US012617752B2

(12) United States Patent
Zhang et al.

(10) Patent No.: US 12,617,752 B2
(45) Date of Patent: May 5, 2026

(54) RAPIDLY METABOLIZED LIPID COMPOUND

(71) Applicants: Beijing Jitai Life Sciences Ltd, Beijing (CN); Melis TechBio Co., Ltd., Beijing (CN)

(72) Inventors: Lin Zhang, Beijing (CN); Feng Shi, Beijing (CN); Andong Liu, Beijing (CN); Liu Yang, Beijing (CN); Shaoli Liu, Beijing (CN); Xuhui Wang, Beijing (CN); Moyan Liu, Beijing (CN); Yan Gong, Beijing (CN); Jeffrey Michael Warrington, Cambridge, MA (US)

(73) Assignees: Beijing Jitai Life Sciences Ltd, Beijing (CN); Metis TechBio Co., Ltd., Beijing (CN)

( * ) Notice: Subject to any disclaimer, the term of this patent is extended or adjusted under 35 U.S.C. 154(b) by 0 days.

(21) Appl. No.: 18/736,389

(22) Filed: Jun. 6, 2024

(65) Prior Publication Data

US 2025/0026713 A1 Jan. 23, 2025

(30) Foreign Application Priority Data

Jun. 16, 2023 (CN) ......................... 202310720951.5
Jun. 16, 2023 (CN) ......................... 202310723466.3
Dec. 29, 2023 (WO) ................ PCT/CN2023/143111
Jan. 26, 2024 (CN) ......................... 202410115561.X
Mar. 1, 2024 (CN) ......................... 202410239117.9
Apr. 11, 2024 (CN) ......................... 202410437163.X

(51) Int. Cl.
*C07C 229/24* (2006.01)
*A61K 9/51* (2006.01)
*C07C 69/675* (2006.01)

(52) U.S. Cl.
CPC .......... *C07C 229/24* (2013.01); *A61K 9/5123* (2013.01); *C07C 69/675* (2013.01)

(58) Field of Classification Search
CPC .... C07C 229/24; C07C 69/675; A61K 9/5123
See application file for complete search history.

(56) References Cited

U.S. PATENT DOCUMENTS

| | | | | |
|---|---|---|---|---|
| 11,246,933 | B1 | 2/2022 | Maier et al. | |
| 2019/0022247 | A1 | 1/2019 | Ansell et al. | |
| 2020/0129445 | A1 * | 4/2020 | Patel .................... | A61K 9/0019 |
| 2020/0306191 | A1 | 10/2020 | Schariter et al. | |
| 2022/0273693 | A1 | 9/2022 | Packer et al. | |
| 2023/0043677 | A1 | 2/2023 | Kim et al. | |

FOREIGN PATENT DOCUMENTS

| | | | |
|---|---|---|---|
| CA | 2856742 | A1 | 6/2013 |
| CA | 2891911 | A1 | 6/2014 |
| CN | 105873902 | A | 8/2016 |
| CN | 106795096 | A | 5/2017 |
| CN | 108368028 | A | 8/2018 |
| CN | 110520409 | A | 11/2019 |
| CN | 111315359 | A | 6/2020 |
| CN | 111417621 | A | 7/2020 |
| CN | 113164379 | A | 7/2021 |
| CN | 113908292 | A | 1/2022 |
| CN | 114073677 | A | 2/2022 |
| CN | 115521220 | A | 12/2022 |
| CN | 115850104 | A | 3/2023 |
| CN | 115887674 | A | 4/2023 |
| CN | 116348147 | A | 6/2023 |
| CN | 116969851 | A | 10/2023 |
| CN | 117243922 | A | 12/2023 |
| JP | 2015500835 | A | 1/2015 |
| JP | 2015505838 | A | 2/2015 |
| JP | 2018521052 | A | 8/2018 |
| JP | 2021104994 | A | 7/2021 |
| JP | 2023164361 | A | 11/2023 |
| WO | 2008140203 | A1 | 11/2008 |
| WO | 2013086322 | A1 | 6/2013 |
| WO | 2014089239 | A1 | 6/2014 |
| WO | 2017180917 | A2 | 10/2017 |
| WO | 2020051220 | A1 | 3/2020 |

(Continued)

OTHER PUBLICATIONS

Next-Generation Lipids in RNA I Interference Therapeutics.
Berge S. M. et al., "Pharmaceutical Salts," J. Pharm. Sci., 1977; 66: 1-19.
English translation of Taiwan First Office Action issued on Apr. 9, 2025 in TW Patent Application No. 113121943.
English translation of International Search Report and Written Opinion mailed on May 20, 2025 in PCT/CN2025/079791, 2 pages.
English translation of International Search Report and Written Opinion mailed on Jun. 16, 2025 in PCT/CN2025/079792, 2 pages.

(Continued)

*Primary Examiner* — Andrew D Kosar
*Assistant Examiner* — Blaine G Doletski
(74) *Attorney, Agent, or Firm* — Fox Rothschild LLP

(57) ABSTRACT

Provided herein is a class of a rapidly metabolized lipid compound, and particularly relates to compounds represented by formula (I), or pharmaceutically acceptable salts, isotopic variants, tautomers, or stereoisomers thereof. Also provided is a nanoparticle pharmaceutical composition comprising said compound, and the application of said compound and its composition in the delivery of nucleic acids.

(I)

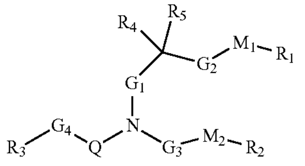

42 Claims, No Drawings

(56) References Cited

FOREIGN PATENT DOCUMENTS

| | | | |
|---|---|---|---|
| WO | 2021030701 | A1 | 2/2021 |
| WO | 2022013443 | A1 | 1/2022 |
| WO | 2022076547 | A1 | 4/2022 |
| WO | 2022153211 | A1 | 7/2022 |
| WO | 2022204288 | A1 | 9/2022 |
| WO | 2022251665 | A1 | 12/2022 |
| WO | 2023056914 | A1 | 4/2023 |
| WO | 2023086465 | A1 | 5/2023 |
| WO | 2024026482 | A1 | 2/2024 |

OTHER PUBLICATIONS

Maier et al., "Biodegradable Lipids Enabling Rapidly Eliminated Lipid Nanoparticles for Systemic Delivery of RNAi Therapeutics", e-published Jun. 25, 2013, Molecular Therapy, vol. 21, Issue 8, pp. 1570-1578.

English translation of Eurasian First Office Action, mailed on Feb. 19, 2026 in Eurasian Patent Application No. 1 202690064.

* cited by examiner

RAPIDLY METABOLIZED LIPID COMPOUND

CROSS-REFERENCE TO RELATED APPLICATIONS

The present application claims the priority of the Chinese Patent Application No. 202310720951.5 filed on Jun. 16, 2023, Chinese Patent Application No. 202310723466.3 filed on Jun. 16, 2023, Chinese Patent Application No. 202410115561.X filed on Jan. 26, 2024, Chinese Patent Application No. 202410437163.X filed on Apr. 11, 2024, Patent Cooperation Treaty Application No. PCT/CN2023/143111 filed on Dec. 29, 2023, and Chinese Patent Application No. 202410239117.9 filed on Mar. 1, 2024. The Patent Applications mentioned above are incorporated herein by reference as part of the disclosure of the present application.

TECHNICAL FIELD

The present disclosure relates to a novel class of ionizable cationic lipid compounds, or pharmaceutically acceptable salts, isotopic variants, tautomers, or stereoisomers thereof. The present disclosure also relates to lipid nanoparticles and pharmaceutical compositions comprising said compound, and the application of the lipid nanoparticles in the delivery of biologically active substances such as nucleic acids (e.g., mRNA, siRNA, ASO, and DNA).

BACKGROUND

Gene therapy refers to the introduction of exogenous genes into target cells to correct or compensate for genetic defects or abnormalities within the cell, so as to achieve the purpose of treatment. In the past few decades, research related to the treatment of clinical diseases through gene therapy has received more and more attention. Especially in recent years, siRNA-related drugs and mRNA vaccines have been approved by the FDA for clinical treatment, which has further promoted research and related investment in the field of gene therapy.

Nucleic acid substances are easily degraded by nucleases in organisms, and nucleic acid substances themselves are negatively charged, which makes it difficult for them to enter the cell through the cell membrane. As a nucleic acid delivery material, lipid nanoparticles (LNP) are one of the most important nucleic acid delivery systems with the advantages of easy to prepare, good biodegradability, no immunogenicity and good safety. The main components of LNP include cationic lipids, cholesterol, neutral lipids and polyethylene glycol-conjugated lipids. Among them, cationic lipid molecules are the core of LNP delivery system, and their molecular structure plays a decisive role in the delivery efficiency, targeting, and formulation stability, and the like, of the entire liposome nanoparticles.

Due to the different requirements of the delivery system for the delivery of different kinds of nucleic acid substances and the specific delivery of different targets, in order to meet the different needs of gene therapy, new lipid molecules need to be further developed.

SUMMARY

The present disclosure develops a new class of ionizable cationic lipid compounds that can be used to deliver various biologically active substances with high delivery efficiency.

The inventor's prior patent CN115850104A discloses that a class of cationic lipid compounds with a pair of geminal dialkyl in each tail has high delivery efficiency. Unexpectedly, after further research, it was found that when the geminal dialkyl structure was applied to cationic lipids containing central nitrogen atoms, the cationic lipids degraded slowly in the liver, making them suitable for applications with slow degradation. For some application scenarios that require accelerating metabolism in vivo, a new class of ionizable lipid compounds is developed.

The present disclosure provides a compound of formula (I) or a pharmaceutically acceptable salt, isotopic variant, tautomer or stereoisomer thereof:

(I)

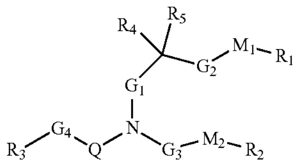

wherein each group is as defined herein.

In another aspect, the present disclosure provides a nanoparticle composition comprising lipid components, and optionally a load, wherein the lipid component comprises the compound of the present disclosure.

U.S. Ser. No. 11/246,933B1 discloses that incorporation of a biodegradable group into the tail chain of a lipid compound in a lipid nanoparticle results in faster metabolism and removal of the lipid from the body following delivery of the active agent to a target area. As a result, these lipids which contain the biodegradable groups have lower toxicity than similar lipids without the biodegradable groups. The tail chain of the cationic lipid compound of the present disclosure has biodegradable group(s), thereby has superior toxicity profile to similar lipids without biodegradable groups, such as DLin-MC3-DMA.

In another aspect, the present disclosure provides a pharmaceutical composition comprising a compound of the present disclosure or a nanoparticle composition of the present disclosure, and optionally pharmaceutically acceptable excipient(s), such as carrier(s), adjuvant(s) or vehicle(s).

In another aspect, the present disclosure provides use of the compound of the present disclosure, a nanoparticle composition of the present disclosure, or a pharmaceutical composition of the present disclosure in the manufacture of a medicament for treating, diagnosing, or preventing a disease. In one embodiment, the medicament for treating, diagnosing, or preventing a disease is a therapeutic or prophylactic mRNA vaccine.

In another aspect, the present disclosure provides use of the compound of the present disclosure, the nanoparticle composition of the present disclosure, or the pharmaceutical composition of the present disclosure in preparing a medicament for delivering a loading. In another aspect, the present disclosure provides the use of a compound of the present disclosure, a nanoparticle composition of the present disclosure, or a pharmaceutical composition of the present disclosure in the manufacture of a medicament for delivering a load.

In another aspect, the present disclosure provides a method of treating, diagnosing, or preventing a disease in a subject, comprising administering to the subject a compound of the present disclosure, a nanoparticle composition of the present disclosure, or a pharmaceutical composition of the present disclosure.

In another aspect, the present disclosure provides a compound of the present disclosure, a nanoparticle composition of the present disclosure, or a pharmaceutical composition of the present disclosure, for use in treating, diagnosing, and/or preventing a disease.

In another aspect, the present disclosure provides a method of delivering a load in a subject, comprising administering to the subject a compound of the present disclosure, a nanoparticle composition of the present disclosure, or a pharmaceutical composition of the present disclosure.

In another aspect, the present disclosure provides a compound of the present disclosure, a nanoparticle composition of the present disclosure, or a pharmaceutical composition of the present disclosure, for use in delivering a load.

In a specific embodiment, the load is selected from one or more of therapeutic agents, prophylactic agents, and diagnostic agents; alternatively, the therapeutic agent, prophylactic agent, or diagnostic agent is a nucleic acid.

In a more specific embodiment, the nucleic acid is selected from one or more of ASO, RNA and DNA.

In a more specific embodiment, the RNA is selected from one or more of small interfering RNA (siRNA), short hairpin RNA (shRNA), antisense RNA (aRNA), messenger RNA (mRNA), long non-coding RNA (lncRNA), microRNA (miRNA), small activating RNA (saRNA), multimeric coding nucleic acid (MCNA), polymeric coding nucleic acid (PCNA), guide RNA (gRNA), CRISPRRNA (crRNA), and a ribozyme, alternatively mRNA, and more alternatively modified mRNA.

DEFINITIONS

Chemical Definitions

Definitions of specific functional groups and chemical terms are described in more detail below.

When a range of values is listed, it is intended to encompass each value and sub-range within the range. For example, "$C_{1-6}$ alkyl" includes $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"$C_{1-20}$ alkyl" refers to a linear or branched saturated hydrocarbon group having 1 to 20 carbon atoms. In some embodiments, $C_{4-20}$ alkyl, $C_{6-14}$ alkyl, $C_{7-12}$ alkyl, $C_{8-12}$ alkyl, $C_{9-12}$ alkyl, $C_{4-10}$ alkyl, $C_{7-11}$ alkyl, $C_{8-11}$ alkyl, $C_{9-11}$ alkyl, $C_{10-11}$ alkyl, $C_{6-10}$ alkyl, $C_{7-10}$ alkyl, $C_{8-10}$ alkyl, $C_{9-10}$ alkyl, $C_{10}$ alkyl, $C_{8-9}$ alkyl, $C_{4-9}$ alkyl, $C_{6-9}$ alkyl, $C_{7-9}$ alkyl, $C_9$ alkyl, $C_{10}$ alkyl, $C_{11}$ alkyl, $C_{2-8}$ alkyl, $C_{4-8}$ alkyl, $C_{5-8}$ alkyl, $C_{6-8}$ alkyl, $C_{7-8}$ alkyl, $C_8$ alkyl, $C_{6-7}$ alkyl, $C_7$ alkyl, $C_{4-6}$ alkyl, $C_{1-20}$ alkyl, $C_{1-14}$ alkyl, $C_{2-14}$ alkyl, $C_{1-13}$ alkyl, $C_{1-12}$ alkyl, $C_{1-10}$ alkyl, $C_{1-9}$ alkyl, $C_{1-8}$ alkyl, $C_{1-7}$ alkyl, $C_{2-7}$ alkyl, $C_{1-6}$ alkyl, $C_{2-6}$ alkyl, $C_{1-5}$ alkyl, $C_5$ alkyl, $C_{1-4}$ alkyl, $C_{2-4}$ alkyl, $C_{1-3}$ alkyl, $C_{2-3}$ alkyl, $C_{1-2}$ alkyl, and Me are preferred. Examples of $C_{1-6}$ alkyl include: methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$), and n-hexyl ($C_6$). The term "$C_{1-6}$ alkyl" also includes heteroalkyl, wherein one or more (e.g., 1, 2, 3, or 4) carbon atoms are substituted with heteroatoms (e.g., oxygen, sulfur, nitrogen, boron, silicon, or phosphorus). An alkyl group may optionally be substituted with one or more substituents, for example, 1 to 5 substituents, 1 to 3 substituents, or 1 substituent. Conventional abbreviations of alkyl groups include: Me ($-CH_3$), Et ($-CH_2CH_3$), iPr ($-CH(CH_3)_2$), nPr ($-CH_2CH_2CH_3$), n-Bu ($-CH_2CH_2CH_2CH_3$), or i-Bu ($-CH_2CH(CH_3)_2$). In some embodiments, alkyl is preferably linear alkyl.

"$C_{2-13}$ alkenyl" refers to a linear or branched hydrocarbon group having 2 to 13 carbon atoms and at least one carbon-carbon double bond. "$C_{4-20}$ alkenyl" refers to a linear or branched hydrocarbon group having 4 to 20 carbon atoms and at least one carbon-carbon double bond. In some embodiments, $C_{4-14}$ alkenyl, $C_{6-14}$ alkenyl, $C_{7-12}$ alkenyl, $C_{4-10}$ alkenyl, $C_{2-10}$ alkenyl, $C_{2-9}$ alkenyl, $C_{2-6}$ alkenyl, and $C_{2-4}$ alkenyl are preferred. Examples of $C_{2-6}$ alkenyl include: ethenyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl where one or more (e.g., 1, 2, 3, or 4) carbon atoms are replaced with heteroatoms (e.g., oxygen, sulfur, nitrogen, boron, silicon, or phosphorus). An alkenyl group may optionally be substituted with one or more substituents, for example, 1 to 5 substituents, 1 to 3 substituents, or 1 substituent.

"$C_{2-13}$ alkynyl" refers to a linear or branched hydrocarbon group having 2 to 13 carbon atoms, at least one carbon-carbon triple bond, and optionally one or more carbon-carbon double bonds. "$C_{4-20}$ alkynyl" refers to a linear or branched hydrocarbon group having 4 to 20 carbon atoms, at least one carbon-carbon triple bond, and optionally one or more carbon-carbon double bonds. In some embodiments, $C_{4-14}$ alkynyl, $C_{6-14}$ alkynyl, $C_{7-12}$ alkynyl, $C_{4-10}$ alkynyl, $C_{2-10}$ alkynyl, $C_{2-9}$ alkynyl, $C_{2-6}$ alkynyl, and $C_{2-4}$ alkynyl are preferred. Examples of $C_{2-6}$ alkynyl include, but are not limited to: ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), and the like. The term "$C_{2-6}$ alkynyl" also includes heteroalkynyl where one or more (e.g., 1, 2, 3, or 4) carbon atoms are replaced with heteroatoms (e.g., oxygen, sulfur, nitrogen, boron, silicon, or phosphorus). An alkynyl group may optionally be substituted with one or more substituents, for example, 1 to 5 substituents, 1 to 3 substituents, or 1 substituent.

"$C_{1-20}$ alkylene" refers to a bivalent group formed by removing another hydrogen of $C_{1-20}$ alkyl, and can be substituted or unsubstituted. In some embodiments, $C_{4-20}$ alkylene, $C_{6-14}$ alkylene, $C_{7-12}$ alkylene, $C_{8-12}$ alkylene, $C_{4-10}$ alkylene, $C_{7-11}$ alkylene, $C_{8-11}$ alkylene, $C_{8-10}$ alkylene, $C_{9-10}$ alkylene, $C_{8-9}$ alkylene, $C_{4-9}$ alkylene, $C_{6-9}$ alkylene, $C_{7-9}$ alkylene, $C_9$ alkylene, $C_{2-8}$ alkylene, $C_{5-8}$ alkylene, $C_{7-8}$ alkylene, $C_{4-6}$ alkylene, $C_{1-20}$ alkylene, $C_{1-14}$ alkylene, $C_{2-14}$ alkylene, $C_{1-13}$ alkylene, $C_{1-12}$ alkylene, $C_{1-10}$ alkylene, $C_{1-9}$ alkyl, $C_{1-8}$ alkylene, $C_{1-7}$ alkylene, $C_{2-7}$ alkylene, $C_{1-6}$ alkylene, $C_{2-6}$ alkylene, $C_{1-5}$ alkylene, $C_5$ alkylene, $C_{1-4}$ alkylene, $C_{2-4}$ alkylene, $C_{1-3}$ alkylene, $C_{2-3}$ alkylene, $C_{1-2}$ alkylene, and methylene are preferred. Unsubstituted alkylene groups include, but are not limited to: methylene ($-CH_2-$), ethylene ($-CH_2CH_2-$), propylene ($-CH_2CH_2CH_2-$), butylene ($-CH_2CH_2CH_2CH_2-$), pentylene ($-CH_2CH_2CH_2CH_2CH_2-$), hexylene ($-CH_2CH_2CH_2CH_2CH_2CH_2-$), etc. Exemplary of substituted alkylene groups, such as those substituted with one or more alkyl (methyl) groups, include, but are not limited to: substituted methylene ($-CH(CH_3)-$, and $-C(CH_3)_2-$), substituted ethylene ($-CH(CH_3)CH_2-$, $-CH_2CH(CH_3)-$, $-C(CH_3)_2CH_2-$, $-CH_2C(CH_3)_2$.), substituted propylene ($-CH(CH_3)CH_2CH_2-$, $-CH_2CH(CH_3)CH_2-$, $-CH_2CH_2CH(CH_3)-$, $-C(CH_3)_2CH_2CH_2-$, $-CH_2C(CH_3)_2CH_2-$, $-CH_2CH_2C(CH_3)_2-$), etc.

"$C_{2-13}$ alkenylene" refers to a bivalent group formed by removing another hydrogen of $C_{2-13}$ alkenyl, and can be substituted or unsubstituted. "$C_{4-14}$ alkenylene" refers to a bivalent group formed by removing another hydrogen of $C_{4-14}$ alkenyl, and can be substituted or unsubstituted. In some embodiments, $C_{6-14}$ alkenylene, $C_{4-10}$ alkenylene, $C_{2-10}$ alkenylene, $C_{2-9}$ alkenylene, $C_{2-6}$ alkenylene, and $C_{2-4}$ alkenylene are particularly preferred. Exemplary unsubstituted forms of the alkenylene include, but are not limited to: ethenylene (—CH═CH—) and propenylene (e.g., —CH═CHCH$_2$— and —CH$_2$—CH═CH—). Exemplary substituted alkenylene groups, for example, alkenylene substituted with one or more alkyl (methyl), include, but are not limited to: substituted ethenylene (—C(CH$_3$)═CH— and —CH═C(CH$_3$)—), substituted propenylene (—C(CH$_3$)═CHCH$_2$—, —CH═C(CH$_3$)CH$_2$—, —CH═CHCH(CH$_3$)—, —CH═CHC(CH$_3$)$_2$—, —CH(CH$_3$)—CH═CH—, —C(CH$_3$)$_2$—CH═CH—, —CH$_2$—C(CH$_3$)═CH—, —CH$_2$—CH═C(CH$_3$)—), etc.

"$C_{2-13}$ alkynylene" refers to a bivalent group formed by removing another hydrogen of $C_{2-13}$ alkynyl, and can be substituted or unsubstituted. "$C_{4-14}$ alkynylene" refers to a bivalent group formed by removing another hydrogen of $C_{4-14}$ alkynyl, and can be substituted or unsubstituted. In some embodiments, $C_{6-14}$ alkynylene, $C_{4-10}$ alkynylene, $C_{2-10}$ alkynylene, $C_{2-9}$ alkynylene, $C_{2-6}$ alkynylene, and $C_{2-4}$ alkynylene are particularly preferred. Exemplary alkynylene groups include, but are not limited to: ethynylene (—C≡C—), substituted or unsubstituted propynylene (—C≡CCH$_2$—), etc.

"$C_{0-6}$ alkylene" refers to a chemical bond and the "$C_{1-6}$ alkylene" described above. "$C_{0-4}$ alkylene" refers to a chemical bond and the "$C_{1-4}$ alkylene" described above.

The term "variable A and variable B have a total length of x carbon atoms" means that the total number of carbon atoms of the main chain in the group represented by variable A and the number of carbon atoms of the main chain in the group represented by variable B is x.

The term "the substitution site of $R_{1s}$ on $R_2$ is separated from $M_2$ by x carbon atoms" means that the sum of the number of carbon atoms (including N atoms replaced by —NR'—) between the sites substituted by variable $R_{1s}$ on variable $R_2$, and so on for other situations. For example:

11b

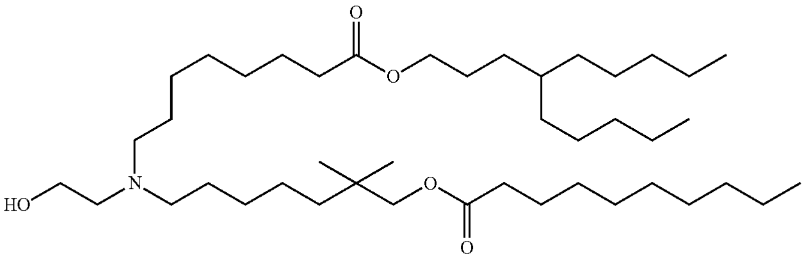

, in compound 11 b, the substitution site of $R_{1s}$ on $R_2$ is separated from $M_2$ by 3 carbon atoms.

"Halo" or "halogen" refers to fluorine (F), chlorine (Cl), bromine (Br), and iodine (I).

Thus, "$C_{1-10}$ haloalkyl" refers to the above "$C_{1-10}$ alkyl", which is substituted with one or more halogen. In some embodiments, $C_{1-8}$ haloalkyl, $C_{1-6}$ haloalkyl, $C_{1-4}$ haloalkyl, and $C_{1-3}$ haloalkyl are particularly preferred, still alternatively $C_{1-2}$ haloalkyl. Exemplary haloalkyl groups include, but are not limited to: —CF$_3$, —CH$_2$F, —CHF$_2$, —CHFCH$_2$F, —CH$_2$CHF$_2$, —CF$_2$CF$_3$, —CCl$_3$, —CH$_2$Cl, —CHCl$_2$, 2,2,2-trifluoro-1,1-dimethyl-ethyl, etc. A haloalkyl group can be substituted at any accessible point of attachment with, for example, 1 to 5 substituents, 1 to 3 substituents, or 1 substituent.

"$C_{3-14}$ cycloalkyl" or "3- to 14-membered cycloalkyl" refers to a radical of a non-aromatic cyclic hydrocarbon group having 3 to 14 ring carbon atoms and zero heteroatoms, optionally containing 1, 2, or 3 double or triple bonds. In some embodiments, 3- to 10-membered cycloalkyl, 5- to 10-membered cycloalkyl, 3- to 8-membered cycloalkyl, 3- to 7-membered cycloalkyl, and 3- to 6-membered cycloalkyl are particularly preferred, still alternatively 5- to 7-membered cycloalkyl, 4- to 6-membered cycloalkyl, 3- to 5-membered cycloalkyl, 3- to 4-membered cycloalkyl, and 5- to 6-membered cycloalkyl, still alternatively 5-membered cycloalkyl, still alternatively 6-membered cycloalkyl, and still alternatively cyclopropyl. The cycloalkyl also includes a ring system in which the cycloalkyl ring described above is fused with one or more aryl or heteroaryl groups, wherein the point of attachment is on the cycloalkyl ring, and in such case, the number of carbon atoms continues to represent the number of carbon atoms in the cycloalkyl system. The cycloalkyl further comprises the cycloalkyl described above, in which the substituents on any non-adjacent carbon atoms are connected to form a bridged ring, together forming a polycyclic alkane sharing two or more carbon atoms. The cycloalkyl further comprises the cycloalkyl described above, in which the substituents on the same carbon atom are connected to form a ring, together forming a polycyclic alkane sharing one carbon atom. Exemplary cycloalkyl groups include, but are not limited to: cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc. A cycloalkyl can optionally be substituted with one or more substituents, for example, 1 to 5 substituents, 1 to 3 substituents, or 1 substituent.

"$C_{3-14}$ cycloalkylene" refers to a bivalent group formed by removing another hydrogen of $C_{3-14}$ cycloalkyl and may be substituted or unsubstituted. In some embodiments, $C_{3-10}$ cycloalkylene, $C_{3-7}$ cycloalkylene, $C_{3-6}$ cycloalkylene, $C_{3-5}$ cycloalkylene, and $C_{3-4}$ cycloalkylene are particularly preferred, even still alternatively cyclopropylene.

"3-14 membered heterocyclyl" or "3- to 14-membered heterocyclyl" refers to a saturated or unsaturated group of a 3- to 14-membered non-aromatic ring system having ring carbon atoms and 1 to 5 ring heteroatoms, wherein each heteroatom is independently selected from nitrogen, oxygen, sulfur, boron, phosphorus, and silicon, optionally wherein 1, 2 or 3 double or triple bonds are contained. In a heterocyclyl containing one or more nitrogen atoms, the point of attachment can be a carbon atom or a nitrogen atom as long as the valence permits. In some embodiments, 3- to 10-membered heterocyclyl is preferred, which is a radical of 3- to 10-membered non-aromatic ring system having ring carbon atoms and 1 to 5 ring heteroatoms; in some embodiments, 5- to 10-membered heterocyclyl is preferred, which is a radical of 5- to 10-membered non-aromatic ring system having ring carbon atoms and 1 to 5 ring heteroatoms; in some embodiments, 3- to 8-membered heterocyclyl is preferred, which is a radical of 3- to 8-membered non-aromatic ring system having ring carbon atoms and 1 to 4 ring heteroatoms; in some embodiments, 3- to 7-membered heterocyclyl is preferred, which is a radical of 3- to 7-membered non-aromatic ring system having ring carbon atoms and 1 to 4 ring heteroatoms; 5- to 7-membered heterocyclyl is preferred, which is a radical of 5- to 7-membered non-aromatic ring system having ring carbon atoms and 1 to 3 ring heteroatoms; 3- to 6-membered heterocyclyl is preferred, which is a radical of 3- to 6-membered non-aromatic ring system having ring carbon atoms and 1 to 3 ring heteroatoms; 4- to 6-membered heterocyclyl is preferred, which is a radical of 4- to 6-membered non-aromatic ring system having ring carbon atoms and 1 to 3 ring heteroatoms; 5- to 6-membered heterocyclyl is more preferred, which is a radical of 5- to 6-membered non-aromatic ring system having ring carbon atoms and 1 to 3 ring heteroatoms; 5-membered heterocyclyl is preferred, which is a radical of 5-membered non-aromatic ring system having ring carbon atoms and 1 to 3 ring heteroatoms; 6-membered heterocyclyl is preferred, which is a radical of 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the heterocyclyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. The heterocyclyl further comprises the heterocyclyl described above, in which the substituents on any non-adjacent carbon or nitrogen atoms are connected to form a bridge ring, together forming a polycyclic heteroalkane sharing two or more carbon or nitrogen atoms. The heterocyclyl further comprises the heterocyclyl described above, in which the substituents on the same carbon atom are connected to form a ring, together forming a polycyclic heteroalkane sharing one carbon atom. Exemplary 3-membered heterocyclyl groups containing one heteroatom include, but are not limited to: aziridinyl, oxiranyl, and thiorenyl. Exemplary 4-membered heterocyclyl groups containing one heteroatom include, but are not limited to: azetidinyl, oxetanyl, and thietanyl. Exemplary 5-membered heterocyclyl groups containing one heteroatom include, but are not limited to: tetrahydrofuranyl, dihydrofuranyl, tetrahydrothienyl, dihydrothienyl, pyrrolidinyl, dihydropyrrolyl, and pyrrolyl-2,5-dione. Exemplary 5-membered heterocyclyl groups containing two heteroatoms include, but are not limited to: pyrazolidinyl, dioxolanyl, oxasulfuranyl, disulfuranyl, and oxazolidin-2-one. Exemplary 5-membered heterocyclyl groups containing three heteroatoms include, but are not limited to: triazolinyl, oxadiazolinyl, and thiadiazolinyl. Exemplary 6-membered heterocyclyl groups containing one heteroatom include, but are not limited to: piperidinyl, tetrahydropyranyl, dihydropyridinyl, and thianyl. Exemplary 6-membered heterocyclyl groups containing two heteroatoms include, but are not limited to: piperazinyl, morpholinyl, dithianyl, and dioxanyl. Exemplary 6-membered heterocyclyl groups containing three heteroatoms include, but are not limited to: triazinanyl. Exemplary 7-membered heterocyclyl groups containing one heteroatom include, but are not limited to: azepanyl, oxepanyl, and thiepanyl. Exemplary 5-membered heterocyclyl groups fused with a $C_6$ aryl ring (also referred to as 5,6-bicyclic heterocyclyl herein) include, but are not limited to: indolinyl, isoindolinyl, dihydrobenzofuranyl, dihydrobenzothienyl, benzoxazolinonyl, and the like. Exemplary 6-membered heterocyclyl groups fused with a $C_6$ aryl ring (also referred to as 6,6-bicyclic heterocyclyl herein) include, but are not limited to: tetrahydroquinolinyl, tetrahydroisoquinolinyl, etc. Heterocyclyl also includes the above heterocyclyl that shares one or two atoms with one cycloalkyl, heterocyclyl, aryl, or heteroaryl to form a bridged or spiro ring, where the shared atom may be a carbon or nitrogen atom as long as the valency permits. The heterocyclyl further includes the heterocyclyl described above, which optionally can be substituted with one or more substituents, e.g., with 1 to 5 substituents, 1 to 3 substituents or 1 substituent.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"5- to 14-membered heteroaryl" refers to a radical of 5- to 14-membered monocyclic or bicyclic 4n+2 aromatic ring system (e.g., having 6, 10 or 14 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. heteroaryl bicyclic systems may include one or more heteroatoms in one or two rings. heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 10-membered heteroaryl groups are alternative, which are radicals of 5- to 10-membered monocyclic or bicyclic 4n+2 aromatic ring systems having ring carbon atoms and 1-4 ring heteroatoms. In other embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1,2,4-oxadiazolyl), and thiadiazolyl.

Exemplary 5-membered heteroaryl groups containing four heteroatoms include, but are not limited to, tetrazolyl. Exemplary 6-membered heteroaryl groups containing one heteroatom include, but are not limited to, pyridyl or pyridonyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl. The heteroaryl can be substituted with one or more substituents, for example, with 1 to 5 substituents, 1 to 3 substituents or 1 substituent.

"Hydroxyalkyl" refers to an alkyl group that is substituted with one or more hydroxy groups.

"Alkoxy" refers to an oxyether form of a linear or branched-chain alkyl group, i.e., an —O-alkyl group. Similarly, "methoxy" refers to —O—$CH_3$.

"Optionally substituted with . . . " means it can be substituted with the specified substituents or unsubstituted.

Bivalent groups formed by removing another hydrogen from the groups defined above such as alkyl, alkenyl, alkynyl, cycloalkyl, heterocyclyl, aryl, heteroaryl are collectively referred to as "ylene". Ring-forming groups such as cycloalkyl, heterocyclyl, aryl, and heteroaryl are collectively referred to as "cyclic groups".

alkyl, alkenyl, alkynyl, cycloalkyl, heterocyclyl, aryl, heteroaryl, etc, as defined herein are optionally substituted groups.

Exemplary substituents on carbon atoms include, but are not limited to: halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X$—, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{a}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{a}$, —$SO_2OR^{a}$, —$OSO_2R^{a}$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{a}$, —$OP(=O)_2R^{a}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, alkyl, haloalkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{a}$, =$NR^{bb}$, or =$NOR^{cc}$;

each of the $R^{aa}$ is independently selected from alkyl, haloalkyl, alkenyl, alkynyl, cycloalkyl, heterocyclyl, aryl, and heteroaryl, or two $R^{aa}$ groups are joined to form a heterocyclyl or heteroaryl ring, wherein each of the alkyl, alkenyl, alkynyl, cycloalkyl, heterocyclyl, aryl, and heteroaryl is independently substituted with 0, 1, 2, 3, 4, or 5 $R^{dd}$ groups;

each of the $R^{bb}$ is independently selected from hydrogen, —OH, —$OR^{a}$, —$N(R^{cc})_2$, —CN, —$C(=O)R^{aa}$, —$C(=O)N(R^{cc})_2$, —$CO_2R^{aa}$, —$SO_2R^{a}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{c})_2$, —$C(=O)SR^{cc}$, —$C(=S)SR^{c}$, —$P(=O)_2R^{a}$, —$P(=O)(R^{aa})_2$, —$P(=O)_2N(R^{cc})_2$, —$P(=O)(NR^{cc})_2$, alkyl, haloalkyl, alkenyl, alkynyl, cycloalkyl, heterocyclyl, aryl, and heteroaryl, or two $R^{bb}$ groups are combined to form a heterocyclyl or heteroaryl ring, wherein each of the alkyl, alkenyl, alkynyl, cycloalkyl, heterocyclyl, aryl, and heteroaryl is independently substituted with 0, 1, 2, 3, 4, or 5 $R^{dd}$ groups;

each of the $R^{cc}$ is independently selected from hydrogen, alkyl, haloalkyl, alkenyl, alkynyl, cycloalkyl, heterocyclyl, aryl, and heteroaryl, or two $R^{cc}$ groups are joined to form a heterocyclyl or heteroaryl ring, wherein each of the alkyl, alkenyl, alkynyl, cycloalkyl, heterocyclyl, aryl, and heteroaryl is independently substituted with 0, 1, 2, 3, 4, or 5 $R^{dd}$ groups;

Each of the $R^{dd}$ is independently selected from: halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X$—, —$N(OR^{ee})R^{ff}$, —SH, —$SR^{ee}$, —$SSR^{ff}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(Rr)_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)_2R^{ee}$, —$P(=O)(R^{ee})_2$, —$OP(=O)(R^{ee})_2$, —$OP(=O)(OR^{ee})_2$, alkyl, haloalkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl is independently substituted with 0, 1, 2, 3, 4, or 5 $R^{gg}$ groups, or two geminal $R^{dd}$ substituents may be combined to form =O or =S;

each of the $R^{cc}$ is independently selected from alkyl, haloalkyl, alkenyl, alkynyl, cycloalkyl, aryl, heterocyclyl, and heteroaryl, wherein each of the alkyl, alkenyl, alkynyl, cycloalkyl, heterocyclyl, aryl, and heteroaryl is independently substituted with 0, 1, 2, 3, 4, or 5 $R^{gg}$ groups;

each of the $R^{ff}$ is independently selected from hydrogen, alkyl, haloalkyl, alkenyl, alkynyl, cycloalkyl, heterocyclyl, aryl, and heteroaryl, or two $R^{ff}$ groups are combined to form a heterocyclyl or heteroaryl ring, wherein each of the alkyl, alkenyl, alkynyl, cycloalkyl, heterocyclyl, aryl, and heteroaryl is independently substituted with 0, 1, 2, 3, 4, or 5 $R^{gg}$ groups;

each of the $R^{gg}$ is independently: halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X$—, —$NH(C_{1-6}$ alkyl$)_2{}^+X$—, —$NH_2(C_{1-6}$ alkyl)+X—, —$NH_3{}^+X$—, —$N(OC_{1-6}$ alkyl)($C_{1-6}$ alkyl), —N(OH)

($C_{1-6}$ alkyl), —NH(OH), —SH, —$SC_{1-6}$ alkyl, —SS($C_{1-6}$ alkyl), —C(═O)($C_{1-6}$ alkyl), —$CO_2$H, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$, —C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)$_2$($C_{1-6}$ alkyl), —P(═O)($C_{1-6}$ alkyl)$_2$, —OP(═O)($C_{1-6}$ alkyl)$_2$, —OP(═O)($OC_{1-6}$ alkyl)$_2$, $C_{1-6}$ alkyl, $C_{1-6}$ haloalkyl, $C_2$-$C_6$ alkenyl, $C_2$-$C_6$ alkynyl, $C_3$-$C_7$ cycloalkyl, $C_6$-$C_{10}$ aryl, 3-7 membered heterocyclyl, or 5-10 membered heteroaryl; or two geminal $R^{gg}$ substituents may be combined to form ═O or ═S; wherein, X— is a counter ion.

exemplary substituents on nitrogen atoms include, but are not limited to: hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^c$, —$SOR^{aa}$, —C(═S)N($R^c$)$_2$, —C(═O)$SR^{cc}$, —C(═S)$SR^{cc}$, —P(═O)$_2R^{aa}$, —P(═O)($R^{aa}$)$_2$, —P(═O)$_2$N($R^{cc}$)$_2$, —P(═O)($NR^{cc}$)$_2$, alkyl, haloalkyl, alkenyl, alkynyl, cycloalkyl, heterocyclyl, aryl, and heteroaryl, or two $R^{cc}$ groups attached to a nitrogen atom are combined to form a heterocyclyl or heteroaryl ring, wherein each of the alkyl, alkenyl, alkynyl, cycloalkyl, heterocyclyl, aryl, and heteroaryl is independently substituted with 0, 1, 2, 3, 4, or 5 $R^{dd}$ groups, and wherein $R^a$, $R^{bb}$, $R^{cc}$, and $R^{dd}$ are as described above.

"Nucleic acids" refers to single- or double-stranded deoxyribonucleic acid (DNA) or ribonucleic acid (RNA) molecules and their heterozygous molecules. Examples of nucleic acid molecules include, but are not limited to, messenger RNA (mRNA), microRNA (miRNA), small interfering RNA (siRNA), self-amplified RNA (saRNA), and antisense oligonucleotides (ASO), etc. Nucleic acids may be further chemically modified, and the chemical modifier selected from one of, or a combination of pseudouridine, N1-methyl-pseudouridine, 5-methoxyuridine, 5-methylcytosine. mRNA molecules contain protein coding regions and may further contain expression regulatory sequences. Typical expression regulatory sequences include, but are not limited to, 5' cap, 5' untranslated region (5' UTR), 3' untranslated region (3' UTR), polyadenylate sequence (PolyA), miRNA binding sites.

"Cationic lipid" refers to a lipid molecule capable of being positively charged at physiological pH. In some embodiments, the cationic lipid is an amino lipid.

"Neutral lipid" refers to a lipid molecule that is not charged at specific pH, e.g., physiological pH. Examples of neutral lipids include, but are not limited to, 1,2-distearoyl-sn-glycero-3-phosphocholine (DSPC), 1,2-dimyristoyl-sn-glycero-3-phosphocholine (DMPC), 1,2-dioleoyl-sn-glycero-3-phosphocholine (DOPC), 1,2-dipalmitoyl-sn-glycero-3-phosphocholine (DPPC), 1-palmitoyl-2-oleoyl-sn-glycero-3-phosphocholine (POPC), 1,2-dioleoyl-sn-glycero-3-phosphoethanolamine (DOPE), 1,2-dimyristoyl-sn-glycero-3-phosphoethanolamine (DMPE), 1-palmitoyl-2-oleoyl-sn-glycero-3-phosphoethanolamine (POPE), and 1,2-dipalmitoyl-sn-glycero-3-phosphoethanolamine (DPPE).

"Structure lipids" refers to lipids that enhance the stability of nanoparticles by filling the gaps between lipids, commonly such as steroids. The steroid is a compound having a perhydrocyclopentanophenanthrene carbon framework. In an alternative embodiment, the steroid is selected from cholesterol, sitosterol, coprosterol, fucosterol, brassicasterol, ergosterol, tomatine, ursolic acid, α-tocopherol, stigmasterol, avenasterol, ergocalciferol and campesterol.

"Polymer lipids" refers to molecules containing a polymer moiety and a lipid moiety. In some embodiments, the polymer lipid is a polyethylene glycol (PEG) lipid. Other lipids that can reduce aggregation, such as products of compounds having uncharged, hydrophilic, space-barrier moieties coupled with lipid may also be used.

"Lipid nanoparticles" refers to particles containing lipid components of nanoscale size.

"Biodegradable groups" refers to functional groups that contain biodegradable bonds, such as esters, disulfide bonds and amides, etc. Biodegradation may affect the process of removing compounds from the body. The biodegradable groups of the present disclosure are oriented from the head to the tail in ionizable lipid molecules.

Other Definitions

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable salt" as used herein refers to those carboxylate and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such as solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19 for reference).

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease", "disorder", and "condition" can be used interchangeably herein.

Unless otherwise indicated, the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a pharmaceutical composition refers to an amount sufficient to elicit a target biological response. As understood by those skilled in the art, the effective amount of the pharmaceutical composition of the disclosure can vary depending on the following factors, such as the desired biological endpoint, the pharmacokinetics of the pharmaceutical composition, the diseases being treated, the mode of administration, and the age, health status and symptoms of the subjects. The effective amount includes therapeutically effective amount and prophylactically effective amount.

Unless otherwise indicated, the "therapeutically effective amount" of the pharmaceutical composition as used herein is an amount sufficient to provide therapeutic benefits in the course of treating a disease, disorder or condition, or to delay or minimize one or more symptoms associated with the disease, disorder or condition. The therapeutically effective amount of a pharmaceutical composition refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless otherwise indicated, the "prophylactically effective amount" of the pharmaceutical composition as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a pharmaceutical composition refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the pharmaceutical compositions of the present disclosure and other therapeutic agents. For example, the pharmaceutical compositions of the present disclosure can be administered simultaneously or sequentially in separate unit dosage with other therapeutic agents, or simultaneously in a single unit dosage with other therapeutic agents.

DETAILED DESCRIPTION

As used herein, "compounds of the present disclosure" refers to the following compounds, pharmaceutically acceptable salts, isotopic variants, tautomers or stereoisomers thereof.

In the present disclosure, compounds are named using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E. Compounds which exist in different tautomeric forms, one of which is not limited to any particular tautomer, but is intended to cover all tautomeric forms.

In one embodiment, the present disclosure relates to a compound of formula (I), or a pharmaceutically acceptable salt, isotopic variant, tautomer or stereoisomer thereof:

(I)

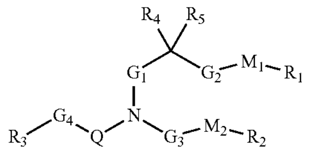

wherein $G_1$ and $G_2$ are independently selected from a chemical bond, $C_{1-13}$ linear alkylene, $C_{2-13}$ linear alkenylene, and $C_{2-13}$ linear alkynylene, each of which is optionally substituted with one or more $R_{G1}$;

$G_1$ and $G_2$ have a total length of 3, 4, 5, 6, 7, 8, 9, 10, 11, 12, or 13 carbon atoms;

$R_{G1}$ is independently H, $C_{1-14}$ alkyl, $-L_a-OR_a$, $-L_a-SR_a$, or $-L_a-NR_aR'_a$;

$G_3$ is $C_{4-14}$ linear alkylene, $C_{4-14}$ linear alkenylene, or $C_{4-14}$ linear alkynylene, each of which is optionally substituted with one or more $R_{G3}$;

$R_{G3}$ is independently H, $-L_a-OR_a$, $-L_a-SR_a$, or $-L_a-NR_aR'_a$;

$L_a$ is independently a chemical bond or $C_{1-14}$ alkylene;

$R_a$ and $R'_a$ are independently selected from H, $C_{1-14}$ alkyl, $C_{3-14}$ cycloalkyl, and 3- to 14-membered heterocyclyl;

$G_4$ is a chemical bond, $C_{1-6}$ alkylene, $C_{2-6}$ alkenylene, or $C_{2-6}$ alkynylene, each of which is optionally substituted with one or more $R_{G4}$;

$R_{G4}$ is independently H, $C_{1-6}$ alkyl, $-L_b-OR_b$, $-L_b-SR_b$, or $-L_b-NR_bR'_b$;

$L_b$ is independently a chemical bond or $C_{1-6}$ alkylene;

$R_b$ and $R'_b$ are independently selected from H, $C_{1-6}$ alkyl, $C_{3-10}$ cycloalkyl, and 3- to 10-membered heterocyclyl;

or, two $R_{G4}$ attached to the same carbon atom are taken together with the carbon atom to which they are attached to form $C_{3-14}$ cycloalkylene or 3- to 14-membered heterocyclylene, each of which is optionally substituted with one or more $R_{4g}$;

$R_{4g}$ is independently H, halogen, cyano, $C_{1-8}$ alkyl, $C_{1-8}$ haloalkyl, $-L_e-OR_e$, $-L_e-SR_e$, or $-L_e-NR_eR'_e$;

$L_e$ is independently a chemical bond or $C_{1-8}$ alkylene;

$R_e$ and $R'_e$ are independently selected from H, $C_{1-8}$ alkyl, $C_{3-14}$ cycloalkyl, and 3- to 14-membered heterocyclyl;

$M_1$ and $M_2$ are independently selected from —C(O)O—, —OC(O)—, —O—, —SC(O)O—, —OC(O)NR—, —NRC(O)NR—, —OC(O)S—, —OC(O)O—, —NRC(O)O—, —SC(O)—, —C(O)S—, —NR—, —C(O)NR—, —NRC(O)—, —NRC(O)S—, —SC(O)NR—, —C(O)—, —OC(S)—, —C(S)O—, —OC(S)NR—, —NRC(S)O—, —S—S—, and $—S(O)_{0-2}—$;

Q is selected from a chemical bond, —C(O)O—, —O—, —SC(O)O—, $—OC(O)NR_f—$, $—NR_fC(O)NR_f—$, —OC(O)S—, —OC(O)O—, $—NR_fC(O)O—$, —OC(O)—, —SC(O)—, —C(O)S—, $—NR_f—$, $—C(O)NR_f—$, $—NR_fC(O)—$, $—NR_fC(O)S—$, $—SC(O)NR_f—$, —C(O)—, —OC(S)—, —C(S)O—, $—OC(S)NR_f—$, $—NR_fC(S)O—$, —S—S—, $—S(O)_{0-2}—$, phenylene, and pyridinylene, wherein the phenylene or the pyridinylene is optionally substituted with one or more R*;

R* is independently H, halogen, cyano, $C_{1-10}$ alkyl, $C_{1-10}$ haloalkyl, $-L_f-OR_f$, $-L_f-SR_f$, or $-L_f-NR_fR'_f$;

$L_f$ is independently a chemical bond or $C_{1-8}$ alkylene;

$R_f$ and $R'_f$ are independently selected from H, $C_{1-10}$ alkyl, $C_{3-14}$ cycloalkyl, and 3- to 14-membered heterocyclyl;

$R_1$ and $R_2$ are independently selected from $C_{4-20}$ alkyl, $C_{4-20}$ alkenyl, and $C_{4-20}$ alkynyl, each of which is optionally substituted with one or more $R_{1s}$, and wherein one or more methylene units are optionally and independently replaced with —NR'—;

$R_{1s}$ is independently H, $C_{1-20}$ alkyl, $-L_c-OR$, $-L_c-SR$, or $-L_c-NR_cR'_c$;

R and R' are independently H or $C_{1-20}$ alkyl;

$L_c$ is independently a chemical bond or $C_{1-20}$ alkylene;

$R_c$ and $R'_c$ are independently selected from H, $C_{1-20}$ alkyl, $C_{3-14}$ cycloalkyl, and 3- to 14-membered heterocyclyl;

$R_3$ is selected from CN, $—OR_g$, $—C(O)R_g$, $—OC(O)R_g$, $—NR''C(O)R_g$, $—NR_gR'_g$, $—NR''C(O)NR_gR'_g$, $—NR''C(O)R_g$, $—NR''S(O)_2R_g$, $—OC(O)NR_gR'_g$, $—NR''C(O)OR_g$, $—N(OR_g)C(O)R_g$, $—N(OR_g)S(O)_2R_g$, $—N(OR_g)C(O)OR_g$, $—N(OR_g)C(O)R_gR'_g$, 3- to 14-membered heterocyclyl, and 5- to 14-membered heteroaryl;

$R_g$ and $R'_g$ are independently H, $C_{1-10}$ alkyl, $C_{3-10}$ cycloalkyl, or 3- to 10-membered heterocyclyl;

R" is independently H or $C_{1-6}$ alkyl;

$R_4$ and $R_5$ are independently $C_{1-8}$ alkyl, which is optionally substituted with one or more $R_{4s}$;

or, $R_4$ and $R_5$ are taken together with the carbon atom to which they are attached to form $C_{3-14}$ cycloalkylene or 3- to 14-membered heterocyclylene, each of which is optionally substituted with one or more $R_{4s}$;

$R_{4s}$ is independently H, halogen, cyano, $C_{1-8}$ alkyl, $C_{1-8}$ haloalkyl, $-L_d-OR_d$, $-L_d-SR_d$, or $-L_d-NR_dR'_d$;

$L_d$ is independently a chemical bond or $C_{1-8}$ alkylene;

$R_d$ and $R'_d$ are independently H, $C_{1-8}$ alkyl, $C_{3-14}$ cycloalkyl, or 3- to 14-membered heterocyclyl.

In another embodiment, the present disclosure relates to a compound of formula (I), or a pharmaceutically acceptable salt, isotopic variant, tautomer, or stereoisomer thereof, which has a structure of formula (II):

(II)

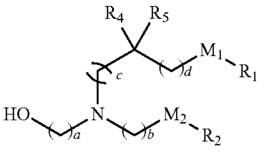

wherein a=1, 2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9;

the other groups are as defined herein.

$G_1$ and $G_2$

In one embodiment, $G_1$ is a chemical bond; in another embodiment, $G_1$ is $C_{1-13}$ linear alkylene, alternatively $C_{1-9}$ linear alkylene, alternatively $C_{1-6}$ linear alkylene, and alternatively $C_{2-6}$ linear alkylene; in another embodiment, $G_1$ is $C_{2-13}$ linear alkenylene, alternatively $C_{2-9}$ linear alkenylene, and alternatively $C_{2-6}$ linear alkenylene; in another embodiment, $G_1$ is $C_{2-13}$ linear alkynylene, alternatively $C_{2-9}$ linear alkynylene, and alternatively $C_{2-6}$ linear alkynylene; in another embodiment, $G_1$ is optionally substituted with one or more $R_{G1}$; in another embodiment, $G_1$ is optionally substituted with 1, 2, 3, or 4 $R_{G1}$; in another embodiment, $G_1$ is unsubstituted.

In a more specific embodiment, $G_1$ is a chemical bond, $C_{1-9}$ linear alkylene, $C_{2-9}$ linear alkenylene, or $C_{2-9}$ linear alkynylene; in another more specific embodiment, $G_1$ is $C_{1-6}$ linear alkylene, $C_{2-6}$ linear alkenylene, or $C_{2-6}$ linear alkynylene; in another more specific embodiment, $G_1$ is $C_{1-6}$ linear alkylene; in another more specific embodiment, $G_1$ is $C_{2-6}$ linear alkylene.

In one embodiment, $G_2$ is a chemical bond; in another embodiment, $G_2$ is $C_{1-3}$ linear alkylene, alternatively $C_{1-9}$ linear alkylene, alternatively $C_{1-6}$ linear alkylene, and alternatively $C_{1-4}$ linear alkylene; in another embodiment, $G_2$ is $C_{2-13}$ linear alkenylene, alternatively $C_{2-9}$ linear alkenylene, and alternatively $C_{2-6}$ linear alkenylene; in another embodiment, $G_2$ is $C_{2-13}$ linear alkynylene, alternatively $C_{2-9}$ linear alkynylene, and alternatively $C_{2-6}$ linear alkynylene; in another embodiment, $G_2$ is optionally substituted with one or more $R_{G1}$; in another embodiment, $G_2$ is optionally substituted with 1, 2, 3, or 4 $R_{G1}$; in another embodiment, $G_2$ is unsubstituted.

In a more specific embodiment, $G_2$ is a chemical bond, $C_{1-9}$ linear alkylene, $C_{2-9}$ linear alkenylene, or $C_{2-9}$ linear alkynylene; in another more specific embodiment, $G_2$ is a chemical bond, $C_{1-6}$ linear alkylene, $C_{2-6}$ linear alkenylene, or $C_{2-6}$ linear alkynylene; in another more specific embodiment, $G_2$ is a chemical bond or $C_{1-6}$ linear alkylene; in another more specific embodiment, $G_2$ is a chemical bond or $C_{1-4}$ linear alkylene.

In one embodiment, $G_1$ and $G_2$ have a total length of 3 carbon atoms; in another embodiment, $G_1$ and $G_2$ have a total length of 4 carbon atoms; in another embodiment, $G_1$ and $G_2$ have a total length of 5 carbon atoms; in another embodiment, $G_1$ and $G_2$ have a total length of 6 carbon atoms; in another embodiment, $G_1$ and $G_2$ have a total length of 7 carbon atoms; in another embodiment, $G_1$ and $G_2$ have a total length of 8 carbon atoms; in another embodiment, $G_1$ and $G_2$ have a total length of 9 carbon atoms; in another embodiment, $G_1$ and $G_2$ have a total length of 10 carbon atoms; in another embodiment, $G_1$ and $G_2$ have a total length of 11 carbon atoms; in another embodiment, $G_1$ and $G_2$ have a total length of 12 carbon atoms; in another embodiment, $G_1$ and $G_2$ have a total length of 13 carbon atoms.

In a more specific embodiment, $G_1$ and $G_2$ have a total length of 3, 4, 5, 6, 7, 8, or 9 carbon atoms; in another more specific embodiment, $G_1$ and $G_2$ have a total length of 4, 5, or 6 carbon atoms; in another more specific embodiment, $G_1$ and $G_2$ have a total length of 5 or 6 carbon atoms; in another more specific embodiment, $G_1$ and $G_2$ have a total length of 5, 6, or 7 carbon atoms; in another more specific embodiment, $G_1$ and $G_2$ have a total length of 6 or 7 carbon atoms.

$R_{G1}$

In one embodiment, $R_{G1}$ is H; in another embodiment, $R_{G1}$ is $C_{1-14}$ alkyl, alternatively $C_{1-10}$ alkyl, and alternatively $C_{1-6}$ alkyl; in another embodiment, $R_{G1}$ is $-L_a-OR_a$; in another embodiment, $R_{G1}$ is $-L_a-SR_a$; in another embodiment, $R_{G1}$ is $-L_a-NR_aR'_a$.

In a more specific embodiment, $R_{G1}$ is independently H or $C_{1-10}$ alkyl; in another more specific embodiment, $R_{G1}$ is independently H or $C_{1-6}$ alkyl.

$G_3$

In one embodiment, $G_3$ is $C_{4-14}$ linear alkylene, alternatively $C_{4-10}$ linear alkylene, alternatively $C_{4-9}$ linear alkylene, and alternatively $C_{5-8}$ linear alkylene; in another embodiment, $G_3$ is $C_{4-14}$ linear alkenylene; in another embodiment, $G_3$ is $C_{4-14}$ linear alkynylene; in another embodiment, $G_3$ is optionally substituted with one or more $R_{G3}$; in another embodiment, $G_3$ is optionally substituted with 1, 2, 3, or 4 $R_{G3}$; in another embodiment, $G_3$ is unsubstituted.

In a more specific embodiment, $G_3$ is $C_{4-10}$ linear alkylene, $C_{4-10}$ linear alkenylene, or $C_{4-10}$ linear alkynylene; in another more specific embodiment, $G_3$ is $C_{4-9}$ linear alkylene; in another more specific embodiment, $G_3$ is $C_{5-8}$ linear alkylene.

$R_{G3}$

In one embodiment, $R_{G3}$ is H; in another embodiment, $R_{G3}$ is $-L_a-OR_a$; in another embodiment, $R_{G3}$ is $-L_a-SR_a$; in another embodiment, $R_{G3}$ is $-L_a-NR_aR'_a$.

$L_a$, $R_a$, and $R'_a$

In one embodiment, $L_a$ is a chemical bond; in another embodiment, $L_a$ is $C_{1-14}$ alkylene, alternatively $C_{1-10}$ alkylene, and alternatively $C_{1-6}$ alkylene.

In a more specific embodiment, $L_a$ is independently a chemical bond or $C_{1-10}$ alkylene; in another more specific embodiment, $L_a$ isa chemical bond or $C_{1-6}$ alkylene.

In one embodiment, $R_a$ is H; in another embodiment, $R_a$ is $C_{1-14}$ alkyl, alternatively $C_{1-10}$ alkyl, alternatively $C_{1-6}$ alkyl; in another embodiment, $R_a$ is $C_{3-14}$ cycloalkyl, alternatively $C_{3-10}$ cycloalkyl; in another embodiment, $R_a$ is 3- to 14-membered heterocyclyl, alternatively 3- to 10-membered heterocyclyl.

In one embodiment, $R'_a$ is H; in another embodiment, $R'_a$ is $C_{1-14}$ alkyl, alternatively $C_{1-10}$ alkyl, and alternatively $C_{1-6}$ alkyl; in another embodiment, $R'_a$ is $C_{3-14}$ cycloalkyl, alternatively $C_{3-10}$ cycloalkyl; in another embodiment, $R'_a$ is 3- to 14-membered heterocyclyl, alternatively 3- to 10-membered heterocyclyl.

In a more specific embodiment, $R_a$ and $R'_a$ are independently H, $C_{1-10}$ alkyl, $C_{3-10}$ cycloalkyl, or 3- to 10-membered heterocyclyl; in another more specific embodiment, $R_a$ and $R'_a$ are independently H or $C_{1-6}$ alkyl.

$G_4$

In one embodiment, $G_4$ is a chemical bond; in another embodiment, $G_4$ is $C_{1-6}$ alkylene, alternatively $C_{1-4}$ alkylene, alternatively $C_{2-4}$ alkylene, and alternatively $C_{2-3}$ alkylene; in another embodiment, $G_4$ is $C_{2-6}$ alkenylene; in another embodiment, $G_4$ is $C_{2-6}$ alkynylene; in another embodiment, $G_4$ is optionally substituted with one or more $R_{G4}$; in another embodiment, $G_4$ is optionally substituted with 1, 2, 3, or 4 $R_{G4}$; in another embodiment, $G_4$ is unsubstituted.

In a more specific embodiment, $G_4$ is $C_{1-4}$alkylene, $C_{2-4}$ alkenylene, or $C_{2-4}$ alkynylene; in another more specific embodiment, $G_4$ is $C_{2-4}$ alkylene; in another more specific embodiment, $G_4$ is $C_{2-3}$ alkylene.

$R_{G4}$

In one embodiment, $R_{G4}$ is H; in another embodiment, $R_{G4}$ is $C_{1-6}$ alkyl, alternatively $C_{1-4}$ alkyl; in another embodiment, $R_{G4}$ is $-L_b-OR_b$; in another embodiment, $R_{G4}$ is $-L_b-SR_b$; in another embodiment, $R_{G4}$ is $-L_b-NR_bR'_b$.

In a more specific embodiment, $R_{G4}$ is independently H or $C_{1-6}$ alkyl.

In one embodiment, two $R_{G4}$ attached to the same carbon atom are taken together with the carbon atom to which they are attached to form $C_{3-14}$ cycloalkylene, alternatively $C_{3-10}$ cycloalkylene, alternatively $C_{3-7}$ cycloalkylene; in another embodiment, two $R_{G4}$ attached to the same carbon atom are taken together with the carbon atom to which they are attached to form 3- to 14-membered heterocyclylene, alternatively 3- to 10-membered heterocyclylene, alternatively 3- to 7-membered heterocyclylene; in another embodiment, a ring formed by two $R_{G4}$ taken together with the carbon atom to which they are attached is optionally substituted with one or more $R_{4g}$; in another embodiment, a ring formed by two $R_{G4}$ taken together with the carbon atom to which they are attached is optionally substituted with 1, 2, or 3 $R_{4g}$; in another embodiment, a ring formed by two $R_{G4}$ taken together with the carbon atom to which they are attached is unsubstituted.

In a more specific embodiment, two $R_{G4}$ attached to the same carbon atom are taken together with the carbon atom to which they are attached to form $C_{3-10}$ cycloalkylene or 3- to 10-membered heterocyclylene; in another more specific embodiment, two $R_{G4}$ attached to the same carbon atom are taken together with the carbon atom to which they are attached to form $C_{3-7}$ cycloalkylene or 3- to 7-membered heterocyclylene.

$L_b$, $R_b$, and $R'_b$

In one embodiment, $L_b$ is a chemical bond; in another embodiment, $L_b$ is $C_{1-6}$ alkylene, alternatively $C_{1-4}$ alkylene.

In a more specific embodiment, $L_b$ is independently a chemical bond or $C_{1-4}$ alkylene.

In one embodiment, $R_b$ is H; in another embodiment, $R_b$ is $C_{1-6}$ alkyl, alternatively $C_{1-4}$ alkyl; in another embodiment, $R_b$ is $C_{3-10}$ cycloalkyl, alternatively $C_{3-7}$ cycloalkyl; in another embodiment, $R_b$ is 3- to 10-membered heterocyclyl, alternatively 3- to 7-membered heterocyclyl.

In one embodiment, $R'_b$ is H; in another embodiment, $R'_b$ is $C_{1-6}$ alkyl, alternatively $C_{1-4}$ alkyl; in another embodiment, $R'_b$ is $C_{3-10}$ cycloalkyl, alternatively $C_{3-7}$ cycloalkyl; in another embodiment, $R'_b$ is 3- to 10-membered heterocyclyl, alternatively 3- to 7-membered heterocyclyl.

In a more specific embodiment, $R_b$ and $R'_b$ are independently H, $C_{1-6}$ alkyl, $C_{3-7}$ cycloalkyl, or 3- to 7-membered heterocyclyl; in another more specific embodiment, $R_b$ and $R'_b$ are independently H or $C_{1-6}$ alkyl; in another more specific embodiment, $R_b$ and $R'_b$ are independently H or $C_{1-4}$ alkyl.

$R_{4g}$

In one embodiment, $R_{4g}$ is H; in another embodiment, $R_{4g}$ is halogen; in another embodiment, $R_{4g}$ is cyano; in another embodiment, $R_{4g}$ is $C_{1-8}$ alkyl, alternatively $C_{1-6}$ alkyl; in another embodiment, $R_{4g}$ is $C_{1-8}$ haloalkyl, alternatively $C_{1-6}$ haloalkyl; in another embodiment, $R_{4g}$ is $-L_e-OR_e$; in another embodiment, $R_{4g}$ is $-L_e-SR_e$; in another embodiment, $R_{4g}$ is $-L_e-NR_eR'_e$.

In a more specific embodiment, $R_{4g}$ is independently H, halogen, cyano, $C_{1-6}$ alkyl, or $C_{1-6}$ haloalkyl.

$L_e$, $R_e$, and $R'_e$

In one embodiment, $L_e$ is a chemical bond; in another embodiment, $L_e$ is $C_{1-8}$ alkylene, alternatively $C_{1-6}$ alkylene, and alternatively $C_{1-4}$ alkylene.

In a more specific embodiment, $L_e$ is independently a chemical bond or $C_{1-6}$ alkylene; in another more specific embodiment, $L_a$ isa chemical bond or $C_{1-4}$ alkylene.

In one embodiment, $R_e$ is H; in another embodiment, $R_e$ is $C_{1-8}$ alkyl, alternatively $C_{1-6}$ alkylene, and alternatively $C_{1-4}$ alkylene; in another embodiment, $R_e$ is $C_{3-14}$ cycloalkyl, alternatively $C_{3-10}$ cycloalkyl; in another embodiment, $R_e$ is 3- to 14-membered heterocyclyl, alternatively 3- to 10-membered heterocyclyl.

In one embodiment, $R'_e$ is H; in another embodiment, $R'_e$ is $C_{1-8}$ alkyl, alternatively $C_{1-6}$ alkylene, and alternatively $C_{1-4}$ alkylene; in another embodiment, $R'_e$ is $C_{3-14}$ cycloalkyl, alternatively $C_{3-10}$ cycloalkyl; in another embodiment, $R'_e$ is 3- to 14-membered heterocyclyl, alternatively 3- to 10-membered heterocyclyl.

In a more specific embodiment, $R_e$ and $R'_e$ are independently H, $C_{1-6}$ alkyl, $C_{3-10}$ cycloalkyl, or 3- to 10-membered heterocyclyl; in another more specific embodiment, $R_e$ and $R'_e$ are independently H or $C_{1-4}$ alkyl.

$M_1$ and $M_2$

In one embodiment, $M_1$ is —C(O)O—; in another embodiment, $M_1$ is —OC(O)—; in another embodiment, $M_1$ is —O—; in another embodiment, $M_1$ is —SC(O)O—; in another embodiment, $M_1$ is —OC(O)NR—; in another embodiment, $M_1$ is —NRC(O)NR—; in another embodiment, $M_1$ is —OC(O)S—; in another embodiment, $M_1$ is —OC(O)O—; in another embodiment, $M_1$ is —NRC(O)O—; in another embodiment, $M_1$ is —SC(O)—; in another embodiment, $M_1$ is —C(O)S—; in another embodiment, $M_1$ is —NR—; in another embodiment, $M_1$ is —C(O)NR—, for example, —C(O)NH—; in another embodiment, $M_1$ is —NRC(O)—, for example, —NHC(O)—; in another embodiment, $M_1$ is —NRC(O)S—; in another embodiment, $M_1$ is —SC(O)NR—; in another embodiment, $M_1$ is —C(O)—; in another embodiment, $M_1$ is —OC(S)—; in another embodiment, $M_1$ is —C(S)O—; in another embodiment, $M_1$ is —OC(S)NR—; in another embodiment, $M_1$ is —NRC(S)O—; in another embodiment, $M_1$ is —S—S—; in another embodiment, $M_1$ is $—S(O)_{0-2}—$, such as —S—, —S(O)—, and $—S(O)_2—$;

In one embodiment, $M_2$ is —C(O)O—; in another embodiment, $M_2$ is —OC(O)—; in another embodiment, $M_2$ is —O—; in another embodiment, $M_2$ is —SC(O)O—; in another embodiment, $M_2$ is —OC(O)NR—; in another embodiment, $M_2$ is —NRC(O)NR—; in another embodiment, $M_2$ is —OC(O)S—; in another embodiment, $M_2$ is —OC(O)O—; in another embodiment, $M_2$ is —NRC(O)O—; in another embodiment, $M_2$ is —SC(O)—; in another embodiment, $M_2$ is —C(O)S—; in another embodiment, $M_2$ is —NR—; in another embodiment, $M_2$ is —C(O)NR—; in another embodiment, $M_2$ is —NRC(O)—; in another embodiment, $M_2$ is —NRC(O)S—; in another embodiment, $M_2$ is —SC(O)NR—; in another embodiment, $M_2$ is —C(O)—; in another embodiment, $M_2$ is —OC(S)—; in another embodiment, $M_2$ is —C(S)O—; in another embodiment, $M_2$ is —OC(S)NR—; in another embodiment, $M_2$ is —NRC(S)O—; in another embodiment, $M_2$ is —S—S—; in another embodiment, $M_2$ is $—S(O)_{0-2}—$, such as —S—, —S(O)—, and $—S(O)_2—$.

In a more specific embodiment, $M_1$ and $M_2$ are independently selected from —C(O)O—, —OC(O)—, —OC(O)O—, —SC(O)—, —C(O)S—, —C(O)NR—, and —NRC(O)—; in another more specific embodiment, $M_1$ and $M_2$ are independently selected from —C(O)O—, —OC(O)O—, —OC(O)—, —SC(O)—, and —C(O)S—; in another more specific embodiment, $M_1$ and $M_2$ are independently selected from —C(O)O—, —OC(O)—, —SC(O)—, and —C(O)S—; in another more specific embodiment, $M_1$ and $M_2$ are independently selected from —C(O)O— and —OC(O)—.

In a more specific embodiment, $M_1$ and $M_2$ are independently selected from —C(O)O— and —C(O)S—; in another more specific embodiment, $M_1$ and $M_2$ are —C(O)O—.

In a more specific embodiment, one of $M_1$ and $M_2$ is —C(O)O— or —C(O)S—, and the other is —OC(O)— or —SC(O)—; in another more specific embodiment, one of $M_1$ and $M_2$ is —C(O)O—, and the other is —OC(O)—.

In a more specific embodiment, $M_1$ is —OC(O)— or —SC(O)—; in another more specific embodiment, $M_1$ is —OC(O)—; in another more specific embodiment, $M_2$ is —C(O)O— or —C(O)S—; in another more specific embodiment, $M_2$ is —C(O)O—.

In a more specific embodiment, $M_1$ and $M_2$ are independently selected from —C(O)O—, —OC(O)—, —SC(O)—, —C(O)S—, —NHC(O)—, and —C(O)NH—; in another more specific embodiment, $M_1$ and $M_2$ are independently selected from —C(O)O—, —OC(O)—, —C(O)S—, and —C(O)NH—; in another more specific embodiment, $M_1$ and $M_2$ are independently selected from —C(O)O—, —OC(O)—, and —C(O)S—; in another more specific embodiment, one of $M_1$ and $M_2$ is —C(O)O— or —C(O)S—, alternatively —C(O)O—, and the other is —C(O)O—, —C(O)S—, —C(O)NH—, —OC(O)—, or —SC(O)—, alternatively —C(O)O—, —C(O)S—, —C(O)NH—, or —OC(O)—, alternatively —C(O)O—, —C(O)S—, —OC(O)—, or —SC(O)—, alternatively —C(O)O—, —C(O)S—, or —OC(O)—; in another more specific embodiment, one of $M_1$ and $M_2$ is —OC(O)O—, and the other is —C(O)O—, —OC(O)—, —SC(O)—, or —C(O)S—, alternatively —C(O)O— or —OC(O)—; in another more specific embodiment, $M_1$ is —C(O)O—, —OC(O)—, —SC(O)—, or —C(O)S—, alternatively —C(O)O— or —OC(O)—, alternatively —C(O)O—, alternatively —OC(O)—, and $M_2$ is —OC(O)O—; in another more specific embodiment, $M_1$ is —OC(O)O—, and $M_2$ is —OC(O)— or —C(O)O—, alternatively —OC(O)—; in another more specific embodiment, $M_1$ and $M_2$ are independently —C(O)O—, —C(O)S—, —OC(O)—, —SC(O)—, or —OC(O)O—; in another more specific embodiment, $M_1$ and $M_2$ are independently —C(O)O—, —OC(O)—, or —OC(O)O—; in another more specific embodiment, $M_1$ and $M_2$ are not simultaneously —OC(O)O—.

Q

In one embodiment, Q is a chemical bond; in another more specific embodiment, Q is —C(O)O—; in another more specific embodiment, Q is —O—; in another more specific embodiment, Q is —SC(O)O—; in another more specific embodiment, Q is —OC(O)$NR_f$—; in another more specific embodiment, Q is —$NR^{ff}$C(O)$NR_f$—; in another more specific embodiment, Q is —OC(O)S—; in another more specific embodiment, Q is —OC(O)O—; in another more specific embodiment, Q is —$NR^{ff}$C(O)O—; in another more specific embodiment, Q is —OC(O)—; in another more specific embodiment, Q is —SC(O)—; in another more specific embodiment, Q is —C(O)S—; in another more specific embodiment, Q is —$NR_f$—; in another more specific embodiment, Q is —C(O)$NR_f$—; in another more specific embodiment, Q is —$NR_f$C(O)—; in another more specific embodiment, Q is —$NR_f$C(O)S—; in another more specific embodiment, Q is —SC(O)$NR_f$—; in another more specific embodiment, Q is —C(O)—; in another more specific embodiment, Q is —OC(S)—; in another more specific embodiment, Q is —C(S)O—; in another more specific embodiment, Q is —OC(S)$NR_f$—; in another more specific embodiment, Q is —$NR_f$C(S)O—; in another more specific embodiment, Q is —S—S—; in another more specific embodiment, Q is —$S(O)_{0-2}$—; in another more specific embodiment, Q is phenylene; in another more specific embodiment, Q is pyridinylene; in another more specific embodiment, when Q is phenylene, Q is optionally substituted with one or more R*, alternatively optionally substituted with 1, 2 or 3 R*; in another more specific embodiment, Q is unsubstituted phenylene; in another more specific embodiment, when Q is pyridinylene, Q is optionally substituted with one or more R*, alternatively optionally substituted with 1, 2 or 3 R*; in another more specific embodiment, Q is unsubstituted pyridinylene.

in another more specific embodiment, Q is a chemical bond, —OC(O)—, or —SC(O)—; in another more specific embodiment, Q is a chemical bond or —SC(O)—; in another more specific embodiment, Q is phenylene or pyridinylene, which is optionally substituted with 1, 2 or 3 R*.

R*

In one embodiment, R* is H; in another more specific embodiment, Q is halogen; in another more specific embodiment, R* is cyano; in another more specific embodiment, R* is $C_{1-10}$ alkyl, alternatively $C_{1-6}$ alkyl; in another more specific embodiment, R* is $C_{1-10}$ haloalkyl, alternatively $C_{1-6}$ haloalkyl; in another more specific embodiment, R* is -$L_f$-$OR_f$; in another more specific embodiment, R* is -$L_f$-$SR_f$; in another more specific embodiment, R* is -$L_f$-$NR_fR'_f$.

In a more specific embodiment, R* is independently H, halogen, cyano, $C_{1-6}$ alkyl, or $C_{1-6}$ haloalkyl.

$L_f$, $R_f$, and $R'_f$

In one embodiment, $L_f$ is a chemical bond; in another embodiment, $L_f$ is $C_{1-8}$ alkylene, alternatively $C_{1-6}$ alkylene, alternatively $C_{1-4}$ alkylene.

In a more specific embodiment, $L_f$ is independently a chemical bond or $C_{1-6}$ alkylene; in another more specific embodiment, $L_f$ is independently a chemical bond or $C_{1-4}$ alkylene.

In one embodiment, $R_f$ is H; in another embodiment, $R_f$ is $C_{1-10}$ alkyl, alternatively $C_{1-6}$ alkyl, and alternatively $C_{1-4}$ alkyl; in another embodiment, $R_f$ is $C_{3-14}$ cycloalkyl, alternatively $C_{3-10}$ cycloalkyl; in another embodiment, $R_f$ is 3- to 14-membered heterocyclyl, alternatively 3- to 10-membered heterocyclyl.

In one embodiment, $R'_f$ is H; in another embodiment, $R'_f$ is $C_{1-10}$ alkyl, alternatively $C_{1-6}$ alkyl, alternatively $C_{1-4}$ alkyl; in another embodiment, $R'_f$ is $C_{3-14}$ cycloalkyl, alternatively $C_{3-10}$ cycloalkyl; in another embodiment, $R'_f$ is 3- to 14-membered heterocyclyl, alternatively 3- to 10-membered heterocyclyl.

In a more specific embodiment, $R_f$ and $R'_f$ are independently H, $C_{1-6}$ alkyl, $C_{3-10}$ cycloalkyl, or 3- to 10-membered heterocyclyl; in another more specific embodiment, $R_f$ and $R'_f$ are independently H or $C_{1-6}$ alkyl; in another more specific embodiment, $R_f$ and $R'_f$ are independently H or $C_{1-4}$ alkyl.

$R_1$ and $R_2$

In one embodiment, $R_1$ is $C_{4-20}$ alkyl, alternatively $C_{6-14}$ alkyl, alternatively $C_{7-12}$ alkyl, alternatively $C_{8-12}$ alkyl, alternatively $C_{8-11}$ alkyl, alternatively $C_{9-10}$ alkyl, alternatively $C_{8-10}$ alkyl, alternatively $C_{9-10}$ alkyl, alternatively $C_{8-9}$ alkyl, alternatively $C_9$ alkyl, alternatively $C_{8-12}$ linear alkyl, alternatively $C_{7-11}$ linear alkyl, alternatively $C_{8-11}$ linear alkyl, alternatively $C_{9-11}$ linear alkyl, alternatively $C_{10-11}$ linear alkyl, alternatively $C_{8-10}$ linear alkyl, alternatively $C_{9-10}$ linear alkyl, alternatively $C_{8-9}$ linear alkyl, alternatively $C_{8-10}$ linear alkyl, alternatively $C_{10}$ linear alkyl, and alternatively $C_9$ linear alkyl; in another embodiment, $R_1$ is $C_{4-20}$ alkenyl, alternatively $C_{6-14}$ alkenyl, alternatively $C_{7-12}$ alkenyl; alternatively $C_{8-12}$ alkenyl; in another embodiment, $R_1$ is $C_{4-20}$ alkynyl, alternatively $C_{6-14}$ alkynyl, alternatively $C_{7-12}$ alkynyl, alternatively $C_{8-12}$ alkynyl; in another embodiment, $R_1$ is optionally substituted with one or more $R_{1s}$; in another embodiment, $R_1$ is optionally substituted with 1, 2, 3, or 4 $R_{1s}$, alternatively optionally substituted with 1 $R_{1s}$; in another embodiment, $R_1$ is unsubstituted; in another embodiment, one or more methylene units in $R_1$ are optionally and independently replaced with —NR'—, alternatively one methylene unit in $R_1$ is optionally replaced with —NR'—; in another embodiment, $R_1$ is optionally substituted with 1 $C_{1-9}$ alkyl(alternatively $C_{6-9}$ alkyl, alternatively $C_{6-7}$ alkyl).

In one embodiment, $R_1$ is —$(CH_2)_5CH_3$; in another embodiment, $R_1$ is —$(CH_2)_6CH_3$; in another embodiment, $R_1$ is —$(CH_2)_7CH_3$; in another embodiment, $R_1$ is —$(CH_2)_8CH_3$; in another embodiment, $R_1$ is —$(CH_2)_9CH_3$; in another embodiment, $R_1$ is —$(CH_2)_{10}CH_3$; in another embodiment, $R_1$ is —$(CH_2)_{11}CH_3$; in another embodiment, $R_1$ is —$CH_2$—C≡C—$(CH_2)_5CH_3$; in another embodiment, $R_1$ is —$CH_2$—C≡C—$(CH_2)_6CH_3$; in another embodiment, $R_1$ is —$(CH_2)_2$—C≡C—$(CH_2)_5CH_3$; in another embodiment, $R_1$ is —$(CH_2)_4$—C≡C—$(CH_2)_3CH_3$; in another embodiment, $R_1$ is —$CH_2$—CH═CH—$(CH_2)_5CH_3$; in another embodiment, $R_1$ is —$CH_2$—CH═CH—$(CH_2)_6CH_3$; in another embodiment, $R_1$ is —$(CH_2)_2$—CH═CH—$(CH_2)_5CH_3$; in another embodiment, $R_1$ is —$(CH_2)_4$—CH═CH—$(CH_2)_3CH_3$; in another embodiment, $R_1$ is $-(CH_2)_5-CH=CH-CH_2CH_3$; in another embodiment, $R_1$ is

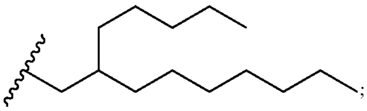 [SMILES: *CC(CCCCC)CCCCCCC]
;

in another embodiment, $R_1$ is

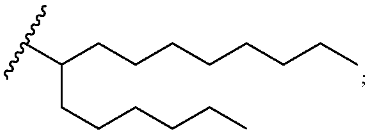 [SMILES: *C(CCCCCC)CCCCCCCC]
;

in another embodiment, $R_1$ is

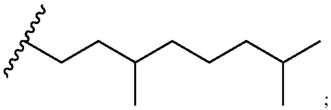 [SMILES: *CCC(C)CCCC(C)C]
;

in another embodiment, $R_1$ is

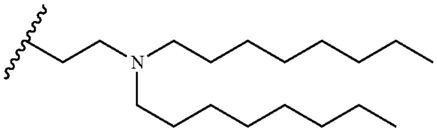
;

in another embodiment, $R_1$ is

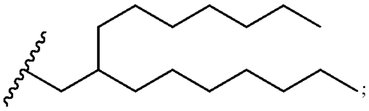 [SMILES: *CC(CCCCCCC)CCCCCCC]
;

in another embodiment, $R_1$ is

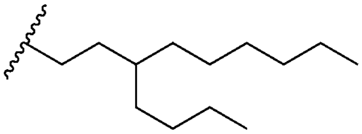
;

in another embodiment, $R_1$ is

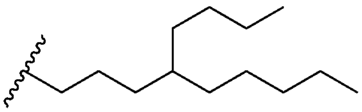
;

in another embodiment, $R_1$ is

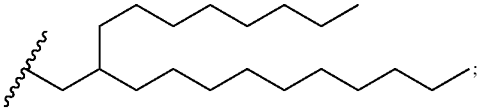 [SMILES: *CC(CCCCCCCC)CCCCCCCCCC]
;

in another embodiment, $R_1$ is

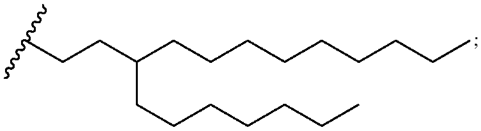 [SMILES: *CCC(CCCCCCC)CCCCCCCCC]
;

in another embodiment, $R_1$ is

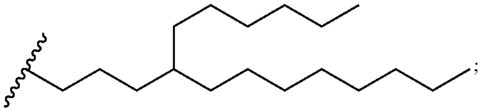 [SMILES: *CCCC(CCCCCC)CCCCCCCC]
;

in another embodiment, $R_1$ is

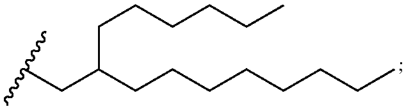 [SMILES: *CC(CCCCCC)CCCCCCCC]
;

in another embodiment, $R_1$ is

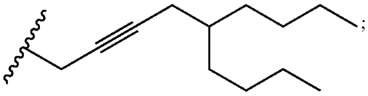 [SMILES: *CC#CCC(CCCC)CCCC]
;

in another embodiment, $R_1$ is

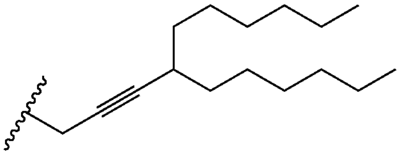
;

in another embodiment, $R_1$ is

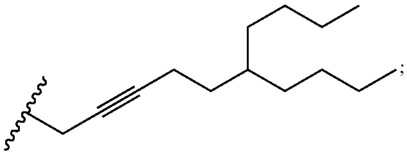 [SMILES: *CC#CCCC(CCCC)CCCC]
;

in another embodiment, $R_1$ is

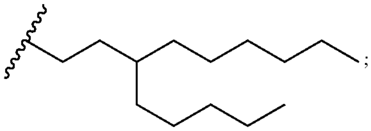 [SMILES: *CCC(CCCCC)CCCCCC];

in another embodiment, $R_1$ is

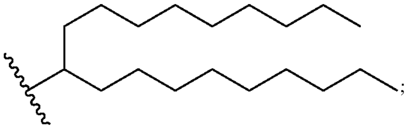 [SMILES: *C(CCCCCCCCC)CCCCCCCCC];

in another embodiment, $R_1$ is

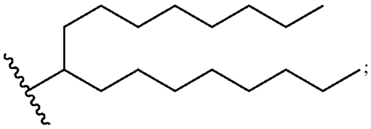 [SMILES: *C(CCCCCCCC)CCCCCCCC];

in another embodiment, $R_1$ is

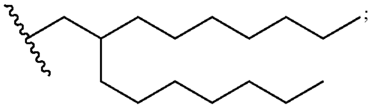 [SMILES: *CC(CCCCCCC)CCCCCCC];

in another embodiment, $R_1$ is

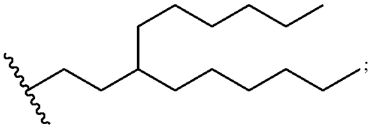 [SMILES: *CCC(CCCCCC)CCCCCC];

in another embodiment, $R_1$ is

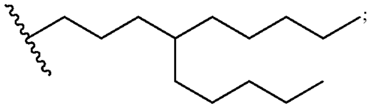 [SMILES: *CCCC(CCCCC)CCCCC];

in another embodiment, $R_1$ is

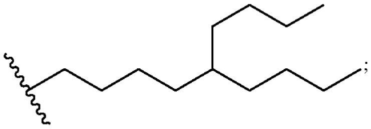 [SMILES: *CCCCC(CCCC)CCCC];

in another embodiment, $R_1$ is

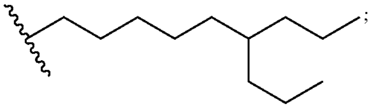 [SMILES: *CCCCCC(CCC)CCC];

in another embodiment, $R_1$ is

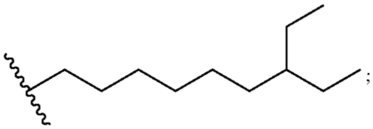 [SMILES: *CCCCCCC(CC)CC];

in another embodiment, $R_1$ is

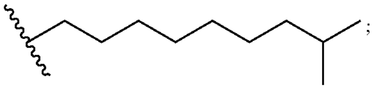 [SMILES: *CCCCCCCC(C)C];

in another embodiment, $R_1$ is

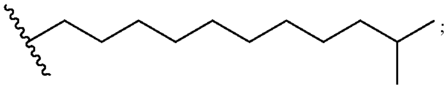 [SMILES: *CCCCCCCCCC(C)C];

in another embodiment, $R_1$ is

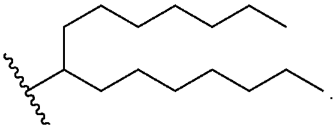 [SMILES: *C(CCCCCCC)CCCCCCC].

In one embodiment, $R_1$ is $-(CH_2)_2-C{\equiv}C-(CH_2)_4CH_3$, in another embodiment, $R_1$ is $-(CH_2)_3-C{\equiv}C-(CH_2)_3CH_3$, in another embodiment, $R_1$ is

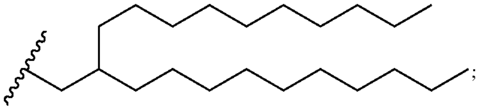 [SMILES: *CC(CCCCCCCCCC)CCCCCCCCCC];

in another embodiment, $R_1$ is

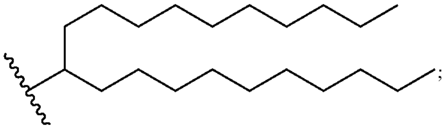 [SMILES: *C(CCCCCCCCCC)CCCCCCCCCC];

in another embodiment, $R_1$ is

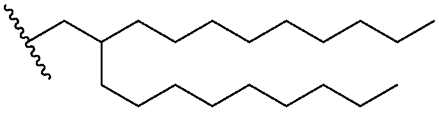

;

in another embodiment, $R_1$ is

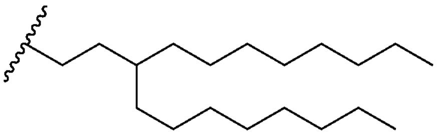

;

in another embodiment, $R_1$ is

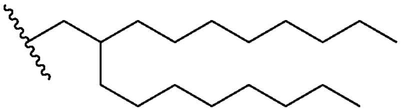

;

in another embodiment, $R_1$ is

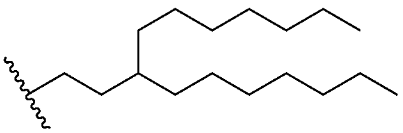

;

in another embodiment, $R_1$ is

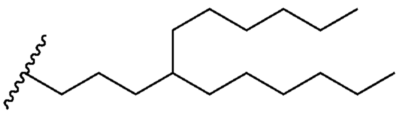

;

in another embodiment, $R_1$ is

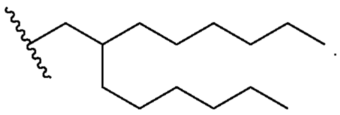 [SMILES: *CC(CCCCCC)CCCCCC]

.

In one embodiment, $R_2$ is $C_{4-20}$ alkyl, alternatively $C_{6-14}$ alkyl, alternatively $C_{7-12}$ alkyl, alternatively $C_{8-12}$ alkyl, alternatively $C_{9-12}$ alkyl, alternatively $C_{8-11}$ alkyl, alternatively $C_{9-10}$ alkyl, alternatively $C_{8-10}$ alkyl, alternatively $C_{9-10}$ alkyl, alternatively $C_{10}$ alkyl, alternatively $C_9$ alkyl, alternatively $C_{8-12}$ linear alkyl, alternatively $C_{7-11}$ linear alkyl, alternatively $C_{8-11}$ linear alkyl, alternatively $C_{10-11}$ linear alkyl, alternatively $C_{8-10}$ linear alkyl, alternatively $C_{10}$ linear alkyl, alternatively $C_{8-10}$ linear alkyl, alternatively $C_{9-10}$ linear alkyl, and alternatively $C_9$ linear alkyl; in another embodiment, $R_2$ is $C_{4-20}$ alkenyl, alternatively $C_{6-14}$ alkenyl, alternatively $C_{7-12}$ alkenyl, alternatively $C_{8-12}$ alkenyl; in another embodiment, $R_2$ is $C_{4-20}$ alkynyl, alternatively $C_{6-14}$ alkynyl, alternatively $C_{7-12}$ alkynyl, alternatively $C_{8-12}$ alkynyl; in another embodiment, $R_2$ is optionally substituted with one or more $R_{1s}$; in another embodiment, $R_2$ is optionally substituted with 1, 2, 3, or 4 $R_{1s}$, alternatively optionally substituted with 1 $R_{1s}$, alternatively optionally substituted with 1 $C_{1-3}$ alkyl, alternatively optionally substituted with 1 methyl; in another embodiment, $R_2$ is unsubstituted; in another embodiment, one or more methylene units in $R_2$ are optionally and independently replaced with —NR'—, alternatively one methylene unit in $R_2$ is optionally replaced with —NR'—.

In one embodiment, only one of $R_1$ and $R_2$ is substituted; in another embodiment, $R_1$ is substituted with $R_{1s}$, and $R_2$ is not substituted with $R_{1s}$; in another embodiment, $R_2$ is substituted with $R_{1s}$, and $R_1$ is not substituted with $R_{1s}$;

In one embodiment, $R_2$ is $—(CH_2)_5CH_3$; in another embodiment, $R_2$ is $—(CH_2)_6CH_3$; in another embodiment, $R_2$ is $—(CH_2)_7CH_3$; in another embodiment, $R_2$ is $—(CH_2)_8CH_3$; in another embodiment, $R_2$ is $—(CH_2)_9CH_3$; in another embodiment, $R_2$ is $—(CH_2)_{10}CH_3$; in another embodiment, $R_2$ is $—(CH_2)_1CH_3$; in another embodiment, $R_2$ is $—CH_2—C{\equiv}C—(CH_2)_5CH_3$; in another embodiment, $R_2$ is $—CH_2—C{\equiv}C—(CH_2)_6CH_3$; in another embodiment, $R_2$ is $—(CH_2)_2—C{\equiv}C—(CH_2)_5CH_3$; in another embodiment, $R_2$ is $—(CH_2)_4—C{\equiv}C—(CH_2)_3CH_3$; in another embodiment, $R_2$ is $—CH_2—CH{=}CH—(CH_2)_5CH_3$; in another embodiment, $R_2$ is $—CH_2—CH{=}CH—(CH_2)_6CH_3$; in another embodiment, $R_2$ is $—(CH_2)_2—CH{=}CH—(CH_2)_5CH_3$; in another embodiment, $R_2$ is $—(CH_2)_4—CH{=}CH—(CH_2)_3CH_3$; in another embodiment, $R_2$ is $—(CH_2)_5—CH{=}CH—CH_2CH_3$; in another embodiment, $R_2$ is

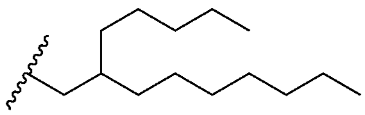

;

in another embodiment, $R_2$ is

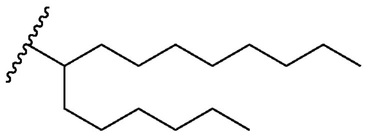

;

in another embodiment, $R_2$ is

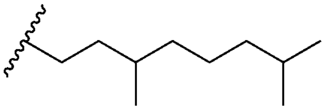

;

in another embodiment, $R_2$ is

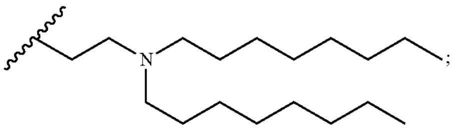 [SMILES: *CCN(CCCCCCCC)CCCCCCCC]

;

in another embodiment, $R_2$ is

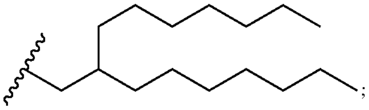 [SMILES: *CC(CCCCCCC)CCCCCCC]
;

in another embodiment, $R_2$ is

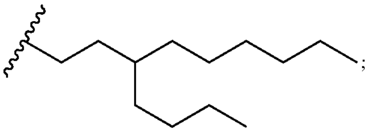 [SMILES: *CCC(CCCC)CCCCCC]
;

in another embodiment, $R_2$ is

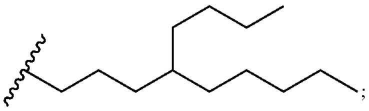 [SMILES: *CCCC(CCCC)CCCCC]
;

in another embodiment, $R_2$ is

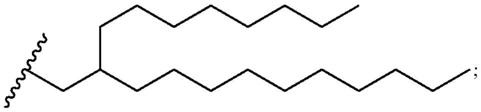 [SMILES: *CC(CCCCCCCC)CCCCCCCCCC]
;

in another embodiment, $R_2$ is

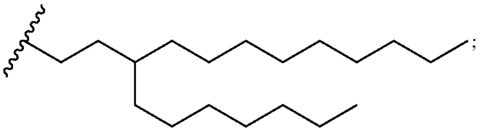 [SMILES: *CCC(CCCCCCC)CCCCCCCCC]
;

in another embodiment, $R_2$ is

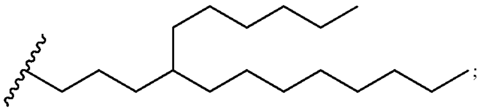 [SMILES: *CCCC(CCCCCC)CCCCCCCC]
;

in another embodiment, $R_2$ is

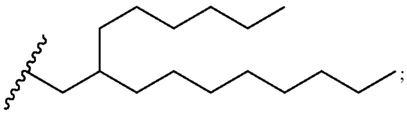 [SMILES: *CC(CCCCCC)CCCCCCCC]
;

in another embodiment, $R_2$ is

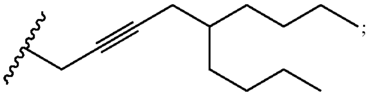 [SMILES: *CC#CCC(CCCC)CCCC]
;

in another embodiment, $R_2$ is

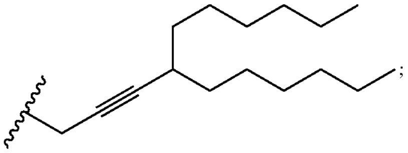 [SMILES: *CC#CC(CCCCCC)CCCCCC]
;

in another embodiment, $R_2$ is

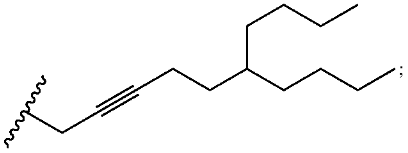 [SMILES: *CC#CCCC(CCCC)CCCC]
;

in another embodiment, $R_2$ is

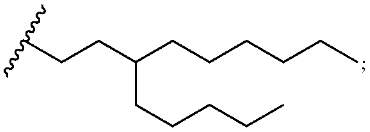 [SMILES: *CCC(CCCCC)CCCCCC]
;

in another embodiment, $R_2$ is

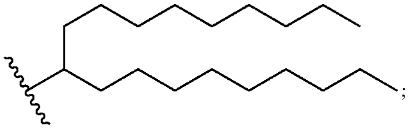 [SMILES: *C(CCCCCCCCC)CCCCCCCCC]
;

in another embodiment, $R_2$ is

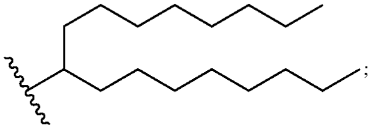 [SMILES: *C(CCCCCCCC)CCCCCCCC]
;

in another embodiment, $R_2$ is

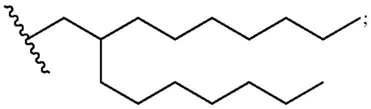 [SMILES: *CC(CCCCCCC)CCCCCCC]
;

in another embodiment, $R_2$ is

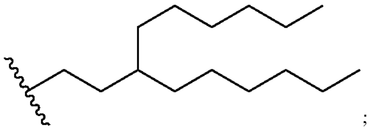 [SMILES: *CCC(CCCCCC)CCCCCC]

;

in another embodiment, $R_2$ is

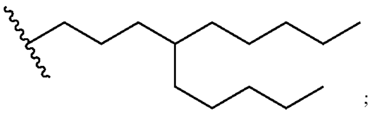 [SMILES: *CCCC(CCCCC)CCCCC]

;

in another embodiment, $R_2$ is

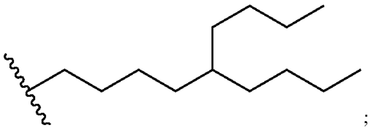 [SMILES: *CCCCC(CCCC)CCCC]

;

in another embodiment, $R_2$ is

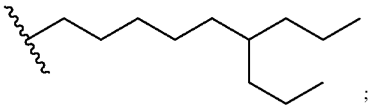 [SMILES: *CCCCCC(CCC)CCC]

;

in another embodiment, $R_2$ is

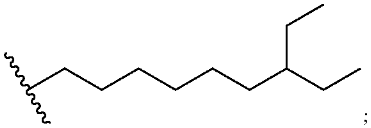

;

in another embodiment, $R_2$ is

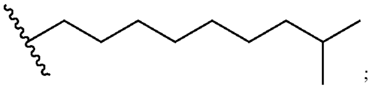 [SMILES: *CCCCCCCC(C)C]

;

in another embodiment, $R_2$ is

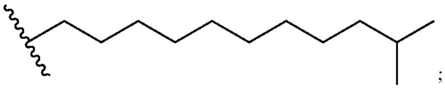 [SMILES: *CCCCCCCCCC(C)C]

;

in another embodiment, $R_2$ is

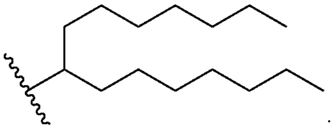 [SMILES: *C(CCCCCCC)CCCCCCC]

.

In one embodiment, $R_2$ is $-(CH_2)_2-C-C-(CH_2)_4CH_3$, in another embodiment, $R_2$ is $-(CH_2)_3-C{\equiv}C-(CH_2)_3CH_3$, in another embodiment, $R_2$ is

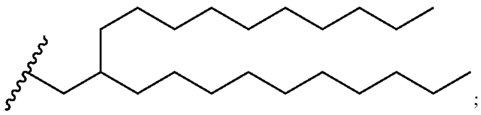 [SMILES: *CC(CCCCCCCCCC)CCCCCCCCCC]

;

in another embodiment, $R_2$ is

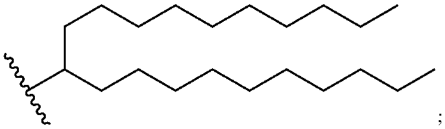 [SMILES: *C(CCCCCCCCCC)CCCCCCCCCC]

;

in another embodiment, $R_2$ is

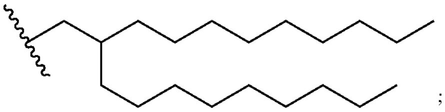 [SMILES: *CC(CCCCCCCCC)CCCCCCCCC]

;

in another embodiment, $R_2$ is

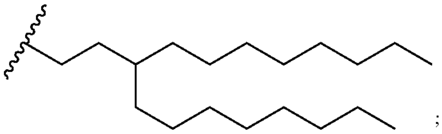 [SMILES: *CCC(CCCCCCCC)CCCCCCCC]

;

in another embodiment, $R_2$ is

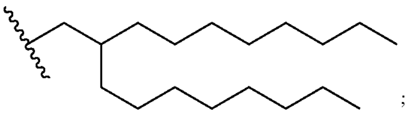 [SMILES: *CC(CCCCCCCC)CCCCCCCC]

;

in another embodiment, $R_2$ is

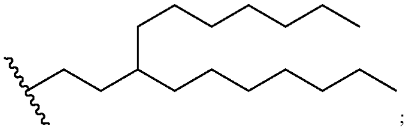 [SMILES: *CCC(CCCCCCC)CCCCCCC]

;

in another embodiment, $R_2$ is

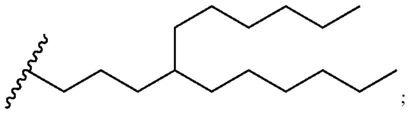 [SMILES: *CCCC(CCCCCC)CCCCCC]

;

in another embodiment, $R_2$ is

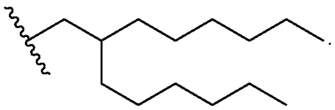 [SMILES: *CC(CCCCCC)CCCCCC]

.

In a more specific embodiment, $R_1$ and $R_2$ are independently selected from $C_{6-14}$ alkyl, $C_{6-14}$ alkenyl, and $C_{6-14}$ alkynyl; in another more specific embodiment, $R_1$ and $R_2$ are independently selected from $C_{7-12}$ alkyl, $C_{7-12}$ alkenyl, and $C_{7-12}$ alkynyl; in another more specific embodiment, $R_1$ and $R_2$ are independently selected from $C_{8-12}$ alkyl, $C_{8-12}$ alkenyl, and $C_{8-12}$ alkynyl; in another more specific embodiment, $R_1$ and $R_2$ are independently selected from the following groups: $—(CH_2)_5CH_3$, $—(CH_2)_6CH_3$, $—(CH_2)_7CH_3$, $—(CH_2)_8CH_3$, $—(CH_2)_9CH_3$, $—(CH_2)_{10}CH_3$, $—(CH_2)_{11}CH_3$, $—CH_2—C{\equiv}C—(CH_2)_5CH_3$, $—CH_2—C—C—(CH_2)_6CH_3$, $—(CH_2)_2—C—C—(CH_2)_5CH_3$, $—(CH_2)_4—C—C—(CH_2)_3CH_3$, $—CH_2—CH{=}CH—(CH_2)_5CH_3$, $—CH_2—CH{=}CH—(CH_2)_6CH_3$, $—(CH_2)_2—CH{=}CH—(CH_2)_5CH_3$, $—(CH_2)_4—CH{=}CH—(CH_2)_3CH_3$, $—(CH_2)_5—CH{=}CH—CH_2CH_3$,

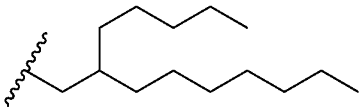

,

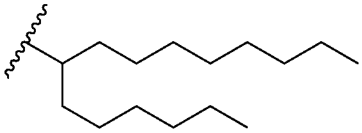

,

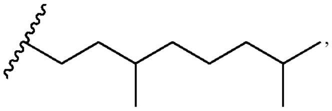

,

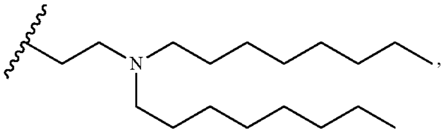

,

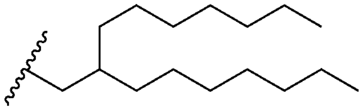

,

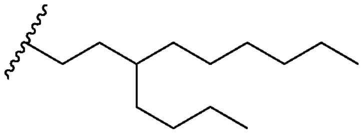

,

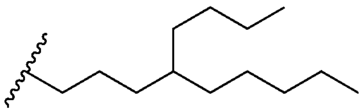

,

-continued

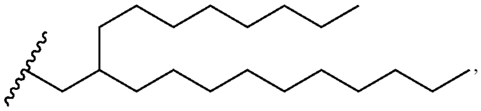

,

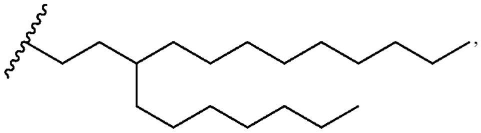

,

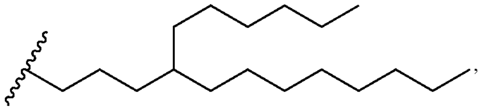

,

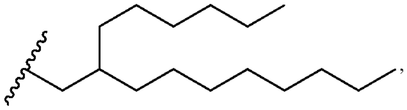

,

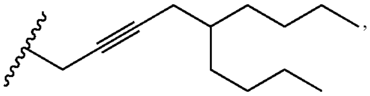

,

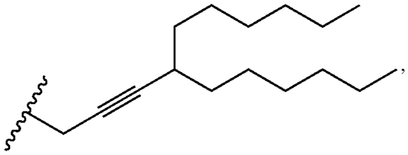

,

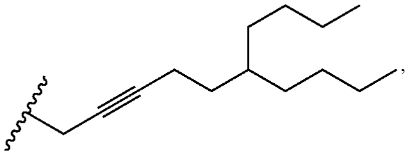

,

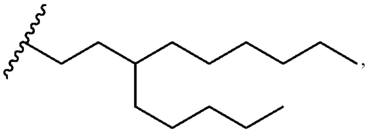

,

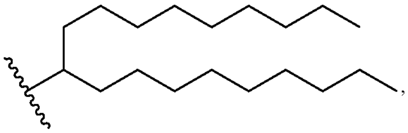

,

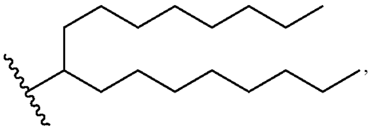

,

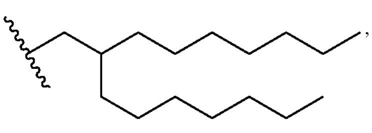

,

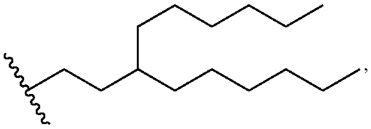

,

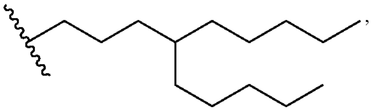

,

-continued

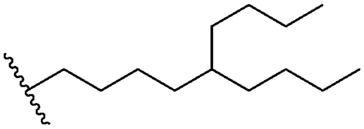,

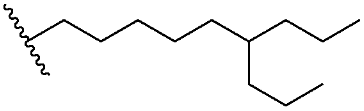,

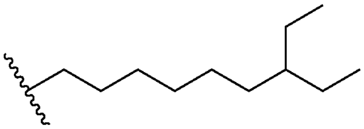,

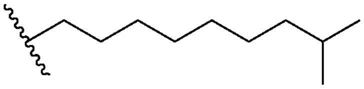,

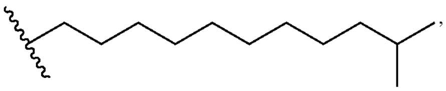, and

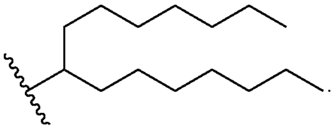.

In a more specific embodiment, $R_1$ and $R_2$ are independently selected from $C_{7-12}$ alkyl, alternatively $C_{8-12}$ alkyl, alternatively $C_{9-10}$ alkyl, alternatively $C_{9-10}$ alkyl, which is optionally substituted with 1 $R_{1s}$; and only one of $R_1$ and $R_2$ is substituted.

In a more specific embodiment, $R_1$ and $R_2$ are independently selected from: $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$,

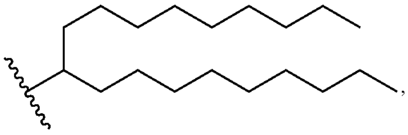,

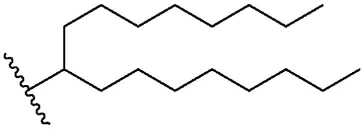,

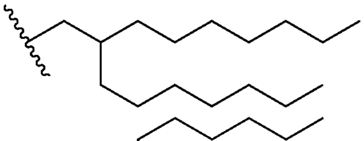,

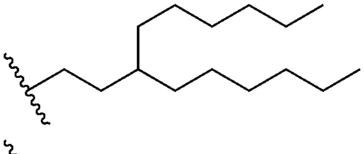,

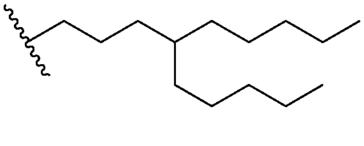,

-continued

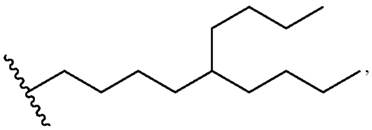,

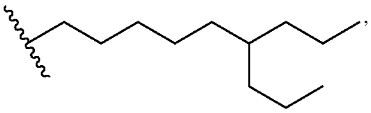,

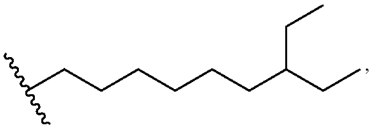,

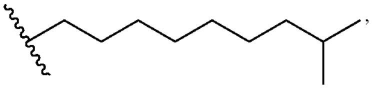,

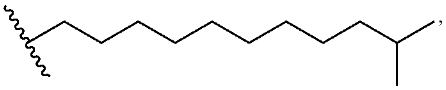, and

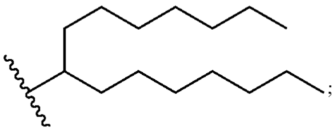;

in another more specific embodiment, $R_1$ and $R_2$ are independently selected from: $-(CH_2)_7CH_3$, $-(CH_2)_8CH_3$, $-(CH_2)_9CH_3$, $-(CH_2)_{10}CH_3$, $-(CH_2)_{11}CH_3$,

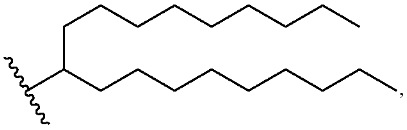,

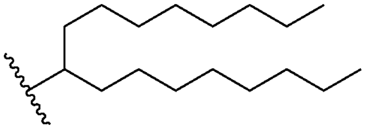,

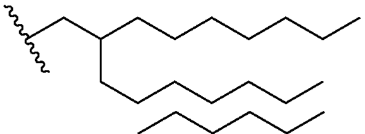,

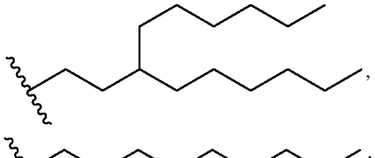,

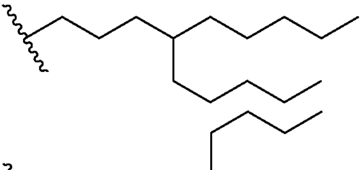,

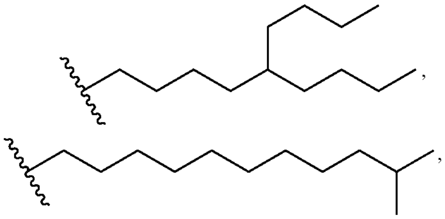,

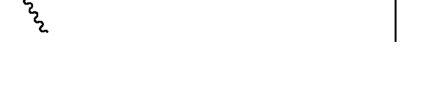, and

-continued
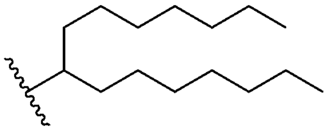
;
and in another more specific embodiment, $R_1$ and $R_2$ are independently selected from: $—(CH_2)_8CH_3$, $—(CH_2)_9CH_3$, $—(CH_2)_{10}CH_3$, $—(CH_2)_{11}CH_3$,
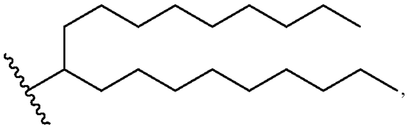
,
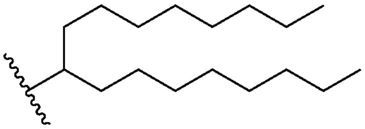
,
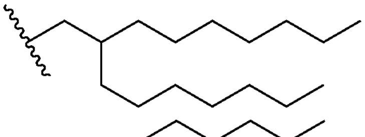
,
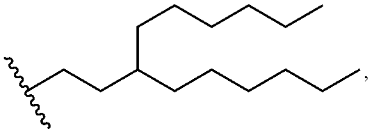
,
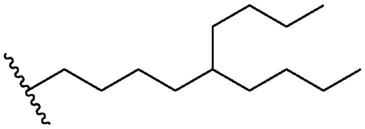
,
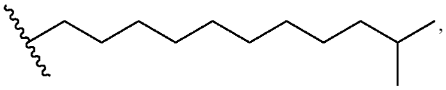
, and
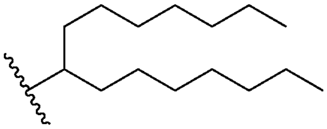
.
In a more specific embodiment, $R_1$ and $R_2$ are independently selected from: $—(CH_2)_6CH_3$, $—(CH_2)_7CH_3$, $—(CH_2)_8CH_3$, $—(CH_2)_9CH_3$, $—(CH_2)_{10}CH_3$, $—(CH_2)_{11}CH_3$, $—CH_2—CH{=}CH—(CH_2)_5CH_3$, $—CH_2—C{\equiv}C—(CH_2)_5CH_3$, $—(CH_2)_2—C—C—(CH_2)_4CH_3$, $—(CH_2)_3—C{\equiv}C—(CH_2)_3CH_3$,
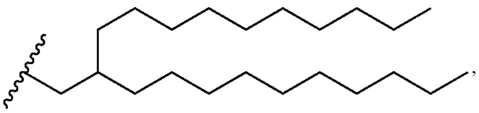
,
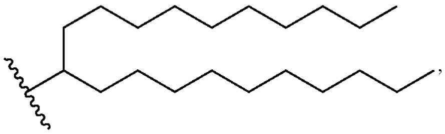
,
-continued
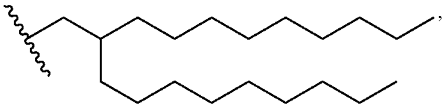
,
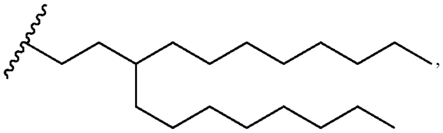
,
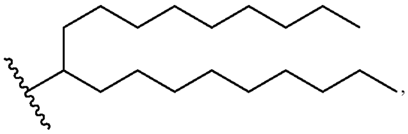
,
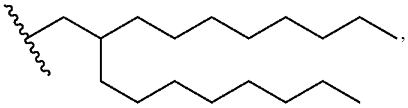
,
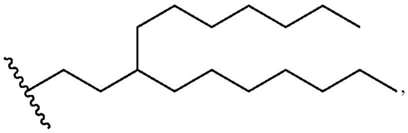
,
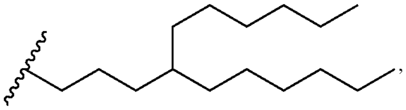
,
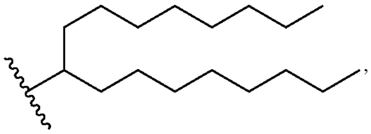
,
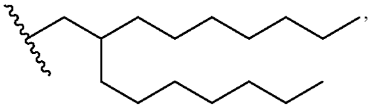
,
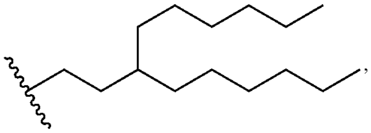
,
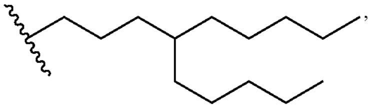
,
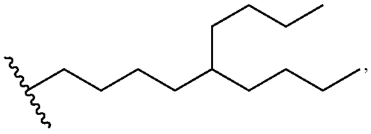
,
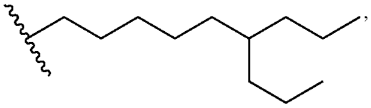
,
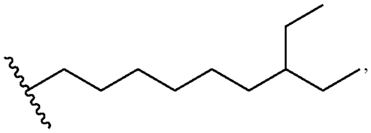
,
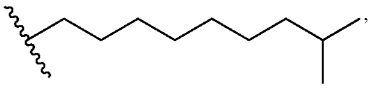
, -continued

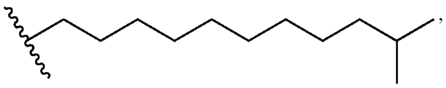,

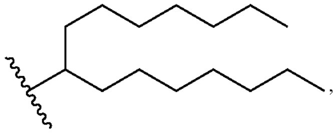, and

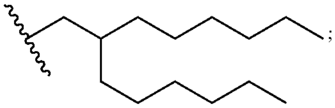;

and in another more specific embodiment, $R_1$ and $R_2$ are independently selected from: $—(CH_2)_7CH_3$, $—(CH_2)_8CH_3$, $—(CH_2)_9CH_3$, $—(CH_2)_{10}CH_3$, $—(CH_2)_{11}CH_3$, $—CH_2—CH{=}CH—(CH_2)_5CH_3$, $—CH_2—C{\equiv}C—(CH_2)_5CH_3$, $—(CH_2)_2—C{\equiv}C—(CH_2)_4CH_3$, $—(CH_2)_3—C{\equiv}C—(CH_2)_3CH_3$,

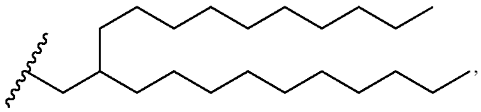,

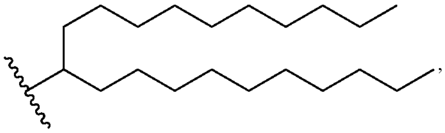,

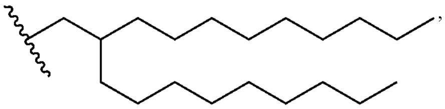,

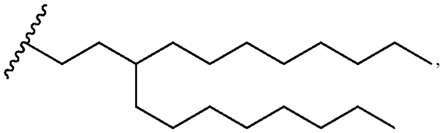,

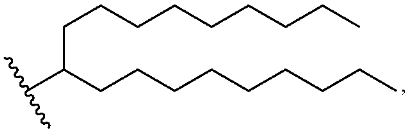,

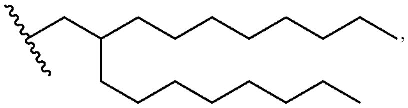,

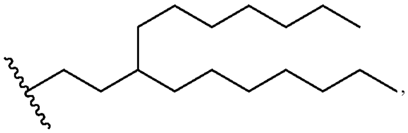,

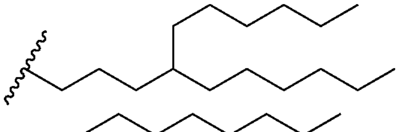,

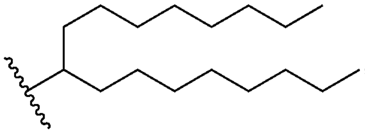,

-continued

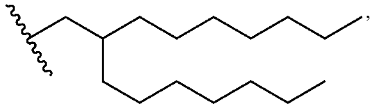,

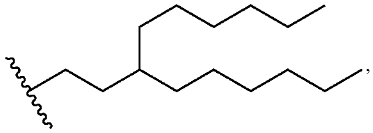,

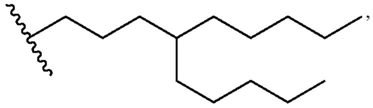,

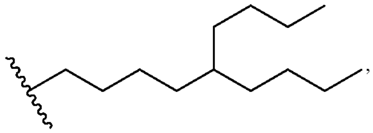,

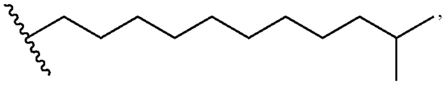,

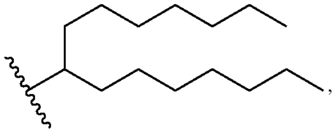, and

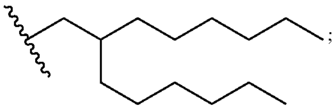;

in another more specific embodiment, $R_1$ and $R_2$ are independently selected from: $—(CH_2)_8CH_3$, $—(CH_2)_9CH_3$, $—(CH_2)_{10}CH_3$, $—(CH_2)_{11}CH_3$, $—CH_2—CH{=}CH—(CH_2)_5 CH_3$, $—CH_2—C—C—(CH_2)_5CH_3$, $—(CH_2)_2—C—C—(CH_2)_4CH_3$, $—(CH_2)_3—C—C—(CH_2)_3CH_3$,

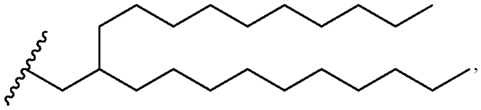,

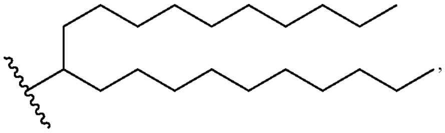,

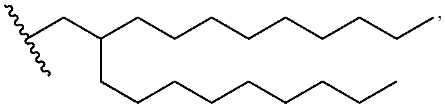,

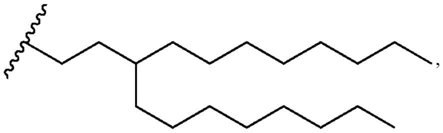,

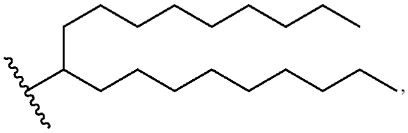,

-continued
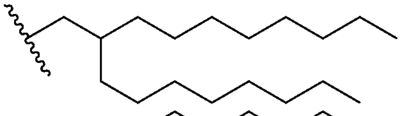
,
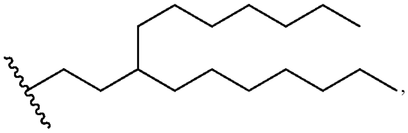
,
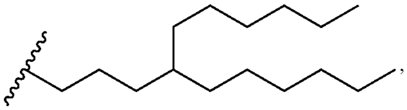
,
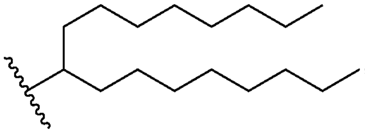
,
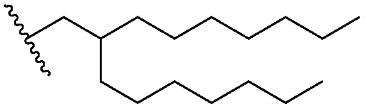
,
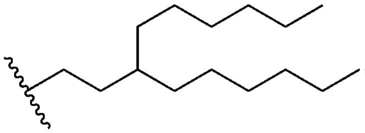
,
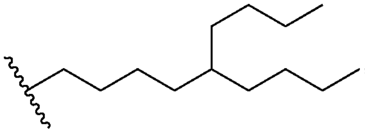
,
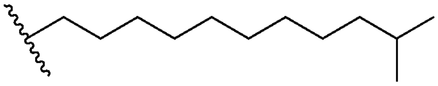
,
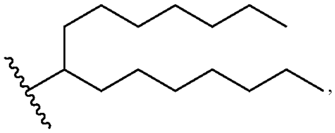
, and
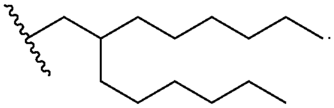
.
In a more specific embodiment, $R_1$ and $R_2$ are independently selected from: $-(CH_2)_8CH_3$, $-(CH_2)_9CH_3$, $-(CH_2)_{10}CH_3$
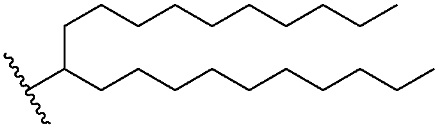
,
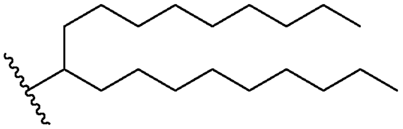
,
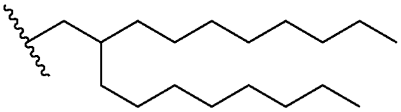
,
-continued
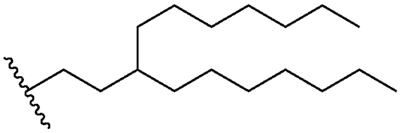
,
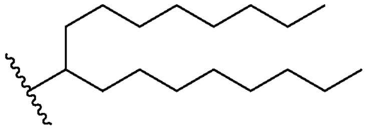
,
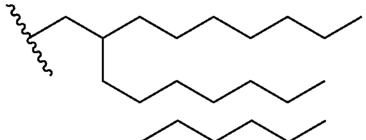
,
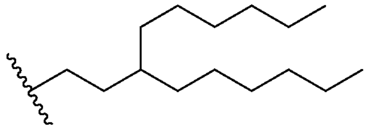
,
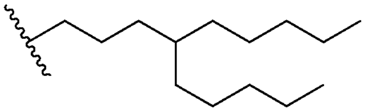
, and
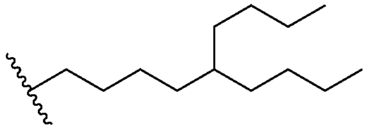
;
in another more specific embodiment $R_1$ and $R_2$ are independently selected from: $-(CH_2)_7CH_3$, $-(CH_2)_8CH_3$, $-(CH_2)_9CH_3$, and
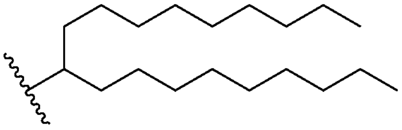
,
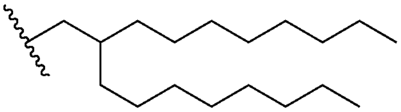
,
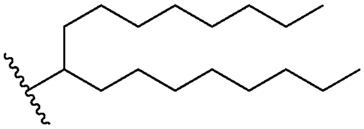
, and
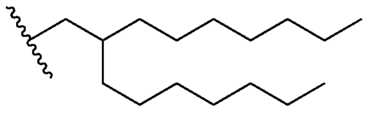
.
In a more specific embodiment, $R_1$ is selected from:
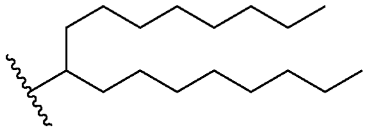
, -continued

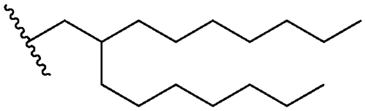

,

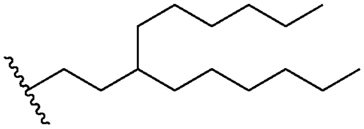

,

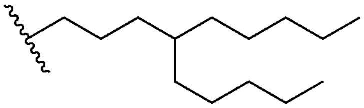

, and

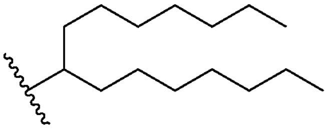

;

in another more specific embodiment, $R_1$ is selected from:

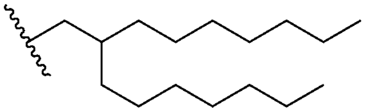

and

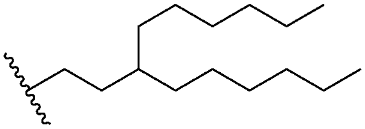

.

In a more specific embodiment, $R_1$ is selected from:

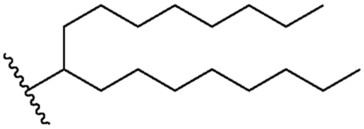

,

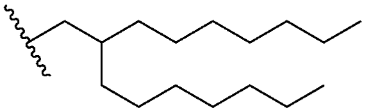

,

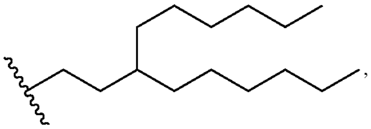

, and

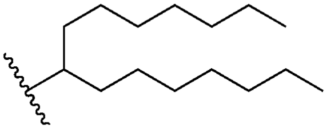

;

in another more specific embodiment, $R_1$ is selected from:

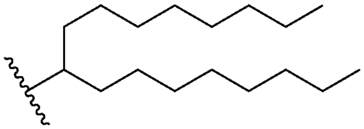

and

-continued

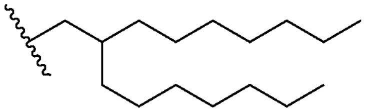

;

in another more specific embodiment, $R_1$ is selected from: $-(CH_2)_8CH_3$, $-(CH)_9CH_3$,

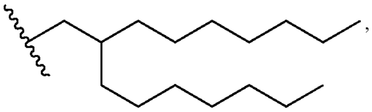

, and

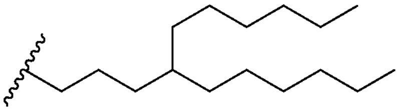

;

in another more specific embodiment, $R_1$ is selected from:

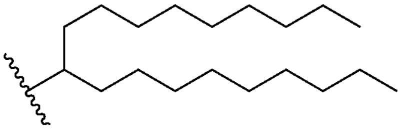

,

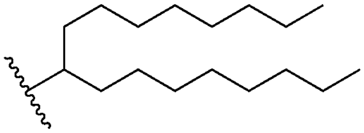

, and

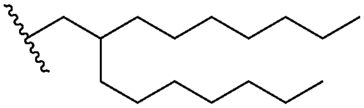

;

in another more specific embodiment, $R_1$ is selected from: and

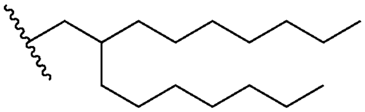

and

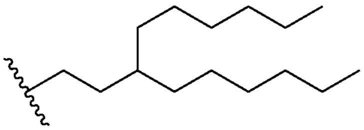

.

In a more specific embodiment, $R_2$ is selected from: $-(CH_2)_9CH_3$, $-(CH_2)_{10}CH_3$, and

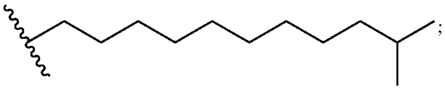 [SMILES: *CCCCCCCCCC(C)C]

;

in another more specific embodiment, $R_2$ is selected from:

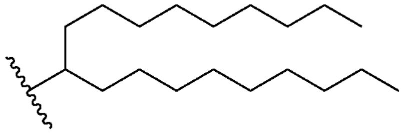

,

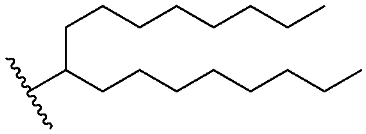

,

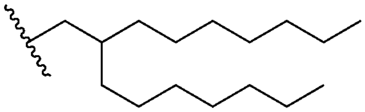

, and

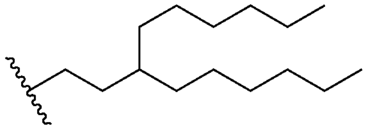

;

in another more specific embodiment, $R_2$ is selected from:

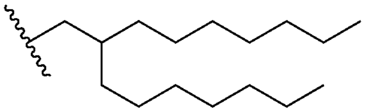

and

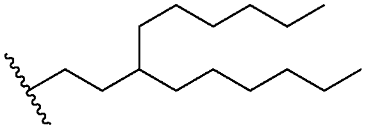

;

in another more specific embodiment, $R_2$ is selected from:

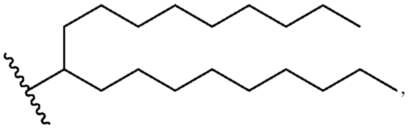

,

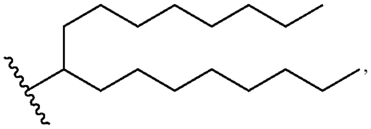

, and

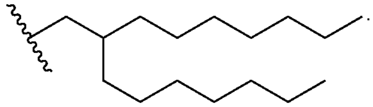

.

In a more specific embodiment, $R_2$ is selected from:

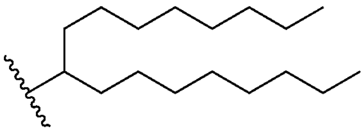

and

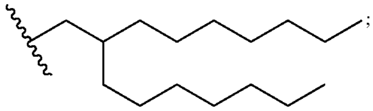

;

in another more specific embodiment, $R_2$ is selected from:

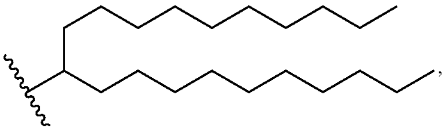

,

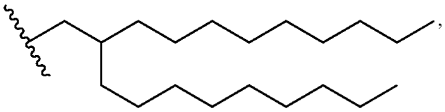

,

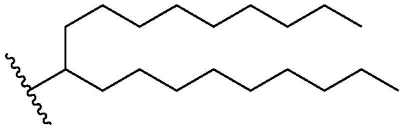

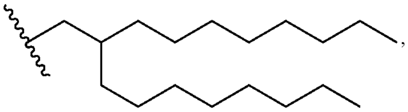

,

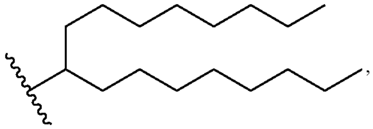

,

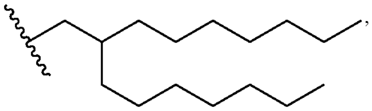 [SMILES: *CC(CCCCCCC)CCCCCCC]

, and

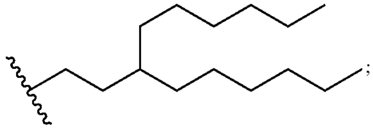

;

in another more specific embodiment, $R_2$ is selected from:

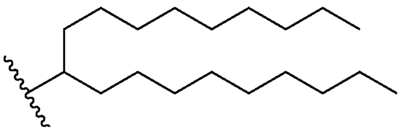

,

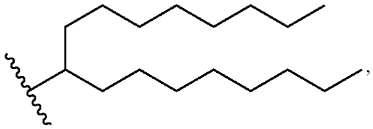

, and

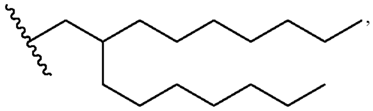

, in another more specific embodiment, $R_2$ is selected from:

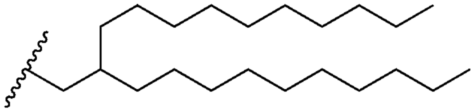

,

-continued

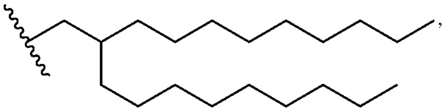
,

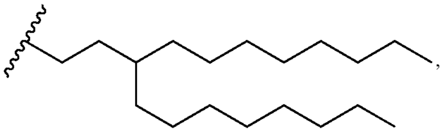
,

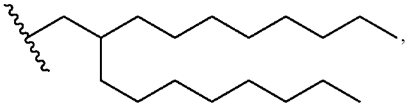
,

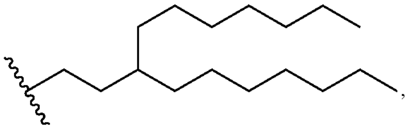
, and

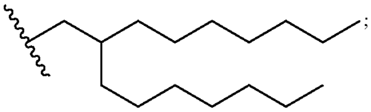
;

in another more specific embodiment, $R_2$ is selected from:

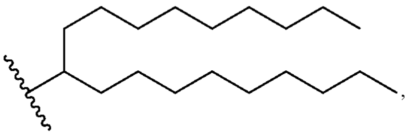
,

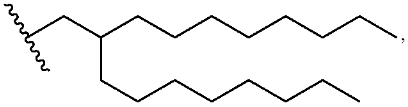
, and

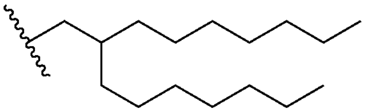
;

in another more specific embodiment, $R_2$ is selected from:

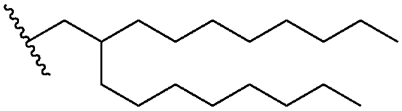
and

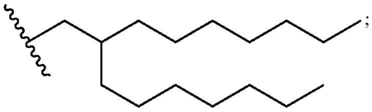
;

in another more specific embodiment, $R_2$ is selected from:

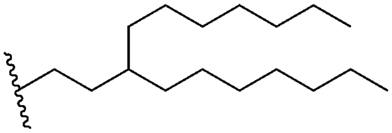
and

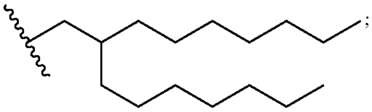
;

in another more specific embodiment, $R_2$ is selected from:

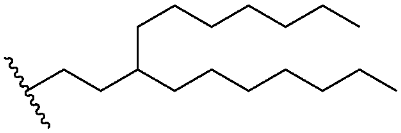
and

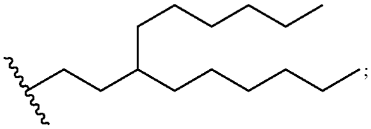
;

in another more specific embodiment, $R_2$ is selected from:

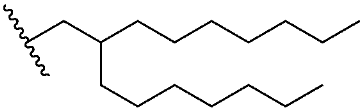
and

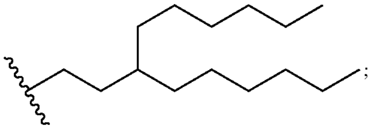
;

in another more specific embodiment, $R_2$ is selected from:

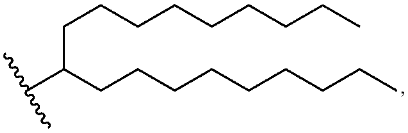
,

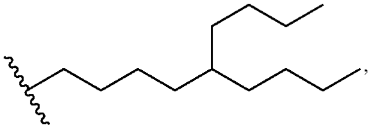
,

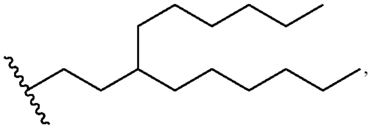
,

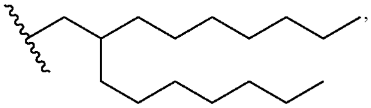
, and

-continued

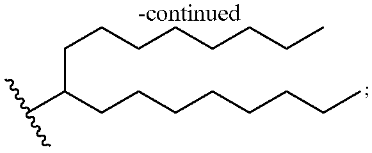;

in another more specific embodiment, $R_2$ is selected from:

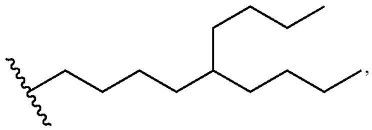,

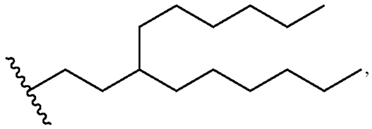,

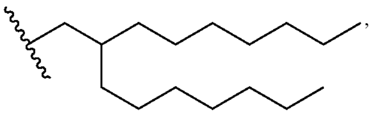, and

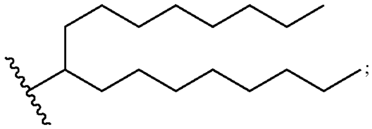;

in another more specific embodiment, $R_2$ is selected from:

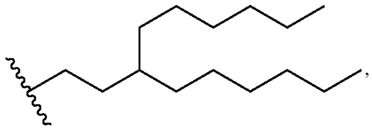,

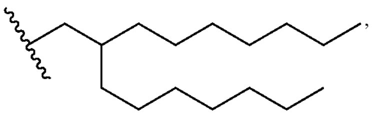, and

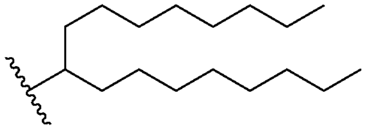.

$R_{1s}$

In one embodiment, $R_{1s}$ is H; in another embodiment, $R_{1s}$ is H; in another embodiment, $R_{1s}$ is $C_{1-20}$ alkyl, alternatively $C_{1-14}$ alkyl, alternatively $C_{1-10}$ alkyl, alternatively $C_{1-9}$ alkyl, alternatively $C_{7-9}$ alkyl, alternatively $C_{8-9}$ alkyl, alternatively $C_{1-6}$ alkyl, and alternatively $C_{1-4}$ alkyl, alternatively $C_{7-11}$ alkyl, alternatively $C_{4-10}$ alkyl, alternatively $C_{6-10}$ alkyl, alternatively $C_{7-11}$ alkyl, alternatively $C_{9-10}$ alkyl, alternatively $C_{4-9}$ alkyl, alternatively $C_{6-9}$ alkyl, alternatively $C_{1-8}$ alkyl, alternatively $C_{4-8}$ alkyl, alternatively $C_{6-8}$ alkyl, alternatively $C_{7-8}$ alkyl, alternatively $C_{6-7}$ alkyl, alternatively $C_9$ alkyl, alternatively $C_8$ alkyl, alternatively $C_7$ alkyl; in another embodiment, $R_{1s}$ is $-L_c-OR_c$; in another embodiment, $R_{1s}$ is $-L_c-SR_c$; in another embodiment, $R_{1s}$ is $-L_c-NR_cR'_c$.

In one embodiment, the substitution site of $R_{1s}$ on $R_1$ is separated from $M_1$ by 0 carbon atom; in another embodiment, the substitution site of $R_{1s}$ on $R_1$ is separated from $M_1$ by 1 carbon atom; in another embodiment, the substitution site of $R_{1s}$ on $R_1$ is separated from $M_1$ by 2 carbon atoms; in another embodiment, the substitution site of $R_{1s}$ on $R_1$ is separated from $M_1$ by 3 carbon atoms; in another embodiment, the substitution site of $R_{1s}$ on $R_1$ is separated from $M_1$ by 4 carbon atoms; in another embodiment, the substitution site of $R_{1s}$ on $R_1$ is separated from $M_1$ by 5 carbon atoms; in another embodiment, the substitution site of $R_{1s}$ on $R_1$ is separated from $M_1$ by 6 carbon atoms; in another embodiment, the substitution site of $R_{1s}$ on $R_1$ is separated from $M_1$ by 7 carbon atoms; in another embodiment, the substitution site of $R_{1s}$ on $R_1$ is separated from $M_1$ by 8 carbon atoms; in another embodiment, the substitution site of $R_{1s}$ on $R_1$ is separated from $M_1$ by 9 carbon atoms; in another embodiment, the substitution site of $R_{1s}$ on $R_1$ is separated from $M_1$ by 10 carbon atoms.

In one embodiment, the substitution site of $R_{1s}$ on $R_2$ is separated from $M_2$ by 0 carbon atom; in another embodiment, the substitution site of $R_{1s}$ on $R_2$ is separated from $M_2$ by 1 carbon atom; in another embodiment, the substitution site of $R_{1s}$ on $R_2$ is separated from $M_2$ by 2 carbon atoms; in another embodiment, the substitution site of $R_{1s}$ on $R_2$ is separated from $M_2$ by 3 carbon atoms; in another embodiment, the substitution site of $R_{1s}$ on $R_2$ is separated from $M_2$ by 4 carbon atoms; in another embodiment, the substitution site of $R_{1s}$ on $R_2$ is separated from $M_2$ by 5 carbon atoms; in another embodiment, the substitution site of $R_{1s}$ on $R_2$ is separated from $M_2$ by 6 carbon atoms; in another embodiment, the substitution site of $R_{1s}$ on $R_2$ is separated from $M_2$ by 7 carbon atoms; in another embodiment, the substitution site of $R_{1s}$ on $R_2$ is separated from $M_2$ by 8 carbon atoms; in another embodiment, the substitution site of $R_{1s}$ on $R_2$ is separated from $M_2$ by 9 carbon atoms; in another embodiment, the substitution site of $R_{1s}$ on $R_2$ is separated from $M_2$ by 10 carbon atoms.

In a more specific embodiment, $R_{1s}$ is independently H, $C_{1-14}$ alkyl, $-L_c-OR$, or $-L_c-NR_cR'_c$; in another more specific embodiment, $R_{1s}$ is independently H or $C_{1-14}$ alkyl; in another more specific embodiment, $R_{1s}$ is independently H or $C_{1-10}$ alkyl; in another more specific embodiment, $R_{1s}$ is independently H or $C_{1-9}$ alkyl; in another more specific embodiment, $R_{1s}$ is independently H or $C_{1-6}$ alkyl; in another more specific embodiment, $R_{1s}$ is independently H or $C_{1-4}$ alkyl.

In a more specific embodiment, the substitution site of $R_{1s}$ on $R_1$ or $R_2$ is separated from $M_1$ or $M_2$ by 0-10 carbon atoms; in another more specific embodiment, the substitution site of $R_{1s}$ on $R_1$ or $R_2$ is separated from $M_1$ or $M_2$ by 0-6 carbon atoms; in another more specific embodiment, the substitution site of $R_{1s}$ on $R_1$ or $R_2$ is separated from $M_1$ or $M_2$ by 0-4 carbon atoms; in another more specific embodiment, the substitution site of $R_{1s}$ on $R_1$ or $R_2$ is separated from $M_1$ or $M_2$ by 0-2 carbon atoms; in another more specific embodiment, the substitution site of $R_{1s}$ on $R_1$ or $R_2$ is separated from $M_1$ or $M_2$ by 0 carbon atom.

In a more specific embodiment, the substitution site of $R_{1s}$ on $R_1$ or $R_2$ is separated from $M_1$ or $M_2$ by 1-10 carbon atoms; in another more specific embodiment, the substitution site of $R_{1s}$ on $R_1$ or $R_2$ is separated from $M_1$ or $M_2$ by 1-6 carbon atoms; in another more specific embodiment, the substitution site of $R_{1s}$ on $R_1$ or $R_2$ is separated from $M_1$ or $M_2$ by 1-4 carbon atoms; in another more specific embodiment, the substitution site of $R_{1s}$ on $R_1$ or $R_2$ is separated from $M_1$ or $M_2$ by 1-2 carbon atoms; in another more specific embodiment, the substitution site of $R_{1s}$ on $R_1$ or $R_2$ is separated from $M_1$ or $M_2$ by 2-10 carbon atoms; in another more specific embodiment, the substitution site of $R_{1s}$ on $R_1$ or $R_2$ is separated from $M_1$ or $M_2$ by 2-6 carbon atoms; in another more specific embodiment, the substitution site of $R_{1s}$ on $R_1$ or $R_2$ is separated from $M_1$ or $M_2$ by 2-4 carbon atoms.

In another more specific embodiment, $R_1$ is not substituted with $R_{1s}$, and the substitution site of $R_{1s}$ on $R_2$ is separated from $M_2$ by 0-10 carbon atoms, alternatively 1-10 carbon atoms, alternatively 1-6 carbon atoms, alternatively 1-4 carbon atoms, alternatively 1-2 carbon atoms; In another more specific embodiment, $R_1$ is not substituted with $R_{1s}$, and the substitution site of $R_{1s}$ on $R_2$ is separated from $M_2$ by 0-10 carbon atoms, alternatively 0-6 carbon atom, alternatively 0-4 carbon atoms, alternatively 0-2 carbon atoms; alternatively 0 carbon atom; In another more specific embodiment, $R_1$ is not substituted with $R_{1s}$, and the substitution site of $R_{1s}$ on $R_2$ is separated from $M_2$ by 2-10 carbon atoms, alternatively 2-6 carbon atom, alternatively 2-4 carbon atoms.

R and R'

In one embodiment, R is H; in another embodiment, R is $C_{1-20}$ alkyl, alternatively $C_{1-14}$ alkyl, alternatively $C_{1-9}$ alkyl, and alternatively $C_{1-6}$ alkyl.

In one embodiment, R' is H; in another embodiment, R' is $C_{1-20}$ alkyl, alternatively $C_{1-14}$ alkyl, alternatively $C_{1-9}$ alkyl, and alternatively $C_{1-6}$ alkyl.

In a more specific embodiment, R and R' are each independently H or $C_{1-20}$ alkyl; in another more specific embodiment, R and R' are each independently H or $C_{1-14}$ alkyl; in another more specific embodiment, R and R' are each independently H or $C_{1-9}$ alkyl; in another more specific embodiment, R and R' are each independently H or $C_{1-6}$ alkyl; in another more specific embodiment, R is H.

$L_c$, $R_c$, and $R'_c$

In one embodiment, $L_c$ is a chemical bond; in another embodiment, $L_c$ is $C_{1-20}$ alkylene, alternatively $C_{1-14}$ alkylene, alternatively $C_{1-10}$ alkylene, and alternatively $C_{1-6}$ alkylene.

In a more specific embodiment, $L_c$ is independently a chemical bond or $C_{1-14}$ alkylene; in another more specific embodiment, $L_c$ is independently a chemical bond or $C_{1-10}$ alkylene; in another more specific embodiment, $L_c$ is independently a chemical bond or $C_{1-6}$ alkylene.

In one embodiment, $R_c$ is H; in another embodiment, $R_c$ is $C_{1-20}$ alkyl, alternatively $C_{1-14}$ alkyl, alternatively $C_{1-10}$ alkyl, and alternatively $C_{1-6}$ alkyl; in another embodiment, $R_c$ is $C_{3-14}$ cycloalkyl, alternatively $C_{3-10}$ cycloalkyl; in another embodiment, $R_c$ is 3- to 14-membered heterocyclyl, alternatively 3- to 10-membered heterocyclyl.

In one embodiment, $R'_c$ is H; in another embodiment, $R'_c$ is $C_{1-20}$ alkyl, alternatively $C_{1-14}$ alkyl, alternatively $C_{1-10}$ alkyl, and alternatively $C_{1-6}$ alkyl; in another embodiment, $R'_c$ is $C_{3-14}$ cycloalkyl, alternatively $C_{3-10}$ cycloalkyl; in another embodiment, $R'_c$ is 3- to 14-membered heterocyclyl, alternatively 3- to 10-membered heterocyclyl.

In a more specific embodiment, $R_c$ and $R'_c$ are independently H or $C_{1-14}$ alkyl; in another more specific embodiment, $R_c$ and $R'_c$ are independently H or $C_{1-10}$ alkyl; in another more specific embodiment, $R_c$ and $R'_c$ are independently H or $C_{1-6}$ alkyl.

$R_3$

In one embodiment, $R_3$ is CN; in another embodiment, $R_3$ is —$OR_g$, for example, —OH; in another embodiment, $R_3$ is —$C(O)R_g$; in another embodiment, $R_3$ is —$OC(O)R_g$; in another embodiment, $R_3$ is —$NR''C(O)R_g$; in another embodiment, $R_3$ is —$NR_gR'_g$, for example, —$N(CH_3)_2$; in another embodiment, $R_3$ is —$NR''C(O)NR_gR'_g$; in another embodiment, $R_3$ is —$NR''C(O)R_g$; in another embodiment, $R_3$ is —$NR''S(O)_2R_g$; in another embodiment, $R_3$ is —$OC(O)NR_gR'_g$; in another embodiment, $R_3$ is —$NR''C(O)OR_g$; in another embodiment, $R_3$ is —$N(OR_g)C(O)R_g$; in another embodiment, $R_3$ is —$N(OR_g)S(O)_2R_g$; in another embodiment, $R_3$ is —$N(OR_g)C(O)OR_g$; in another embodiment, $R_3$ is —$N(OR_g)C(O)R_gR'_g$; in another embodiment, $R_3$ is 3- to 14-membered heterocyclyl; in another embodiment, $R_3$ is 5- to 14-membered heteroaryl.

In a more specific embodiment, $R_3$ is CN, —$OR_g$, or —$NR_gR'_g$; in another more specific embodiment, $R_3$ is —$OR_g$ or —$NR_gR'_g$; in another more specific embodiment, $R_3$ is —OH or —$N(CH_3)_2$; in another more specific embodiment, $R_3$ is —$OR_g$; in another more specific embodiment, $R_3$ is —OH.

$R_g$ and $R'_g$

In one embodiment, $R_g$ is H; in another embodiment, $R_g$ is $C_{1-10}$ alkyl, alternatively $C_{1-6}$ alkyl, alternatively $C_{1-4}$ alkyl, for example, methyl; in another embodiment, $R_g$ is $C_{3-10}$ cycloalkyl, alternatively $C_{3-7}$ cycloalkyl; in another embodiment, $R_g$ is 3-to 10-membered heterocyclyl, alternatively 3- to 7-membered heterocyclyl.

In one embodiment, $R'_g$ is H; in another embodiment, $R'_g$ is $C_{1-10}$ alkyl, alternatively $C_{1-6}$ alkyl, and alternatively $C_{1-4}$ alkyl; in another embodiment, $R'_g$ is $C_{3-10}$ cycloalkyl, alternatively $C_{3-7}$ cycloalkyl; in another embodiment, $R'_g$ is 3- to 10-membered heterocyclyl, alternatively 3- to 7-membered heterocyclyl.

In a more specific embodiment, $R_g$ and $R'_g$ are independently H, $C_{1-6}$ alkyl, $C_{3-7}$ cycloalkyl, or 3- to 7-membered heterocyclyl; in another more specific embodiment, $R_g$ and $R'_g$ are independently H or $C_{1-6}$ alkyl; in another more specific embodiment, $R_g$ and $R'_g$ are independently H or $C_{1-4}$ alkyl; in another more specific embodiment, $R_g$ and $R'_g$ are independently H or methyl.

R''

In one embodiment, R'' is H; in another embodiment, R'' is $C_{1-6}$ alkyl, alternatively $C_{1-4}$ alkyl.

$R_4$ and $R_5$

In one embodiment, $R_4$ is $C_{1-8}$ alkyl, alternatively $C_{1-6}$ alkyl, alternatively $C_{1-3}$ alkyl, and alternatively methyl; in another embodiment, $R_4$ is optionally substituted with one or more $R_{4s}$; in another embodiment, $R_4$ is optionally substituted with 1, 2, or 3 $R_{4s}$; in another embodiment, $R_4$ is unsubstituted.

In one embodiment, $R_5$ is $C_{1-8}$ alkyl, alternatively $C_{1-6}$ alkyl, alternatively $C_{1-3}$ alkyl, and alternatively methyl; in another embodiment, $R_5$ is optionally substituted with one or more $R_{4s}$; in another embodiment, $R_5$ is optionally substituted with 1, 2, or 3 $R_{4s}$; in another embodiment, $R_5$ is unsubstituted.

In one embodiment, $R_4$ and $R_5$ are taken together with the carbon atom to which they are attached to form $C_{3-14}$ cycloalkylene, alternatively $C_{3-10}$ cycloalkylene, alternatively $C_{3-6}$ cycloalkylene (e.g., cyclopropylene, cyclobutylene, cyclopentylene, and cyclohexylene), alternatively $C_{3-5}$ cycloalkylene, alternatively $C_{3-4}$ cycloalkylene, alternatively cyclopropylene, alternatively cyclopentylene; in another embodiment, $R_4$ and $R_5$ are taken together with the carbon atom to which they are attached to form 3- to 14-membered heterocyclylene, alternatively 3- to 10-membered heterocyclylene, alternatively 3- to 6-membered heterocyclylene; in another embodiment, a ring formed by $R_4$, $R_5$ taken together with the carbon atom to which they are attached is optionally substituted with one or more $R_{4s}$; in another embodiment, a ring formed by $R_4$, $R_5$ taken together with the carbon atom to which they are attached is optionally substituted with 1, 2, or 3 $R_{4s}$; in another embodiment, a ring formed by $R_4$, $R_5$ taken together with the carbon atom to which they are attached is unsubstituted.

In a more specific embodiment, $R_4$ and $R_5$ are taken together with the carbon atom to which they are attached to form $C_{3-10}$ cycloalkylene or 3- to 10-membered heterocyclylene; in another more specific embodiment, $R_4$ and $R_5$ are taken together with the carbon atom to which they are attached to form $C_{3-6}$ cycloalkylene or 3- to 6-membered heterocyclylene; in another more specific embodiment, $R_4$ and $R_5$ are taken together with the carbon atom to which they are attached to form $C_{3-6}$ cycloalkylene (e.g., cyclopropylene, cyclobutylene, cyclopentylene, or cyclohexylene); in another more specific embodiment, $R_4$ and $R_5$ are taken together with the carbon atom to which they are attached to form $C_{3-5}$ cycloalkylene; in another more specific embodiment, $R_4$ and $R_5$ are taken together with the carbon atom to which they are attached to form cyclopropylene or cyclopentylene; in another more specific embodiment, $R_4$ and $R_5$ are taken together with the carbon atom to which they are attached to form cyclopropylene; in another more specific embodiment, $R_4$ and $R_5$ are not taken together with the carbon atom to which they are attached to form a ring.

$R_{4s}$

In one embodiment, $R_{4s}$ is H; in another embodiment, $R_{4s}$ is halogen; in another embodiment, $R_{4s}$ is cyano; in another embodiment, $R_{4s}$ is $C_{1-8}$ alkyl, alternatively $C_{1-6}$ alkyl, alternatively $C_{1-3}$ alkyl; in another embodiment, $R_{4s}$ is $C_{1-8}$ haloalkyl, alternatively $C_{1-6}$ haloalkyl, and alternatively $C_{1-3}$ haloalkyl; in another embodiment, $R_{4s}$ is $-L_d-OR_d$; in another embodiment, $R_{4s}$ is $-L_d-SR_d$; in another embodiment, $R_{4s}$ is $-L_d-NR_dR'_d$.

In a more specific embodiment, $R_{4s}$ is independently H, halogen, cyano, $C_{1-6}$ alkyl, $C_{1-6}$ haloalkyl, $-L_d-OR_d$, $-L_d-SR_d$, or $-L_d-NR_dR'_d$; in another more specific embodiment, $R_{4s}$ is independently H, halogen, cyano, $C_{1-6}$ alkyl, or $C_{1-6}$ haloalkyl; in another more specific embodiment, $R_{4s}$ is independently H, $C_{1-3}$ alkyl, or $C_{1-3}$ haloalkyl.

$L_d$, $R_d$, and $R'_d$

In one embodiment, $L_d$ is a chemical bond; in another embodiment, $L_d$ is $C_{1-8}$ alkylene, alternatively $C_{1-6}$ alkylene, and alternatively $C_{1-3}$ alkylene.

In a more specific embodiment, $L_d$ is independently a chemical bond or $C_{1-6}$ alkylene; in another more specific embodiment, $L_d$ is independently a chemical bond or $C_{1-3}$ alkylene.

In one embodiment, $R_d$ is H; in another embodiment, $R_d$ is $C_{1-8}$ alkyl, alternatively $C_{1-6}$ alkyl; in another embodiment, $R_d$ is $C_{3-14}$ cycloalkyl, alternatively $C_{3-10}$ cycloalkyl; in another embodiment, $R_d$ is 3- to 14-membered heterocyclyl, alternatively 3- to 10-membered heterocyclyl.

In one embodiment, $R'_d$ is H; in another embodiment, $R'_d$ is $C_{1-8}$ alkyl, alternatively $C_{1-6}$ alkyl; in another embodiment, $R'_d$ is $C_{3-14}$ cycloalkyl, alternatively $C_{3-10}$ cycloalkyl; in another embodiment, $R'_d$ is 3- to 14-membered heterocyclyl, alternatively 3- to 10-membered heterocyclyl.

In a more specific embodiment, $R_d$ and $R'_d$ are independently H, $C_{1-6}$ alkyl, $C_{3-10}$ cycloalkyl, or 3- to 10-membered heterocyclyl; in another more specific embodiment, $R_d$ and $R'_d$ are independently H or $C_{1-6}$ alkyl.

a. b, c, and d

In one embodiment, a is 1; in another embodiment, a is 2; in another embodiment, a is 3; in another embodiment, a is 4; in another embodiment, a is 5; in another embodiment, a is 6.

In a more specific embodiment, a=2, 3, 4, 5, or 6; in another more specific embodiment, a=2, 3, or 4; in another more specific embodiment, a=2 or 4; in another more specific embodiment, a=2 or 3; in another more specific embodiment, a=3 or 4.

In one embodiment, b is 4; in another embodiment, b is 5; in another embodiment, b is 6; in another embodiment, b is 7; in another embodiment, b is 8; in another embodiment, b is 9; in another embodiment, b is 10.

In a more specific embodiment, b=5, 6, 7, or 8; in another more specific embodiment, b=5, 6, or 7; in another more specific embodiment, b=5 or 7; in another more specific embodiment, b=6 or 7.

In a more specific embodiment, b=4, 5, 6, 7, 8, 9, or 10; in another more specific embodiment, b=4, 5, 6, 7, 8, or 9; in another more specific embodiment, b=4, 5, 6, or 7; in another more specific embodiment, b=5 or 6; in another more specific embodiment, b=6, 7, or 8; in another more specific embodiment, b=5, 6, 7, or 8.

In one embodiment, c is 1; in another embodiment, c is 2; in another embodiment, c is 3; in another embodiment, c is 4; in another embodiment, c is 5; in another embodiment, c is 6.

In a more specific embodiment, c=2, 3, 4, 5, or 6; in another more specific embodiment, c=2, 3, or 4; in another more specific embodiment, c=3 or 4; in another more specific embodiment, c=5 or 6.

In a more specific embodiment, c=2, 4, 5, or 6; in another more specific embodiment, c=4, 5, or 6; in another more specific embodiment, c=4 or 6; in another more specific embodiment, c=2, 3, 4, or 5; in another more specific embodiment, c=2, 4, or 5; in another more specific embodiment, c=2 or 5.

In one embodiment, d is 0; in another embodiment, d is 1; in another embodiment, d is 2; in another embodiment, d is 3; in another embodiment, d is 4.

In a more specific embodiment, d=0, 1, 2, or 4; in another more specific embodiment, d=2, 3, or 4; in another more specific embodiment, d=0 or 1.

In a more specific embodiment, d=0, 1, 2, 3, or 4; in another more specific embodiment, d=0, 1, or 2; in another more specific embodiment, d=0 or 2; in another more specific embodiment, d is not 0; in another more specific embodiment, d=1, 2, 3, or 4; in another more specific embodiment, d=1 or 2; in another more specific embodiment, d=1, 2 or 4; in another more specific embodiment, d=1 or 4.

In one embodiment, c+d=3; in another embodiment, c+d=4; in another embodiment, c+d=5; in another embodiment, c+d=6; in another embodiment, c+d=7; in another embodiment, c+d=8; in another embodiment, c+d=9.

In a more specific embodiment, c+d=4, 5, or 6; in another more specific embodiment, c+d=5 or 6.

In a more specific embodiment, c+d=3, 4, 5, 6, 7, 8, or 9; in another more specific embodiment, c+d=4, 5, 6, or 7; in another more specific embodiment, c+d=4, 5, or 6; in another more specific embodiment, c+d=5, 6, or 7; in another more specific embodiment, c+d=6, 7, or 8; in another more specific embodiment, c+d=6 or 7.

Any of the above technical solutions in any specific embodiment or any combination thereof may be combined with any technical solution or any combination thereof in other specific embodiments. For example, any technical solutions of $G_1$, or any combination thereof, may be combined with any technical solution of $G_2$, $R_{G1}$, $G_3$, $R_{G3}$, $L_a$, $R_a$, $R'_a$, $G_4$, $R_{G4}$, $L_b$, Rb, $R'_b$, $R_{4g}$, $L_e$, $R_e$, $R'_e$, $M_1$, $M_2$, Q, R*, $L_f$, Rf, $R'_f$, $R_1$, $R_2$, $R_{1s}$, R, R', $L_c$, $R_c$, $R'_c$, $R_3$, $R_g$, $R'_g$, R", $R_4$, $R_5$, $R_{4s}$, $L_d$, $R_d$, $R'_d$, a, b, c, and d, etc. The present disclosure is intended to include all of these combinations of technical solutions and, for reasons of space, will not be listed.

In a more specific embodiment, the present disclosure provides a compound of formula (I), or a pharmaceutically acceptable salt, isotopic variant, tautomer, or stereoisomer thereof:

(I)

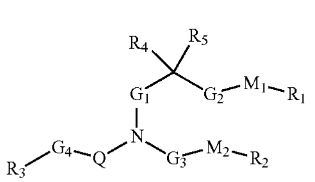

wherein $G_1$ and $G_2$ are independently selected from a chemical bond, $C_{1-13}$ linear alkylene, $C_{2-13}$ linear alkenylene, and $C_{2-13}$ linear alkynylene, each of which is optionally substituted with one or more $R_{G1}$;

$G_1$ and $G_2$ have a total length of 3, 4, 5, 6, 7, 8, 9, 10, 11, 12, or 13 carbon atoms;

$R_{G1}$ is independently H, $C_{1-14}$ alkyl, $-L_a-OR_a$, $-L_a-SR_a$, or $-L_a-NR_aR'_a$;

$G_3$ is $C_{4-14}$ linear alkylene, $C_{4-14}$ linear alkenylene, or $C_{4-14}$ linear alkynylene, each of which is optionally substituted with one or more $R_{G3}$;

$R_{G3}$ is independently H, —La—$OR^a$, $-L_a-SR_a$, or $-L_a-NR_aR'_a$;

$L_a$ is independently a chemical bond or $C_{1-14}$ alkylene;

$R_a$ and $R'_a$ are independently selected from H, $C_{1-14}$ alkyl, $C_{3-14}$ cycloalkyl, and 3- to 14-membered heterocyclyl;

$G_4$ is a chemical bond, $C_{1-6}$ alkylene, $C_{2-6}$ alkenylene, or $C_{2-6}$ alkynylene, each of which is optionally substituted with one or more $R_{G4}$;

$R_{G4}$ is independently H, $C_{1-6}$ alkyl, $-L_b-OR_b$, $-L_b-SR_b$, or $-L_b-NR_bR'_b$;

$L_b$ is independently a chemical bond or $C_{1-6}$ alkylene;

$R_b$ and $R'_b$ are independently selected from H, $C_{1-6}$ alkyl, $C_{3-10}$ cycloalkyl, and 3- to 10-membered heterocyclyl;

or, two $R_{G4}$ attached to the same carbon atom are taken together with the carbon atom to which they are attached to form $C_{3-14}$ cycloalkylene or 3- to 14-membered heterocyclylene, each of which is optionally substituted with one or more $R_{4g}$;

$R_{4g}$ is independently H, halogen, cyano, $C_{1-8}$ alkyl, $C_{1-8}$ haloalkyl, $-L_e-OR_e$, $-L_e-SR_e$, or $-L_e-NR_eR'_e$;

$L_e$ is independently a chemical bond or $C_{1-8}$ alkylene;

$R_e$ and $R'_e$ are independently selected from H, $C_{1-8}$ alkyl, $C_{3-14}$ cycloalkyl, and 3- to 14-membered heterocyclyl;

$M_1$ and $M_2$ are independently selected from —C(O)O—, —OC(O)—, —O—, —SC(O)O—, —OC(O)NR—, —NRC(O)NR—, —OC(O)S—, —OC(O)O—, —NRC(O)O—, —SC(O)—, —C(O)S—, —NR—, —C(O)NR—, —NRC(O)—, —NRC(O)S—, —SC(O)NR—, —C(O)—, —OC(S)—, —C(S)O—, —OC(S)NR—, —NRC(S)O—, —S—S—, and $—S(O)_{0-2}—$;

Q is selected from a chemical bond, —C(O)O—, —O—, —SC(O)O—, $—OC(O)NR_f—$, $—NR_fC(O)NR_f—$, —OC(O)S—, —OC(O)O—, $—NR_fC(O)O—$, —OC(O)—, —SC(O)—, —C(O)S—, $—NR_f—$, $—C(O)NR_f—$, $—NR_fC(O)—$, $—NR_fC(O)S—$, $—SC(O)NR_f—$, —C(O)—, —OC(S)—, —C(S)O—, $—OC(S)NR_f—$, $—NR_fC(S)O—$, —S—S—, $—S(O)_{0-2}—$, phenylene, and pyridinylene, wherein the phenylene or the pyridinylene is optionally substituted with one or more R*;

R* is independently H, halogen, cyano, $C_{1-10}$ alkyl, $C_{1-10}$ haloalkyl, $-L_f-OR_f$, $-L_f-SR_f$, or $-L_f-NR_fR'_f$;

$L_f$ is independently a chemical bond or $C_{1-8}$ alkylene;

$R_f$ and $R'_f$ are independently selected from H, $C_{1-10}$ alkyl, $C_{3-14}$ cycloalkyl, and 3- to 14-membered heterocyclyl;

$R_1$ and $R_2$ are independently selected from $C_{4-20}$ alkyl, $C_{4-20}$ alkenyl, and $C_{4-20}$ alkynyl, each of which is optionally substituted with one or more $R_{1s}$, and wherein one or more methylene units are optionally and independently replaced with —NR'—;

$R_{1s}$ is independently H, $C_{1-20}$ alkyl, $-L_c-OR$, $-L_c-SR$, or $-L_c-NR_cR'_c$;

R and R' are independently H or $C_{1-20}$ alkyl;

$L_c$ is independently a chemical bond or $C_{1-20}$ alkylene;

$R_c$ and $R'_c$ are independently selected from H, $C_{1-20}$ alkyl, $C_{3-14}$ cycloalkyl, and 3- to 14-membered heterocyclyl;

$R_3$ is selected from CN, $—OR_g$, $—C(O)R_g$, $—OC(O)R_g$, $—NR''C(O)R_g$, $—NR_gR'_g$, $—NR''C(O)NR_gR'_g$, $—NR''C(O)R_g$, $—NR''S(O)_2R_g$, $—OC(O)NR_gR'_g$, $—NR''C(O)OR_g$, $—N(OR_g)C(O)R_g$, $—N(OR_g)S(O)_2R_g$, $—N(OR_g)C(O)OR_g$, $—N(OR_g)C(O)R_gR'_g$, 3- to 14-membered heterocyclyl, and 5- to 14-membered heteroaryl;

$R_g$ and $R'_g$ are independently H, $C_{1-10}$ alkyl, $C_{3-10}$ cycloalkyl, or 3- to 10-membered heterocyclyl;

R" is independently H or $C_{1-6}$ alkyl;

$R_4$ and $R_5$ are independently $C_{1-8}$ alkyl, which is optionally substituted with one or more $R_{4s}$;

or, $R_4$ and $R_5$ are taken together with the carbon atom to which they are attached to form $C_{3-14}$ cycloalkylene or 3- to 14-membered heterocyclylene, each of which is optionally substituted with one or more $R_{4s}$;

$R_{4s}$ is independently H, halogen, cyano, $C_{1-8}$ alkyl, $C_{1-8}$ haloalkyl, $-L_d-OR_d$, $-L_d-SR_d$, or $-L_d-NR_dR'_d$;

$L_d$ is independently a chemical bond or $C_{1-8}$ alkylene;

$R_d$ and $R'_d$ are independently H, $C_{1-8}$ alkyl, $C_{3-14}$ cycloalkyl, or 3- to 14-membered heterocyclyl.

In a more specific embodiment, the present disclosure provides the compound of formula (I), or a pharmaceutically acceptable salt, isotopic variant, tautomer, or stereoisomer thereof, wherein $G_1$ and $G_2$ are independently a chemical bond, $C_{1-9}$ linear alkylene, $C_{2-9}$ linear alkenylene, or $C_{2-9}$ linear alkynylene.

In a more specific embodiment, $G_1$ is $C_{1-6}$ linear alkylene, $C_{2-6}$ linear alkenylene, or $C_{2-6}$ linear alkynylene, alternatively $C_{1-6}$ linear alkylene, alternatively $C_{2-6}$ linear alkylene.

In a more specific embodiment, $G_2$ is a chemical bond, $C_{1-6}$ linear alkylene, $C_{2-6}$ linear alkenylene, or $C_{2-6}$ linear alkynylene, alternatively a chemical bond or $C_{1-6}$ linear alkylene, alternatively a chemical bond or $C_{1-4}$ linear alkylene.

In a more specific embodiment, $G_1$ and $G_2$ have a total length of 3, 4, 5, 6, 7, 8, or 9 carbon atoms, alternatively a total length of 4, 5, or 6 carbon atoms, alternatively a total length of 5 or 6 carbon atoms; alternatively a total length of 5, 6 or 7 carbon atoms; alternatively a total length of 6 or 7 carbon atoms.

alternatively, $G_1$ and $G_2$ are optionally substituted with 1, 2, 3, or 4 $R_{G1}$.

In a more specific embodiment, the present disclosure provides the compound of formula (I), or a pharmaceutically acceptable salt, isotopic variant, tautomer, or stereoisomer thereof, wherein $R_{G1}$ is independently H or $C_{1-10}$ alkyl, alternatively H or $C_{1-6}$ alkyl.

In a more specific embodiment, the present disclosure provides the compound of formula (I), or a pharmaceutically acceptable salt, isotopic variant, tautomer, or stereoisomer thereof, wherein $G_3$ is $C_{4-10}$ linear alkylene, $C_{4-10}$ linear alkenylene, or $C_{4-10}$ linear alkynylene, alternatively $C_{4-9}$ linear alkylene, alternatively $C_{5-8}$ linear alkylene.

In a more specific embodiment, $G_3$ is optionally substituted with 1, 2, 3, or 4 $R_{G3}$.

In a more specific embodiment, the present disclosure provides the compound of formula (I), or a pharmaceutically acceptable salt, isotopic variant, tautomer, or stereoisomer thereof, wherein $L_a$ is independently a chemical bond or $C_{1-10}$ alkylene, alternatively a chemical bond or $C_{1-6}$ alkylene.

In a more specific embodiment, $R_a$ and $R'_a$ are independently H, $C_{1-10}$ alkyl, $C_{3-10}$ cycloalkyl, or 3- to 10-membered heterocyclyl, alternatively H or $C_{1-6}$ alkyl.

In a more specific embodiment, the present disclosure provides the compound of formula (I), or a pharmaceutically acceptable salt, isotopic variant, tautomer, or stereoisomer thereof, wherein $G_4$ is $C_{1-4}$ alkylene, $C_{2-4}$ alkenylene, or $C_{2-4}$ alkynylene, alternatively $C_{2-4}$ alkylene, alternatively $C_{2-3}$ alkylene.

In a more specific embodiment, $G_4$ is optionally substituted with 1, 2, 3, or 4 $R_{G4}$.

In a more specific embodiment, the present disclosure provides the compound of formula (I), or a pharmaceutically acceptable salt, isotopic variant, tautomer, or stereoisomer thereof, wherein $R_{G4}$ is independently H or $C_{1-6}$ alkyl, alternatively $C_{1-4}$ alkyl.

In a more specific embodiment, two $R_{G4}$ attached to the same carbon atom are taken together with the carbon atom to which they are attached to form $C_{3-10}$ cycloalkylene or 3- to 10-membered heterocyclylene, alternatively $C_{3-7}$ cycloalkylene or 3- to 7-membered heterocyclylene, each of which is optionally substituted with 1, 2, or 3 $R_{4g}$.

In a more specific embodiment, $R_{4g}$ is independently H, halogen, cyano, $C_{1-6}$ alkyl, or $C_{1-6}$ haloalkyl.

In a more specific embodiment, the present disclosure provides the compound of formula (I), or a pharmaceutically acceptable salt, isotopic variant, tautomer, or stereoisomer thereof, wherein $L_b$ is independently a chemical bond or $C_{1-4}$ alkylene.

In a more specific embodiment, $R_b$ and $R'_b$ are independently H, $C_{1-6}$ alkyl, $C_{3-7}$ cycloalkyl, or 3- to 7-membered heterocyclyl, alternatively H or $C_{1-6}$ alkyl, alternatively H or $C_{1-4}$ alkyl.

In a more specific embodiment, the present disclosure provides the compound of formula (I), or a pharmaceutically acceptable salt, isotopic variant, tautomer, or stereoisomer thereof, wherein $M_1$ and $M_2$ are independently selected from —C(O)O—, —OC(O)—, —OC(O)O—, —SC(O)—, —C(O)S—, —C(O)NR—, and —NRC(O)—, alternatively —C(O)O—, —OC(O)O—, —OC(O)—, —SC(O)—, and —C(O)S—, alternatively —C(O)O—, —OC(O)—, —SC(O)—, and —C(O)S—, alternatively —C(O)O— and —OC(O)—.

In a more specific embodiment, $M_1$ and $M_2$ are independently selected from —C(O)O— and —C(O)S—, alternatively —C(O)O—.

In a more specific embodiment, one of $M_1$ and $M_2$ is —C(O)O— or —C(O)S—, alternatively —C(O)O—, and the other is —OC(O)— or —SC(O)—, alternatively —OC(O)—.

In a more specific embodiment, $M_1$ is —OC(O)— or —SC(O)—, alternatively —OC(O)—; and $M_2$ is —C(O)O— or —C(O)S—, alternatively —C(O)O—.

In a more specific embodiment, $M_1$ is —C(O)O—, and $M_2$ is —C(O)O— or —C(O)S—.

In a more specific embodiment, $M_1$ and $M_2$ are independently selected from —C(O)O—, —OC(O)—, —SC(O)—, —C(O)S—, —NHC(O)—, and —C(O)NH—.

In a more specific embodiment, $M_1$ and $M_2$ are independently selected from —C(O)O—, —OC(O)—, —C(O)S—, and —C(O)NH—, alternatively —C(O)O—, —OC(O)—, and —C(O)S—.

In a more specific embodiment, one of $M_1$ and $M_2$ is —C(O)O— or —C(O)S—, alternatively —C(O)O—, and the other is selected from —C(O)O—, —C(O)S—, —C(O)NH—, —OC(O)—, and —SC(O)—, alternatively —C(O)O—, —C(O)S—, —C(O)NH—, and —OC(O)—, alternatively —C(O)O—, —C(O)S—, —OC(O)— and —SC(O)—, alternatively —C(O)O—, —C(O)S—, and —OC(O)—.

In a more specific embodiment, one of $M_1$ and $M_2$ is —OC(O)O—, and the other is selected from —C(O)O—, —OC(O)—, —SC(O)—, and —C(O)S—, alternatively —C(O)O— and —OC(O)—.

In a more specific embodiment, $M_1$ is selected from —C(O)O—, —OC(O)—, —SC(O)—, and —C(O)S—, alternatively —C(O)O— and —OC(O)—, alternatively —C(O)O—, alternatively —OC(O)—, $M_2$ is —OC(O)O—.

In a more specific embodiment, $M_1$ is —OC(O)O—, $M_2$ is —OC(O)— or —C(O)O—, alternatively —OC(O)—.

In a more specific embodiment, $M_1$ and $M_2$ are independently selected from —C(O)O—, —C(O)S—, —OC(O)—, —SC(O)—, and —OC(O)O—, alternatively —C(O)O—, —OC(O)—, and —OC(O)O—; alternatively $M_1$ and $M_2$ are not simultaneously —OC(O)O—.

In a more specific embodiment, the present disclosure provides the compound of formula (I), or a pharmaceutically acceptable salt, isotopic variant, tautomer, or stereoisomer thereof, wherein $R_1$ and $R_2$ are independently $C_{6-14}$ alkyl, $C_{6-14}$ alkenyl, or $C_{6-14}$ alkynyl, alternatively $C_{6-14}$ alkyl, alternatively $C_{7-12}$ alkyl, alternatively $C_{8-12}$ alkyl.

In a more specific embodiment, $R_1$ and $R_2$ are independently $C_{7-12}$ alkyl, $C_{7-12}$ alkenyl, or $C_{7-12}$ alkynyl, alternatively $C_{8-12}$ alkyl, $C_{8-12}$ alkenyl, or $C_{8-12}$ alkynyl.

In a more specific embodiment, $R_1$ and $R_2$ are optionally substituted with 1, 2, 3, or 4 $R_{1s}$, alternatively optionally substituted with 1 $R_{1s}$.

In a more specific embodiment, $R_1$ and $R_2$ are independently selected from the following groups: $—(CH_2)_5CH_3$, $—(CH_2)_6CH_3$, $—(CH_2)_7CH_3$, $—(CH_2)_8CH_3$, $—(CH_2)_9CH_3$, $—(CH_2)_{10}CH_3$, $—(CH_2)_{11}CH_3$, $—CH_2—C{\equiv}C—(CH_2)_5CH_3$, $—CH_2—C{\equiv}C—(CH_2)_6CH_3$, $—(CH_2)_2—C{\equiv}C—(CH_2)_5CH_3$, $—(CH_2)_4—C{\equiv}C—(CH_2)_3CH_3$, $—CH_2—CH{=}CH—(CH_2)_5CH_3$, $—CH_2—CH{=}CH—(CH_2)_6CH_3$, $—(CH_2)_2—CH{=}CH—(CH_2)_5CH_3$, $—(CH_2)_4—CH{=}CH—(CH_2)_3CH_3$, $—(CH_2)_5—CH{=}CH—CH_2CH_3$,

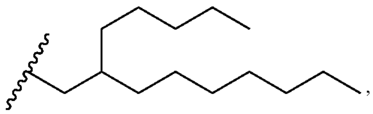
,
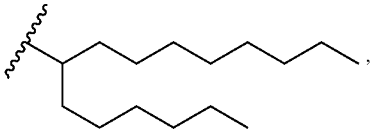
,

-continued

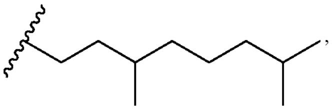,

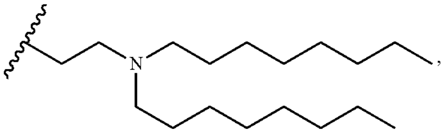,

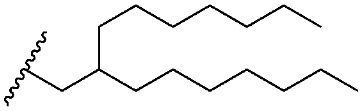,

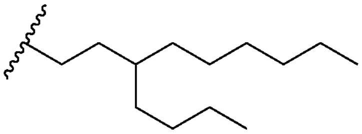,

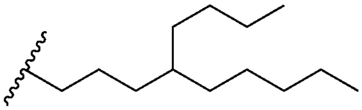,

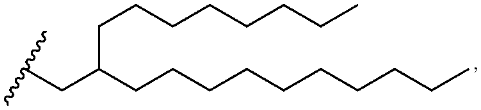,

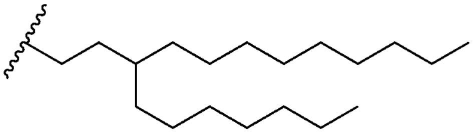,

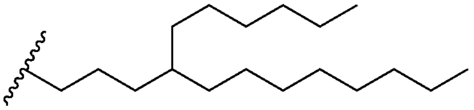,

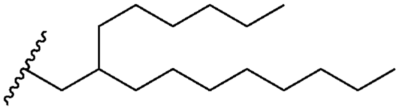,

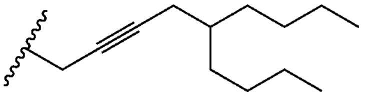,

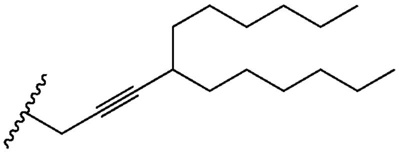,

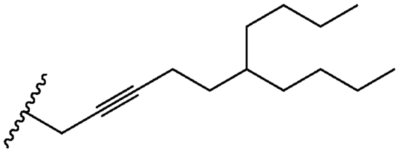,

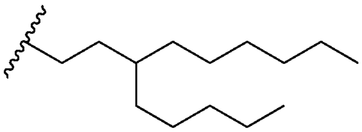,

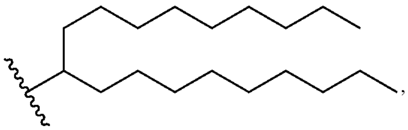,

-continued

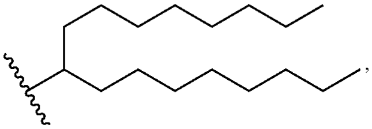,

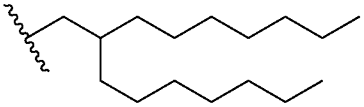,

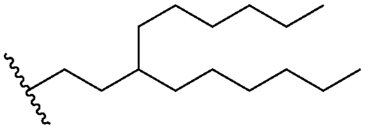,

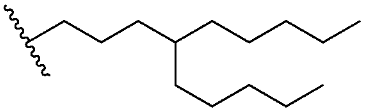,

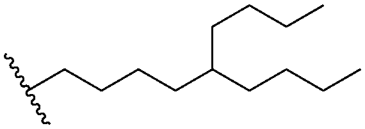,

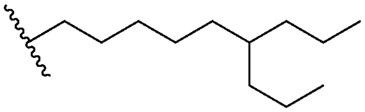,

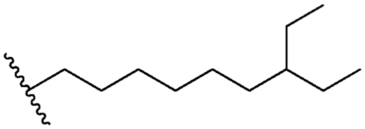,

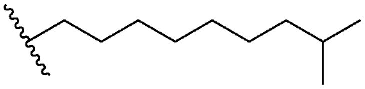,

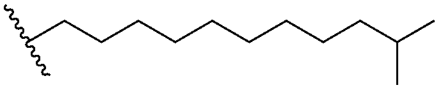, and

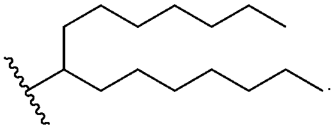.

In a more specific embodiment, $R_1$ and $R_2$ are independently selected from the following groups: $-(CH_2)_5CH_3$, $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$, $-CH_2-C{\equiv}C-(CH_2)_5CH_3$, $-CH_2-C{\equiv}C-(CH_2)_6CH_3$, $-(CH_2)_2-C{\equiv}C-(CH_2)_5CH_3$, $-(CH_2)_2-C{\equiv}C-(CH_2)_4CH_3$, $-(CH_2)_3-C{\equiv}C-(CH_2)_3CH_3$, $-(CH_2)_4-C{\equiv}C-(CH_2)_3CH_3$, $-CH_2-CH{=}CH-(CH_2)_5CH_3$, $-CH_2-CH{=}CH-(CH_2)_6CH_3$, $-(CH_2)_2-CH{=}CH-(CH_2)_5CH_3$, $-(CH_2)_4-CH{=}CH-(CH_2)_3CH_3$, $-(CH_2)_5-CH{=}CH-CH_2CH_3$

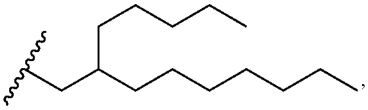,

-continued
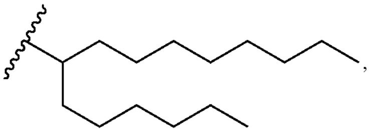
,
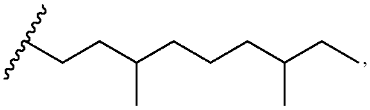
,
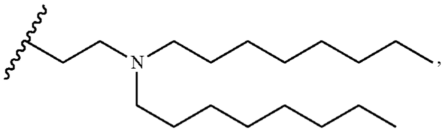
,
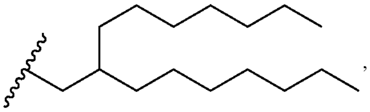
,
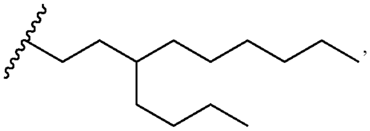
,
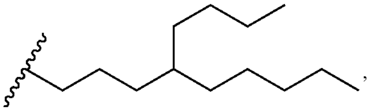
,
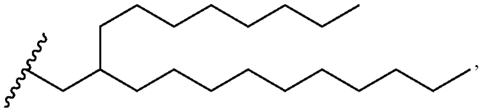
,
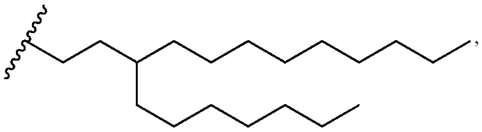
,
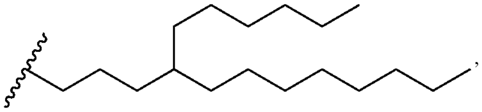
,
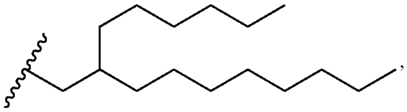
,
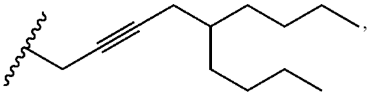
,
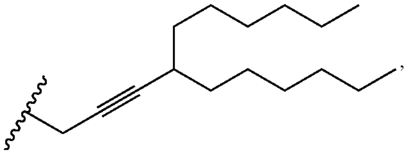
,
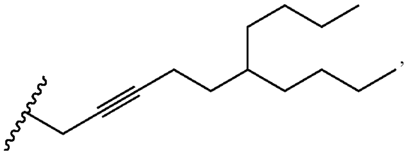
,
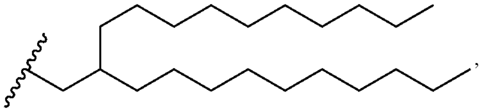
,
-continued
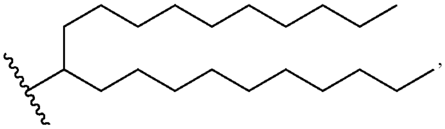
,
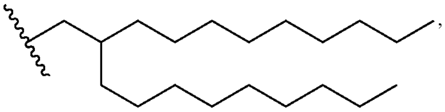
,
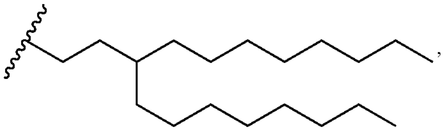
,
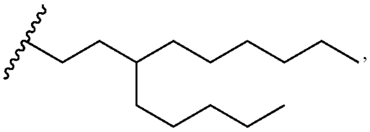
,
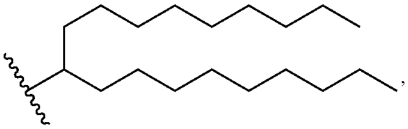
,
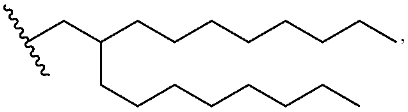
,
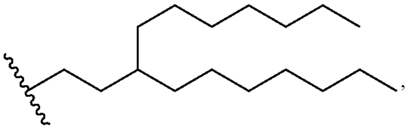
,
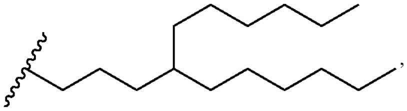
,
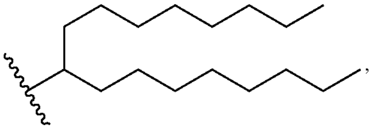
,
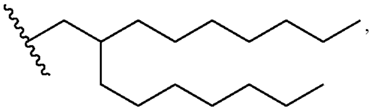
,
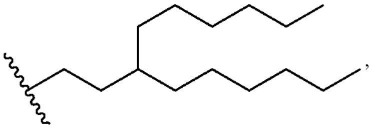
,
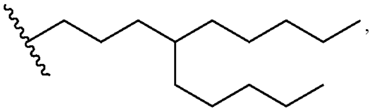
,
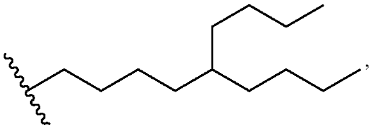
,
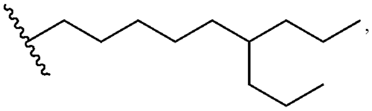
, -continued

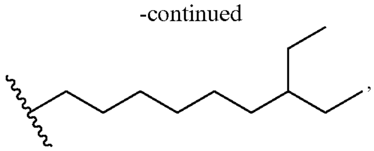

,

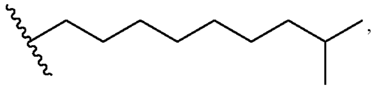

,

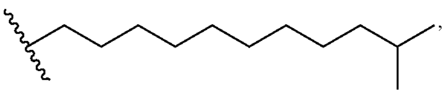

,

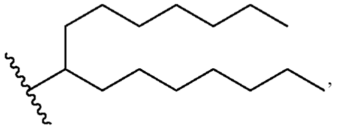

, and

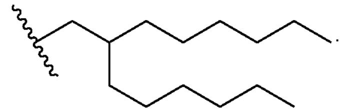

.

In a more specific embodiment, the present disclosure provides the compound of formula (I), or a pharmaceutically acceptable salt, isotopic variant, tautomer, or stereoisomer thereof, wherein $R_{1s}$ is independently H, $C_{1-14}$ alkyl, -$L_c$-$OR_c$, or -$L_c$-$NR_cR'_c$, alternatively H or $C_{1-14}$ alkyl, alternatively H or $C_{1-10}$ alkyl, alternatively H or $C_{1-9}$ alkyl, alternatively H or $C_{1-6}$ alkyl, alternatively H or $C_{1-14}$ alky.

In a more specific embodiment, the present disclosure provides the compound of formula (I), or a pharmaceutically acceptable salt, isotopic variant, tautomer, or stereoisomer thereof, wherein R and R' are each independently H or $C_{1-20}$ alkyl, alternatively H or $C_{1-14}$ alkyl, alternatively H or $C_{1-9}$ alkyl, alternatively H or $C_{1-6}$ alkyl; alternatively, R is H.

In a more specific embodiment, the present disclosure provides the compound of formula (I), or a pharmaceutically acceptable salt, isotopic variant, tautomer, or stereoisomer thereof, wherein $L_c$ is independently a chemical bond or $C_{1-14}$ alkylene, alternatively a chemical bond or $C_{1-10}$ alkylene, alternatively a chemical bond or $C_{1-6}$ alkylene.

In a more specific embodiment, $R_c$ and $R'_c$ are independently H or $C_{1-14}$ alkyl, alternatively H or $C_{1-10}$ alkyl, alternatively H or $C_{1-6}$ alkyl.

In a more specific embodiment, the present disclosure provides the compound of formula (I), or a pharmaceutically acceptable salt, isotopic variant, tautomer, or stereoisomer thereof, wherein $R_3$ is CN, —$OR_g$, or —$NR_gR'_g$, alternatively —$OR_g$ or —$NR_gR'_g$, alternatively —$OR_g$, alternatively —OH.

In a more specific embodiment, $R_3$ is OH or —$N(CH_3)_2$

In a more specific embodiment, $R_g$ and $R'_g$ are independently H, $C_{1-6}$ alkyl, $C_{3-7}$ cycloalkyl, or 3- to 7-membered heterocyclyl, alternatively H or $C_{1-6}$ alkyl, alternatively H or $C_{1-4}$ alkyl, alternatively H or methyl.

In a more specific embodiment, the present disclosure provides the compound of formula (I), or a pharmaceutically acceptable salt, isotopic variant, tautomer, or stereoisomer thereof, wherein $R_4$ and $R_5$ are independently $C_{1-6}$ alkyl, alternatively $C_{1-3}$ alkyl, alternatively methyl.

In a more specific embodiment, $R_4$ and $R_5$ are optionally substituted with 1, 2, or 3 $R_{4s}$.

In a more specific embodiment, $R_4$ and $R_5$ are taken together with the carbon atom to which they are attached to form $C_{3-10}$ cycloalkylene or 3- to 10-membered heterocyclylene, alternatively $C_{3-6}$ cycloalkylene or 3- to 6-membered heterocyclylene, alternatively $C_{3-6}$ cycloalkylene (e.g., cyclopropylene, cyclobutylene, cyclopentylene, or cyclohexylene), alternatively $C_{3-5}$ cycloalkylene, alternatively cyclopropylene or cyclopentylene, alternatively cyclopropylene.

In a more specific embodiment, a ring formed by $R_4$ and $R_5$ with the carbon atom to which they are attached to is optionally substituted with 1, 2, or 3 $R_{4s}$.

In a more specific embodiment, the present disclosure provides the compound of formula (I), or a pharmaceutically acceptable salt, isotopic variant, tautomer, or stereoisomer thereof, wherein $R_{4s}$ is independently H, halogen, cyano, $C_{1-6}$ alkyl, $C_{1-6}$ haloalkyl, —La—$OR_d$, —La—$SR_d$, or -$L_d$-$NR_dR'_d$, alternatively H, halogen, cyano, $C_{1-6}$ alkyl, or $C_{1-6}$ haloalkyl, alternatively H, $C_{1-3}$ alkyl, or $C_{1-3}$ haloalkyl.

In a more specific embodiment, the present disclosure provides the compound of formula (I), or a pharmaceutically acceptable salt, isotopic variant, tautomer, or stereoisomer thereof, wherein La is independently a chemical bond or $C_{1-6}$ alkylene, alternatively a chemical bond or $C_{1-3}$ alkylene.

In a more specific embodiment, $R_d$ and $R'_d$ are independently H, $C_{1-6}$ alkyl, $C_{3-10}$ cycloalkyl, or 3- to 10-membered heterocyclyl, alternatively H or $C_{1-6}$ alkyl.

In a more specific embodiment, the present disclosure provides the compound of formula (I), or a pharmaceutically acceptable salt, isotopic variant, tautomer, or stereoisomer thereof, wherein $L_e$ is independently a chemical bond or $C_{1-6}$ alkylene, alternatively a chemical bond or $C_{1-4}$ alkylene.

In a more specific embodiment, $R_e$ and $R'_e$ are independently H, $C_{1-6}$ alkyl, $C_{3-10}$ cycloalkyl, or 3- to 10-membered heterocyclyl, alternatively H or $C_{1-6}$ alkyl, alternatively H or $C_{1-4}$ alkyl.

In a more specific embodiment, the present disclosure provides the compound of formula (I), or a pharmaceutically acceptable salt, isotopic variant, tautomer, or stereoisomer thereof, wherein Q is a chemical bond, —OC(O)—, or —SC(O)—, alternatively a chemical bond or —SC(O)—.

In a more specific embodiment, when Q is phenylene or pyridinylene, Q is optionally substituted with 1, 2, or 3 R*.

In a more specific embodiment, R* is independently H, halogen, cyano, $C_{1-6}$ alkyl, or $C_{1-6}$ haloalkyl.

In a more specific embodiment, $L_f$ is independently a chemical bond or $C_{1-6}$ alkylene, alternatively a chemical bond or $C_{1-4}$ alkylene.

In a more specific embodiment, $R_f$ and $R'_f$ are independently H, $C_{1-6}$ alkyl, $C_{3-10}$ cycloalkyl, or 3- to 10-membered heterocyclyl, alternatively H or $C_{1-6}$ alkyl, alternatively H or $C_{1-4}$ alkyl.

In a more specific embodiment, the present disclosure provides the compound of formula (I), or a pharmaceutically acceptable salt, isotopic variant, tautomer, or stereoisomer thereof, which has a structure of formula (II) or formula (III):

(II)

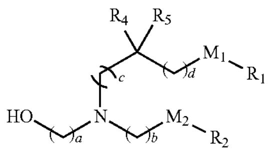

or

-continued (III)

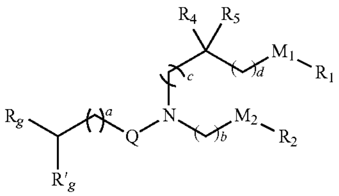

wherein a=1, 2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9;

the other groups are as defined herein.

In a more specific embodiment, the present disclosure provides the compound of formula (II) or formula (III), or a pharmaceutically acceptable salt, isotopic variant, tautomer, or stereoisomer thereof, (II)

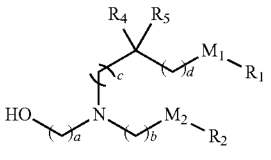

or (III)

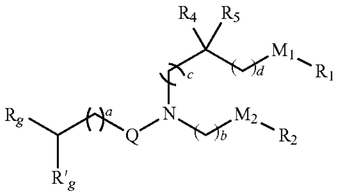

wherein, the substitution site of $R_{1s}$ on $R_1$ or $R_2$ is separated from $M_1$ or $M_2$ by 0-10 carbon atoms, alternatively 0-6 carbon atoms, alternatively 0-4 carbon atoms, alternatively 0-2 carbon atoms, alternatively 0 carbon atom.

In a more specific embodiment, the substitution site of $R_{1s}$ on $R_2$ is separated from $M_2$ by 1-10 carbon atoms, alternatively 1-6 carbon atoms, alternatively 1-4 carbon atoms, alternatively 1-2 carbon atoms; alternatively 2-10 carbon atoms, alternatively 2-6 carbon atoms, alternatively 2-4 carbon atoms.

In a more specific embodiment, $R_1$ is not substituted with $R_{1s}$, and the substitution site of $R_{1s}$ on $R_2$ is separated from $M_2$ by 0-10 carbon atoms, alternatively 1-10 carbon atoms, alternatively 1-6 carbon atoms, alternatively 1-4 carbon atoms, alternatively 1-2 carbon atoms; alternatively 2-10 carbon atoms, alternatively 2-6 carbon atoms, alternatively 2-4 carbon atoms.

In a more specific embodiment, $R_1$ is substituted with $R_{1s}$, and $R_2$ is not substituted with $R_{1s}$.

In a more specific embodiment, $R_4$ and $R_5$ are not taken together with the carbon atom to which they are attached to form a ring.

In a more specific embodiment, d is not 0.

In a more specific embodiment, the present disclosure provides the compound of formula (II), or a pharmaceutically acceptable salt, isotopic variant, tautomer, or stereoisomer thereof, (II)

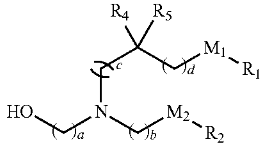

wherein a=2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9; alternatively c+d=4, 5, or 6;

$M_1$ and $M_2$ are independently selected from —C(O)O—, —OC(O)—, —SC(O)—, and —C(O)S—;

alternatively, $M_1$ and $M_2$ are independently selected from —C(O)O— and —C(O)S—; alternatively, one of $M_1$ and $M_2$ is —C(O)O— or —C(O)S—, and the other is —OC(O)— or —SC(O)—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, $-L_c-OR_c$, or $-L_c-NR_cR'_c$, alternatively H or $C_{1-14}$alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-6}$ alkyl;

or, $R_4$ and $R_5$ are taken together with the carbon atom to which they are attached to form $C_{3-6}$ cycloalkylene or 3- to 6-membered heterocyclylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, 7, 8, or 9; alternatively b=5, 6, 7, or 8; alternatively b=5, 6, or 7;

c=2, 3, 4, 5, or 6;

d=0, 1, 2, 3, or 4;

c+d=5 or 6;

$M_1$ and $M_2$ are independently —C(O)O— or —OC(O)—; alternatively, $M_1$ and $M_2$ are —C(O)O—; alternatively, one of $M_1$ and $M_2$ is —C(O)O—, and the other is —OC(O)—;

$R_1$ and $R_2$ are independently $C_{7-12}$ alkyl, alternatively $C_{8-12}$ alkyl, which is optionally substituted with 1 $R_{1s}$;

$R_{1s}$ is independently H or $C_{1-10}$ alkyl, alternatively H or $C_{1-9}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene, alternatively $C_{3-5}$ cycloalkylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, 7, 8, or 9; alternatively b=5, 6, 7, or 8; alternatively b=5 or 7;

c=2, 3, 4, 5, or 6;

d=0, 1, 2, 3, or 4; alternatively d=0, 1, 2, or 4;

c+d=5 or 6; alternatively c+d=6;

$M_1$ and $M_2$ are —C(O)O—;

or, one of $M_1$ and $M_2$ is —C(O)O—, and the other is —OC(O)—;

$R_1$ and $R_2$ are independently selected from: $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$,
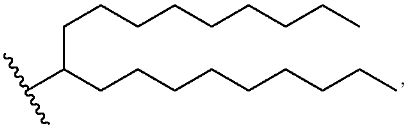,
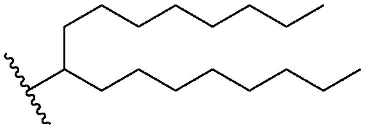,
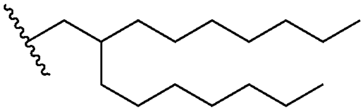,
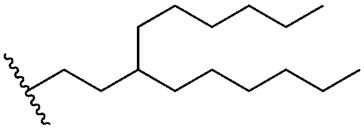,
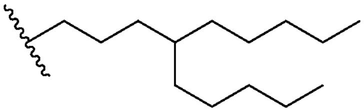,
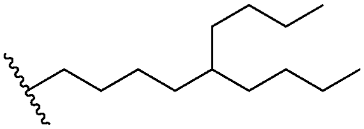,
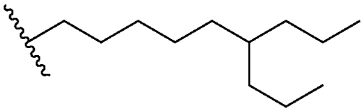,
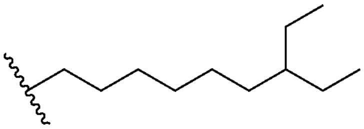,
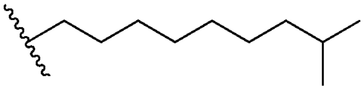,
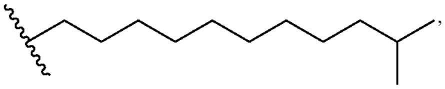, and
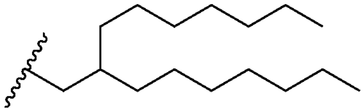,
alternatively: $-(CH_2)_7CH_3$, $-(CH_2)_5CH_3$, $-(CH_2)_9CH_3$, $-(CH_2)_{10}CH_3$, $-(CH_2)_{11}CH_3$,
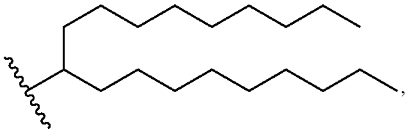,
-continued
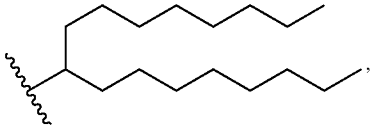,
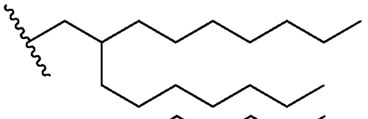,
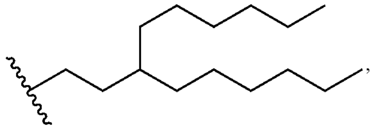,
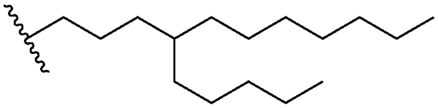,
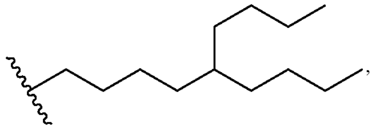,
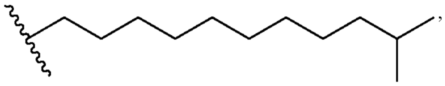 [SMILES: *CCCCCCCCCC(C)C], and
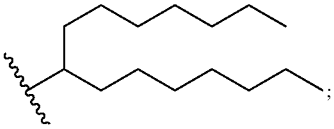;
alternatively: $-(CH_2)_8CH_3$, $-(CH_2)_9CH_3$, $-(CH_2)_{10}CH_3$, $-(CH_2)_{11}CH_3$,
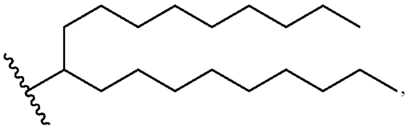,
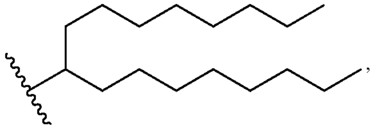,
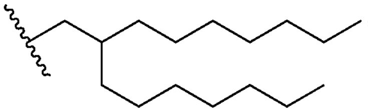,
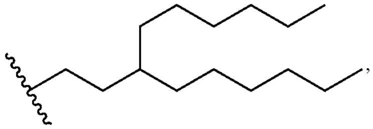,
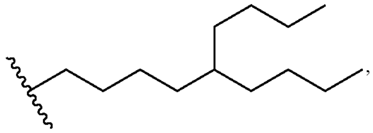,
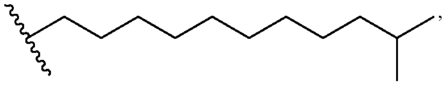 [SMILES: *CCCCCCCCCC(C)C], and -continued

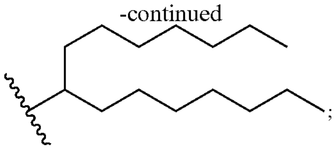

;

$R_4$ and $R_5$ are methyl;

or, $R_4$ and $R_5$ are taken together with the carbon atom to which they are attached to form cyclopropylene, cyclobutylene, cyclopentylene, or cyclohexylene, alternatively cyclopropylene or cyclopentylene, alternatively cyclopropylene.

In a more specific embodiment, only one of $R_1$ and $R_2$ is substituted.

In a more specific embodiment, the present disclosure provides the compound of formula (II), or a pharmaceutically acceptable salt, isotopic variant, tautomer, or stereoisomer thereof, wherein a=2;

b=5;

c=2, 3, 4, 5, or 6; alternatively c=6;

d=0, 1, 2, 3, or 4; alternatively d=0;

c+d=5 or 6, alternatively 6;

$M_1$ and $M_2$ are —C(O)O—;

$R_1$ is $C_{7-12}$ alkyl, alternatively $C_{8-12}$ alkyl, alternatively $C_{8-9}$ alkyl, or alternatively $C_9$ alkyl, which is optionally substituted with 1 $R_{1s}$;

$R_{1s}$ is independently H or $C_{1-10}$ alkyl, alternatively H or $C_{1-9}$ alkyl, alternatively $C_{5-8}$ alkyl, alternatively $C_{6-8}$ alkyl, alternatively $C_{7-8}$ alkyl;

$R_2$ is $C_{7-11}$ linear alkyl, alternatively $C_{10-11}$ linear alkyl, alternatively $C_{11}$ linear alkyl, which is optionally substituted with 1 $C_{1-3}$ alkyl, alternatively optionally substituted with 1 methyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, $R_1$ is

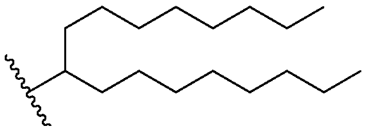

,

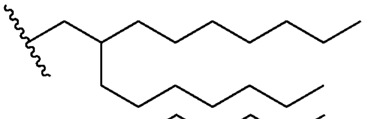

,

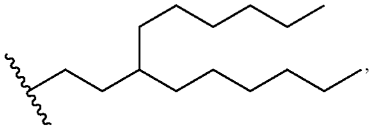

,

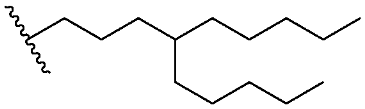

, or

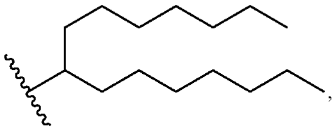

, alternatively

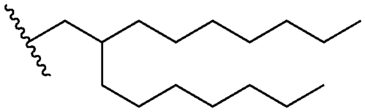

or

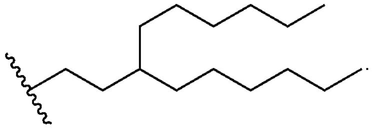

.

In a more specific embodiment, $R_1$ is

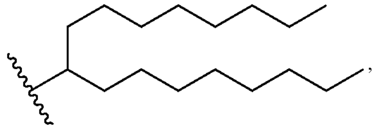

,

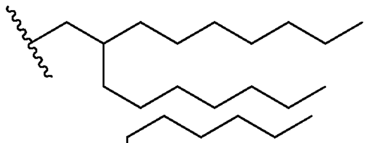

,

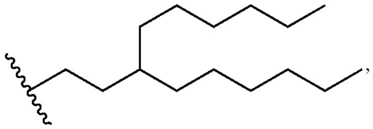

, or

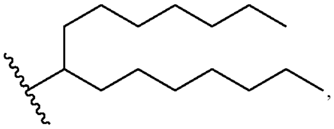

, alternatively

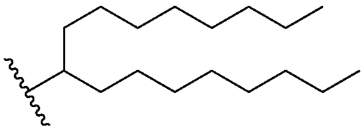

or

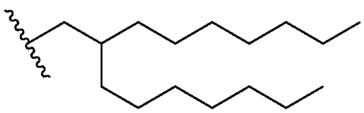

.

In a more specific embodiment, $R_2$ is $—(CH_2)_9CH_3$, $—(CH_2)_{10}CH_3$, or

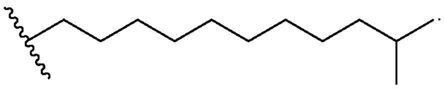

.

In a more specific embodiment, the present disclosure provides the compound of formula (II), or a pharmaceutically acceptable salt, isotopic variant, tautomer, or stereoisomer thereof, wherein a=2, 3, or 4; alternatively a=2;

b=7;

c=2, 3, 4, 5, or 6; alternatively c=2, 3, or 4; alternatively c=2;

d=0, 1, 2, 3, or 4; alternatively d=2, 3, or 4; alternatively d=4;

c+d=5 or 6, alternatively 6;

$M_1$ and $M_2$ are —C(O)O—;

$R_1$ is $C_{8-11}$ linear alkyl, alternatively $C_{9-10}$ linear alkyl, alternatively $C_9$ linear alkyl;

$R_2$ is $C_{7-12}$ alkyl, alternatively $C_{8-12}$ alkyl, alternatively $C_{9-10}$ alkyl, which is optionally substituted with 1 $R_{1s}$;

$R_{1s}$ is independently H or $C_{1-10}$ alkyl, alternatively H or $C_{1-9}$ alkyl, alternatively $C_{6-9}$ alkyl, alternatively $C_{7-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, $R_2$ is

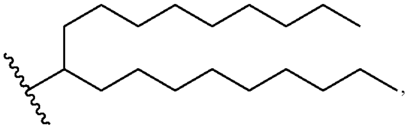

,

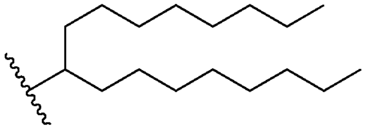

,

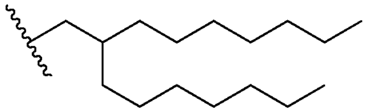

, or

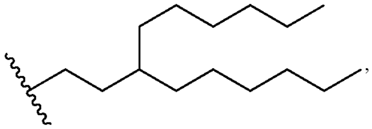

, alternatively

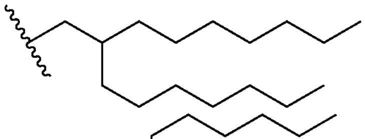

or

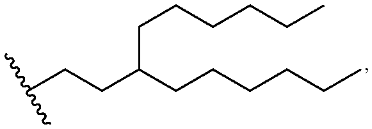

, alternatively

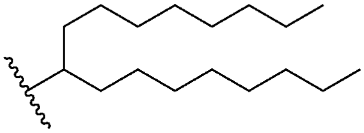

and

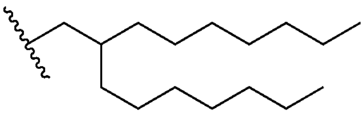

.

In a more specific embodiment, the present disclosure provides the compound of formula (II), or a pharmaceutically acceptable salt, isotopic variant, tautomer, or stereoisomer thereof, wherein a=2;

b=7;

c=3 or 4; alternatively c=4;

d=2;

$M_1$ and $M_2$ are —C(O)O—;

$R_1$ is $C_{7-12}$ alkyl, alternatively $C_{8-12}$ alkyl, alternatively $C_{8-10}$ alkyl, which is optionally substituted with 1 $R_{1s}$;

$R_{1s}$ is independently H or $C_{1-10}$ alkyl, alternatively H or $C_{1-9}$ alkyl;

$R_2$ is $C_{7-11}$ linear alkyl, alternatively $C_9$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, the present disclosure provides the compound of formula (II), or a pharmaceutically acceptable salt, isotopic variant, tautomer, or stereoisomer thereof, wherein a=2, 3, or 4; alternatively a=2 or 4;

b=6 or 7; alternatively b=7;

c=2, 3, 4, 5, or 6; alternatively c=5 or 6;

d=0, 1, 2, 3, or 4; alternatively d=0 or 1;

c+d=5 or 6, alternatively 6;

$M_1$ is —OC(O)—; and $M_2$ is —C(O)O—;

$R_1$ is $C_{7-11}$ linear alkyl, alternatively $C_{9-10}$ linear alkyl;

$R_2$ is $C_{7-12}$ alkyl, alternatively $C_{8-12}$ alkyl, alternatively $C_{9-10}$ linear alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, when a=4, $R_4$ and $R_5$ are not taken together with the carbon atom to which they are attached to form a ring; alternatively, $R_{1s}$ is independently $C_{8-9}$ alkyl.

In a more specific embodiment, $R_2$ is, or

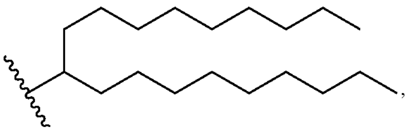

,

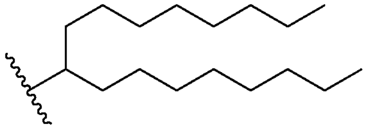

, or

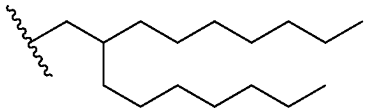

.

In a more specific embodiment, the present disclosure provides the compound of formula (II), or a pharmaceutically acceptable salt, isotopic variant, tautomer, or stereoisomer thereof, (II)

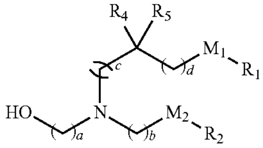

wherein a=2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9; alternatively c+d=4, 5, 6, or 7;

$M_1$ and $M_2$ are independently selected from —C(O)O—, —OC(O)—, —SC(O)—, —C(O)S—, —NHC(O)—, and —C(O)NH—, alternatively —C(O)O—, —OC(O)—, —SC(O)—, and —C(O)S—; alternatively, one of $M_1$ and $M_2$ is —C(O)O— or —C(O)S—, and the other is —C(O)O—, —C(O)S—, —C(O)NH—, —OC(O)— or —SC(O)—, alternatively —C(O)O—, —C(O)S—, —OC(O)— or —SC(O)—;

$R_1$ and $R_2$ are independently $C_{6-14}$ alkyl, $C_{6-14}$ alkenyl, or $C_{6-14}$ alkynyl, each of which is optionally substituted with 1, 2, 3, or 4 $R_{1s}$;

$R_{1s}$ is independently H, $C_{1-14}$ alkyl, $-L_c-OR$, or $-L_c-NR_cR'_c$, alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-6}$ alkyl;

or, $R_4$ and $R_5$ are taken together with the carbon atom to which they are attached to form $C_{3-6}$ cycloalkylene or 3- to 6-membered heterocyclylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, 7, 8, or 9, alternatively b=5, 6, 7, or 8, alternatively b=5, 6, or 7;

c=2, 3, 4, 5, or 6;

d=0, 1, 2, 3, or 4;

c+d=5, 6, or 7;

$M_1$ and $M_2$ are independently —C(O)O—, —OC(O)—, —C(O)S— or —C(O)NH—, alternatively —C(O)O—, —OC(O)—, or —C(O)S—; alternatively, one of $M_1$ and $M_2$ is —C(O)O—, and the other is —C(O)O—, —C(O)S—, —C(O)NH—, or —OC(O)—, alternatively —C(O)O—, —C(O)S—, or —OC(O)—;

$R_1$ and $R_2$ are independently $C_{7-12}$ alkyl, $C_{7-12}$ alkenyl, or $C_{7-12}$ alkynyl, alternatively $C_{8-12}$ alkyl, $C_{8-12}$ alkenyl, or $C_{8-12}$ alkynyl, each of which is optionally substituted with 1 $R_{1s}$;

$R_{1s}$ is independently H or $C_{1-10}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene, alternatively $C_{3-5}$ cycloalkylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, 7, 8, or 9; alternatively b=5, 6, 7, or 8; alternatively b=5 or 7;

c=2, 3, 4, 5, or 6;

d=0, 1, 2, 3, or 4;

c+d=5, 6, or 7; alternatively c+d=6;

one of $M_1$ and $M_2$ is —C(O)O—, and the other is —C(O)O—, —C(O)S—, —C(O)NH—, or —OC(O)—, alternatively —C(O)O—, —C(O)S—, or —OC(O)—;

$R_1$ and $R_2$ are independently selected from: $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$, $-CH_2-CH=CH-(CH_2)_5CH_3$, $-CH_2-C\equiv C-(CH_2)_5CH_3$, $-(CH_2)_2-C\equiv C-(CH_2)_4CH_3$, $-(CH_2)_3-C\equiv C-(CH_2)_3CH_3$

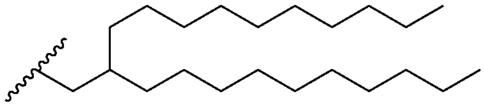
,
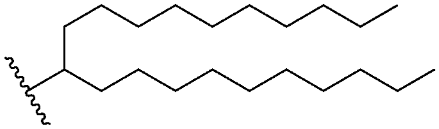
,
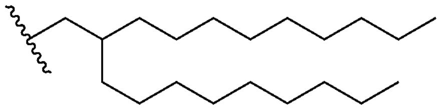
,
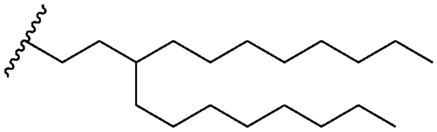
,
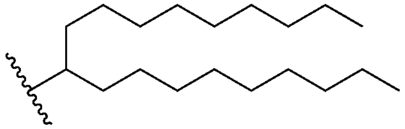
,
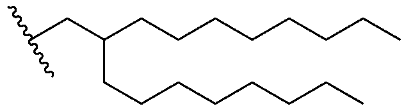
,
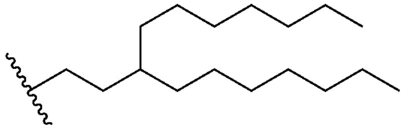
,
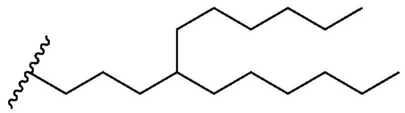
,
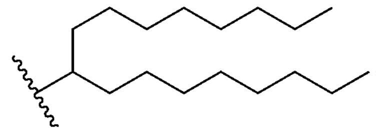
,
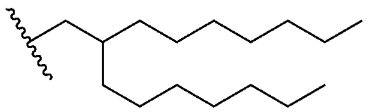
,
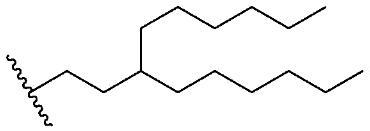
, -continued
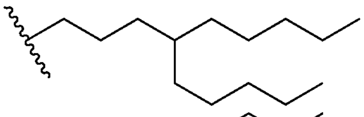,
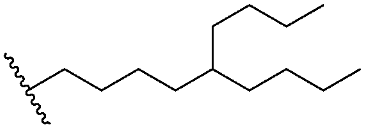,
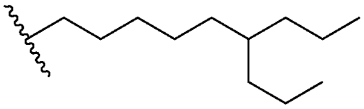,
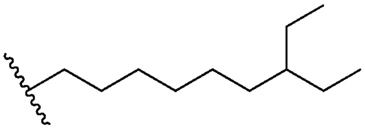,
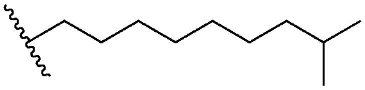,
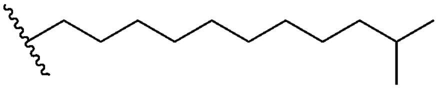,
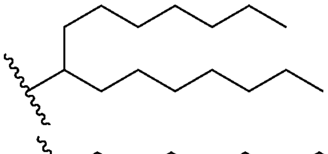, and
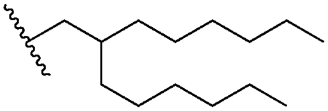,
alternatively: —$(CH_2)_7CH_3$, —$(CH_2)_8CH_3$, —$(CH_2)_9CH_3$, —$(CH_2)_{10}CH_3$, —$(CH_2)_{11}CH_3$, —$CH_2$—CH═CH—$(CH_2)_5$ $CH_3$, —$CH_2$—C—C—$(CH_2)_5CH_3$, —$(CH_2)_2$—C—C—$(CH_2)_4CH_3$, —$(CH_2)_3$—C—C—$(CH_2)_3CH_3$,
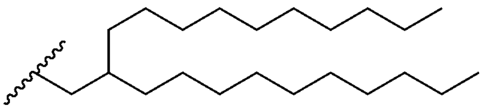,
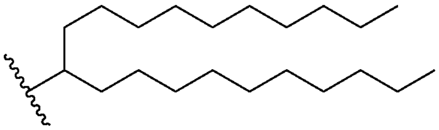,
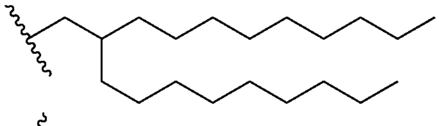,
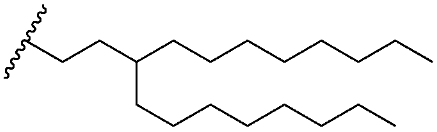,
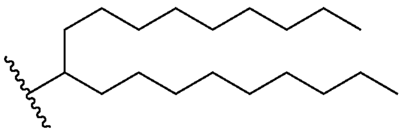,
-continued
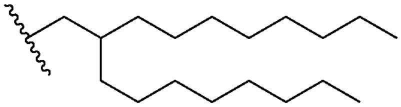,
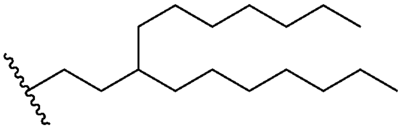,
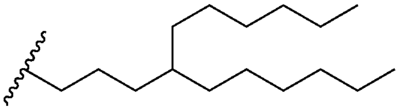,
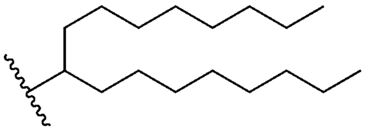,
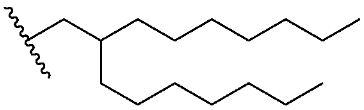,
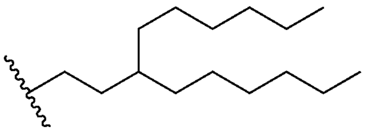,
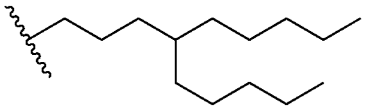,
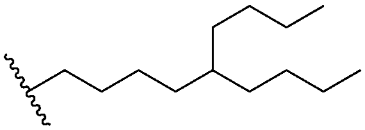,
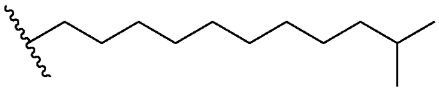,
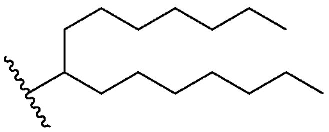, and
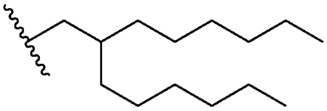;
alternatively:—$(CH_2)_8CH_3$, —$(CH_2)_9CH_3$, —$(CH_2)_{10}CH_3$, —$(CH_2)_{11}CH_3$, —$CH_2$—CH═CH—$(CH_2)_5CH_3$, —$CH_2$—C═C—$(CH_2)_5CH_3$, —$(CH_2)_2$—C—C—$(CH_2)_4CH_3$, —$(CH_2)_3$—C—C—$(CH_2)_3CH_3$,
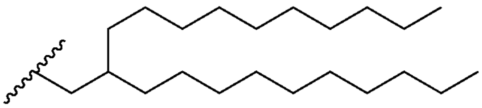,
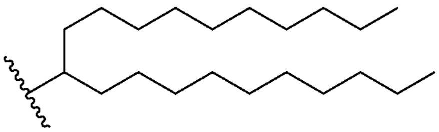, -continued

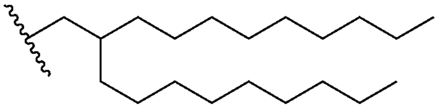

,

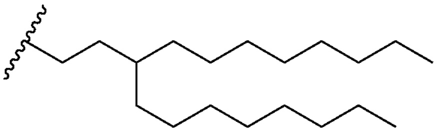

,

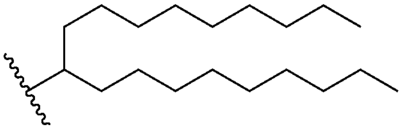

,

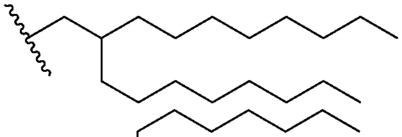

,

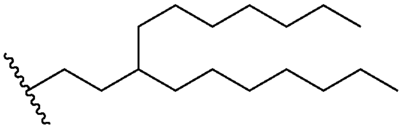

,

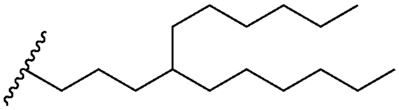

,

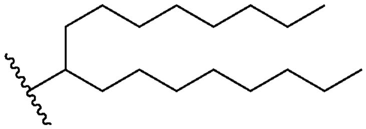

,

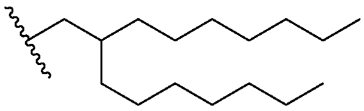

,

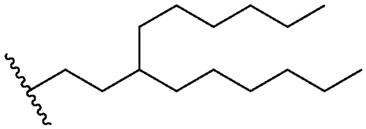

,

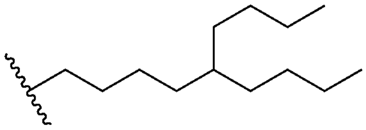

,

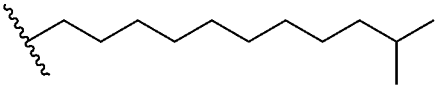

,

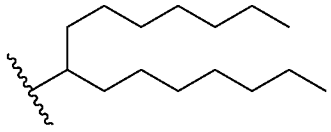

, and

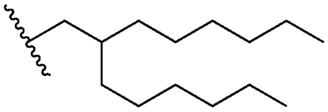

;

$R_4$ and $R_5$ are methyl;

or, $R_4$ and $R_5$ are taken together with the carbon atom to which they are attached to form cyclopropylene, cyclobutylene, cyclopentylene, or cyclohexylene, alternatively cyclopropylene or cyclopentylene, alternatively cyclopropylene;

In a more specific embodiment, only one of $R_1$ and $R_2$ is substituted.

In a more specific embodiment, the present disclosure provides the compound of formula (II), or a pharmaceutically acceptable salt, isotopic variant, tautomer, or stereoisomer thereof, wherein a=2;

b=5;

c=5 or 6; alternatively c=6;

d=0 or 1; alternatively d=0;

c+d=5 or 6, alternatively 6;

$M_1$ is —C(O)O—, and $M_2$ is —C(O)O— or —C(O)S—; alternatively $M_1$ and $M_2$ are —C(O)O—;

$R_1$ is $C_{7-12}$ alkyl, alternatively $C_{8-12}$ alkyl, alternatively $C_{8-9}$ alkyl, or alternatively $C_9$ alkyl, which is optionally substituted with 1 $R_{1s}$;

$R_{1s}$ is independently H or $C_{1-10}$ alkyl, alternatively H or $C_{1-9}$ alkyl, alternatively $C_{6-8}$ alkyl, alternatively $C_{7-8}$ alkyl;

$R_2$ is $C_{7-11}$ linear alkyl, alternatively $C_{10-11}$ linear alkyl, alternatively $C_{11}$ linear alkyl, which is optionally substituted with 1 $C_{1-3}$ alkyl, alternatively optionally substituted with 1 methyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

In a more specific embodiment, $R_1$ is

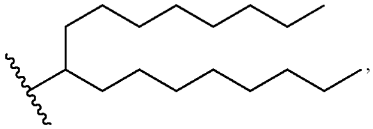

,

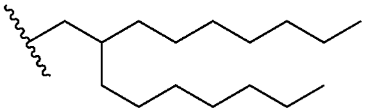

,

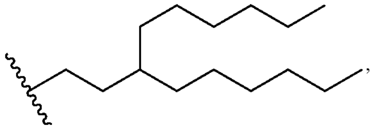

,

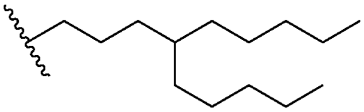

, or

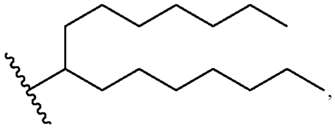

, alternatively

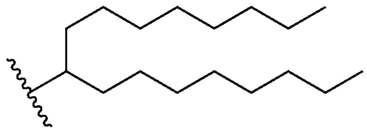

or

-continued

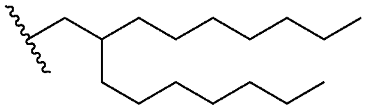

;

In a more specific embodiment, $R_2$ is $—(CH_2)_9CH_3$, $—(CH_2)_{10}CH_3$, or

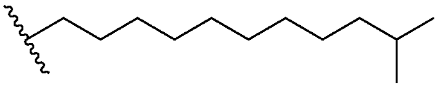

.

In a more specific embodiment, the present disclosure provides the compound of formula (II), or a pharmaceutically acceptable salt, isotopic variant, tautomer, or stereoisomer thereof, wherein a=2, 3, or 4; alternatively a=2;

b=5, 6, or 7; alternatively b=7;

c=2, 3, 4, 5, or 6; alternatively c=2, 3, or 4; alternatively c=2;

d=0, 1, 2, 3, or 4; alternatively d=2, 3, or 4; alternatively d=4;

c+d=5 or 6, alternatively 6;

$M_1$ and $M_2$ are —C(O)O—;

$R_1$ and $R_2$ are independently $C_{7-12}$ alkyl, alternatively $C_{8-12}$ alkyl, alternatively $C_{9-11}$ alkyl, alternatively $C_{9-10}$ alkyl, which is optionally substituted with 1 $R_{1s}$; and only one of $R_1$ and $R_2$ is substituted;

$R_{1s}$ is independently H or $C_{1-10}$ alkyl, alternatively $C_{6-10}$ alkyl, alternatively $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring;

In a more specific embodiment, $R_1$ is $C_{8-12}$ linear alkyl, alternatively $C_{9-11}$ linear alkyl, alternatively $C_{9-10}$ linear alkyl;

$R_2$ is $C_{7-12}$ alkyl, alternatively $C_{8-12}$ alkyl, alternatively $C_{9-11}$ alkyl, alternatively $C_{9-10}$ alkyl, which is optionally substituted with 1 $R_{1s}$; when $R_2$ is $C_{10}$ linear alkyl, $R_{1s}$ is $C_{9-10}$ alkyl, alternatively $C_9$ alkyl.

In a more specific embodiment, $R_2$ is

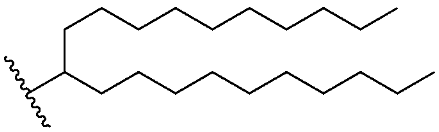

,

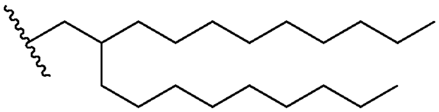

,

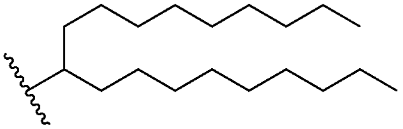

,

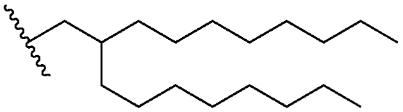

,

-continued

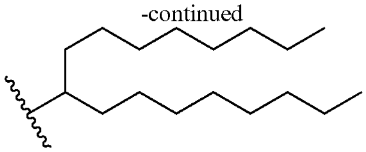

,

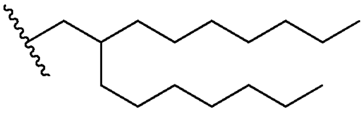

, or

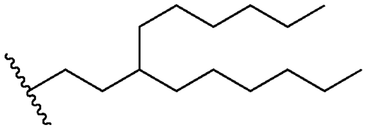

, or alternatively

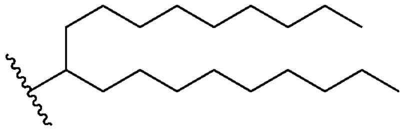

,

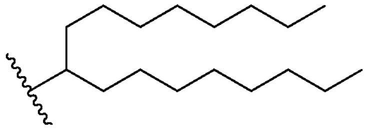

, or

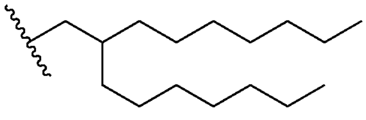

.

In a more specific embodiment, the present disclosure provides the compound of formula (II), or a pharmaceutically acceptable salt, isotopic variant, tautomer, or stereoisomer thereof, wherein a=2, 3, or 4;

b=6;

c=4, 5, or 6; alternatively c=5 or 6; alternatively c=5;

d=1 or 2; alternatively d=1;

c+d=6, 7, or 8; alternatively 6 or 7; alternatively 6;

$M_1$ is —OC(O)—; $M_2$ is —C(O)O—;

$R_1$ is $C_{7-12}$ linear alkyl, alternatively $C_{8-12}$ linear alkyl, alternatively $C_{9-11}$ linear alkyl;

$R_2$ is $C_{7-12}$ alkyl, alternatively $C_{8-12}$ alkyl, alternatively $C_{9-12}$ alkyl, which is optionally substituted with 1 $R_{1s}$;

$R_{1s}$ is independently $C_{7-11}$ alkyl, alternatively $C_{7-10}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

provided that, when c=4, a=2 or 3.

In a more specific embodiment, $R_2$ is

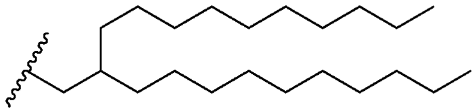

,

-continued

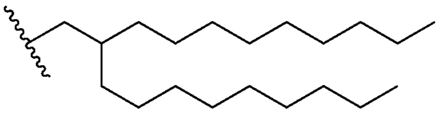

,

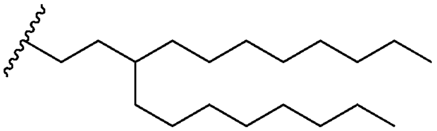

,

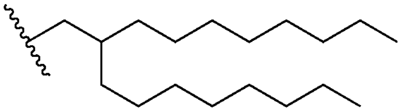

,

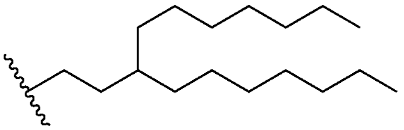

, or

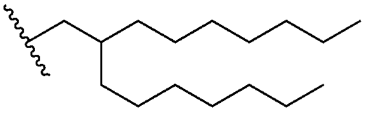

.

In a more specific embodiment, a=2 or 4; b=6; c=5 or 6, alternatively c=5; d=1;

$R_1$ is $C_{8-9}$ linear alkyl, alternatively $C_9$ linear alkyl;

$R_2$ is $C_{9-10}$ alkyl, alternatively $C_{10}$ alkyl, which is optionally substituted with 1 $R_{1s}$;

$R_{1s}$ is independently $C_{7-8}$ alkyl;

$R_4$ and $R_5$ are independently $C_{1-3}$ alkyl, alternatively methyl.

In a more specific embodiment, a=2, 3 or 4, alternatively 2 or 4; b=6; c=5; d=2;

$R_1$ is $C_{9-10}$ linear alkyl, alternatively $C_9$ linear alkyl;

$R_2$ is $C_{9-11}$ alkyl, which is optionally substituted with 1 $R_{1s}$;

$R_{1s}$ is independently $C_{7-9}$ alkyl, $R_4$ and $R_5$ are independently $C_{1-3}$ alkyl, alternatively methyl.

In a more specific embodiment, the present disclosure provides the compound of formula (II), or a pharmaceutically acceptable salt, isotopic variant, tautomer, or stereoisomer thereof, wherein a=2, 3, or 4; alternatively a=2 or 4;

b=7;

c=5 or 6; alternatively c=5;

d=0 or 1; alternatively d=1;

c+d=5 or 6, alternatively 6;

$M_1$ is —OC(O)—; $M_2$ is —C(O)O—;

$R_1$ is $C_{8-11}$ linear alkyl, alternatively $C_{9-10}$ linear alkyl, which is optionally substituted with 1 $C_{1-9}$ alkyl (alternatively $C_{6-9}$ alkyl, alternatively $C_{6-7}$ alkyl);

$R_2$ is $C_{7-12}$ alkyl, alternatively $C_{8-12}$ alkyl, alternatively $C_{9-10}$ alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, $R_1$ is $—(CH_2)_5CH_3$, $—(CH_2)_9CH_3$,

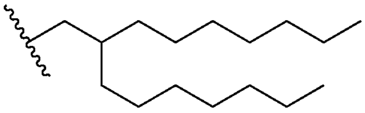

, or

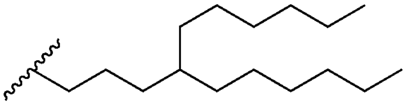

;

$R_2$ is

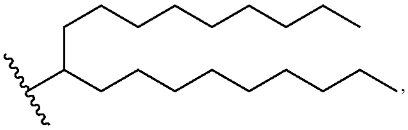

,

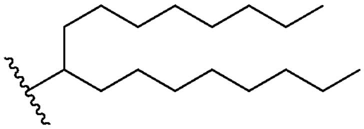

, or

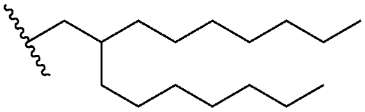

.

In a more specific embodiment, when a=4, $R_1$ is $C_{9-10}$ linear alkyl;

$R_2$ is $C_{9-10}$ alkyl, which is optionally substituted with 1 $R_{1s}$;

$R_{1s}$ is $C_{8-9}$ alkyl;

$R_4$ and $R_5$ are not taken together with the carbon atom to which they are attached to form a ring.

In a more specific embodiment, when a=2, $R_1$ is $C_{10}$ linear alkyl;

alternatively $R_{1s}$ is $C_{8-9}$ alkyl, alternatively $C_9$ alkyl.

In a more specific embodiment, the present disclosure provides the compound of formula (II), or a pharmaceutically acceptable salt, isotopic variant, tautomer, or stereoisomer thereof, wherein a=2, 3, or 4; alternatively a=2 or 4;

b=7;

c=4;

d=2;

$M_1$ is —OC(O)—; $M_2$ is —C(O)O—;

$R_1$ is $C_{8-12}$ linear alkyl, alternatively $C_{9-10}$ linear alkyl;

$R_2$ is $C_{8-11}$ alkyl, alternatively $C_{9-10}$ alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring.

In a more specific embodiment, $R_2$ is

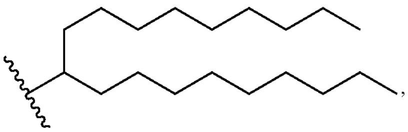

,

-continued

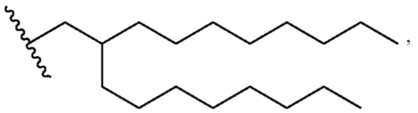

or

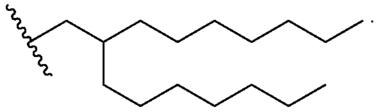

In a more specific embodiment, the present disclosure provides the compound of formula (II), or a pharmaceutically acceptable salt, isotopic variant, tautomer, or stereoisomer thereof, wherein a=2, 3, or 4; alternatively a=2;

b=8;

c=5;

d=1;

$M_1$ is —OC(O)—; $M_2$ is —C(O)O—;

$R_1$ is $C_{8-12}$ linear alkyl, alternatively $C_{9-10}$ linear alkyl, alternatively $C_{0-11}$ linear alkyl;

$R_2$ is $C_{8-11}$ alkyl, alternatively $C_{9-10}$ alkyl, which is optionally substituted with 1 $R_{1s}$;

$R_{1s}$ is independently $C_{7-9}$ alkyl, alternatively $C_{7-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring.

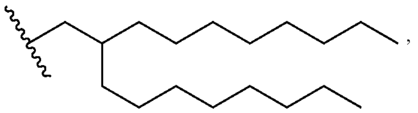

or

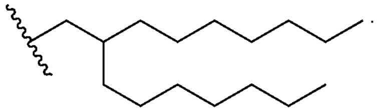 [SMILES: *CC(CCCCCCC)CCCCCCC]

In a more specific embodiment, $R_2$ is, or

In a more specific embodiment, the present disclosure provides the compound of formula (II), or a pharmaceutically acceptable salt, isotopic variant, tautomer, or stereoisomer thereof, wherein a=2;

b=6, 7, or 8, alternatively b=7;

c=5;

d=1;

$M_1$ is —OC(O)—; $M_2$ is —C(O)O—;

$R_1$ is $C_{8-11}$ linear alkyl, alternatively $C_{9-10}$ linear alkyl, alternatively $C_9$ linear alkyl;

$R_2$ is $C_{8-11}$ alkyl, alternatively $C_{9-10}$ alkyl, alternatively $C_9$ alkyl, which is optionally substituted with 1 $R_{1s}$;

$R_{1s}$ is independently $C_7$ alkyl;

$R_4$ and $R_5$ are independently $C_{1-3}$ alkyl, alternatively methyl.

In a more specific embodiment, $R_2$ is

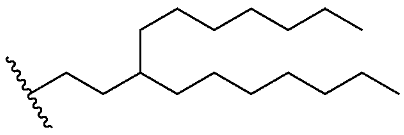

or

-continued

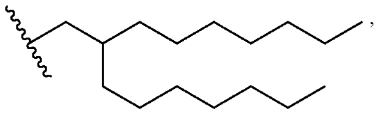

alternatively

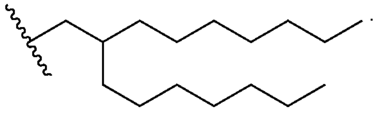

In a more specific embodiment, the present disclosure provides the compound of formula (II), or a pharmaceutically acceptable salt, isotopic variant, tautomer, or stereoisomer thereof, wherein a=2 or 3, alternatively a=2;

b=7;

c=3;

d=3;

$M_1$ is —OC(O)—; $M_2$ is —C(O)O—;

$R_1$ is $C_{8-11}$ linear alkyl, alternatively $C_{9-10}$ linear alkyl, alternatively $C_9$ linear alkyl;

$R_2$ is $C_{8-11}$ alkyl, alternatively $C_{9-10}$ alkyl, alternatively $C_9$ alkyl, which is optionally substituted with 1 $R_{1s}$;

$R_{1s}$ is independently $C_{6-7}$ alkyl, alternatively $C_7$ alkyl;

$R_4$ and $R_5$ are independently $C_{1-3}$ alkyl, alternatively methyl.

In a more specific embodiment, $R_2$ is

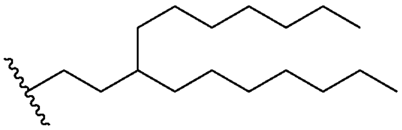

or

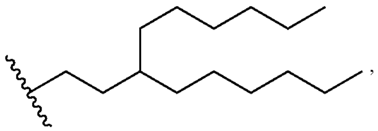 [SMILES: *CCC(CCCCCC)CCCCCC]

alternatively

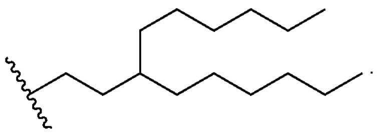

In a more specific embodiment, the present disclosure provides the compound of formula (II), or a pharmaceutically acceptable salt, isotopic variant, tautomer, or stereoisomer thereof,

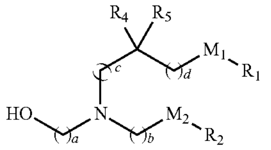

(II)

wherein a=2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9, alternatively c+d=4, 5, or 6;

one of $M_1$ and $M_2$ is —OC(O)O—, and the other is —C(O)O—, —OC(O)—, —SC(O)—, or —C(O)S—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, -$L_c$-$OR_c$, or -$L_c$-$NR_cR'_c$; alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-6}$ alkyl;

or, $R_4$ and $R_5$ are taken together with the carbon atom to which they are attached to form $C_{3-6}$ cycloalkylene or 3- to 6-membered heterocyclylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, or 7, alternatively b=5 or 6, alternatively b=6;

c=2, 3, 4, 5, or 6; alternatively c=2, 4, 5, or 6;

d=0, 1, 2, 3, or 4; alternatively d=0, 1, 2, or 4;

c+d=5 or 6, alternatively c+d=6;

one of $M_1$ and $M_2$ is —OC(O)O—, and the other is —C(O)O— or —OC(O)—;

$R_1$ and $R_2$ are independently $C_{7-12}$ alkyl, alternatively $C_{9-11}$ alkyl, which is optionally substituted with 1 $R_{1s}$;

$R_{1s}$ is independently H or $C_{1-10}$ alkyl; alternatively H or $C_{4-10}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene, alternatively $C_{3-4}$ cycloalkylene.

In a more specific embodiment, the present disclosure provides the compound of formula (II), or a pharmaceutically acceptable salt, isotopic variant, tautomer, or stereoisomer thereof, wherein a=2, 3, or 4;

b=4, 5, 6, or 7, alternatively b=5 or 6, alternatively b=6;

c=2, 3, 4, 5, or 6; alternatively c=2, 4, 5, or 6;

d=0, 1, 2, 3, or 4; alternatively d=0, 1, 2, or 4;

c+d=5 or 6, alternatively c+d=6;

one of $M_1$ and $M_2$ is —OC(O)O—, and the other is —C(O)O— or —OC(O)—;

$R_1$ and $R_2$ are independently selected from $—(CH_2)_8CH_3$, $—(CH_2)_9CH_3$, $—(CH_2)_{10}CH_3$,

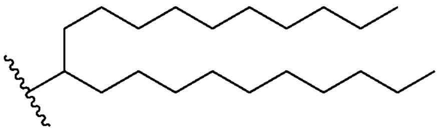,

-continued

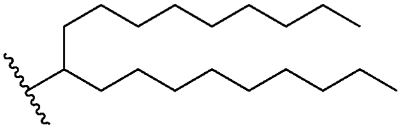,

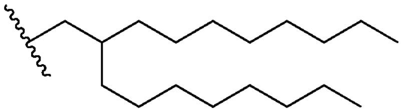,

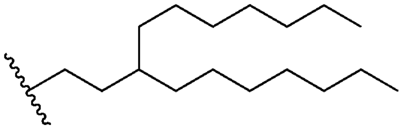,

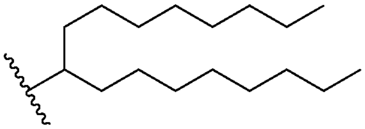,

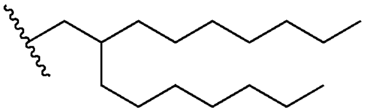,

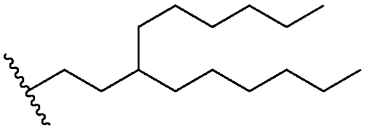,

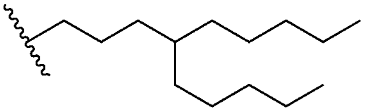, and

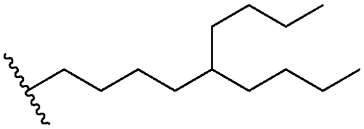;

$R_4$ and $R_5$ are methyl;

or, $R_4$ and $R_5$ are taken together with the carbon atom to which they are attached to form cyclopropylene.

In a more specific embodiment, only one of $R_1$ and $R_2$ is substituted;

In a more specific embodiment, $M_1$ is —C(O)O— or —OC(O)—, alternatively —C(O)O—, and $M_2$ is —OC(O)O—.

In a more specific embodiment, $M_1$ is —OC(O)O—, and $M_2$ is —OC(O)—.

In a more specific embodiment, the present disclosure provides the compound of formula (II), or a pharmaceutically acceptable salt, isotopic variant, tautomer, or stereoisomer thereof, wherein a=2;

b=5 or 6, alternatively b=6;

c=4, 5, or 6; alternatively c=4 or 6; alternatively c=6;

d=0, 1, or 2; alternatively d=0 or 2;

c+d=6;

$M_1$ is —C(O)O—, and $M_2$ is —OC(O)O—;

$R_1$ is $C_{8-11}$ alkyl, alternatively $C_{9-10}$ alkyl, alternatively $C_9$ alkyl, which is optionally substituted with 1 $R_{1s}$;

$R_{1s}$ is $C_{7-9}$ alkyl, alternatively $C_7$ alkyl;

$R_2$ is $C_{8-11}$ linear alkyl, alternatively $C_{9-10}$ linear alkyl, alternatively $C_9$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring.

In a more specific embodiment, $R_1$ is

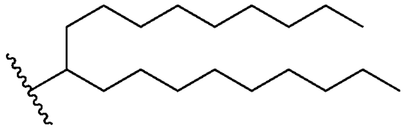

,

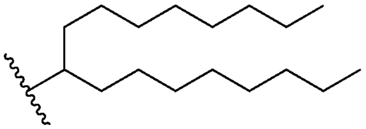

, or

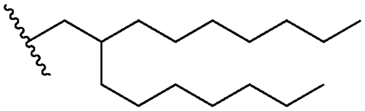

, alternatively

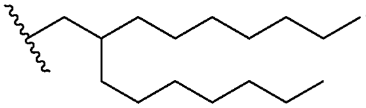

.

In a more specific embodiment, the present disclosure provides the compound of formula (II), or a pharmaceutically acceptable salt, isotopic variant, tautomer, or stereoisomer thereof, wherein a=2;

b=6;

c=4, 5, or 6; alternatively c=5 or 6; alternatively c=6;

d=0, 1, or 2; alternatively d=0 or 1;

c+d=6;

$M_1$ is —C(O)O—, and $M_2$ is —OC(O)O—;

$R_1$ is $C_{8-10}$ linear alkyl, alternatively $C_{9-10}$ linear alkyl, alternatively $C_9$ linear alkyl;

$R_2$ is $C_{8-10}$ alkyl, alternatively $C_{9-10}$ alkyl, alternatively $C_9$ alkyl, which is optionally substituted with 1 $R_{1s}$;

$R_{1s}$ is $C_{6-7}$ alkyl, alternatively $C_7$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring.

In a more specific embodiment, $R_2$ is or

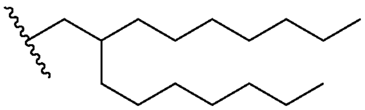

or

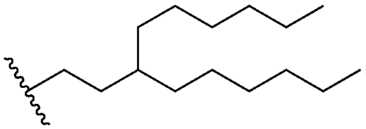

, alternatively

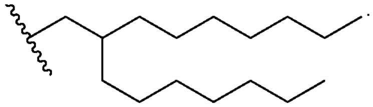 [SMILES: *CC(CCCCCCC)CCCCCCC]

.

In a more specific embodiment, the present disclosure provides the compound of formula (II), or a pharmaceutically acceptable salt, isotopic variant, tautomer, or stereoisomer thereof, wherein a=2;

b=5 or 6; alternatively b=6;

c=5;

d=1;

$M_1$ is —OC(O)—, and $M_2$ is —OC(O)O—;

$R_1$ is $C_{8-10}$ alkyl, alternatively $C_{9-10}$ alkyl, alternatively $C_9$ alkyl, which is optionally substituted with 1 $R_{1s}$;

$R_{1s}$ is $C_{6-8}$ alkyl, alternatively $C_{6-7}$ alkyl;

$R_2$ is $C_{8-12}$ linear alkyl, alternatively $C_{0-1}$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring.

In a more specific embodiment, $R_1$ is

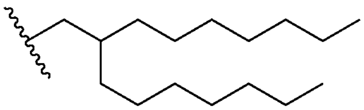

or

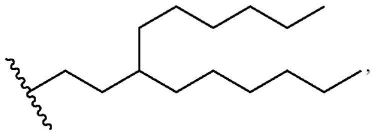

, alternatively

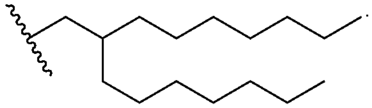 [SMILES: *CC(CCCCCCC)CCCCCCC]

.

In a more specific embodiment, the present disclosure provides the compound of formula (II), or a pharmaceutically acceptable salt, isotopic variant, tautomer, or stereoisomer thereof, wherein a=2, 3 or 4; alternatively a=2;

b=5, 6, 7, or 8; alternatively b=6 or 7; alternatively b=7;

c=4, 5, or 6; alternatively c=4;

d=0, 1, or 2; alternatively d=1;

c+d=5 or 6; alternatively c+d=5;

$M_1$ is —OC(O)O—, $M_2$ is —OC(O)—;

$R_1$ is $C_{8-12}$ alkyl, alternatively $C_{8-10}$ alkyl, which is optionally substituted with 1 $R_{1s}$;

$R_{1s}$ is $C_{6-10}$ alkyl, alternatively $C_{6-8}$ alkyl;

$R_2$ is $C_{8-12}$ linear alkyl, alternatively $C_{8-10}$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring.

In a more specific embodiment, $R_1$ is

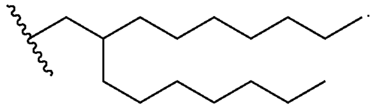 [SMILES: *CC(CCCCCCC)CCCCCCC]

In a more specific embodiment, the present disclosure provides the compound of formula (II), or a pharmaceutically acceptable salt, isotopic variant, tautomer, or stereoisomer thereof, wherein In a more specific embodiment, the present disclosure provides the compound of formula (III), or a pharmaceutically acceptable salt, isotopic variant, tautomer, or stereoisomer thereof, (III)

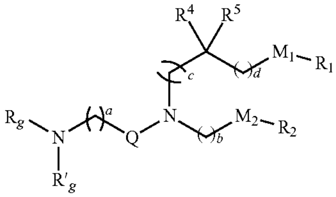

wherein

Q is —SC(O)— or —OC(O)—;

$R_g$ and $R'_g$ are independently $C_{1-6}$ alkyl;

a=2, 3, 4, 5, or 6; alternatively a=2, 3, or 4;

b=4, 5, 6, 7, 8, or 9; alternatively b=5, 6, or 7;

c=2, 3, 4, 5, or 6;

d=0, 1, 2, 3, or 4;

c+d=5 or 6;

$M_1$ and $M_2$ are independently selected from —C(O)O—, —C(O)S—, —OC(O)—, —SC(O)—, and —OC(O)O—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, -$L_c$-OR, or -$L_c$-$NR_cR'_c$; alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-6}$ alkyl, or, $R_4$ and $R_5$ are taken together with the carbon atom to which they are attached to form $C_{3-6}$ cycloalkylene or 3- to 6-membered heterocyclylene.

In a more specific embodiment, the present disclosure provides the compound of formula (III), or a pharmaceutically acceptable salt, isotopic variant, tautomer, or stereoisomer thereof, wherein Q is —SC(O)— or —OC(O)—;

$R_g$ and $R'_g$ are independently $C_{1-3}$ alkyl;

a=3 or 4;

b=6 or 7;

c=2, 3, 4, or 5; alternatively 2 or 5;

d=1, 2, 3, or 4; alternatively 1 or 4;

c+d=5 or 6;

$M_1$ and $M_2$ are independently selected from —C(O)O—, —OC(O)—, and —OC(O)O—;

alternatively, $M_1$ and $M_2$ are not simultaneously —OC(O)O—;

$R_1$ and $R_2$ are independently $C_{7-12}$ alkyl, alternatively $C_{8-10}$ alkyl, which is optionally substituted with 1 $R_{1s}$;

$R_{1s}$ is independently H or $C_{1-10}$ alkyl; alternatively H or $C_{1-9}$ alkyl;

$R_4$ and $R_5$ are independently $C_{1-3}$ alkyl, or, $R_4$ and $R_5$ are taken together with the carbon atom to which they are attached to form $C_{3-6}$ cycloalkylene.

In a more specific embodiment, the present disclosure provides the compound of formula (III), or a pharmaceutically acceptable salt, isotopic variant, tautomer, or stereoisomer thereof, wherein Q is —SC(O)—;

$R_g$ and $R'_g$ are methyl;

a=3 or 4;

b=6 or 7;

c=2, 4, or 5; alternatively 2 or 5;

d=1, 2, or 4; alternatively 1 or 4;

c+d=6;

$M_1$ and $M_2$ are independently selected from —C(O)O—, —OC(O)—, and —OC(O)O—;

alternatively, $M_1$ and $M_2$ are not simultaneously —OC(O)O—;

$R_1$ and $R_2$ are independently $—(CH_2)_7CH_3$, $—(CH_2)_8CH_3$, $—(CH_2)_9CH_3$,

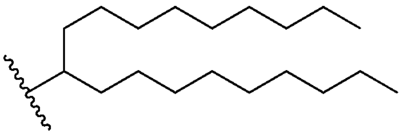

,

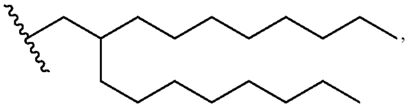

,

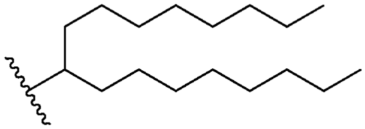

, or

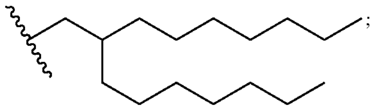 [SMILES: *CC(CCCCCCC)CCCCCCC]

;

$R_4$ and $R_5$ are methyl;

or, $R_4$ and $R_5$ are taken together with the carbon atom to which they are attached to form cyclopropylene, alternatively not to form a ring.

In a more specific embodiment, only one of $R_1$ and $R_2$ is substituted; alternatively, $R_1$ is unsubstituted, and $R_2$ is substituted.

In a more specific embodiment, the present disclosure provides the compound of formula (II), or a pharmaceutically acceptable salt, isotopic variant, tautomer, or stereoisomer thereof, (II)

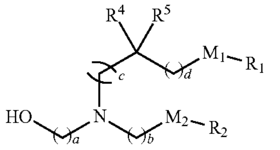

wherein $M_1$ and $M_2$ are independently selected from —C(O)O— and —C(O)S—, alternatively —C(O)O—; the other groups are as defined herein.

In a more specific embodiment, the present disclosure provides the compound of formula (II) or a pharmaceutically acceptable salt, isotopic variant, tautomer, or stereoisomer thereof, (II)

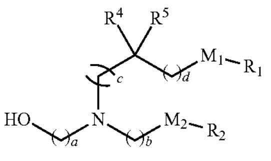

wherein one of $M_1$ and $M_2$ is —C(O)O— or —C(O)S—, alternatively —C(O)O—, and the other is —OC(O)— or —SC(O)—, alternatively —OC(O)—;

the other groups are as defined herein.

In a more specific embodiment, $R_{1s}$ is independently H or $C_{1-6}$ alkyl, alternatively H or $C_{1-4}$ alkyl.

In a more specific embodiment, $M_1$ is —OC(O)— or —SC(O)—, alternatively —OC(O)—; and $M_2$ is —C(O)O— or —C(O)S—, alternatively —C(O)O—.

In a more specific embodiment, $R_{1s}$ is independently $C_{1-8}$ alkyl, alternatively $C_{4-8}$ alkyl, alternatively $C_{6-8}$ alkyl, alternatively $C_{7-8}$ alkyl, alternatively $C_8$ alkyl;

In a more specific embodiment, the present disclosure provides the compound of formula (II) or formula (III), or a pharmaceutically acceptable salt, isotopic variant, tautomer, or stereoisomer thereof, (II)

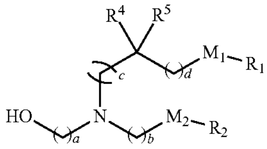

or (III)

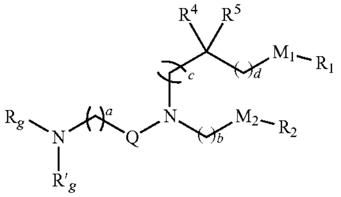

wherein

Q is a chemical bond, —SC(O)— or —OC(O)—;

$R_g$ and $R'_g$ are independently $C_{1-6}$ alkyl;

a=2, 3, 4, 5, or 6;

b=6 or 7;

c=5 or 6;

d=0 or 1;

c+d=5 or 6;

$M_1$ is —OC(O)— or —SC(O)—; and $M_2$ is —C(O)O— or —C(O)S—;

$R_1$ and $R_2$ are independently $C_{7-12}$ alkyl, alternatively $C_{8-12}$ alkyl, which is optionally substituted with 1 $R_{1s}$;

$R_{1s}$ is independently H or $C_{1-10}$ alkyl;

$R_4$ and $R_5$ are independently $C_{1-6}$ alkyl, or, $R_4$ and $R_5$ are taken together with the carbon atom to which they are attached to form $C_{3-6}$ cycloalkylene.

In a more specific embodiment, only one of $R_1$ and $R_2$ is substituted; alternatively, $R_1$ is unsubstituted, and $R_2$ is substituted.

In a more specific embodiment, the present disclosure provides the compound of formula (II) or formula (III), or a pharmaceutically acceptable salt, isotopic variant, tautomer, or stereoisomer thereof, wherein Q is —SC(O)— or —OC(O)—, alternatively —SC(O)—;

$R_g$ and $R'_g$ are independently $C_{1-3}$ alkyl, alternatively methyl;

a=2, 3, or 4; alternatively a=2 or 4; alternatively a=4;

b=6 or 7; alternatively b=7;

c=5 or 6; alternatively c=5;

d=0 or 1; alternatively d=1;

c+d=5 or 6; alternatively c+d=6;

$M_1$ is —OC(O)—; $M_2$ is —C(O)O—;

$R_1$ is $C_{7-11}$ linear alkyl, alternatively $C_{9-10}$ linear alkyl; alternatively $C_9$ linear alkyl;

$R_2$ is $C_{7-12}$ alkyl, alternatively $C_{8-12}$ alkyl, alternatively $C_{9-10}$ alkyl, alternatively $C_9$ alkyl, which is optionally substituted with 1 $R_{1s}$;

$R_{1s}$ is independently $C_{1-9}$ alkyl, alternatively $C_{1-8}$ alkyl, alternatively $C_{4-9}$ alkyl, alternatively $C_{4-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene.

In a more specific embodiment, the substitution site of $R_{1s}$ on $R_1$ or $R_2$ is separated from $M_1$ or $M_2$ by 0-10 carbon atoms, alternatively 0-6 carbon atoms, alternatively 0-4 carbon atoms, alternatively 0-2 carbon atoms, alternatively 0 carbon atom.

In a more specific embodiment, $R_1$ is not substituted with $R_{1s}$, and the substitution site of $R_{1s}$ on $R_2$ is separated from $M_2$ by 0-10 carbon atoms, alternatively 1-10 carbon atoms, alternatively 1-6 carbon atoms, 1-4 carbon atoms, 1-2 carbon atoms; alternatively 2-10 carbon atoms, alternatively 2-6 carbon atoms, 2-4 carbon atoms.

In a more specific embodiment, $R_2$ is

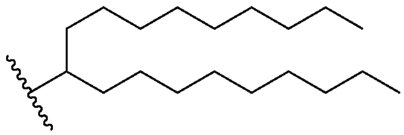

,

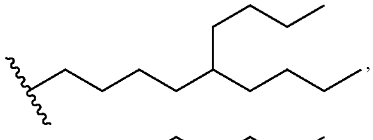

,

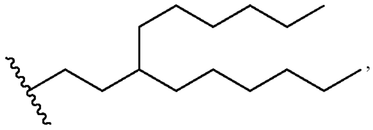

,

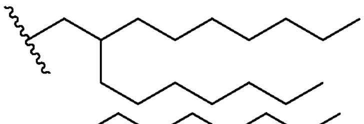

, or

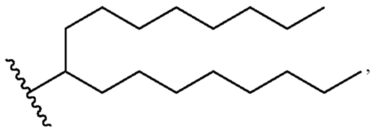

, alternatively

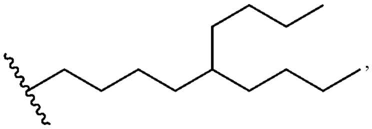

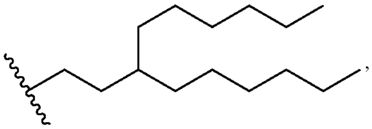

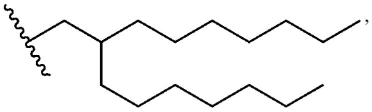

, or

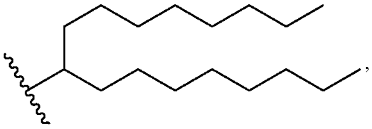 [SMILES: *C(CCCCCCCC)CCCCCCCC]

alternatively

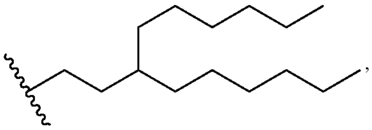

-continued

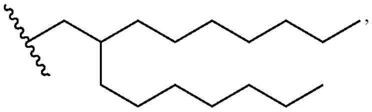

, or

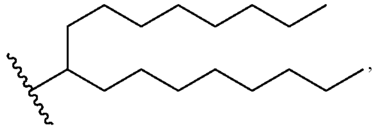

alternatively

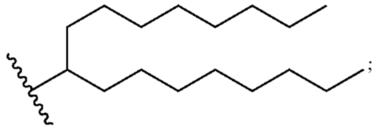

In a more specific embodiment, $R_4$ and $R_5$ are not taken together with the carbon atom to which they are attached to form a ring.

In a more specific embodiment, the present disclosure provides the compound of formula (I), or a pharmaceutically acceptable salt, isotopic variant, tautomer, or stereoisomer thereof, wherein the compound is selected from the compounds in Table (I).

TABLE I

| | |
|---|---|
| 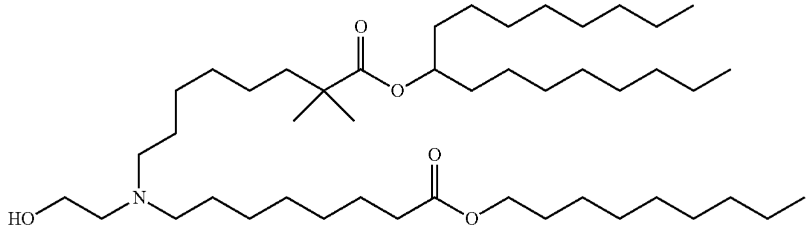 [SMILES: CCCCCCCCCOC(=O)CCCCCCCN(CCO)CCCCCCC(C)(C)C(=O)OC(CCCCCCCC)CCCCCCCC] | 1a |
| 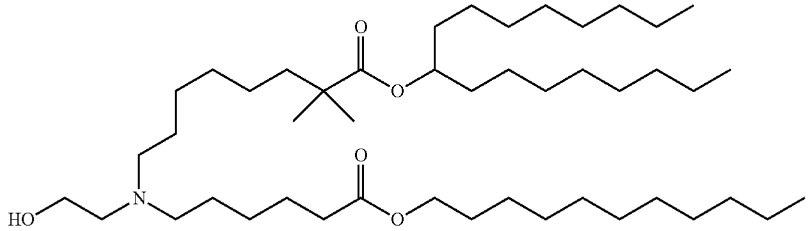 [SMILES: CCCCCCCCCCCOC(=O)CCCCCN(CCO)CCCCCCC(C)(C)C(=O)OC(CCCCCCCC)CCCCCCCC] | 3a |
| 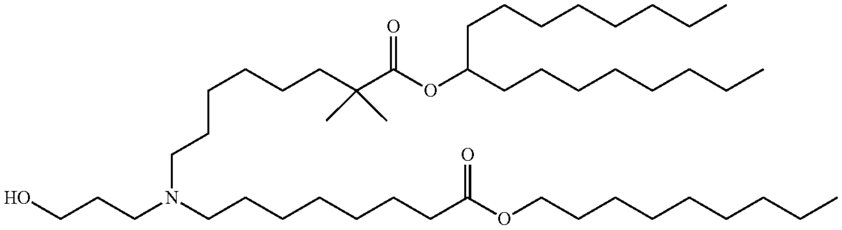 | 4a |

TABLE I-continued
5a
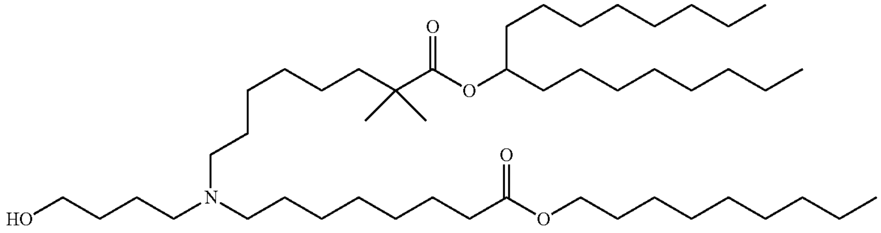
6a
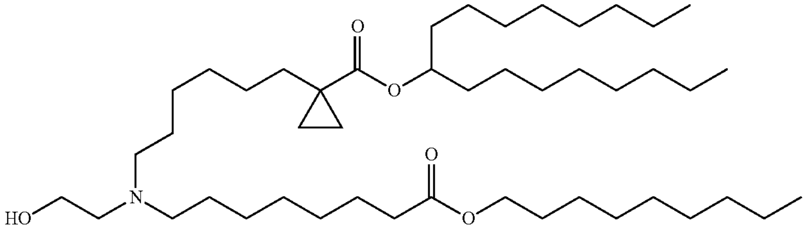 [SMILES: CCCCCCCCCOC(=O)CCCCCCCN(CCO)CCCCCCC1(C(=O)OC(CCCCCCCC)CCCCCCCC)CC1]
7a
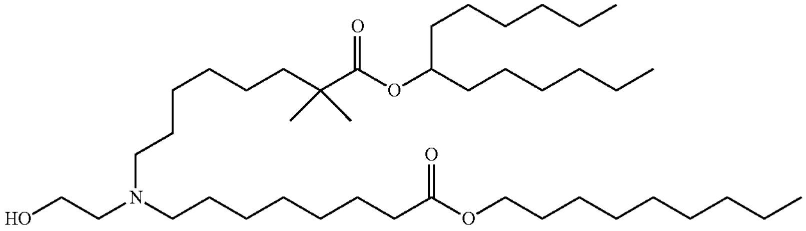 [SMILES: CCCCCCCCCOC(=O)CCCCCCCN(CCO)CCCCCCC(C)(C)C(=O)OC(CCCCCC)CCCCCC]
8a
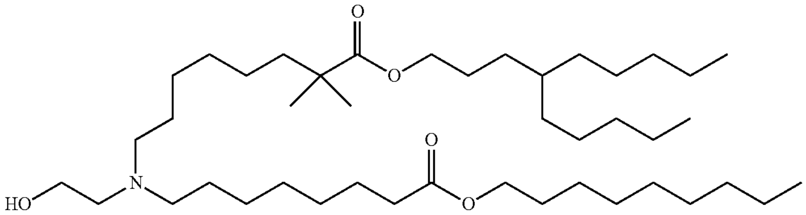 [SMILES: CCCCCCCCCOC(=O)CCCCCCCN(CCO)CCCCCCC(C)(C)C(=O)OCCCC(CCCCC)CCCCC]
9a
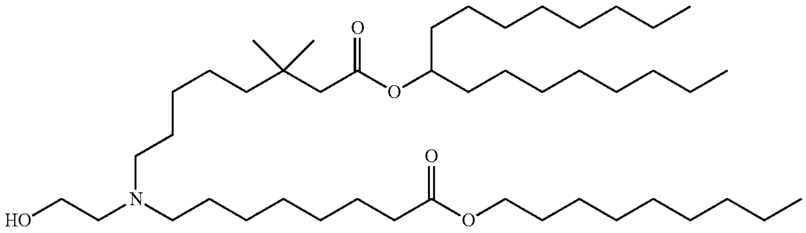 [SMILES: CCCCCCCCCOC(=O)CCCCCCCN(CCO)CCCCCC(C)(C)CC(=O)OC(CCCCCCCC)CCCCCCCC]
10a
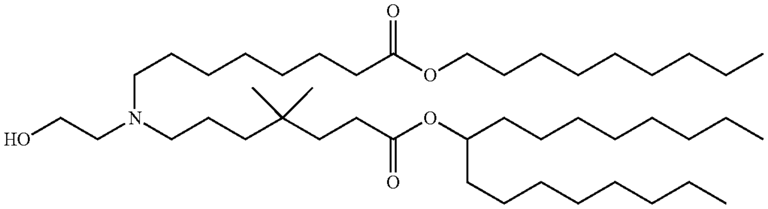 [SMILES: CCCCCCCCCOC(=O)CCCCCCCN(CCO)CCCC(C)(C)CCC(=O)OC(CCCCCCCC)CCCCCCCC]
11a
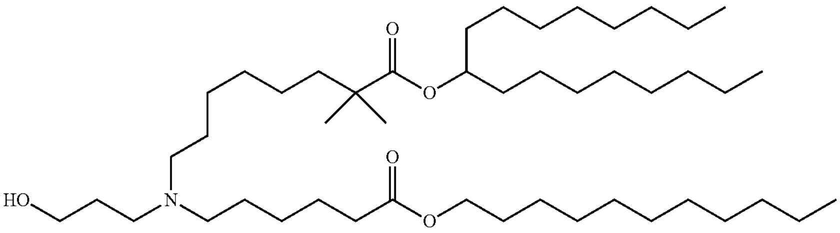 [SMILES: CCCCCCCCCCCOC(=O)CCCCCN(CCCO)CCCCCCC(C)(C)C(=O)OC(CCCCCCCC)CCCCCCCC]

TABLE I-continued
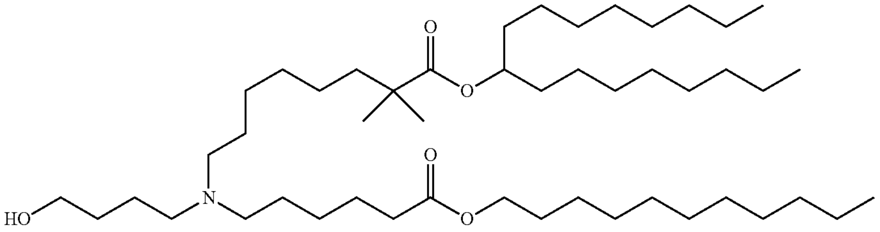 [SMILES: CCCCCCCCCCCOC(=O)CCCCCN(CCCCO)CCCCCCC(C)(C)C(=O)OC(CCCCCCCC)CCCCCCCC]
12a
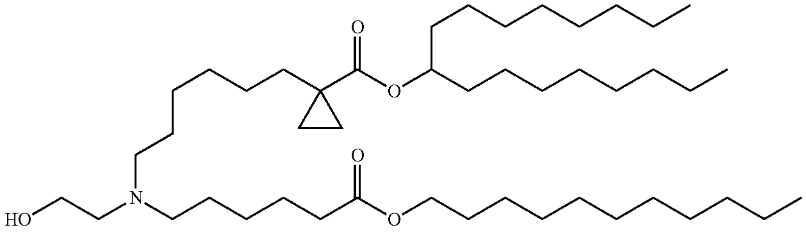 [SMILES: CCCCCCCCCCCOC(=O)CCCCCN(CCO)CCCCCCC1(C(=O)OC(CCCCCCCC)CCCCCCCC)CC1]
13a
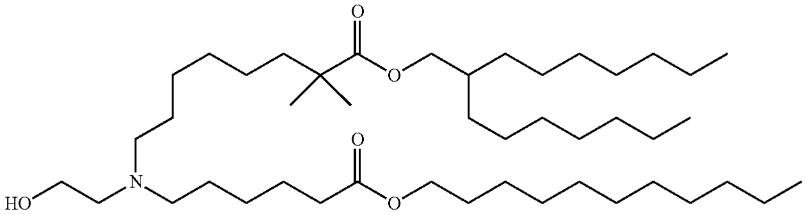 [SMILES: CCCCCCCCCCCOC(=O)CCCCCN(CCO)CCCCCCC(C)(C)C(=O)OCC(CCCCCCC)CCCCCCC]
14a
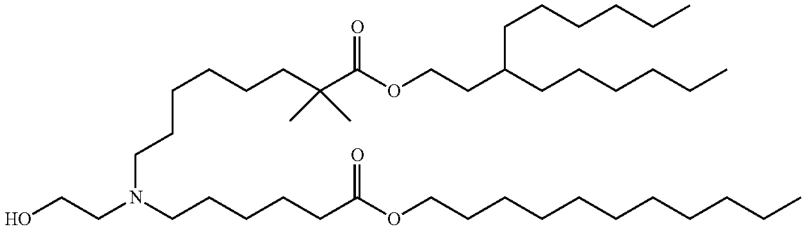 [SMILES: CCCCCCCCCCCOC(=O)CCCCCN(CCO)CCCCCCC(C)(C)C(=O)OCCC(CCCCCC)CCCCCC]
15a
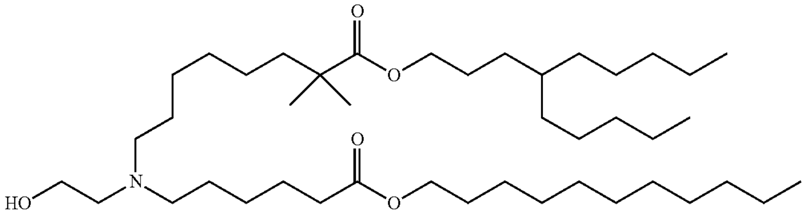 [SMILES: CCCCCCCCCCCOC(=O)CCCCCN(CCO)CCCCCCC(C)(C)C(=O)OCCCC(CCCCC)CCCCC]
16a
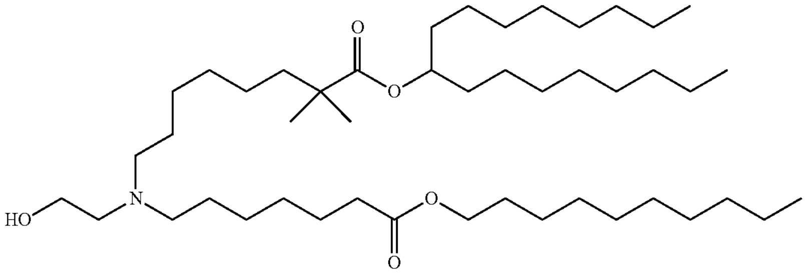 [SMILES: CCCCCCCCCCOC(=O)CCCCCCN(CCO)CCCCCCC(C)(C)C(=O)OC(CCCCCCCC)CCCCCCCC]
17a TABLE I-continued
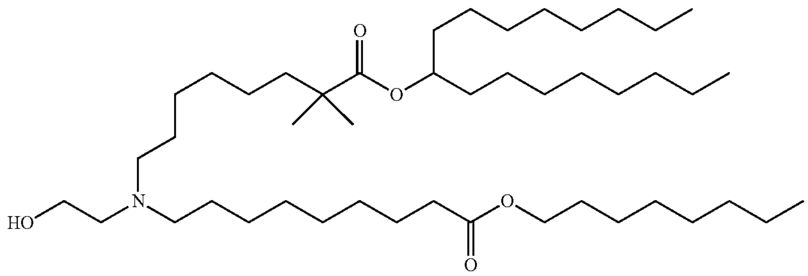 [SMILES: CCCCCCCCOC(=O)CCCCCCCCN(CCO)CCCCCCC(C)(C)C(=O)OC(CCCCCCCC)CCCCCCCC]
18a
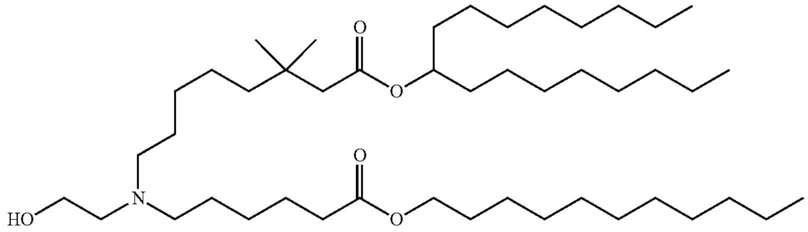 [SMILES: CCCCCCCCCCCOC(=O)CCCCCN(CCO)CCCCCC(C)(C)CC(=O)OC(CCCCCCCC)CCCCCCCC]
19a
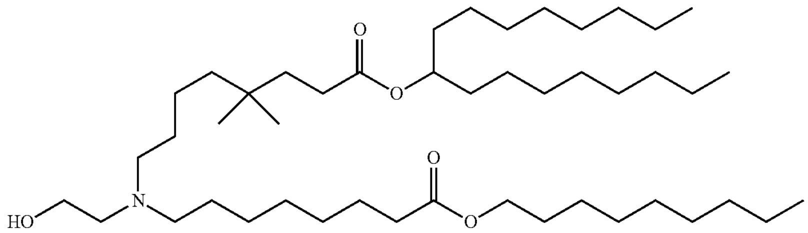 [SMILES: CCCCCCCCCOC(=O)CCCCCCCN(CCO)CCCCC(C)(C)CCC(=O)OC(CCCCCCCC)CCCCCCCC]
20a
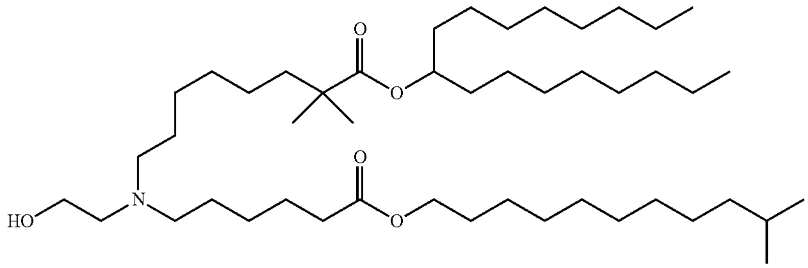 [SMILES: CCCCCCCCC(CCCCCCCC)OC(=O)C(C)(C)CCCCCCN(CCO)CCCCCC(=O)OCCCCCCCCCC(C)C]
21a
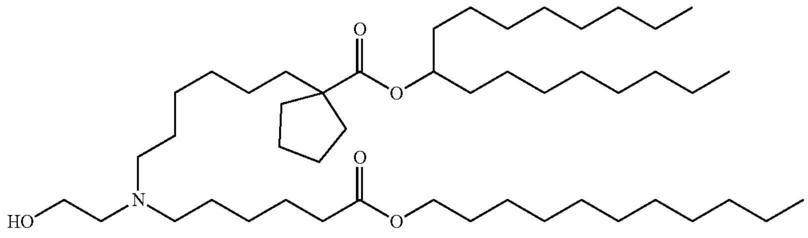 [SMILES: CCCCCCCCCCCOC(=O)CCCCCN(CCO)CCCCCCC1(C(=O)OC(CCCCCCCC)CCCCCCCC)CCCC1]
22a
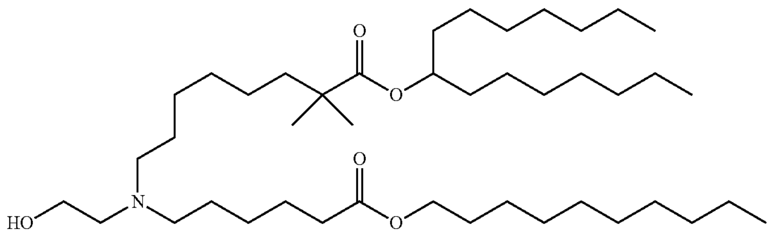 [SMILES: CCCCCCCCCCOC(=O)CCCCCN(CCO)CCCCCCC(C)(C)C(=O)OC(CCCCCCC)CCCCCCC]
23a TABLE I-continued
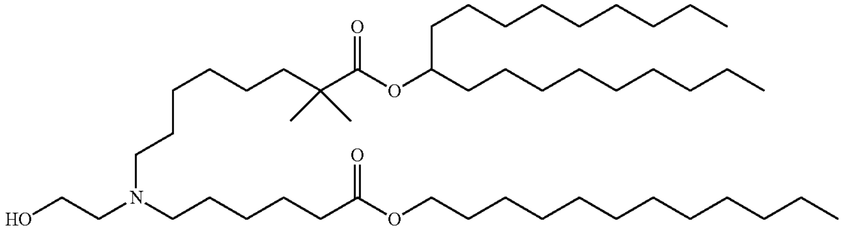 [SMILES: CCCCCCCCCCCCOC(=O)CCCCCN(CCO)CCCCCCC(C)(C)C(=O)OC(CCCCCCCCC)CCCCCCCCC]
24a
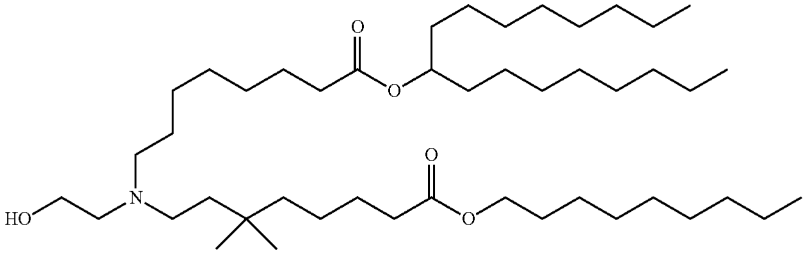 [SMILES: CCCCCCCCCOC(=O)CCCCC(C)(C)CCN(CCO)CCCCCCCC(=O)OC(CCCCCCCC)CCCCCCCC]
25a
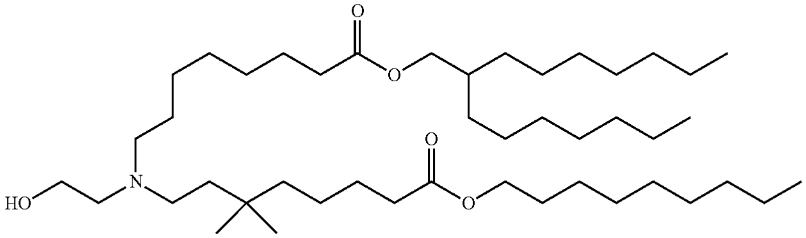 [SMILES: CCCCCCCCCOC(=O)CCCCC(C)(C)CCN(CCO)CCCCCCCC(=O)OCC(CCCCCCC)CCCCCCC]
26a
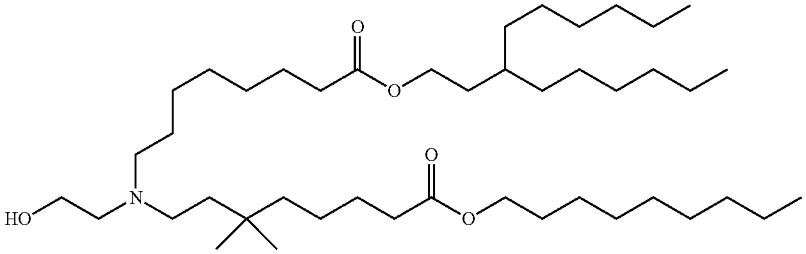 [SMILES: CCCCCCCCCOC(=O)CCCCC(C)(C)CCN(CCO)CCCCCCCC(=O)OCCC(CCCCCC)CCCCCC]
27a
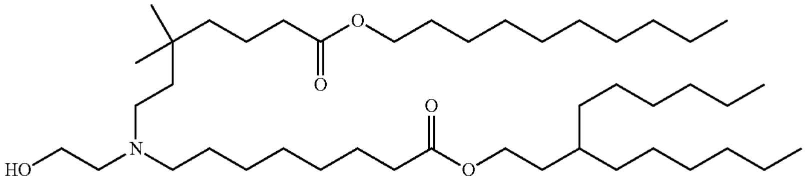 [SMILES: CCCCCCCCCCOC(=O)CCCC(C)(C)CCN(CCO)CCCCCCCC(=O)OCCC(CCCCCC)CCCCCC]
28a
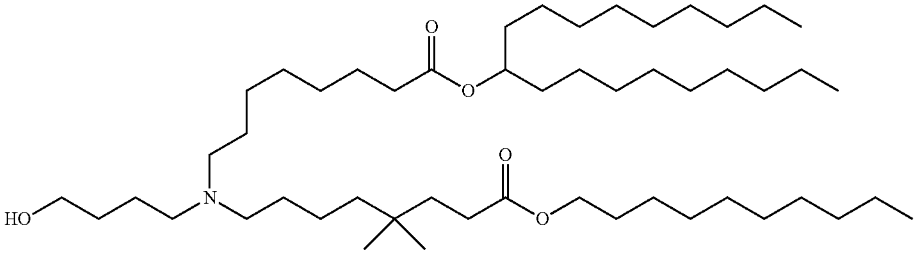 [SMILES: CCCCCCCCCCOC(=O)CCC(C)(C)CCCCN(CCCCO)CCCCCCCC(=O)OC(CCCCCCCCC)CCCCCCCCC]
29a TABLE I-continued
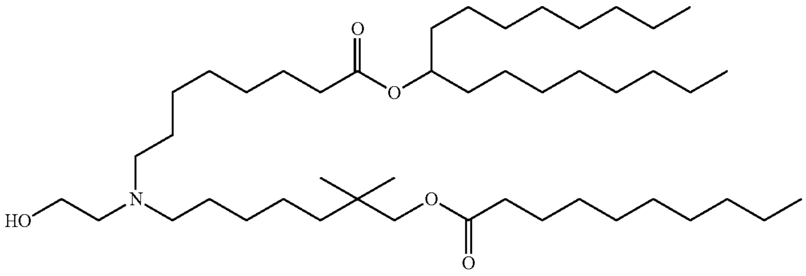 [SMILES: CCCCCCCCCC(=O)OCC(C)(C)CCCCCN(CCO)CCCCCCCC(=O)OC(CCCCCCCC)CCCCCCCC]
1b
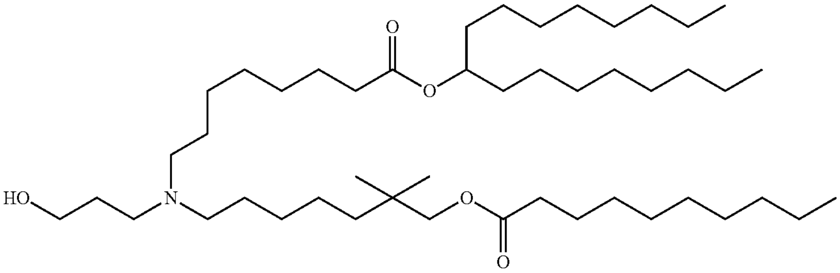 [SMILES: CCCCCCCCCC(=O)OCC(C)(C)CCCCCN(CCCO)CCCCCCCC(=O)OC(CCCCCCCC)CCCCCCCC]
2b
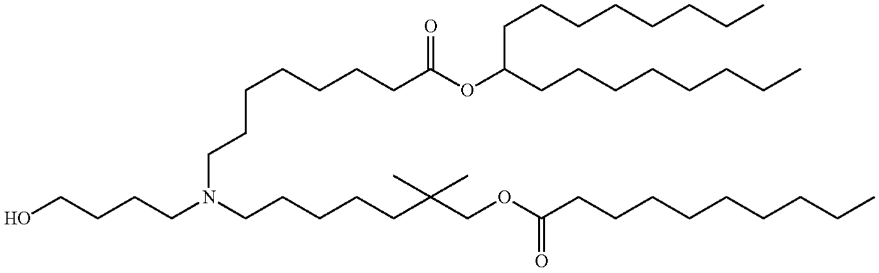 [SMILES: CCCCCCCCCC(=O)OCC(C)(C)CCCCCN(CCCCO)CCCCCCCC(=O)OC(CCCCCCCC)CCCCCCCC]
3b
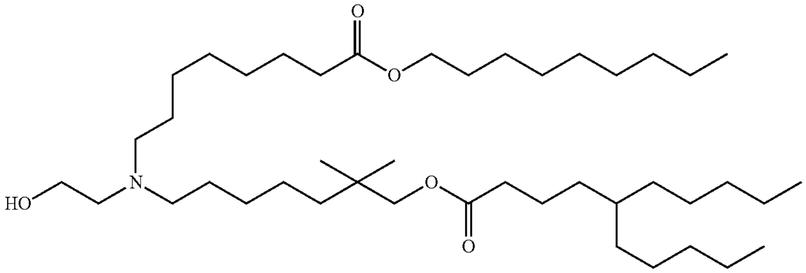 [SMILES: CCCCCCCCCOC(=O)CCCCCCCN(CCO)CCCCCC(C)(C)COC(=O)CCCC(CCCCC)CCCCC]
5b
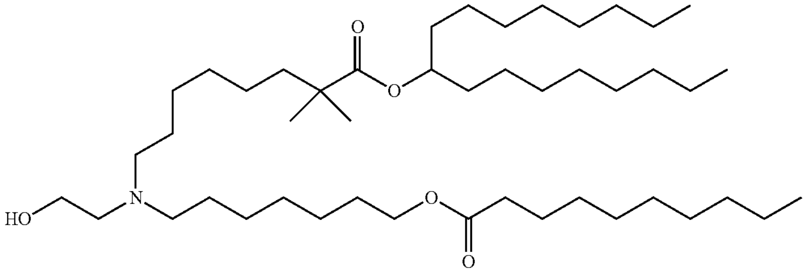 [SMILES: CCCCCCCCCC(=O)OCCCCCCCN(CCO)CCCCCCC(C)(C)C(=O)OC(CCCCCCCC)CCCCCCCC]
6b TABLE I-continued
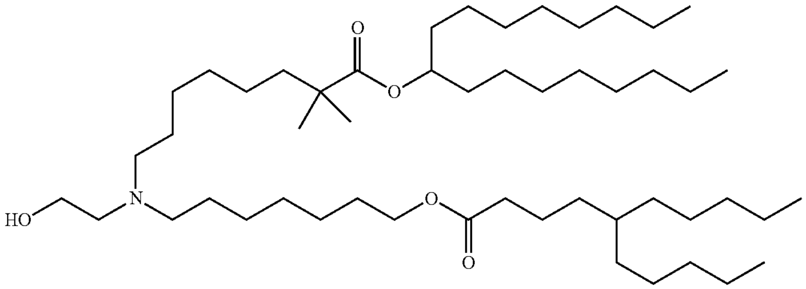 [SMILES: CCCCCCCCC(CCCCCCCC)OC(=O)C(C)(C)CCCCCCN(CCO)CCCCCCCOC(=O)CCCC(CCCCC)CCCCC]
7b
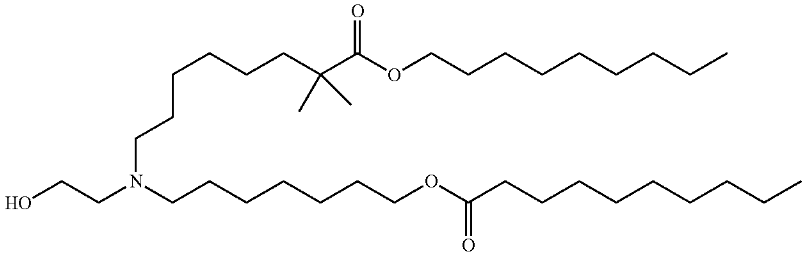 [SMILES: CCCCCCCCCOC(=O)C(C)(C)CCCCCCN(CCO)CCCCCCCOC(=O)CCCCCCCCC]
8b
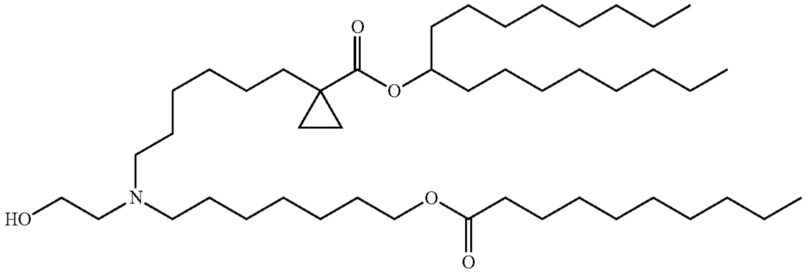 [SMILES: CCCCCCCCCC(=O)OCCCCCCCN(CCO)CCCCCCC1(C(=O)OC(CCCCCCCC)CCCCCCCC)CC1]
9b
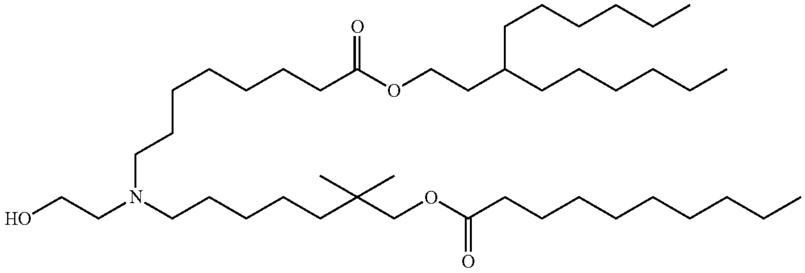 [SMILES: CCCCCCCCCC(=O)OCC(C)(C)CCCCCN(CCO)CCCCCCCC(=O)OCCC(CCCCCC)CCCCCC]
10b
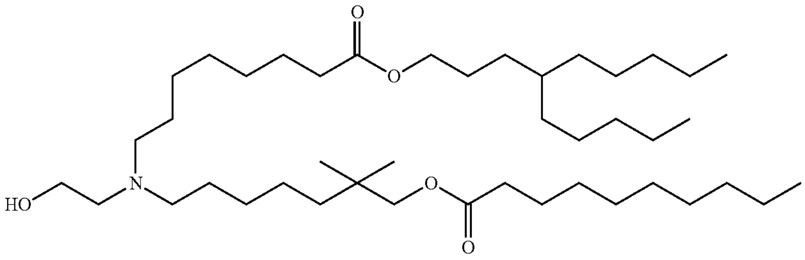 [SMILES: CCCCCCCCCC(=O)OCC(C)(C)CCCCCN(CCO)CCCCCCCC(=O)OCCCC(CCCCC)CCCCC]
11b TABLE I-continued
12b
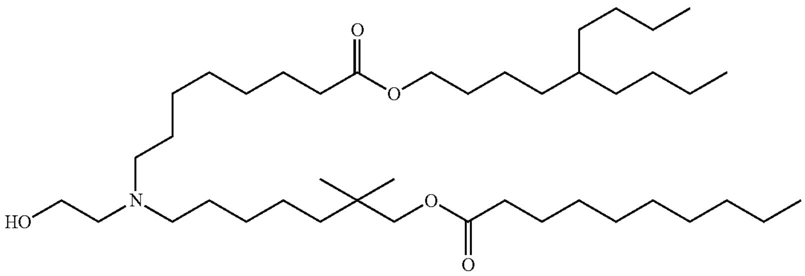 [SMILES: CCCCCCCCCC(=O)OCC(C)(C)CCCCCN(CCO)CCCCCCCC(=O)OCCCCC(CCCC)CCCC]
13b
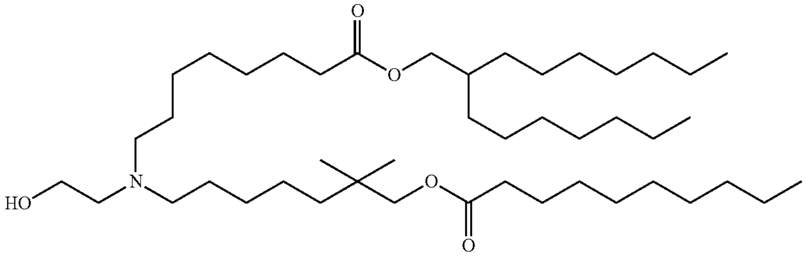 [SMILES: CCCCCCCCCC(=O)OCC(C)(C)CCCCCN(CCO)CCCCCCCC(=O)OCC(CCCCCCC)CCCCCCC]
14b
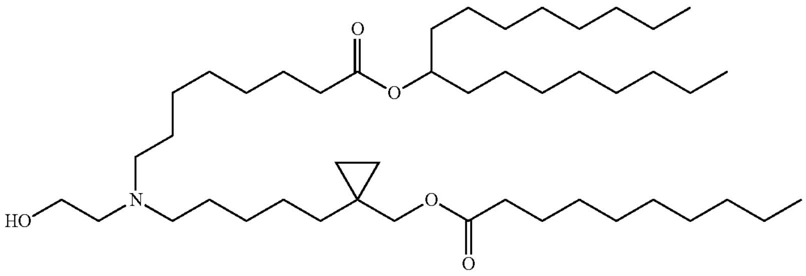 [SMILES: CCCCCCCCCC(=O)OCC1(CCCCCN(CCO)CCCCCCCC(=O)OC(CCCCCCCC)CCCCCCCC)CC1]
15b
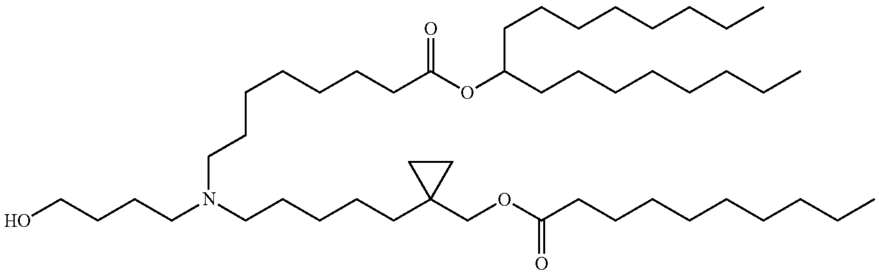 [SMILES: CCCCCCCCCC(=O)OCC1(CCCCCN(CCCCO)CCCCCCCC(=O)OC(CCCCCCCC)CCCCCCCC)CC1]
16b
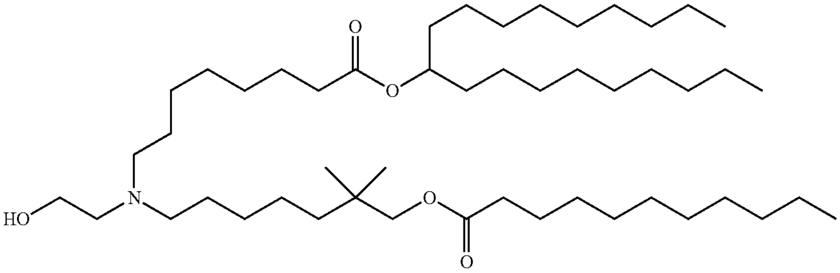 [SMILES: CCCCCCCCCCC(=O)OCC(C)(C)CCCCCN(CCO)CCCCCCCC(=O)OC(CCCCCCCCC)CCCCCCCCC]

TABLE I-continued
17b
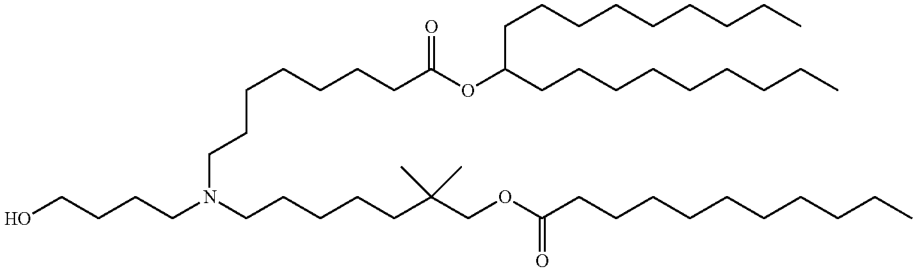 [SMILES: CCCCCCCCCCC(=O)OCC(C)(C)CCCCCN(CCCCO)CCCCCCCC(=O)OC(CCCCCCCCC)CCCCCCCCC]
18b
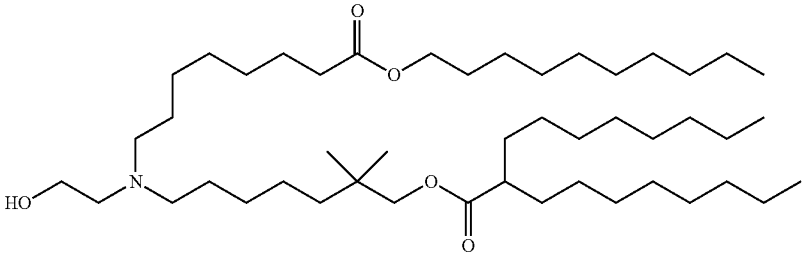 [SMILES: CCCCCCCCCCOC(=O)CCCCCCCN(CCO)CCCCCC(C)(C)COC(=O)C(CCCCCCCC)CCCCCCCC]
19b
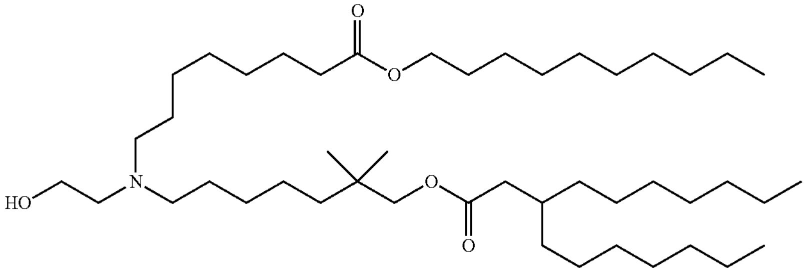 [SMILES: CCCCCCCCCCOC(=O)CCCCCCCN(CCO)CCCCCC(C)(C)COC(=O)CC(CCCCCCC)CCCCCCC]
20b
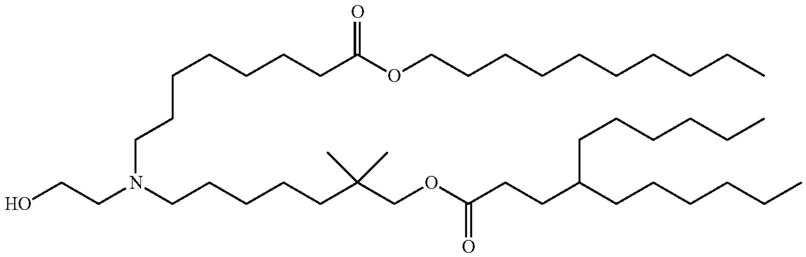 [SMILES: CCCCCCCCCCOC(=O)CCCCCCCN(CCO)CCCCCC(C)(C)COC(=O)CCC(CCCCCC)CCCCCC]
21b
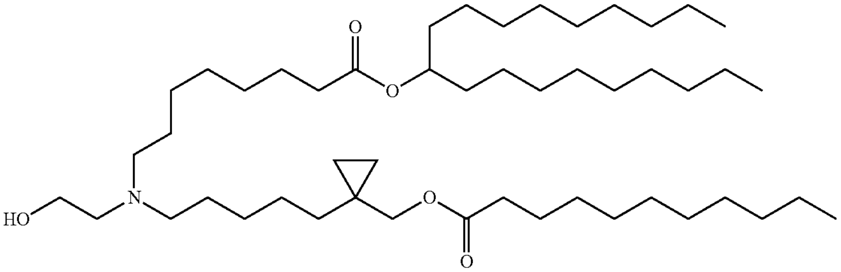 [SMILES: CCCCCCCCCCC(=O)OCC1(CCCCCN(CCO)CCCCCCCC(=O)OC(CCCCCCCCC)CCCCCCCCC)CC1]
22b
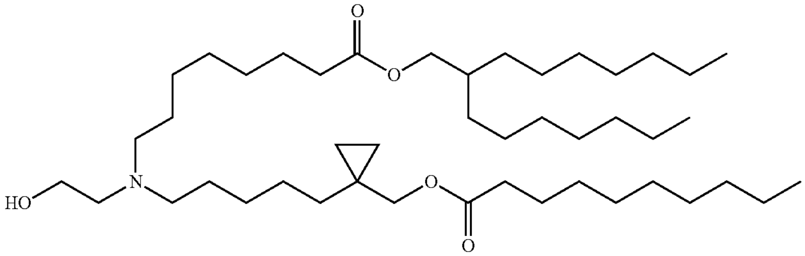 [SMILES: CCCCCCCCCC(=O)OCC1(CCCCCN(CCO)CCCCCCCC(=O)OCC(CCCCCCC)CCCCCCC)CC1]

TABLE I-continued
23b
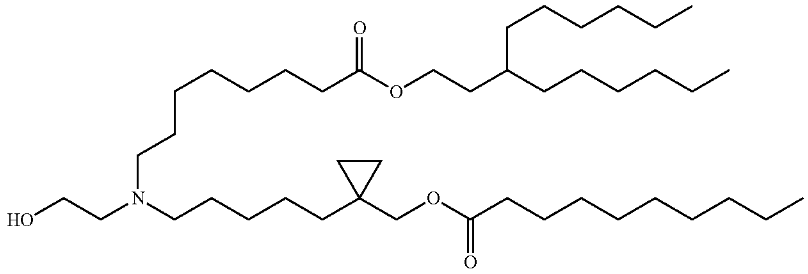 [SMILES: CCCCCCCCCC(=O)OCC1(CCCCCN(CCO)CCCCCCCC(=O)OCCC(CCCCCC)CCCCCC)CC1]
24b
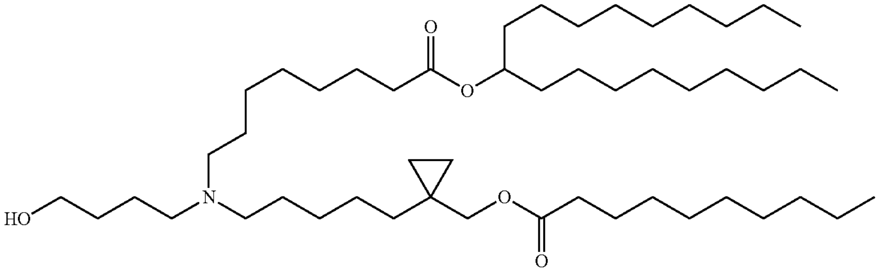 [SMILES: CCCCCCCCCC(=O)OCC1(CCCCCN(CCCCO)CCCCCCCC(=O)OC(CCCCCCCCC)CCCCCCCCC)CC1]
30a
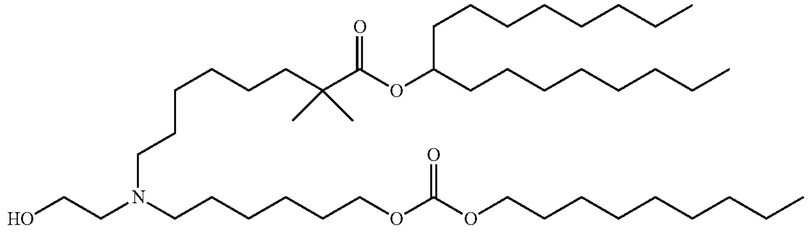 [SMILES: CCCCCCCCCOC(=O)OCCCCCCN(CCO)CCCCCCC(C)(C)C(=O)OC(CCCCCCCC)CCCCCCCC]
31a
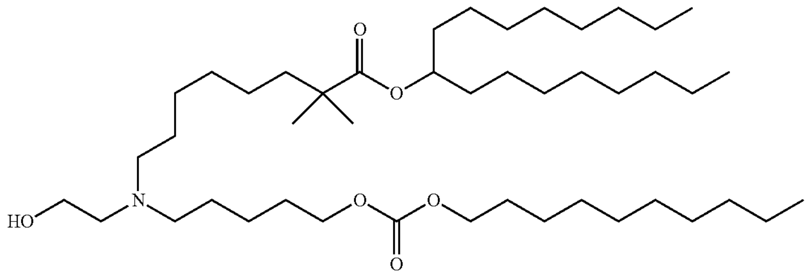
32a
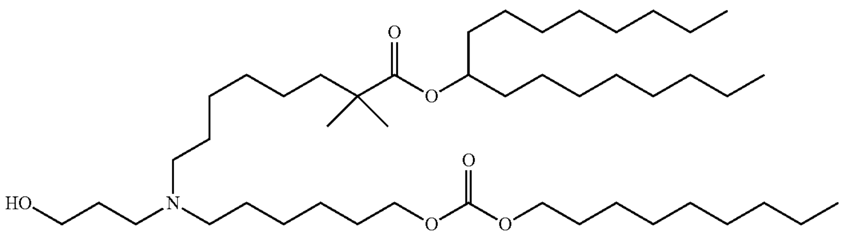 [SMILES: CCCCCCCCCOC(=O)OCCCCCCN(CCCO)CCCCCCC(C)(C)C(=O)OC(CCCCCCCC)CCCCCCCC]
33a
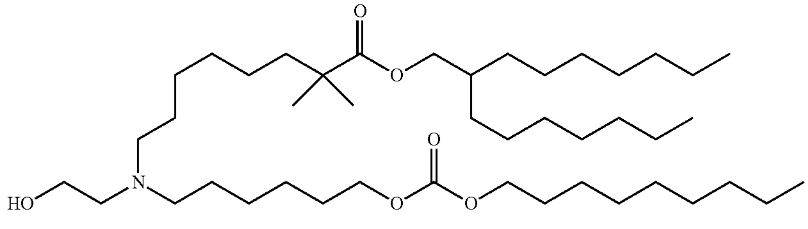 [SMILES: CCCCCCCCCOC(=O)OCCCCCCN(CCO)CCCCCCC(C)(C)C(=O)OCC(CCCCCCC)CCCCCCC]

TABLE I-continued
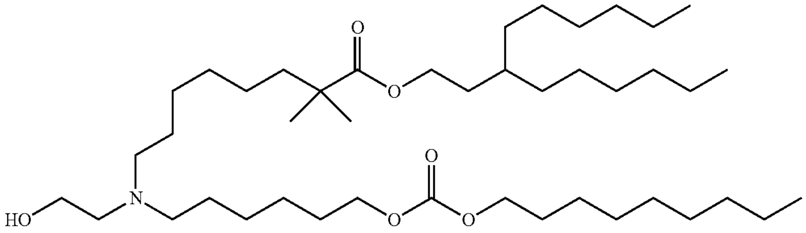 [SMILES: CCCCCCCCCOC(=O)OCCCCCCN(CCO)CCCCCCC(C)(C)C(=O)OCCC(CCCCCC)CCCCCC]
34a
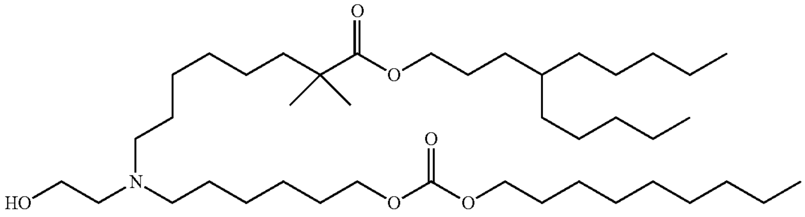 [SMILES: CCCCCCCCCOC(=O)OCCCCCCN(CCO)CCCCCCC(C)(C)C(=O)OCCCC(CCCCC)CCCCC]
35a
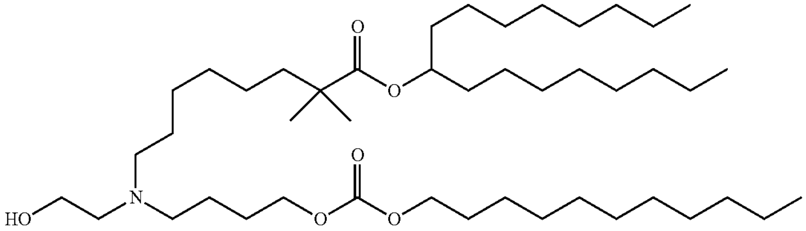 [SMILES: CCCCCCCCCCCOC(=O)OCCCCN(CCO)CCCCCCC(C)(C)C(=O)OC(CCCCCCCC)CCCCCCCC]
36a
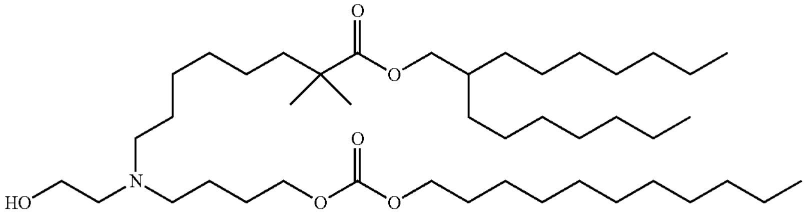 [SMILES: CCCCCCCCCCCOC(=O)OCCCCN(CCO)CCCCCCC(C)(C)C(=O)OCC(CCCCCCC)CCCCCCC]
37a
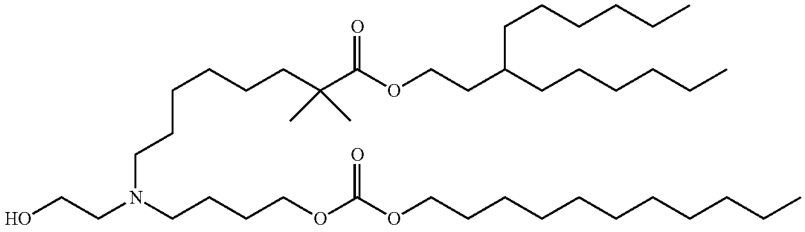 [SMILES: CCCCCCCCCCCOC(=O)OCCCCN(CCO)CCCCCCC(C)(C)C(=O)OCCC(CCCCCC)CCCCCC]
38a
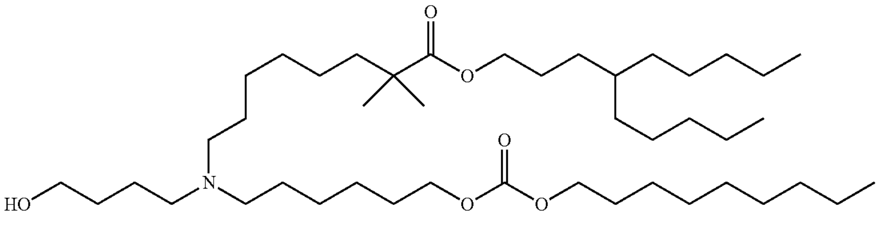 [SMILES: CCCCCCCCCOC(=O)OCCCCCCN(CCCCO)CCCCCCC(C)(C)C(=O)OCCCC(CCCCC)CCCCC]
39a
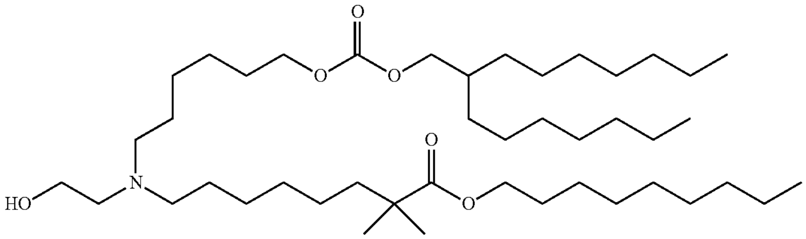 [SMILES: CCCCCCCCCOC(=O)C(C)(C)CCCCCCN(CCO)CCCCCCOC(=O)OCC(CCCCCCC)CCCCCCC]
40a TABLE I-continued
41a
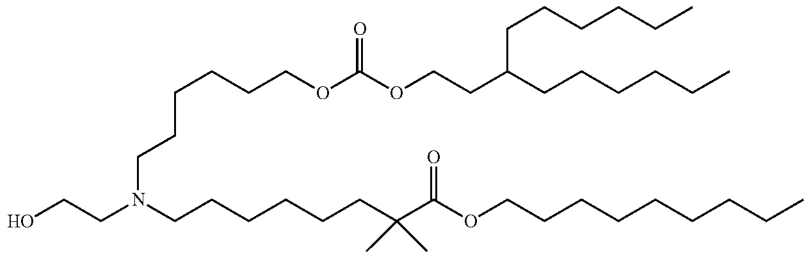 [SMILES: CCCCCCCCCOC(=O)C(C)(C)CCCCCCN(CCO)CCCCCCOC(=O)OCCC(CCCCCC)CCCCCC]
42a
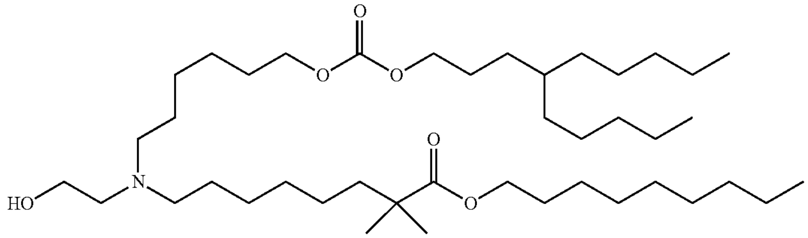 [SMILES: CCCCCCCCCOC(=O)C(C)(C)CCCCCCN(CCO)CCCCCCOC(=O)OCCCC(CCCCC)CCCCC]
43a
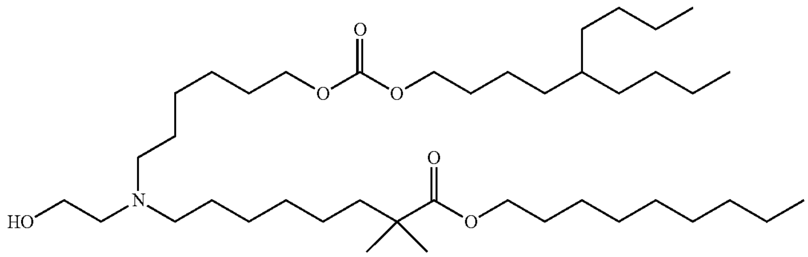 [SMILES: CCCCCCCCCOC(=O)C(C)(C)CCCCCCN(CCO)CCCCCCOC(=O)OCCCCC(CCCC)CCCC]
44a
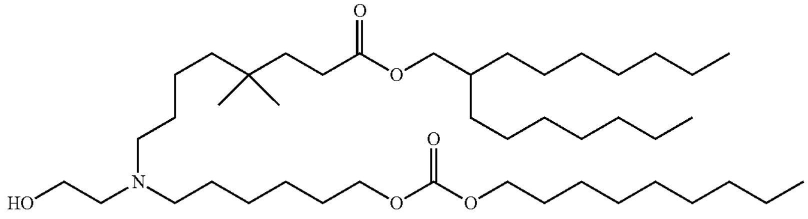 [SMILES: CCCCCCCCCOC(=O)OCCCCCCN(CCO)CCCCC(C)(C)CCC(=O)OCC(CCCCCCC)CCCCCCC]
45a
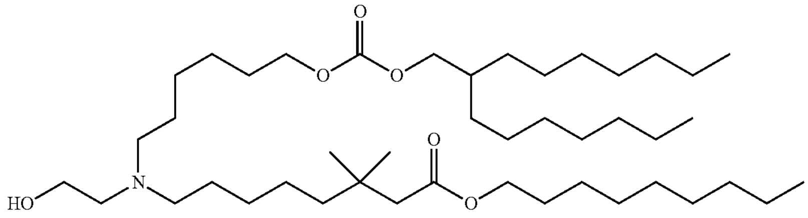 [SMILES: CCCCCCCCCOC(=O)CC(C)(C)CCCCCN(CCO)CCCCCCOC(=O)OCC(CCCCCCC)CCCCCCC]
46a
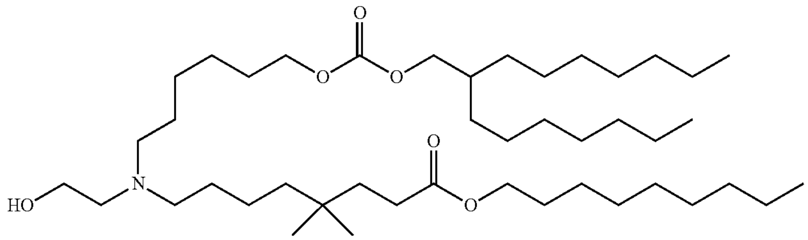 [SMILES: CCCCCCCCCOC(=O)CCC(C)(C)CCCCN(CCO)CCCCCCOC(=O)OCC(CCCCCCC)CCCCCCC]

TABLE I-continued
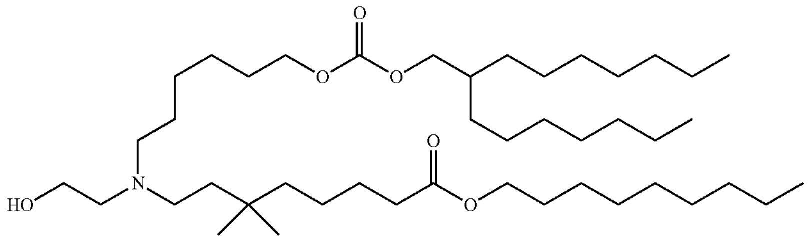
47a
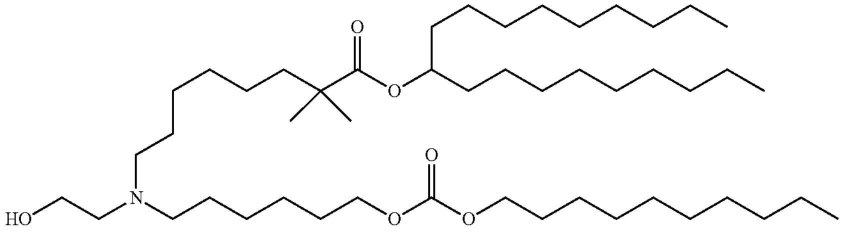 [SMILES: CCCCCCCCCCOC(=O)OCCCCCCN(CCO)CCCCCCC(C)(C)C(=O)OC(CCCCCCCCC)CCCCCCCCC]
48a
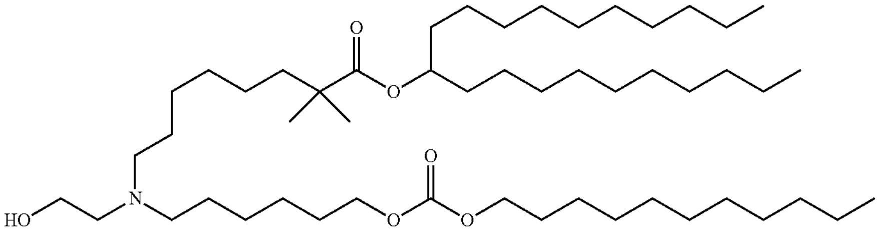 [SMILES: CCCCCCCCCCCOC(=O)OCCCCCCN(CCO)CCCCCCC(C)(C)C(=O)OC(CCCCCCCCCC)CCCCCCCCCC]
49a
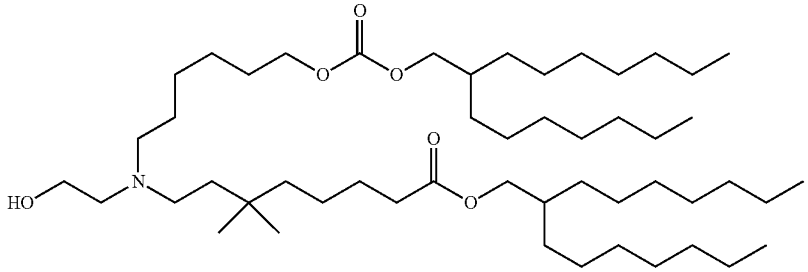 [SMILES: CCCCCCCC(CCCCCCC)COC(=O)CCCCC(C)(C)CCN(CCO)CCCCCCOC(=O)OCC(CCCCCCC)CCCCCCC]
50a
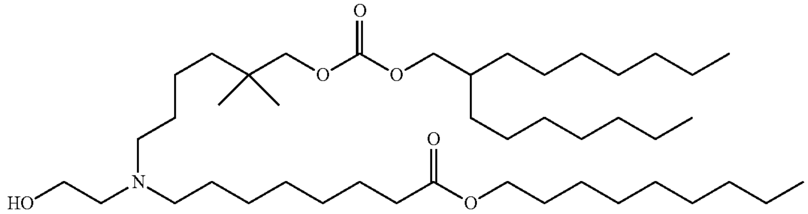 [SMILES: CCCCCCCCCOC(=O)CCCCCCCN(CCO)CCCCC(C)(C)COC(=O)OCC(CCCCCCC)CCCCCCC]
51a
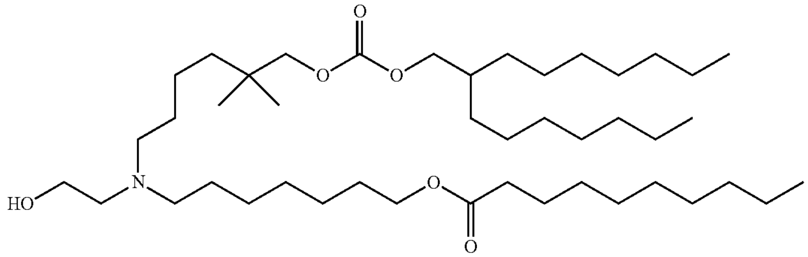 [SMILES: CCCCCCCCCC(=O)OCCCCCCCN(CCO)CCCCC(C)(C)COC(=O)OCC(CCCCCCC)CCCCCCC]
25b TABLE I-continued
26b
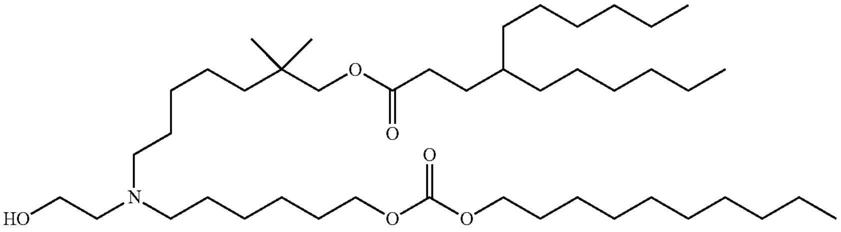 [SMILES: CCCCCCCCCCOC(=O)OCCCCCCN(CCO)CCCCCC(C)(C)COC(=O)CCC(CCCCCC)CCCCCC]
27b
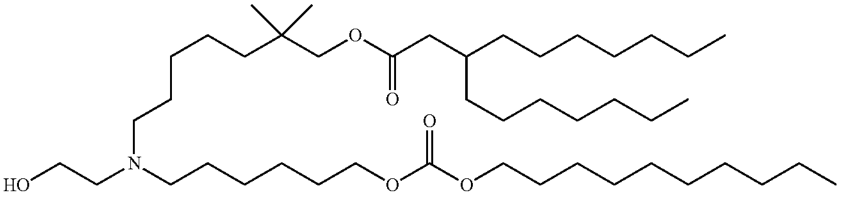 [SMILES: CCCCCCCCCCOC(=O)OCCCCCCN(CCO)CCCCCC(C)(C)COC(=O)CC(CCCCCCC)CCCCCCC]
28b
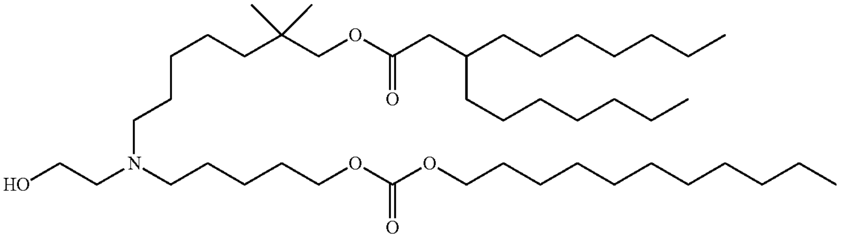 [SMILES: CCCCCCCCCCCOC(=O)OCCCCCN(CCO)CCCCCC(C)(C)COC(=O)CC(CCCCCCC)CCCCCCC]
29b
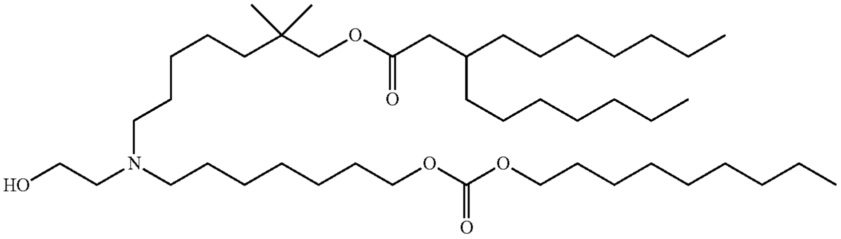 [SMILES: CCCCCCCCCOC(=O)OCCCCCCCN(CCO)CCCCCC(C)(C)COC(=O)CC(CCCCCCC)CCCCCCC]
30b
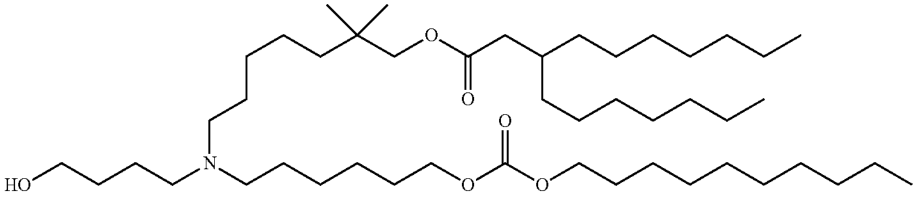 [SMILES: CCCCCCCCCCOC(=O)OCCCCCCN(CCCCO)CCCCCC(C)(C)COC(=O)CC(CCCCCCC)CCCCCCC]
31b
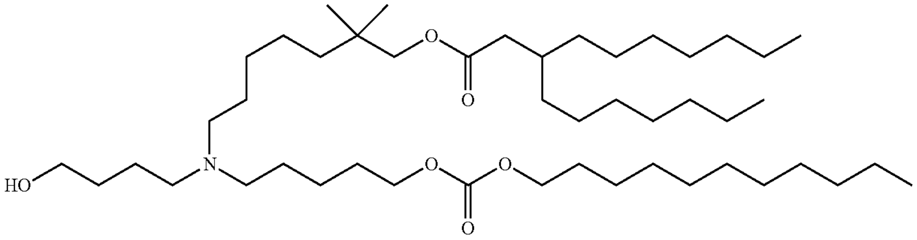 [SMILES: CCCCCCCCCCCOC(=O)OCCCCCN(CCCCO)CCCCCC(C)(C)COC(=O)CC(CCCCCCC)CCCCCCC]
32b
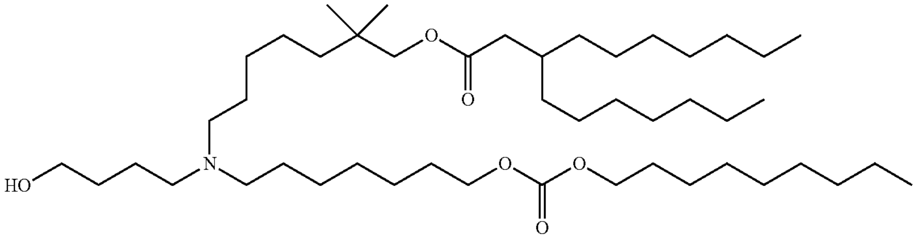 [SMILES: CCCCCCCCCOC(=O)OCCCCCCCN(CCCCO)CCCCCC(C)(C)COC(=O)CC(CCCCCCC)CCCCCCC]

TABLE I-continued
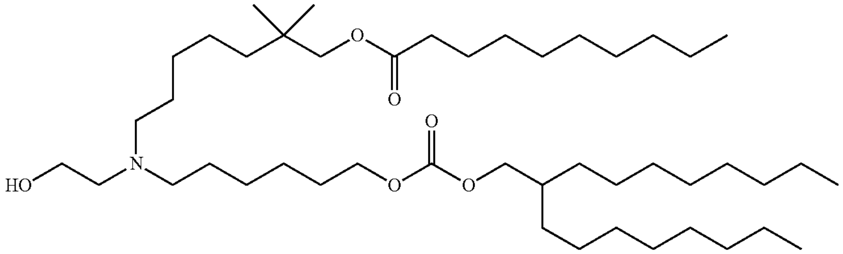 [SMILES: CCCCCCCCCC(=O)OCC(C)(C)CCCCCN(CCO)CCCCCCOC(=O)OCC(CCCCCCCC)CCCCCCCC]
33b
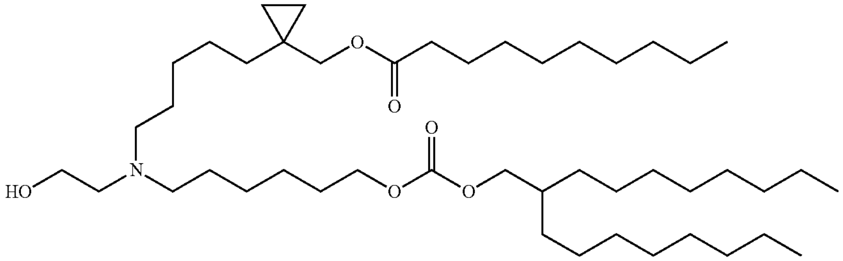 [SMILES: CCCCCCCCCC(=O)OCC1(CCCCCN(CCO)CCCCCCOC(=O)OCC(CCCCCCCC)CCCCCCCC)CC1]
34b
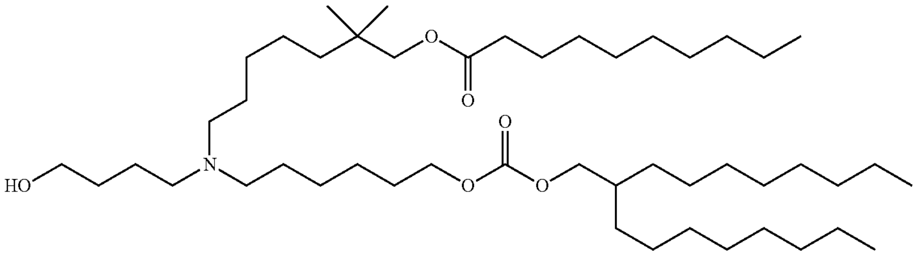 [SMILES: CCCCCCCCCC(=O)OCC(C)(C)CCCCCN(CCCCO)CCCCCCOC(=O)OCC(CCCCCCCC)CCCCCCCC]
35b
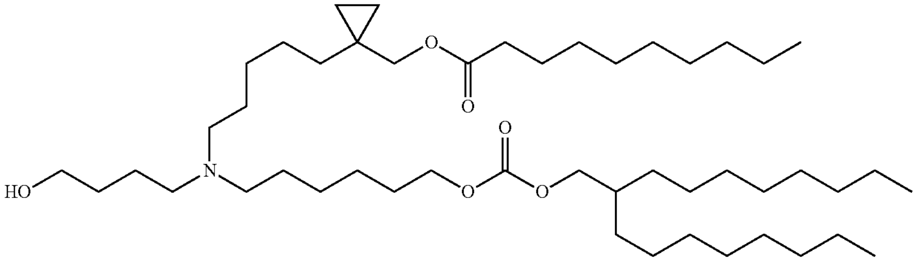 [SMILES: CCCCCCCCCC(=O)OCC1(CCCCCN(CCCCO)CCCCCCOC(=O)OCC(CCCCCCCC)CCCCCCCC)CC1]
36b
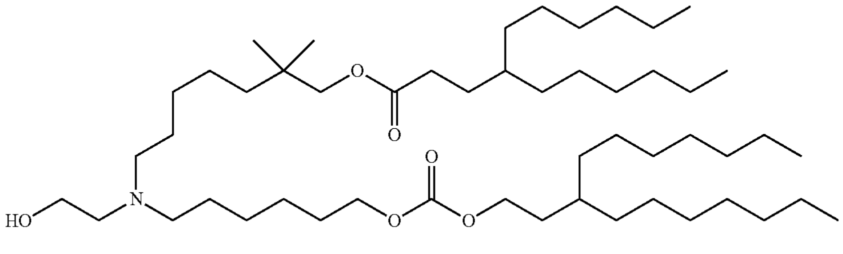 [SMILES: CCCCCCCC(CCCCCCC)CCOC(=O)OCCCCCCN(CCO)CCCCCC(C)(C)COC(=O)CCC(CCCCCC)CCCCCC]
37b
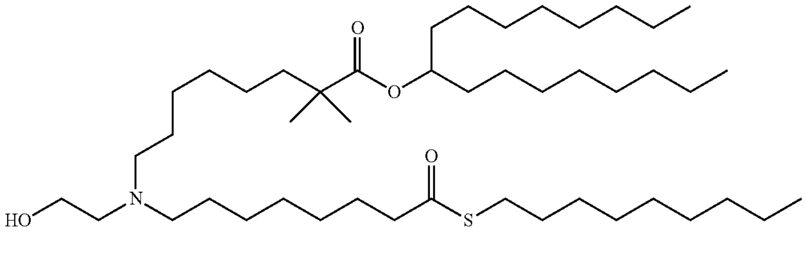
52a TABLE I-continued
53a
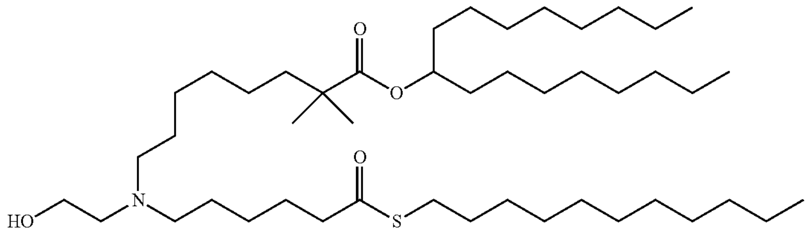
54a
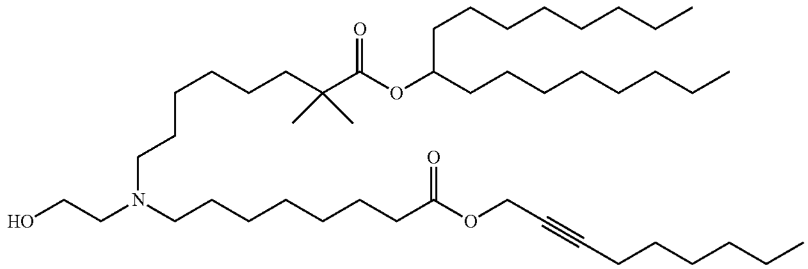 [SMILES: CCCCCCC#CCOC(=O)CCCCCCCN(CCO)CCCCCCC(C)(C)C(=O)OC(CCCCCCCC)CCCCCCCC]
55a
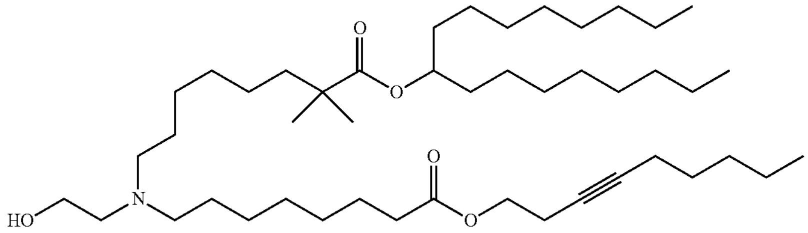 [SMILES: CCCCCC#CCCOC(=O)CCCCCCCN(CCO)CCCCCCC(C)(C)C(=O)OC(CCCCCCCC)CCCCCCCC]
56a
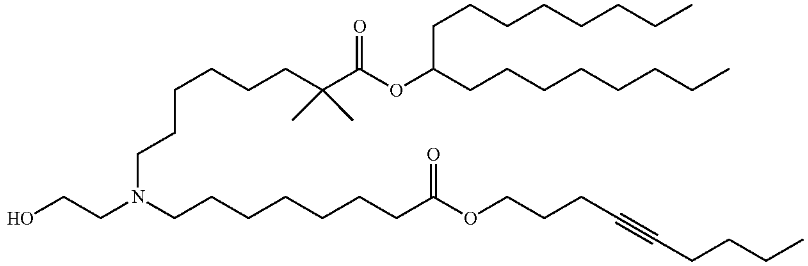 [SMILES: CCCCC#CCCCOC(=O)CCCCCCCN(CCO)CCCCCCC(C)(C)C(=O)OC(CCCCCCCC)CCCCCCCC]
57a
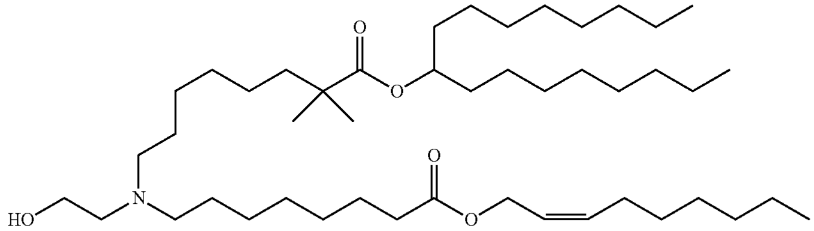 [SMILES: CCCCCC/C=C\COC(=O)CCCCCCCN(CCO)CCCCCCC(C)(C)C(=O)OC(CCCCCCCC)CCCCCCCC]
58a
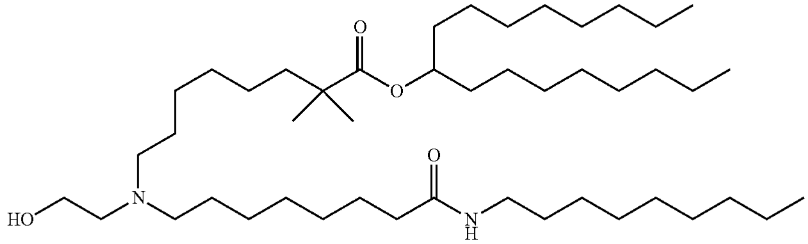 [SMILES: CCCCCCCCCNC(=O)CCCCCCCN(CCO)CCCCCCC(C)(C)C(=O)OC(CCCCCCCC)CCCCCCCC]

TABLE I-continued
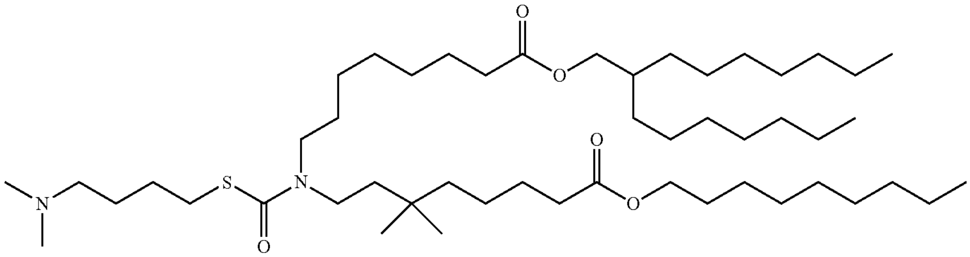 [SMILES: CCCCCCCCCOC(=O)CCCCC(C)(C)CCN(CCCCCCCC(=O)OCC(CCCCCCC)CCCCCCC)C(=O)SCCCCN(C)C]
59a
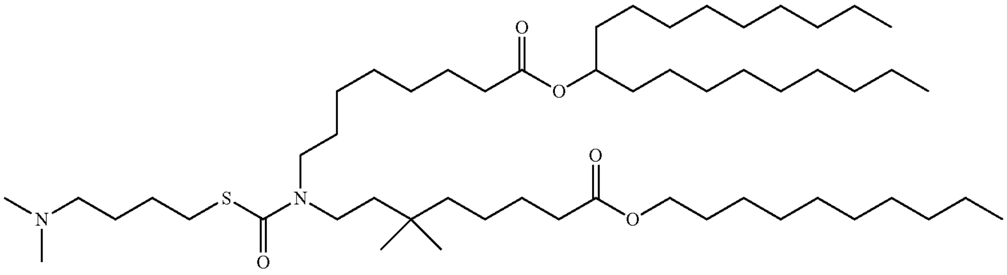 [SMILES: CCCCCCCCCCOC(=O)CCCCC(C)(C)CCN(CCCCCCCC(=O)OC(CCCCCCCCC)CCCCCCCCC)C(=O)SCCCCN(C)C]
60a
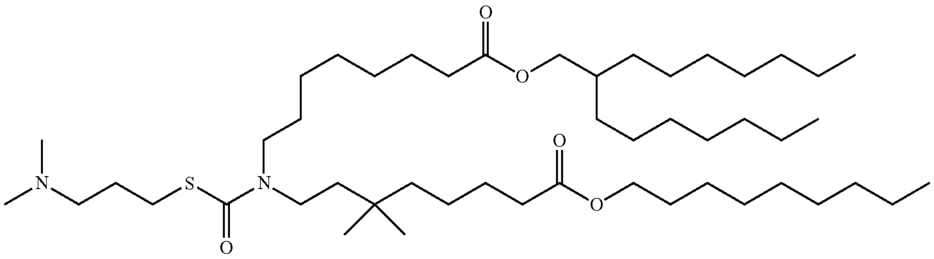 [SMILES: CCCCCCCCCOC(=O)CCCCC(C)(C)CCN(CCCCCCCC(=O)OCC(CCCCCCC)CCCCCCC)C(=O)SCCCN(C)C]
61a
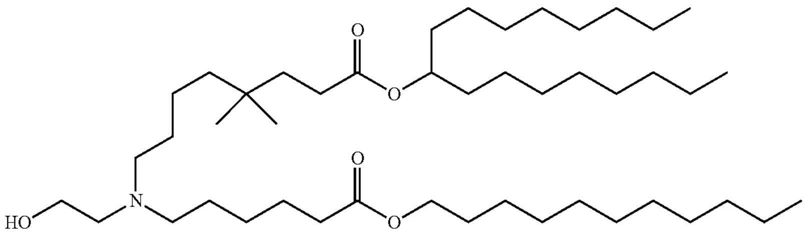 [SMILES: CCCCCCCCCCCOC(=O)CCCCCN(CCO)CCCCC(C)(C)CCC(=O)OC(CCCCCCCC)CCCCCCCC]
62a
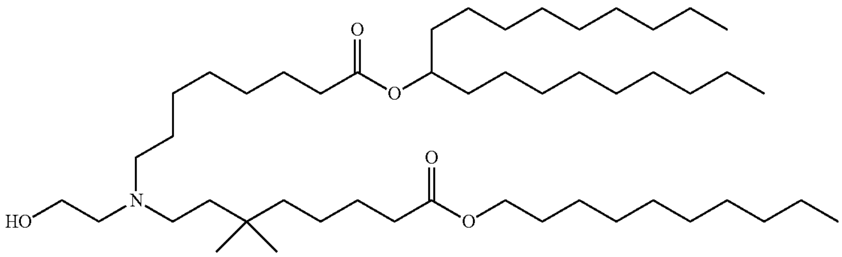 [SMILES: CCCCCCCCCCOC(=O)CCCCC(C)(C)CCN(CCO)CCCCCCCC(=O)OC(CCCCCCCCC)CCCCCCCCC]
63a
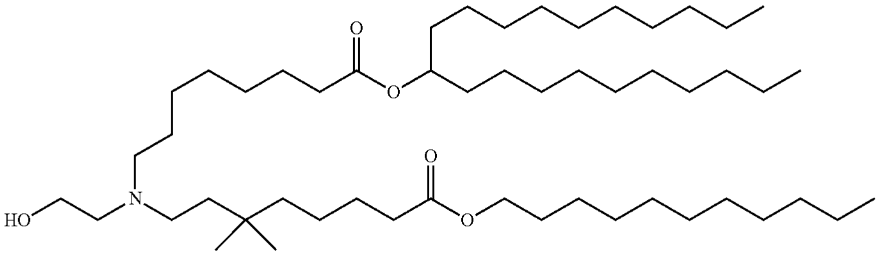 [SMILES: CCCCCCCCCCCOC(=O)CCCCC(C)(C)CCN(CCO)CCCCCCCC(=O)OC(CCCCCCCCCC)CCCCCCCCCC]
64a TABLE I-continued
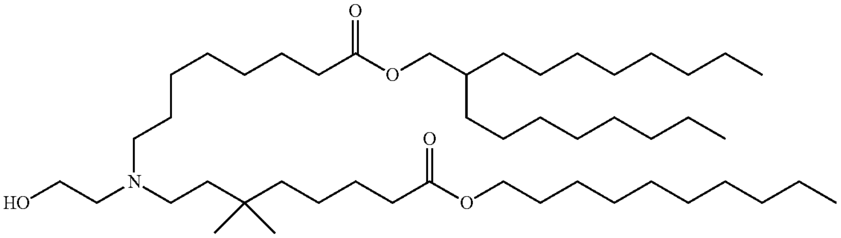 [SMILES: CCCCCCCCCCOC(=O)CCCCC(C)(C)CCN(CCO)CCCCCCCC(=O)OCC(CCCCCCCC)CCCCCCCC]
65a
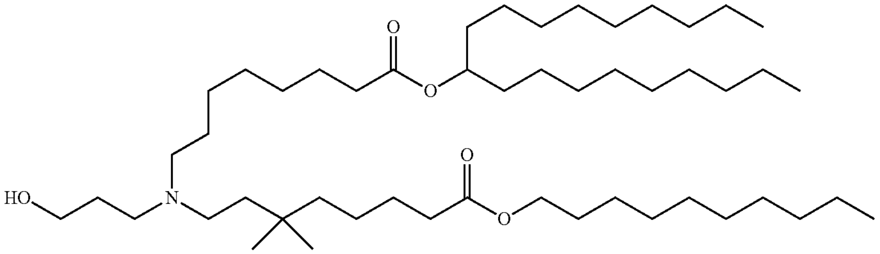 [SMILES: CCCCCCCCCCOC(=O)CCCCC(C)(C)CCN(CCCO)CCCCCCCC(=O)OC(CCCCCCCCC)CCCCCCCCC]
66a
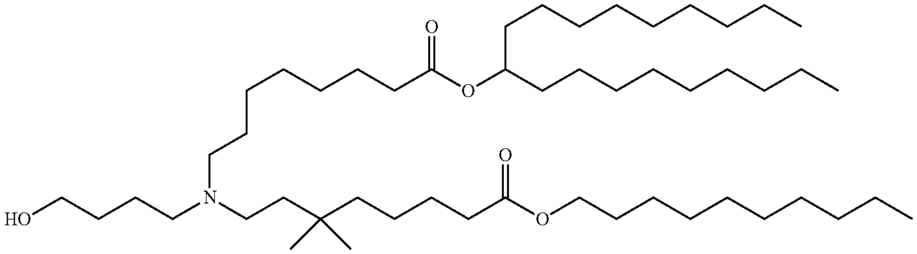 [SMILES: CCCCCCCCCCOC(=O)CCCCC(C)(C)CCN(CCCCO)CCCCCCCC(=O)OC(CCCCCCCCC)CCCCCCCCC]
67a
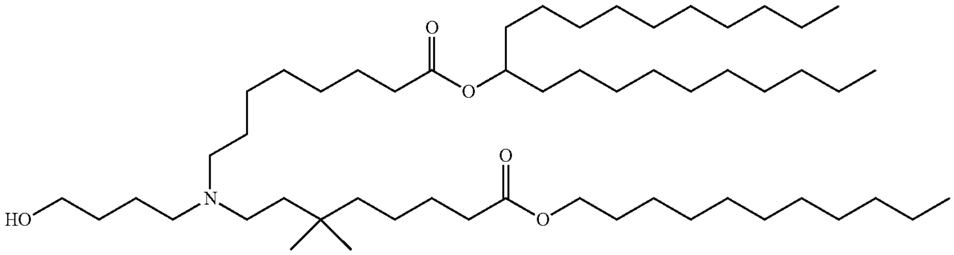 [SMILES: CCCCCCCCCCCOC(=O)CCCCC(C)(C)CCN(CCCCO)CCCCCCCC(=O)OC(CCCCCCCCCC)CCCCCCCCCC]
68a
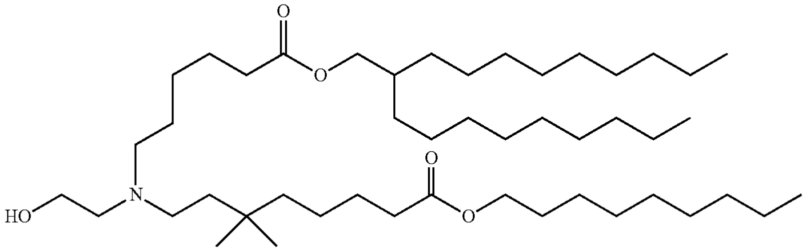 [SMILES: CCCCCCCCCOC(=O)CCCCC(C)(C)CCN(CCO)CCCCCC(=O)OCC(CCCCCCCCC)CCCCCCCCC]
69a
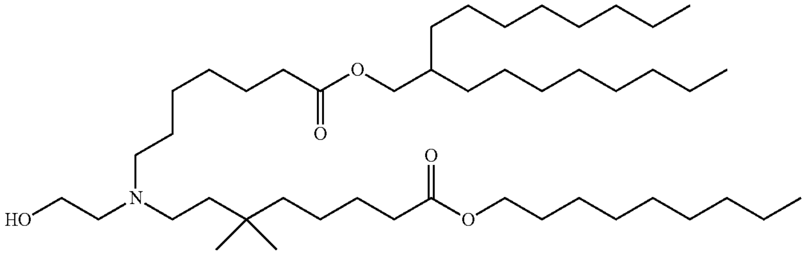 [SMILES: CCCCCCCCCOC(=O)CCCCC(C)(C)CCN(CCO)CCCCCCC(=O)OCC(CCCCCCCC)CCCCCCCC]
70a TABLE I-continued
38b
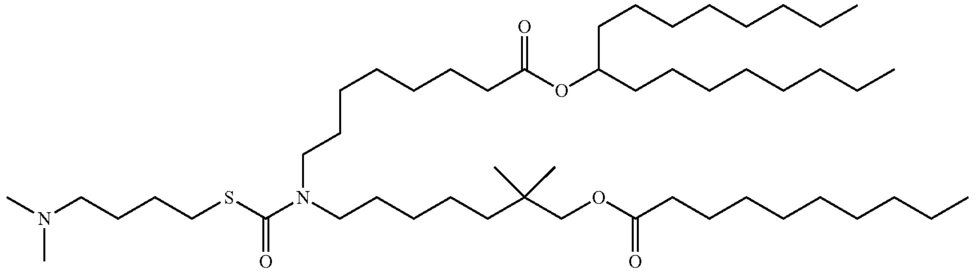 [SMILES: CCCCCCCCCC(=O)OCC(C)(C)CCCCCN(CCCCCCCC(=O)OC(CCCCCCCC)CCCCCCCC)C(=O)SCCCCN(C)C]
39b
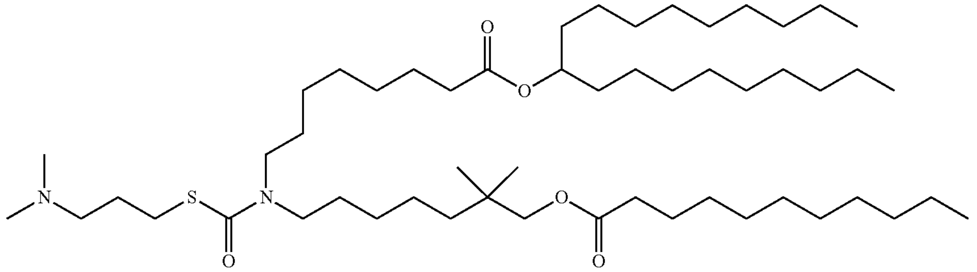 [SMILES: CCCCCCCCCCC(=O)OCC(C)(C)CCCCCN(CCCCCCCC(=O)OC(CCCCCCCCC)CCCCCCCCC)C(=O)SCCCN(C)C]
40b
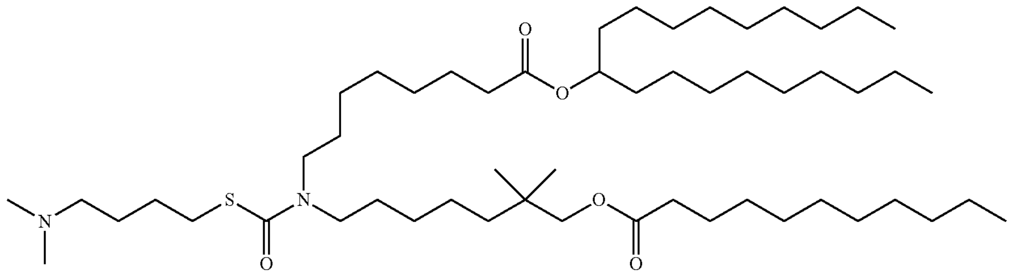 [SMILES: CCCCCCCCCCC(=O)OCC(C)(C)CCCCCN(CCCCCCCC(=O)OC(CCCCCCCCC)CCCCCCCCC)C(=O)SCCCCN(C)C]
41b
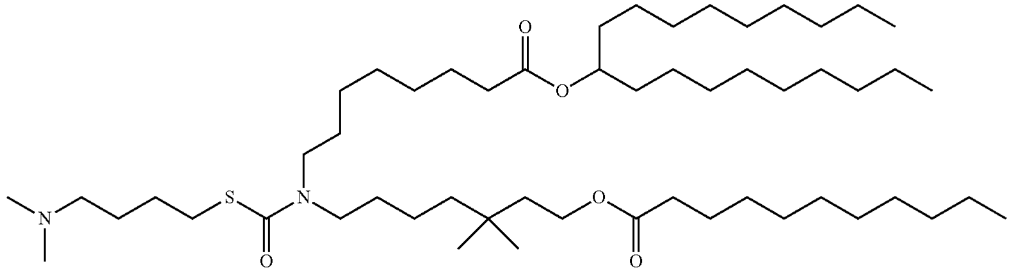 [SMILES: CCCCCCCCCCC(=O)OCCC(C)(C)CCCCN(CCCCCCCC(=O)OC(CCCCCCCCC)CCCCCCCCC)C(=O)SCCCCN(C)C]
42b
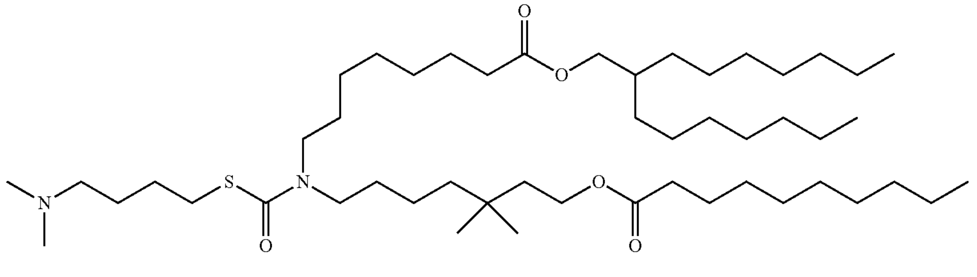 [SMILES: CCCCCCCCCC(=O)OCCC(C)(C)CCCCN(CCCCCCCC(=O)OCC(CCCCCCC)CCCCCCC)C(=O)SCCCCN(C)C]
43b
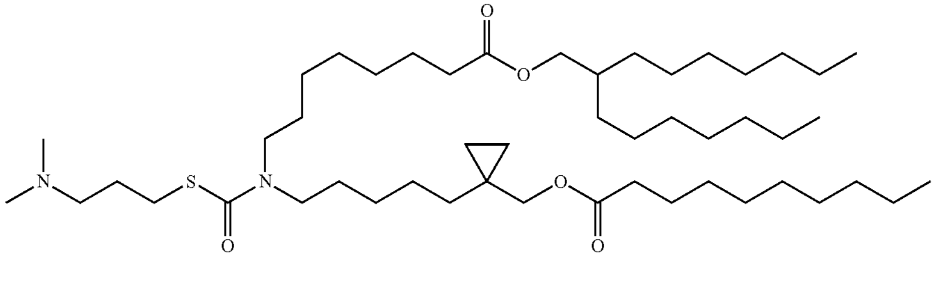 [SMILES: CCCCCCCCCC(=O)OCC1(CCCCCN(CCCCCCCC(=O)OCC(CCCCCCC)CCCCCCC)C(=O)SCCCN(C)C)CC1]

TABLE I-continued
44b
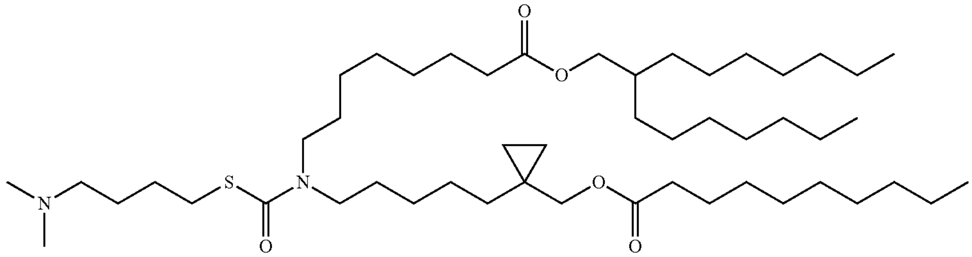 [SMILES: CCCCCCCCCC(=O)OCC1(CCCCCN(CCCCCCCC(=O)OCC(CCCCCCC)CCCCCCC)C(=O)SCCCCN(C)C)CC1]
45b
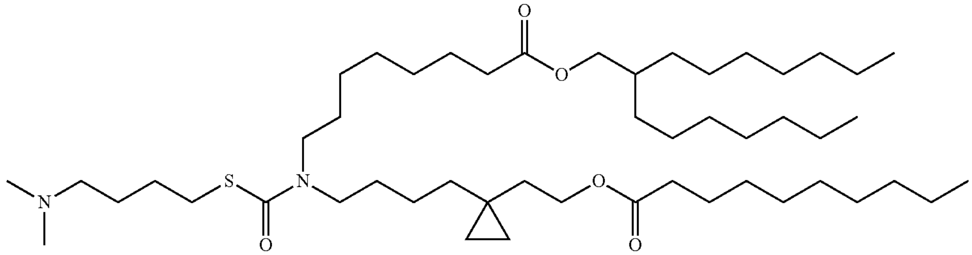 [SMILES: CCCCCCCCCC(=O)OCCC1(CCCCN(CCCCCCCC(=O)OCC(CCCCCCC)CCCCCCC)C(=O)SCCCCN(C)C)CC1]
46b
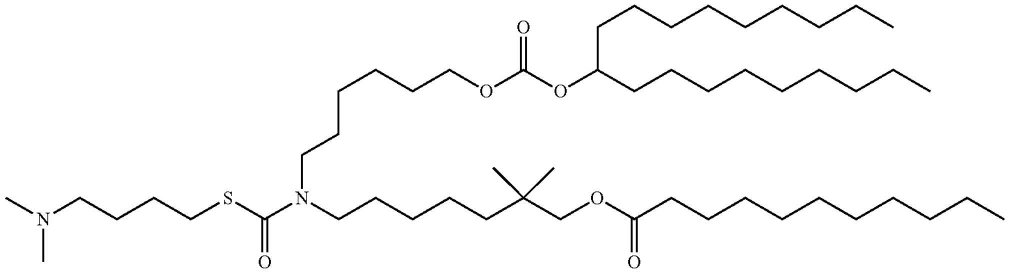 [SMILES: CCCCCCCCCCC(=O)OCC(C)(C)CCCCCN(CCCCCCOC(=O)OC(CCCCCCCCC)CCCCCCCCC)C(=O)SCCCCN(C)C]
47b
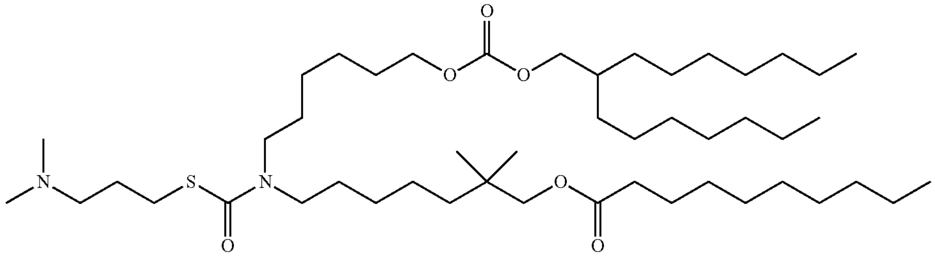 [SMILES: CCCCCCCCCC(=O)OCC(C)(C)CCCCCN(CCCCCCOC(=O)OCC(CCCCCCC)CCCCCCC)C(=O)SCCCN(C)C]
48b
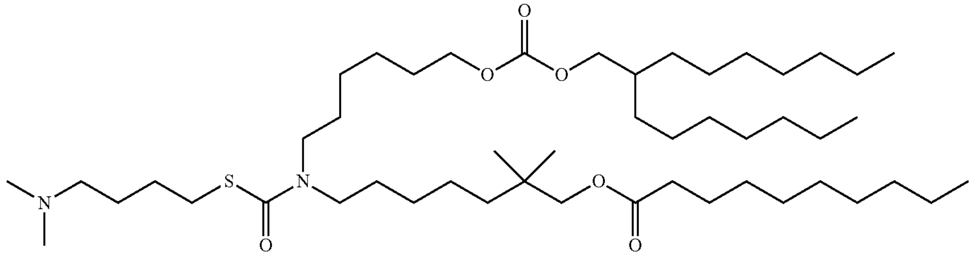 [SMILES: CCCCCCCCCC(=O)OCC(C)(C)CCCCCN(CCCCCCOC(=O)OCC(CCCCCCC)CCCCCCC)C(=O)SCCCCN(C)C]
49b
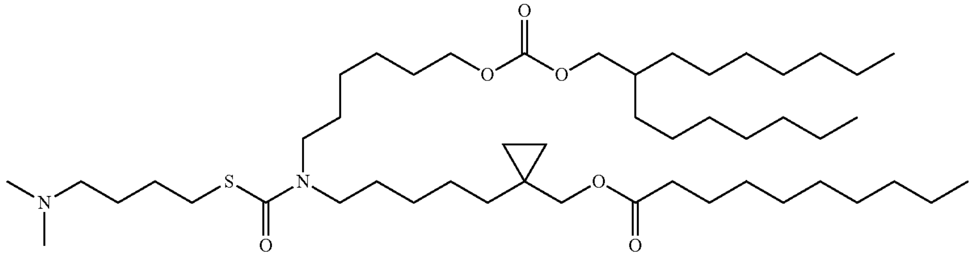

TABLE I-continued
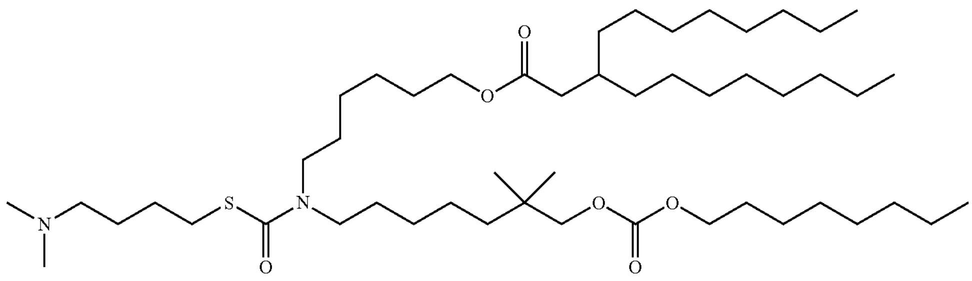 [SMILES: CCCCCCCCOC(=O)OCC(C)(C)CCCCCN(CCCCCCOC(=O)CC(CCCCCCCC)CCCCCCCC)C(=O)SCCCCN(C)C]
50b
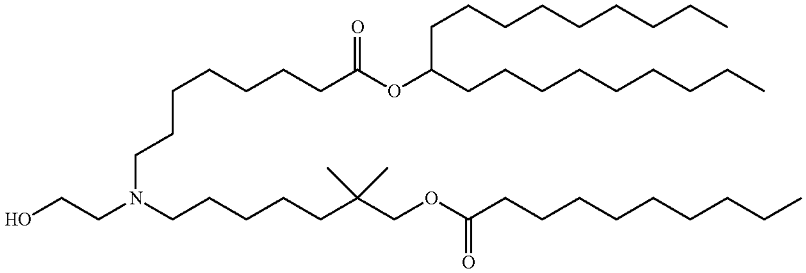 [SMILES: CCCCCCCCCC(=O)OCC(C)(C)CCCCCN(CCO)CCCCCCCC(=O)OC(CCCCCCCCC)CCCCCCCCC]
51b
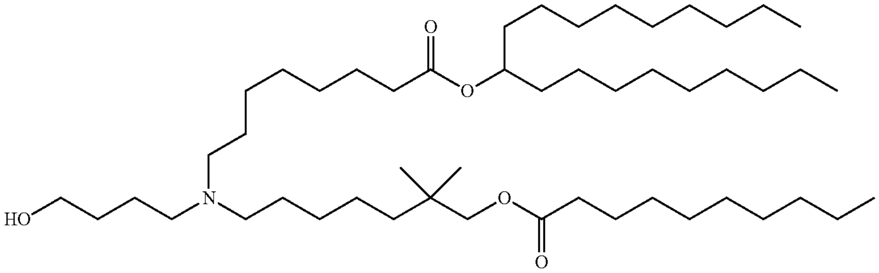 [SMILES: CCCCCCCCCC(=O)OCC(C)(C)CCCCCN(CCCCO)CCCCCCCC(=O)OC(CCCCCCCCC)CCCCCCCCC]
52b
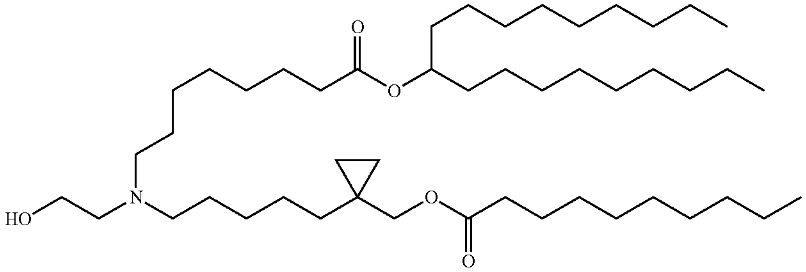 [SMILES: CCCCCCCCCC(=O)OCC1(CCCCCN(CCO)CCCCCCCC(=O)OC(CCCCCCCCC)CCCCCCCCC)CC1]
53b
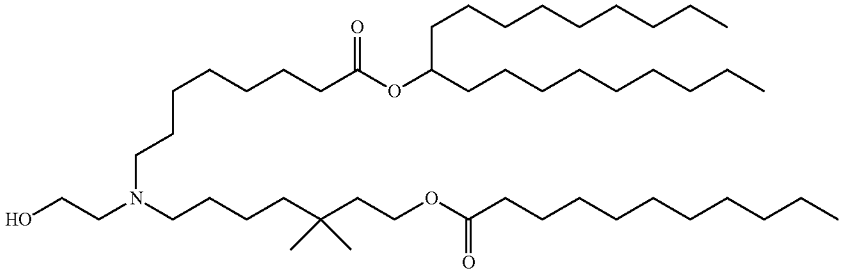 [SMILES: CCCCCCCCCCC(=O)OCCC(C)(C)CCCCN(CCO)CCCCCCCC(=O)OC(CCCCCCCCC)CCCCCCCCC]
54b TABLE I-continued
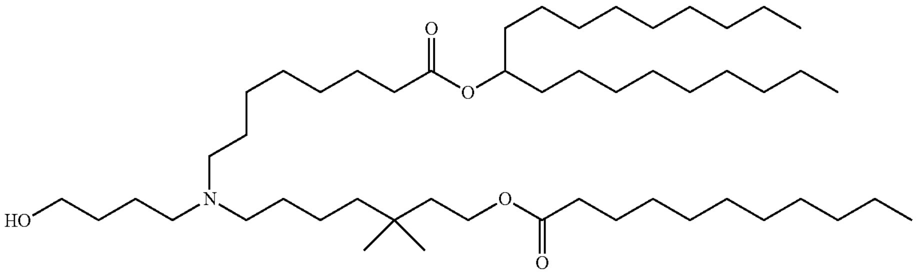 [SMILES: CCCCCCCCCCC(=O)OCCC(C)(C)CCCCN(CCCCO)CCCCCCCC(=O)OC(CCCCCCCCC)CCCCCCCCC]
55b
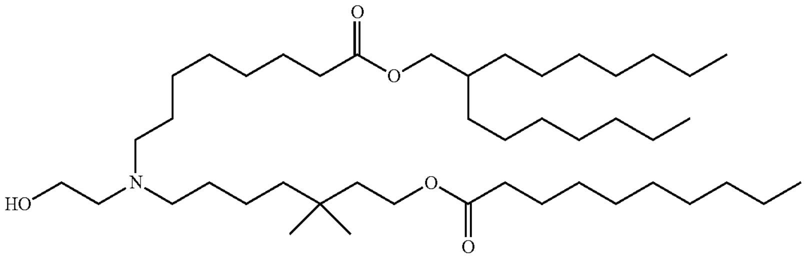 [SMILES: CCCCCCCCCC(=O)OCCC(C)(C)CCCCN(CCO)CCCCCCCC(=O)OCC(CCCCCCC)CCCCCCC]
56b
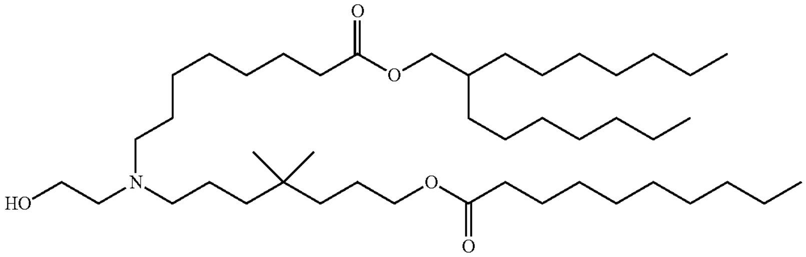 [SMILES: CCCCCCCCCC(=O)OCCCC(C)(C)CCCN(CCO)CCCCCCCC(=O)OCC(CCCCCCC)CCCCCCC]
57b
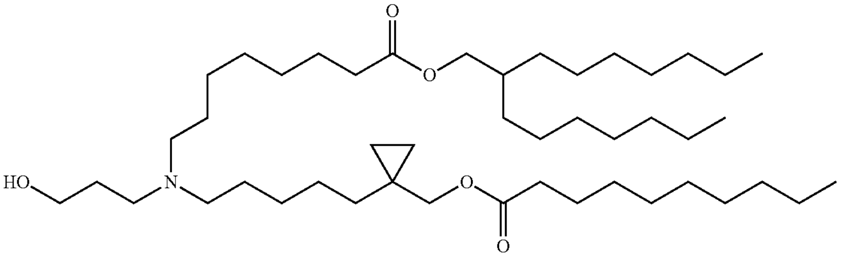 [SMILES: CCCCCCCCCC(=O)OCC1(CCCCCN(CCCO)CCCCCCCC(=O)OCC(CCCCCCC)CCCCCCC)CC1]
58b
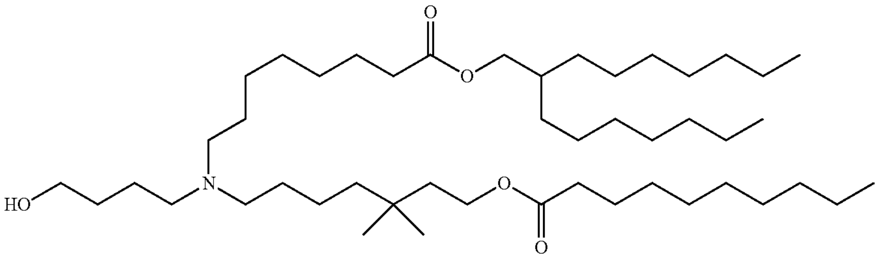 [SMILES: CCCCCCCCCC(=O)OCCC(C)(C)CCCCN(CCCCO)CCCCCCCC(=O)OCC(CCCCCCC)CCCCCCC]
59b
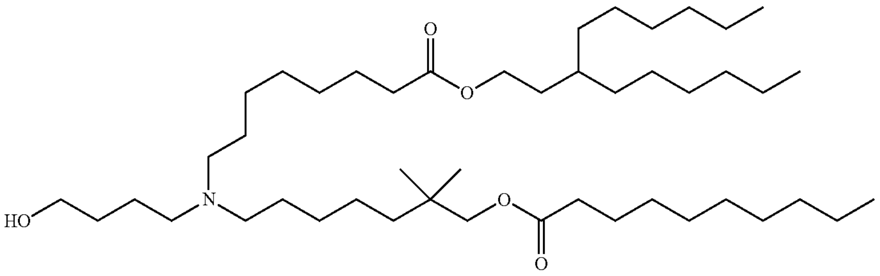 [SMILES: CCCCCCCCCC(=O)OCC(C)(C)CCCCCN(CCCCO)CCCCCCCC(=O)OCCC(CCCCCC)CCCCCC]
60b TABLE I-continued
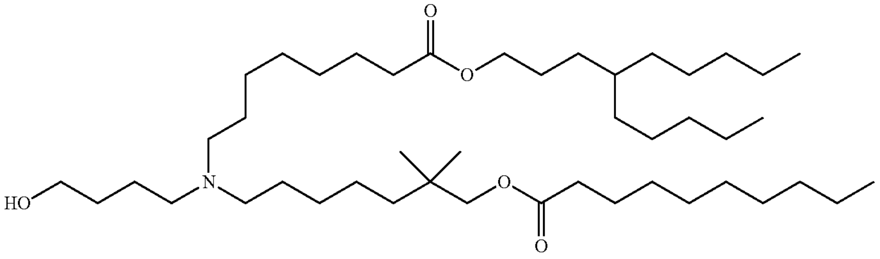 [SMILES: CCCCCCCCCC(=O)OCC(C)(C)CCCCCN(CCCCO)CCCCCCCC(=O)OCCCC(CCCCC)CCCCC]
61b
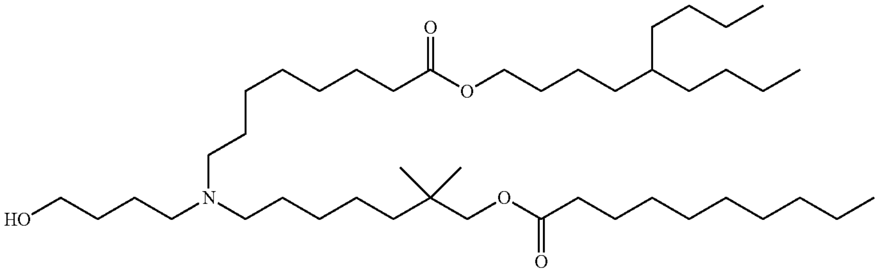 [SMILES: CCCCCCCCCC(=O)OCC(C)(C)CCCCCN(CCCCO)CCCCCCCC(=O)OCCCCC(CCCC)CCCC]
62b
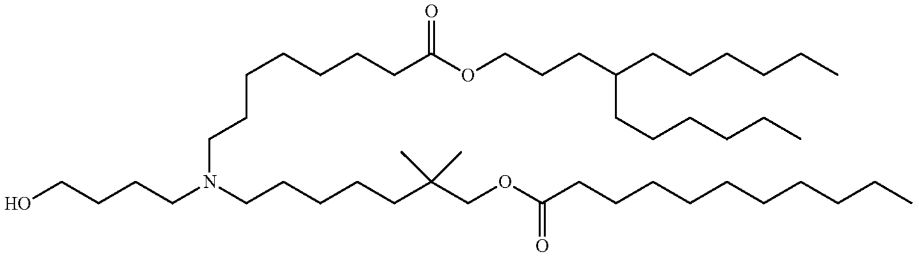 [SMILES: CCCCCCCCCCC(=O)OCC(C)(C)CCCCCN(CCCCO)CCCCCCCC(=O)OCCCC(CCCCCC)CCCCCC]
63b
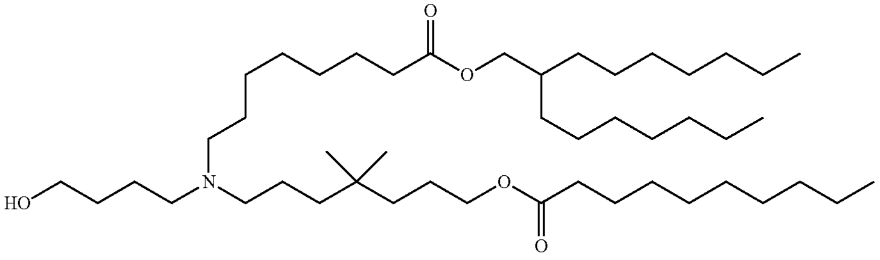 [SMILES: CCCCCCCCCC(=O)OCCCC(C)(C)CCCN(CCCCO)CCCCCCCC(=O)OCC(CCCCCCC)CCCCCCC]
64b
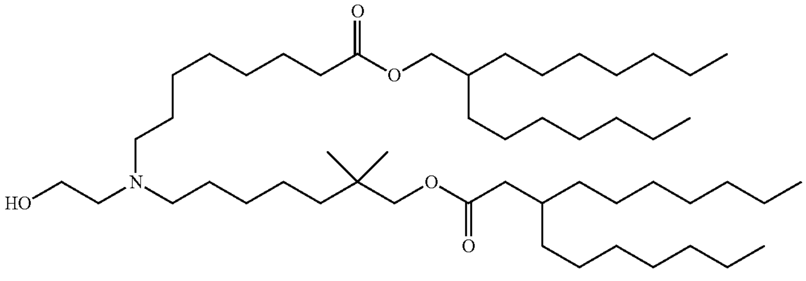 [SMILES: CCCCCCCC(CCCCCCC)COC(=O)CCCCCCCN(CCO)CCCCCC(C)(C)COC(=O)CC(CCCCCCC)CCCCCCC]
65b
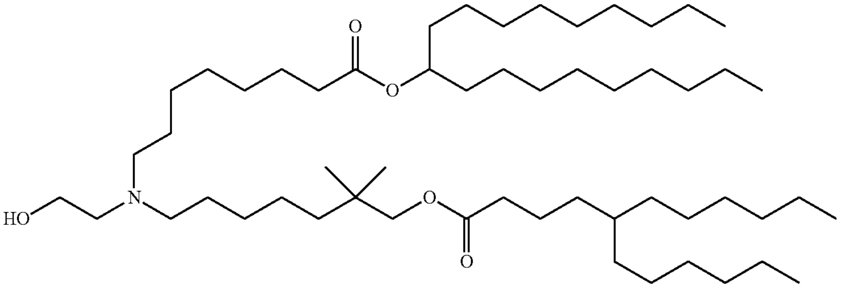 [SMILES: CCCCCCCCCC(CCCCCCCCC)OC(=O)CCCCCCCN(CCO)CCCCCC(C)(C)COC(=O)CCCC(CCCCCC)CCCCCC]
66b TABLE I-continued
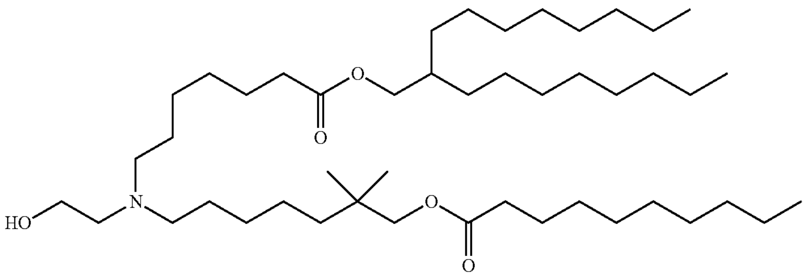 [SMILES: CCCCCCCCCC(=O)OCC(C)(C)CCCCCN(CCO)CCCCCCC(=O)OCC(CCCCCCCC)CCCCCCCC]
67b
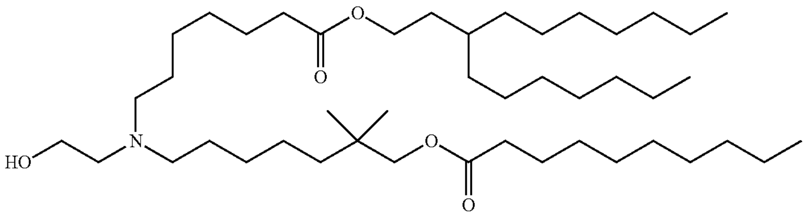 [SMILES: CCCCCCCCCC(=O)OCC(C)(C)CCCCCN(CCO)CCCCCCC(=O)OCCC(CCCCCCC)CCCCCCC]
68b
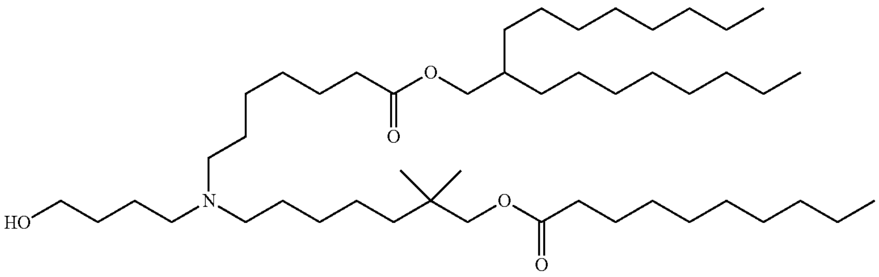 [SMILES: CCCCCCCCCC(=O)OCC(C)(C)CCCCCN(CCCCO)CCCCCCC(=O)OCC(CCCCCCCC)CCCCCCCC]
69b
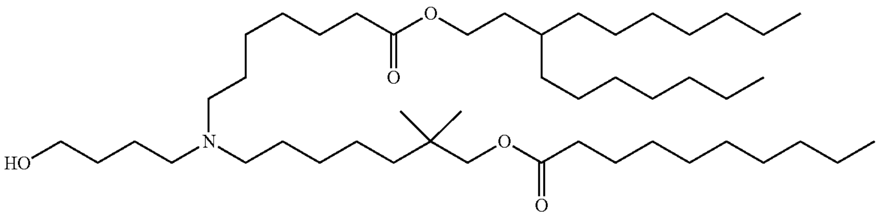 [SMILES: CCCCCCCCCC(=O)OCC(C)(C)CCCCCN(CCCCO)CCCCCCC(=O)OCCC(CCCCCCC)CCCCCCC]
70b
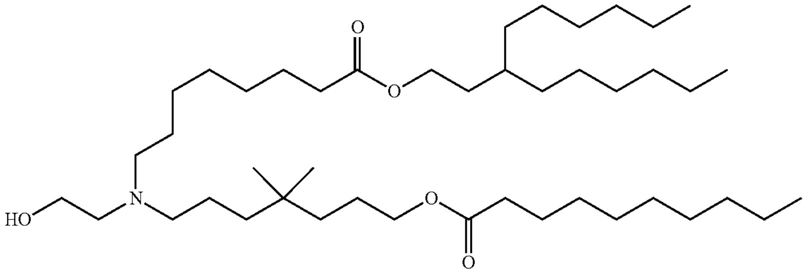 [SMILES: CCCCCCCCCC(=O)OCCCC(C)(C)CCCN(CCO)CCCCCCCC(=O)OCCC(CCCCCC)CCCCCC]
71b
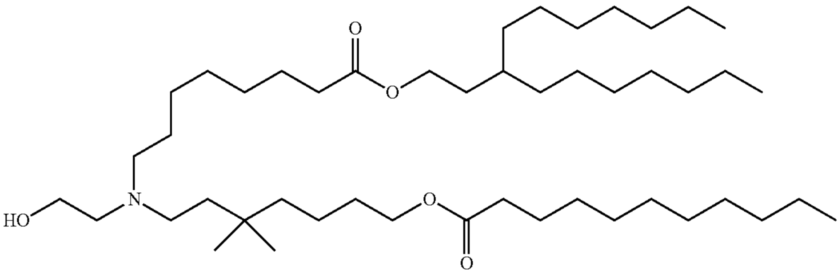 [SMILES: CCCCCCCCCCC(=O)OCCCCC(C)(C)CCN(CCO)CCCCCCCC(=O)OCCC(CCCCCCC)CCCCCCC]
72b TABLE I-continued
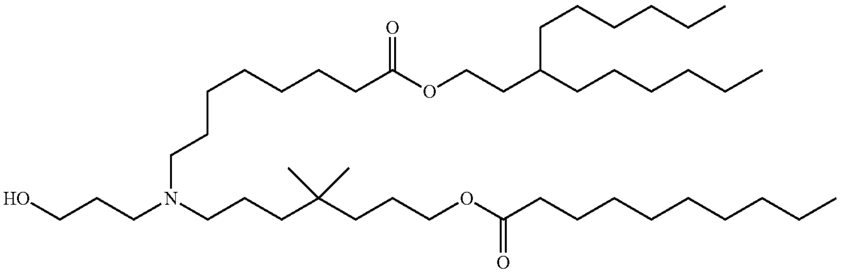 [SMILES: CCCCCCCCCC(=O)OCCCC(C)(C)CCCN(CCCO)CCCCCCCC(=O)OCCC(CCCCCC)CCCCCC]
73b
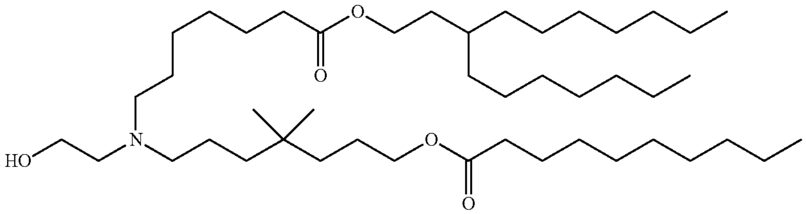 [SMILES: CCCCCCCCCC(=O)OCCCC(C)(C)CCCN(CCO)CCCCCCC(=O)OCCC(CCCCCCC)CCCCCCC]
74b
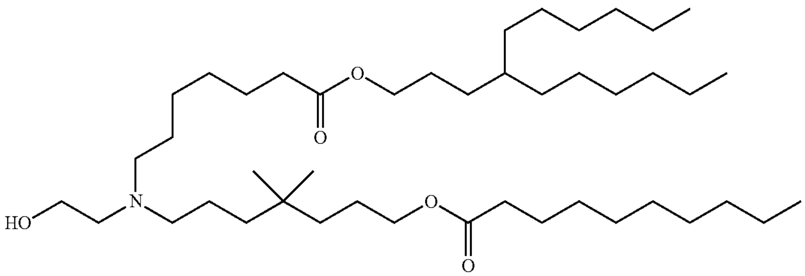 [SMILES: CCCCCCCCCC(=O)OCCCC(C)(C)CCCN(CCO)CCCCCCC(=O)OCCCC(CCCCCC)CCCCCC]
75b
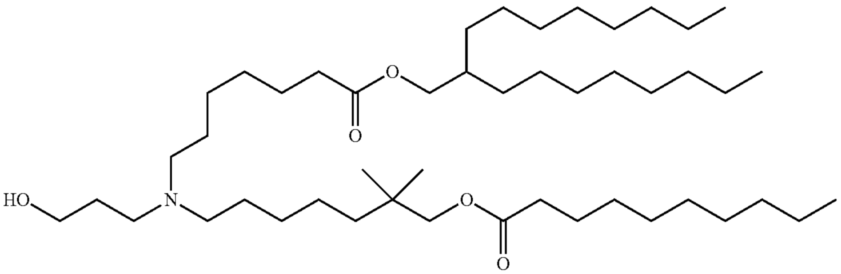 [SMILES: CCCCCCCCCC(=O)OCC(C)(C)CCCCCN(CCCO)CCCCCCC(=O)OCC(CCCCCCCC)CCCCCCCC]
76b
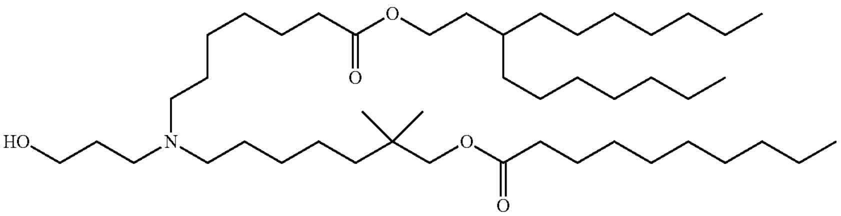 [SMILES: CCCCCCCCCC(=O)OCC(C)(C)CCCCCN(CCCO)CCCCCCC(=O)OCCC(CCCCCCC)CCCCCCC]
77b
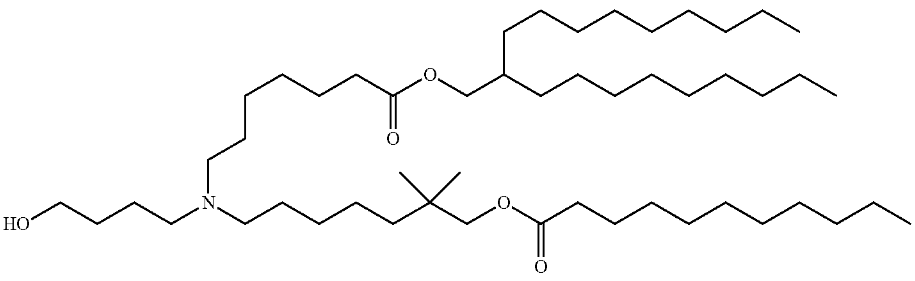 [SMILES: CCCCCCCCCCC(=O)OCC(C)(C)CCCCCN(CCCCO)CCCCCCC(=O)OCC(CCCCCCCCC)CCCCCCCCC]
78b TABLE I-continued
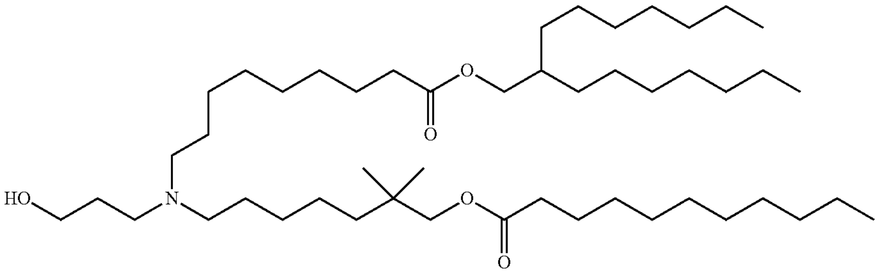 [SMILES: CCCCCCCCCCC(=O)OCC(C)(C)CCCCCN(CCCO)CCCCCCCCC(=O)OCC(CCCCCCC)CCCCCCC]
79b
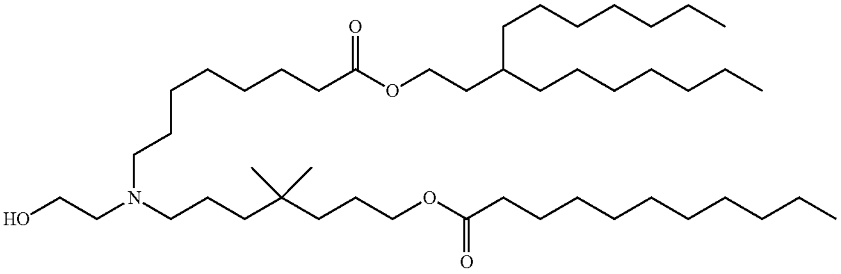 [SMILES: CCCCCCCCCCC(=O)OCCCC(C)(C)CCCN(CCO)CCCCCCCC(=O)OCCC(CCCCCCC)CCCCCCC]
80b
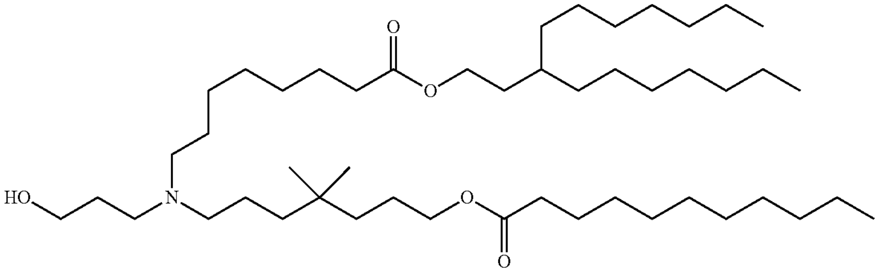 [SMILES: CCCCCCCCCCC(=O)OCCCC(C)(C)CCCN(CCCO)CCCCCCCC(=O)OCCC(CCCCCCC)CCCCCCC]
81b
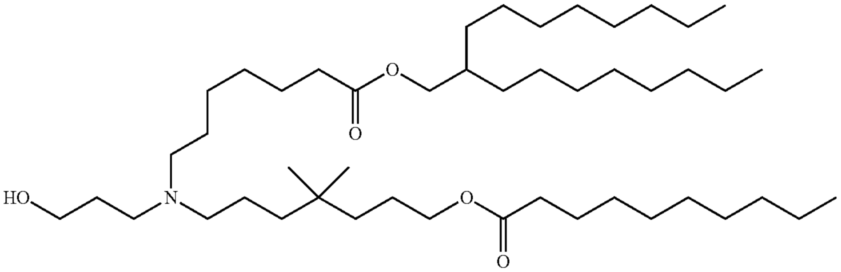 [SMILES: CCCCCCCCCC(=O)OCCCC(C)(C)CCCN(CCCO)CCCCCCC(=O)OCC(CCCCCCCC)CCCCCCCC]
82b
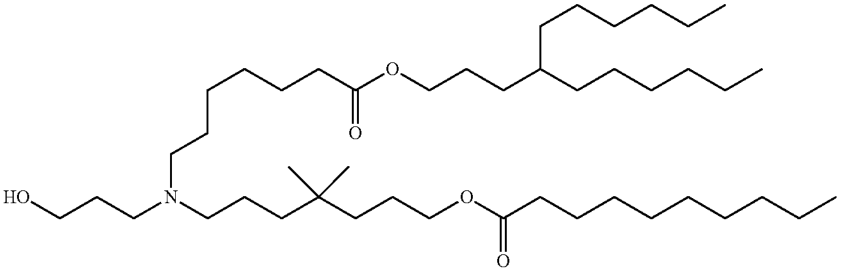 [SMILES: CCCCCCCCCC(=O)OCCCC(C)(C)CCCN(CCCO)CCCCCCC(=O)OCCCC(CCCCCC)CCCCCC]
83b TABLE I-continued
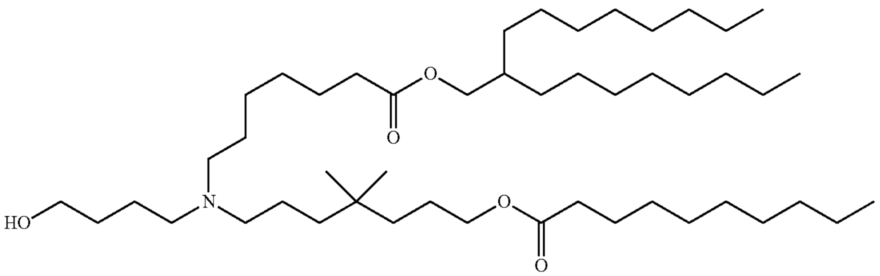 [SMILES: CCCCCCCCCC(=O)OCCCC(C)(C)CCCN(CCCCO)CCCCCCC(=O)OCC(CCCCCCCC)CCCCCCCC]
84b
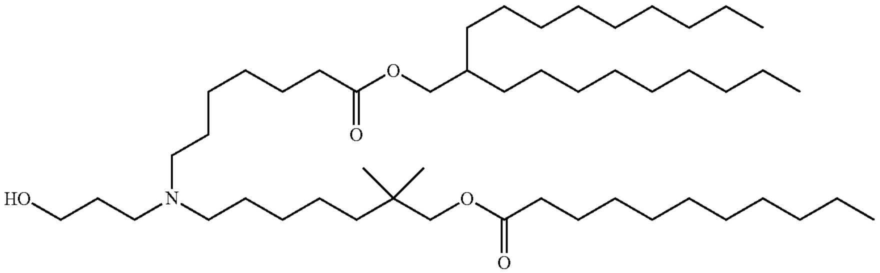 [SMILES: CCCCCCCCCCC(=O)OCC(C)(C)CCCCCN(CCCO)CCCCCCC(=O)OCC(CCCCCCCCC)CCCCCCCCC]
85b
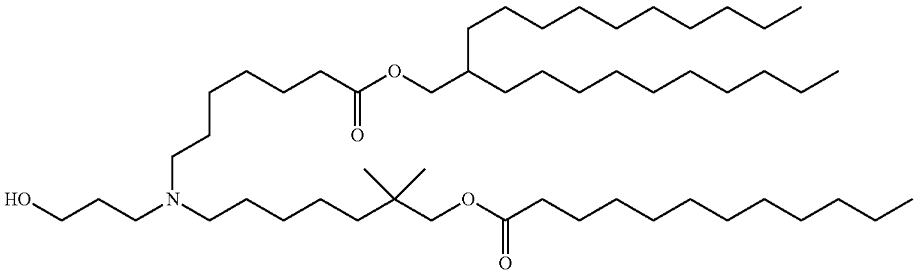 [SMILES: CCCCCCCCCCCC(=O)OCC(C)(C)CCCCCN(CCCO)CCCCCCC(=O)OCC(CCCCCCCCCC)CCCCCCCCCC]
86b
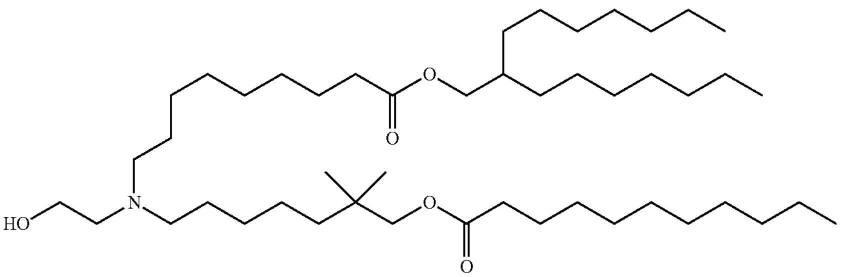 [SMILES: CCCCCCCCCCC(=O)OCC(C)(C)CCCCCN(CCO)CCCCCCCCC(=O)OCC(CCCCCCC)CCCCCCC]
87b
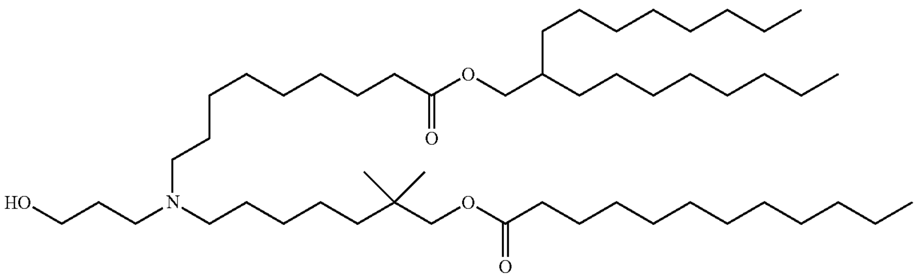 [SMILES: CCCCCCCCCCCC(=O)OCC(C)(C)CCCCCN(CCCO)CCCCCCCCC(=O)OCC(CCCCCCCC)CCCCCCCC]
88b TABLE I-continued
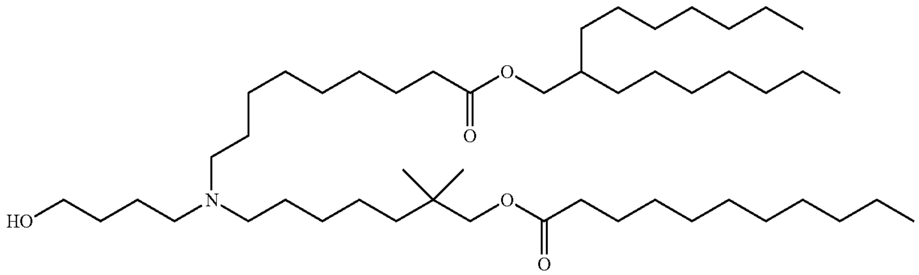 [SMILES: CCCCCCCCCCC(=O)OCC(C)(C)CCCCCN(CCCCO)CCCCCCCCC(=O)OCC(CCCCCCC)CCCCCCC]
89b
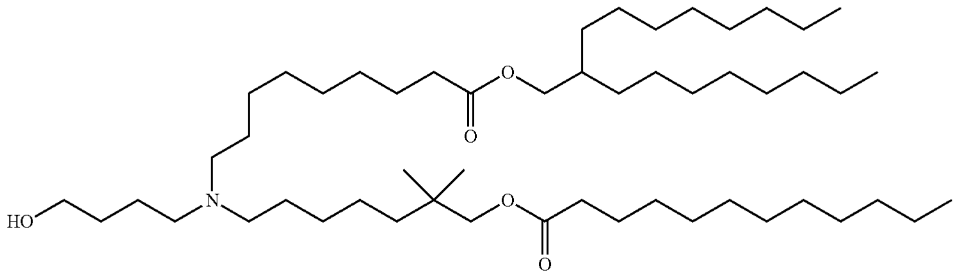 [SMILES: CCCCCCCCCCCC(=O)OCC(C)(C)CCCCCN(CCCCO)CCCCCCCCC(=O)OCC(CCCCCCCC)CCCCCCCC]
90b
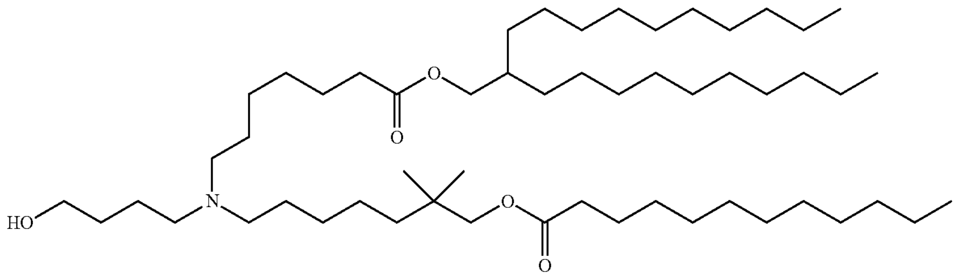 [SMILES: CCCCCCCCCCCC(=O)OCC(C)(C)CCCCCN(CCCCO)CCCCCCC(=O)OCC(CCCCCCCCCC)CCCCCCCCCC]
91b
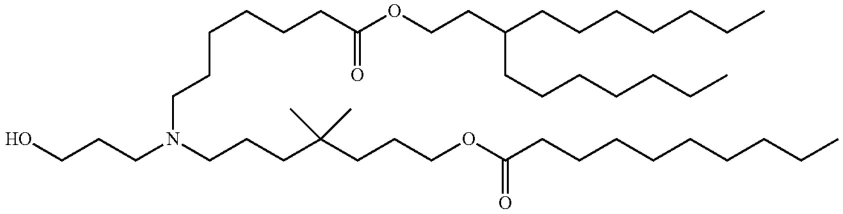 [SMILES: CCCCCCCCCC(=O)OCCCC(C)(C)CCCN(CCCO)CCCCCCC(=O)OCCC(CCCCCCC)CCCCCCC]
92b
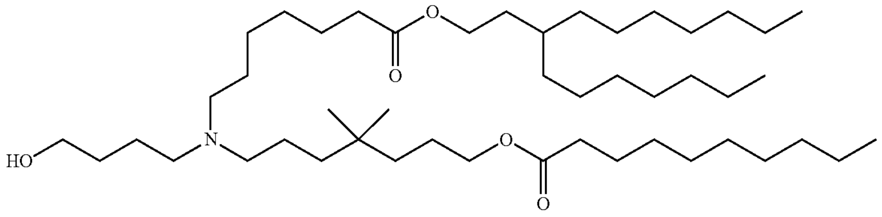 [SMILES: CCCCCCCCCC(=O)OCCCC(C)(C)CCCN(CCCCO)CCCCCCC(=O)OCCC(CCCCCCC)CCCCCCC]
93b
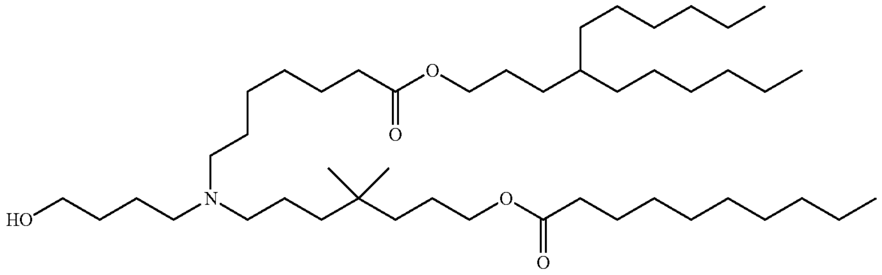 [SMILES: CCCCCCCCCC(=O)OCCCC(C)(C)CCCN(CCCCO)CCCCCCC(=O)OCCCC(CCCCCC)CCCCCC]
94b TABLE I-continued
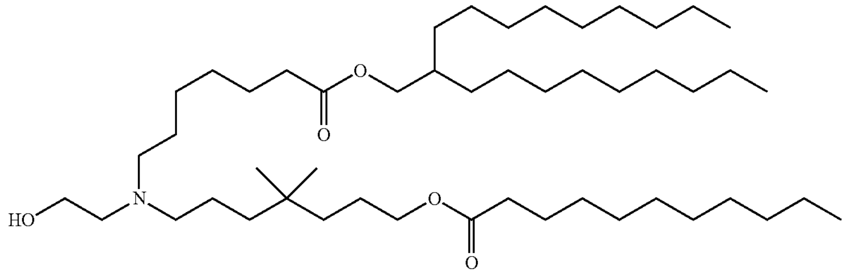 [SMILES: CCCCCCCCCCC(=O)OCCCC(C)(C)CCCN(CCO)CCCCCCC(=O)OCC(CCCCCCCCC)CCCCCCCCC]
95b
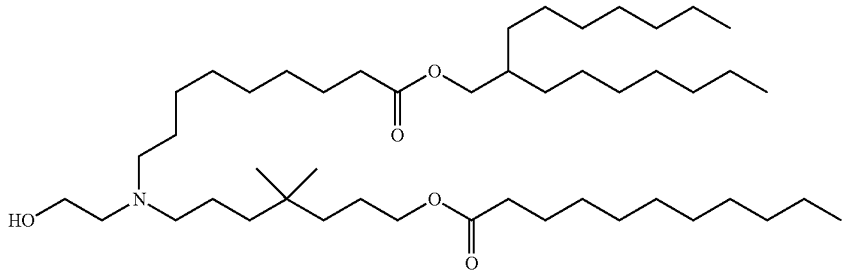 [SMILES: CCCCCCCCCCC(=O)OCCCC(C)(C)CCCN(CCO)CCCCCCCCC(=O)OCC(CCCCCCC)CCCCCCC]
96b
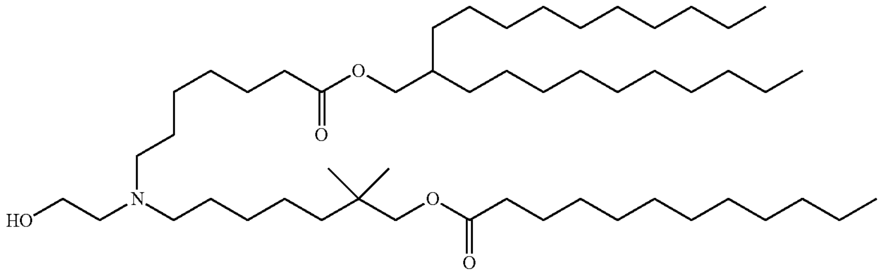 [SMILES: CCCCCCCCCCCC(=O)OCC(C)(C)CCCCCN(CCO)CCCCCCC(=O)OCC(CCCCCCCCCC)CCCCCCCCCC]
97b
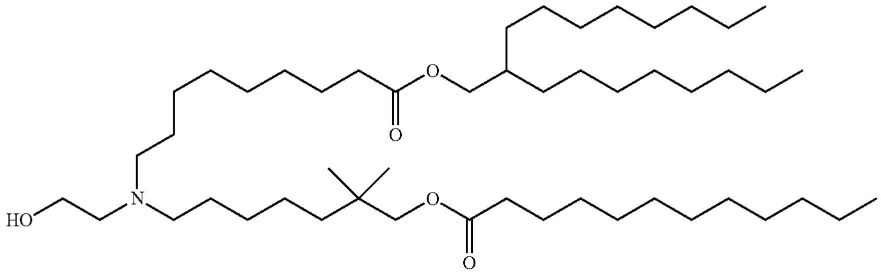 [SMILES: CCCCCCCCCCCC(=O)OCC(C)(C)CCCCCN(CCO)CCCCCCCCC(=O)OCC(CCCCCCCC)CCCCCCCC]
98b
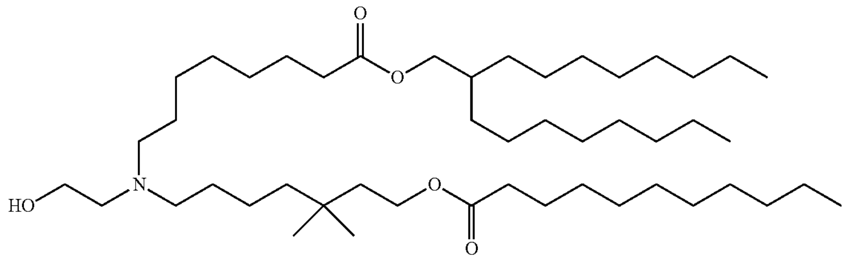 [SMILES: CCCCCCCCCCC(=O)OCCC(C)(C)CCCCN(CCO)CCCCCCCC(=O)OCC(CCCCCCCC)CCCCCCCC]
99b
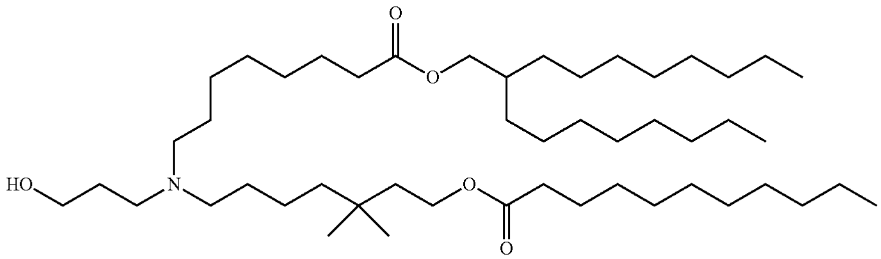 [SMILES: CCCCCCCCCCC(=O)OCCC(C)(C)CCCCN(CCCO)CCCCCCCC(=O)OCC(CCCCCCCC)CCCCCCCC]
100b TABLE I-continued
101b
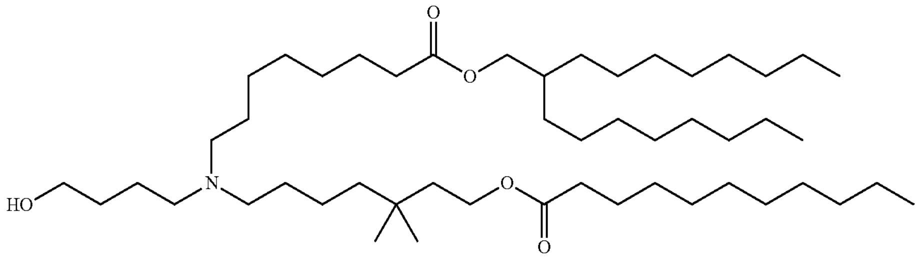 [SMILES: CCCCCCCCCCC(=O)OCCC(C)(C)CCCCN(CCCCO)CCCCCCCC(=O)OCC(CCCCCCCC)CCCCCCCC]
102b
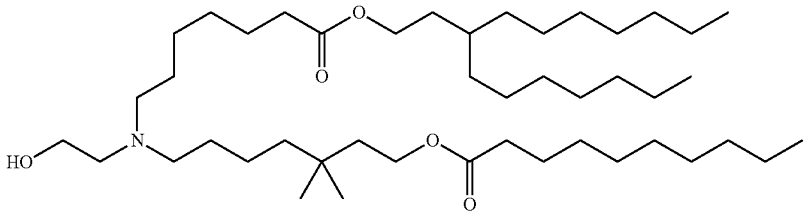 [SMILES: CCCCCCCCCC(=O)OCCC(C)(C)CCCCN(CCO)CCCCCCC(=O)OCCC(CCCCCCC)CCCCCCC]
103b
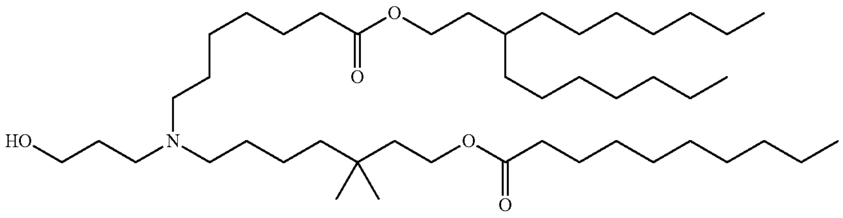 [SMILES: CCCCCCCCCC(=O)OCCC(C)(C)CCCCN(CCCO)CCCCCCC(=O)OCCC(CCCCCCC)CCCCCCC]
104b
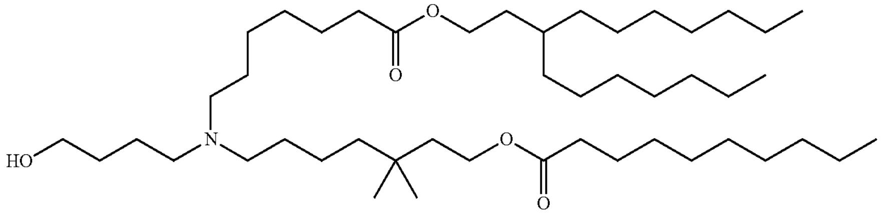 [SMILES: CCCCCCCCCC(=O)OCCC(C)(C)CCCCN(CCCCO)CCCCCCC(=O)OCCC(CCCCCCC)CCCCCCC]
105b
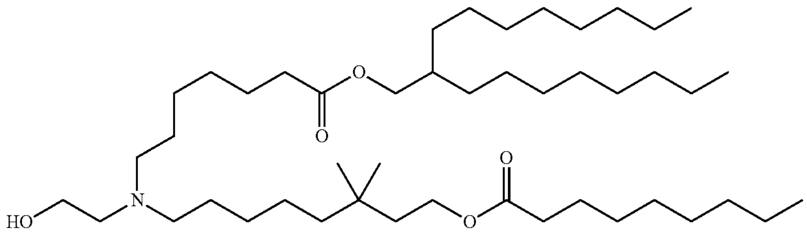 [SMILES: CCCCCCCCC(=O)OCCC(C)(C)CCCCCN(CCO)CCCCCCC(=O)OCC(CCCCCCCC)CCCCCCCC]
106b
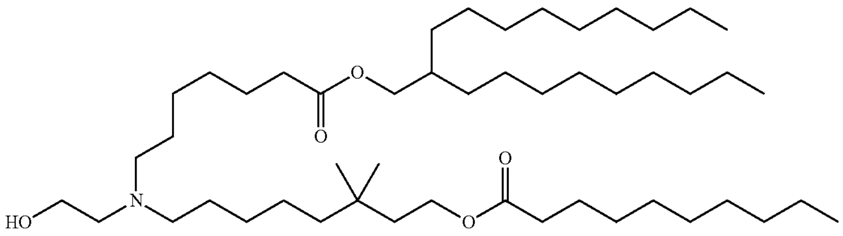 [SMILES: CCCCCCCCCC(=O)OCCC(C)(C)CCCCCN(CCO)CCCCCCC(=O)OCC(CCCCCCCCC)CCCCCCCCC]

TABLE I-continued
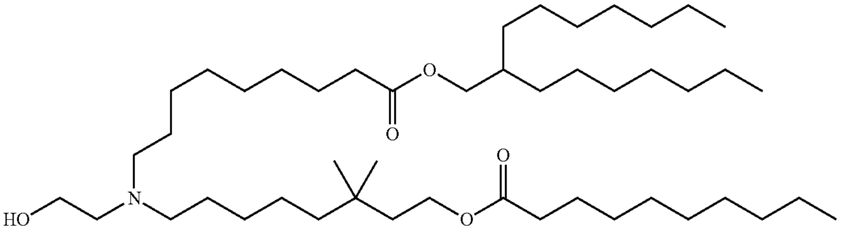 [SMILES: CCCCCCCCCC(=O)OCCC(C)(C)CCCCCN(CCO)CCCCCCCCC(=O)OCC(CCCCCCC)CCCCCCC]
107b
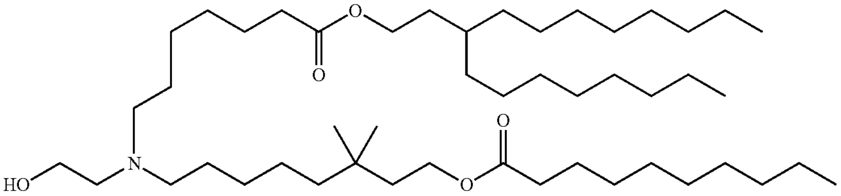 [SMILES: CCCCCCCCCC(=O)OCCC(C)(C)CCCCCN(CCO)CCCCCCC(=O)OCCC(CCCCCCCC)CCCCCCCC]
108b
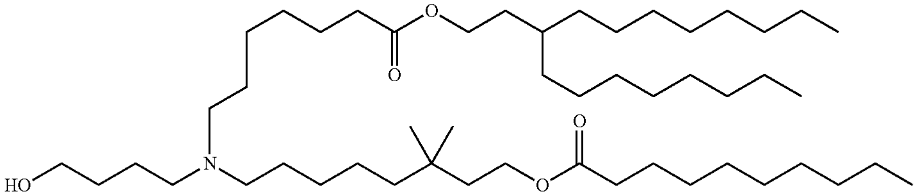 [SMILES: CCCCCCCCCC(=O)OCCC(C)(C)CCCCCN(CCCCO)CCCCCCC(=O)OCCC(CCCCCCCC)CCCCCCCC]
109b
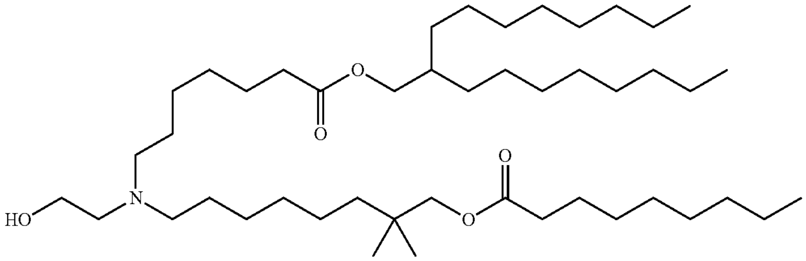 [SMILES: CCCCCCCCC(=O)OCC(C)(C)CCCCCCN(CCO)CCCCCCC(=O)OCC(CCCCCCCC)CCCCCCCC]
110b
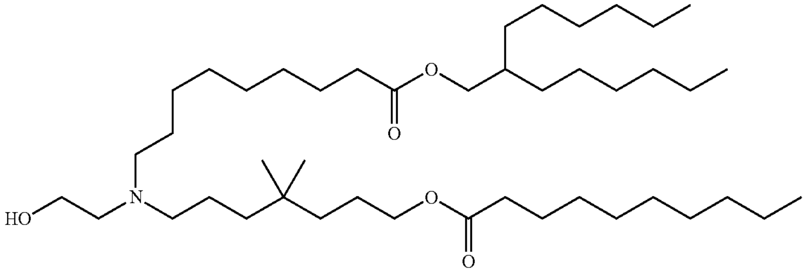 [SMILES: CCCCCCCCCC(=O)OCCCC(C)(C)CCCN(CCO)CCCCCCCCC(=O)OCC(CCCCCC)CCCCCC]
111b
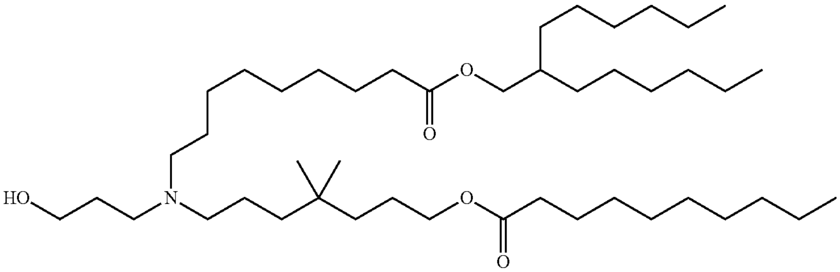 [SMILES: CCCCCCCCCC(=O)OCCCC(C)(C)CCCN(CCCO)CCCCCCCCC(=O)OCC(CCCCCC)CCCCCC]
112b TABLE I-continued
113b
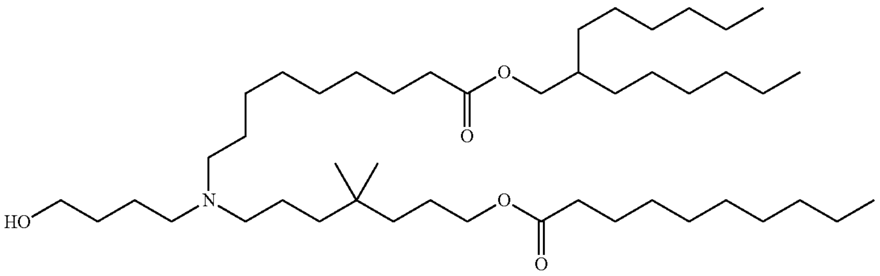 [SMILES: CCCCCCCCCC(=O)OCCCC(C)(C)CCCN(CCCCO)CCCCCCCCC(=O)OCC(CCCCCC)CCCCCC]
114b
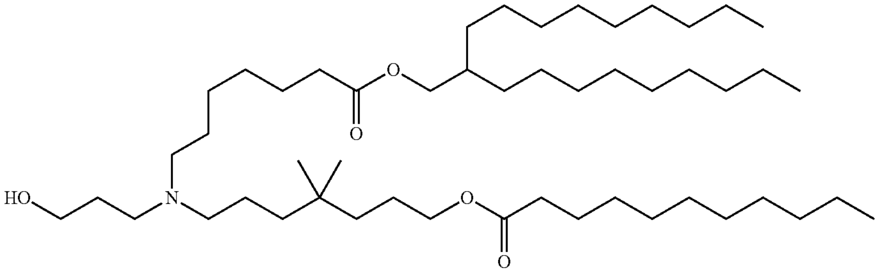 [SMILES: CCCCCCCCCCC(=O)OCCCC(C)(C)CCCN(CCCO)CCCCCCC(=O)OCC(CCCCCCCCC)CCCCCCCCC]
115b
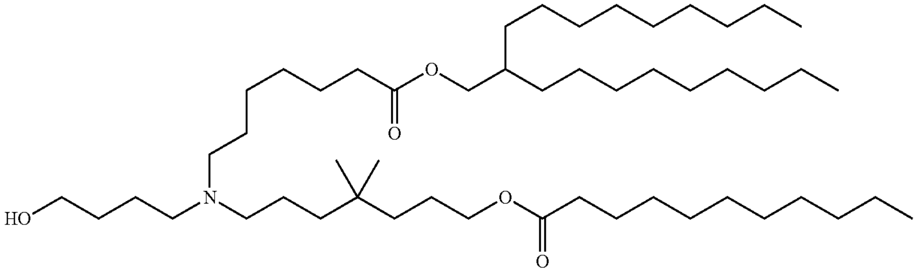 [SMILES: CCCCCCCCCCC(=O)OCCCC(C)(C)CCCN(CCCCO)CCCCCCC(=O)OCC(CCCCCCCCC)CCCCCCCCC]
116b
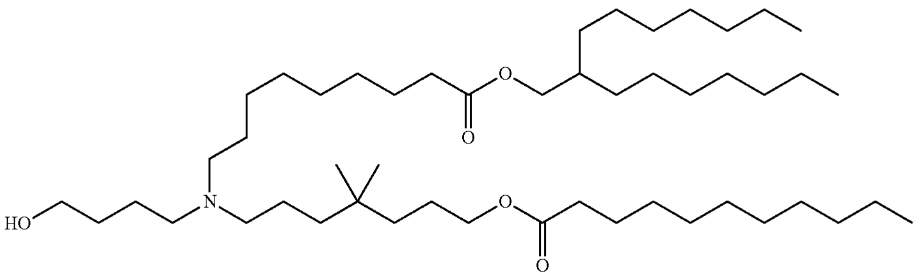 [SMILES: CCCCCCCCCCC(=O)OCCCC(C)(C)CCCN(CCCCO)CCCCCCCCC(=O)OCC(CCCCCCC)CCCCCCC]
117b
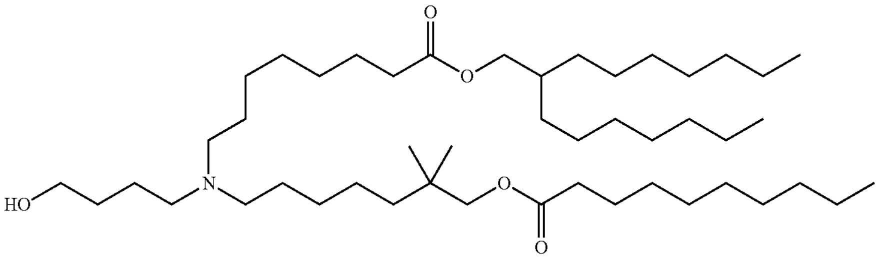 [SMILES: CCCCCCCCCC(=O)OCC(C)(C)CCCCCN(CCCCO)CCCCCCCC(=O)OCC(CCCCCCC)CCCCCCC]
1c
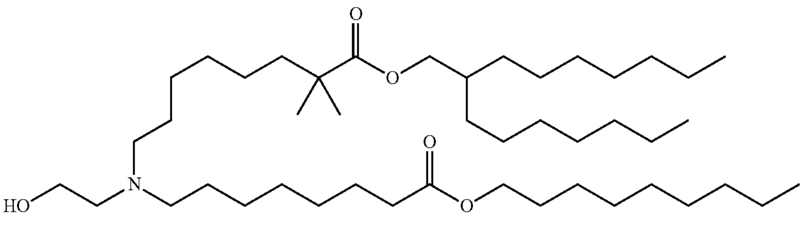 [SMILES: CCCCCCCCCOC(=O)CCCCCCCN(CCO)CCCCCCC(C)(C)C(=O)OCC(CCCCCCC)CCCCCCC]

TABLE I-continued
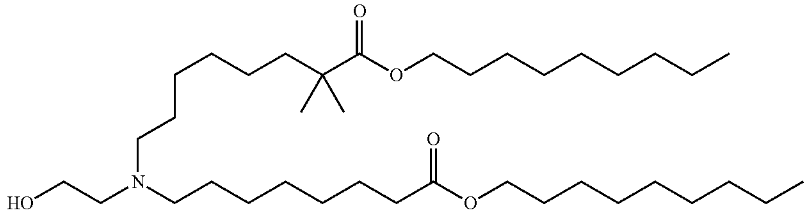 [SMILES: CCCCCCCCCOC(=O)CCCCCCCN(CCO)CCCCCCC(C)(C)C(=O)OCCCCCCCCC]
2c
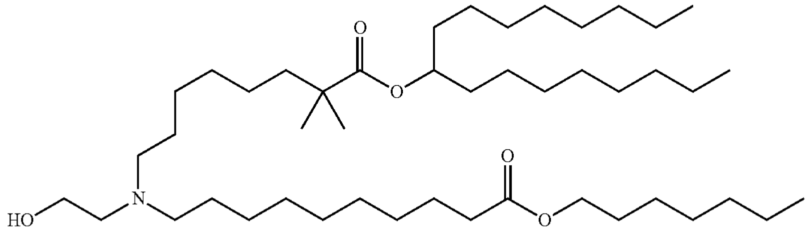 [SMILES: CCCCCCCCC(CCCCCCCC)OC(=O)C(C)(C)CCCCCCN(CCO)CCCCCCCCCC(=O)OCCCCCCC]
3c
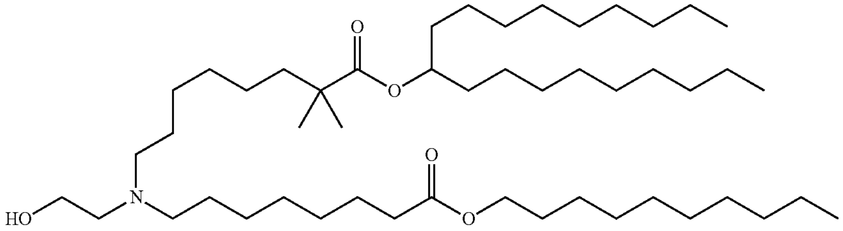 [SMILES: CCCCCCCCCCOC(=O)CCCCCCCN(CCO)CCCCCCC(C)(C)C(=O)OC(CCCCCCCCC)CCCCCCCCC]
4c
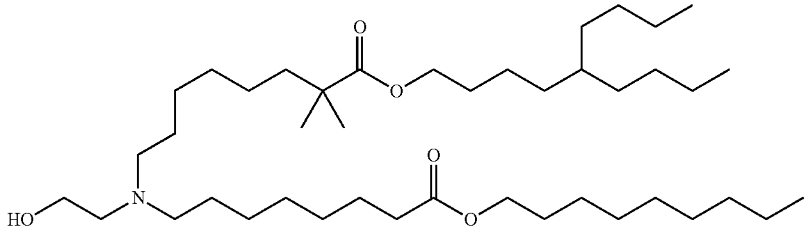 [SMILES: CCCCCCCCCOC(=O)CCCCCCCN(CCO)CCCCCCC(C)(C)C(=O)OCCCCC(CCCC)CCCC]
5c
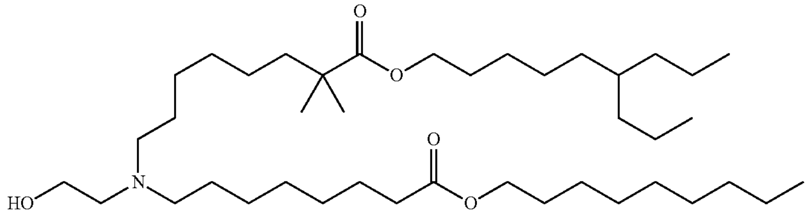 [SMILES: CCCCCCCCCOC(=O)CCCCCCCN(CCO)CCCCCCC(C)(C)C(=O)OCCCCCC(CCC)CCC]
6c
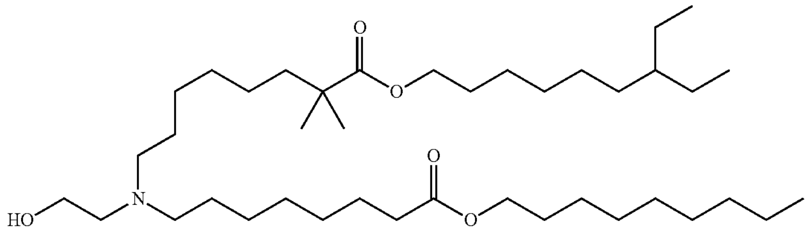 [SMILES: CCCCCCCCCOC(=O)CCCCCCCN(CCO)CCCCCCC(C)(C)C(=O)OCCCCCCC(CC)CC]
7c
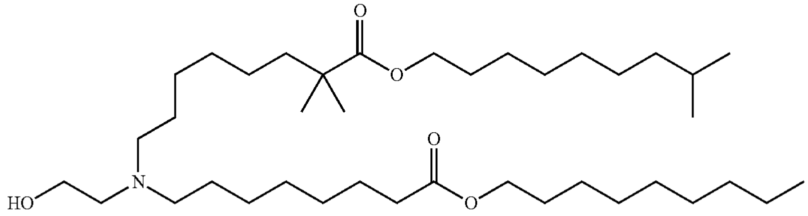 [SMILES: CCCCCCCCCOC(=O)CCCCCCCN(CCO)CCCCCCC(C)(C)C(=O)OCCCCCCCC(C)C]
8c TABLE I-continued
9c
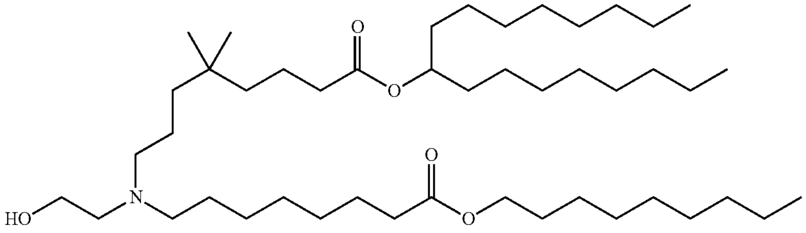 [SMILES: CCCCCCCCCOC(=O)CCCCCCCN(CCO)CCCC(C)(C)CCCC(=O)OC(CCCCCCCC)CCCCCCCC]
10c
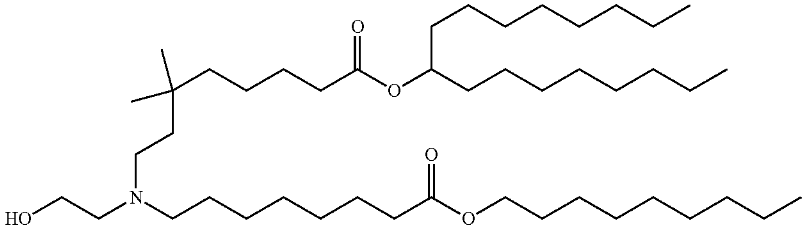 [SMILES: CCCCCCCCCOC(=O)CCCCCCCN(CCO)CCC(C)(C)CCCCC(=O)OC(CCCCCCCC)CCCCCCCC]
11c
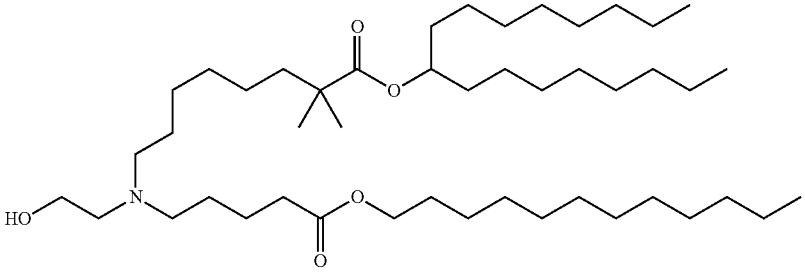 [SMILES: CCCCCCCCCCCCOC(=O)CCCCN(CCO)CCCCCCC(C)(C)C(=O)OC(CCCCCCCC)CCCCCCCC]
12c
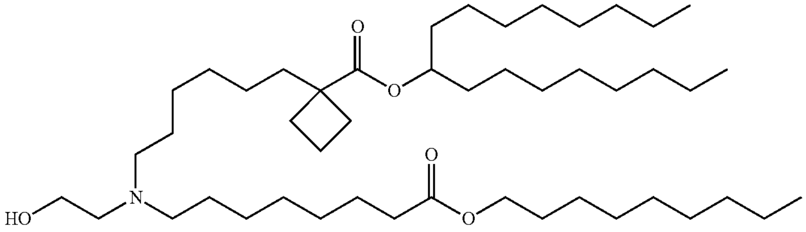 [SMILES: CCCCCCCCCOC(=O)CCCCCCCN(CCO)CCCCCCC1(C(=O)OC(CCCCCCCC)CCCCCCCC)CCC1]
13c
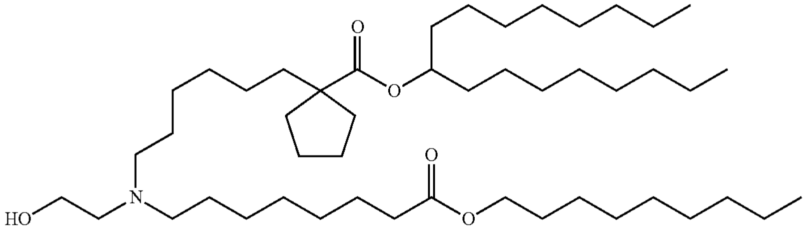 [SMILES: CCCCCCCCCOC(=O)CCCCCCCN(CCO)CCCCCCC1(C(=O)OC(CCCCCCCC)CCCCCCCC)CCCC1]
14c
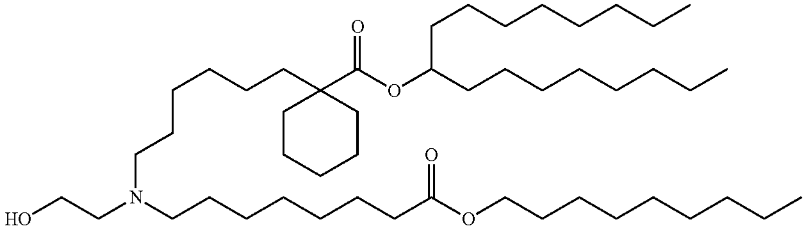 [SMILES: CCCCCCCCCOC(=O)CCCCCCCN(CCO)CCCCCCC1(C(=O)OC(CCCCCCCC)CCCCCCCC)CCCCC1]

TABLE I-continued
15c
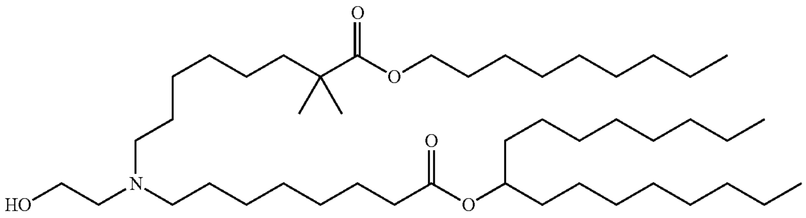 [SMILES: CCCCCCCCCOC(=O)C(C)(C)CCCCCCN(CCO)CCCCCCCC(=O)OC(CCCCCCCC)CCCCCCCC]
16c
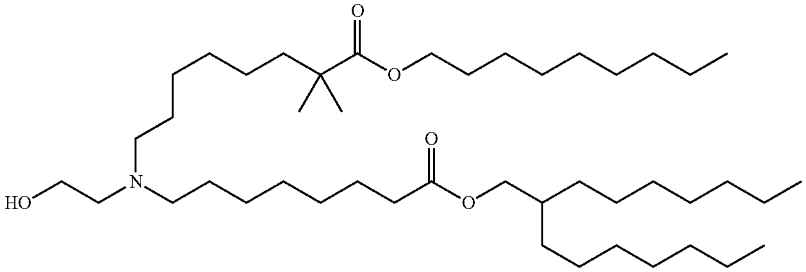 [SMILES: CCCCCCCCCOC(=O)C(C)(C)CCCCCCN(CCO)CCCCCCCC(=O)OCC(CCCCCCC)CCCCCCC]
17c
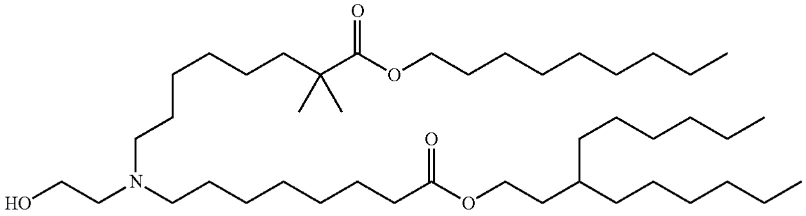 [SMILES: CCCCCCCCCOC(=O)C(C)(C)CCCCCCN(CCO)CCCCCCCC(=O)OCCC(CCCCCC)CCCCCC]
18c
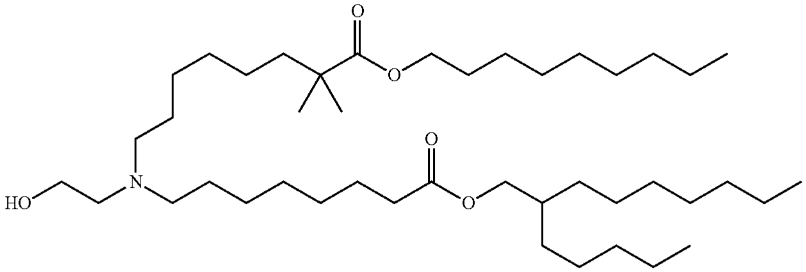 [SMILES: CCCCCCCCCOC(=O)C(C)(C)CCCCCCN(CCO)CCCCCCCC(=O)OCC(CCCCC)CCCCCCC]
19c
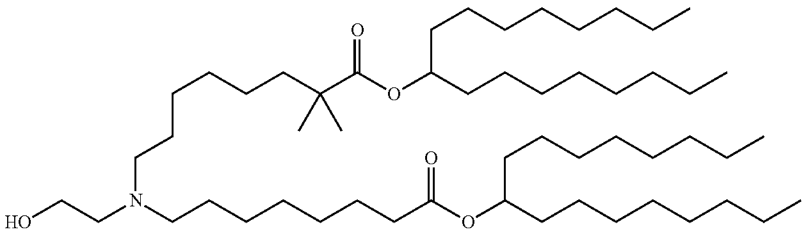 [SMILES: CCCCCCCCC(CCCCCCCC)OC(=O)CCCCCCCN(CCO)CCCCCCC(C)(C)C(=O)OC(CCCCCCCC)CCCCCCCC]
20c
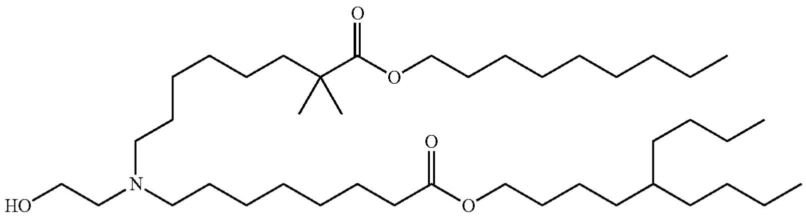 [SMILES: CCCCCCCCCOC(=O)C(C)(C)CCCCCCN(CCO)CCCCCCCC(=O)OCCCCC(CCCC)CCCC]

TABLE I-continued
21c
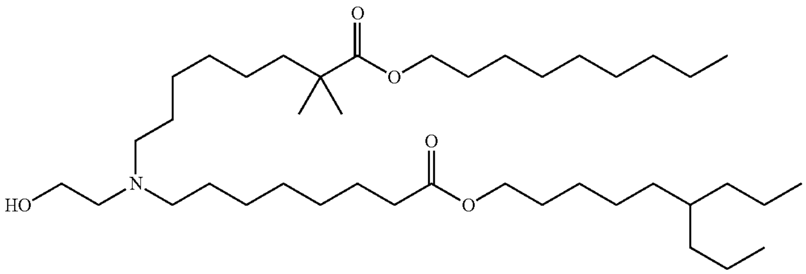 [SMILES: CCCCCCCCCOC(=O)C(C)(C)CCCCCCN(CCO)CCCCCCCC(=O)OCCCCCC(CCC)CCC]
22c
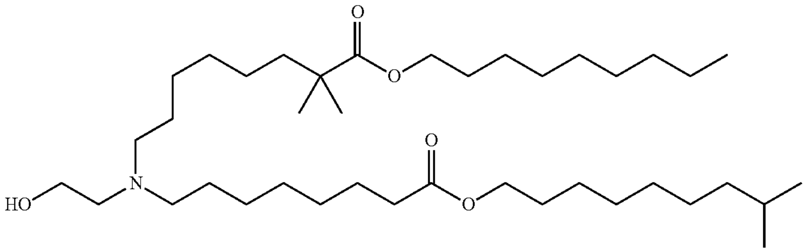 [SMILES: CCCCCCCCCOC(=O)C(C)(C)CCCCCCN(CCO)CCCCCCCC(=O)OCCCCCCCC(C)C]
23c
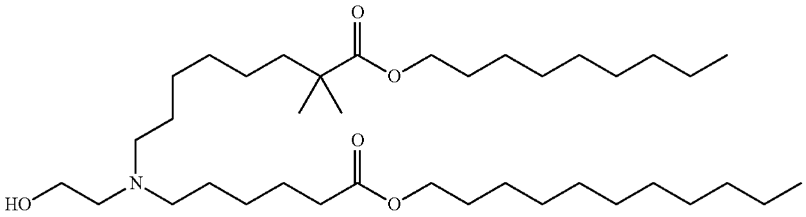 [SMILES: CCCCCCCCCCCOC(=O)CCCCCN(CCO)CCCCCCC(C)(C)C(=O)OCCCCCCCCC]
24c
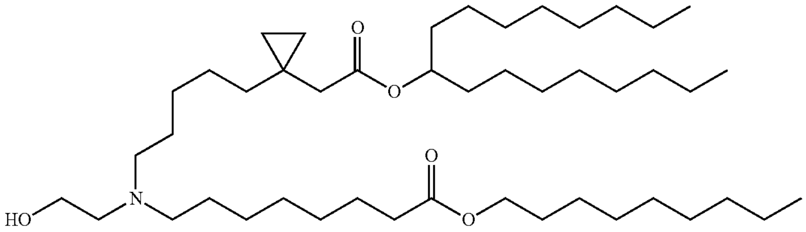 [SMILES: CCCCCCCCCOC(=O)CCCCCCCN(CCO)CCCCCC1(CC(=O)OC(CCCCCCCC)CCCCCCCC)CC1]
25c
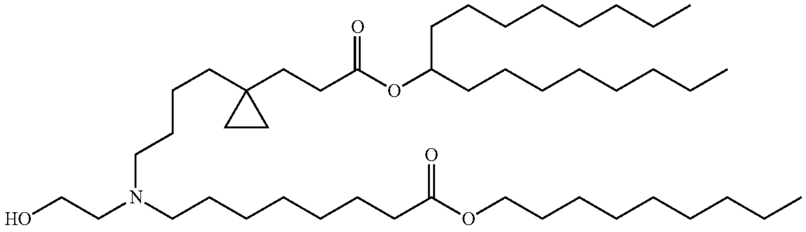 [SMILES: CCCCCCCCCOC(=O)CCCCCCCN(CCO)CCCCC1(CCC(=O)OC(CCCCCCCC)CCCCCCCC)CC1]
26c
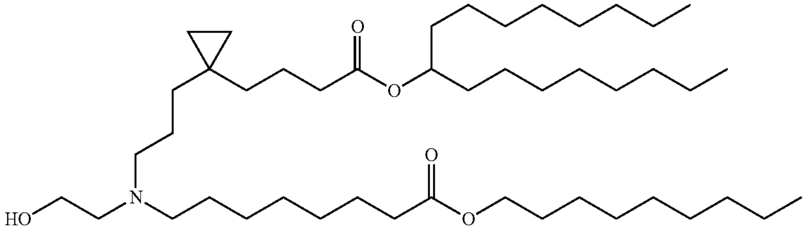 [SMILES: CCCCCCCCCOC(=O)CCCCCCCN(CCO)CCCC1(CCCC(=O)OC(CCCCCCCC)CCCCCCCC)CC1]

TABLE I-continued
27c
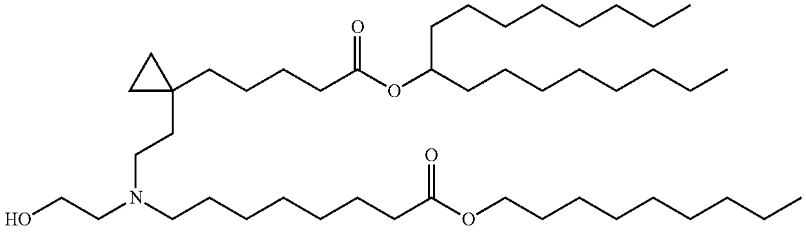 [SMILES: CCCCCCCCCOC(=O)CCCCCCCN(CCO)CCC1(CCCCC(=O)OC(CCCCCCCC)CCCCCCCC)CC1]
28c
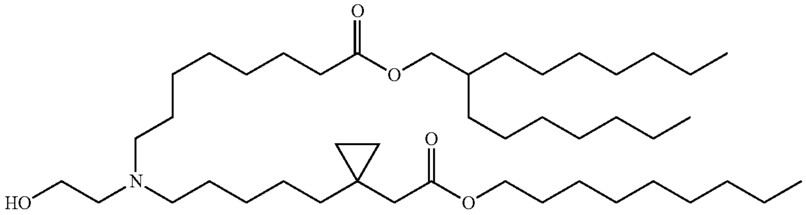 [SMILES: CCCCCCCCCOC(=O)CC1(CCCCCN(CCO)CCCCCCCC(=O)OCC(CCCCCCC)CCCCCCC)CC1]
29c
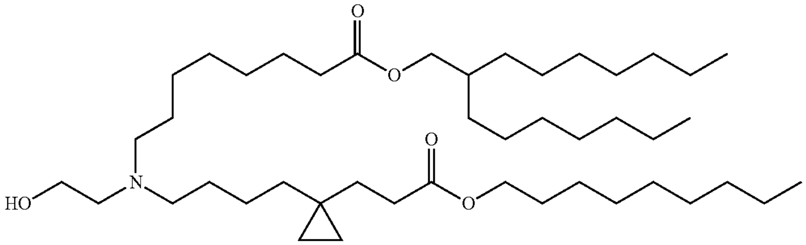 [SMILES: CCCCCCCCCOC(=O)CCC1(CCCCN(CCO)CCCCCCCC(=O)OCC(CCCCCCC)CCCCCCC)CC1]
30c
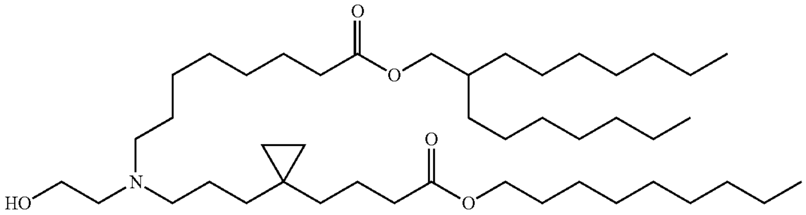 [SMILES: CCCCCCCCCOC(=O)CCCC1(CCCN(CCO)CCCCCCCC(=O)OCC(CCCCCCC)CCCCCCC)CC1]
31c
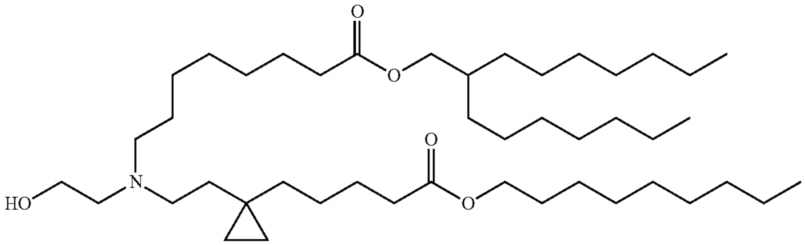 [SMILES: CCCCCCCCCOC(=O)CCCCC1(CCN(CCO)CCCCCCCC(=O)OCC(CCCCCCC)CCCCCCC)CC1]
32c
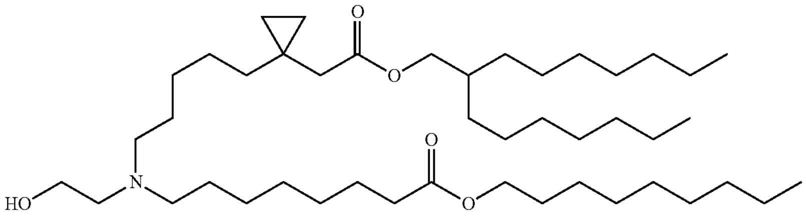 [SMILES: CCCCCCCCCOC(=O)CCCCCCCN(CCO)CCCCCC1(CC(=O)OCC(CCCCCCC)CCCCCCC)CC1]
33c
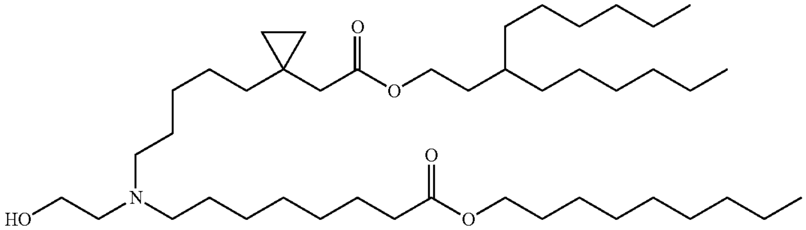 [SMILES: CCCCCCCCCOC(=O)CCCCCCCN(CCO)CCCCCC1(CC(=O)OCCC(CCCCCC)CCCCCC)CC1]

TABLE I-continued
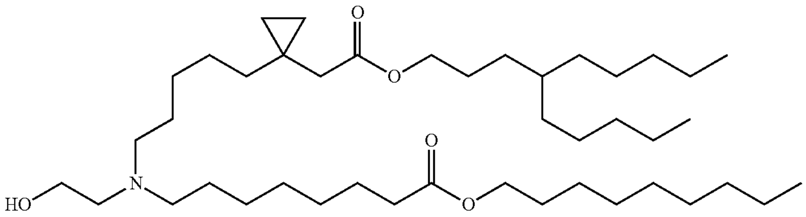 [SMILES: CCCCCCCCCOC(=O)CCCCCCCN(CCO)CCCCCC1(CC(=O)OCCCC(CCCCC)CCCCC)CC1]
34c
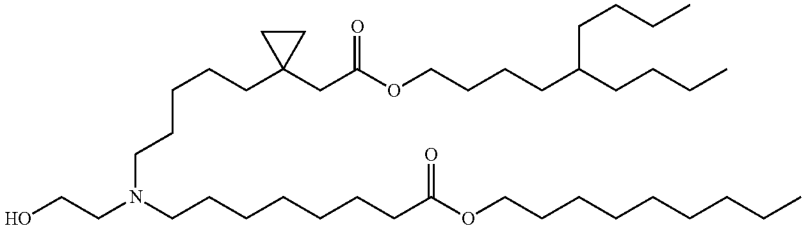 [SMILES: CCCCCCCCCOC(=O)CCCCCCCN(CCO)CCCCCC1(CC(=O)OCCCCC(CCCC)CCCC)CC1]
35c
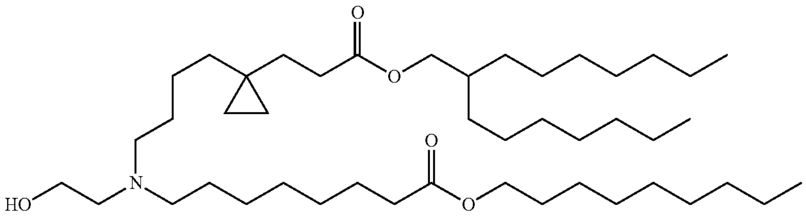 [SMILES: CCCCCCCCCOC(=O)CCCCCCCN(CCO)CCCCC1(CCC(=O)OCC(CCCCCCC)CCCCCCC)CC1]
36c
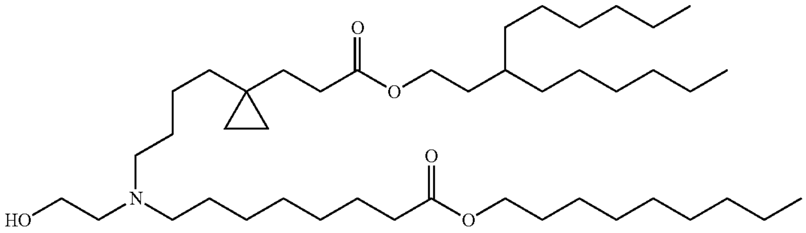 [SMILES: CCCCCCCCCOC(=O)CCCCCCCN(CCO)CCCCC1(CCC(=O)OCCC(CCCCCC)CCCCCC)CC1]
37c
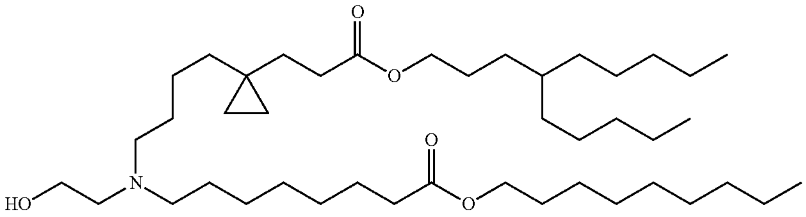 [SMILES: CCCCCCCCCOC(=O)CCCCCCCN(CCO)CCCCC1(CCC(=O)OCCCC(CCCCC)CCCCC)CC1]
38c
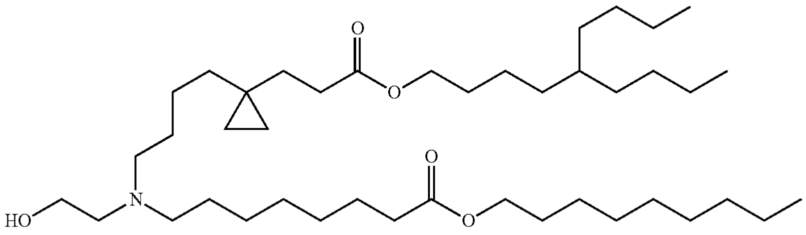 [SMILES: CCCCCCCCCOC(=O)CCCCCCCN(CCO)CCCCC1(CCC(=O)OCCCCC(CCCC)CCCC)CC1]
39c
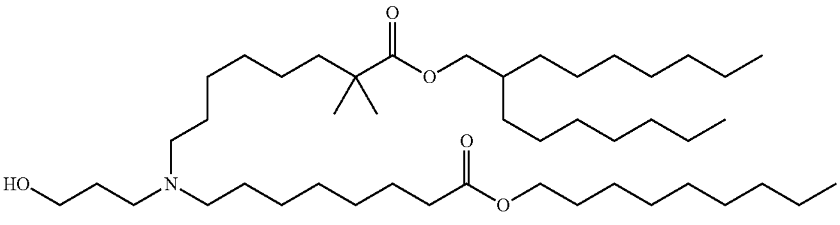 [SMILES: CCCCCCCCCOC(=O)CCCCCCCN(CCCO)CCCCCCC(C)(C)C(=O)OCC(CCCCCCC)CCCCCCC]
40c TABLE I-continued
41c
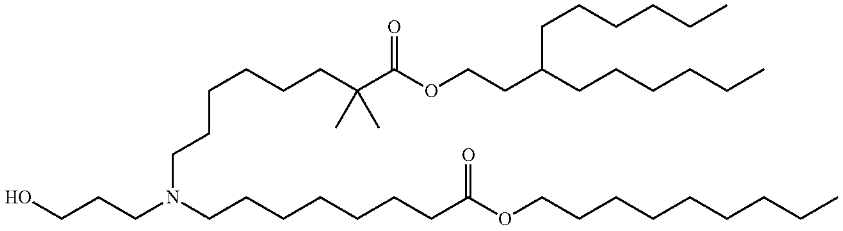 [SMILES: CCCCCCCCCOC(=O)CCCCCCCN(CCCO)CCCCCCC(C)(C)C(=O)OCCC(CCCCCC)CCCCCC]
42c
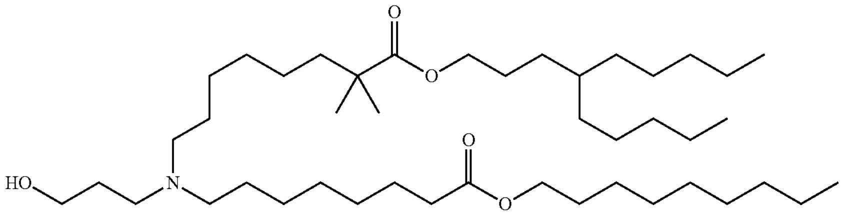 [SMILES: CCCCCCCCCOC(=O)CCCCCCCN(CCCO)CCCCCCC(C)(C)C(=O)OCCCC(CCCCC)CCCCC]
43c
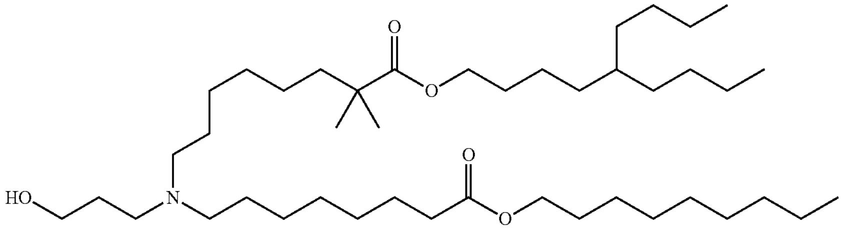 [SMILES: CCCCCCCCCOC(=O)CCCCCCCN(CCCO)CCCCCCC(C)(C)C(=O)OCCCCC(CCCC)CCCC]
44c
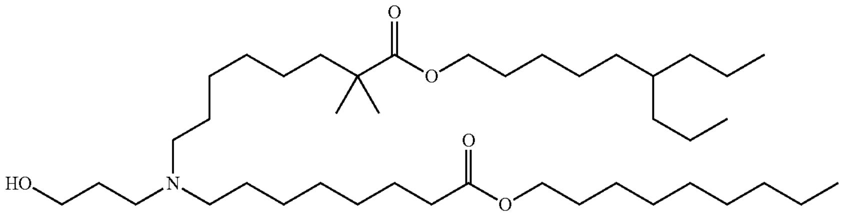 [SMILES: CCCCCCCCCOC(=O)CCCCCCCN(CCCO)CCCCCCC(C)(C)C(=O)OCCCCCC(CCC)CCC]
45c
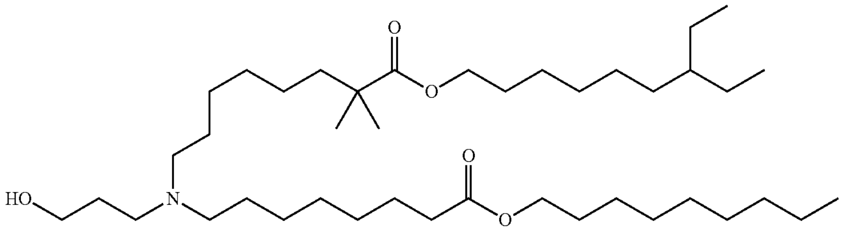 [SMILES: CCCCCCCCCOC(=O)CCCCCCCN(CCCO)CCCCCCC(C)(C)C(=O)OCCCCCCC(CC)CC]
46c
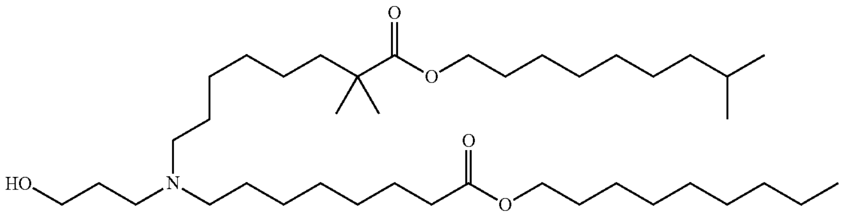 [SMILES: CCCCCCCCCOC(=O)CCCCCCCN(CCCO)CCCCCCC(C)(C)C(=O)OCCCCCCCC(C)C]
47c
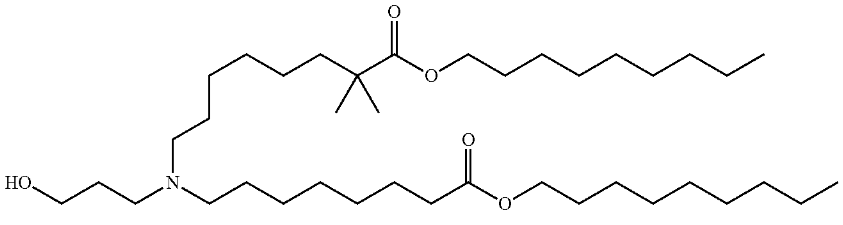 [SMILES: CCCCCCCCCOC(=O)CCCCCCCN(CCCO)CCCCCCC(C)(C)C(=O)OCCCCCCCCC]

TABLE I-continued
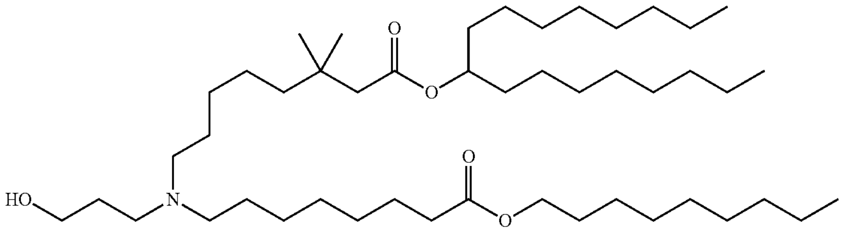 [SMILES: CCCCCCCCCOC(=O)CCCCCCCN(CCCO)CCCCCC(C)(C)CC(=O)OC(CCCCCCCC)CCCCCCCC]
48c
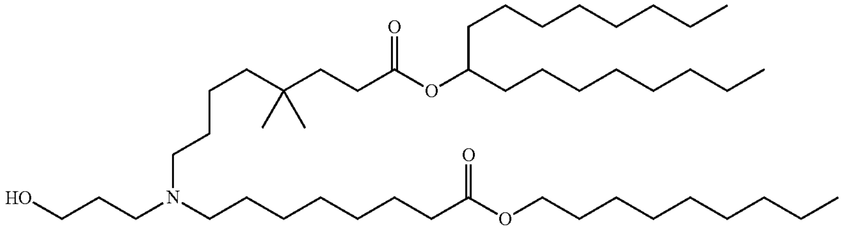 [SMILES: CCCCCCCCCOC(=O)CCCCCCCN(CCCO)CCCCC(C)(C)CCC(=O)OC(CCCCCCCC)CCCCCCCC]
49c
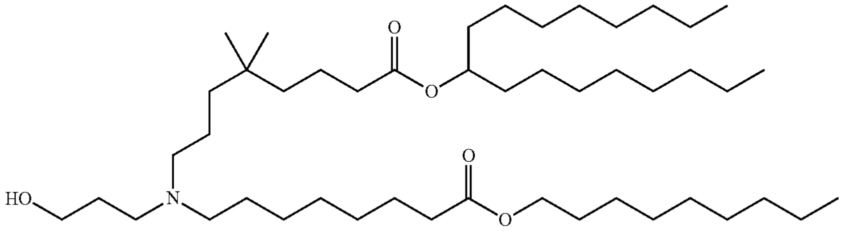 [SMILES: CCCCCCCCCOC(=O)CCCCCCCN(CCCO)CCCC(C)(C)CCCC(=O)OC(CCCCCCCC)CCCCCCCC]
50c
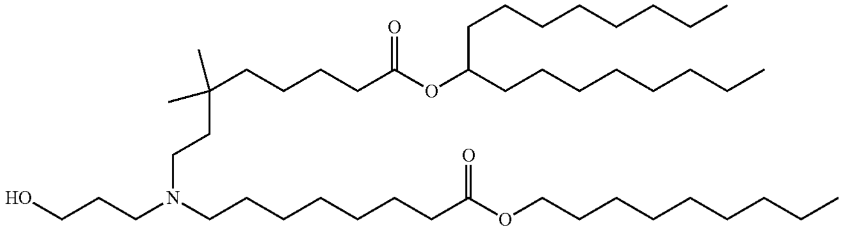 [SMILES: CCCCCCCCCOC(=O)CCCCCCCN(CCCO)CCC(C)(C)CCCCC(=O)OC(CCCCCCCC)CCCCCCCC]
51c
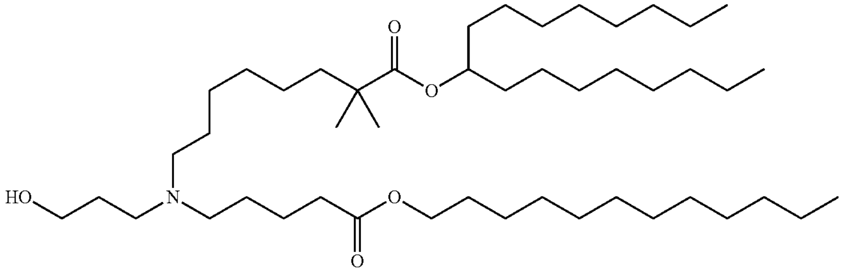 [SMILES: CCCCCCCCCCCCOC(=O)CCCCN(CCCO)CCCCCCC(C)(C)C(=O)OC(CCCCCCCC)CCCCCCCC]
52c
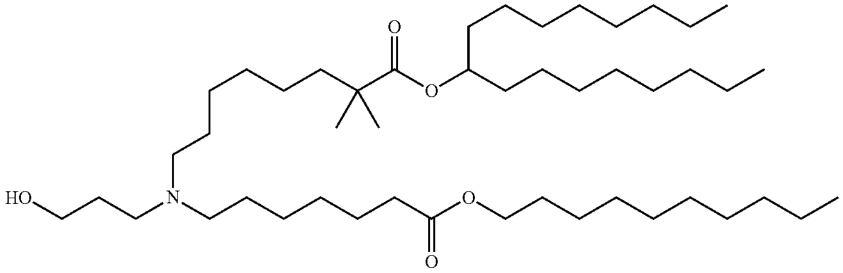 [SMILES: CCCCCCCCCCOC(=O)CCCCCCN(CCCO)CCCCCCC(C)(C)C(=O)OC(CCCCCCCC)CCCCCCCC]
53c TABLE I-continued
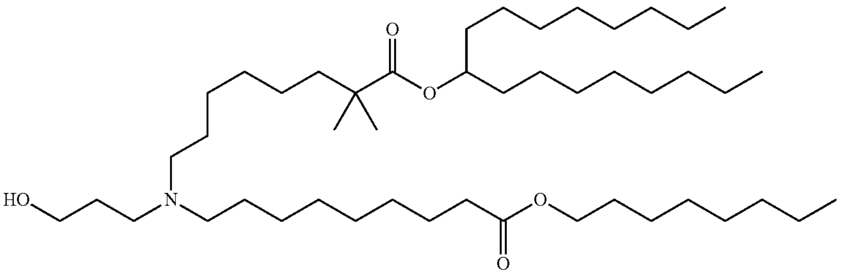 [SMILES: CCCCCCCCOC(=O)CCCCCCCCN(CCCO)CCCCCCC(C)(C)C(=O)OC(CCCCCCCC)CCCCCCCC]
54c
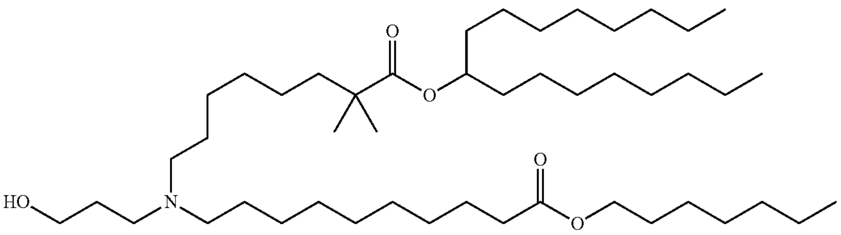 [SMILES: CCCCCCCCC(CCCCCCCC)OC(=O)C(C)(C)CCCCCCN(CCCO)CCCCCCCCCC(=O)OCCCCCCC]
55c
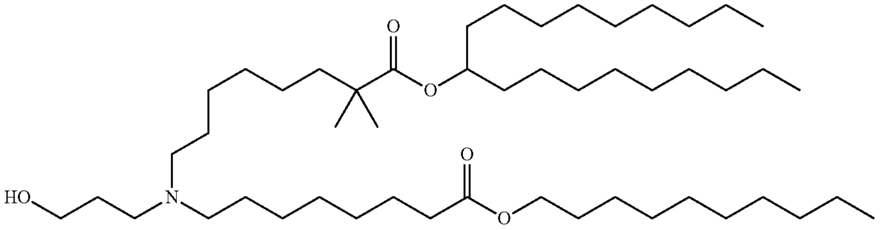 [SMILES: CCCCCCCCCCOC(=O)CCCCCCCN(CCCO)CCCCCCC(C)(C)C(=O)OC(CCCCCCCCC)CCCCCCCCC]
56c
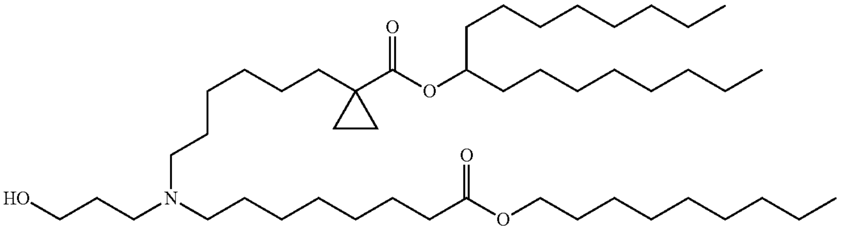 [SMILES: CCCCCCCCCOC(=O)CCCCCCCN(CCCO)CCCCCCC1(C(=O)OC(CCCCCCCC)CCCCCCCC)CC1]
57c
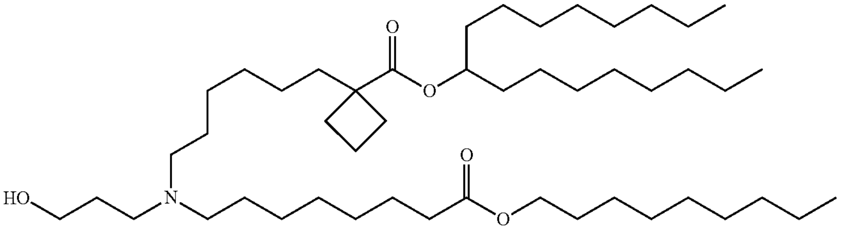 [SMILES: CCCCCCCCCOC(=O)CCCCCCCN(CCCO)CCCCCCC1(C(=O)OC(CCCCCCCC)CCCCCCCC)CCC1]
58c
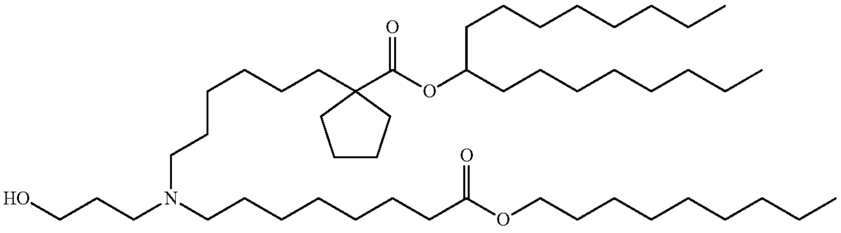 [SMILES: CCCCCCCCCOC(=O)CCCCCCCN(CCCO)CCCCCCC1(C(=O)OC(CCCCCCCC)CCCCCCCC)CCCC1]
59c TABLE I-continued
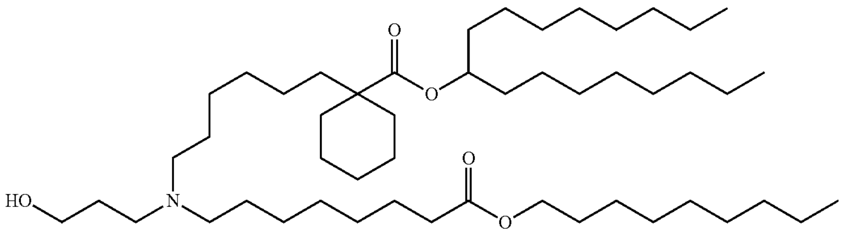 [SMILES: CCCCCCCCCOC(=O)CCCCCCCN(CCCO)CCCCCCC1(C(=O)OC(CCCCCCCC)CCCCCCCC)CCCCC1]
60c
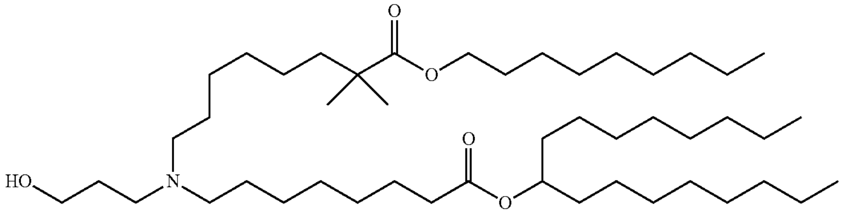 [SMILES: CCCCCCCCCOC(=O)C(C)(C)CCCCCCN(CCCO)CCCCCCCC(=O)OC(CCCCCCCC)CCCCCCCC]
61c
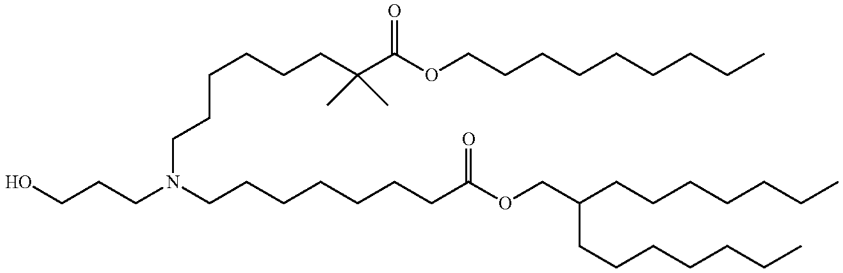 [SMILES: CCCCCCCCCOC(=O)C(C)(C)CCCCCCN(CCCO)CCCCCCCC(=O)OCC(CCCCCCC)CCCCCCC]
62c
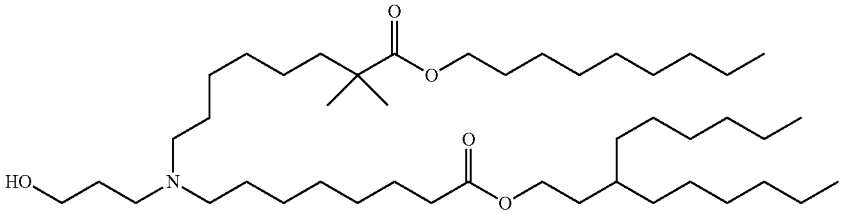 [SMILES: CCCCCCCCCOC(=O)C(C)(C)CCCCCCN(CCCO)CCCCCCCC(=O)OCCC(CCCCCC)CCCCCC]
63c
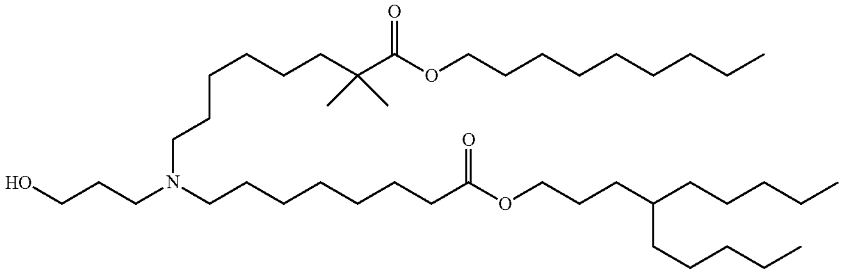 [SMILES: CCCCCCCCCOC(=O)C(C)(C)CCCCCCN(CCCO)CCCCCCCC(=O)OCCCC(CCCCC)CCCCC]
64c
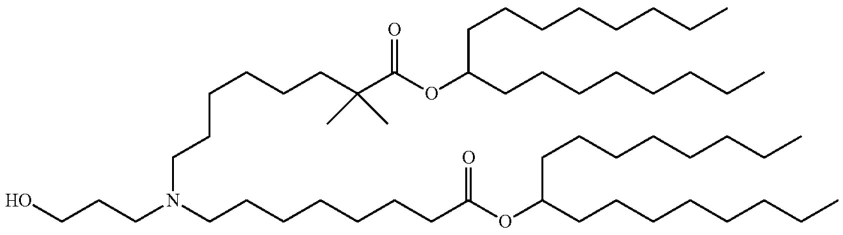 [SMILES: CCCCCCCCC(CCCCCCCC)OC(=O)CCCCCCCN(CCCO)CCCCCCC(C)(C)C(=O)OC(CCCCCCCC)CCCCCCCC]
65c TABLE I-continued
66c
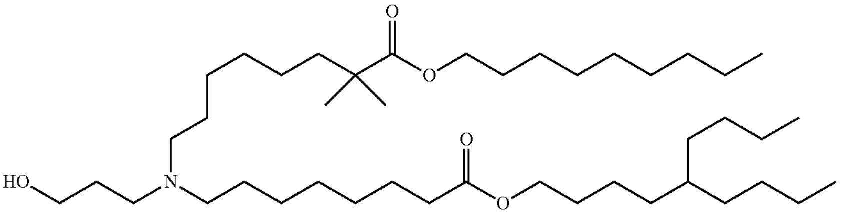 [SMILES: CCCCCCCCCOC(=O)C(C)(C)CCCCCCN(CCCO)CCCCCCCC(=O)OCCCCC(CCCC)CCCC]
67c
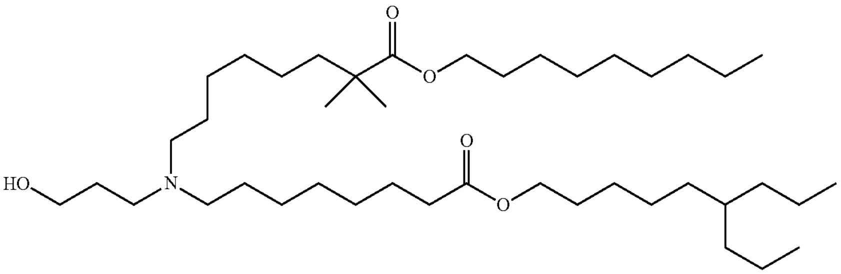 [SMILES: CCCCCCCCCOC(=O)C(C)(C)CCCCCCN(CCCO)CCCCCCCC(=O)OCCCCCC(CCC)CCC]
68c
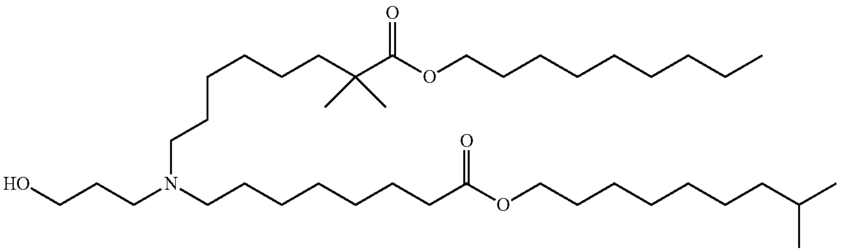 [SMILES: CCCCCCCCCOC(=O)C(C)(C)CCCCCCN(CCCO)CCCCCCCC(=O)OCCCCCCCC(C)C]
69c
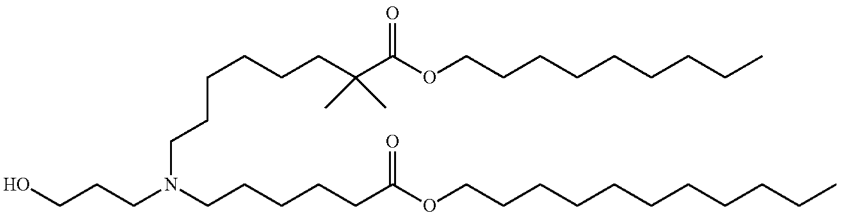 [SMILES: CCCCCCCCCCCOC(=O)CCCCCN(CCCO)CCCCCCC(C)(C)C(=O)OCCCCCCCCC]
70c
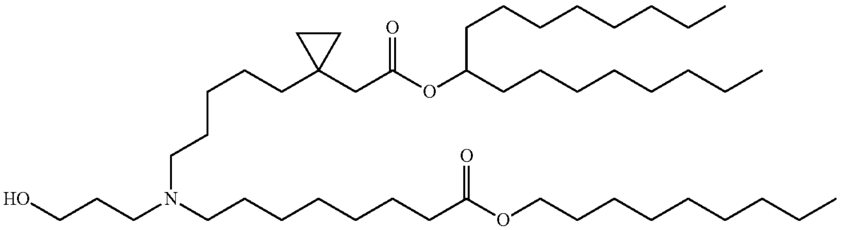 [SMILES: CCCCCCCCCOC(=O)CCCCCCCN(CCCO)CCCCCC1(CC(=O)OC(CCCCCCCC)CCCCCCCC)CC1]
71c
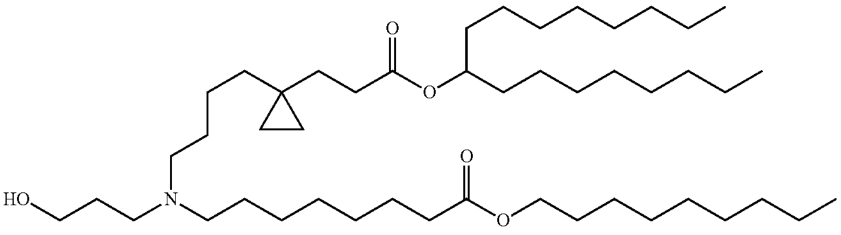 [SMILES: CCCCCCCCCOC(=O)CCCCCCCN(CCCO)CCCCC1(CCC(=O)OC(CCCCCCCC)CCCCCCCC)CC1]

TABLE I-continued
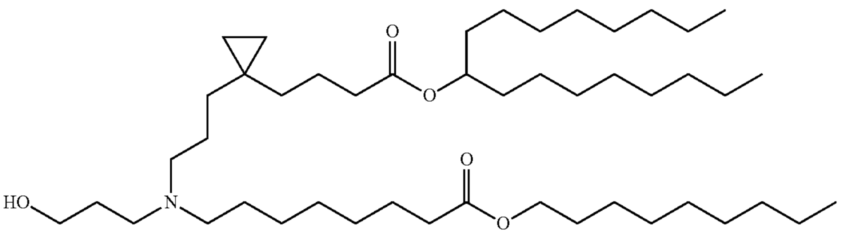 [SMILES: CCCCCCCCCOC(=O)CCCCCCCN(CCCO)CCCC1(CCCC(=O)OC(CCCCCCCC)CCCCCCCC)CC1]
72c
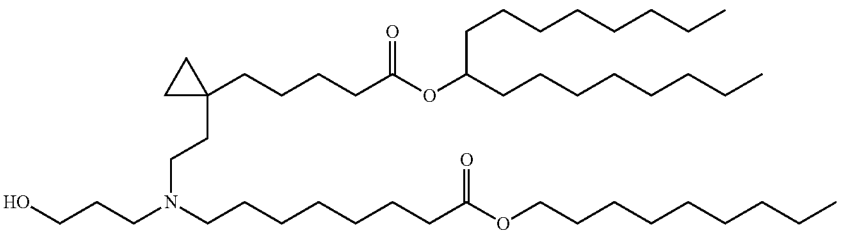 [SMILES: CCCCCCCCCOC(=O)CCCCCCCN(CCCO)CCC1(CCCCC(=O)OC(CCCCCCCC)CCCCCCCC)CC1]
73c
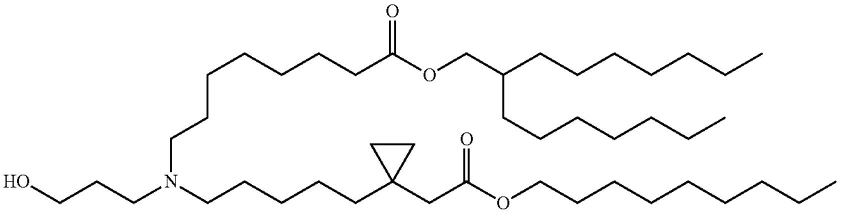 [SMILES: CCCCCCCCCOC(=O)CC1(CCCCCN(CCCO)CCCCCCCC(=O)OCC(CCCCCCC)CCCCCCC)CC1]
74c
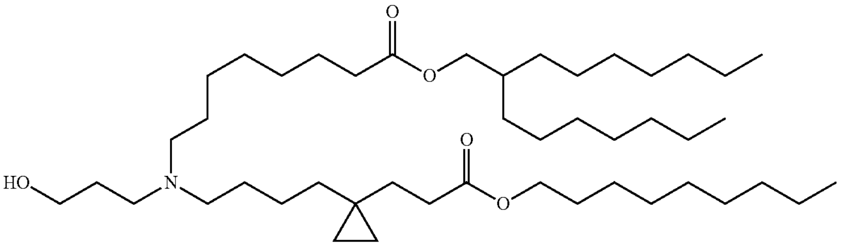 [SMILES: CCCCCCCCCOC(=O)CCC1(CCCCN(CCCO)CCCCCCCC(=O)OCC(CCCCCCC)CCCCCCC)CC1]
75c
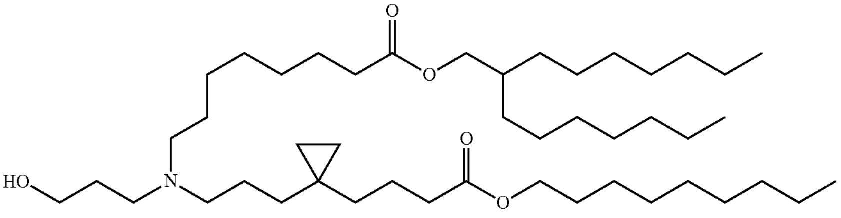 [SMILES: CCCCCCCCCOC(=O)CCCC1(CCCN(CCCO)CCCCCCCC(=O)OCC(CCCCCCC)CCCCCCC)CC1]
76c
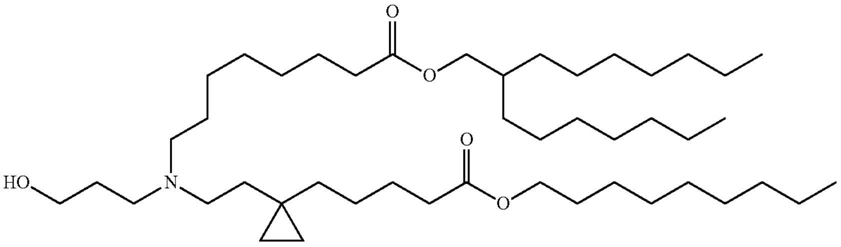 [SMILES: CCCCCCCCCOC(=O)CCCCC1(CCN(CCCO)CCCCCCCC(=O)OCC(CCCCCCC)CCCCCCC)CC1]
77c TABLE I-continued
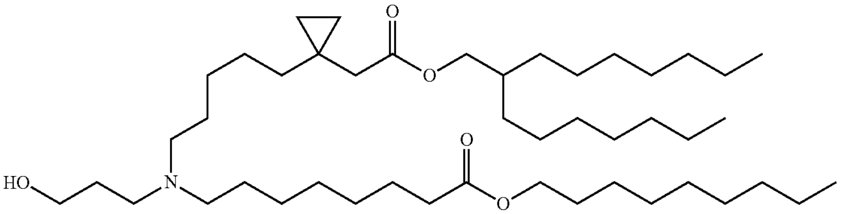 [SMILES: CCCCCCCCCOC(=O)CCCCCCCN(CCCO)CCCCCC1(CC(=O)OCC(CCCCCCC)CCCCCCC)CC1]
78c
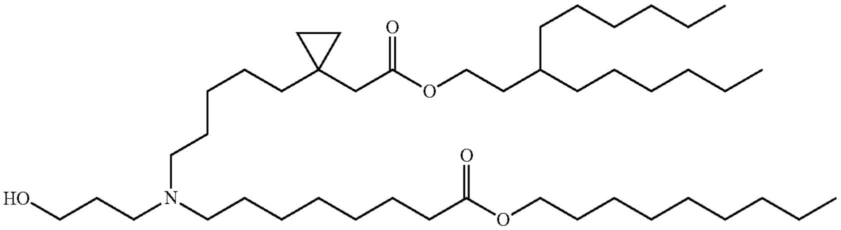 [SMILES: CCCCCCCCCOC(=O)CCCCCCCN(CCCO)CCCCCC1(CC(=O)OCCC(CCCCCC)CCCCCC)CC1]
79c
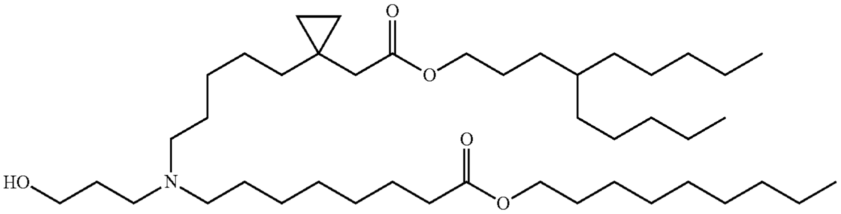 [SMILES: CCCCCCCCCOC(=O)CCCCCCCN(CCCO)CCCCCC1(CC(=O)OCCCC(CCCCC)CCCCC)CC1]
80c
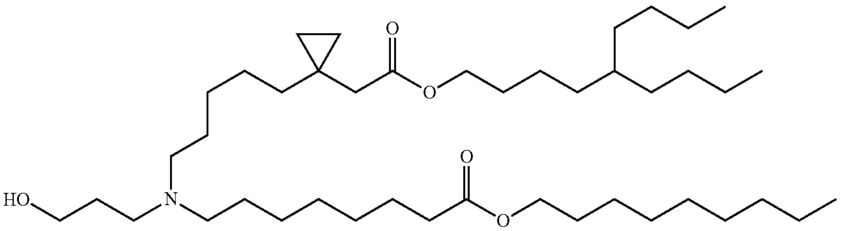 [SMILES: CCCCCCCCCOC(=O)CCCCCCCN(CCCO)CCCCCC1(CC(=O)OCCCCC(CCCC)CCCC)CC1]
81c
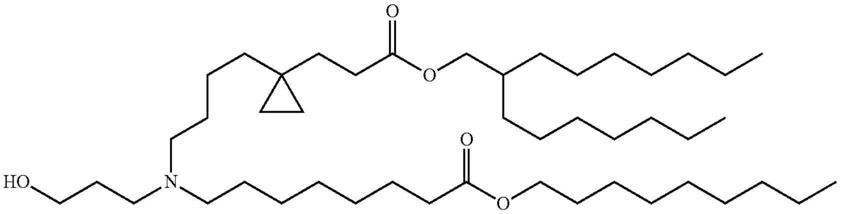 [SMILES: CCCCCCCCCOC(=O)CCCCCCCN(CCCO)CCCCC1(CCC(=O)OCC(CCCCCCC)CCCCCCC)CC1]
82c
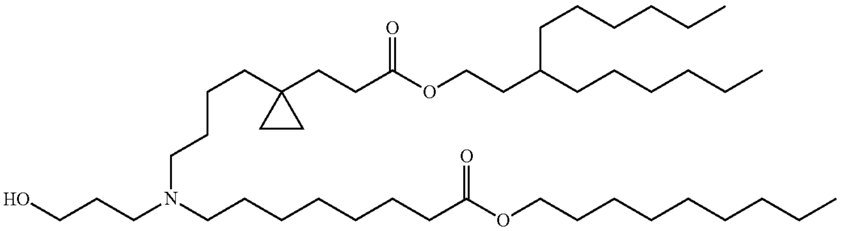 [SMILES: CCCCCCCCCOC(=O)CCCCCCCN(CCCO)CCCCC1(CCC(=O)OCCC(CCCCCC)CCCCCC)CC1]
83c
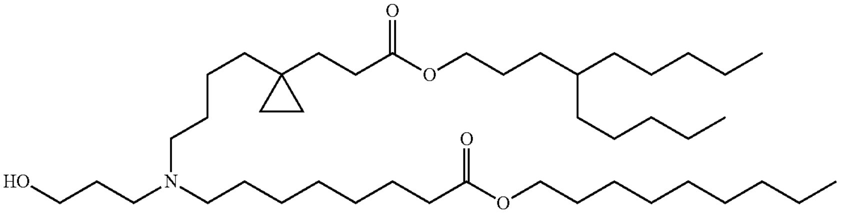 [SMILES: CCCCCCCCCOC(=O)CCCCCCCN(CCCO)CCCCC1(CCC(=O)OCCCC(CCCCC)CCCCC)CC1]
84c TABLE I-continued
85c
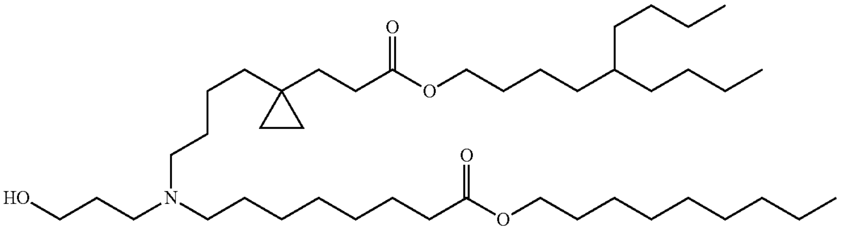 [SMILES: CCCCCCCCCOC(=O)CCCCCCCN(CCCO)CCCCC1(CCC(=O)OCCCCC(CCCC)CCCC)CC1]
86c
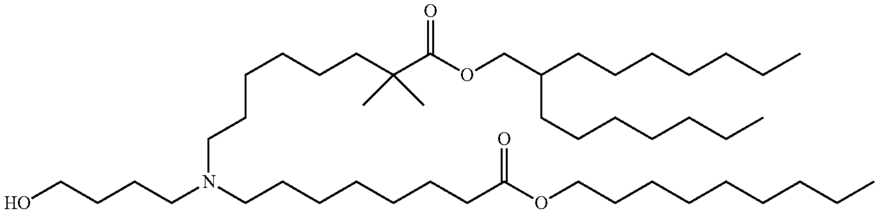 [SMILES: CCCCCCCCCOC(=O)CCCCCCCN(CCCCO)CCCCCCC(C)(C)C(=O)OCC(CCCCCCC)CCCCCCC]
87c
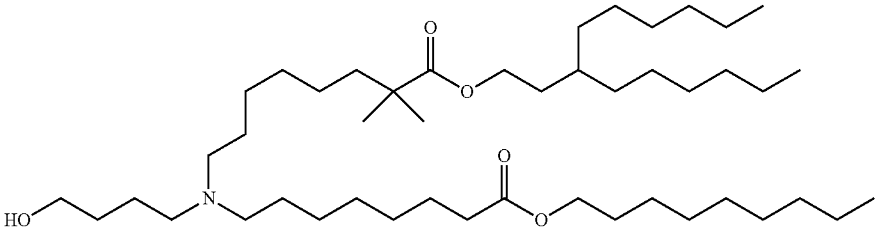 [SMILES: CCCCCCCCCOC(=O)CCCCCCCN(CCCCO)CCCCCCC(C)(C)C(=O)OCCC(CCCCCC)CCCCCC]
88c
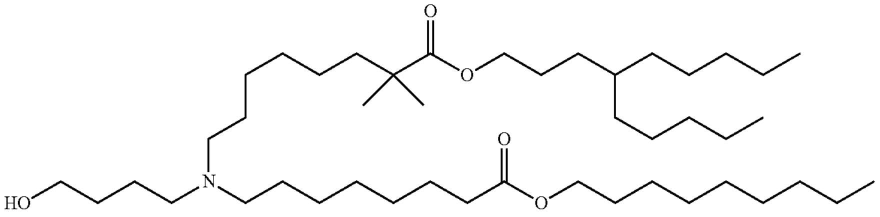 [SMILES: CCCCCCCCCOC(=O)CCCCCCCN(CCCCO)CCCCCCC(C)(C)C(=O)OCCCC(CCCCC)CCCCC]
89c
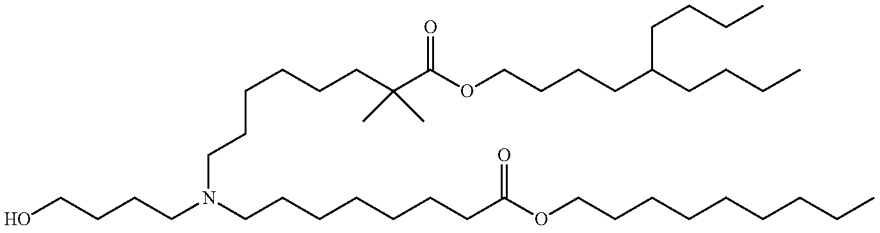 [SMILES: CCCCCCCCCOC(=O)CCCCCCCN(CCCCO)CCCCCCC(C)(C)C(=O)OCCCCC(CCCC)CCCC]
90c
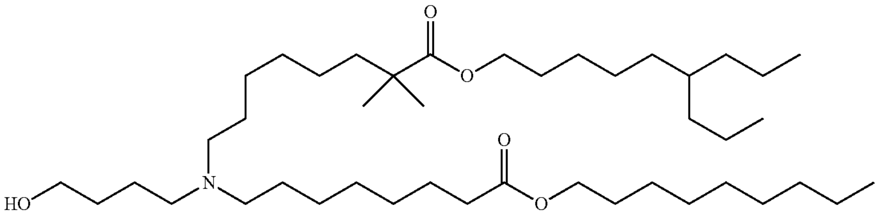 [SMILES: CCCCCCCCCOC(=O)CCCCCCCN(CCCCO)CCCCCCC(C)(C)C(=O)OCCCCCC(CCC)CCC]
91c
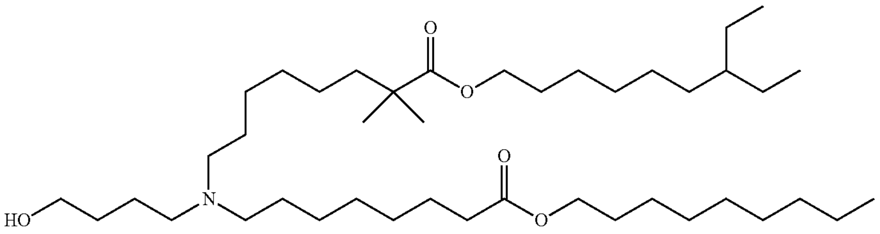 [SMILES: CCCCCCCCCOC(=O)CCCCCCCN(CCCCO)CCCCCCC(C)(C)C(=O)OCCCCCCC(CC)CC]

TABLE I-continued
92c
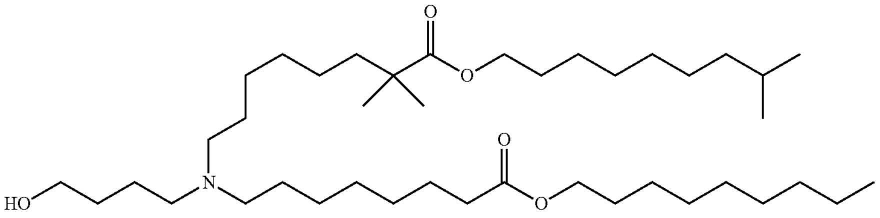 [SMILES: CCCCCCCCCOC(=O)CCCCCCCN(CCCCO)CCCCCCC(C)(C)C(=O)OCCCCCCCC(C)C]
93c
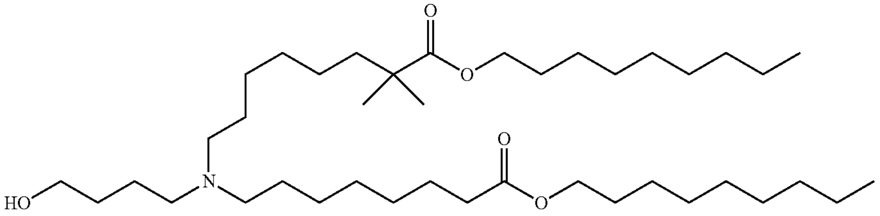 [SMILES: CCCCCCCCCOC(=O)CCCCCCCN(CCCCO)CCCCCCC(C)(C)C(=O)OCCCCCCCCC]
94c
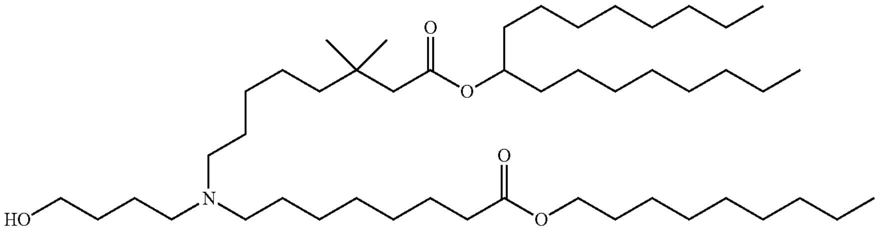 [SMILES: CCCCCCCCCOC(=O)CCCCCCCN(CCCCO)CCCCCC(C)(C)CC(=O)OC(CCCCCCCC)CCCCCCCC]
95c
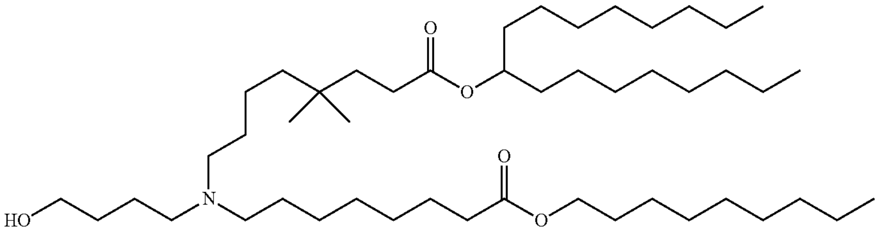 [SMILES: CCCCCCCCCOC(=O)CCCCCCCN(CCCCO)CCCCC(C)(C)CCC(=O)OC(CCCCCCCC)CCCCCCCC]
96c
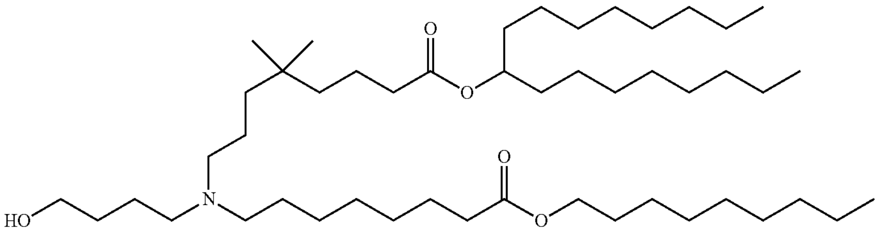 [SMILES: CCCCCCCCCOC(=O)CCCCCCCN(CCCCO)CCCC(C)(C)CCCC(=O)OC(CCCCCCCC)CCCCCCCC]
97c
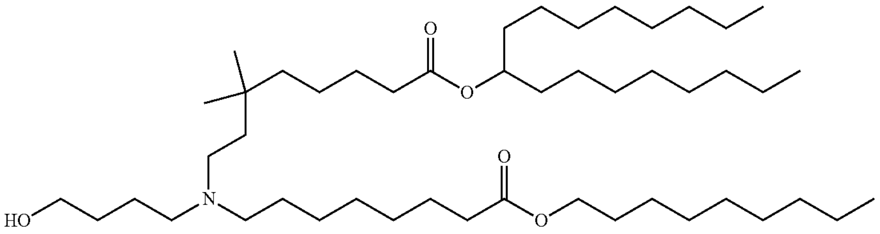 [SMILES: CCCCCCCCCOC(=O)CCCCCCCN(CCCCO)CCC(C)(C)CCCCC(=O)OC(CCCCCCCC)CCCCCCCC]

TABLE I-continued
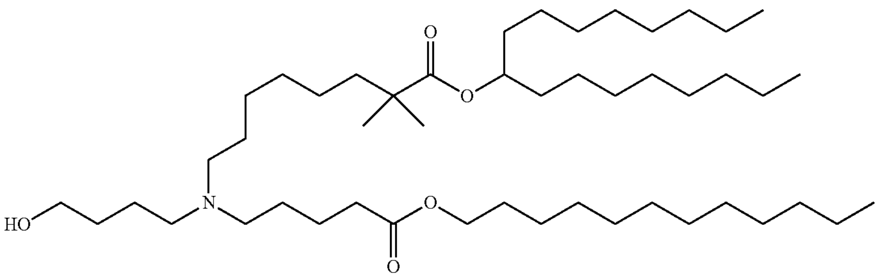 [SMILES: CCCCCCCCCCCCOC(=O)CCCCN(CCCCO)CCCCCCC(C)(C)C(=O)OC(CCCCCCCC)CCCCCCCC]
98c
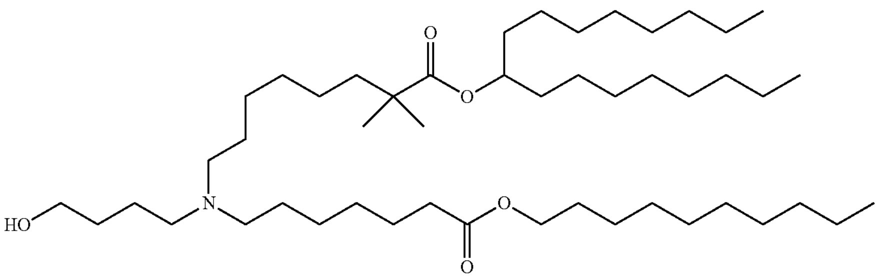
99c
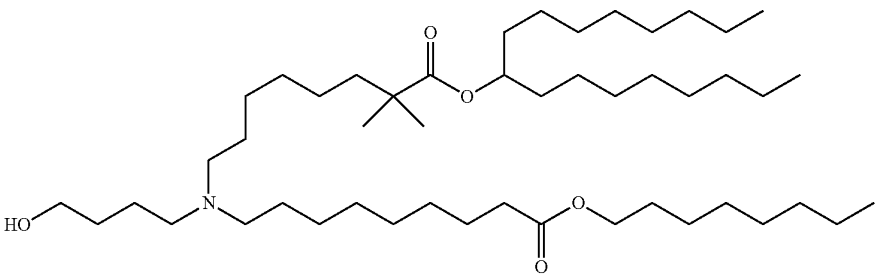
100c
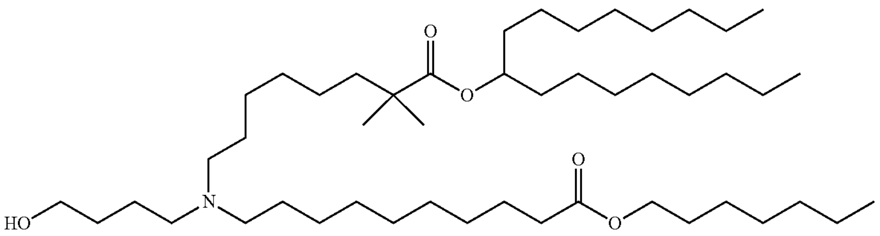 [SMILES: CCCCCCCCC(CCCCCCCC)OC(=O)C(C)(C)CCCCCCN(CCCCO)CCCCCCCCCC(=O)OCCCCCCC]
101c
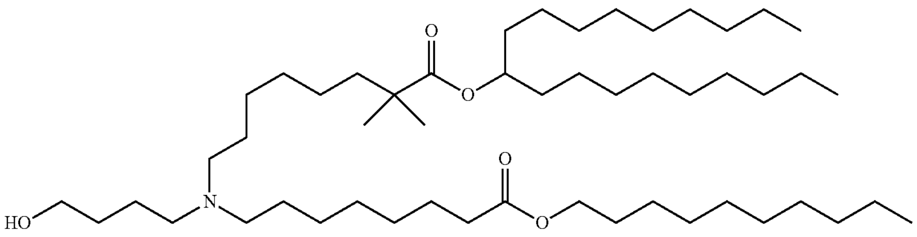 [SMILES: CCCCCCCCCCOC(=O)CCCCCCCN(CCCCO)CCCCCCC(C)(C)C(=O)OC(CCCCCCCCC)CCCCCCCCC]
102c
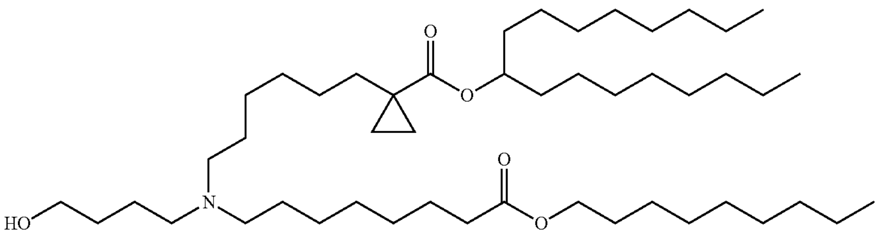 [SMILES: CCCCCCCCCOC(=O)CCCCCCCN(CCCCO)CCCCCCC1(C(=O)OC(CCCCCCCC)CCCCCCCC)CC1]
103c TABLE I-continued
104c
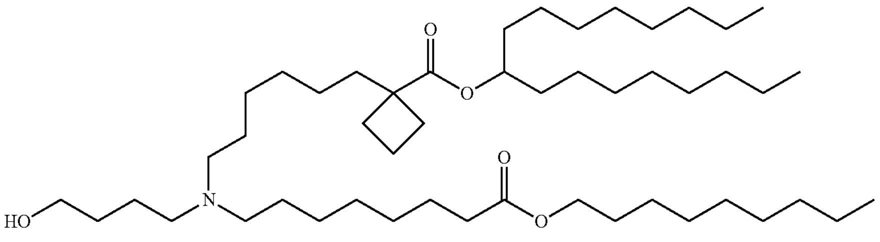 [SMILES: CCCCCCCCCOC(=O)CCCCCCCN(CCCCO)CCCCCCC1(C(=O)OC(CCCCCCCC)CCCCCCCC)CCC1]
105c
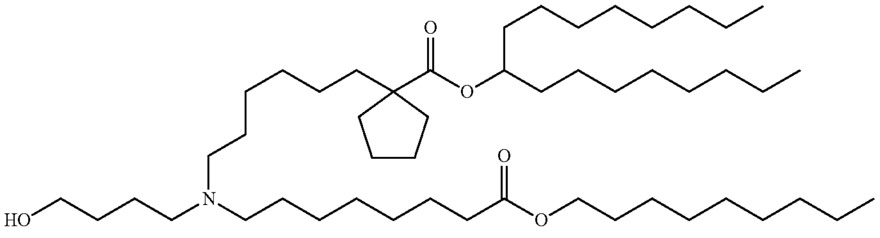 [SMILES: CCCCCCCCCOC(=O)CCCCCCCN(CCCCO)CCCCCCC1(C(=O)OC(CCCCCCCC)CCCCCCCC)CCCC1]
106c
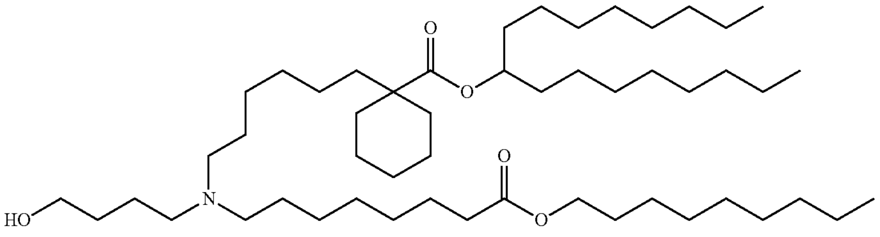 [SMILES: CCCCCCCCCOC(=O)CCCCCCCN(CCCCO)CCCCCCC1(C(=O)OC(CCCCCCCC)CCCCCCCC)CCCCC1]
107c
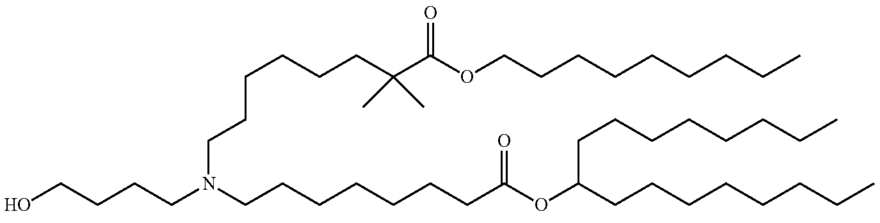 [SMILES: CCCCCCCCCOC(=O)C(C)(C)CCCCCCN(CCCCO)CCCCCCCC(=O)OC(CCCCCCCC)CCCCCCCC]
108c
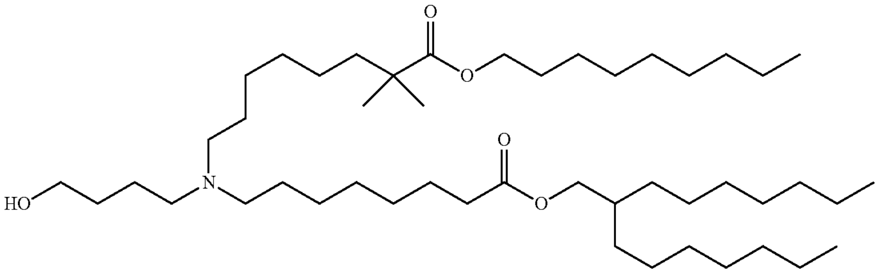 [SMILES: CCCCCCCCCOC(=O)C(C)(C)CCCCCCN(CCCCO)CCCCCCCC(=O)OCC(CCCCCCC)CCCCCCC]
109c
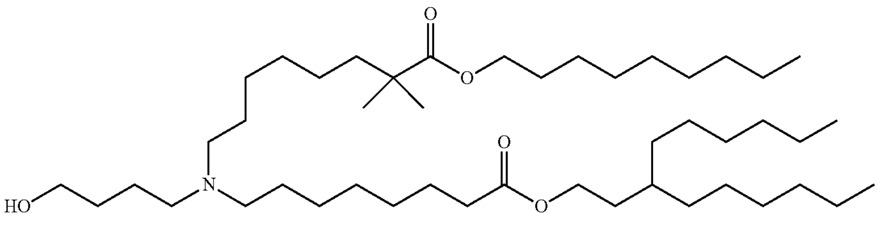 [SMILES: CCCCCCCCCOC(=O)C(C)(C)CCCCCCN(CCCCO)CCCCCCCC(=O)OCCC(CCCCCC)CCCCCC]

TABLE I-continued
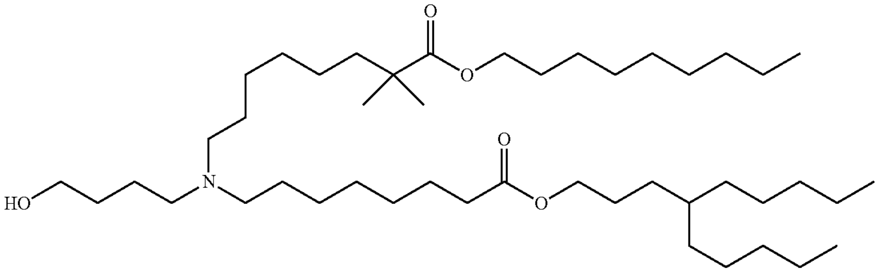 [SMILES: CCCCCCCCCOC(=O)C(C)(C)CCCCCCN(CCCCO)CCCCCCCC(=O)OCCCC(CCCCC)CCCCC]
110c
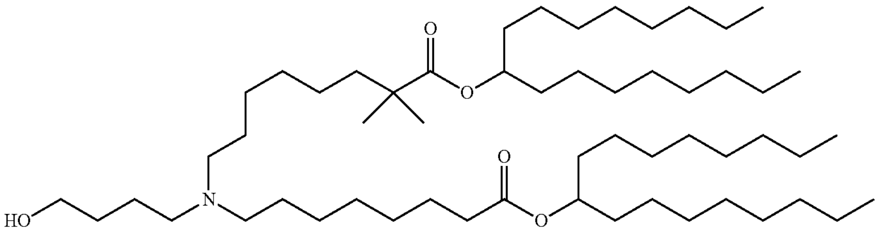 [SMILES: CCCCCCCCC(CCCCCCCC)OC(=O)CCCCCCCN(CCCCO)CCCCCCC(C)(C)C(=O)OC(CCCCCCCC)CCCCCCCC]
111c
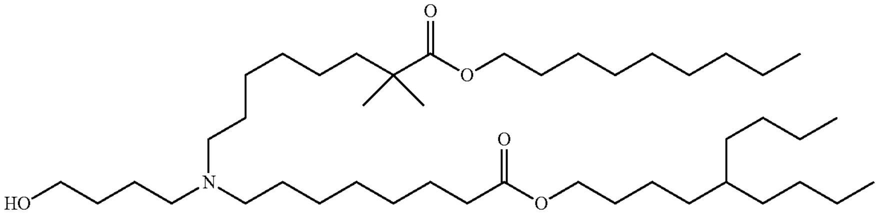 [SMILES: CCCCCCCCCOC(=O)C(C)(C)CCCCCCN(CCCCO)CCCCCCCC(=O)OCCCCC(CCCC)CCCC]
112c
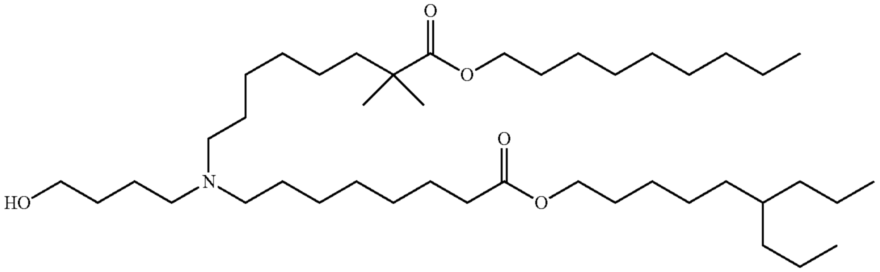 [SMILES: CCCCCCCCCOC(=O)C(C)(C)CCCCCCN(CCCCO)CCCCCCCC(=O)OCCCCCC(CCC)CCC]
113c
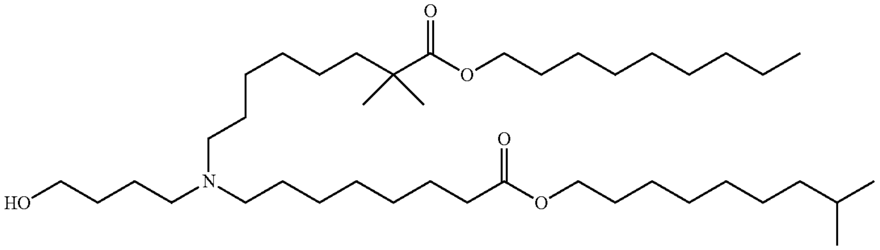 [SMILES: CCCCCCCCCOC(=O)C(C)(C)CCCCCCN(CCCCO)CCCCCCCC(=O)OCCCCCCCC(C)C]
114c
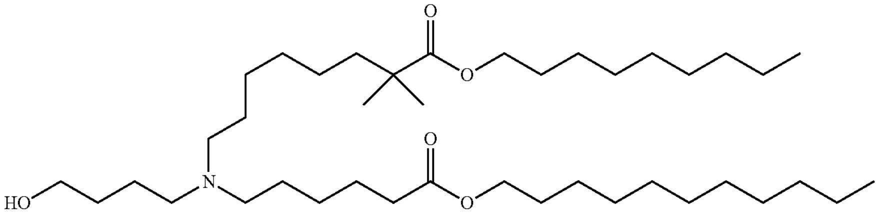 [SMILES: CCCCCCCCCCCOC(=O)CCCCCN(CCCCO)CCCCCCC(C)(C)C(=O)OCCCCCCCCC]
115c TABLE I-continued
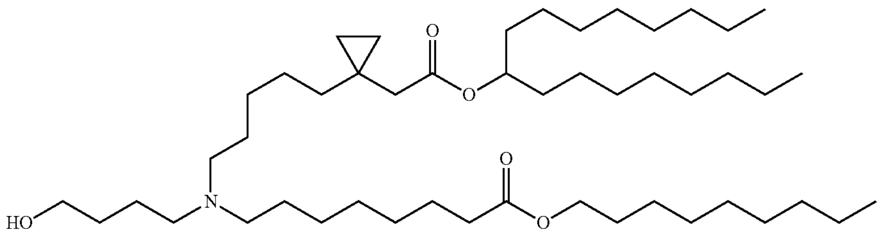 [SMILES: CCCCCCCCCOC(=O)CCCCCCCN(CCCCO)CCCCCC1(CC(=O)OC(CCCCCCCC)CCCCCCCC)CC1]
116c
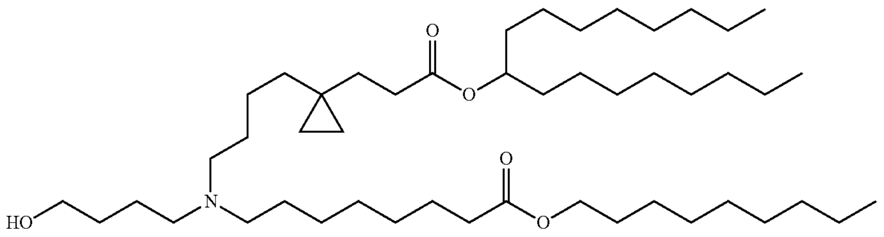 [SMILES: CCCCCCCCCOC(=O)CCCCCCCN(CCCCO)CCCCC1(CCC(=O)OC(CCCCCCCC)CCCCCCCC)CC1]
117c
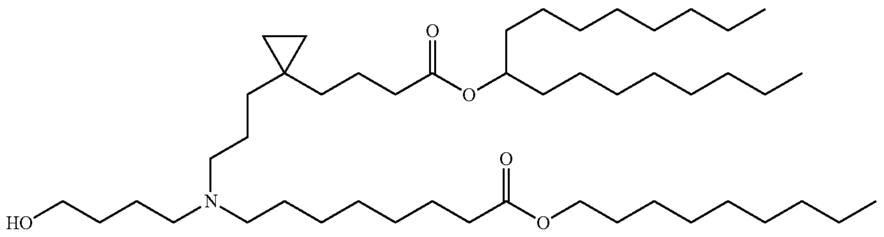 [SMILES: CCCCCCCCCOC(=O)CCCCCCCN(CCCCO)CCCC1(CCCC(=O)OC(CCCCCCCC)CCCCCCCC)CC1]
118c
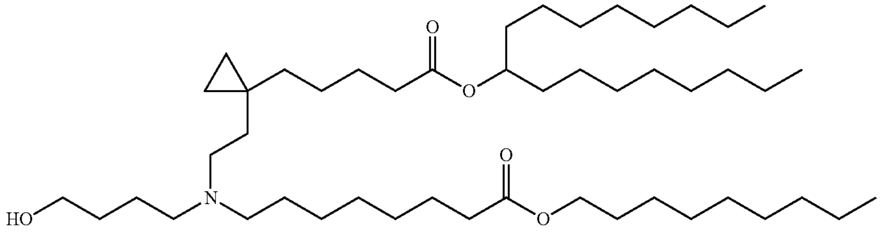 [SMILES: CCCCCCCCCOC(=O)CCCCCCCN(CCCCO)CCC1(CCCCC(=O)OC(CCCCCCCC)CCCCCCCC)CC1]
119c
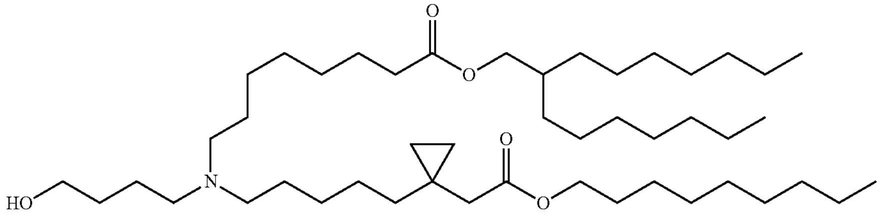 [SMILES: CCCCCCCCCOC(=O)CC1(CCCCCN(CCCCO)CCCCCCCC(=O)OCC(CCCCCCC)CCCCCCC)CC1]
120c
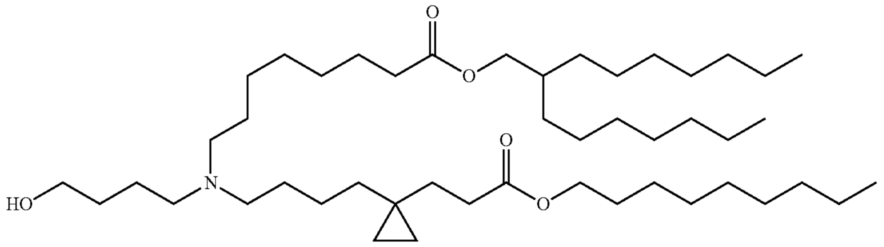 [SMILES: CCCCCCCCCOC(=O)CCC1(CCCCN(CCCCO)CCCCCCCC(=O)OCC(CCCCCCC)CCCCCCC)CC1]
121c TABLE I-continued
122c
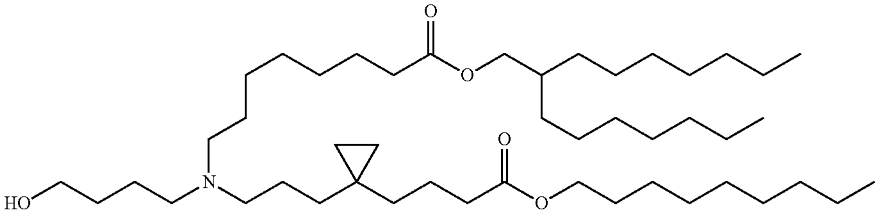 [SMILES: CCCCCCCCCOC(=O)CCCC1(CCCN(CCCCO)CCCCCCCC(=O)OCC(CCCCCCC)CCCCCCC)CC1]
123c
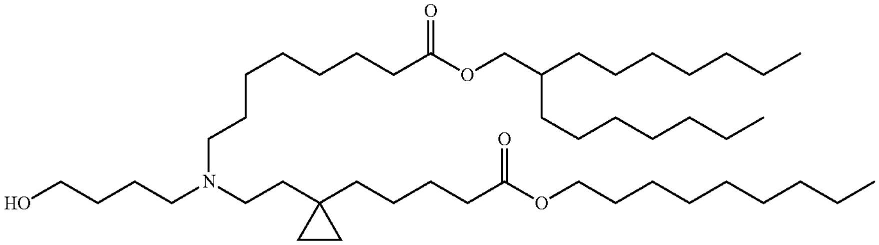 [SMILES: CCCCCCCCCOC(=O)CCCCC1(CCN(CCCCO)CCCCCCCC(=O)OCC(CCCCCCC)CCCCCCC)CC1]
124c
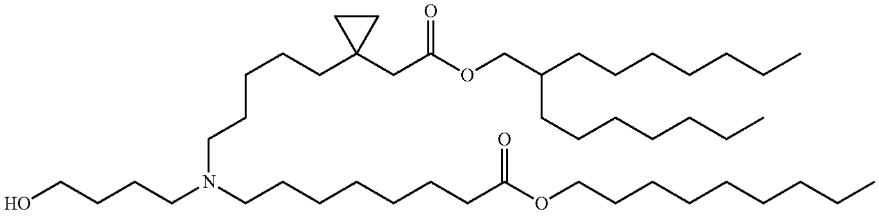 [SMILES: CCCCCCCCCOC(=O)CCCCCCCN(CCCCO)CCCCCC1(CC(=O)OCC(CCCCCCC)CCCCCCC)CC1]
125c
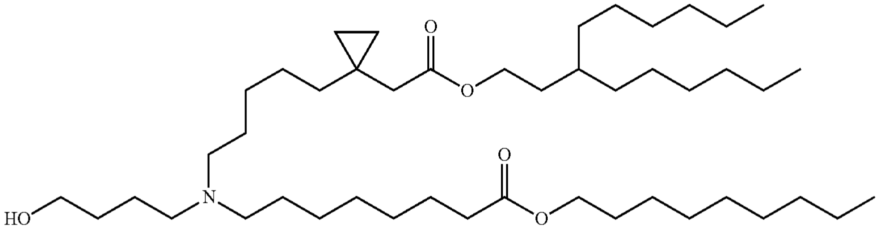 [SMILES: CCCCCCCCCOC(=O)CCCCCCCN(CCCCO)CCCCCC1(CC(=O)OCCC(CCCCCC)CCCCCC)CC1]
126c
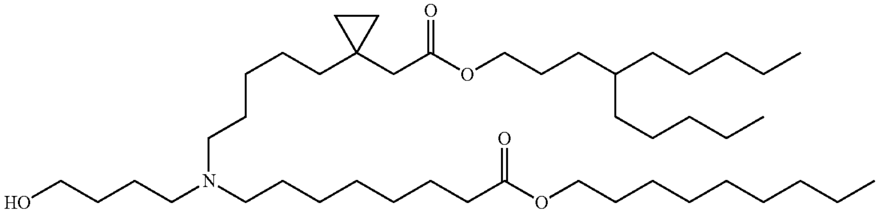 [SMILES: CCCCCCCCCOC(=O)CCCCCCCN(CCCCO)CCCCCC1(CC(=O)OCCCC(CCCCC)CCCCC)CC1]
127c
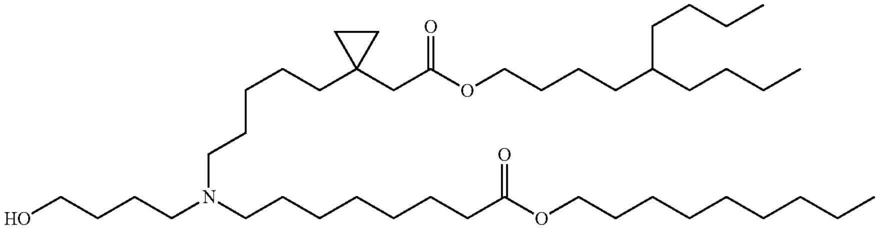 [SMILES: CCCCCCCCCOC(=O)CCCCCCCN(CCCCO)CCCCCC1(CC(=O)OCCCCC(CCCC)CCCC)CC1]
128c
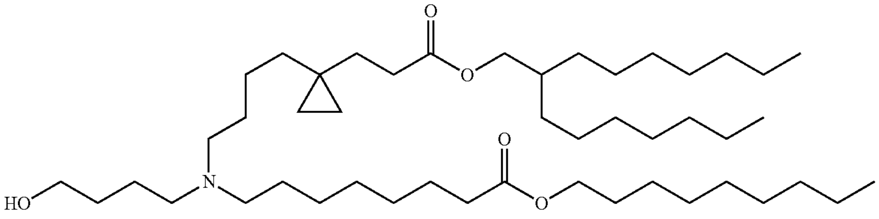 [SMILES: CCCCCCCCCOC(=O)CCCCCCCN(CCCCO)CCCCC1(CCC(=O)OCC(CCCCCCC)CCCCCCC)CC1]

TABLE I-continued
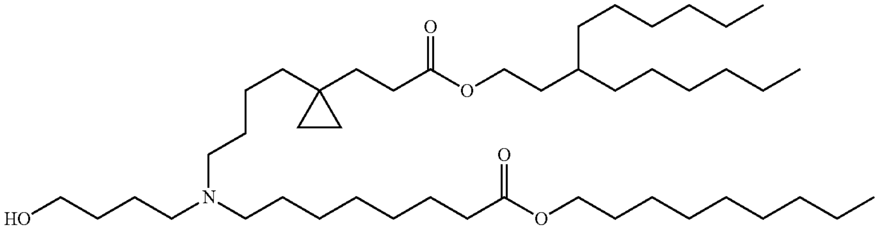 [SMILES: CCCCCCCCCOC(=O)CCCCCCCN(CCCCO)CCCCC1(CCC(=O)OCCC(CCCCCC)CCCCCC)CC1]
129c
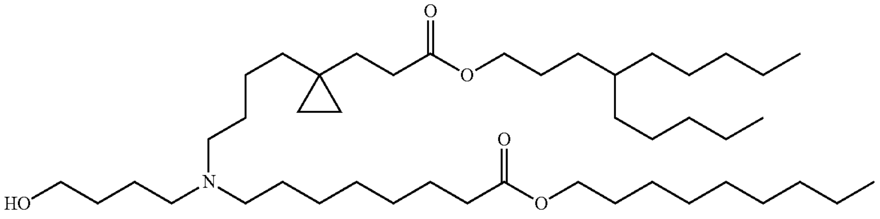 [SMILES: CCCCCCCCCOC(=O)CCCCCCCN(CCCCO)CCCCC1(CCC(=O)OCCCC(CCCCC)CCCCC)CC1]
130c
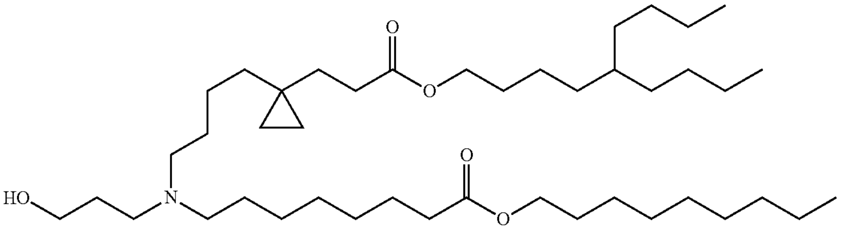 [SMILES: CCCCCCCCCOC(=O)CCCCCCCN(CCCO)CCCCC1(CCC(=O)OCCCCC(CCCC)CCCC)CC1]
131c
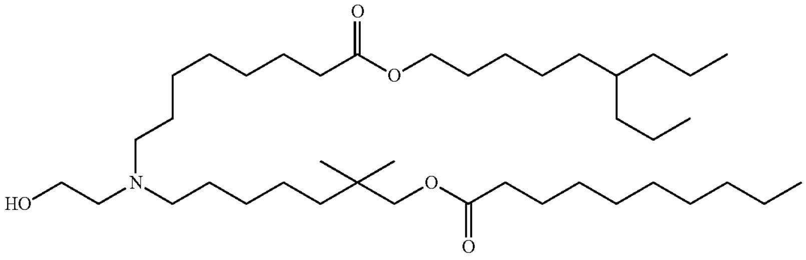 [SMILES: CCCCCCCCCC(=O)OCC(C)(C)CCCCCN(CCO)CCCCCCCC(=O)OCCCCCC(CCC)CCC]
132c
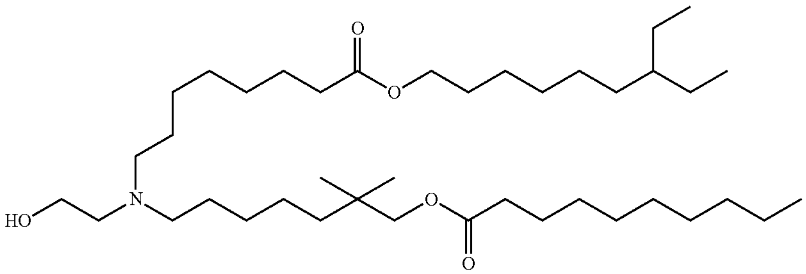 [SMILES: CCCCCCCCCC(=O)OCC(C)(C)CCCCCN(CCO)CCCCCCCC(=O)OCCCCCCC(CC)CC]
133c
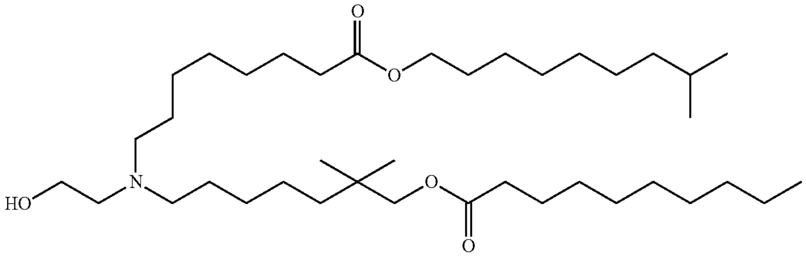 [SMILES: CCCCCCCCCC(=O)OCC(C)(C)CCCCCN(CCO)CCCCCCCC(=O)OCCCCCCCC(C)C]
134c TABLE I-continued
135c
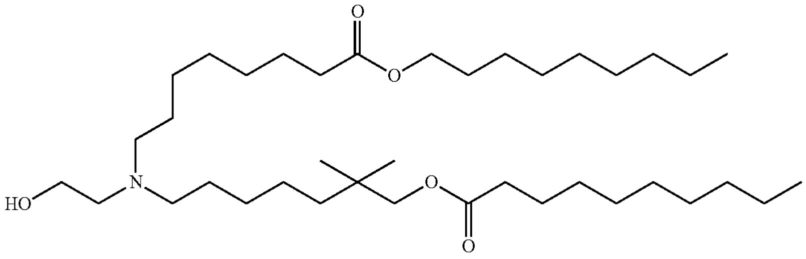 [SMILES: CCCCCCCCCOC(=O)CCCCCCCN(CCO)CCCCCC(C)(C)COC(=O)CCCCCCCCC]
136c
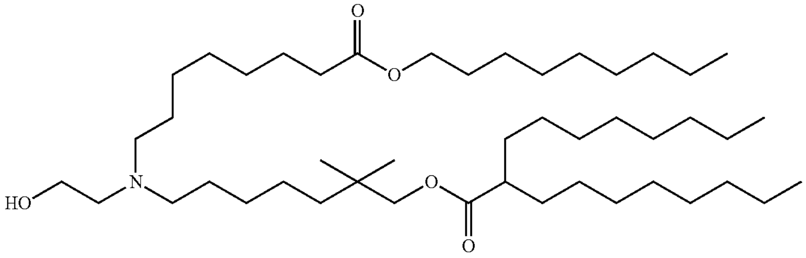 [SMILES: CCCCCCCCCOC(=O)CCCCCCCN(CCO)CCCCCC(C)(C)COC(=O)C(CCCCCCCC)CCCCCCCC]
137c
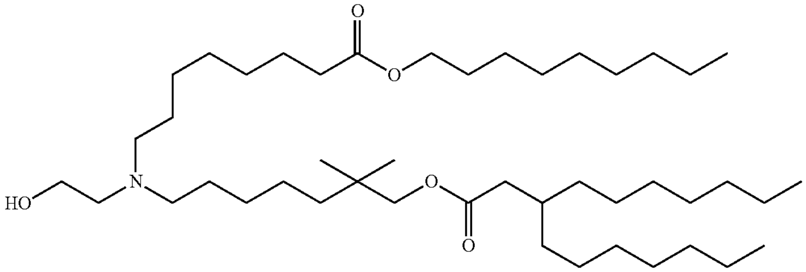 [SMILES: CCCCCCCCCOC(=O)CCCCCCCN(CCO)CCCCCC(C)(C)COC(=O)CC(CCCCCCC)CCCCCCC]
138c
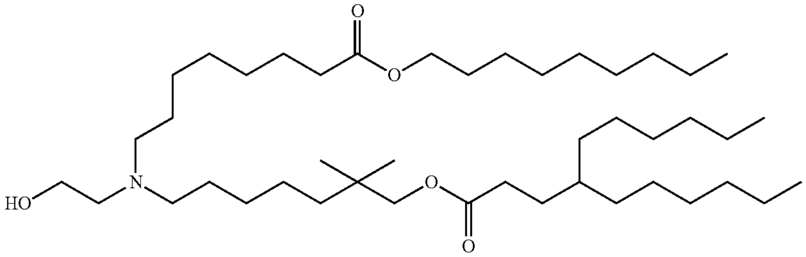 [SMILES: CCCCCCCCCOC(=O)CCCCCCCN(CCO)CCCCCC(C)(C)COC(=O)CCC(CCCCCC)CCCCCC]
139c
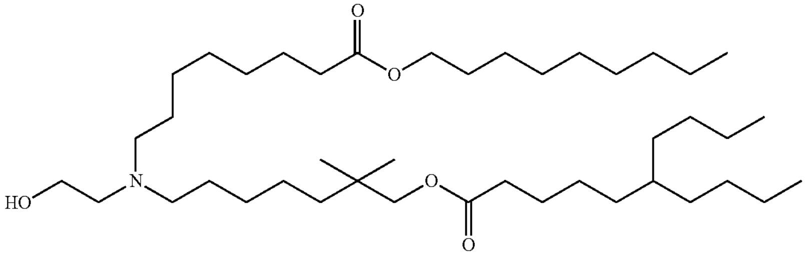 [SMILES: CCCCCCCCCOC(=O)CCCCCCCN(CCO)CCCCCC(C)(C)COC(=O)CCCCC(CCCC)CCCC]
140c
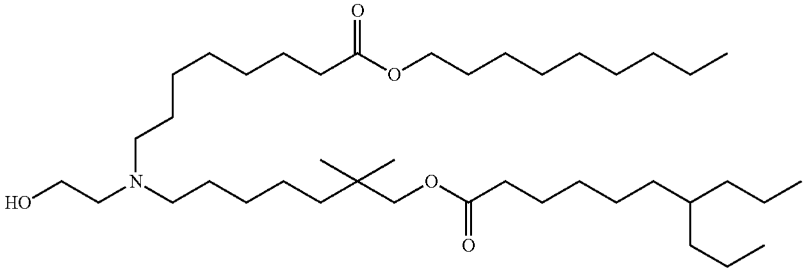 [SMILES: CCCCCCCCCOC(=O)CCCCCCCN(CCO)CCCCCC(C)(C)COC(=O)CCCCCC(CCC)CCC]

TABLE I-continued
141c
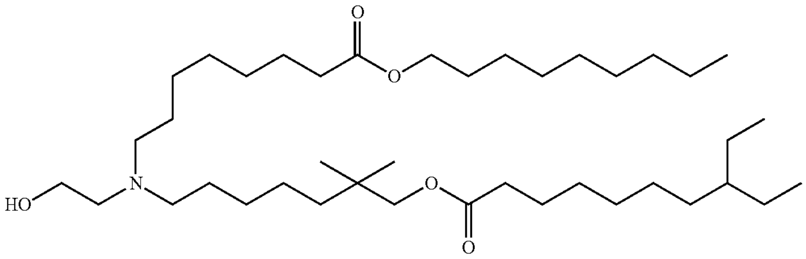 [SMILES: CCCCCCCCCOC(=O)CCCCCCCN(CCO)CCCCCC(C)(C)COC(=O)CCCCCCC(CC)CC]
142c
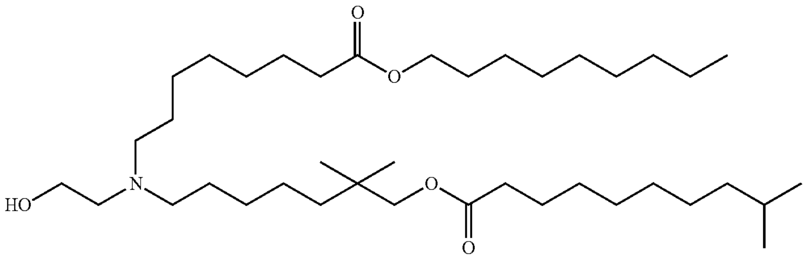 [SMILES: CCCCCCCCCOC(=O)CCCCCCCN(CCO)CCCCCC(C)(C)COC(=O)CCCCCCCC(C)C]
143c
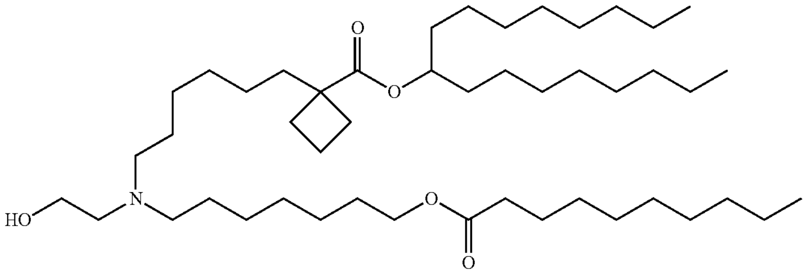 [SMILES: CCCCCCCCCC(=O)OCCCCCCCN(CCO)CCCCCCC1(C(=O)OC(CCCCCCCC)CCCCCCCC)CCC1]
144c
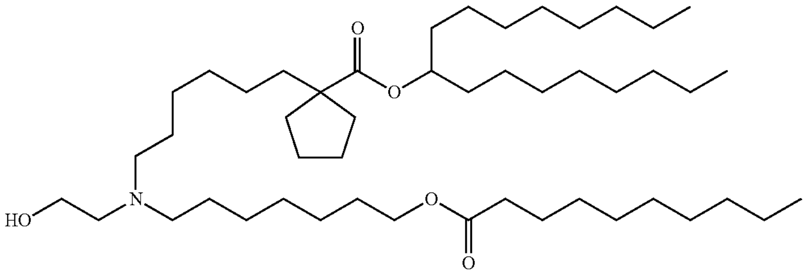 [SMILES: CCCCCCCCCC(=O)OCCCCCCCN(CCO)CCCCCCC1(C(=O)OC(CCCCCCCC)CCCCCCCC)CCCC1]
145c
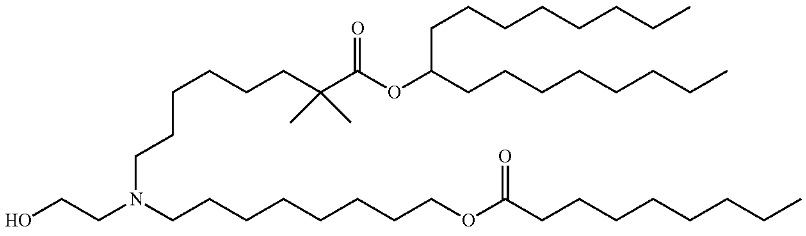 [SMILES: CCCCCCCCC(=O)OCCCCCCCCN(CCO)CCCCCCC(C)(C)C(=O)OC(CCCCCCCC)CCCCCCCC]
146c
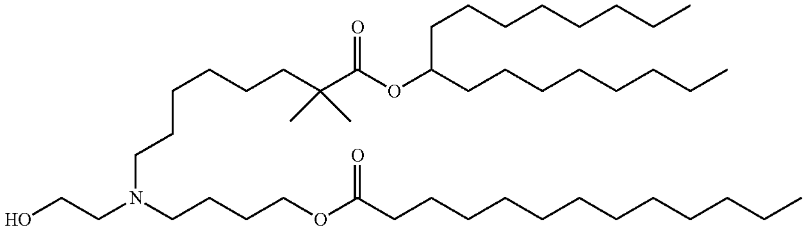

TABLE I-continued
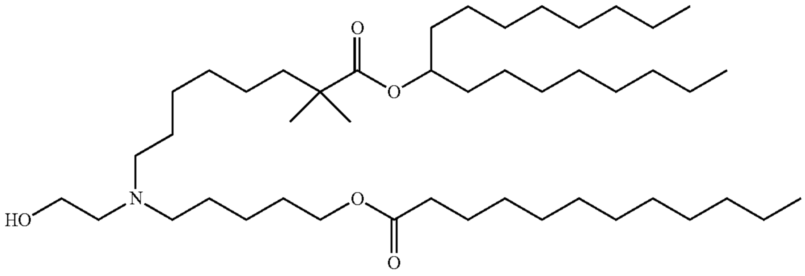 [SMILES: CCCCCCCCCCCC(=O)OCCCCCN(CCO)CCCCCCC(C)(C)C(=O)OC(CCCCCCCC)CCCCCCCC]
147c
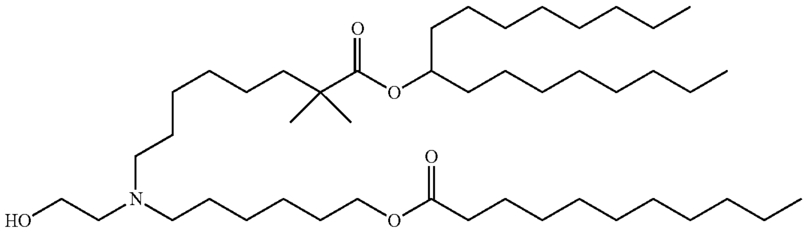
148c
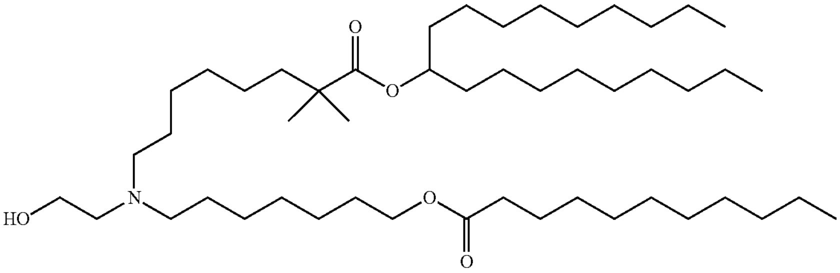 [SMILES: CCCCCCCCCCC(=O)OCCCCCCCN(CCO)CCCCCCC(C)(C)C(=O)OC(CCCCCCCCC)CCCCCCCCC]
149c
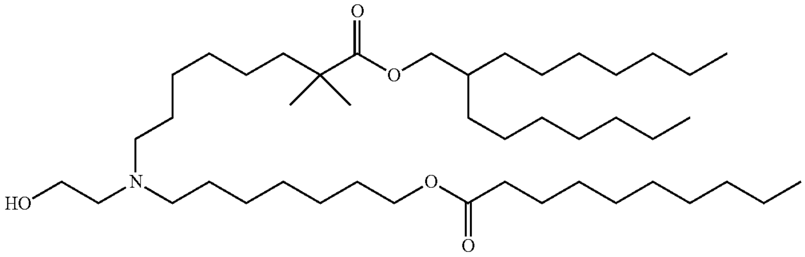 [SMILES: CCCCCCCCCC(=O)OCCCCCCCN(CCO)CCCCCCC(C)(C)C(=O)OCC(CCCCCCC)CCCCCCC]
150c
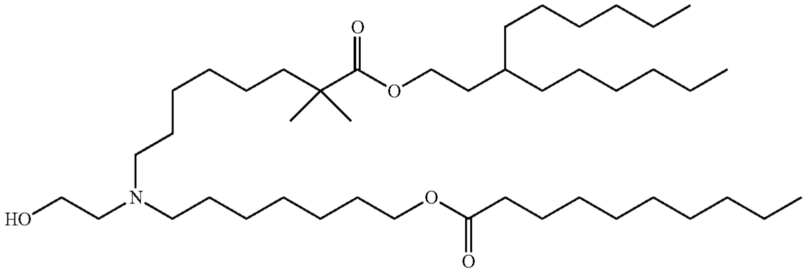 [SMILES: CCCCCCCCCC(=O)OCCCCCCCN(CCO)CCCCCCC(C)(C)C(=O)OCCC(CCCCCC)CCCCCC]
151c
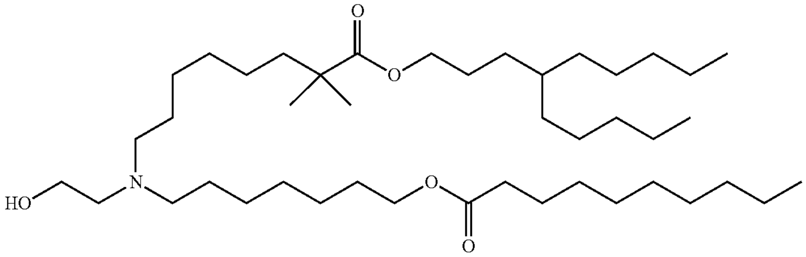 [SMILES: CCCCCCCCCC(=O)OCCCCCCCN(CCO)CCCCCCC(C)(C)C(=O)OCCCC(CCCCC)CCCCC]
152c TABLE I-continued
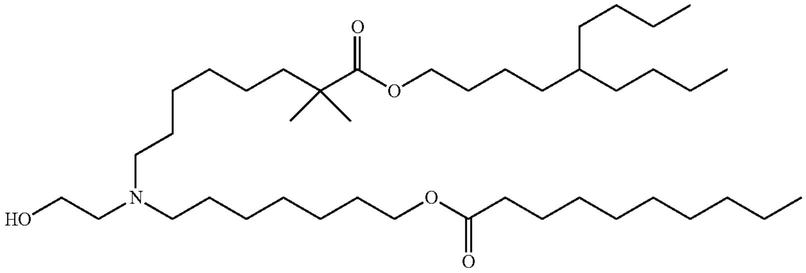 [SMILES: CCCCCCCCCC(=O)OCCCCCCCN(CCO)CCCCCCC(C)(C)C(=O)OCCCCC(CCCC)CCCC]
153c
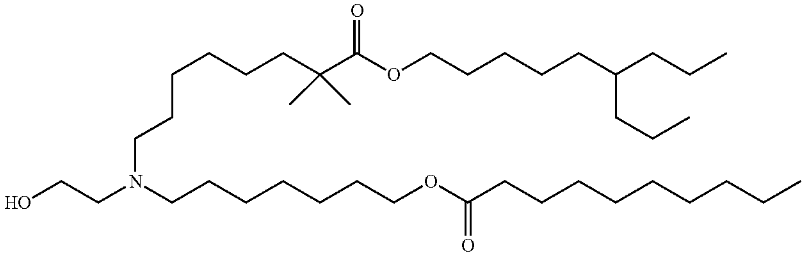 [SMILES: CCCCCCCCCC(=O)OCCCCCCCN(CCO)CCCCCCC(C)(C)C(=O)OCCCCCC(CCC)CCC]
154c
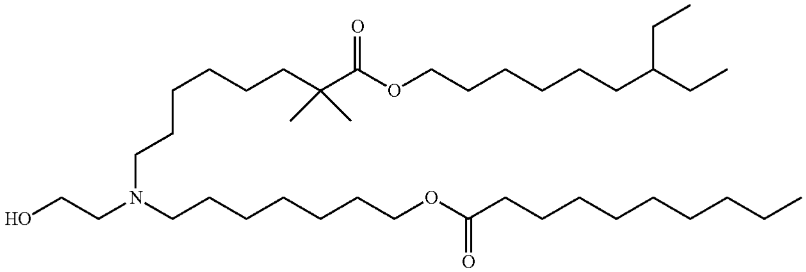 [SMILES: CCCCCCCCCC(=O)OCCCCCCCN(CCO)CCCCCCC(C)(C)C(=O)OCCCCCCC(CC)CC]
155c
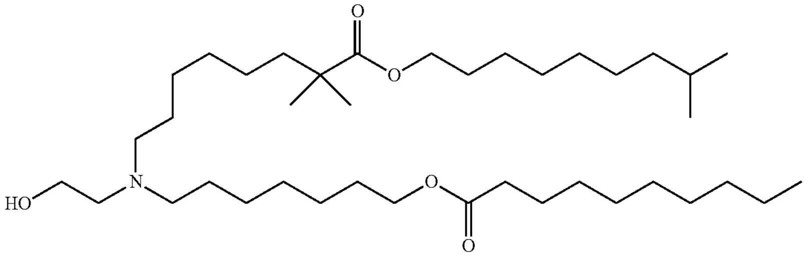 [SMILES: CCCCCCCCCC(=O)OCCCCCCCN(CCO)CCCCCCC(C)(C)C(=O)OCCCCCCCC(C)C]
156c
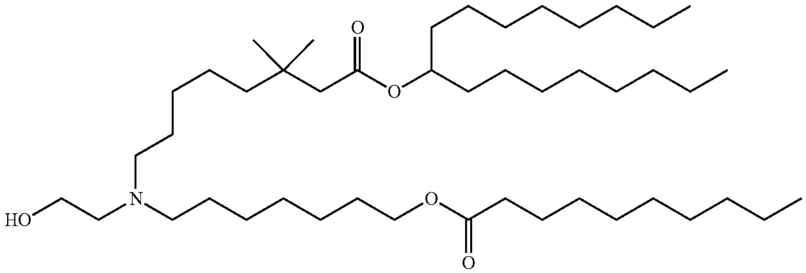 [SMILES: CCCCCCCCCC(=O)OCCCCCCCN(CCO)CCCCCC(C)(C)CC(=O)OC(CCCCCCCC)CCCCCCCC]
157c
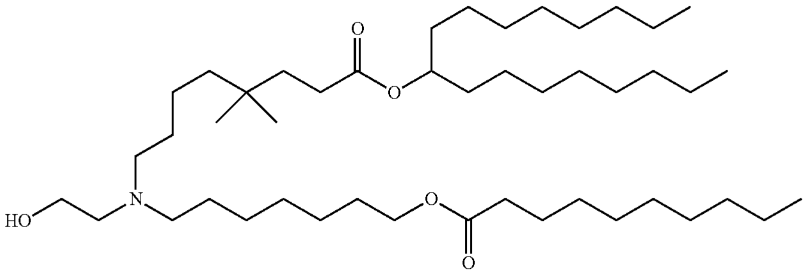 [SMILES: CCCCCCCCCC(=O)OCCCCCCCN(CCO)CCCCC(C)(C)CCC(=O)OC(CCCCCCCC)CCCCCCCC]
158c TABLE I-continued
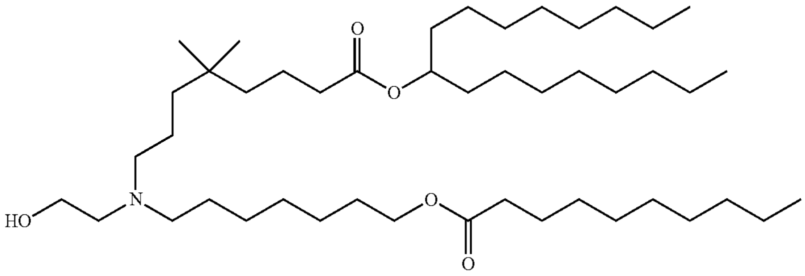 [SMILES: CCCCCCCCCC(=O)OCCCCCCCN(CCO)CCCC(C)(C)CCCC(=O)OC(CCCCCCCC)CCCCCCCC]
159c
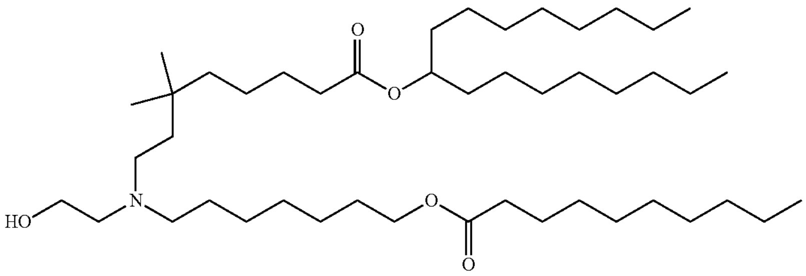 [SMILES: CCCCCCCCCC(=O)OCCCCCCCN(CCO)CCC(C)(C)CCCCC(=O)OC(CCCCCCCC)CCCCCCCC]
160c
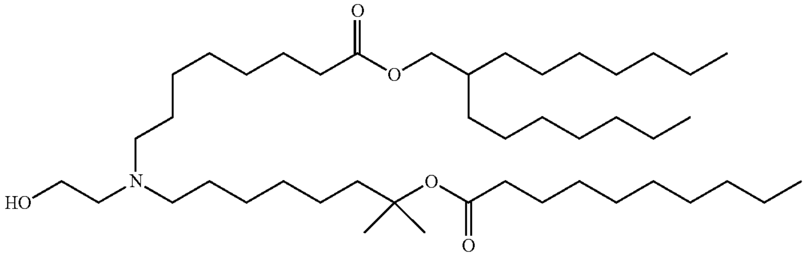 [SMILES: CCCCCCCCCC(=O)OC(C)(C)CCCCCCN(CCO)CCCCCCCC(=O)OCC(CCCCCCC)CCCCCCC]
161c
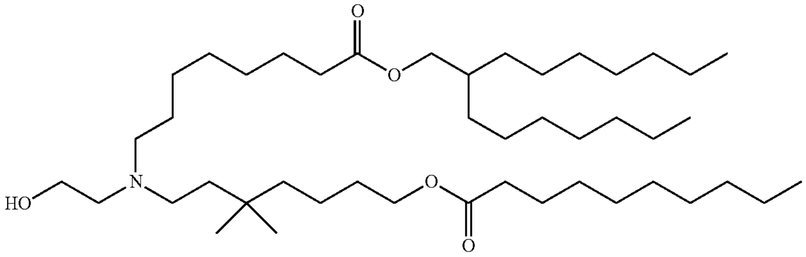 [SMILES: CCCCCCCCCC(=O)OCCCCC(C)(C)CCN(CCO)CCCCCCCC(=O)OCC(CCCCCCC)CCCCCCC]
162c
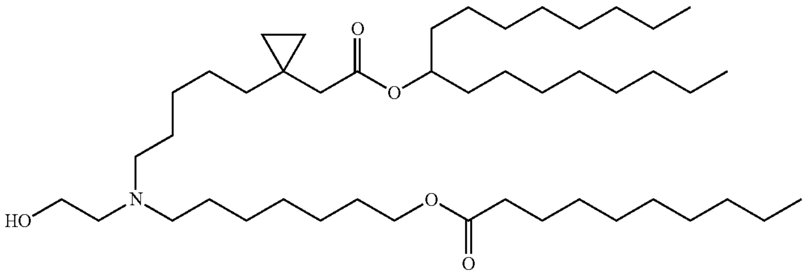 [SMILES: CCCCCCCCCC(=O)OCCCCCCCN(CCO)CCCCCC1(CC(=O)OC(CCCCCCCC)CCCCCCCC)CC1]
163c TABLE I-continued
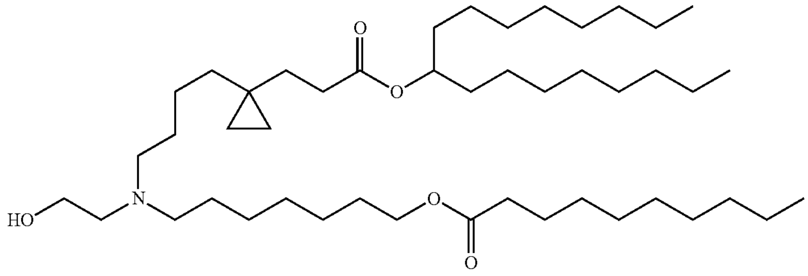 [SMILES: CCCCCCCCCC(=O)OCCCCCCCN(CCO)CCCCC1(CCC(=O)OC(CCCCCCCC)CCCCCCCC)CC1]
164c
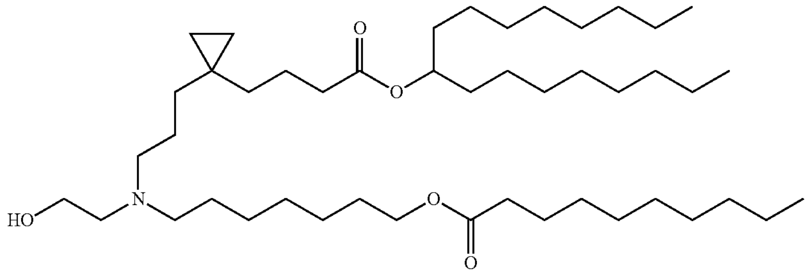 [SMILES: CCCCCCCCCC(=O)OCCCCCCCN(CCO)CCCC1(CCCC(=O)OC(CCCCCCCC)CCCCCCCC)CC1]
165c
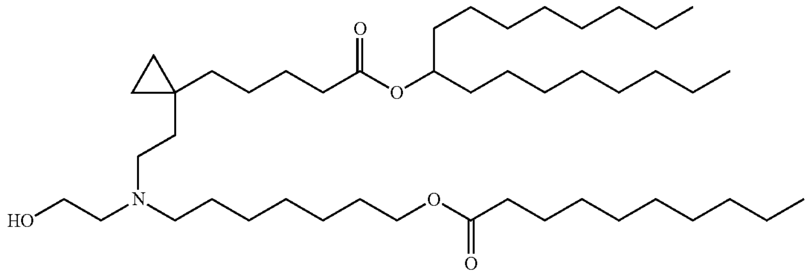 [SMILES: CCCCCCCCCC(=O)OCCCCCCCN(CCO)CCC1(CCCCC(=O)OC(CCCCCCCC)CCCCCCCC)CC1]
166c
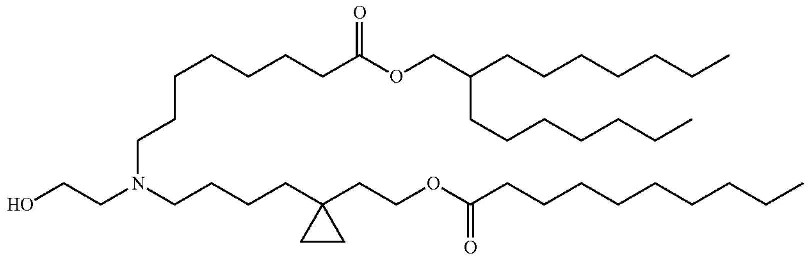 [SMILES: CCCCCCCCCC(=O)OCCC1(CCCCN(CCO)CCCCCCCC(=O)OCC(CCCCCCC)CCCCCCC)CC1]
167c
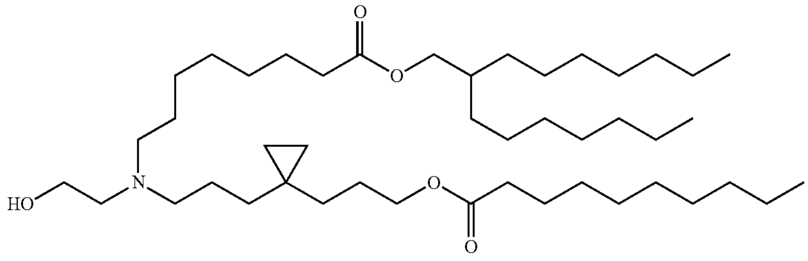 [SMILES: CCCCCCCCCC(=O)OCCCC1(CCCN(CCO)CCCCCCCC(=O)OCC(CCCCCCC)CCCCCCC)CC1]
168c
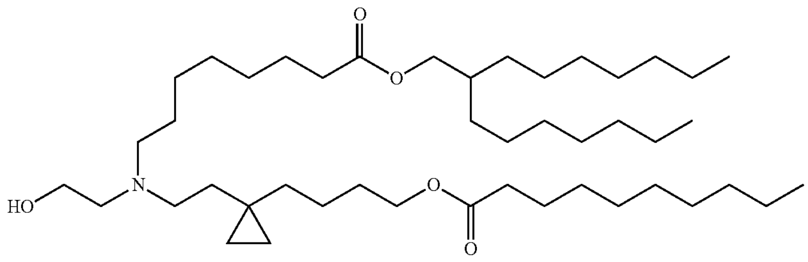 [SMILES: CCCCCCCCCC(=O)OCCCCC1(CCN(CCO)CCCCCCCC(=O)OCC(CCCCCCC)CCCCCCC)CC1]
169c TABLE I-continued
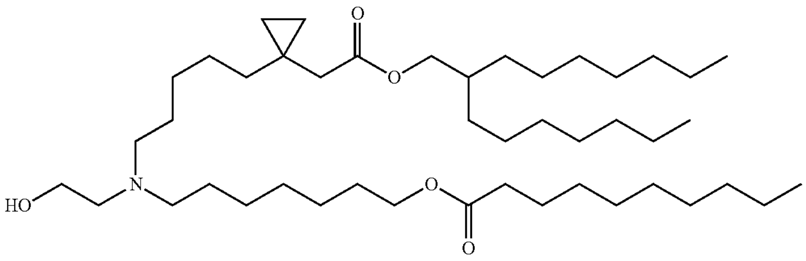 [SMILES: CCCCCCCCCC(=O)OCCCCCCCN(CCO)CCCCCC1(CC(=O)OCC(CCCCCCC)CCCCCCC)CC1]
170c
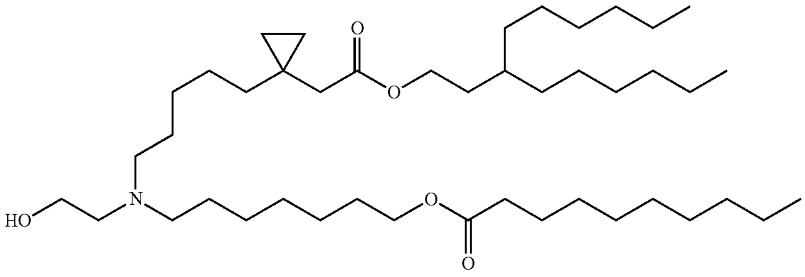 [SMILES: CCCCCCCCCC(=O)OCCCCCCCN(CCO)CCCCCC1(CC(=O)OCCC(CCCCCC)CCCCCC)CC1]
171c
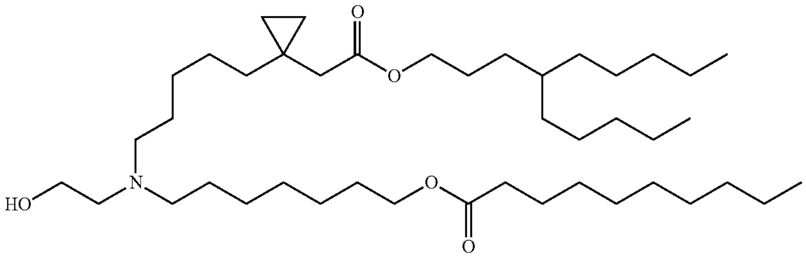 [SMILES: CCCCCCCCCC(=O)OCCCCCCCN(CCO)CCCCCC1(CC(=O)OCCCC(CCCCC)CCCCC)CC1]
172c
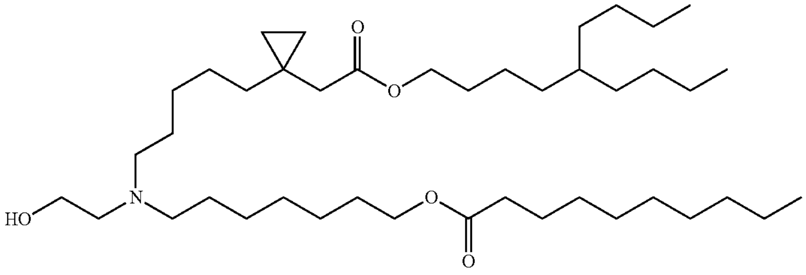 [SMILES: CCCCCCCCCC(=O)OCCCCCCCN(CCO)CCCCCC1(CC(=O)OCCCCC(CCCC)CCCC)CC1]
173c
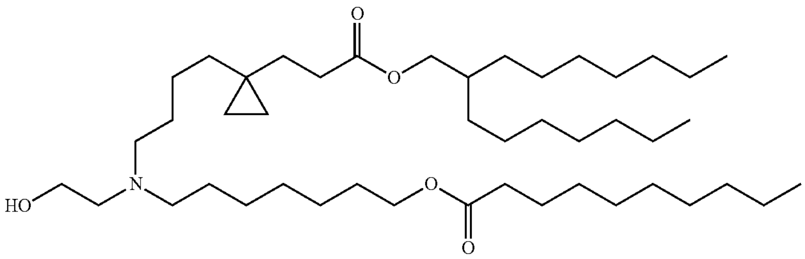 [SMILES: CCCCCCCCCC(=O)OCCCCCCCN(CCO)CCCCC1(CCC(=O)OCC(CCCCCCC)CCCCCCC)CC1]
174c TABLE I-continued
175c
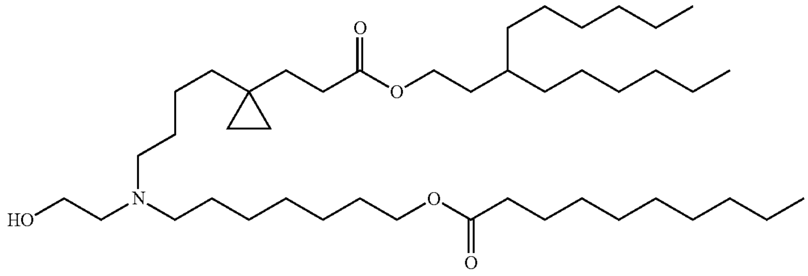 [SMILES: CCCCCCCCCC(=O)OCCCCCCCN(CCO)CCCCC1(CCC(=O)OCCC(CCCCCC)CCCCCC)CC1]
176c
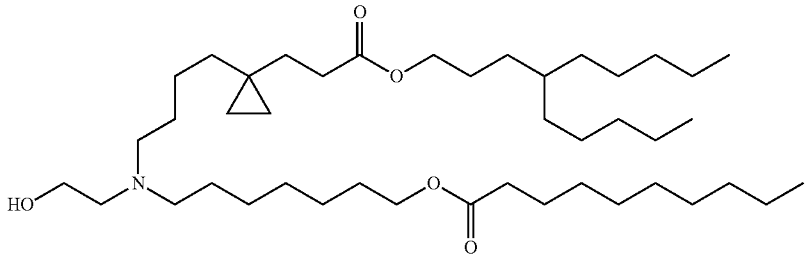 [SMILES: CCCCCCCCCC(=O)OCCCCCCCN(CCO)CCCCC1(CCC(=O)OCCCC(CCCCC)CCCCC)CC1]
177c
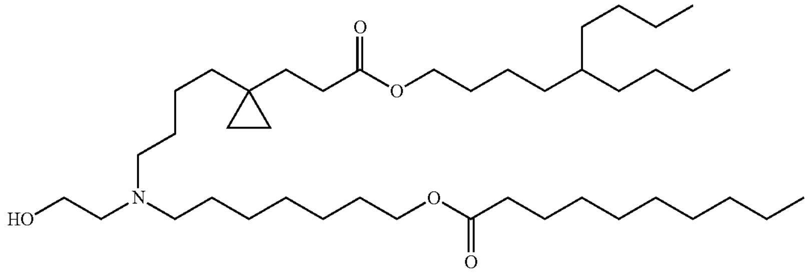 [SMILES: CCCCCCCCCC(=O)OCCCCCCCN(CCO)CCCCC1(CCC(=O)OCCCCC(CCCC)CCCC)CC1]
178c
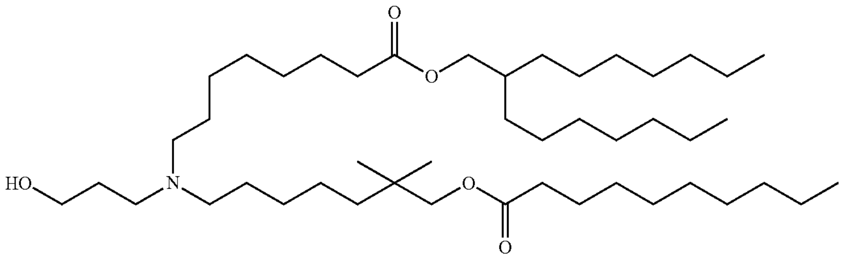 [SMILES: CCCCCCCCCC(=O)OCC(C)(C)CCCCCN(CCCO)CCCCCCCC(=O)OCC(CCCCCCC)CCCCCCC]
179c
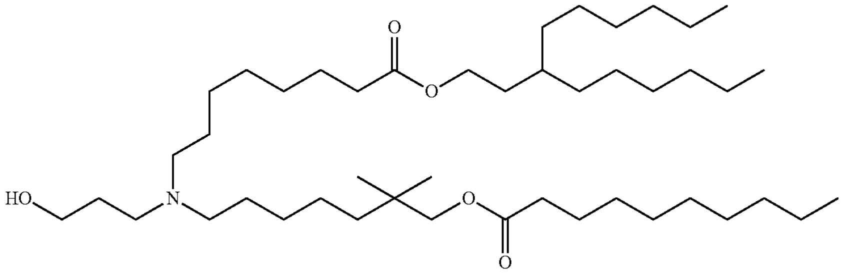 [SMILES: CCCCCCCCCC(=O)OCC(C)(C)CCCCCN(CCCO)CCCCCCCC(=O)OCCC(CCCCCC)CCCCCC]
180c
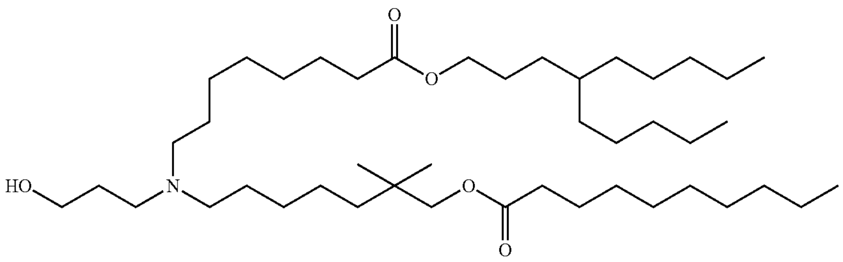 [SMILES: CCCCCCCCCC(=O)OCC(C)(C)CCCCCN(CCCO)CCCCCCCC(=O)OCCCC(CCCCC)CCCCC]

TABLE I-continued
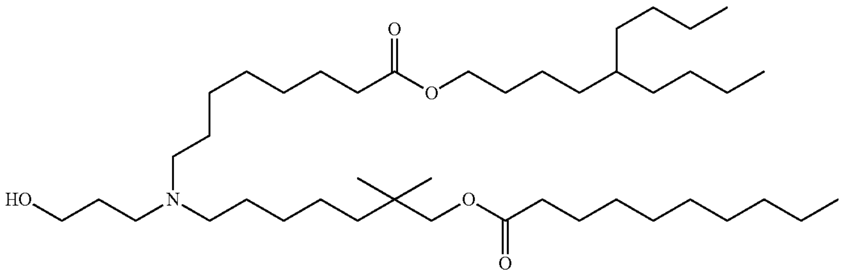 [SMILES: CCCCCCCCCC(=O)OCC(C)(C)CCCCCN(CCCO)CCCCCCCC(=O)OCCCCC(CCCC)CCCC]
181c
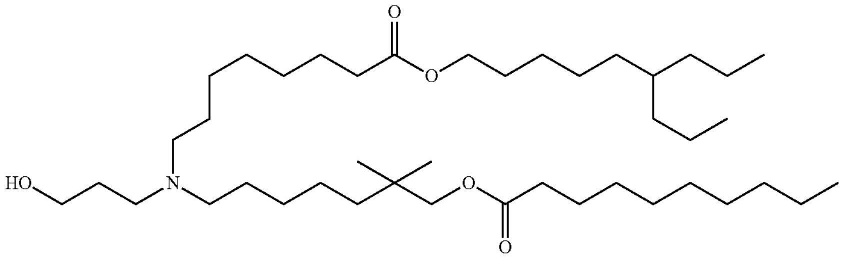 [SMILES: CCCCCCCCCC(=O)OCC(C)(C)CCCCCN(CCCO)CCCCCCCC(=O)OCCCCCC(CCC)CCC]
182c
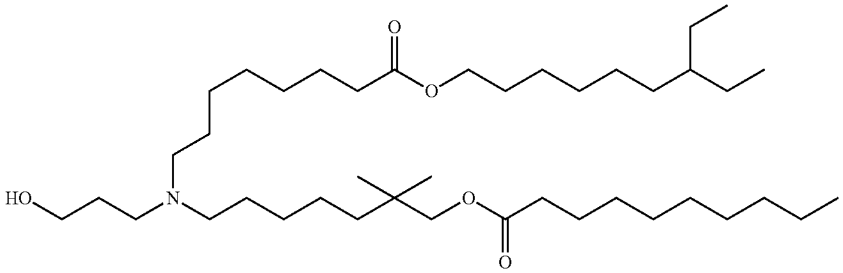 [SMILES: CCCCCCCCCC(=O)OCC(C)(C)CCCCCN(CCCO)CCCCCCCC(=O)OCCCCCCC(CC)CC]
183c
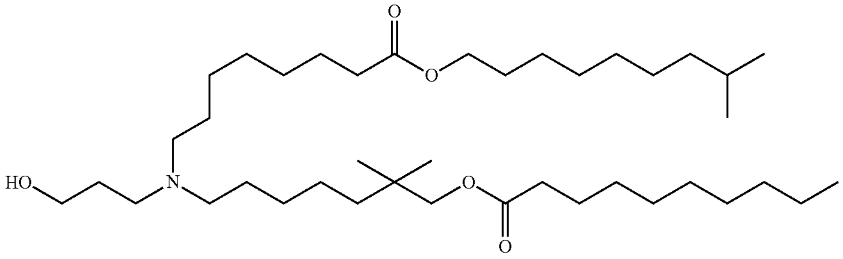 [SMILES: CCCCCCCCCC(=O)OCC(C)(C)CCCCCN(CCCO)CCCCCCCC(=O)OCCCCCCCC(C)C]
184c
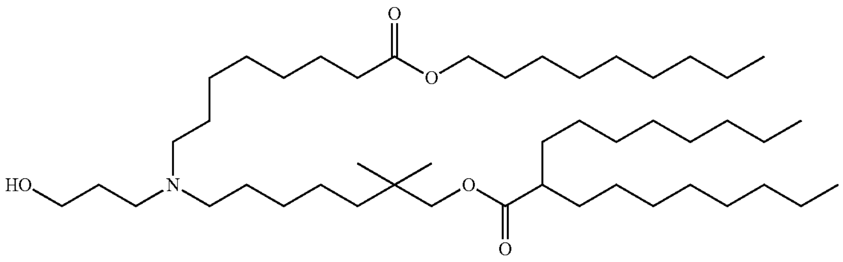 [SMILES: CCCCCCCCCOC(=O)CCCCCCCN(CCCO)CCCCCC(C)(C)COC(=O)C(CCCCCCCC)CCCCCCCC]
185c TABLE I-continued
186c
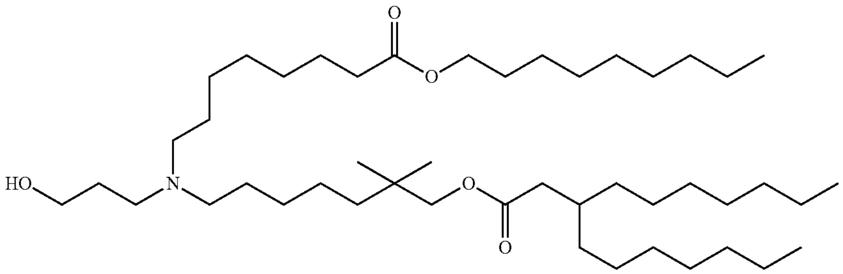 [SMILES: CCCCCCCCCOC(=O)CCCCCCCN(CCCO)CCCCCC(C)(C)COC(=O)CC(CCCCCCC)CCCCCCC]
187c
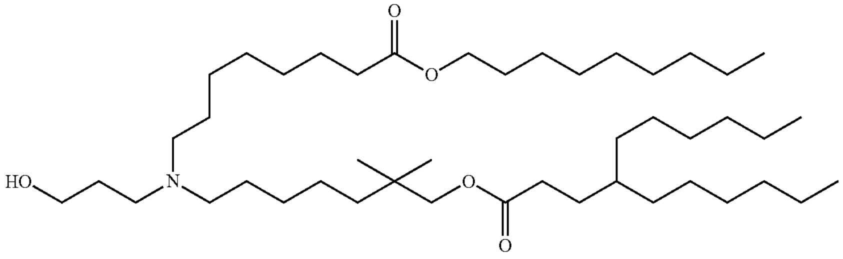 [SMILES: CCCCCCCCCOC(=O)CCCCCCCN(CCCO)CCCCCC(C)(C)COC(=O)CCC(CCCCCC)CCCCCC]
188c
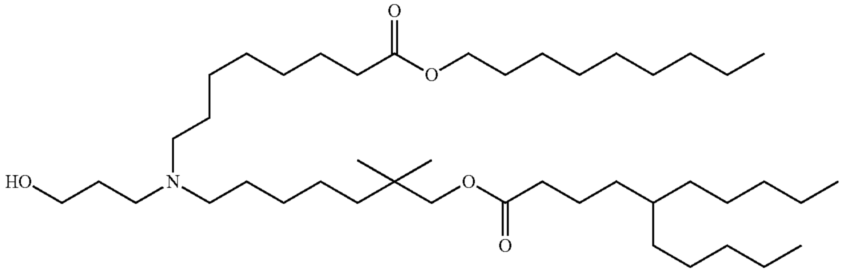 [SMILES: CCCCCCCCCOC(=O)CCCCCCCN(CCCO)CCCCCC(C)(C)COC(=O)CCCC(CCCCC)CCCCC]
189c
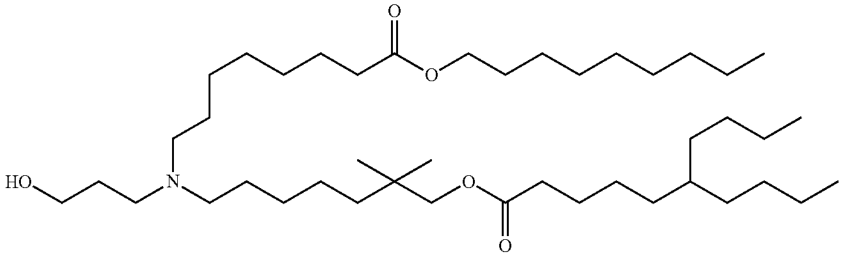 [SMILES: CCCCCCCCCOC(=O)CCCCCCCN(CCCO)CCCCCC(C)(C)COC(=O)CCCCC(CCCC)CCCC]
190c
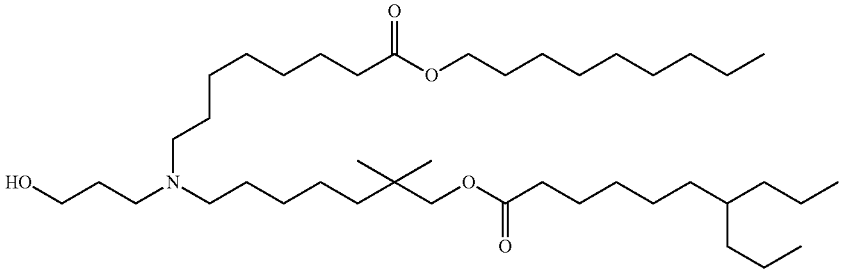 [SMILES: CCCCCCCCCOC(=O)CCCCCCCN(CCCO)CCCCCC(C)(C)COC(=O)CCCCCC(CCC)CCC]
191c
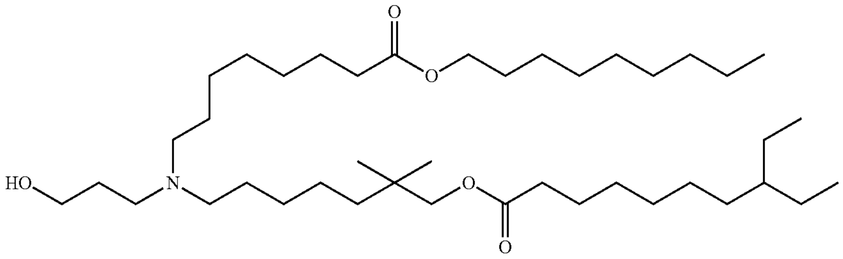 [SMILES: CCCCCCCCCOC(=O)CCCCCCCN(CCCO)CCCCCC(C)(C)COC(=O)CCCCCCC(CC)CC]

TABLE I-continued
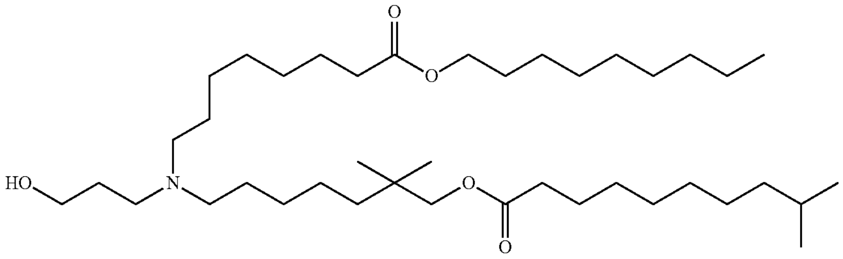 [SMILES: CCCCCCCCCOC(=O)CCCCCCCN(CCCO)CCCCCC(C)(C)COC(=O)CCCCCCCC(C)C]
192c
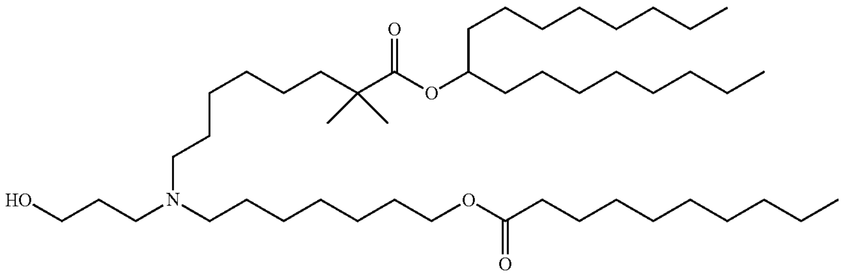 [SMILES: CCCCCCCCCC(=O)OCCCCCCCN(CCCO)CCCCCCC(C)(C)C(=O)OC(CCCCCCCC)CCCCCCCC]
193c
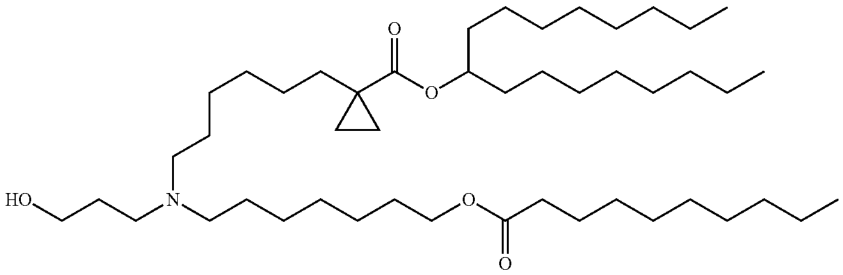 [SMILES: CCCCCCCCCC(=O)OCCCCCCCN(CCCO)CCCCCCC1(C(=O)OC(CCCCCCCC)CCCCCCCC)CC1]
194c
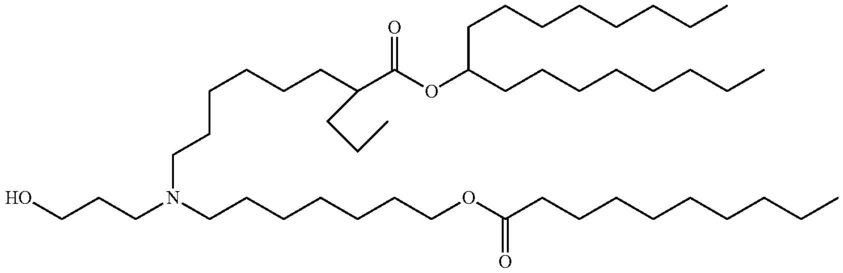 [SMILES: CCCCCCCCCC(=O)OCCCCCCCN(CCCO)CCCCCCC(CCC)C(=O)OC(CCCCCCCC)CCCCCCCC]
195c
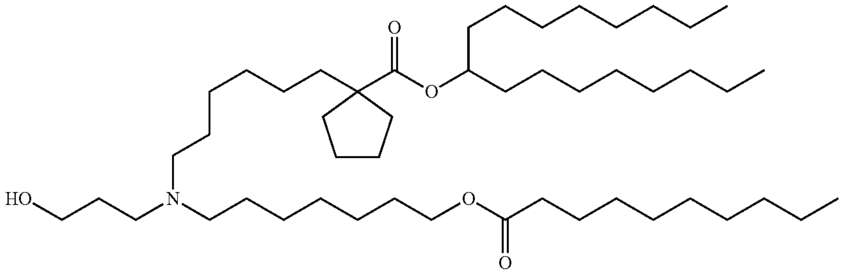 [SMILES: CCCCCCCCCC(=O)OCCCCCCCN(CCCO)CCCCCCC1(C(=O)OC(CCCCCCCC)CCCCCCCC)CCCC1]
196c
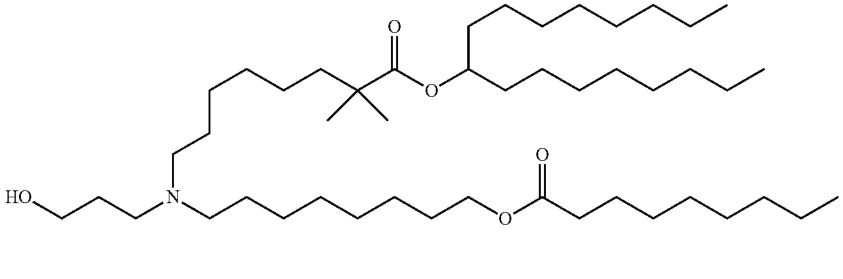 [SMILES: CCCCCCCCC(=O)OCCCCCCCCN(CCCO)CCCCCCC(C)(C)C(=O)OC(CCCCCCCC)CCCCCCCC]
197c TABLE I-continued
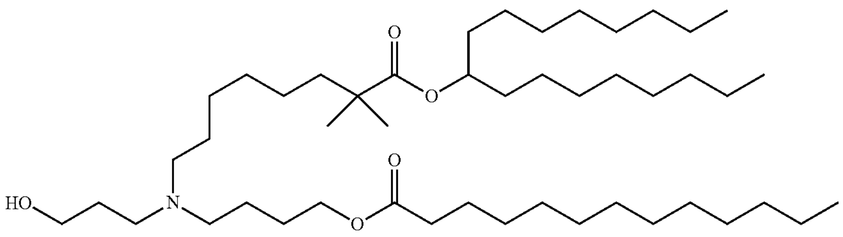 [SMILES: CCCCCCCCCCCCC(=O)OCCCCN(CCCO)CCCCCCC(C)(C)C(=O)OC(CCCCCCCC)CCCCCCCC]
198c
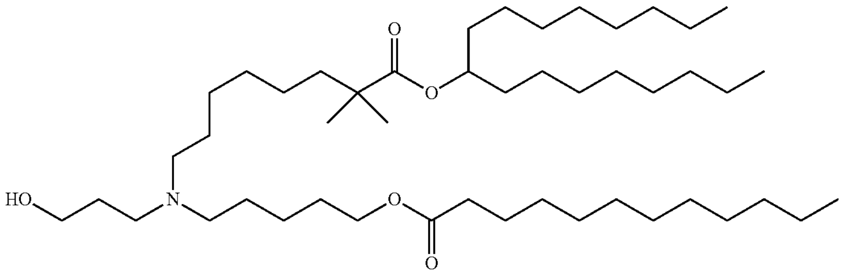 [SMILES: CCCCCCCCCCCC(=O)OCCCCCN(CCCO)CCCCCCC(C)(C)C(=O)OC(CCCCCCCC)CCCCCCCC]
199c
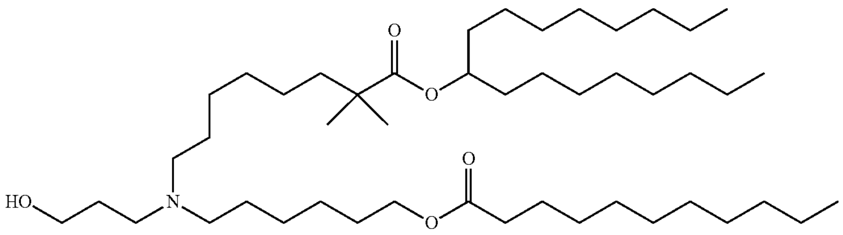
200c
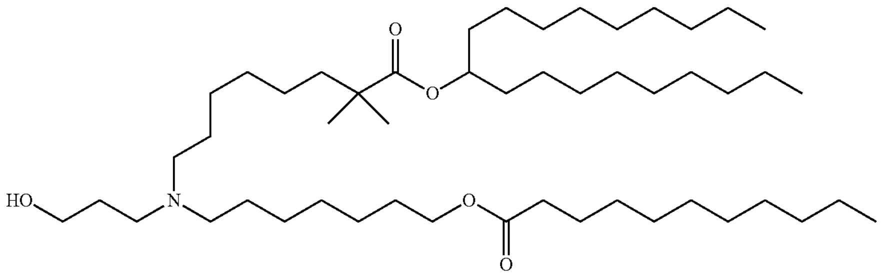 [SMILES: CCCCCCCCCCC(=O)OCCCCCCCN(CCCO)CCCCCCC(C)(C)C(=O)OC(CCCCCCCCC)CCCCCCCCC]
201c
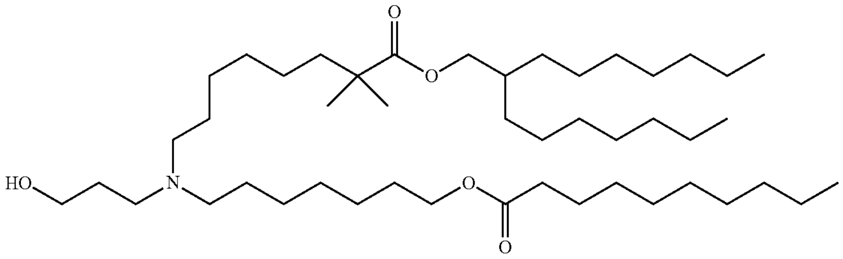 [SMILES: CCCCCCCCCC(=O)OCCCCCCCN(CCCO)CCCCCCC(C)(C)C(=O)OCC(CCCCCCC)CCCCCCC]
202c
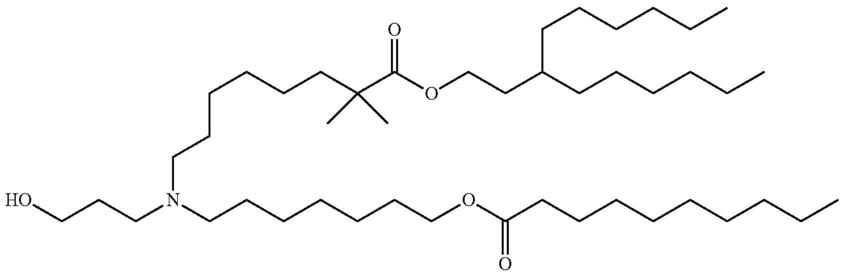 [SMILES: CCCCCCCCCC(=O)OCCCCCCCN(CCCO)CCCCCCC(C)(C)C(=O)OCCC(CCCCCC)CCCCCC]
203c TABLE I-continued
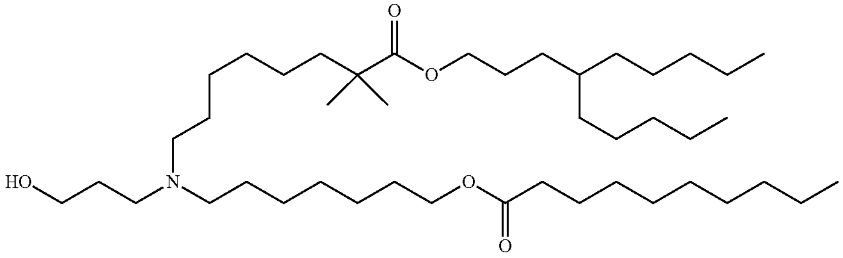 [SMILES: CCCCCCCCCC(=O)OCCCCCCCN(CCCO)CCCCCCC(C)(C)C(=O)OCCCC(CCCCC)CCCCC]
204c
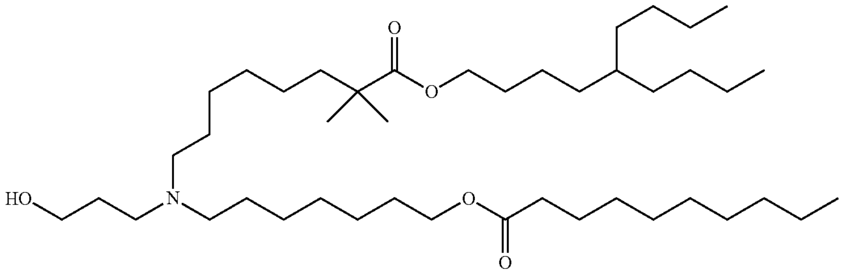 [SMILES: CCCCCCCCCC(=O)OCCCCCCCN(CCCO)CCCCCCC(C)(C)C(=O)OCCCCC(CCCC)CCCC]
205c
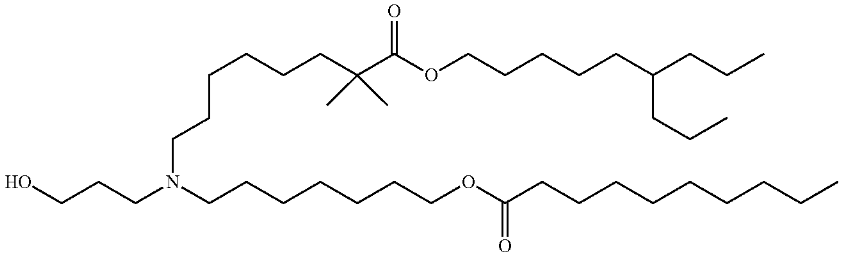 [SMILES: CCCCCCCCCC(=O)OCCCCCCCN(CCCO)CCCCCCC(C)(C)C(=O)OCCCCCC(CCC)CCC]
206c
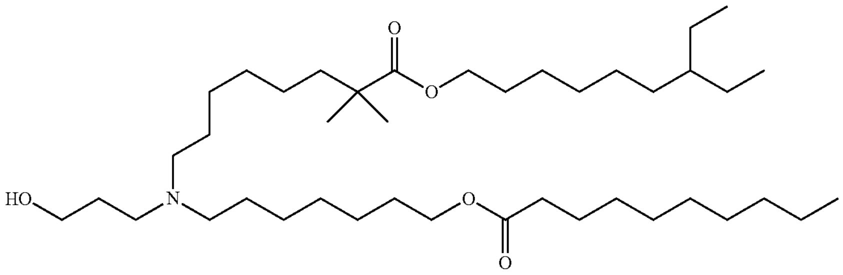 [SMILES: CCCCCCCCCC(=O)OCCCCCCCN(CCCO)CCCCCCC(C)(C)C(=O)OCCCCCCC(CC)CC]
207c
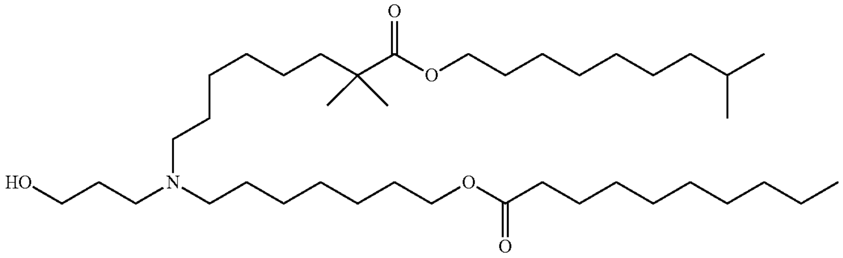 [SMILES: CCCCCCCCCC(=O)OCCCCCCCN(CCCO)CCCCCCC(C)(C)C(=O)OCCCCCCCC(C)C]
208c
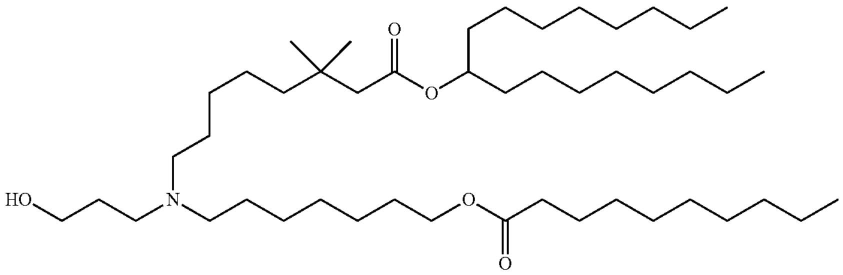 [SMILES: CCCCCCCCCC(=O)OCCCCCCCN(CCCO)CCCCCC(C)(C)CC(=O)OC(CCCCCCCC)CCCCCCCC]
209c TABLE I-continued
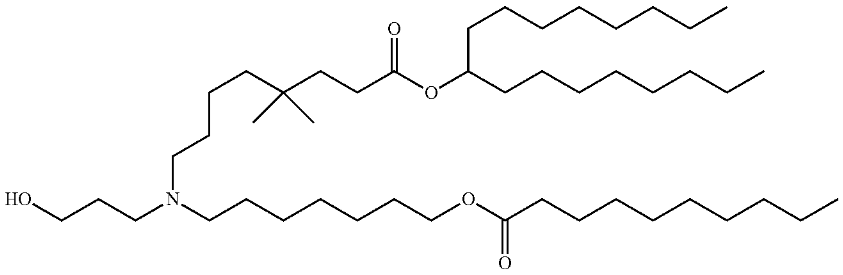 [SMILES: CCCCCCCCCC(=O)OCCCCCCCN(CCCO)CCCCC(C)(C)CCC(=O)OC(CCCCCCCC)CCCCCCCC]
210c
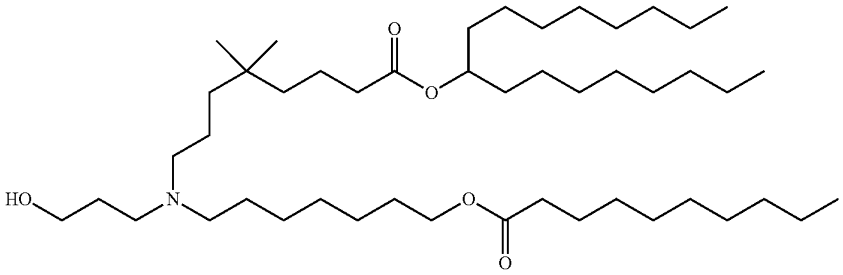 [SMILES: CCCCCCCCCC(=O)OCCCCCCCN(CCCO)CCCC(C)(C)CCCC(=O)OC(CCCCCCCC)CCCCCCCC]
211c
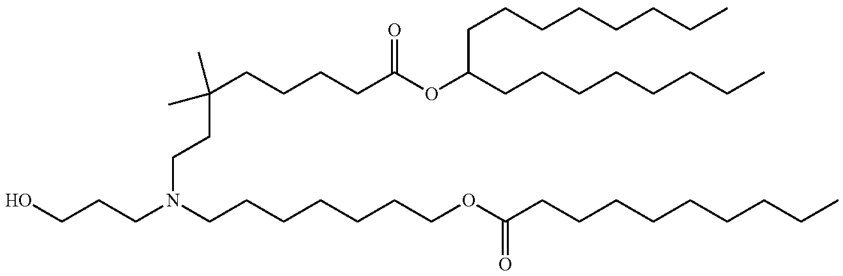 [SMILES: CCCCCCCCCC(=O)OCCCCCCCN(CCCO)CCC(C)(C)CCCCC(=O)OC(CCCCCCCC)CCCCCCCC]
212c
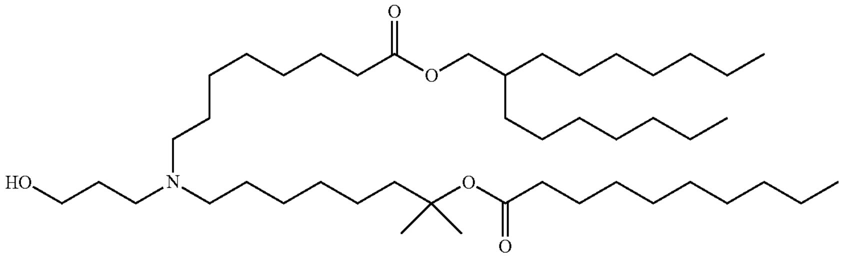 [SMILES: CCCCCCCCCC(=O)OC(C)(C)CCCCCCN(CCCO)CCCCCCCC(=O)OCC(CCCCCCC)CCCCCCC]
213c
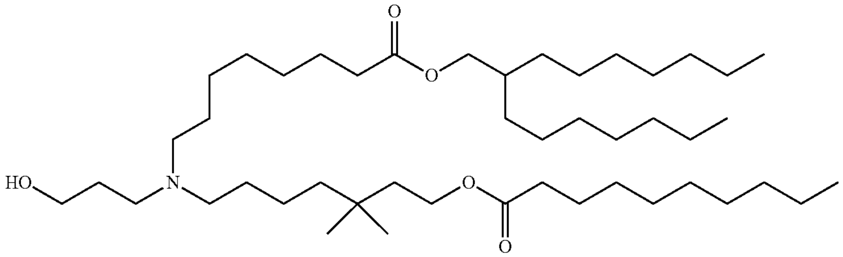 [SMILES: CCCCCCCCCC(=O)OCCC(C)(C)CCCCN(CCCO)CCCCCCCC(=O)OCC(CCCCCCC)CCCCCCC]
214c
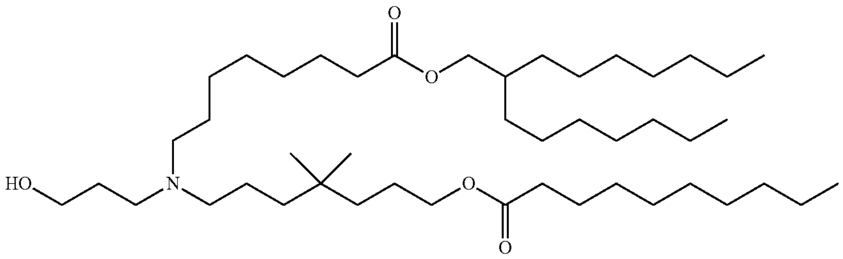 [SMILES: CCCCCCCCCC(=O)OCCCC(C)(C)CCCN(CCCO)CCCCCCCC(=O)OCC(CCCCCCC)CCCCCCC]
215c TABLE I-continued
216c
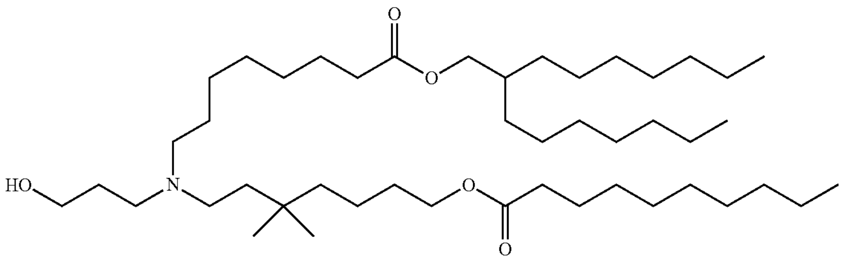 [SMILES: CCCCCCCCCC(=O)OCCCCC(C)(C)CCN(CCCO)CCCCCCCC(=O)OCC(CCCCCCC)CCCCCCC]
217c
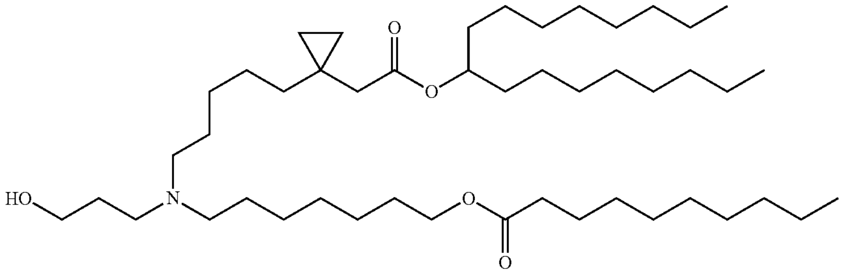 [SMILES: CCCCCCCCCC(=O)OCCCCCCCN(CCCO)CCCCCC1(CC(=O)OC(CCCCCCCC)CCCCCCCC)CC1]
218c
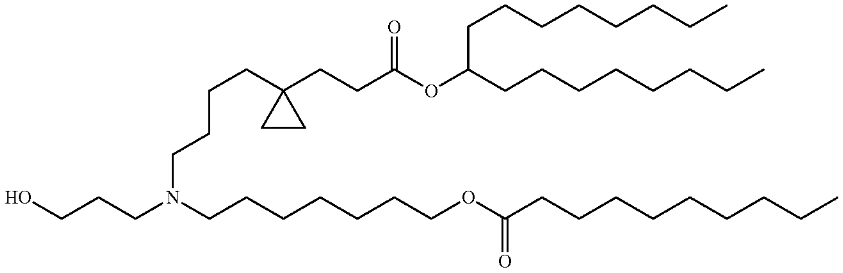 [SMILES: CCCCCCCCCC(=O)OCCCCCCCN(CCCO)CCCCC1(CCC(=O)OC(CCCCCCCC)CCCCCCCC)CC1]
219c
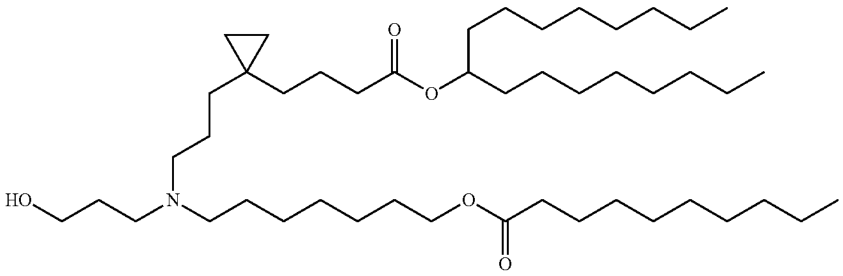 [SMILES: CCCCCCCCCC(=O)OCCCCCCCN(CCCO)CCCC1(CCCC(=O)OC(CCCCCCCC)CCCCCCCC)CC1]
220c
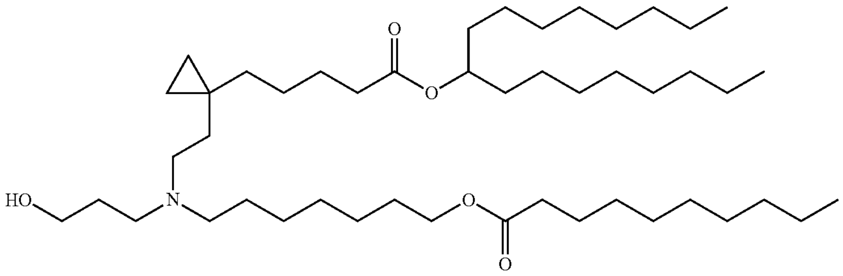 [SMILES: CCCCCCCCCC(=O)OCCCCCCCN(CCCO)CCC1(CCCCC(=O)OC(CCCCCCCC)CCCCCCCC)CC1]

TABLE I-continued
221c
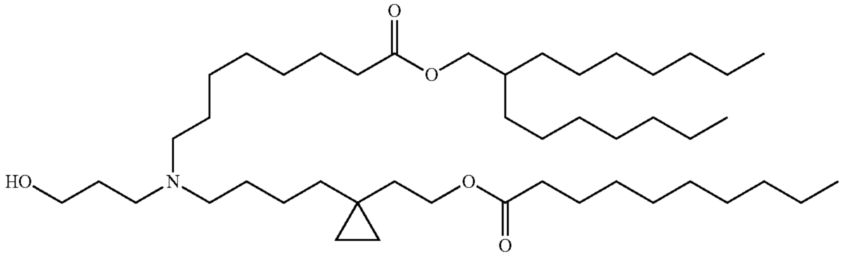 [SMILES: CCCCCCCCCC(=O)OCCC1(CCCCN(CCCO)CCCCCCCC(=O)OCC(CCCCCCC)CCCCCCC)CC1]
222c
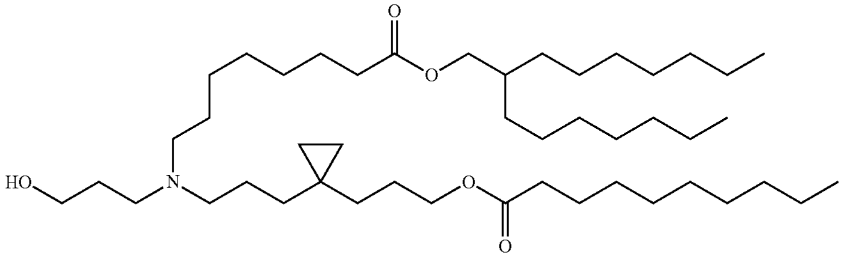 [SMILES: CCCCCCCCCC(=O)OCCCC1(CCCN(CCCO)CCCCCCCC(=O)OCC(CCCCCCC)CCCCCCC)CC1]
223c
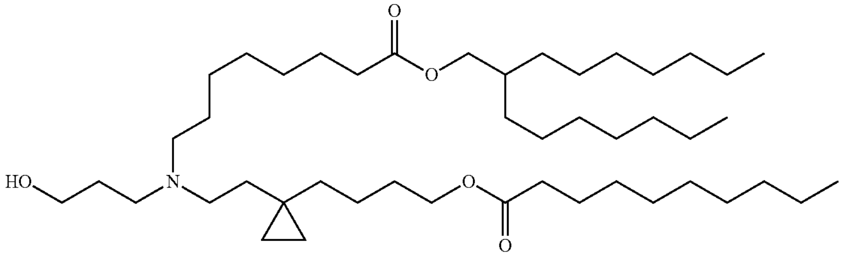 [SMILES: CCCCCCCCCC(=O)OCCCCC1(CCN(CCCO)CCCCCCCC(=O)OCC(CCCCCCC)CCCCCCC)CC1]
224c
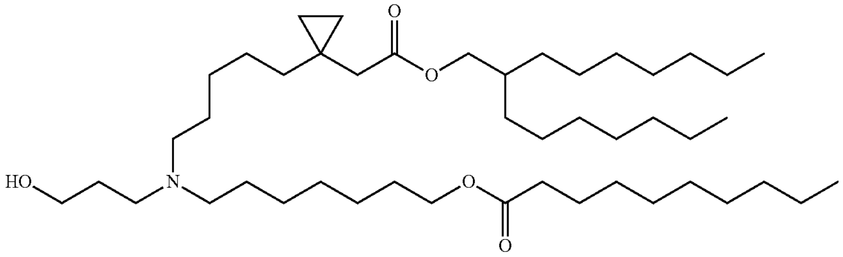 [SMILES: CCCCCCCCCC(=O)OCCCCCCCN(CCCO)CCCCCC1(CC(=O)OCC(CCCCCCC)CCCCCCC)CC1]
225c
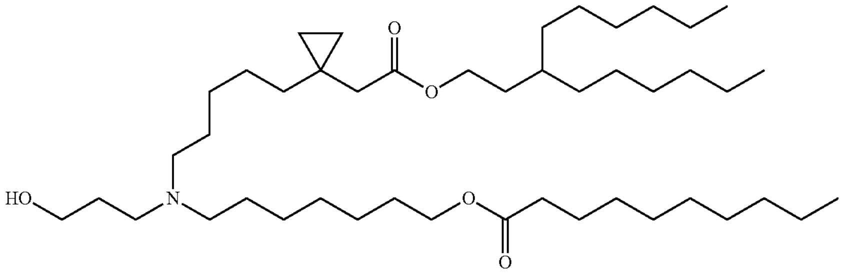 [SMILES: CCCCCCCCCC(=O)OCCCCCCCN(CCCO)CCCCCC1(CC(=O)OCCC(CCCCCC)CCCCCC)CC1]
226c
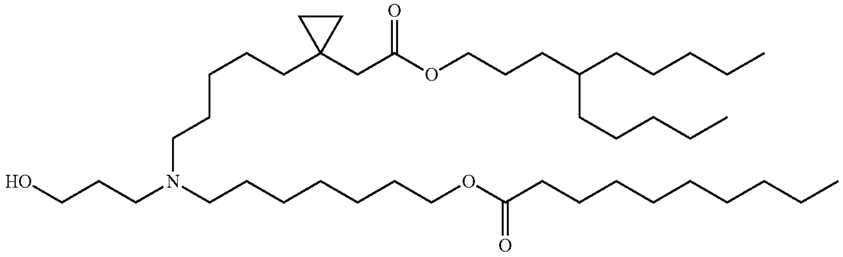 [SMILES: CCCCCCCCCC(=O)OCCCCCCCN(CCCO)CCCCCC1(CC(=O)OCCCC(CCCCC)CCCCC)CC1]

TABLE I-continued
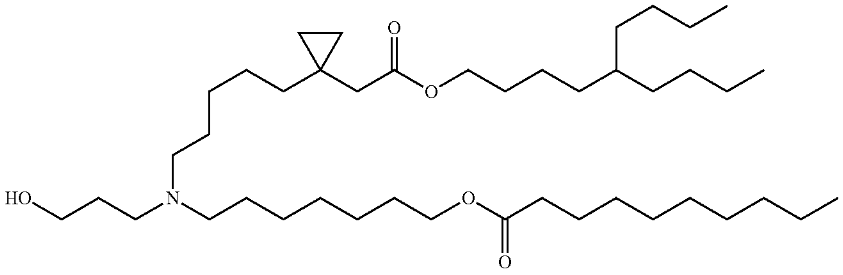 [SMILES: CCCCCCCCCC(=O)OCCCCCCCN(CCCO)CCCCCC1(CC(=O)OCCCCC(CCCC)CCCC)CC1]
227c
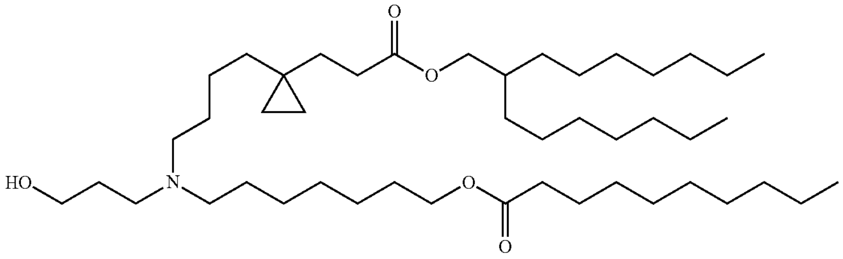 [SMILES: CCCCCCCCCC(=O)OCCCCCCCN(CCCO)CCCCC1(CCC(=O)OCC(CCCCCCC)CCCCCCC)CC1]
228c
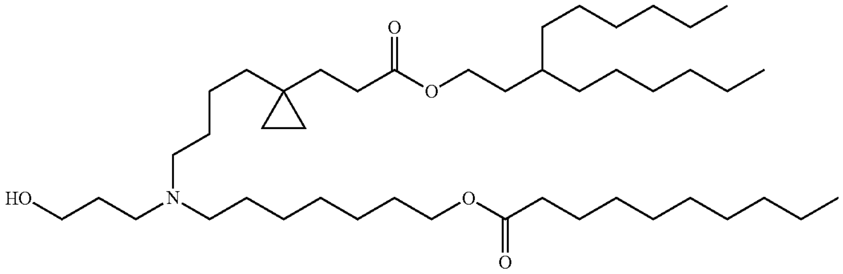 [SMILES: CCCCCCCCCC(=O)OCCCCCCCN(CCCO)CCCCC1(CCC(=O)OCCC(CCCCCC)CCCCCC)CC1]
229c
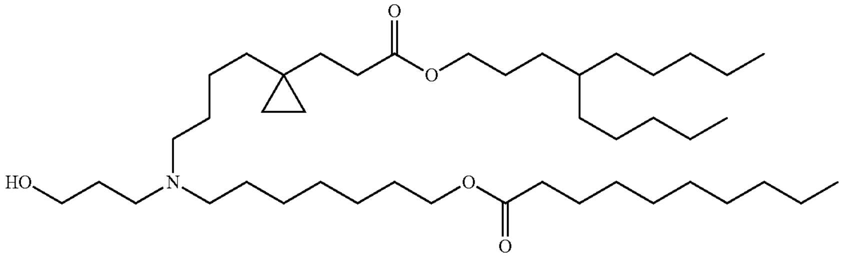 [SMILES: CCCCCCCCCC(=O)OCCCCCCCN(CCCO)CCCCC1(CCC(=O)OCCCC(CCCCC)CCCCC)CC1]
230c
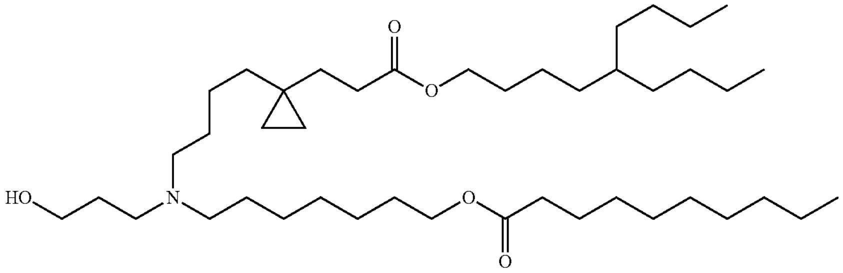 [SMILES: CCCCCCCCCC(=O)OCCCCCCCN(CCCO)CCCCC1(CCC(=O)OCCCCC(CCCC)CCCC)CC1]
231c
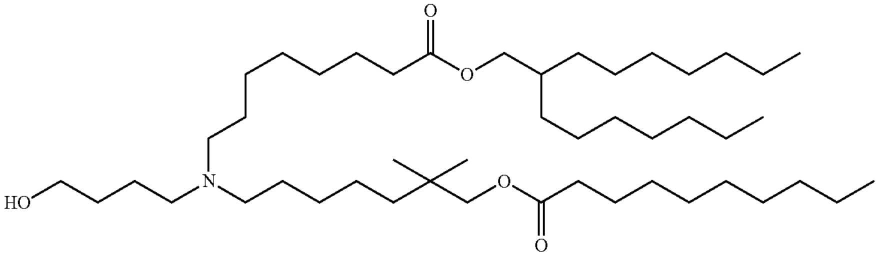 [SMILES: CCCCCCCCCC(=O)OCC(C)(C)CCCCCN(CCCCO)CCCCCCCC(=O)OCC(CCCCCCC)CCCCCCC]
232c TABLE I-continued
233c
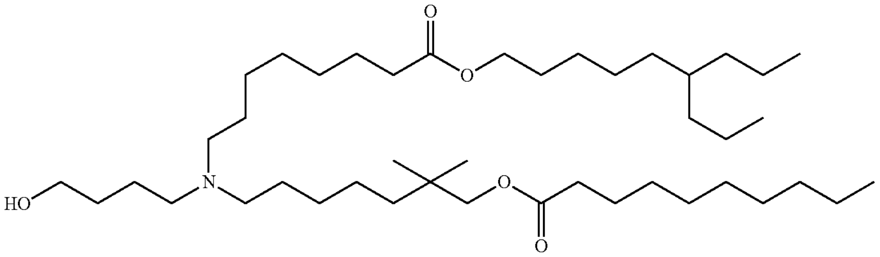 [SMILES: CCCCCCCCCC(=O)OCC(C)(C)CCCCCN(CCCCO)CCCCCCCC(=O)OCCCCCC(CCC)CCC]
234c
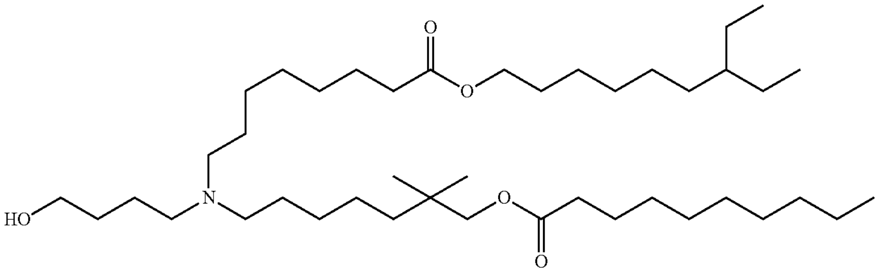 [SMILES: CCCCCCCCCC(=O)OCC(C)(C)CCCCCN(CCCCO)CCCCCCCC(=O)OCCCCCCC(CC)CC]
235c
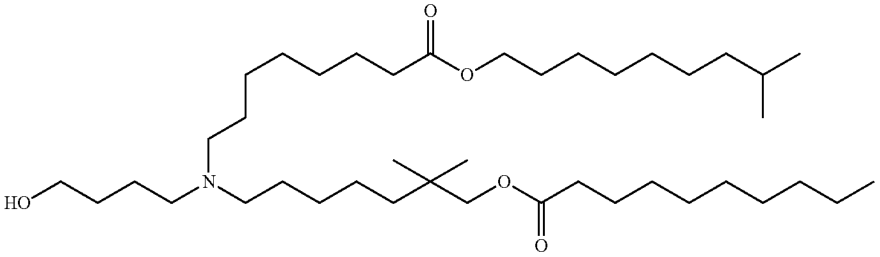 [SMILES: CCCCCCCCCC(=O)OCC(C)(C)CCCCCN(CCCCO)CCCCCCCC(=O)OCCCCCCCC(C)C]
236c
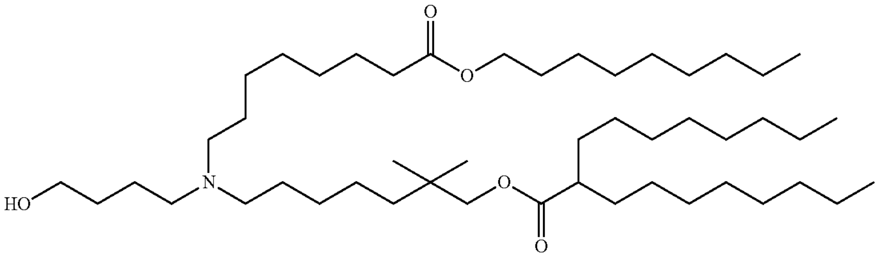 [SMILES: CCCCCCCCCOC(=O)CCCCCCCN(CCCCO)CCCCCC(C)(C)COC(=O)C(CCCCCCCC)CCCCCCCC]
237c
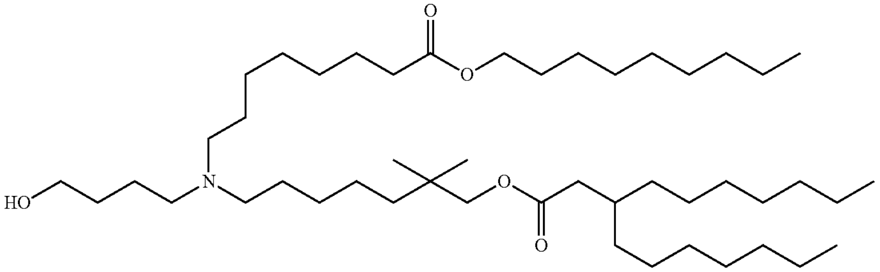 [SMILES: CCCCCCCCCOC(=O)CCCCCCCN(CCCCO)CCCCCC(C)(C)COC(=O)CC(CCCCCCC)CCCCCCC]
238c
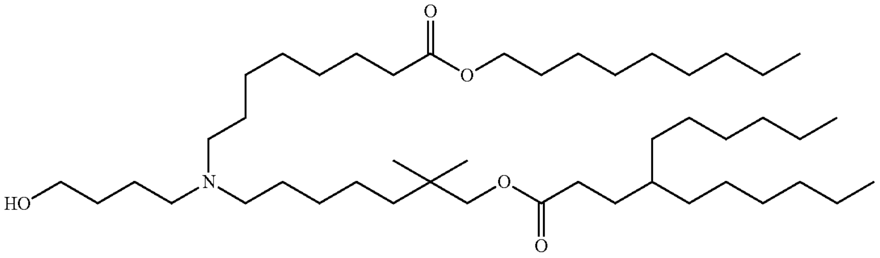 [SMILES: CCCCCCCCCOC(=O)CCCCCCCN(CCCCO)CCCCCC(C)(C)COC(=O)CCC(CCCCCC)CCCCCC]

TABLE I-continued
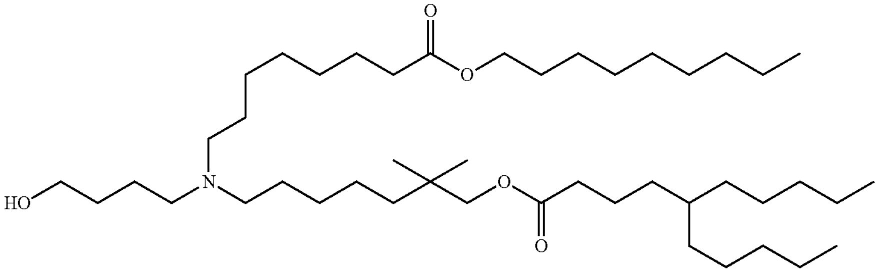 [SMILES: CCCCCCCCCOC(=O)CCCCCCCN(CCCCO)CCCCCC(C)(C)COC(=O)CCCC(CCCCC)CCCCC]
239c
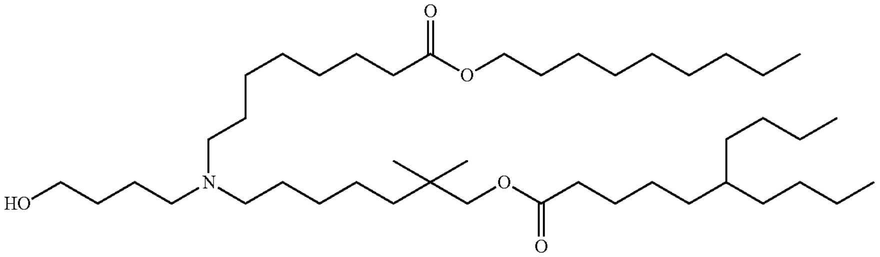 [SMILES: CCCCCCCCCOC(=O)CCCCCCCN(CCCCO)CCCCCC(C)(C)COC(=O)CCCCC(CCCC)CCCC]
240c
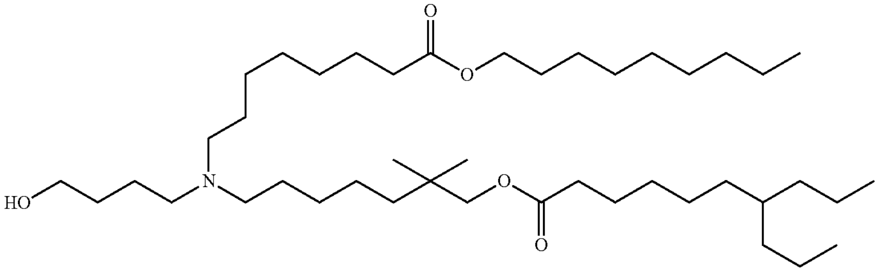 [SMILES: CCCCCCCCCOC(=O)CCCCCCCN(CCCCO)CCCCCC(C)(C)COC(=O)CCCCCC(CCC)CCC]
241c
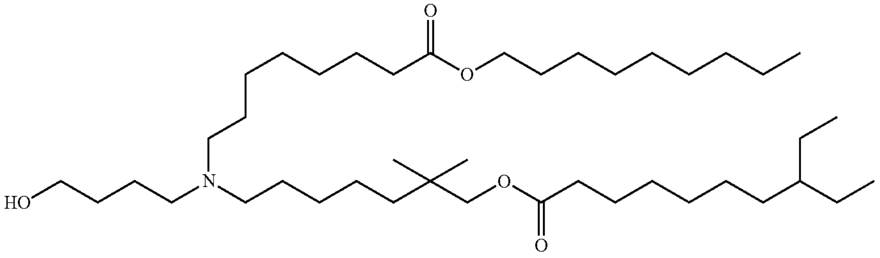 [SMILES: CCCCCCCCCOC(=O)CCCCCCCN(CCCCO)CCCCCC(C)(C)COC(=O)CCCCCCC(CC)CC]
242c
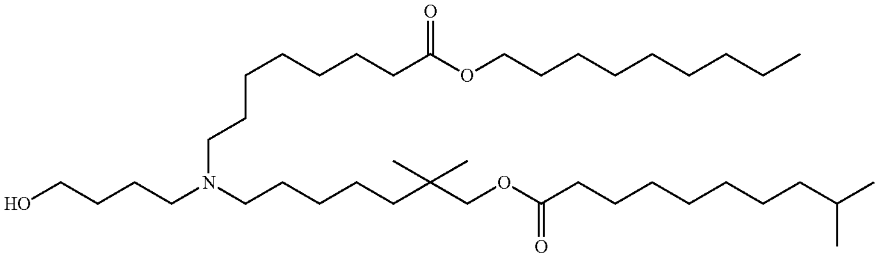 [SMILES: CCCCCCCCCOC(=O)CCCCCCCN(CCCCO)CCCCCC(C)(C)COC(=O)CCCCCCCC(C)C]
243c
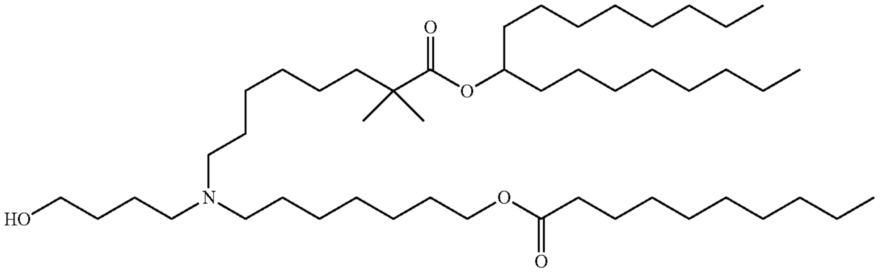 [SMILES: CCCCCCCCCC(=O)OCCCCCCCN(CCCCO)CCCCCCC(C)(C)C(=O)OC(CCCCCCCC)CCCCCCCC]
244c TABLE I-continued
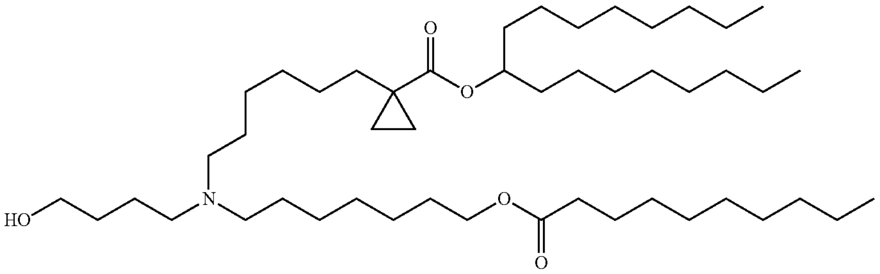 [SMILES: CCCCCCCCCC(=O)OCCCCCCCN(CCCCO)CCCCCCC1(C(=O)OC(CCCCCCCC)CCCCCCCC)CC1]
245c
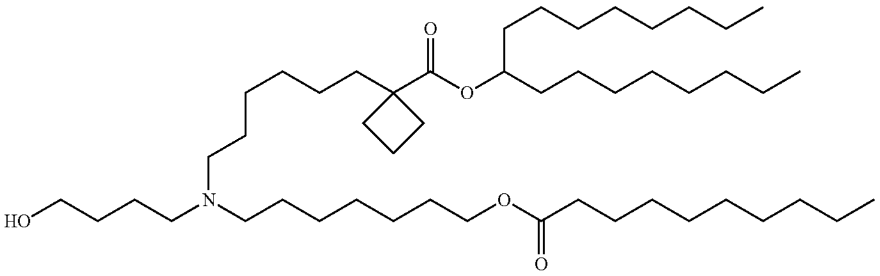 [SMILES: CCCCCCCCCC(=O)OCCCCCCCN(CCCCO)CCCCCCC1(C(=O)OC(CCCCCCCC)CCCCCCCC)CCC1]
246c
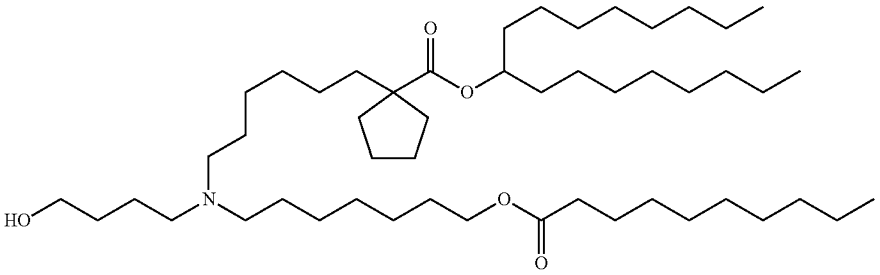 [SMILES: CCCCCCCCCC(=O)OCCCCCCCN(CCCCO)CCCCCCC1(C(=O)OC(CCCCCCCC)CCCCCCCC)CCCC1]
247c
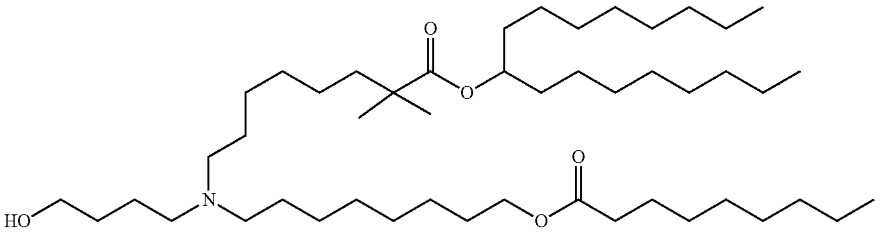 [SMILES: CCCCCCCCC(=O)OCCCCCCCCN(CCCCO)CCCCCCC(C)(C)C(=O)OC(CCCCCCCC)CCCCCCCC]
248c
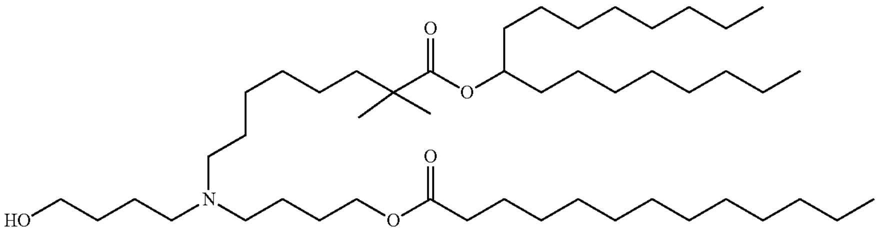 [SMILES: CCCCCCCCCCCCC(=O)OCCCCN(CCCCO)CCCCCCC(C)(C)C(=O)OC(CCCCCCCC)CCCCCCCC]
249c
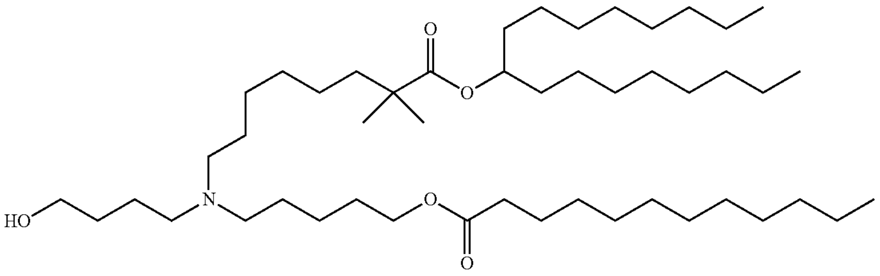 [SMILES: CCCCCCCCCCCC(=O)OCCCCCN(CCCCO)CCCCCCC(C)(C)C(=O)OC(CCCCCCCC)CCCCCCCC]
250c TABLE I-continued
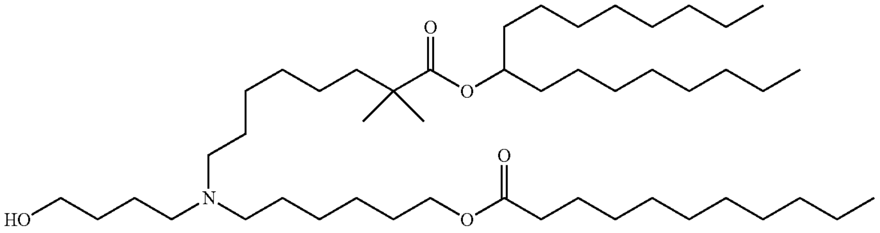 [SMILES: CCCCCCCCCCC(=O)OCCCCCCN(CCCCO)CCCCCCC(C)(C)C(=O)OC(CCCCCCCC)CCCCCCCC]
251c
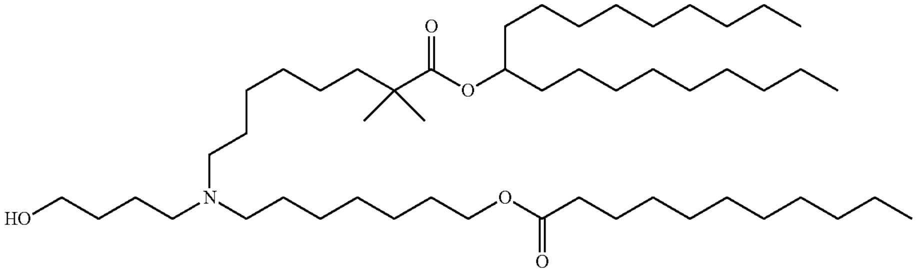 [SMILES: CCCCCCCCCCC(=O)OCCCCCCCN(CCCCO)CCCCCCC(C)(C)C(=O)OC(CCCCCCCCC)CCCCCCCCC]
252c
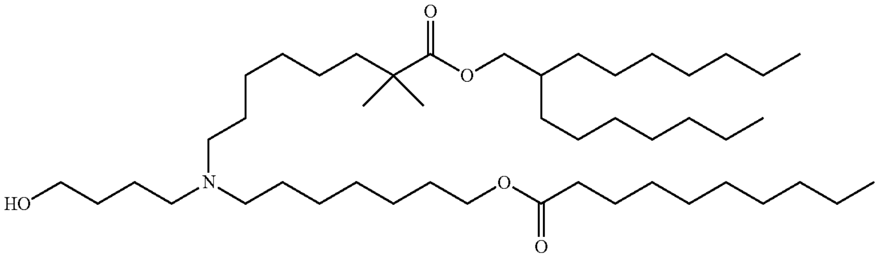 [SMILES: CCCCCCCCCC(=O)OCCCCCCCN(CCCCO)CCCCCCC(C)(C)C(=O)OCC(CCCCCCC)CCCCCCC]
253c
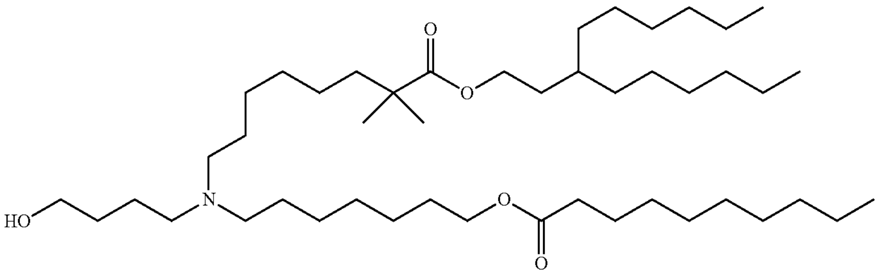 [SMILES: CCCCCCCCCC(=O)OCCCCCCCN(CCCCO)CCCCCCC(C)(C)C(=O)OCCC(CCCCCC)CCCCCC]
254c
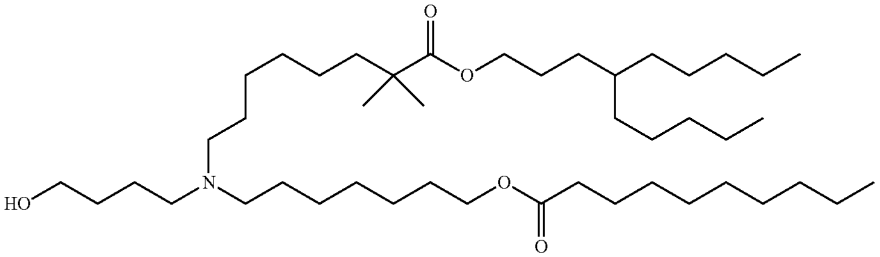 [SMILES: CCCCCCCCCC(=O)OCCCCCCCN(CCCCO)CCCCCCC(C)(C)C(=O)OCCCC(CCCCC)CCCCC]
255c
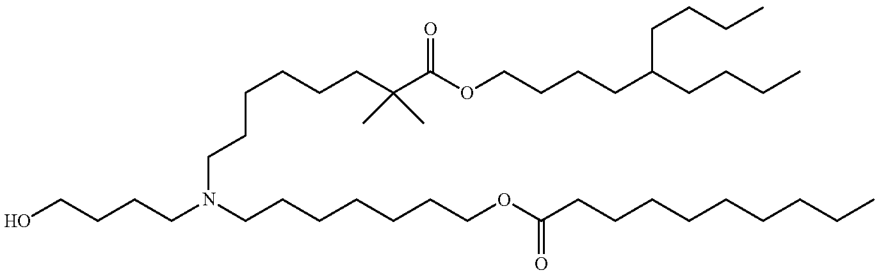 [SMILES: CCCCCCCCCC(=O)OCCCCCCCN(CCCCO)CCCCCCC(C)(C)C(=O)OCCCCC(CCCC)CCCC]
256c TABLE I-continued
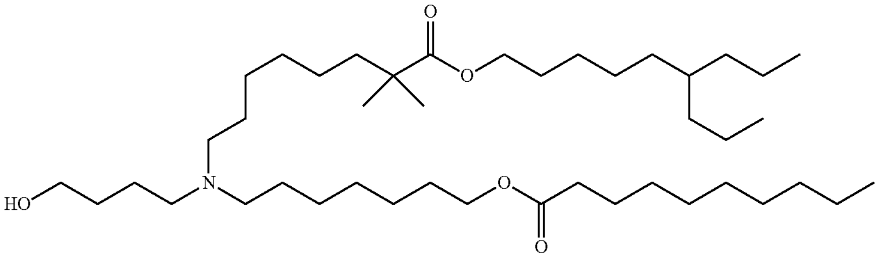 [SMILES: CCCCCCCCCC(=O)OCCCCCCCN(CCCCO)CCCCCCC(C)(C)C(=O)OCCCCCC(CCC)CCC]
257c
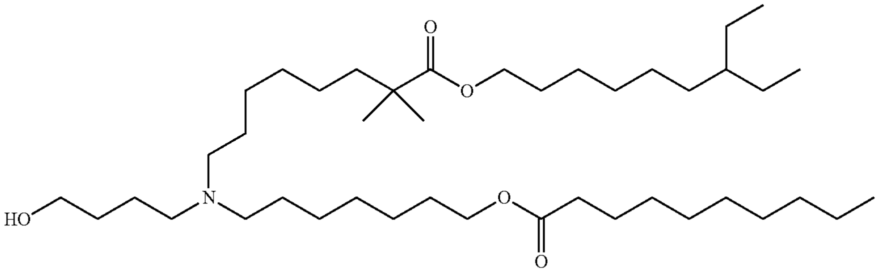 [SMILES: CCCCCCCCCC(=O)OCCCCCCCN(CCCCO)CCCCCCC(C)(C)C(=O)OCCCCCCC(CC)CC]
258c
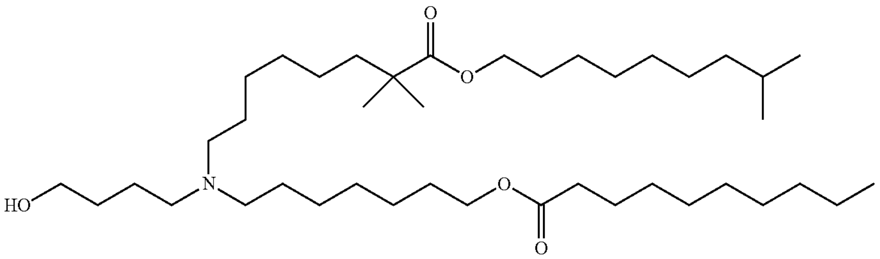 [SMILES: CCCCCCCCCC(=O)OCCCCCCCN(CCCCO)CCCCCCC(C)(C)C(=O)OCCCCCCCC(C)C]
259c
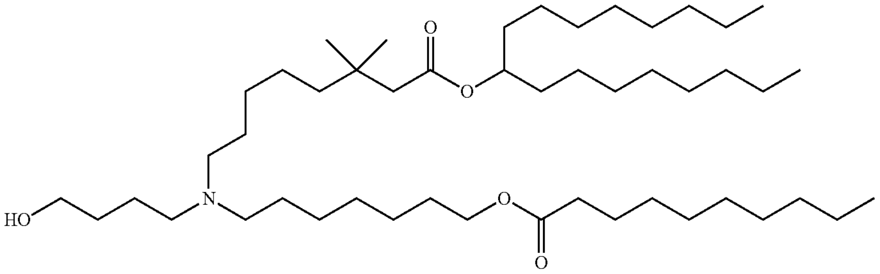 [SMILES: CCCCCCCCCC(=O)OCCCCCCCN(CCCCO)CCCCCC(C)(C)CC(=O)OC(CCCCCCCC)CCCCCCCC]
260c
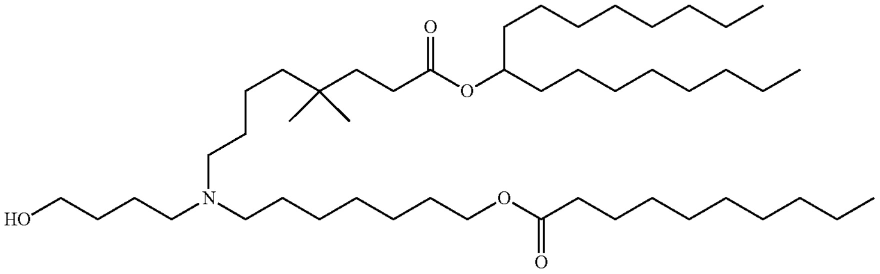 [SMILES: CCCCCCCCCC(=O)OCCCCCCCN(CCCCO)CCCCC(C)(C)CCC(=O)OC(CCCCCCCC)CCCCCCCC]
261c
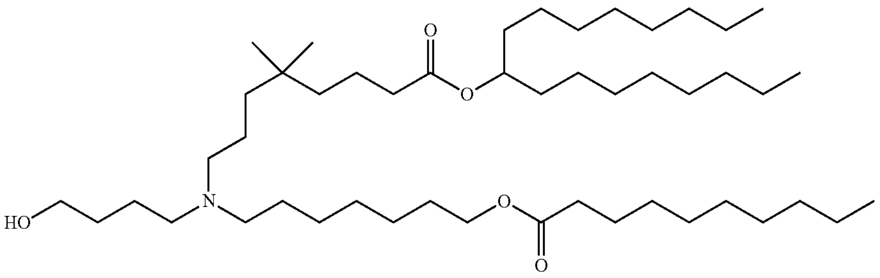 [SMILES: CCCCCCCCCC(=O)OCCCCCCCN(CCCCO)CCCC(C)(C)CCCC(=O)OC(CCCCCCCC)CCCCCCCC]
262c TABLE I-continued
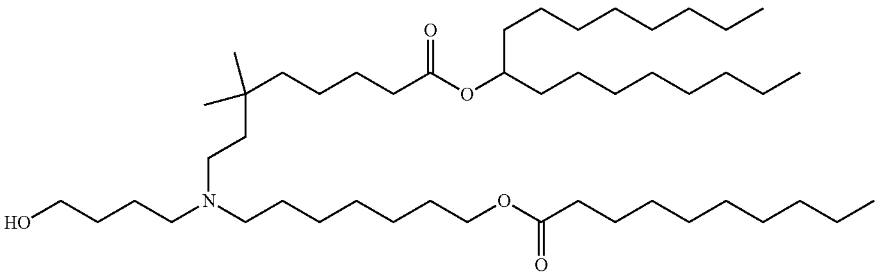 [SMILES: CCCCCCCCCC(=O)OCCCCCCCN(CCCCO)CCC(C)(C)CCCCC(=O)OC(CCCCCCCC)CCCCCCCC]
263c
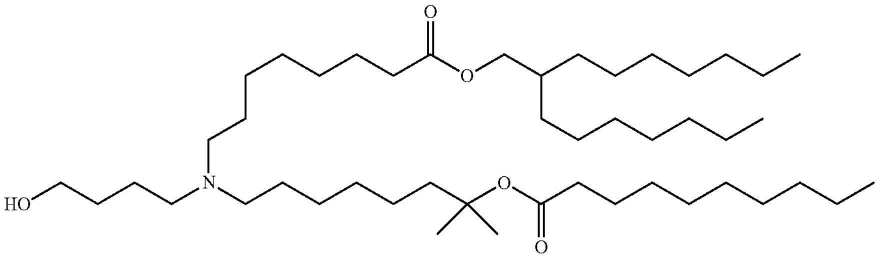 [SMILES: CCCCCCCCCC(=O)OC(C)(C)CCCCCCN(CCCCO)CCCCCCCC(=O)OCC(CCCCCCC)CCCCCCC]
264c
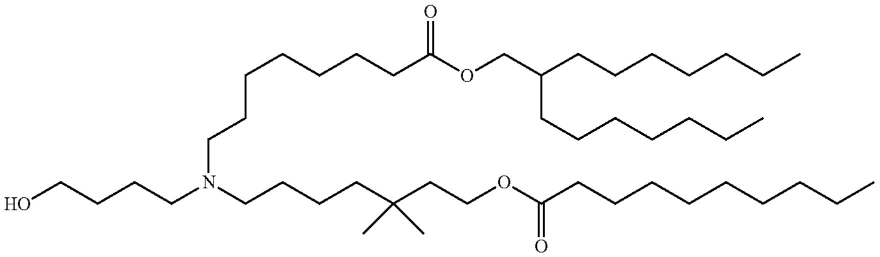 [SMILES: CCCCCCCCCC(=O)OCCC(C)(C)CCCCN(CCCCO)CCCCCCCC(=O)OCC(CCCCCCC)CCCCCCC]
265c
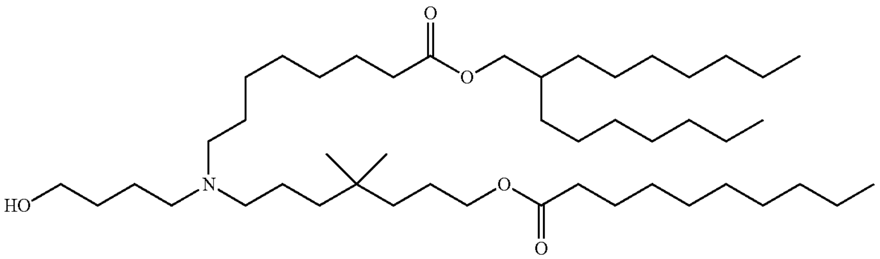 [SMILES: CCCCCCCCCC(=O)OCCCC(C)(C)CCCN(CCCCO)CCCCCCCC(=O)OCC(CCCCCCC)CCCCCCC]
266c
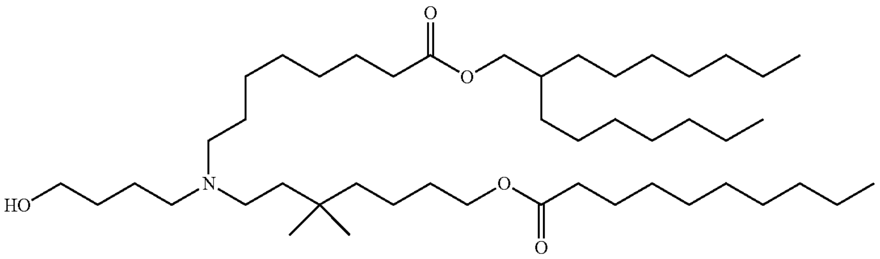 [SMILES: CCCCCCCCCC(=O)OCCCCC(C)(C)CCN(CCCCO)CCCCCCCC(=O)OCC(CCCCCCC)CCCCCCC]
267c
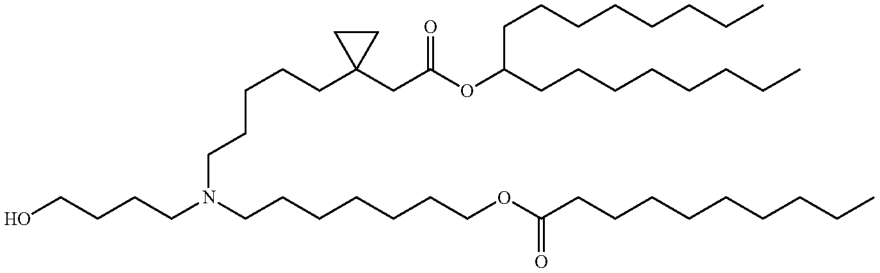 [SMILES: CCCCCCCCCC(=O)OCCCCCCCN(CCCCO)CCCCCC1(CC(=O)OC(CCCCCCCC)CCCCCCCC)CC1]
268c TABLE I-continued
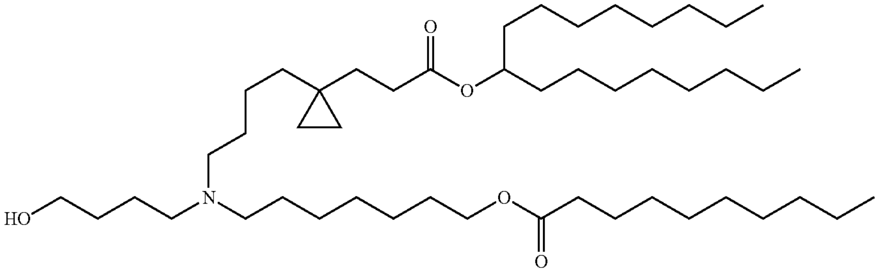 [SMILES: CCCCCCCCCC(=O)OCCCCCCCN(CCCCO)CCCCC1(CCC(=O)OC(CCCCCCCC)CCCCCCCC)CC1]
269c
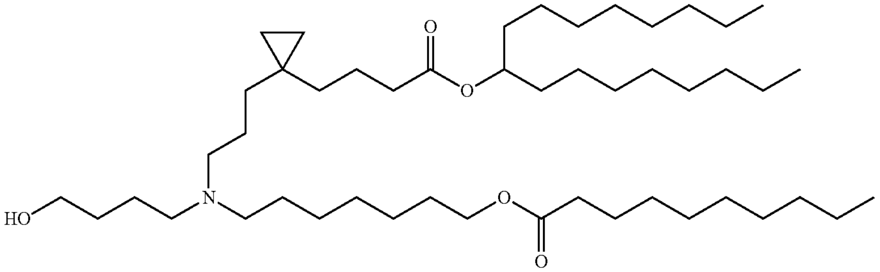 [SMILES: CCCCCCCCCC(=O)OCCCCCCCN(CCCCO)CCCC1(CCCC(=O)OC(CCCCCCCC)CCCCCCCC)CC1]
270c
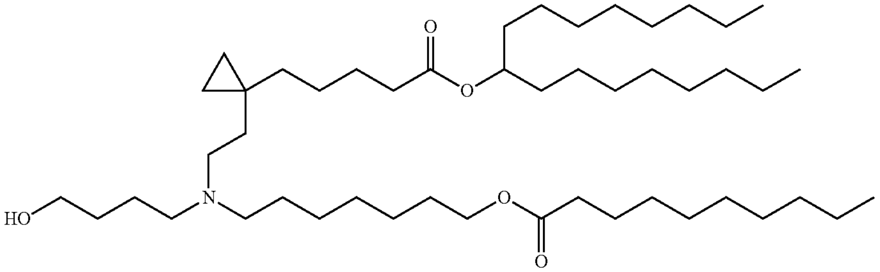 [SMILES: CCCCCCCCCC(=O)OCCCCCCCN(CCCCO)CCC1(CCCCC(=O)OC(CCCCCCCC)CCCCCCCC)CC1]
271c
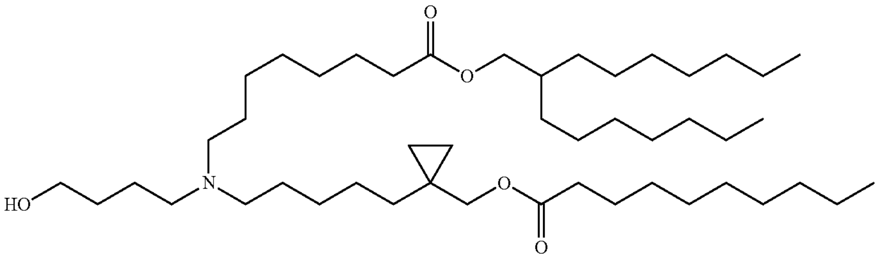 [SMILES: CCCCCCCCCC(=O)OCC1(CCCCCN(CCCCO)CCCCCCCC(=O)OCC(CCCCCCC)CCCCCCC)CC1]
272c
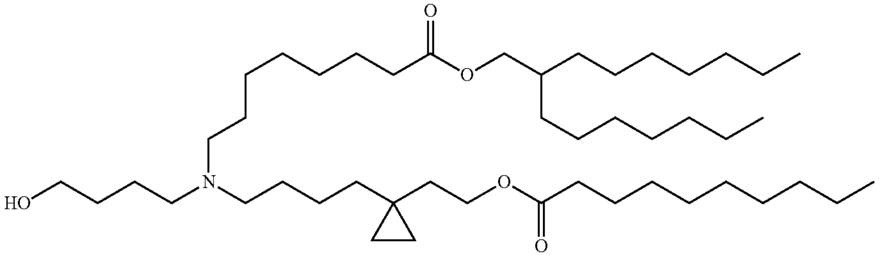 [SMILES: CCCCCCCCCC(=O)OCCC1(CCCCN(CCCCO)CCCCCCCC(=O)OCC(CCCCCCC)CCCCCCC)CC1]
273c
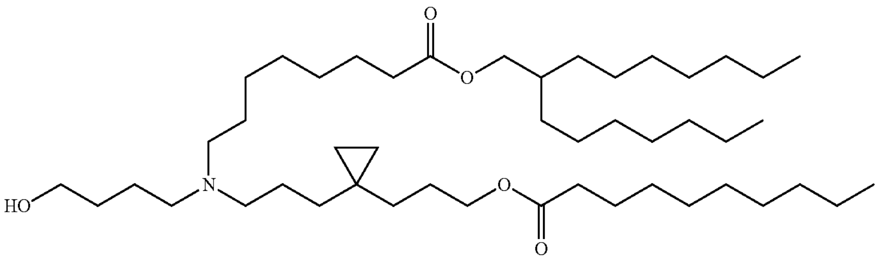 [SMILES: CCCCCCCCCC(=O)OCCCC1(CCCN(CCCCO)CCCCCCCC(=O)OCC(CCCCCCC)CCCCCCC)CC1]
274c TABLE I-continued
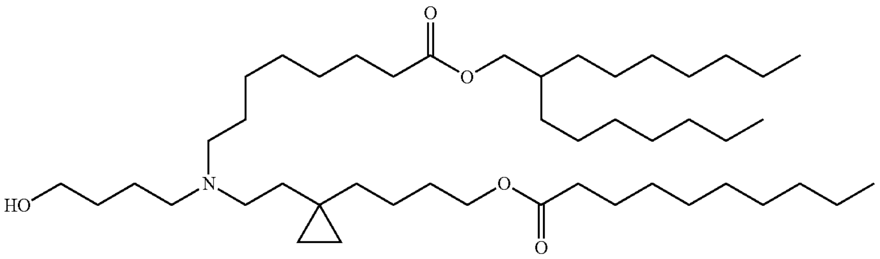 [SMILES: CCCCCCCCCC(=O)OCCCCC1(CCN(CCCCO)CCCCCCCC(=O)OCC(CCCCCCC)CCCCCCC)CC1]
275c
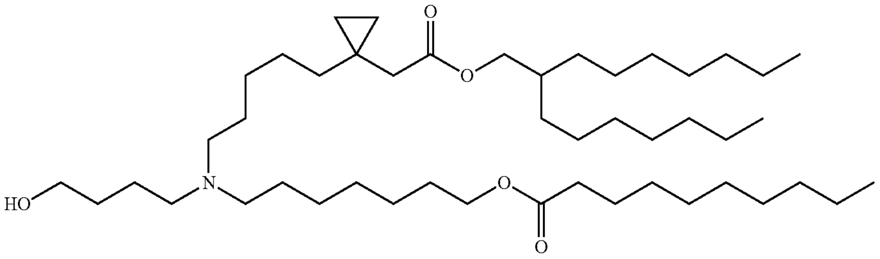 [SMILES: CCCCCCCCCC(=O)OCCCCCCCN(CCCCO)CCCCCC1(CC(=O)OCC(CCCCCCC)CCCCCCC)CC1]
276c
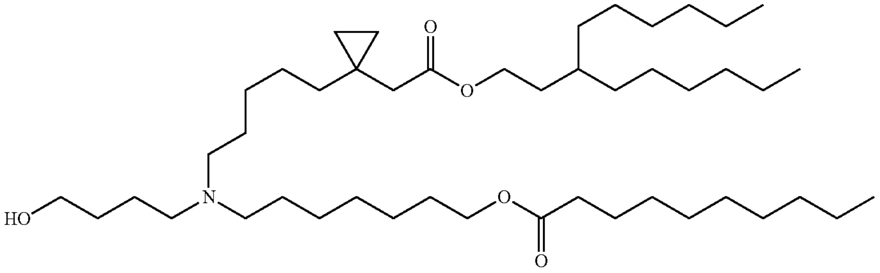 [SMILES: CCCCCCCCCC(=O)OCCCCCCCN(CCCCO)CCCCCC1(CC(=O)OCCC(CCCCCC)CCCCCC)CC1]
277c
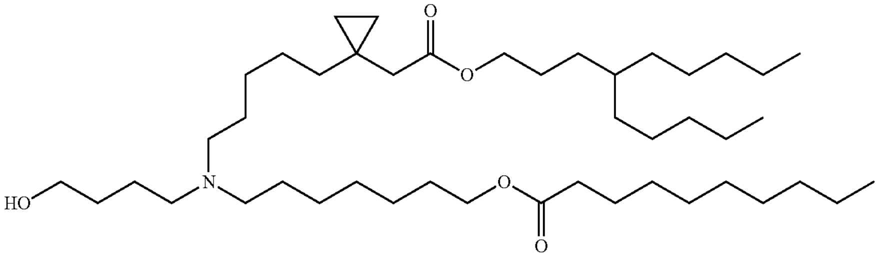 [SMILES: CCCCCCCCCC(=O)OCCCCCCCN(CCCCO)CCCCCC1(CC(=O)OCCCC(CCCCC)CCCCC)CC1]
278c
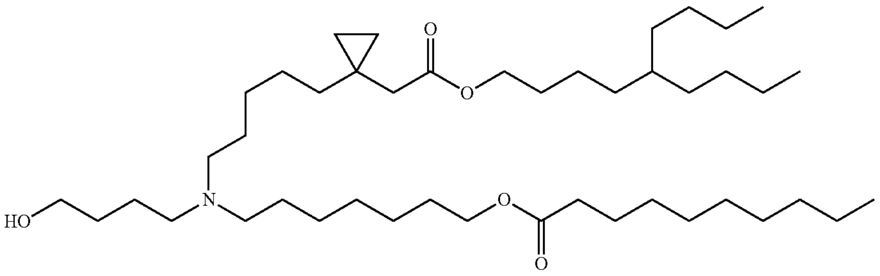 [SMILES: CCCCCCCCCC(=O)OCCCCCCCN(CCCCO)CCCCCC1(CC(=O)OCCCCC(CCCC)CCCC)CC1]
279c
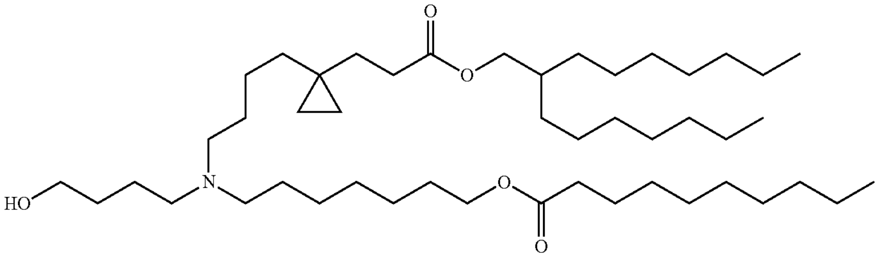 [SMILES: CCCCCCCCCC(=O)OCCCCCCCN(CCCCO)CCCCC1(CCC(=O)OCC(CCCCCCC)CCCCCCC)CC1]
280c TABLE I-continued

| | |
|---|---|
| 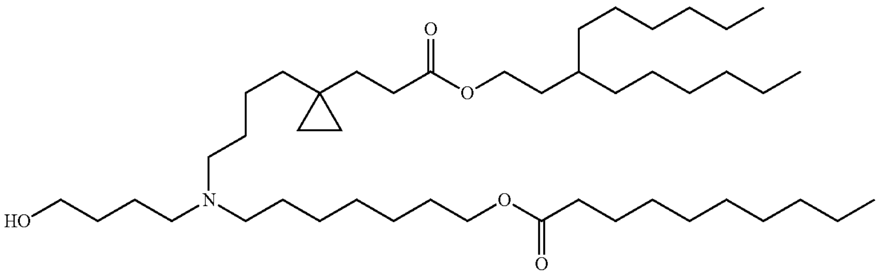 [SMILES: CCCCCCCCCC(=O)OCCCCCCCN(CCCCO)CCCCC1(CCC(=O)OCCC(CCCCCC)CCCCCC)CC1] | 281c |
| 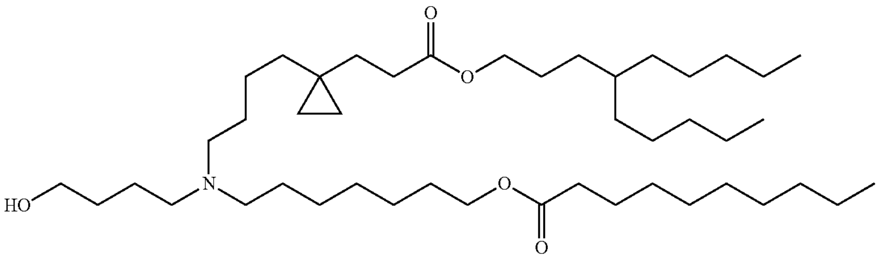 [SMILES: CCCCCCCCCC(=O)OCCCCCCCN(CCCCO)CCCCC1(CCC(=O)OCCCC(CCCCC)CCCCC)CC1] | 282c |
| 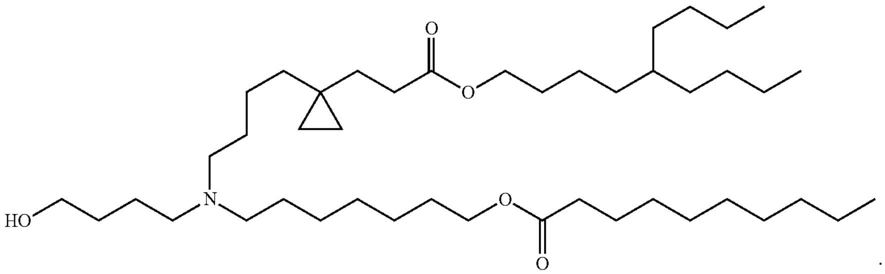 [SMILES: CCCCCCCCCC(=O)OCCCCCCCN(CCCCO)CCCCC1(CCC(=O)OCCCCC(CCCC)CCCC)CC1] | 283c |

The present disclosure further provides a method for preparing a compound of formula (II), comprising:

reacting a compound of formula (IIA) with a compound of formula (IIB) to give the compound of formula (II),

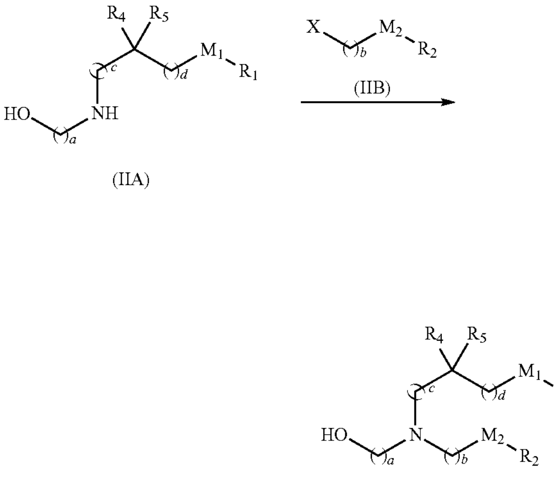

(IIA) (IIB) (II)

wherein X is halogen, and the other variables are as defined herein.

The present disclosure further provides a method for preparing a compound of formula (II), comprising:

reacting a compound of formula (IIC) with a compound of formula (IID) to give the compound of formula (II),

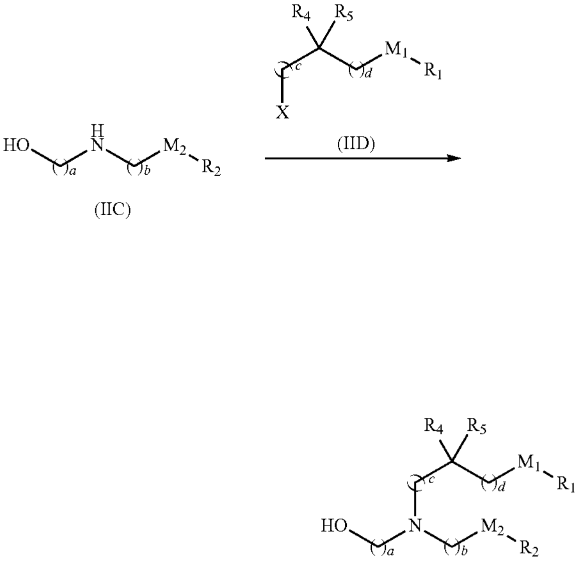

(IIC) (IID) (II)

wherein X is halogen, and the other variables are as defined herein.

In a specific embodiment, the compound is selected from:
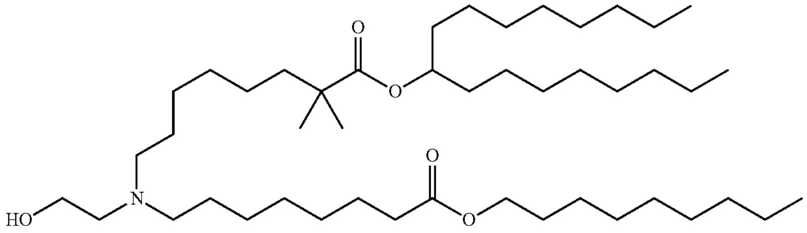
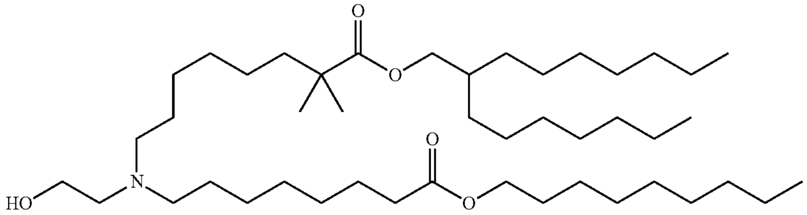
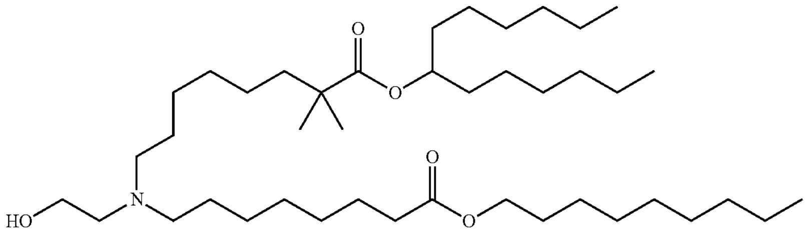
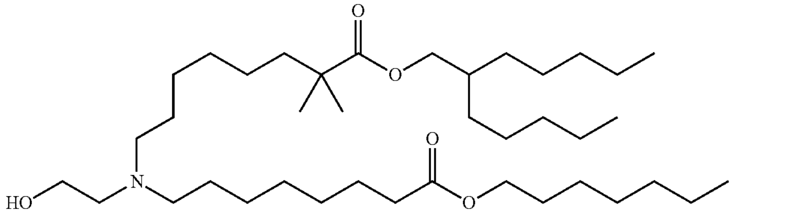
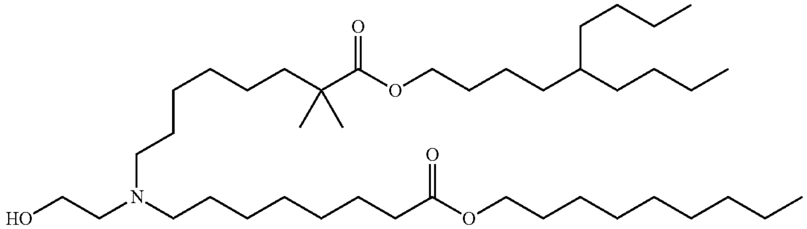
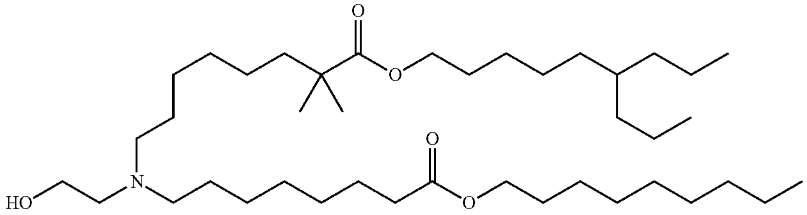
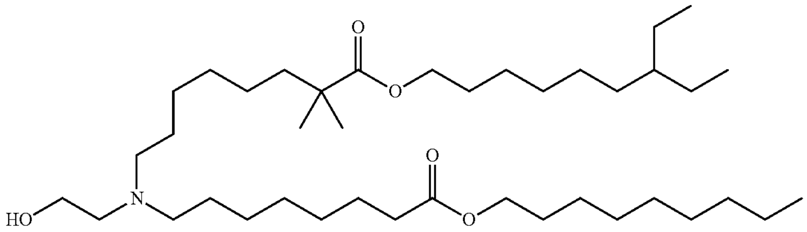

-continued
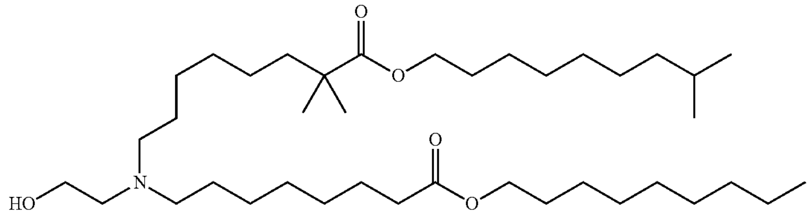
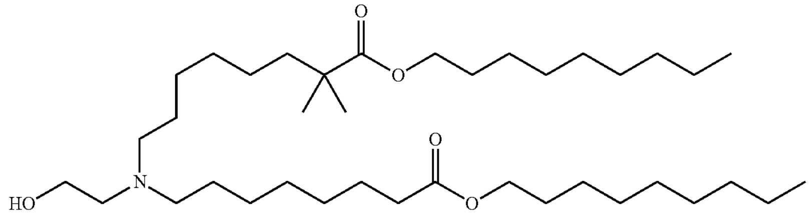
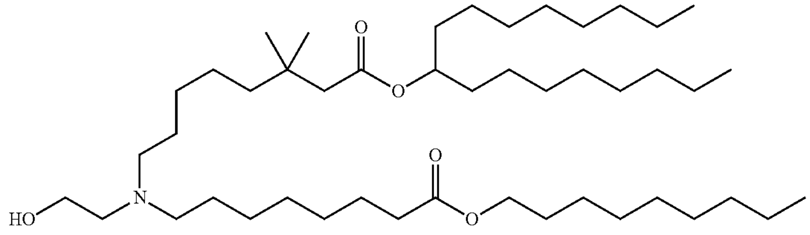
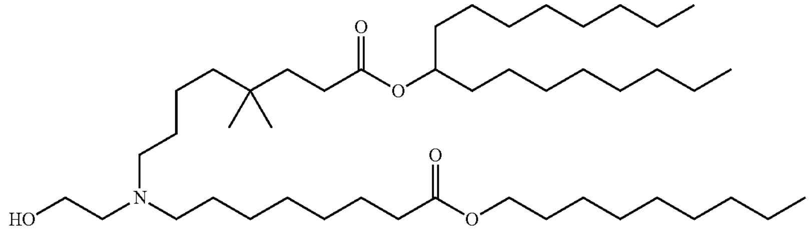
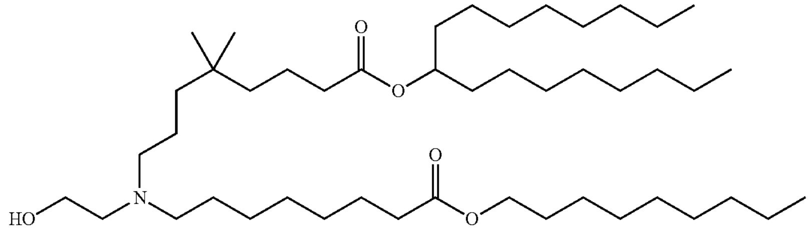
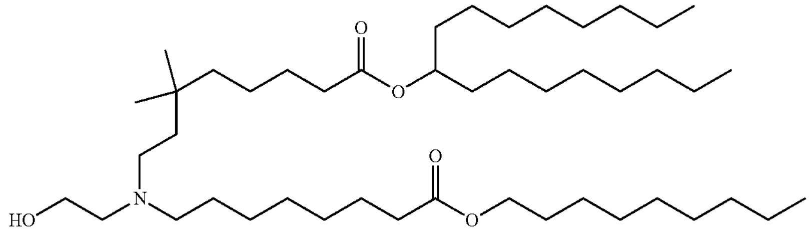
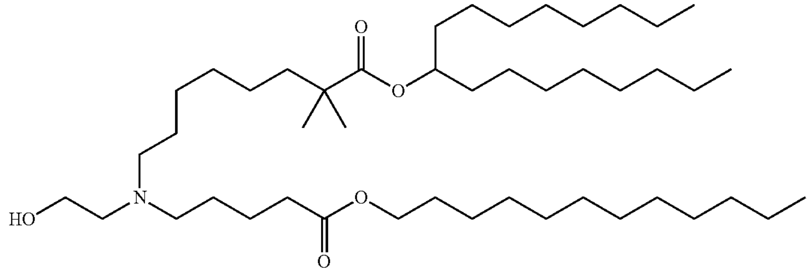

-continued
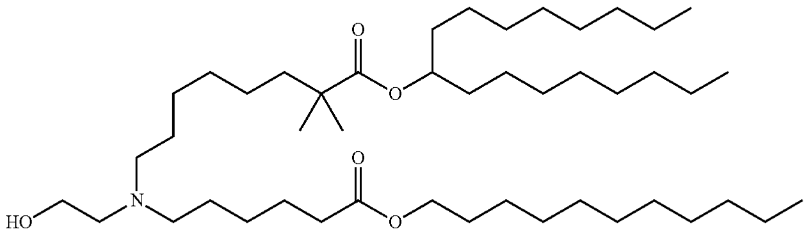
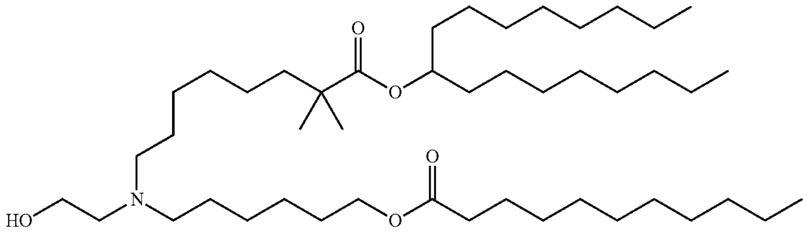
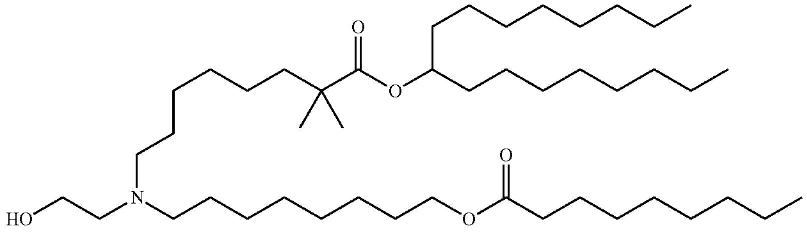
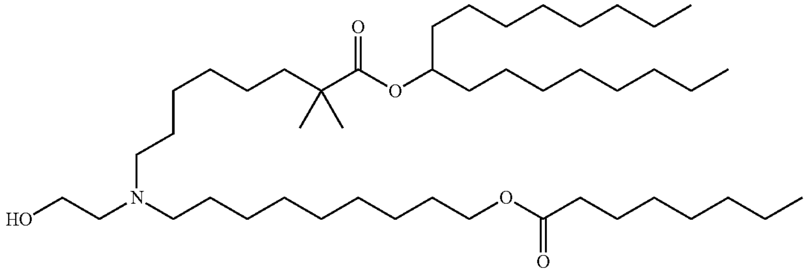
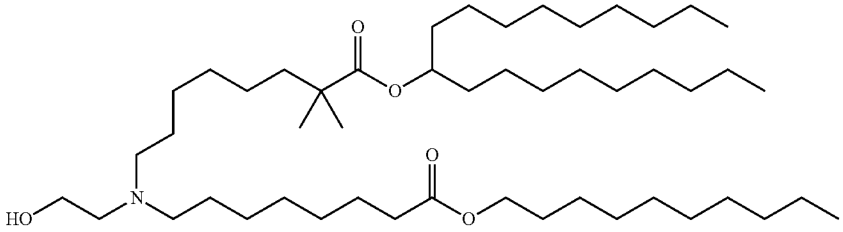
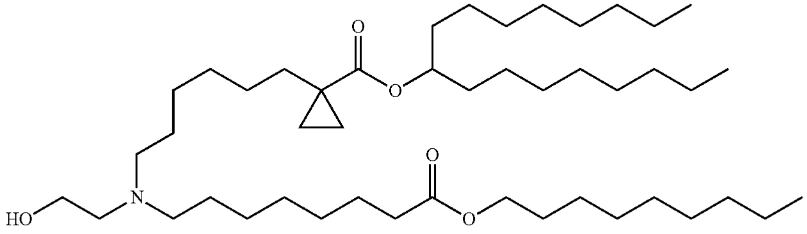
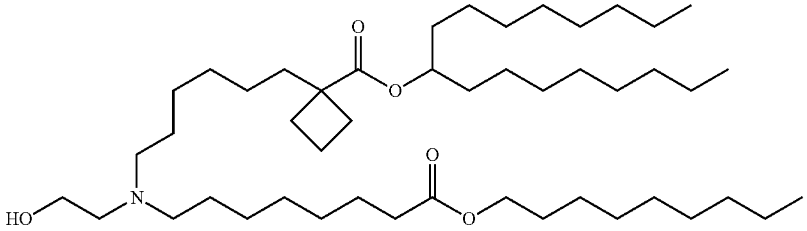

-continued
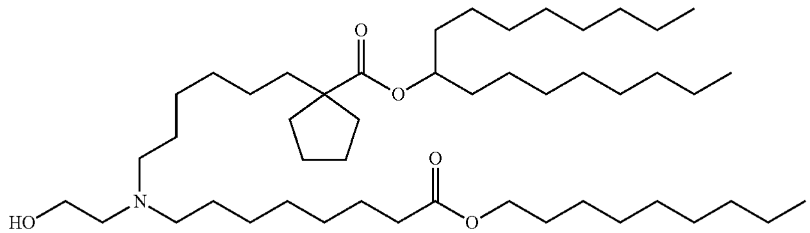
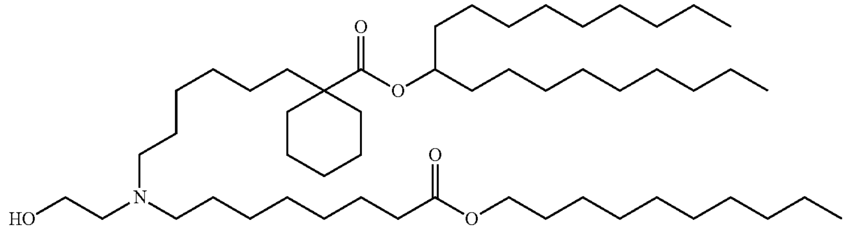
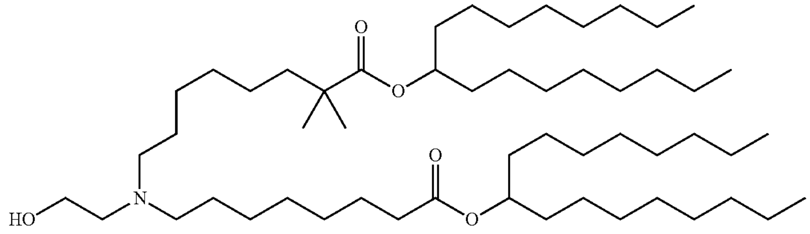
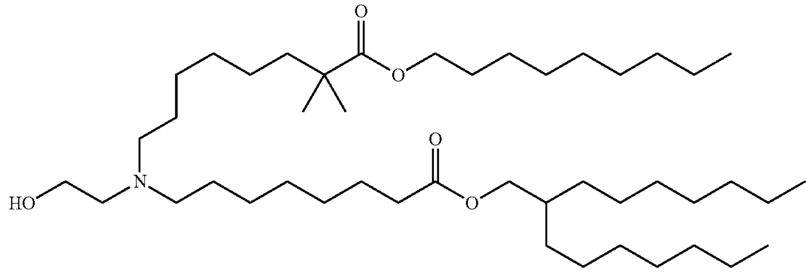
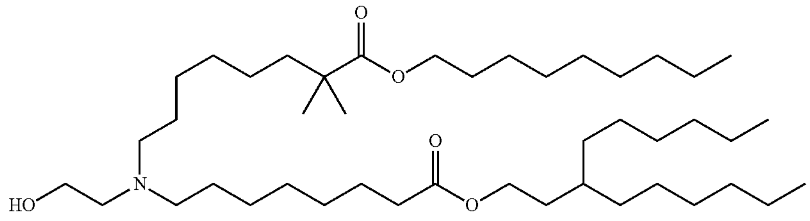
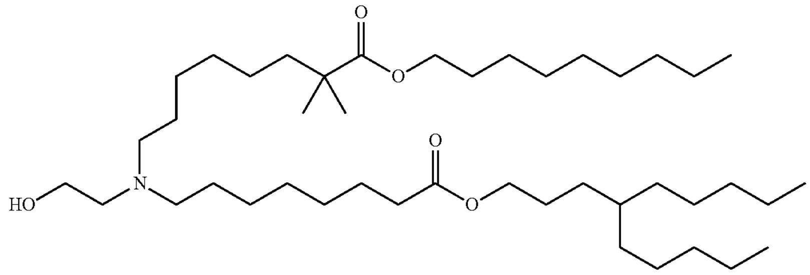
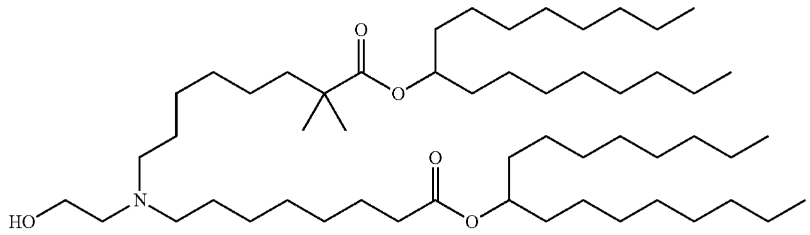

-continued
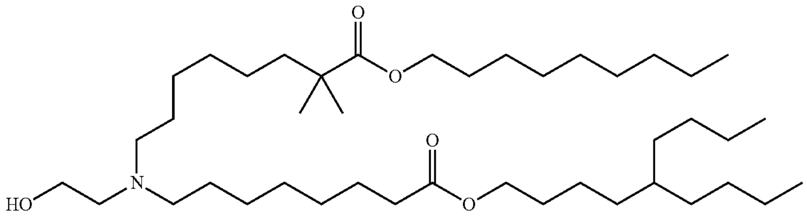
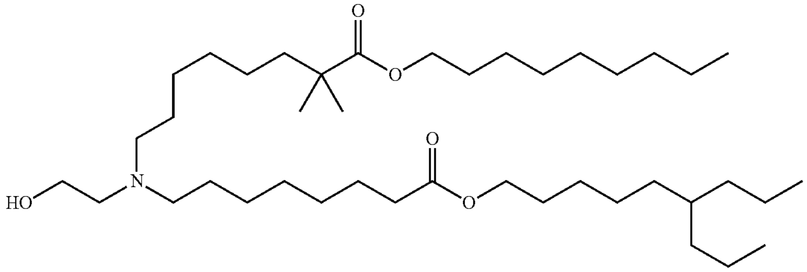
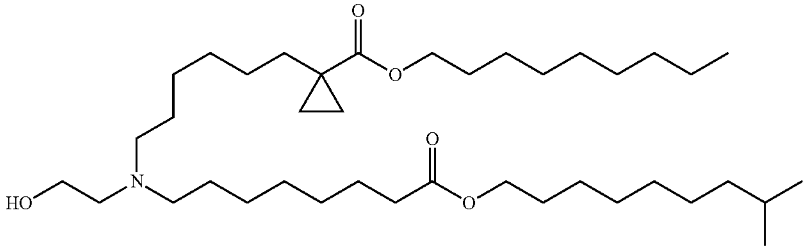
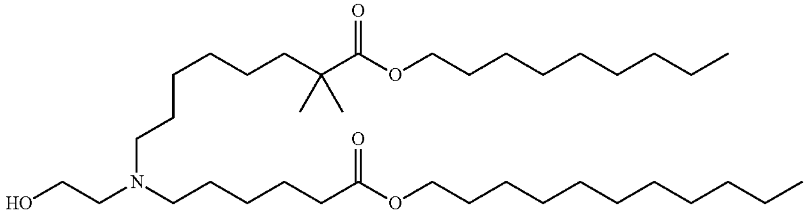
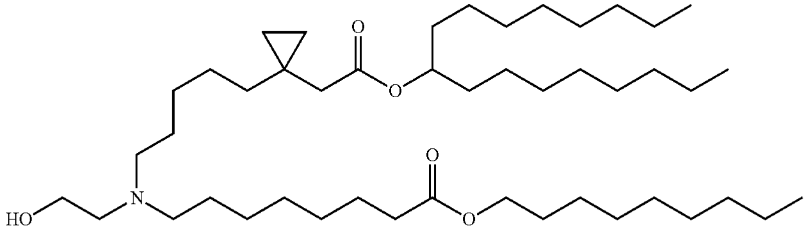
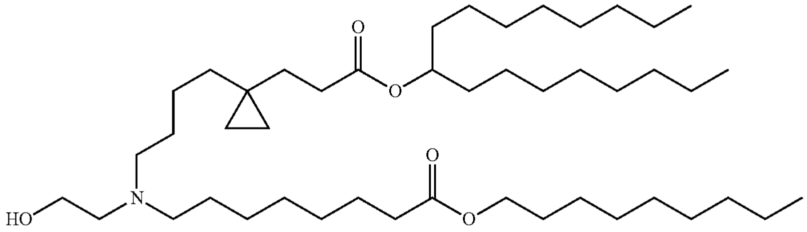
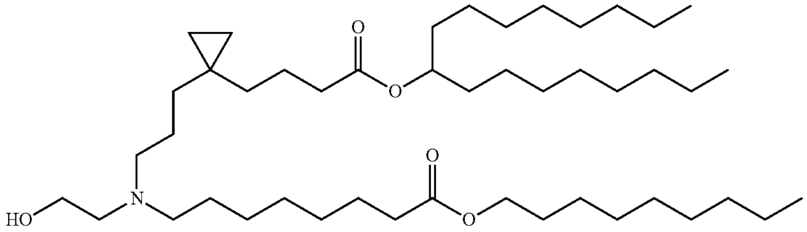

-continued
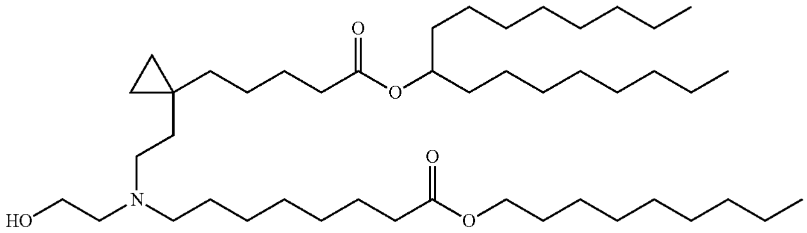
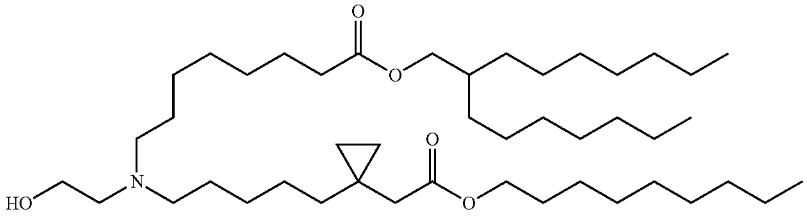
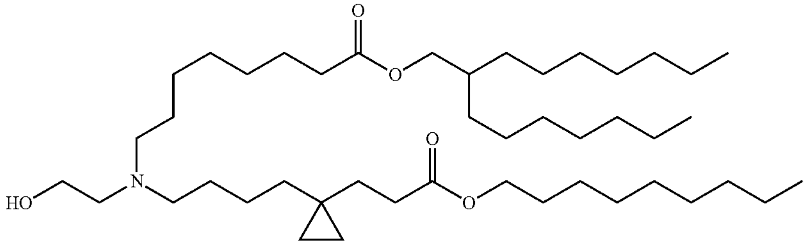
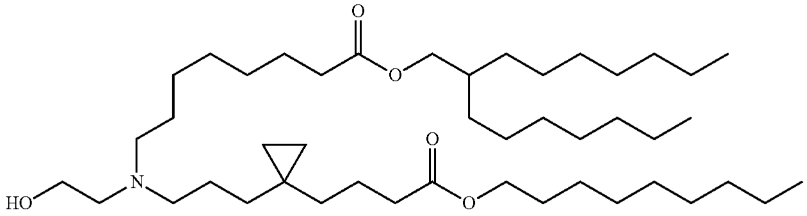
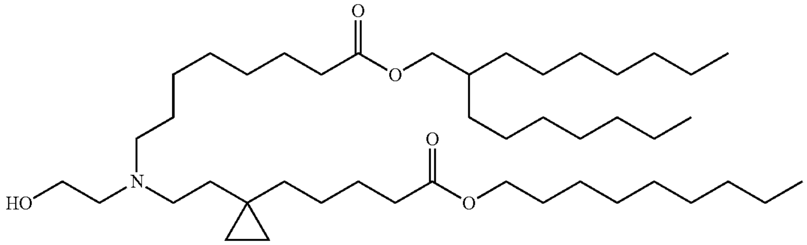
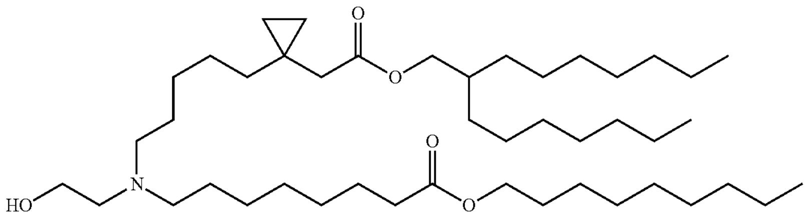
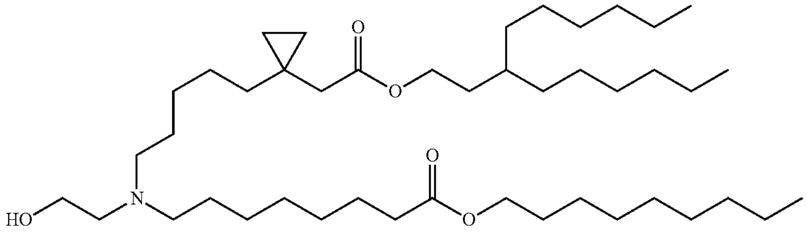

-continued
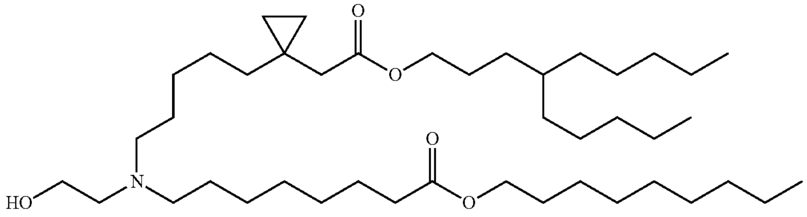
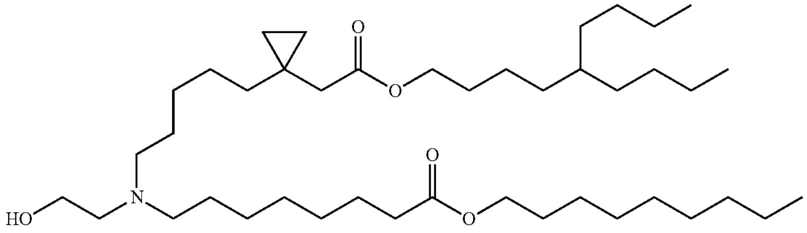
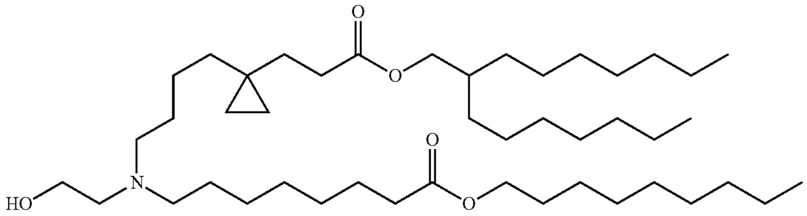
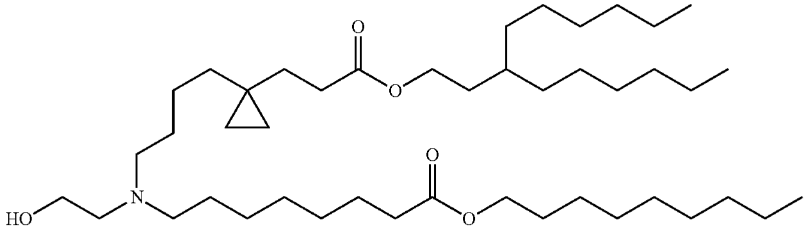
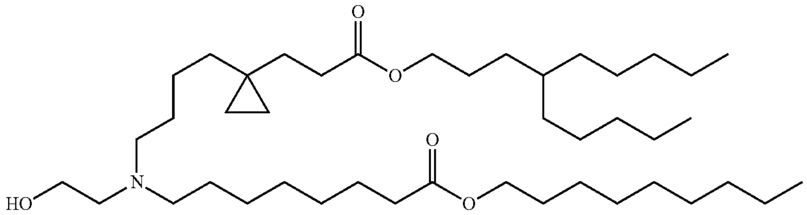
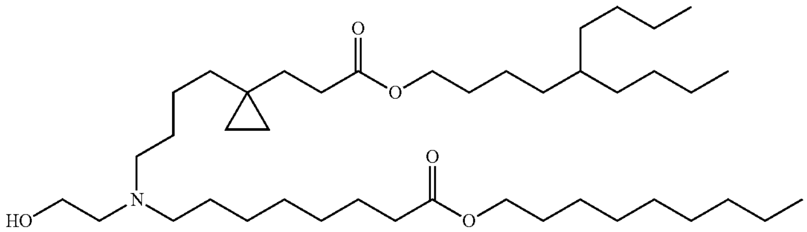
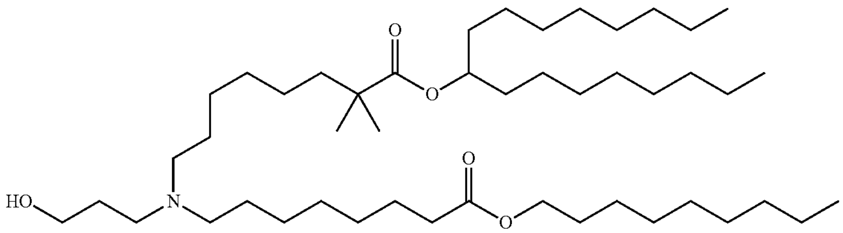

-continued
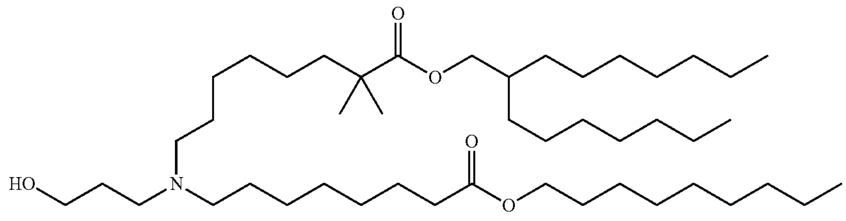
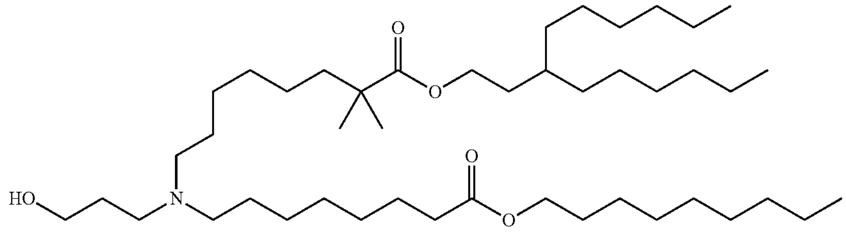
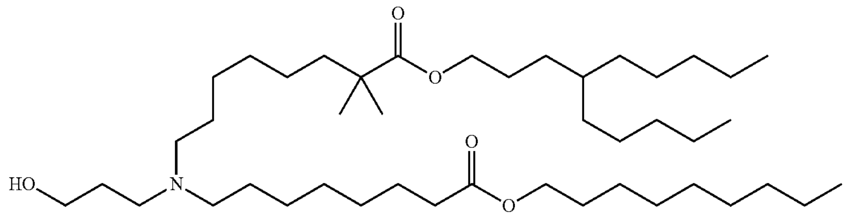
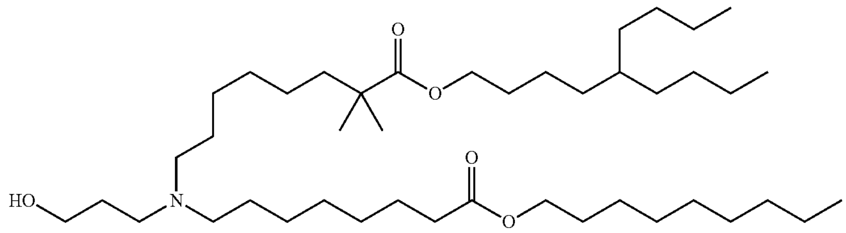
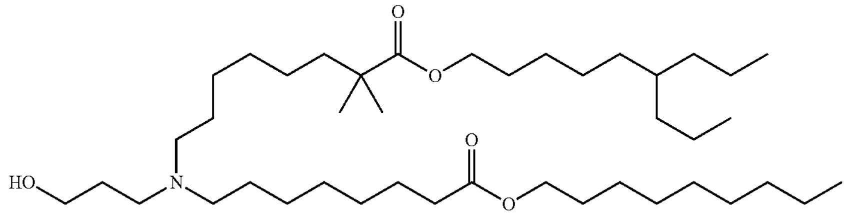
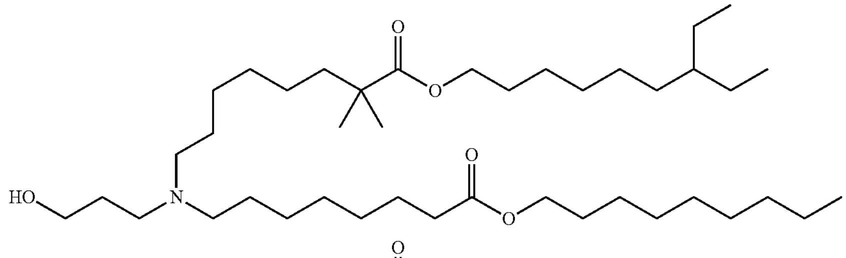
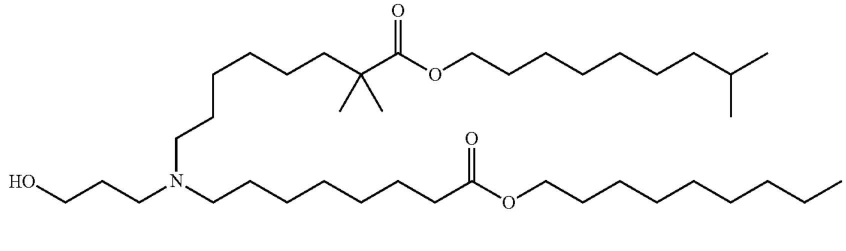

-continued
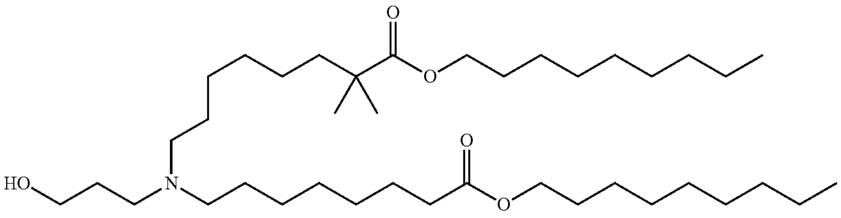
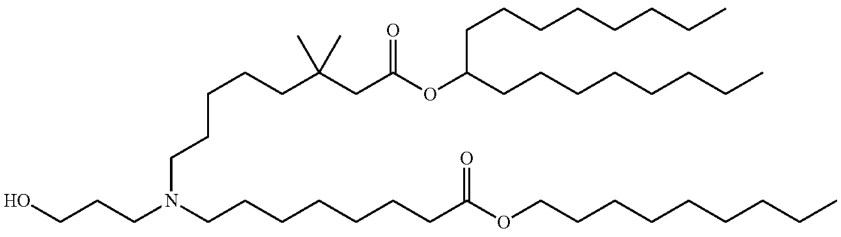
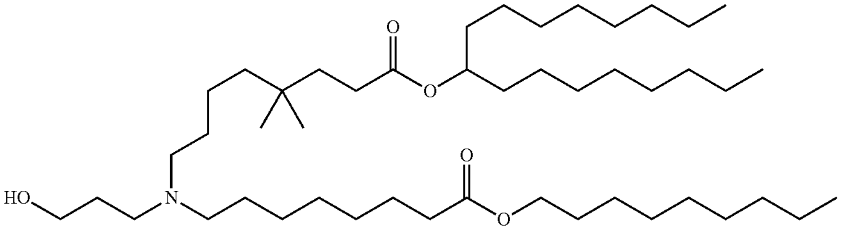
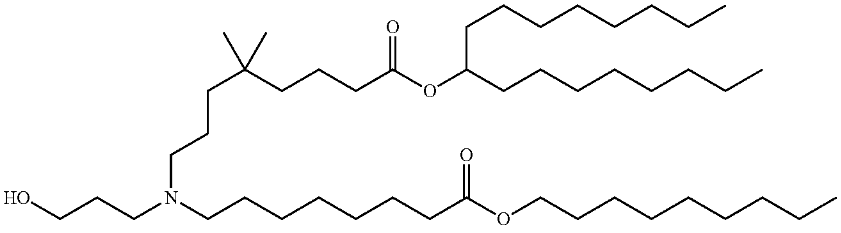
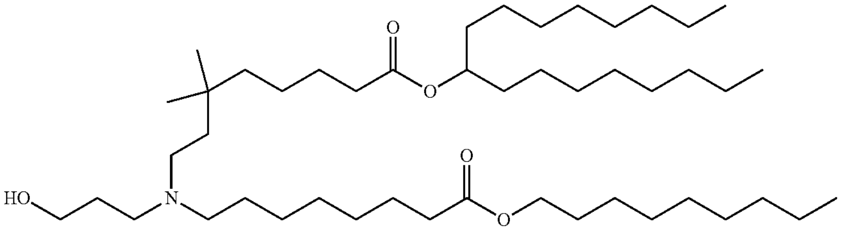
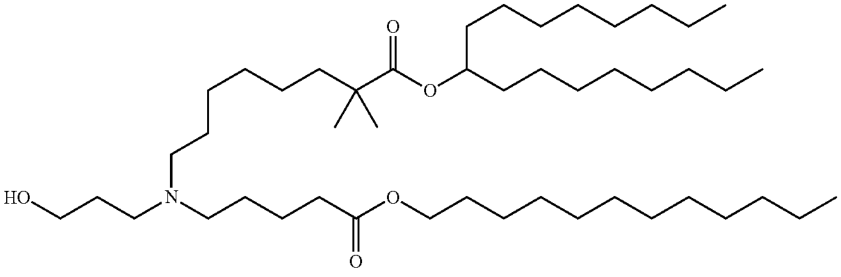
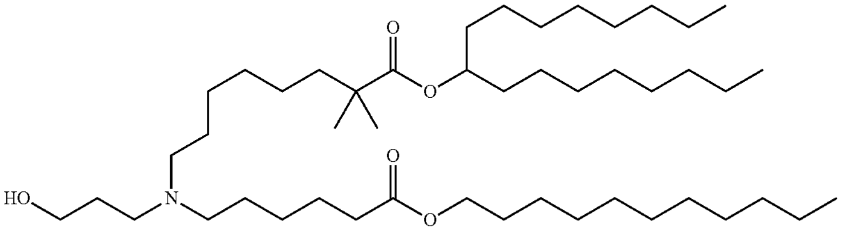

-continued
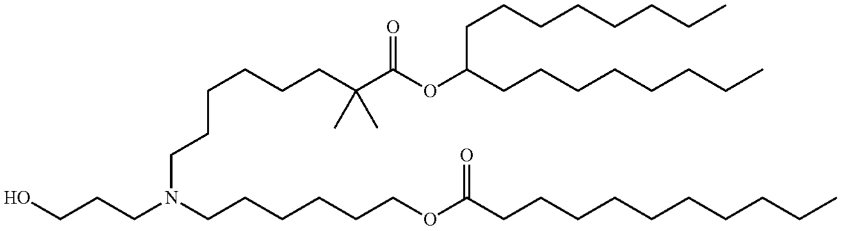
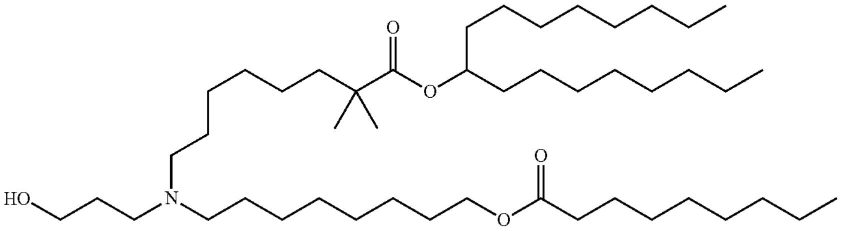
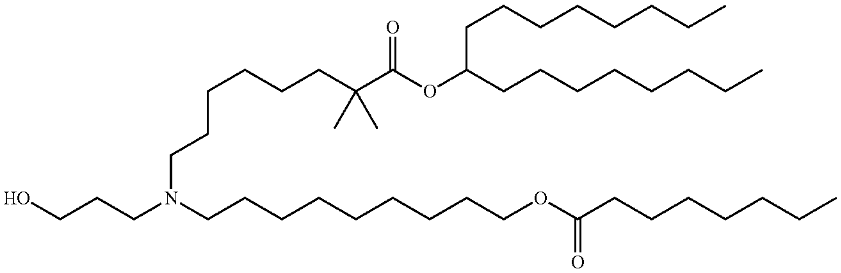
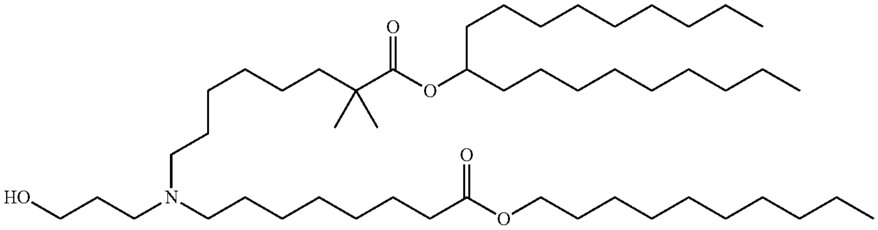
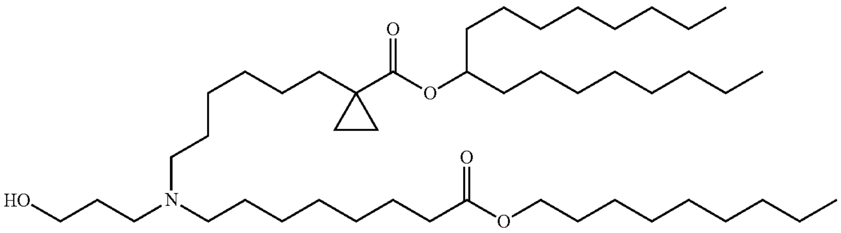
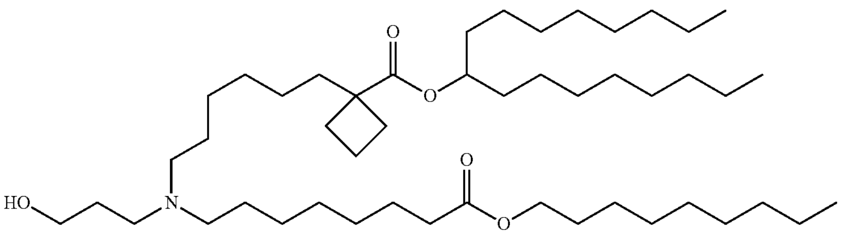
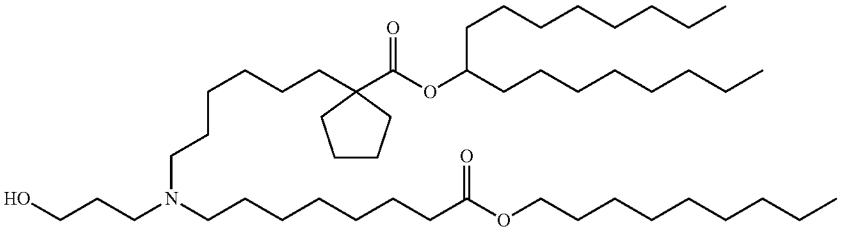

-continued
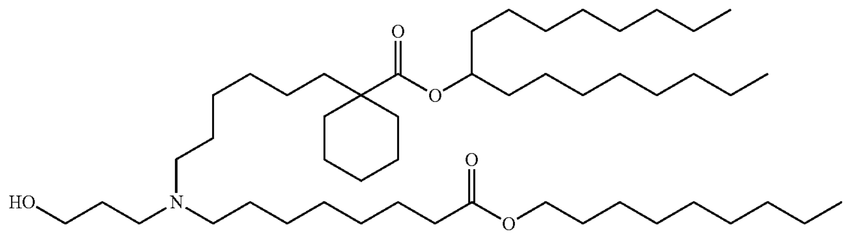
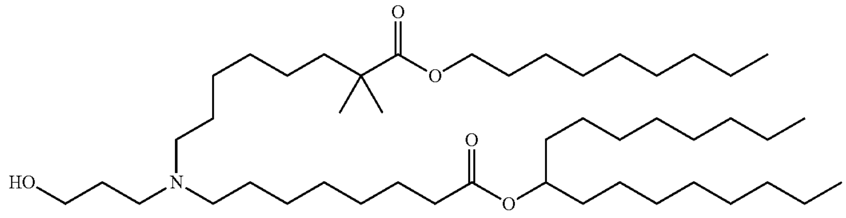
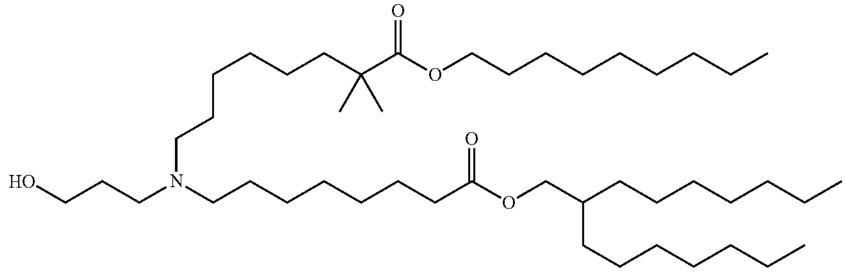
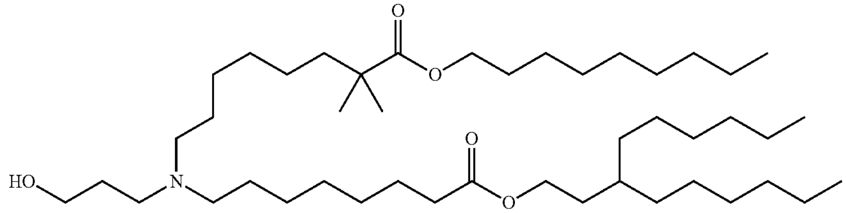
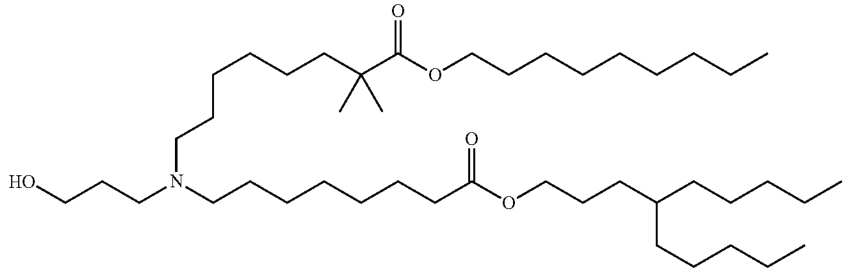
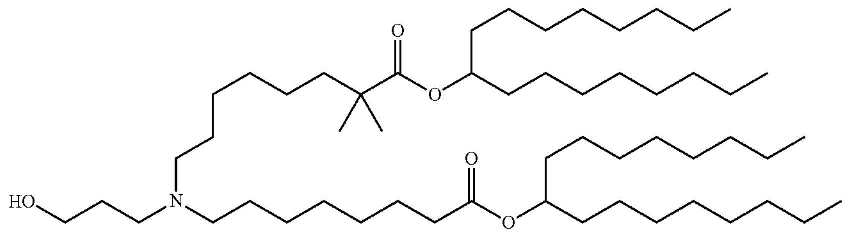
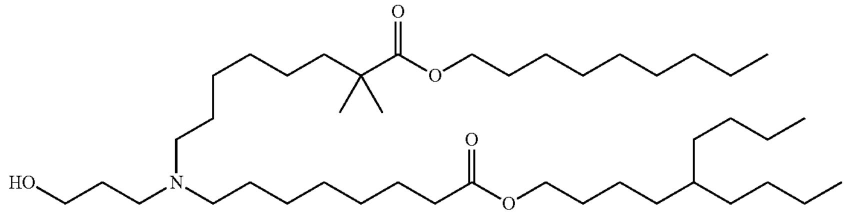

-continued
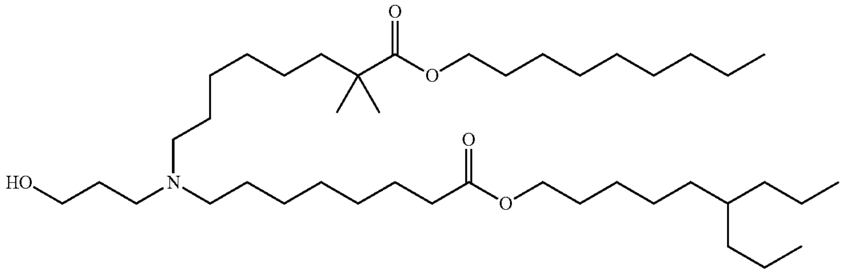
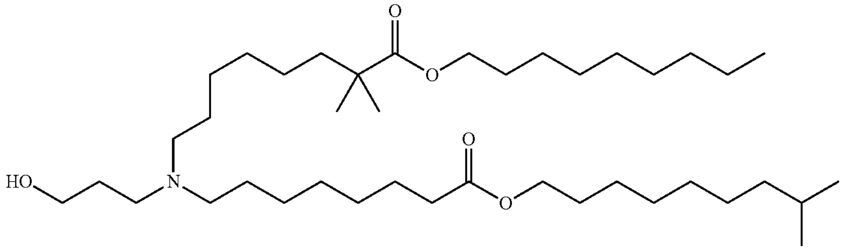
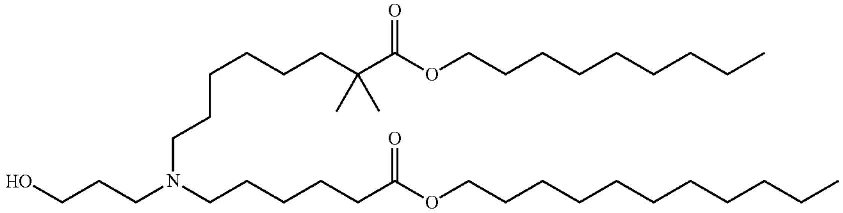
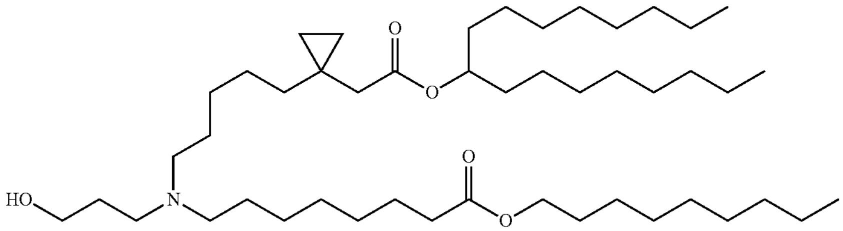
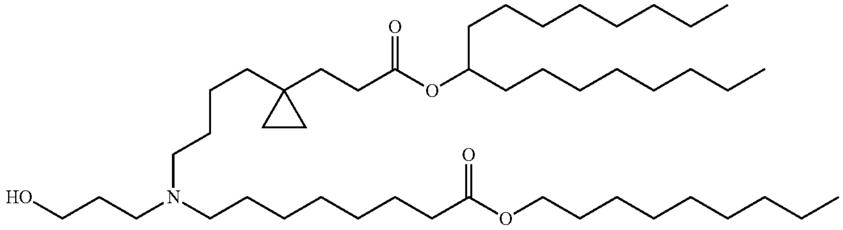
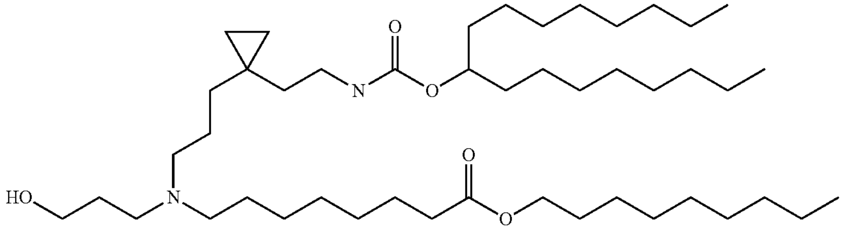
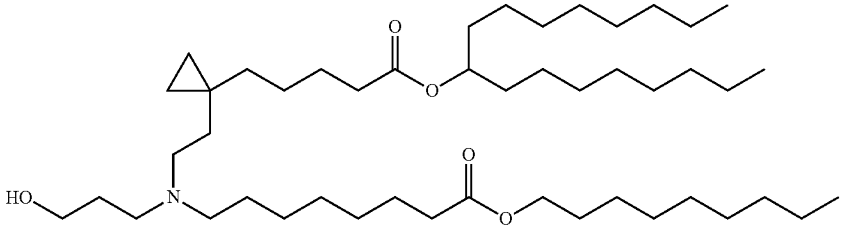

-continued
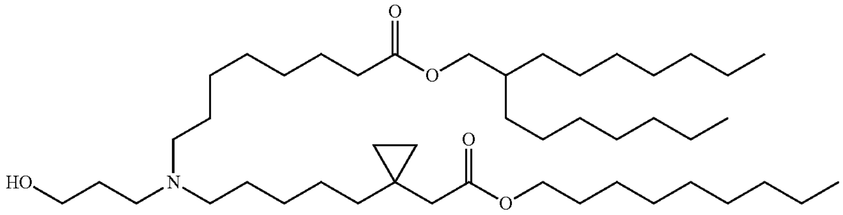
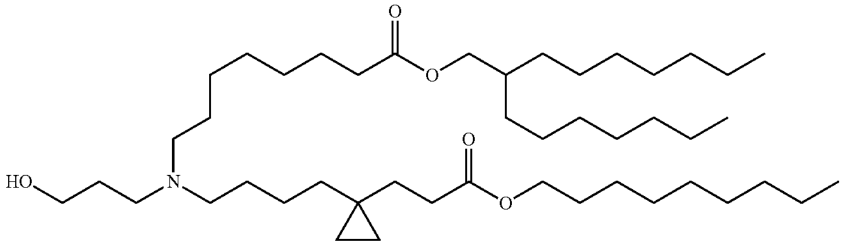
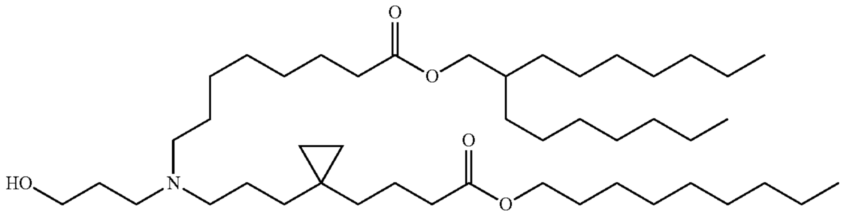
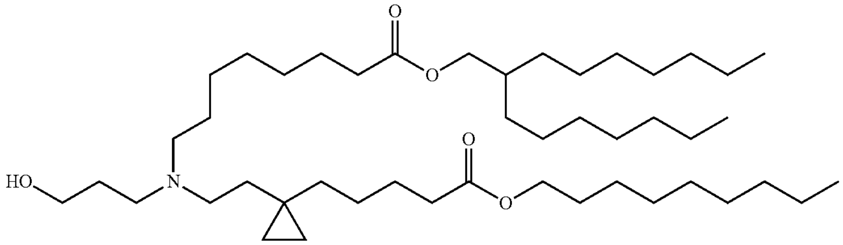
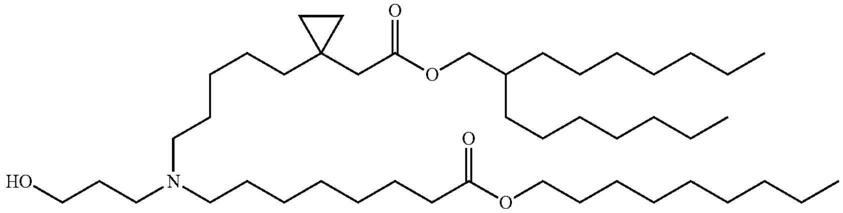
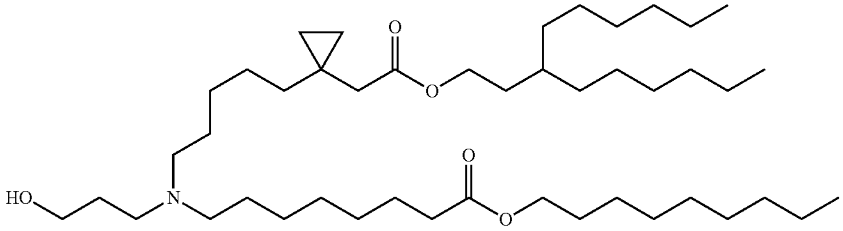
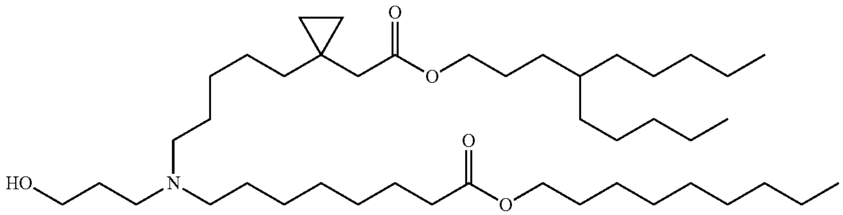

-continued
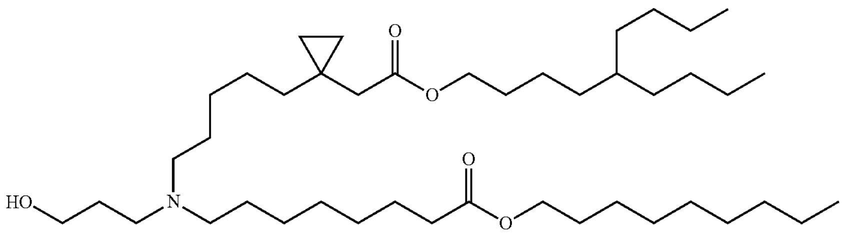
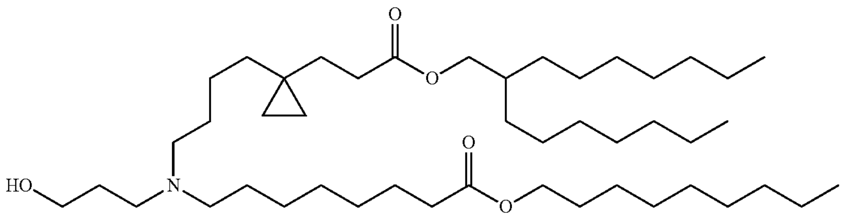
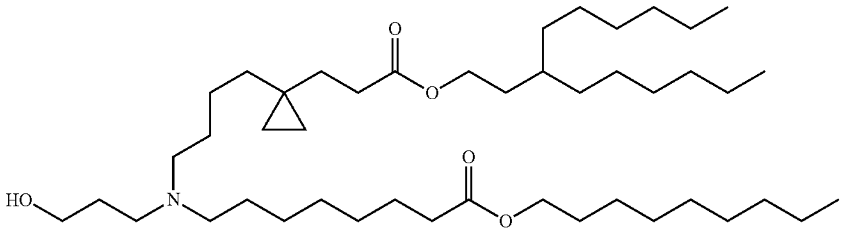
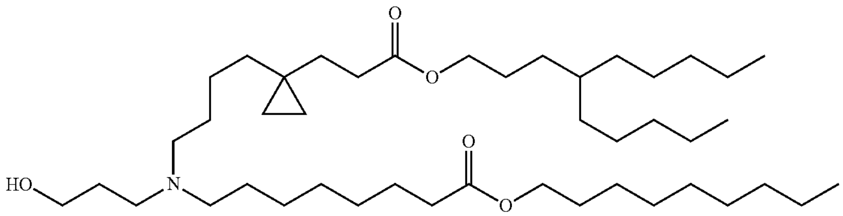
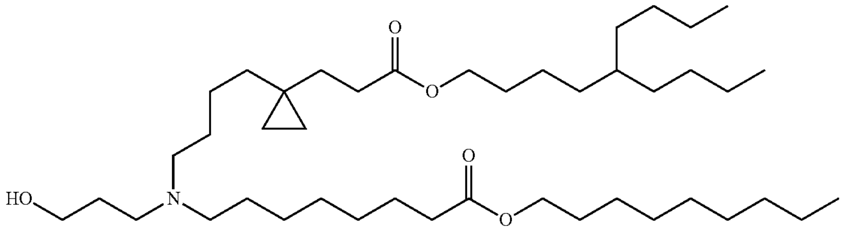
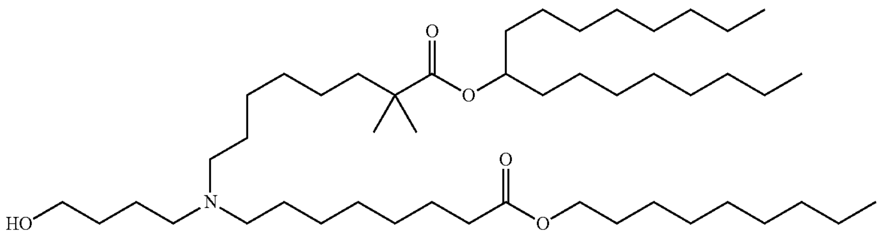
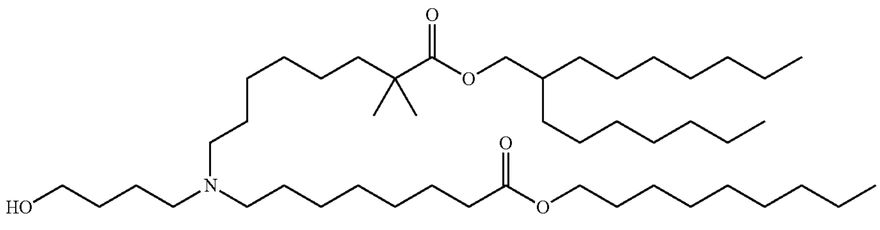

-continued
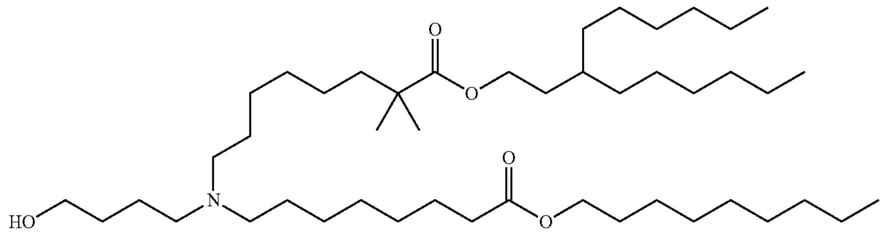
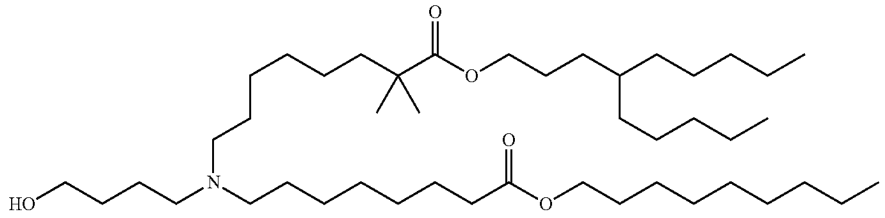
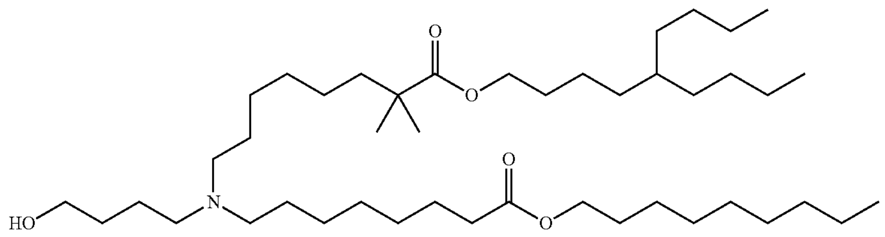
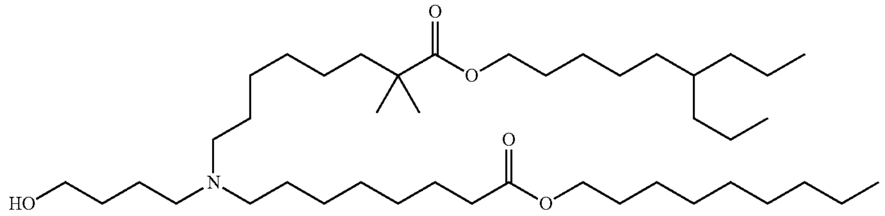
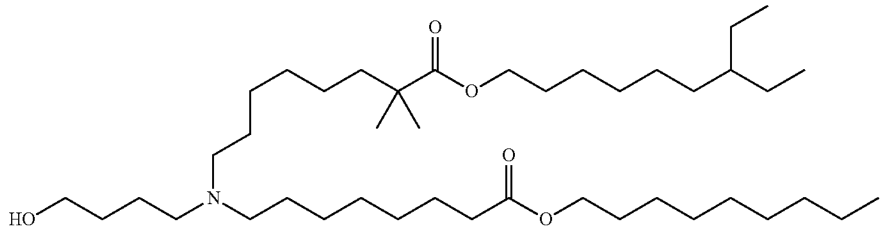
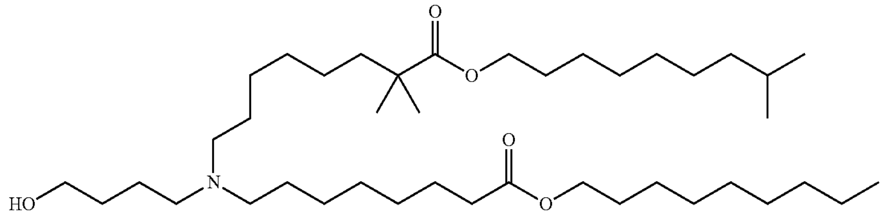
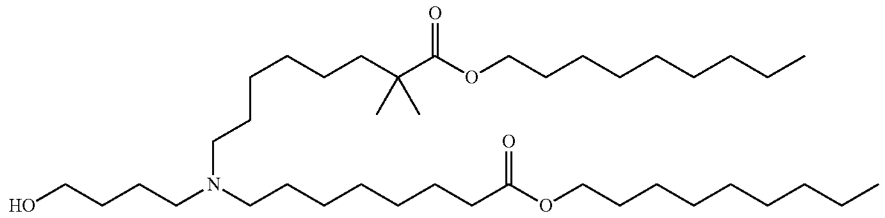

-continued
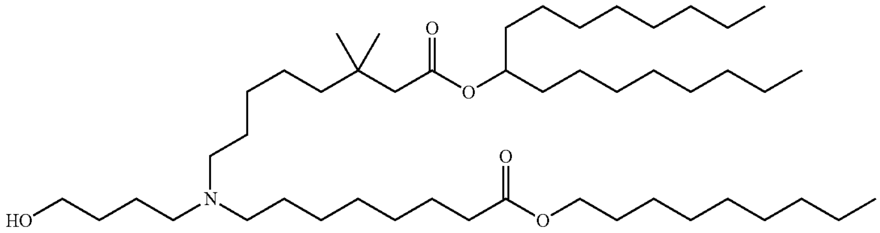
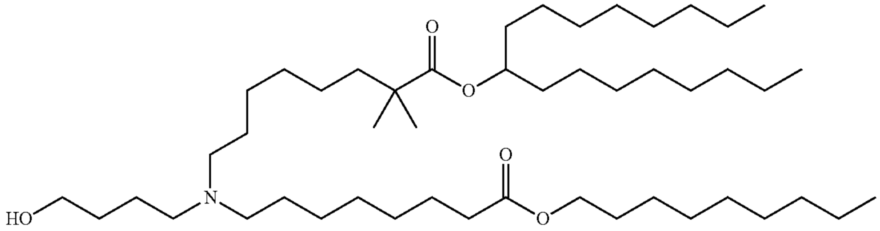
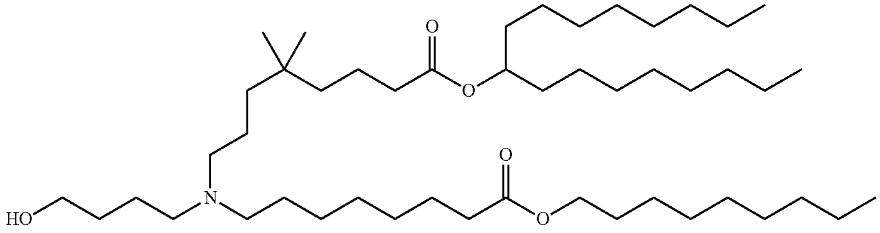
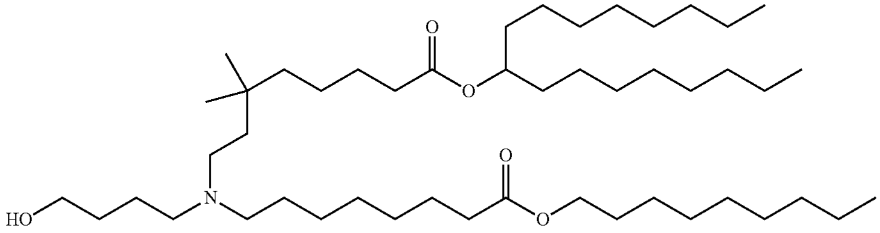
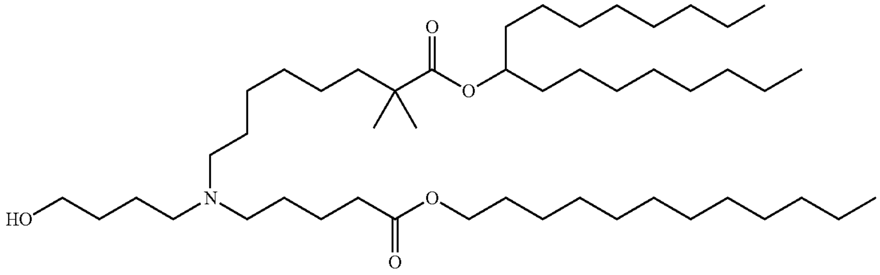
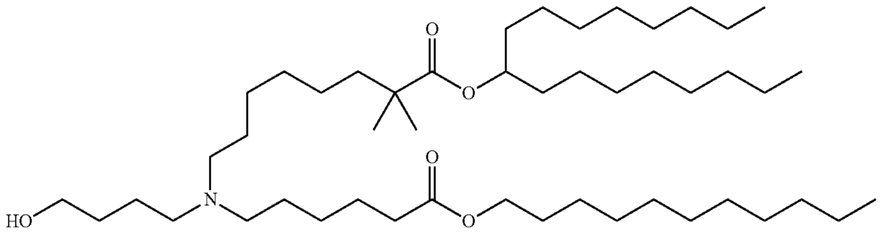
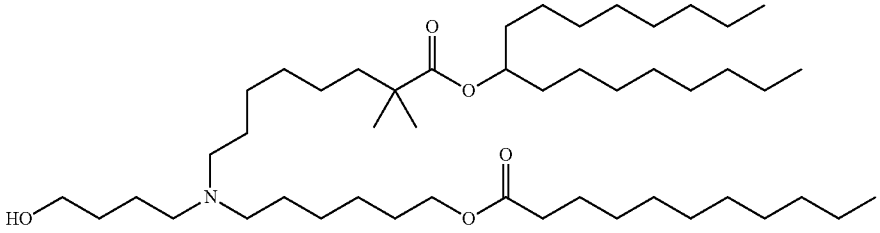

-continued
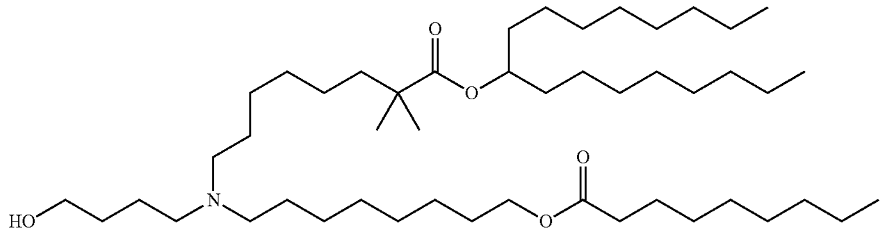
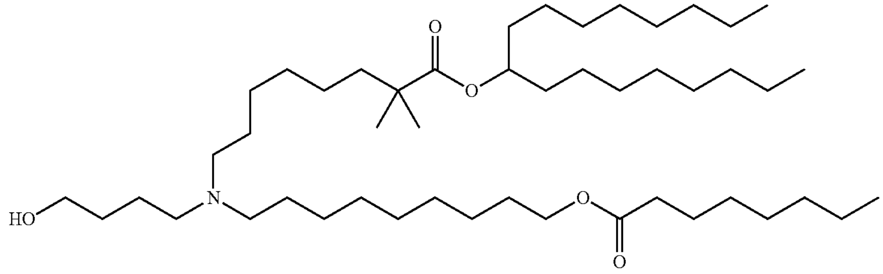
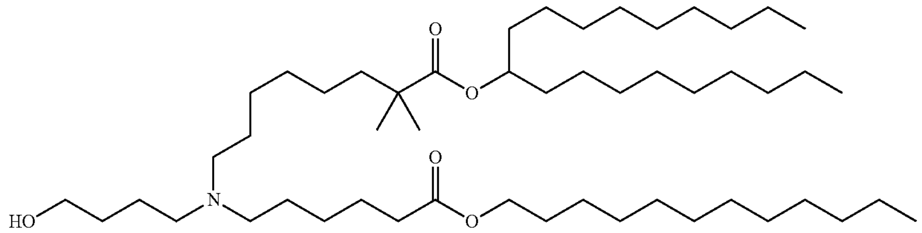
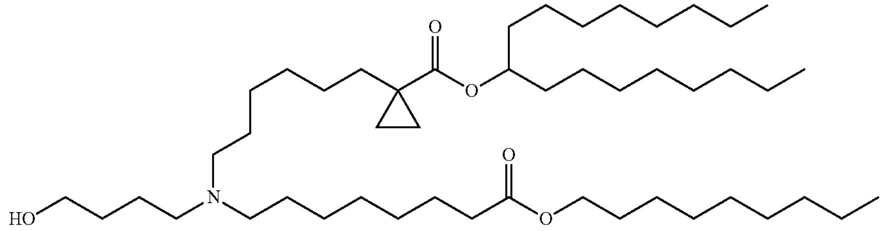
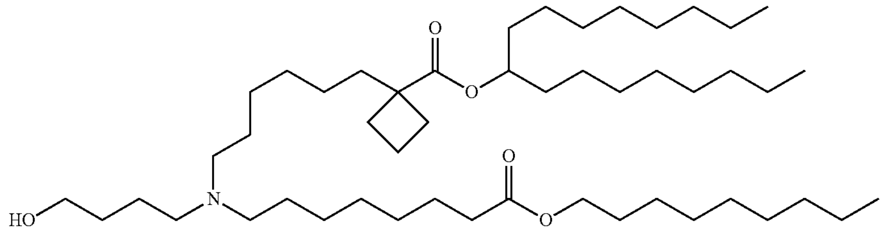
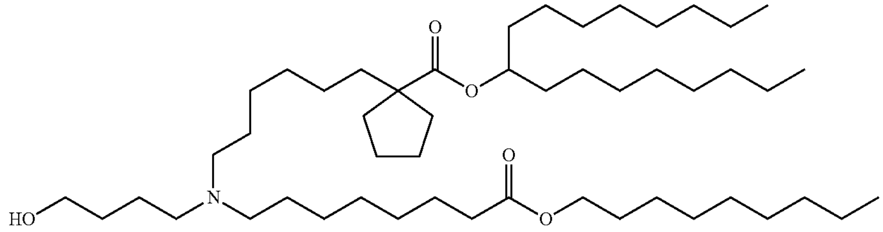
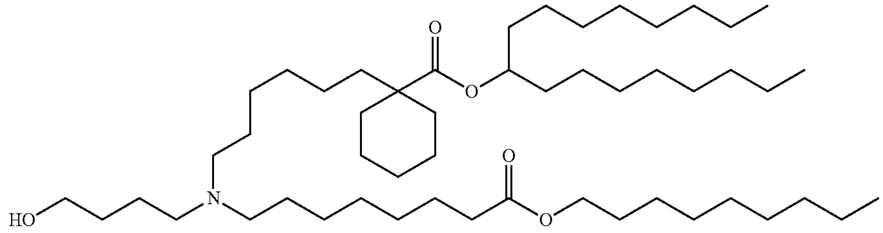

-continued
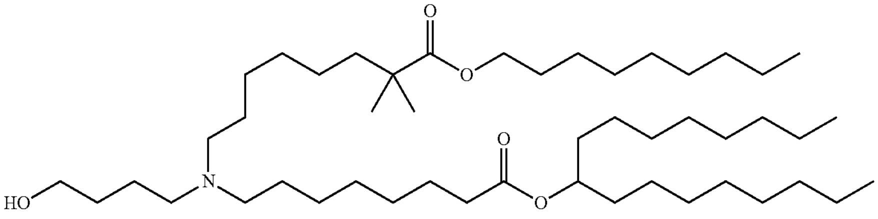
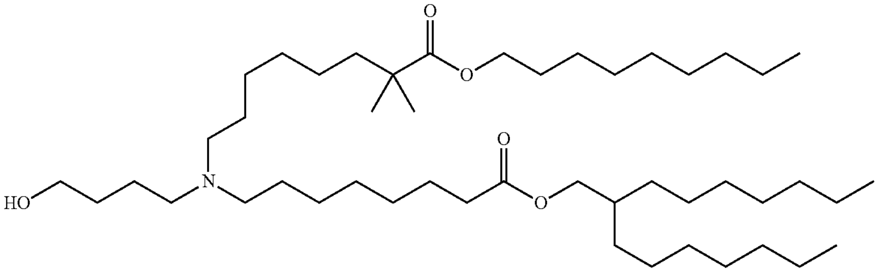
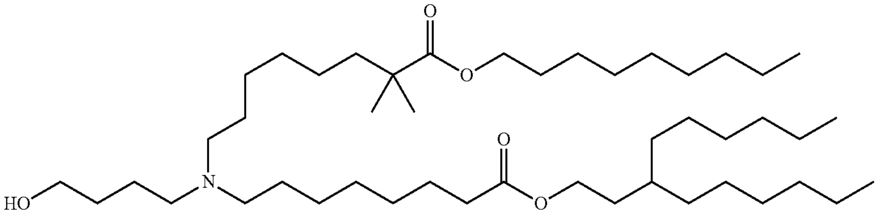
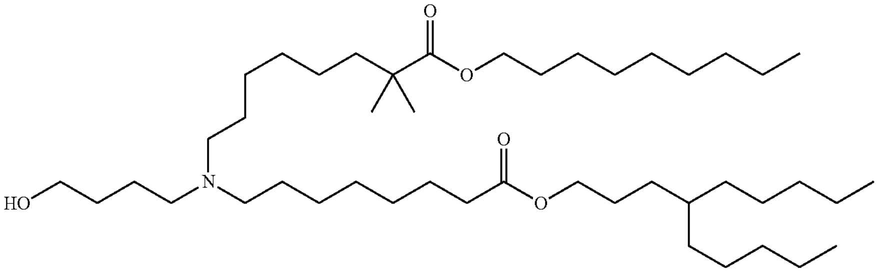
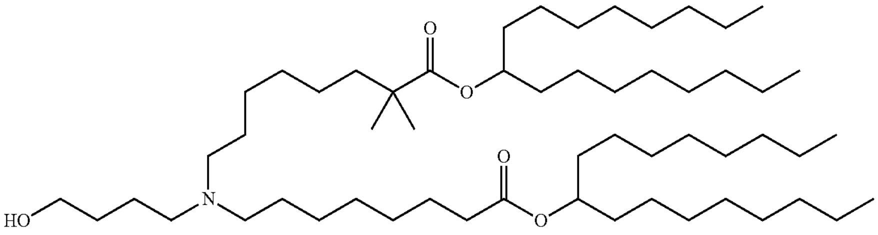
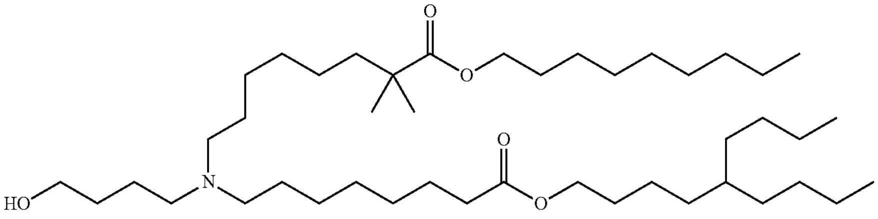
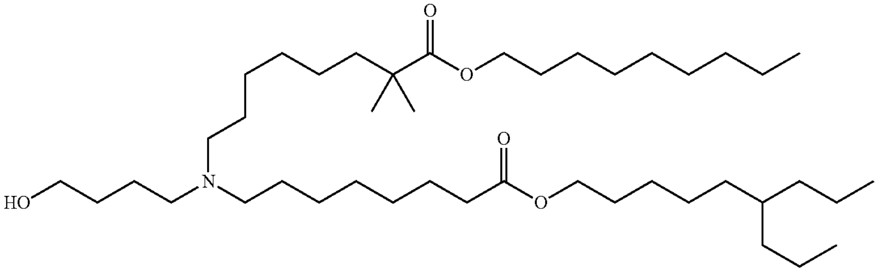

-continued
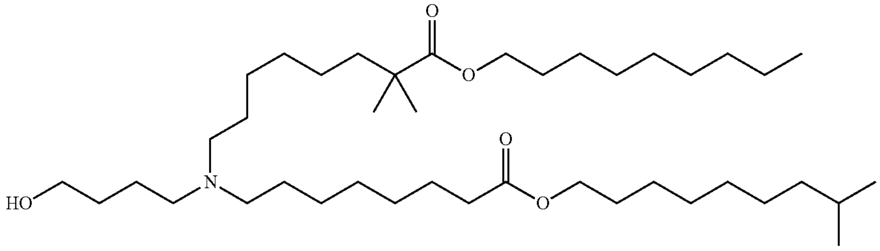
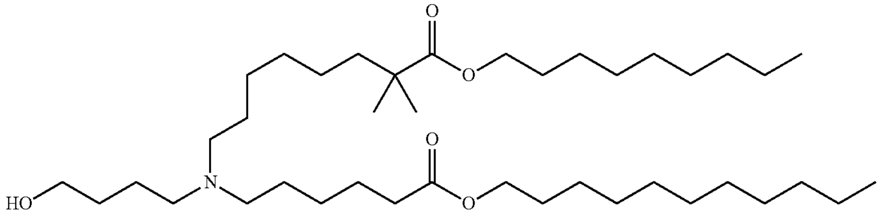
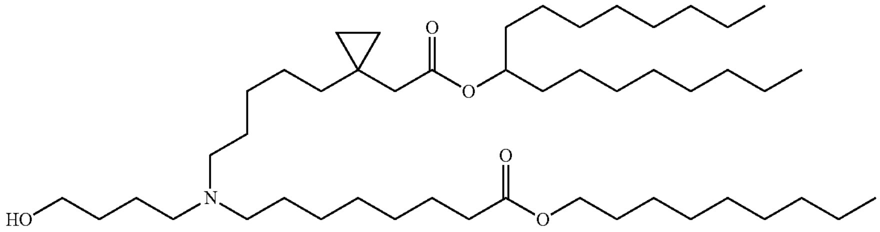
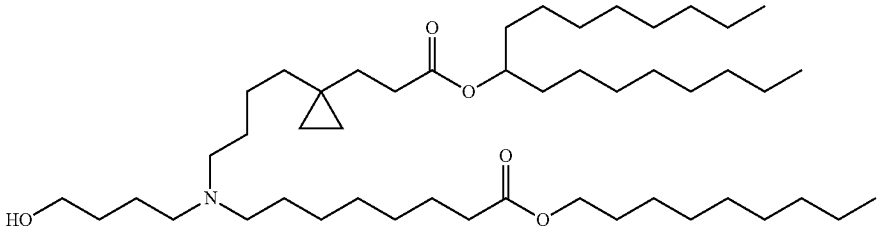
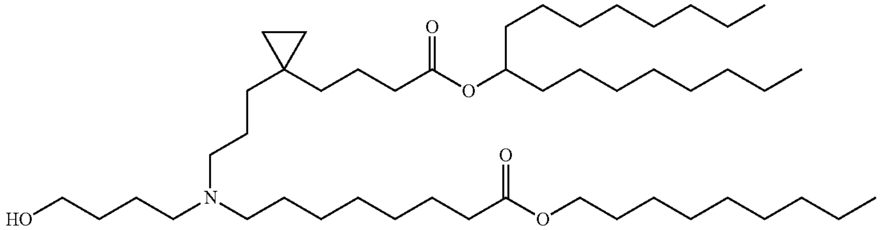
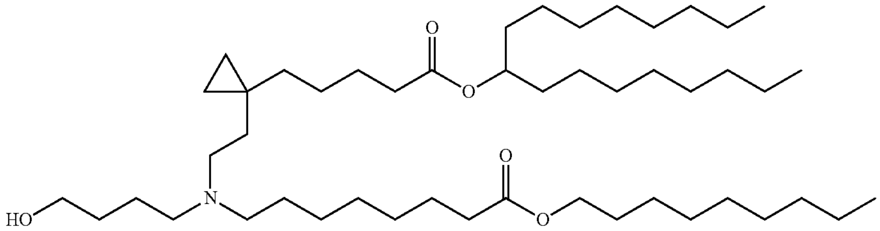
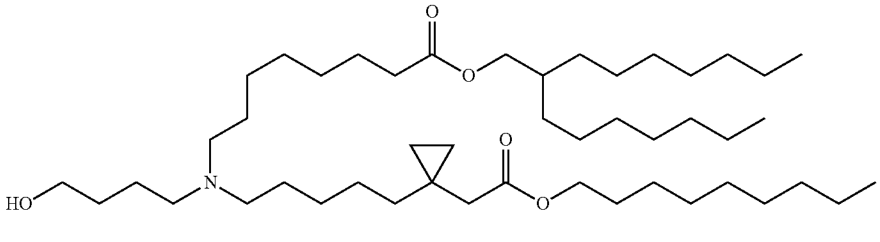

-continued
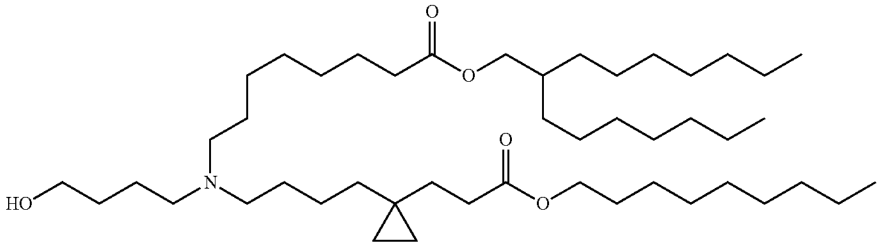
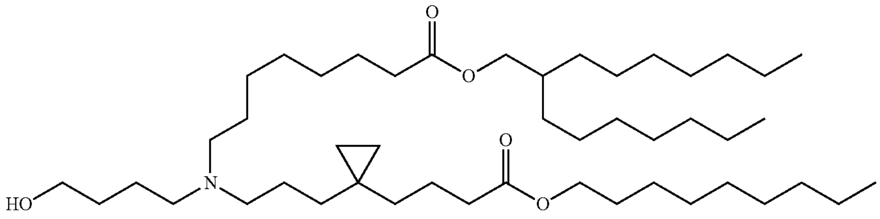
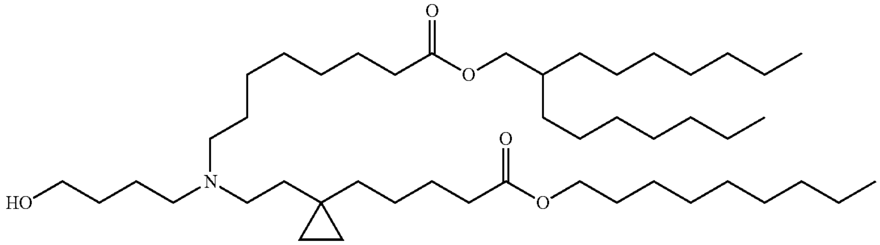
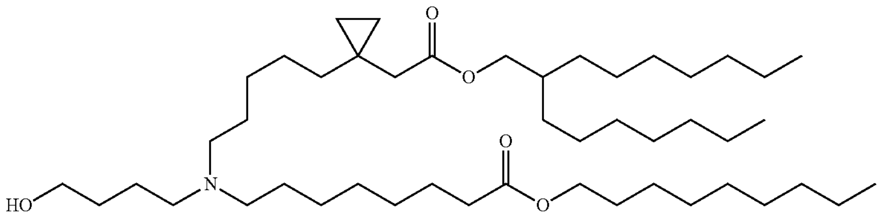
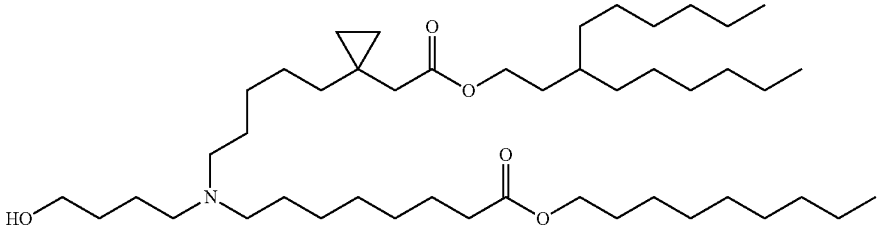
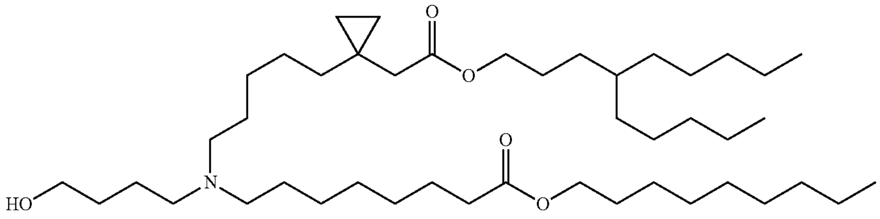
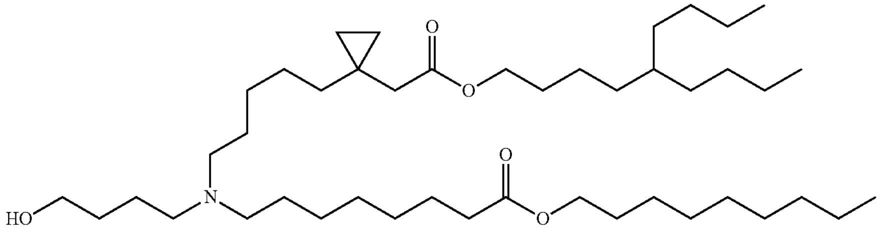

-continued

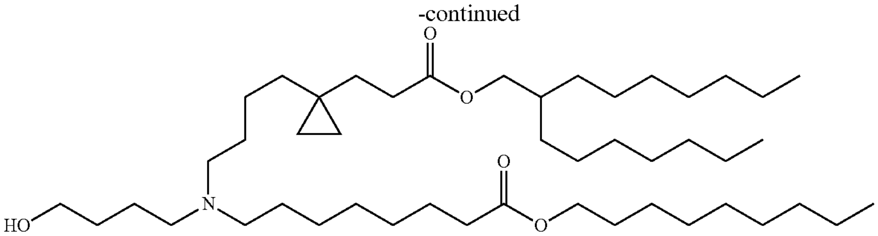

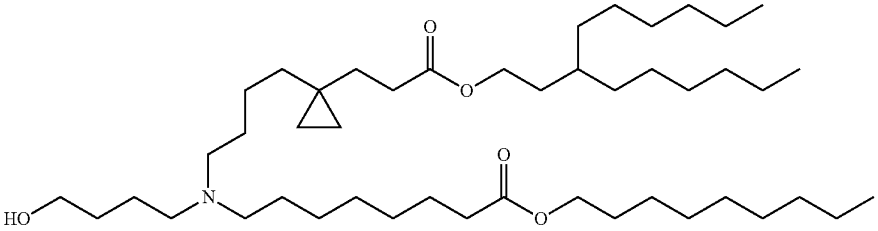

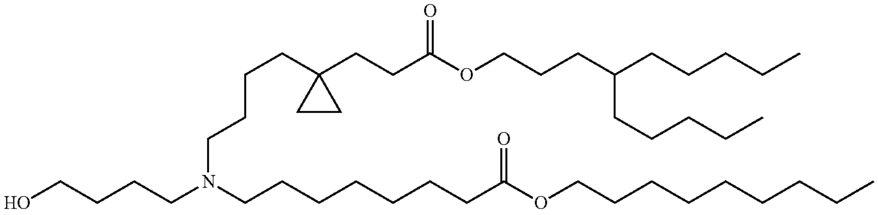

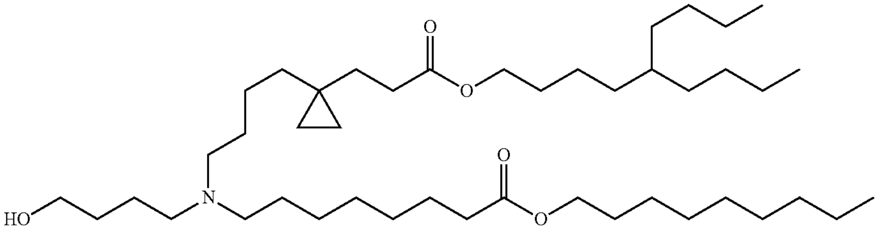

In a more specific embodiment, the present disclosure provides a nanoparticle composition comprising a lipid component, and optionally a load, wherein the lipid component comprises the compound of the present disclosure.

In a more specific embodiment, the present disclosure provides the nanoparticle composition described above, wherein, the lipid component comprises the following components in molar percentage:

ionizable cationic lipids 20 mol %-85 mol %;
structural lipids 10 mol %-75 mol %;
neutral lipids 1.0 mol %-30 mol %;
polymeric lipids 0.25 mol %-10 mol %.

In a more specific embodiment, the present disclosure provides the nanoparticle composition described above, wherein, the lipid component comprises the following components in molar percentage:

any of the above-mentioned compound of the present disclosure 50 mol %;
neutral lipids 10 mol %;
structural lipids 38.5 mol %;
polymeric lipids 1.5 mol %.

In a more specific embodiment, the present disclosure provides the nanoparticle composition described above, wherein, the neutral lipids are selected from one or more of DSPC, DMPC, DOPC, DPPC, POPC, DOPE, DMPE, POPE and DPPE, alternatively DSPC and/or DOPE.

In a more specific embodiment, the present disclosure provides the nanoparticle composition described above, wherein, the structure lipids are selected from one or more of cholesterol, sitosterol, coprosterol, fucosterol, brassicasterol, ergosterol, tomatine, ursolic acid, α-tocopherol, stigmasterol, avenasterol, ergocalciferol and campesterol, alternatively cholesterol and/or D-sitosterol, still alternatively cholesterol.

In a more specific embodiment, the present disclosure provides the nanoparticle composition described above, wherein, the polymer lipids are polyethylene glycolated lipids.

In a more specific embodiment, the present disclosure provides the nanoparticle composition described above, wherein, the polyethylene glycolated lipids are selected from one or more of: PEG modified phosphatidylethanolamine, PEG modified phosphatidic acid, PEG modified ceramide, PEG modified dialkyl amine, PEG modified diacylglycerol, and PEG modified dialkylglycerol.

In a more specific embodiment, the present disclosure provides the nanoparticle composition described above, wherein, the polyethylene glycolated lipids contain a PEG moiety of about 1000 Da to about 20 kDa, alternatively a PEG moiety of about 1000 Da to about 5000 Da.

In a more specific embodiment, the present disclosure provides the nanoparticle composition described above, wherein, the polyethylene glycolated lipids are selected from one or more of DMPE-PEG1000, DPPE-PEG1000, DSPE-PEG1000, DOPE-PEG1000, DMG-PEG2000, Ceramide-PEG2000, DMPE-PEG2000, DPPE-PEG2000, DSPE-PEG2000, Azido-PEG2000, DSPE-PEG2000-Mannose, Ceramide-PEG5000, and DSPE-PEG5000, alternatively DMG-PEG2000.

In a more specific embodiment, the present disclosure provides the nanoparticle composition described above, wherein, the load is selected from one or more of therapeutic, prophylactic and diagnostic agents.

In a more specific embodiment, the present disclosure provides the nanoparticle composition described above, wherein, the therapeutic, prophylactic or diagnostic agent is a nucleic acid.

In a more specific embodiment, the present disclosure provides the nanoparticle composition described above, wherein, the nucleic acid is selected from one or more of ASO, RNA and DNA.

In a more specific embodiment, the present disclosure provides the nanoparticle composition described above, wherein, the RNA is selected from one or more of interfering RNA (RNAi), small interfering RNA (siRNA), short hairpin RNA (shRNA), antisense RNA (aRNA), messenger RNA (mRNA), modified messenger RNA (mmRNA), long non-coding RNA (lncRNA), microRNA (miRNA), small activating RNA (saRNA), multimeric coding nucleic acid (MCNA), polymeric coding nucleic acid (PCNA), guide RNA (gRNA), CRISPRRNA (crRNA), and nucleases, alternatively mRNA, still alternatively, modified mRNA.

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

The compounds of the present disclosure may exist in tautomer forms. The tautomer is a functional group isomer resulting from the rapid shift of an atom between two positions in a molecule. The tautomer is a special functional group isomer, wherein a pair of tautomers can convert between each other, but usually exist in a relatively stable isomer as its main form. The most important examples are the enol and keto tautomers.

The present disclosure also comprises compounds that are labeled with isotopes (isotope variants), which are equivalent to those described in formula (IV), but one or more atoms are replaced with atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are yet alternative, because they are easy to prepare and detect. Furthermore, replaced with heavier isotopes, such as deuterium, which is $^{2}H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

Pharmaceutical Compositions and Kits

In another aspect, the present disclosure provides a pharmaceutical composition comprising nanoparticle compositions of the present disclosure and pharmaceutically acceptable excipient(s), the nanoparticle composition comprises the compounds of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a nanoparticle composition of the present disclosure and other therapeutic, or diagnostic, or prophylactic agents, and a first and a second containers (e.g., vials, ampoules, bottles, syringes, and/or dispersible packages or other materials) containing the nanoparticle composition of the present disclosure or other therapeutic, or diagnostic, or prophylactic agents. In some embodiments, kits provided can also optionally include a third container containing a pharmaceutically acceptable excipient for diluting or suspending the nanoparticle composition of the present disclosure and/or other therapeutic, or diagnostic, or prophylactic agent. In some embodiments, the nanoparticle composition of the present disclosure provided in the first container and the other therapeutic, or diagnostic, or prophylactic agents provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the pharmaceutical compositions provided herein are administered in an effective amount. The amount of the pharmaceutical composition actually administered will typically be determined by a physician, in the light of the relevant circumstances, including the condition to be treated or prevented, the chosen route of administration, the actual pharmaceutical composition administered, the age, weight, and response of the individual patient, the severity of the patient's symptoms, and the like.

When used to prevent the disorder of the present disclosure, the pharmaceutical compositions provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and still alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Injectable compositions are typically based upon injectable sterile saline or phosphate-buffered saline or other injectable excipients known in the art. As before, the active compound in such compositions is typically a minor component, often being from about 0.05 to 1000 by weight with the remainder being the injectable excipient and the like.

EXAMPLE

In order to make the technical solutions of the present disclosure clearer and more explicit, the present disclosure is further elaborated through the following examples. The following examples are used only to illustrate specific embodiments of the present disclosure so that a person skilled in the art can understand the present disclosure, but are not intended to limit the scope of protection of the present disclosure. The technical means or methods, etc. not specifically described in the specific embodiments of the present disclosure are conventional technical means or methods, etc. in the art. The materials, reagents, etc. used in examples are commercially available if not otherwise specified.

TABLE 1

| Chemical formula or abbreviation | Full Name |
|---|---|
| THF | Tetrahydrofuran |
| ACN | Acetonitrile |
| DCM | Dichloromethane |
| MeOH | Methanol |
| DMF | N,N-dimethylformamide |
| DMSO | Dimethyl sulfoxide |
| MTBE | tert-Butyl methyl ether |
| $CDCl_3$ | Deuterated chloroform |
| TBAF | Tetrabutylammonium fluoride |
| TBAI | Tetrabutylammonium iodide |
| LDA | Lithium diisopropylamide |
| DMAP | 4-Dimethylaminopyridine |
| $(COCl)_2$ | Oxalyl chloride |
| NaI | Sodium iodide |
| NaH | Sodium hydride |
| $K_2CO_3$ | Potassium carbonate |
| EDCI | 1-(3-Dimethylaminopropyl)-3-ethylcarbodiimide |
| DIEA | N,N-diisopropylethylamine |
| $LiAlH_4$ | Lithium aluminum hydride |
| CMPE | Cyclopentyl methyl ether |
| DMPU | N,N-dimethylpropyleneurea |
| TMSCl | Trimethylchlorosilane |
| TMSOK | Potassium trimethylsilanolate |
| TEA | Triethylamine |

Example 1: Synthesis of Compound 1a

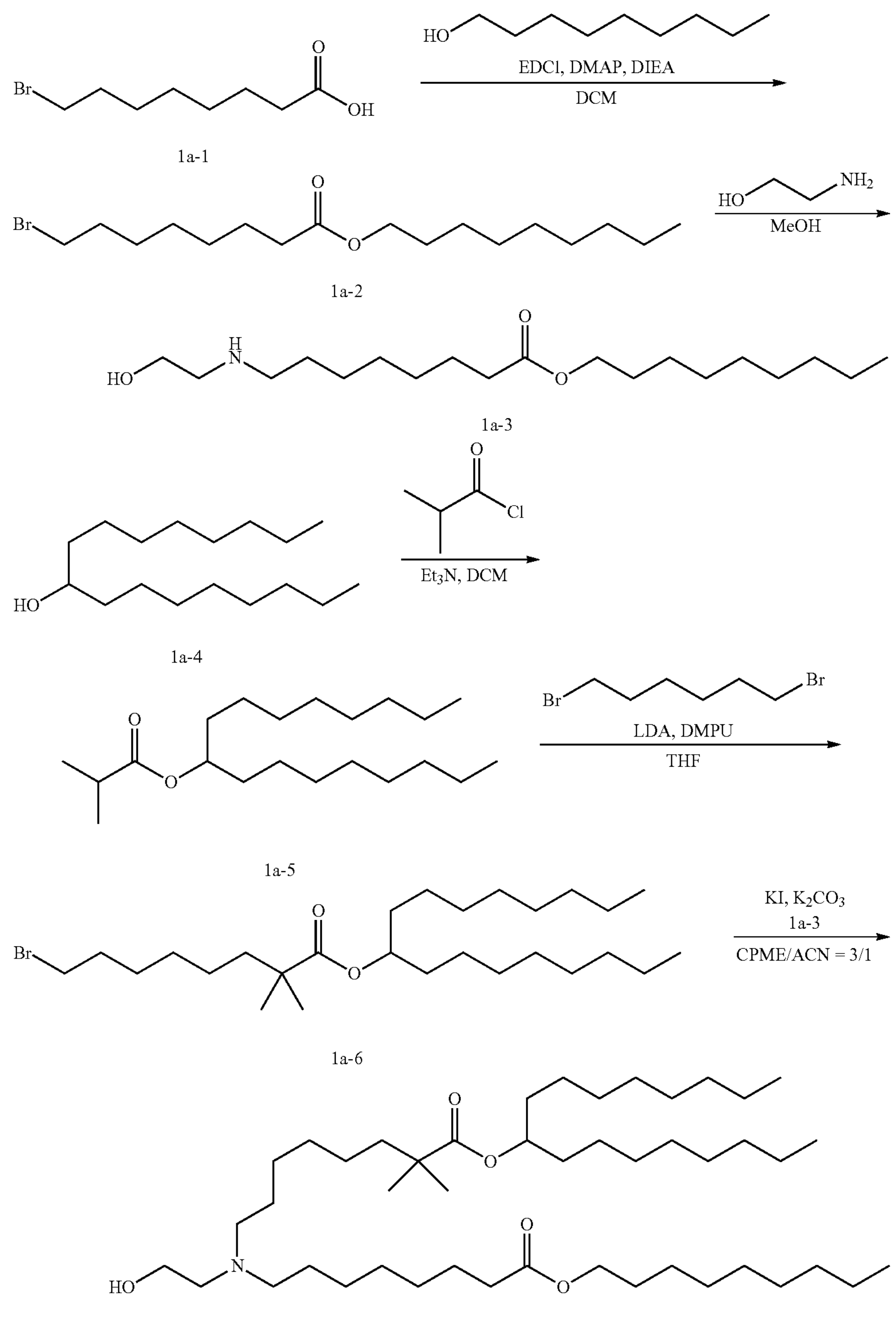

1a-1

1a-2

1a-3

1a-4

1a-5

1a-6

1a

To a 500 mL three-neck round-bottom flask were added 1-nonanol (15 g, 104.0 mmol, 1.0 eq.), 8-bromooctanoic acid (25.5 g, 114.0 mmol, 1.1 eq.), DMAP (2.54 g, 20.8 mmol, 0.2 eq.), DIEA (40.3 g, 312.0 mmol, 3.0 eq.), and EDCI (25.9 g, 135 mmol, 1.3 eq.) at room temperature, and 250 mL of DCM was added. The reaction liquid was stirred at room temperature for 4 h, and the reaction was completed as monitored by TLC. The reaction liquid was poured into 200 mL of a saturated aqueous ammonium chloride solution, and the mixture was extracted with 3×100 mL of DCM. The organic phases were combined and dried over anhydrous sodium sulfate. The mixture was filtered, and the filtrate was concentrated to dryness to give a crude product, which was purified by silica gel column chromatography to give 21 g of a yellow oily compound 1a-2.

To a 250 mL three-neck round-bottom flask were added compound 1a-2 (21 g, 60.1 mmol, 1.0 eq.) and 2-aminoethanol (110 g, 1.80 mol, 30.0 eq.) at room temperature, and the mixture was dissolved in 100 mL of methanol. The mixture was heated to 60° C., stirred for reaction for 18 h, and concentrated to remove the reaction solvent. Then a saturated aqueous ammonium chloride solution and ethyl acetate were added thereto, and the mixture was extracted after layer separation. The organic phases were combined and dried over anhydrous sodium sulfate. The mixture was filtered, and the filtrate was concentrated to dryness to give a crude product, which was purified by silica gel column chromatography to give 14 g of a yellow oily compound 1a-3.

To a 250 mL three-neck round-bottom flask were added 9-heptadecanol (9.8 g, 38.2 mmol, 1.0 eq.) and triethylamine (15.5 g, 152.8 mmol, 4.0 eq.) at room temperature, and the mixture was dissolved in 100 mL of DCM. The reaction system was cooled in an ice bath, and then 2-methylpropionyl chloride (9.8 g, 91.7 mmol, 2.4 eq.) was slowly added. The mixture was warmed to room temperature and reacted overnight. After the reaction was completed as monitored by TLC, a saturated aqueous ammonium chloride solution was added to quench the reaction, and the mixture was extracted with DCM. The organic phases were combined and dried over anhydrous sodium sulfate. The mixture was filtered, and the filtrate was concentrated to dryness to give a crude product, which was purified by silica gel column chromatography to give 8.7 g of a yellow oily compound 1a-5.

To a 250 mL three-neck round-bottom flask was added compound 1a-5 (8.7 g, 26.6 mmol, 1.0 eq.) at room temperature, and the mixture was dissolved in 60 mL of THF. The reaction system was cooled to −40° C., and then LDA (13.1 mL, 26.2 mmol, 0.98 eq.) was slowly added dropwise. The mixture was stirred for reaction for 1 h, and then 1,6-dibromohexane (9.03 g, 37.0 mmol, 1.39 eq.) and DMPU (0.48 g, 3.73 mmol, 0.14 eq.) were added to the reaction system. The mixture was warmed to room temperature and reacted overnight. After the reaction was completed as monitored by TLC, a saturated ammonium chloride ice water solution was added to quench the reaction, and the mixture was extracted with ethyl acetate. The organic phases were combined and dried over anhydrous sodium sulfate. The mixture was filtered, and the filtrate was concentrated to dryness to give a crude product, which was purified by silica gel column chromatography to give 10.1 g of a yellow oily compound 1a-6.

To a 20 mL round-bottom flask were added compound 1a-6 (1.48 g, 3.04 mmol, 2.0 eq.), compound 1a-3 (500 mg, 1.52 mmol, 1.0 eq.), $K_2CO_3$ (628.2 mg, 4.55 mmol, 3.0 eq.), KI (302.3 mg, 1.82 mmol, 1.2 eq.), cyclopentyl methyl ether (7.5 mL), and acetonitrile (2.5 mL). The mixture was warmed to 80° C. and reacted. After the reaction was completed as monitored by TLC, a saturated ammonium chloride ice water solution was added to quench the reaction, and the mixture was extracted with DCM. The organic phases were combined and dried over anhydrous sodium sulfate. The mixture was filtered, and the filtrate was concentrated to dryness to give a crude product, which was purified by silica gel column chromatography to give 96.98 mg of an oily compound 1a.

$^1H$ NMR (400 MHz, $CDCl_3$) δ: 4.86-4.80 (m, 1H), 4.04 (t, J=7.2 Hz, 2H), 3.57 (m, 2H), 2.62 (t, J=7.2 Hz, 2H), 2.49 (t, J=7.2 Hz, 4H), 2.29 (t, J=7.2 Hz, 2H), 1.62 (m, 4H), 1.51-1.45 (m, 10H), 1.38-1.23 (m, 49H), 1.15 (s, 6H), 0.88 (t, J=7.2 Hz, 9H); ESI-MS m/z: 738.60 $[M+H]^+$.

Example 2: Synthesis of Compound 2a

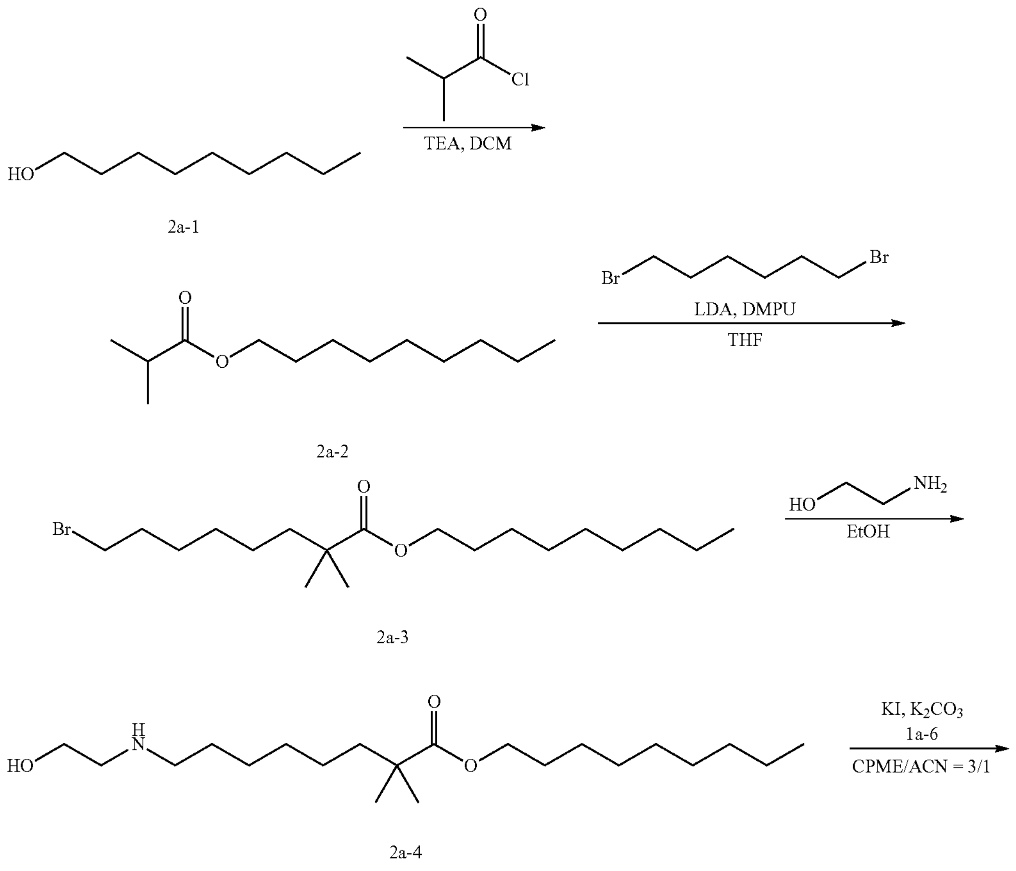

-continued

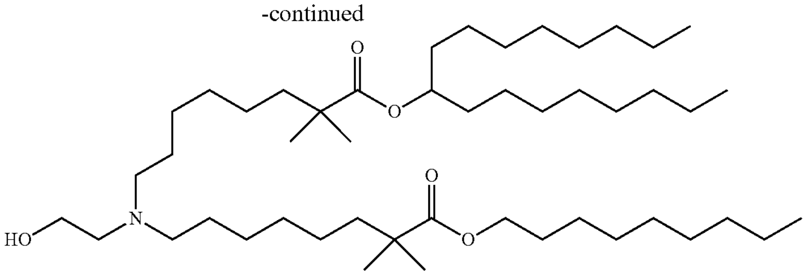

2a

To a 250 mL three-neck round-bottom flask were added 1-nonanol (8.8 g, 61.0 mmol, 1.0 eq.) and triethylamine (24.7 g, 244.0 mmol, 4.0 eq.) at room temperature, and the mixture was dissolved in 100 mL of DCM. The reaction system was cooled in an ice bath, and then 2-methylpropionyl chloride (15.6 g, 146.4 mmol, 2.4 eq.) was slowly added. The mixture was warmed to room temperature and reacted. After the reaction was completed as monitored by TLC, a saturated aqueous ammonium chloride solution was added to quench the reaction, and the mixture was extracted with DCM. The organic phases were combined and dried over anhydrous sodium sulfate. The mixture was filtered, and the filtrate was concentrated to dryness to give a crude product, which was purified by silica gel column chromatography to give 10.8 g of a yellow oily compound 2a-2.

To a 250 mL three-neck round-bottom flask was added compound 2a-2 (4.8 g, 22.4 mmol, 1.0 eq.) at room temperature, and the mixture was dissolved in 50 mL of THF. The reaction system was cooled to −40° C., and then LDA (11.0 mL, 21.9 mmol, 0.98 eq.) was slowly added dropwise. The mixture was stirred for reaction for 1 h, and then 1,6-dibromohexane (7.59 g, 31.1 mmol, 1.39 eq.) and DMPU (0.57 g, 4.48 mmol, 0.2 eq.) were added to the reaction system. The mixture was warmed to room temperature and reacted overnight. After the reaction was completed as monitored by TLC, a saturated ammonium chloride ice water solution was added to quench the reaction, and the mixture was extracted with ethyl acetate. The organic phases were combined and dried over anhydrous sodium sulfate. The mixture was filtered, and the filtrate was concentrated to dryness to give a crude product, which was purified by silica gel column chromatography to give 4.6 g of a yellow oily compound 2a-3.

To a 250 mL three-neck round-bottom flask were added compound 2a-3 (4.6 g, 12.2 mmol, 1.0 eq.) and 2-aminoethanol (14.9 g, 244.0 mmol, 20.0 eq.) at room temperature, and the mixture was dissolved in 50 mL of ethanol. The mixture was heated to 60° C., stirred for reaction for 18 h, and concentrated to remove the reaction solvent. Then a saturated aqueous ammonium chloride solution and ethyl acetate were added thereto, and the mixture was extracted after layer separation. The organic phases were combined and dried over anhydrous sodium sulfate. The mixture was filtered, and the filtrate was concentrated to dryness to give a crude product, which was purified by silica gel column chromatography to give 2.2 g of a yellow oily compound 2a-4.

To a 20 mL round-bottom flask were added compound 2a-4 (500 mg, 1.4 mmol, 1.0 eq.), compound 1a-6 (1.37 g, 2.8 mmol, 2.0 eq.), $K_2CO_3$ (579 mg, 4.2 mmol, 3.0 eq.), KI (279 mg, 1.68 mmol, 1.2 eq.), cyclopentyl methyl ether (7.5 mL), and acetonitrile (2.5 mL). The mixture was warmed to 80° C. and reacted. After the reaction was completed as monitored by TLC, a saturated ammonium chloride ice water solution was added to quench the reaction, and the mixture was extracted with DCM. The organic phases were combined and dried over anhydrous sodium sulfate. The mixture was filtered, and the filtrate was concentrated to dryness to give a crude product, which was purified by silica gel column chromatography to give 137.9 mg of an oily compound 2a.

$^1H$ NMR (400 MHz, $CDCl_3$) δ: 4.83 (m, 1H), 4.04 (t, J=7.2 Hz, 2H), 3.55 (t, J=5.6 Hz, 2H), 2.60 (t, J=5.6 Hz, 2H), 2.47 (t, J=7.2 Hz, 4H), 1.62 (m, 2H), 1.52-1.40 (m, 12H), 1.36-1.20 (m, 48H), 1.15 (m, 12H), 0.88 (t, J=7.2 Hz, 9H); ESI-MS m/z: 766.50 $[M+H]^+$.

Example 3: Synthesis of Compound 3a

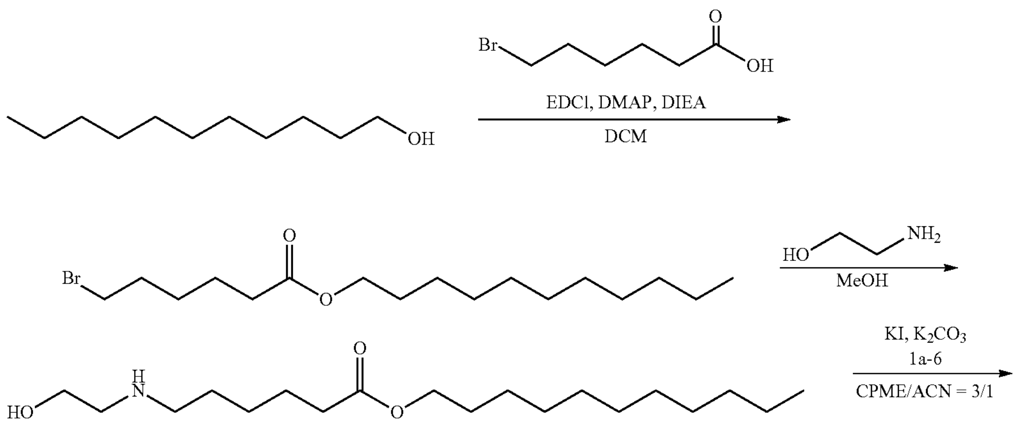

-continued

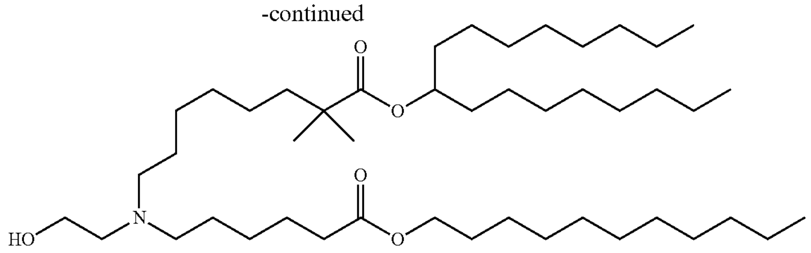

3a

Compound 3a was prepared referring to the method of Example 1 to give 114.7 mg of an oily product.

$^1$H NMR (400 MHz, $CDCl_3$) δ: 4.83 (m, 1H), 4.06 (t, J=7.2 Hz, 2H), 3.59 (m, 2H), 2.66 (m, 2H), 2.54 (m, 4H), 2.30 (t, J=7.2 Hz, 2H), 1.70-1.56 (m, 4H), 1.50 (m, 10H), 1.32-1.26 (m, 49H), 1.15 (s, 6H), 0.88 (t, J=7.2 Hz, 9H); ESI-MS m/z: 738.55 $[M+H]^+$.

Example 4: Synthesis of Compound 4a

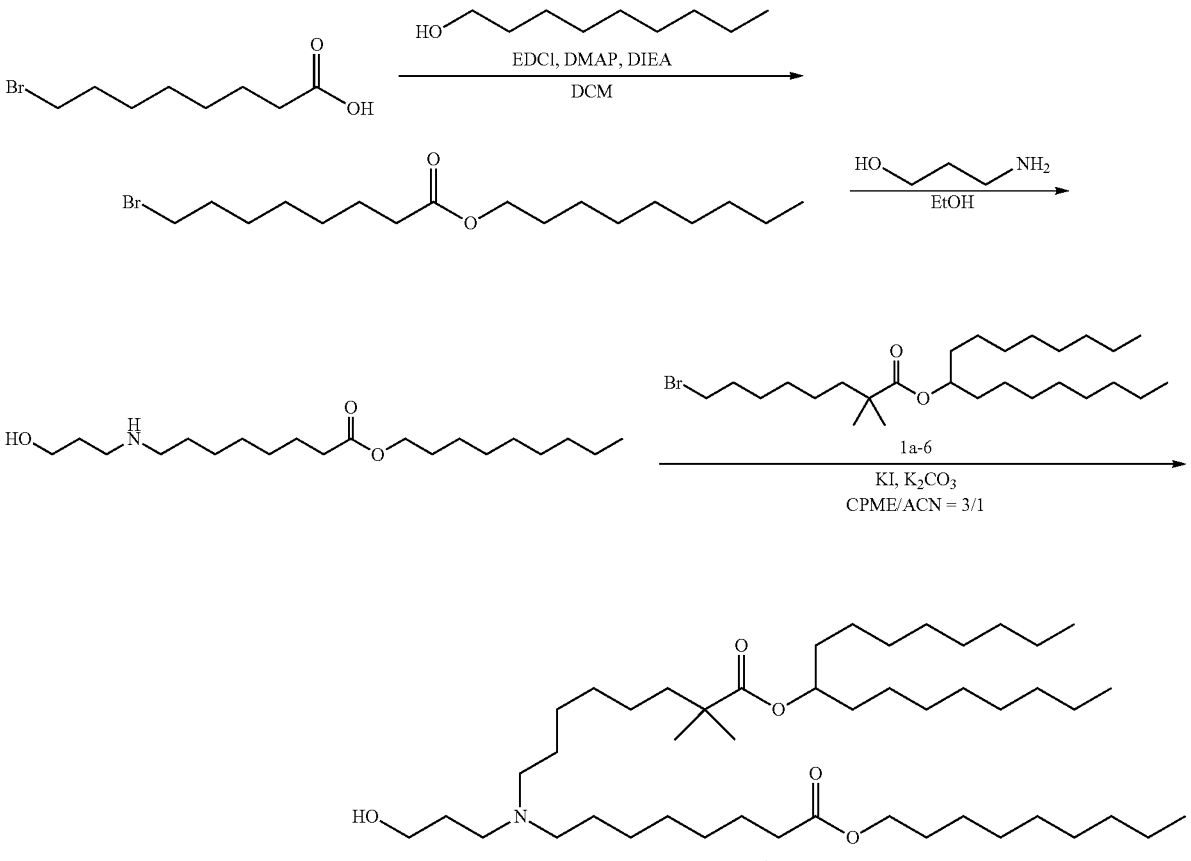

4a

Compound 4a was prepared referring to the method of Example 1 to give 112.1 mg of an oily product.

$^1$H NMR (400 MHz, $CDCl_3$) δ: 4.83 (m, 1H), 4.05 (t, J=7.2 Hz, 2H), 3.80 (t, J=5.4 Hz, 2H), 2.51-2.73 (m, 6H), 2.29 (t, J=7.2 Hz, 2H), 1.65-1.44 (m, 16H), 1.26 (m, 49H), 1.15 (s, 6H), 0.93-0.82 (m, 9H); ESI-MS m/z: 752.70 $[M+H]^+$.

Example 5: Synthesis of Compound 5a
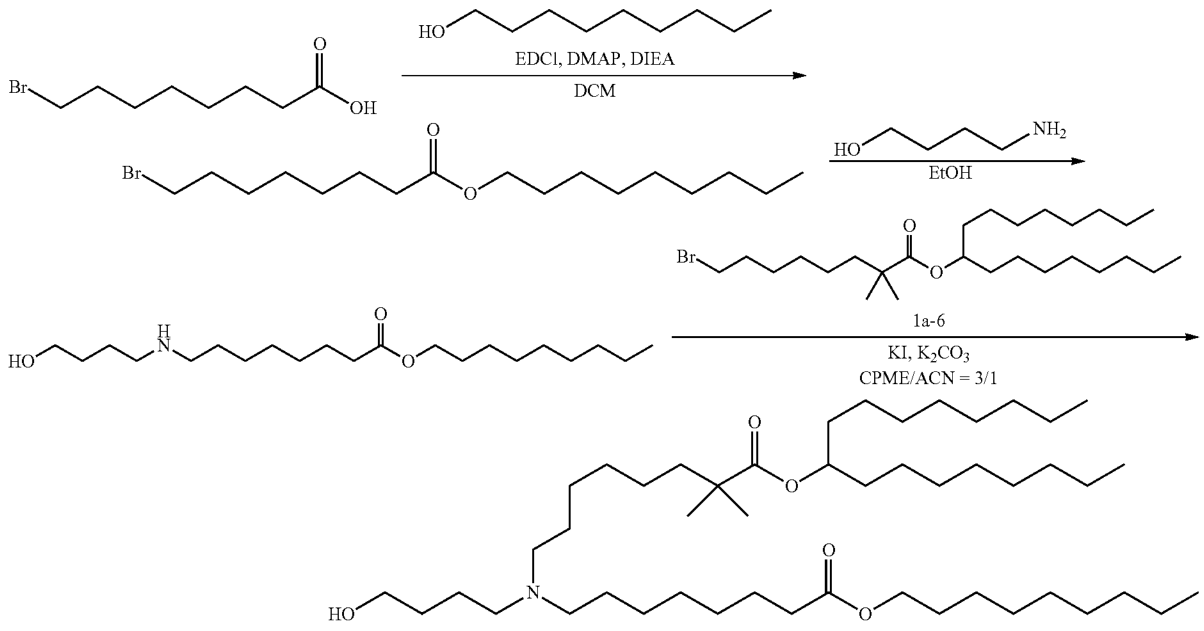
5a
Compound 5a was prepared referring to the method of Example 1 to give 150.8 mg of an oily product.
$^1$H NMR (300 MHz, $CDCl_3$) δ: 4.84 (m, 1H), 4.05 (t, J=7.2 Hz, 2H), 3.60 (m, 2H), 2.41-2.63 (m, 4H), 2.29 (t, J=7.2 Hz, 2H), 1.65-1.44 (m, 18H), 1.26-1.34 (m, 51H), 1.14 (s, 6H), 0.93-0.82 (m, 9H); ESI-MS m/z: 766.70 $[M+H]^+$.
Example 6: Synthesis of Compound 6a
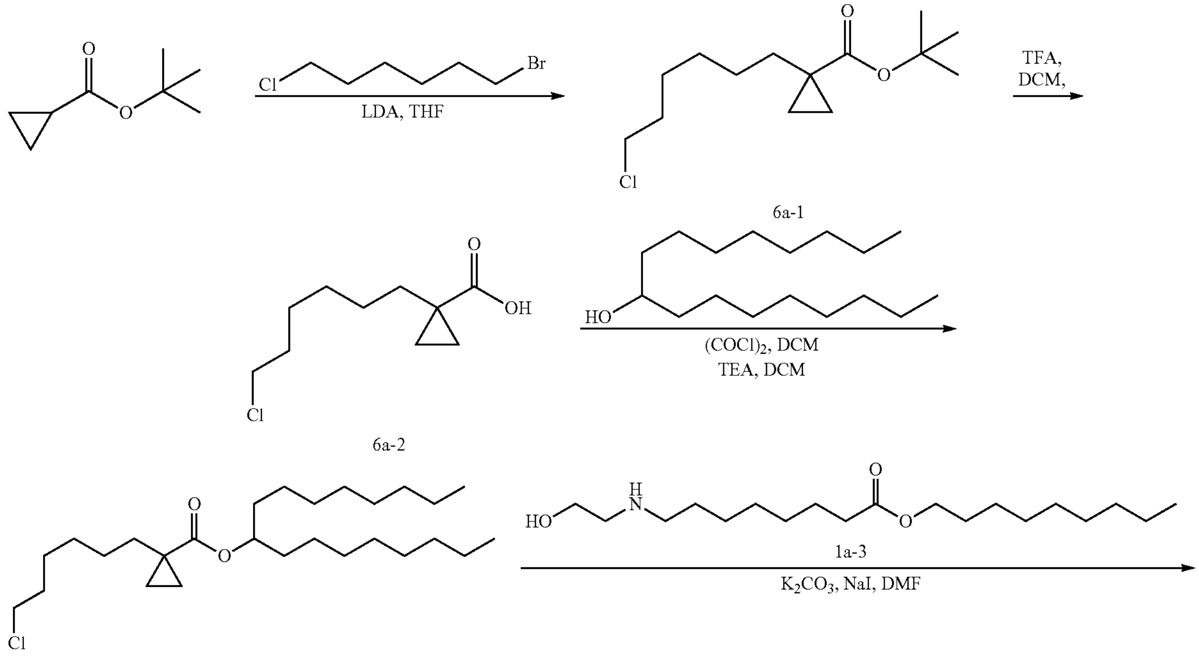
6a-3

-continued

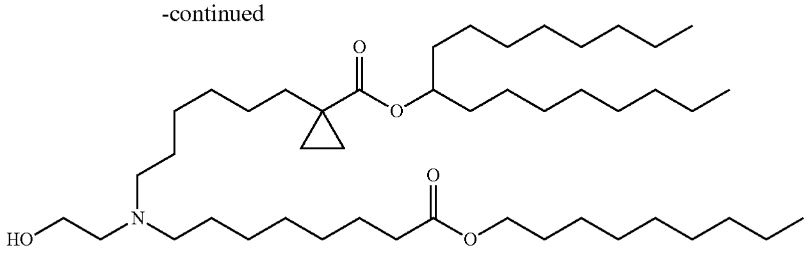

6a tert-Butyl cyclopropanecarboxylate (15.0 g, 150.0 mmol, 1.0 eq.) was dissolved in 150 mL of anhydrous tetrahydrofuran, and the mixture was cooled to −60° C. LDA (150.0 mL, 300.0 mmol, 2.0 eq.) was added to the reaction liquid under nitrogen atmosphere. After the mixture was stirred at the same temperature for reaction for 1 h, 1-bromo-6-chlorohexane (44.9 g, 225.0 mmol, 1.5 eq.) was added, and the mixture was stirred at room temperature for reaction for another 3 h. After the reaction was completed as monitored by TLC, the reaction was quenched with a saturated aqueous ammonium chloride solution, and the mixture was extracted with DCM. The organic phases were combined and dried over anhydrous sodium sulfate. The mixture was filtered, and the filtrate was concentrated to dryness to give a crude product, which was purified by silica gel column chromatography to give 19 g of a colorless oily compound 6a-1.

To a solution of compound 6a-1 (10.0 g, 38.3 mmol) in DCM (30.0 mL) was added 10.0 mL of trifluoroacetic acid, and the mixture was stirred at room temperature for 3 h. The reaction solvent was removed by pressurized rotary evaporation to give a crude product, which was purified by silica gel column chromatography to give 6.9 g of a colorless oily compound 6a-2.

Compound 6a-2 (500.0 mg, 2.45 mmol, 2.0 eq.) was dissolved in DCM (5.0 mL), and 2-3 drops of DMF and oxalyl chloride (311.1 mg, 2.45 mmol, 2.0 eq.) were added to the reaction system under an ice bath. After the mixture was stirred for 30 min, the solvent was removed by rotary evaporation under reduced pressure to give an acyl chloride intermediate. The resulting acyl chloride was dissolved in DCM (5.0 mL), then 9-heptadecanol (312.3 mg, 1.22 mmol, 1.0 eq.) and triethylamine (247.5 mg, 2.45 mmol, 2.0 eq.) were added, and the mixture was reacted at room temperature for 5 h. After the reaction was completed, the reaction liquid was poured into 50 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 240 mg of an oily compound 6a-3.

To a solution of compound 6a-3 (200.0 mg, 0.45 mmol, 1.5 eq.) in DMF (3.0 mL) were added potassium carbonate (124.2 mg, 0.90 mmol, 3.0 eq.), sodium iodide (112.5 mg, 0.75 mmol, 2.5 eq.), and compound 1a-3 (99.0 mg, 0.30 mmol, 1.0 eq.). The reaction liquid was heated to 80° C. and stirred for reaction for 5 h. After the reaction was completed, the reaction system was cooled to room temperature. The reaction was quenched with a saturated aqueous sodium chloride solution, and the mixture was extracted with DCM. The organic phases were combined and dried over anhydrous sodium sulfate. The mixture was filtered, and the filtrate was concentrated to dryness to give a crude product, which was purified by preparative liquid chromatography to give 75.2 mg of compound 6a. (Column model: XSelect C18 (19×150 mm, 5 m), mobile phase A: water:acetonitrile=90:10 (10 mmol/L ammonium bicarbonate+0.5% aqueous ammonia), mobile phase B: isopropanol:acetonitrile=90:10; flow rate: 25 mL/min; gradient: the proportion of B was 75%-80% in 0-12 min, and the proportion of B was 90% after 12 min).

$^1H$ NMR (400 MHz, $CDCl_3$) δ: 4.82 (m, 1H), 4.05 (t, J=7.2 Hz, 2H), 2.57 (m, 6H), 2.29 (t, J=7.2 Hz, 2H), 1.61 (m, 7H), 1.52 (m, 13H); 1.21-1.37 (m, 45H), 1.16 (q, J=4.4 Hz, 2H), 0.88 (t, J=7.2 Hz, 9H), 0.64 (q, J=4.4 Hz, 2H); ESI-MS m/z: 736.55 $[M+H]^+$.

Example 7: Synthesis of Compound 7a

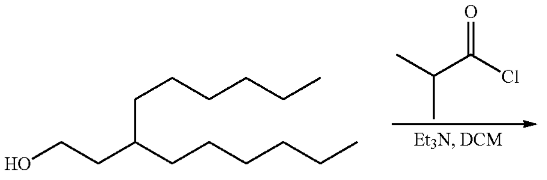

7a-1

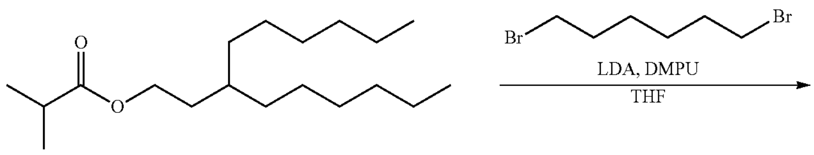

7a-2

-continued
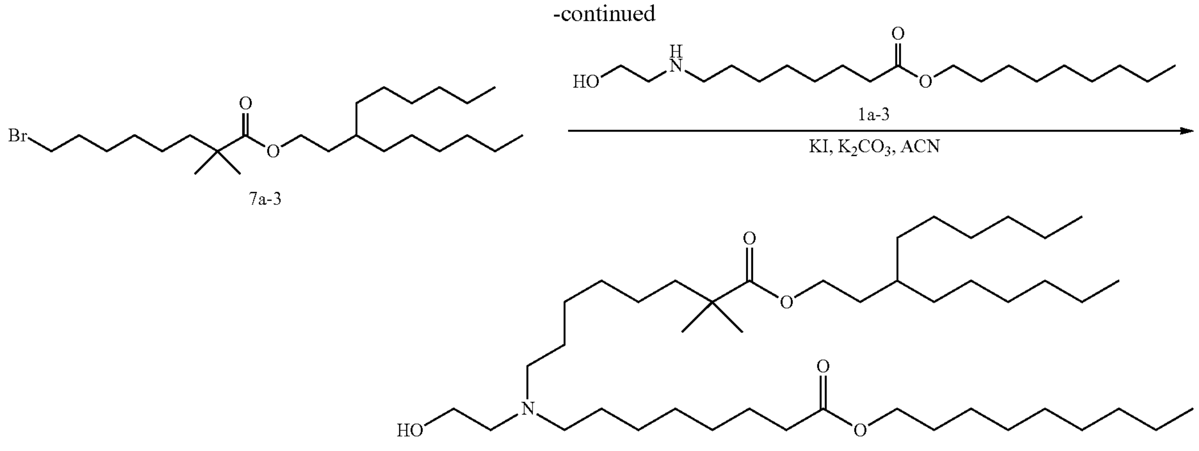
7a
Compound 7a was prepared referring to the method of Example 1 to give 102.4 mg of an oily product.
$^1H$ NMR (300 MHz, $CDCl_3$) δ: 4.08 (td, J=7.2 Hz, 4H), 3.58 (m, 2H), 2.57 (d, J=40.6 Hz, 6H), 2.31 (t, J=7.2 Hz, 2H), 1.73-1.40 (m, 14H), 1.20-1.39 (m, 45H), 1.17 (s, 6H), 0.96-0.85 (m, 9H); ESI-MS m/z: 710.55 $[M+H]^+$.
Example 8: Synthesis of Compound 8a
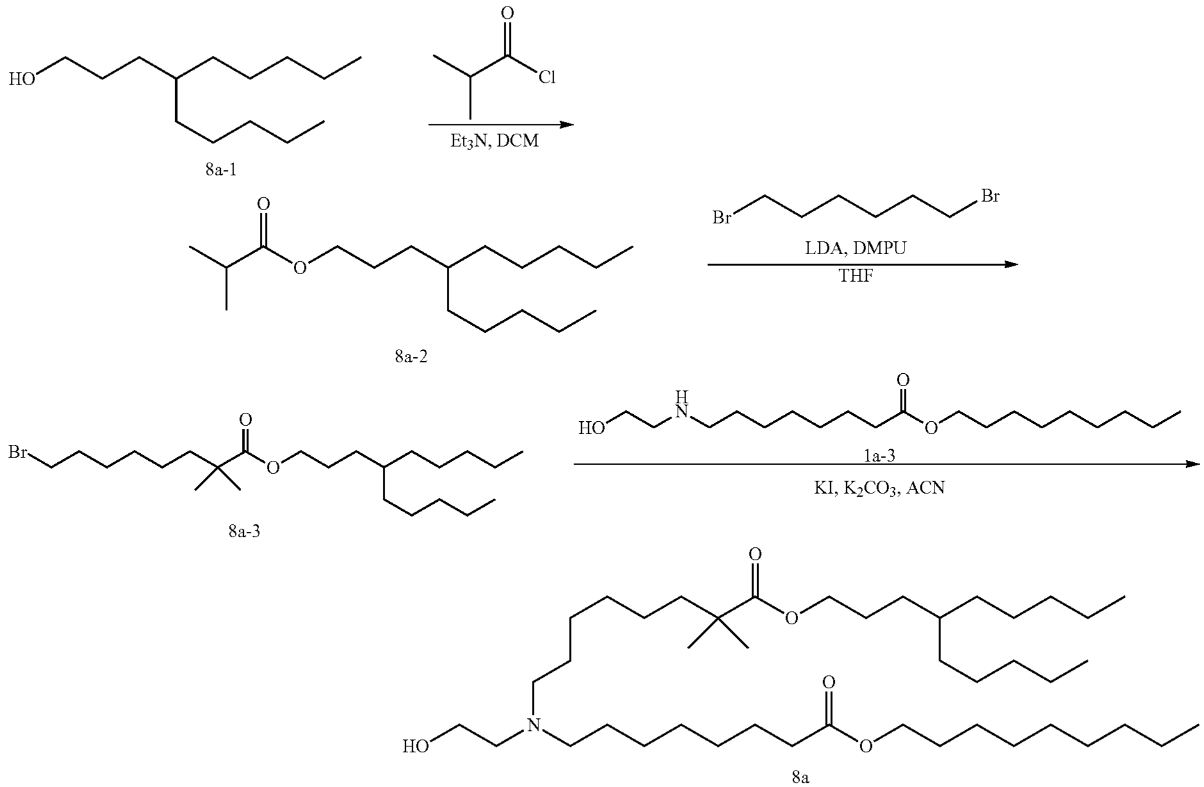
8a
Compound 8a was prepared referring to the method of Example 1 to give 44.9 mg of an oily product.
$^1H$ NMR (300 MHz, $CDCl_3$) δ: 4.07-3.91 (m, 4H), 3.56 (m, 2H), 2.31-2.62 (m, 6H), 2.29 (t, J=7.2 Hz, 2H), 1.73-1.40 (m, 12H), 1.39-1.20 (m, 44H), 1.16 (s, 6H), 0.93-0.82 (m, 9H); ESI-MS m/z: 696.50 $[M+H]^+$.

Example 9: Synthesis of Compound 9a

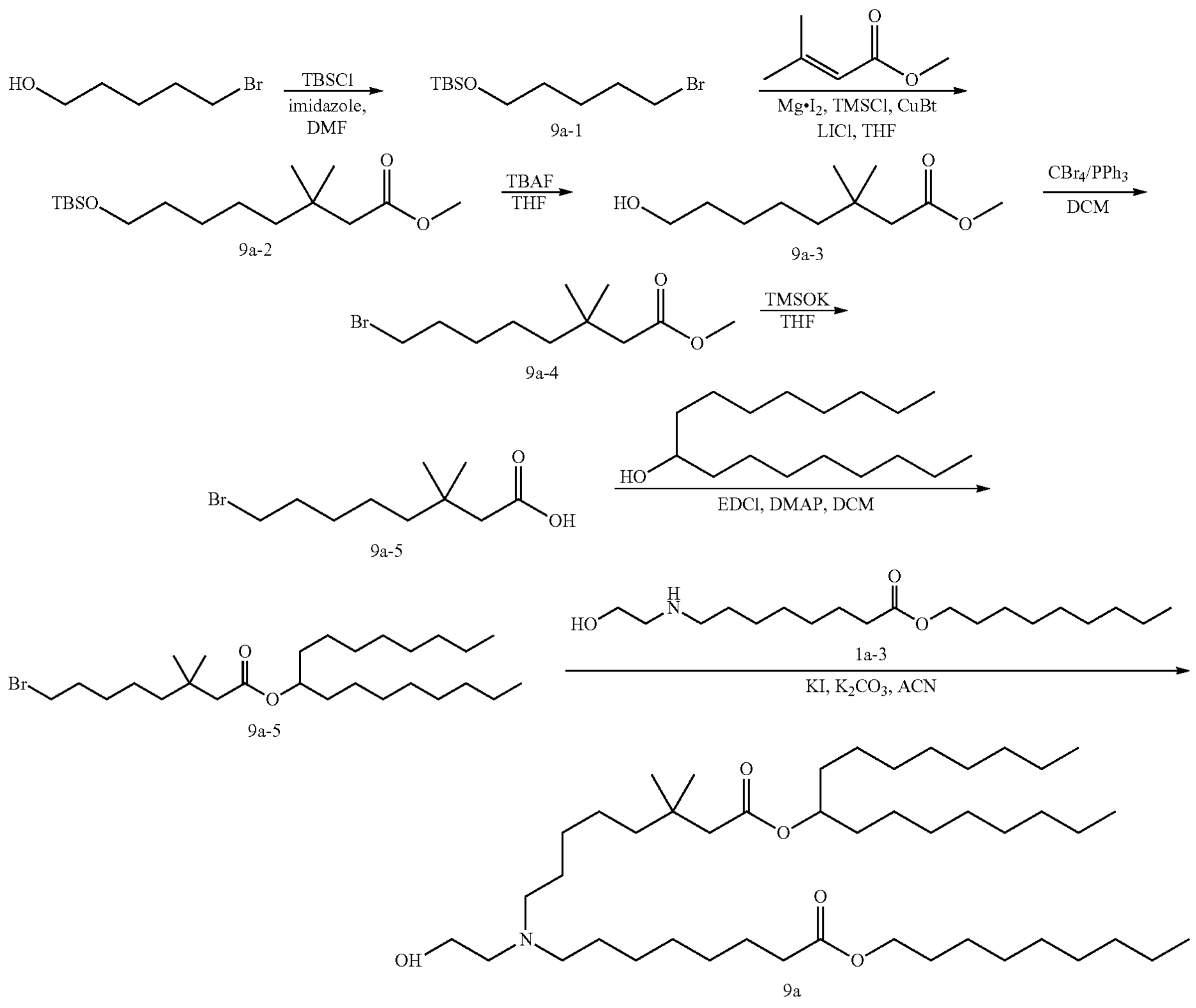

In a 250 mL round-bottom flask, 5-bromo-1-pentanol (30 g, 180.0 mmol, 1.0 eq.) and imidazole (30.6 g, 449.0 mmol, 2.5 eq.) were dissolved in 120 mL of DMF. The reaction system was placed in an ice bath, and TBSCl (29.8 g, 198 mmol, 1.1 eq.) was added to the reaction system. The mixture was warmed to room temperature and reacted overnight. After the reaction was completed as monitored by TLC, a saturated aqueous sodium bicarbonate solution was added to quench the reaction, and the mixture was extracted with DCM. The organic phases were combined and dried over anhydrous sodium sulfate. The mixture was filtered, and the filtrate was concentrated to dryness to give a crude product, which was purified by silica gel column chromatography to give 26 g of a light yellow oily compound 9a-1.

In a 250 mL three-neck round-bottom flask, Mg (1.70 g, 70.1 mmol, 1.6 eq.), $I_2$ (0.01 g, 0.039 mmol), and 50 mL of anhydrous THF were added. The reaction system was warmed to 37° C., then compound 9a-1 (18.5 g, 65.7 mmol, 1.5 eq.) was slowly added within 30 min, and the mixture was reacted until magnesium powder almost disappeared completely to give a Grignard reagent. In a 250 mL three-neck round-bottom flask, CuBr (0.63 g, 4.38 mmol, 0.1 eq.), LiCl (0.37 g, 8.76 mmol, 0.2 eq.), and 50 mL of anhydrous THF were added under nitrogen atmosphere. After the mixture was stirred at 0° C. for 30 min, to the obtained copper-lithium reagent solution were added methyl 3,3-dimethacrylate (5 g, 43.8 mmol, 1.0 eq.) and TMSCl (7.14 g, 65.7 mmol, 1.5 eq.) dropwise. After the dropwise addition was completed, the mixture was stirred at 0° C. for another 30 min. The prepared Grignard reagent was slowly added dropwise to the reaction liquid, and after the dropwise addition was completed, the mixture was reacted for another 2 h. After the reaction was completed as monitored by TLC, the reaction was quenched with a saturated aqueous ammonium chloride solution, and the mixture was extracted with ethyl acetate. The organic phases were combined and dried over anhydrous sodium sulfate. The mixture was filtered, and the filtrate was concentrated to dryness to give a crude product, which was purified by silica gel column chromatography to give 13 g of a light yellow oily compound 9a-2.

To a solution of compound 9a-2 (13 g, 41.1 mmol, 1.0 eq.) in THF was added TBAF (21.5 g, 82.1 mmol, 2.0 eq.) in batches under an ice bath, and the mixture was stirred at room temperature for 2 h. A saturated aqueous ammonium chloride solution was added to quench the reaction, and the mixture was extracted with ethyl acetate. The organic phases were combined and dried over anhydrous sodium sulfate. The mixture was filtered, and the filtrate was concentrated to dryness to give a crude product of 9a-3, which was directly used in the next step without purification.

Compound 9a-3 (14 g, 69.2 mmol, 1.0 eq.) and $PPh_3$ (21.8 g, 83.0 mmol, 1.2 eq.) were dissolved in 140 mL of dichloromethane, the reaction system was cooled to 0° C., and then $CBr_4$ (25.3 g, 76.1 mmol, 1.1 eq.) was added in batches. The mixture was stirred at room temperature for reaction until the reaction was completed as monitored by TLC. The reaction was quenched with an ice saturated aqueous sodium chloride solution, and the mixture was extracted with ethyl acetate. The organic phases were combined and dried over anhydrous sodium sulfate. The mixture was filtered, and the filtrate was concentrated to dryness to give a crude product, which was purified by silica gel column chromatography to give 7.6 g of a light yellow oily compound 9a-4.

To 60 mL of a solution of compound 9a-4 (6 g, 22.6 mmol, 1 eq.) in THF was added TMSOK (4.35 g, 33.9 mmol, 1.5 eq.). The mixture was stirred at room temperature for reaction until the reaction was completed as monitored by TLC, the pH of the reaction system was adjusted to 4.0 with 2.0 M hydrochloric acid, and the mixture was extracted with ethyl acetate. The organic phases were combined and dried over anhydrous sodium sulfate. The mixture was filtered, and the filtrate was concentrated to dryness to give a crude product, which was purified by silica gel column chromatography to give 2.5 g of a light yellow oily compound 9a-5.

Compound 9a was prepared referring to the method of Example 1 to give 81.7 mg of an oily product.

$^1H$ NMR (300 MHz, $CDCl_3$) δ: 4.85 (m, 1H), 4.05 (t, J=7.2 Hz, 2H), 3.66 (s, 2H), 2.59 (m, 4H), 2.31 (t, J=7.2 Hz, 2H), 2.19 (s, 2H), 1.64-1.43 (m, 12H), 1.22-1.38 (m, 51H), 1.12 (s, 6H), 0.95-0.85 (m, 9H); ESI-MS m/z: 738.65 $[M+H]^+$.

Example 10: Synthesis of Compound 10a

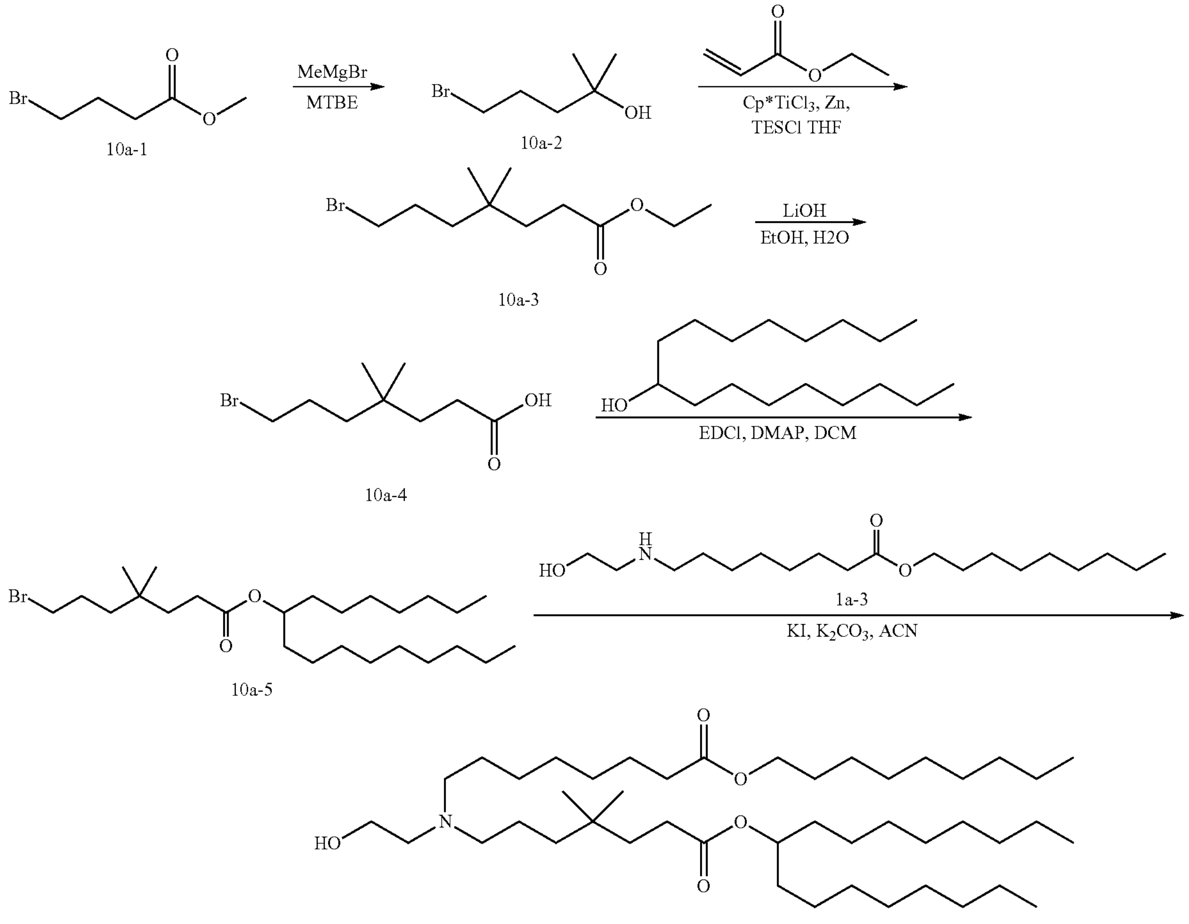

10a-1, 10a-2, 10a-3, 10a-4, 10a-5, 1a-3, 10a

In a 100 mL round-bottom flask, methyl 4-bromobutyrate (4 g, 22.1 mmol, 1.0 eq.) was dissolved in 40 mL of MTBE, the reaction system was placed in an ice bath, and methylmagnesium bromide (22.1 mL, 66.3 mmol, 3.0 eq.) was added to the reaction system. The mixture was warmed to room temperature and reacted until the reaction was completed as monitored by TLC, a saturated aqueous ammonium chloride solution was added to quench the reaction, and the mixture was extracted with EtOAc. The organic phases were combined and dried over anhydrous sodium sulfate. The mixture was filtered, and the filtrate was concentrated to dryness to give a crude product, which was purified by silica gel column chromatography to give 3.5 g of compound 10a-2.

To a 100 mL round-bottom flask were added compound 10a-2 (3 g, 16.6 mmol, 1.0 eq.) triethylchlorosilane (7.49 g, 49.7 mmol, 3.0 eq.), zinc powder (3.25 g, 49.7 mmol, 3.0 eq.), Cp*$TiCl_3$ (519 mg, 1.80 mmol, 0.1 eq.), and 5A molecular sieves (2.4 g) under nitrogen atmosphere, and then 24 mL of anhydrous THF was added. The reaction system was heated to 50° C., and then ethyl acrylate (2.49 g, 24.9 mmol, 1.5 eq.) was added to the reaction system. The mixture was heated to 60° C. for reaction for another 12 h. The reaction liquid was cooled to room temperature, a saturated aqueous sodium chloride solution was added to quench the reaction, and the mixture was extracted with EtOAc. The organic phases were combined and dried over anhydrous sodium sulfate. The mixture was filtered, and the filtrate was concentrated to dryness to give a crude product, which was purified by silica gel column chromatography to give 2.4 g of compound 10a-3.

In a 40 mL reaction flask, compound 10a-3 (1 g, 3.77 mmol, 1.0 eq.) was dissolved in a mixed solution of 10 mL ethanol and 2 mL water, and then lithium hydroxide (0.27 g, 11.3 mmol, 3.0 eq.) was added to the reaction system. The mixture was reacted at room temperature until the reaction was completed as monitored by TLC, the organic solvent was removed by rotary evaporation, and the pH of the solution was adjusted to about 4 with 2.0 M dilute hydrochloric acid. A saturated aqueous ammonium chloride solution was added to quench the reaction, and the mixture was extracted with EtOAc. The organic phases were combined and dried over anhydrous sodium sulfate. The mixture was filtered, and the filtrate was concentrated to dryness to give a crude product, which was purified by silica gel column chromatography to give 800 mg of compound 10a-4.

Compound 10a was prepared referring to the method of Example 1 to give 93.4 mg of an oily product.

$^1$H NMR (300 MHz, $CDCl_3$) δ: 4.92-4.72 (m, 1H), 4.05 (t, J=7.2 Hz, 2H), 3.59 (m, 2H), 2.64-2.51 (m, 6H), 2.33-2.18 (m, 4H), 1.55 (m, 14H), 1.34-1.24 (m, 45H), 0.83 (m, 15H); ESI-MS m/z: 724.55 $[M+H]^+$.

Example 11: Synthesis of Compound 11a

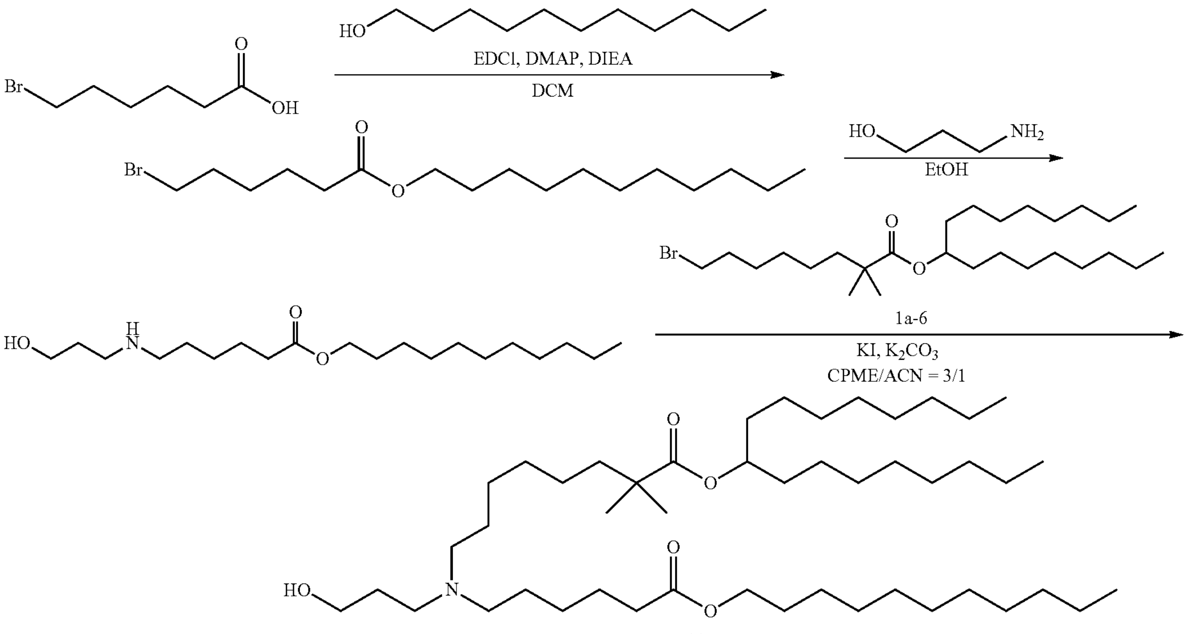

11a

Compound 11a was prepared referring to the method of Example 1 to give 69.5 mg of an oily product.

$^1$H NMR (400 MHz, $CDCl_3$) δ: 4.90-4.80 (m, 1H), 4.08 (t, J=7.2 Hz, 2H), 3.81 (t, J=5.2 Hz, 2H), 2.55 (m, 6H), 2.33 (t, J=7.2 Hz, 2H), 1.71-1.46 (m, 16H), 1.40-1.26 (m, 49H), 1.17 (s, 6H), 0.90 (t, J=7.2 Hz, 9H); ESI-MS m/z: 752.60 $[M+H]^+$.

Example 12: Synthesis of Compound 12a

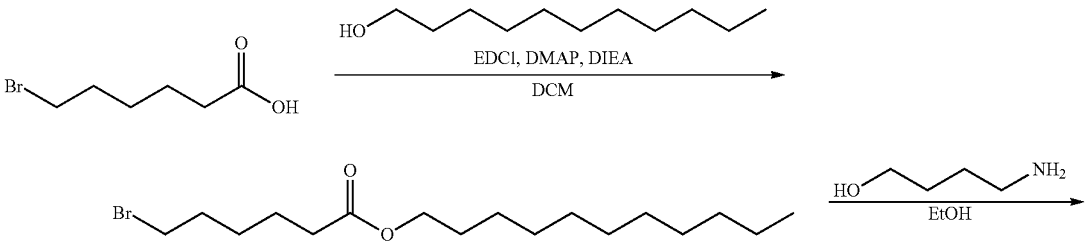

-continued

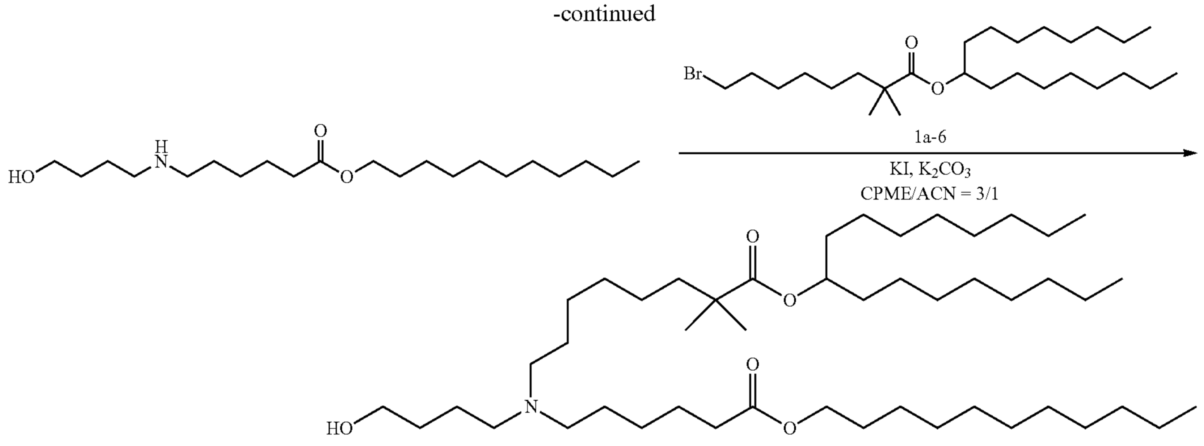

12a

Compound 12a was prepared referring to the method of Example 1 to give 178.6 mg of an oily product.

$^1$H NMR (400 MHz, $CDCl_3$) δ: 4.88-4.77 (m, 1H), 4.05 (t, J=7.2 Hz, 2H), 3.60 (t, J=5.6 Hz, 2H), 2.57 (m, 6H), 2.30 (t, J=7.2 Hz, 2H), 1.71-1.46 (m, 12H), 1.43-1.15 (m, 55H), 1.11 (s, 6H), 0.89 (t, J=7.2 Hz, 9H); ESI-MS m/z: 766.70 $[M+H]^+$.

Example 13: Synthesis of Compound 13a

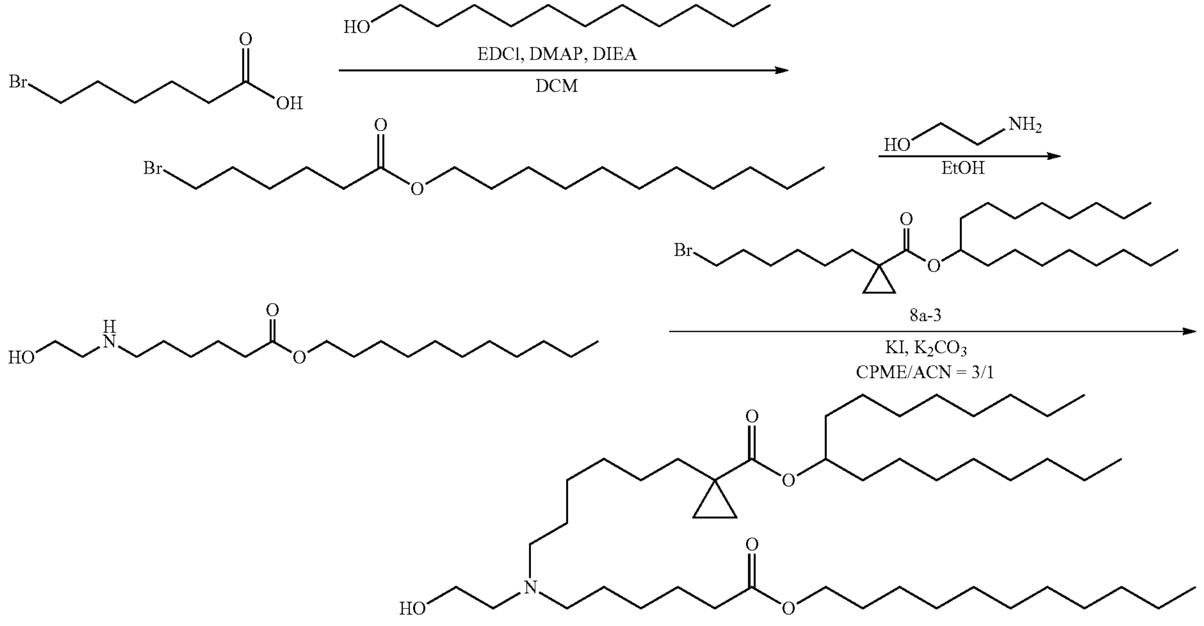

13a

Compound 13a was prepared referring to the method of Example 1 to give 43.5 mg of an oily product.

$^1$H NMR (400 MHz, $CDCl_3$) δ: 4.81 (p, J=6.4 Hz, 1H), 4.06 (t, J=6.8 Hz, 2H), 3.58 (m, 2H), 2.58-2.36 (m, 6H), 2.30 (t, J=7.6 Hz, 2H), 1.70-1.51 (m, 16H), 1.48-1.16 (m, 47H), 1.14 (t, J=4.0 Hz, 2H), 0.88 (t, J=7.2 Hz, 9H), 0.64 (t, J=4.0 Hz, 2H); ESI-MS m/z: 736.60 $[M+H]^+$.

Example 14: Synthesis of Compound 14a
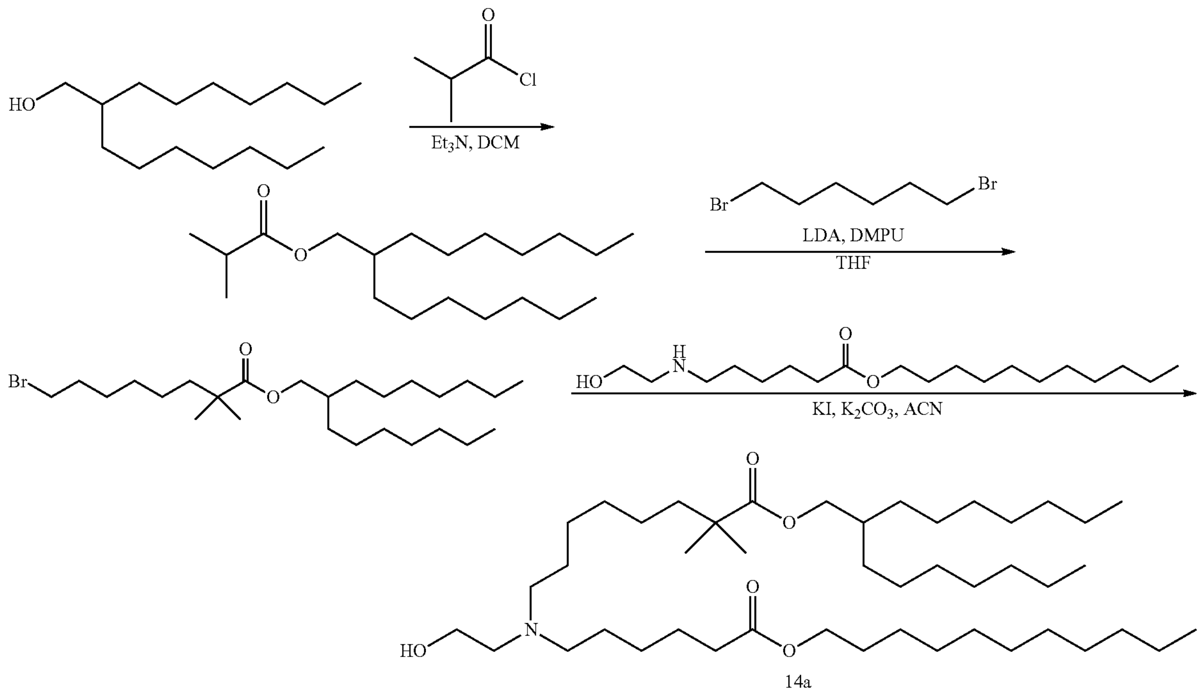
14a
Compound 14a was prepared referring to the method of Example 1 to give 56.3 mg of an oily product.
$^1$H NMR (400 MHz, $CDCl_3$) δ: 4.08 (t, J=6.8 Hz, 2H), 4.01 (d, J=4.8 Hz, 2H), 3.97 (d, J=5.6 Hz, 2H), 3.17-3.06 (m, 5H), 2.36 (t, J=7.2 Hz, 2H), 1.87-1.63 (m, 16), 1.57-1.29 (m, 45H), 1.19 (s, 6H), 0.91 (t, J=7.2 Hz, 9H); ESI-MS m/z: 724.55 $[M+H]^+$.
Example 15: Synthesis of Compound 15a
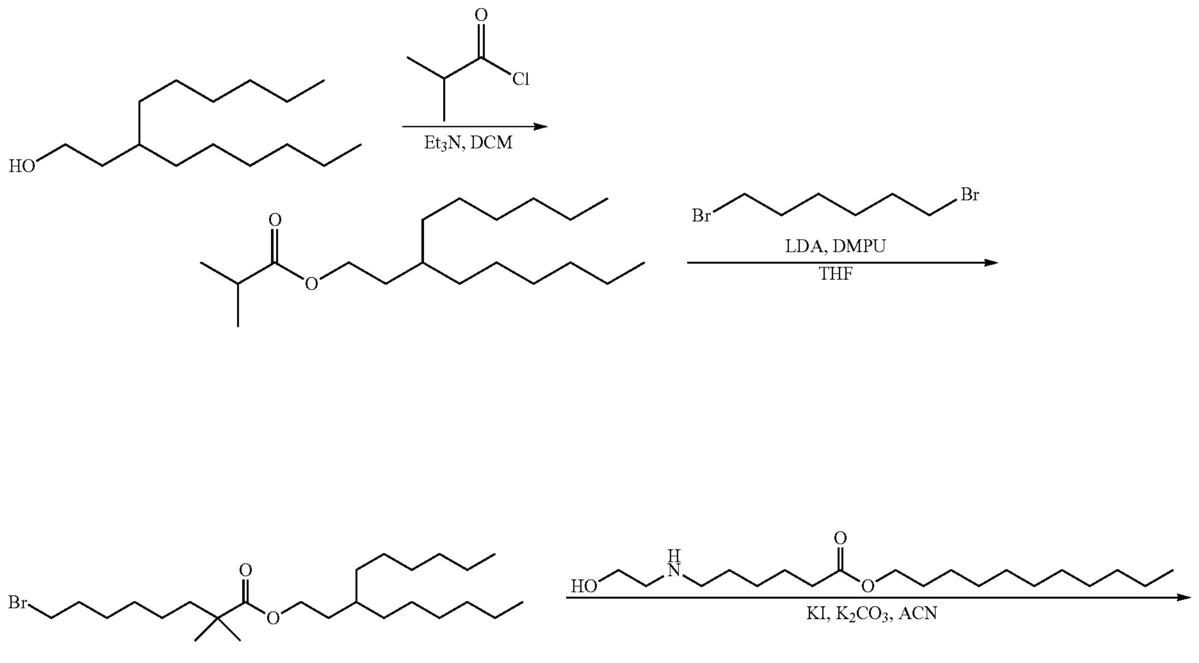

-continued
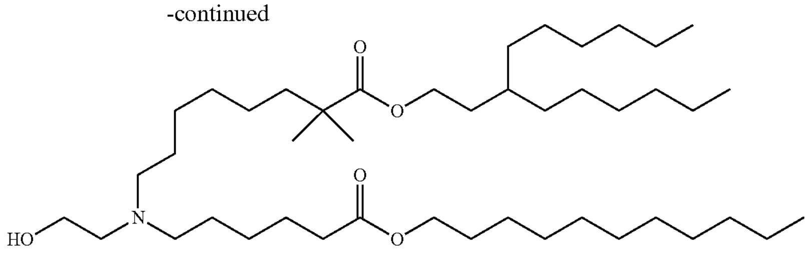
15a
Compound 15a was prepared referring to the method of Example 1 to give 120.3 mg of an oily product.
$^{1}$H NMR (400 MHz, $CDCl_3$) δ: 4.09-4.03 (m, 4H), 3.56 (m, 2H), 2.62-2.49 (m, 5H), 2.30 (t, J=6.0 Hz, 2H), 1.66-1.55 (m, 14H), 1.52-1.26 (m, 45H), 1.15 (s, 6H), 0.88 (t, J=7.2 Hz, 9H); ESI-MS m/z: 710.55 $[M+H]^+$.
Example 16: Synthesis of Compound 16a
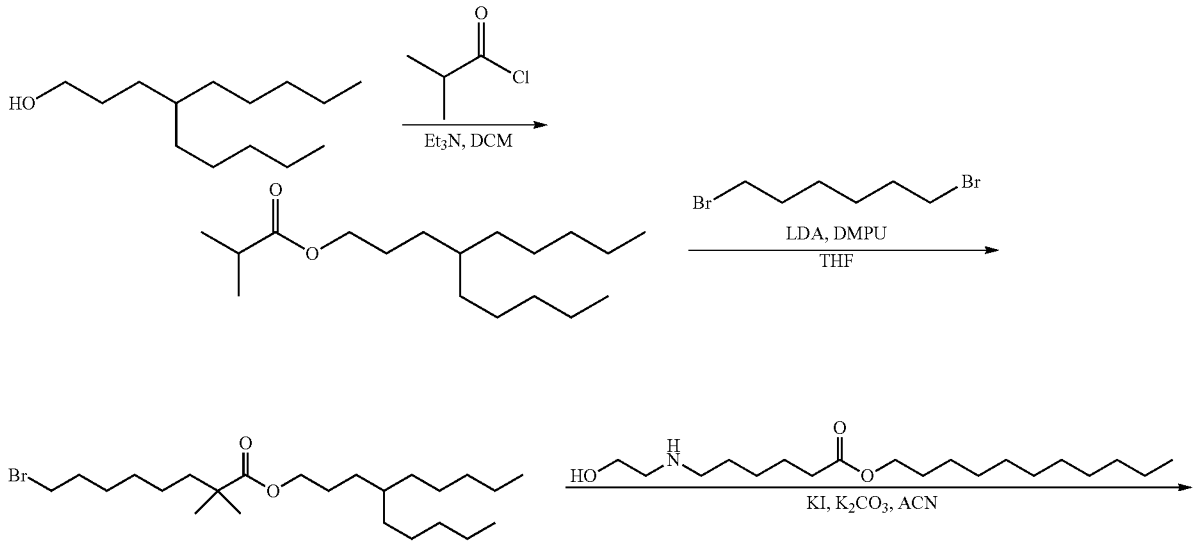
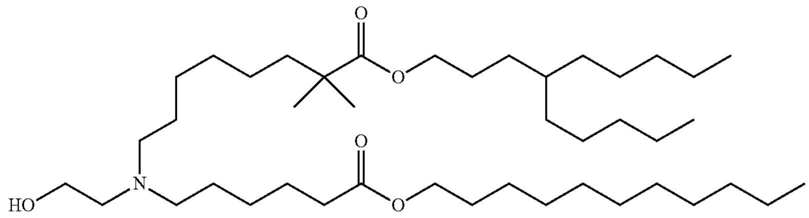
16a
Compound 16a was prepared referring to the method of Example 1 to give 80.8 mg of an oily product.
$^{1}$H NMR (400 MHz, $CDCl_3$) δ: 4.07-3.92 (m, 4H), 3.60 (m, 2H), 2.66-2.46 (m, 6H), 2.30 (t, J=7.6 Hz, 2H), 1.68-1.44 (m, 12H), 1.38-1.07 (m, 44H), 1.05 (s, 6H), 0.88 (t, J=7.2 Hz, 9H); ESI-MS m/z: 696.55 $[M+H]^+$.

Example 17: Synthesis of Compound 17a
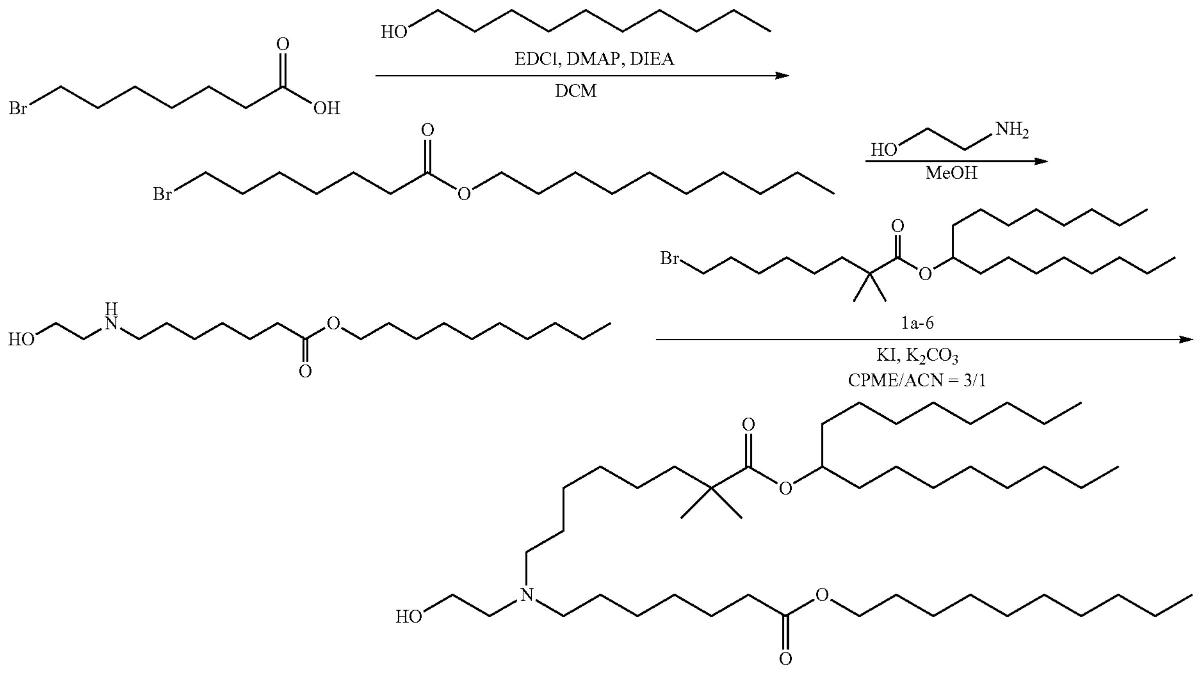
17a
Compound 17a was prepared referring to the method of Example 1 to give 125.7 mg of an oily product.
$^1$H NMR (400 MHz, $CDCl_3$) δ: 4.86-4.80 (m, 1H), 4.05 (t, J=6.8 Hz, 2H), 3.55 (m, 2H), 2.60-2.47 (m, 6H), 2.29 (t, J=7.6 Hz, 2H), 1.66-1.48 (m, 14H), 1.43-1.26 (m, 49H), 1.15 (s, 6H), 0.88 (t, J=7.2 Hz, 9H); ESI-MS m/z: 738.65 $[M+H]^+$.
Example 18: Synthesis of Compound 18a
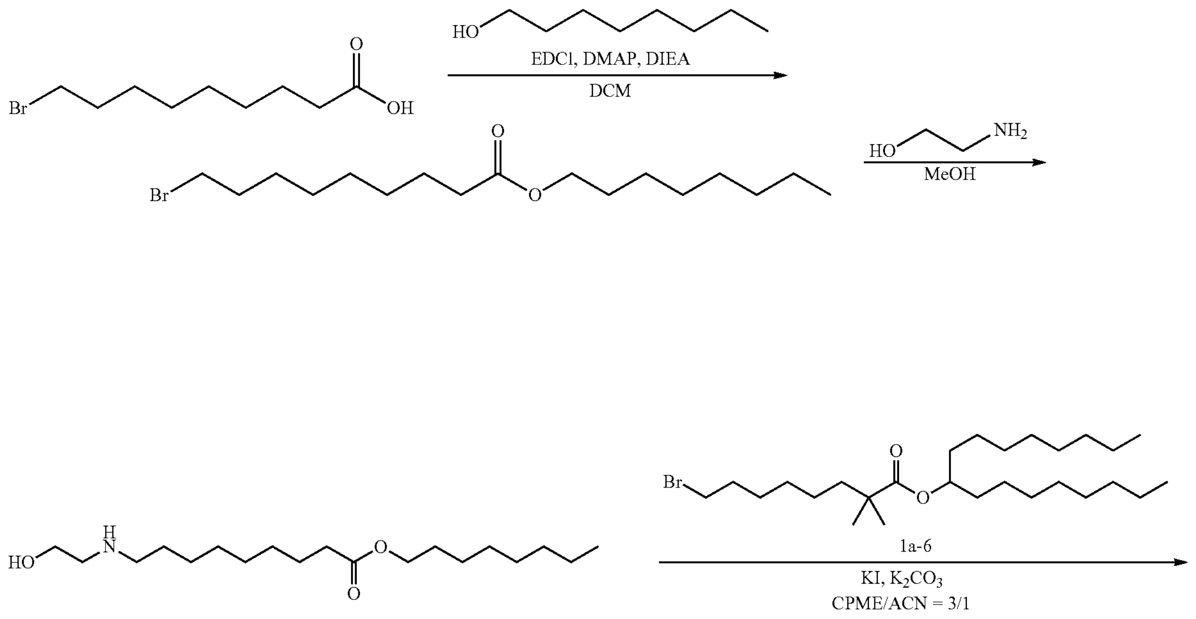

-continued

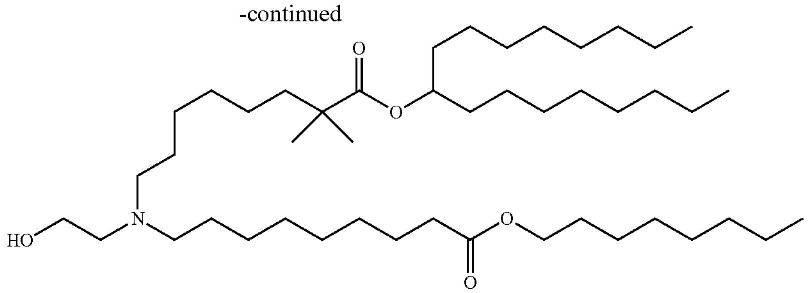

18a

Compound 18a was prepared referring to the method of Example 1 to give 127.4 mg of an oily product.

$^1$H NMR (400 MHz, $CDCl_3$) δ: 4.86-4.80 (m, 1H), 4.06 (t, J=6.8 Hz, 2H), 3.53 (t, J=4.8 Hz, 2H), 2.58 (t, J=4.8 Hz, 2H), 2.43 (t, J=4.8 Hz, 4H), 2.29 (t, J=7.6 Hz, 2H), 1.65-1.43 (m, 14H), 1.38-1.18 (m, 49H), 1.15 (s, 6H), 0.88 (t, J=7.2 Hz, 9H); ESI-MS m/z: 738.66 $[M+H]^+$.

Example 19: Synthesis of Compound 19a

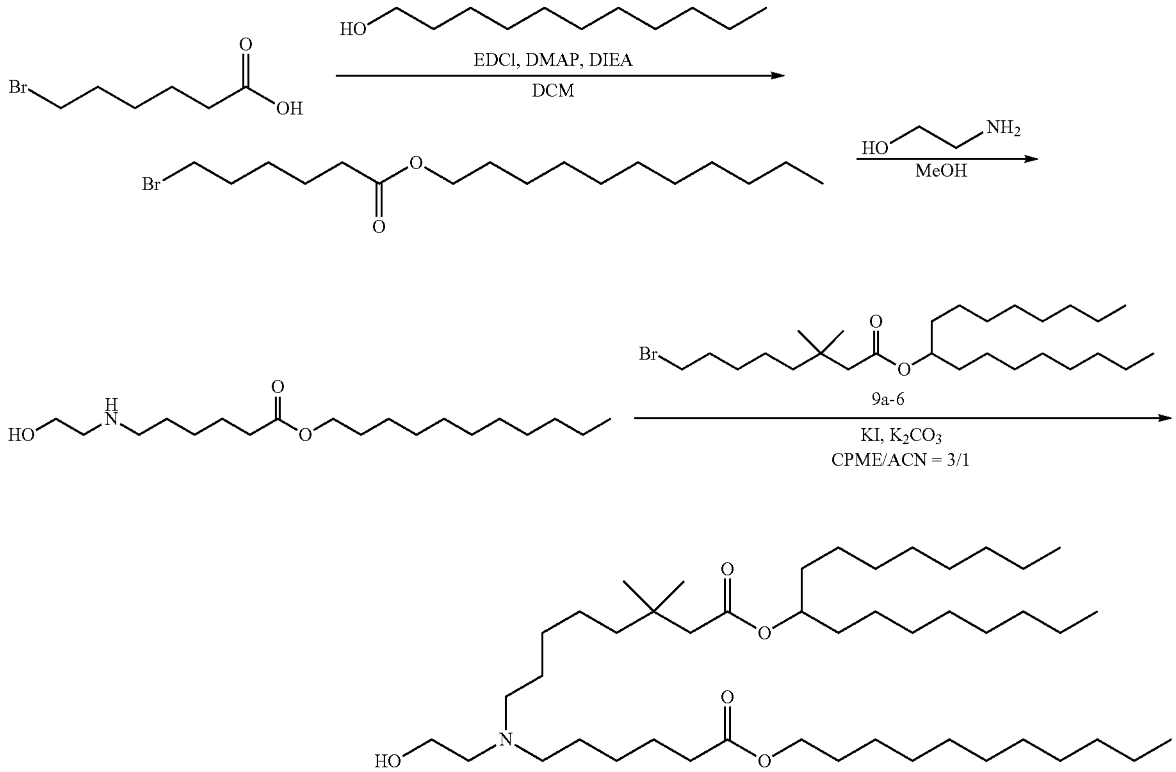

19a

Compound 19a was prepared referring to the method of Example 9 to give 79.7 mg of an oily product.

$^1$H NMR (300 MHz, $CDCl_3$) δ: 4.89-4.82 (m, 1H), 4.06 (t, J=6.9 Hz, 2H), 3.67 (m, 2H), 2.70-2.34 (m, 4H), 2.31 (t, J=7.5 Hz, 2H), 2.17 (s, 2H), 1.70-1.49 (m, 12H), 1.38-1.18 (m, 49H), 0.99 (s, 6H), 0.88 (t, J=6.9 Hz, 9H); ESI-MS m/z: 738.65 $[M+H]^+$.

Example 20: Synthesis of Compound 20a

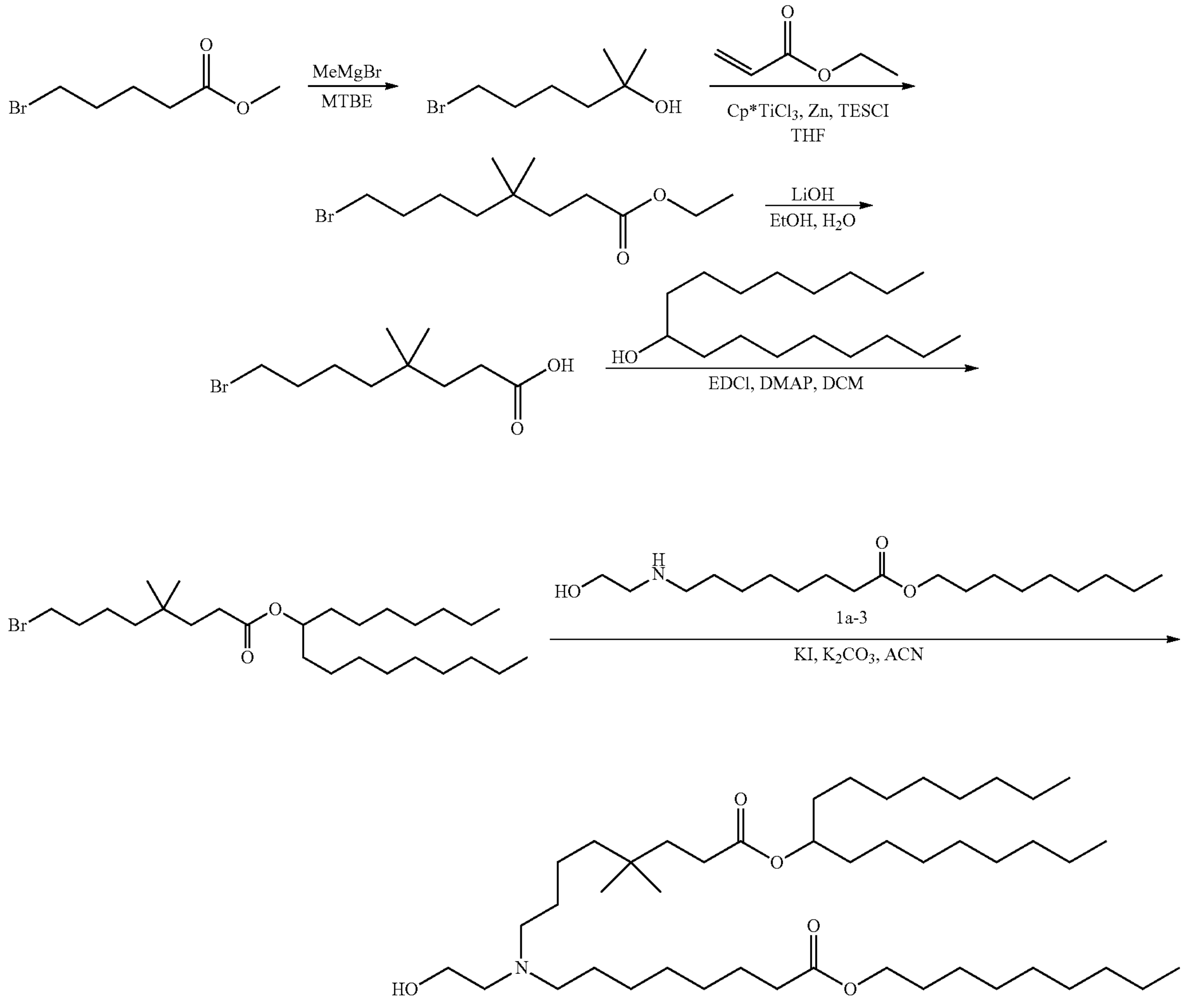

20a

Compound 20a was prepared referring to the method of Example 10 to give 74.5 mg of an oily product.

$^{1}$H NMR (400 MHz, $CDCl_3$) δ: 4.89-4.85 (m, 1H), 4.06 (t, J=7.2 Hz, 2H), 3.63 (m, 2H), 2.69-2.57 (m, 6H), 2.35-2.20 (m, 4H), 1.71-1.53 (m, 15H), 1.39-1.19 (m, 46H), 0.94-0.85 (in, 15H); ESI-MS m/z: 738.45 $[M+H]^+$.

The compounds in Table 2 were synthesized using the methods of the above examples, or using similar methods of the corresponding intermediates.

TABLE 2

| |
|---|
| 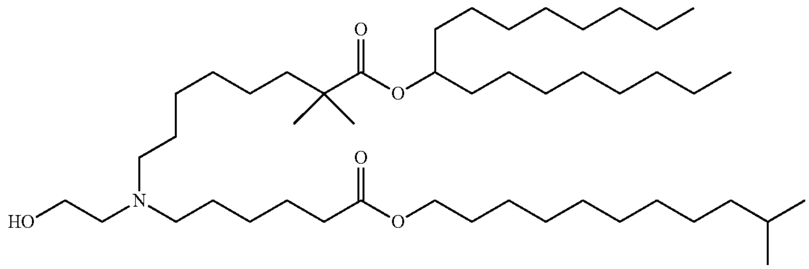 [SMILES: CCCCCCCCC(CCCCCCCC)OC(=O)C(C)(C)CCCCCCN(CCO)CCCCCC(=O)OCCCCCCCCCC(C)C]<br>Example 21: Compound 21a<br>$[M + H]^+$: 752.65 |

TABLE 2-continued
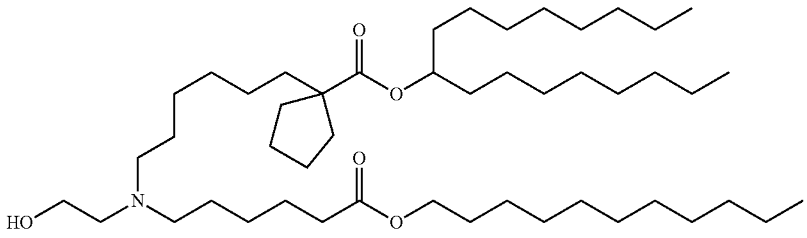 [SMILES: CCCCCCCCCCCOC(=O)CCCCCN(CCO)CCCCCCC1(C(=O)OC(CCCCCCCC)CCCCCCCC)CCCC1]
Example 22: Compound 22a
[M + H]+: 764.65
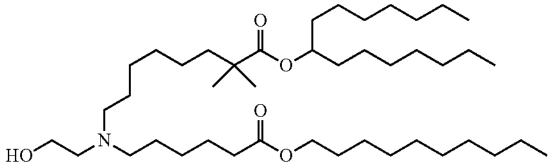 [SMILES: CCCCCCCCCCOC(=O)CCCCCN(CCO)CCCCCCC(C)(C)C(=O)OC(CCCCCCC)CCCCCCC]
Example 23: Compound 23a
[M + H]+: 696.65
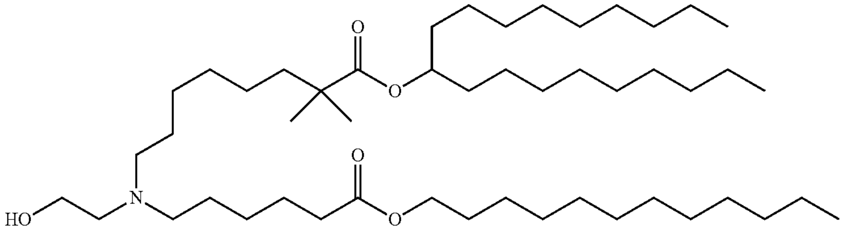 [SMILES: CCCCCCCCCCCCOC(=O)CCCCCN(CCO)CCCCCCC(C)(C)C(=O)OC(CCCCCCCCC)CCCCCCCCC]
Example 24: Compound 24a
[M + H]+: 780.65
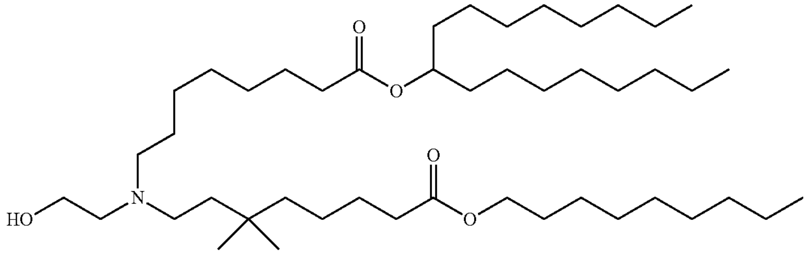 [SMILES: CCCCCCCCCOC(=O)CCCCC(C)(C)CCN(CCO)CCCCCCCC(=O)OC(CCCCCCCC)CCCCCCCC]
Example 25: Compound 25a
[M + H]+: 738.60
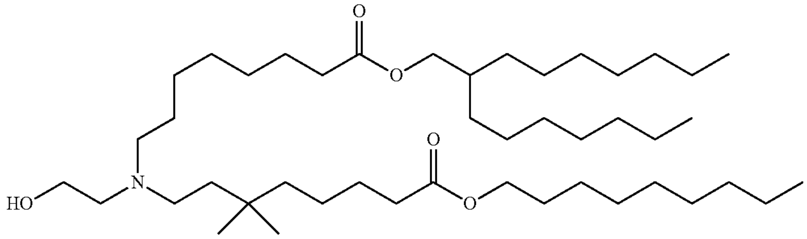 [SMILES: CCCCCCCCCOC(=O)CCCCC(C)(C)CCN(CCO)CCCCCCCC(=O)OCC(CCCCCCC)CCCCCCC]
Example 26: Compound 26a
[M + H]+: 724.55

TABLE 2-continued
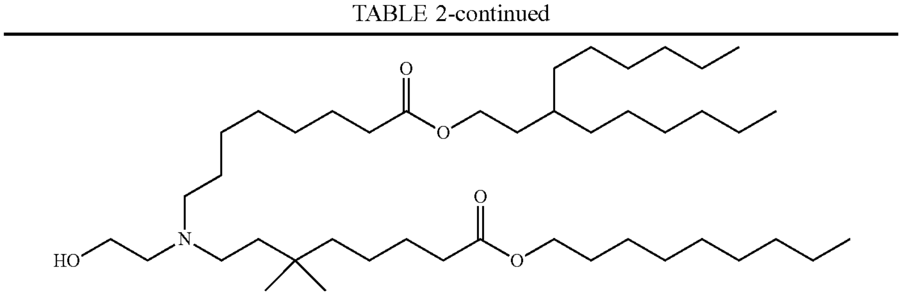
Example 27: Compound 27a
$[M+H]^+$: 710.50
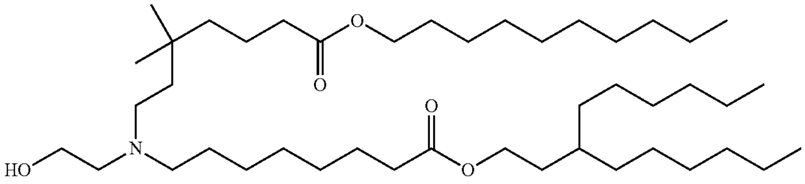 [SMILES: CCCCCCCCCCOC(=O)CCCC(C)(C)CCN(CCO)CCCCCCCC(=O)OCCC(CCCCCC)CCCCCC]
Example 28: Compound 28a
$[M+H]^+$: 710.50
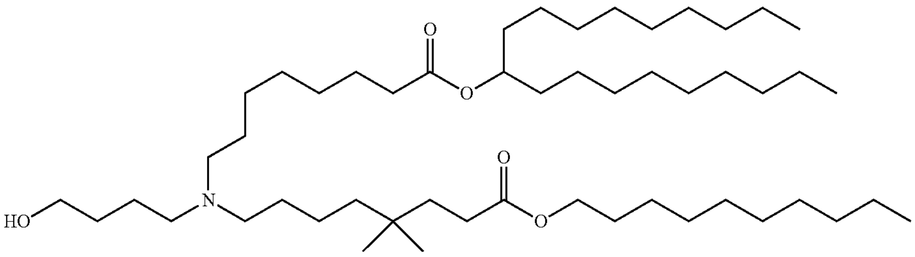 [SMILES: CCCCCCCCCCOC(=O)CCC(C)(C)CCCCN(CCCCO)CCCCCCCC(=O)OC(CCCCCCCCC)CCCCCCCCC]
Example 29: Compound 29a
$[M+H]^+$: 808.70
Example 30: Synthesis of Compound 1b
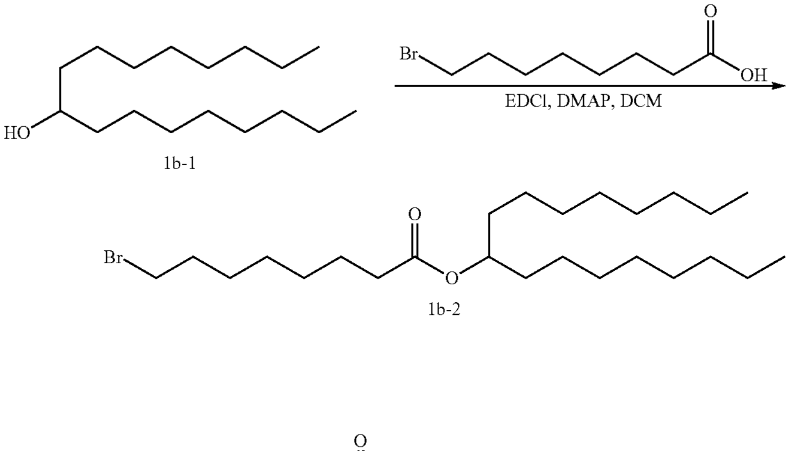
1b-1
1b-2
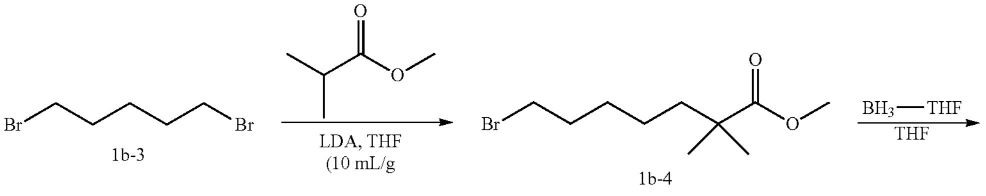
1b-3
1b-4

-continued

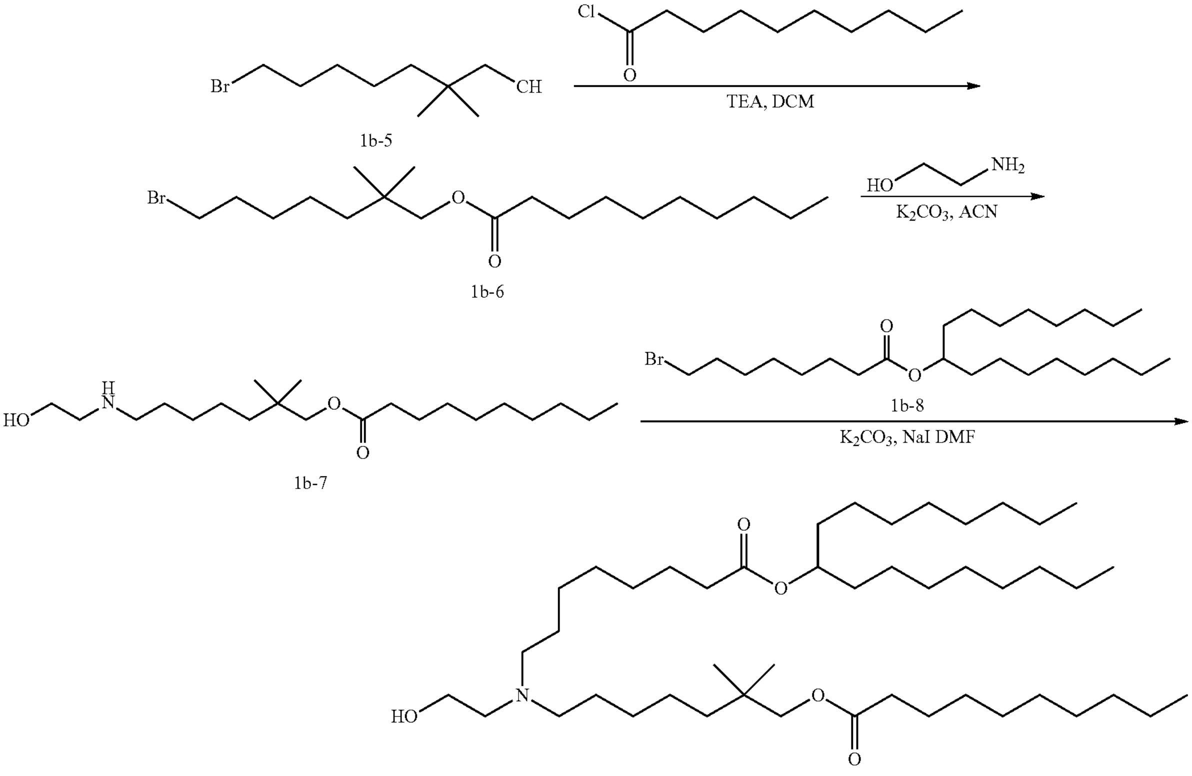

1b-5

1b-6

1b-7

1b-8

1b

9-Heptadecanol 1b-1 (200.0 mg, 0.78 mmol, 1.0 eq.) was dissolved in DCM (2.0 mL), and 8-bromooctanoic acid (226.2 mg, 1.01 mmol, 1.3 eq.), EDCI (179.4 mg, 0.94 mmol, 1.2 eq.), and DMAP (42.9 mg, 1.17 mmol, 1.5 eq.) were added to the solution. The reaction liquid was stirred at room temperature for 3 h, the reaction liquid was poured into 10 mL of a saturated aqueous sodium chloride solution, and the mixture was extracted with 3×20 mL of DCM. The organic phases were combined and dried over anhydrous sodium sulfate. The mixture was filtered, and the filtrate was concentrated to dryness to give a crude product, which was purified by silica gel column chromatography to give 300 mg of a yellow oily compound 1b-2.

Methyl isobutyrate (21 g, 205.0 mmol, 1.0 eq.) was dissolved in 200 mL of anhydrous THF, the mixture was cooled to 0° C., and LDA (205 mL, 410.0 mmol, 2.0 eq.) was added to the reaction liquid under nitrogen atmosphere. The reaction was heated to room temperature. After stirring for 30 min, 1,5-dibromopentane (47 g, 205.0 mmol, 1.0 eq.) was added. After the reaction was completed as monitored by TLC, a saturated aqueous ammonium chloride solution was added to quench the reaction, and the mixture was extracted with 3×300 mL of DCM. The organic phases were combined and dried over anhydrous sodium sulfate. The mixture was filtered, and the filtrate was concentrated to dryness to give a crude product, which was purified by silica gel column chromatography to give 30 g of a yellow oily compound 1b-4.

Compound 1b-4 (15.0 g, 40.0 mmol, 1.0 eq.) was dissolved in 30 mL of THF, the mixture was cooled to 0° C., and a borane-tetrahydrofuran solution (1 M, 100.0 mL) was added dropwise to the reaction system under nitrogen atmosphere. The mixture was heated to 75° C. and stirred for reaction for 3 h. After the reaction was completed, the reaction system was cooled to room temperature. The reaction was quenched with a saturated aqueous ammonium chloride solution, and the mixture was extracted with 3×300 mL of DCM. The organic phases were combined and dried over anhydrous sodium sulfate. The mixture was filtered, and the filtrate was concentrated to dryness to give a crude product of 1b-5 (13.6 g), which was directly used in the next step without purification.

Caprinoyl chloride (11.0 g, 58.0 mmol, 1.3 eq.) was added to a solution of compound 1b-5 (10.0 g, 44.0 mmol, 1.0 eq.) in DCM (100 mL), triethylamine (13.5 g, 134.0 mmol, 3.0 eq.) was added to the reaction system, and the mixture was reacted at room temperature for 3 h. The reaction liquid was poured into 100 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 10 g of compound 1b-6.

Potassium carbonate (1.5 g, 11.1 mmol, 3.0 eq.) and compound 1b-6 (1.4 g, 3.7 mmol, 1.0 eq.) were added to a solution of ethanolamine (2.3 g, 37.2 mmol, 10.0 eq.) in acetonitrile (15.0 mL). The mixture was heated to 70° C. and stirred for reaction for 3 h. The reaction liquid was poured into 30 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 1.4 g of compound 1b-7. $^1$H NMR (300 MHz, $CD_3Cl$) δ: 0.85-0.89 (m, 9H), 1.20-1.26 (m, 21H), 1.59-1.62 (m, 4H), 2.29-2.34 (m, 2H), 2.73-2.76 (m, 2H), 2.87-2.91 (m, 2H), 3.72-3.77 (m, 3H).

Compound 1b-2 (300.0 mg, 0.84 mmol, 1.0 eq.) and compound 1b-7 (503.4 mg, 1.09 mmol, 1.3 eq.) were dissolved in DMF (3.0 mL), then potassium carbonate (289.9 mg, 2.1 mmol, 2.5 eq.) and sodium iodide (314.4 mg, 2.1 mmol, 2.5 eq.) were added, and the mixture was heated to 70° C. and stirred for reaction for 2 h. The reaction liquid was poured into 20 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give compound 1b (158.9 mg).

$^1$H NMR (400 MHz, Methanol-$d_4$) δ: 0.85-0.95 (m, 15H), 1.17-1.34 (m, 48H), 1.52-1.59 (m, 8H), 1.62-1.64 (m, 4H), 2.27-2.35 (m, 4H), 2.48-2.53 (m, 4H), 2.63 (t, J=6.3 Hz, 2H), 3.61 (t, J=6.3 Hz, 2H), 3.80 (s, 2H), 4.84-4.89 (m, 1H); ESI-MS m/z: 738.65 [M+H]$^+$.

Example 31: Synthesis of Compound 2b

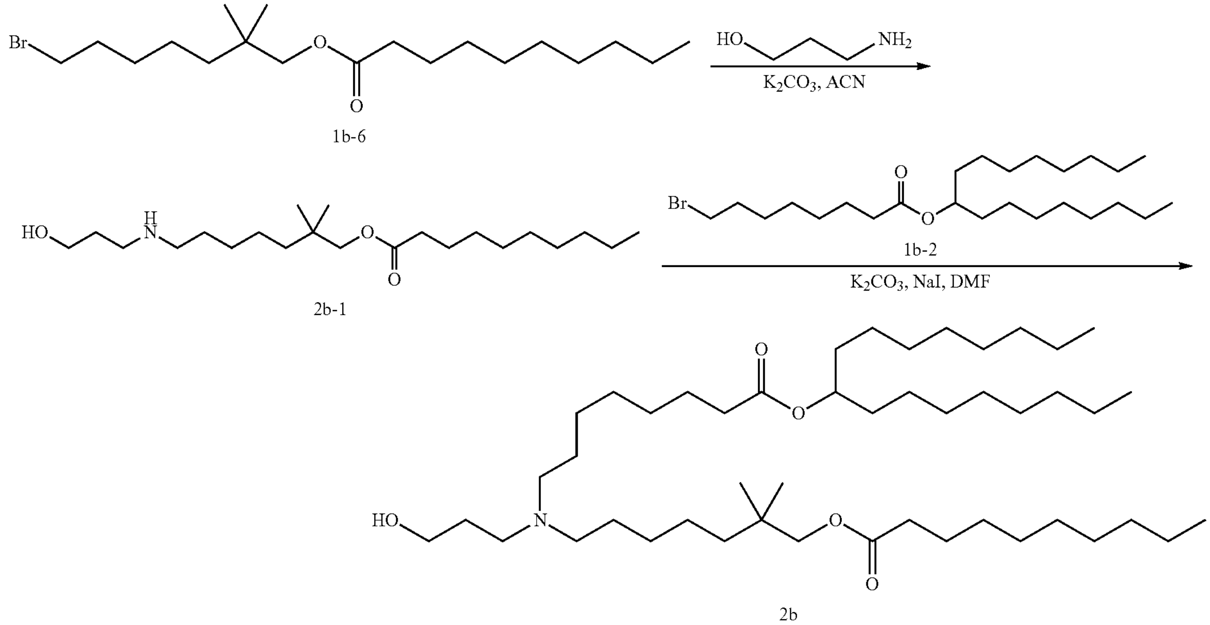

Potassium carbonate (549.3 mg, 4.0 mmol, 3.0 eq.) and compound 1b-6 (500.0 mg, 1.33 mmol, 1.0 eq.) were added to a solution of 3-amino-1-propanol (1.0 g, 13.3 mmol, 10.0 eq.) in acetonitrile (10.0 mL). The mixture was heated to 70° C. and stirred for reaction for 3 h. The reaction liquid was poured into 30 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 350 mg of a colorless oily compound 2b-1.

Compound 1b-2 (565 mg, 1.22 mmol, 1.3 eq.) and compound 2b-1 (350 mg, 0.94 mmol, 1.0 eq.) were dissolved in DMF (5.0 mL), then potassium carbonate (389 mg, 2.82 mmol, 3.0 eq.) and sodium iodide (353 mg, 2.35 mmol, 2.5 eq.) were added, and the mixture was heated to 70° C. and stirred for reaction for 5 h. The reaction liquid was poured into 20 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give compound 2b (160 mg).

$^1$H NMR (400 MHz, Methanol-$d_4$) δ: 0.85-0.95 (m, 15H), 1.20-1.40 (m, 48H), 1.62-1.70 (m, 12H), 1.72-1.78 (m, 2H), 2.28-2.35 (m, 4H), 2.60-2.66 (m, 4H), 2.74-2.79 (m, 2H), 3.64 (t, J=6.0 Hz, 2H), 3.80 (s, 2H), 4.82-4.89 (m, 1H); ESI-MS m/z: 752.65 [M+H]$^+$.

Example 32: Synthesis of Compound 3b

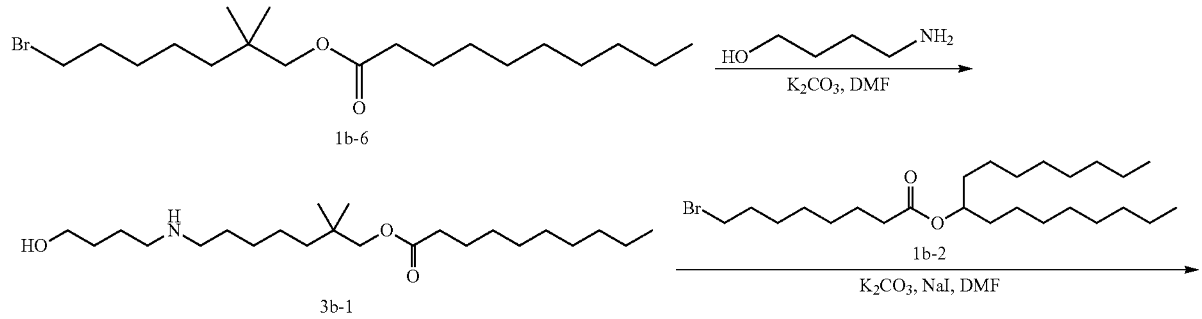

-continued

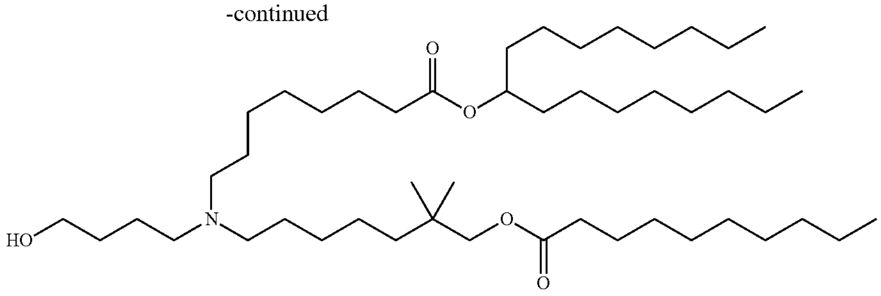

3b

Potassium carbonate (549 mg, 4.0 mmol, 3.0 eq.) and compound 1b-6 (500 mg, 1.33 mmol, 1.0 eq.) were added to a solution of 4-amino-1-butanol (1.2 g, 13.3 mmol, 10.0 eq.) in DMF (10.0 mL). The mixture was heated to 70° C. and stirred for reaction for 3 h. The reaction liquid was poured into 30 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 300 mg of a colorless oily compound 3b-1.

Compound 1b-2 (462 mg, 1.0 mmol, 1.3 eq.) and compound 3b-1(297 mg, 0.77 mmol, 1.0 eq.) were dissolved in DMF (5.0 mL), then potassium carbonate (269 mg, 1.9 mmol, 2.5 eq.) and sodium iodide (285 mg, 1.9 mmol, 2.5 eq.) were added, and the mixture was heated to 70° C. and stirred for reaction for 5 h. The reaction liquid was poured into 20 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give compound 3b (228 mg).

$^1$H NMR (400 MHz, $CDCl_3$) δ: 0.80-0.90 (m, 15H), 1.25-1.40 (m, 48H), 1.49-1.66 (m, 8H), 1.74-1.81 (m, 8H), 2.24-2.37 (m, 4H), 2.47-2.58 (m, 6H), 3.56 (s, 2H), 3.77 (s, 2H), 4.81-4.88 (m, 1H); ESI-MS m/z: 766.85 $[M+H]^+$.

Example 33: Synthesis of Compound 4b

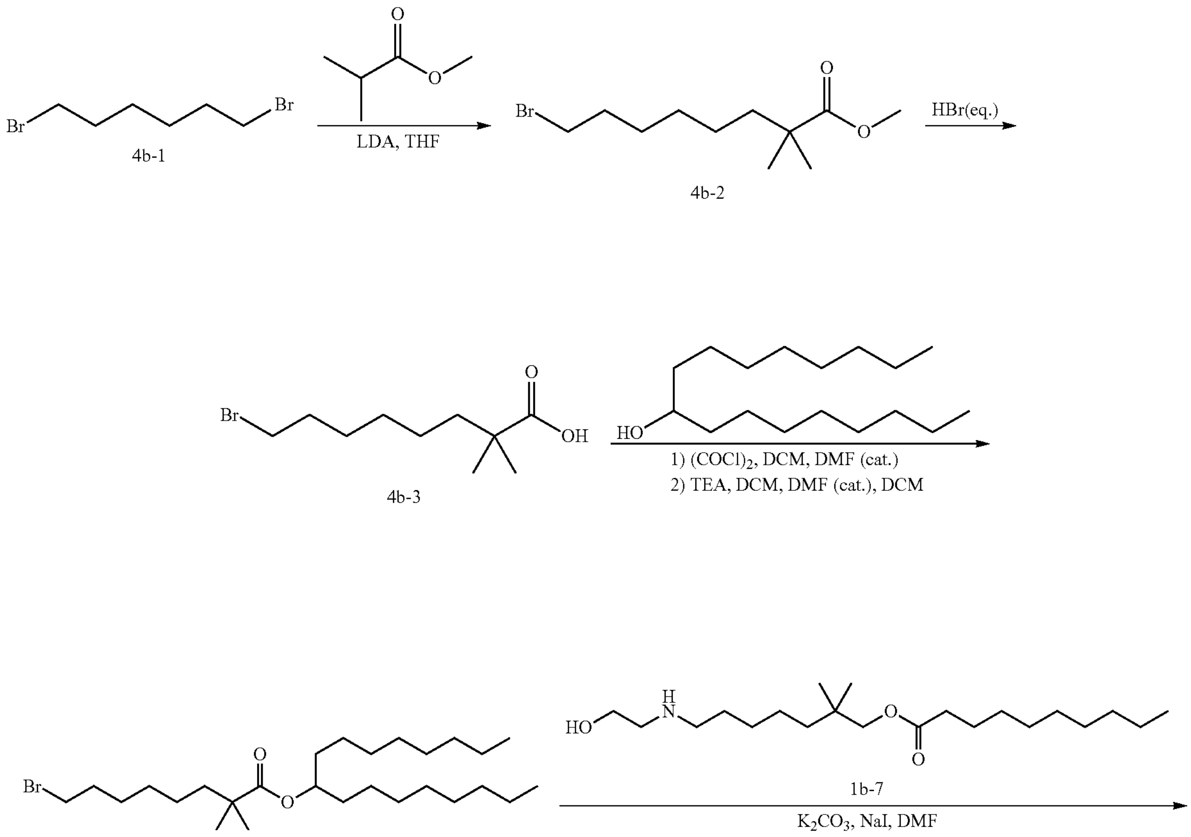

4b-1

4b-2

4b-3

4b-4

-continued

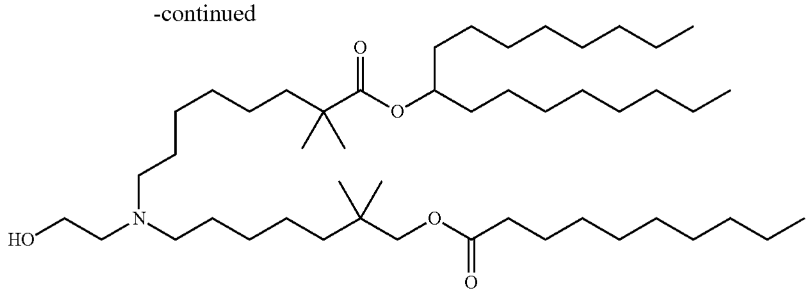

4b

Methyl isobutyrate (21 g, 205 mmol, 1.0 eq.) was dissolved in 200 mL of anhydrous THF, the mixture was cooled to 0° C., and LDA (205 mL, 410 mmol, 2.0 eq.) was added to the reaction liquid under nitrogen atmosphere. The reaction was heated to room temperature. After stirring for 30 min, 1,6-dibromohexane (50 g, 205 mmol, 1.0 eq.) was added. After the reaction was completed as monitored by TLC, a saturated aqueous ammonium chloride solution was added to quench the reaction, and the mixture was extracted with 3×300 mL of DCM. The organic phases were combined and dried over anhydrous sodium sulfate. The mixture was filtered, and the filtrate was concentrated to dryness to give a crude product, which was purified by silica gel column chromatography to give 34 g of a yellow oily compound 4b-2. $^1$H NMR (400 MHz, $CD_3Cl$) δ: 1.05-1.52 (m, 14H), 1.78-1.91 (m, 2H), 3.36-3.42 (m, 2H), 3.71 (s, 3H).

Compound 4b-2 (10.0 g, 37.6 mmol, 1.0 eq.) was added to a hydrobromic acid aqueous solution (50.0 mL). The reaction liquid was heated to 100° C. and stirred for reaction for 24 h. After the reaction was completed, the reaction system was cooled to room temperature. The reaction was quenched with a saturated aqueous sodium chloride solution, and the mixture was extracted with DCM. The organic phases were combined and dried over anhydrous sodium sulfate. The mixture was filtered, and the filtrate was concentrated to dryness to give a crude product, which was purified by silica gel column chromatography to give 7.4 g of a yellow oily compound 4b-3. $^1$H NMR (400 MHz, $CD_3Cl$) δ: 1.19 (s, 6H), 1.25-1.28 (m, 4H), 1.30-1.56 (m, 4H), 1.80-1.89 (m, 2H), 3.37-3.42 (m, 2H).

Compound 4b-3 (5.0 g, 19.9 mmol, 1.0 eq.) was dissolved in DCM (50.0 mL), and DMF (291.0 mg, 3.98 mmol, 0.2 eq.) and oxalyl chloride (5.1 g, 39.8 mmol, 2.0 eq.) were added to the reaction system under an ice bath. After the mixture was stirred for 30 min, the solvent was removed by rotary evaporation under reduced pressure to give an acyl chloride intermediate. The resulting acyl chloride was dissolved in DCM (50.0 mL), then 9-heptadecanol (4.08 g, 15.9 mmol, 0.8 eq.) and triethylamine (6.03 g, 59.7 mmol, 3.0 eq.) were added, and the mixture was reacted at room temperature overnight. After the reaction was completed, the reaction liquid was poured into 300 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 4.3 g of an oily compound 4b-4.

To a solution of compound 4b-4 (492.9 mg, 1.0 mmol, 1.2 eq.) in DMF (3.0 mL) were added potassium carbonate (347.8 mg, 2.5 mmol, 3.0 eq.), sodium iodide (314.4 mg, 2.1 mmol, 2.5 eq.), and compound 1b-7 (300.0 mg, 0.8 mmol, 1.0 eq.). The reaction liquid was heated to 70° C. and stirred for reaction for 2 h. After the reaction was completed, the reaction system was cooled to room temperature. The reaction was quenched with a saturated aqueous sodium chloride solution, and the mixture was extracted with DCM. The organic phases were combined and dried over anhydrous sodium sulfate. The mixture was filtered, and the filtrate was concentrated to dryness to give a crude product, which was purified by preparative liquid chromatography to give 106 mg of compound 4b. (Column model: XBridge Shield RP18 OBD Column 19×150 mm, 5 μm; mobile phase A: acetonitrile: water (10 mmol/L ammonium bicarbonate+0.05% aqueous ammonia), mobile phase B: isopropanol: acetonitrile; flow rate: 20 mL/min; gradient: the proportion of mobile phase B was gradually increased from 75% B to 95% B within 9 min).

$^1$H NMR (400 MHz, Methanol-$d_4$) δ: 0.85-0.95 (m, 15H), 1.15 (s, 6H), 1.20-1.40 (m, 48H), 1.47-1.54 (m, 10H), 1.60-1.64 (m, 2H), 2.31-2.34 (m, 2H), 2.47-2.51 (m, 4H), 2.61 (t, J=6.4 Hz, 2H), 3.61 (t, J=6.4 Hz, 2H), 3.80 (s, 2H), 4.81-4.88 (m, 1H); ESI-MS m/z: 766.70 $[M+H]^+$.

Example 34: Synthesis of Compound 5b

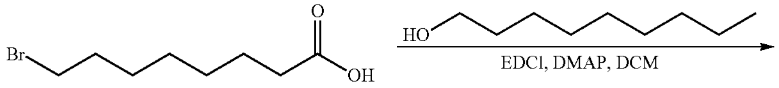

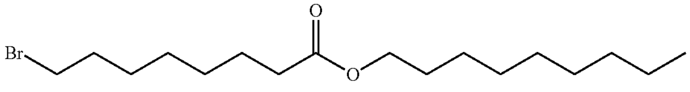

5b-1

-continued
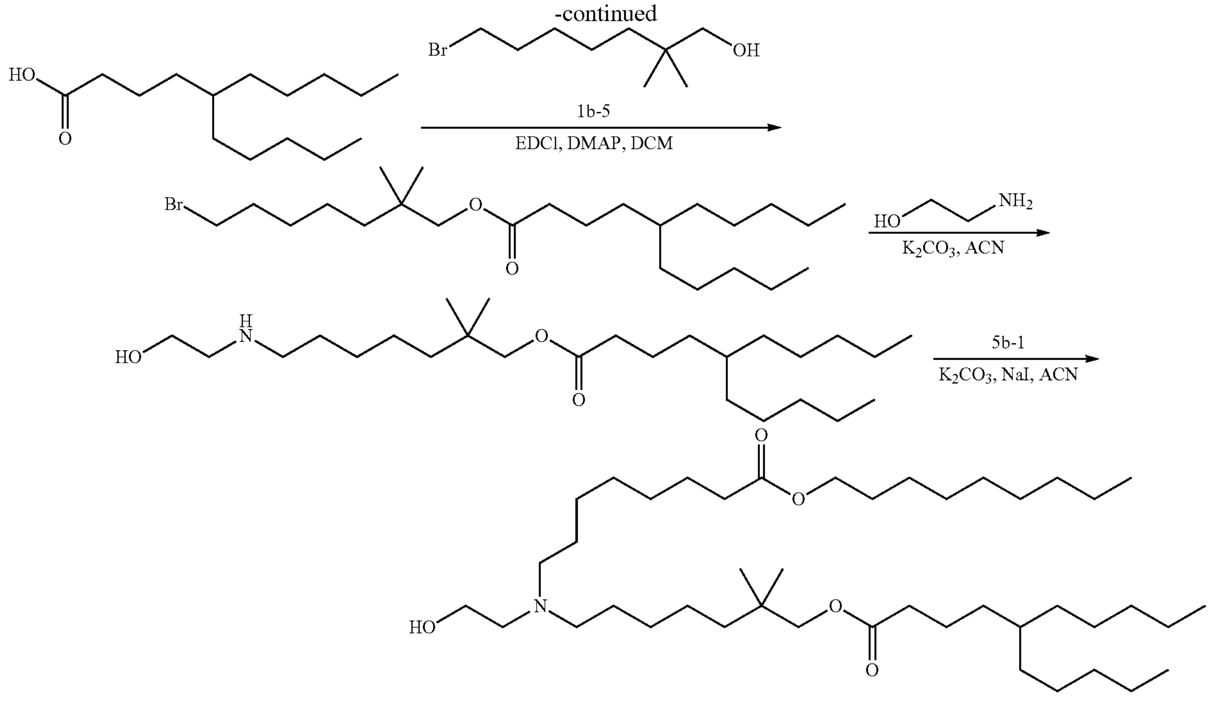
5b
Compound 5b was prepared referring to the method of Example 30 to give 174 mg of an oily product.
$^1$H NMR (400 MHz, Methanol-d$_4$) δ: 0.85-0.95 (m, 15H), 1.20-1.40 (m, 43H), 1.50-1.60 (m, 4H), 1.61-1.70 (m, 7H), 2.28-2.33 (m, 4H), 2.48-2.64 (m, 5H), 3.51-3.63 (m, 2H), 3.80 (s, 2H), 4.04-4.08 (m, 2H); ESI-MS m/z: 696.60 [M+H]$^+$.
Example 35: Synthesis of Compound 6b
Compound 6b was prepared referring to the method of Example 30 to give 113 mg of an oily product.
$^1$H NMR (400 MHz, Methanol-d$_4$) δ: 0.85-0.95 (m, 9H), 1.25 (s, 6H), 1.35-1.55 (m, 48H), 1.58-1.65 (m, 14H), 2.27-2.32 (m, 2H), 2.46-2.51 (m, 4H), 2.58-2.62 (m, 2H), 3.58-3.64 (m, 2H), 4.04-4.08 (m, 2H), 4.83-4.87 (m, 1H); ESI-MS m/z: 738.65 [M+H]$^+$.
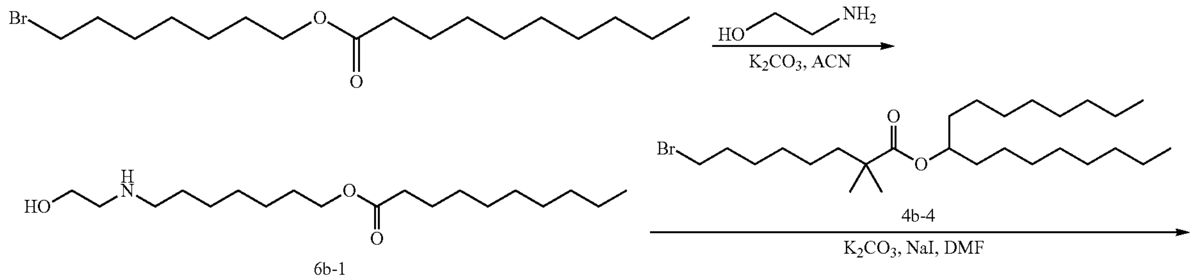
6b-1
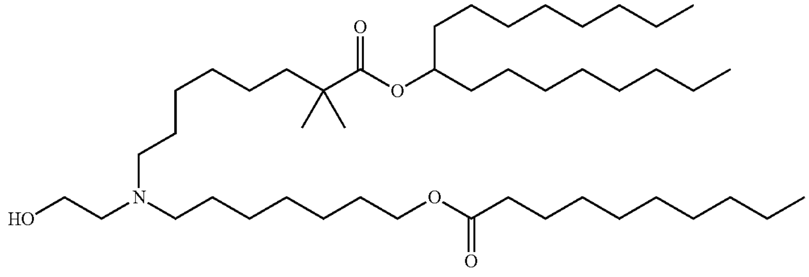
6b Example 36: Synthesis of Compound 7b
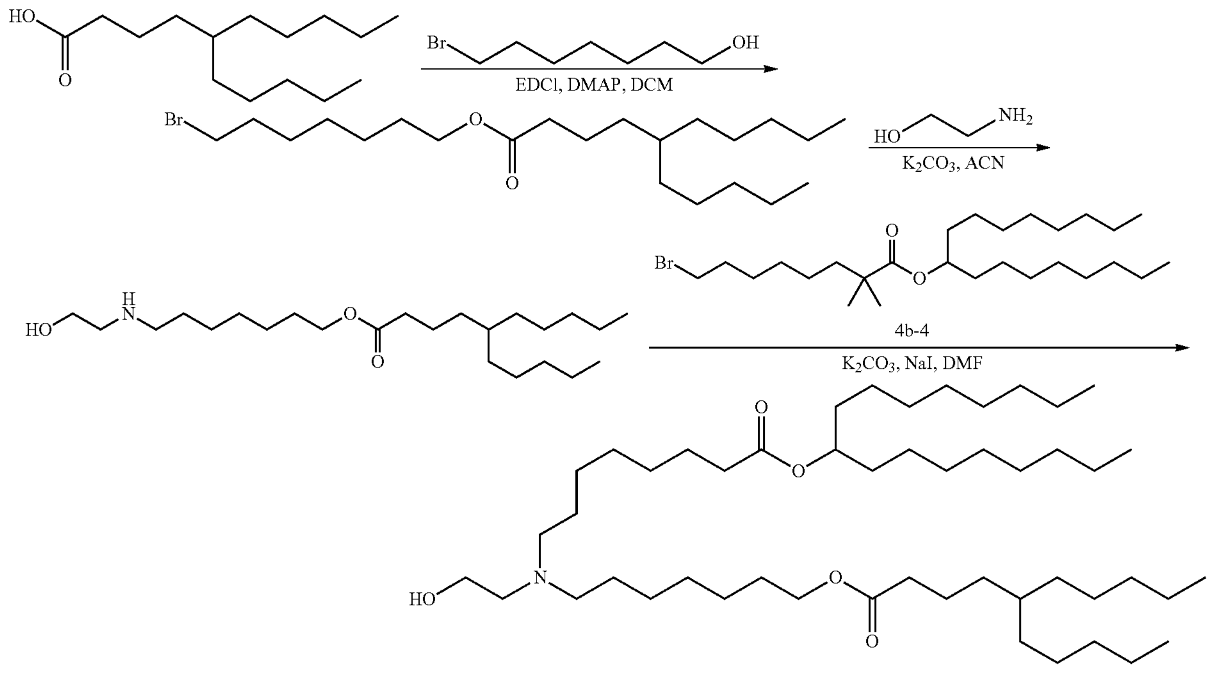
7b
Compound 7b was prepared referring to the method of Example 30 to give 91 mg of an oily product.
$^1$H NMR (400 MHz, $CDCl_3$) δ: 0.85-0.90 (m, 12H), 1.14 (s, 6H), 1.23-1.49 (m, 56H), 1.56-1.64 (m, 14H), 2.24-2.29 (m, 2H), 2.51-2.65 (m, 5H), 3.60 (s, 2H), 4.03-4.07 (m, 2H), 4.80-4.84 (m, 1H); ESI-MS m/z: 809.05 $[M+H]^+$.
Example 37: Synthesis of Compound 8b
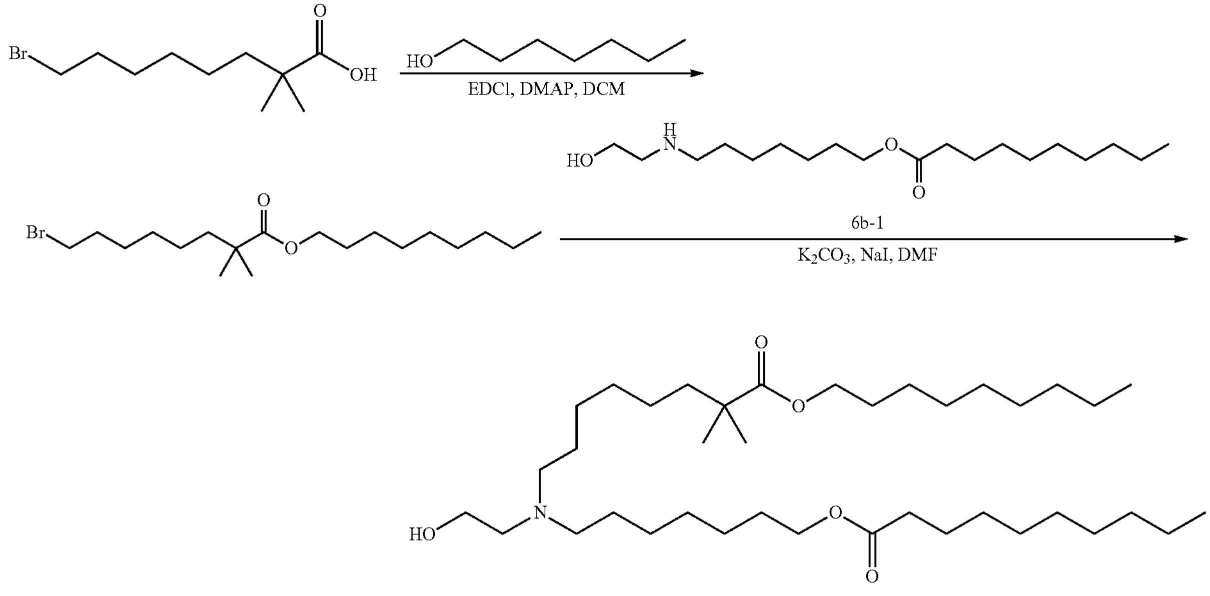
8b
Compound 8b was prepared referring to the method of Example 30 to give 124 mg of an oily product.
$^1$H NMR (400 MHz, $CDCl_3$) δ: 0.85-0.95 (m, 6H), 1.27-1.49 (m, 42H), 1.52-1.63 (m, 12H), 2.26-2.31 (m, 2H), 2.52-2.57 (m, 4H), 2.65-2.68 (m, 2H), 3.47-3.64 (m, 2H), 4.01-4.07 (m, 4H); ESI-MS m/z: 626.65 $[M+H]^+$.

Example 38: Synthesis of Compound 9b

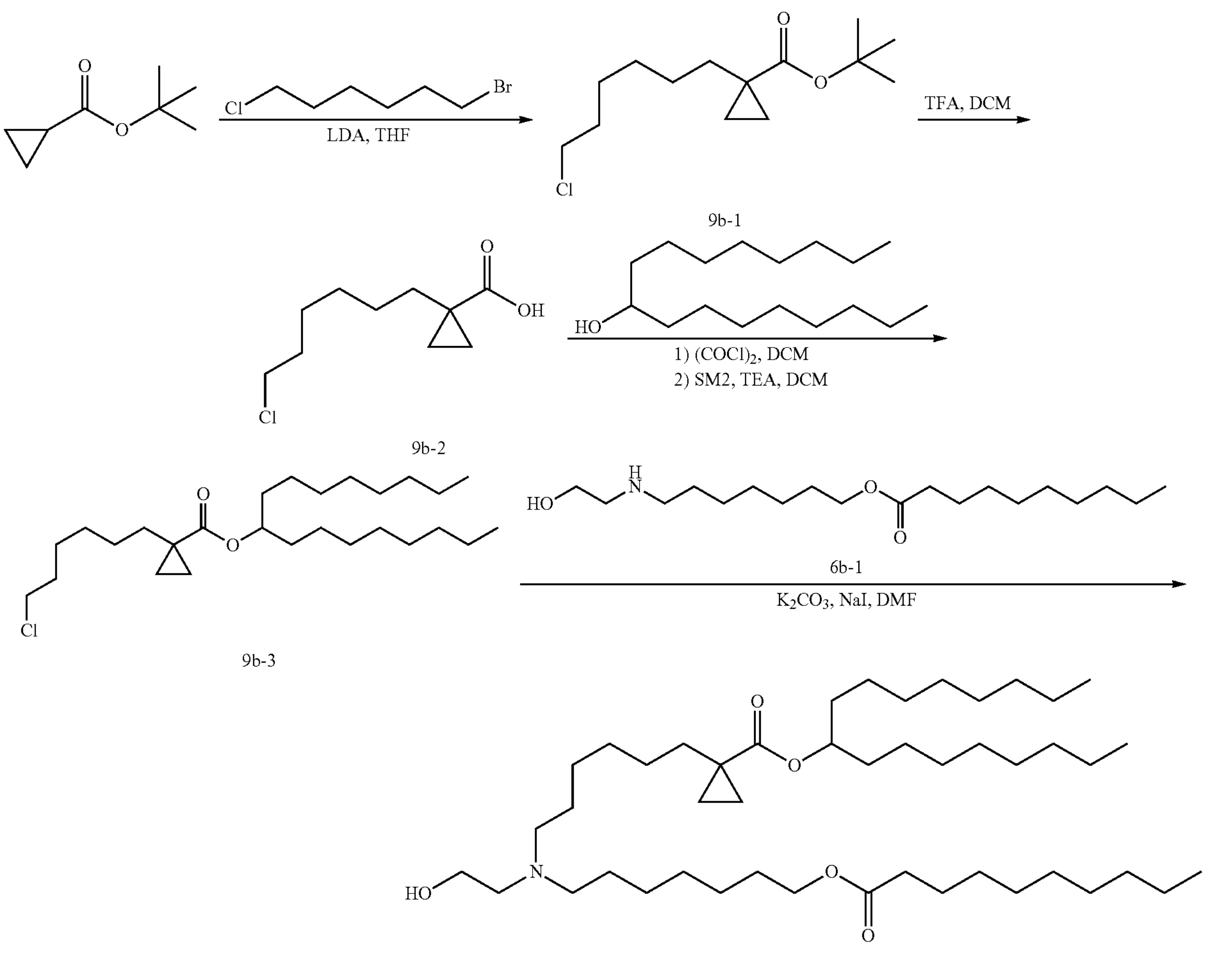

9b-1

9b-2

9b-3

9b tert-Butyl cyclopropanecarboxylate (15.0 g, 150.0 mmol, 1.0 eq.) was dissolved in 150 mL of anhydrous tetrahydrofuran, and the mixture was cooled to −60° C. LDA (150.0 mL, 300.0 mmol, 2.0 eq.) was added to the reaction liquid under nitrogen atmosphere. After the mixture was stirred at the same temperature for reaction for 1 h, 1-bromo-6-chlorohexane (44.9 g, 225.0 mmol, 1.5 eq.) was added, and the mixture was stirred at room temperature for reaction for another 3 h. After the reaction was completed as monitored by TLC, the reaction was quenched with a saturated aqueous ammonium chloride solution, and the mixture was extracted with 3×300 mL of DCM. The organic phases were combined and dried over anhydrous sodium sulfate. The mixture was filtered, and the filtrate was concentrated to dryness to give a crude product, which was purified by silica gel column chromatography to give 19 g of a colorless oily compound 9b-1.

To a solution of compound 9b-1 (10.0 g, 38.3 mmol) in DCM (30.0 mL) was added 10.0 mL of trifluoroacetic acid, and the mixture was stirred at room temperature for 3 h. The reaction solvent was removed by pressurized rotary evaporation to give a crude product, which was purified by silica gel column chromatography to give 6.9 g of a colorless oily compound 9b-2.

Compound 9b-2 (500.0 mg, 2.45 mmol, 2.0 eq.) was dissolved in DCM (5.0 mL), and 2-3 drops of DMF and oxalyl chloride (311.1 mg, 2.45 mmol, 2.0 eq.) were added to the reaction system under an ice bath. After the mixture was stirred for 30 min, the solvent was removed by rotary evaporation under reduced pressure to give an acyl chloride intermediate. The resulting acyl chloride was dissolved in DCM (5.0 mL), then 9-heptadecanol (312.3 mg, 1.22 mmol, 1.0 eq.) and triethylamine (247.5 mg, 2.45 mmol, 2.0 eq.) were added, and the mixture was reacted at room temperature for 5 h. After the reaction was completed, the reaction liquid was poured into 50 mL of water, and the mixture was extracted with DCM. The organic phases were combined and dried over anhydrous sodium sulfate. The mixture was filtered, and the filtrate was concentrated to dryness to give a crude product, which was purified by silica gel column chromatography to give 240 mg of an oily compound 9b-3.

To a solution of compound 9b-3 (200.0 mg, 0.45 mmol, 1.5 eq.) in DMF (3.0 mL) were added potassium carbonate (124.2 mg, 0.90 mmol, 3.0 eq.), sodium iodide (112.5 mg, 0.75 mmol, 2.5 eq.), and compound 6b-1 (99.0 mg, 0.30 mmol, 1.0 eq.). The reaction liquid was heated to 70° C. and stirred for reaction for 5 h. After the reaction was completed, the reaction system was cooled to room temperature. The reaction was quenched with a saturated aqueous sodium chloride solution, and the mixture was extracted with DCM. The organic phases were combined and dried over anhydrous sodium sulfate. The mixture was filtered, and the filtrate was concentrated to dryness to give a crude product, which was purified by preparative liquid chromatography to give 85.4 mg of compound 9b. (Column model: XBridge Shield RP18 OBD Column 19×150 mm, 5 μm; mobile phase A: acetonitrile: water (10 mmol/L ammonium bicarbonate+0.05% aqueous ammonia), mobile phase B: isopropanol: acetonitrile; flow rate: 20 mL/min; gradient: 75% B to 95% B in 9 min).

$^{1}$H NMR (400 MHz, $CDCl_3$) δ: 0.60-0.70 (m, 2H), 0.85-0.95 (m, 9H), 1.13-1.31 (m, 48H), 1.46-1.48 (m, 12H), 1.57-1.63 (m, 4H), 2.26-2.31 (m, 2H), 2.42-2.47 (m, 4H), 2.56-2.59 (m, 2H), 3.50-3.54 (m, 2H), 4.03-4.07 (m, 2H), 4.80-4.84 (m, 1H); ESI-MS m/z: 736.65 $[M+H]^+$.

Example 39: Synthesis of Compound 10b

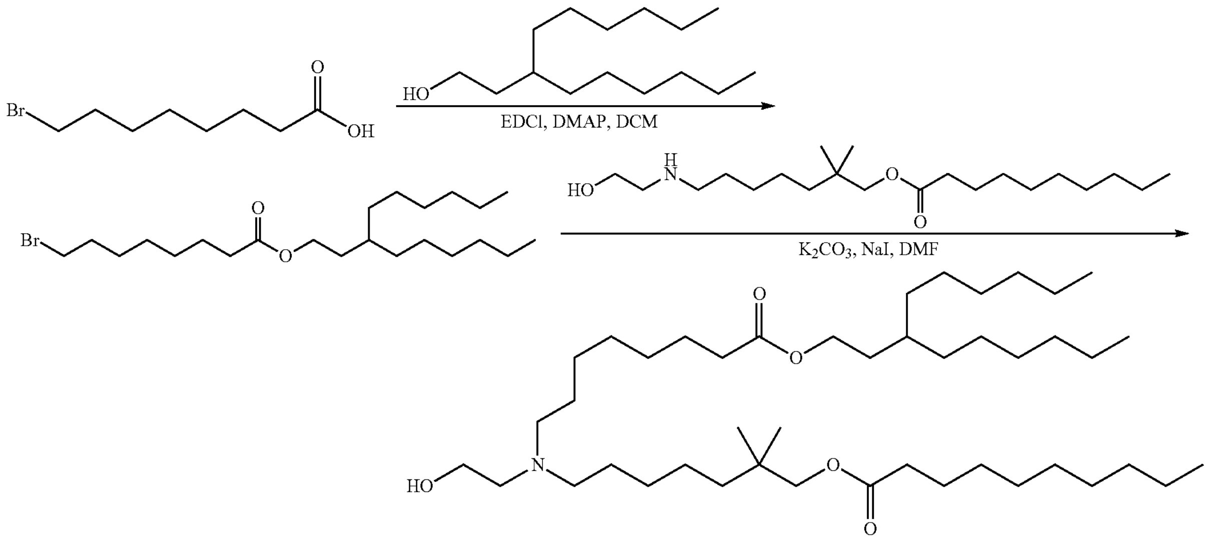

10b

Compound 10b was prepared referring to the method of Example 30 to give 128 mg of an oily product.

$^{1}$H NMR (300 MHz, $CDCl_3$) δ: 0.85-0.95 (m, 15H), 1.12-1.36 (m, 43H), 1.40-1.63 (m, 12H), 2.26-2.31 (m, 4H), 2.42-2.65 (m, 6H), 3.50-3.54 (m, 2H), 3.78 (s, 2H), 4.08 (t, J=7.2 Hz, 2H); ESI-MS m/z: 710.80 $[M+H]^+$.

Example 40: Synthesis of Compound 11b

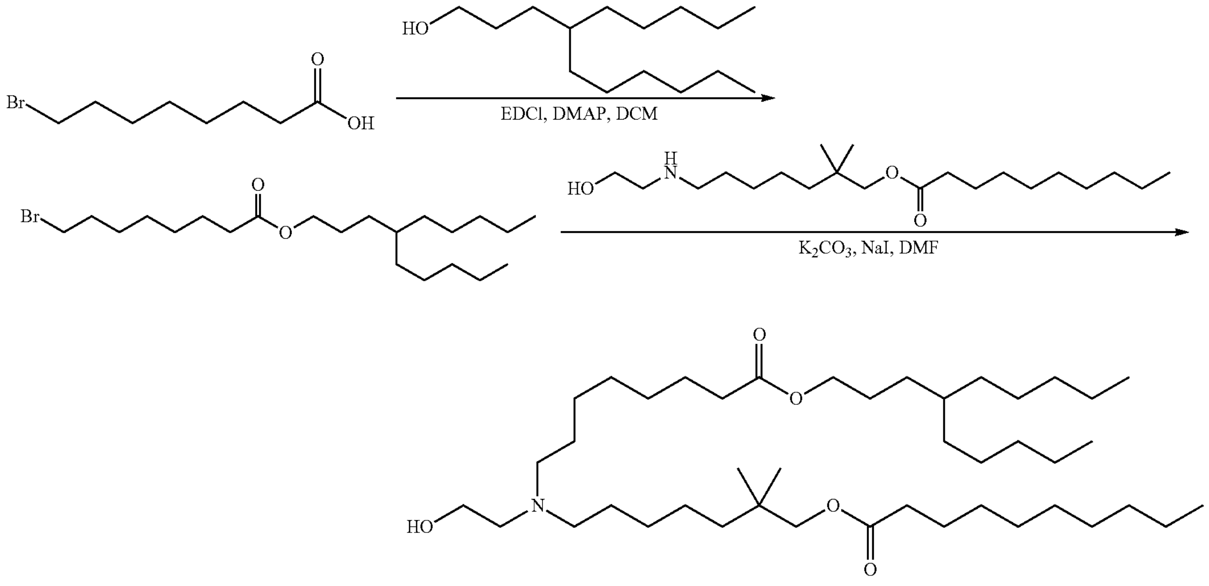

11b

Compound 11b was prepared referring to the method of Example 30 to give 92 mg of an oily product.

$^1H$ NMR (300 MHz, $CDCl_3$) δ: 0.83-0.94 (m, 15H), 1.18-1.42 (m, 43H), 1.48-1.67 (m, 10H), 2.28-2.35 (m, 4H), 2.46-2.52 (m, 4H), 2.61 (t, J=6.6 Hz, 2H), 3.61 (t, J=6.6 Hz, 2H), 3.80 (s, 2H), 4.05 (t, J=6.6 Hz, 2H); ESI-MS m/z: 696.60 $[M+H]^+$.

Example 41: Synthesis of Compound 12b

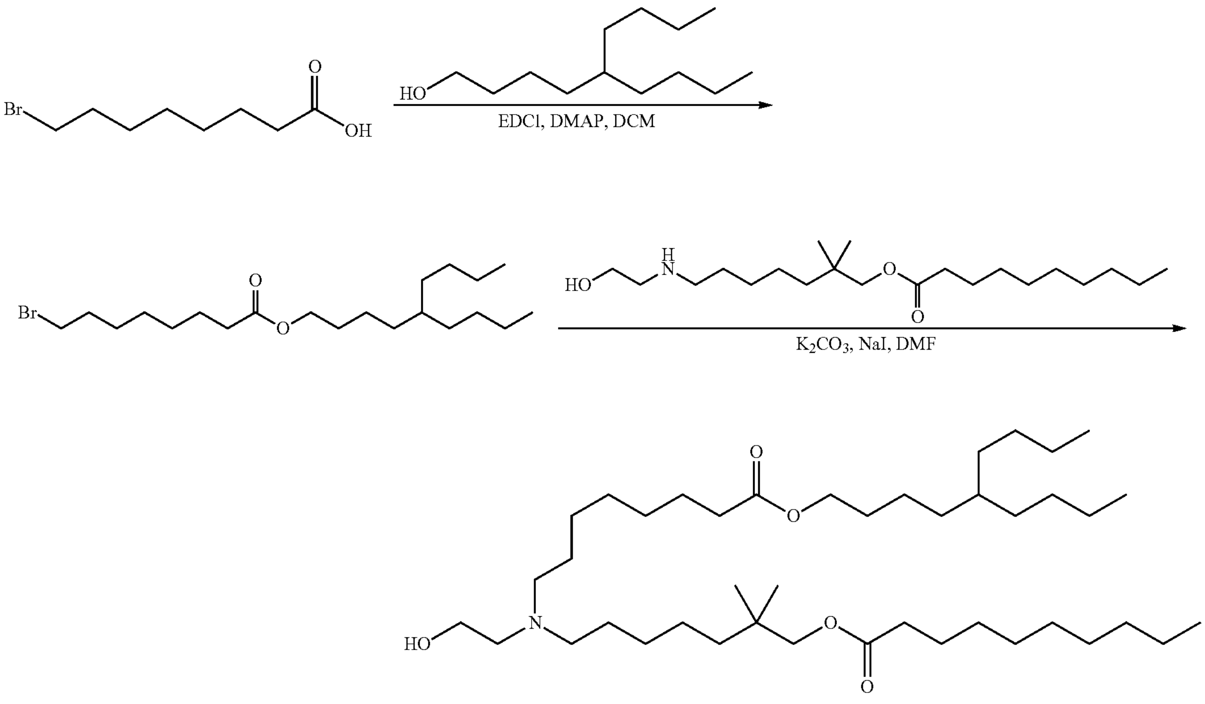

12b

Compound 12b was prepared referring to the method of Example 30 to give 105 mg of an oily product.

$^1H$ NMR (400 MHz, $CDCl_3$) δ: 0.85-0.95 (m, 15H), 1.19-1.34 (m, 41H), 1.42-1.58 (m, 4H), 1.59-1.63 (m, 6H), 2.23 (q, J=7.6 Hz, 4H), 2.53 (q, J=7.6 Hz, 4H), 2.62 (q, J=7.6 Hz, 2H), 3.62 (t, J=6.4 Hz, 2H), 3.80 (s, 2H), 4.07 (t, J=6.4 Hz, 2H); ESI-MS m/z: 682.60 $[M+H]^+$.

The compounds in Table 3 were synthesized using the methods of the above examples, or using similar methods of the corresponding intermediates.

TABLE 3

| |
|---|
| 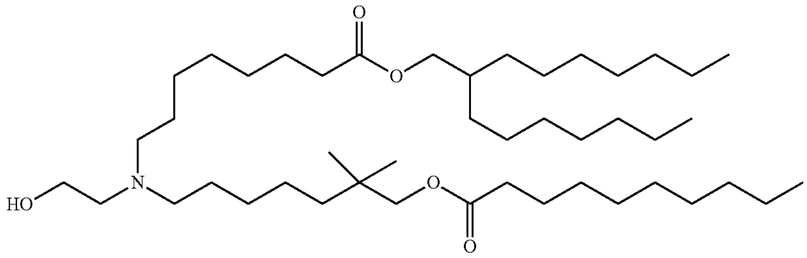 [SMILES: CCCCCCCCCC(=O)OCC(C)(C)CCCCCN(CCO)CCCCCCCC(=O)OCC(CCCCCCC)CCCCCCC] Example 42: Compound 13b $[M + H]^+$: 724.80 |

TABLE 3-continued
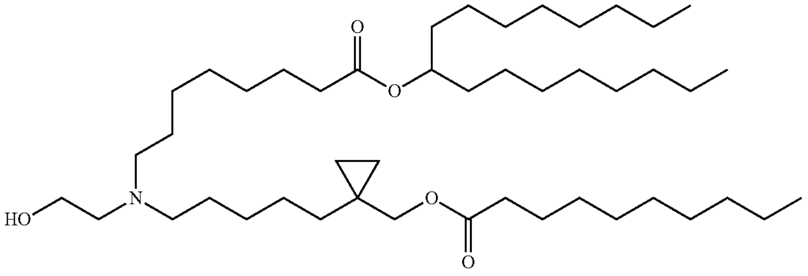 [SMILES: CCCCCCCCCC(=O)OCC1(CCCCCN(CCO)CCCCCCCC(=O)OC(CCCCCCCC)CCCCCCCC)CC1]
Example 43: Compound 14b
[M + H]+: 736.70
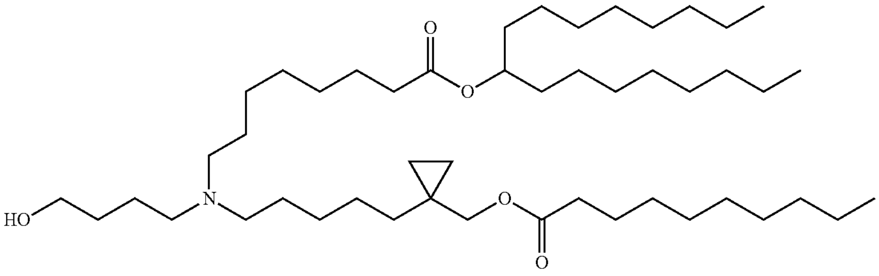 [SMILES: CCCCCCCCCC(=O)OCC1(CCCCCN(CCCCO)CCCCCCCC(=O)OC(CCCCCCCC)CCCCCCCC)CC1]
Example 44: Compound 15b
[M + H]+: 764.70
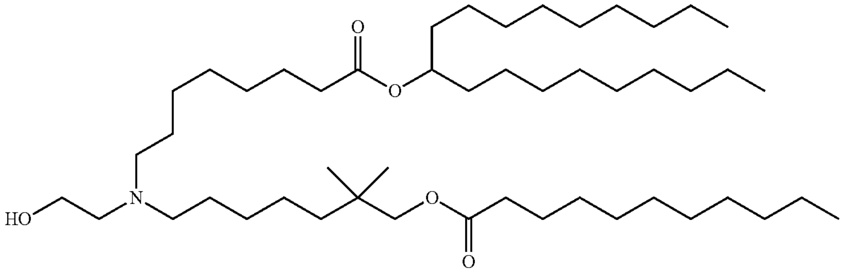 [SMILES: CCCCCCCCCCC(=O)OCC(C)(C)CCCCCN(CCO)CCCCCCCC(=O)OC(CCCCCCCCC)CCCCCCCCC]
Example 45: Compound 16b
[M + H]+: 780.80
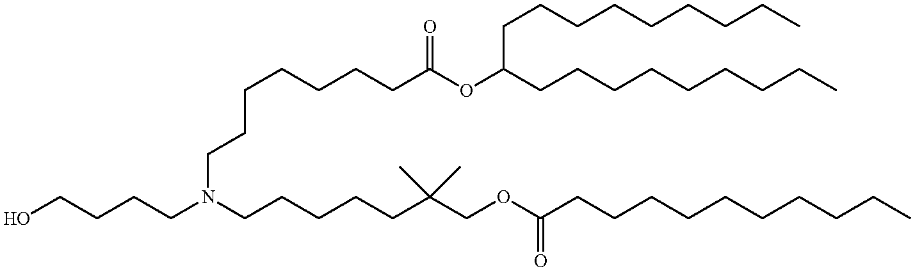 [SMILES: CCCCCCCCCCC(=O)OCC(C)(C)CCCCCN(CCCCO)CCCCCCCC(=O)OC(CCCCCCCCC)CCCCCCCCC]
Example 46: Compound 17b
[M + H]+: 808.80

TABLE 3-continued
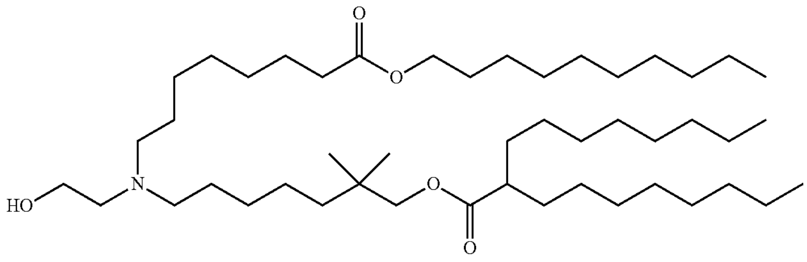 [SMILES: CCCCCCCCCCOC(=O)CCCCCCCN(CCO)CCCCCC(C)(C)COC(=O)C(CCCCCCCC)CCCCCCCC]
Example 47: Compound 18b
$[M + H]^+$: 752.85
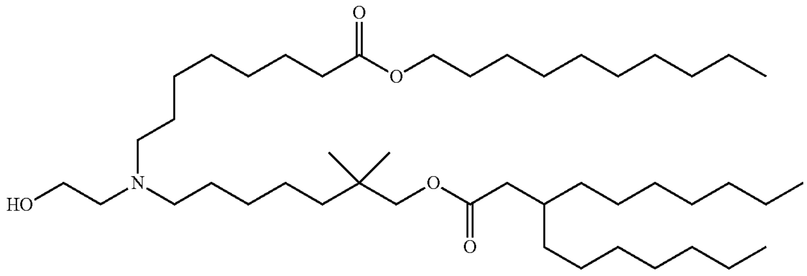 [SMILES: CCCCCCCCCCOC(=O)CCCCCCCN(CCO)CCCCCC(C)(C)COC(=O)CC(CCCCCCC)CCCCCCC]
Example 48: Compound 19b
$[M + H]^+$: 738.65
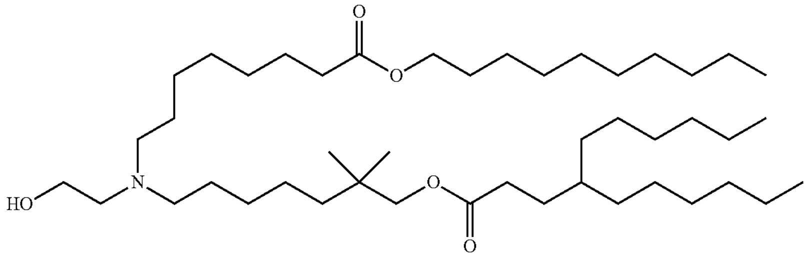 [SMILES: CCCCCCCCCCOC(=O)CCCCCCCN(CCO)CCCCCC(C)(C)COC(=O)CCC(CCCCCC)CCCCCC]
Example 49: Compound 20b
$[M + H]^+$: 724.80
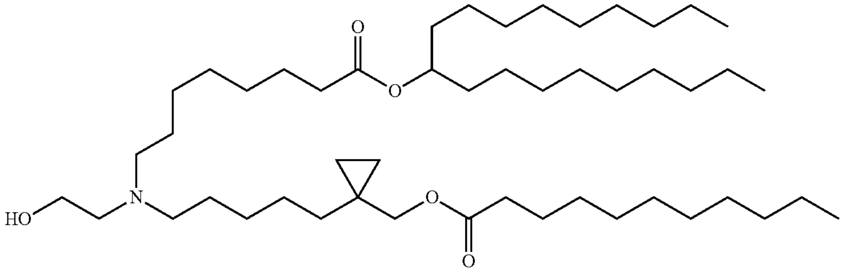 [SMILES: CCCCCCCCCCC(=O)OCC1(CCCCCN(CCO)CCCCCCCC(=O)OC(CCCCCCCCC)CCCCCCCCC)CC1]
Example 50: Compound 21b
$[M + H]^+$: 778.75
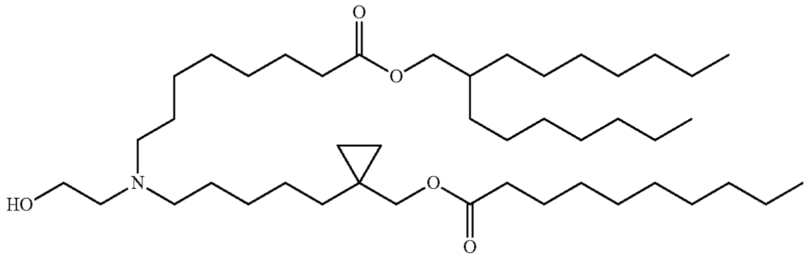 [SMILES: CCCCCCCCCC(=O)OCC1(CCCCCN(CCO)CCCCCCCC(=O)OCC(CCCCCCC)CCCCCCC)CC1]
Example 51: Compound 22b
$[M + H]^+$: 722.75

TABLE 3-continued
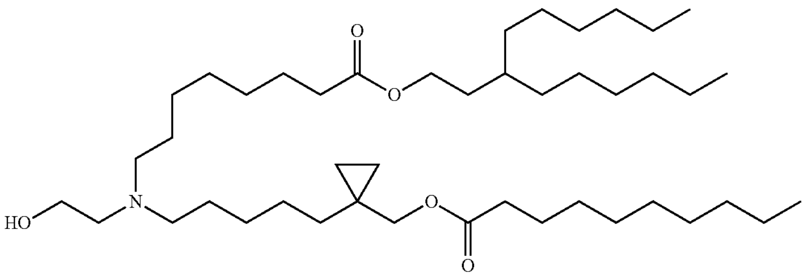 [SMILES: CCCCCCCCCC(=O)OCC1(CCCCCN(CCO)CCCCCCCC(=O)OCCC(CCCCCC)CCCCCC)CC1]
Example 52: Compound 23b
[M + H]+: 708.70
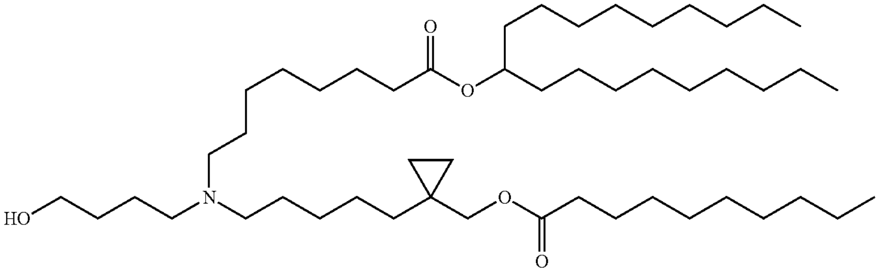 [SMILES: CCCCCCCCCC(=O)OCC1(CCCCCN(CCCCO)CCCCCCCC(=O)OC(CCCCCCCCC)CCCCCCCCC)CC1]
Example 53: Compound 24b
[M + H]+: 792.70
Example 54: Synthesis of Compound 30a
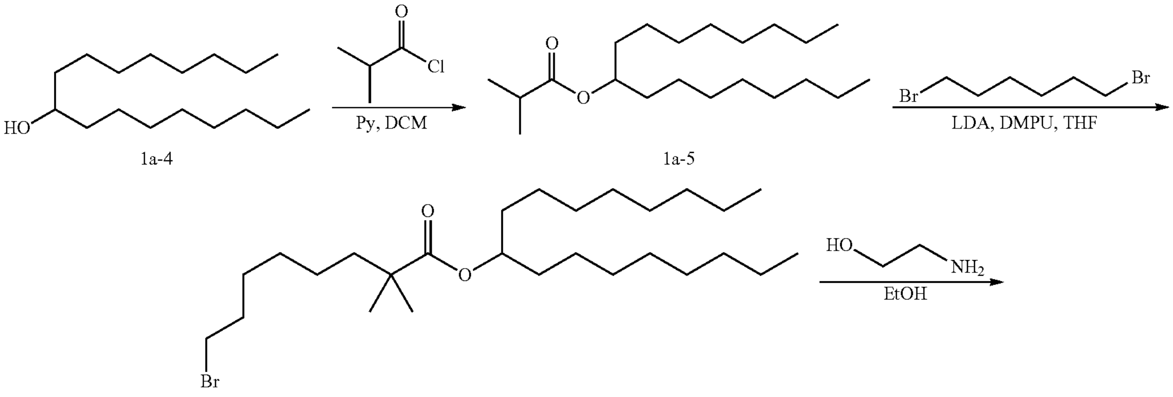
1a-4
1a-5
1a-6
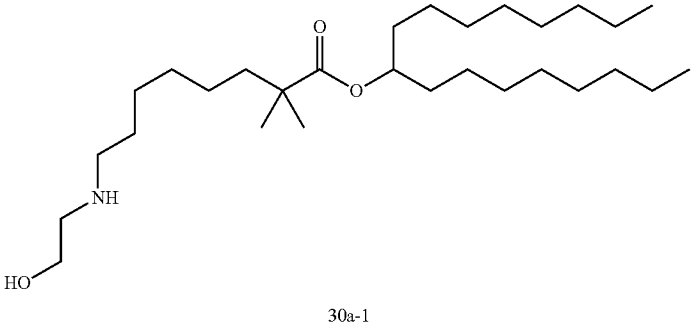
30a-1

-continued

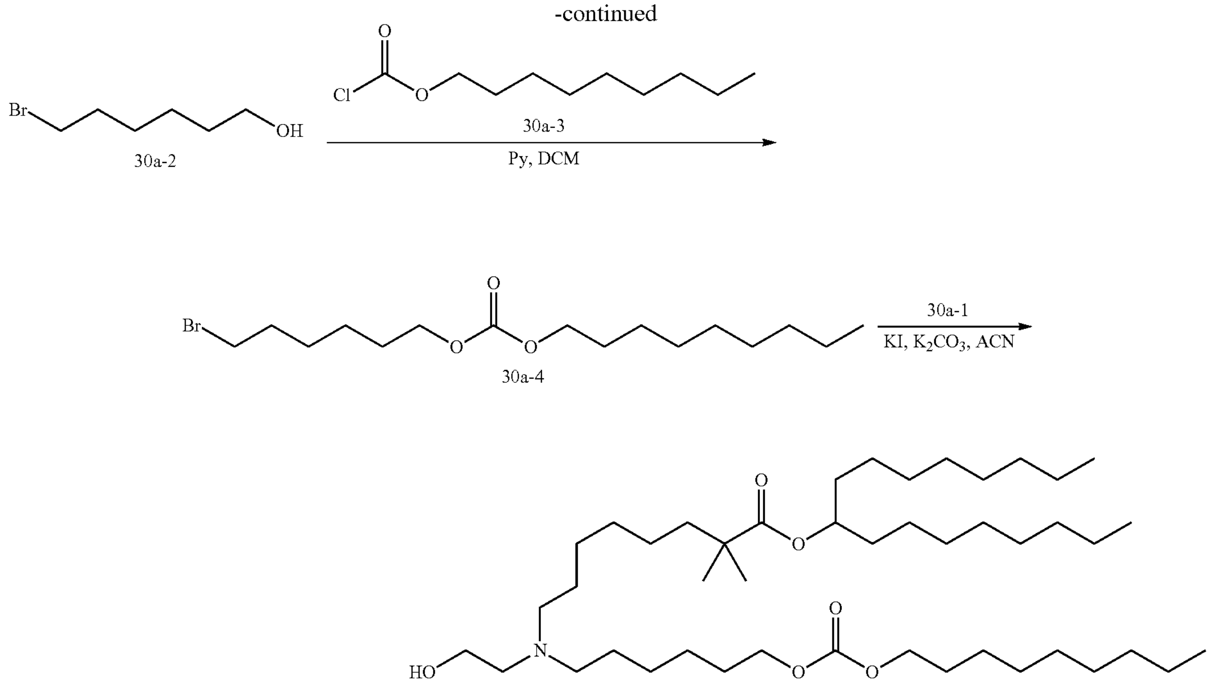

30a-2

30a-3

30a-4

30a

In a 250 mL round-bottom flask, 9-heptadecanol (10.0 g, 39.0 mmol, 1.0 eq.) and pyridine (6.17 g, 78.0 mmol, 2.0 eq.) were dissolved in 100 mL of dichloromethane, and then the reaction system was cooled to 0° C. Isobutyryl chloride (10.39 g, 97.5 mmol, 2.5 eq.) was slowly added to the reaction liquid, and then the mixture was stirred at room temperature for 2 h. Water was added to quench the reaction at 0° C., and the mixture was extracted with DCM. The organic phases were combined, dried over anhydrous $Na_2SO_4$, and filtered to remove the drying agent, and the solvent was removed by rotary evaporation. The resulting crude product was purified by silica gel column chromatography to give a yellow oily compound 1a-5 (10.4 g).

Compound 1a-5 (10.0 g, 30.62 mmol, 1.0 eq.) was dissolved in anhydrous THF (100 mL), the reaction system was cooled to −40° C., and LDA (15.3 mL, 30.6 mmol, 1.0 eq.) was added to the reaction liquid under nitrogen atmosphere. After the mixture was stirred for reaction at −40° C. for 1 h, 1,6-dibromohexane (14.9 g, 61.2 mmol, 2.0 eq.) and DMPU (471 mg, 3.7 mmol, 0.12 eq.) were added at the same temperature. The reaction system was slowly warmed to room temperature and then reacted overnight. After the reaction was completed, the reaction liquid was added to a saturated $NH_4C_1$ solution, and the mixture was extracted with DCM. The organic phases were combined, dried over anhydrous $Na_2SO_4$, and filtered to remove the drying agent, and the solvent was removed by rotary evaporation to give a crude compound 1a-6, which was directly used in the next step without purification.

Compound 1a-6 (15 g, 30.6 mmol, 1.0 eq.) and ethanolamine (37.4 g, 612.0 mmol, 20.0 eq.) were dissolved in 80 mL of ethanol, and the reaction system was heated to 60° C. and reacted for 2 h. After the reaction was completed, the reaction system was cooled to room temperature, the ethanol solvent was removed by rotary evaporation, the crude product was dissolved in ethyl acetate, and then a saturated sodium chloride solution was added. After extraction, the organic phases were combined, dried over anhydrous $Na_2SO_4$, and filtered to remove the drying agent, and the solvent was removed by rotary evaporation. The resulting crude product was purified by silica gel column chromatography to give a yellow oily compound 30a-1 (12.4 g).

In a 50 mL reaction flask, 6-bromo-1-hexanol (1.5 g, 8.3 mmol, 1.0 eq.) and pyridine (1.31 g, 16.6 mmol, 2.0 eq.) were dissolved in 15 mL of DCM, n-nonyl chloroformate (1.88 g, 9.1 mmol, 1.1 eq.) was added dropwise within 15 min under an ice bath, and the mixture was left at room temperature overnight. A saturated aqueous ammonium chloride solution was added to quench the reaction, and the mixture was extracted with DCM. The organic phases were combined, dried over anhydrous $Na_2SO_4$, and filtered to remove the drying agent, and the solvent was removed by rotary evaporation. The resulting crude product was purified by silica gel column chromatography to give a yellow oily compound 30a-4 (2.5 g).

In an 8 mL sealed tube, compound 30a-4 (200 mg, 0.57 mmol, 1.0 eq.), compound 30a-1 (294.2 mg, 0.63 mmol, 1.1 eq.), KI (113.4 mg, 0.68 mmol, 1.2 eq.), $K_2CO_3$ (236.0 mg, 1.71 mmol, 3.0 eq.), and 5.0 mL of anhydrous acetonitrile were added. The mixture was heated to 80° C., stirred for reaction overnight, cooled to room temperature, and filtered. After the filter cake was washed with acetonitrile, the organic phases were combined, and the solvent was removed by rotary evaporation to give a reaction crude product. The crude product was purified by preparative liquid chromatography to give compound 30a (87.9 mg).

$^1H$ NMR (400 MHz, $CDCl_3$) δ: 4.83 (m, 1H), 4.12 (t, J=6.6 Hz, 4H), 3.61 (m, 2H), 2.62 (m, 6H), 1.70-1.63 (m, 4H), 1.50 (m, 8H), 1.26 (m, 49H), 1.15 (s, 6H), 0.88 (t, J=6.6 Hz, 9H); ESI-MS m/z: 740.55 $[M+H]^+$.

Example 55: Synthesis of Compound 31a

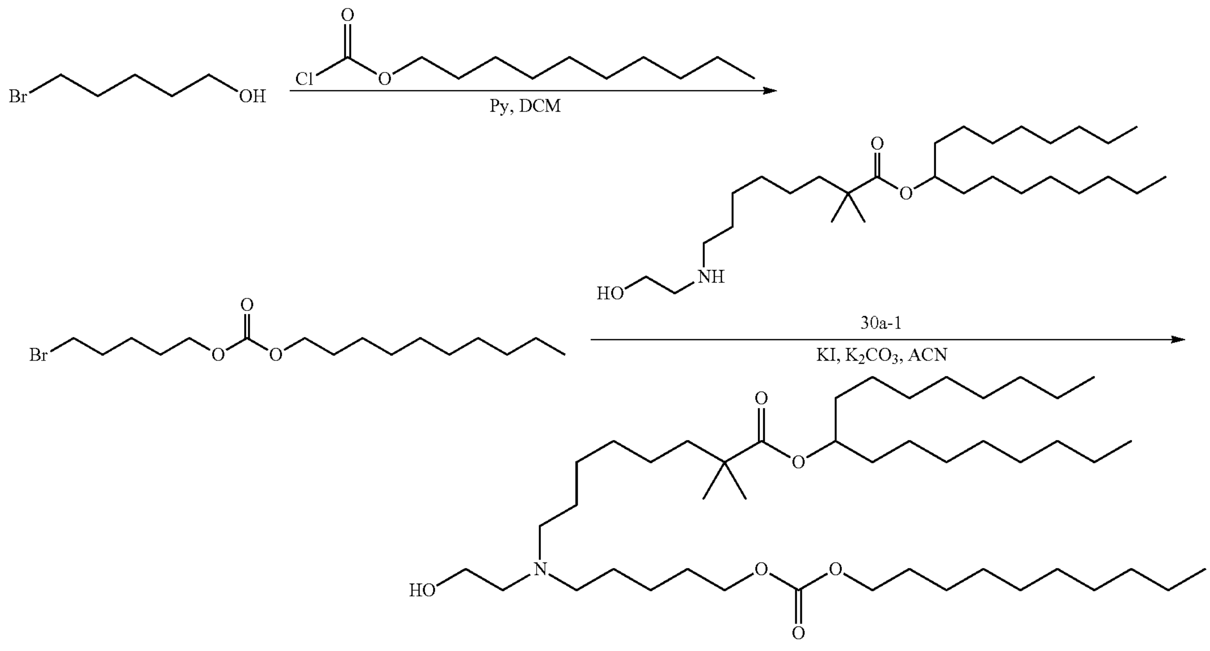

31a

Compound 31a was prepared referring to the method of Example 54 to give 80.7 mg of an oily product.

$^1$H NMR (400 MHz, $CDCl_3$) δ: 4.83 (p, J=6.6 Hz, 1H), 4.12 (td, J=7.2, 2.4 Hz, 4H), 3.61 (m, 2H), 2.61 (m, 6H), 1.68 (m, 4H), 1.50 (m, 8H), 1.26 (m, 49H), 1.15 (s, 6H), 0.88 (t, J=6.6 Hz, 9H); ESI-MS m/z: 740.65 [M+H]$^+$.

Example 56: Synthesis of Compound 32a

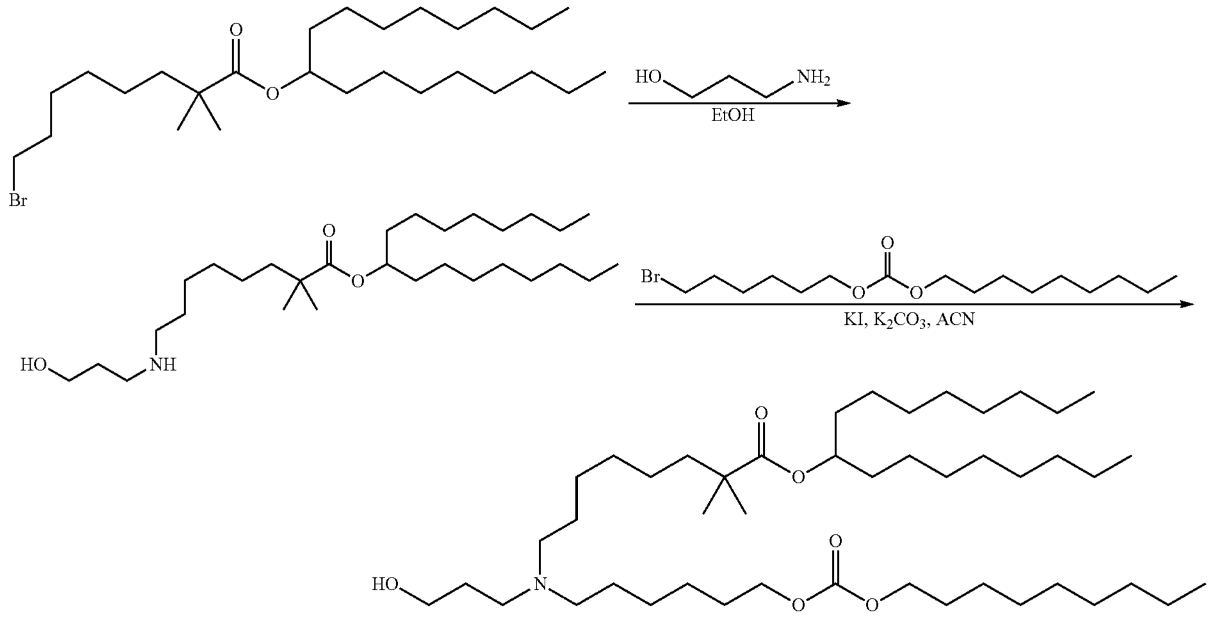

32a

Compound 32a was prepared referring to the method of Example 54 to give 93.9 mg of an oily product.

$^1$H NMR (300 MHz, $CDCl_3$) δ: 4.85 (p, J=6.6 Hz, 1H), 4.12 (t, J=6.6 Hz, 4H), 3.79 (t, J=5.1 Hz, 2H), 2.65 (m, 2H), 2.42 (m, 4H), 1.77-1.64 (m, 6H), 1.51 (t, J=6.0 Hz, 10H), 1.28 (d, J=4.5 Hz, 47H), 1.17 (s, 6H), 0.88 (t, J=6.6 Hz, 9H); ESI-MS m/z: 754.60 [M+H]$^+$.

Example 57: Synthesis of Compound 33a
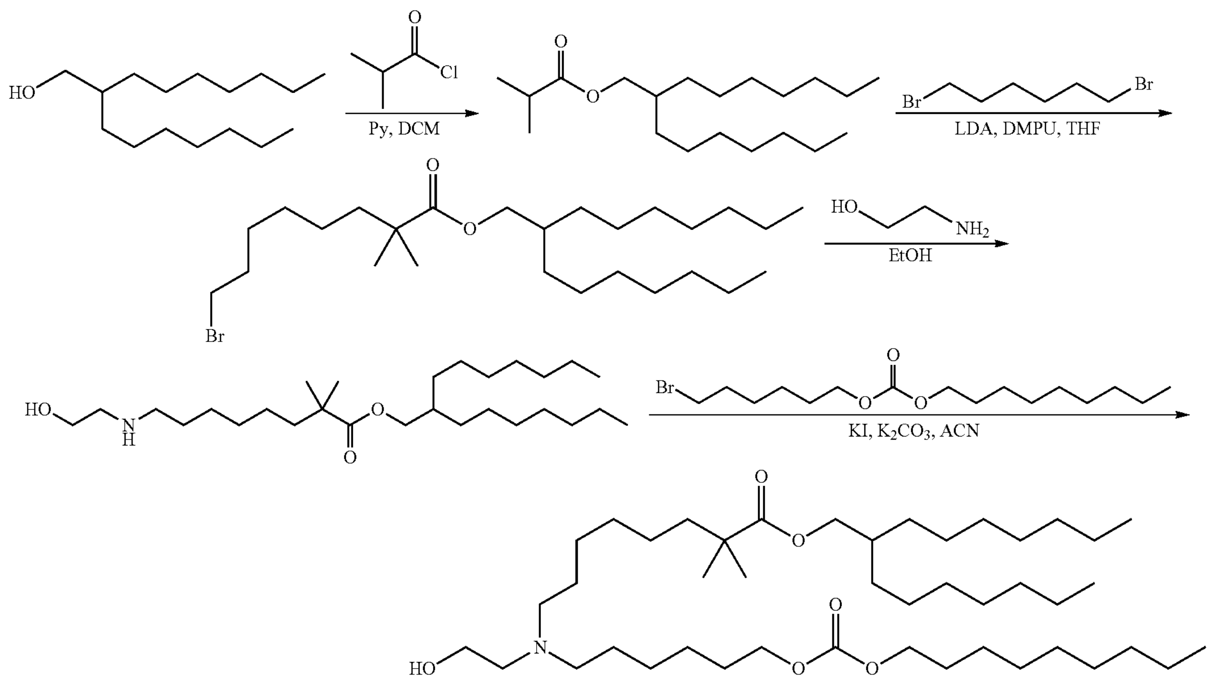
33a
Compound 33a was prepared referring to the method of Example 54 to give 164.2 mg of an oily product.
$^1$H NMR (400 MHz, $CDCl_3$) δ: 4.12 (t, J=6.8 Hz, 4H), 3.95 (d, J=5.6 Hz, 2H), 3.54 (t, J=5.2 Hz, 2H), 2.59 (t, J=5.2 Hz, 2H), 2.50-2.41 (m, 4H), 1.67 (m, 5H), 1.53-1.19 (m, 53H), 1.16 (s, 6H), 0.88 (t, J=6.8 Hz, 9H); ESI-MS m/z: 726.50 $[M+H]^+$.
Example 58: Synthesis of Compound 34a
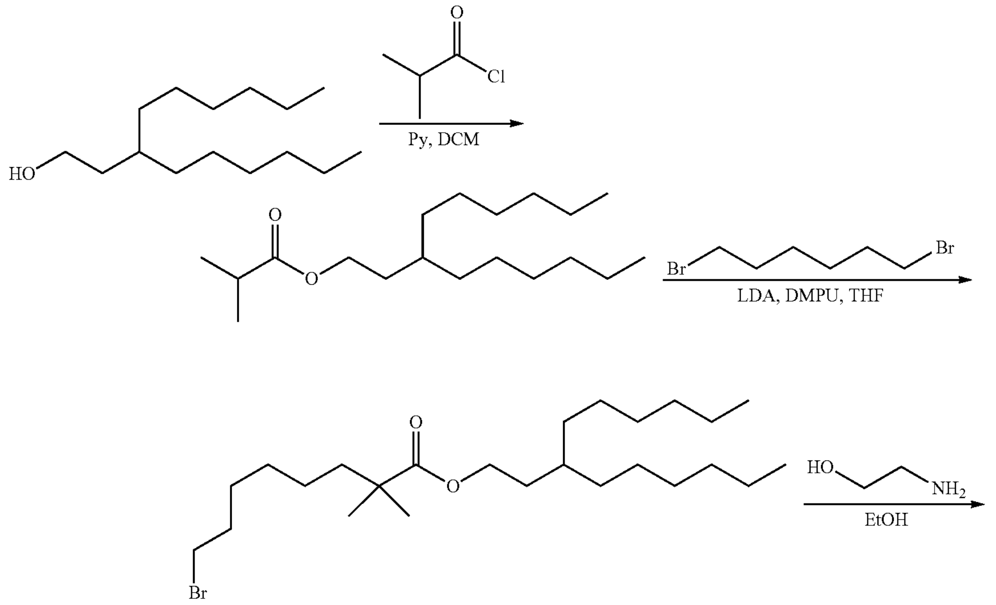

-continued

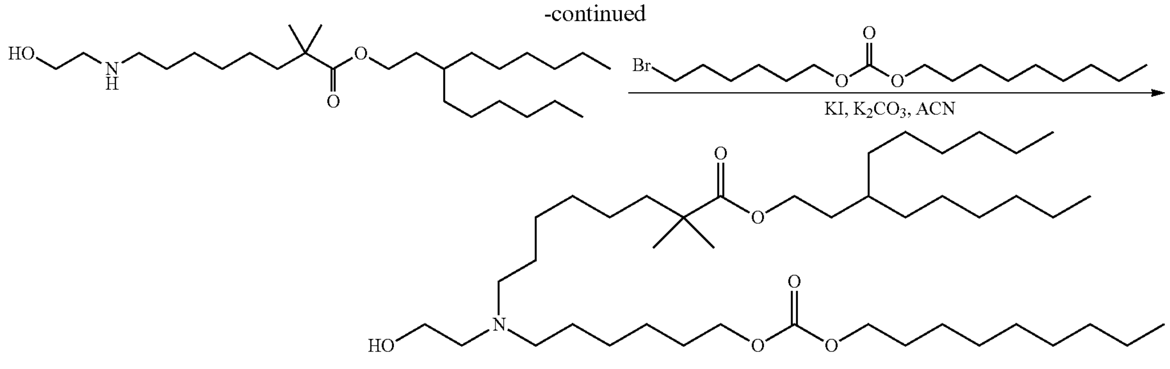

34a

Compound 34a was prepared referring to the method of Example 54 to give 150.1 mg of an oily product.

$^1$H NMR (400 MHz, $CDCl_3$) δ: 4.12 (t, J=6.8 Hz, 4H), 4.08 (t, J=6.8 Hz, 2H), 3.56 (m, 2H), 2.61-2.48 (m, 6H), 1.66 (m, 5H), 1.61-1.26 (m, 51H), 1.15 (s, 6H), 0.88 (t, J=6.8 Hz, 9H); ESI-MS m/z: 712.60 $[M+H]^+$.

Example 59: Synthesis of Compound 35a

Compound 35a was prepared referring to the method of Example 54 to give 217.9 mg of an oily product.

$^1$H NMR (400 MHz, $CDCl_3$) δ: 4.12 (t, J=6.8 Hz, 4H), 4.03 (t, J=6.8 Hz, 2H), 3.53 (t, J=5.2 Hz, 2H), 2.58 (t, J=5.2 Hz, 2H), 2.47-2.40 (m, 4H), 1.73-1.62 (m, 6H), 1.60-1.19 (m, 48H), 1.16 (s, 6H), 0.88 (t, J=6.8 Hz, 9H); ESI-MS m/z: 698.55 $[M+H]^+$.

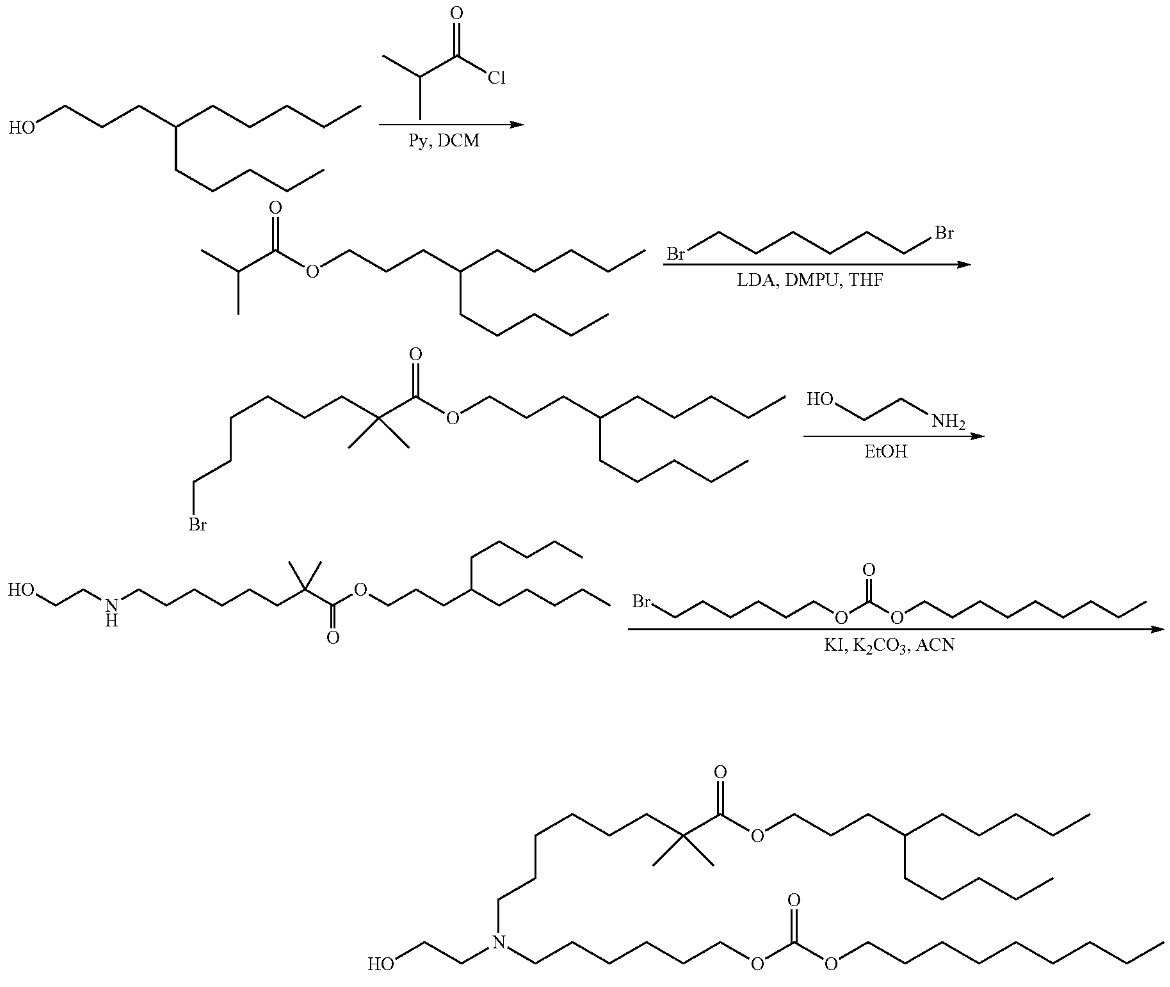

35a

Example 60: Synthesis of Compound 36a

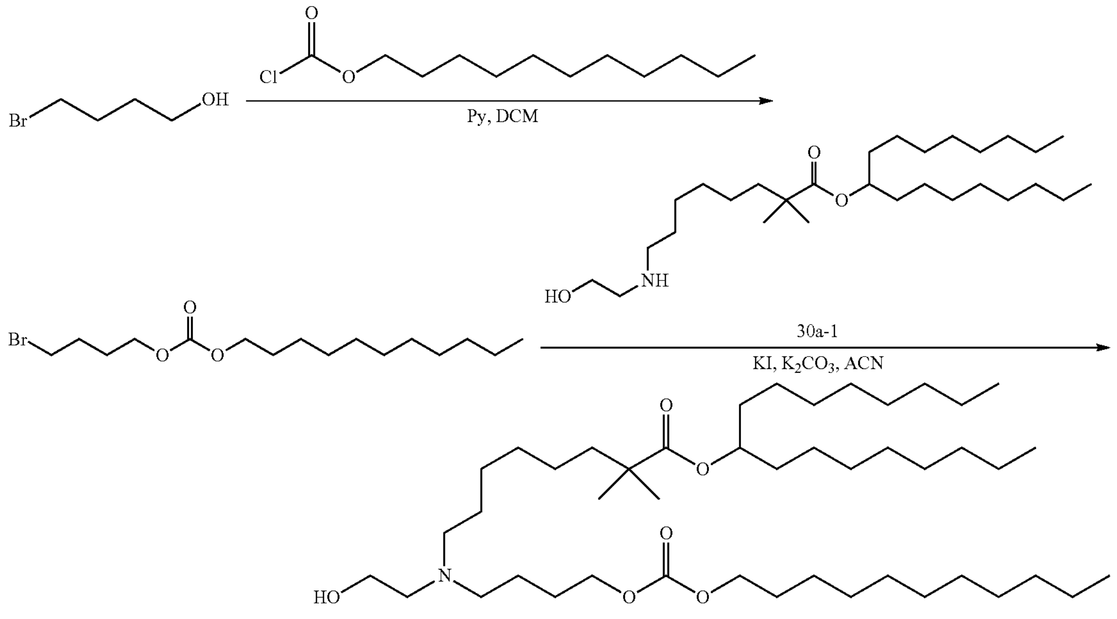

36a

Compound 36a was prepared referring to the method of Example 54 to give 169.7 mg of an oily product.

$^1$H NMR (300 MHz, $CDCl_3$) δ: 4.83 (p, J=6.6 Hz, 1H), 4.16-4.10 (m, 4H), 3.53 (t, J=5.1 Hz, 2H), 2.58 (t, J=5.1 Hz, 2H), 2.52-2.42 (m, 4H), 1.67 (m, 4H), 1.59-1.18 (m, 57H), 1.15 (s, 6H), 0.89 (t, J=6.6 Hz, 9H); ESI-MS m/z: 740.60 $[M+H]^+$.

Example 61: Synthesis of Compound 37a

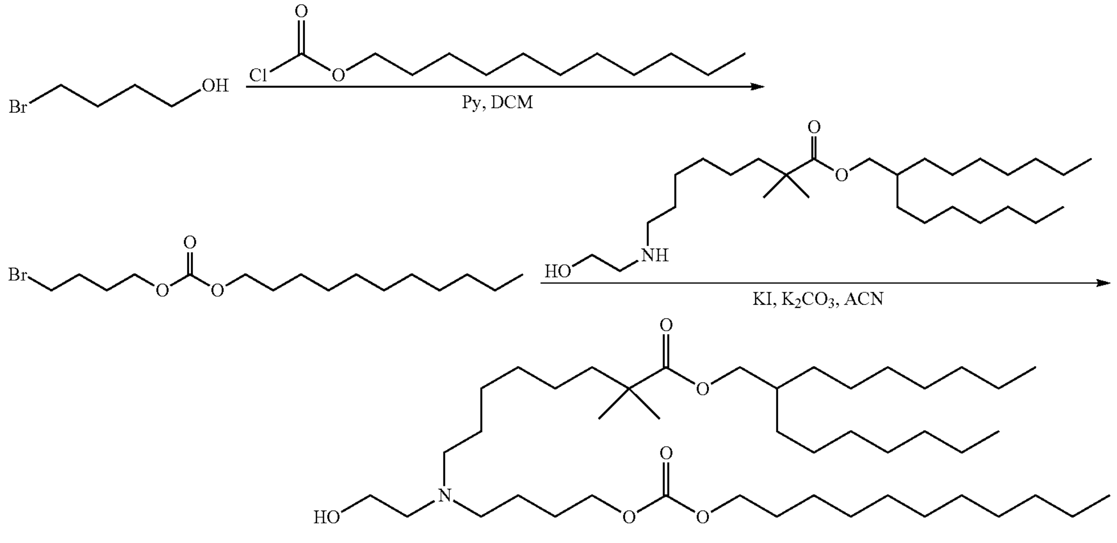

37a

Compound 37a was prepared referring to the method of Example 54 to give 59.4 mg of an oily product.

$^1$H NMR (400 MHz, $CDCl_3$) δ: 4.12 (q, J=6.8 Hz, 4H), 3.95 (d, J=5.2 Hz, 2H), 3.58 (m, 2H), 2.64-2.51 (m, 6H), 1.74-1.43 (m, 12H), 1.39-1.19 (m, 46H), 1.16 (s, 6H), 0.88 (t, J=6.8 Hz, 9H); ESI-MS m/z: 726.50 $[M+H]^+$.

Example 62: Synthesis of Compound 38a
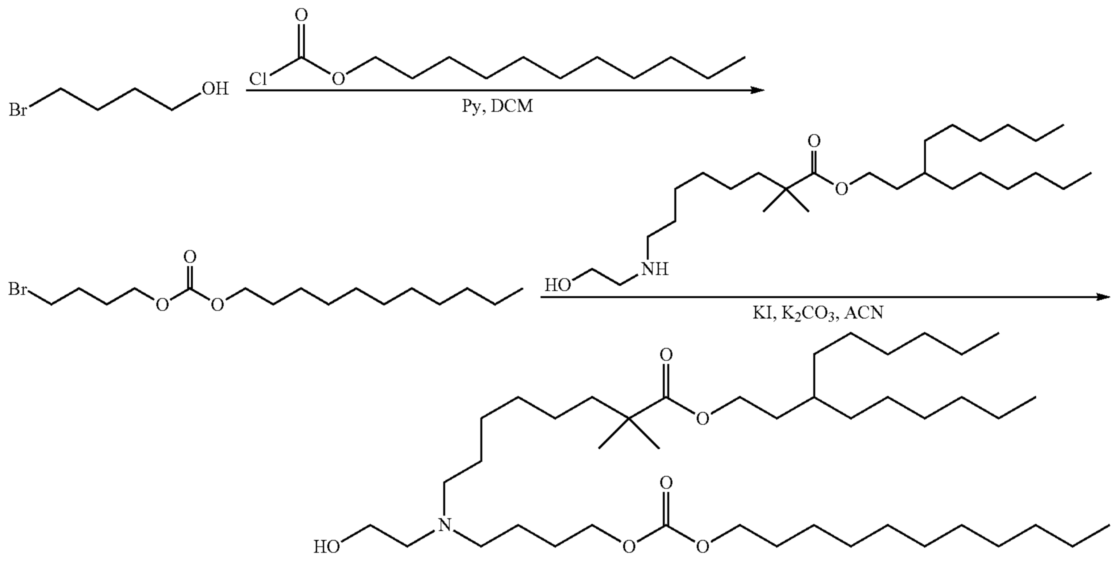
38a
Compound 38a was prepared referring to the method of Example 54 to give 44.8 mg of an oily product.
$^1$H NMR (300 MHz, $CDCl_3$) δ: 4.16-4.04 (m, 6H), 3.62 (m, 2H), 2.69-2.58 (m, 6H), 1.74-1.41 (m, 12H), 1.39-1.18 (m, 44H), 1.15 (s, 6H), 0.92-0.87 (m, 9H); ESI-MS m/z: 712.55 $[M+H]^+$.
Example 63: Synthesis of Compound 39a
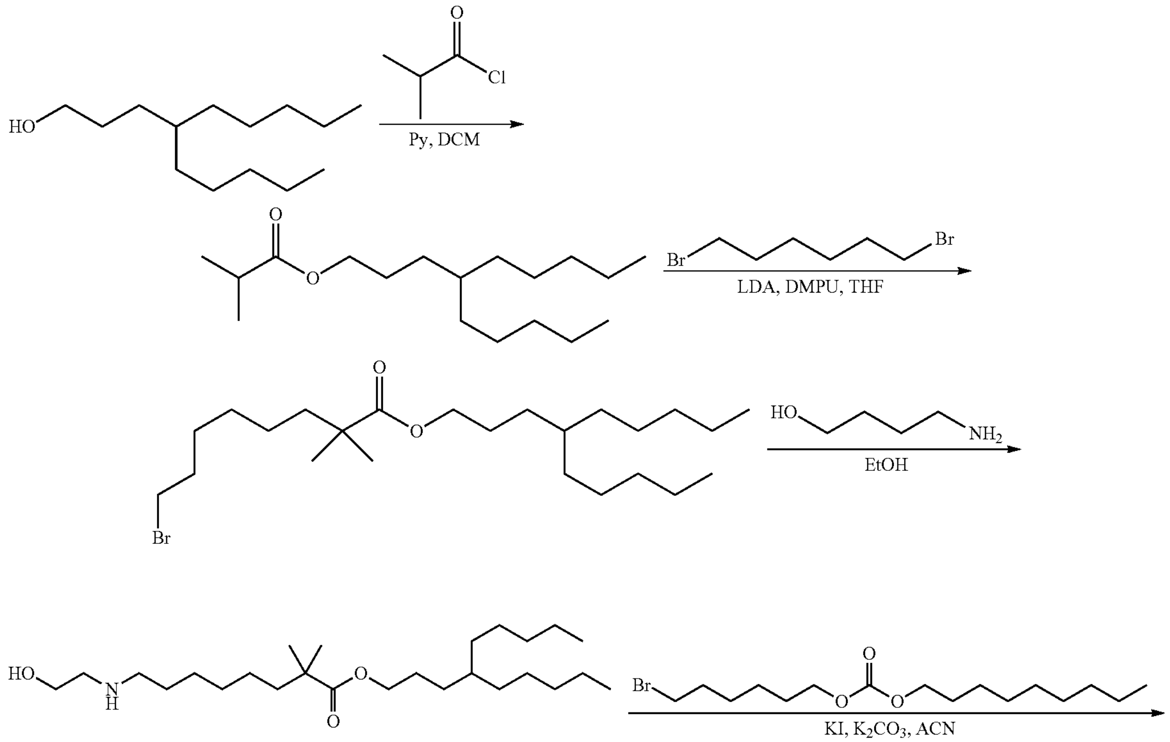

-continued

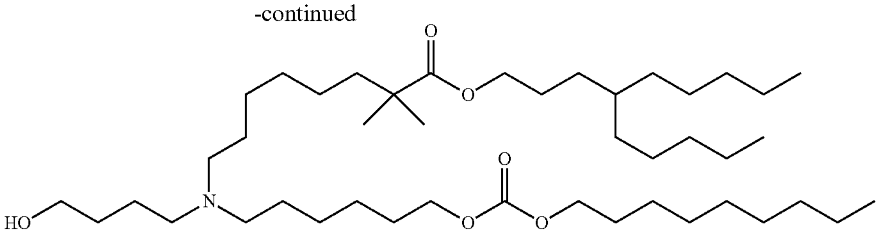

39a

Compound 39a was prepared referring to the method of Example 54 to give 105.4 mg of an oily product.

$^1H$ NMR (400 MHz, $CDCl_3$) δ: 4.13-4.10 (m, 4H), 4.03 (t, J=6.8 Hz, 2H), 3.56 (m, 2H), 2.46 (m, 6H), 1.73-1.67 (m, 8H), 1.64-1.19 (m, 50H), 1.15 (s, 6H), 0.88 (m, 9H); ESI-MS m/z: 726.50 $[M+H]^+$.

Example 64: Synthesis of Compound 40a

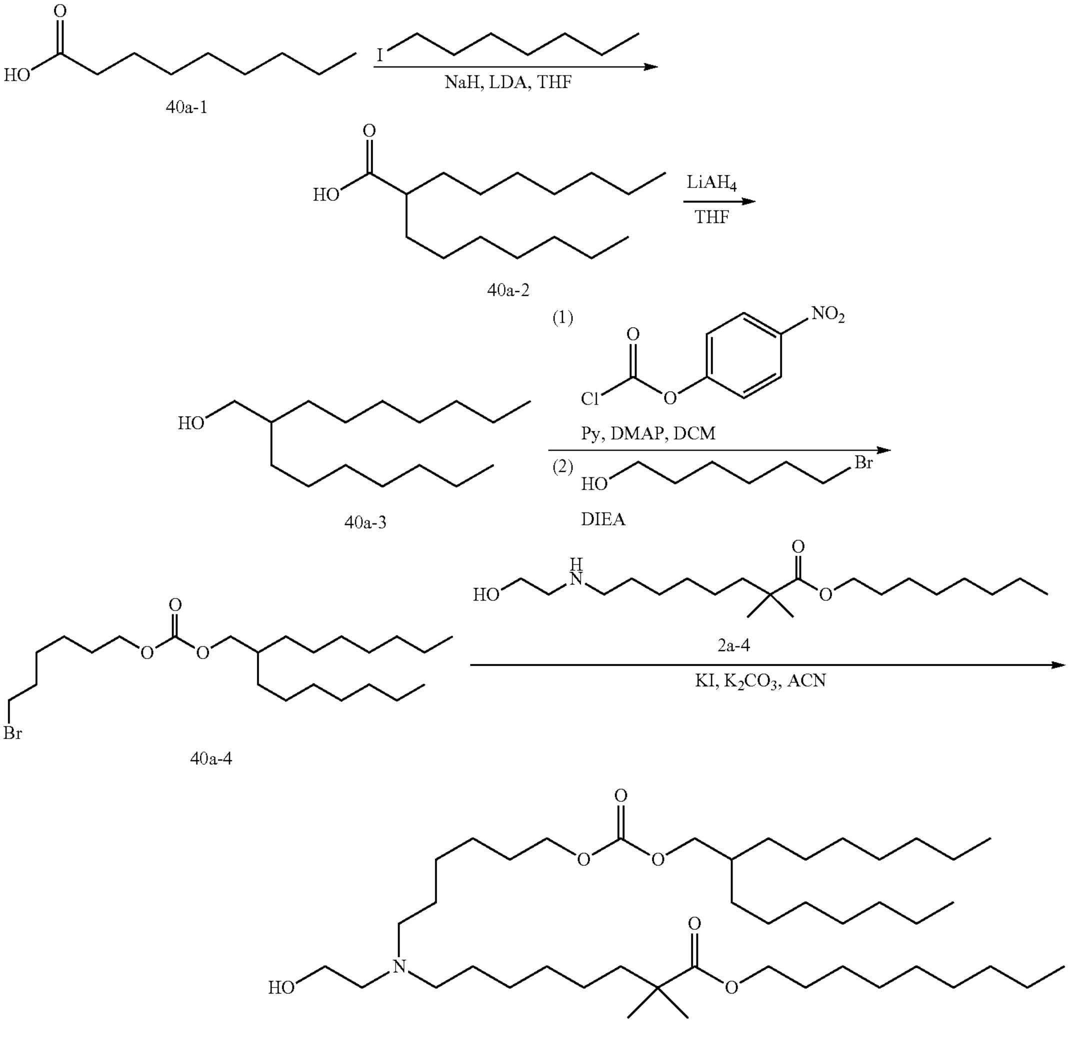

40a

In a 500 mL round-bottom flask, nonanoic acid (15.0 g, 94.8 mmol, 1.0 eq.) and THF (150 mL), were added at room temperature under nitrogen atmosphere. The system was cooled to 0° C., NaH (3.64 g, 151.7 mmol, 1.6 eq.) was sequentially added in batches, and LDA (85.3 mL, 170.6 mmol, 1.8 eq., 2 M in THF) was added dropwise. The mixture was stirred at room temperature for 1 h, and 1-iodoheptane (23.6 g, 104.3 mmol, 1.1 eq.) was added to the system at 0° C. The system was stirred at 80° C. overnight. The reaction was monitored by TLC, and a new spot of the product was found. The reaction was cooled to room temperature, ice water was added to quench the reaction, and the mixture was extracted 3 times with DCM. The organic phases were combined and washed once with a saturated NaCl solution, dried over $Na_2SO_4$, filtered, and concentrated. The crude product was purified by silica gel column chromatography to give yellow oily 2-heptylnonanoic acid (16.36 g).

In a 250 mL round-bottom flask, 2-heptylnonanoic acid (7.0 g, 27.3 mmol, 1.0 eq.) was dissolved in 70 mL of anhydrous THF at room temperature, the system was cooled to 0° C., and $LiAlH_4$ (16.38 mL, 2.5 M in THF) was added dropwise within 30 min. After the dropwise addition was completed, the mixture was warmed to room temperature and stirred for 2 h. The reaction was monitored by TLC, and the conversion of the starting material was completed. The reaction liquid was poured into a saturated sodium chloride solution to quench the reaction, the mixture was extracted with ethyl acetate, and the organic phases were combined, dried over $Na_2SO_4$, filtered, and concentrated. The crude product was purified by silica gel column chromatography to give a light yellow oily product of 2-heptylnonanol (6.97 g).

eq.) and DIEA (639.7 mg, 4.95 mmol, 3.0 eq.) were added to the reaction system. The system was stirred at room temperature overnight. The mixture was diluted with DCM (4 mL) and washed once with a saturated sodium bicarbonate solution (6 mL). The organic phase was washed once with saturated NaCl (5 mL), dried over anhydrous $Na_2SO_4$, filtered, and concentrated. The crude product was purified by silica gel column chromatography to give a light yellow oily carbonate intermediate compound 40a-4 (325 mg).

In an 8 mL sealed tube, compound 40a-4 (250 mg, 0.56 mmol, 1.0 eq.) obtained in the previous step, compound 2a-4 (179.0 mg, 0.50 mmol, 0.9 eq.), potassium iodide (110.8 mg, 0.67 mmol, 1.2 eq.), potassium carbonate (230.6 mg, 1.68 mmol, 3.0 eq.), and acetonitrile (2.5 mL) were added at room temperature. The mixture was heated to 80° C. and stirred for reaction overnight. The reaction was monitored by LC-MS, and the reaction system was cooled to room temperature. The mixture was filtered, concentrated, and purified by Prep-HPLC to give a light yellow oily product of compound 40a (84.3 mg).

$^1H$ NMR (400 MHz, $CDCl_3$) δ: 4.14 (t, J=6.8 Hz, 2H), 4.06 (dd, J=8.0, 6.0 Hz, 4H), 3.60 (m, 2H), 2.65-2.53 (m, 6H), 1.73-1.60 (m, 12H), 1.42-1.22 (m, 46H), 1.18 (s, 6H), 0.90 (t, J=6.8 Hz, 9H); ESI-MS m/z: 726.50 $[M+H]^+$.

Example 65: Synthesis of Compound 41a

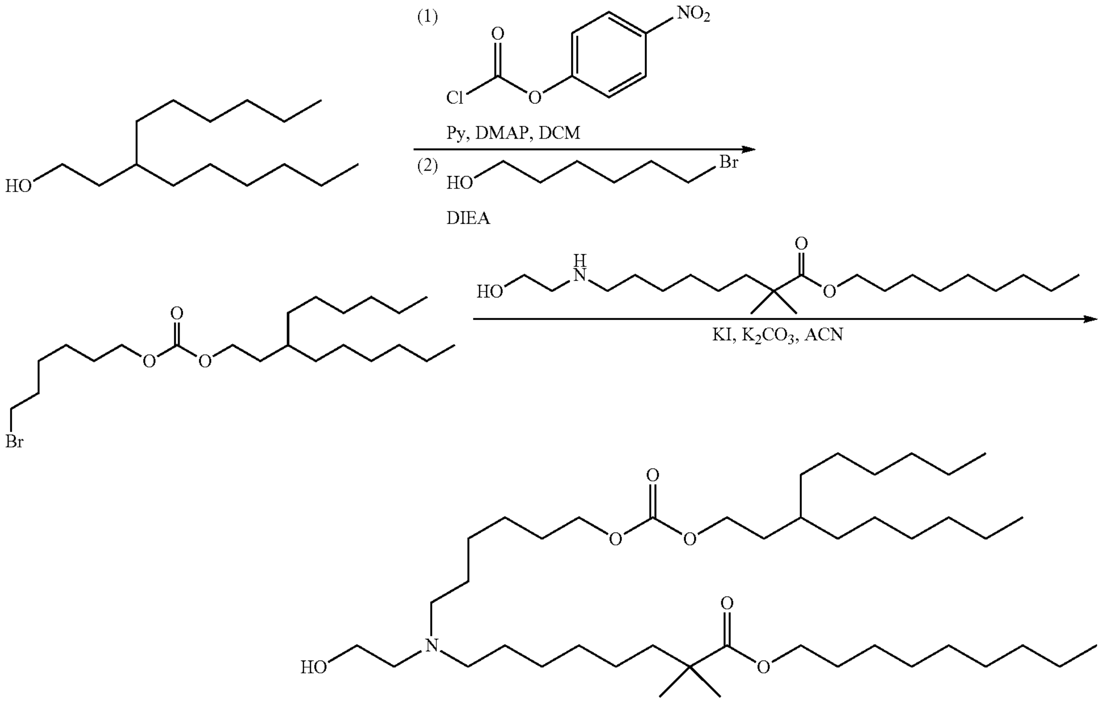

41a

In a 50 mL three-neck round-bottom flask, 2-heptylnonanol (400 mg, 1.65 mmol, 1.0 eq.), pyridine (261.0 mg, 3.30 mmol, 2.0 eq.), DMAP (40.3 mg, 0.33 mmol, 0.2 eq.), p-nitrophenyl chloroformate (399.0 mg, 1.98 mmol, 1.2 eq.), and DCM (4 mL) were added at room temperature. The reaction system was stirred at room temperature for 1 h. Thereafter, 6-bromo-1-hexanol (896.2 mg, 4.95 mmol, 3.0

Compound 41a was prepared referring to the method of Example 64 to give 113.3 mg of an oily product.

$^1H$ NMR (400 MHz, $CDCl_3$) δ: 4.14 (td, J=9.2, 6.8 Hz, 4H), 4.06 (t, J=6.8 Hz, 2H), 3.57 (m, 2H), 2.62-2.49 (m, 6H), 1.71-1.63 (m, 6H), 1.57-1.22 (m, 50H), 1.17 (s, 6H), 0.90 (t, J=6.8 Hz, 9H); ESI-MS m/z: 712.55 $[M+H]^+$.

Example 66: Synthesis of Compound 42a

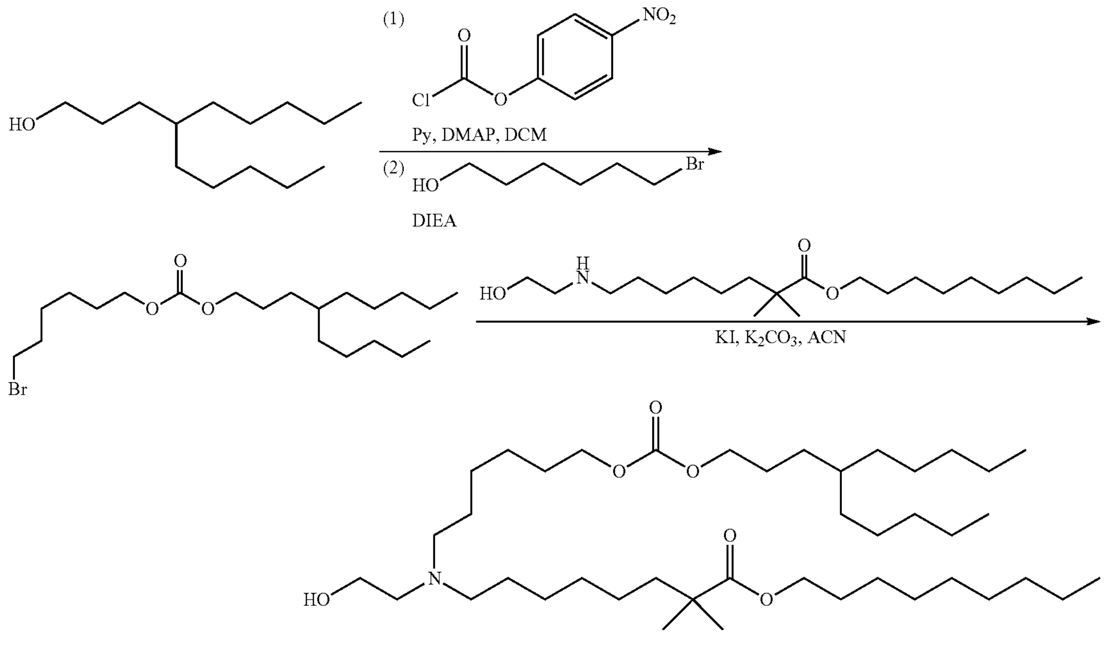

42a

Compound 42a was prepared referring to the method of Example 64 to give 124.2 mg of an oily product.

$^1$H NMR (300 MHz, $CDCl_3$) δ: 4.12 (td, J=6.6, 4.8 Hz, 4H), 4.04 (t, J=6.6 Hz, 2H), 3.55 (t, J=5.7 Hz, 2H), 2.60-2.47 (m, 6H), 1.72-1.62 (m, 6H), 1.59-1.19 (m, 48H), 1.15 (s, 6H), 0.93-0.83 (m, 9H); ESI-MS m/z: 698.55 $[M+H]^+$.

Example 67: Synthesis of Compound 43a

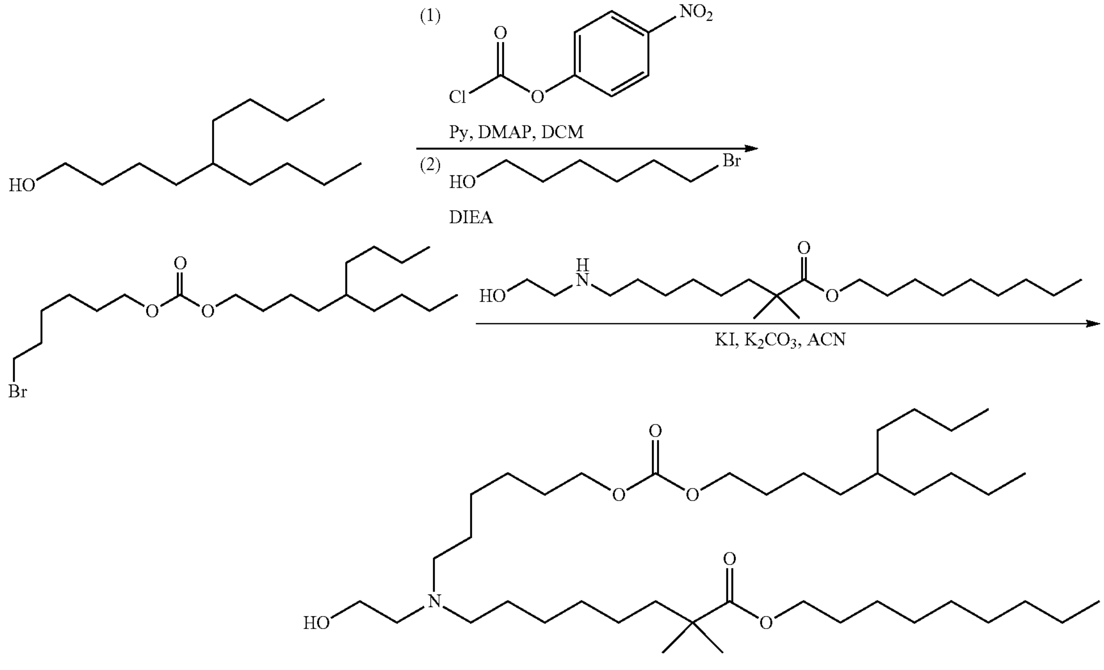

43a

Compound 43a was prepared referring to the method of Example 64 to give 97.7 mg of an oily product.

$^1$H NMR (400 MHz, $CDCl_3$) δ: 4.15 (td, J=6.8, 1.6 Hz, 4H), 4.06 (t, J=6.8 Hz, 2H), 3.64 (m, 2H), 2.68-2.56 (m, 6H), 1.76-1.60 (m, 8H), 1.54-1.22 (m, 44H), 1.18 (s, 6H), 0.96-0.86 (m, 9H); ESI-MS m/z: 684.45 $[M+H]^+$.

Example 68: Synthesis of Compound 44a

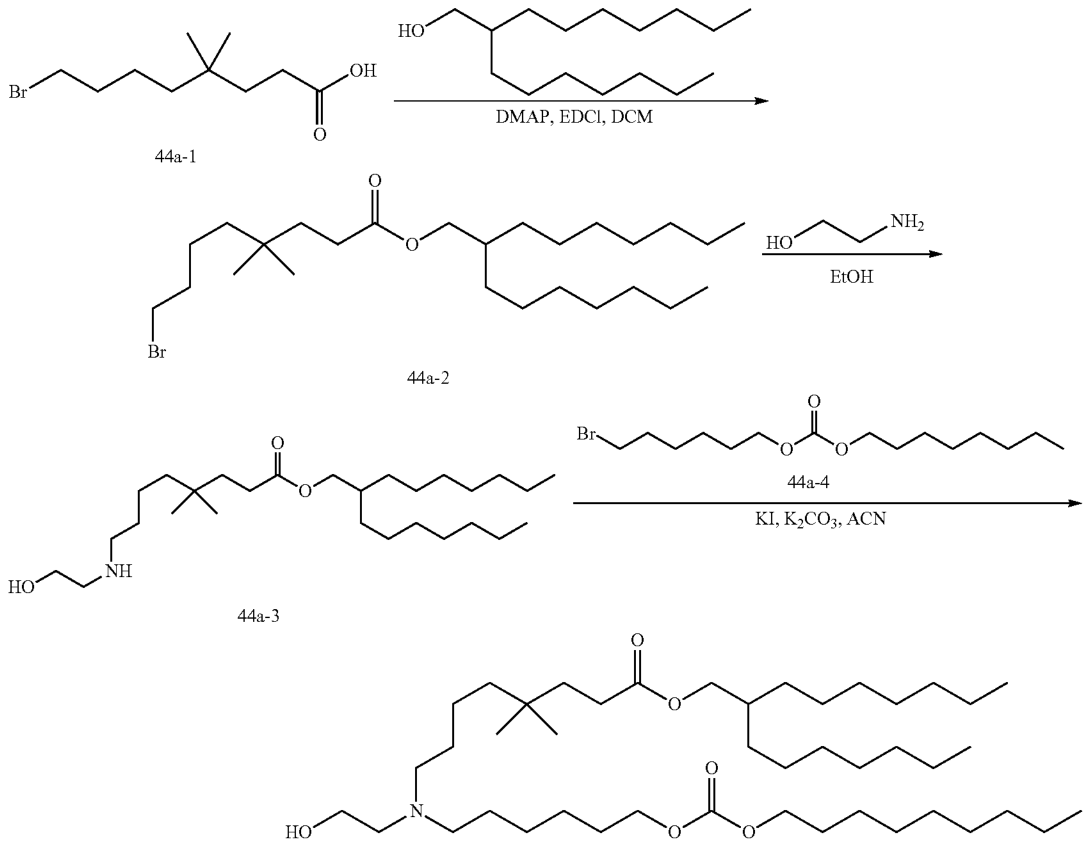

44a-1

44a-2

44a-3

44a

In a 20 mL round-bottom flask, compound 44a-1 (587.58 mg, 2.34 mmol, 1.2 eq.), 2-heptylnonanol (500 mg, 1.95 mmol, 1.0 eq.), EDCI (560.58 mg, 2.93 mmol, 1.5 eq.), and DMAP (47.63 mg, 0.39 mmol, 0.2 eq.) were dissolved in 5 mL of dichloromethane, and the mixture was reacted at room temperature overnight. After the reaction was completed, a saturated aqueous sodium chloride solution was added to quench the reaction, the mixture was extracted with dichloromethane, and the organic phases were combined, dried over $Na_2SO_4$, filtered, and concentrated to give 1 g of crude 44a-2, which was directly used in the subsequent reaction.

Compound 44a was prepared referring to the method of Example 54 to give 165.3 mg of an oily product.

$^1H$ NMR (400 MHz, $CDCl_3$) δ: 4.12 (t, J=6.8 Hz, 4H), 3.96 (d, J=5.6 Hz, 2H), 3.59 (m, 2H), 2.53-2.42 (m, 6H), 2.26-2.20 (m, 2H), 1.70-1.63 (m, 7H), 1.56-1.19 (m, 49H), 0.92-0.83 (m, 15H); ESI-MS m/z: 726.50 $[M+H]^+$.

Example 69: Synthesis of Compound 45a

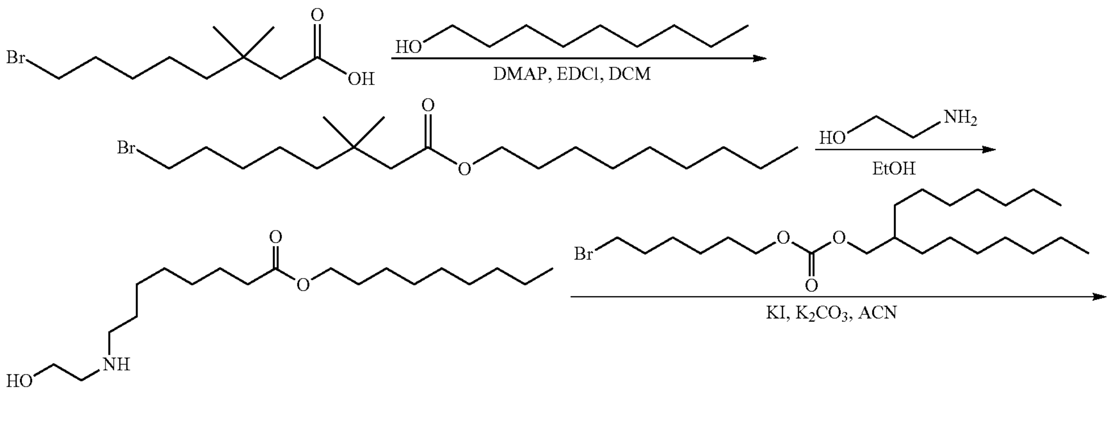

-continued
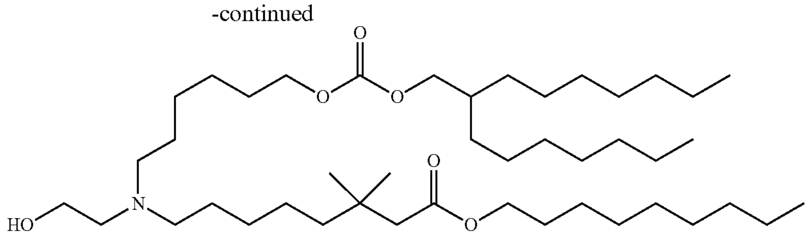
45a
Compound 45a was prepared referring to the method of Example 68 to give 107.2 mg of an oily product.
$^1H$ NMR (300 MHz, $CDCl_3$) δ: 4.12 (t, J=6.6 Hz, 2H), 4.04 (t, J=6.6 Hz, 4H), 3.57 (m, 2H), 2.63-2.51 (m, 6H), 2.18 (s, 2H), 1.73-1.61 (m, 5H), 1.59-1.21 (m, 51H), 0.98 (s, 6H), 0.93-0.83 (m, 9H); ESI-MS m/z: 726.55 $[M+H]^+$.
Example 70: Synthesis of Compound 46a
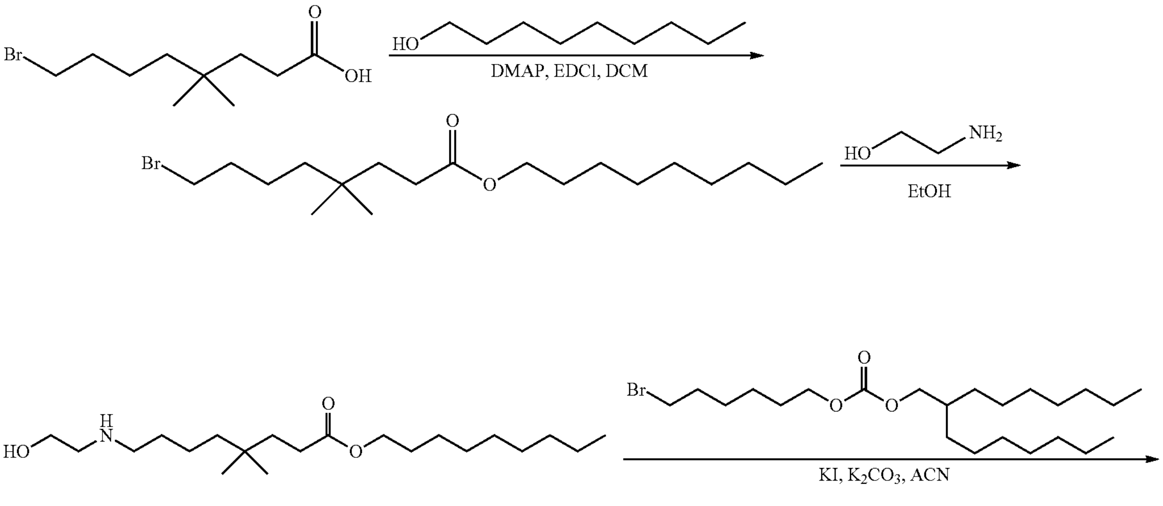
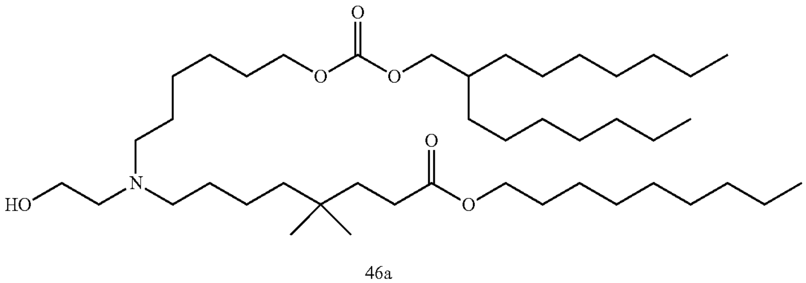
46a
Compound 46a was prepared referring to the method of Example 68 to give 116.7 mg of an oily product.
$^1H$ NMR (300 MHz, $CDCl_3$) δ: 4.12 (t, J=6.6 Hz, 2H), 4.07-4.02 (m, 4H), 3.58 (m, 2H), 2.64-2.49 (m, 6H), 2.27-2.21 (m, 2H), 1.73-1.60 (m, 5H), 1.56-1.21 (m, 51H), 0.93-0.82 (m, 15H); ESI-MS m/z: 726.45 $[M+H]^+$.

Example 71: Synthesis of Compound 47a
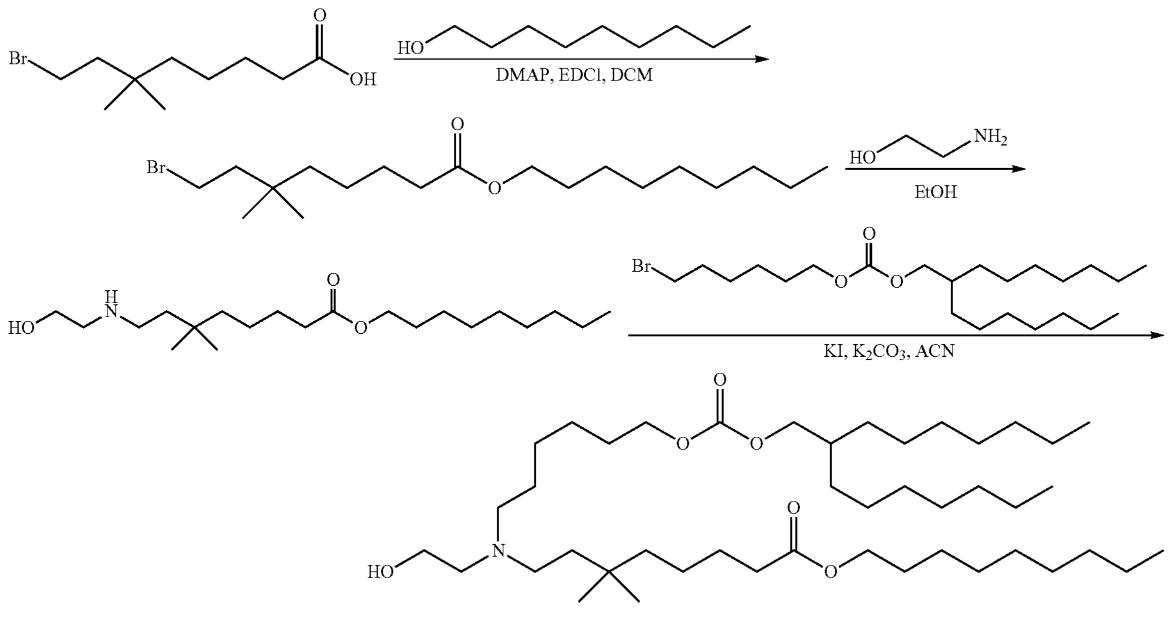
47a
Compound 47a was prepared referring to the method of Example 68 to give 24.2 mg of an oily product.
$^{1}$H NMR (400 MHz, $CDCl_3$) δ: 4.12 (t, J=6.8 Hz, 2H), 4.07-4.02 (m, 4H), 3.73 (m, 2H), 2.81-2.63 (m, 6H), 2.31 (t, J=6.8 Hz, 2H), 1.76-1.59 (m, 10H), 1.58-1.22 (m, 46H), 0.92-0.87 (m, 15H); ESI-MS m/z: 726.55 $[M+H]^+$.
Example 72: Synthesis of Compound 48a
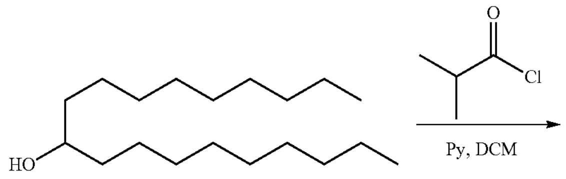
48a-1
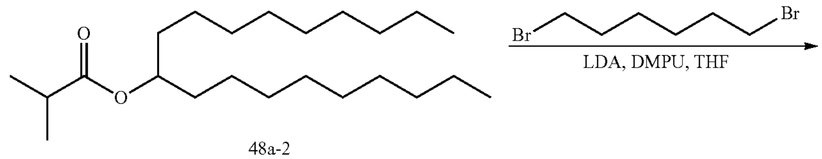
48a-2
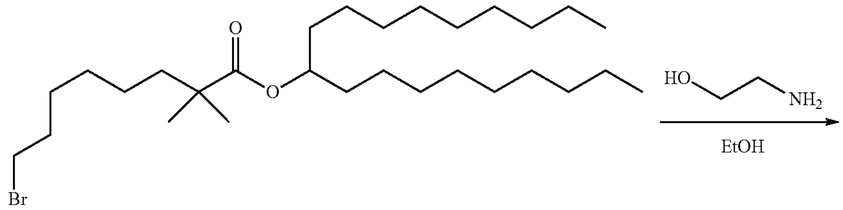
48a-3

-continued
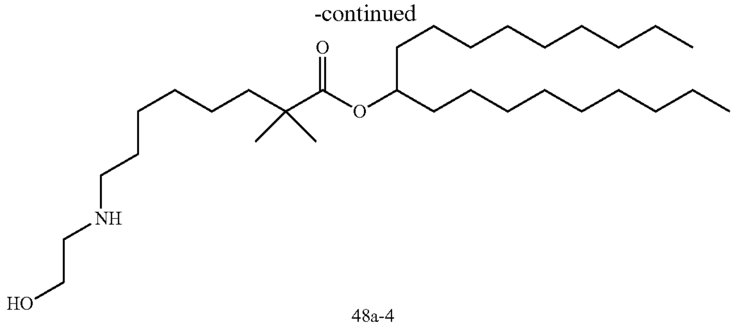
48a-4
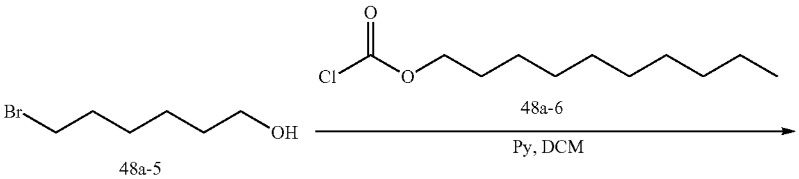
48a-5
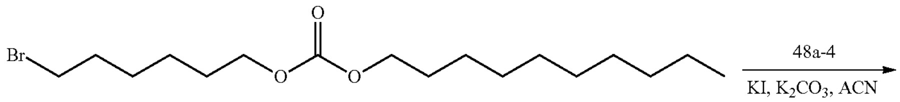
48a-7
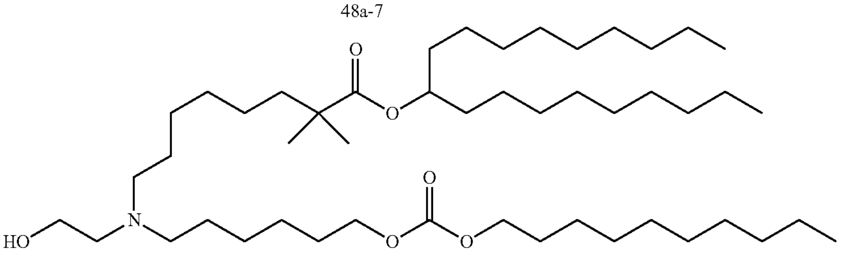
48a
Compound 48a was prepared referring to the method of Example 54 to give 258.1 mg of an oily product.
$^1$H NMR (300 MHz, $CDCl_3$) δ: 4.85 (p, J=6.0 Hz, 1H), 4.12 (t, J=6.6 Hz, 4H), 3.59 (m, 2H), 2.65-2.52 (m, 6H), 1.67-1.62 (m, 5H), 1.49-1.20 (m, 60H), 1.15 (s, 6H), 0.88 (t, J=6.6 Hz, 9H); ESI-MS m/z: 782.72 $[M+H]^+$.
Example 73: Synthesis of Compound 49a
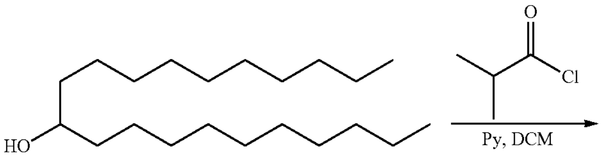
49a-1
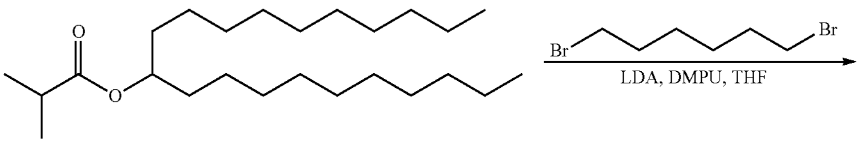
49a-2

-continued
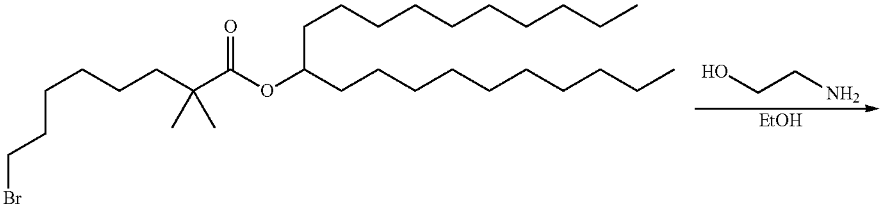
49a-3
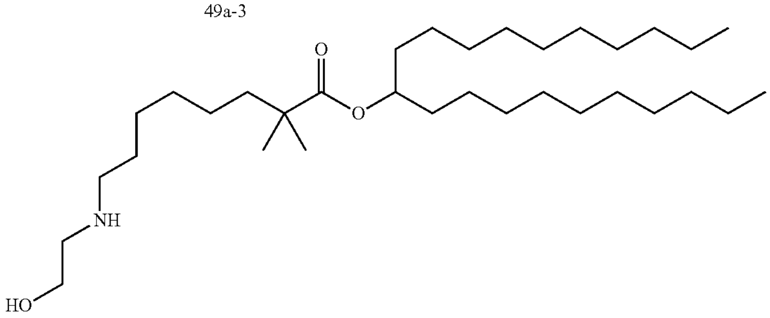
49a-4
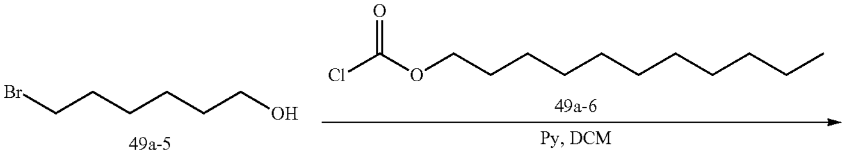
49a-5 49a-6
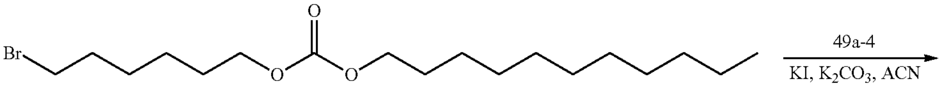
49a-7
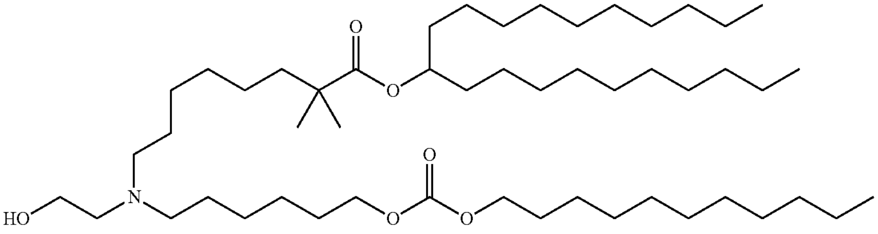
49a
Compound 49a was prepared referring to the method of Example 54 to give 27.9 mg of an oily product.
$^1$H NMR (300 MHz, $CDCl_3$) δ: 4.82 (p, J=6.0 Hz, 1H), 4.12 (t, J=6.6 Hz, 4H), 3.65 (m, 2H), 2.73-2.61 (m, 6H), 1.83-1.62 (m, 9H), 1.51-1.19 (m, 64H), 1.15 (s, 6H), 0.89 (t, J=6.6 Hz, 9H); ESI-MS m/z: 824.70 $[M+H]^+$.
Example 74: Synthesis of Compound 50a
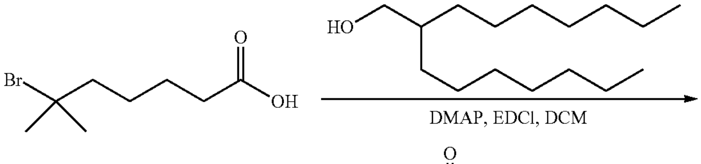
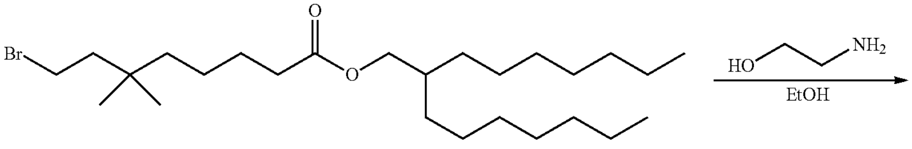

-continued
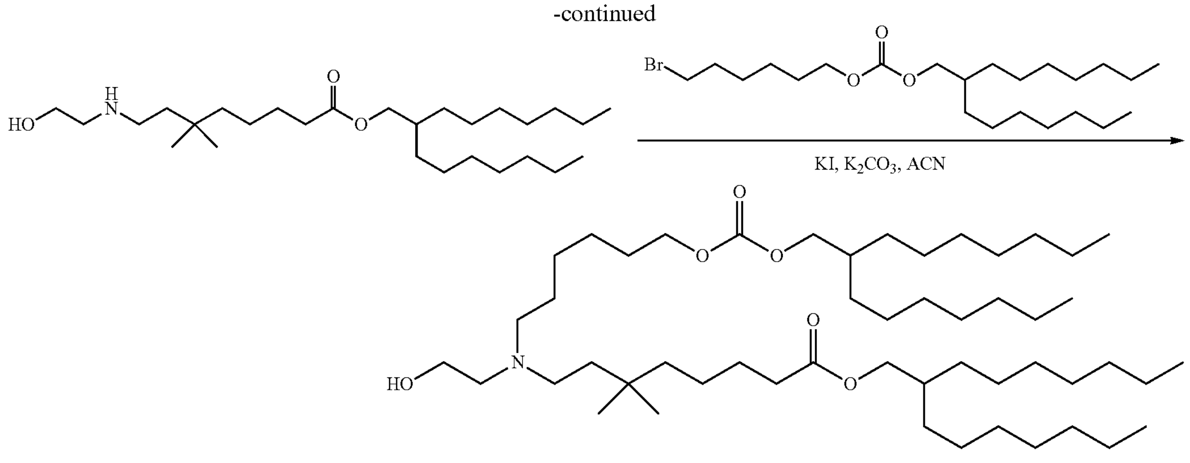
50a
Compound 50a was prepared referring to the method of Example 68 to give 75.9 mg of an oily product.
$^1$H NMR (400 MHz, $CDCl_3$) δ: 4.12 (t, J=6.6 Hz, 2H), 4.03 (d, J=6.0 Hz, 2H), 3.96 (d, J=6.0 Hz, 2H), 3.61 (m, 2H), 2.67-2.55 (m, 6H), 2.32 (t, J=7.2 Hz, 2H), 1.72-1.54 (m, 10H), 1.52-1.20 (m, 57H), 0.89 (m, 18H); ESI-MS m/z: 824.65 $[M+H]^+$.
Example 75: Synthesis of Compound 51a
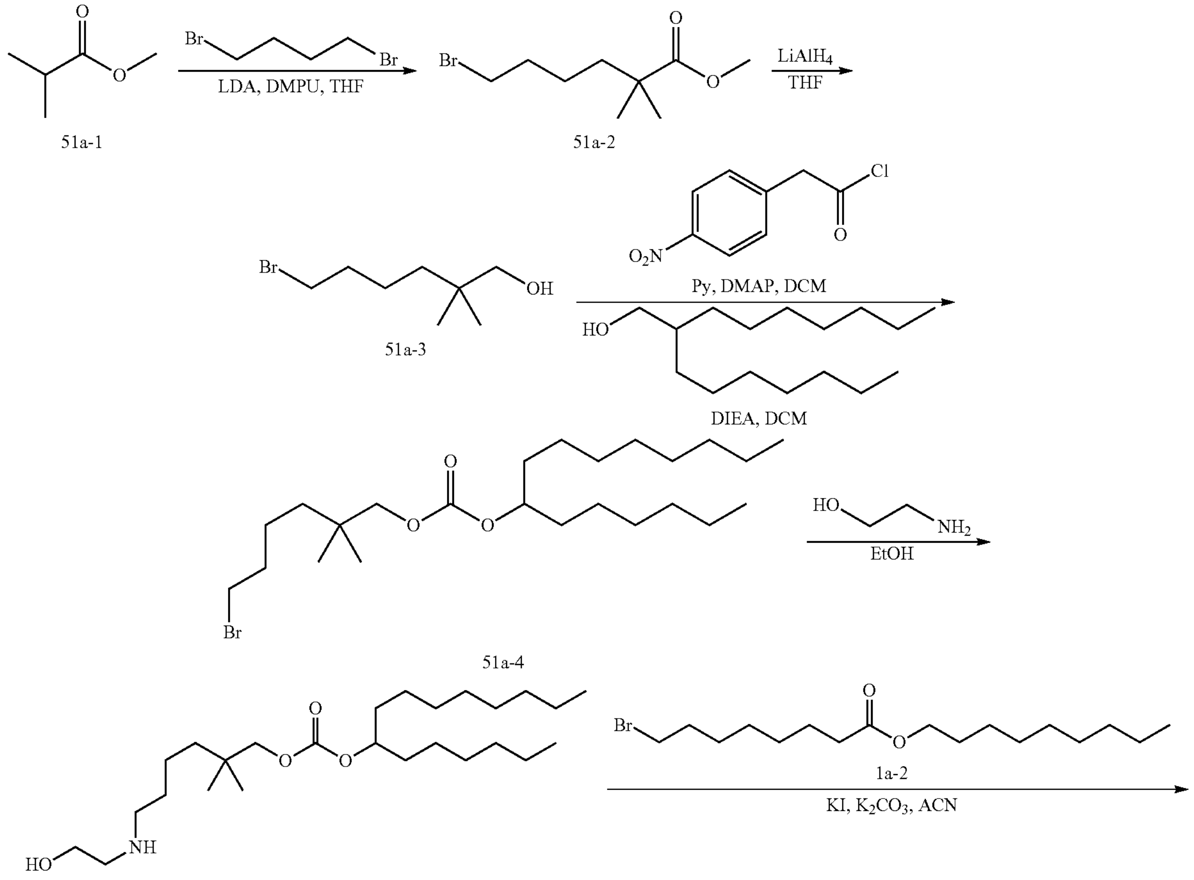
51a-1 51a-2 51a-3 51a-4 51a-5

-continued

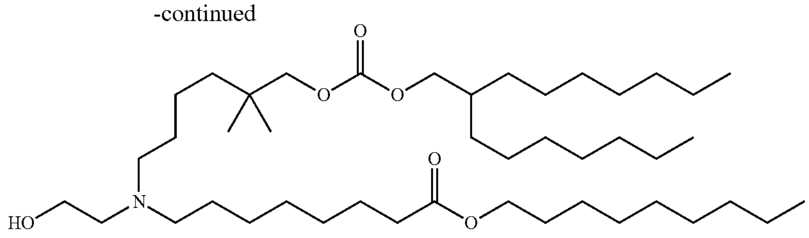

51a

In a 250 mL reaction flask, methyl isobutyrate (3.5 g, 34.3 mmol, 1.0 eq.) and THF (40 mL) were added under nitrogen atmosphere, and the mixture was cooled to −40° C. LDA (17.2 mL, 34.3 mmol, 1.0 eq., 2 M in THF) was added dropwise within 10 min, and after the dropwise addition was completed, the mixture was reacted for another 1.5 h. Then 1,4-dibromobutane (14.80 g, 68.5 mmol, 2.0 eq.) and DMPU (0.88 g, 6.85 mmol, 0.2 eq.) were added dropwise within 5 min at the same temperature, and the mixture was slowly warmed to room temperature and reacted overnight. After the reaction was completed, a saturated aqueous ammonium chloride solution was added to quench the reaction, the mixture was extracted with ethyl acetate, the organic phases were combined, dried over $Na_2SO_4$, filtered, and concentrated, and the organic solvent was removed by rotary evaporation to give 7.5 g of a crude compound of methyl 2,2-dimethyl-6-bromohexanoate.

In a 250 mL round-bottom flask, methyl 2,2-dimethyl-6-bromohexanoate (7.5 g, crude) was dissolved in 75 mL of anhydrous THF. After the mixture was cooled to 0° C., $LiAlH_4$ (10.12 mL, 25.3 mmol, 2.5 M in THF) was added dropwise. After the dropwise addition was completed, the mixture was reacted for another 30 min. After the reaction was completed, a saturated aqueous ammonium chloride solution was added to quench the reaction, the mixture was extracted with ethyl acetate, the organic phases were combined, dried over $Na_2SO_4$, filtered, and concentrated, and the organic solvent was removed by rotary evaporation to give 7.5 g of a crude product, which was purified by silica gel column chromatography to give 2.5 g of the compound 2,2-dimethyl-6-bromohexanol.

Compound 51a was prepared referring to the method of Example 64 to give 205.5 mg of an oily product.

$^1H$ NMR (300 MHz, $CDCl_3$) δ: 4.08-4.02 (m, 4H), 3.85 (s, 2H), 3.54 (t, J=5.1 Hz, 2H), 2.59 (t, J=5.1 Hz, 2H), 2.49-2.43 (m, 4H), 2.29 (t, J=7.5 Hz, 2H), 1.66-1.57 (m, 6H), 1.55-1.22 (m, 50H), 0.92-0.83 (m, 15H); ESI-MS m/z: 726.80 $[M+H]^+$.

Example 76: Synthesis of Compound 25b

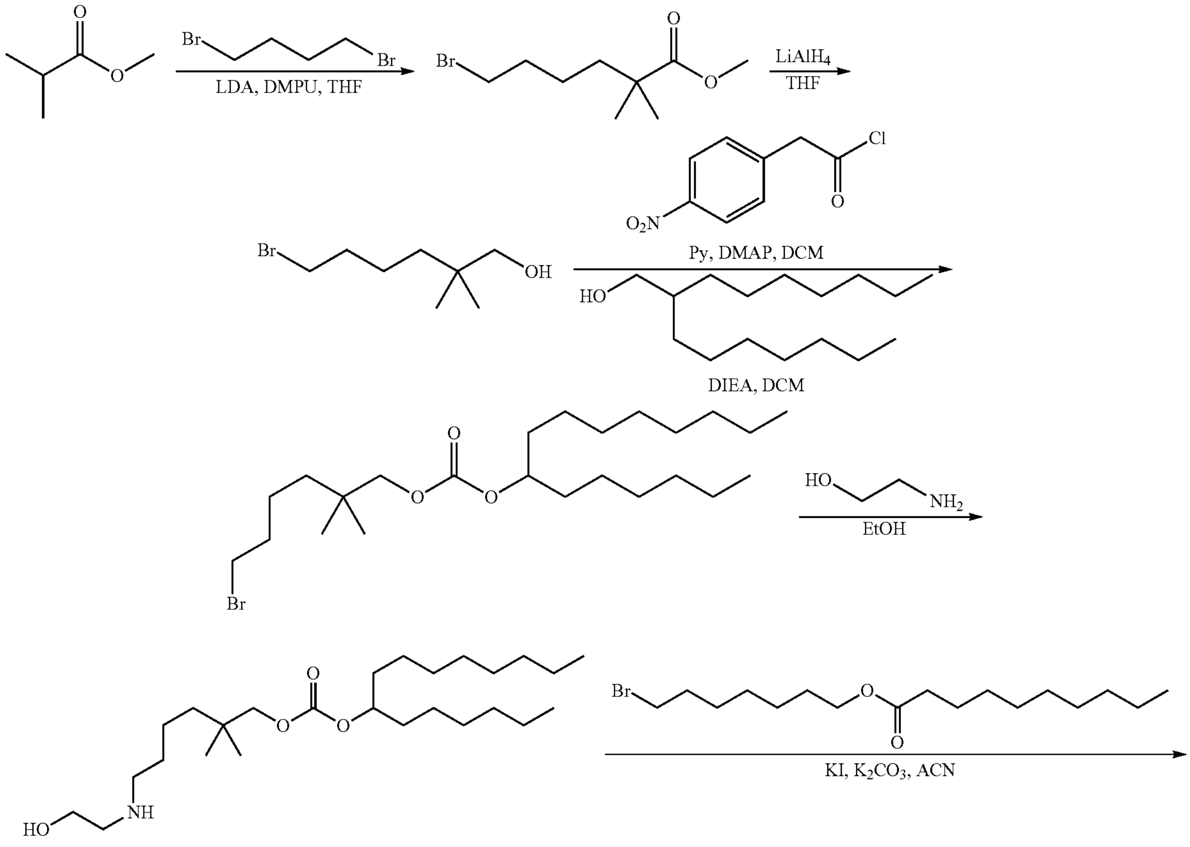

-continued

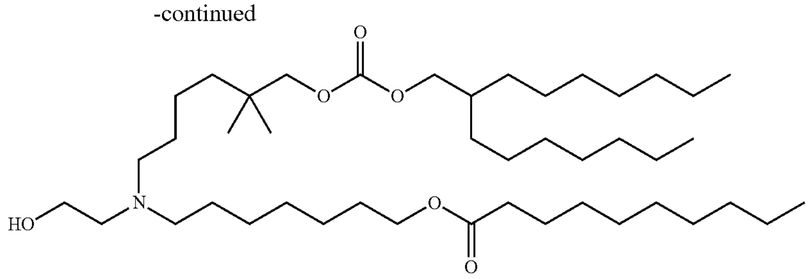

28b

Compound 25b was prepared referring to the method of Example 75 to give 152.1 mg of an oily product.

$^1$H NMR (300 MHz, $CDCl_3$) δ: 4.08-4.02 (m, 4H), 3.85 (s, 2H), 3.58 (m, 2H), 2.64-2.51 (m, 6H), 2.29 (t, J=7.5 Hz, 2H), 1.79-1.59 (m, 6H), 1.47-1.24 (m, 50H), 0.95-0.85 (m, 15H); ESI-MS m/z: 726.50 $[M+H]^+$.

Example 77: Synthesis of Compound 26b

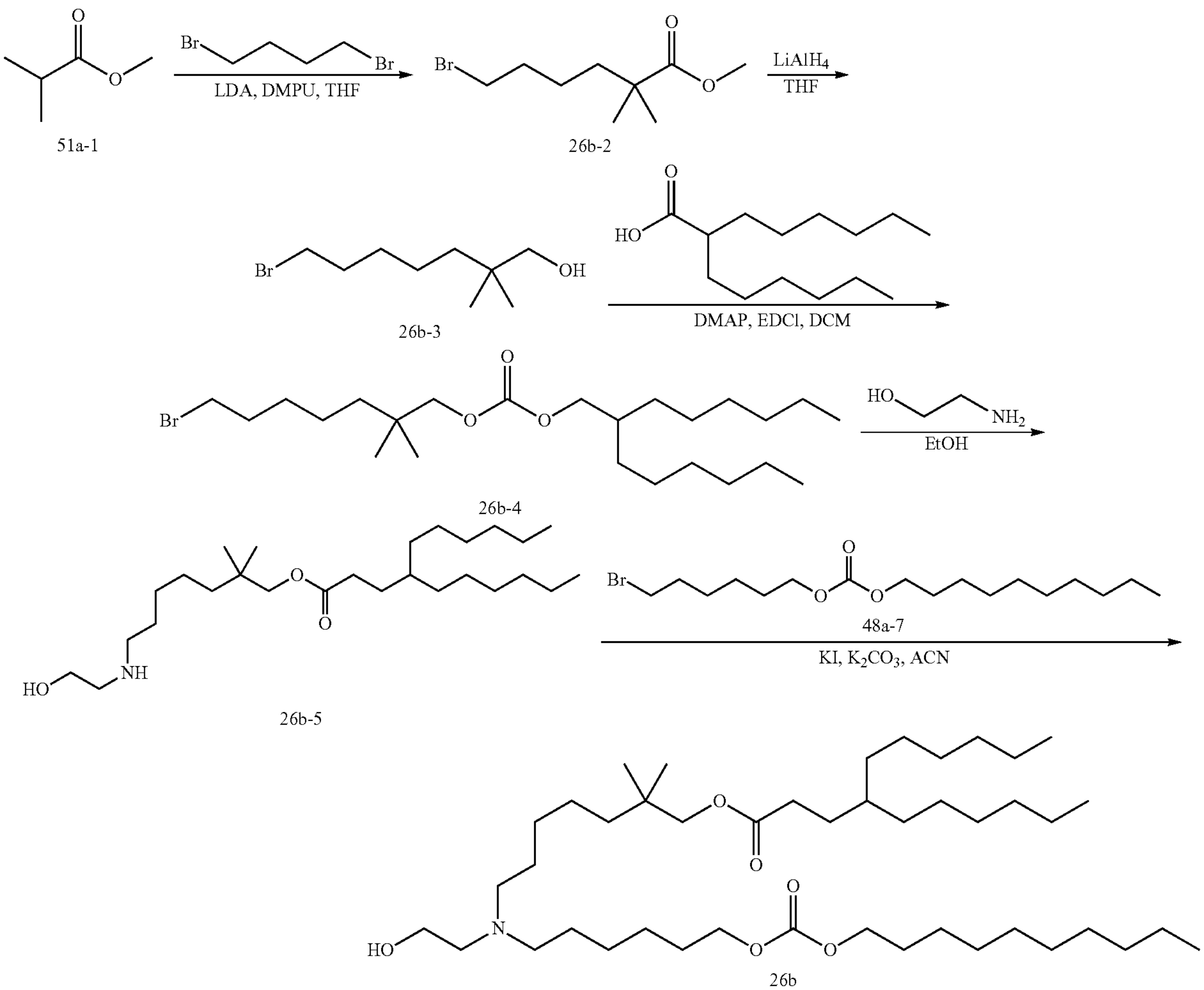

Methyl isobutyrate (21 g, 205.0 mmol, 1.0 eq.) was dissolved in 200 mL of anhydrous THF, the mixture was cooled to 0° C., and LDA (205 mL, 410.0 mmol, 2.0 eq.) was added to the reaction liquid under nitrogen atmosphere. The reaction was heated to room temperature. After stirring for 30 min, 1,5-dibromopentane (47 g, 205.0 mmol, 1.0 eq.) was added. After the reaction was completed as monitored by TLC, a saturated aqueous ammonium chloride solution was added to quench the reaction, and the mixture was extracted with DCM (3×300 mL). The organic phases were combined and dried over anhydrous sodium sulfate. The mixture was filtered, and the filtrate was concentrated to dryness to give a crude product, which was purified by silica gel column chromatography to give 30 g of a yellow oily compound methyl 2,2-dimethyl-7-bromoheptanoate.

Methyl 2-dimethyl-7-bromoheptanoate (15.0 g, 40.0 mmol, 1.0 eq.) was dissolved in 30 mL of THF, the mixture was cooled to 0° C., and a lithium aluminum hydride solution (2 M, 50.0 mL) was added dropwise to the reaction system under nitrogen atmosphere. The mixture was stirred for reaction for 3 h. After the reaction was completed, the reaction was quenched with a saturated aqueous ammonium chloride solution, and the mixture was extracted with DCM (3×300 mL). The organic phases were combined and dried over anhydrous sodium sulfate. The mixture was filtered, and the filtrate was concentrated to dryness to give a crude product of 2,2-dimethyl-7-bromoheptanol (13.6 g), which was directly used in the next step without purification.

organic phases were combined and dried over anhydrous sodium sulfate. The mixture was filtered, and the filtrate was concentrated to dryness to give a crude product, which was purified by silica gel column chromatography to give 858 mg of a yellow oily compound 26b-4.

Compound 26b was prepared referring to the method of Example 64 to give 99.0 mg of an oily product.

$^1H$ NMR (300 MHz, MeOH-$d_4$) δ: 0.86-0.91 (m, 15H), 1.21-1.40 (m, 50H), 1.58-1.71 (m, 6H), 2.32 (t, J=7.5 Hz, 2H), 2.48-2.53 (m, 4H), 2.62 (t, J=6.6 Hz, 2H), 3.61 (t, J=6.3 Hz, 2H), 3.80 (s, 2H), 4.10 (td, J=2.7, 6.3 Hz, 4H); ESI-MS m/z: 726.70 $[M+H]^+$.

Example 78: Synthesis of Compound 27b

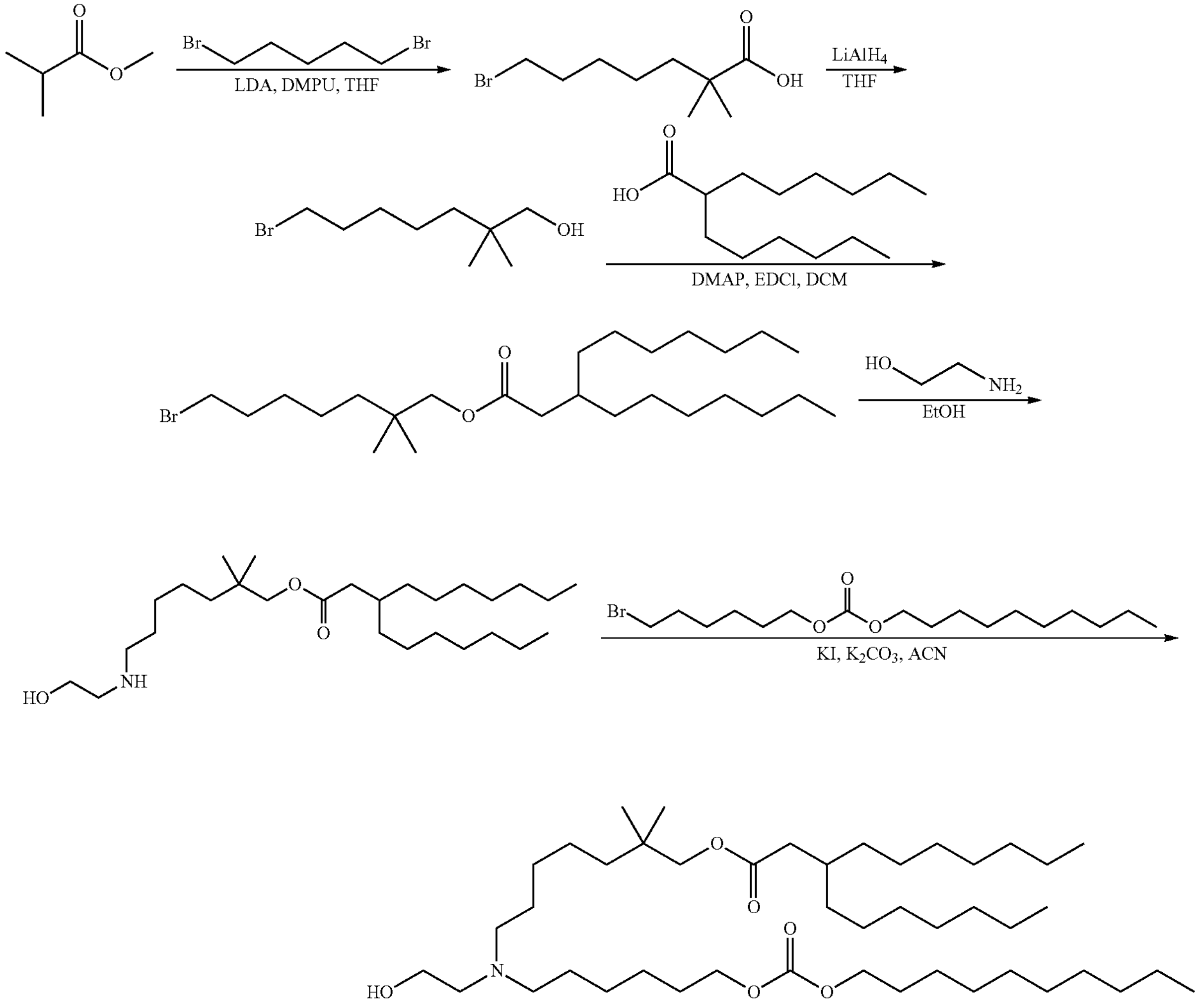

27b 2,2-Dimethyl-7-bromoheptanol (500.0 mg, 2.24 mmol, 1.0 eq.) was dissolved in DCM (10.0 mL), and 4-hexyldecanoic acid (746.2 mg, 2.91 mmol, 1.3 eq.), EDCI (515.7 mg, 2.69 mmol, 1.2 eq.), and DMAP (410.5 mg, 3.36 mmol, 1.5 eq.) were added to the solution. The reaction liquid was stirred at room temperature for 3 h, the reaction liquid was poured into 10 mL of a saturated aqueous sodium chloride solution, and the mixture was extracted with DCM. The Compound 27b was prepared referring to the method of Example 77 to give 70.0 mg of an oily product.

$^1H$ NMR (300 MHz, MeOH-$d_4$) δ: 0.85-0.95 (m, 15H), 1.25-1.55 (m, 48H), 1.59-1.83 (m, 10H), 2.25 (d, J=6.6 Hz, 2H), 2.48-2.53 (m, 4H), 2.62 (t, J=6.3 Hz, 2H), 3.61 (t, J=6.3 Hz, 2H), 3.79 (s, 2H), 4.11 (td, J=3.0, 6.6 Hz, 4H); ESI-MS m/z: 740.65 $[M+H]^+$.

Example 79: Synthesis of Compound 28b
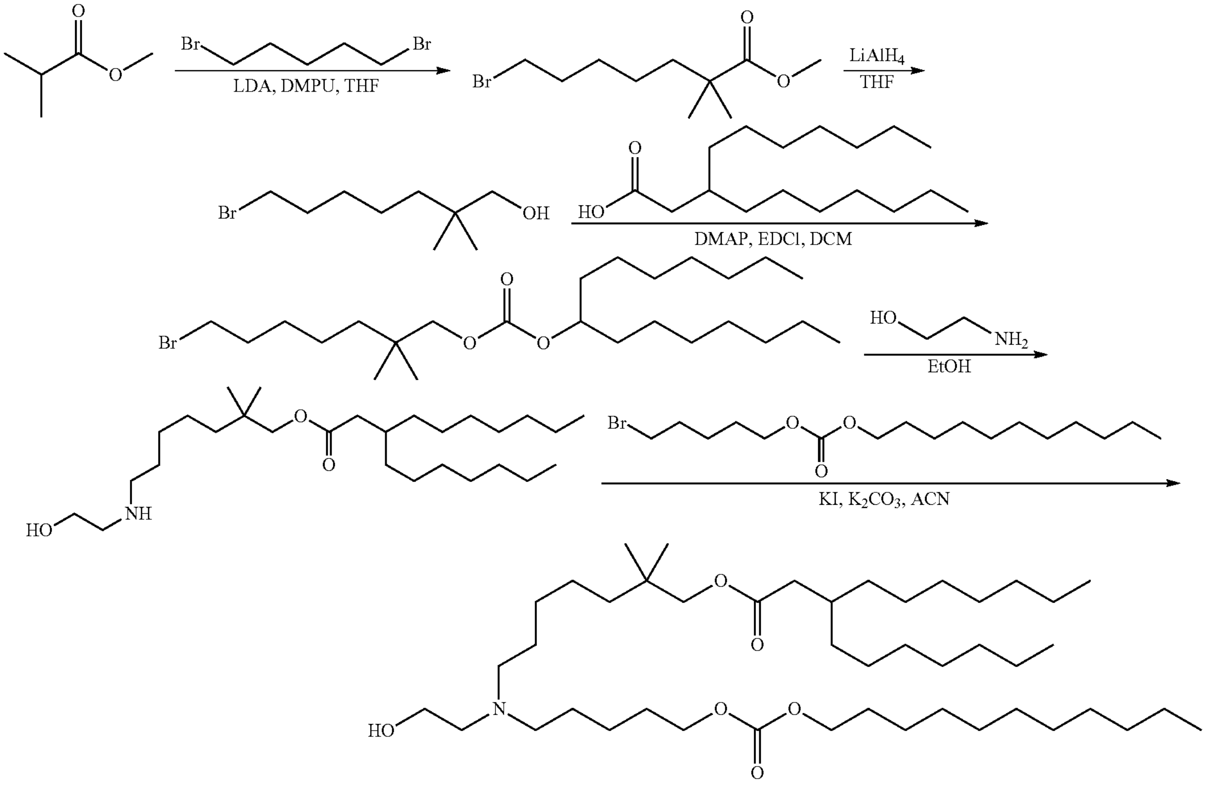
28b
Compound 28b was prepared referring to the method of Example 77 to give 97.8 mg of an oily product.
$^1$H NMR (300 MHz, MeOH-$d_4$) δ: 0.85-0.95 (m, 15H), 1.21-1.55 (m, 48H), 1.60-1.84 (m, 10H), 2.25 (d, J=6.6 Hz, 2H), 2.47-2.53 (m, 4H), 2.61 (t, J=6.3 Hz, 2H), 3.61 (t, J=6.3 Hz, 2H), 3.79 (s, 2H), 4.11 (td, J=4.5, 6.3 Hz, 4H); ESI-MS m/z: 740.80 $[M+H]^+$.
Example 80: Synthesis of Compound 29b
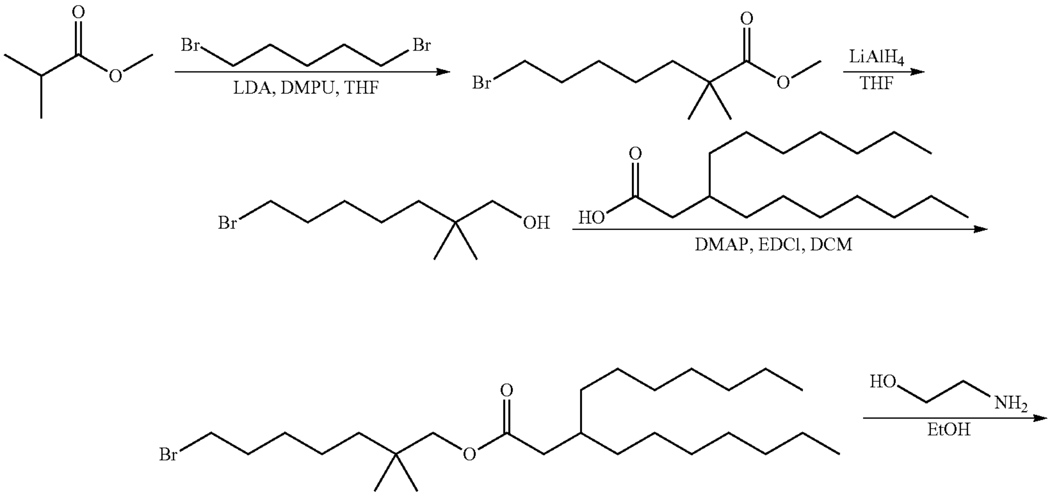

-continued

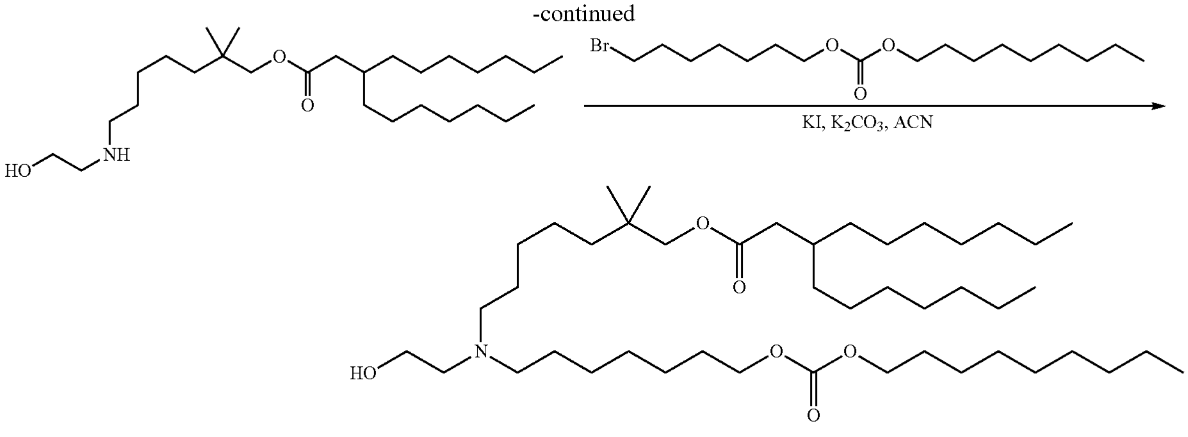

29b

Compound 29b was prepared referring to the method of Example 77 to give 107.7 mg of an oily product.

$^1$H NMR (300 MHz, MeOH-$d_4$) δ: 0.85-0.95 (m, 15H), 1.21-1.55 (m, 53H), 1.60-1.84 (m, 5H), 2.25 (d, J=6.6 Hz, 2H), 2.50-2.55 (m, 4H), 2.64 (t, J=6.3 Hz, 2H), 3.60 (t, J=6.3 Hz, 2H), 3.79 (s, 2H), 4.11 (td, J=1.8, 6.6 Hz, 4H); ESI-MS m/z: 740.60 $[M+H]^+$.

Example 81: Synthesis of Compound 30b

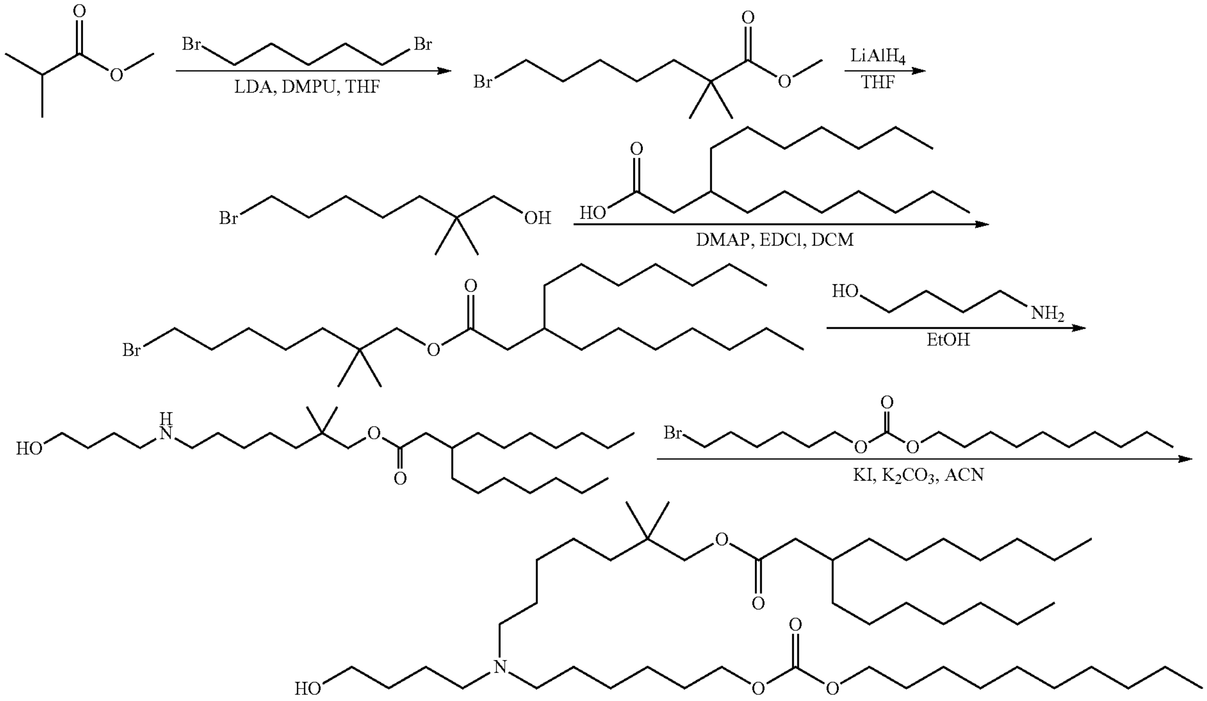

30b

Compound 30b was prepared referring to the method of Example 77 to give 82.4 mg of an oily product.

$^1$H NMR (300 MHz, MeOH-$d_4$) δ: 0.87-0.92 (m, 15H), 1.21-1.53 (m, 49H), 1.55-1.83 (m, 13H), 2.25 (d, J=6.9 Hz, 2H), 2.46-2.52 (m, 6H), 3.55 (t, J=5.7 Hz, 2H), 3.79 (s, 2H), 4.11 (td, J=3.0, 6.6 Hz, 4H); ESI-MS m/z: 768.70 $[M+H]^+$.

Example 82: Synthesis of Compound 31b
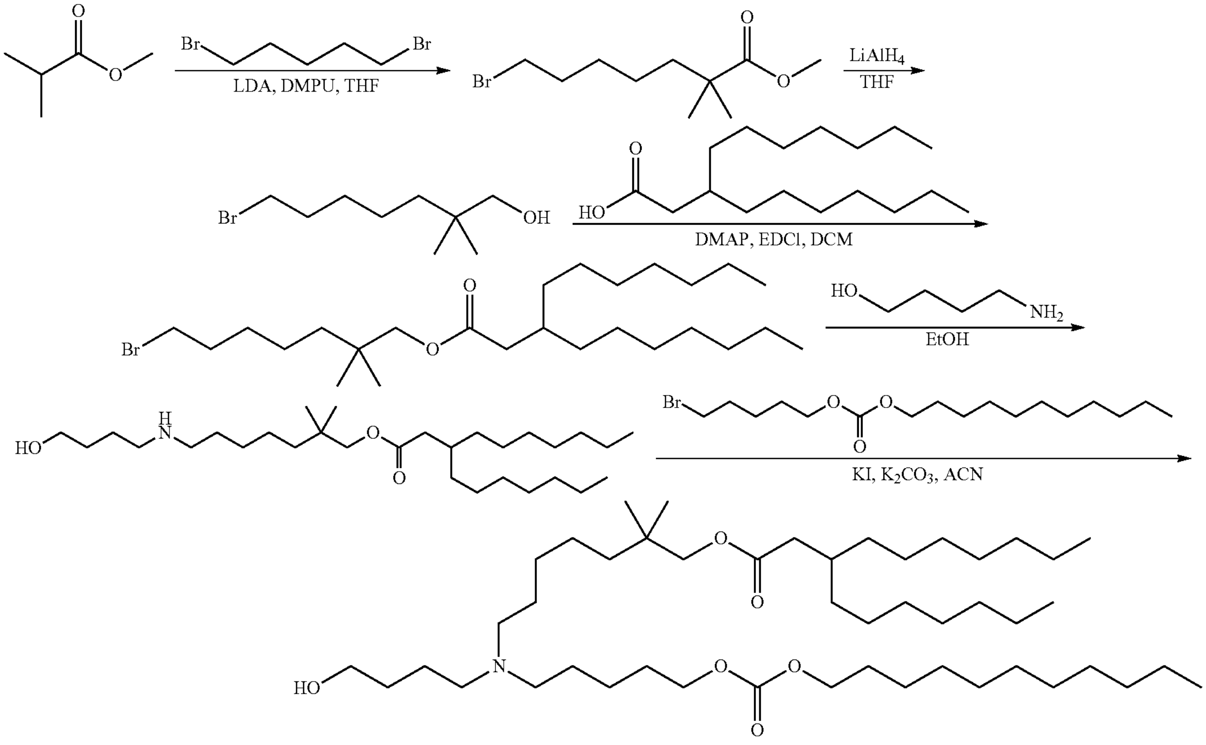
31b
Compound 31b was prepared referring to the method of Example 77 to give 107.7 mg of an oily product.
$^{1}H$ NMR (300 MHz, MeOH-$d_4$) δ: 0.86-0.92 (m, 15H), 1.21-1.53 (m, 49H), 1.55-1.83 (m, 13H), 2.25 (d, J=6.6 Hz, 2H), 2.47-2.54 (m, 6H), 3.55 (t, J=5.7 Hz, 2H), 3.79 (s, 2H), 4.10 (td, J=6.6, 12.3 Hz, 4H); ESI-MS m/z: 768.70 $[M+H]^+$.
Example 83: Synthesis of Compound 32b
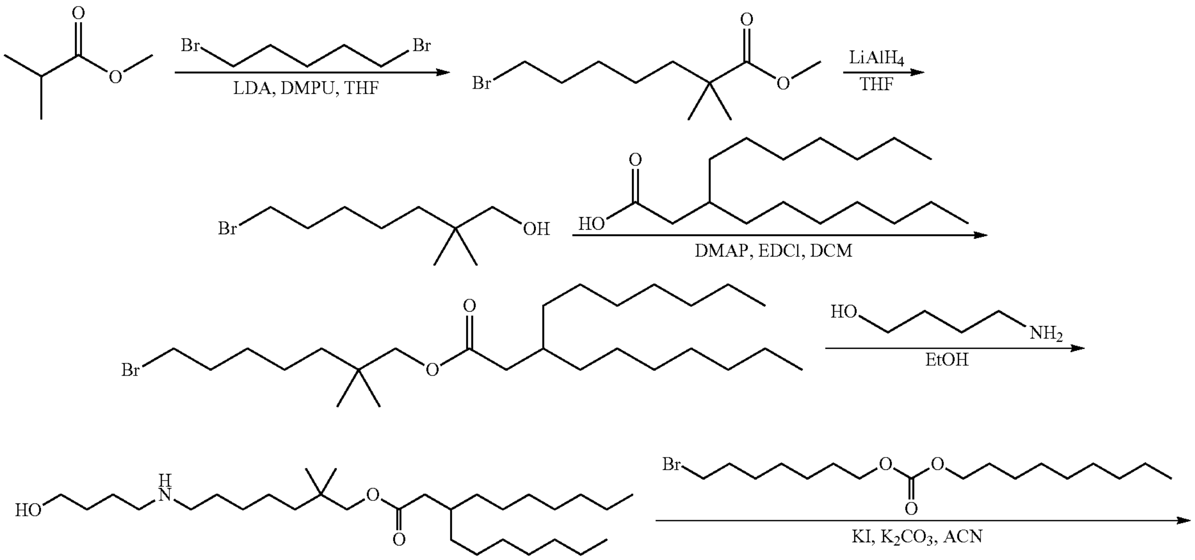

-continued

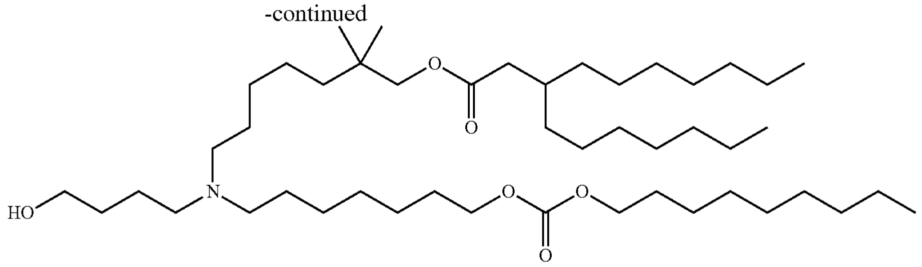

32b

Compound 32b was prepared referring to the method of Example 77 to give 84.3 mg of an oily product.

$^1$H NMR (300 MHz, MeOH-$d_4$) δ: 0.88-0.93 (m, 15H), 1.22-1.53 (m, 49H), 1.56-1.83 (m, 13H), 2.25 (d, J=6.6 Hz, 2H), 2.49-2.54 (m, 6H), 3.55 (t, J=5.4 Hz, 2H), 3.79 (s, 2H), 4.10 (td, J=2.1, 6.6 Hz, 4H); ESI-MS m/z: 768.65 $[M+H]^+$.

Example 84: Synthesis of Compound 33b

Compound 33b was prepared referring to the method of Example 77 to give 74.9 mg of an oily product.

$^1$H NMR (300 MHz, MeOH-$d_4$) δ: 0.88-0.92 (m, 15H), 1.22-1.53 (m, 51H), 1.48-1.69 (m, 9H), 2.33 (t, J=7.5 Hz, 2H), 2.50-2.55 (m, 4H), 2.63 (t, J=6.3 Hz, 2H), 3.62 (t, J=6.6 Hz, 2H), 3.80 (s, 2H), 4.02 (d, J=5.7 Hz, 2H), 4.11 (t, J=6.6 Hz, 2H); ESI-MS m/z: 754.60 $[M+H]^+$.

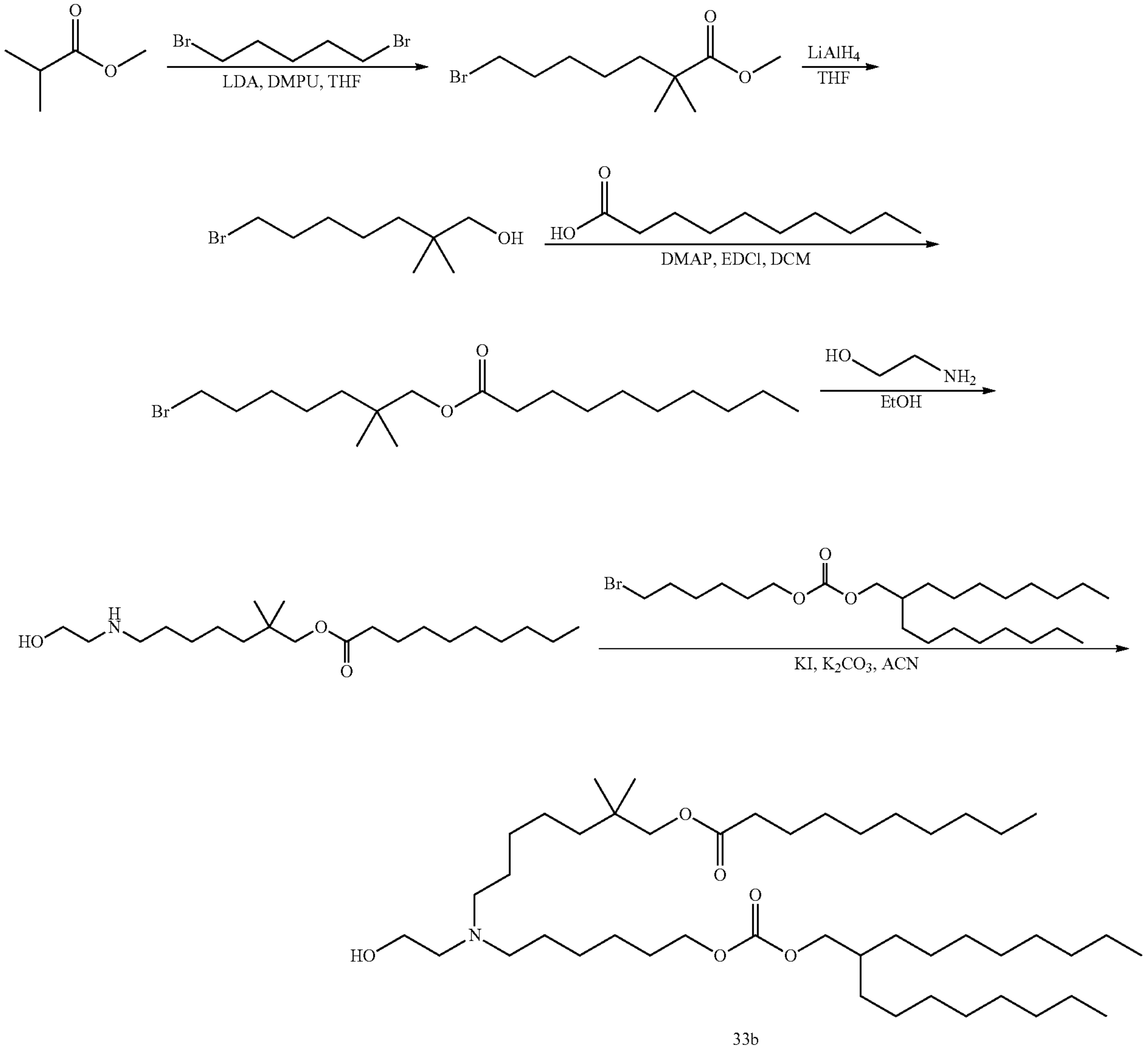

33b

Example 85: Synthesis of Compound 34b
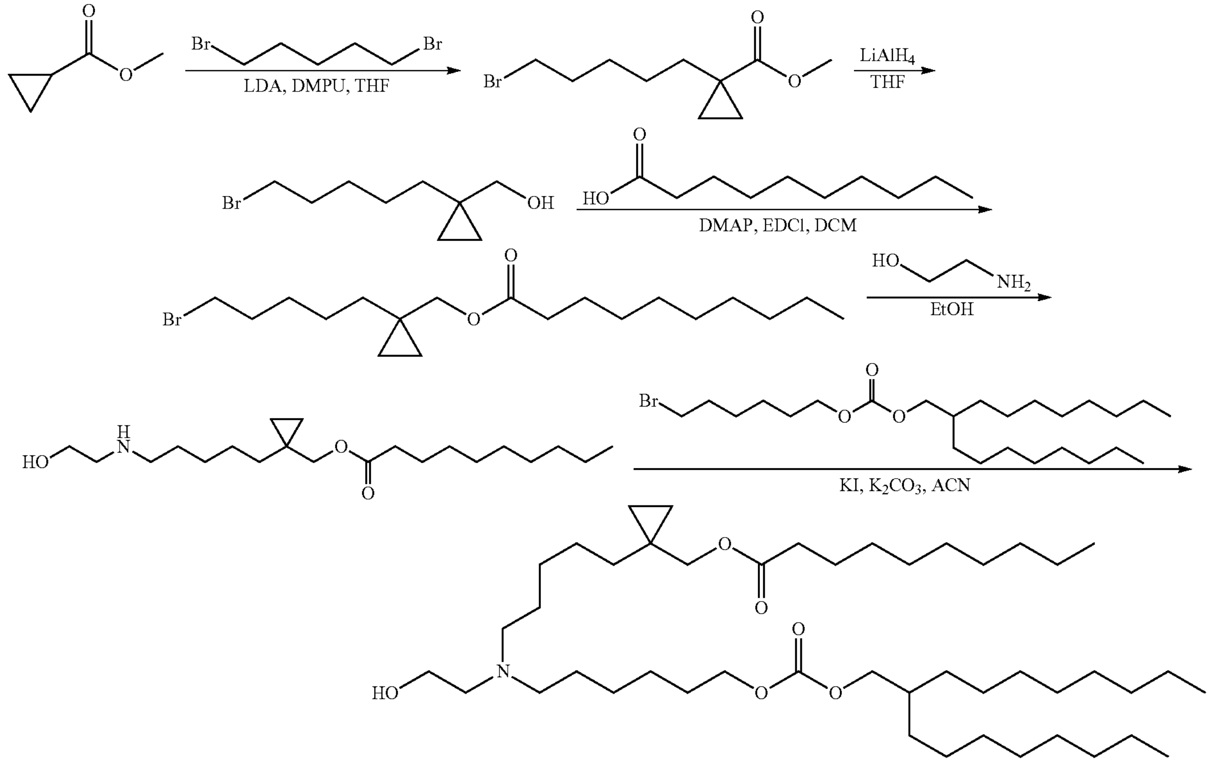
34b
Compound 34b was prepared referring to the method of Example 77 to give 76.6 mg of an oily product.
$^1$H NMR (300 MHz, MeOH-$d_4$) δ: 0.36-0.46 (m, 4H), 0.88-0.92 (m, 9H), 1.20-1.51 (m, 55H), 1.56-1.69 (m, 5H), 2.32 (t, J=7.5 Hz, 2H), 2.51-2.55 (m, 4H), 2.64 (t, J=6.3 Hz, 2H), 3.62 (t, J=6.3 Hz, 2H), 3.92 (s, 2H), 4.02 (d, J=5.7 Hz, 2H), 4.11 (t, J=6.6 Hz, 2H); ESI-MS m/z: 752.60 $[M+H]^+$.
Example 86: Synthesis of Compound 35b
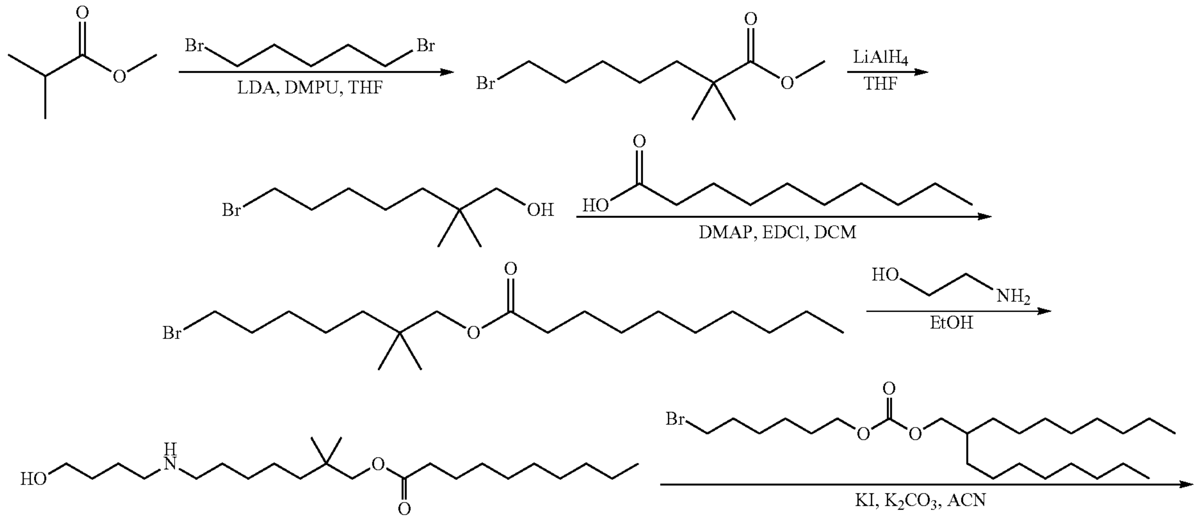

-continued

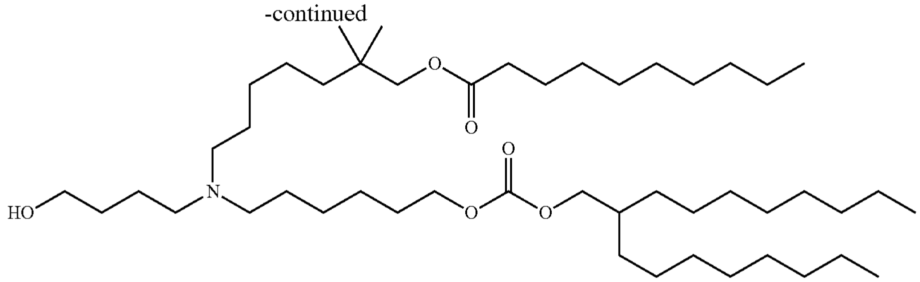

35b

Compound 35b was prepared referring to the method of Example 77 to give 100.0 mg of an oily product.

$^1$H NMR (300 MHz, MeOH-$d_4$) δ: 0.88-0.92 (m, 15H), 1.24-1.72 (m, 64H), 2.33 (t, J=7.5 Hz, 2H), 2.45-2.51 (m, 6H), 3.55 (t, J=6.0 Hz, 2H), 3.80 (s, 2H), 4.02 (d, J=5.7 Hz, 2H), 4.11 (t, J=6.3 Hz, 2H); ESI-MS m/z: 782.65 [M+H]$^+$.

Example 87: Synthesis of Compound 36b

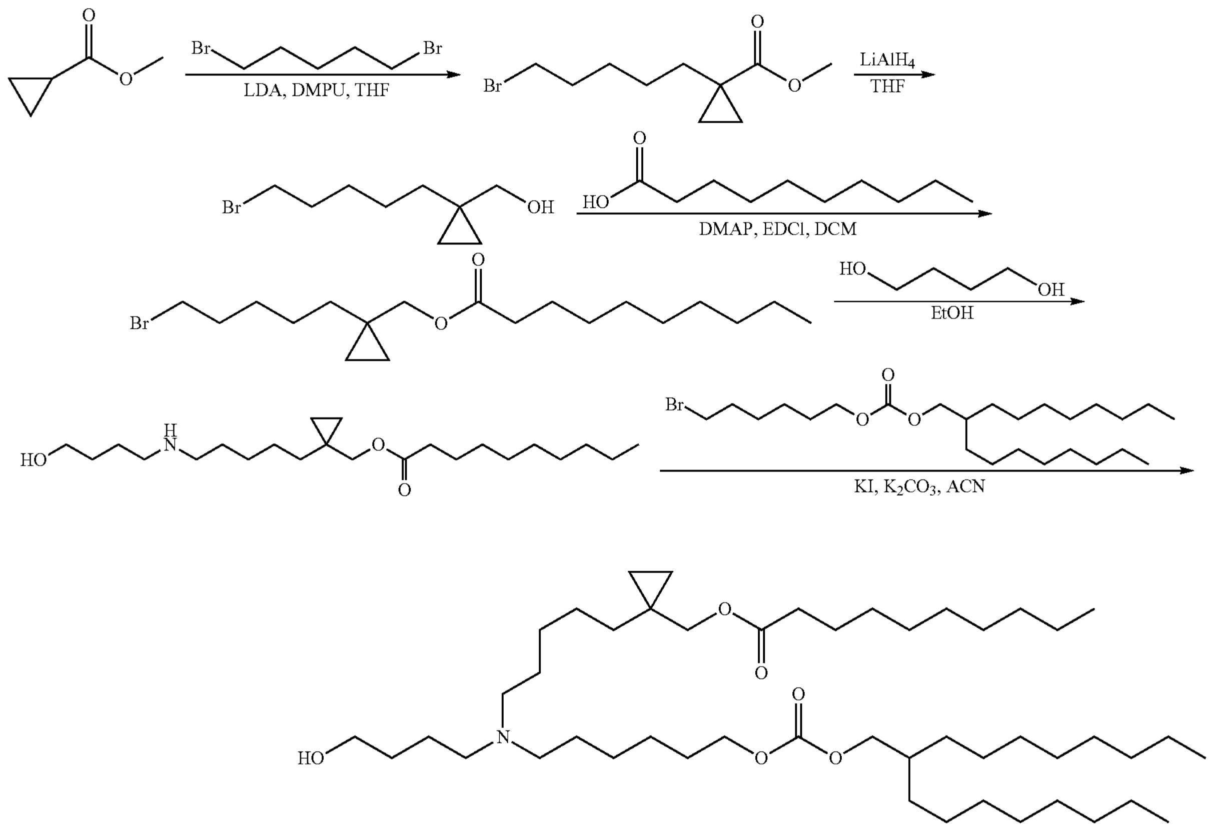

36b

Compound 36b was prepared referring to the method of Example 77 to give 107.0 mg of an oily product.

$^1$H NMR (300 MHz, MeOH-$d_4$) δ: 0.34-0.46 (m, 4H), 0.87-0.92 (m, 9H), 1.22-1.72 (m, 64H), 2.32 (t, J=7.2 Hz, 2H), 2.45-2.51 (m, 6H), 3.55 (t, J=5.7 Hz, 2H), 3.92 (s, 2H), 4.02 (d, J=5.7 Hz, 2H), 4.11 (t, J=6.3 Hz, 2H); ESI-MS m/z: 780.80 [M+H]$^+$.

Example 88: Synthesis of Compound 37b
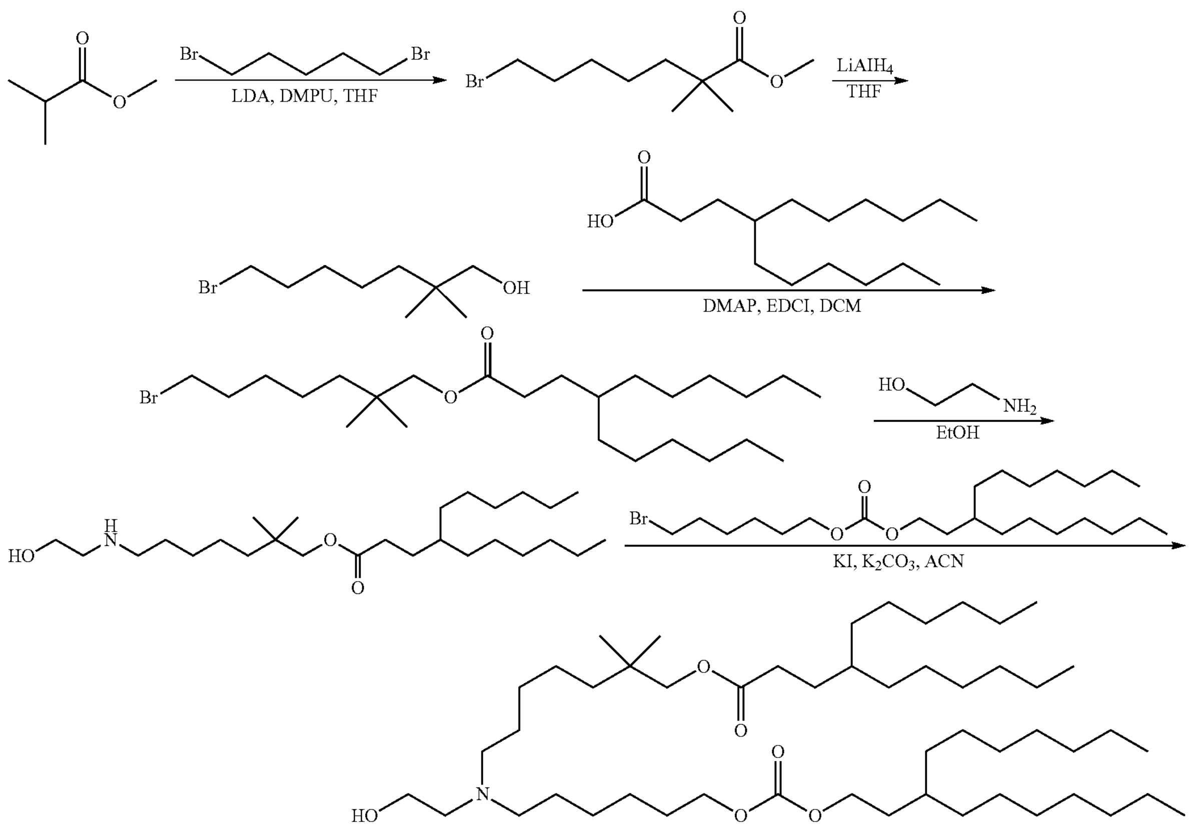
37b
Compound 37b was prepared referring to the method of Example 77 to give 71.6 mg of an oily product.
$^1$H NMR (300 MHz, MeOH-d$_4$) δ: 0.89-0.94 (m, 18H), 1.24-1.69 (m, 67H), 2.32 (t, J=7.5 Hz, 2H), 2.50-2.55 (m, 4H), 2.64 (t, J=6.3 Hz, 2H), 3.62 (t, J=6.3 Hz, 2H), 3.80 (s, 2H), 4.11 (td, J=6.3, 14.7 Hz, 4H); ESI-MS m/z: 824.70 [M+H]$^+$.
Example 89: Synthesis of Compound 52a
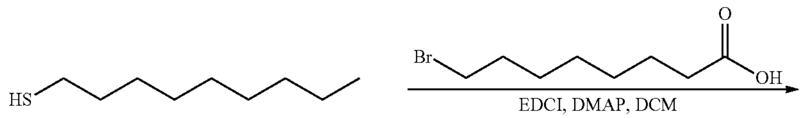
52a-1
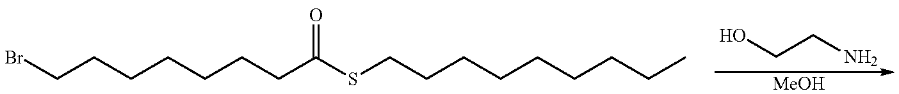
52a-2
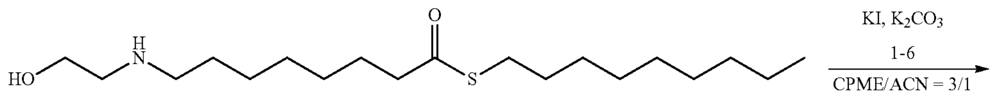
52a-3

-continued

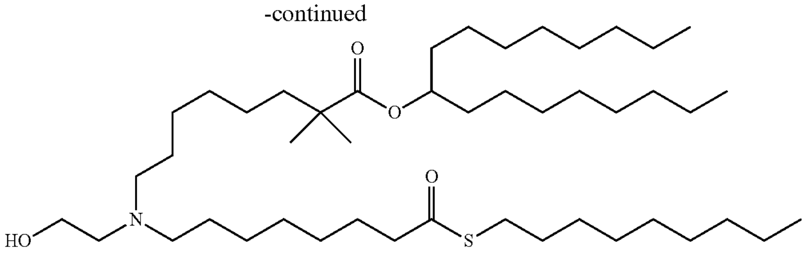

52a

Compound 52a was prepared referring to the method of Example 1 to give 243.8 mg of an oily product.

$^1$H NMR (300 MHz, $CDCl_3$) δ: 4.87-4.81 (m, 1H), 3.59 (m, 2H), 2.86 (t, J=7.2 Hz, 2H), 2.65-2.51 (m, 8H), 1.64-1.58 (m, 4H), 1.57-1.43 (m, 11H), 1.39-1.19 (m, 48H), 1.15 (s, 6H), 0.90 (t, J=7.2 Hz, 9H); ESI-MS m/z: 754.60 $[M+H]^+$.

Example 90: Synthesis of Compound 53a

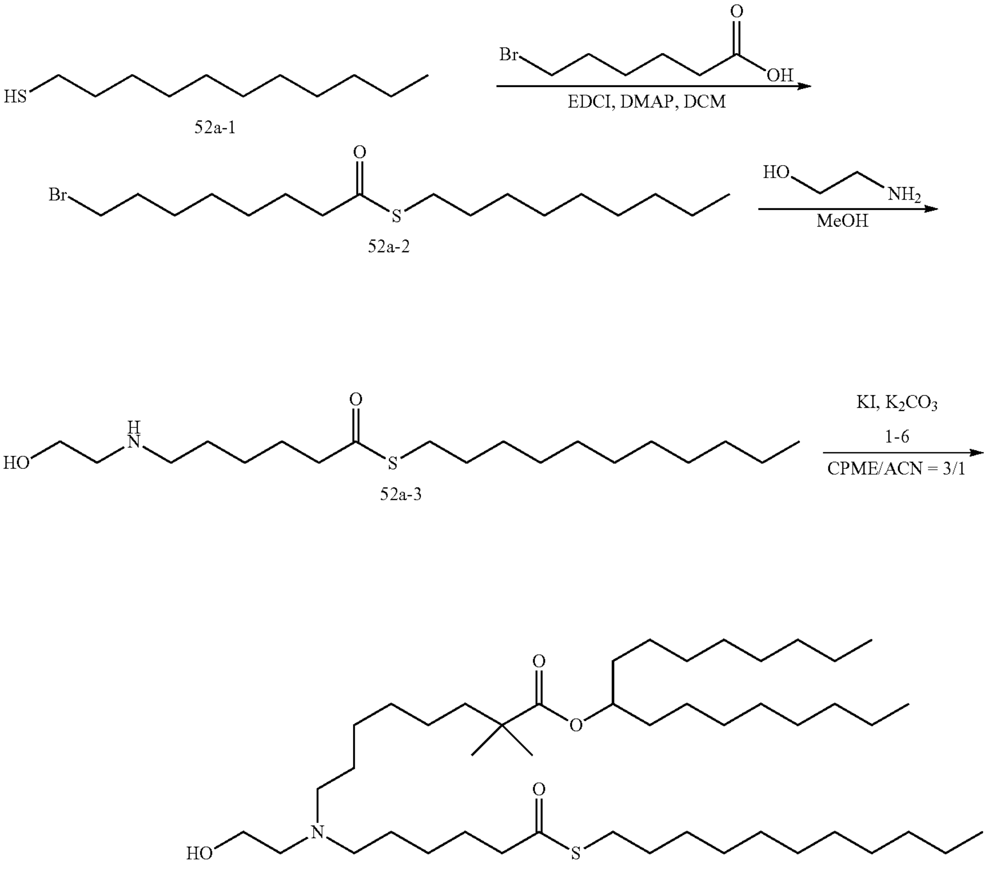

52a-1

52a-2

52a-3

52a

Compound 53a was prepared referring to the method of Example 1 to give 262.7 mg of an oily product.

$^1$H NMR (300 MHz, $CDCl_3$) δ: 4.90-4.78 (m, 1H), 3.56 (t, J=5.1 Hz, 2H), 2.86 (t, J=7.2 Hz, 2H), 2.63-2.48 (m, 8H), 1.81-1.19 (m, 63H), 1.16 (s, 6H), 0.89 (t, J=7.2 Hz, 9H); ESI-MS m/z: 754.60 $[M+H]^+$.

Example 91: Synthesis of Compound 54a
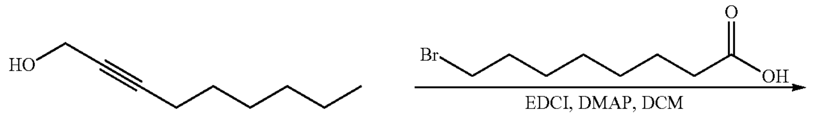
54a-1
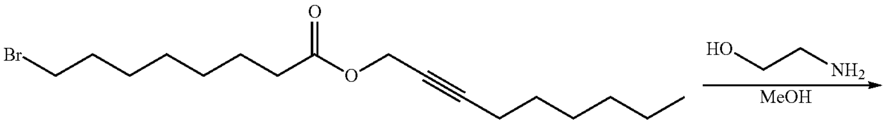
54a-2
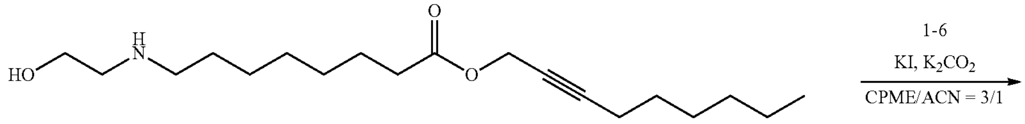
54a-3
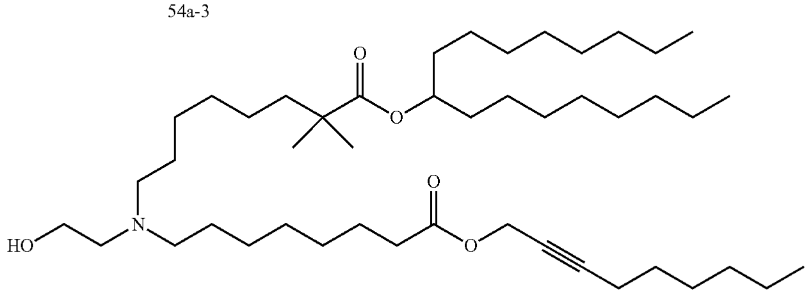
54a
Compound 54a was prepared referring to the method of Example 1 to give 287.7 mg of an oily product.
$^1$H NMR (300 MHz, $CDCl_3$) δ: 4.89-4.79 (m, 1H), 4.66 (t, J=2.1 Hz, 2H), 3.53 (t, J=5.4 Hz, 2H), 2.58 (t, J=5.4 Hz, 2H), 2.45 (t, J=7.2 Hz, 4H), 2.34 (t, J=7.2 Hz, 2H), 2.24-2.20 (m, 2H), 1.79-1.17 (m, 57H), 1.15 (s, 6H), 0.88 (t, J=7.2 Hz, 9H); ESI-MS m/z: 734.60 [M+H].
Example 92: Synthesis of Compound 55a
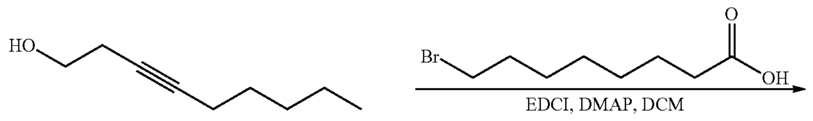
55a-1
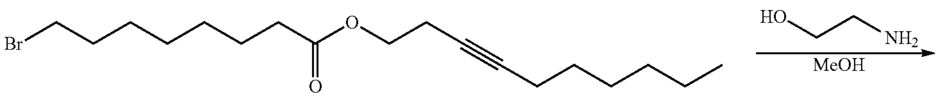
55a-2
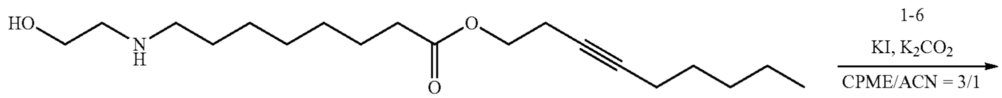
55a-3

-continued

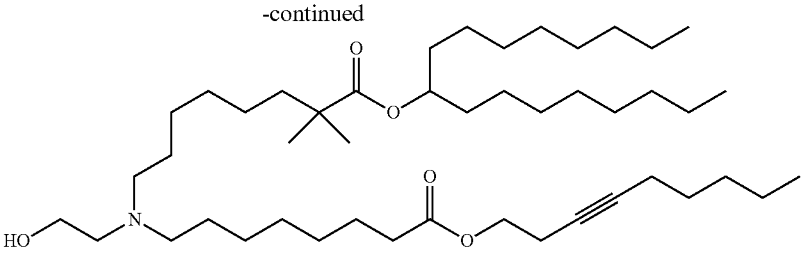

55a

Compound 55a was prepared referring to the method of Example 1 to give 173.5 mg of an oily product.

$^1$H NMR (300 MHz, $CDCl_3$) δ: 4.89-4.78 (m, 1H), 4.13 (t, J=7.2 Hz, 2H), 3.56 (m, 2H), 2.63 (m, 2H), 2.51-2.45 (m, 6H), 2.31 (t, J=7.2 Hz, 2H), 2.16-2.10 (m, 2H), 1.78-1.17 (m, 55H), 1.15 (s, 6H), 0.90 (m, 9H); ESI-MS m/z: 734.50 $[M+H]^+$.

Example 93: Synthesis of Compound 56a

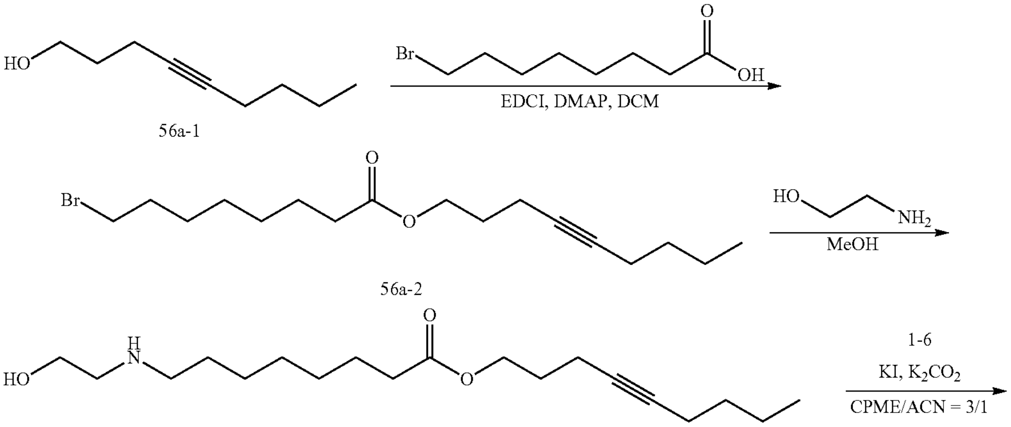

56a-1

56a-2

56a-3

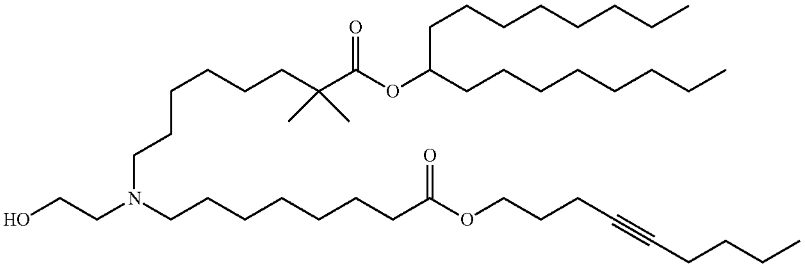

56a

Compound 56a was prepared referring to the method of Example 1 to give 112.2 mg of an oily product.

$^1$H NMR (300 MHz, $CDCl_3$) δ: 4.87-4.79 (m, 1H), 4.16 (t, J=6.6 Hz, 2H), 3.60 (m, 2H), 2.67-2.53 (m, 6H), 2.32-2.11 (m, 6H), 2.32-2.11 (m, 6H), 1.85-1.76 (m, 2H), 1.66-1.18 (m, 53H), 1.14 (s, 6H), 0.88 (m, 9H); ESI-MS m/z: 734.55 $[M+H]^+$.

Example 94: Synthesis of Compound 57a
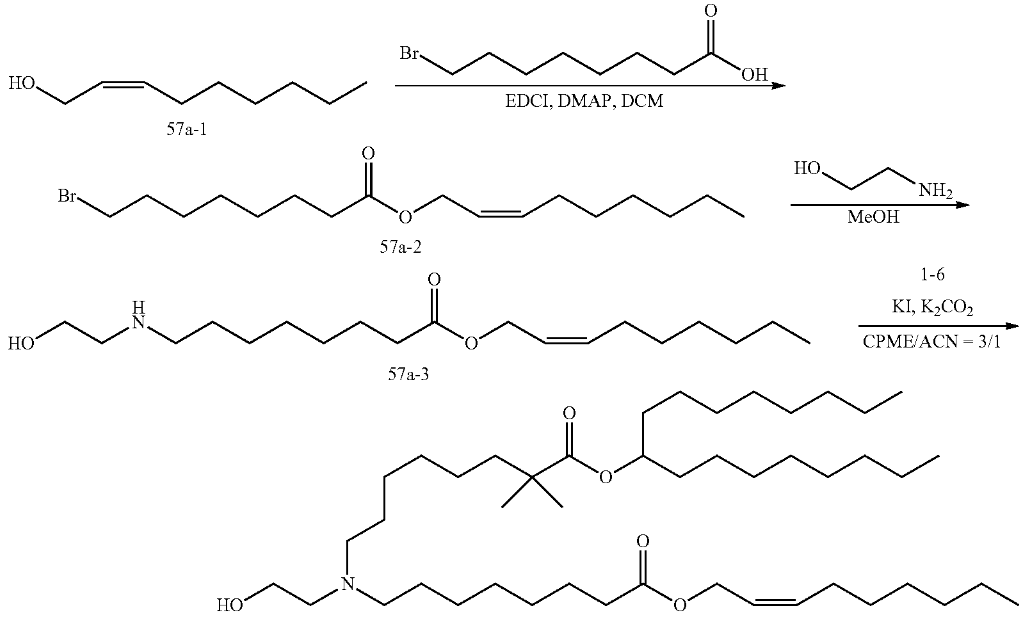
57a-1
57a-2
57a-3
57a
Compound 57a was prepared referring to the method of Example 1 to give 45.0 mg of an oily product.
$^1$H NMR (400 MHz, $CDCl_3$) δ: 5.68-5.49 (m, 2H), 4.85-4.79 (m, 1H), 4.63 (d, J=6.8 Hz, 2H), 3.84 (m, 2H), 2.95-2.76 (m, 6H), 2.31 (t, J=7.2 Hz, 2H), 2.12-2.07 (m, 2H), 1.66-1.18 (m, 57H), 1.16 (s, 6H), 0.88 (m, 9H); ESI-MS m/z: 736.60 $[M+H]^+$.
Example 95: Synthesis of Compound 58a
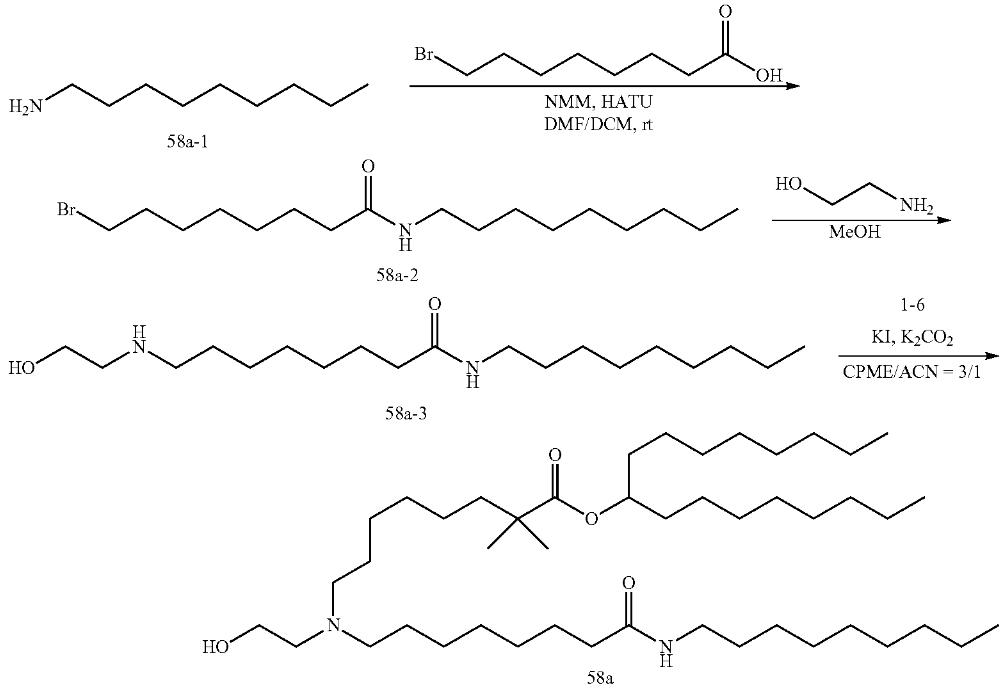
58a-1
58a-2
58a-3
58a In a 50 mL round-bottom flask, the reactants 1-nonanamine (286.5 mg, 2.0 mmol, 1.0 eq.), 8-bromooctanoic acid (535.5 mg, 2.4 mmol, 1.2 eq.), NMM (202.3 mg, 2.0 mmol, 1.0 eq.), and HATU (1.14 g, 3.0 mmol, 1.5 eq.) were dissolved in a mixed solution of DMF (2.0 mL) and DCM (10.0 mL), and the mixture was stirred at room temperature for reaction until the reaction of 1-nonanamine was completed as monitored by TLC. The reaction liquid was introduced into 100 mL of a saturated sodium chloride solution, and the mixture was extracted with DCM (30 mL×3). The organic phases were combined and dried over anhydrous sodium sulfate. The mixture was filtered, and the filtrate was concentrated to dryness to give a crude product, which was purified by silica gel column chromatography to give 610 mg of compound 58a-2.

Compound 58a was prepared referring to the method of Example 1 to give 104.0 mg of an oily product.

$^1H$ NMR (300 MHz, $CDCl_3$) δ: 5.53 (s, 1H), 4.87-4.79 (m, 1H), 3.22 (dd, J=6.9 Hz, 13.2 Hz, 2H), 2.67-2.52 (m, 6H), 2.15 (t, J=7.2 Hz, 2H), 1.65-1.19 (m, 63H), 1.15 (s, 6H), 0.88 (t, J=6.9 Hz, 9H); ESI-MS m/z: 737.60 [M+H].

Example 96: Synthesis of Compound 59a

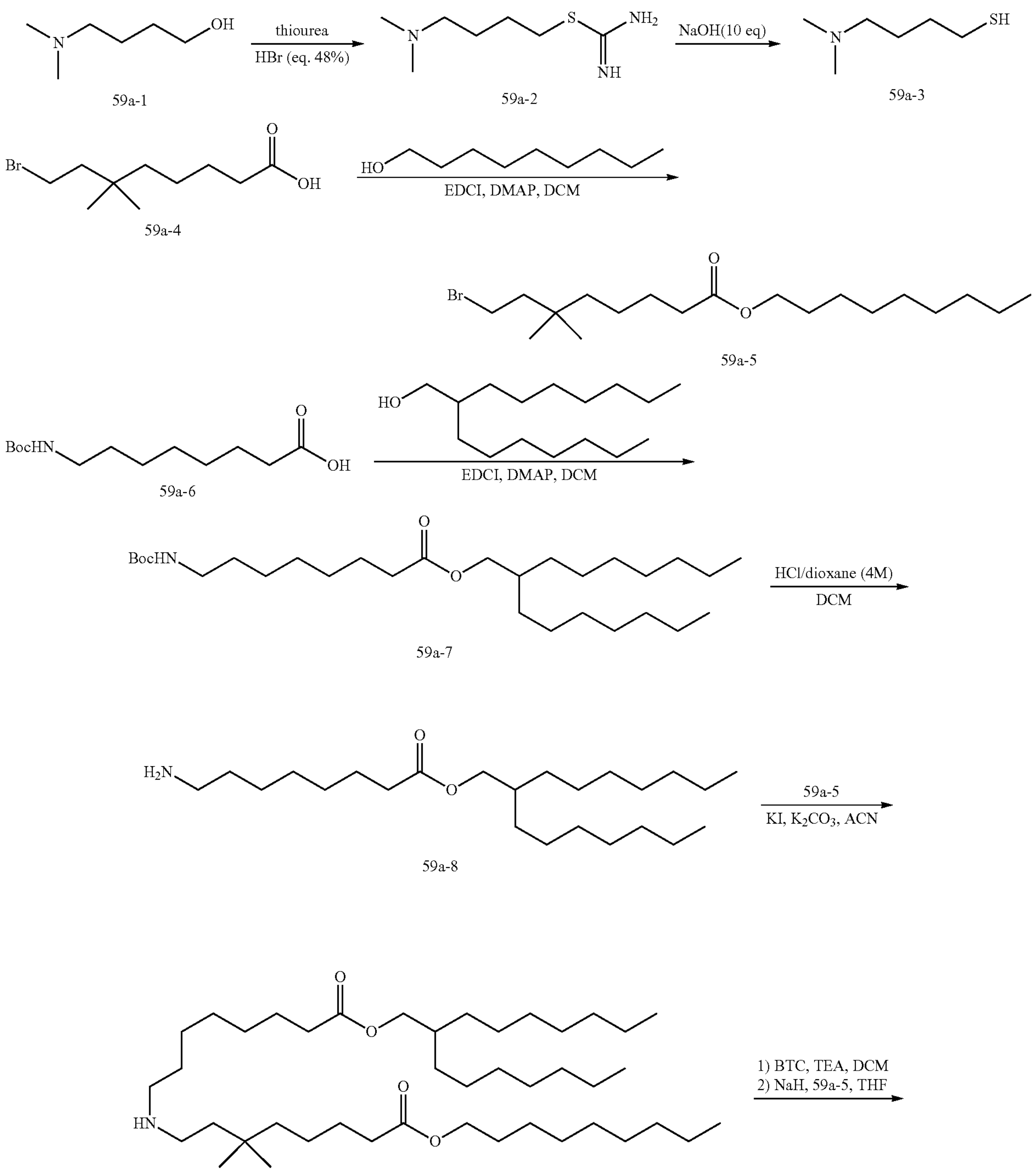

59a-1 59a-2 59a-3 59a-4 59a-5 59a-6 59a-7 59a-8 59a-9

-continued

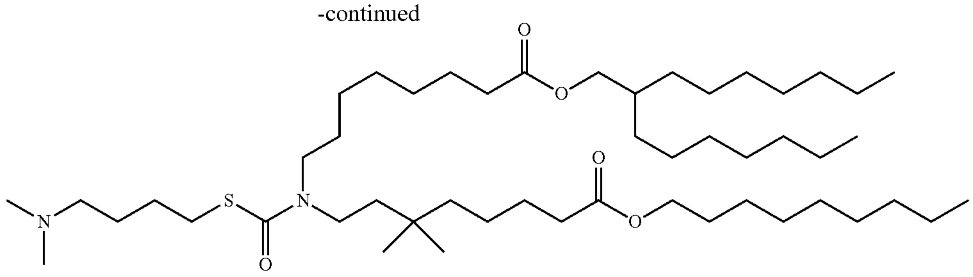

59a

In a 100 mL sealed tube, 4-dimethylamino-1-butanol (3.0 g, 25.5 mmol, 1.0 eq.) and thiourea (8.4 g, 110.0 mmol, 4.3 eq.) were added, then an aqueous HBr solution (48%, 60 mL) was added, and the mixture was heated to 120° C. and stirred for overnight, which was directly used in the next step without purification.

The system described above was cooled to 0° C., NaOH (10.2 g, 255.0 mmol, 10.0 eq.) was added in batches, and the mixture was heated to 120° C. and reacted for 2 h. The mixture was cooled to room temperature and extracted with dichloromethane. The organic phases were combined, dried over anhydrous sodium sulfate, and filtered to remove the drying agent, and the solvent was removed to give 2.45 g of a colorless oily compound 59a-3.

In a 100 mL three-neck flask, compound 59a-6 (1.5 g, 5.8 mmol, 1.0 eq.), 2-heptyl-1-nonanol (1.40 g, 5.8 mmol, 1.0 eq.), EDCI (1.66 g, 8.7 mmol, 1.5 eq.), and DMAP (0.35 g, 2.9 mmol, 0.5 eq.) were dissolved in 20 mL of dichloromethane, and the mixture was stirred at room temperature overnight. The mixture was washed with water (3×15 mL). The organic phase was subjected to rotary evaporation under reduced pressure, directly mixed with silica gel, and purified by silica gel column chromatography to give 3.3 g of compound 59a-7.

In a 100 mL three-neck flask, compound 59a-7 (2.8 g, 5.8 mmol, 1.0 eq.) was dissolved in 20 mL of dichloromethane, HCl/dioxane (4 M, 14 mL) was added, and the mixture was stirred at room temperature overnight. The organic solvent was removed by rotary evaporation, the reaction liquid was adjusted to neutrality with a saturated sodium bicarbonate solution, and the mixture was extracted with DCM (3×20 mL). The organic phase was collected and dried over anhydrous $Na_2SO_4$. The organic phase was purified by silica gel column chromatography to give 1.95 g of compound 8.

In a 40 mL sealed tube, compound 59a-8 (680 mg, 1.8 mmol, 1.0 eq.), KI (365 mg, 2.2 mmol, 1.2 eq.), $K_2CO_3$ (745 mg, 5.4 mmol, 3.0 eq.), and 59a-5 (668.9 mg, 1.8 mmol, 1.0 eq.) were dissolved in 10 mL of acetonitrile. The mixture was heated to 80° C. and stirred for reaction overnight. After the reaction was completed, the mixture was cooled to room temperature and filtered, and the filter cake was washed with acetonitrile (5 mL×2). The filtrate was collected and concentrated by rotary evaporation to dryness. The residue was purified by column chromatography to give 580 mg of a yellow oily compound 59a-9.

In a 20 mL sealed tube, compound 59a-9 (200 mg, 0.29 mmol, 1.0 eq.) was dissolved in 5 mL of DCM. After the reaction system was cooled to 5° C., TEA (59.5 mg, 0.59 mmol, 2.0 eq.) and BTC (87.3 mg, 0.29 mmol, 1.0 eq.) were added dropwise. The temperature was kept at 5° C., the mixture was stirred for reaction for 1 h and concentrated to remove DCM, and 5 mL of tetrahydrofuran was added. In another 20 mL sealed tube, compound 59a-3 (101.9 mg, 0.76 mmol, 2.6 eq.) was dissolved in 5 mL of tetrahydrofuran. After the mixture was cooled to 0° C., NaH (60%, 58.0 mg, 1.45 mmol, 5.0 eq.) was added. After stirring at 0° C. for 1 h, the above prepared THF mixed solution was added dropwise, and the mixture was reacted for another 1 h. The reaction liquid was poured into 10 mL of ice water, and the mixture was extracted with ethyl acetate. The organic phases were combined, dried over anhydrous sodium sulfate, and filtered to remove the drying agent, and the solvent was removed to give a crude product. The crude product was purified by Prep-HPLC (Column: XSelect C18 (30×150 mm, 5 μm); Eluent A: $H_2O$/ACN 60/40, 10 mM $NH_4HCO_3$+ 1% $NH_3 \cdot H_2O$; Eluent B: IPA/ACN 90/10; Flow rate: 60 mL/min; Gradient program: 65%-85% B in 0-12 min) to give 126.9 mg of a light yellow oily compound 59a.

$^1H$ NMR (300 MHz, $CDCl_3$) δ: 4.06 (t, J=6.6 Hz, 2H), 3.96 (d, J=5.7 Hz, 2H), 3.36-3.15 (m, 4H), 2.90 (t, J=6.9 Hz, 2H), 2.41 (s, 2H), 2.31-2.24 (m, 10H), 1.64-1.16 (m, 61H), 0.93-0.77 (m, 15H); ESI-MS m/z: 839.65 $[M+H]^+$.

Example 97: Synthesis of Compound 60a

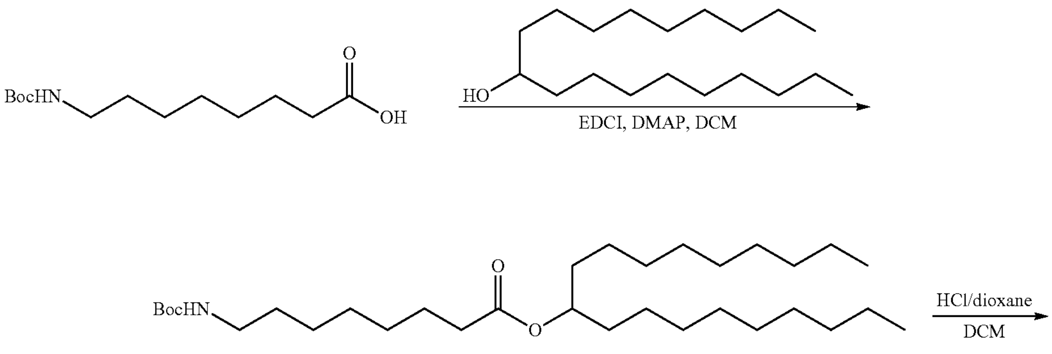

-continued
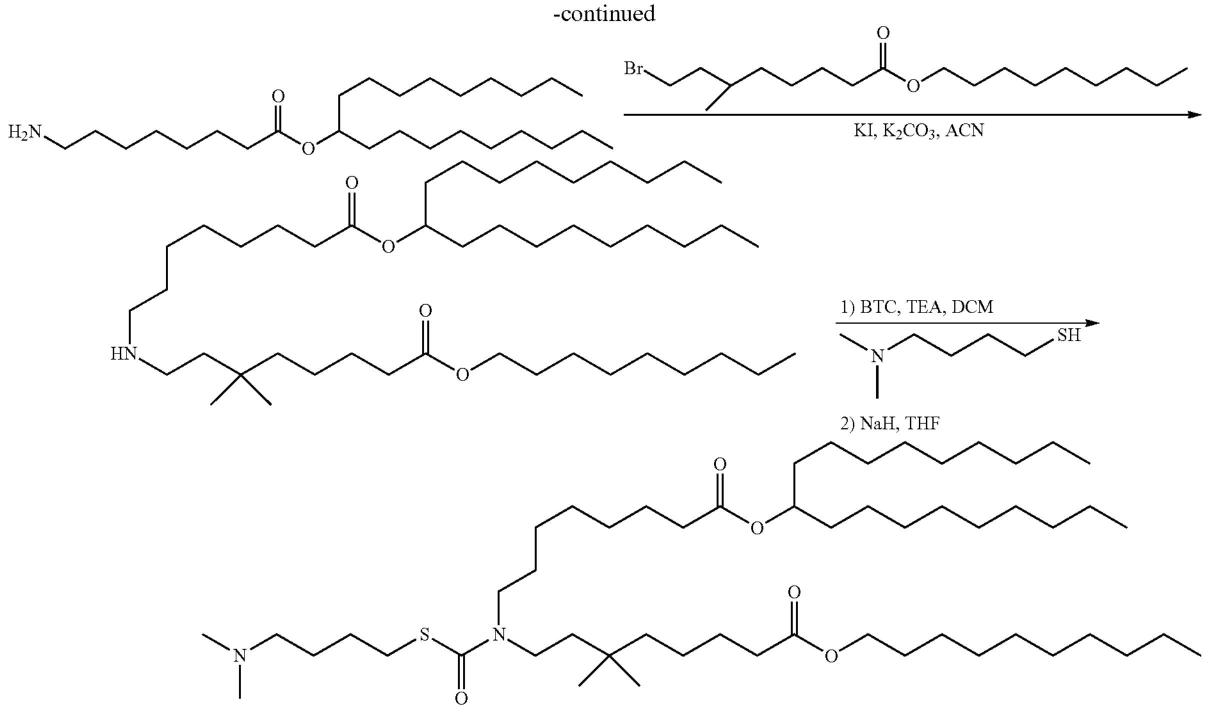
60a
Compound 60a was prepared referring to the method of Example 96 to give 157.3 mg of an oily product.
$^1$H NMR (300 MHz, $CDCl_3$) δ: 4.86 (p, J=6.3 Hz, 1H), 4.06 (t, J=6.9 Hz, 2H), 3.37-3.17 (m, 4H), 2.90 (t, J=6.9 Hz, 2H), 2.39-2.25 (m, 12H), 1.79-1.18 (m, 70H), 0.93-0.83 (m, 15H); ESI-MS m/z: 895.80 $[M+H]^+$.
Example 98: Synthesis of Compound 61a
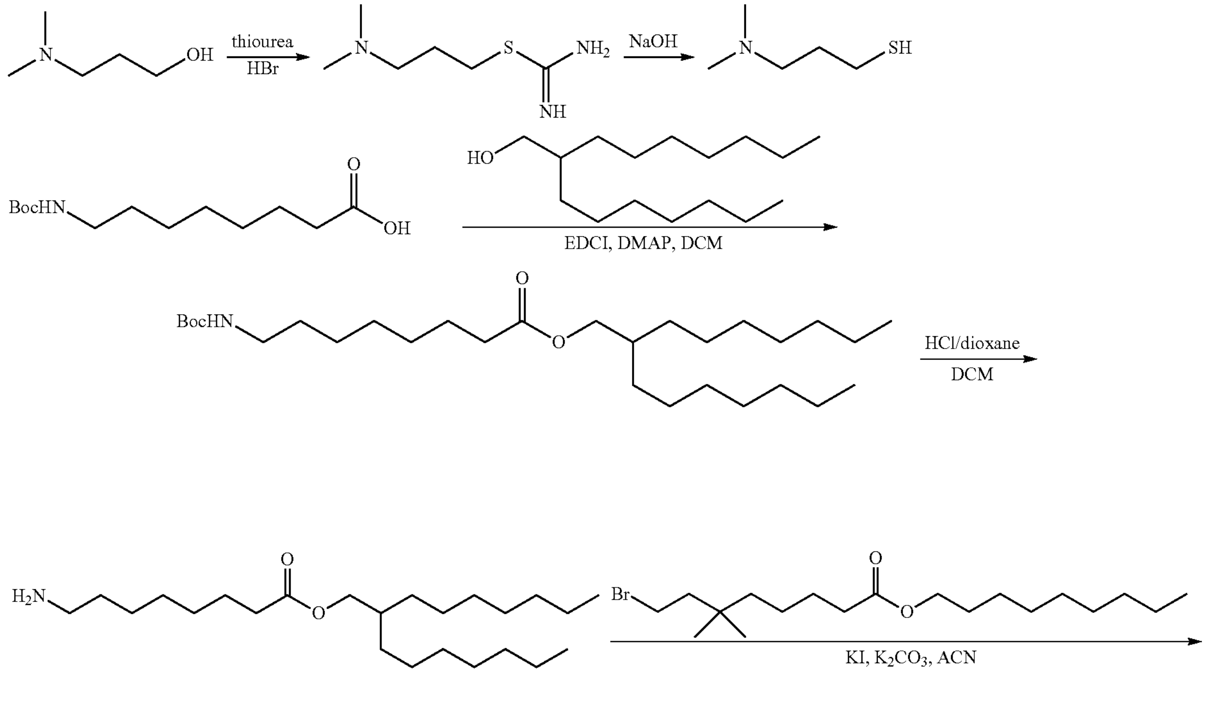

-continued
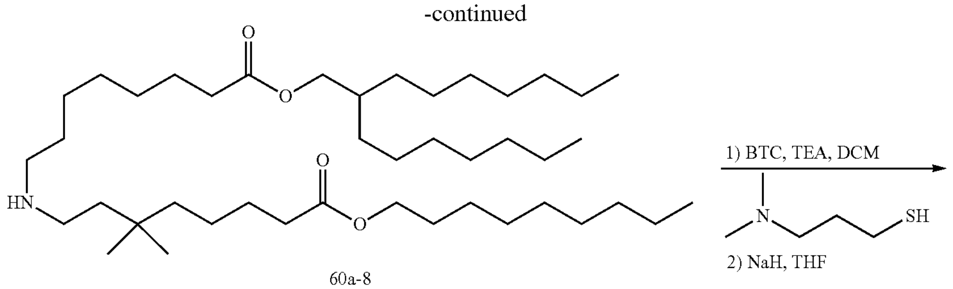
60a-8
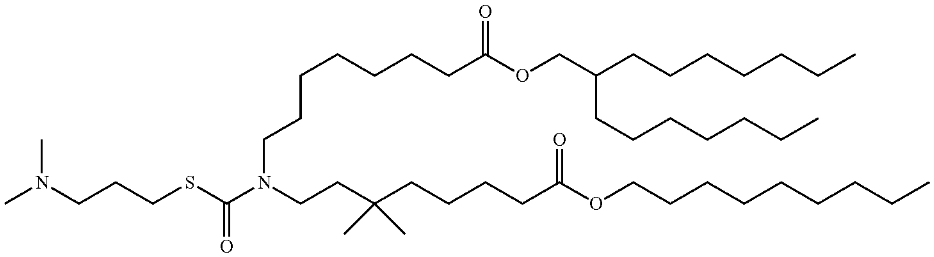
61a
Compound 61a was prepared referring to the method of Example 96 to give 184.0 mg of an oily product.
$^1$H NMR (300 MHz, $CDCl_3$) δ: 4.06 (t, J=6.9 Hz, 2H), 3.96 (d, J=5.7 Hz, 2H), 3.35-3.18 (m, 4H), 2.91 (t, J=7.2 Hz, 2H), 2.43-2.27 (m, 12H), 1.87-1.77 (m, 2H), 1.61-1.18 (m, 57H), 0.93-0.84 (m, 15H); ESI-MS m/z: 825.55 $[M+H]^+$.
Example 99: Synthesis of Compound 38b
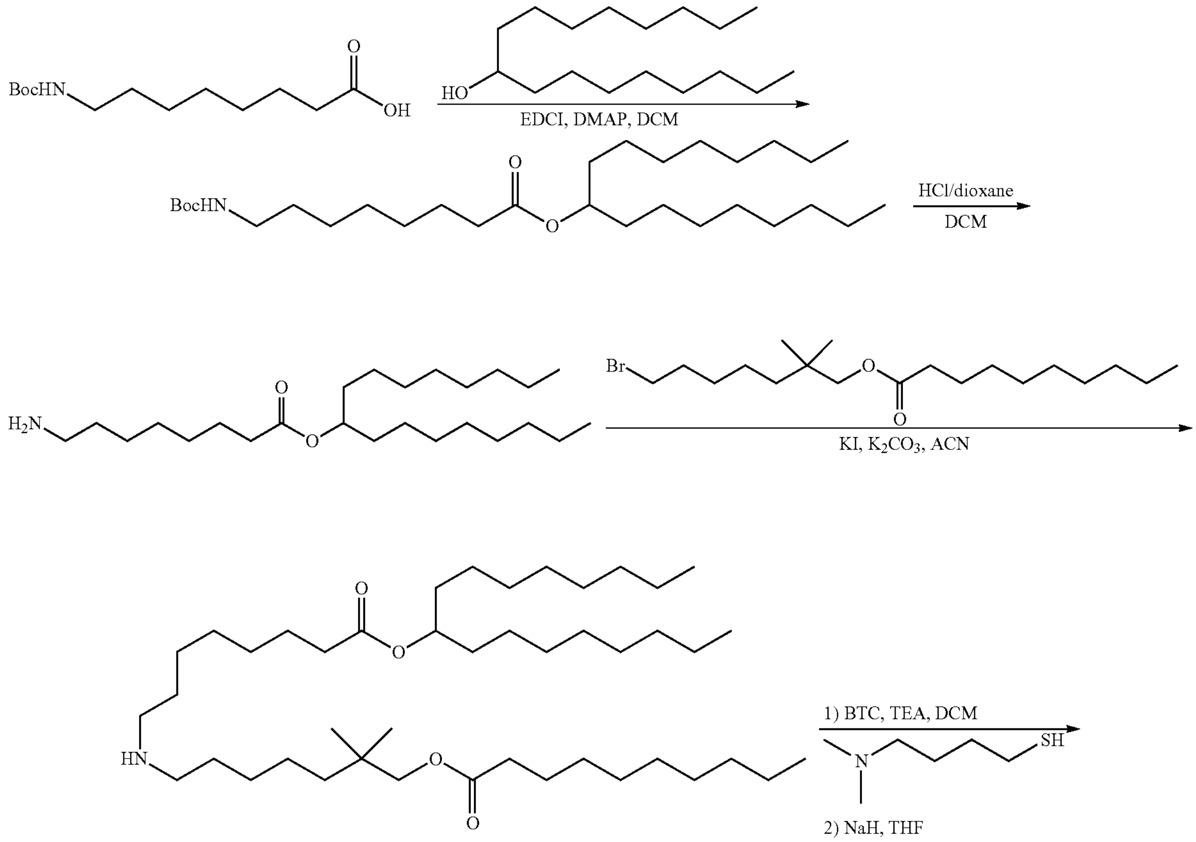

-continued

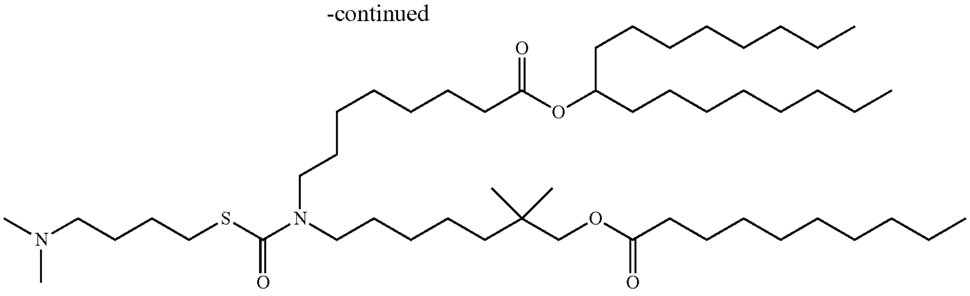

38b

Compound 38b was prepared referring to the method of Example 96 to give 228 mg of an oily product.

$^1$H NMR (300 MHz, $CDCl_3$) δ: 4.86 (p, J=6.3 Hz, 1H), 3.78 (s, 2H), 3.33-3.18 (m, 4H), 2.90 (t, J=6.6 Hz, 2H), 2.38-2.25 (m, 12H), 1.69-1.44 (m, 16H), 1.34-1.17 (m, 48H), 0.90-0.85 (m, 15H); ESI-MS m/z: 853.65 $[M+H]^+$.

Example 100: Synthesis of Compound 39b

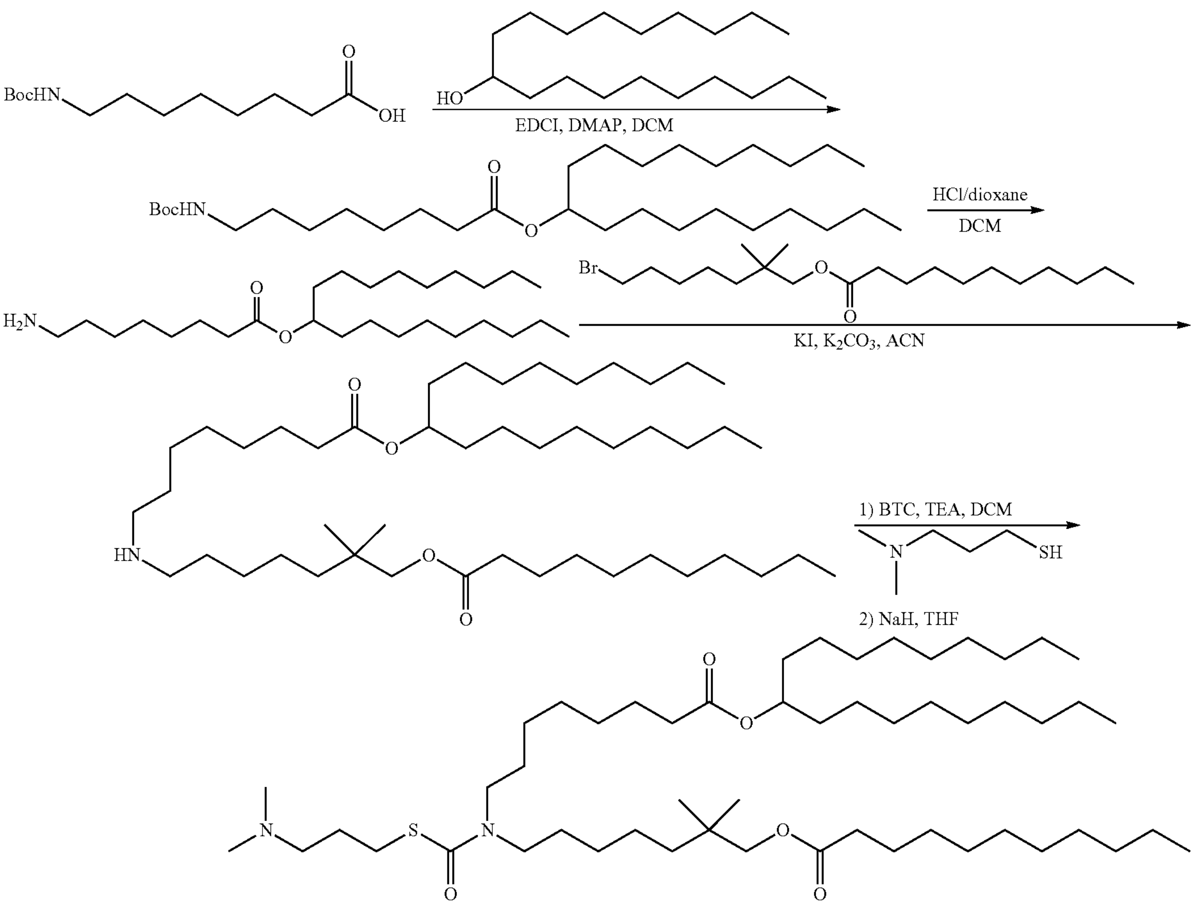

39b

Compound 39b was prepared referring to the method of Example 96 to give 117.9 mg of an oily product.

$^1$H NMR (300 MHz, $CDCl_3$) δ: 4.86 (p, J=6.3 Hz, 1H), 3.78 (s, 2H), 3.36-3.17 (m, 4H), 2.92 (t, J=7.2 Hz, 2H), 2.46 (t, J=7.2 Hz, 2H), 2.34-2.22 (m, 10H), 1.90-1.80 (m, 3H), 1.62-1.49 (m, 14H), 1.34-1.17 (m, 51H), 0.93-0.86 (m, 15H); ESI-MS m/z: 881.65 $[M+H]^+$.

Example 101: Synthesis of Compound 40b
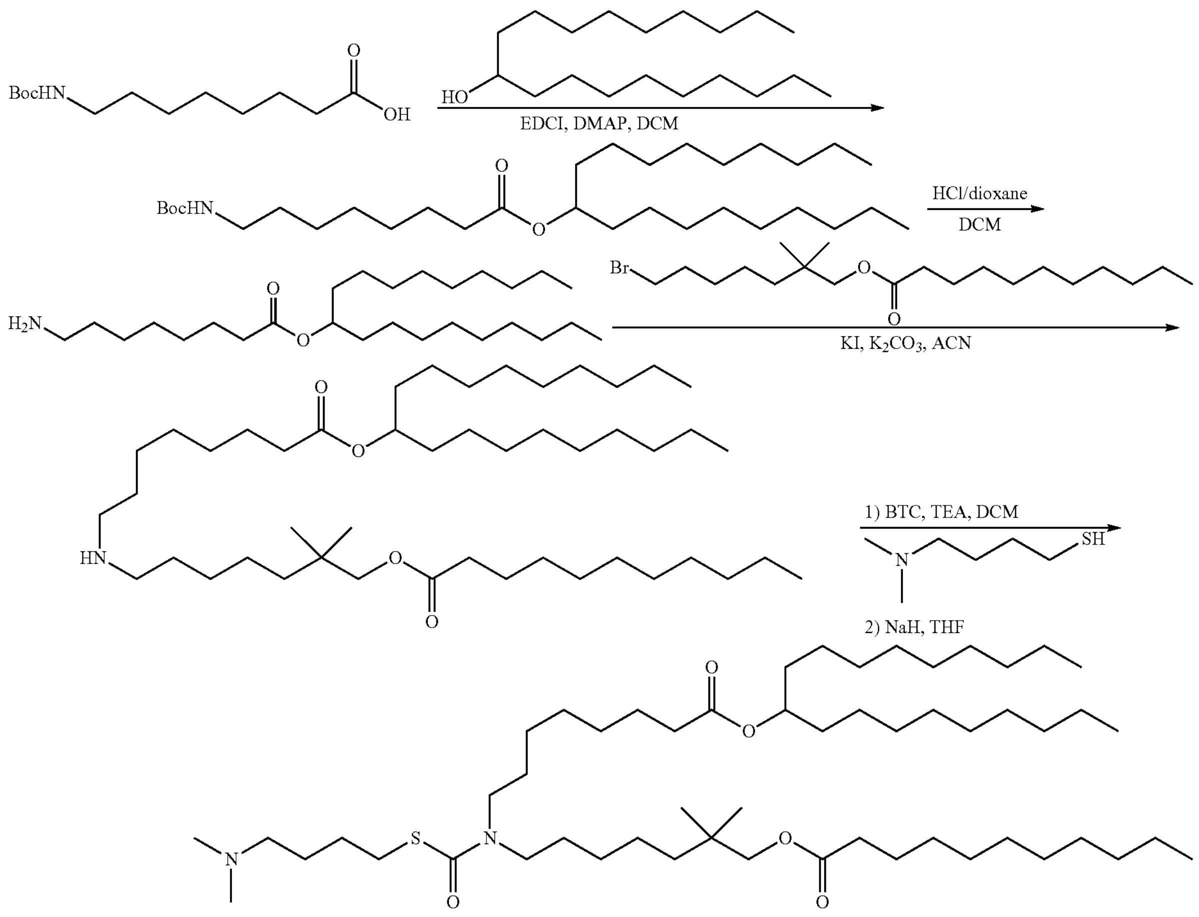
40b
Compound 40b was prepared referring to the method of Example 96 to give 75.3 mg of an oily product.
$^1$H NMR (300 MHz, $CDCl_3$) δ: 4.86 (p, J=6.3 Hz, 1H), 3.78 (s, 2H), 3.36-3.17 (m, 4H), 2.91 (t, J=6.6 Hz, 2H), 2.48-2.28 (m, 12H), 1.89-1.60 (m, 10H), 1.51-1.16 (m, 60H), 0.93-0.87 (m, 15H); ESI-MS m/z: 895.70 [M+H]$^+$.
Example 102: Synthesis of Compound 41b
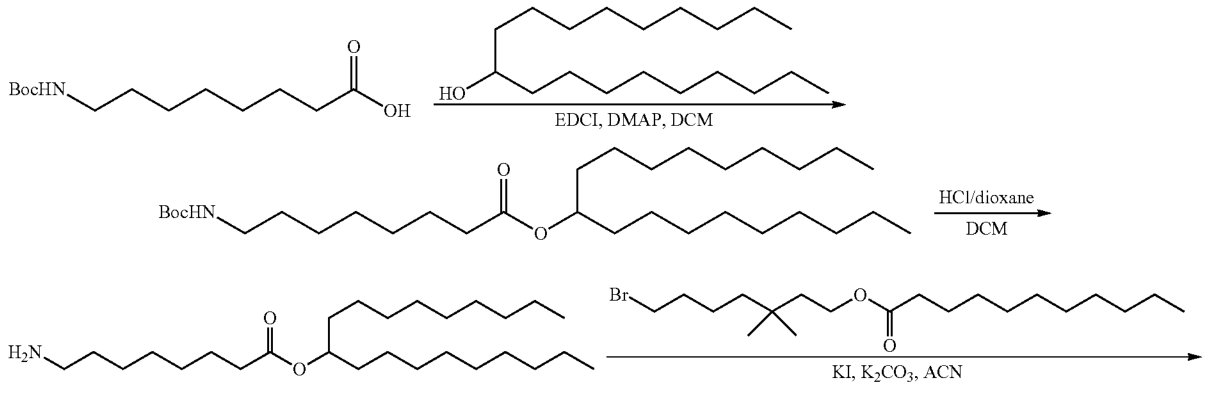

-continued
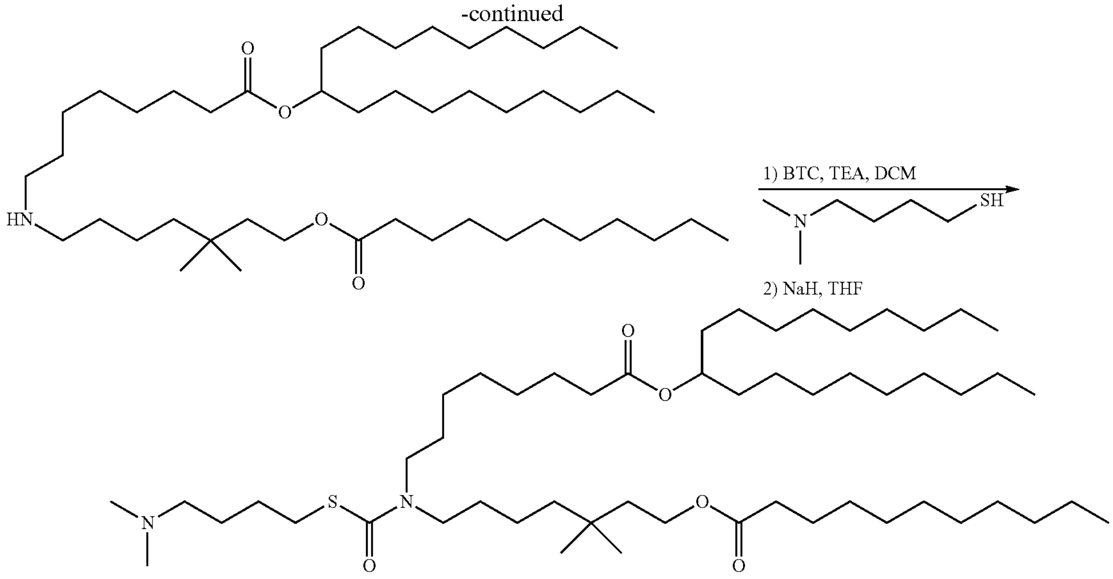
41b
Compound 41b was prepared referring to the method of Example 96 to give 95.1 mg of an oily product.
$^1$H NMR (400 MHz, $CDCl_3$) δ: 4.86 (p, J=6.4 Hz, 1H), 4.09 (t, J=7.6 Hz, 2H), 3.31-3.24 (m, 4H), 2.90 (t, J=7.6 Hz, 2H), 2.40-2.26 (m, 12H), 1.63-1.50 (m, 21H), 1.32-1.16 (m, 49H), 0.90-0.86 (m, 15H); ESI-MS m/z: 895.80 $[M+H]^+$.
Example 103: Synthesis of Compound 42b
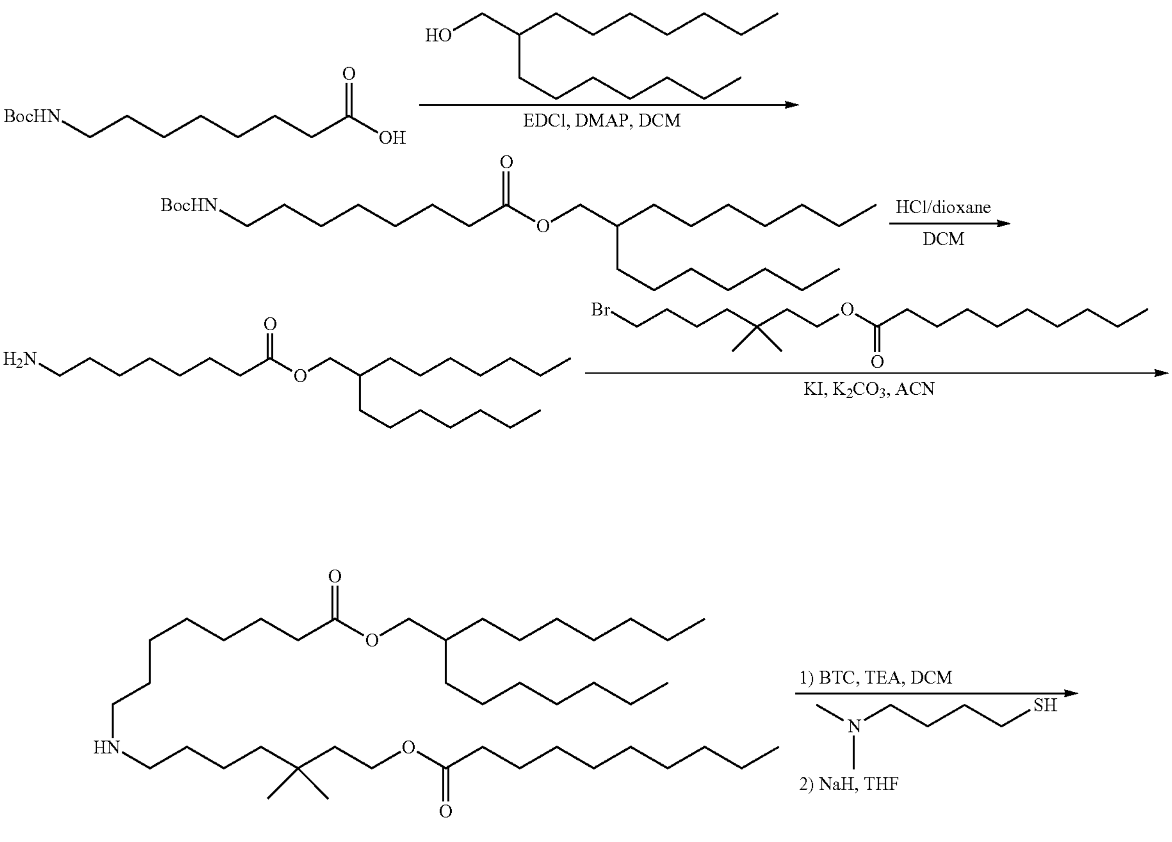

-continued

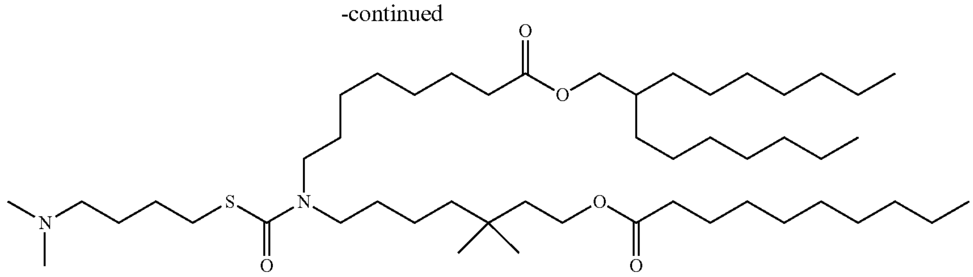

42b

Compound 42b was prepared referring to the method of Example 96 to give 63.6 mg of an oily product.

$^1$H NMR (400 MHz, $CDCl_3$) δ: 4.09 (p, J=7.6 Hz, 2H), 3.96 (d, J=6.0 Hz, 2H), 3.31-3.24 (m, 4H), 2.90 (t, J=7.2 Hz, 2H), 2.57-2.26 (m, 12H), 1.67-1.43 (m, 20H), 1.32-1.16 (m, 41H), 0.90-0.86 (m, 15H); ESI-MS m/z: 839.70 $[M+H]^+$.

Example 104: Synthesis of Compound 43b

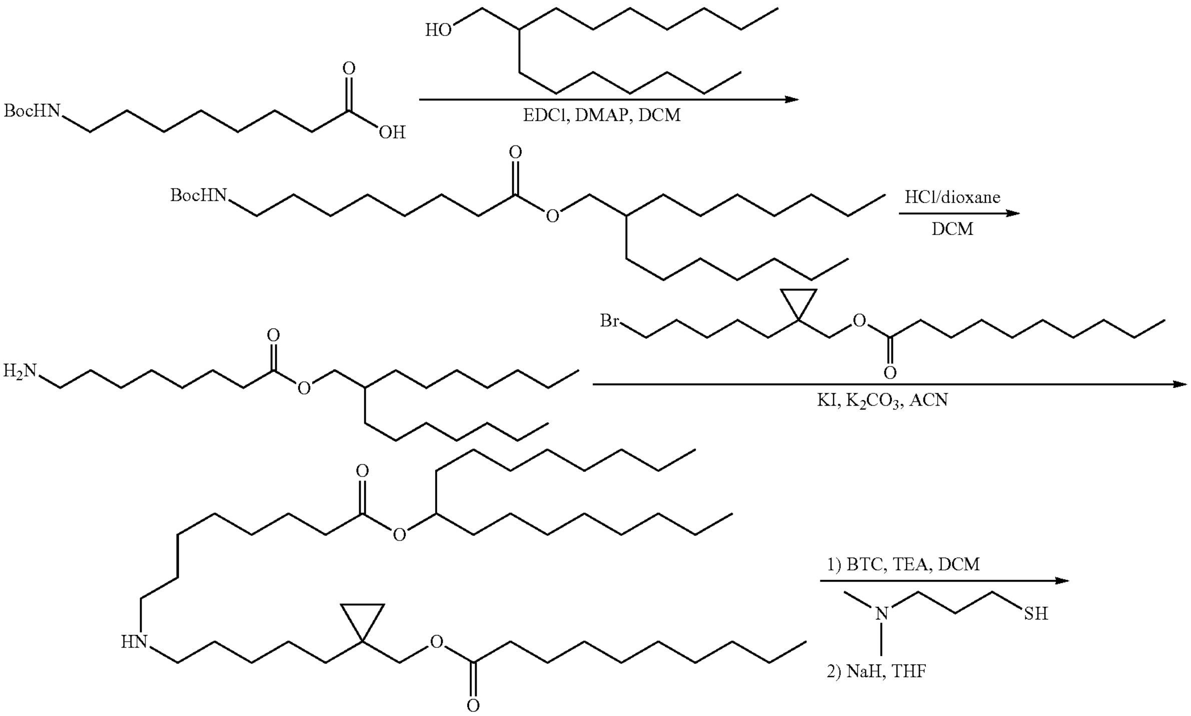

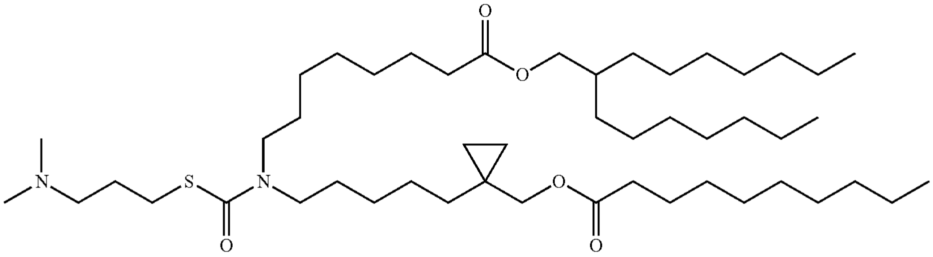

43b

Compound 43b was prepared referring to the method of Example 96 to give 130.5 mg of an oily product.

$^1$H NMR (300 MHz, $CDCl_3$) δ: 3.96 (d, J=6.0 Hz, 2H), 3.89 (s, 2H), 3.35-3.18 (m, 4H), 2.91 (t, J=7.2 Hz, 2H), 2.44-2.28 (m, 12H), 1.87-1.79 (m, 2H), 1.77-1.60 (m, 10H), 1.34-1.17 (m, 47H), 0.90-0.85 (m, 9H), 0.52-0.32 (m, 4H); ESI-MS m/z: 823.60 $[M+H]^+$.

Example 105: Synthesis of Compound 44b
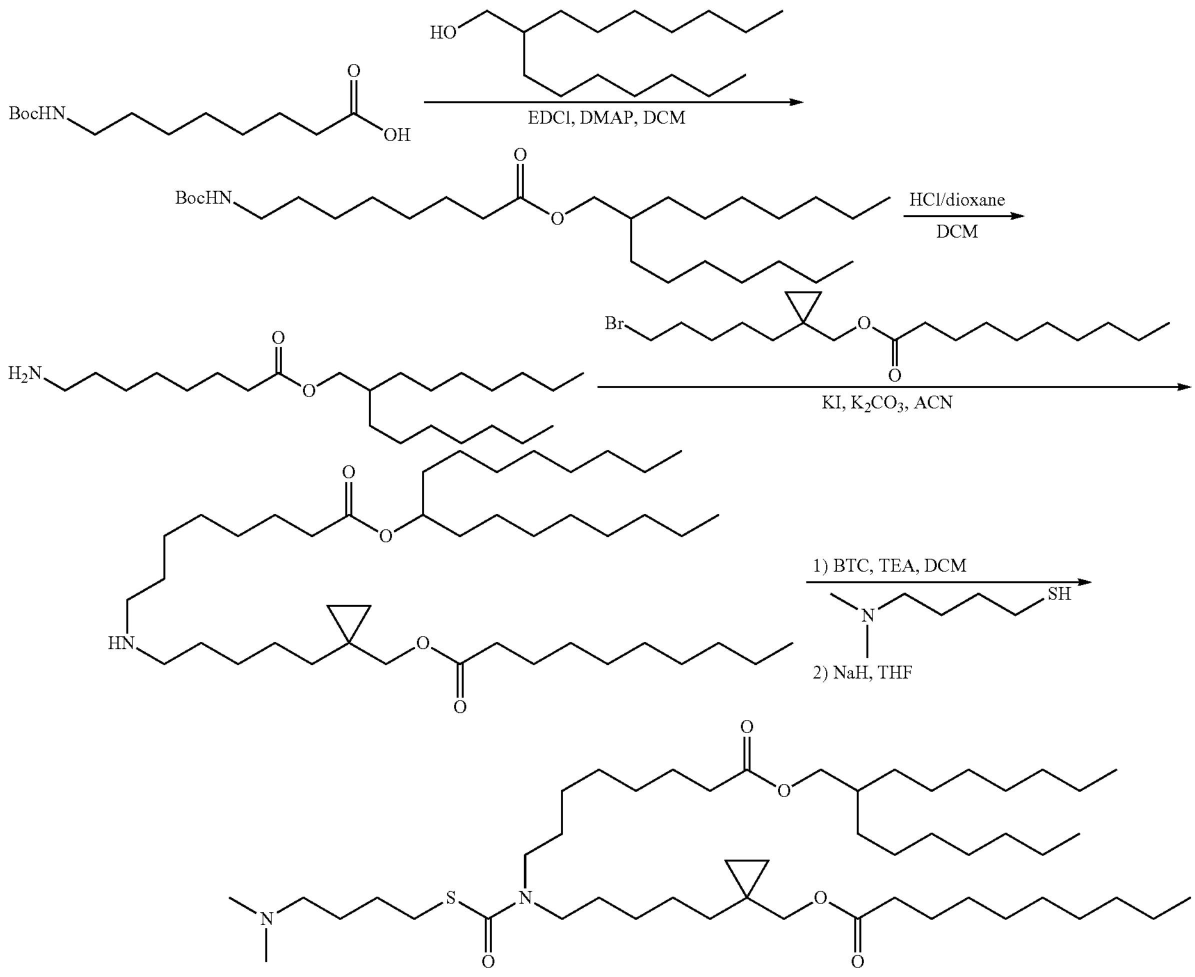
44b
Compound 44b was prepared referring to the method of Example 96 to give 79.4 mg of an oily product.
$^1$H NMR (300 MHz, $CDCl_3$) δ: 3.95 (d, J=5.7 Hz, 2H), 3.90 (s, 2H), 3.35-3.19 (m, 4H), 2.90 (t, J=7.2 Hz, 2H), 2.67 (s, 4H), 2.34-2.27 (m, 4H), 1.72-1.51 (m, 16H), 1.29-1.21 (m, 49H), 0.90-0.83 (m, 9H), 0.46-0.36 (m, 4H); ESI-MS m/z: 837.75 $[M+H]^+$.
Example 106: Synthesis of Compound 45b
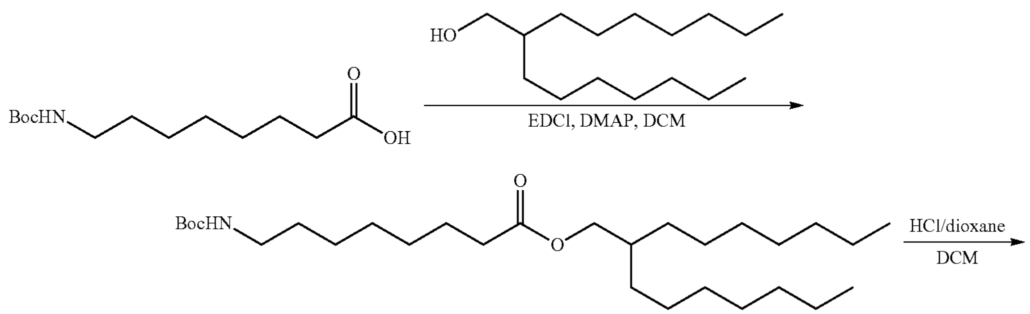

-continued
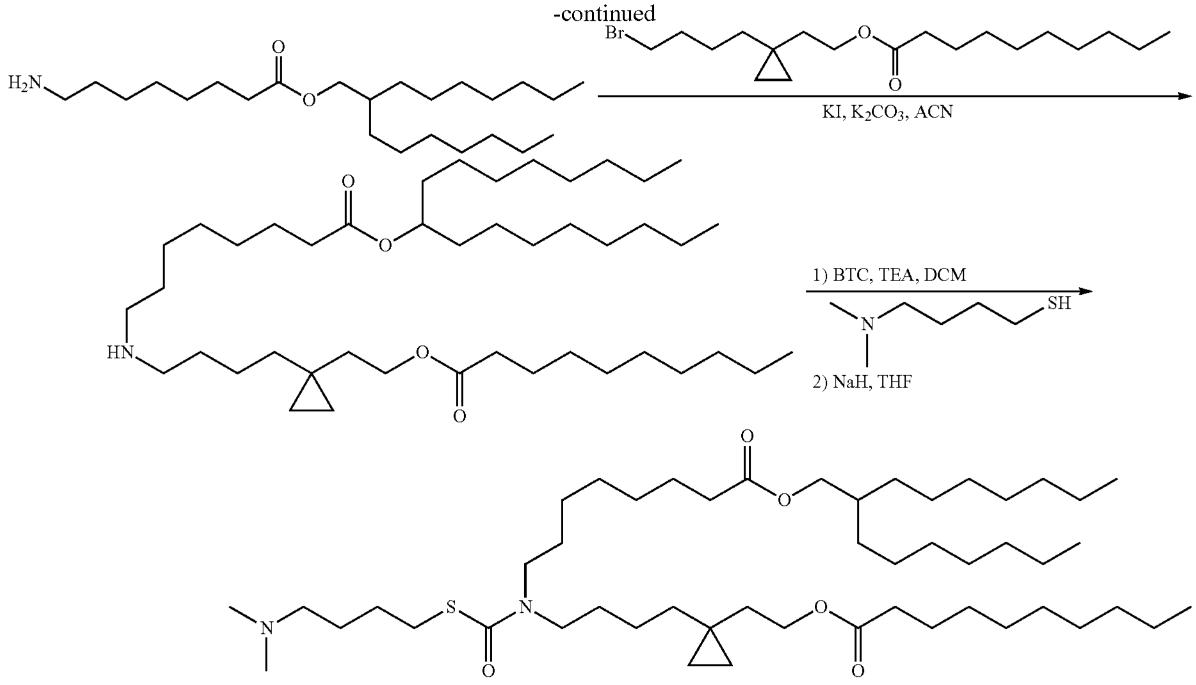
45b
Compound 45b was prepared referring to the method of Example 96 to give 41 mg of an oily product.
$^1$H NMR (400 MHz, $CDCl_3$) δ: 4.13 (s, 2H), 3.96 (d, J=6.0 Hz, 2H), 3.31-3.24 (m, 4H), 2.90 (t, J=6.8 Hz, 2H), 2.54-2.26 (m, 10H), 1.67-1.45 (m, 18H), 1.29-1.21 (m, 45H), 0.90-0.82 (m, 9H), 0.32-0.29 (m, 4H); ESI-MS m/z: 837.70 $[M+H]^+$.
Example 107: Synthesis of Compound 46b
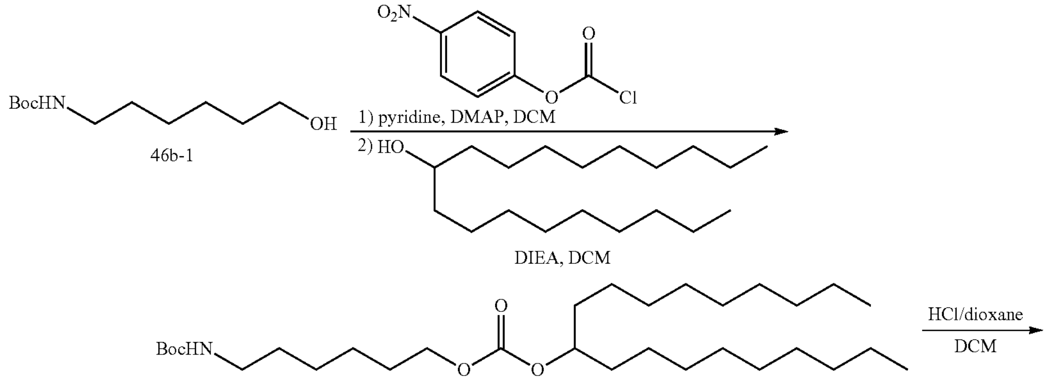
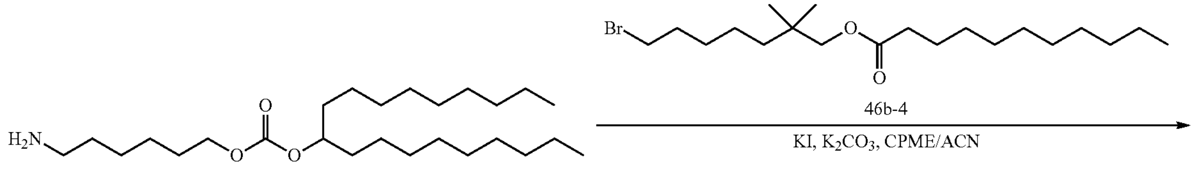

-continued

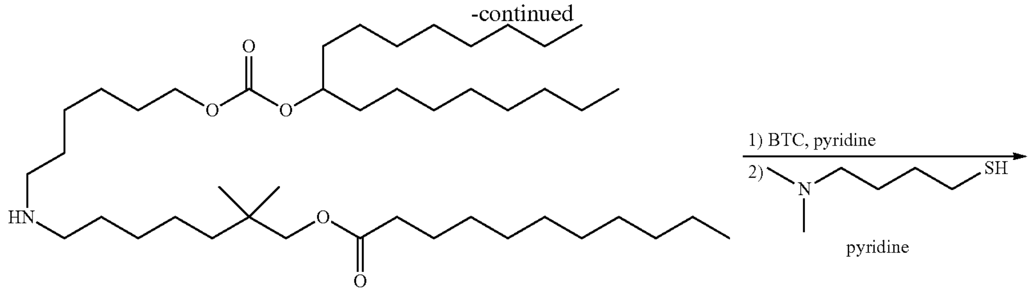

46b-5

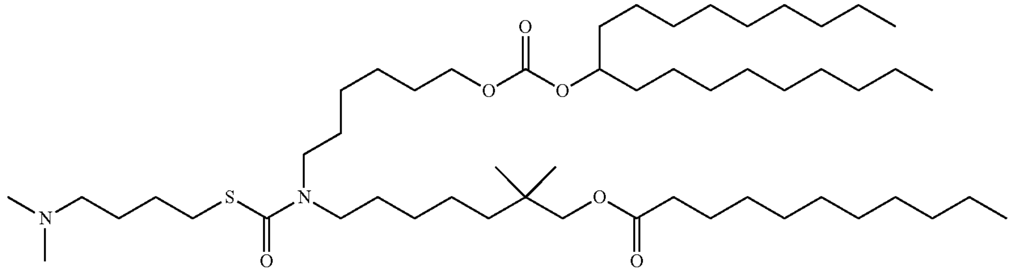

46b

In a 100 mL three-neck round-bottom flask, compound 46b-1 (1.0 g, 4.60 mmol, 1.0 eq.), pyridine (0.74 mL, 9.2 mmol, 2.0 eq.), DMAP (112.4 mg, 0.92 mmol, 0.2 eq.), and p-nitrophenyl chloroformate (1.11 g, 5.52 mmol, 1.2 eq.) were dissolved in 20 mL of dichloromethane at room temperature under nitrogen atmosphere. After the reaction system was stirred at room temperature for 1 h, 2-nonyl-1-decanol (3.93 g, 13.8 mmol, 3.0 eq.) and DIEA (2.40 mL, 13.8 mmol, 3.0 eq.) were added to the reaction system. The reaction system was stirred at room temperature overnight. The reaction was monitored by TLC, and a new spot of the product was found. The mixture was diluted with DCM (20 mL) and washed once with a saturated sodium bicarbonate solution (10 mL). The organic phase was washed 2 times with a saturated NaCl solution (40 mL), dried over anhydrous $Na_2SO_4$, filtered, and concentrated. The crude product was purified by silica gel column chromatography to give a light yellow oily compound 46b-2 (1.68 g).

Compound 46b was prepared referring to the method of Example 96 to give 78.5 mg of an oily product.

$^1$H NMR (300 MHz, $CDCl_3$) δ: 4.68 (p, J=6.0 Hz, 1H), 4.11 (t, J=6.6 Hz, 2H), 3.78 (s, 2H), 3.36-3.22 (m, 4H), 2.90 (t, J=6.9 Hz, 2H), 2.47-2.29 (m, 10H), 1.70-1.56 (m, 18H), 1.29-1.21 (m, 50H), 0.90-0.86 (m, 15H); ESI-MS m/z: 897.70 $[M+H]^+$.

Example 108: Synthesis of Compound 47b

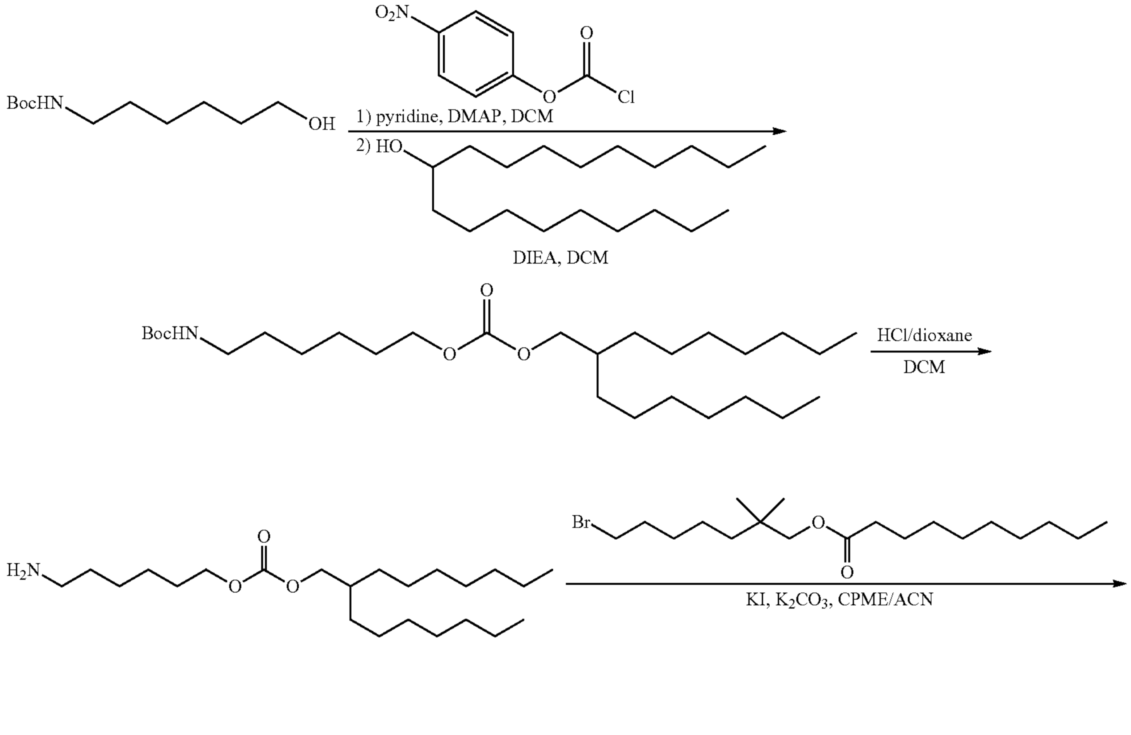

-continued
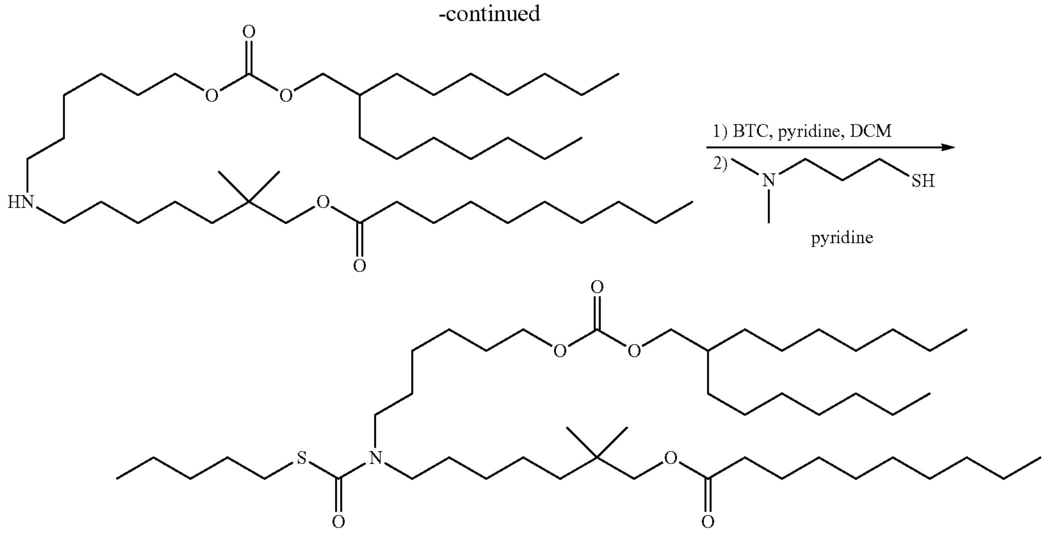
47b
Compound 47b was prepared referring to the method of Example 107 to give 189.8 mg of an oily product.
$^{1}$H NMR (400 MHz, $CDCl_3$) δ: 4.12 (t, J=6.4 Hz, 2H), 4.02 (d, J=5.6 Hz, 2H), 3.78 (s, 2H), 3.32-3.24 (m, 4H), 2.92 (t, J=7.2 Hz, 2H), 2.47-2.30 (m, 10H), 1.85-1.84 (m, 2H), 1.66-1.40 (m, 7H), 1.26-1.18 (m, 48H), 0.93-0.88 (m, 15H); ESI-MS m/z: 827.55 $[M+H]^+$.
Example 109: Synthesis of Compound 48b
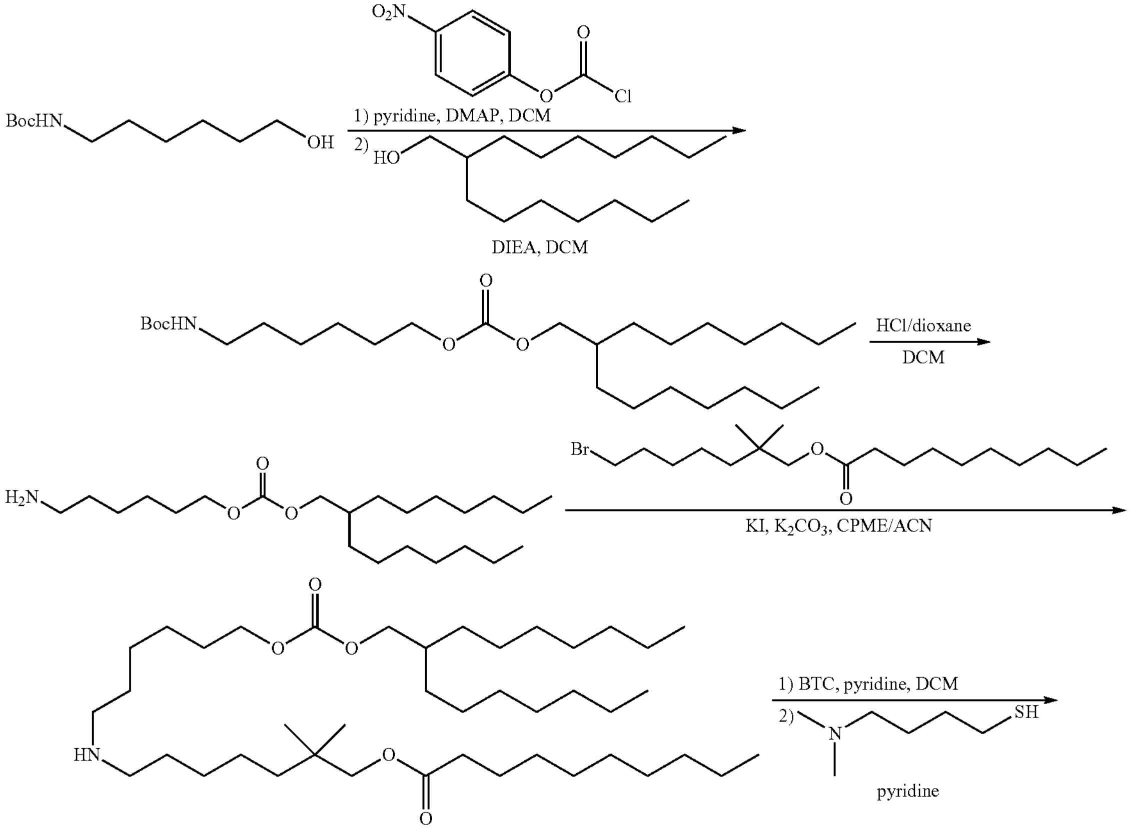

-continued
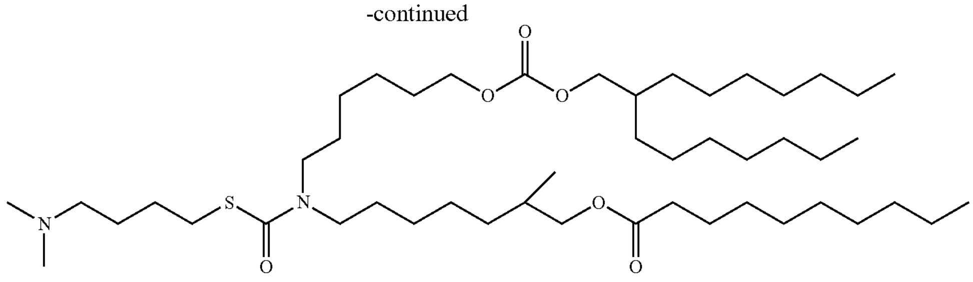
48b
Compound 48b was prepared referring to the method of Example 107 to give 129.4 mg of an oily product.
$^{1}$H NMR (300 MHz, $CDCl_3$) δ: 4.12 (t, J=6.6 Hz, 2H), 4.02 (d, J=5.7 Hz, 2H), 3.78 (s, 2H), 3.36-3.21 (m, 4H), 2.90 (t, J=6.9 Hz, 2H), 2.36-2.26 (m, 10H), 1.63-1.41 (m, 13H), 1.26-1.18 (m, 46H), 0.89-0.86 (m, 15H); ESI-MS m/z: 841.65 $[M+H]^+$.
Example 110: Synthesis of Compound 49b
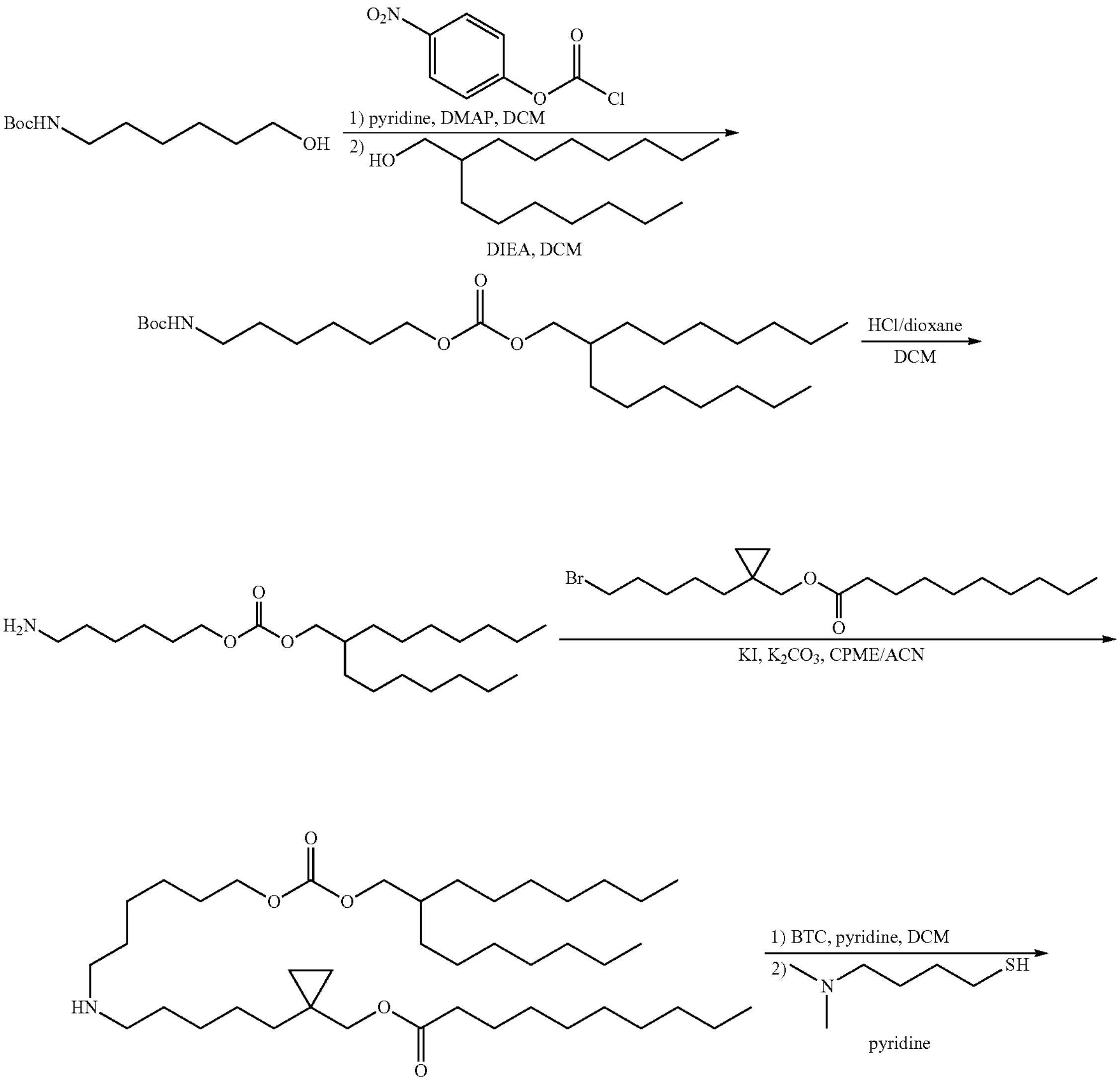

-continued
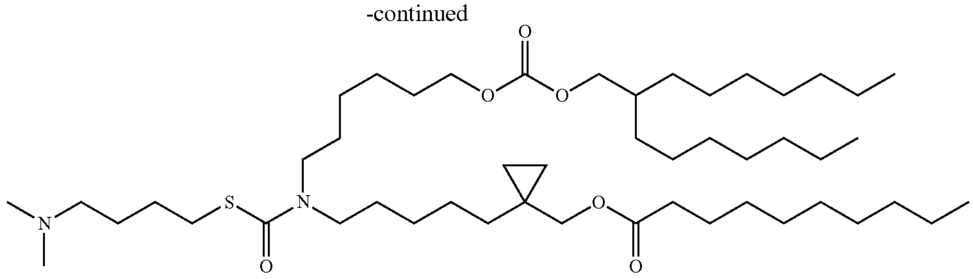
49b
Compound 49b was prepared referring to the method of Example 107 to give 135.6 mg of an oily product.
$^1$H NMR (300 MHz, $CDCl_3$) δ: 4.12 (t, J=6.3 Hz, 2H), 4.02 (d, J=5.7 Hz, 2H), 3.89 (s, 2H), 3.31-3.22 (m, 4H), 2.90 (t, J=6.9 Hz, 2H), 2.34-2.26 (m, 10H), 1.65-1.48 (m, 13H), 1.27-1.19 (m, 46H), 0.90-0.86 (m, 9H), 0.45-0.35 (m, 4H); ESI-MS m/z: 839.50 $[M+H]^+$.
Example 111: Synthesis of Compound 50b
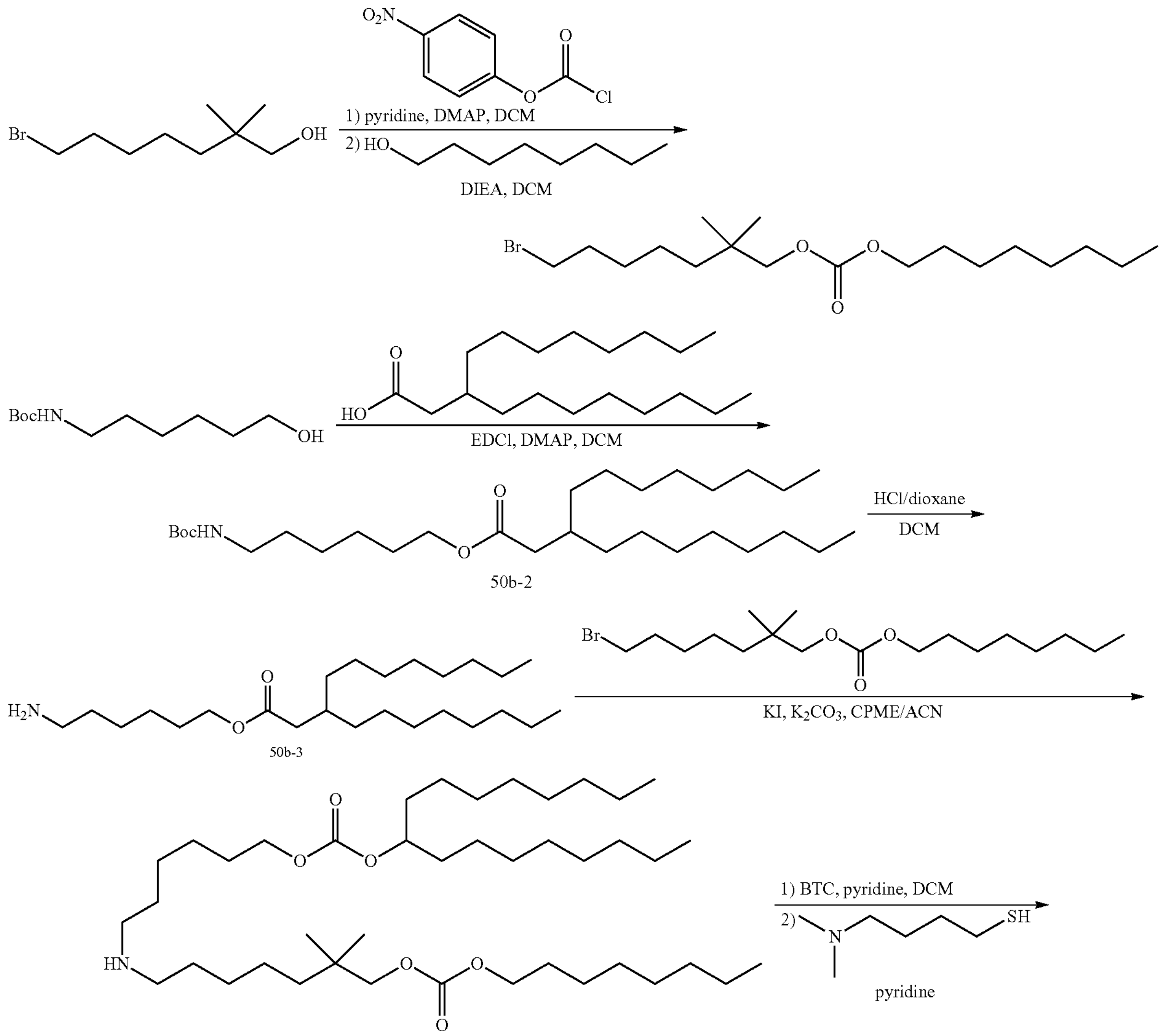
50b-2
50b-3

-continued

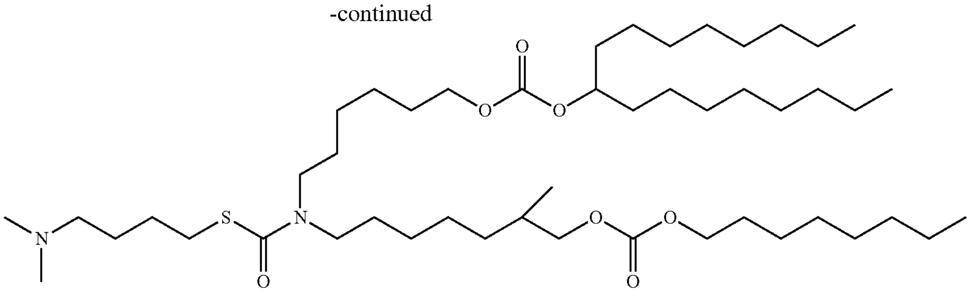

50b

Compound 50b was prepared referring to the method of Example 107 to give 123.1 mg of an oily product.

$^{1}$H NMR (300 MHz, $CDCl_3$) δ: 4.12 (t, J=6.6 Hz, 2H), 4.02 (t, J=6.6 Hz, 2H), 3.84 (s, 2H), 3.34-3.19 (m, 4H), 2.90 (t, J=6.6 Hz, 2H), 2.46-2.20 (m, 10H), 1.84 (m, 2H), 1.65-1.44 (m, 13H), 1.27-1.19 (m, 46H), 0.92-0.86 (m, 15H); ESI-MS m/z: 855.60 $[M+H]^+$.

The compounds in Table below were synthesized using the methods of the above examples, or using similar methods of the corresponding intermediates.

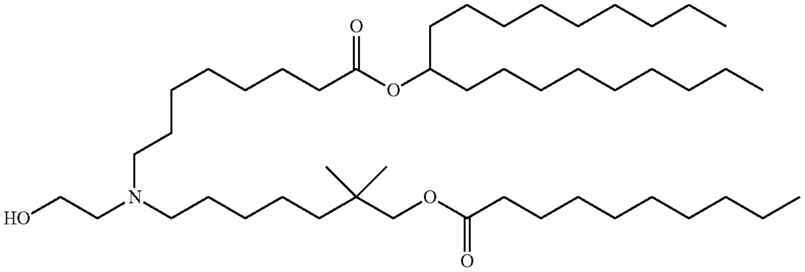 [SMILES: CCCCCCCCCC(=O)OCC(C)(C)CCCCCN(CCO)CCCCCCCC(=O)OC(CCCCCCCCC)CCCCCCCCC]

51b

Example 112
$[M + H]^+$: 766.65

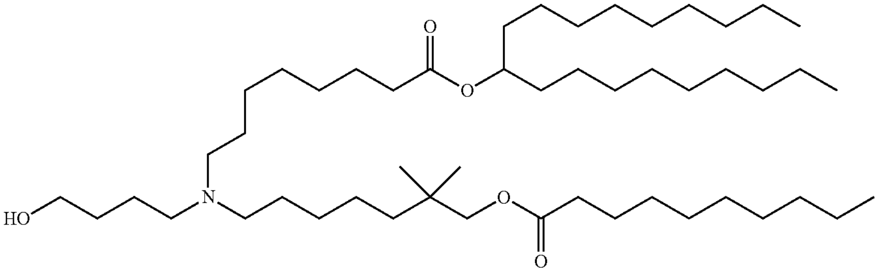 [SMILES: CCCCCCCCCC(=O)OCC(C)(C)CCCCCN(CCCCO)CCCCCCCC(=O)OC(CCCCCCCCC)CCCCCCCCC]

52b

Example 113
$[M + H]^+$: 794.80

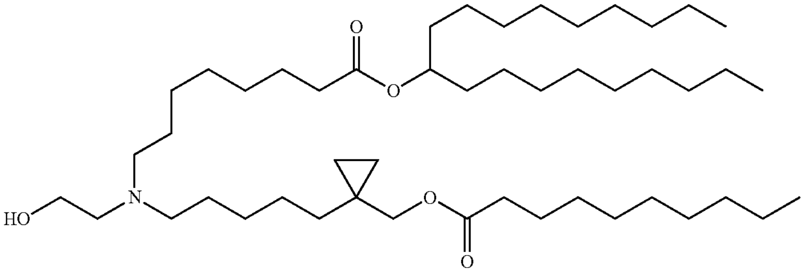 [SMILES: CCCCCCCCCC(=O)OCC1(CCCCCN(CCO)CCCCCCCC(=O)OC(CCCCCCCCC)CCCCCCCCC)CC1]

53b

Example 114
$[M + H]^+$: 764.70

-continued
54b
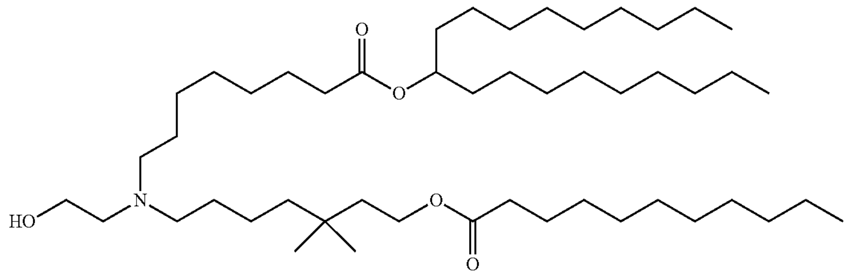 [SMILES: CCCCCCCCCCC(=O)OCCC(C)(C)CCCCN(CCO)CCCCCCCC(=O)OC(CCCCCCCCC)CCCCCCCCC]
Example 115
[M + H]+: 780.85
55b
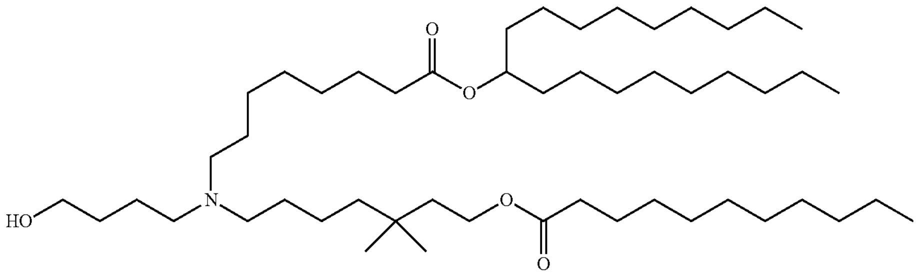 [SMILES: CCCCCCCCCCC(=O)OCCC(C)(C)CCCCN(CCCCO)CCCCCCCC(=O)OC(CCCCCCCCC)CCCCCCCCC]
Example 116
[M + H]+: 808.90
56b
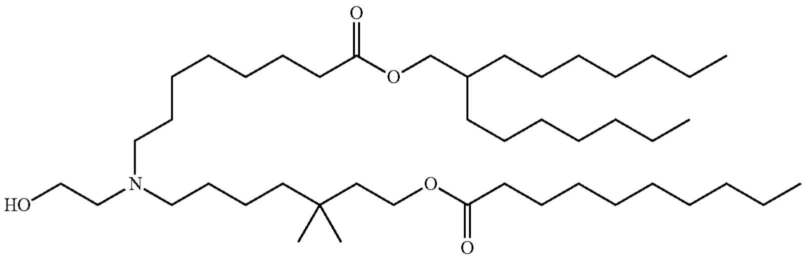 [SMILES: CCCCCCCCCC(=O)OCCC(C)(C)CCCCN(CCO)CCCCCCCC(=O)OCC(CCCCCCC)CCCCCCC]
Example 117
[M + H]+: 724.60
57b
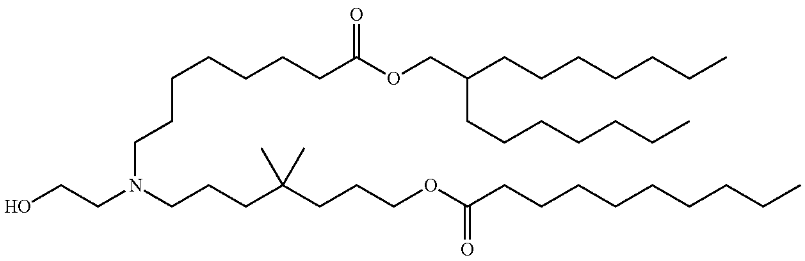 [SMILES: CCCCCCCCCC(=O)OCCCC(C)(C)CCCN(CCO)CCCCCCCC(=O)OCC(CCCCCCC)CCCCCCC]
Example 118
[M + H]+: 724.60

-continued
58b
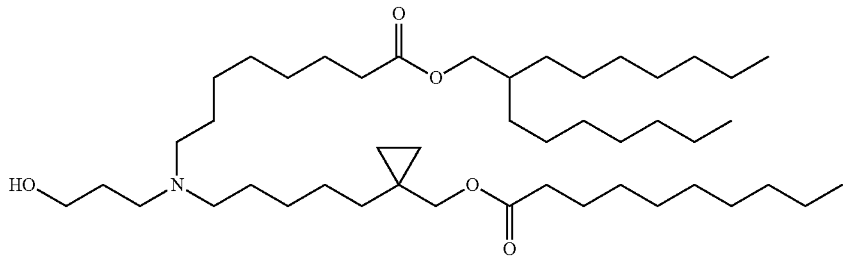 [SMILES: CCCCCCCCCC(=O)OCC1(CCCCCN(CCCO)CCCCCCCC(=O)OCC(CCCCCCC)CCCCCCC)CC1]
Example 119
[M + H]+: 737.60
59b
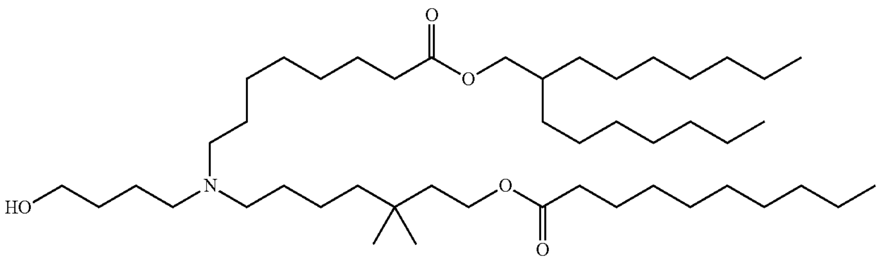 [SMILES: CCCCCCCCCC(=O)OCCC(C)(C)CCCCN(CCCCO)CCCCCCCC(=O)OCC(CCCCCCC)CCCCCCC]
Example 120
[M + H]+: 752.65
62a
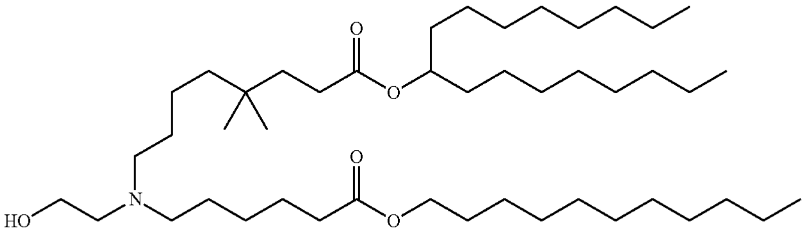 [SMILES: CCCCCCCCCCCOC(=O)CCCCCN(CCO)CCCCC(C)(C)CCC(=O)OC(CCCCCCCC)CCCCCCCC]
Example 121
[M + H]+: 738.60
63a
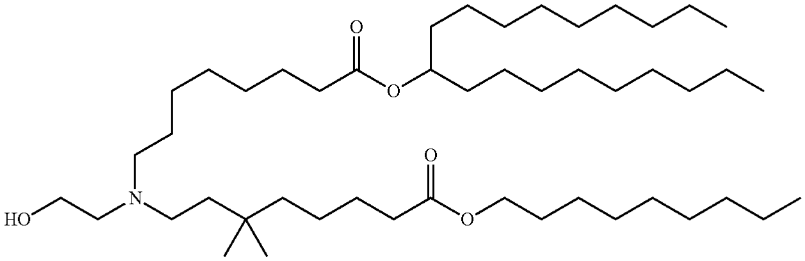 [SMILES: CCCCCCCCCOC(=O)CCCCC(C)(C)CCN(CCO)CCCCCCCC(=O)OC(CCCCCCCCC)CCCCCCCCC]
Example 122
[M + H]+: 780.65
64a
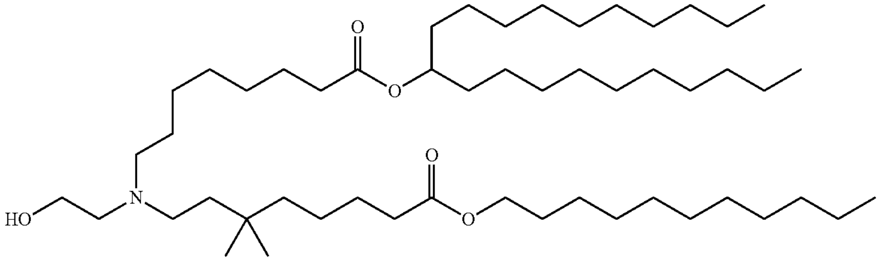 [SMILES: CCCCCCCCCCCOC(=O)CCCCC(C)(C)CCN(CCO)CCCCCCCC(=O)OC(CCCCCCCCCC)CCCCCCCCCC]
Example 123
[M + H]+: 822.70

-continued
65a
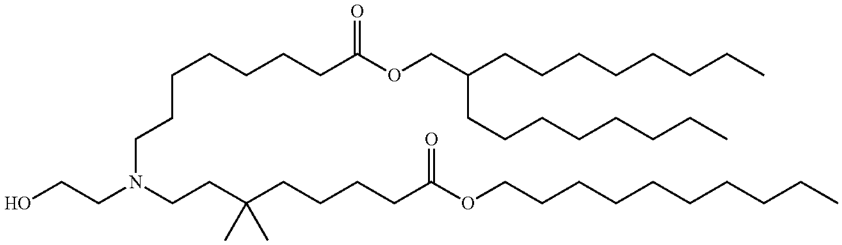 [SMILES: CCCCCCCCCCOC(=O)CCCCC(C)(C)CCN(CCO)CCCCCCCC(=O)OCC(CCCCCCCC)CCCCCCCC]
Example 124
[M + H]$^+$: 766.60
66a
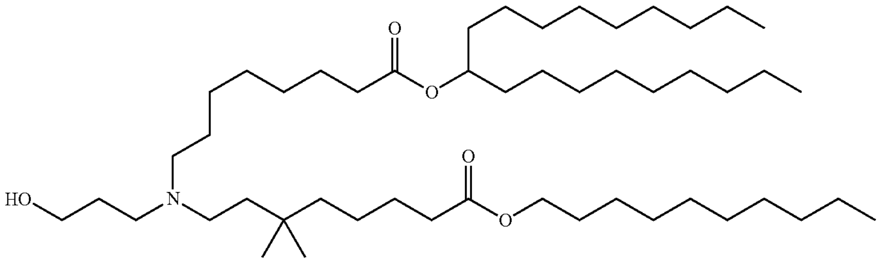 [SMILES: CCCCCCCCCCOC(=O)CCCCC(C)(C)CCN(CCCO)CCCCCCCC(=O)OC(CCCCCCCCC)CCCCCCCCC]
Example 125
[M + H]$^+$: 794.70
67a
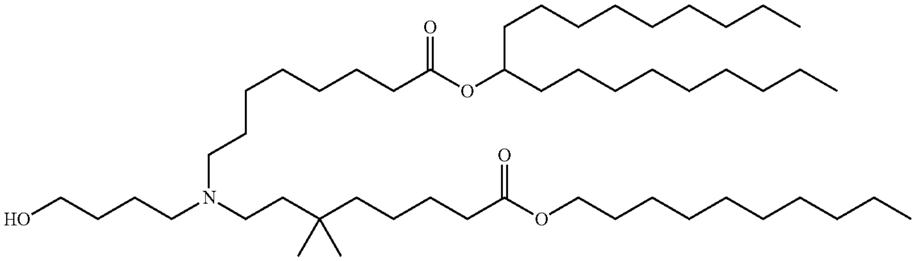 [SMILES: CCCCCCCCCCOC(=O)CCCCC(C)(C)CCN(CCCCO)CCCCCCCC(=O)OC(CCCCCCCCC)CCCCCCCCC]
Example 126
[M + H]$^+$: 808.70
68a
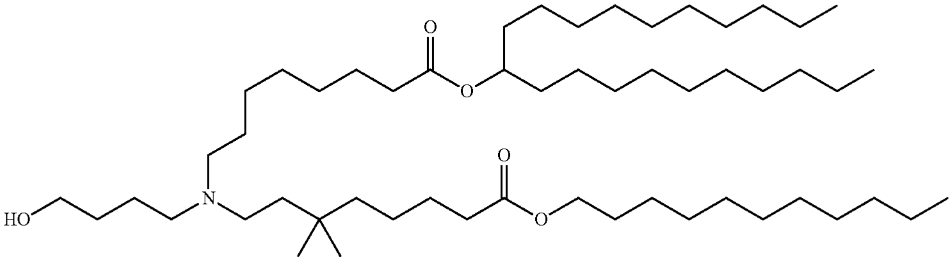 [SMILES: CCCCCCCCCCCOC(=O)CCCCC(C)(C)CCN(CCCCO)CCCCCCCC(=O)OC(CCCCCCCCCC)CCCCCCCCCC]
Example 127
[M + H]$^+$: 850.75

-continued
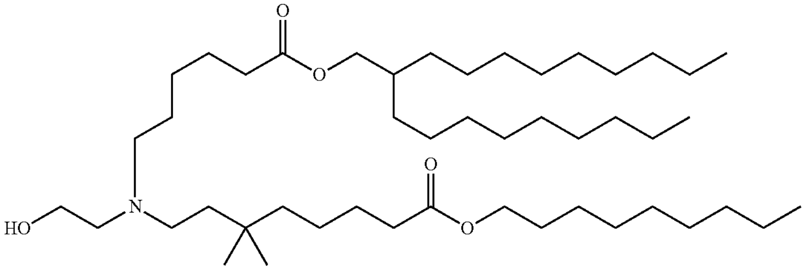 [SMILES: CCCCCCCCCOC(=O)CCCCC(C)(C)CCN(CCO)CCCCCC(=O)OCC(CCCCCCCCC)CCCCCCCCC]
69a
Example 128
[M + H]+: 752.60
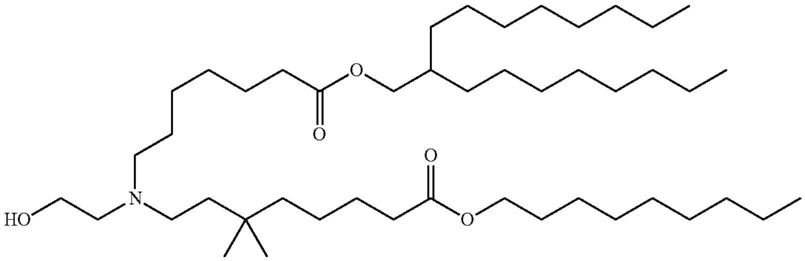 [SMILES: CCCCCCCCCOC(=O)CCCCC(C)(C)CCN(CCO)CCCCCCC(=O)OCC(CCCCCCCC)CCCCCCCC]
70a
Example 129
[M + H]+: 738.55
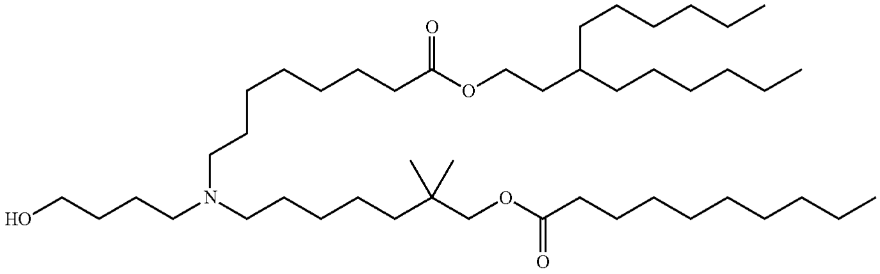 [SMILES: CCCCCCCCCC(=O)OCC(C)(C)CCCCCN(CCCCO)CCCCCCCC(=O)OCCC(CCCCCC)CCCCCC]
60b
Example 130
[M + H]+: 738.75
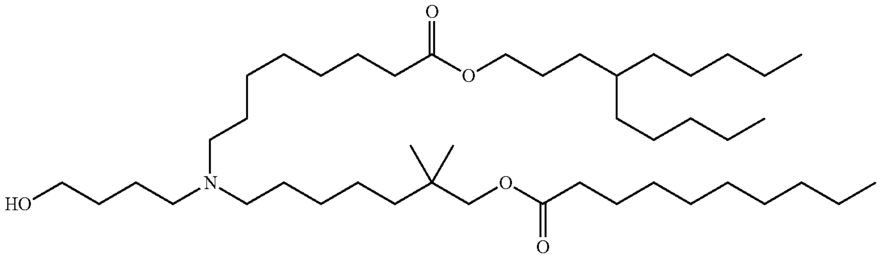 [SMILES: CCCCCCCCCC(=O)OCC(C)(C)CCCCCN(CCCCO)CCCCCCCC(=O)OCCCC(CCCCC)CCCCC]
61b
Example 131
[M + H]+: 724.70

-continued
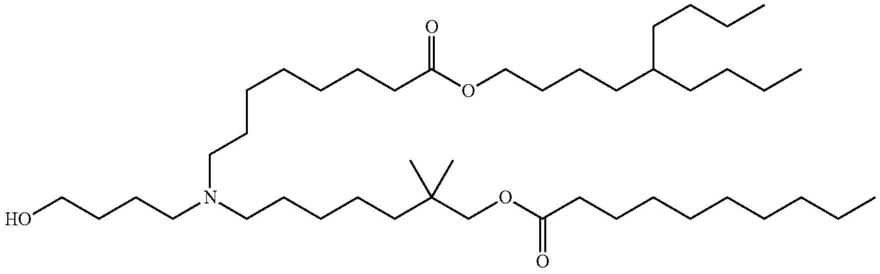 [SMILES: CCCCCCCCCC(=O)OCC(C)(C)CCCCCN(CCCCO)CCCCCCCC(=O)OCCCCC(CCCC)CCCC]
62b
Example 132
[M + H]+: 710.80
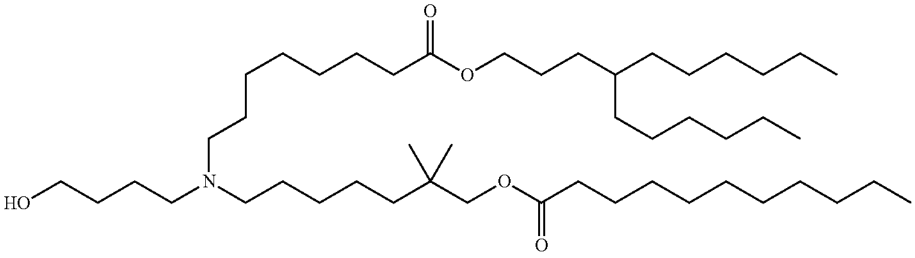 [SMILES: CCCCCCCCCCC(=O)OCC(C)(C)CCCCCN(CCCCO)CCCCCCCC(=O)OCCCC(CCCCCC)CCCCCC]
63b
Example 133
[M + H]+: 766.95
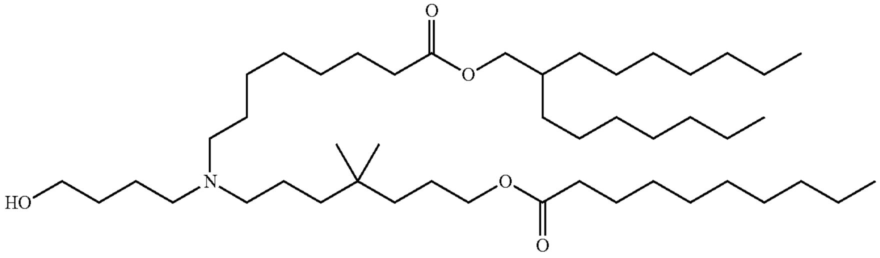 [SMILES: CCCCCCCCCC(=O)OCCCC(C)(C)CCCN(CCCCO)CCCCCCCC(=O)OCC(CCCCCCC)CCCCCCC]
64b
Example 134
[M + H]+: 752.65
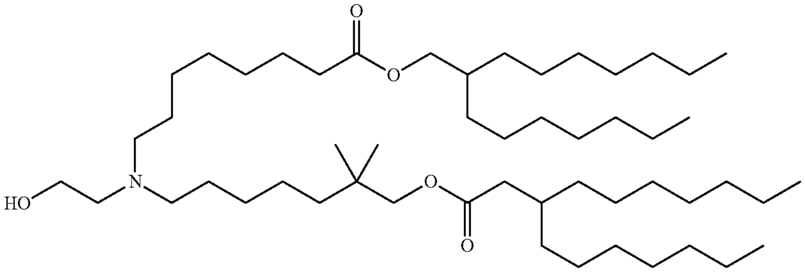 [SMILES: CCCCCCCC(CCCCCCC)COC(=O)CCCCCCCN(CCO)CCCCCC(C)(C)COC(=O)CC(CCCCCCC)CCCCCCC]
65b
Example 135
[M + H]+: 822.75

-continued
66b
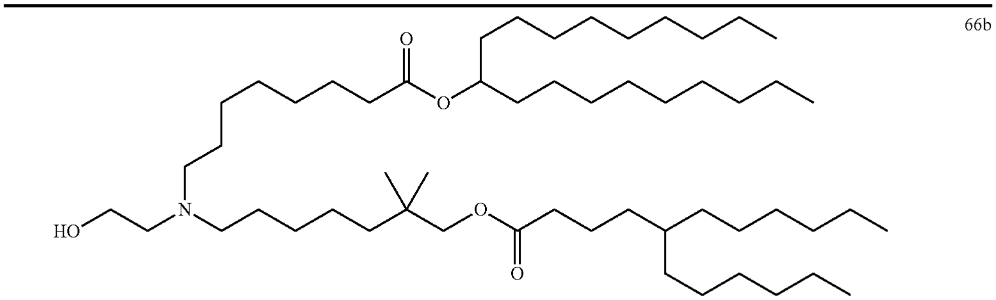
Example 136
[M + H]+: 864.85
67b
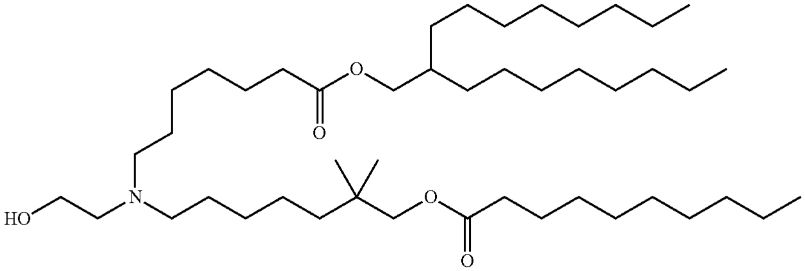 [SMILES: CCCCCCCCCC(=O)OCC(C)(C)CCCCCN(CCO)CCCCCCC(=O)OCC(CCCCCCCC)CCCCCCCC]
Example 137
[M + H]+: 738.55
68b
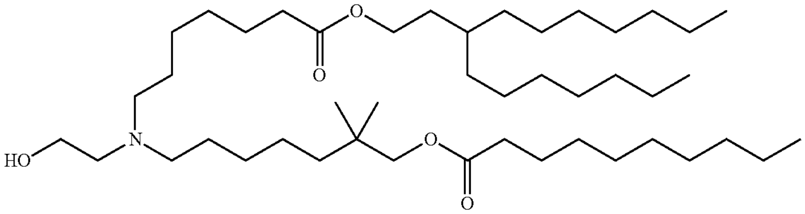 [SMILES: CCCCCCCCCC(=O)OCC(C)(C)CCCCCN(CCO)CCCCCCC(=O)OCCC(CCCCCCC)CCCCCCC]
Example 138
[M + H]+: 724.70
69b
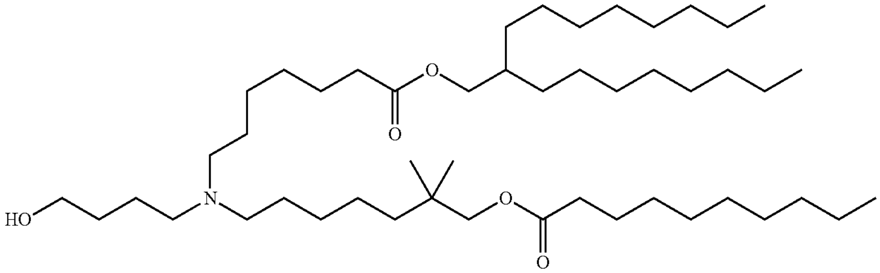 [SMILES: CCCCCCCCCC(=O)OCC(C)(C)CCCCCN(CCCCO)CCCCCCC(=O)OCC(CCCCCCCC)CCCCCCCC]
Example 139
[M + H]+: 766.70
70b
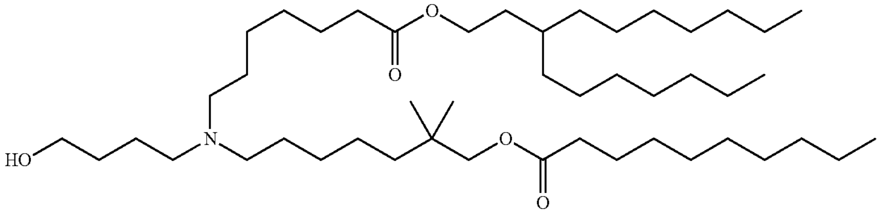 [SMILES: CCCCCCCCCC(=O)OCC(C)(C)CCCCCN(CCCCO)CCCCCCC(=O)OCCC(CCCCCCC)CCCCCCC]
Example 140
[M + H]+: 752.75

-continued
71b
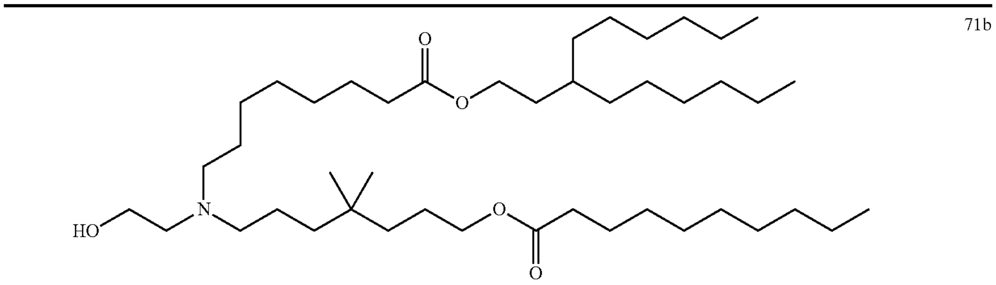
Example 141
[M + H]+: 710.70
72b
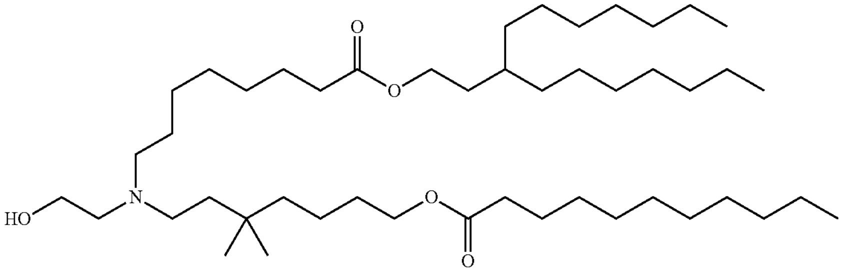 [SMILES: CCCCCCCCCCC(=O)OCCCCC(C)(C)CCN(CCO)CCCCCCCC(=O)OCCC(CCCCCCC)CCCCCCC]
Example 142
[M + H]+: 752.70
73b
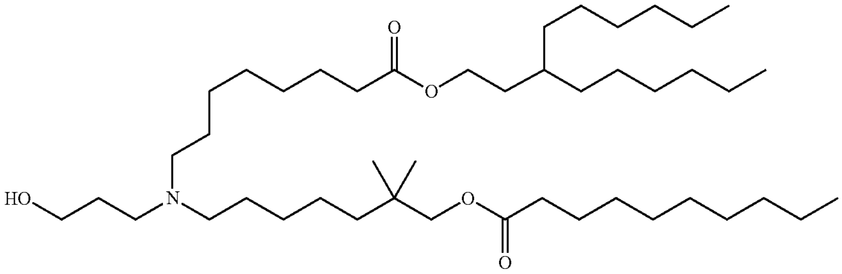 [SMILES: CCCCCCCCCC(=O)OCC(C)(C)CCCCCN(CCCO)CCCCCCCC(=O)OCCC(CCCCCC)CCCCCC]
Example 143
[M + H]+: 724.70
74b
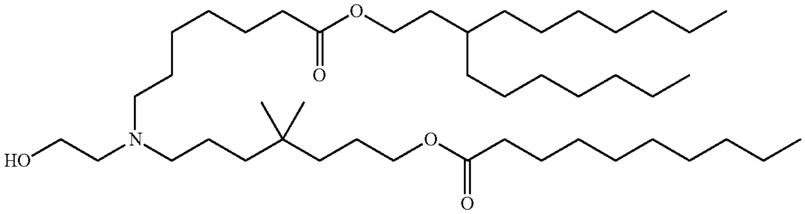 [SMILES: CCCCCCCCCC(=O)OCCCC(C)(C)CCCN(CCO)CCCCCCC(=O)OCCC(CCCCCCC)CCCCCCC]
Example 144
[M + H]+: 724.65
75b
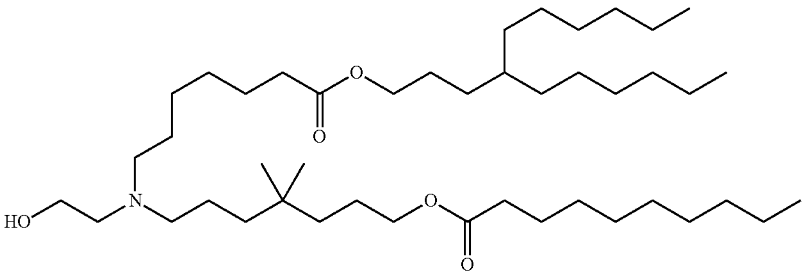 [SMILES: CCCCCCCCCC(=O)OCCCC(C)(C)CCCN(CCO)CCCCCCC(=O)OCCCC(CCCCCC)CCCCCC]
Example 145
[M + H]+: 710.65

-continued
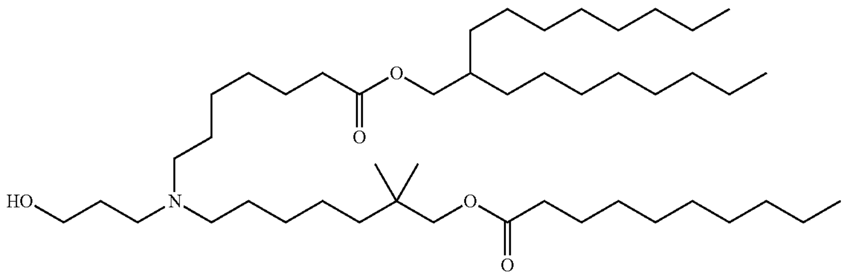 [SMILES: CCCCCCCCCC(=O)OCC(C)(C)CCCCCN(CCCO)CCCCCCC(=O)OCC(CCCCCCCC)CCCCCCCC]
76b
Example 146
[M + H]$^+$: 156
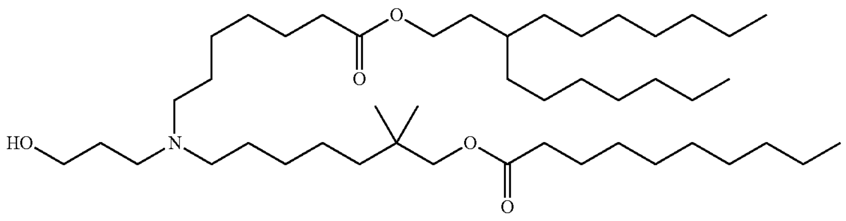 [SMILES: CCCCCCCCCC(=O)OCC(C)(C)CCCCCN(CCCO)CCCCCCC(=O)OCCC(CCCCCCC)CCCCCCC]
77b
Example 147
[M + H]$^+$: 738.80
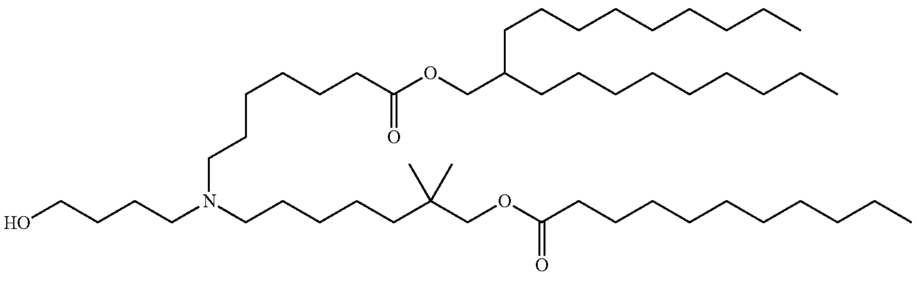 [SMILES: CCCCCCCCCCC(=O)OCC(C)(C)CCCCCN(CCCCO)CCCCCCC(=O)OCC(CCCCCCCCC)CCCCCCCCC]
78b
Example 148
[M + H]$^+$: 808.70
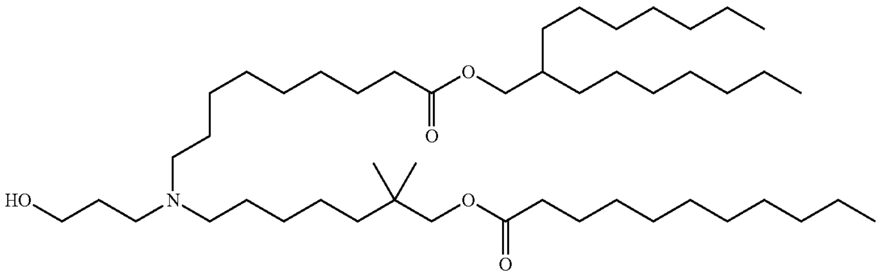 [SMILES: CCCCCCCCCCC(=O)OCC(C)(C)CCCCCN(CCCO)CCCCCCCCC(=O)OCC(CCCCCCC)CCCCCCC]
79b
Example 149
[M + H]$^+$: 766.70

-continued
80b
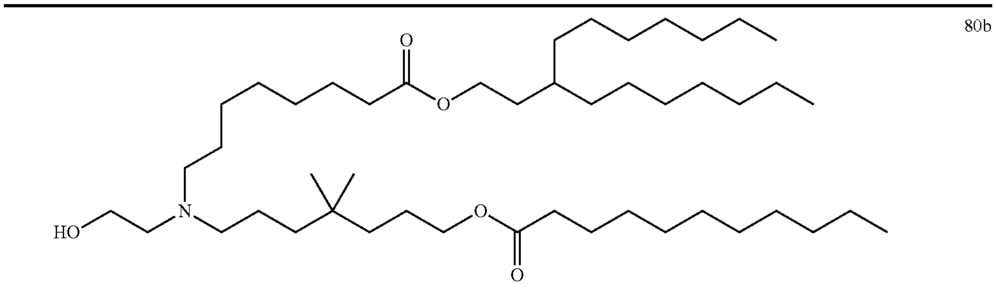
Example 150
[M + H]+: 752.65
81b
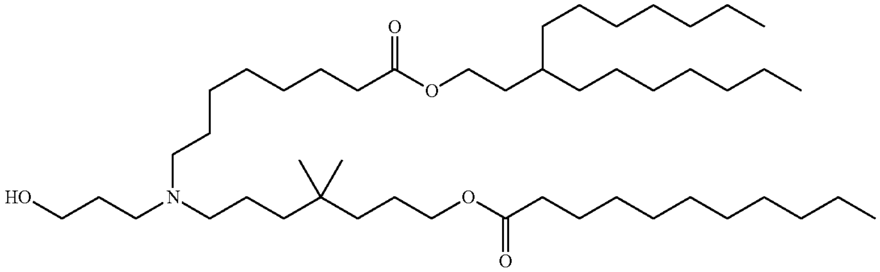 [SMILES: CCCCCCCCCCC(=O)OCCCC(C)(C)CCCN(CCCO)CCCCCCCC(=O)OCCC(CCCCCCC)CCCCCCC]
Example 151
[M + H]+: 766.65
82b
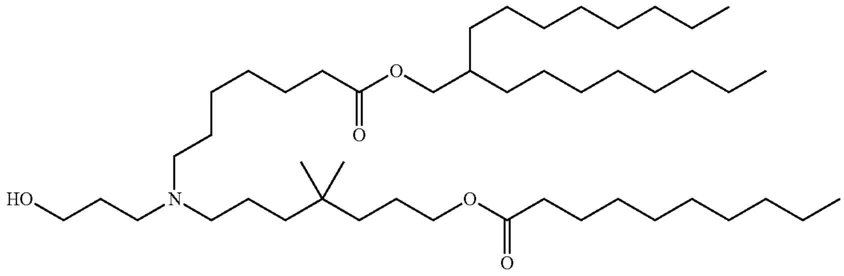 [SMILES: CCCCCCCCCC(=O)OCCCC(C)(C)CCCN(CCCO)CCCCCCC(=O)OCC(CCCCCCCC)CCCCCCCC]
Example 152
[M + H]+: 752.75
83b
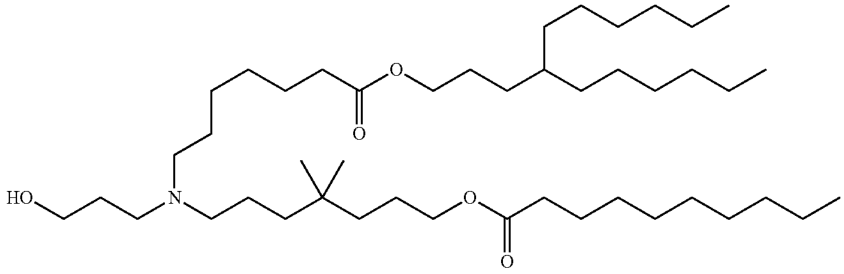 [SMILES: CCCCCCCCCC(=O)OCCCC(C)(C)CCCN(CCCO)CCCCCCC(=O)OCCCC(CCCCCC)CCCCCC]
Example 153
[M + H]+: 724.65

-continued
84b
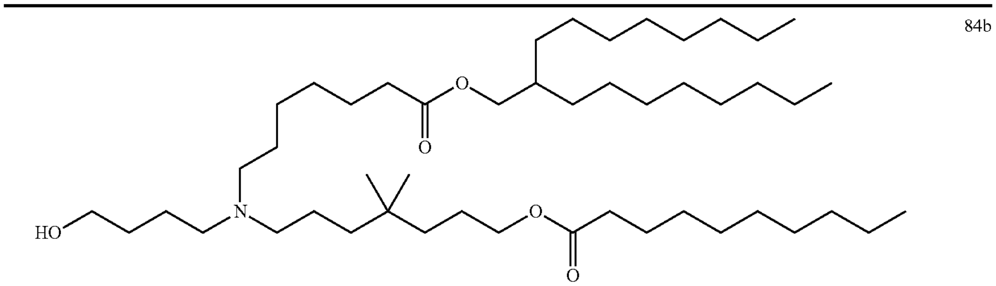
Example 154
[M + H]+: 766.65
85b
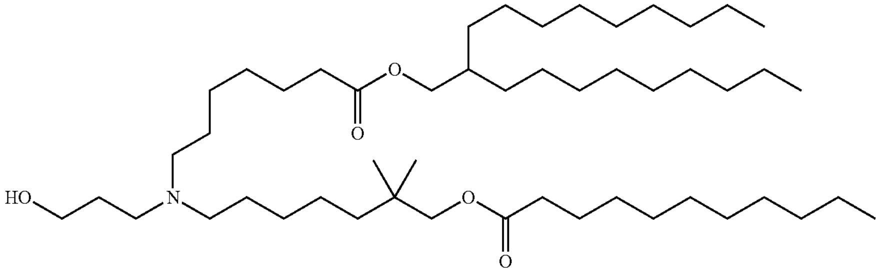 [SMILES: CCCCCCCCCCC(=O)OCC(C)(C)CCCCCN(CCCO)CCCCCCC(=O)OCC(CCCCCCCCC)CCCCCCCCC]
Example 155
[M + H]+: 794.85
86b
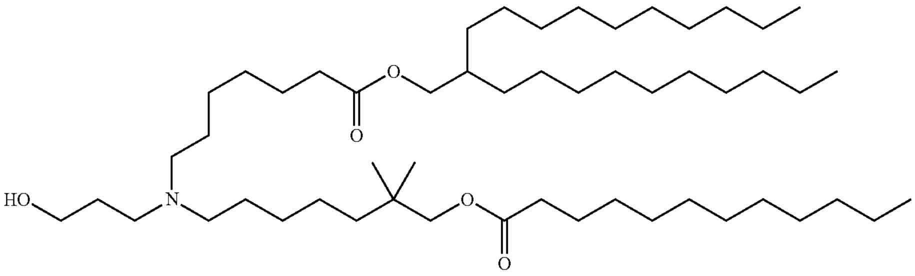 [SMILES: CCCCCCCCCCCC(=O)OCC(C)(C)CCCCCN(CCCO)CCCCCCC(=O)OCC(CCCCCCCCCC)CCCCCCCCCC]
Example 156
[M + H]+: 836.70
87b
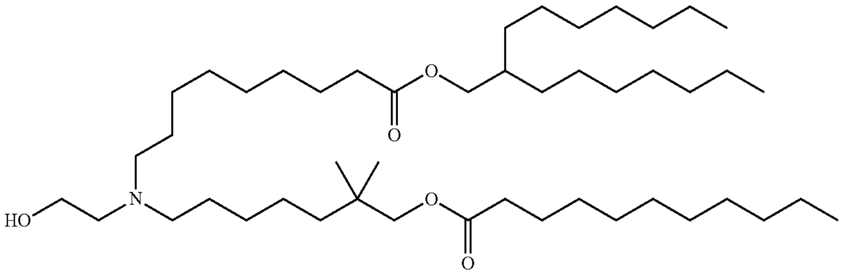 [SMILES: CCCCCCCCCCC(=O)OCC(C)(C)CCCCCN(CCO)CCCCCCCCC(=O)OCC(CCCCCCC)CCCCCCC]
Example 157
[M + H]+: 752.65

-continued
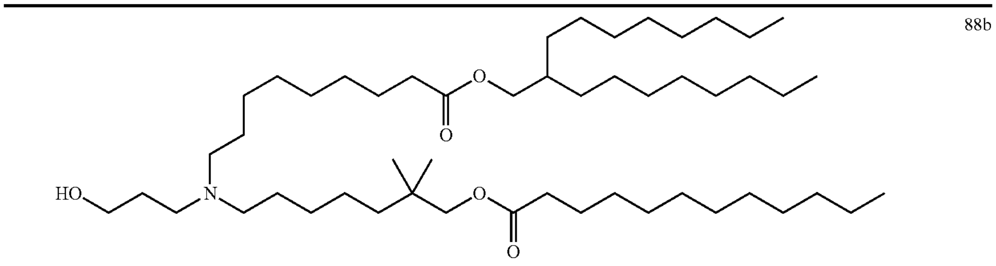
88b
Example 158
[M + H]$^+$: 808.70
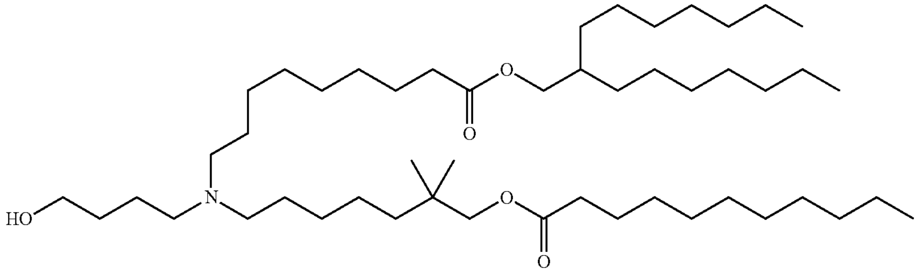 [SMILES: CCCCCCCCCCC(=O)OCC(C)(C)CCCCCN(CCCCO)CCCCCCCCC(=O)OCC(CCCCCCC)CCCCCCC]
89b
Example 159
[M + H]$^+$: 780.65
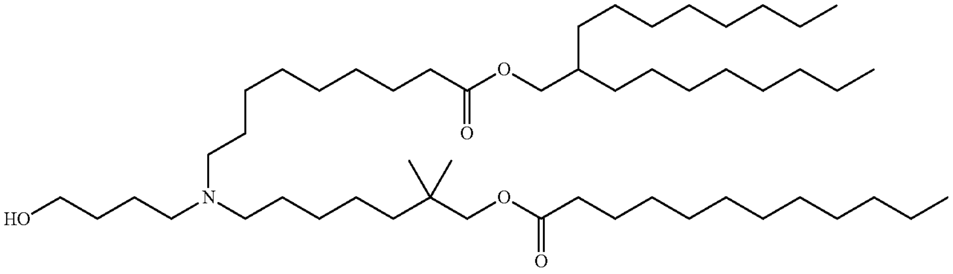 [SMILES: CCCCCCCCCCCC(=O)OCC(C)(C)CCCCCN(CCCCO)CCCCCCCCC(=O)OCC(CCCCCCCC)CCCCCCCC]
90b
Example 160
[M + H]$^+$: 822.75
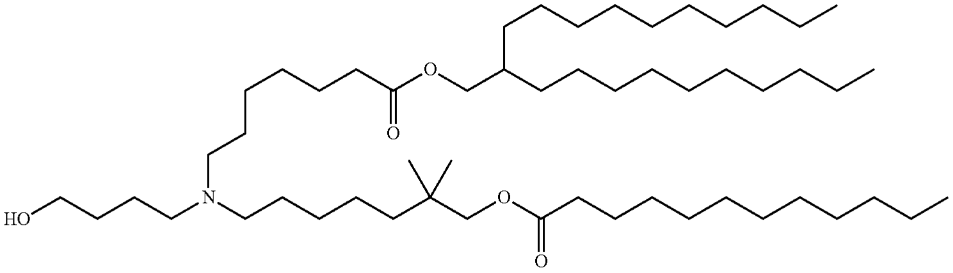 [SMILES: CCCCCCCCCCCC(=O)OCC(C)(C)CCCCCN(CCCCO)CCCCCCC(=O)OCC(CCCCCCCCCC)CCCCCCCCCC]
91b
Example 161
[M + H]$^+$: 850.80
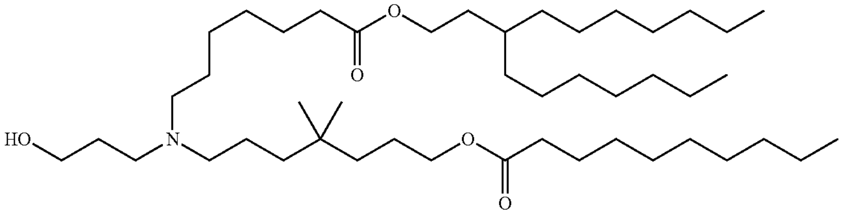 [SMILES: CCCCCCCCCC(=O)OCCCC(C)(C)CCCN(CCCO)CCCCCCC(=O)OCCC(CCCCCCC)CCCCCCC]
92b
Example 162
[M + H]$^+$: 738.65

-continued
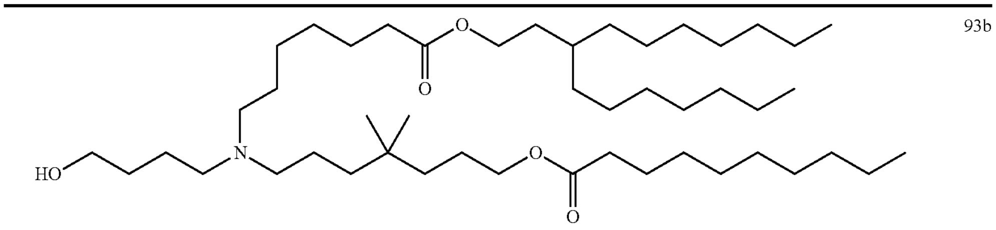
93b
Example 163
[M + H]+: 752.70
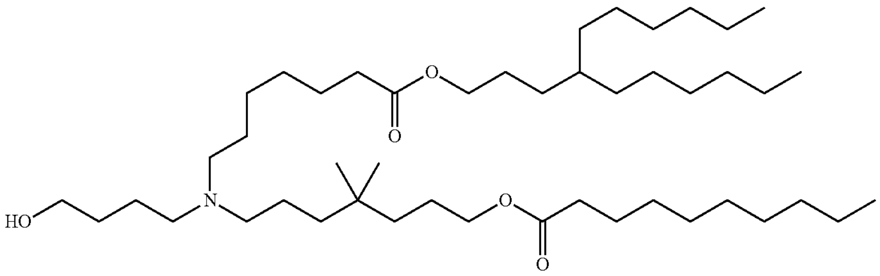 [SMILES: CCCCCCCCCC(=O)OCCCC(C)(C)CCCN(CCCCO)CCCCCCC(=O)OCCCC(CCCCCC)CCCCCC]
94b
Example 164
[M + H]+: 738.65
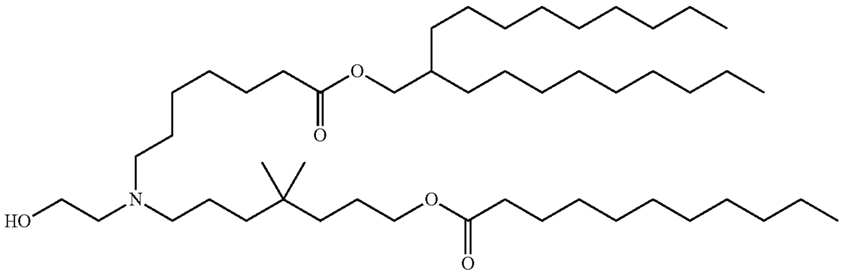 [SMILES: CCCCCCCCCCC(=O)OCCCC(C)(C)CCCN(CCO)CCCCCCC(=O)OCC(CCCCCCCCC)CCCCCCCCC]
95b
Example 165
[M + H]+: 780.90
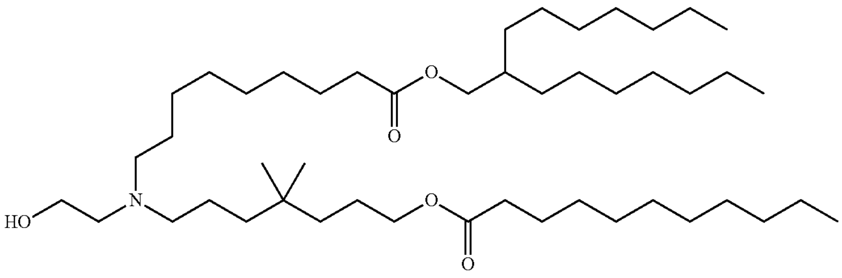 [SMILES: CCCCCCCCCCC(=O)OCCCC(C)(C)CCCN(CCO)CCCCCCCCC(=O)OCC(CCCCCCC)CCCCCCC]
96b
Example 166
[M + H]+: 752.90

-continued
97b
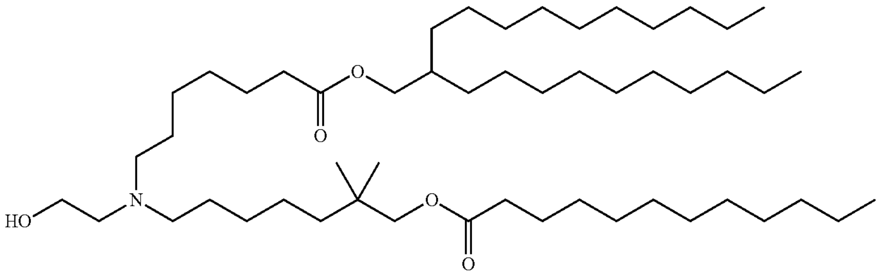 [SMILES: CCCCCCCCCCCC(=O)OCC(C)(C)CCCCCN(CCO)CCCCCCC(=O)OCC(CCCCCCCCCC)CCCCCCCCCC]
Example 167
[M + H]$^+$: 822.75
98b
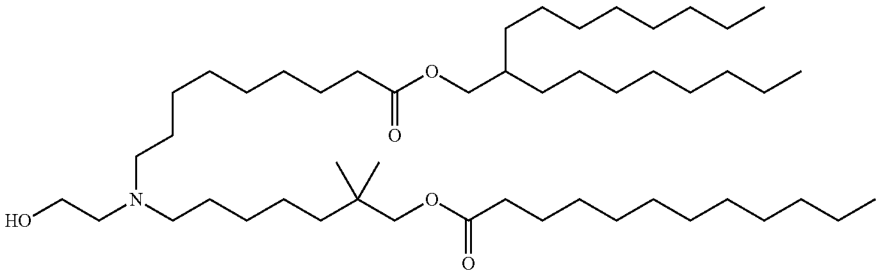 [SMILES: CCCCCCCCCCCC(=O)OCC(C)(C)CCCCCN(CCO)CCCCCCCCC(=O)OCC(CCCCCCCC)CCCCCCCC]
Example 168
[M + H]$^+$: 794.60
99b
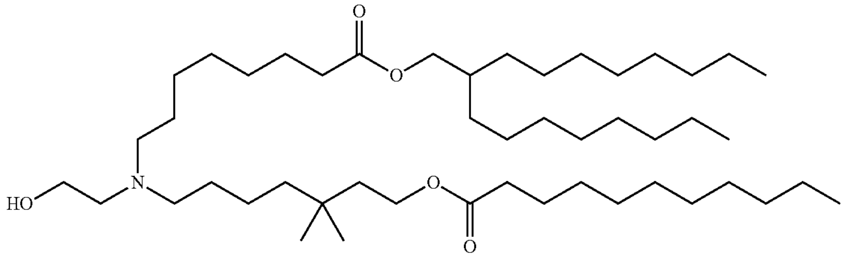 [SMILES: CCCCCCCCCCC(=O)OCCC(C)(C)CCCCN(CCO)CCCCCCCC(=O)OCC(CCCCCCCC)CCCCCCCC]
Example 169
[M + H]$^+$: 766.65
100b
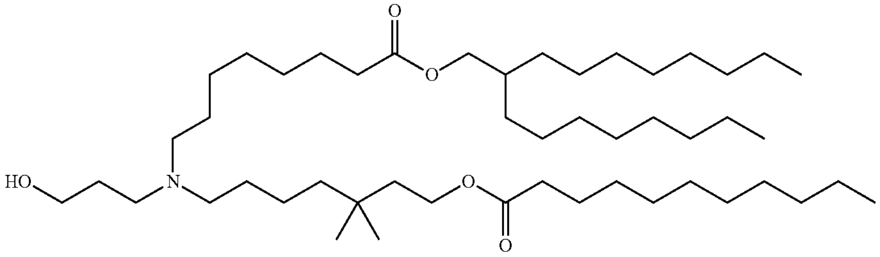 [SMILES: CCCCCCCCCCC(=O)OCCC(C)(C)CCCCN(CCCO)CCCCCCCC(=O)OCC(CCCCCCCC)CCCCCCCC]
Example 170
[M + H]$^+$: 780.70

-continued
101b
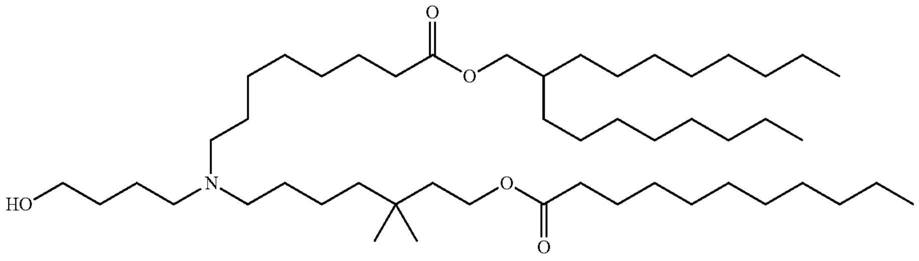 [SMILES: CCCCCCCCCCC(=O)OCCC(C)(C)CCCCN(CCCCO)CCCCCCCC(=O)OCC(CCCCCCCC)CCCCCCCC]
Example 171
[M + H]: 794.75
102b
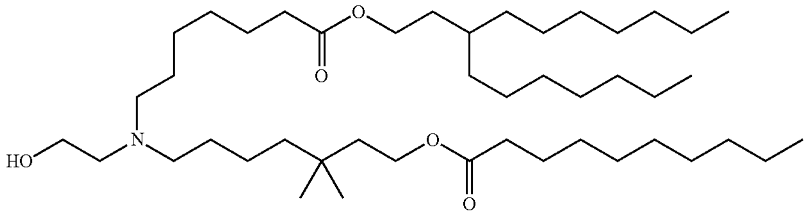 [SMILES: CCCCCCCCCC(=O)OCCC(C)(C)CCCCN(CCO)CCCCCCC(=O)OCCC(CCCCCCC)CCCCCCC]
Example 172
$[M + H]^+$: 724.70
103b
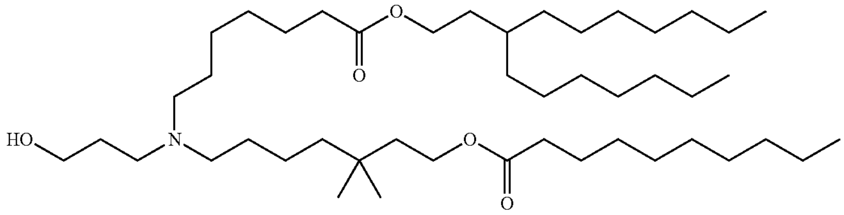 [SMILES: CCCCCCCCCC(=O)OCCC(C)(C)CCCCN(CCCO)CCCCCCC(=O)OCCC(CCCCCCC)CCCCCCC]
Example 173
$[M + H]^+$: 738.65
104b
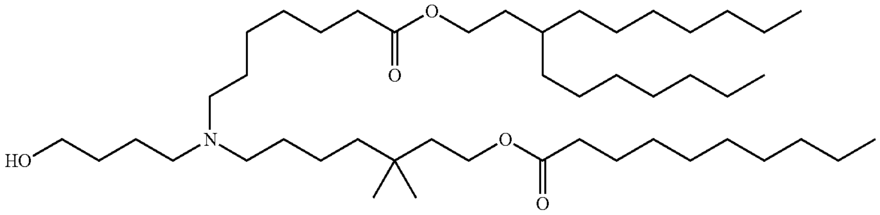 [SMILES: CCCCCCCCCC(=O)OCCC(C)(C)CCCCN(CCCCO)CCCCCCC(=O)OCCC(CCCCCCC)CCCCCCC]
Example 174
$[M + H]^+$: 752.75
105b
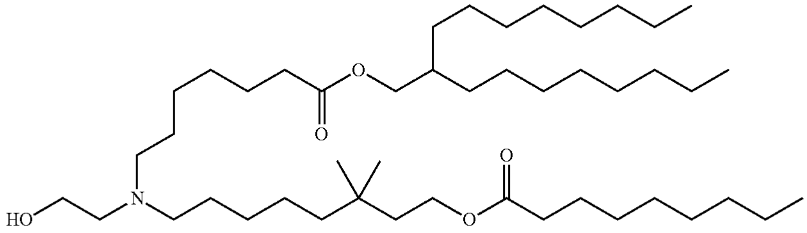 [SMILES: CCCCCCCCC(=O)OCCC(C)(C)CCCCCN(CCO)CCCCCCC(=O)OCC(CCCCCCCC)CCCCCCCC]
Example 175
$[M + H]^+$: 738.60

-continued
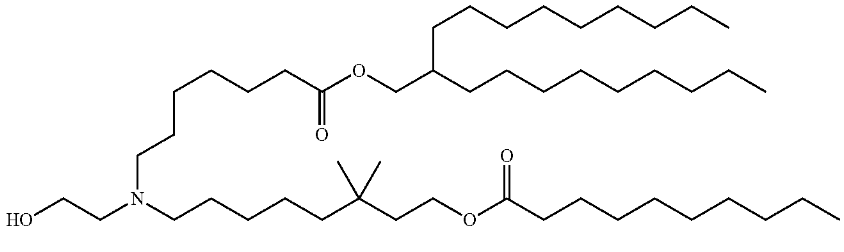 [SMILES: CCCCCCCCCC(=O)OCCC(C)(C)CCCCCN(CCO)CCCCCCC(=O)OCC(CCCCCCCCC)CCCCCCCCC]
106b
Example 176
[M + H]+: 780.70
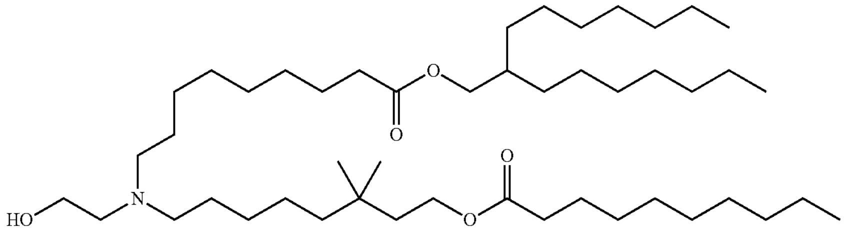 [SMILES: CCCCCCCCCC(=O)OCCC(C)(C)CCCCCN(CCO)CCCCCCCCC(=O)OCC(CCCCCCC)CCCCCCC]
107b
Example 177
[M + H]+: 752.65
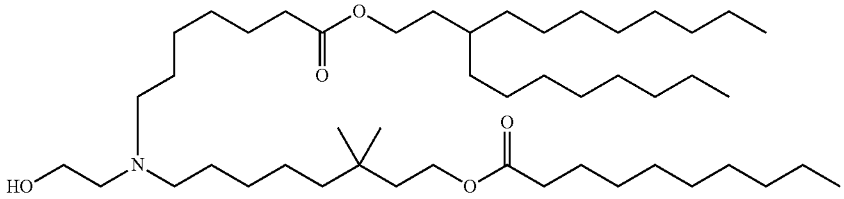 [SMILES: CCCCCCCCCC(=O)OCCC(C)(C)CCCCCN(CCO)CCCCCCC(=O)OCCC(CCCCCCCC)CCCCCCCC]
108b
Example 178
[M + H]+: 766.60
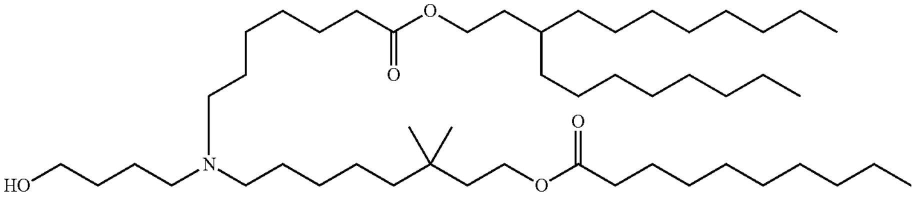 [SMILES: CCCCCCCCCC(=O)OCCC(C)(C)CCCCCN(CCCCO)CCCCCCC(=O)OCCC(CCCCCCCC)CCCCCCCC]
109b
Example 179
[M + H]: 794.75
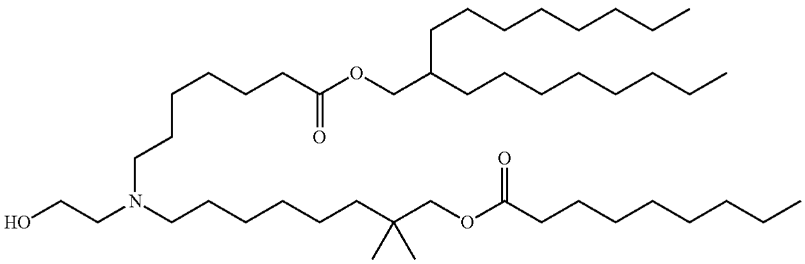 [SMILES: CCCCCCCCC(=O)OCC(C)(C)CCCCCCN(CCO)CCCCCCC(=O)OCC(CCCCCCCC)CCCCCCCC]
110b
Example 180
[M + H]+: 738.70

-continued
111b
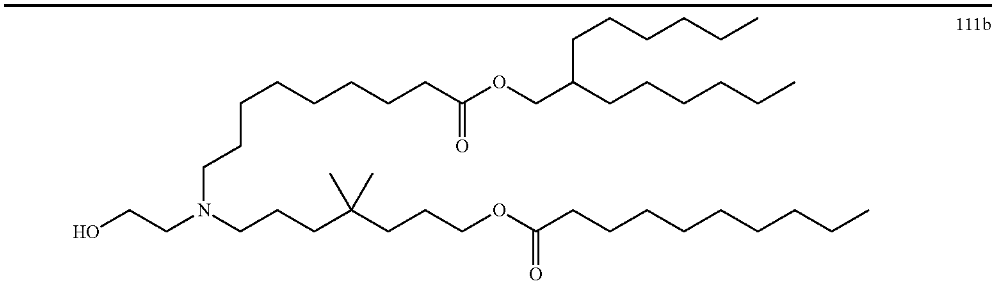
Example 181
[M + H]+: 710.60
112b
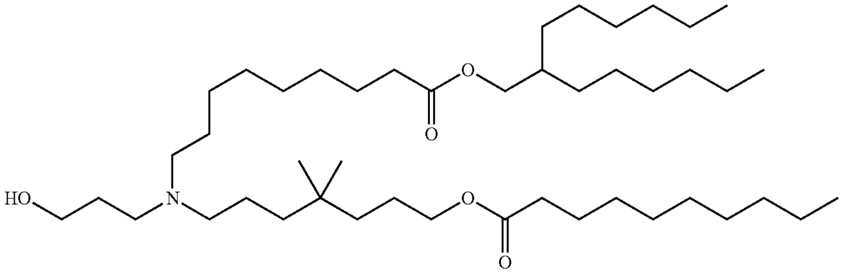 [SMILES: CCCCCCCCCC(=O)OCCCC(C)(C)CCCN(CCCO)CCCCCCCCC(=O)OCC(CCCCCC)CCCCCC]
Example 182
[M + H]+: 724.85
113b
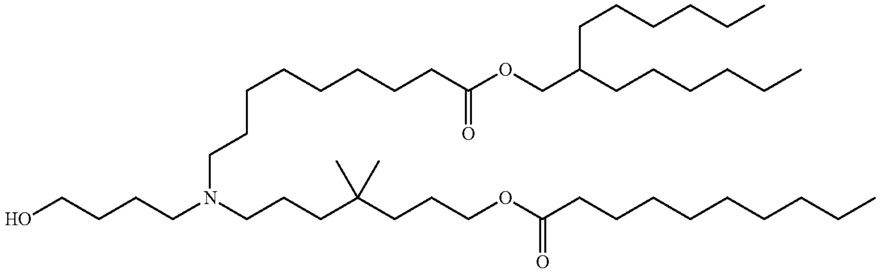 [SMILES: CCCCCCCCCC(=O)OCCCC(C)(C)CCCN(CCCCO)CCCCCCCCC(=O)OCC(CCCCCC)CCCCCC]
Example 183
[M + H]+: 738.85
114b
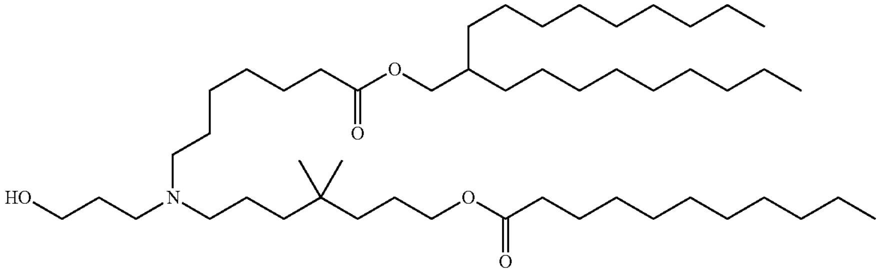 [SMILES: CCCCCCCCCCC(=O)OCCCC(C)(C)CCCN(CCCO)CCCCCCC(=O)OCC(CCCCCCCCC)CCCCCCCCC]
Example 184
[M + H]+: 794.75

-continued

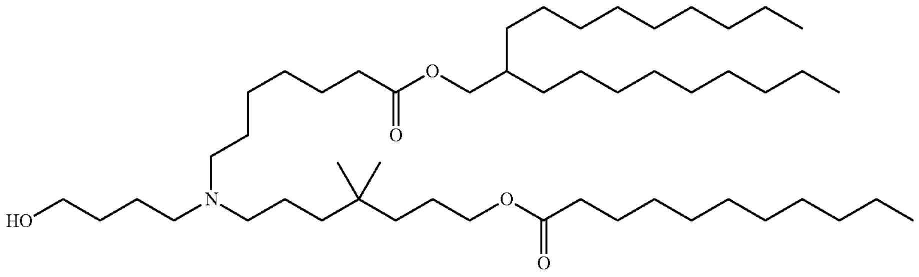 [SMILES: CCCCCCCCCCC(=O)OCCCC(C)(C)CCCN(CCCCO)CCCCCCC(=O)OCC(CCCCCCCCC)CCCCCCCCC]

115b

Example 185
[M + H]+: 808.80

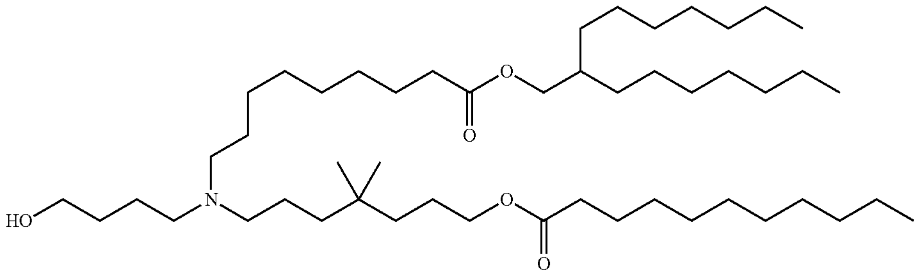 [SMILES: CCCCCCCCCCC(=O)OCCCC(C)(C)CCCN(CCCCO)CCCCCCCCC(=O)OCC(CCCCCCC)CCCCCCC]

116b

Example 186
[M + H]+: 780.75

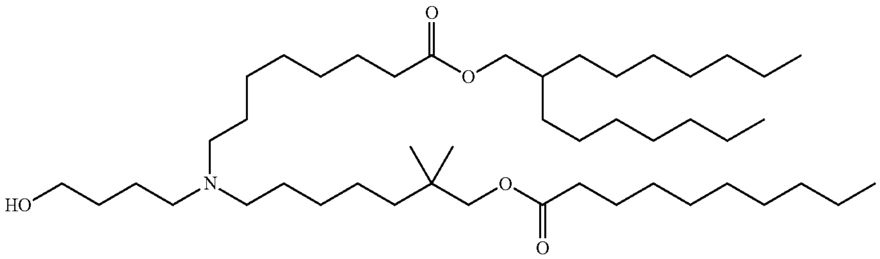 [SMILES: CCCCCCCCCC(=O)OCC(C)(C)CCCCCN(CCCCO)CCCCCCCC(=O)OCC(CCCCCCC)CCCCCCC]

117b

Example 187
[M + H]+: 752.90

Compounds 1c-283c were synthesized using the method as described in the above Examples, or similar methods using corresponding intermediates.

Pharmacological Experiments

Assay Example 1: Preparation of Nanoparticles

Materials used for lipid nanoparticle assembly include: (1) ionizable lipid compounds: e.g., ionizable lipids designed and synthesized in the present disclosure or DLin-MC3-DMA (purchased from AVT) as a control; (2) structure lipids: e.g., Cholesterol (purchased from Sigma-Aldrich); (3) phospholipids: e.g., DSPC i.e., 1,2-distearoyl-SN-glycero-3-phosphocholine (Distearoylphosphatidylcholine, purchased from AVT); (4) polyethylene glycolated lipids: e.g. DMG-PEG2000 i.e., dimyristoylglycero-polyethylene glycol 2000 (1,2-dimyristoyl-rac-glycero-3-methoxypolyethylene glycol-2000, purchased from AVT); (5) active ingredients of nucleic acid fragments: e.g. Luciferase mRNA, siRNA, CRISPR Cas 9 mRNA, etc. (manufactured in-house). The names of materials of the lipid nanoparticle assembly and their structural formulae are detailed in Table 4.

TABLE 4

| No. | Structure name | Structural formula |
|---|---|---|
| 1 | DLin-MC3-DMA (MC3) | 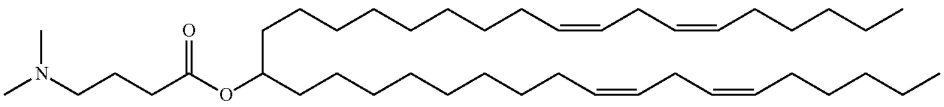 [SMILES: CCCCC/C=C\C/C=C\CCCCCCCCC(CCCCCCCC/C=C\C/C=C\CCCCC)OC(=O)CCCN(C)C] |

TABLE 4-continued

| No. | Structure name | Structural formula |
|---|---|---|
| 2 | Cholesterol | 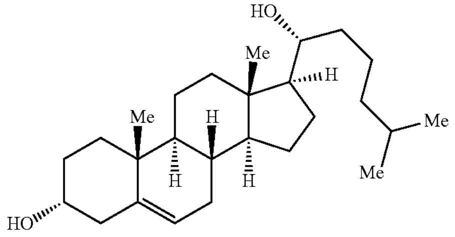 |
| 3 | DSPC | 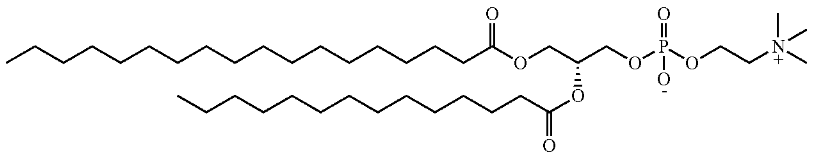 |
| 4 | DMG-PEG2000 | 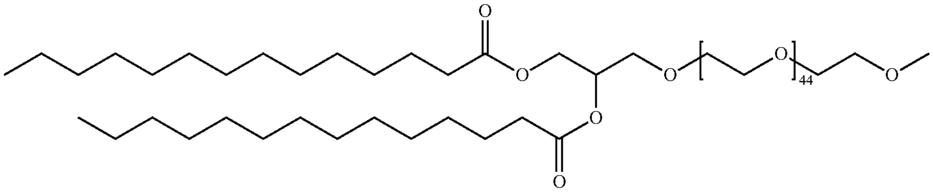 |

Lipid nanoparticles were prepared by (1) dissolving and mixing ionizable lipid compounds, cholesterol, phospholipids and polyethylene glycolated lipids in ethanol at (molar percentages) 50%, 38.5%, 10% and 1.5%, respectively; (2) dissolving the mRNA active ingredient in 25 mM sodium acetate solution (pH=4.5); (3) using an automated high-throughput microfluidic system to mix the organic phase containing the lipid mixture and the aqueous phase containing the mRNA component in the flow ratio range of 1:1 to 1:4 at a mixing speed of 10 mL/min to 18 mL/min; (4) the prepared lipid nanoparticles (N/P ratio=6) were diluted with phosphate buffer solution and the nanoparticle solutions were ultrafiltered to the original preparation volume using ultrafiltration tubes (purchased from Millipore) with a cut-off molecular weight of 30 kDa; and (5) the obtained nanoparticles were filtered through a sterile 0.2 μm filter membrane and then stored in a sealed glass vial at low temperature.

The preparation method of lipid nanoparticles includes microfluidic mixing systems, but is not limited to this method, which also includes T-type mixers and ethanol injection method, and the like.

Assay Example 2: Characterization of Physical Properties of Lipid Nanoparticles The particle size and particle size dispersity index (PDI) of the prepared lipid nanoparticles were measured using a Zetasizer Pro (purchased from Malvern Instruments Ltd) and a DynaPro NanoStar (purchased from Wyatt) dynamic light scattering instrument. The degree of RNA encapsulation by lipid nanoparticles was characterized by the Encapsulation Efficiency %, which reflects the degree of binding of lipid nanoparticles to RNA fragments. This parameter was measured by the method of Quant-it™ RiboGreen RNA Assay (purchased from Invitrogen). Lipid nanoparticle samples were diluted in TE buffer (10 mM Tris-HCl, 1 mM EDTA, pH=7.5). A portion of the sample solution was removed, to which 0.5% Triton (Triton X-100) was added, and then allowed to stand at 37° C. for 30 minutes. Immediately after the addition of RIBOGREEN® reaction solution, the fluorescence values were read on a Varioskan LUX multifunctional microplate reader (purchased from Thermofisher) at 485 nm for absorption and 528 nm for emission to give the encapsulation efficiency values.

Assay Example 3: Animal Experiment

The delivery effect and safety of nanoparticles encapsulated with luciferase mRNA (Trilink, L-7202) in mice were evaluated. The test mice were SPF-grade C57BL/6 mice, female, 6-8 weeks old, weighing 18-22 g, and were purchased from SPF (Beijing) Biotechnology Co., Ltd. All animals were acclimatized for more than 7 days prior to the experiment, and had free access to food and water during the experiment. The conditions include alternating light and dark for 12/12 h, the indoor temperature of 20-26° C. and the humidity of 40-70%. The mice were randomly grouped. The lipid nanoparticles encapsulated with luciferase mRNA prepared above were injected into mice by intravenous administration at a single dose of 0.5 mg/kg mRNA, and the mice were subjected to in vivo bioluminescence assay using a Small Animal In Vivo Imaging System (IVIS LUMINA III, purchased from PerkinElmer) at 6 h after administration. The assay was performed as follows: D-luciferin solution was prepared in saline at a concentration of 15 mg/mL, and each mouse was given the substrate by intraperitoneal injection. At ten minutes after administration of the substrate, the mice were anesthetized in an anesthesia chamber with isoflurane at a concentration of 2.5%. The anesthetized mice were placed in IVIS for fluorescence imaging, and data acquisition and analysis were performed on the concentrated distribution area of fluorescence.

The in vivo delivery efficiency of lipid nanoparticle carriers was expressed as the mean values of fluorescence intensity and total photon count in different animals within the same subject group, as shown in Table 5-Table 11. Higher values of fluorescence intensity and total photon count indicate higher in vivo delivery efficiency of this mRNA fragment by lipid nanoparticles. The lipid nanoparticles containing the cationic lipids of the present disclosure have good in vivo delivery efficiency.

TABLE 5

| Compound | Particle size (nm) | Particle-size distribution (PDI) | Encapsulation efficiency (%) | Total photon count in vivo at 6 hours after administration (Total Flux) |
|---|---|---|---|---|
| 1a | 113.08 | 0.022 | 94.61 | 3.52E+10 |
| 3a | 89.72 | 0.021 | 94.23 | 1.03E+11 |
| 4a | 103.7 | 0.005 | 92.87 | 3.25E+10 |
| 6a | 90.67 | 0.018 | 87.22 | 2.88E+10 |
| 7a | 103.32 | 0.018 | 90.92 | 5.26E+10 |
| 9a | 103.03 | 0.031 | 89.64 | 2.06E+10 |
| 10a | 131.09 | 0.032 | 89.69 | 7.08E+10 |
| 11a | 98.01 | 0.021 | 89.36 | 2.05E+10 |
| 12a | 104.85 | 0.021 | 85.24 | 1.39E+10 |
| 13a | 110.20 | 0.018 | 92.96 | 5.01E+10 |
| 14a | 90.99 | 0.012 | 91.67 | 1.09E+11 |
| 15a | 95.94 | 0.021 | 90.77 | 4.15E+10 |
| 19a | 109.37 | 0.035 | 87.90 | 4.73E+10 |
| 20a | 102.13 | 0.032 | 87.83 | 1.18E+11 |
| 21a | 110.00 | 0.016 | 88.37 | 8.84E+10 |
| 22a | 99.48 | 0.010 | 97.25 | 1.74E+10 |
| 23a | 99.25 | 0.011 | 96.30 | 9.84E+10 |
| 24a | 109.53 | 0.052 | 88.89 | 3.07E+10 |
| 25a | 86.99 | 0.051 | 95.62 | 1.33E+11 |
| 26a | 106.37 | 0.050 | 91.18 | 1.11E+11 |
| 27a | 136.43 | 0.016 | 93.52 | 4.31E+10 |
| 28a | 110.30 | 0.018 | 93.90 | 4.30E+10 |
| 29a | 88.59 | 0.012 | 97.30 | 5.46E+10 |
| MC3 | 96.83 | 0.04 | 95.62 | 8.04E+09 |

TABLE 6

| Compound | Particle size (nm) | Particle-size distribution (PDI) | Encapsulation efficiency (%) | Total photon count in vivo at 6 hours after administration (Total Flux) |
|---|---|---|---|---|
| 1b | 88.59 | 0.031 | 89.89 | 9.34E+10 |
| 2b | 104.61 | 0.013 | 80.17 | 8.31E+10 |
| 3b | 102.32 | 0.015 | 74.43 | 1.41E+11 |
| 6b | 99.55 | 0.029 | 80.01 | 7.42E+10 |
| 7b | 101.67 | 0.030 | 88.68 | 2.00E+10 |
| 10b | 114.72 | 0.052 | 72.72 | 3.15E+10 |
| 12b | 104.60 | 0.031 | 91.04 | 1.19E+10 |
| 13b | 99.02 | 0.018 | 89.27 | 1.81E+11 |
| 14b | 99.73 | 0.013 | 83.54 | 1.05E+11 |
| 15b | 120.27 | 0.015 | 69.69 | 8.22E+10 |
| 16b | 101.90 | 0.028 | 89.09 | 1.28E+11 |
| 17b | 109.87 | 0.030 | 87.72 | 1.74E+11 |
| 18b | 100.46 | 0.037 | 89.34 | 3.91E+10 |
| 19b | 109.53 | 0.036 | 83.01 | 6.13E+10 |
| 20b | 107.83 | 0.032 | 87.69 | 4.82E+10 |
| 21b | 94.58 | 0.051 | 92.37 | 4.95E+10 |
| 22b | 99.44 | 0.050 | 93.03 | 8.78E+10 |
| 23b | 115.70 | 0.031 | 93.14 | 3.92E+10 |
| 24b | 83.05 | 0.019 | 94.52 | 7.06E+10 |
| MC3 | 96.83 | 0.04 | 95.62 | 8.04E+09 |

TABLE 7

| Compound | Particle size (nm) | Particle-size distribution (PDI) | Encapsulation efficiency (%) | Total photon count in vivo at 6 hours after administration (Total Flux) |
|---|---|---|---|---|
| 30a | 107.40 | 0.12 | 86.94 | 8.32E+10 |
| 31a | 115.56 | 0.11 | 86.08 | 7.04E+10 |
| 32a | 129.00 | 0.10 | 83.51 | 1.24E+10 |
| 33a | 111.60 | 0.17 | 86.98 | 1.09E+11 |
| 34a | 116.67 | 0.12 | 95.73 | 3.14E+10 |
| 35a | 126.63 | 0.22 | 95.00 | 3.01E+10 |
| 36a | 104.80 | 0.15 | 92.41 | 2.51E+10 |
| 37a | 110.67 | 0.15 | 92.14 | 3.54E+10 |
| 38a | 114.03 | 0.13 | 94.51 | 1.39E+10 |
| 39a | 144.83 | 0.08 | 93.59 | 2.24E+10 |
| 40a | 120.90 | 0.18 | 95.08 | 2.03E+11 |
| 41a | 114.03 | 0.13 | 94.51 | 1.11E+11 |
| 42a | 104.13 | 0.17 | 95.54 | 3.47E+10 |
| 43a | 105.63 | 0.15 | 97.03 | 2.23E+10 |
| 44a | 92.67 | 0.20 | 96.84 | 1.06E+11 |
| 45a | 114.73 | 0.15 | 94.63 | 1.22E+11 |
| 46a | 110.83 | 0.16 | 93.03 | 9.06E+10 |
| 47a | 104.47 | 0.21 | 93.23 | 3.10E+10 |
| 48a | 81.22 | 0.16 | 96.13 | 8.16E+10 |
| 49a | 100.56 | 0.14 | 94.85 | 2.28E+10 |
| 50a | 78.03 | 0.12 | 98.67 | 2.86E+10 |
| 51a | 92.08 | 0.15 | 94.81 | 3.11E+10 |
| 25b | 94.39 | 0.15 | 95.59 | 1.11E+11 |
| 26b | 113.77 | 0.14 | 94.58 | 6.53E+10 |
| 27b | 91.10 | 0.18 | 97.83 | 5.59E+10 |
| 28b | 94.55 | 0.16 | 96.19 | 4.18E+10 |
| 29b | 112.43 | 0.10 | 96.28 | 3.52E+10 |
| 30b | 115.83 | 0.08 | 95.02 | 4.03E+10 |
| 31b | 118.73 | 0.07 | 95.73 | 1.87E+10 |
| 32b | 116.50 | 0.16 | 95.31 | 3.52E+10 |
| 33b | 85.80 | 0.15 | 94.85 | 8.23E+10 |
| 34b | 85.20 | 0.19 | 97.61 | 2.78E+10 |
| 35b | 100.40 | 0.21 | 96.35 | 3.77E+10 |
| 36b | 112.50 | 0.19 | 96.10 | 3.84E+10 |
| 37b | 83.72 | 0.16 | 95.15 | 3.72E+10 |
| MC3 | 96.83 | 0.04 | 95.62 | 8.04E+09 |

TABLE 8

| Compound | Particle size (nm) | Particle-size distribution (PDI) | Encapsulation efficiency (%) | Total photon count in vivo at 6 hours after administration (Total Flux) |
|---|---|---|---|---|
| 52a | 79.40 | 0.09 | 93.30 | 2.58E+10 |
| 53a | 124.00 | 0.23 | 90.96 | 9.04E+10 |
| 54a | 87.37 | 0.14 | 91.34 | 1.32E+10 |
| 55a | 126.17 | 0.16 | 73.85 | 1.96E+10 |
| 56a | 86.37 | 0.09 | 82.84 | 3.23E+10 |
| 57a | 79.17 | 0.17 | 95.41 | 3.42E+10 |
| 58a | 187.50 | 0.18 | 68.54 | 2.72E+10 |

TABLE 9

| Compound | Particle size (nm) | Particle-size distribution (PDI) | Encapsulation efficiency (%) | Total photon count in vivo at 6 hours after administration (Total Flux) |
|---|---|---|---|---|
| 60a | 92.74 | 0.15 | 97.44 | 1.75E+10 |
| 61a | 111.90 | 0.09 | 95.87 | 1.32E+10 |
| 38b | 102.50 | 0.11 | 98.29 | 1.49E+10 |
| 39b | 102.67 | 0.07 | 93.58 | 7.16E+10 |
| 40b | 97.10 | 0.11 | 96.74 | 3.70E+10 |
| 43b | 121.89 | 0.08 | 95.26 | 1.29E+10 |
| 44b | 92.63 | 0.15 | 97.45 | 1.16E+10 |
| 46b | 98.91 | 0.09 | 97.78 | 2.44E+10 |

TABLE 9-continued

| Compound | Particle size (nm) | Particle-size distribution (PDI) | Encapsulation efficiency (%) | Total photon count in vivo at 6 hours after administration (Total Flux) |
|---|---|---|---|---|
| 47b | 122.40 | 0.07 | 97.27 | 2.84E+10 |
| 50b | 98.36 | 0.13 | 98.50 | 1.01E+10 |

TABLE 10

| Compound | Particle size (nm) | Particle-size distribution (PDI) | Encapsulation efficiency (%) | Total photon count in vivo at 6 hours after administration (Total Flux) |
|---|---|---|---|---|
| 51b | 91.96 | 0.12 | 95.92 | 7.60E+10 |
| 52b | 105.97 | 0.06 | 90.84 | 1.01E+11 |
| 53b | 125.03 | 0.42 | 91.92 | 1.00E+11 |
| 54b | 81.37 | 0.17 | 96.69 | 5.71E+10 |
| 55b | 90.37 | 0.11 | 94.65 | 1.02E+11 |
| 56b | 98.59 | 0.16 | 93.87 | 8.35E+10 |
| 57b | 98.23 | 0.18 | 94.15 | 3.86E+10 |
| 58b | 112.93 | 0.15 | 92.88 | 6.17E+10 |
| 59b | 127.23 | 0.12 | 80.27 | 1.04E+11 |
| 62a | 98.07 | 0.17 | 89.88 | 1.20E+10 |
| 63a | 80.23 | 0.17 | 95.56 | 1.17E+11 |
| 64a | 86.99 | 0.15 | 96.72 | 9.82E+10 |
| 65a | 95.88 | 0.16 | 95.93 | 6.53E+10 |
| 66a | 105.77 | 0.11 | 92.88 | 9.31E+10 |
| 67a | 111.33 | 0.06 | 91.57 | 6.07E+10 |
| 68a | 103.93 | 0.04 | 94.47 | 7.55E+10 |
| 69a | 107.20 | 0.34 | 96.65 | 7.41E+10 |
| 70a | 86.08 | 0.15 | 96.69 | 9.33E+10 |

TABLE 11

| Compound | Particle size (nm) | Particle-size distribution (PDI) | Encapsulation efficiency (%) | Total photon count in vivo at 6 hours after administration (Total Flux) |
|---|---|---|---|---|
| 63b | 165.53 | 0.09 | 84.27 | 2.72E+10 |
| 64b | 143.67 | 0.09 | 89.27 | 3.36E+10 |
| 65b | 80.60 | 0.16 | 97.75 | 1.25E+11 |
| 66b | 81.83 | 0.17 | 97.18 | 4.35E+10 |
| 67b | 88.28 | 0.23 | 96.30 | 1.71E+11 |
| 68b | 88.33 | 0.20 | 96.31 | 2.88E+11 |
| 69b | 99.05 | 0.13 | 93.85 | 1.52E+11 |
| 70b | 96.20 | 0.09 | 96.91 | 1.15E+11 |
| 71b | 95.59 | 0.17 | 95.95 | 1.70E+11 |
| 72b | 92.45 | 0.12 | 95.13 | 7.01E+10 |
| 73b | 119.37 | 0.14 | 92.71 | 4.73E+10 |
| 74b | 93.18 | 0.17 | 94.92 | 7.13E+10 |
| 75b | 91.60 | 0.19 | 95.99 | 7.05E+10 |
| 76b | 91.27 | 0.18 | 94.97 | 9.41E+10 |
| 77b | 93.16 | 0.16 | 95.88 | 9.72E+10 |
| 78b | 98.88 | 0.12 | 92.27 | 5.51E+10 |
| 79b | 99.27 | 0.15 | 92.85 | 1.62E+11 |
| 80b | 93.39 | 0.18 | 93.59 | 8.94E+10 |
| 81b | 107.43 | 0.19 | 92.87 | 5.20E+10 |
| 82b | 99.57 | 0.16 | 90.71 | 5.03E+10 |
| 83b | 100.67 | 0.10 | 95.70 | 1.62E+10 |
| 84b | 123.77 | 0.11 | 89.17 | 6.68E+10 |
| 85b | 92.14 | 0.17 | 95.44 | 9.61E+10 |
| 86b | 92.26 | 0.13 | 94.74 | 1.01E+11 |
| 87b | 92.25 | 0.22 | 94.16 | 1.35E+11 |
| 88b | 98.16 | 0.12 | 94.68 | 4.51E+10 |
| 89b | 122.20 | 0.08 | 84.88 | 5.51E+10 |
| 90b | 109.57 | 0.08 | 91.21 | 4.72E+10 |
| 91b | 96.43 | 0.12 | 91.95 | 8.66E+10 |
| 92b | 99.90 | 0.15 | 92.47 | 3.74E+10 |
| 93b | 141.73 | 0.10 | 90.17 | 2.45E+10 |

TABLE 11-continued

| Compound | Particle size (nm) | Particle-size distribution (PDI) | Encapsulation efficiency (%) | Total photon count in vivo at 6 hours after administration (Total Flux) |
|---|---|---|---|---|
| 94b | 125.60 | 0.11 | 93.55 | 2.23E+10 |
| 95b | 84.62 | 0.15 | 95.41 | 2.44E+10 |
| 96b | 97.75 | 0.15 | 92.10 | 3.77E+10 |
| 97b | 85.56 | 0.14 | 93.79 | 9.01E+10 |
| 98b | 87.99 | 0.18 | 93.04 | 1.07E+11 |
| 99b | 85.13 | 0.15 | 92.70 | 4.78E+10 |
| 100b | 101.50 | 0.12 | 91.14 | 8.51E+10 |
| 101b | 126.00 | 0.10 | 81.76 | 5.39E+10 |
| 102b | 92.12 | 0.16 | 93.92 | 7.52E+10 |
| 103b | 96.82 | 0.11 | 94.07 | 5.95E+10 |
| 104b | 135.57 | 0.09 | 91.51 | 3.20E+10 |
| 105b | 89.73 | 0.16 | 94.38 | 9.24E+10 |
| 106b | 88.22 | 0.15 | 94.89 | 1.42E+11 |
| 107b | 88.13 | 0.16 | 94.05 | 1.98E+11 |
| 108b | 86.61 | 0.16 | 94.16 | 1.38E+11 |
| 109b | 95.32 | 0.13 | 93.00 | 1.90E+11 |
| 110b | 133.93 | 0.21 | 85.48 | 1.36E+11 |
| 111b | 187.13 | 0.21 | 63.26 | 3.98E+10 |
| 112b | 175.67 | 0.17 | 69.74 | 1.31E+10 |
| 113b | 147.03 | 0.09 | 88.21 | 2.09E+10 |
| 114b | 103.40 | 0.13 | 93.55 | 4.53E+10 |
| 115b | 100.25 | 0.12 | 93.91 | 3.71E+10 |
| 116b | 120.13 | 0.09 | 90.71 | 1.96E+10 |
| 117b | 151.17 | 0.09 | 72.51 | 1.73E+10 |

Assay Example 4: Evaluation of Delivery Efficiency and Safety In Vitro

The delivery effect and safety of nanoparticles encapsulated with luciferase mRNA were evaluated at the cellular level in vitro. The cells used in the assay were human embryonic kidney cells 293 (HEK293T cells) cultured in DMEM (Dulbecco's Modified Eagle Medium) (purchased from Thermo Fisher) containing 10% fetal bovine serum and 5% penicillin-streptomycin double antibiotics at a indoor temperature of 37° C. and a $CO_2$ concentration of 5%. The cells were uniformly dispersed and spread in 48-well plates, and incubated in the incubator for 24 h. Then a solution of the lipid nanoparticles encapsulated with luciferase mRNA were added. After 24 h, the cells were lysed, and the intracellular expression intensity and relative light units (RLU) of luciferase in each type of lipid nanoparticles were measured with a luciferase detection reagent (purchased from Promega). The higher the intensity of expression, the higher the delivery efficiency of the lipid material at the cellular level. Meanwhile, CCK-8 reagent (purchased from DOJINDO) was used in cytotoxicity testing for the parallel lipid nanoparticle-treated cell groups after 24 hours. In the test, the group of cells to which only PBS was added was used as a negative control. The procedure was as follows: after the addition of CCK-8 solution, the cells were left to stand in an incubator at 37° C. for 4 h. The absorbance values were read on a multifunctional microplate reader at an absorbance band of 450 nm. The ratio of the absorbance value of the nanoparticle-treated cells to that of the negative control was used as a characterization parameter for cell viability.

The delivery effects and the toxicity data of nanoparticles at the cellular level in vitro are shown in Table 12.

TABLE 12

| Compound | Fluorescence intensity of cells (RLU) | Cell viability (%) |
|---|---|---|
| 20a | 6.55E+06 | 105.11 |
| MC3 | 2.95E+06 | 97.84 |

Assay Example 5: Evaluation of Clearance Rate of Ionizable Lipids In Vivo

The 6-8 weeks old C57 WT female mice (n=3) were injected by tail vein administration of 100 μL of unloaded LNP (0.1 mg/mL) formed from the ionizable lipid, cholesterol, DSPC, and DMG-PEG 2000 at a ratio of 50:38.5:10:1.5. The experimental animals were executed by removing the cervical vertebrae and dissected for the liver at 24 h and 72 h after administration, respectively, while the same batch of non-dosed experimental animal livers were used as a blank control group. Water was added to the liver sample for homogenization, and the protein was precipitated. The content of the ionizable lipid in the sample was quantitatively analyzed using LC-MS/MS in comparison to a calibration standard prepared from matched blank liver tissues.

TABLE 13

| Compound | Percentage of cationic lipids in the liver in the total dose, 24 h after administration (%) | Percentage of cationic lipids in the liver in the total dose, 72 h after administration (%) |
|---|---|---|
| 1a | <1 | 0 |
| 4a | <1 | 0 |
| 1b | 15 ± 4.2 | <1 |
| 3b | 12 ± 3.8 | <1 |
| 10b | 5 ± 3.1 | <1 |
| 12b | <1 | 0 |
| 13b | 8 ± 2.7 | <1 |
| 30a | 4 | <2 |
| 26b | 8 | <1 |
| 22b | 2 | <1 |
| 39b | <1 | <1 |
| 56a | <1 | <1 |
| Control group | 92 ± 3.5 | 89 ± 4.7 |

The control compound is of the following structure:

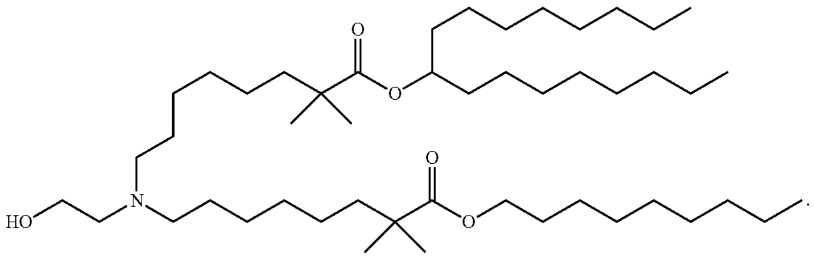 [SMILES: CCCCCCCCCOC(=O)C(C)(C)CCCCCCN(CCO)CCCCCCC(C)(C)C(=O)OC(CCCCCCCC)CCCCCCCC]

Datas in Table 13 show that the geminal dialkyl compound in the control group degrade slowly in the liver, and about 90% of it still remains in the liver 72 hours after administration. The compounds of the present invention has a faster degradation rate, and can be degraded in the liver in about 72 hours.

While the present disclosure has been fully described by way of its embodiments, it is worth noting that various variations and modifications are apparent to those skilled in the art. Such variations and modifications should all be included within the scope of the claims appended to this disclosure.

The invention claimed is:

1. A compound of formula (I), or a pharmaceutically acceptable salt, isotopic variant, tautomer, or stereoisomer thereof:

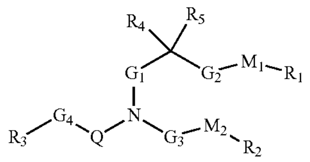

(I)

wherein, $G_1$ and $G_2$ are independently selected from a chemical bond, $C_{1-13}$ linear alkylene, $C_{2-13}$ linear alkenylene, and $C_{2-3}$ linear alkynylene, each of which is optionally substituted with one or more $R_{G1}$;

$G_1$ and $G_2$ have a total length of 3, 4, 5, 6, 7, 8, 9, 10, 11, 12, or 13 carbon atoms;

$R_{G1}$ is independently H, $C_{1-14}$ alkyl, —$L_a$-$OR_a$, $L_a$-$SR_a$, or -$L_a$-$NR_aR'_a$;

$G_3$ is $C_{4-14}$ linear alkylene, $C_{4-14}$ linear alkenylene, or $C_{4-14}$ linear alkynylene, each of which is optionally substituted with one or more $R_3$;

$R_{G3}$ is independently —H, -$L_a$-$OR_a$, -$L_a$-$SR_a$, or -$L_a$-$NR_aR'_a$;

$L_a$ is independently a chemical bond or $C_{1-4}$ alkylene;

$R_a$ and $R'_a$ are independently selected from H, $C_{1-14}$ alkyl, $C_{3-14}$ cycloalkyl, and 3- to 14-membered heterocyclyl;

$G_4$ is a chemical bond, $C_{1-6}$ alkylene, $C_{2-6}$ alkenylene, or $C_{2-6}$ alkynylene, each of which is optionally substituted with one or more $R_{G4}$;

$R_{G4}$ is independently H, $C_{1-6}$ alkyl, -$L_b$-$OR_b$, -$L_b$-$SR_b$, or -$L_b$-$NR_bR'_b$;

$L_b$ is independently a chemical bond or $C_{1-6}$ alkylene;

$R_b$ and $R'_b$ are independently selected from H, and $C_{1-6}$ alkyl;

or, two $R_{G4}$ attached to the same carbon atom are taken together with the carbon atom to which they are attached to form $C_{3-14}$ cycloalkylene or 3- to 14-membered heterocyclylene, each of which is optionally substituted with one or more $R_{4g}$;

$R_{4g}$ is independently H, halogen, cyano, $C_{1-8}$ alkyl, $C_{1-8}$ haloalkyl, -$L_e$-$OR_e$, -$L_e$-$SR_e$, or -$L_e$-$NR_eR'_e$;

$L_e$ is independently a chemical bond or $C_{1-8}$ alkylene;

$R_e$ and $R'_e$ are independently selected from H, $C_{1-8}$ alkyl, $C_{3-14}$ cycloalkyl, and 3- to 14-membered heterocyclyl;

$M_1$ and $M_2$ are independently selected from —C(O)O—, —OC(O)—, —O—, —SC(O)O—, —OC(O)NR—, —NRC(O)NR—, —OC(O)S—, —OC(O)O—, —NRC(O)O—, —SC(O)—, —C(O)S—, —NR—, —C(O)NR—, —NRC(O)—, —NRC(O)S—, —SC(O)NR—, —C(O)—, —OC(S)—, —C(S)O—, —OC(S)NR—, —NRC(S)O—, —S—S—, and —$S(O)_{0\text{-}2}$—; Q is selected from a chemical bond, —C(O)O—, —O—, —SC(O)O—, —OC(O)$NR_f$—, —$NR_f$C(O)$NR_f$—, —OC(O)S—, —OC(O)O—, —$NR_f$C(O)O—, —OC(O)—, —SC(O)—, —C(O)S—, —$NR_f$—, —C(O)$NR_f$—, —$NR_f$C(O)—, —NRC(O)S—, —SC(O)$NR_f$—, —C(O)—, —OC(S)—, —C(S)O—, —OC(S)$NR_f$—, —$NR_f$C(S)O—, —S—S—, —$S(O)_{0\text{-}2}$—, phenylene, and pyridinylene;

$R_{1s}$ independently selected from H, and $C_{1\text{-}10}$ alkyl;

$R_1$ and $R_2$ are independently selected from $C_{4\text{-}20}$ alkyl, $C_{4\text{-}20}$ alkenyl, and $C_{4\text{-}20}$ alkynyl, each of which is optionally substituted with one or more $R_{1s}$ and wherein one or more methylene units are optionally and independently replaced with —NR'—;

$R_{1s}$ is independently H, $C_{1\text{-}20}$ alkyl, -$L_c$-$OR_c$, -$L_c$-$SR_c$, or -$L_c$-$NR_cR'_c$;

R and R' are independently H or $C_{1\text{-}20}$ alkyl;

$L_e$ is independently a chemical bond or $C_{1\text{-}20}$ alkylene;

$R_c$ and $R'_c$ are independently selected from H, $C_{1\text{-}20}$ alkyl, $C_{3\text{-}14}$ cycloalkyl, and 3- to 14-membered heterocyclyl;

$R_3$ is selected from CN, —$OR_g$, —C(O)$R_g$, —OC(O)$R_g$, —NR"C(O)$R_g$, —$NR_gR'_g$, —NR"C(O)$NR_gR'_g$, —NR"C(O)$R_g$, —NR"$S(O)_2R_g$, —OC(O)$NR_gR'_g$, —NR"C(O)$OR_g$, —N($OR_g$)C(O)$R_g$, —N($OR_g$)$S(O)_2$ $R_g$, —N($OR_g$)C(O)$OR_g$, —N($OR_g$)C(O)$R_gR'_g$, 3- to 14-membered heterocyclyl, and 5- to 14-membered heteroaryl;

$R_g$ and $R'_g$ are independently H, $C_{1\text{-}10}$ alkyl, $C_{3\text{-}10}$ cycloalkyl, or 3- to 10-membered heterocyclyl;

R" is independently H or $C_{1\text{-}6}$ alkyl;

$R_4$ and $R_5$ are independently $C_1$ alkyl;

or, $R_4$ and $R_5$ are taken together with the carbon atom to which they are attached to form $C_3$a cycloalkylene or 3- to 6-membered heterocyclylene.

2. The compound of formula (I) of claim 1, or a pharmaceutically acceptable salt, isotopic variant, tautomer, or stereoisomer thereof, which has a structure of formula (II) or formula (III):

(II)

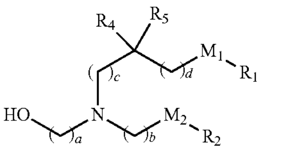

or (III)

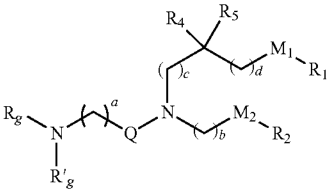

wherein, a=1, 2, 3, 4, 5, or 6;

b=4, 5, 6, 7, 8, 9, or 10;

c=1, 2, 3, 4, 5, or 6;

d===0, 1, 2, 3, or 4;

c+d=3, 4, 5, 6, 7, 8, or 9;

the other groups are as defined in claim 1.

3. The compound of fornnula (II) or formula (III) of claim 2, or a pharmaceutically acceptable salt, isotopic variant, tautomer, or stereoisomer thereof, (II)

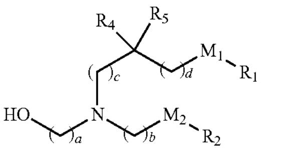

or (III)

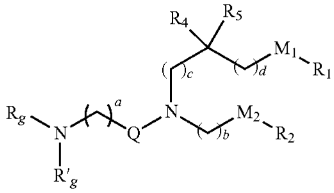

wherein, the substitution site of $R_{1s}$ on $R_1$ or $R_2$ is separated from $M_1$ or $M_2$ by 0-10 carbon atoms, alternatively 0-6 carbon atoms, alternatively 0-4 carbon atoms, alternatively 0-2 carbon atoms, alternatively 0 carbon atoms;

alternatively, the substitution site of $R_{1s}$ on $R_1$ or $R_2$ is separated from $M_1$ or $M_2$ by 1-10 carbon atoms, alternatively 1-6 carbon atoms, alternatively 1-4 carbon atoms, alternatively 1-2 carbon atoms; alternatively 2-10 carbon atoms, alternatively 2-6 carbon atoms, alternatively 2-4 carbon atoms;

alternatively, $R_1$ is not substituted with $R_{1s}$ and the substitution site of $R_{1s}$ on $R_2$ is separated from $M_2$ by 0-10 carbon atoms, alternatively 1-10 carbon atoms, alternatively 1-6 carbon atoms, alternatively 1-4 carbon atoms, alternatively 1-2 carbon atoms; alternatively 2-10 carbon atoms, alternatively 2-6 carbon atoms, alternatively 2-4 carbon atoms;

alternatively, $R_1$ is substituted with $R_{1s}$, and $R_2$ is not substituted with $R_{1s}$;

alternatively, $R_4$ and $R_5$ are not taken together with the carbon atom to which they are attached to form a ring;

alternatively, d is not 0.

4. The compound of formula (II) of claim 2, or a pharmaceutically acceptable salt, isotopic variant, tautomer, or stereoisomer thereof, (II)

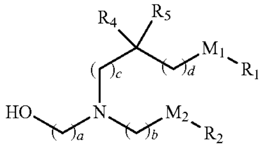

wherein a=2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9; alternatively c+d=4, 5, or 6;

$M_1$ and $M_2$ are independently selected from —C(O)O—, —OC(O)—, —SC(O)—, and —C(O)S—; alternatively, $M_1$ and $M_2$ are independently selected from —C(O)O— and —C(O)S—; alternatively, one of $M_1$ and $M_2$ is —C(O)O— or —C(O)S—, and the other is —OC(O)— or —SCO)—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, -$L_c$-$OR_c$, or -$L_c$-$NR_cR'_c$, alternatively H or $C_{1-4}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene or 3-to 6-membered heterocyclylene;

alternatively, a=2, 3, or 4;

b=4, 5, 6, 7, 8, or 9; alternatively b=5, 6, 7, or 8; alternatively b=5, 6, or 7;

c=2, 3, 4, 5, or 6;

d=0, 1, 2, 3, or 4;

c+d=5 or 6;

$M_1$ and $M_2$ are independently —C(O)O— or —OC(O)—; alternatively, $M_1$ and $M_2$ are —C(O)O—;

alternatively, one of $M_1$ and $M_2$ is —C(O)O—, and the other is —OC(O)—;

$R_1$ and $R_2$ are independently $C_{7-12}$ alkyl, alternatively $C_{8-12}$ alkyl, which is optionally substituted with 1 $R_{1s}$;

$R_{1s}$ is independently H or $C_{1-10}$ alkyl, alternatively H or $C_{1-9}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene, alternatively $C_{3-5}$ cycloalkylene;

alternatively, a=2, 3, or 4;

b=4, 5, 6, 7, 8, or 9; alternatively b=5, 6, 7, or 8; alternatively b=5 or 7;

c=2, 3, 4, 5, or 6;

d=0, 1, 2, 3, or 4; alternatively d=0, 1, 2, or 4;

c+d=5 or 6; alternatively c+d=6;

$M_1$ and $M_2$ are —C(O)O—;

or, one of $M_1$ and $M_2$ is —C(O)O—, and the other is —OC(O)—;

$R_1$ and $R_2$ are independently selected from: $—(CH_2)_6CH_3$, $—(CH_2)_7CH_3$, $—(CH_2)_8CH_3$, $—(CH_2)_9CH_3$, $—(CH_2)_{10}CH_3$, $—(CH_2)_{11}CH_3$,

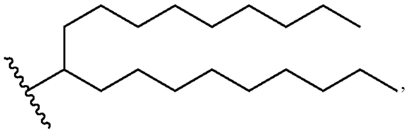,

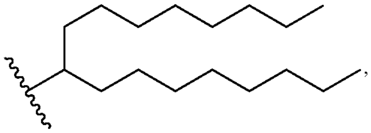,

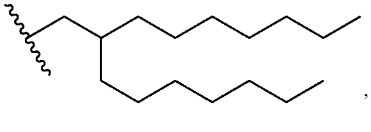,

-continued

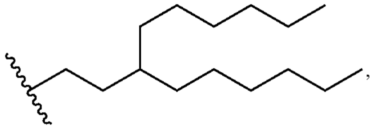,

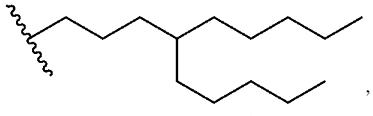,

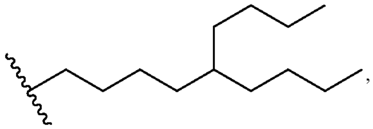,

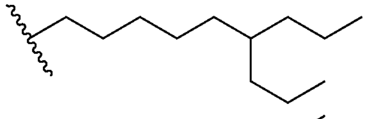,

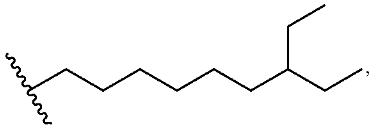,

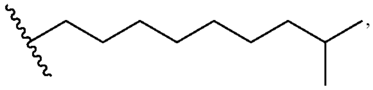,

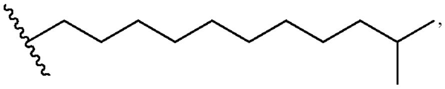, and

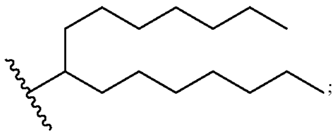;

alternatively $—(CH_2)_7CH_3$, $—(CH_2)_8CH_3$, $—(CH_2)_9CH_3$, $(CH_2)_{10}CH_3$, $—(CH_2)_{11}CH_3$,

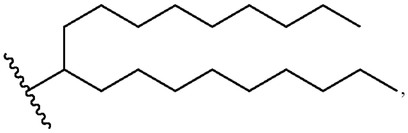,

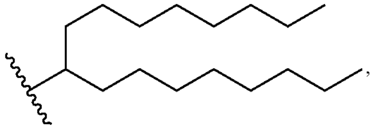,

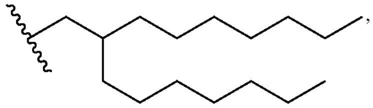,

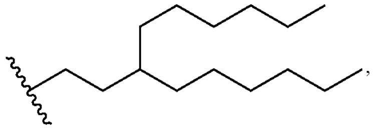,

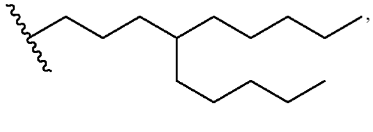,

-continued

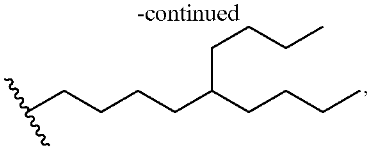

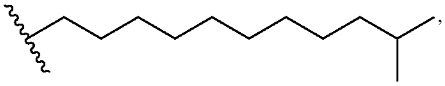 [SMILES: *CCCCCCCCCC(C)C] and

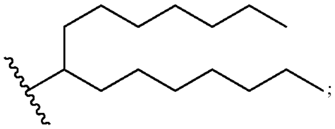

alternatively —$(CH_2)_8CH_3$, —$(CH_2)_9CH_3$, —$(CH_2)_{10}CH$—$(CH_2)_{11}CH_3$,

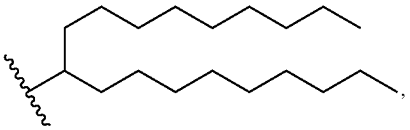

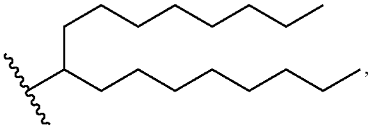

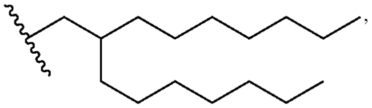

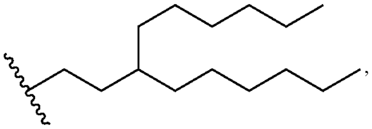

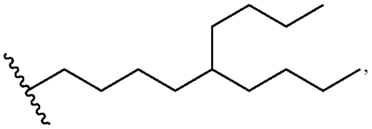

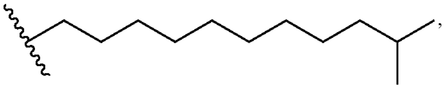 [SMILES: *CCCCCCCCCC(C)C] and

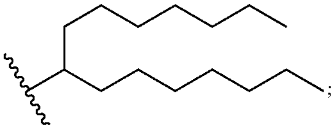

$R_4$ and $R_5$ are methyl;

or, $R_4$ and $R_5$ are taken together with the carbon atom to which they are attached to form cyclopropylene, cyclobutylene, cyclopentylene, or cyclohexylene, alternatively cyclopropylene or cyclopentylene, alternatively cyclopropylene;

alternatively, only one of $R_1$ and $R_2$ is substituted.

5. The compound of formula (II) of claim 4, or a pharmaceutically acceptable salt, isotopic variant, tautomer, or stereoisomer thereof, wherein a=2;

b=5;

c=2, 3, 4, 5, or 6; alternatively c=6;

d=0, 1, 2, 3, or 4; alternatively d 0;

c+d=5 or 6, alternatively 6:

$M_1$ and $M_2$ are —C(O)O—;

$R_1$ is $C_{7-12}$ alkyl, alternatively $C_{8-12}$ alkyl, alternatively $C_{8-9}$ alkyl, or alternatively $C_9$ alkyl, which is optionally substituted with 1 $R_1$;

$R_{1s}$ is independently H or $C_{1-10}$ alkyl, alternatively H or $C_{1-9}$ alkyl, alternatively $C_{6-8}$ alkyl, alternatively $C_{7-8}$ alkyl;

$R_2$ is $C_{7-11}$ linear alkyl, alternatively $C_{10-11}$ linear alkyl, alternatively $C_{11}$ linear alkyl, which is optionally substituted with 1 $C_{1-3}$ alkyl, alternatively optionally substituted with 1 methyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively $R_1$ is

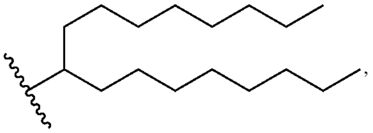

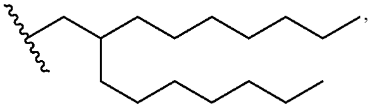 [SMILES: *CC(CCCCCCC)CCCCCCC]

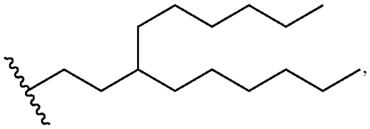 or

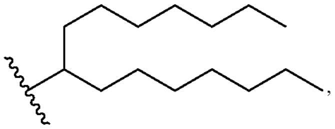

alternatively

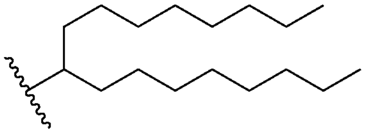 or

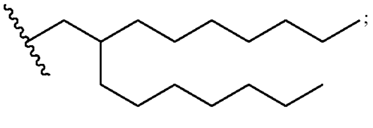

alternatively, $R_2$ is —$(CH_2)_9CH_3$, —$(CH_2)_{10}CH_3$, or

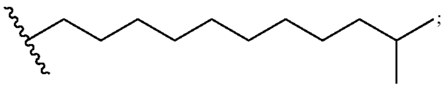

alternatively, a=2, 3, or 4; alternatively a=2;

b=7;

c=2, 3, 4, 5, or 6; alternatively c=2, 3, or 4; alternatively c=2;

d=0, 1, 2, 3, or 4; alternatively d=2, 3, or 4; alternatively d=4;

c+d=5 or 6, alternatively 6;

$M_1$ and $M_2$ are —C(O)O—;

$R_1$ is $C_{8-11}$ linear alkyl, alternatively $C_{9-10}$ linear alkyl, alternatively $C_9$ linear alkyl;

$R_2$ is $C_{7-12}$ alkyl, alternatively $C_{8-12}$ alkyl, alternatively $C_{9-10}$ alkyl, which is optionally substituted with 1 $R_{1s}$;

$R_{1s}$ is independently H or $C_{1-10}$ alkyl, alternatively H or $C_{1-9}$ alkyl, alternatively $C_{6-9}$ alkyl, alternatively $C_{7-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, $R_2$ is

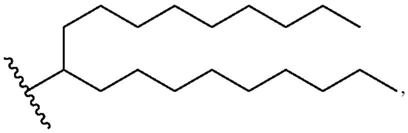
,

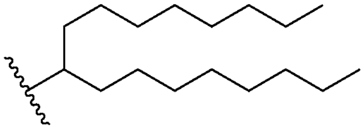
,

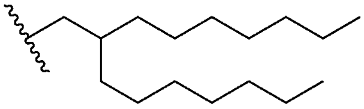
, or

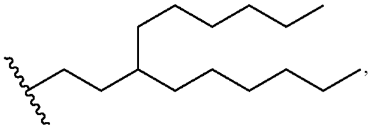
, alternatively

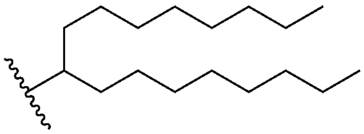
or

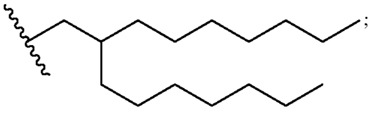
;

alternatively, a=2;

b=7;

c=3 or 4; alternatively c=4;

d=2;

$M_j$ and $M_2$ are —C(O)O—;

$R_1$ is $C_{7-12}$ alkyl, alternatively $C_{8-12}$ alkyl, alternatively $C_{8-10}$ alkyl, which is optionally substituted with 1 $R_{1s}$;

$R_{1s}$ is independently H or $C_{1-10}$ alkyl, alternatively H or $C_{1-9}$ alkyl;

$R_2$ is $C_{7-11}$ linear alkyl, alternatively $C_9$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, a=2, 3, or 4; alternatively a=2 or 4;

b=6 or 7; alternatively b=7;

c=2, 3, 4, 5, or 6; alternatively c=5 or 6;

d=0, 1, 2, 3, or 4; alternatively d=0 or 1;

c+d=5 or 6, alternatively 6;

$M_1$ is —OC(O)—; and $M_2$ is —C(O)O—;

$R_1$ is $C_{7-11}$ linear alkyl, alternatively $C_{9-10}$ linear alkyl;

$R_2$ is $C_{7-12}$ alkyl, alternatively $C_{8-12}$ alkyl, alternatively $C_{9-10}$ linear alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, when a=4, $R_4$ and $R_5$ are not taken together with the carbon atom to which they are attached to form a ring; alternatively, $R_{1s}$ is independently $C_{8-9}$ alkyl;

alternatively, $R_2$ is

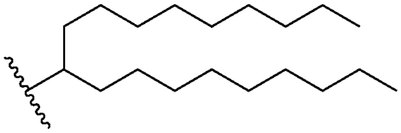
,

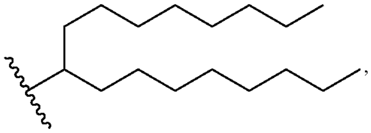
, or

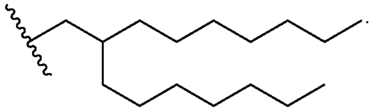
.

6. The compound of formula (II) of claim 2, or a pharmaceutically acceptable salt, isotopic variant, tautomer, or stereoisomer thereof, (II)

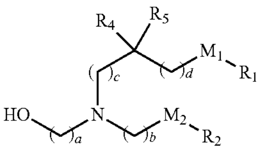

wherein a=2, 3, 4, 5, or 6;

b=4, 5, 6, 7, 8, 9, or 10;

c=1, 2, 3, 4, 5, or 6;

d=0, 1, 2, 3, or 4;

c+d=3, 4, 5, 6, 7, 8, or 9; alternatively c+d=4, 5, 6, or 7;

$M_1$ and $M_2$ are independently selected from —C(O)O—, —OC(O)—, —SC(O)—, —C(O)S—, —N—HC(O)—, and —C(O)NH—, alternatively —C(O)O—, —OC(O)—, —SC(O)—, and —C(O)S—; alternatively, one of $M_1$ and $M_2$ is —C(O)O— or —C(O)S—, and the other is —C(O)O—, —C(O)S—, —C(O)

NH—, —OC(O)— or —SC(O)— alternatively —C(O)O—, —C(O)S—, —OC(O)— or —SC(O)—;

$R_1$ and $R_2$ are independently $C_{6-14}$ alkyl, $C_{6-14}$ alkenyl, or $C_{6-14}$ alkynyl, each of which is optionally substituted with 1, 2, 3, or 4 $R_{1s}$;

$R_{1s}$ is independently H, $C_{1-14}$ alkyl, $-L_c-OR_c$, or $-L_c-NR_cR'_c$, alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently C13 alkyl;

or, $R_4$ and $R_5$ are taken together with the carbon atom to which they are attached to form $C_{3-6}$ cycloalkylene or 3- to 6-membered heterocyclylene;

alternatively, a=2, 3, or 4;

b=4, 5, 6, 7, 8, or 9, alternatively b=5, 6, 7, or 8, alternatively b=5, 6, or 7;

c=2, 3, 4, 5, or 6;

d=0, 1, 2, 3, or 4;

c+d=5, 6, or 7;

$M_1$ and $M_2$ are independently —C(O)O—, —OC(O)—, —C(O)S— or —C(O)NH—, alternatively —C(O)O—, —OC(O)—, or —C(O)S—; alternatively, one of $M_1$ and $M_2$ is —C(O)O—, and the other is —C(O)O—, —(C(O)S—, —C(O)NH—, or —OC(O)—, alternatively —C(O)O—, —C(O)S—, or —OC(O)—;

$R_1$ and $R_2$ are independently $C_{7-12}$ alkyl, $C_{7-12}$ alkenyl, or $C_{7-12}$ alkynyl, alternatively $C_{8-12}$ alkyl, $C_{8-12}$ alkenyl, or $C_{8-12}$ alkynyl, each of which is optionally substituted with 1 $R_{1s}$;

$R_{1s}$ is independently H or $C_{1-10}$ alkyl;

$R_4$ and $R_5$ are independently $C_{1-3}$ alkyl;

or, $R_1$ and $R_5$ are taken together with the carbon atom to which they are attached to form $C_{3-6}$ cycloalkylene, alternatively $C_{3-5}$ cycloalkylene;

alternatively, a=2, 3, or 4;

b=4, 5, 6, 7, 8, or 9; alternatively b=5, 6, 7, or 8; alternatively b=5 or 7;

c=2, 3, 4, 5, or 6;

d=01, 2, 3, or 4;

c+d=5, 6, or 7; alternatively c+d==6;

one of $M_1$ and $M_2$ is —C(O)O—, and the other is —C(O)O—, —C(O)S—, —C(O)NH—, or —OC(O)—, alternatively —C(O)O—, —C(O)S—, or —OC(O)—;

$R_1$ and $R_2$ are independently selected from: $-(CH_2)_6CH_3$, $-(CH_2)_7CH_3$, $-(CH_2)_5CH_3$, $-(CH_2)_9CH_3$, $-(CH_2)_{10}CH_3$, $-(CH_2)_{11}CH_3$, $-CH_2-CH{=}CH-CH-(CH_2)_5CH_3$, $-CH_2-C{\equiv}C-(CH_2)_5CH_3$, $-(CH_2)_2-C{\equiv}C-(CH_2)_{10}CH_3$, $-(CH_2)_3-C{\equiv}C-(CH_2)_3CH_3$,

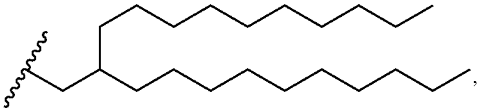
,
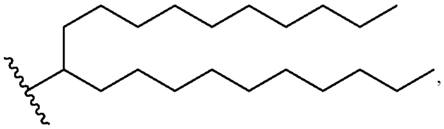
,
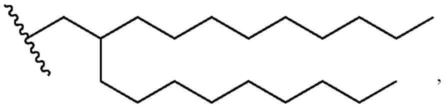
,

-continued

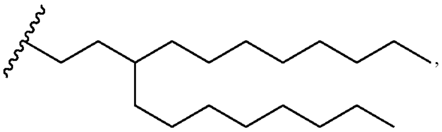
,
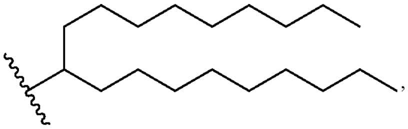
,
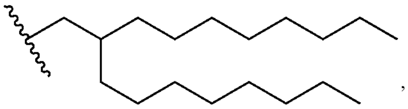
,
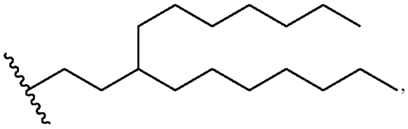
,
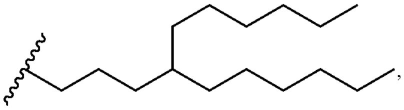
,
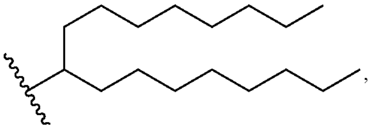
,
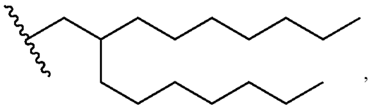 [SMILES: *CC(CCCCCCC)CCCCCCC]
,
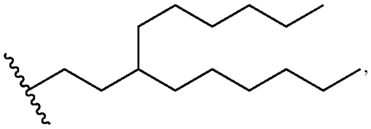
,
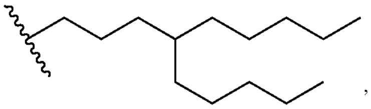
,
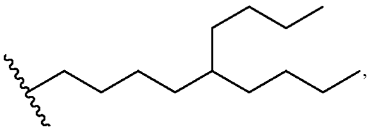
,
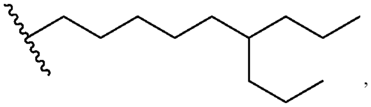
,
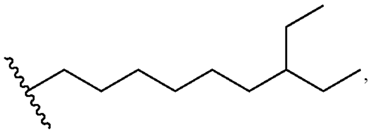
,
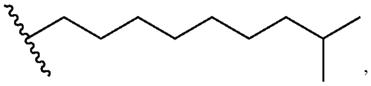
,
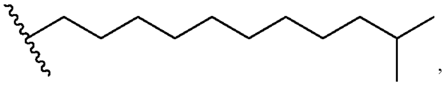
, -continued
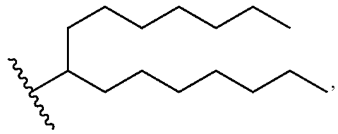
, and
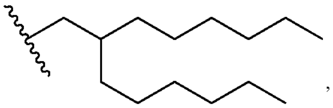
,
alternatively: $—(CH_2)_7CH_3$, $—(CH_2—)_8CH_3$, $—(CH_2)_9CH_3$, $—(CH_2)_{10}CH_3$, $—(CH_2)_{11}CH_3$, $—CH_2—CH{=}CH—(CH_2)CH_5$, $—CH_2—C{\equiv}C—(C_2)CH_3$, $—(CH_2)_2—C{\equiv}C—(CH_2)_4CH_3$, $—(CH_2)_3—C{\equiv}C—(C_2)_3CH_3$,
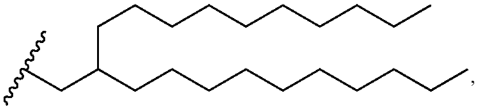
,
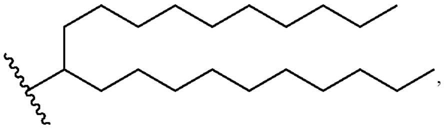
,
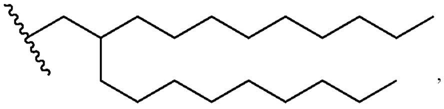
,
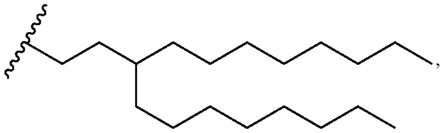
,
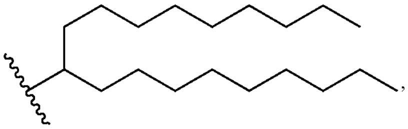
,
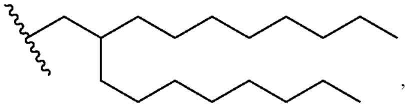
,
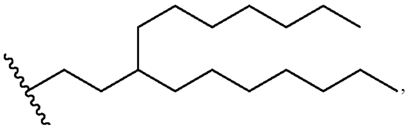
,
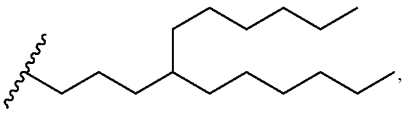
,
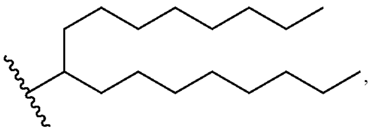
,
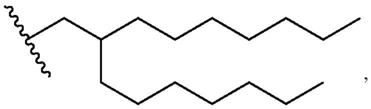 [SMILES: *CC(CCCCCCC)CCCCCCC]
,
-continued
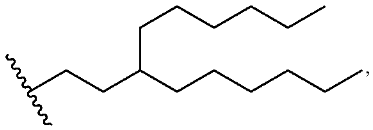
,
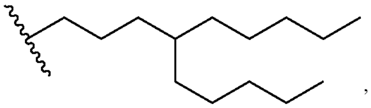
,
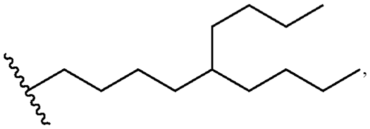
,
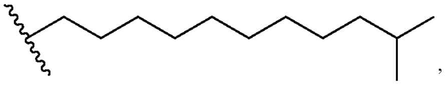
,
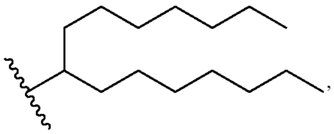
, and
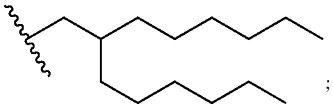
;
alternatively: $—(CH_2)_8CH_3—(CH_2)_9CH_3$, $—(CH_2)_{10}CH_3$, $—(CH_2)_{11}CH_3$, $—CH_2—CH{=}C—(CH_2)_5CH_3$, $—CH_2—C{\equiv}C—(CH_2)_5CH_3$, $—(CH_2)_2—C{\equiv}C—(CH_2)_4CH_3$, $—(CH_2)_3—C{\equiv}C—(CH_2)_3CH_3$,
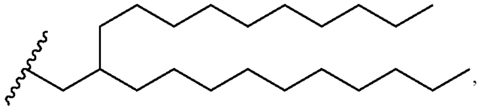
,
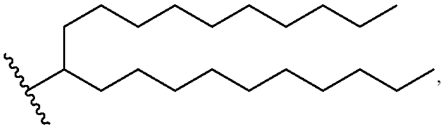
,
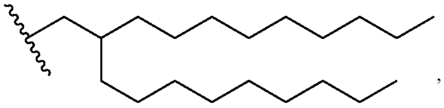
,
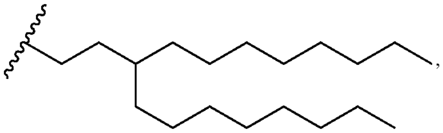
,
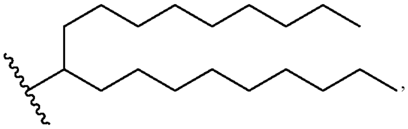
,
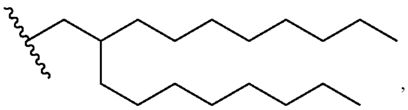
, -continued

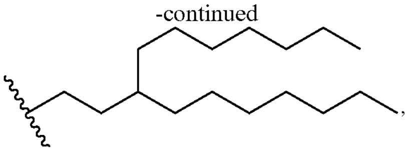
,

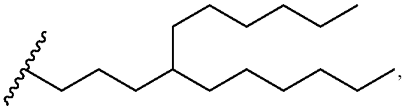
,

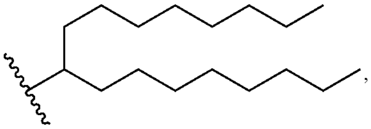
,

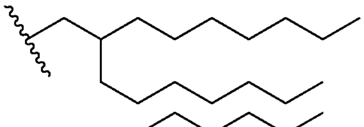
,

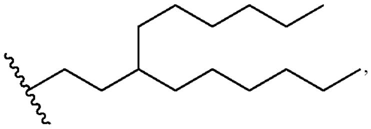
,

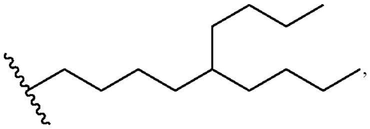
,

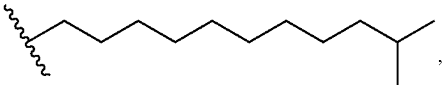
,

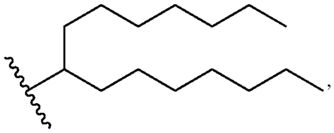
, and

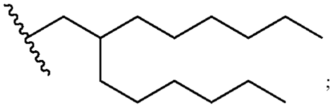
;

$R_4$ and $R_5$ are methyl;

or, $R_4$ and $R_5$ are taken together with the carbon atom to which they are attached to form cyclopropylene, cyclobutylene, cyclopentylene, or cyclohexylene, alternatively cyclopropylene or cyclopentylene, alternatively cyclopropylene;

alternatively, only one of $R_1$ and $R_2$ is substituted.

7. The compound of formula (II) of claim 6, or a pharmaceutically acceptable salt, isotopic variant, tautomer, or stereoisomer thereof, wherein a=2;

b=5;

c=5 or 6; alternatively c=6;

d=0 or 1; alternatively d=0, c+d=5 or 6, alternatively 6;

$M_1$ is —C(O)O—, and $M_2$ is —C(O)O— or —C(O)S—; alternatively $M_1$ and $M_2$ are —C(O)O—;

$R_1$ is $C_{7-12}$ alkyl, alternatively $C_{8-12}$ alkyl, alternatively $C_{8-9}$ alkyl, or alternatively $C_9$ alkyl, which is optionally substituted with 1 $R_{1s}$;

$R_{1s}$ is independently H or $C_{1-10}$ alkyl, alternatively H or $C_{1-9}$ alkyl, alternatively $C_{6-8}$ alkyl, alternatively $C_{7-8}$ alkyl;

$R_2$ is $C_{7-11}$ linear alkyl, alternatively $C_{10-11}$ linear alkyl, alternatively $C_{11}$ linear alkyl, which is optionally substituted with 1 $C_{1-3}$ alkyl, alternatively optionally substituted with 1 methyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, $R_1$ is

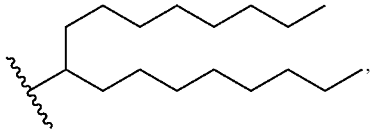
,

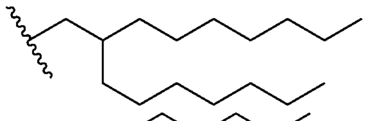
,

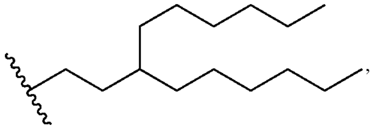
, or

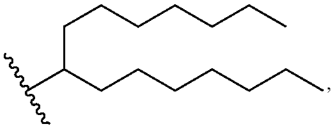
, alternatively

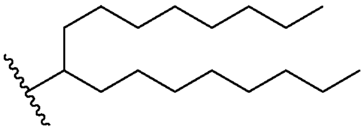
or

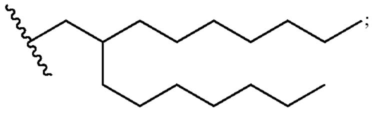
;

alternatively, $R_2$ is $-(CH_2)_9CH_3$, $-(CH_2)_{10}CH$, or

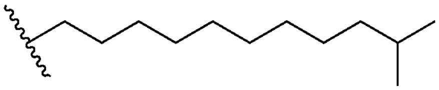
;

alternatively, a=2, 3, or 4; alternatively a=2;

b=5, 6, or 7: alternatively b=7;

c=2, 3, 4, 5, or 6; alternatively c=2, 3, or 4; alternatively c=2;

d=0, 1, 2, 3, or 4; alternatively d=2, 3, or 4; alternatively d=4;

c+d=5 or 6, alternatively 6;

$M_1$ and $M_2$ are —C(O)O—;

$R_1$ and $R_2$ are independently $C_{7-12}$ alkyl, alternatively $C_{8-12}$ alkyl, alternatively $C_{9-11}$ alkyl, alternatively $C_{9-10}$ alkyl, which is optionally substituted with 1 $R_{1s}$; and only one of $R_1$ and $R_2$ is substituted;

$R_{1s}$ is independently H or $C_{1-10}$ alkyl, alternatively $C_{6-10}$ alkyl, alternatively $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring;

alternatively, $R_1$ is $C_{8-12}$ linear alkyl, alternatively $C_{9-11}$ linear alkyl, alternatively $C_{9-10}$ linear alkyl;

$R_1$ is $C_{7-12}$ alkyl, alternatively $C_{8-12}$ alkyl, alternatively $C_{9-11}$ alkyl, alternatively $C_{9-10}$ alkyl, which is optionally substituted with 1 $R_{1s}$; when $R_2$ is $C_{10}$ linear alkyl, $R_{1s}$ is $C_{9-10}$ alkyl, alternatively $C_9$ alkyl;

alternatively, $R_2$ is

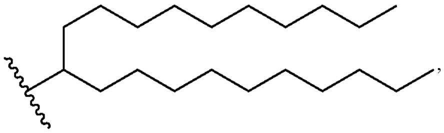,

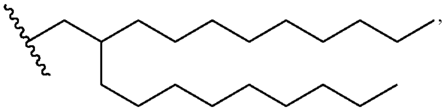,

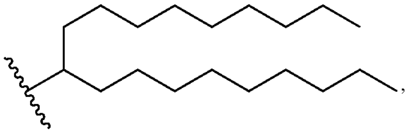,

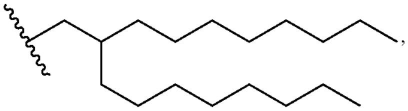,

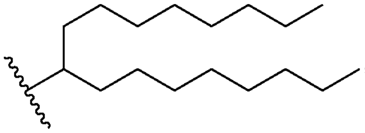,

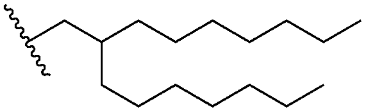, or

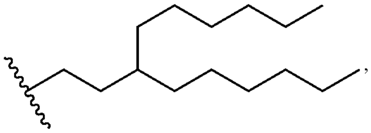, alternatively

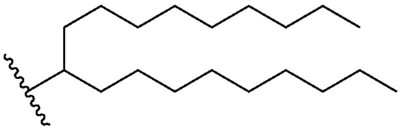,

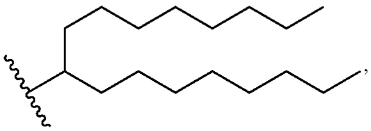, or

-continued

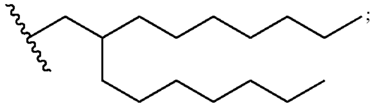 [SMILES: *CC(CCCCCCC)CCCCCCC];

alternatively, a=2, 3, or 4;

b=6;

c=4, 5, or 6; alternatively c=5 or 6; alternatively c=5;

d=1 or 2; alternatively d=1;

c+d=6, 7, or 8; alternatively 6 or 7; alternatively 6;

$M_1$ is —OC(O)—; $M_2$ is —C(O)O—;

$R_1$ is $C_{7-12}$ linear alkyl, alternatively $C_{8-11}$ linear alkyl, alternatively $C_{9-11}$ linear alkyl;

$R_2$ is $C_{7-12}$ alkyl, alternatively $C_{8-12}$ alkyl, alternatively $C_{9-12}$ alkyl, which is optionally substituted with 1 $R_{1s}$;

$R_{1s}$ is independently $C_{7-11}$ alkyl, alternatively $C_{7-10}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

provided that, when c=4, a=2 or 3;

alternatively, $R_2$ is

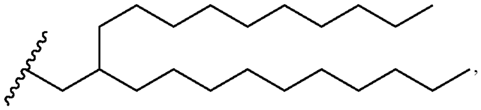,

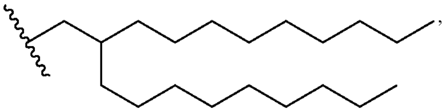,

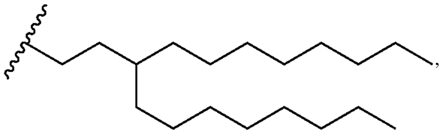,

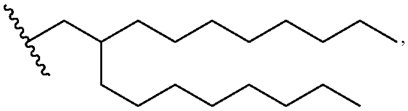,

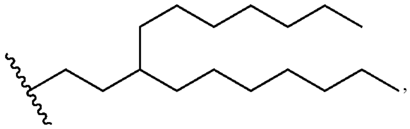, or

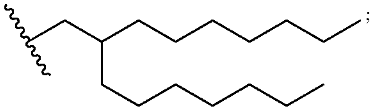;

alternatively, a=2 or 4; b=6; c=5 or 6, alternatively c=5; d=1;

$R_1$ is $C_{8-9}$ linear alkyl, alternatively $C_9$ linear alkyl;

$R_2$ is $C_{9-10}$ alkyl, alternatively $C_{10}$ alkyl, which is optionally substituted with 1 $R_{1s}$;

$R_{1s}$ is independently $C_{7-8}$ alkyl;

$R_4$ and $R^5$ are independently $C_{1-3}$ alkyl, alternatively methyl;

alternatively, a=2, 3 or 4, alternatively 2 or 4; b==6; c=5; d=2;

$R_1$ is $C_{9-10}$ linear alkyl, alternatively $C_9$ linear alkyl;

$R_2$ is $C_{9-11}$ alkyl, which is optionally substituted with 1 Rai;

$R_{1s}$ is independently $C_{7-9}$ alkyl, $R_4$ and $R_5$ are independently $C_{1-3}$ alkyl, alternatively methyl;

alternatively, a=2, 3 or 4; alternatively a=2 or 4;

b=7;

c=5 or 6; alternatively c=5;

d=0 or 1; alternatively d::=1;

c+d=5 or 6, alternatively 6;

$M_1$ is —OC(O)—; $M_2$ is —C(O)O—;

$R_1$ is $C_{8-11}$ linear alkyl, alternatively $C_{9-10}$ linear alkyl, which is optionally substituted with 1 $C_{1-9}$ alkyl (alternatively $C_{6-9}$ alkyl, alternatively $C_{6-7}$ alkyl);

$R_2$ is $C_{7-12}$ alkyl, alternatively $C_{8-12}$ alkyl, alternatively ($C_{9-10}$ alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, $R_1$ is $—(CH_2)_8CH_3$, $—(CH_2)_9CH_3$,

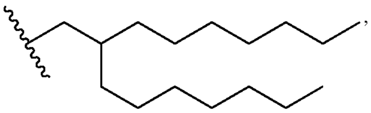
, or

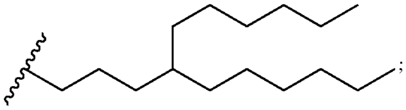
;

$R_2$ is

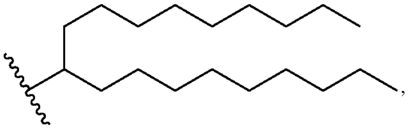
,

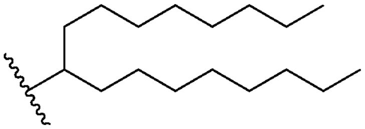
, or

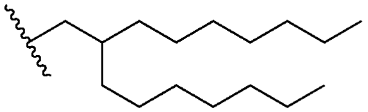
;

alternatively, when a=4, $R_1$ is $C_{9-10}$ linear alkyl;

$R_2$ is $C_{9-10}$ alkyl, which is optionally substituted with 1 $R_{1s}$;

$R_{1s}$ is $C_{8-9}$ alkyl;

$R_4$ and $R_5$ are not taken together with the carbon atom to which they are attached to form a ring;

alternatively, when a=2, $R_1$ is $C_{10}$ linear alkyl;

alternatively $R_{1s}$ is $C_{8-9}$ alkyl, alternatively $C_9$ alkyl;

alternatively, a=2, 3, or 4; alternatively a=2 or 4;

b=7;

c=4;

d=2;

$M_1$ is —OC(O)—; $M_2$ is —C(O)O—;

$R_1$ is $C_{8-11}$ linear alkyl, alternatively $C_{9-10}$ linear alkyl;

$R_2$ is $C_{8-11}$ alkyl, alternatively $C_{9-10}$ alkyl, which is optionally substituted with 1 $R_{1s}$;

$R_{1s}$ is independently $C_{7-9}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring;

alternatively, $R_2$ is

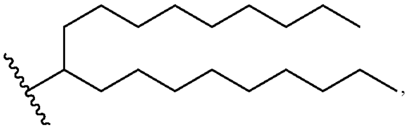
,

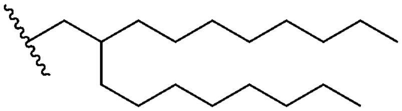
, or

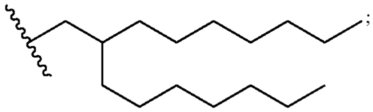
;

alternatively, a=2, 3, or 4; alternatively a=2;

b=8;

c=5;

d=1;

$M_1$ is —OC(O)—; $M_2$ is —C(O)O—;

$R_1$ is $C_{8-12}$ linear alkyl, alternatively $C_{9-11}$ linear alkyl, alternatively $C_{10-11}$ linear alkyl;

$R_2$ is $C_{8-11}$ alkyl, alternatively $C_{9-10}$ alkyl, which is optionally substituted with 1 $R_{1s}$;

$R_{1s}$ is independently $C_{7-9}$ alkyl, alternatively $C_{7-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene, alternatively not to form a ring;

alternatively, $R_2$ is

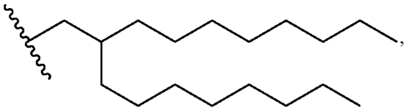
, or

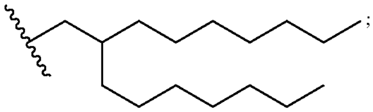
;

alternatively, a=2;

b=6, 7, or 8, alternatively b=7;

c=5;

d=1;

$M_1$ is —OC(O)—; $M_2$ is —C(O)O—;

$R_1$ is $C_{8-11}$ linear alkyl, alternatively $C_{9-10}$ linear alkyl, alternatively $C_9$ linear alkyl;

$R_2$ is $C_{8-11}$ alkyl, alternatively $C_{9-10}$ alkyl, alternatively $C_9$ alkyl, which is optionally substituted with 1 $R_{1s}$;

$R_{1s}$ is independently $C_7$ alkyl;

$R_4$ and $R_5$ are independently $C_{1-3}$ alkyl, alternatively methyl;

alternatively, $R_2$ is

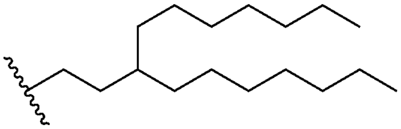

or

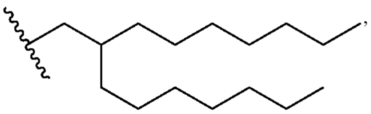

, alternatively

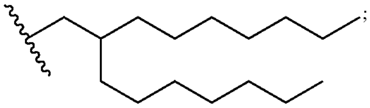

;

alternatively, a=2 or 3, alternatively a=2;

b=7;

c=3;

d=3;

$M_1$ is —OC(O)—; $M_2$ is —C(O)O—;

$R_1$ is $C_{8-11}$ linear alkyl, alternatively $C_{9-10}$ linear alkyl, alternatively $C_9$ linear alkyl;

$R_2$ is $C_{8-11}$ alkyl, alternatively $C_{9-10}$ alkyl, alternatively $C_9$ alkyl, which is optionally substituted with 1 $R_1$, $R_{1s}$ is independently $C_{6-7}$ alkyl, alternatively $C_7$ alkyl;

$R_4$ and $R_5$ are independently $C_{1-3}$ alkyl, alternatively methyl;

alternatively, $R_2$ is

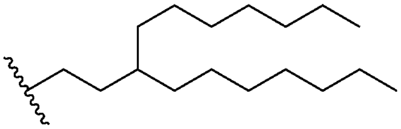

or

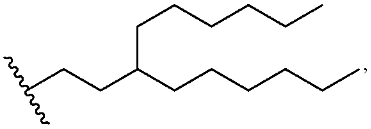

, alternatively

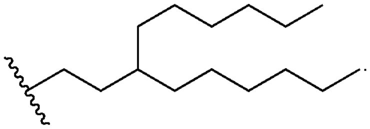

.

8. The compound of formula (I) of claim 2, or a pharmaceutically acceptable salt, isotopic variant, tautomer, or stereoisomer thereof,

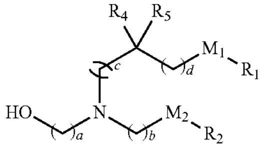

(II)

wherein, a=2, 3, 4, 5, or 6;

b=4, 5, 6, 7, 8, 9 or 10;

c=1, 2, 3, 4, 5, or 6;

d=0, 1, 2, 3, or 4, c+d=3, 4, 5, 6, 7, 8, or 9, alternatively c+d=4, 5, or 6;

one of $M_1$ and $M_2$ is —OC(O)O—, and the other is —C(O)O—, —OC(O)—, —SC(O)—, or —C(O)S—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, -$L_c$-$OR_c$, or -$L_e$-$NR_cR'_c$ alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene or 3- to 6-membered heterocyclylene;

alternatively, a=2, 3, or 4;

b=4, 5, 6, or 7, alternatively b=5 or 6, alternatively b=6;

c=2, 3, 4, 5, or 6; alternatively c=2, 4, 5, or 6;

d=0, 1, 2, 3, or 4; alternatively d=0, 1, 2, or 4;

c+d=5 or 6, alternatively c+d=6;

one of $M_1$ and $M_2$ is —OC(O)O—, and the other is —C(O)O— or —OC(O)—;

$R_1$ and $R_2$ are independently $C_{7-12}$ alkyl, alternatively $C_{9-11}$ alkyl, which is optionally substituted with 1 $R_{1s}$;

$R_{1s}$ is independently H or $C_{1-10}$ alkyl; alternatively H or $C_{4-10}$ alkyl;

$R_4$ and $R_5$ are independently $C_{1-3}$ alkyl;

or, $R_4$ and $R_5$ are taken together with the carbon atom to which they are attached to form $C_{3-6}$ cycloalkylene, alternatively $C_{3-4}$ cycloalkylene;

alternatively, a=2, 3, or 4;

b=4, 5, 6, or 7, alternatively b=5 or 6, alternatively b=6;

c=2, 3, 4, 5, or 6; alternatively c=2, 4, 5, or 6;

d=0, 1, 2, 3, or 4; alternatively d=0, 1, 2, or 4;

c+d=5 or 6, alternatively c+d=6;

one of $M_1$ and $M_2$ is —OC(O)O—, and the other is —C(O)O— or —OC(O)—;

$R_1$ and $R_2$ are independently selected from $—(CH_2)_8CH_3$, $—(CH_2)_9CH_3$, $—(CH_2)_{10}CH_3$,

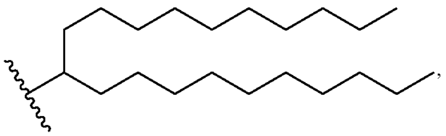

,

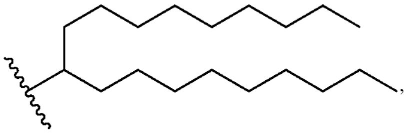

,

-continued

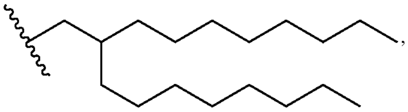
,
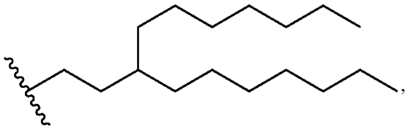
,
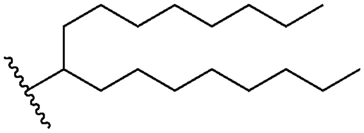
,
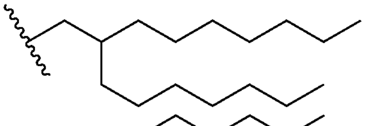
,
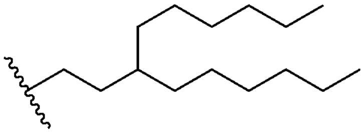
,
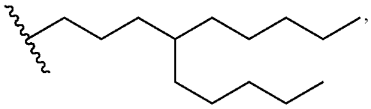
, and
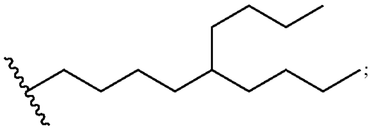
;

$R_4$ and $R^5$ are methyl;

or, $R_4$ and $R_5$ are taken together with the carbon atom to which they are attached to form cyclopropylene;

alternatively, only one of $R_1$ and $R_2$ is substituted;

alternatively, $M_1$ is —C(O)O— or —OC(O)—, alternatively —C(O)O—, and $M_2$ is —OC(O)O—;

alternatively, $M_1$ is —OC(O)O—, and $M_2$ is —OC(O)—.

9. The compound of formula (I) of claim 8, or a pharmaceutically acceptable salt, isotopic variant, tautomer, or stereoisomer thereof, wherein, a=2;

b=5 or 6, alternatively b=6;

c=4, 5, or 6; alternatively c=4 or 6; alternatively c=6;

d=0, 1, or 2; alternatively d=0 or 2;

c+d=6;

$M_1$ is —C(O)O—, and $M_2$ is —OC(O)O—;

$R_1$ is $C_{8-11}$ alkyl, alternatively $C_{9-10}$, alkyl, alternatively $C_9$ alkyl, which is optionally substituted with 1 $R_{1s}$;

$R_{1s}$ is $C_{7-9}$ alkyl, alternatively $C_7$ alkyl;

$R_2$ is $C_{8-11}$ linear alkyl, alternatively $C_{9-10}$ linear alkyl, alternatively $C_9$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring;

alternatively, $R_1$ is

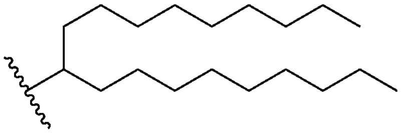
,
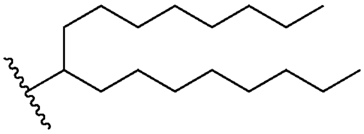
, or
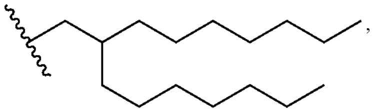
, alternatively

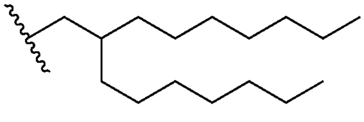
;

alternatively, a=2;

b=6;

c=4, 5, or 6; alternatively c=5 or 6; alternatively c=6;

d=0, 1, or 2; alternatively d=0 or 1;

c+d=6;

$M_1$ is —C(O)O—, and $M_2$ is —OC(O)O—;

$R_1$ is $C_{8-10}$ linear alkyl, alternatively $C_{9-10}$ linear alkyl, alternatively $C_9$ linear alkyl;

$R_2$ is $C_{8-10}$ alkyl, alternatively $C_{9-10}$ alkyl, alternatively $C_9$ alkyl, which is optionally substituted with 1 $R_{1s}$, $R_{1s}$ is $C_{6-7}$ alkyl, alternatively $C_7$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring;

alternatively, $R_2$ is

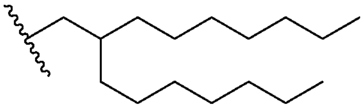
or
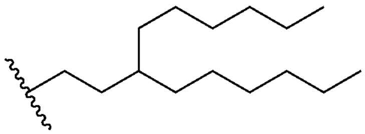
, alternatively

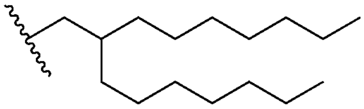
;

alternatively, a=2;

b=5 or 6; alternatively b=6;

c=5;

d=1;

$M_1$ is —OC(O)—, and $M_2$ is —OC(O)O—;

$R_1$ is $C_{8-10}$ alkyl, alternatively $C_{9-10}$ alkyl, alternatively $C_9$ alkyl, which is optionally substituted with 1 $R_{1s}$;

$R_{1s}$ is $C_{6-8}$ alkyl, alternatively $C_{6-7}$ alkyl;

$R_2$ is $C_{8-12}$ linear alkyl, alternatively $C_{10-11}$ linear alkyl;

$R_4$ and $R^5$ are independently C1-alkyl, alternatively methyl;

or, $R_4$ and $R_5$ are taken together with the carbon atom to which they are attached to form $C_{3-4}$ cycloalkylene, alternatively not to form a ring;

alternatively, $R_1$ is

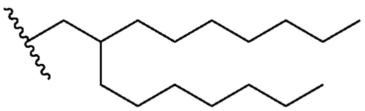

or

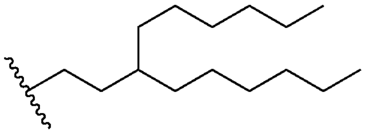

, alternatively

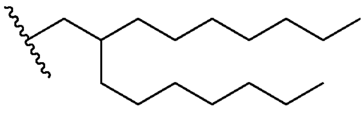

;

alternatively, a=−2, 3 or 4; alternatively a=2;

b=5, 6, 7, or 8; alternatively b=6 or 7; alternatively b=7;

c=4, 5, or 6; alternatively c=4;

d=0, 1, or 2; alternatively d=1;

c+d=5 or 6; alternatively c+d=5;

$M_1$ is —OC(O)O—, $M_2$ is —OC(O)—;

$R_1$ is $C_{8-12}$ alkyl, alternatively $C_{8-10}$ alkyl, which is optionally substituted with 1 $R_{1s}$;

$R_{1s}$ is $C_{6-10}$ alkyl, alternatively $C_{6-8}$ alkyl;

$R_2$ is $C_{8-12}$ linear alkyl, alternatively $C_{8-10}$ linear alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively not to form a ring;

alternatively, $R_1$ is

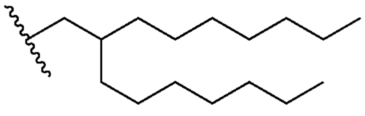

.

10. The compound of formula (III) of claim 2, or a pharmaceutically acceptable salt, isotopic variant, tautomer, or stereoisomer thereof,

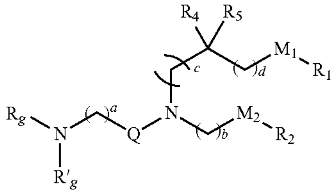

(III)

wherein,

Q is —SC(O)— or —OC(O)—;

$R_g$ and $R'_g$ are independently $C_{1-6}$ alkyl;

a=2, 3, 4, 5, or 6; alternatively a=2, 3, or 4;

b=4, 5, 6, 7, 8, or 9; alternatively b=5, 6, or 7;

c=2, 3, 4, 5, or 6;

d=0, 1, 2, 3, or 4;

c+d=5 or 6;

$M_1$ and $M_2$ are independently selected from —C(O)O—, —C(O)S—, —OC(C)—, —SC(O)—, and —OC(O)O—;

$R_1$ and $R_2$ are independently $C_{6-14}$ alkyl, which is optionally substituted with 1, 2, 3, or 4 $R_{1s}$;

$R_{1s}$ is independently H, $C_{1-14}$ alkyl, -$L_c$-$OR_c$, or -$L_c$-$NR_cR'_c$; alternatively H or $C_{1-14}$ alkyl;

$L_c$ is independently a chemical bond or $C_{1-14}$ alkylene;

$R_c$ and $R'_c$ are independently H or $C_{1-14}$ alkyl;

$R_4$ and $R_5$ are independently $C_{1-3}$ alkyl, or, $R_4$ and $R_5$ are taken together with the carbon atom to which they are attached to form $C_{3-6}$ cycloalkylene or 3- to 6-membered heterocyclylene;

alternatively,

Q is —SC(O)— or —OC(O)—;

$R_g$ and $R'_g$ are independently $C_{1-3}$ alkyl;

a=3 or 4;

b=6 or 7;

c=2, 3, 4, or 5; alternatively 2 or 5;

d=1, 2, 3, or 4; alternatively 1 or 4;

c+d=5 or 6;

$M_y$ and $M_2$ are independently selected from —C(O)O—, —OC(O)—, and —OC(O)O—; alternatively, $M_1$ and $M_2$ are not simultaneously —OC(O)O—;

$R_1$ and $R_2$ are independently $C_{7-12}$ alkyl, alternatively $C_{8-10}$ alkyl, which is optionally substituted with 1 $R_{1s}$;

$R_{1s}$ is independently H or $C_{1-10}$ alkyl; alternatively H or $C_{1-9}$ alkyl;

$R_4$ and $R^5$ are independently $C_{1-3}$ alkyl, or, $R_4$ and $R_5$ are taken together with the carbon atom to which they are attached to form $C_6$ cycloalkylene;

alternatively,

Q is —SC(O)—;

$R_g$ and $R'_g$ are methyl;

a=3 or 4;

b=6 or 7;

c=2, 4, or 5; alternatively 2 or 5;

d=1, 2, or 4; alternatively 1 or 4;

c+d=6;

$M_1$ and $M_2$ are independently selected from —C(O)O—, —OC(O)—, and —OC(O)O—; alternatively, $M_1$ and $M_2$ are not simultaneously —OC(O)O—;

$R_1$ and $R_2$ are independently $—(CH_2)_7CH_3$, $—(CH_2)_8CH—$, $—(CH_2)_9CH_3$,

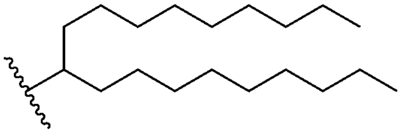
,
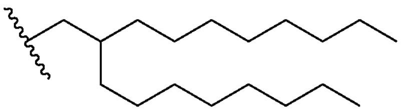
,
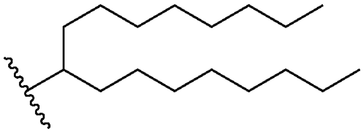
, or
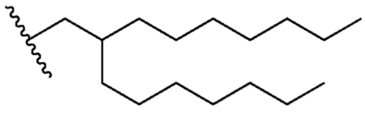
;

$R_4$ and $R_5$ are methyl;

or, $R_4$ and $R_5$ are taken together with the carbon atom to which they are attached to form cyclopropylene, alternatively not to form a ring;

alternatively, only one of $R_1$ and $R_2$ is substituted; alternatively, $R_1$ is unsubstituted, and $R_2$ is substituted.

11. The compound of formula (II) of claim 2, or a pharmaceutically acceptable salt, isotopic variant, tautomer, or stereoisomer thereof, (II)

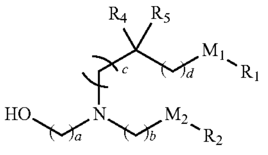

wherein, M, and $M_2$ are independently —C(O)O— or —C(O)S—, alternatively —C(O)O—;

the other groups are as defined in claim 2.

12. The compound of formula (I) of claim 2, or a pharmaceutically acceptable salt, isotopic variant, tautomer, or stereoisomer thereof, (II)

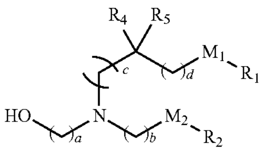

wherein, one of $M_1$ and $M_2$ is —C(O)O— or —C(O)S—, alternatively —C(O)O—, and the other is —OC(O)— or —SC(O)—, alternatively —OC(O)—;

the other groups are as defined in claim 2;

alternatively, $R_{1s}$ is independently H or $C_{1-6}$ alkyl; alternatively H or $C_{1-4}$ alkyl;

alternatively, $R_{1s}$ is independently $C_{1-8}$ alkyl, alternatively $C_{4-8}$ alkyl, alternatively $C_{6-8}$ alkyl, alternatively $C_{7-8}$ alkyl, alternatively $C_8$ alkyl;

alternatively $M_1$ is —OC(O)— or —SC(O)—, alternatively —OC(O)—; and $M_2$ is —C(O)O—Or —C(O)S—, alternatively —C(O)O—.

13. A compound of formula (II) or formula (III), or a pharmaceutically acceptable salt, isotopic variant, tautomer, or stereoisomer thereof:

(II)

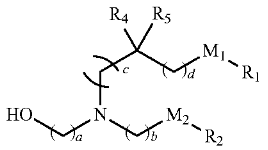

or (III)

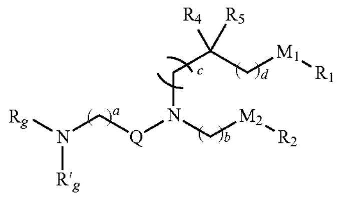

wherein

Q is a chemical bond, —SC(O)— or —OC(O)—;

$R_g$ and $R'_g$ are independently $C_{1-6}$ alkyl;

a=2, 3, 4, 5, or 6;

b=6 or 7;

c=5 or 6;

d=0 or 1;

c+d=5 or 6;

$M_1$ is —OC(O)— or —SC(O)—; and $M_2$ is —C(O)O— or —C(O)S—;

$R_1$ and $R_2$ are independently $C_{7-12}$ alkyl, alternatively $C_{8-12}$ alkyl, which is optionally substituted with 1 $R_{1s}$;

$R_{1s}$ is independently H or $C_{1-10}$ alkyl;

$R_4$ and $R_5$ are independently $C_{1-3}$ alkyl, or, $R_4$ and $R_5$ are taken together with the carbon atom to which they are attached to form $C_{3-6}$ cycloalkylene;

alternatively, only one of $R_1$ and $R_2$ is substituted; alternatively, $R_1$ is unsubstituted, and $R_2$ is substituted;

alternatively,

Q is —SC(O)— or —OC(O)—, alternatively —SC(O)—;

$R_g$ and $R'_g$ are independently $C_{1-3}$ alkyl, alternatively methyl;

a=2, 3, or 4; alternatively a=2 or 4; alternatively a=4;

b=6 or 7; alternatively b=7;

c=5 or 6; alternatively c=5;

d=0 or 1; alternatively d=1;

c+d=5 or 6; alternatively c+d=6;

$M_1$ is —OC(O)—; $M_2$ is —C(O)O—;

$R_1$ is $C_{7-11}$ linear alkyl, alternatively $C_{9-10}$ linear alkyl, alternatively $C_9$ linear alkyl;

$R_2$ is $C_{7-12}$ alkyl, alternatively $C_{8-12}$ alkyl, alternatively $C_{9-10}$ alkyl, alternatively $C_9$ alkyl, which is optionally substituted with 1 $R_{1s}$;

$R_{1s}$ is independently $C_{1-9}$ alkyl, alternatively $C_{1-8}$ alkyl, alternatively $C_{4-9}$ alkyl, alternatively $C_{4-8}$ alkyl;

$R_4$ and $R_5$ are independently $C_{1-3}$ alkyl, alternatively methyl;

or, $R_4$ and $R_5$ are taken together with the carbon atom to which they are attached to form $C_{3-4}$ cycloalkylene, alternatively cyclopropylene;

alternatively, the substitution site of $R_{1s}$ on $R_1$ or $R_2$ is separated from $M_1$ or $M_2$ by 0-10 carbon atoms, alternatively 0-6 carbon atoms, alternatively 0-4 carbon atoms, alternatively 0-2 carbon atoms, alternatively 0 carbon atom;

alternatively, $R_1$ is not substituted with $R_{1s}$, and the substitution site of $R_{1s}$ on $R_2$ is separated from $M_2$ by 0-10 carbon atoms, alternatively 1-10 carbon atoms, alternatively 1-6 carbon atoms, alternatively 1-4 carbon atoms, alternatively 1-2 carbon atoms; alternatively 2-10 carbon atoms, alternatively 2-6 carbon atoms, alternatively 2-4 carbon atoms;

alternatively, $R_2$ is

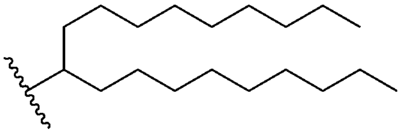
,
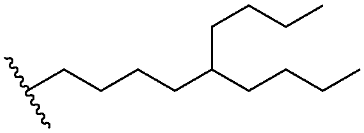
,
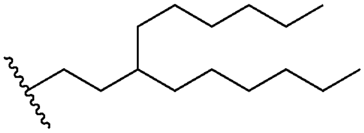
,
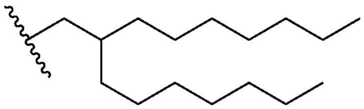
, or
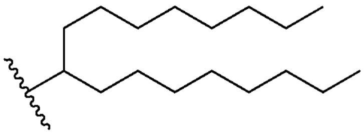
, alternatively

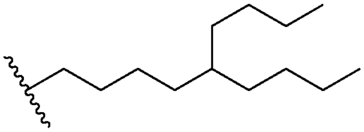
,
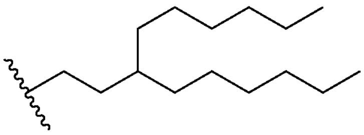
,
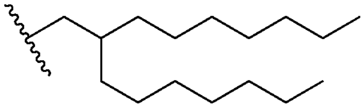
, or
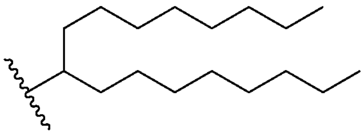
, alternatively

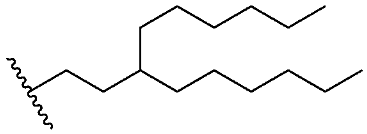
,
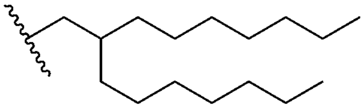
, or
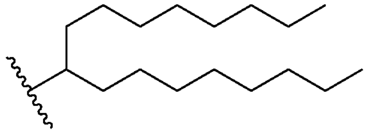
, alternatively

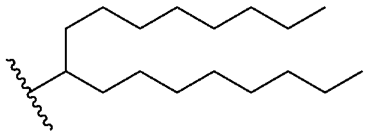
;

alternatively, $R_4$ and $R_5$ are not taken together with the carbon atom to which they are attached to form a ring.

14. A pharmaceutical composition, comprising the compound of claim 1, or a pharmaceutically acceptable salt, isotopic variant, tautomer, or stereoisomer thereof and a pharmaceutically acceptable excipient(s).

15. A nanoparticle composition, comprising a lipid component, and optionally a load, wherein the lipid component comprises the compound of claim 1, or a pharmaceutically acceptable salt, isotopic variant, tautomer, or stereoisomer thereof, and the load is selected from one or more of therapeutic, prophylactic, and diagnostic agents.

16. The nanoparticle composition of claim 15, wherein the therapeutic, prophylactic, or diagnostic agents is a nucleic acid;

alternatively, the nucleic acid is selected from one or more of ASO, RNA, and DNA; alternatively, the RNA is selected from one or more of small interfering RNA (siRNA), short hairpin RNA (shRNA), antisense RNA (aRNA), messenger RNA (mRNA), long non-coding RNA (lncRNA), microRNA (miRNA), small activating RNA (saRNA), multimeric coding nucleic acid (MCNA), polymeric coding nucleic acid (PCNA) guide RNA (gRNA), CRISPRRNA (crRNA), and nucleases, alternatively mRNA, more alternatively modified mRNA.

17. A method for delivering a load in a subject, comprising administering to the subject the nanoparticle composition of claim 15;

wherein the load is selected from one or more of therapeutic, prophylactic, and diagnostic agents.

18. A method for preparing a compound of formula (II), comprising:

reacting a compound of formula (IIA) with a compound of formula (IIB) to give the compound of formula (II),

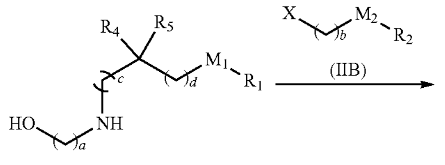

(IIA)

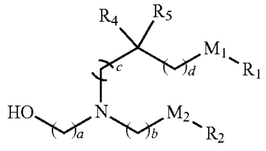
(II)

wherein X is halogen, and the other variables are as defined in claim 2;

or, reacting a compound of formula (TIC) with a compound of formula (IID), to give the compound of formula (II),

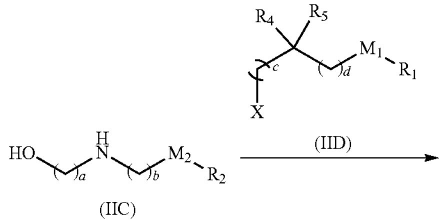

(IIC)

-continued

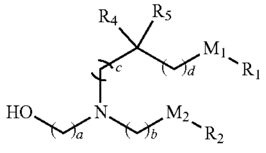
(II)

wherein X is halogen, and the other variables are as defined in claim 2.

19. The compound of formula (I) of claim 1, or a pharmaceutically acceptable salt, isotopic variant, tautomer, or stereoisomer thereof, wherein, $G_1$ is $C_{2-6}$ linear alkylene.

20. The compound of formula (I) of claim 1, or a pharmaceutically acceptable salt, isotopic variant, tautomer, or stereoisomer thereof, wherein, $M_1$ and $M_2$ are independently selected from —C(O)O—, —O(O)—, —OC(O)O—, and —S—S—; alternatively, $M_1$ and $M_2$ are independently selected from —C(O)O—, —OC(O)—, and —OC(O)O—; alternatively, $M_1$ is —OC(O)—, and $M_2$ is —C(O)O—.

21. The compound of formula (I) of claim 1, or a pharmaceutically acceptable salt, isotopic variant, tautomer, or stereoisomer thereof, wherein, $R_4$ and $R_5$ are taken together with the carbon atom to which they are attached to form cyclopropylene.

22. The compound of formula (I) of claim 1, or a pharmaceutically acceptable salt, isotopic variant, tautomer, or stereoisomer thereof, wherein, Q is selected from a chemical bond, —SC(O)— and —OC(O)—.

23. The compound of formula (I) of claim 1, or a pharmaceutically acceptable salt, isotopic variant, tautomer, or stereoisomer thereof, wherein, the compound is selected from the following:

1a

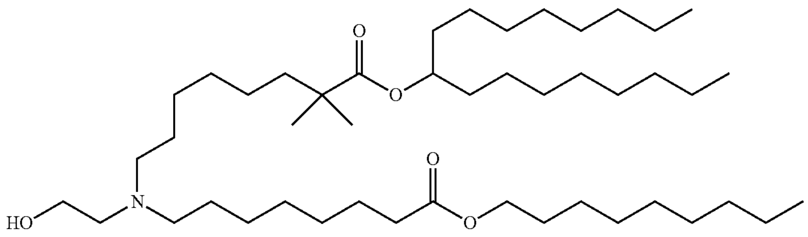

3a

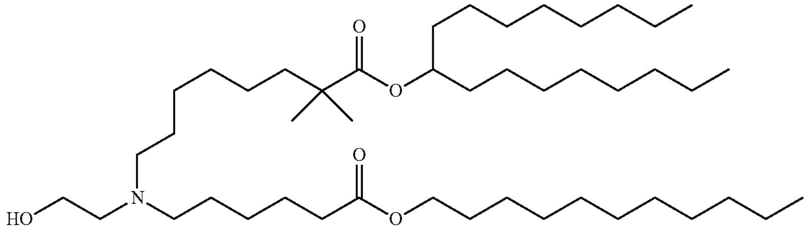

8a

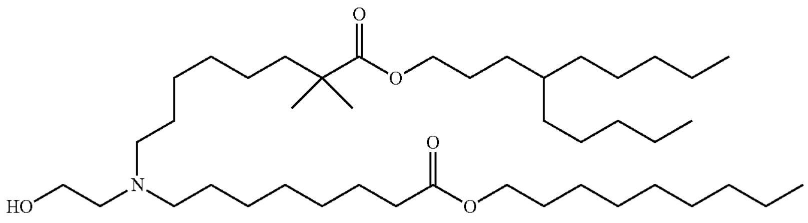

-continued
14a
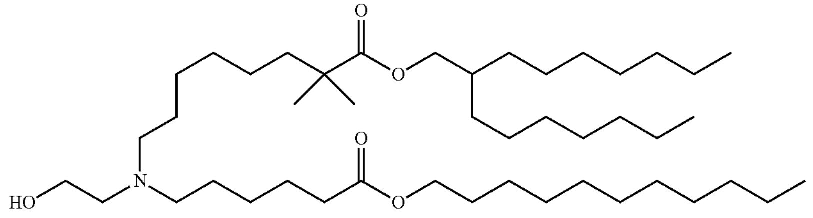
20a
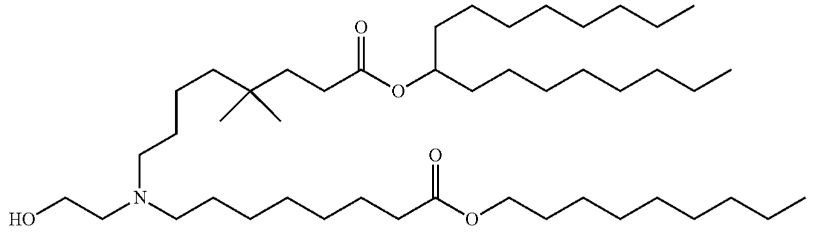
25a
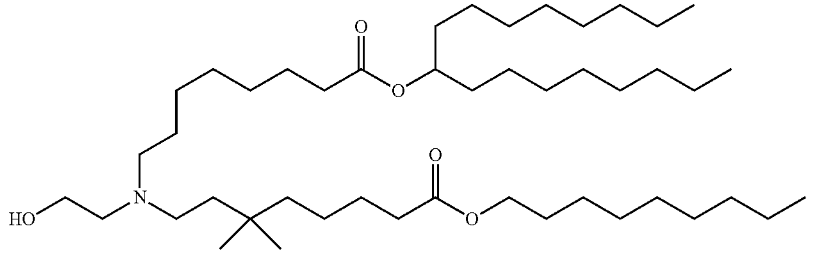
26a
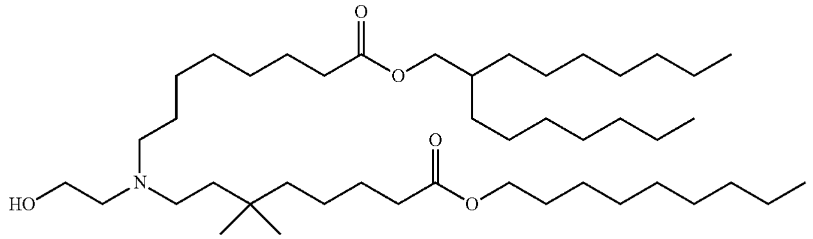
32a
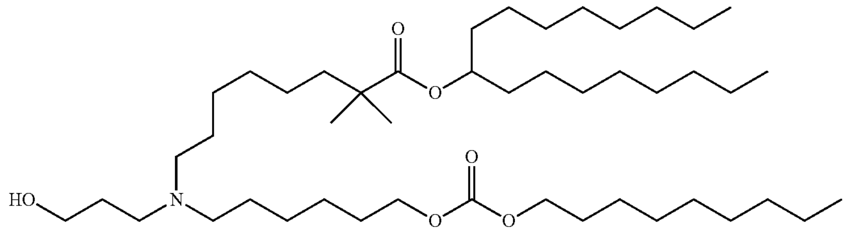
33a
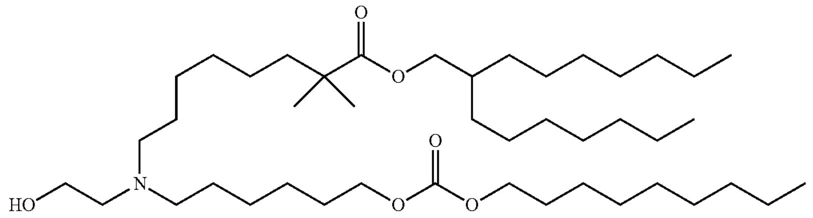

-continued
40a
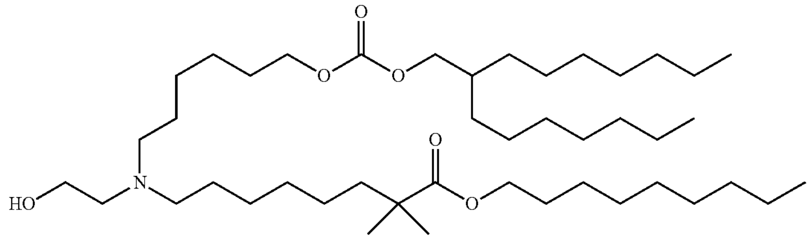
41a
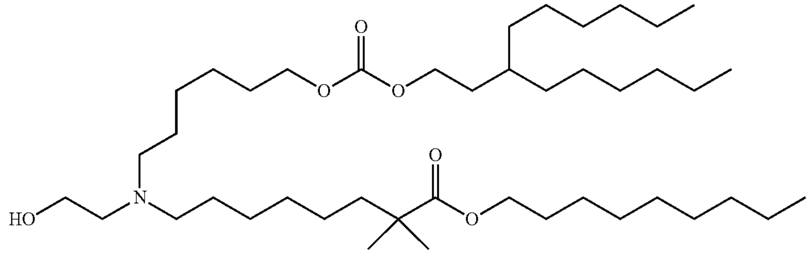
44a
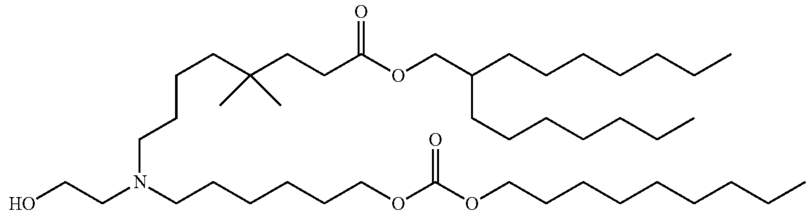
45a
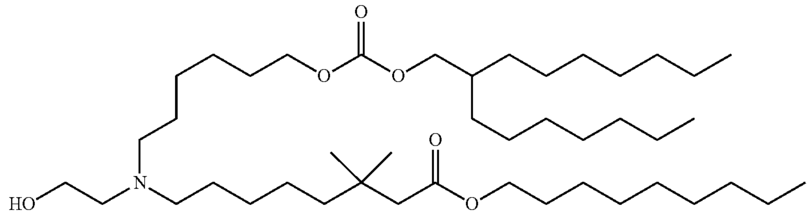
63a
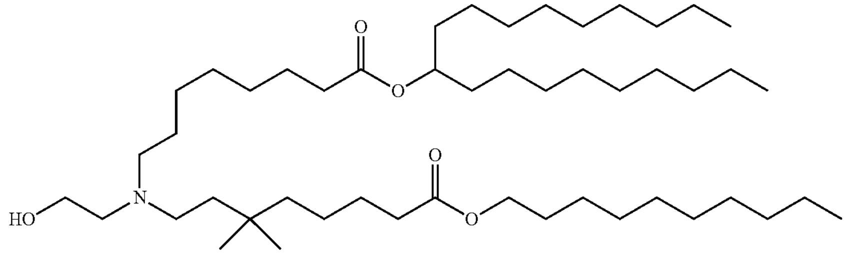
1b
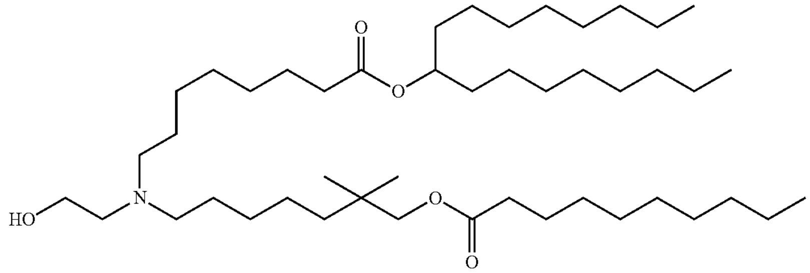

-continued
3b
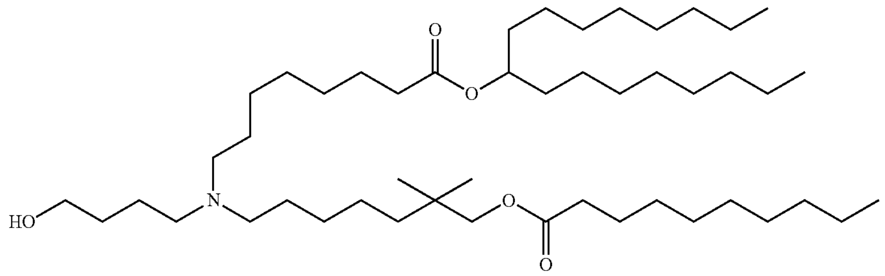
5b
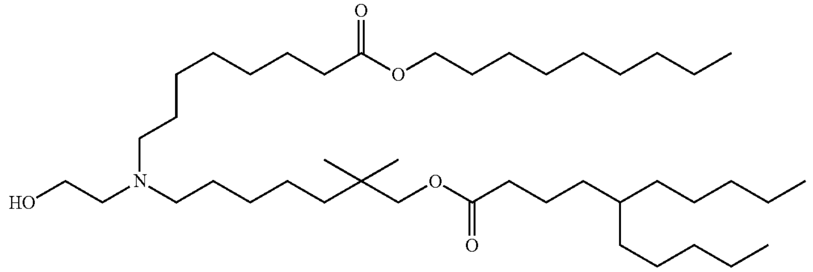
10b
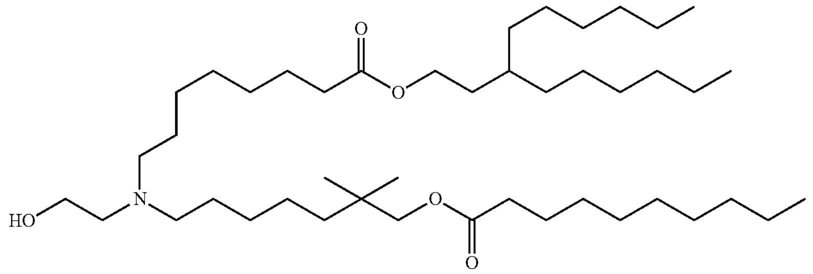
11b
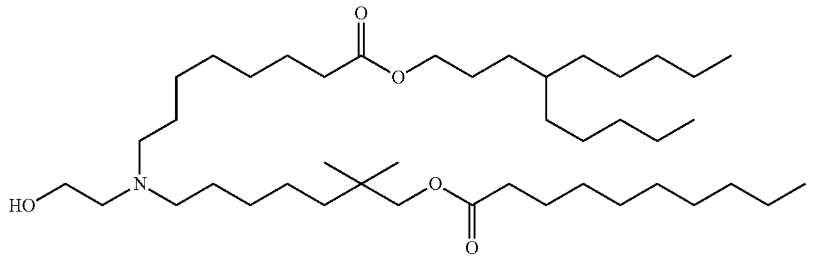
13b
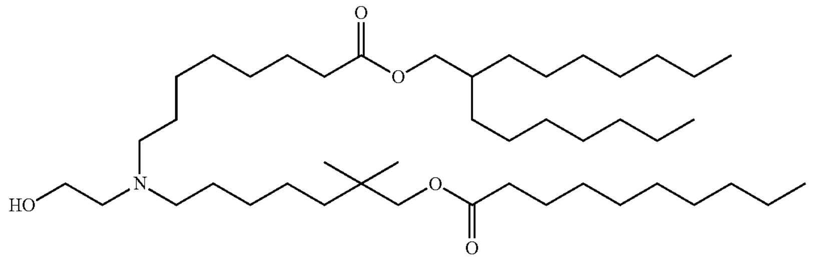
14b
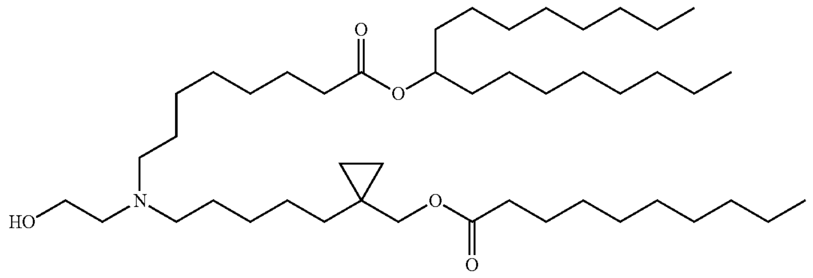

-continued
16b
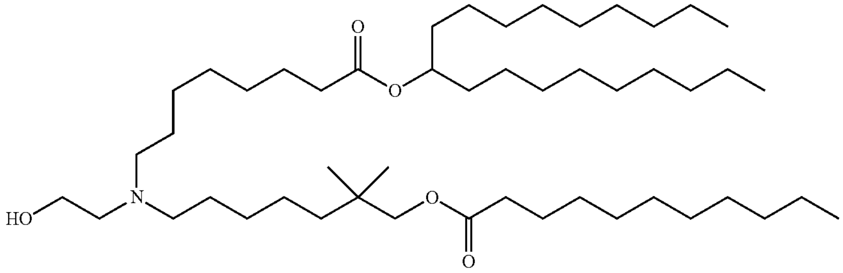
17b
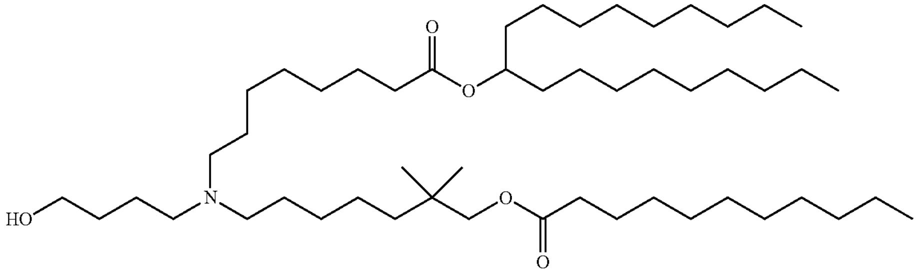
22b
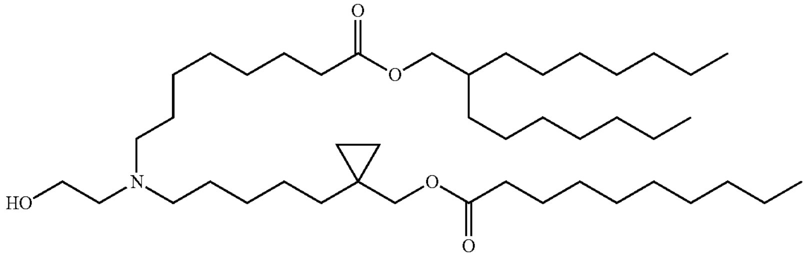
23b
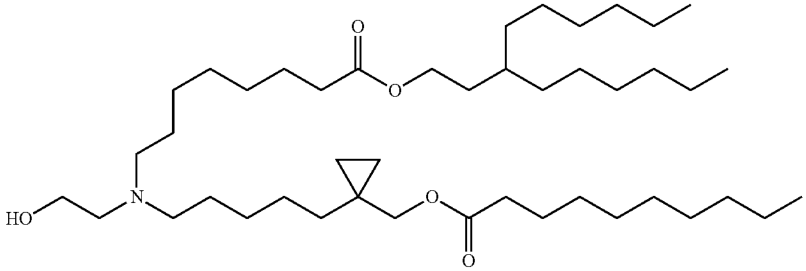
25b
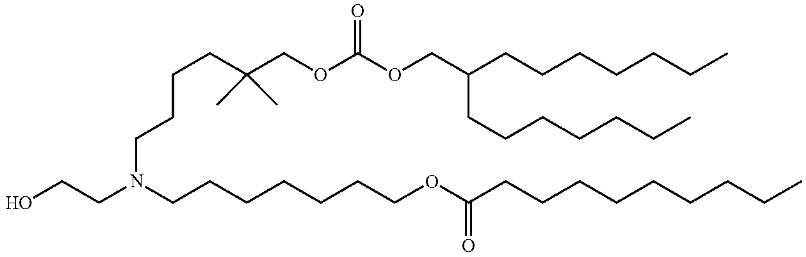
33b
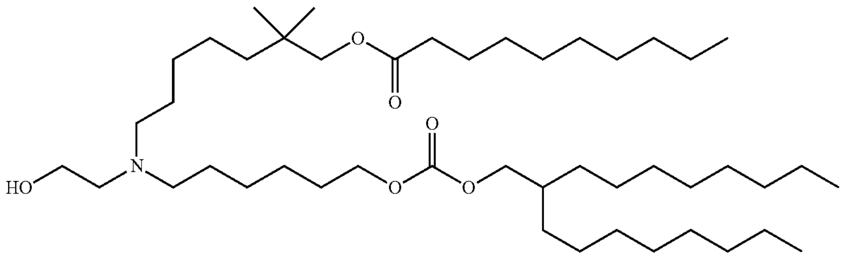

-continued
52b
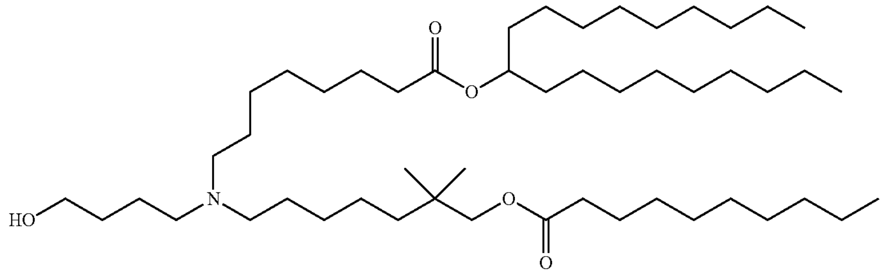
53b
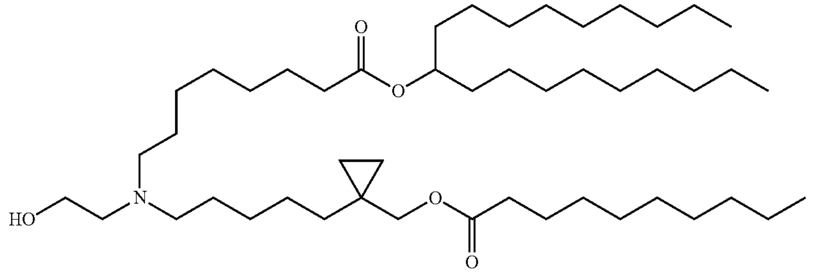
55b
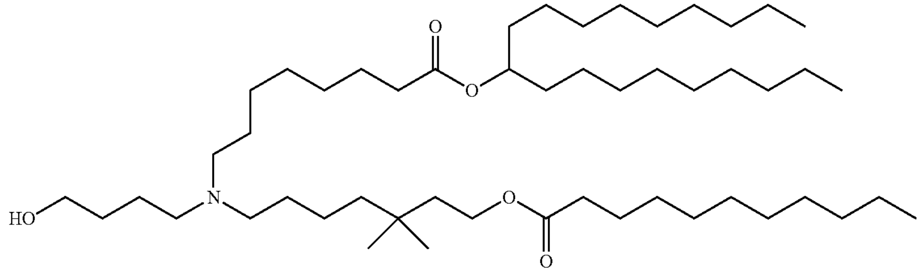
57b
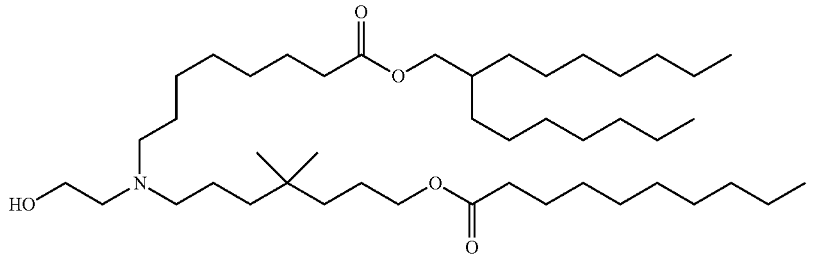
59b
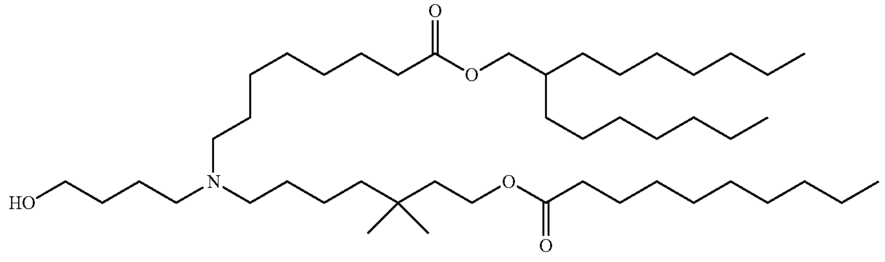
65b
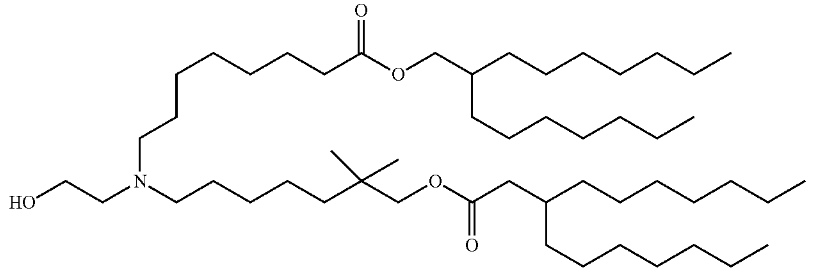

-continued
67b
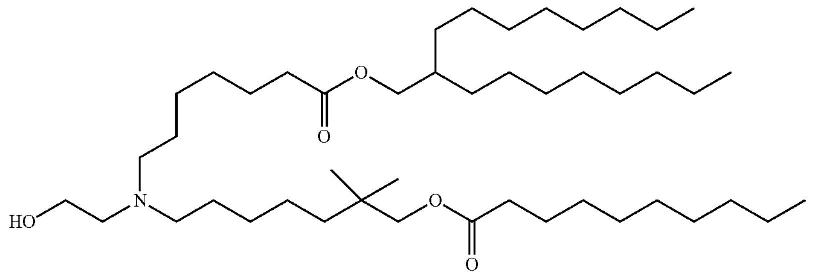
68b
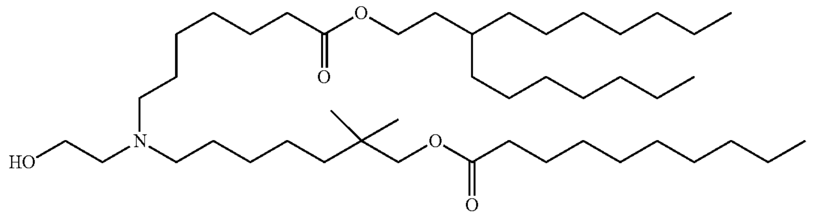
69b
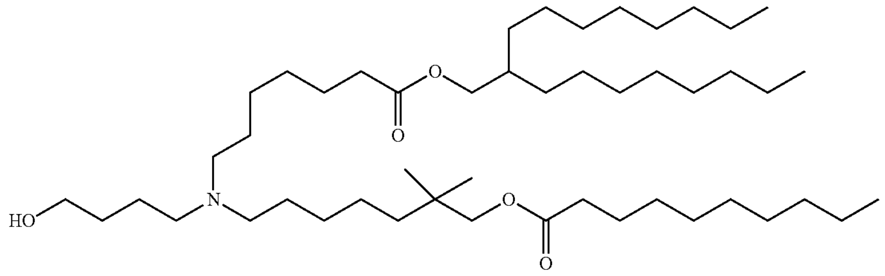
70b
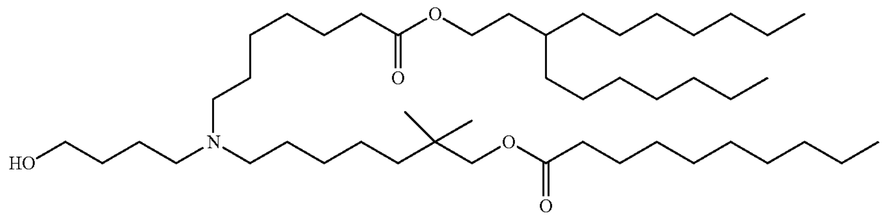
71b
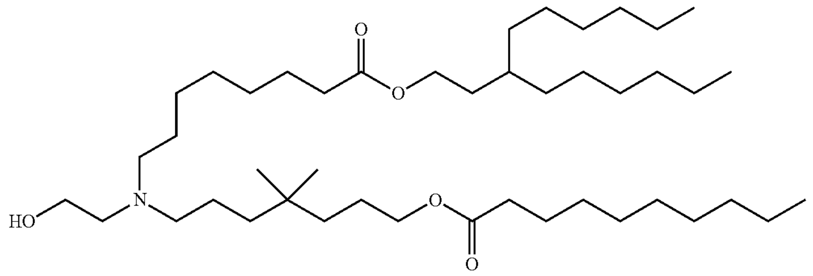
79b
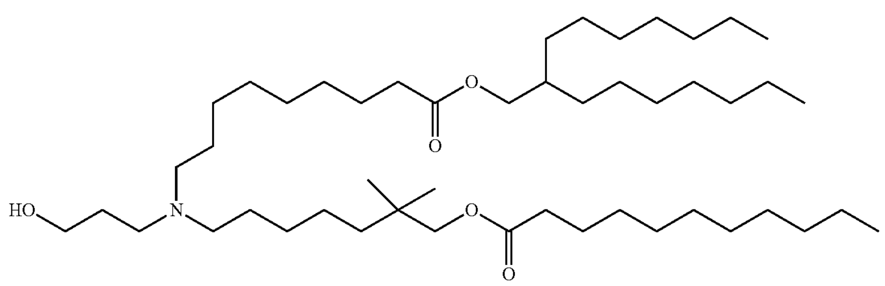

-continued
86b
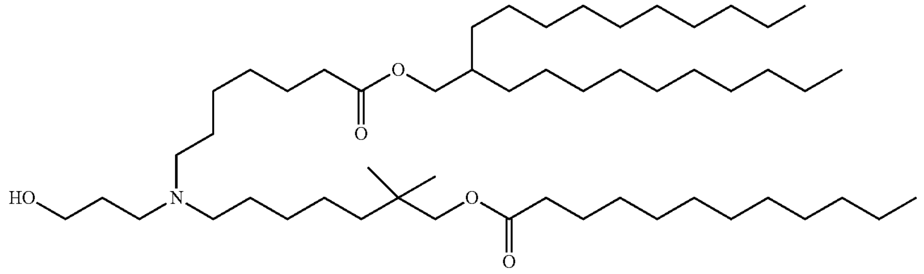
87b
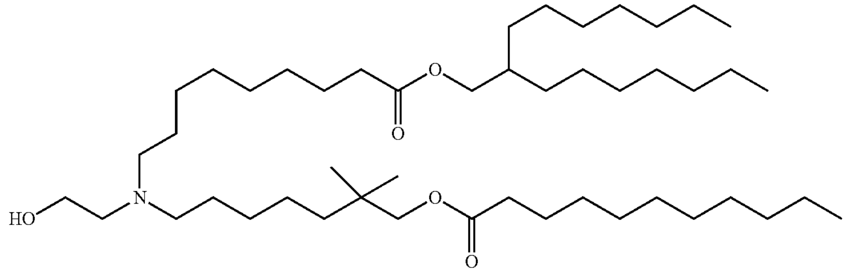
98b
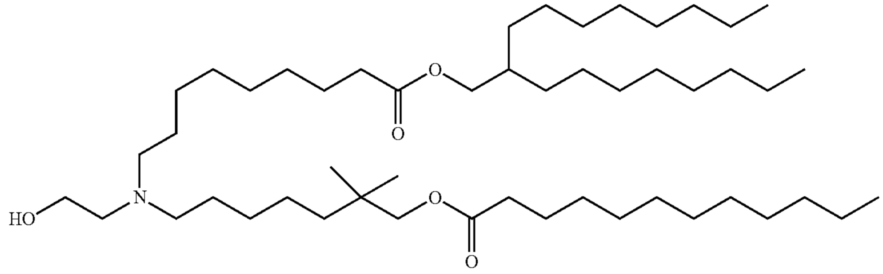
106b
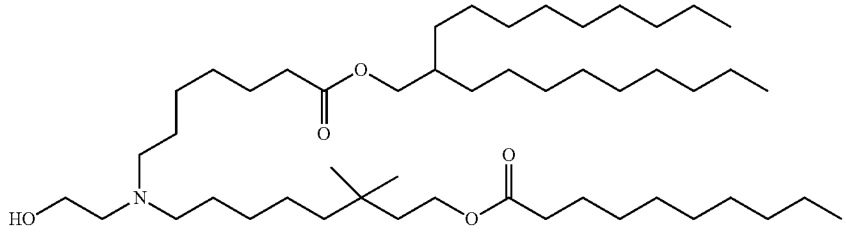
107b
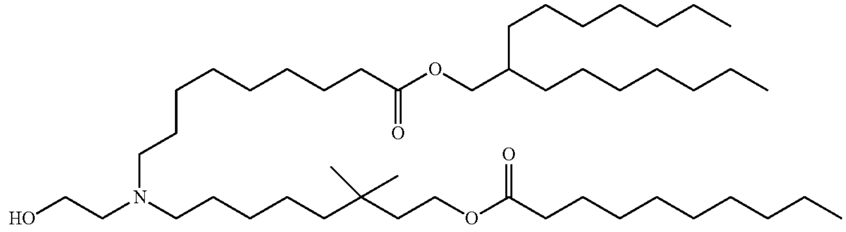
108b
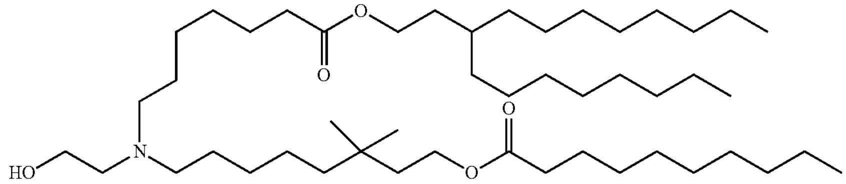

-continued

109b

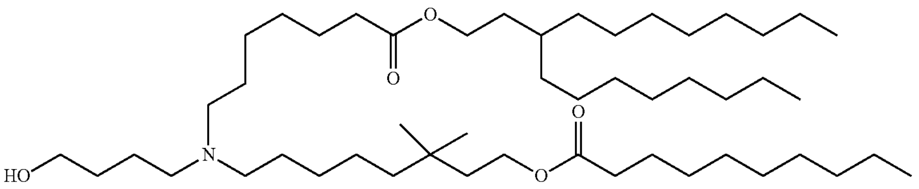

110b

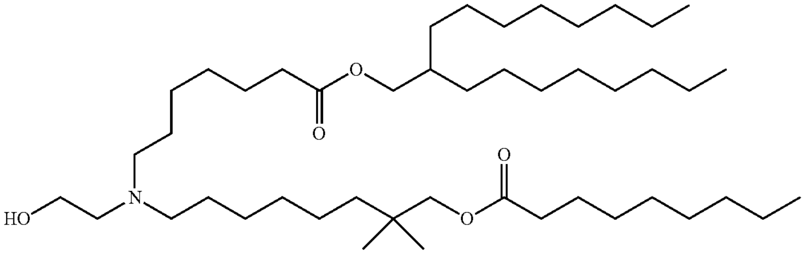

179c

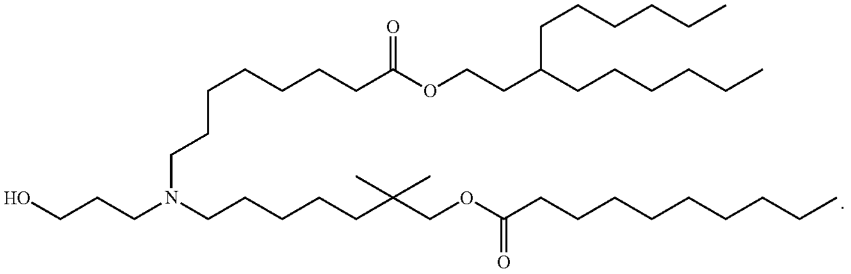

24. The compound of formula (I) of claim 1, or a pharmaceutically acceptable salt, isotopic variant, tautomer, or stereoisomer thereof, wherein, the compound is 1a

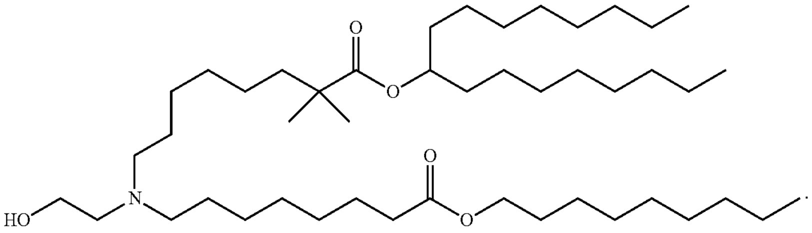

25. The compound of formula (I) of claim 1, or a pharmaceutically acceptable salt, isotopic variant, tautomer, or stereoisomer thereof, wherein, the compound is 8a

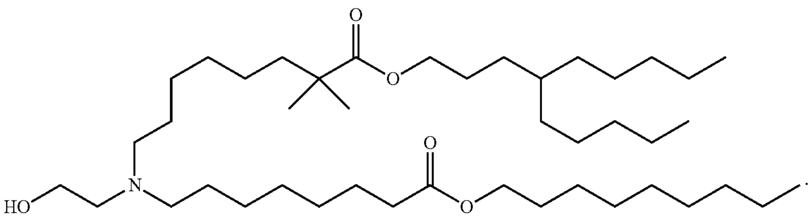

26. The compound of formula (I) of claim 1, or a pharmaceutically acceptable salt, isotopic variant, tautomer, or stereoisomer thereof, wherein, the compound is 32a

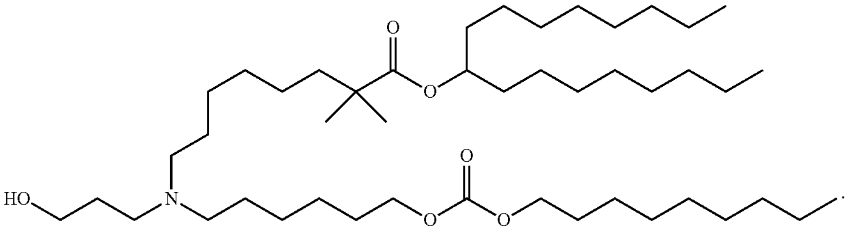

27. The compound of formula (I) of claim 1, or a pharmaceutically acceptable salt, isotopic variant, tautomer, or stereoisomer thereof, wherein, the compound is 44a

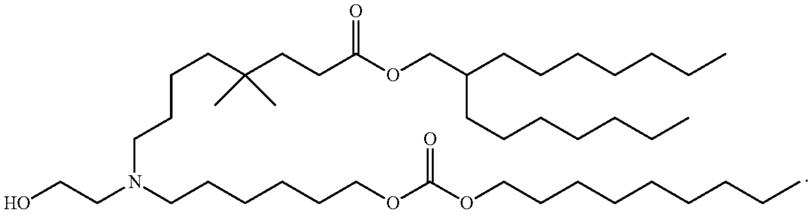

28. The compound of formula (I) of claim 1, or a pharmaceutically acceptable salt, isotopic variant, tautomer, or stereoisomer thereof, wherein, the compound is 1b

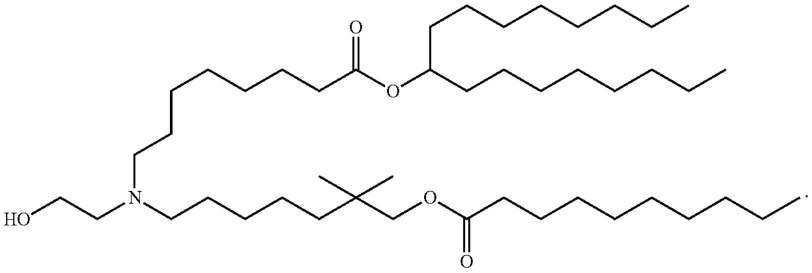

29. The compound of formula (I) of claim 1, or a pharmaceutically acceptable salt, isotopic variant, tautomer, or stereoisomer thereof, wherein, the compound is 5b

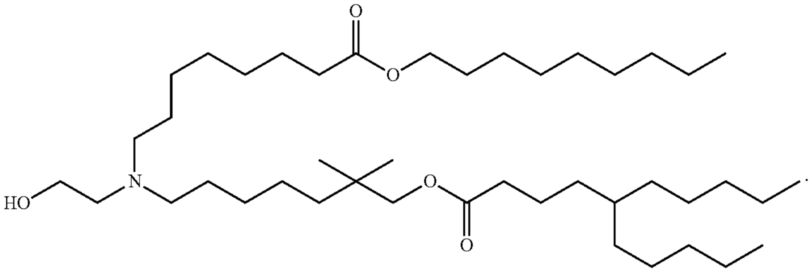

30. The compound of formula (I) of claim 1, or a pharmaceutically acceptable salt, isotopic variant, tautomer, or stereoisomer thereof, wherein, the compound is

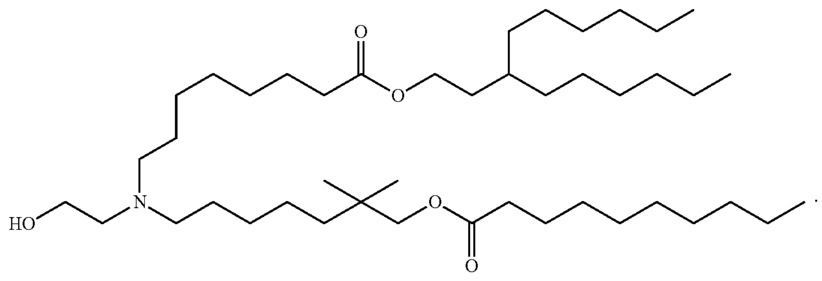

10b

31. The compound of formula (I) of claim 1, or a pharmaceutically acceptable salt, isotopic variant, tautomer, or stereoisomer thereof, wherein, the compound is

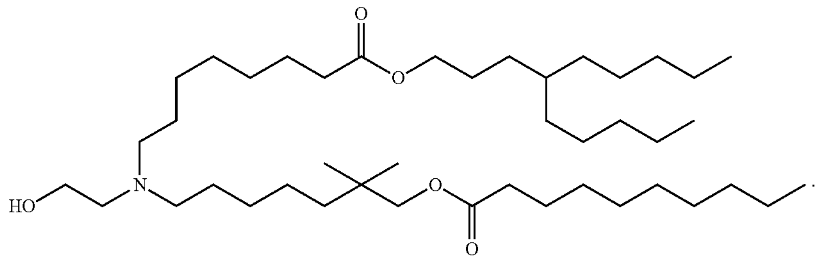

11b

32. The compound of formula (I) of claim 1, or a pharmaceutically acceptable salt, isotopic variant, tautomer, or stereoisomer thereof, wherein, the compound is

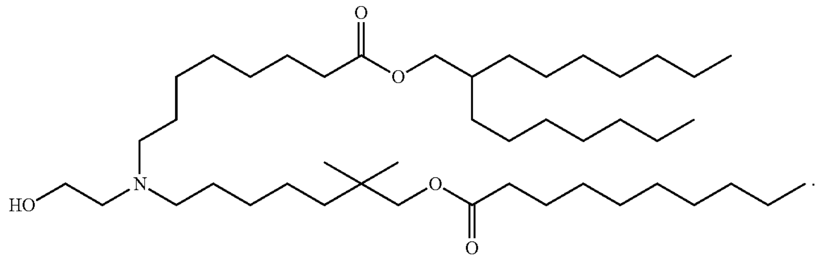

13b

33. The compound of formula (I) of claim 1, or a pharmaceutically acceptable salt, isotopic variant, tautomer, or stereoisomer thereof, wherein, the compound is

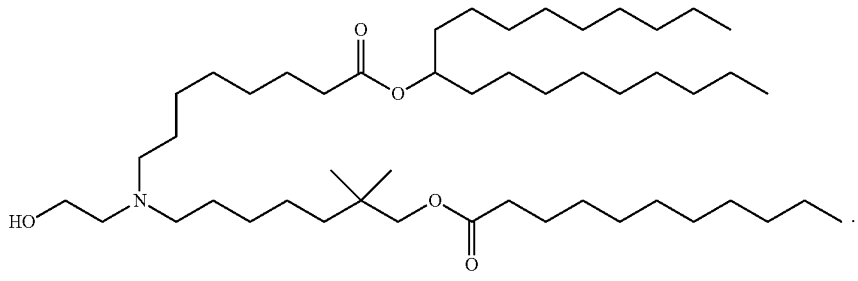

16b

34. The compound of formula (I) of claim 1, or a pharmaceutically acceptable salt, isotopic variant tautomer, or stereoisomer thereof, wherein, the compound is 17b

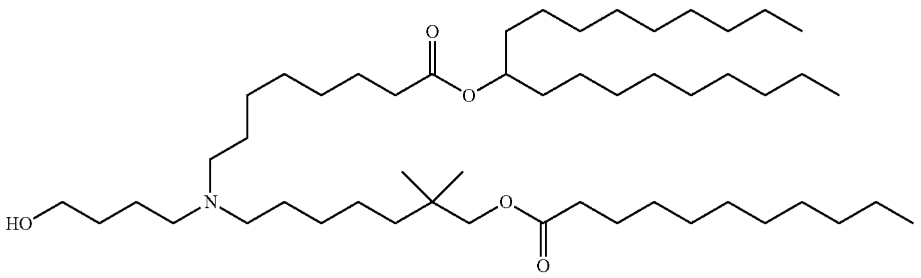

.

35. The compound of formula (I) of claim 1, or a pharmaceutically acceptable salt, isotopic variant tautomer, or stereoisomer thereof, wherein, the compound is 22b

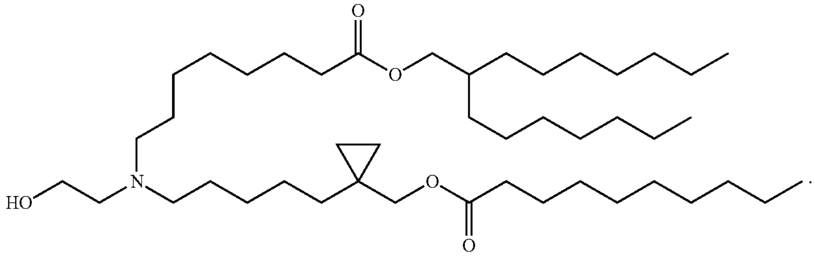

.

36. The compound of formula (I) of claim 1, or a pharmaceutically acceptable salt, isotopic variant, tautomer, or stereoisomer thereof, wherein, the compound is 23b

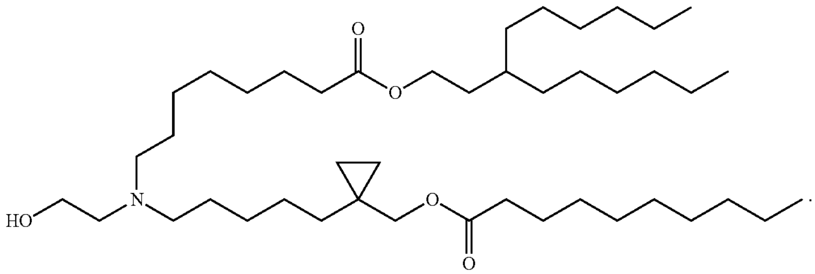

.

37. The compound of formula (I) of claim 1, or a pharmaceutically acceptable salt, isotopic variant, tautomer, or stereoisomer thereof, wherein, the compound is 25b

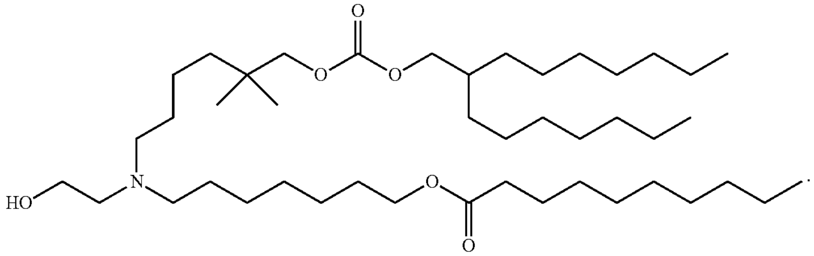

.

38. The compound of formula (I) of claim 1, or a pharmaceutically acceptable salt, isotopic variant, tautomer, or stereoisomer thereof, wherein, the compound is 33b

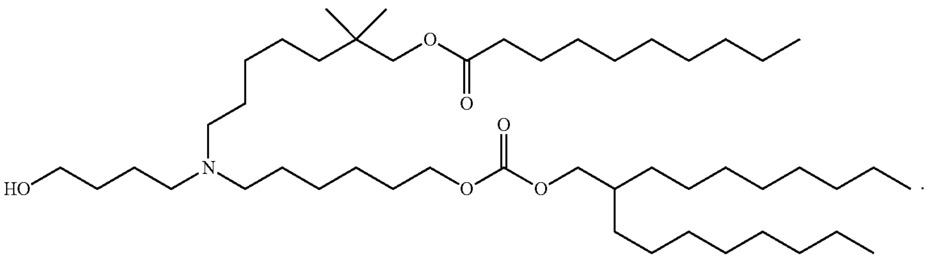

39. The compound of formula (I) of claim 1, or a pharmaceutically acceptable salt, isotopic variant, tautomer, or stereoisomer thereof wherein, the compound is 57b

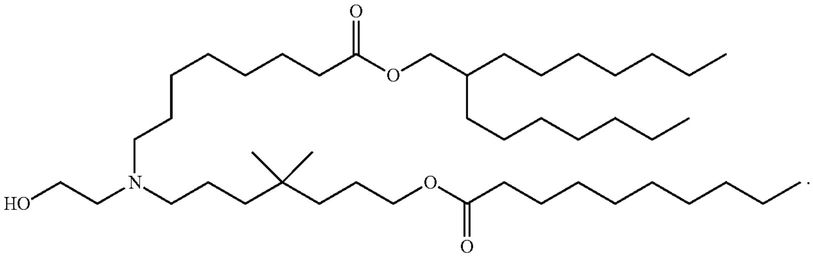

40. The compound of formula (I) of claim 1, or a pharmaceutically acceptable salt, isotopic variant, tautomer, or stereoisomer thereof, wherein, the compound is 68b

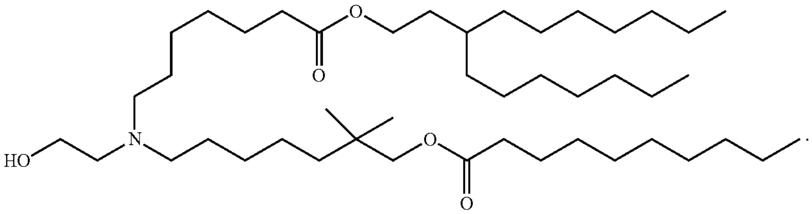

41. The compound of formula (I) of claim 1, or a pharmaceutically acceptable salt, isotopic variant, tautomer, or stereoisomer thereof, wherein, the compound is 179c

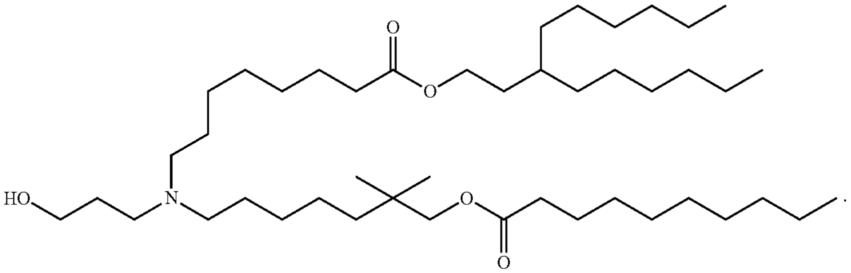

42. The compound of formula (I) of claim 1, or a pharmaceutically acceptable salt, isotopic variant, tautomer, or stereoisomer thereof, wherein the compound is selected from the following:

1a
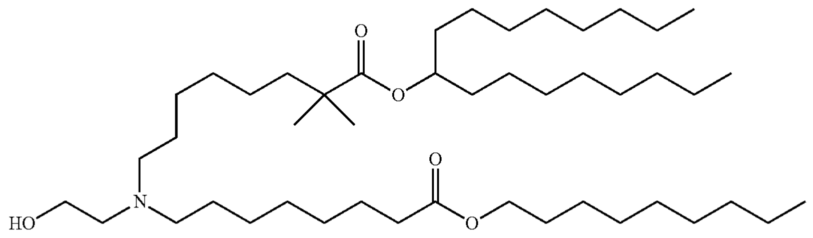
3a
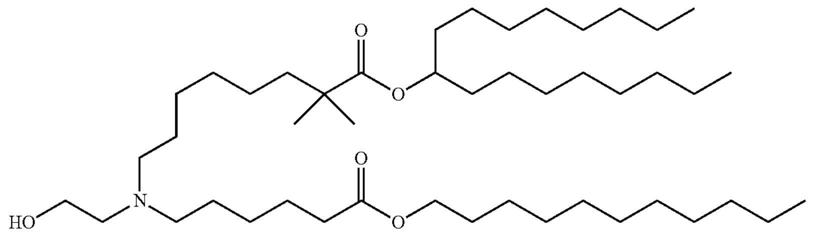
4a
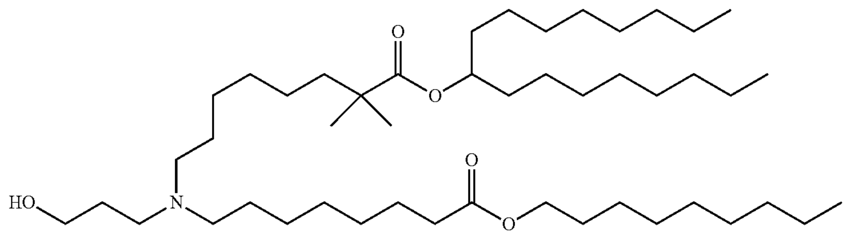
5a
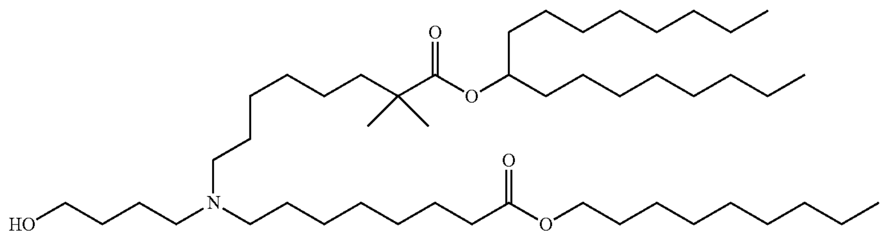
6a
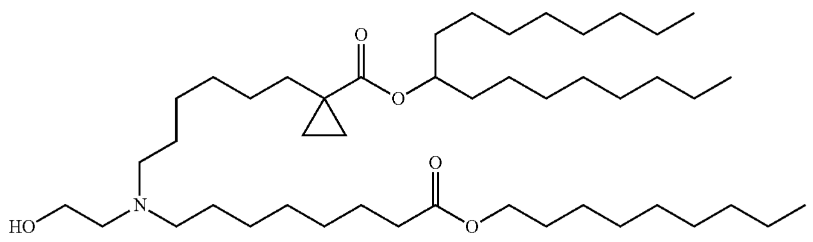
7a
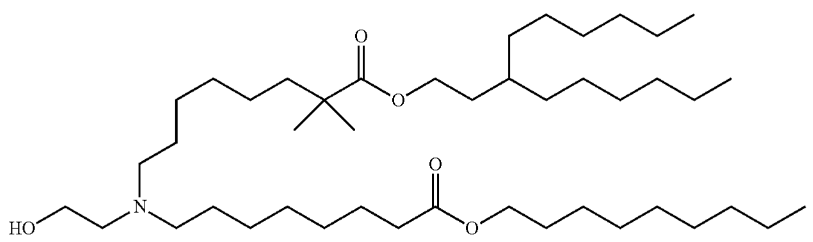

-continued
8a
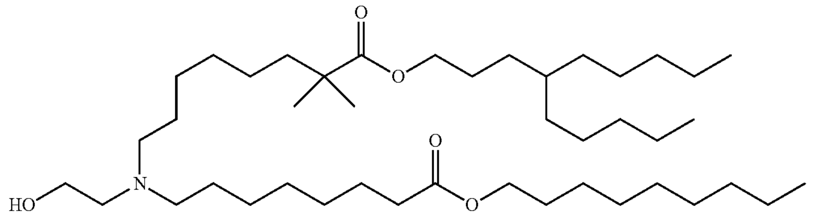
9a
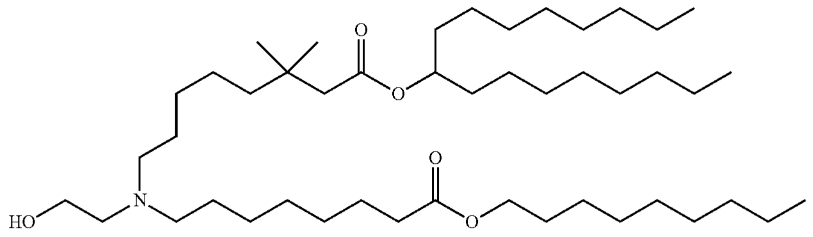
10a
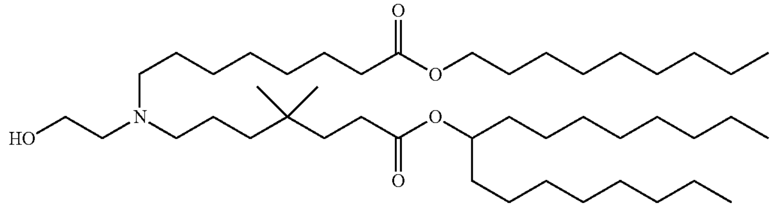
11a
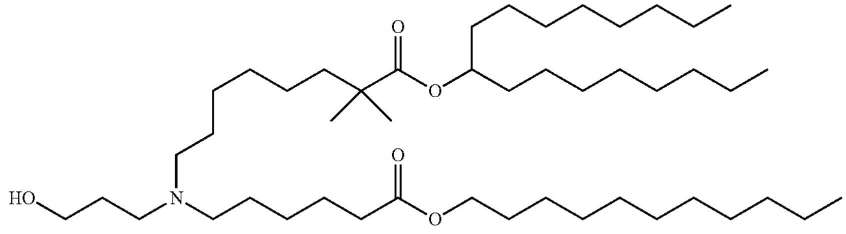
12a
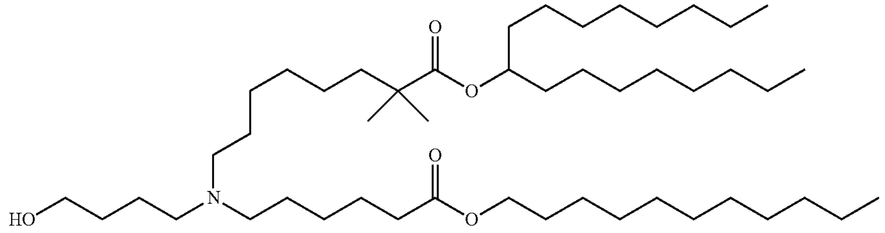
13a
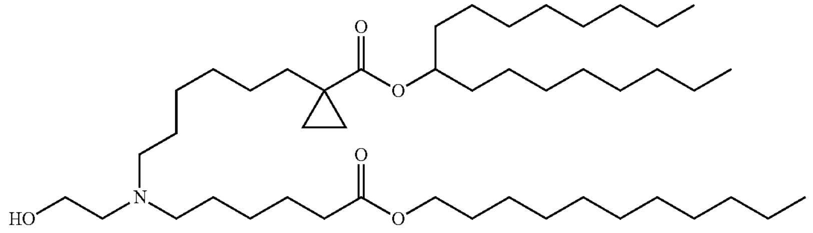
14a
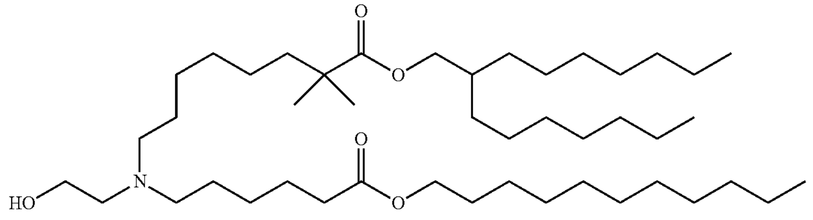

-continued
15a
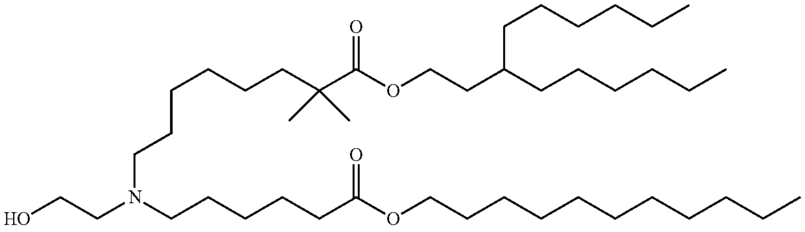
16a
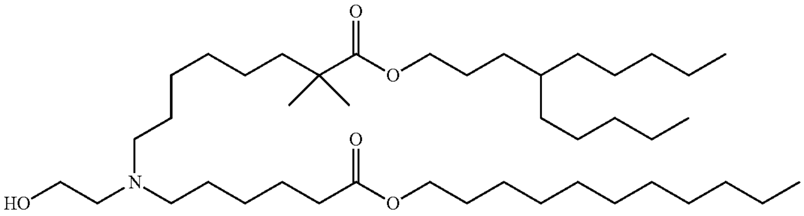
17a
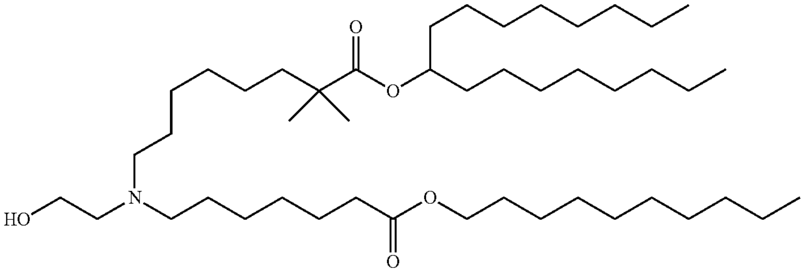
18a
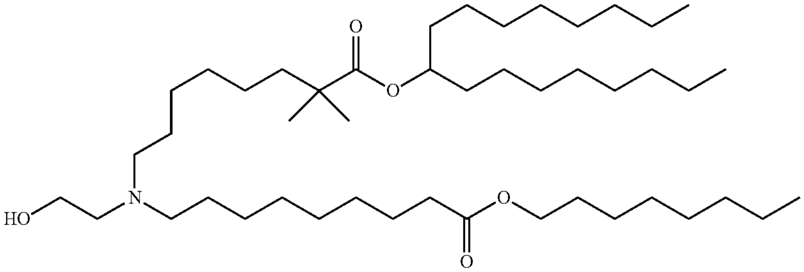
19a
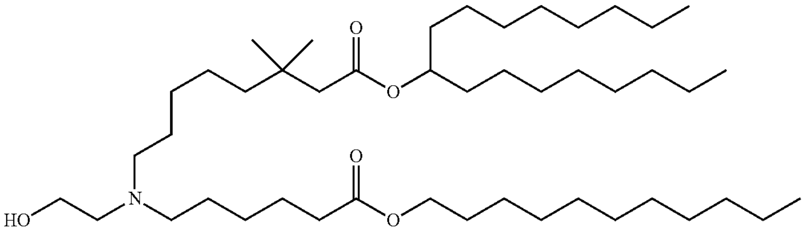
20a
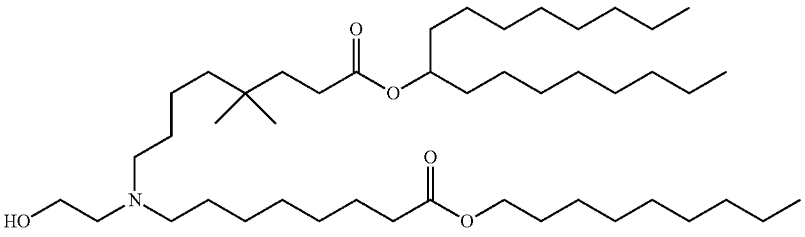

-continued
21a
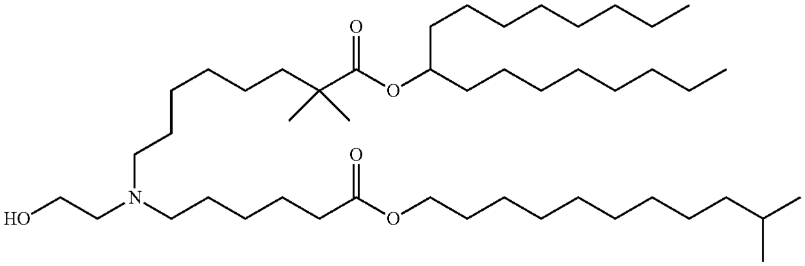
22a
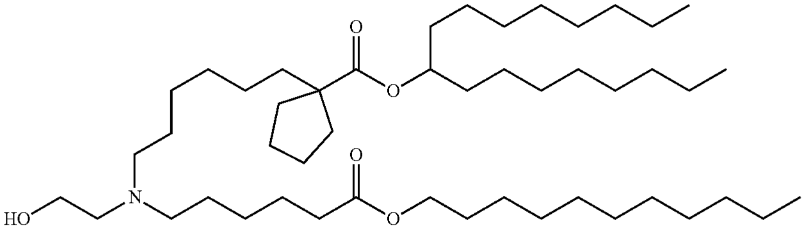
23a
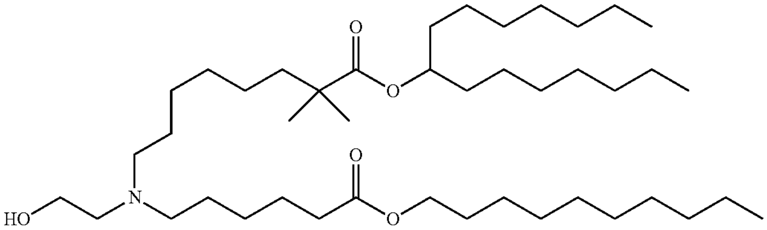
24a
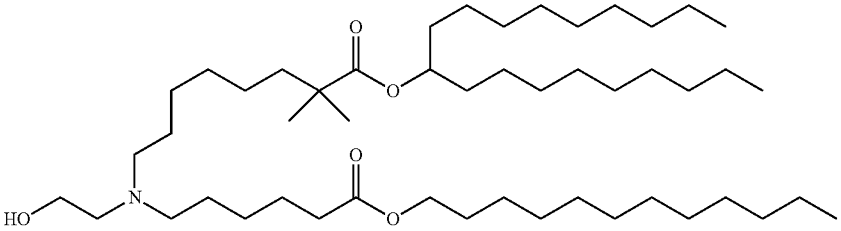
25a
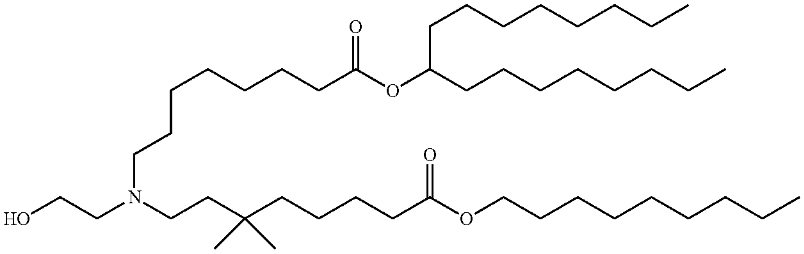
26a
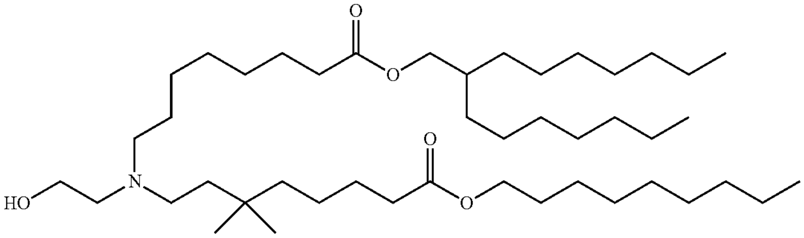

-continued
27a
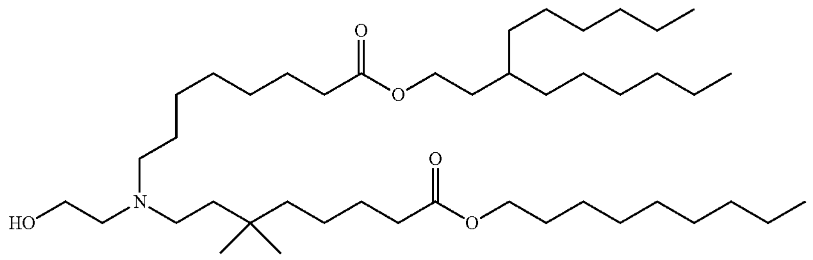
28a
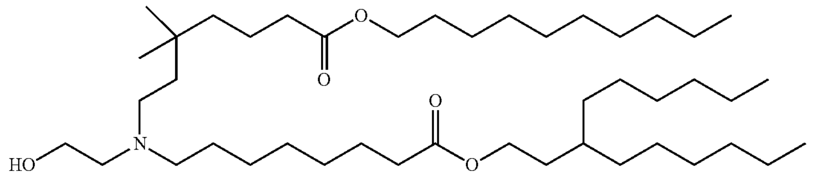
29a
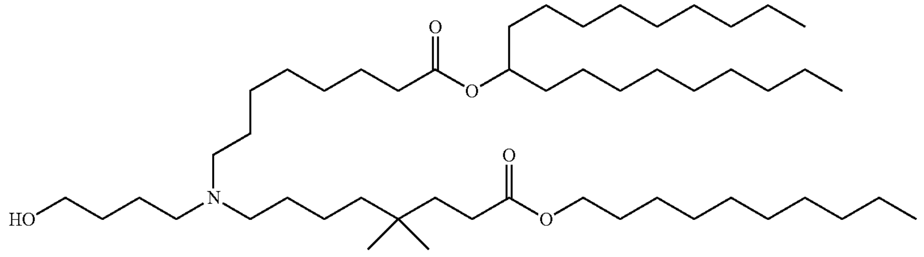
1b
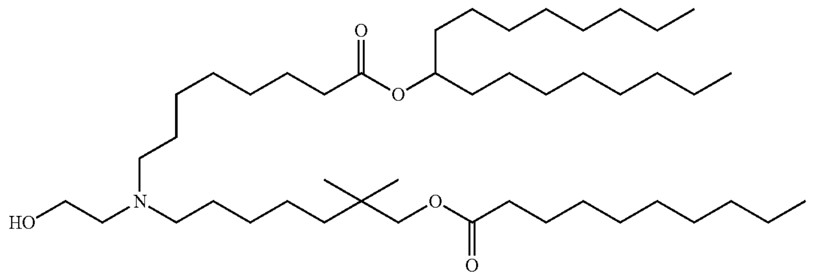
2b
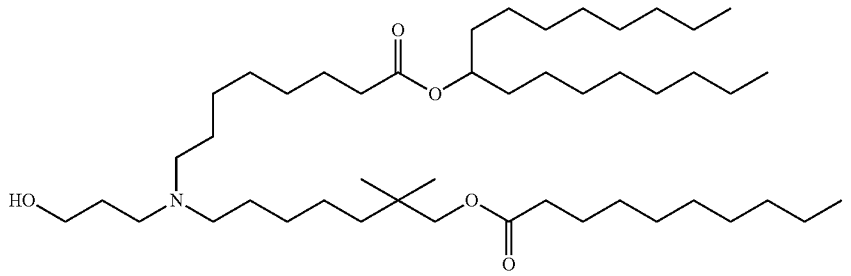
3b
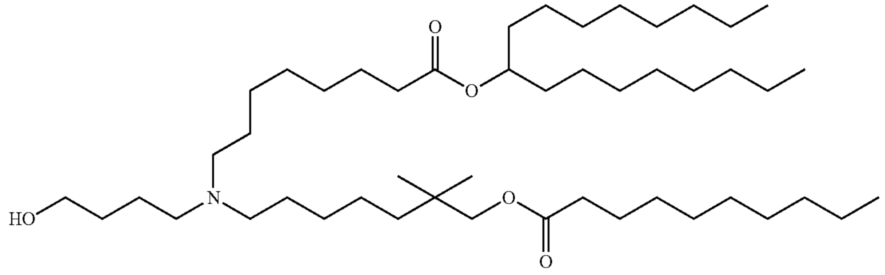

-continued
5b
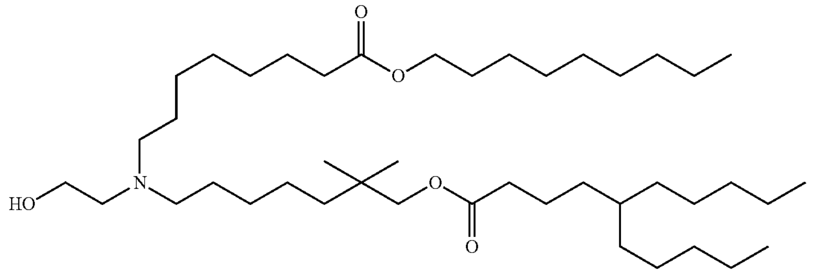
6b
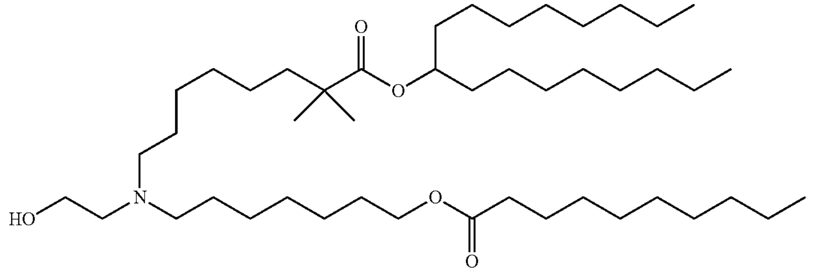
7b
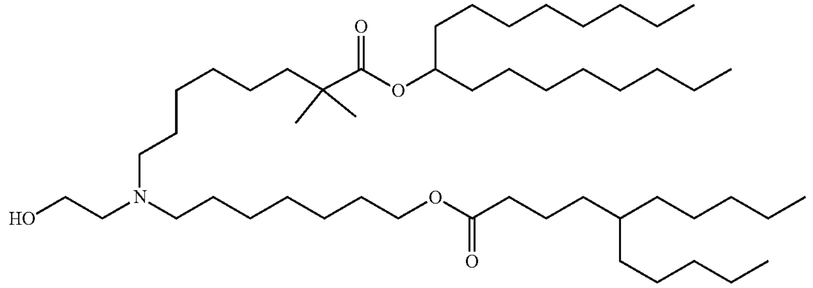
8b
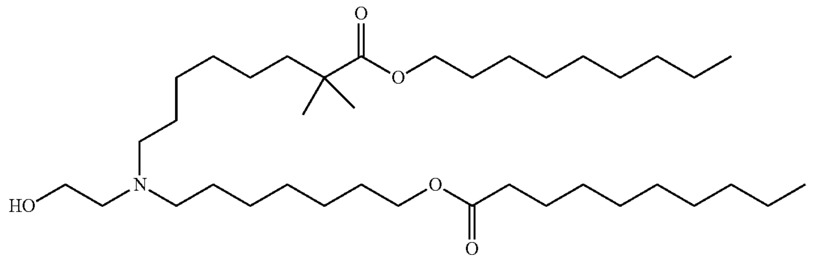
9b
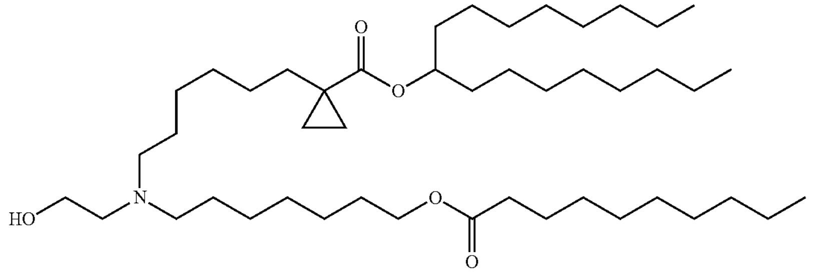

-continued
10b
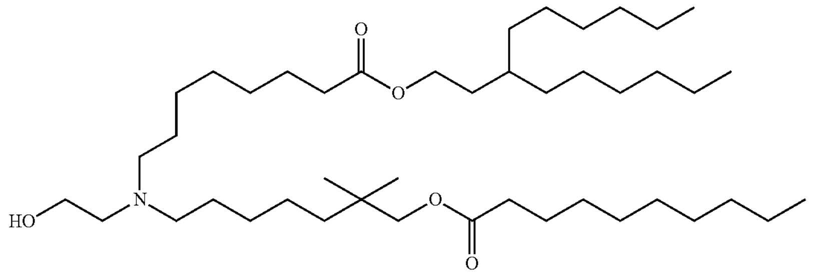
11b
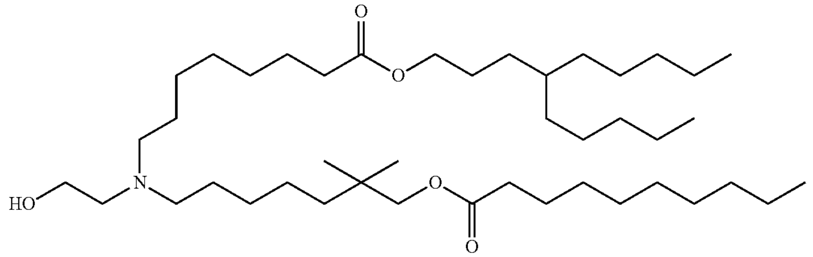
12b
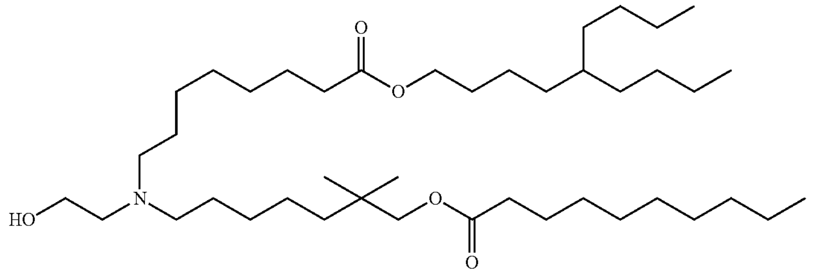
13b
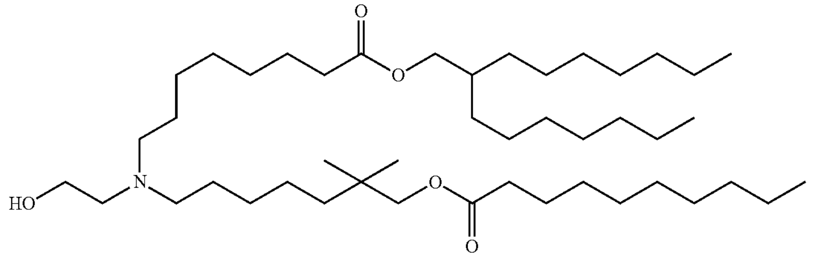
14b
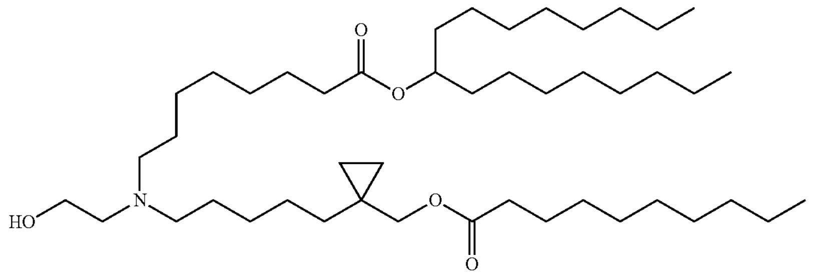
15b
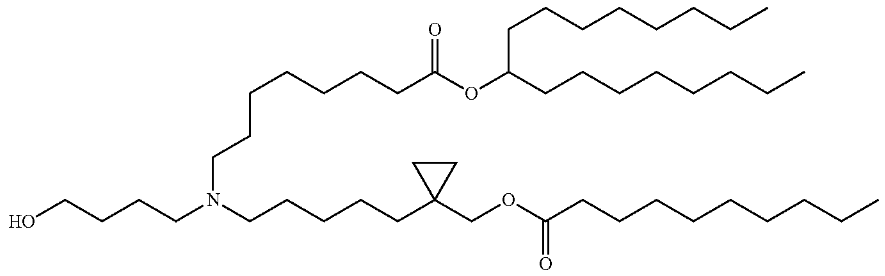

-continued
16b
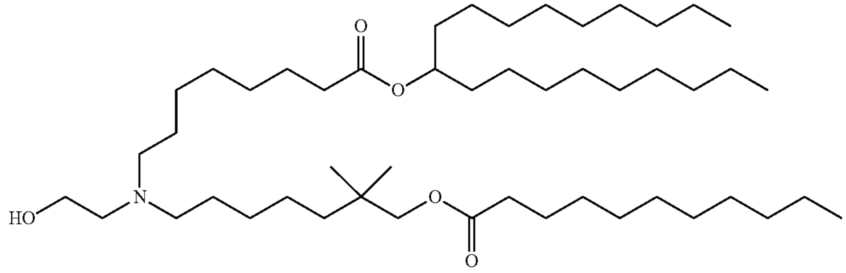
17b
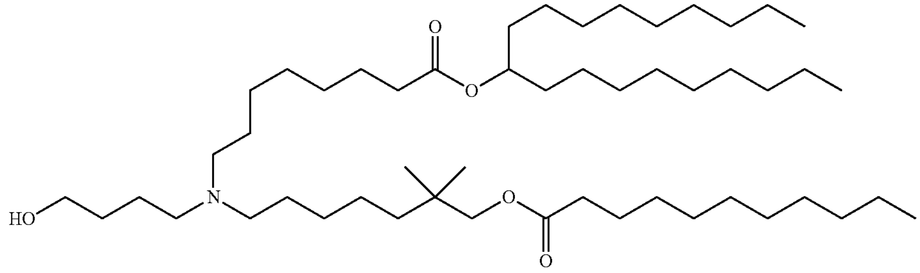
18b
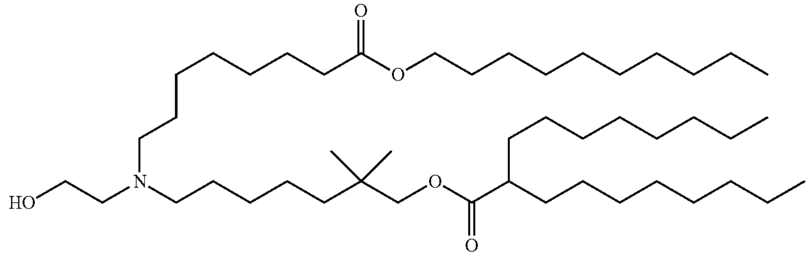
19b
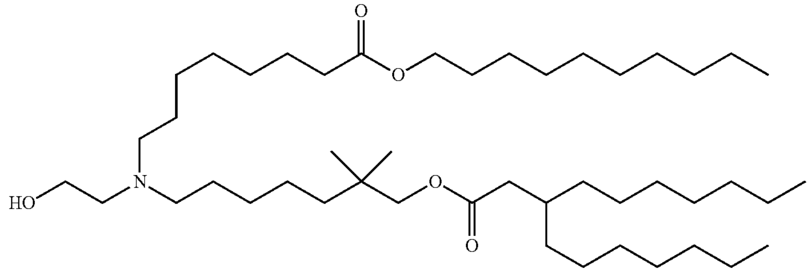
20b
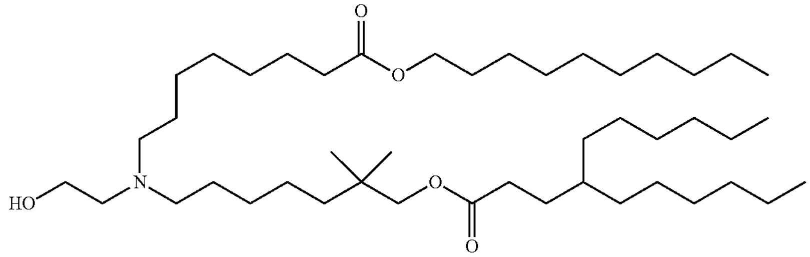
21b
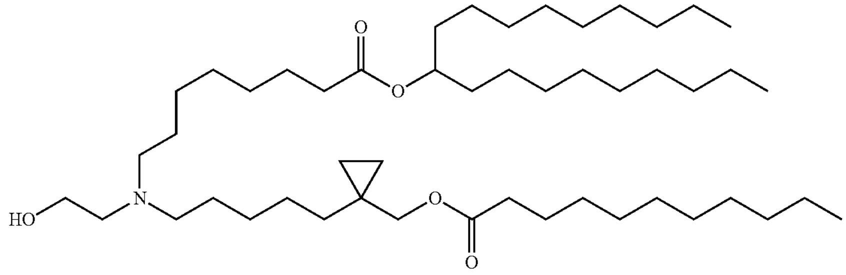

-continued
22b
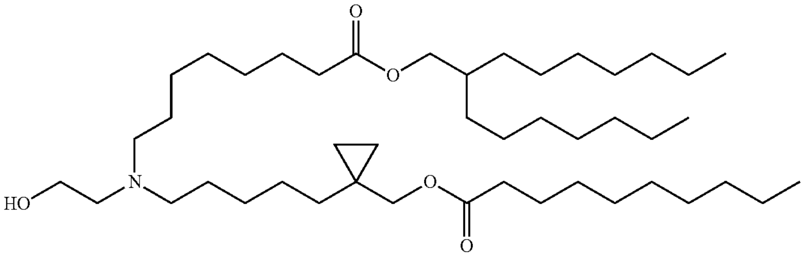
23b
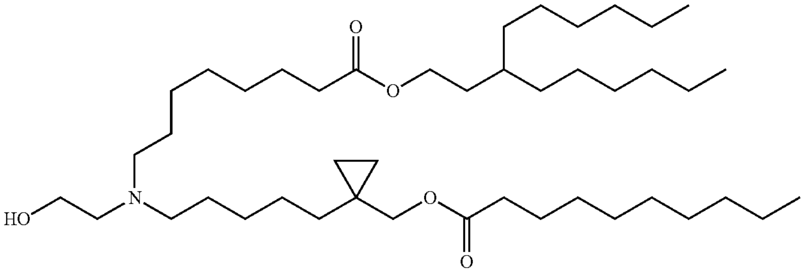
24b
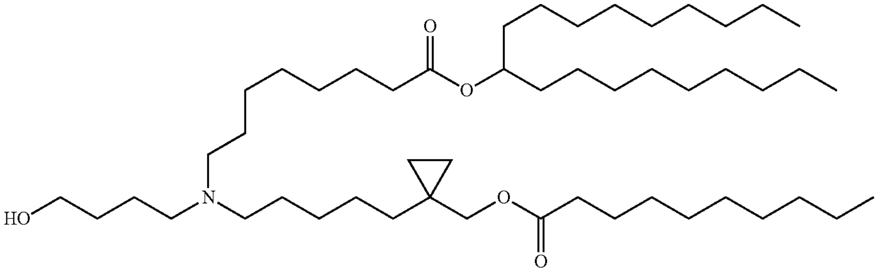
30a
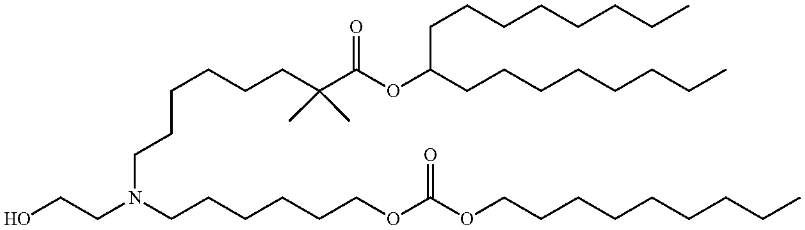
31a
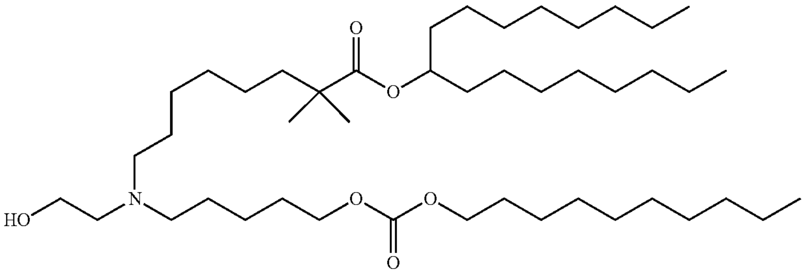
32a
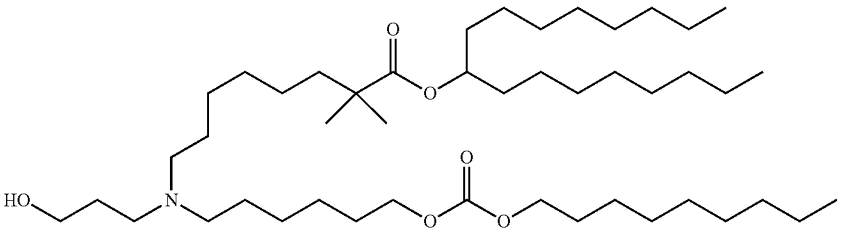

-continued
33a
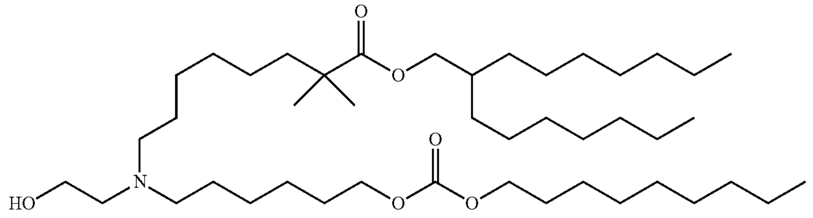
34a
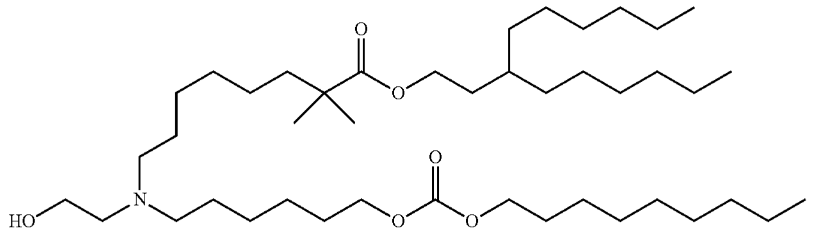
35a
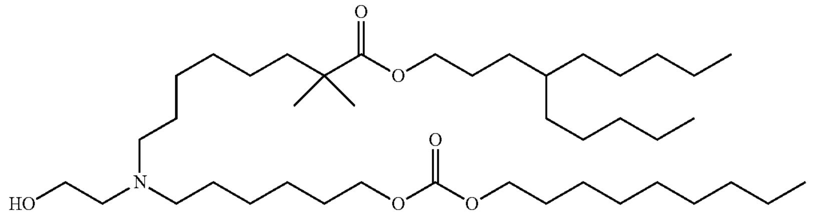
36a
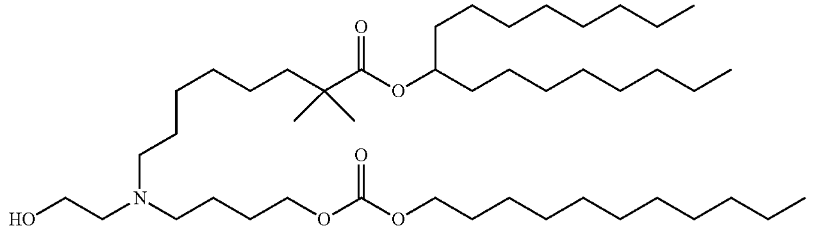
37a
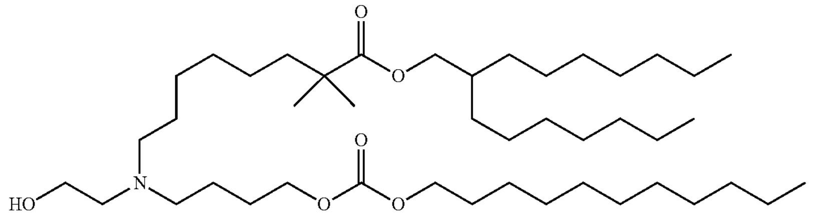
38a
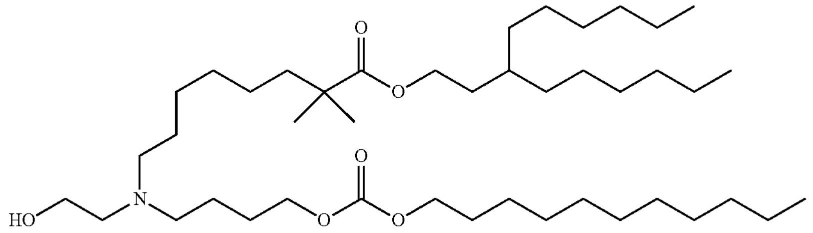
39a
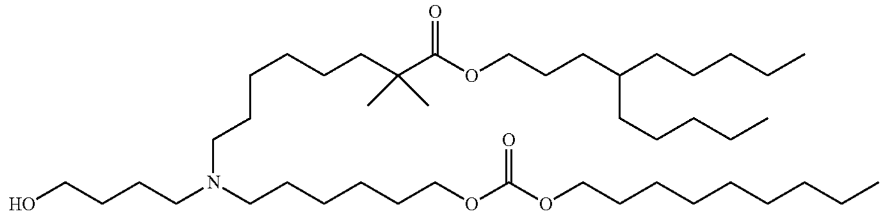

-continued
40a
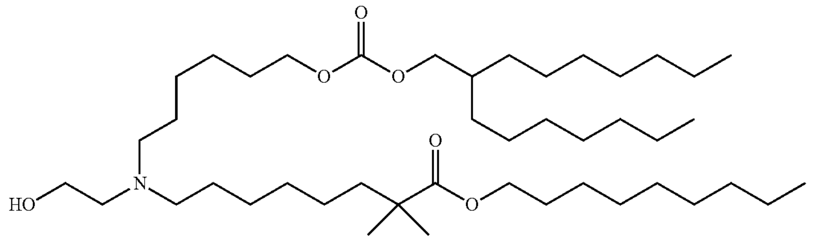
41a
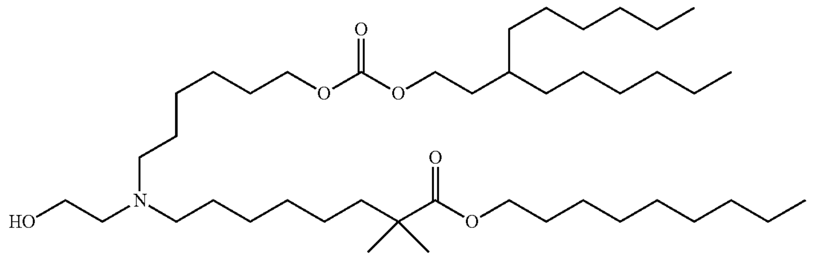
42a
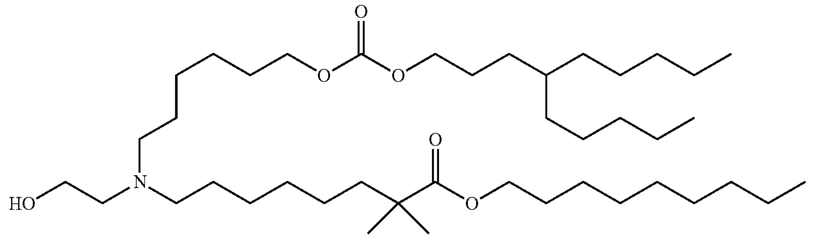
43a
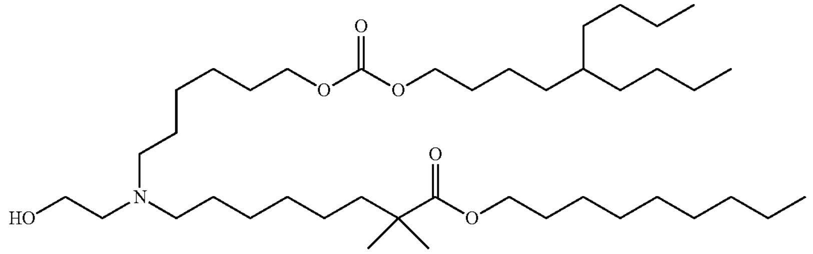
44a
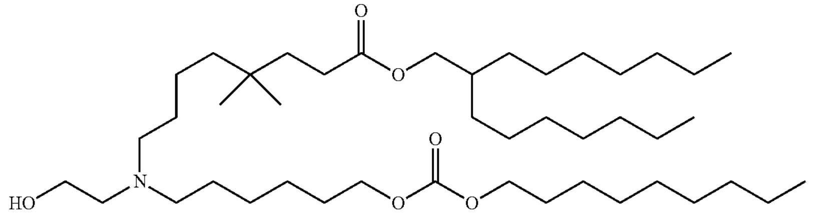
45a
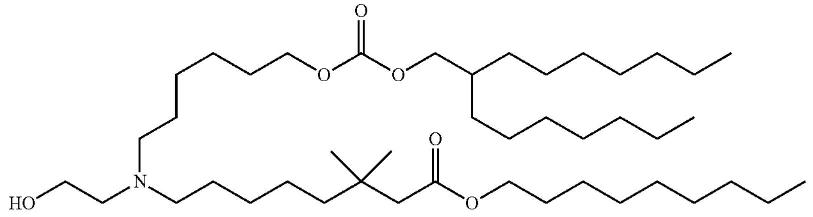

-continued
46a
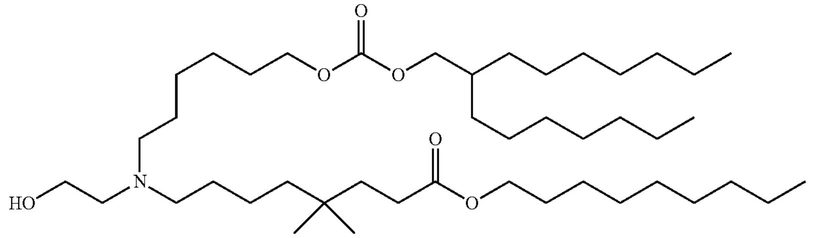
47a
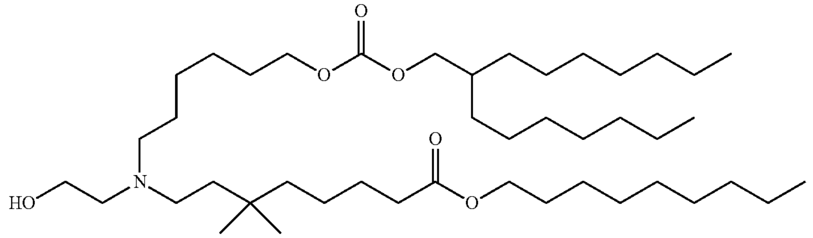
48a
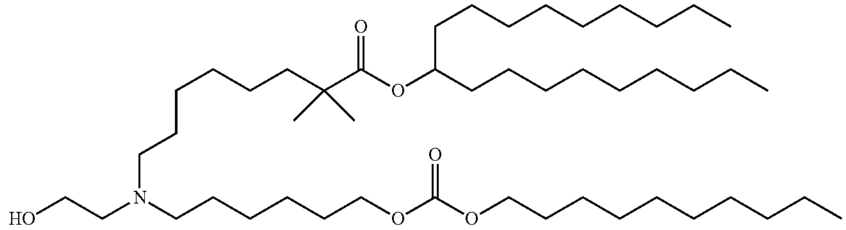
49a
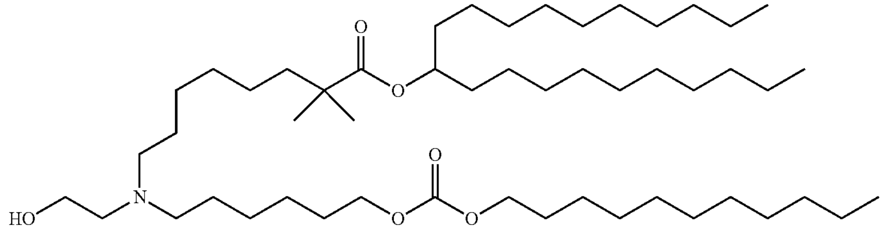
50a
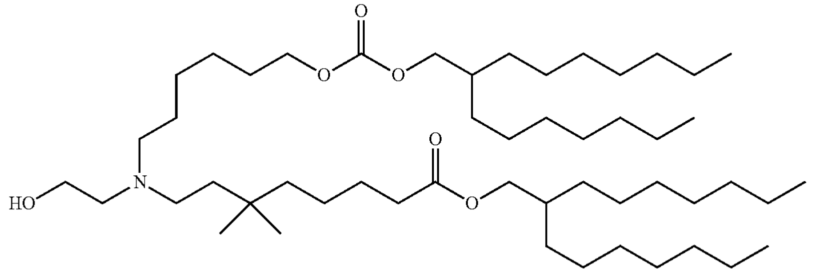
51a
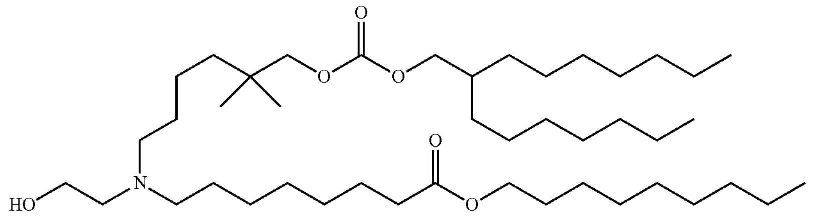

-continued
25b
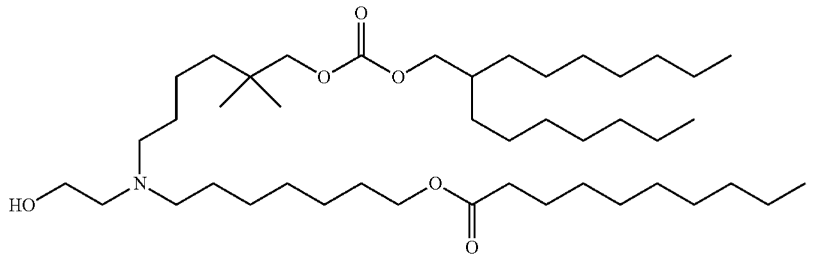
26b
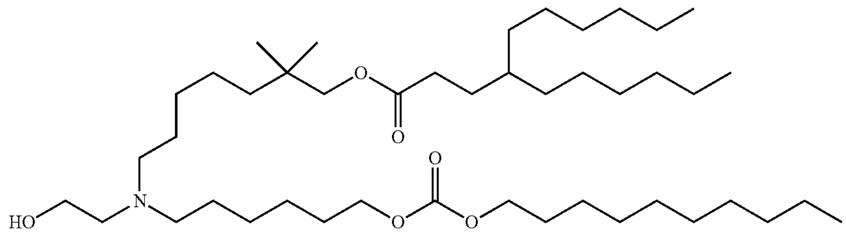
27b
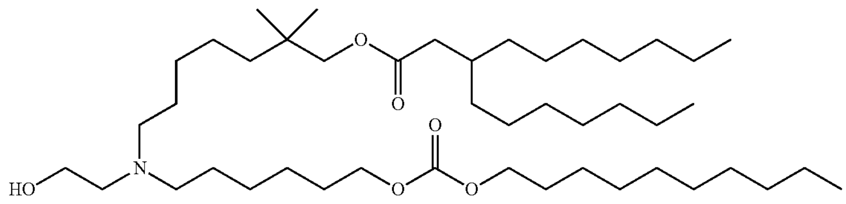
28b
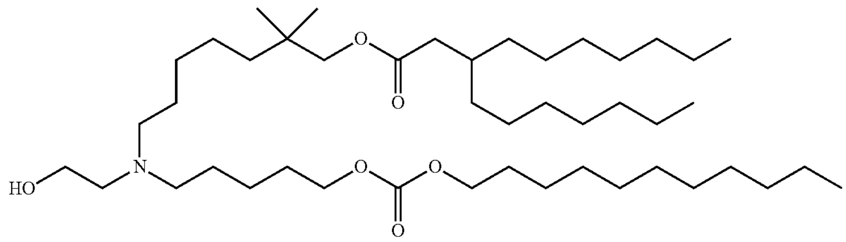
29b
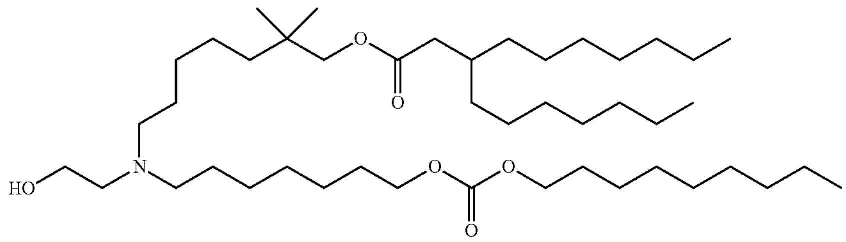
30b
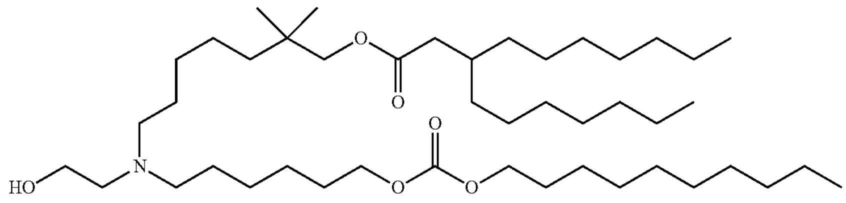

-continued
31b
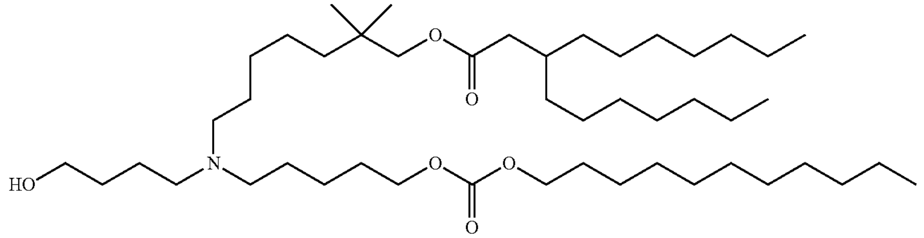
32b
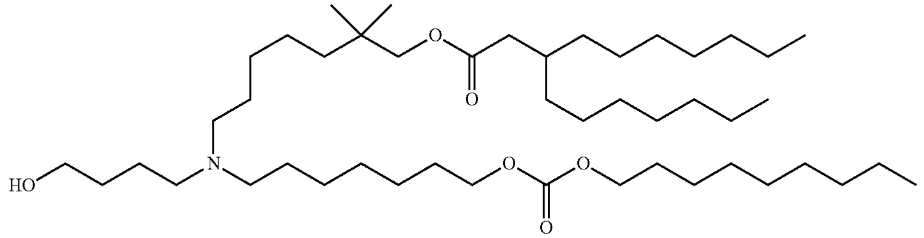
33b
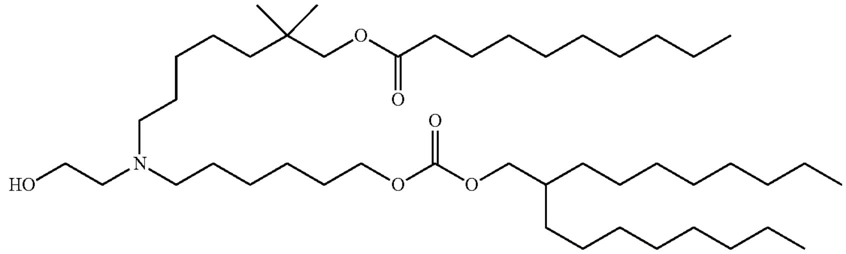
34b
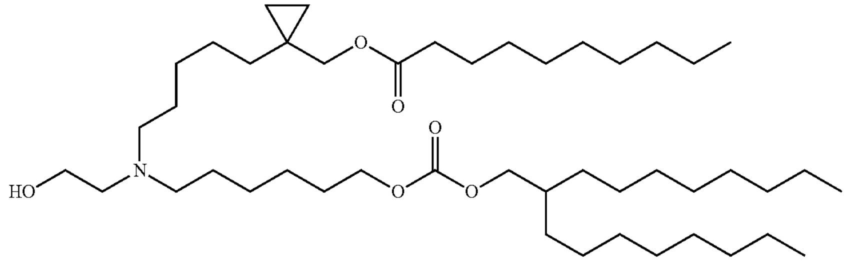
35b
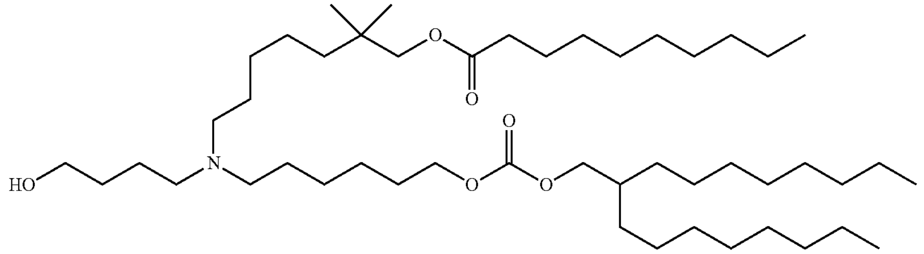
36b
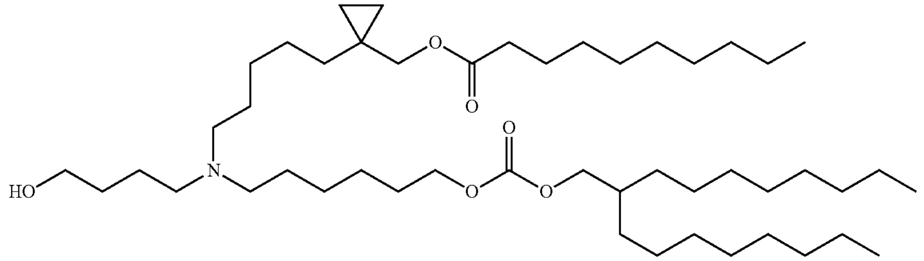

-continued
37b
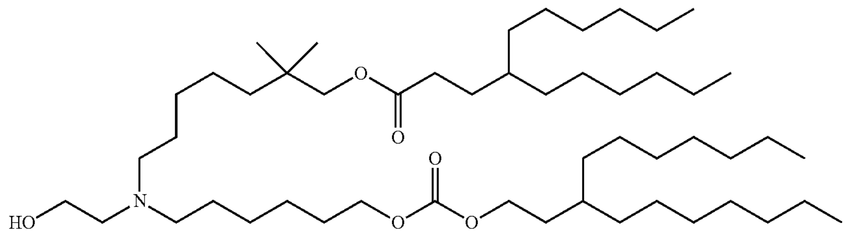
52a
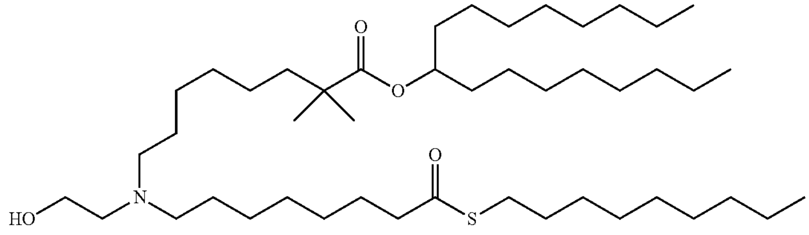
53a
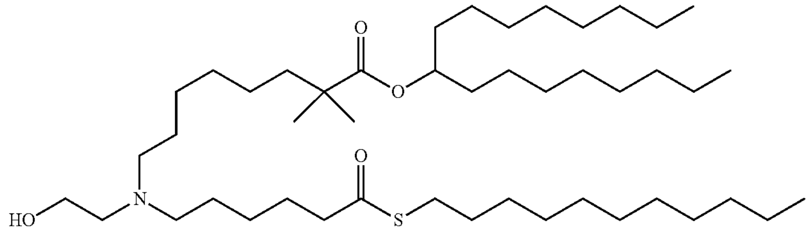
54a
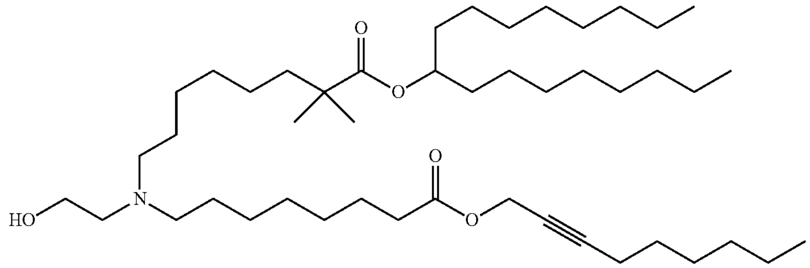
55a
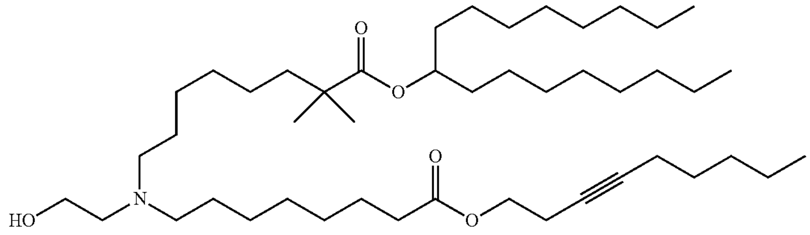
56a
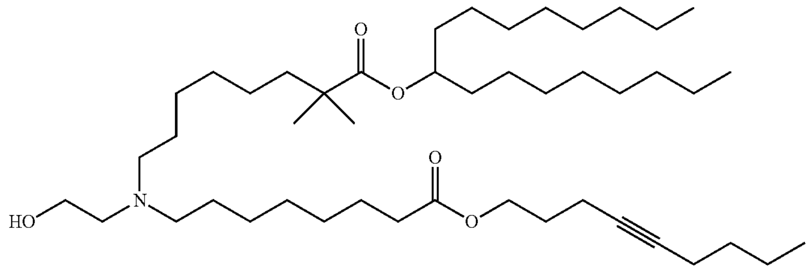

-continued
57a
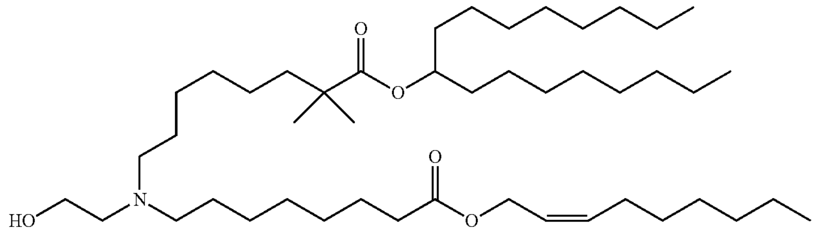
58a
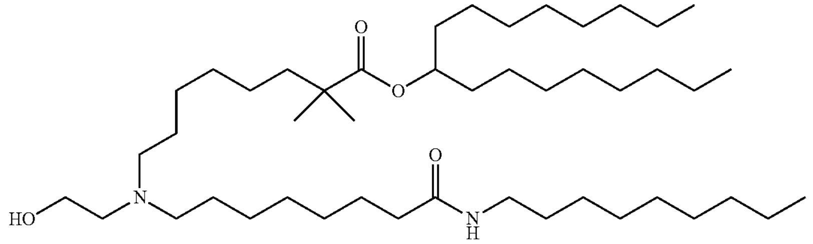
59a
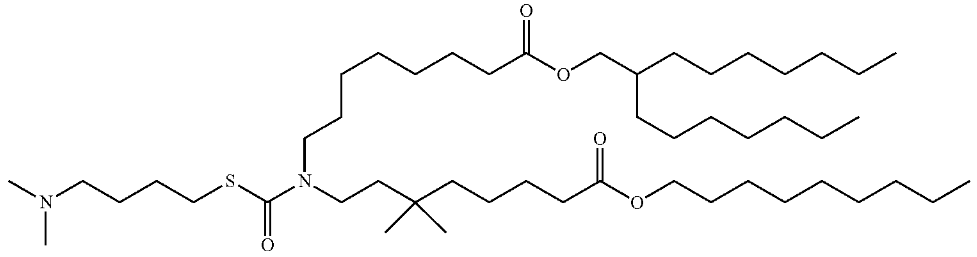
60a
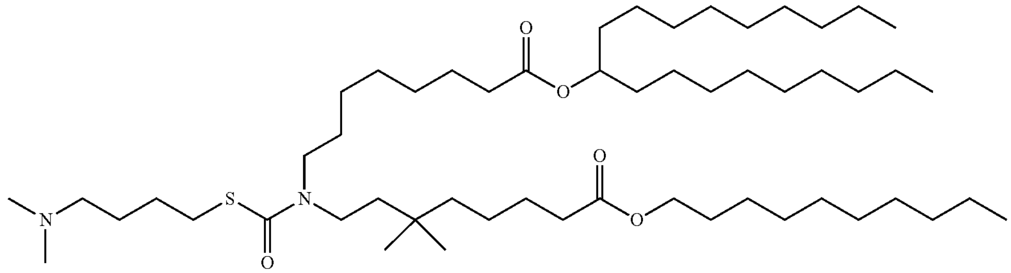
61a
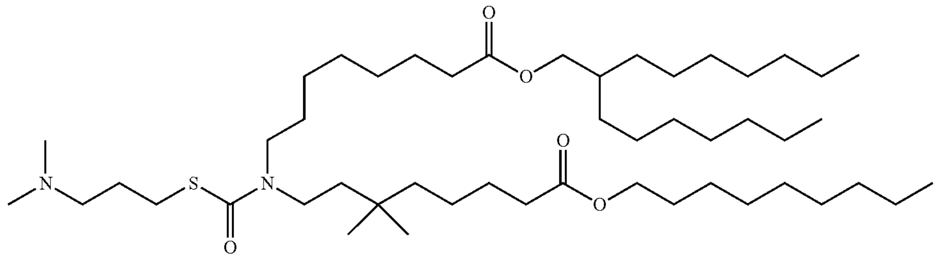
62a
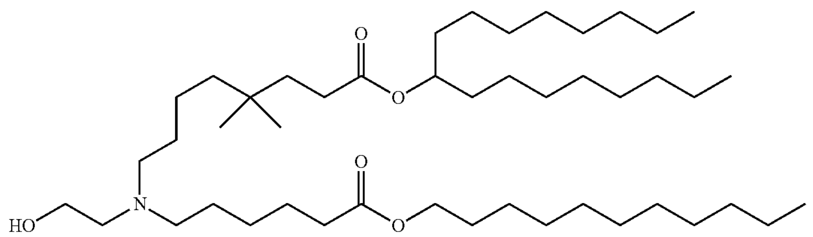

-continued
63a
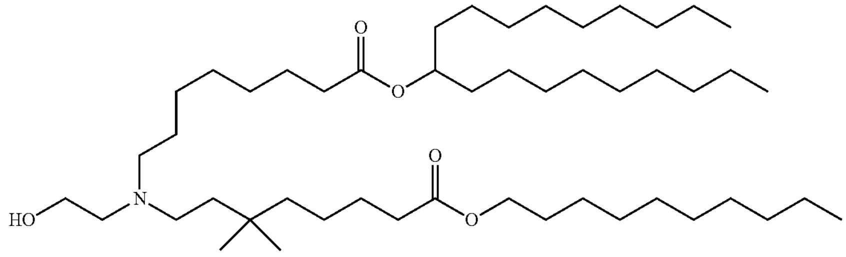
64a
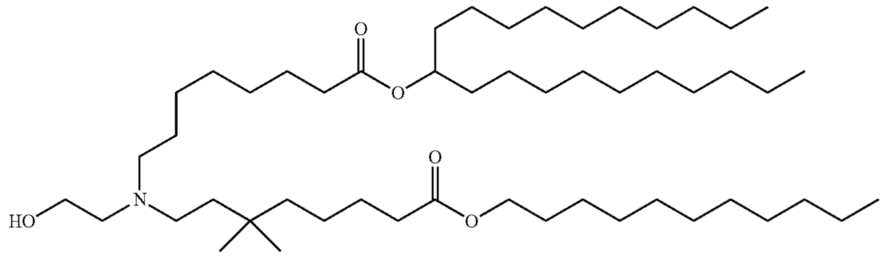
65a
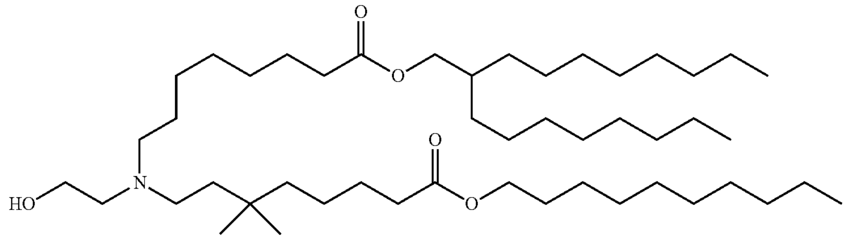
66a
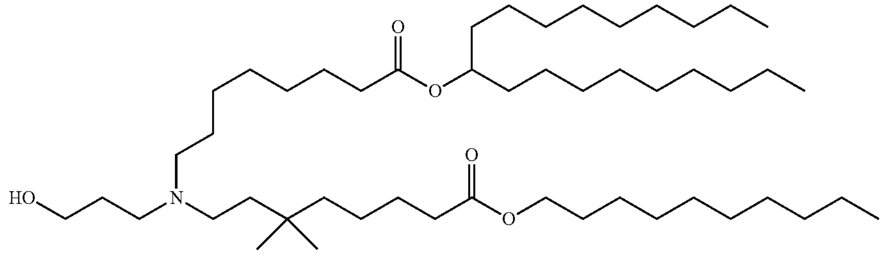
67a
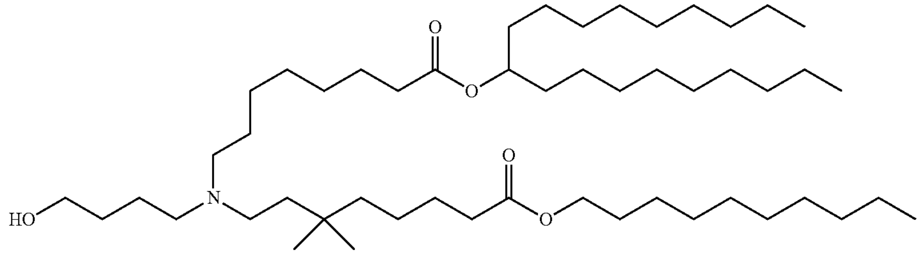
68a
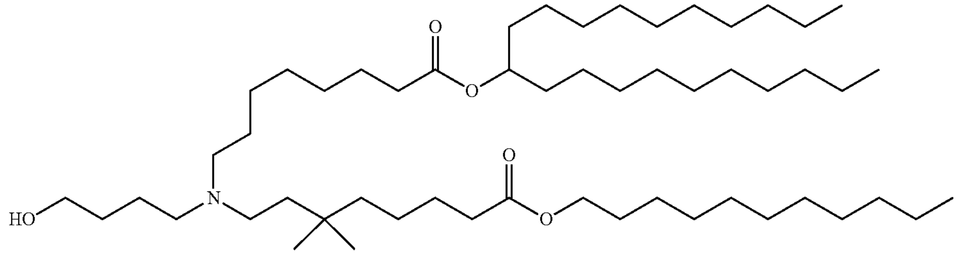

-continued
69a
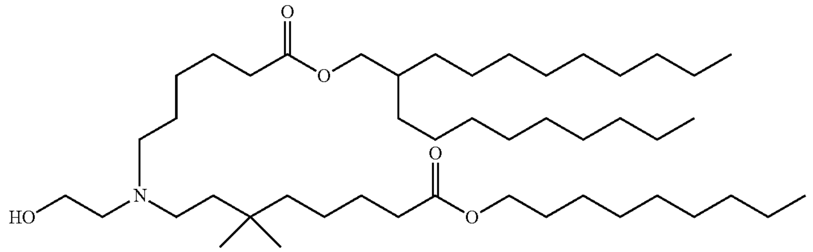
70a
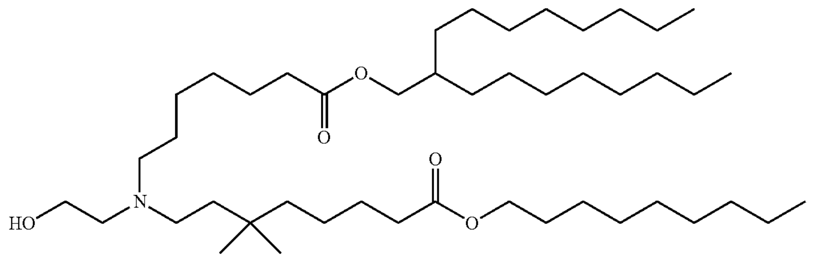
38b
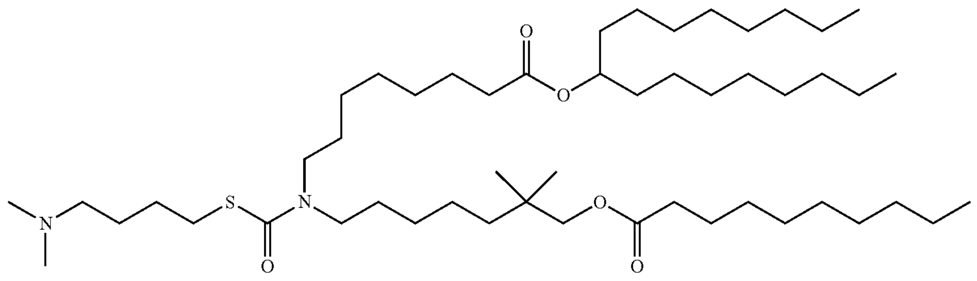
39b
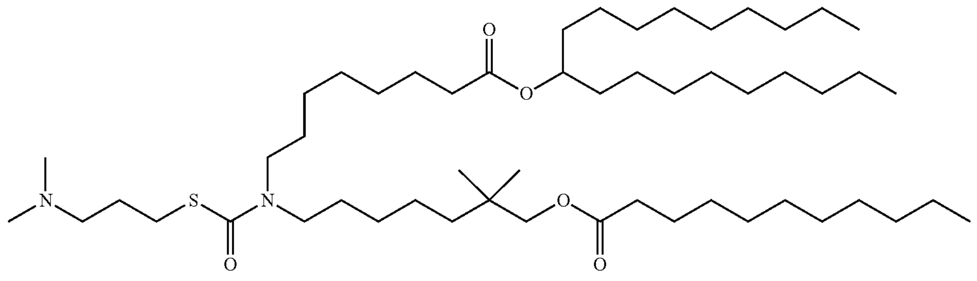
40b
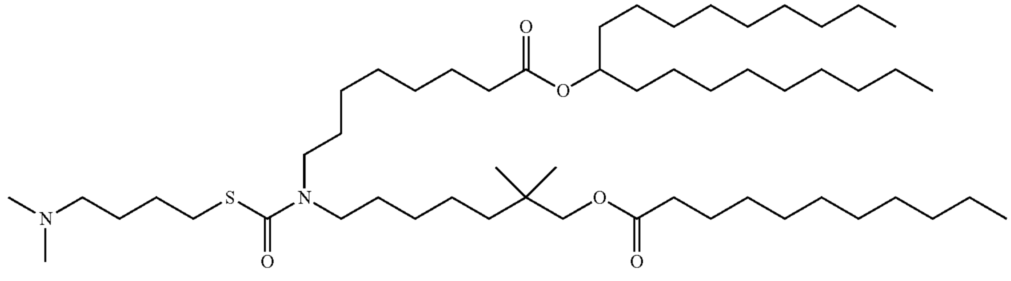

-continued
41b
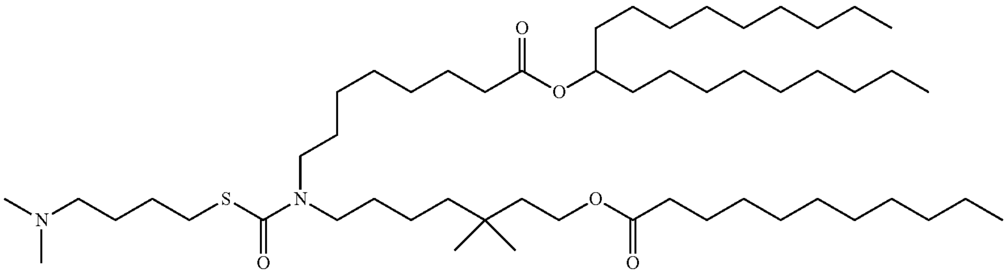
42b
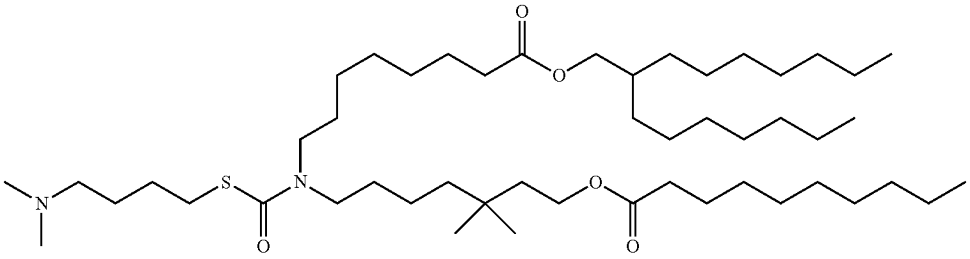
43b
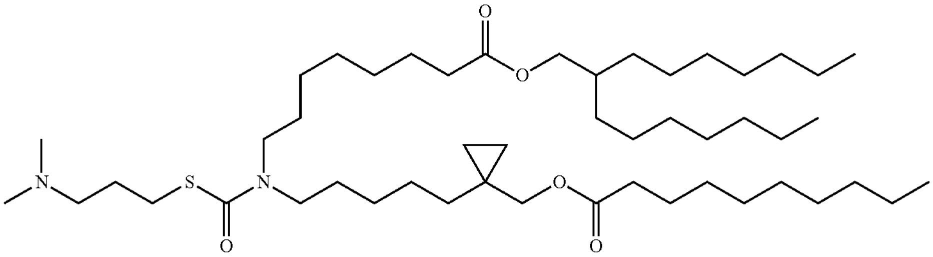
44b
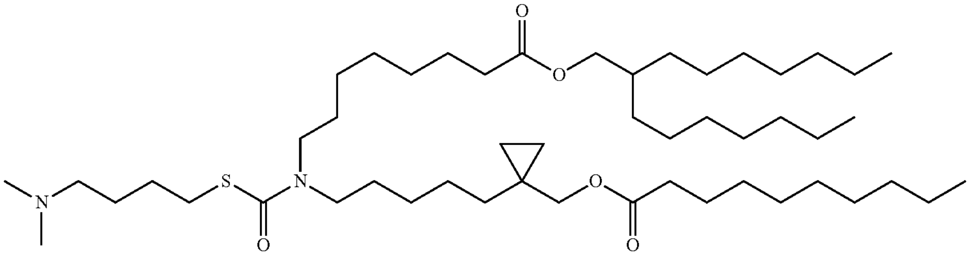
45b
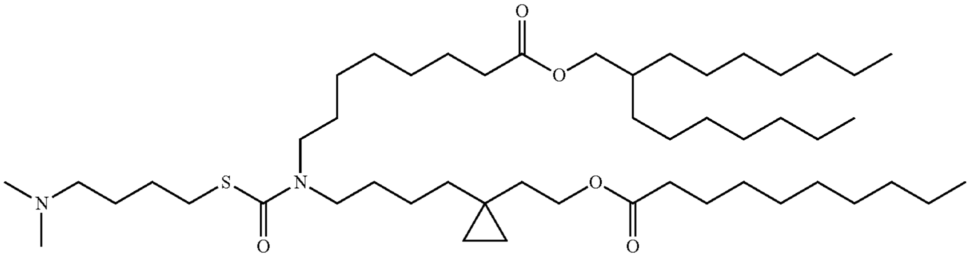
46b
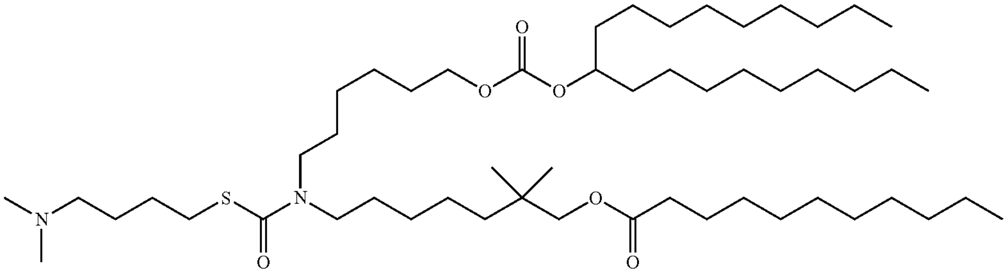

-continued
47b
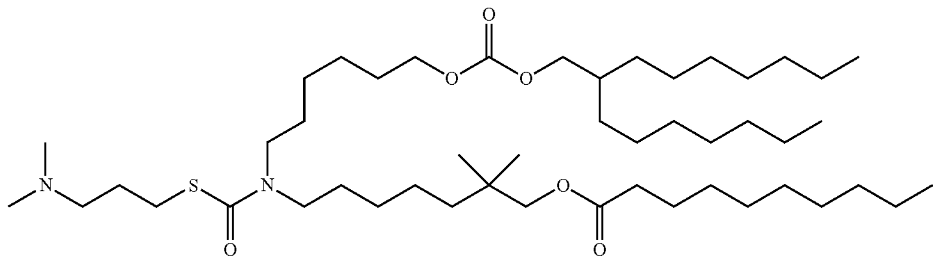
48b
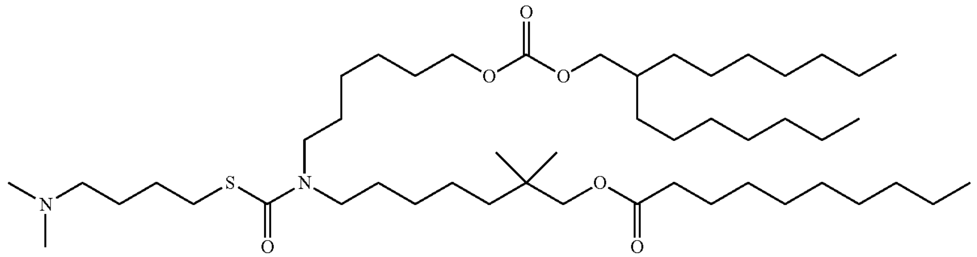
49b
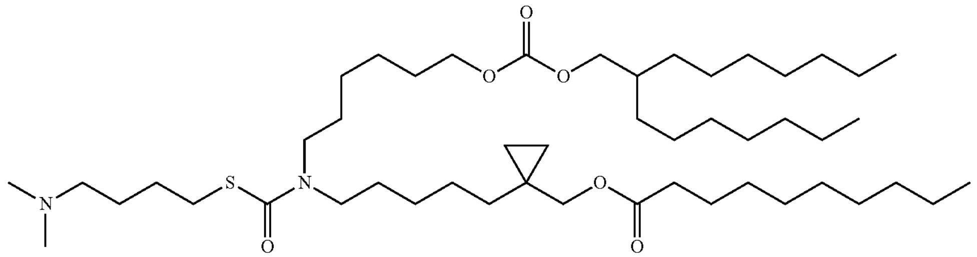
50b
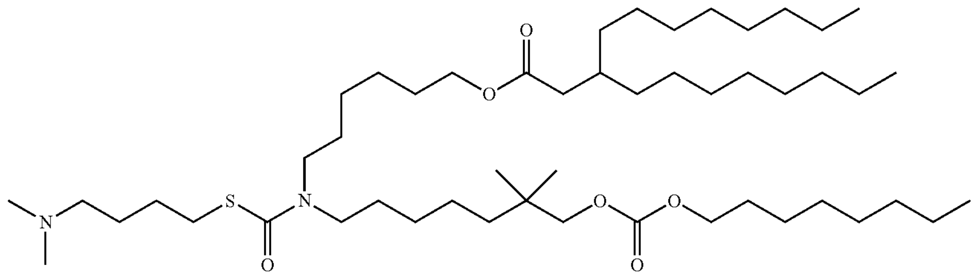
51b
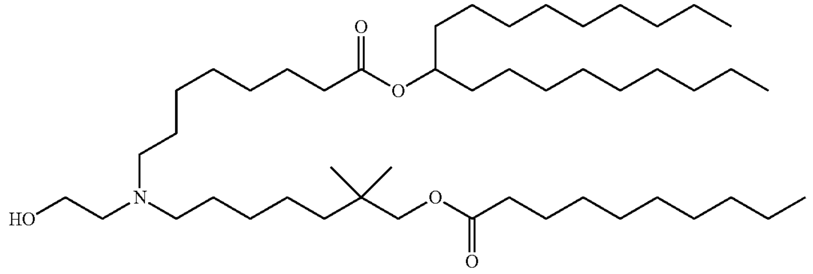

-continued
52b
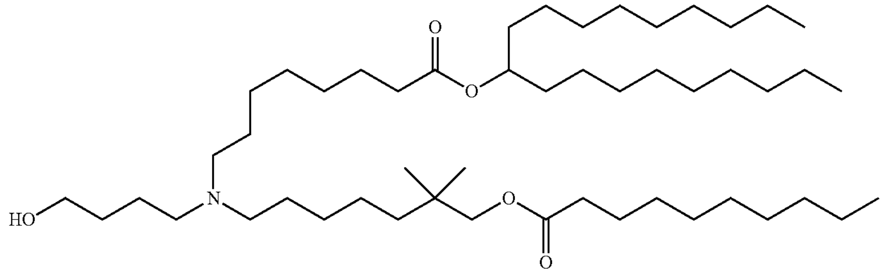
53b
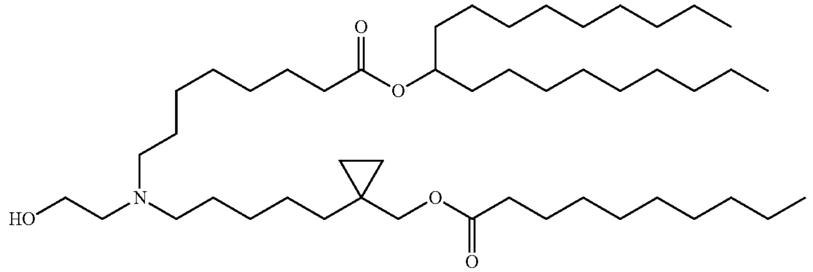
54b
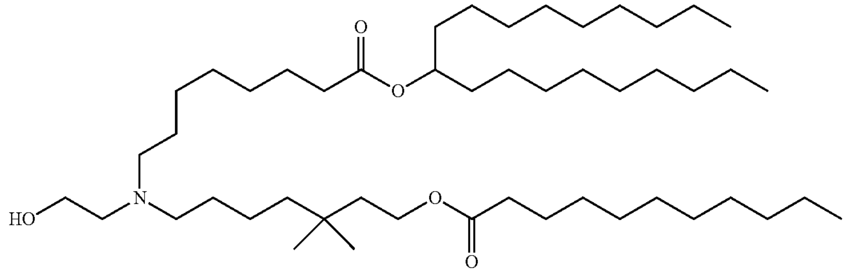
55b
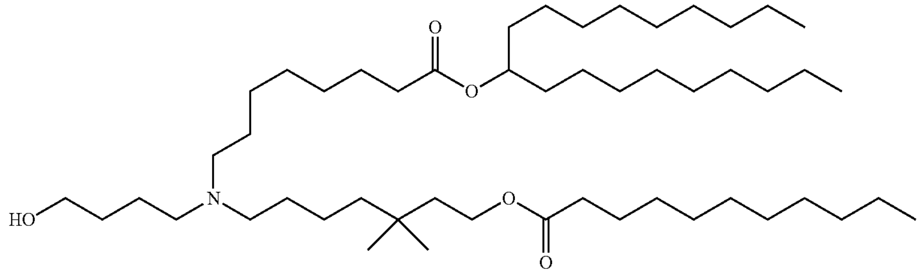
56b
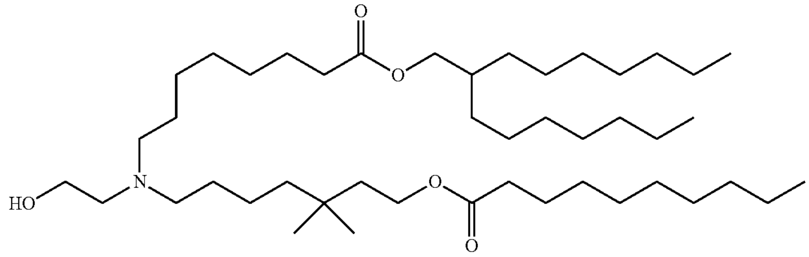
57b
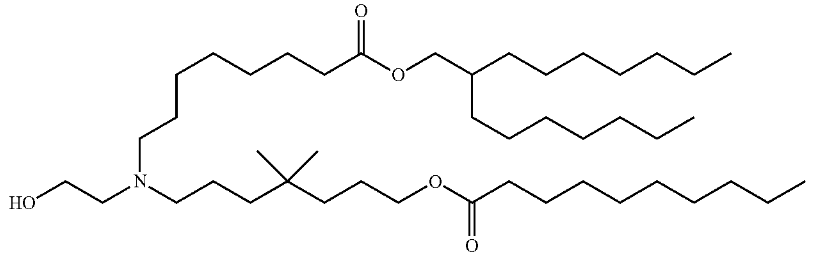

-continued
58b
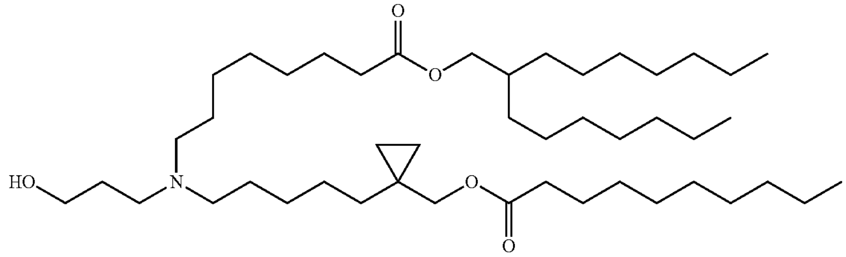
59b
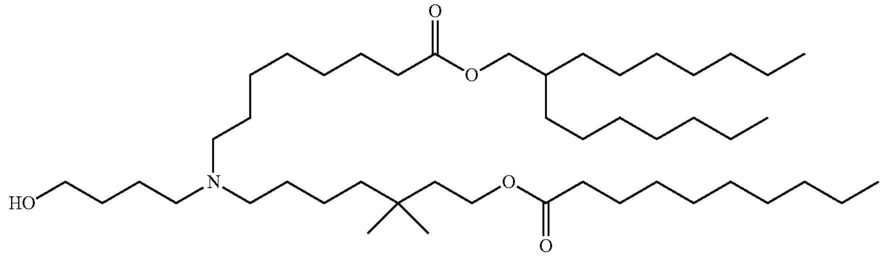
60b
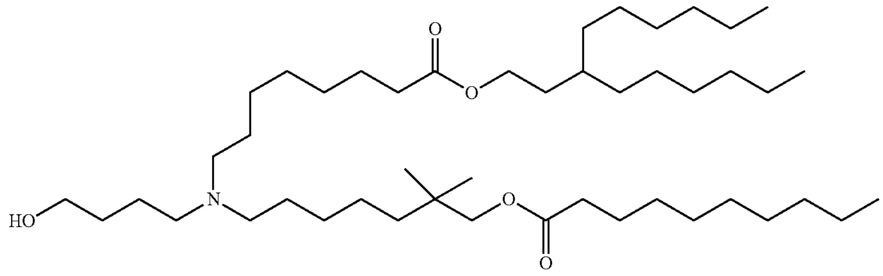
61b
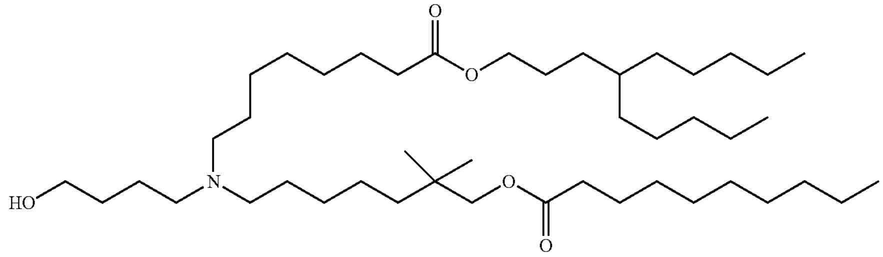
62b
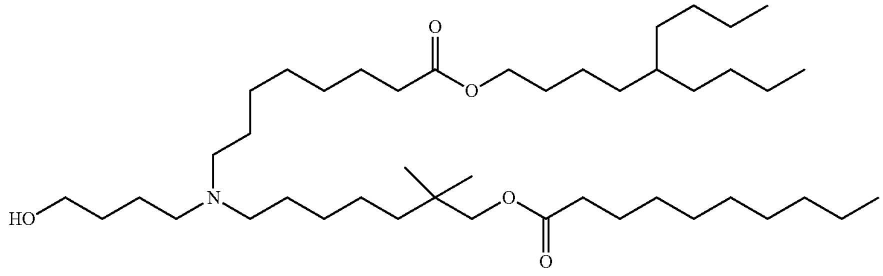
63b
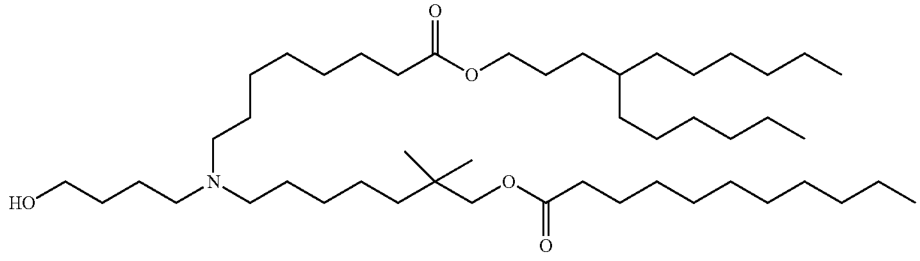

-continued
64b
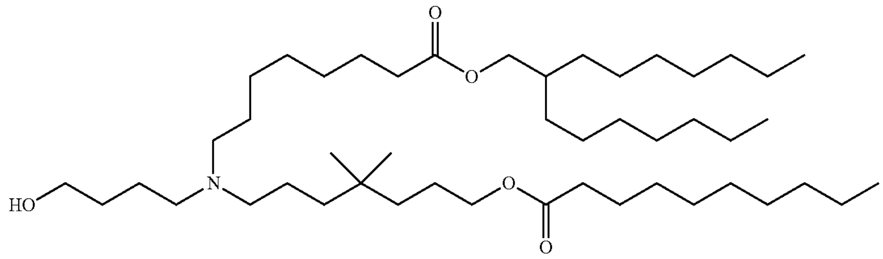
65b
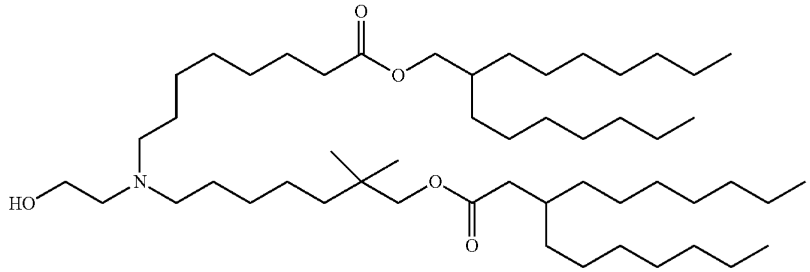
66b
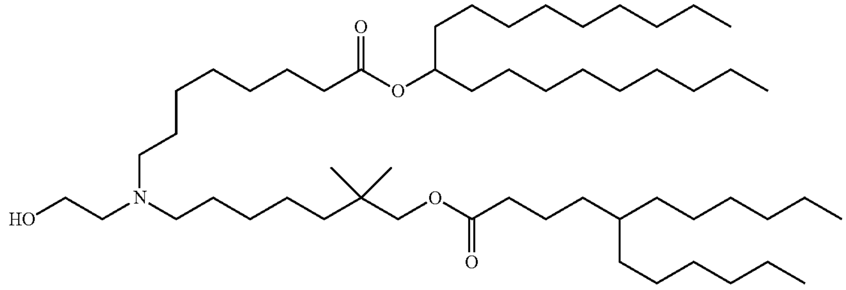
67b
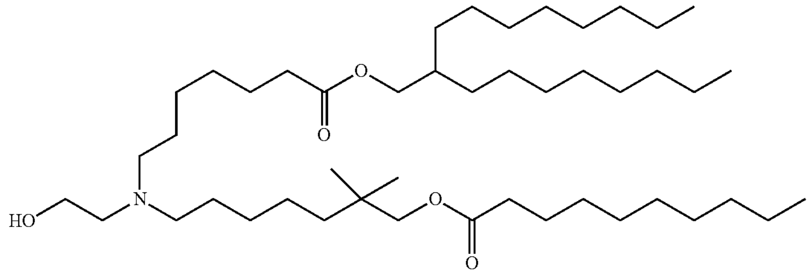
68b
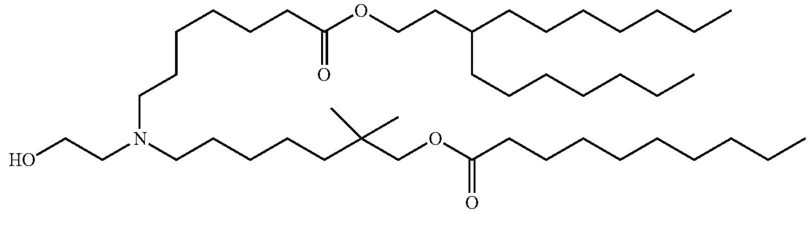
69b
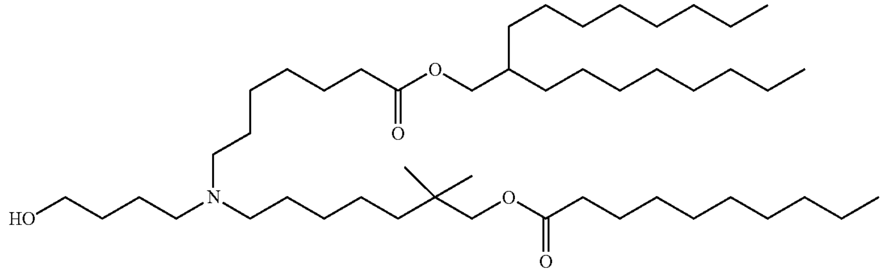

-continued
70b
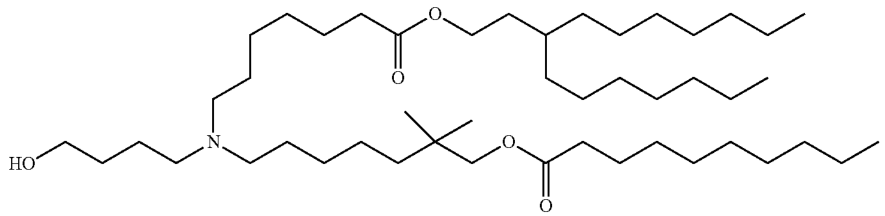
71b
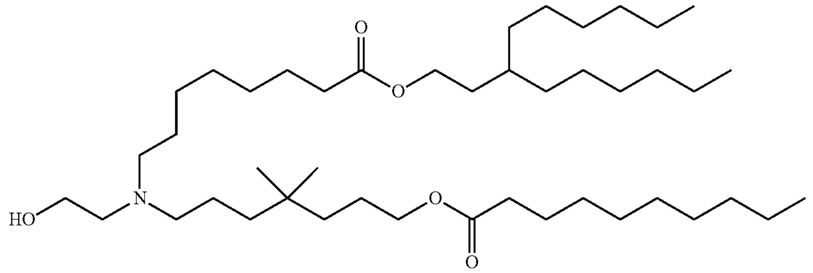
72b
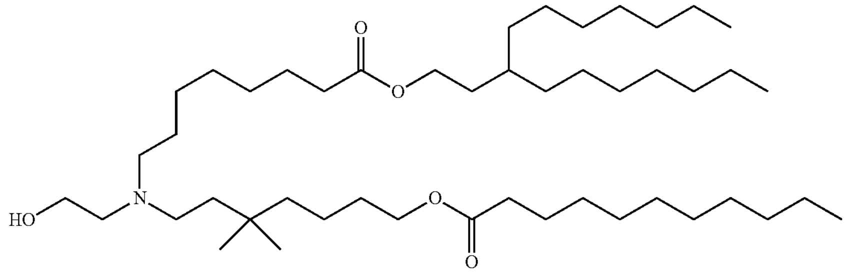
73b
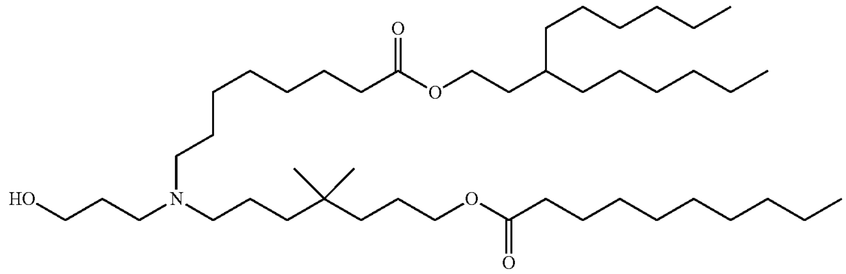
74b
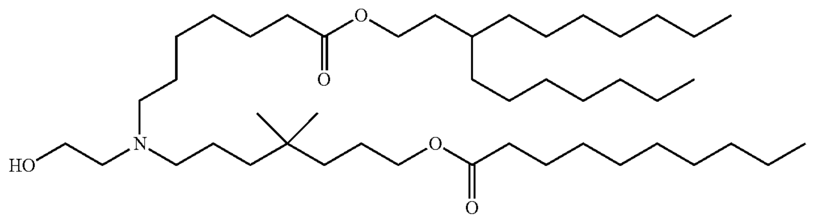
75b
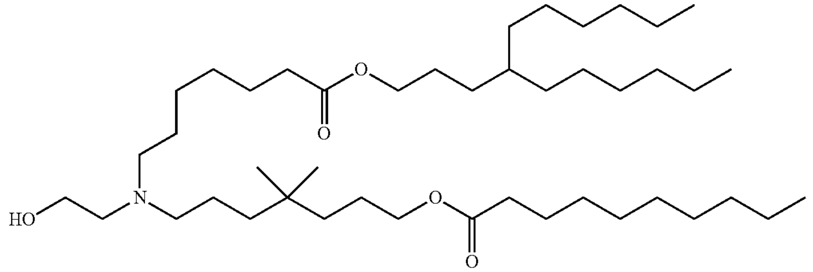

-continued
76b
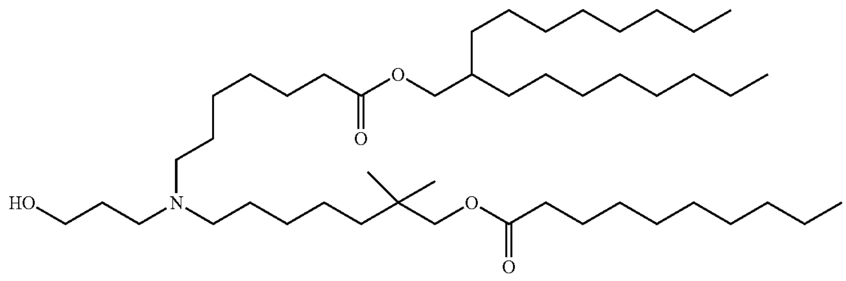
77b
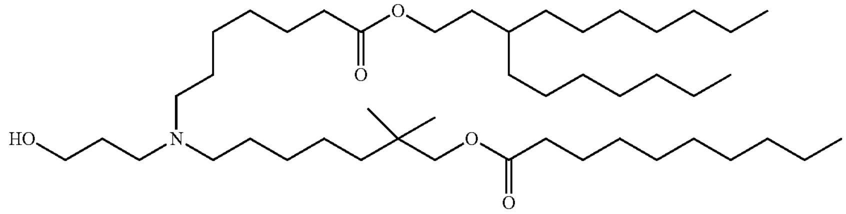
78b
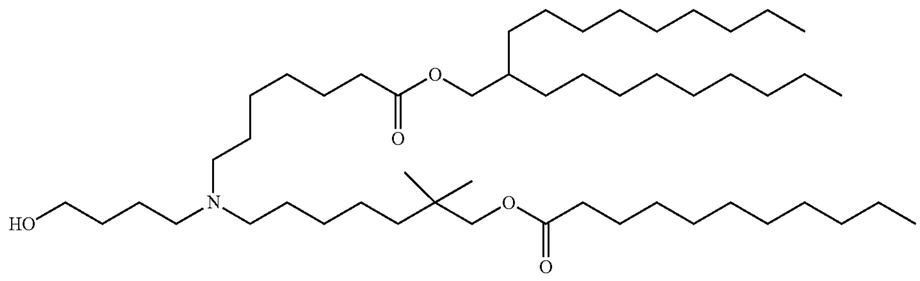
79b
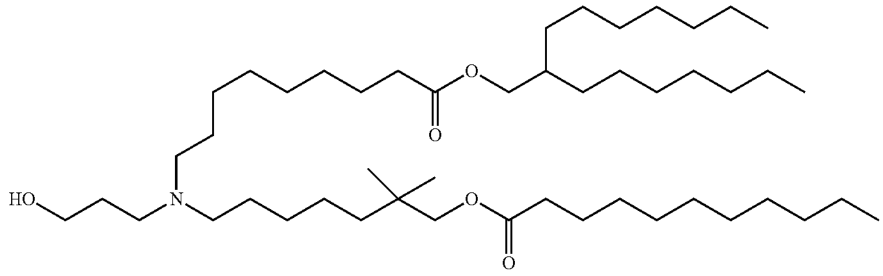
80b
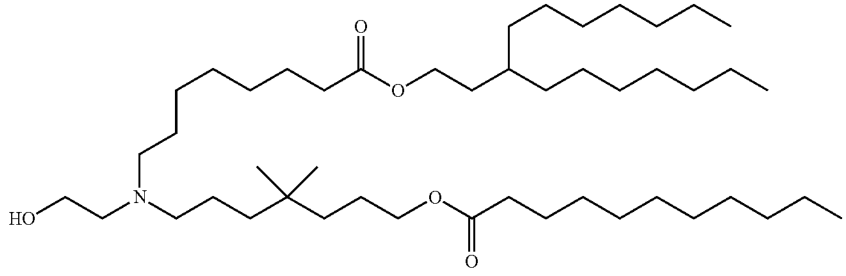

-continued
81b
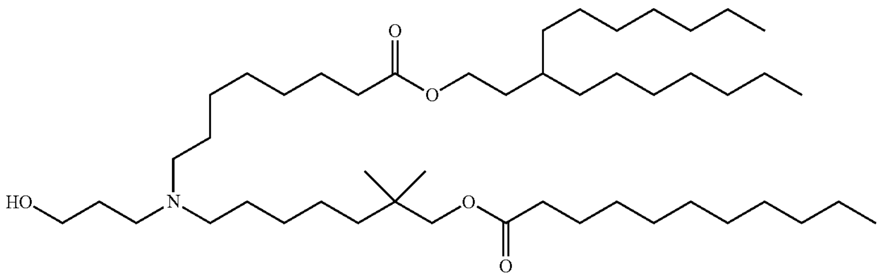
82b
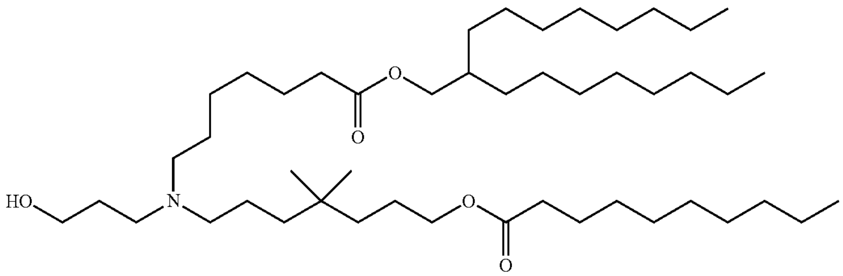
83b
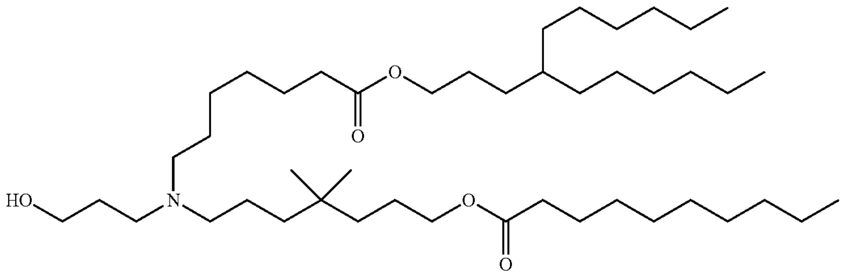
84b
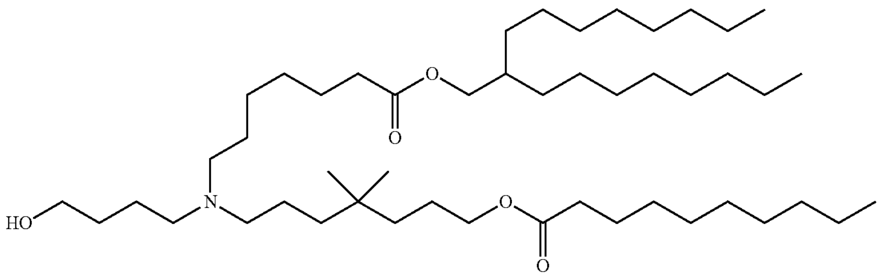
85b
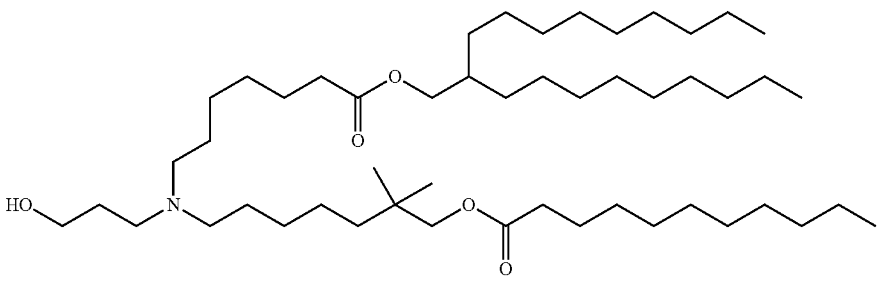

-continued
86b
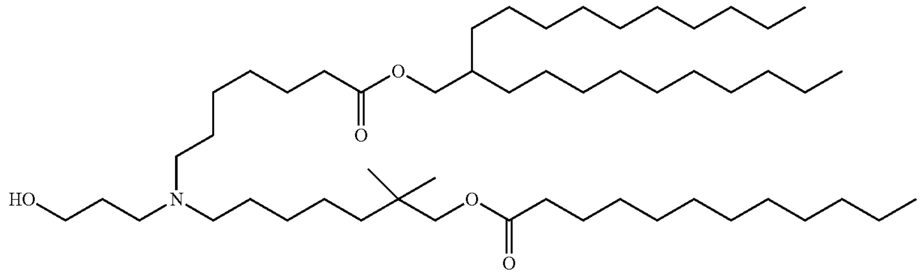
87b
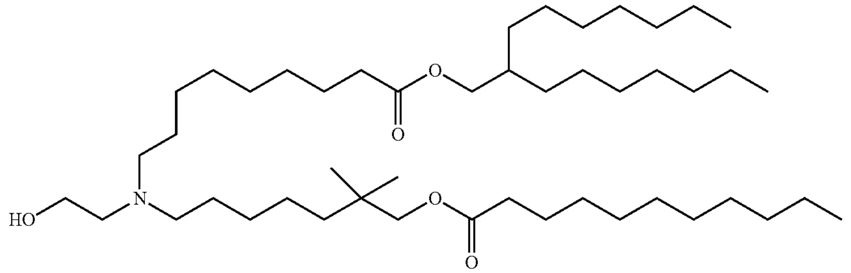
88b
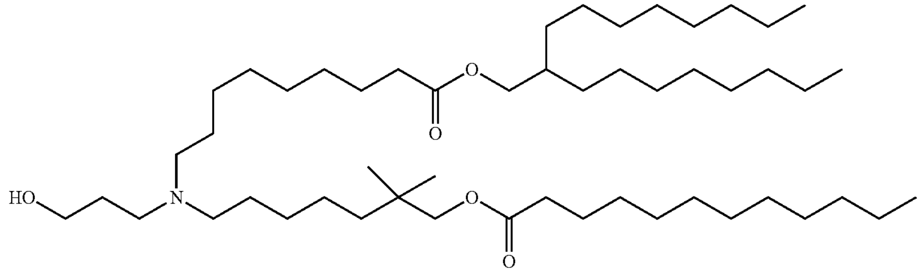
89b
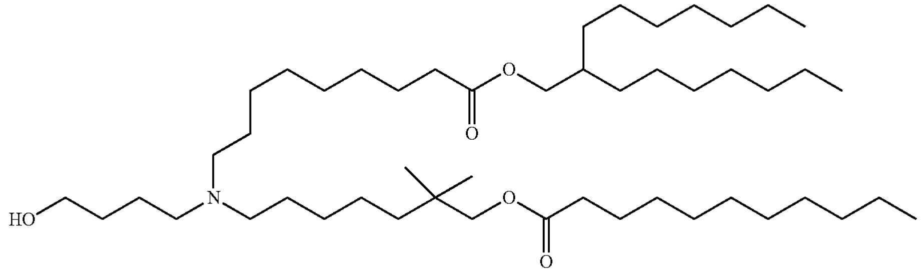
90b
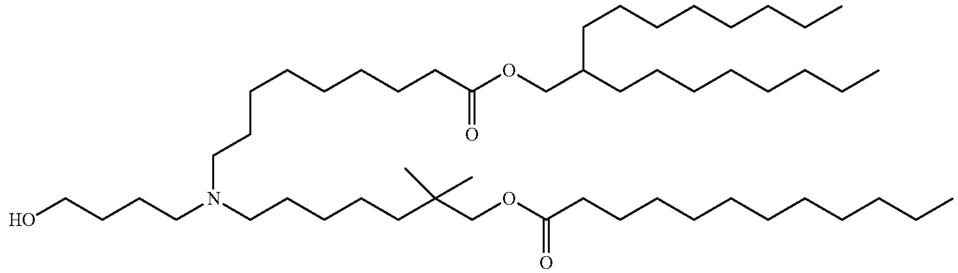

-continued
91b
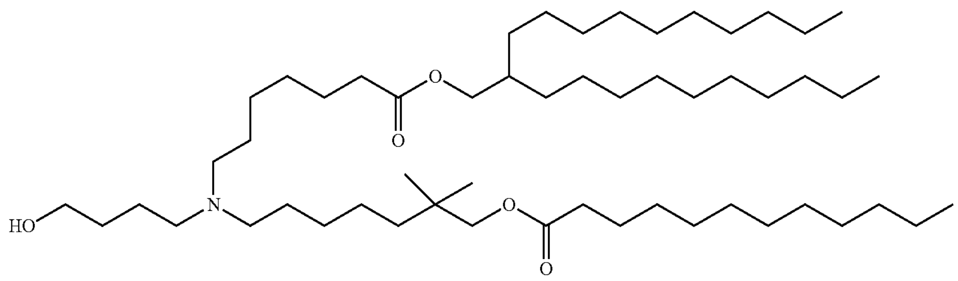
92b
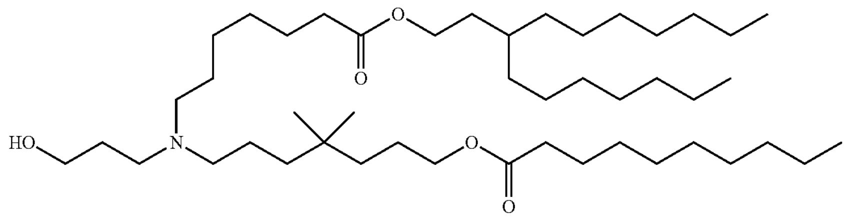
93b
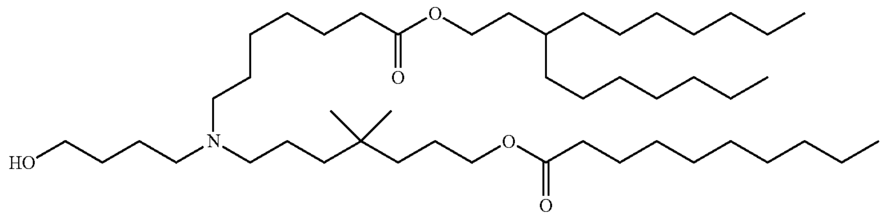
94b
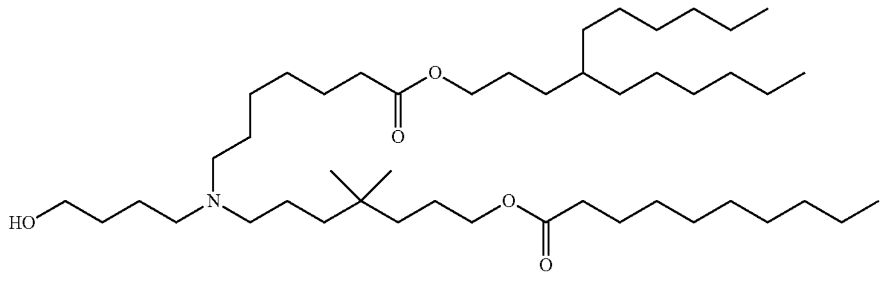
95b
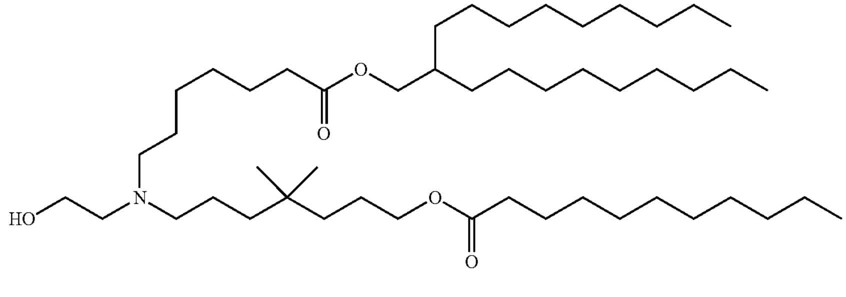

-continued
96b
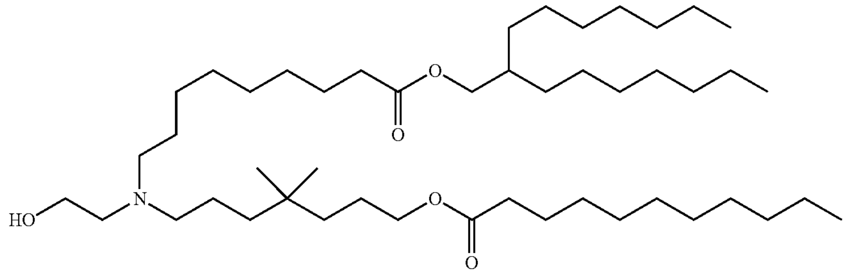
97b
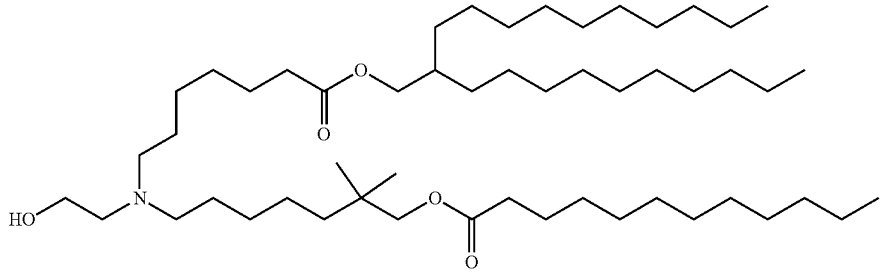
98b
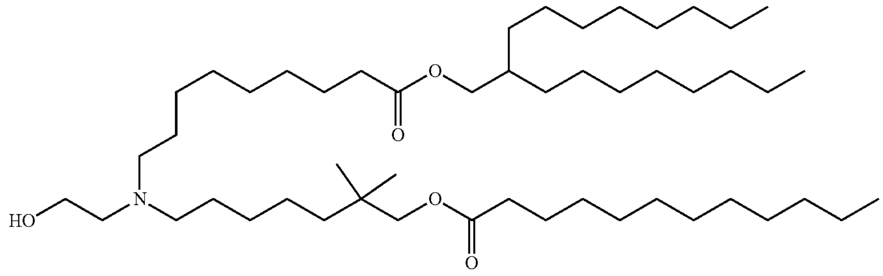
99b
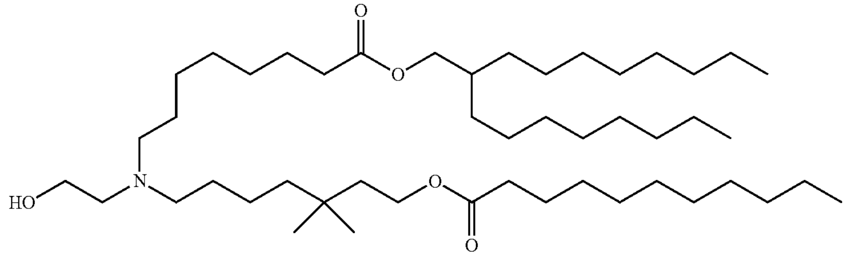
100b
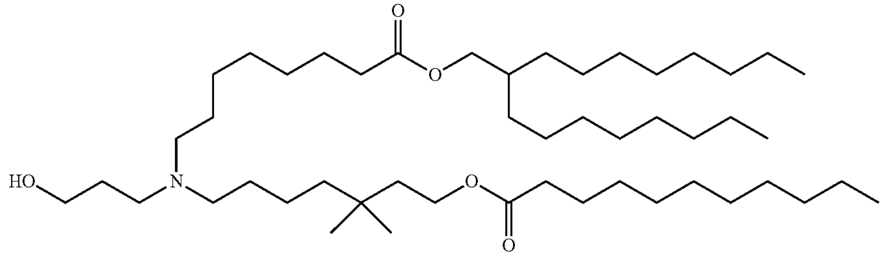
101b
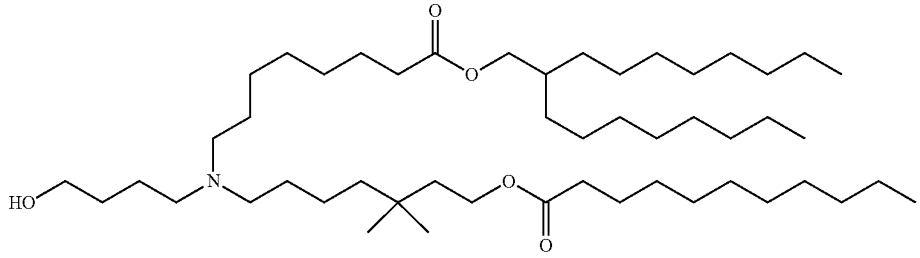

-continued
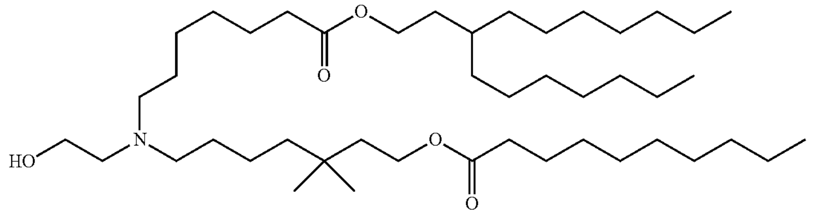
102b
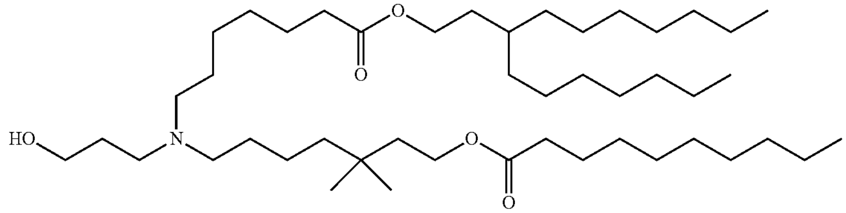
103b
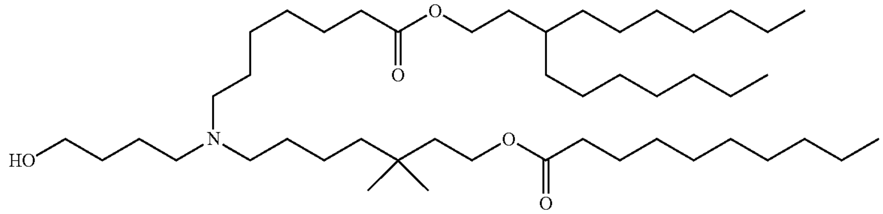
104b
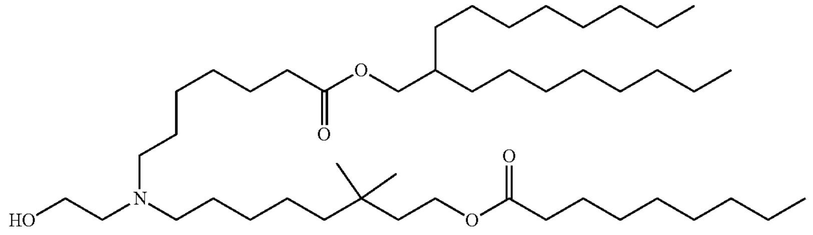
105b
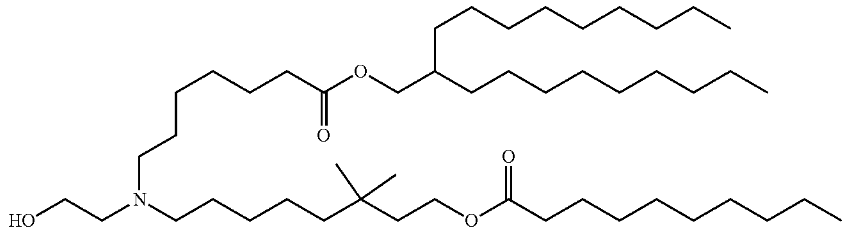
106b
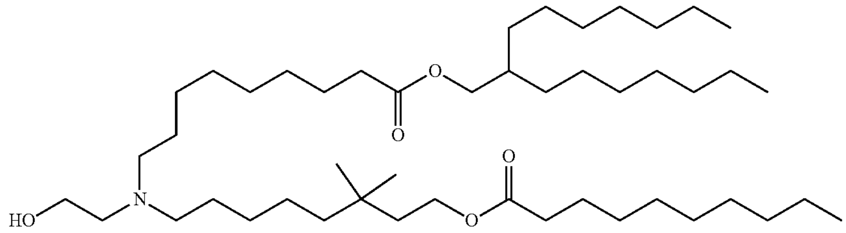
107b
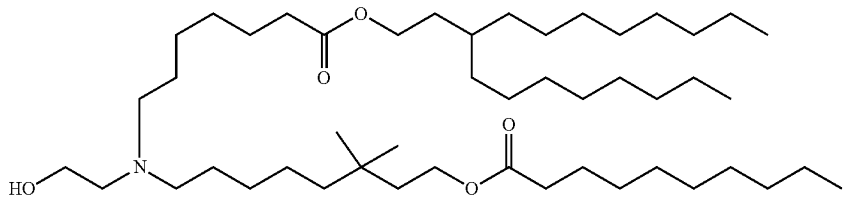
108b -continued
109b
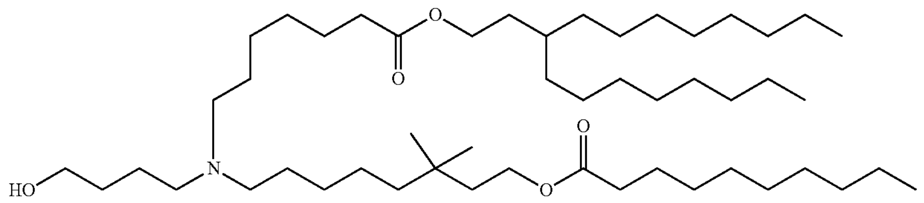
110b
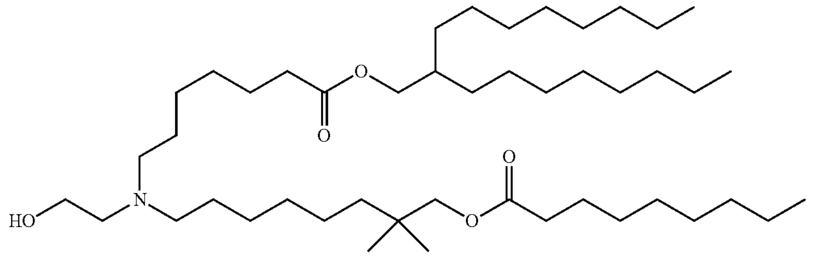
111b
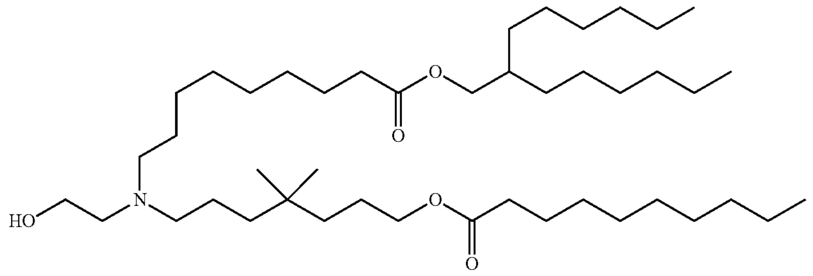
112b
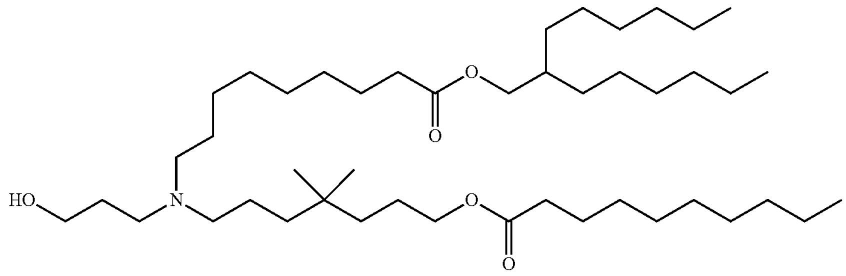
113b
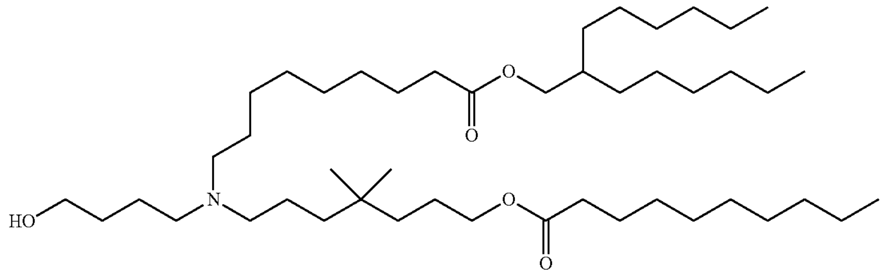
114b
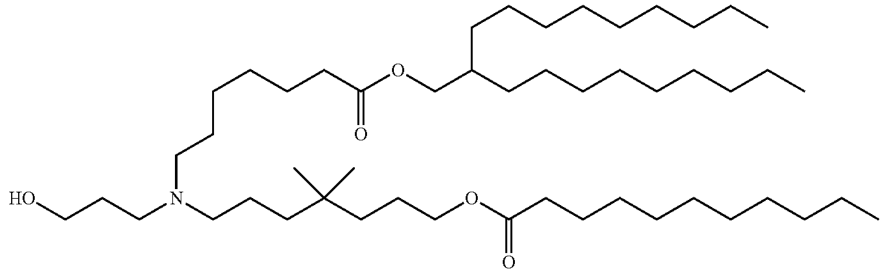

-continued
115b
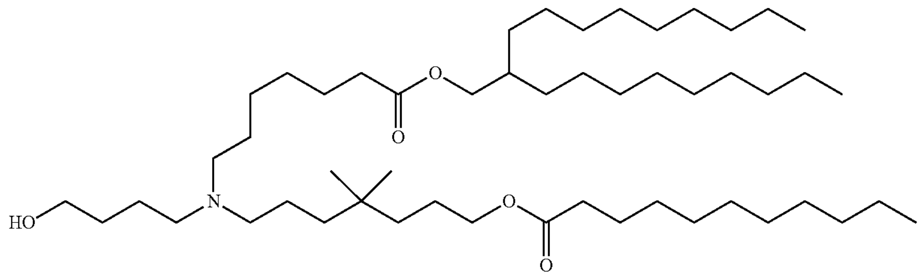
116b
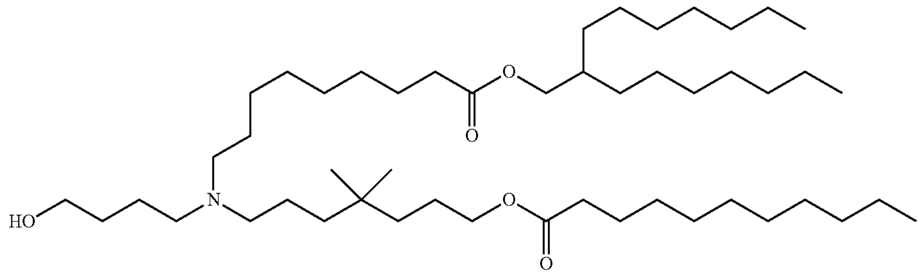
117b
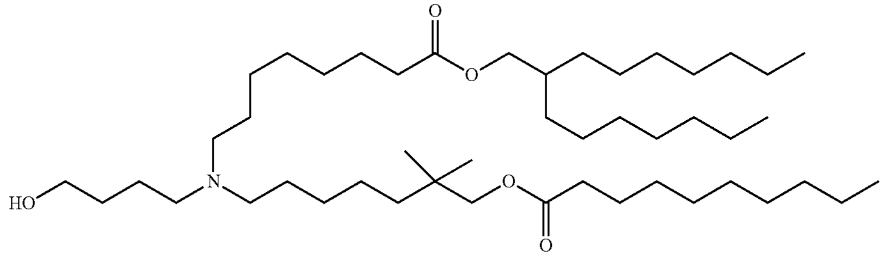
1c
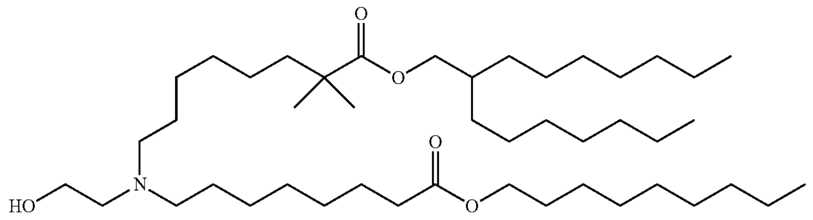
2c
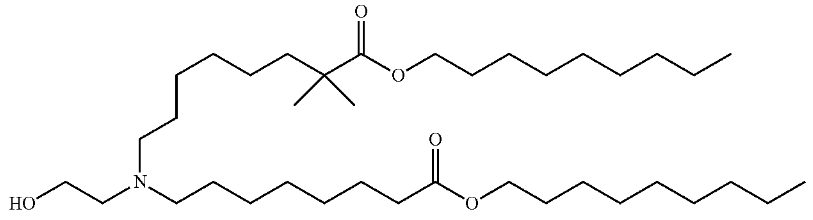
3c
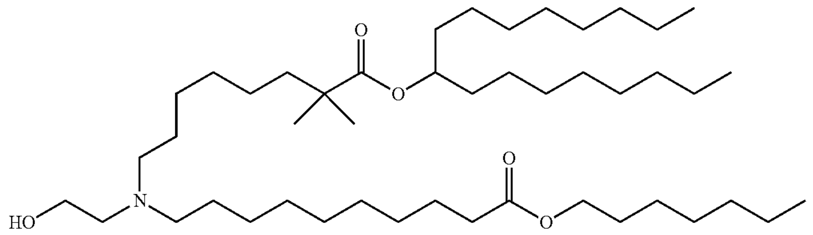

-continued
4c
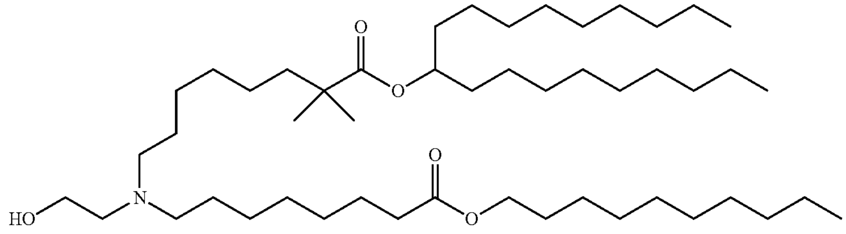
5c
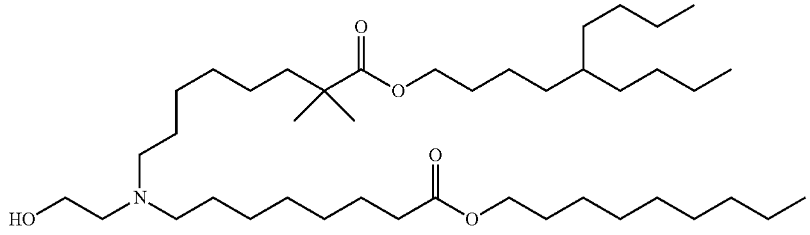
6c
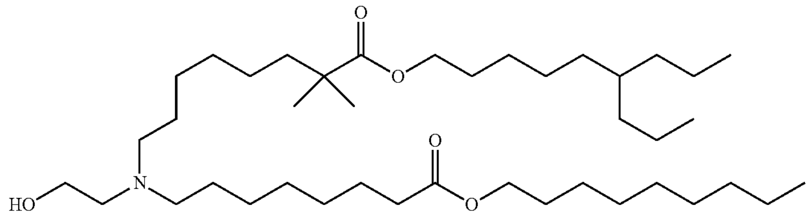
7c
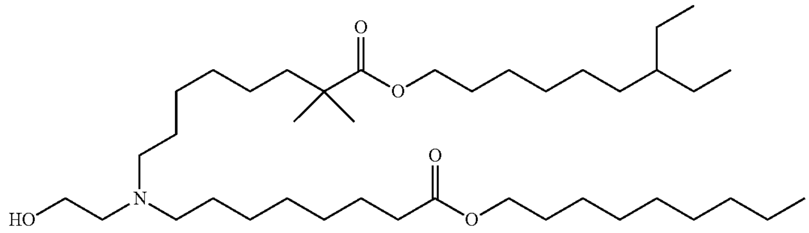
8c
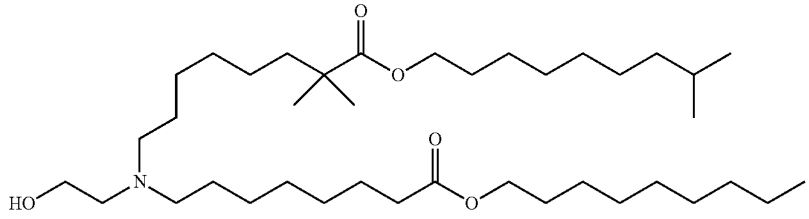
9c
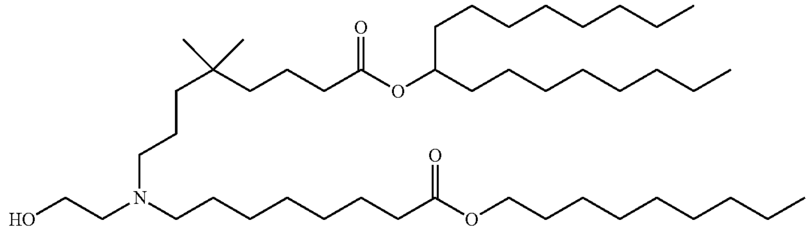
10c
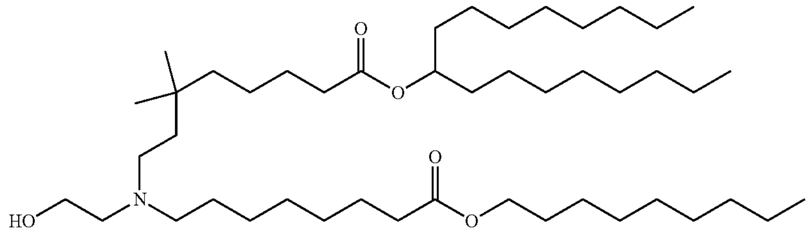

-continued
11c
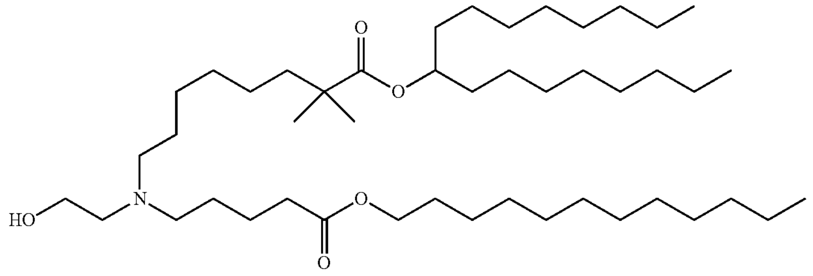
12c
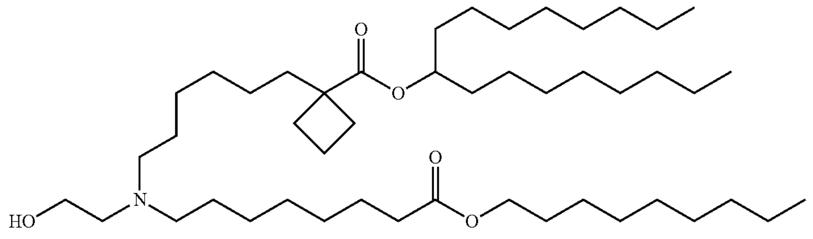
13c
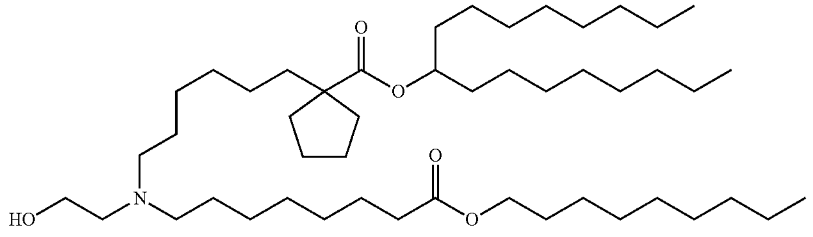
14c
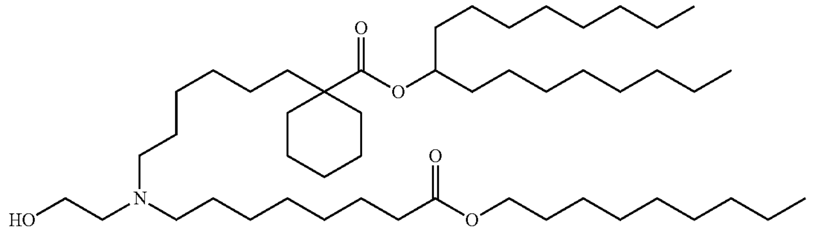
15c
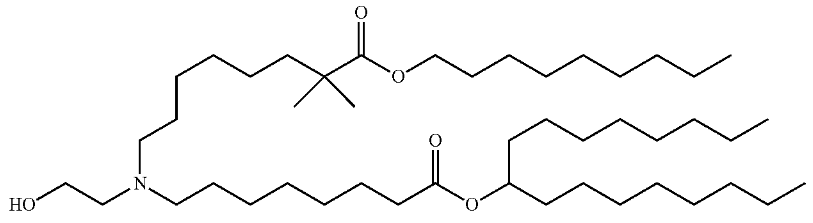
16c
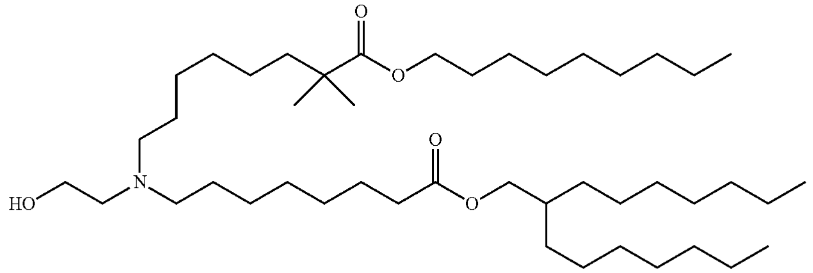

-continued
17c
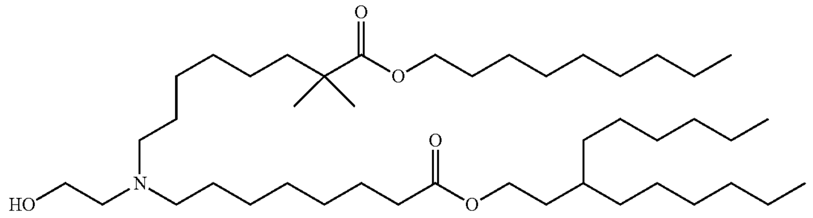
18c
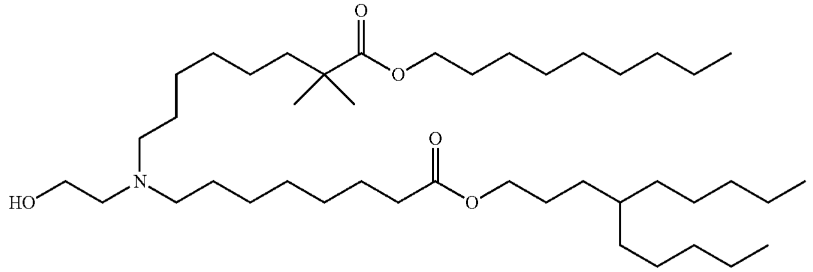
19c
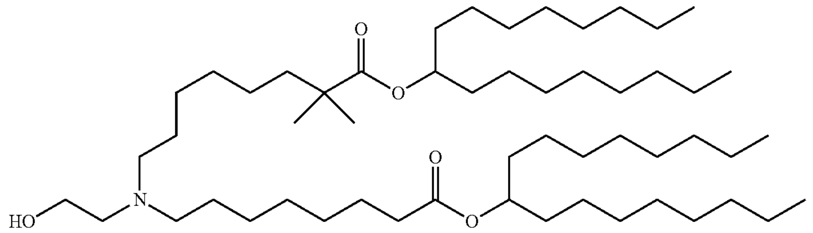
20c
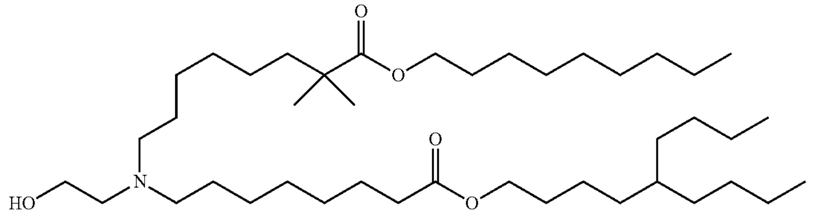
21c
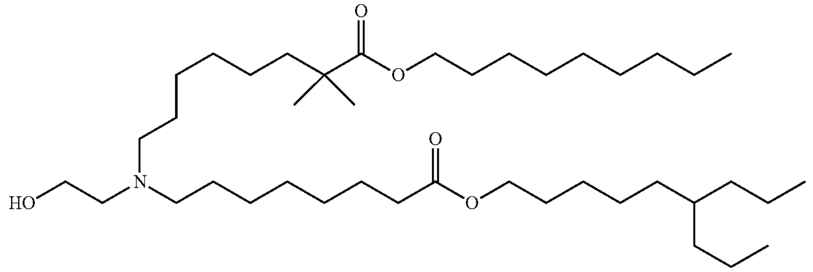
22c
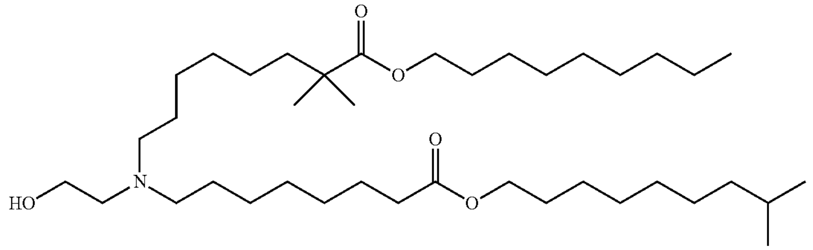

-continued
23c
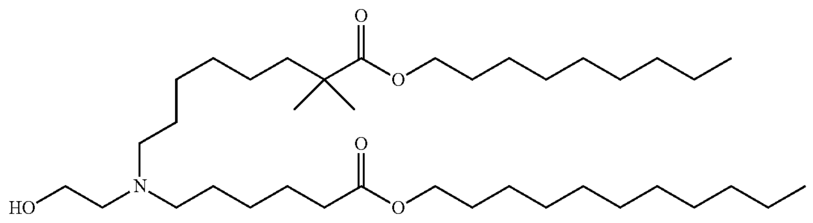
24c
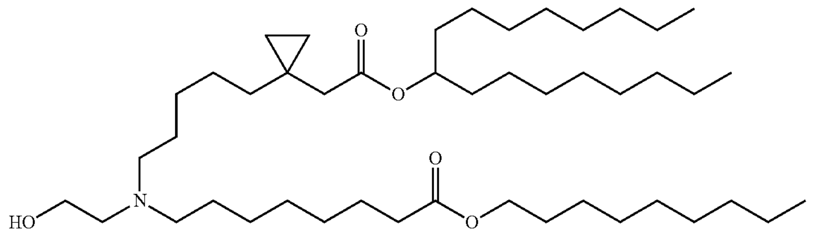
25c
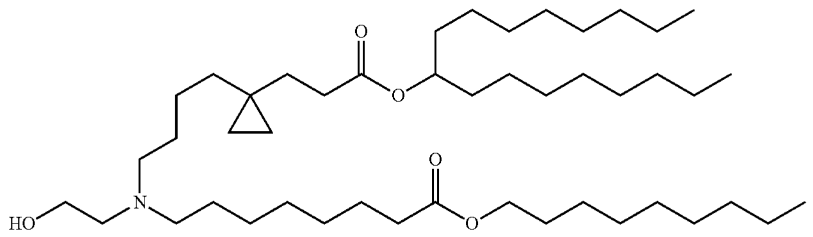
26c
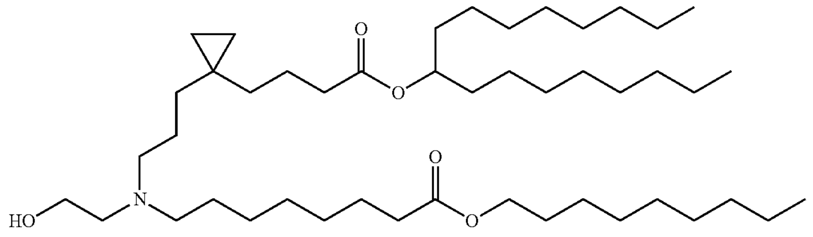
27c
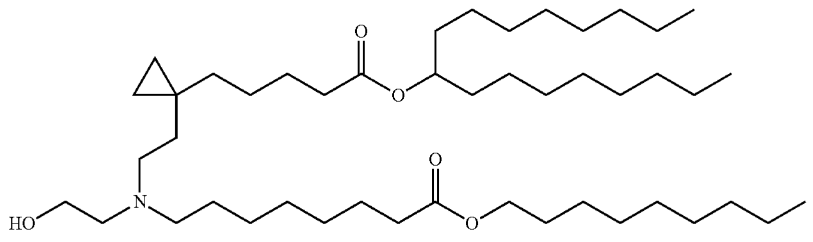
28c
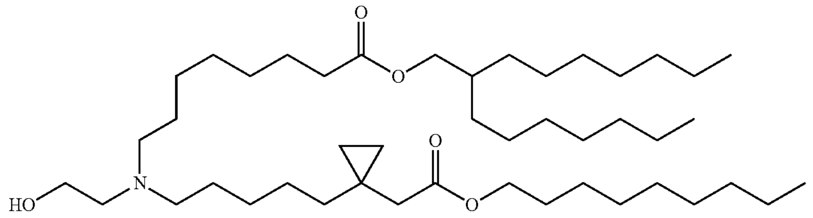

-continued
29c
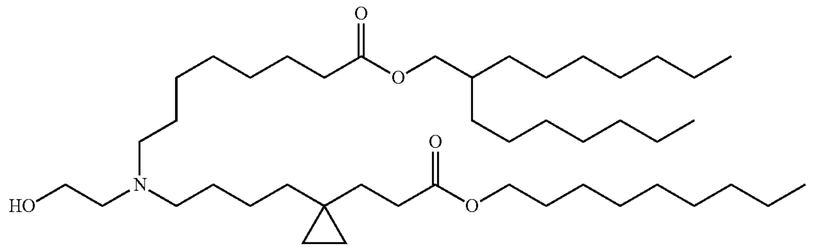
30c
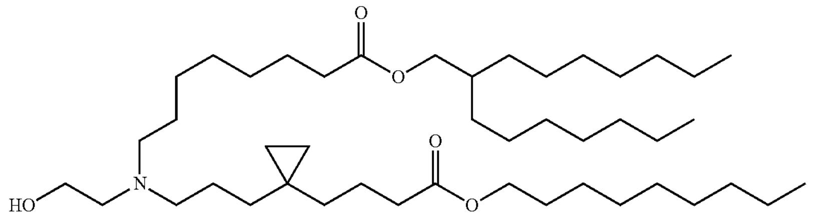
31c
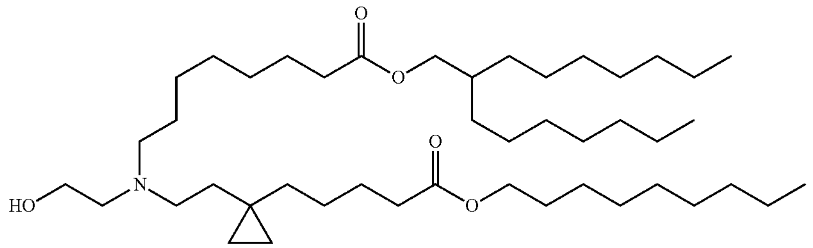
32c
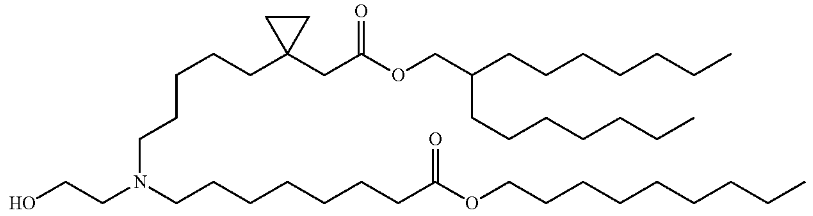
33c
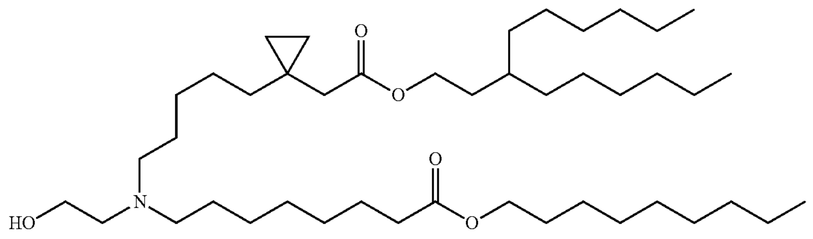
34c
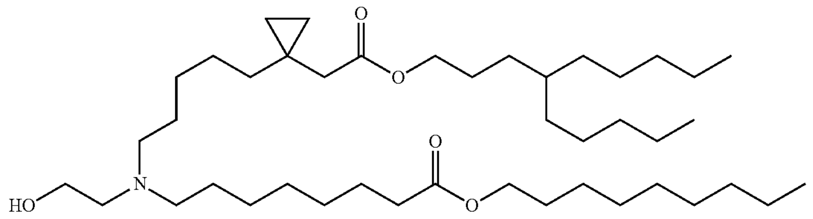

-continued
35c
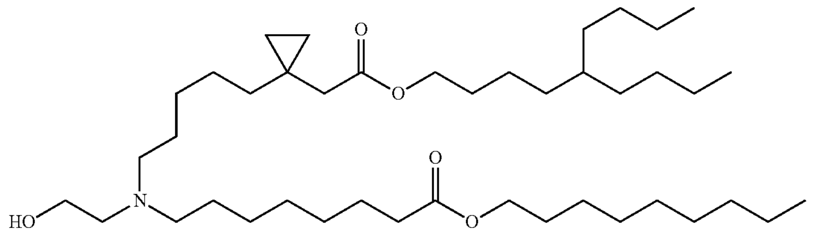
36c
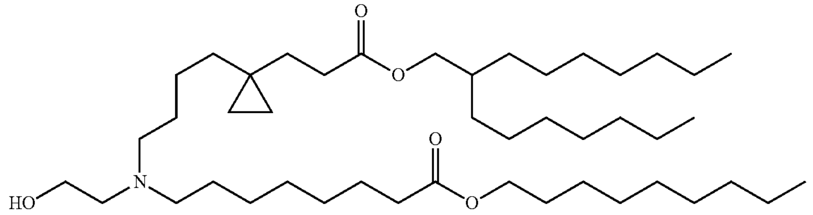
37c
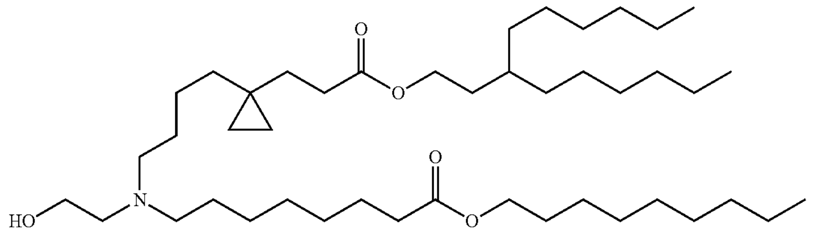
38c
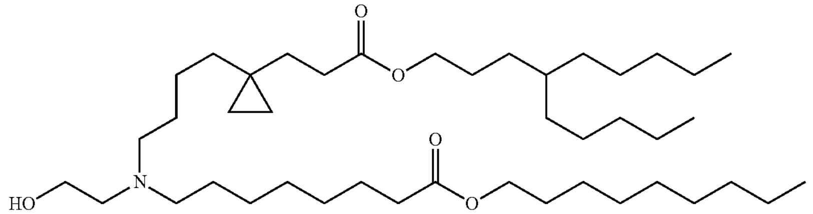
39c
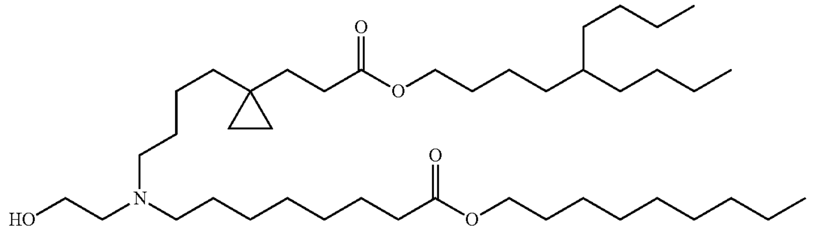
40c
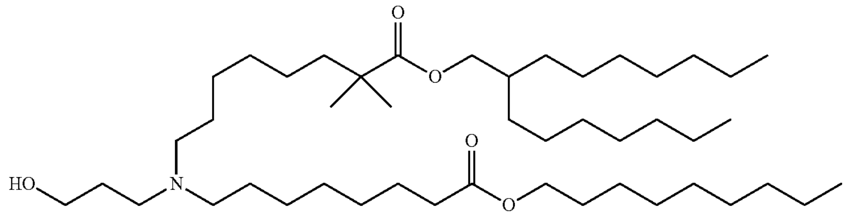
41c
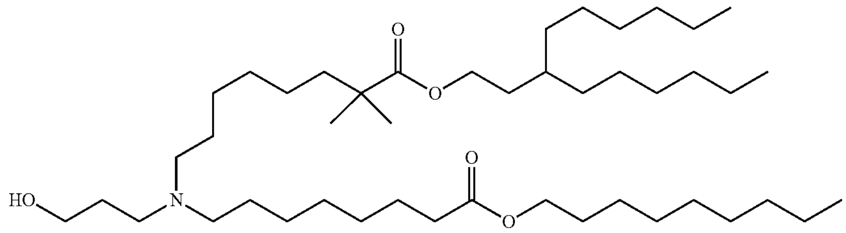

-continued
42c
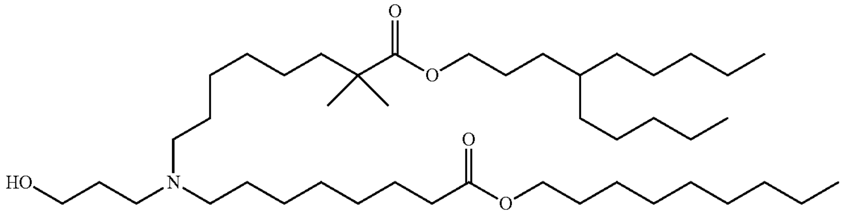
43c
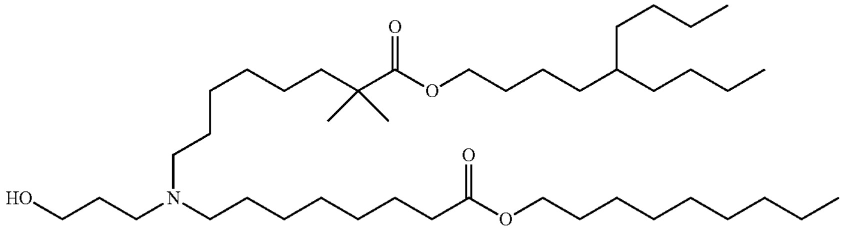
44c
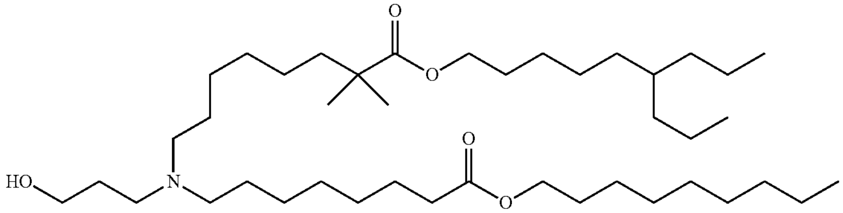
45c
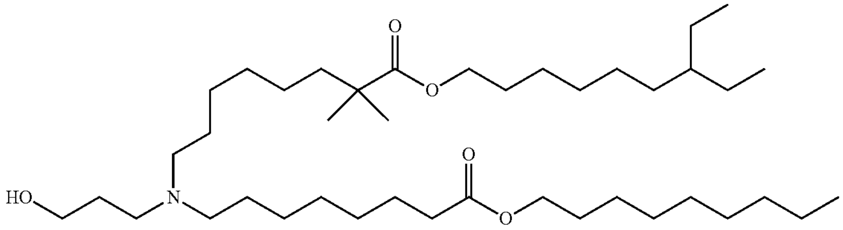
46c
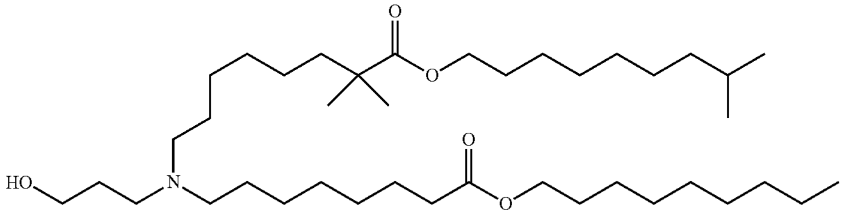
47c
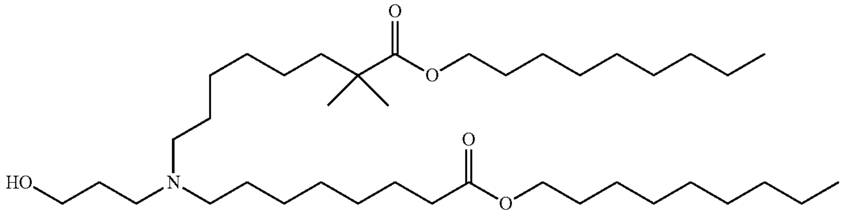
48c
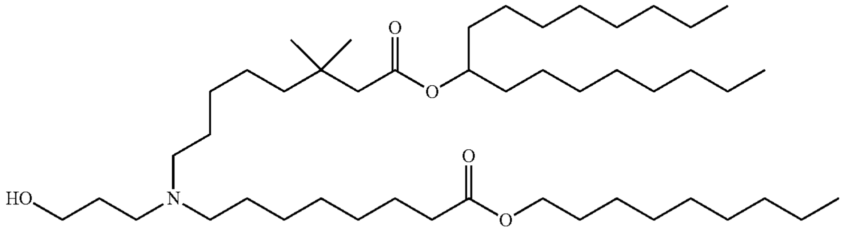

-continued
49c
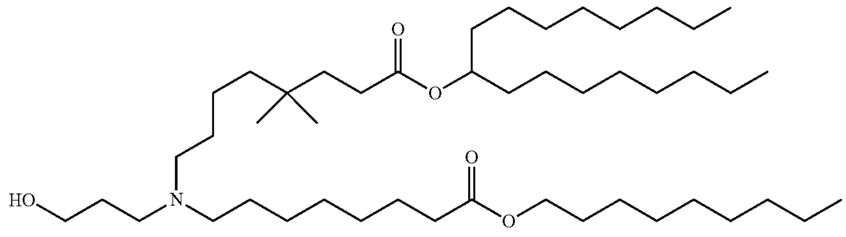
50c
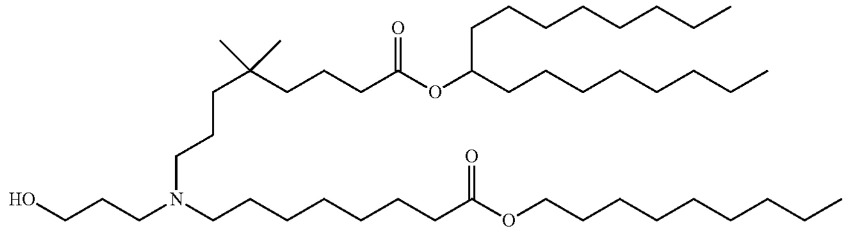
51c
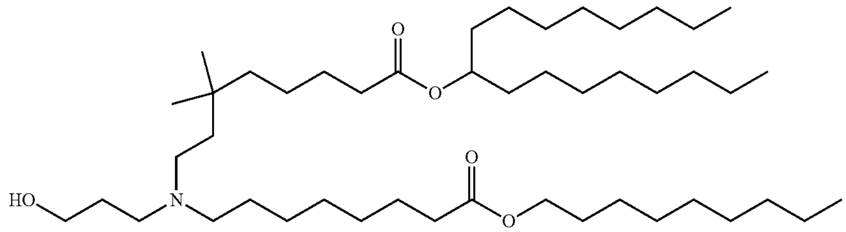
52c
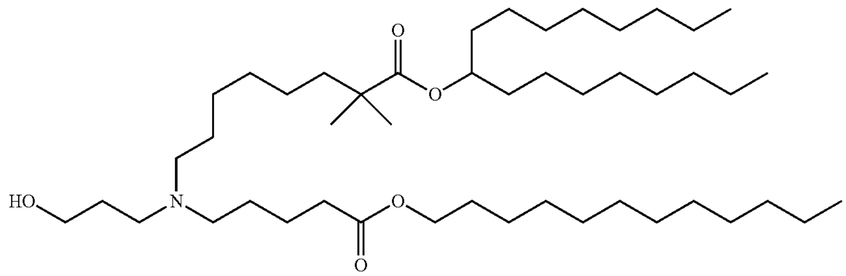
53c
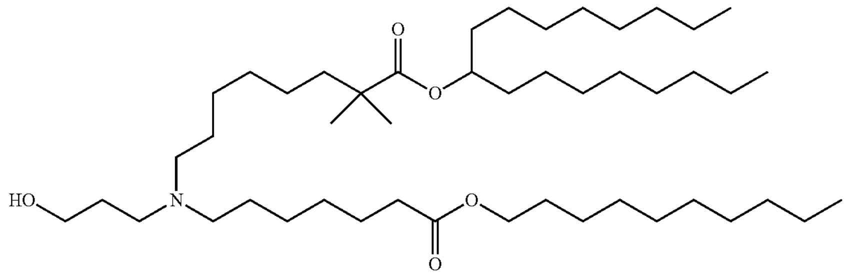
54c
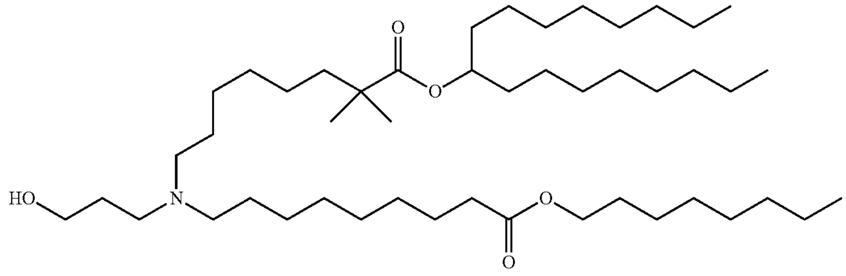

-continued
55c
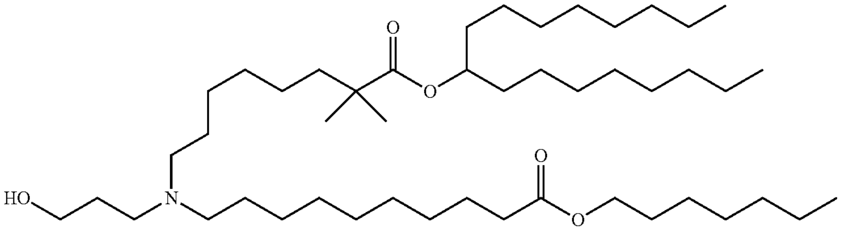
56c
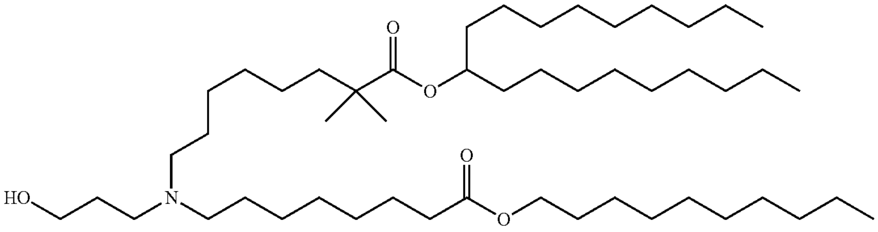
57c
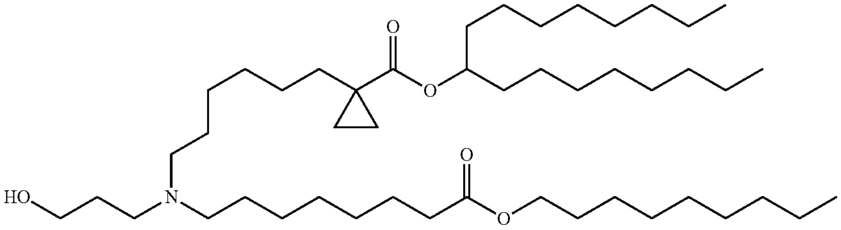
58c
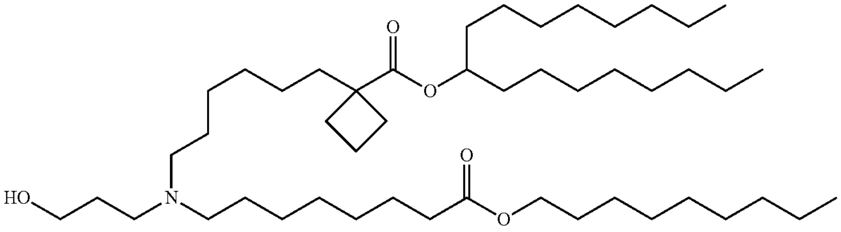
59c
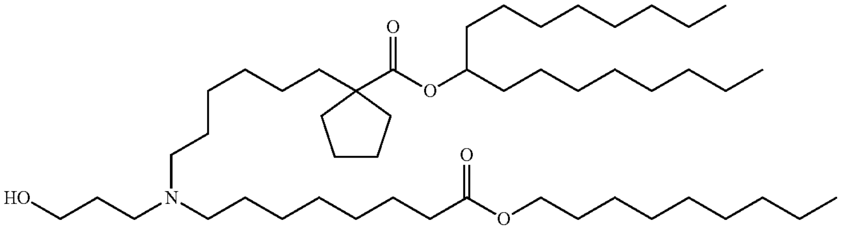
60c
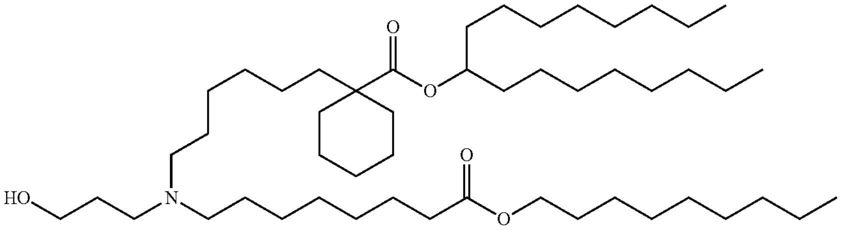

-continued
61c
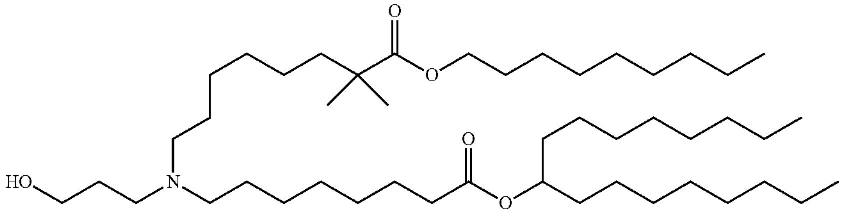
62c
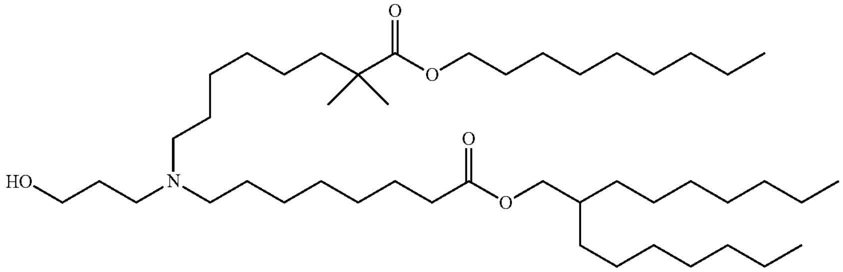
63c
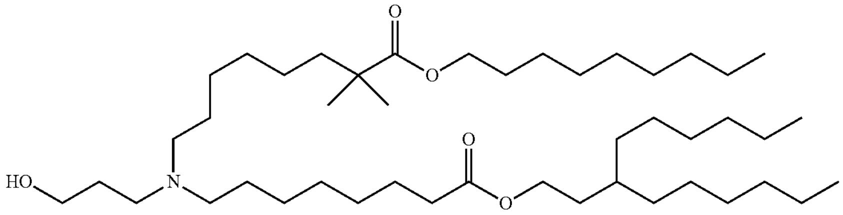
64c
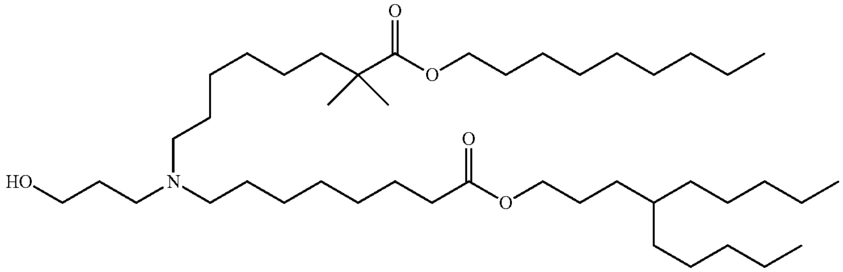
65c
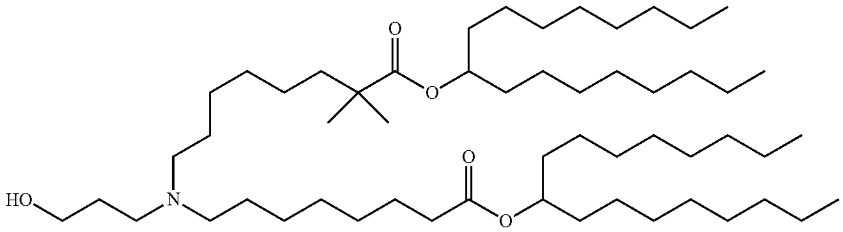
66c
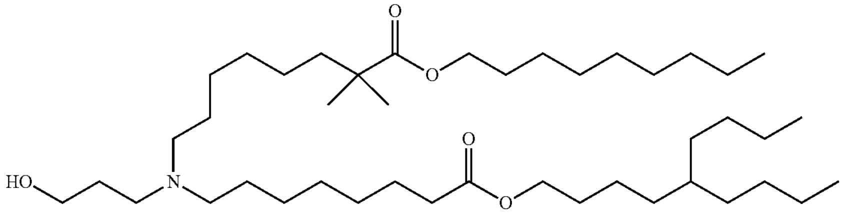

-continued
67c
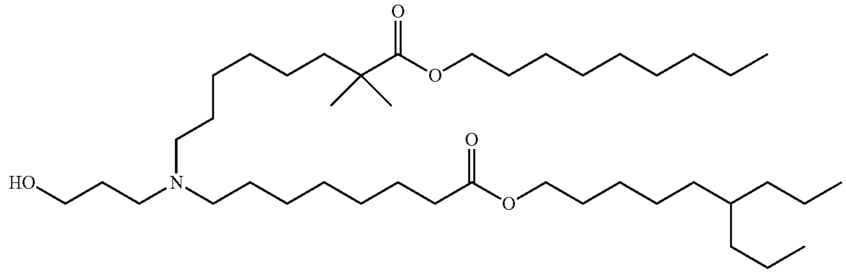
68c
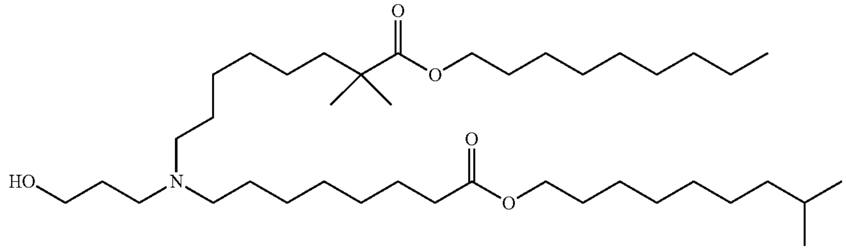
69c
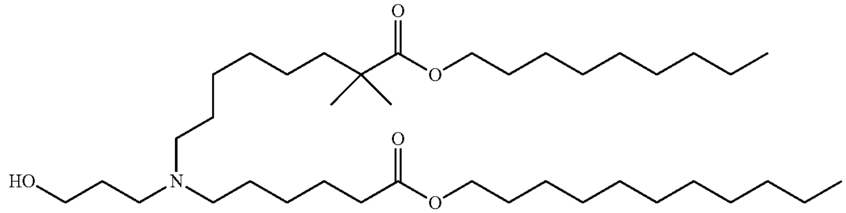
70c
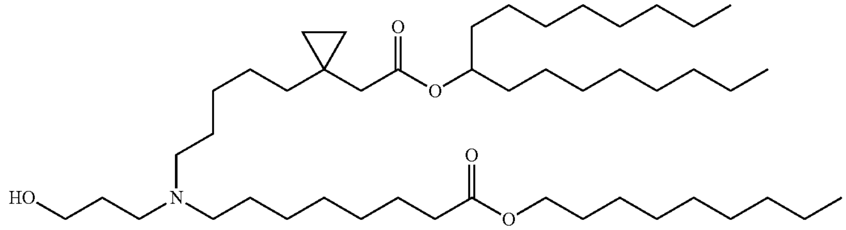
71c
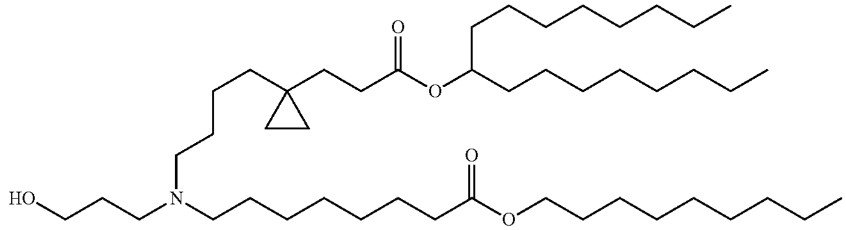
72c
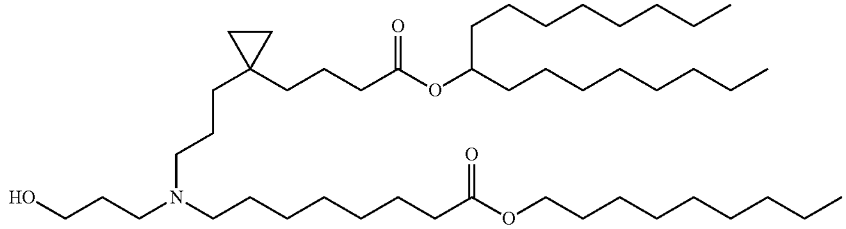

-continued
73c
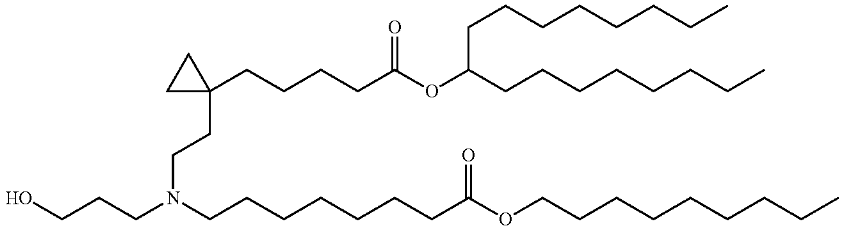
74c
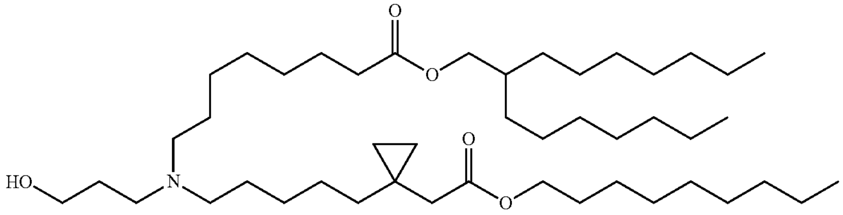
75c
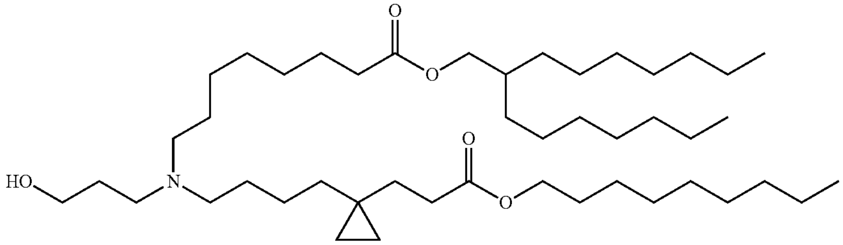
76c
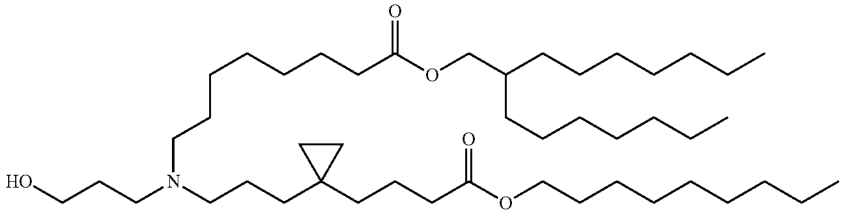
77c
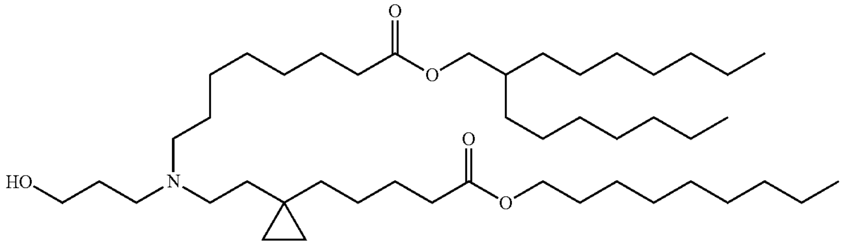
78c
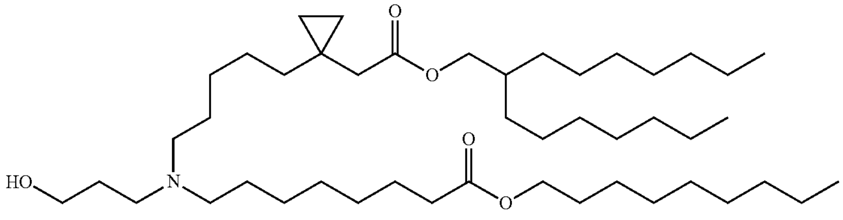
79c
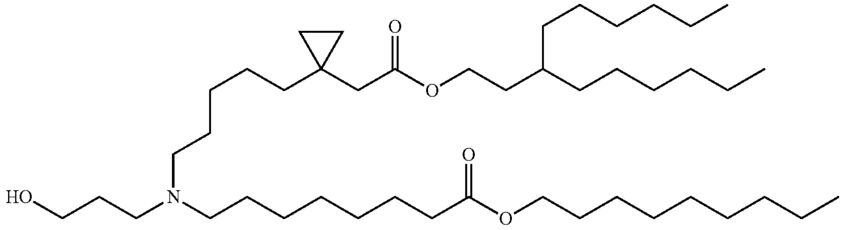

-continued
80c
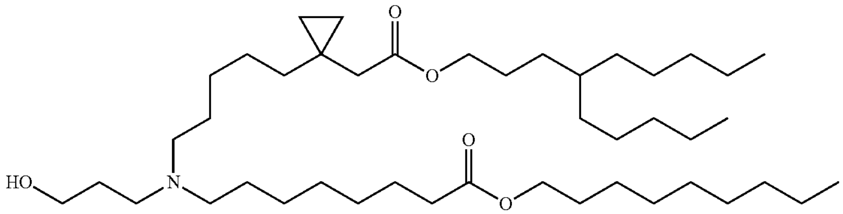
81c
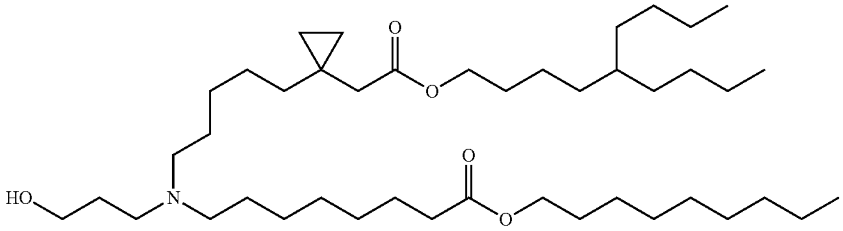
82c
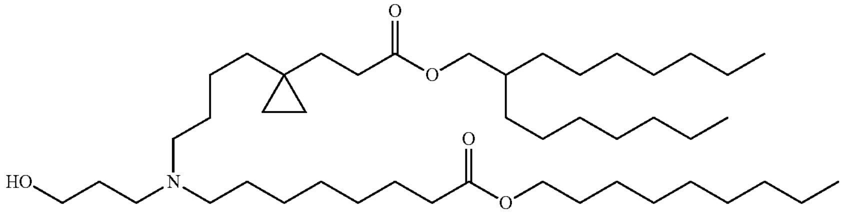
83c
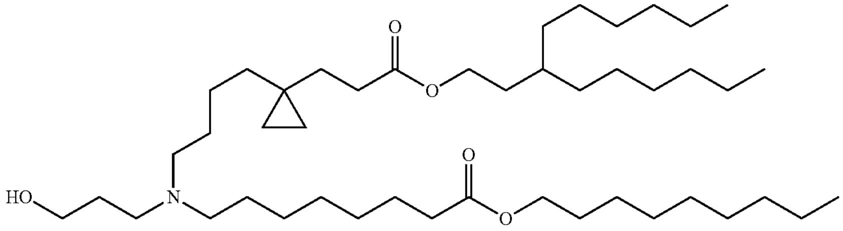
84c
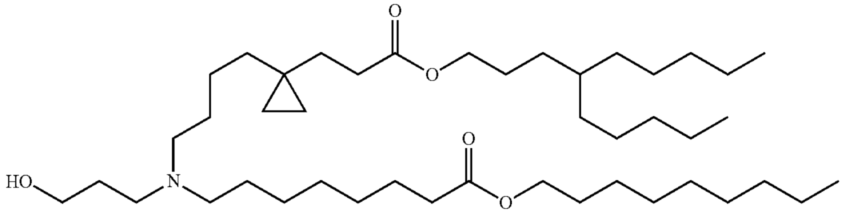
85c
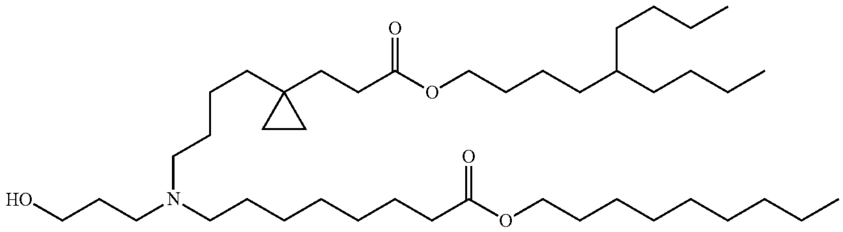
86c
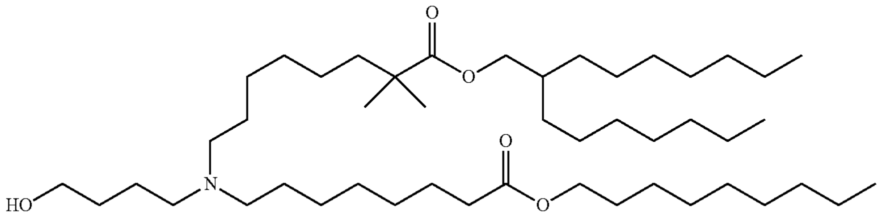

-continued
87c
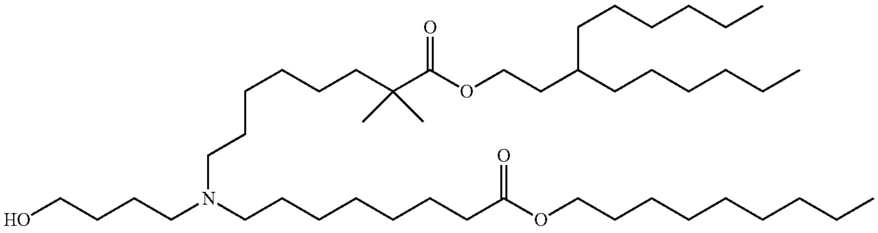
88c
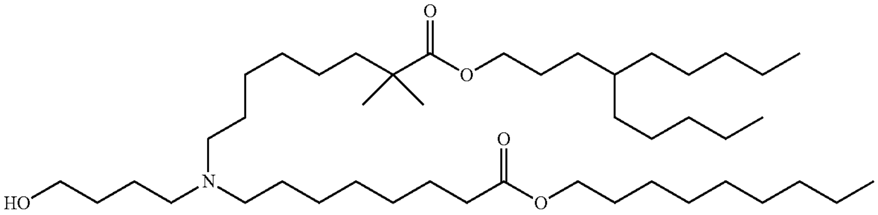
89c
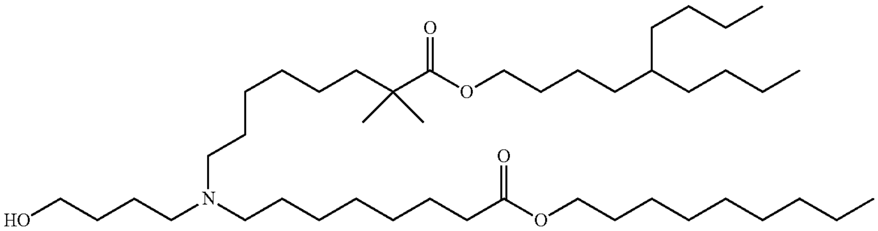
90c
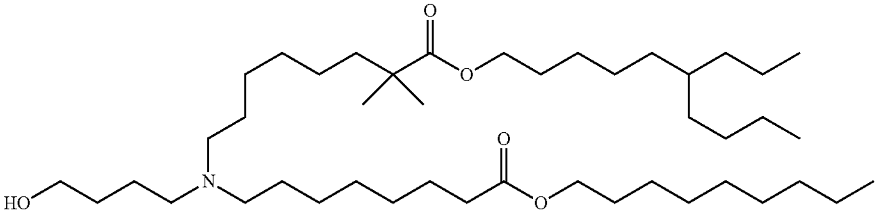
91c
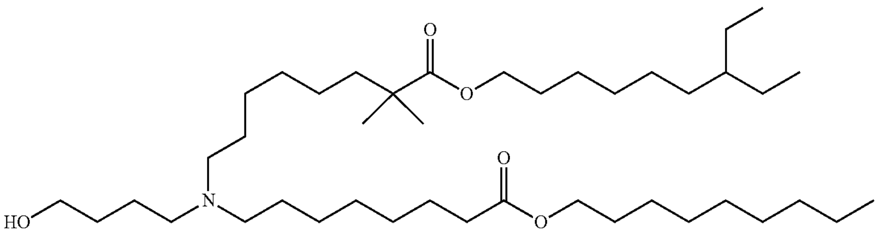
92c
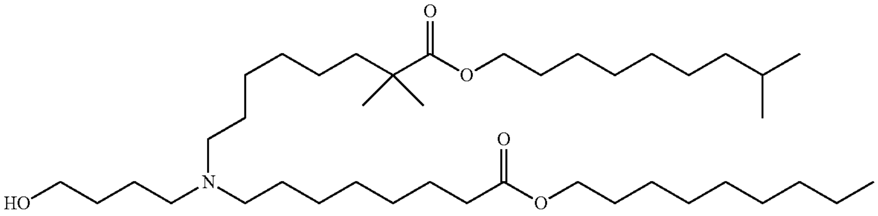
93c
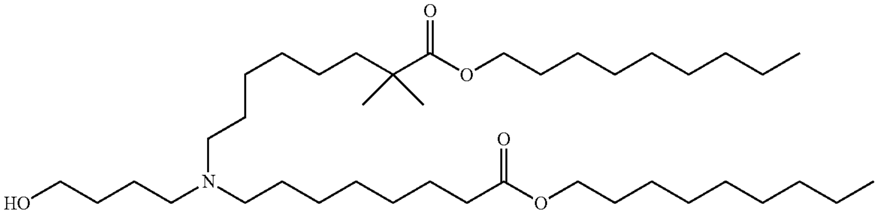

-continued
94c
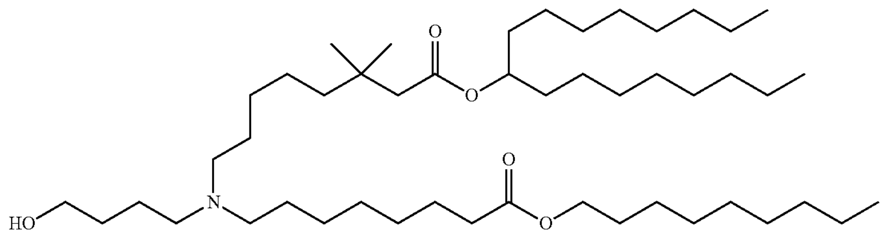
95c
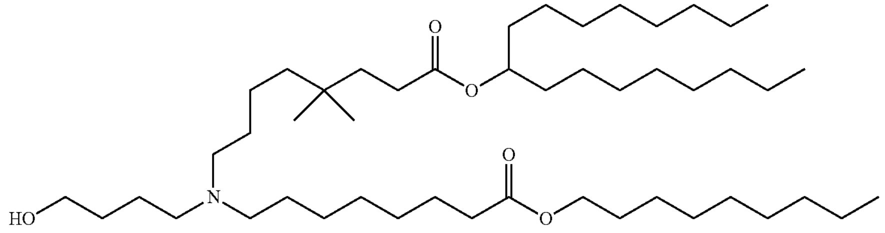
96c
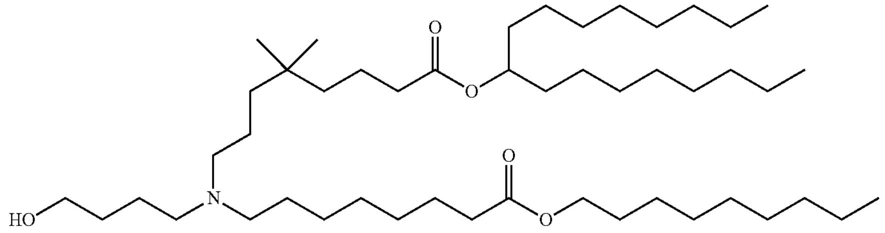
97c
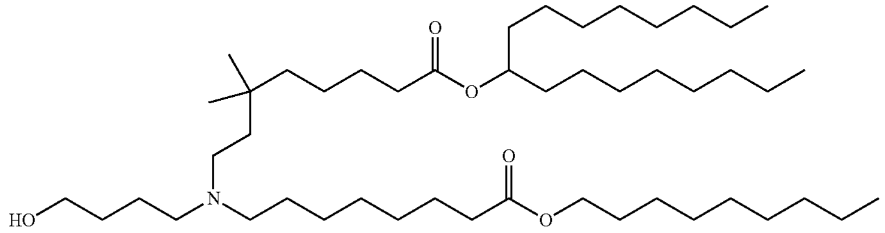
98c
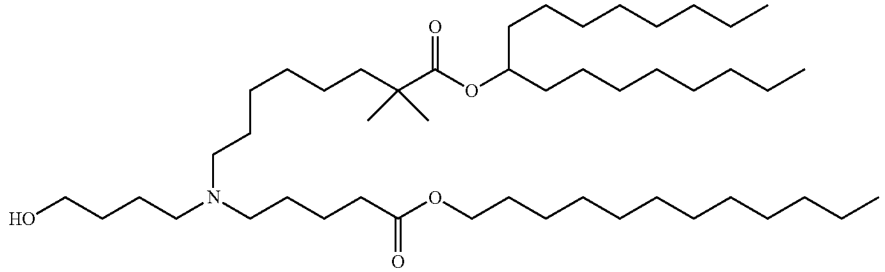
99c
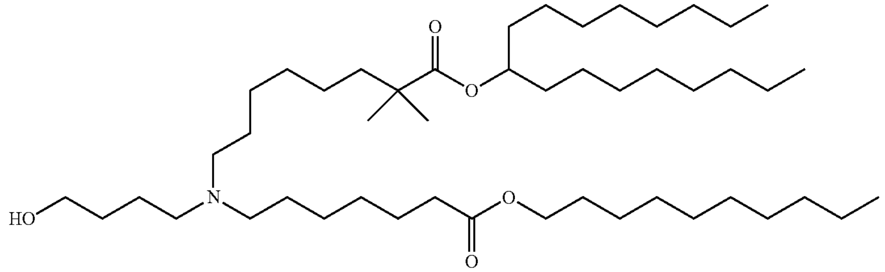

-continued
100c
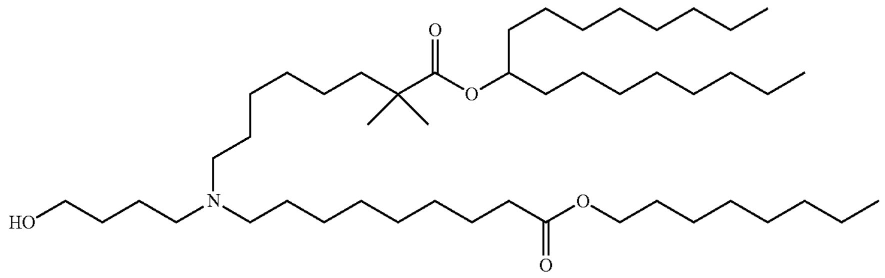
101c
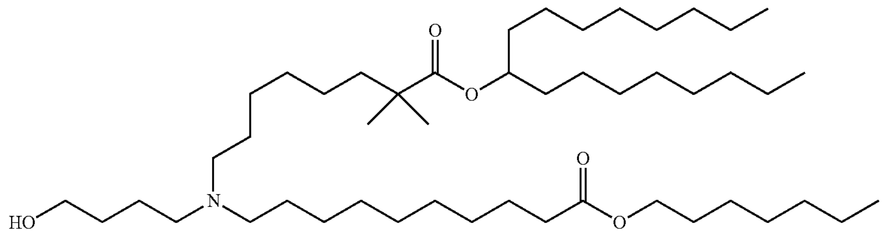
102c
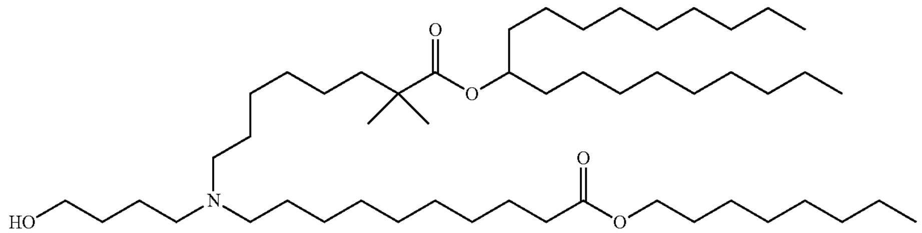
103c
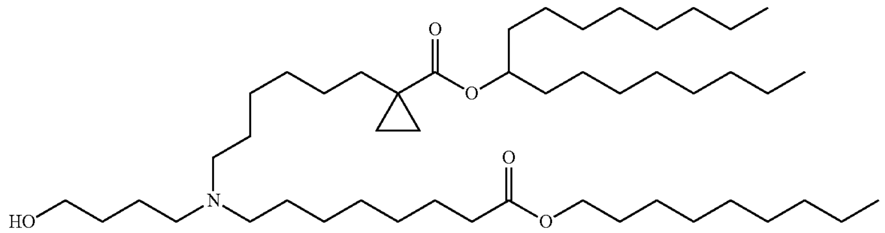
104c
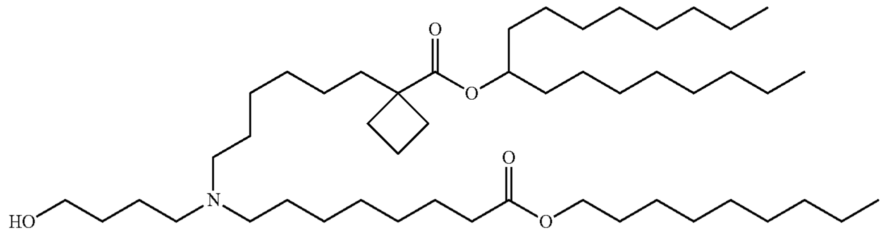
105c
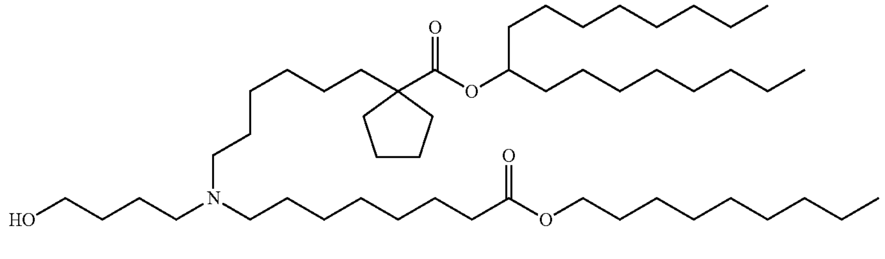

-continued
106c
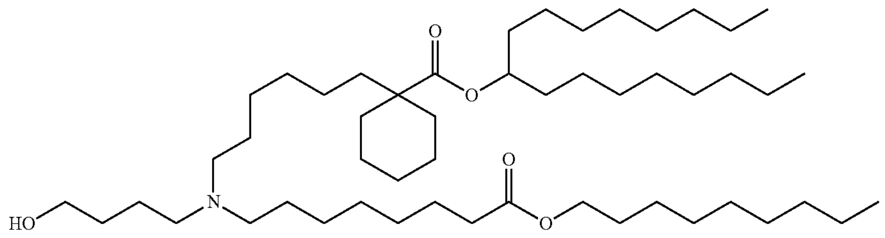
107c
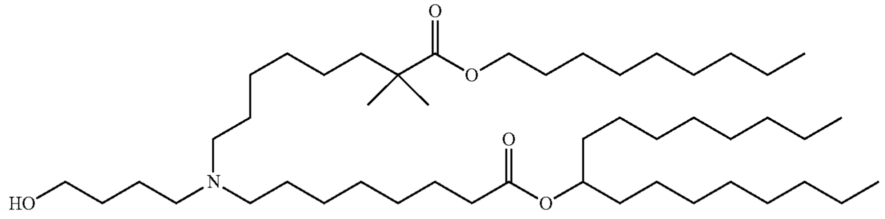
108c
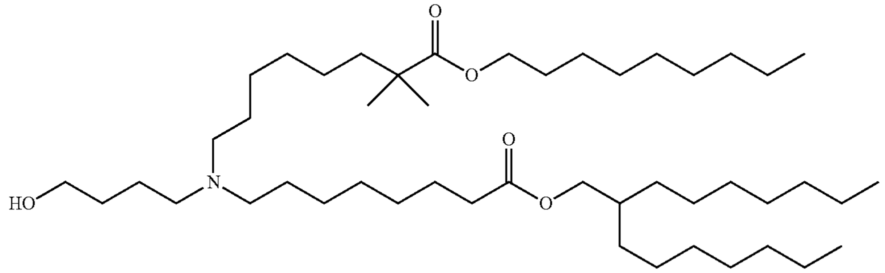
109c
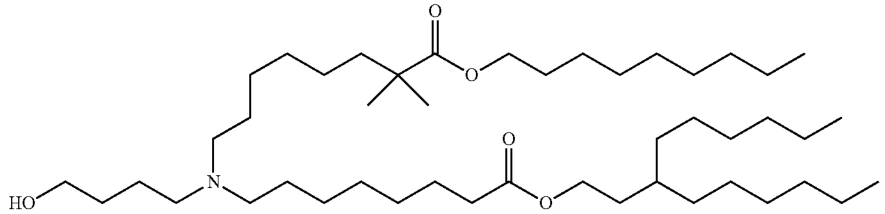
110c
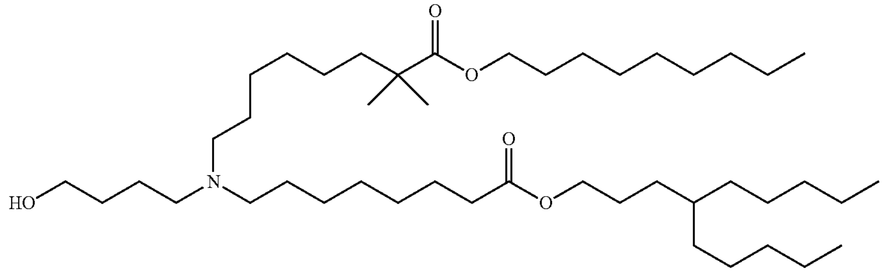
111c
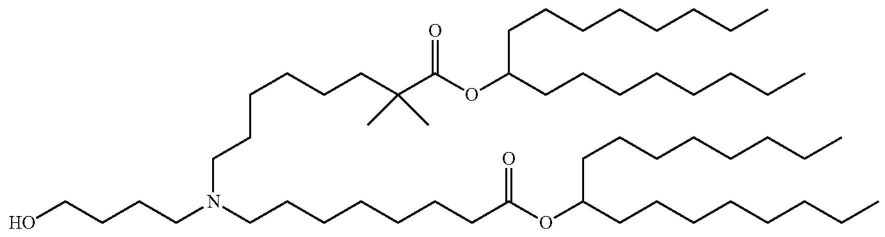

-continued
112c
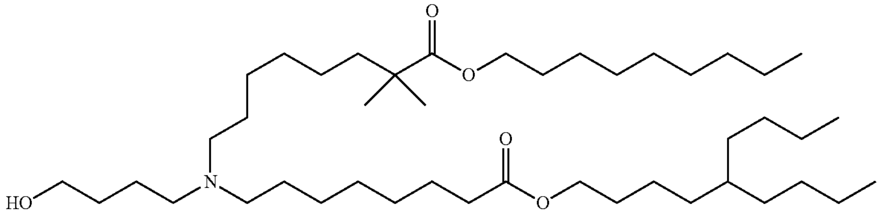
113c
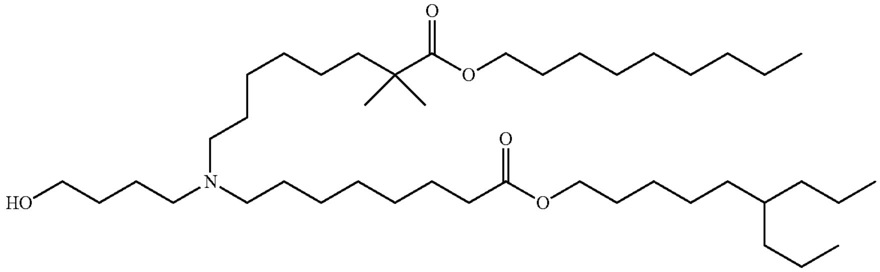
114c
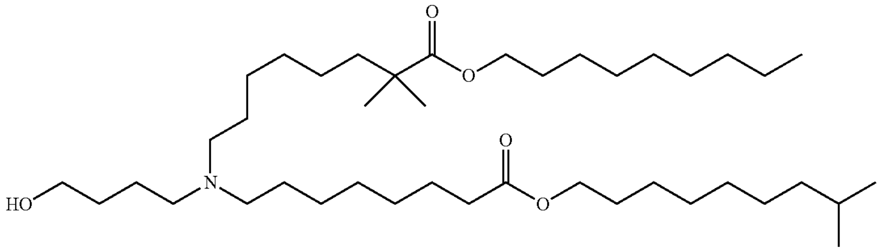
115c
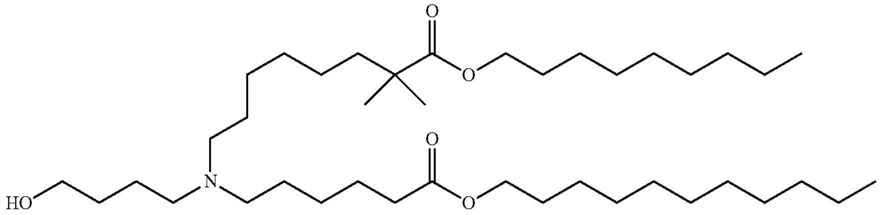
116c
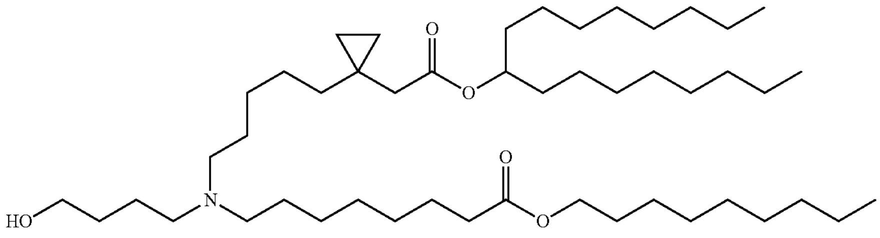
117c
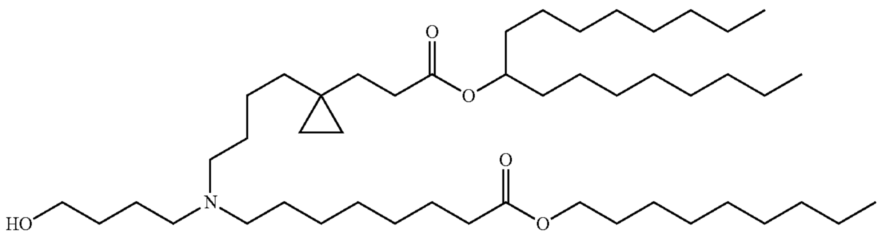

-continued
118c
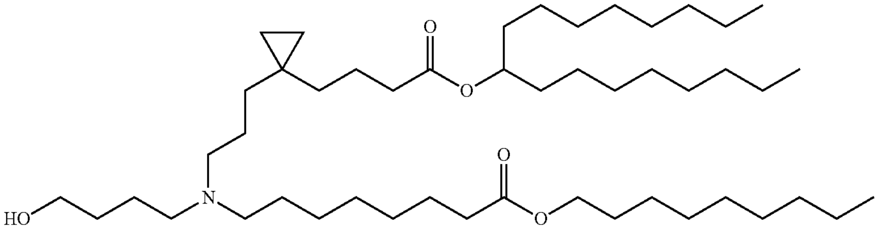
119c
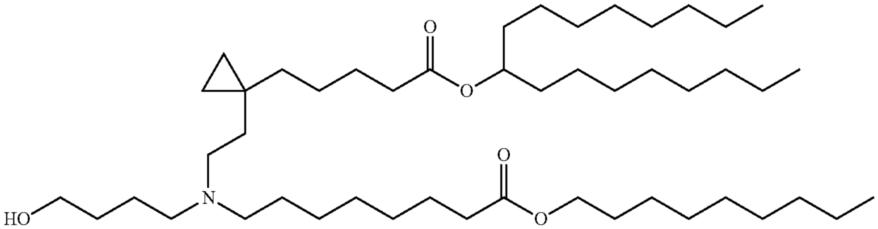
120c
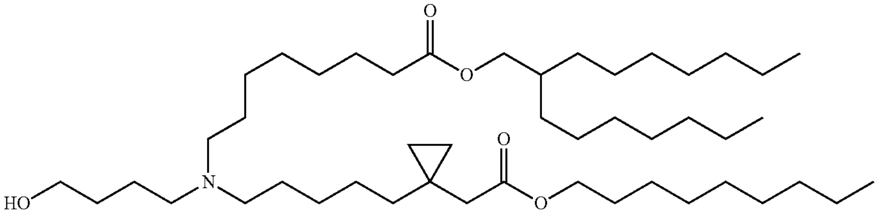
121c
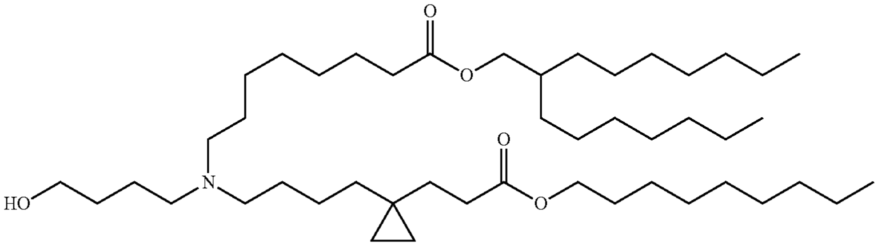
122c
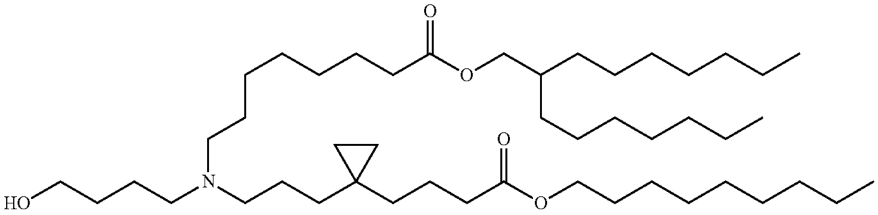
123c
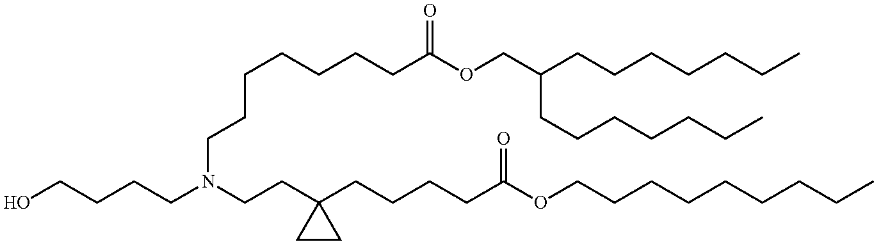
124c
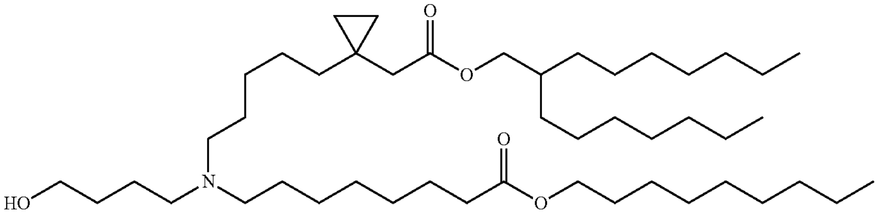

-continued
125c
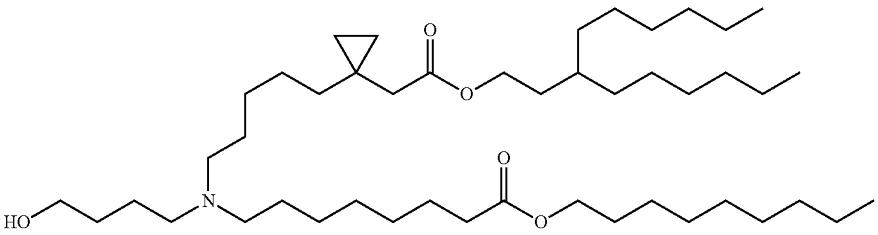
126c
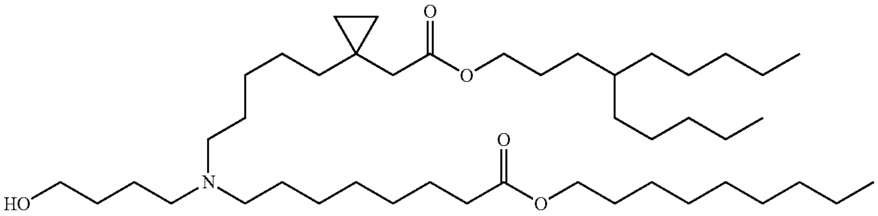
127c
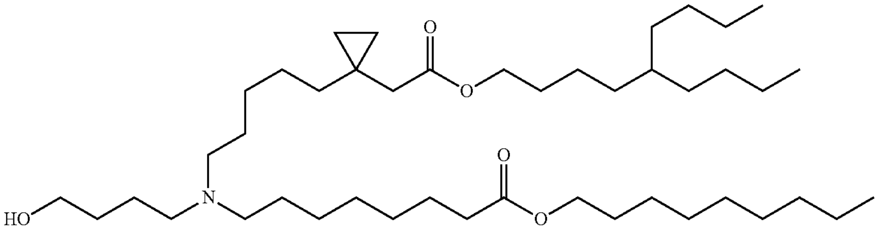
128c
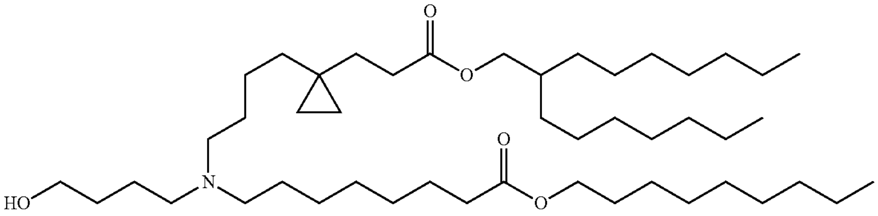
129c
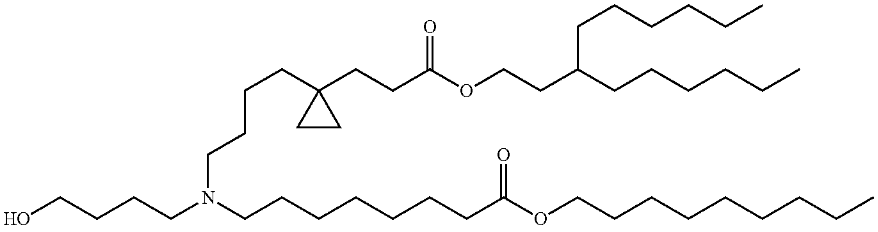
130c
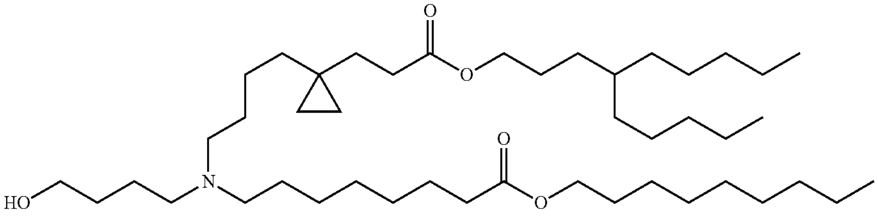
131c
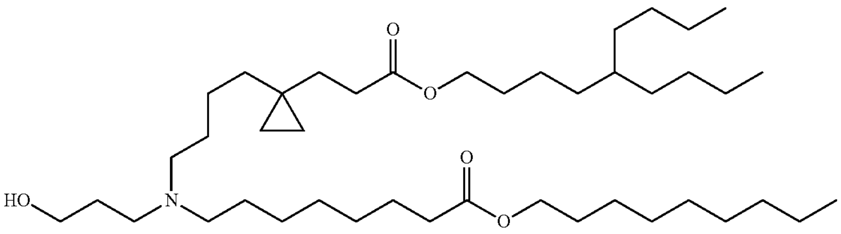

-continued
132c
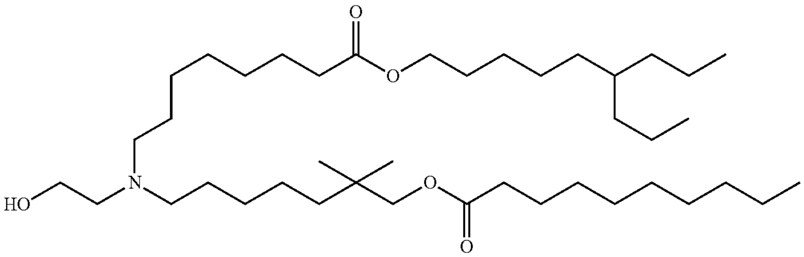
133c
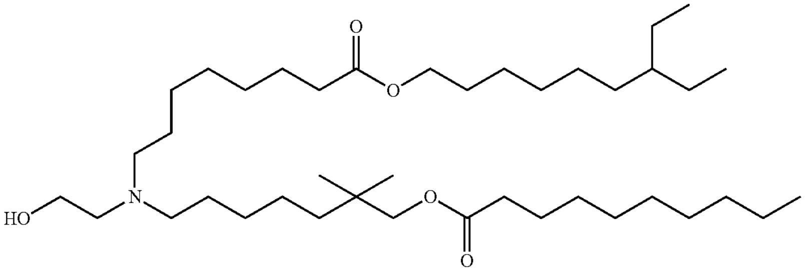
134c
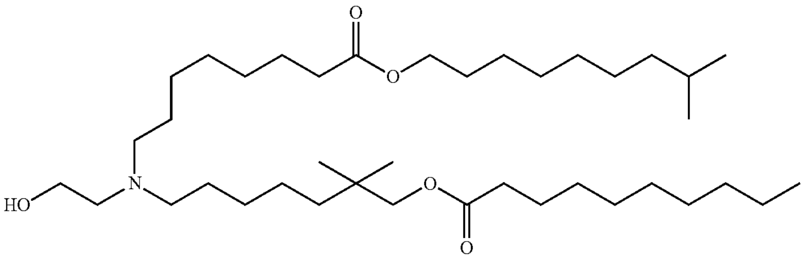
135c
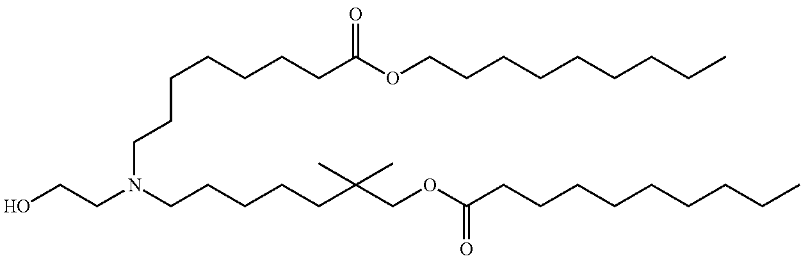
136c
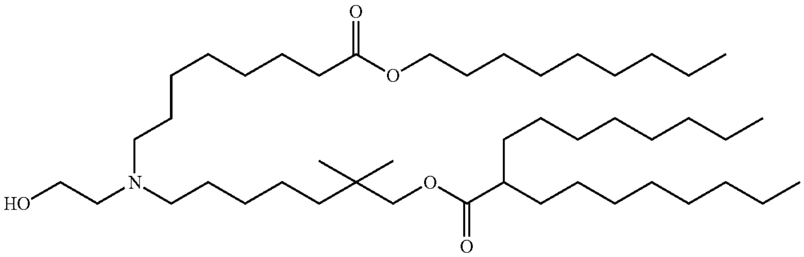
137c
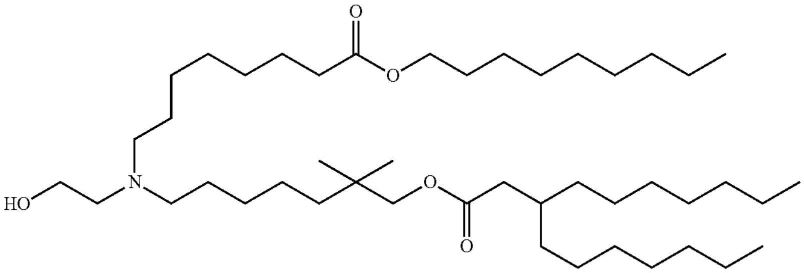

-continued
138c
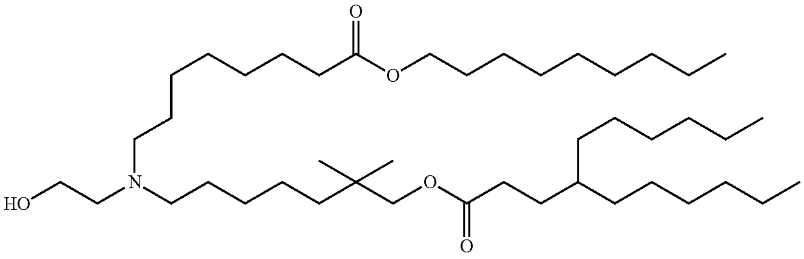
139c
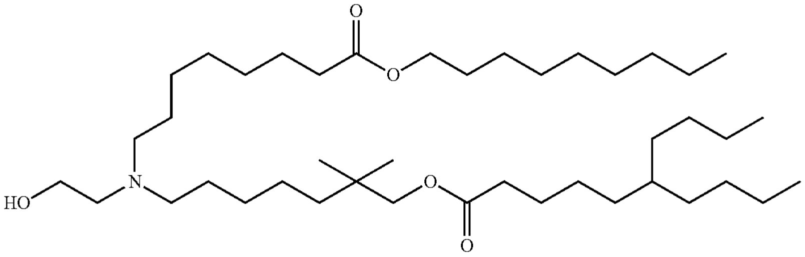
140c
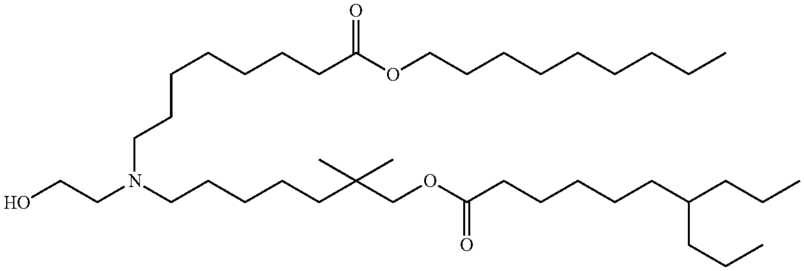
141c
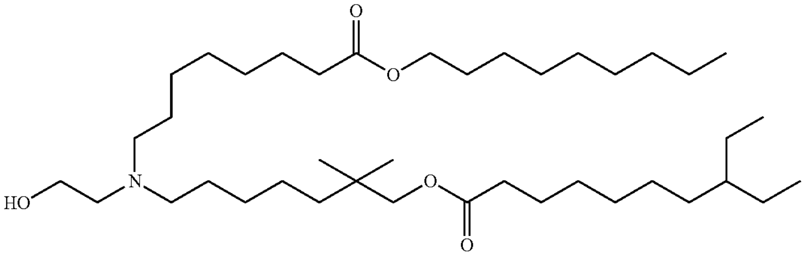
142c
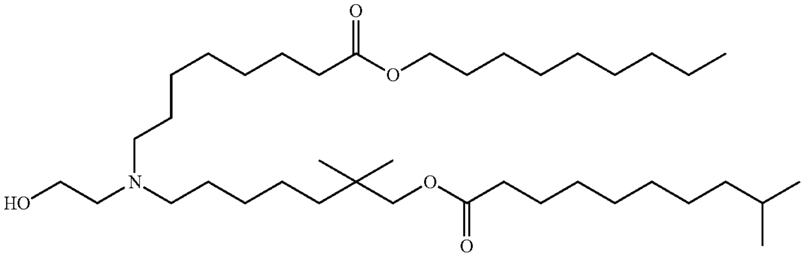
143c
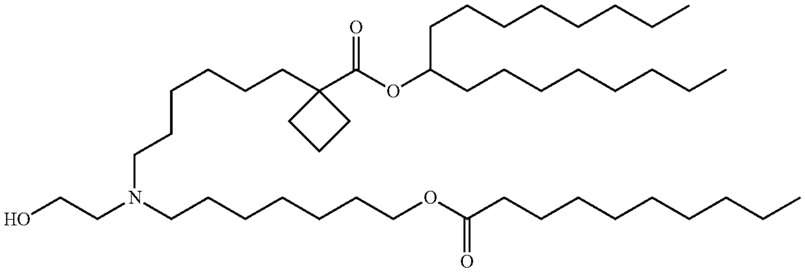

144c
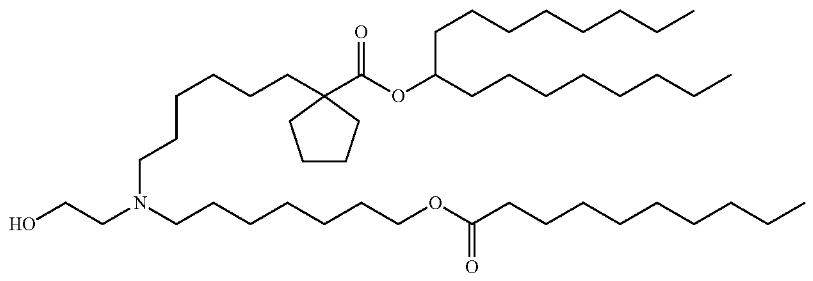
145c
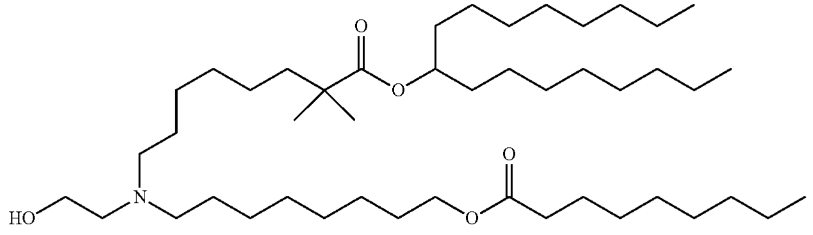
146c
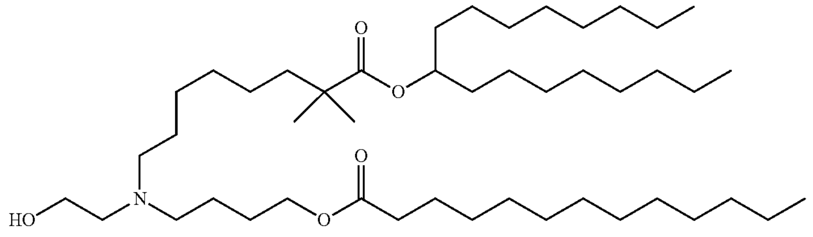
147c
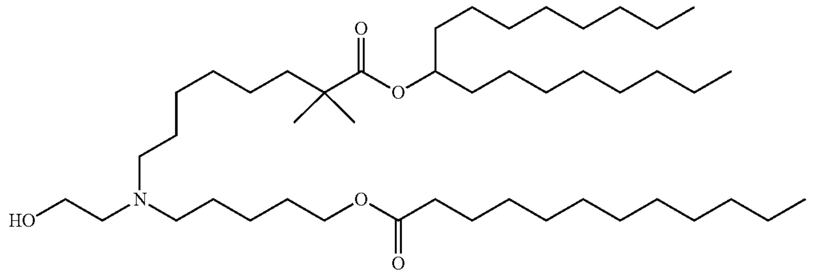
148c
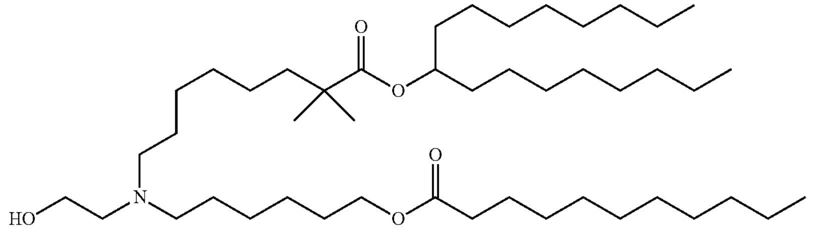
149c
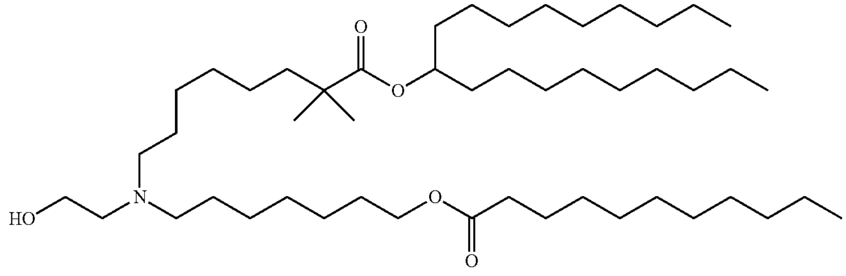

-continued
150c
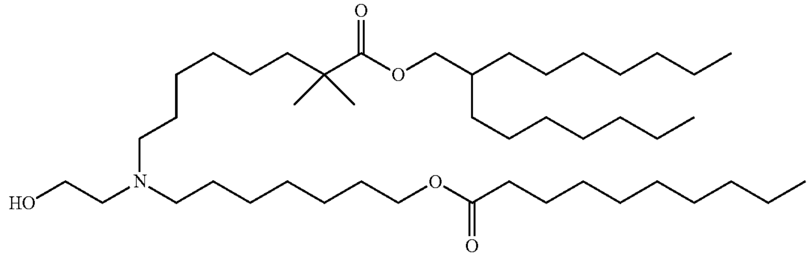
151c
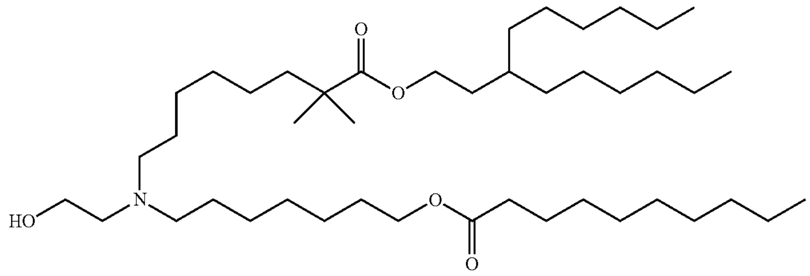
152c
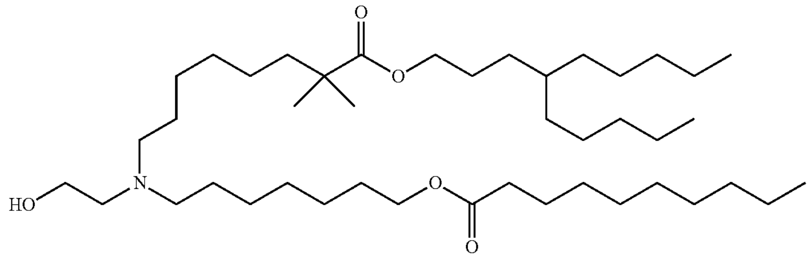
153c
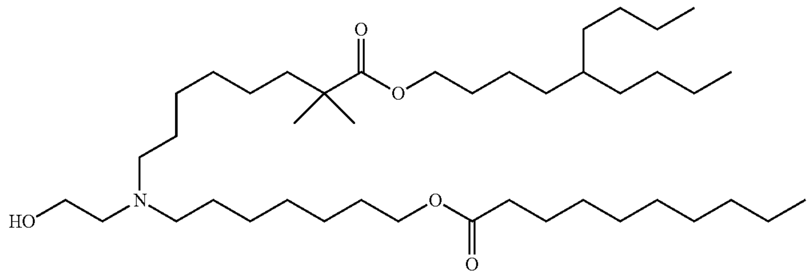
154c
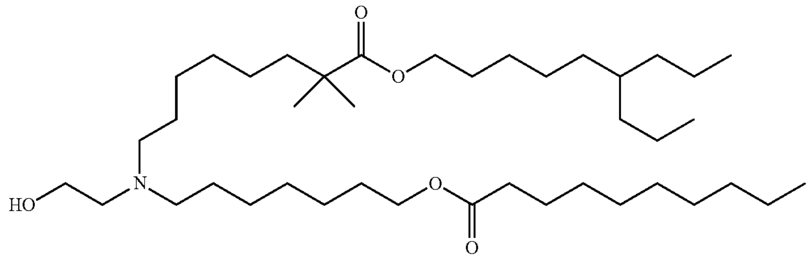
155c
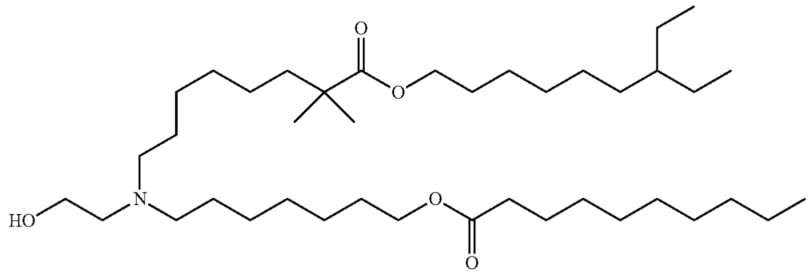

-continued
156c
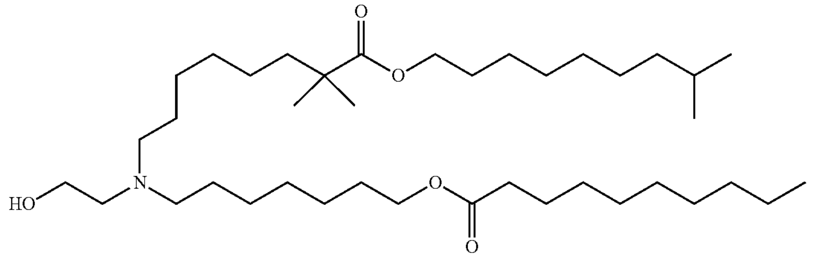
157c
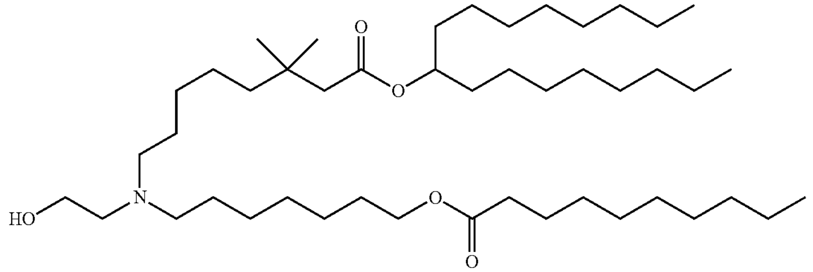
158c
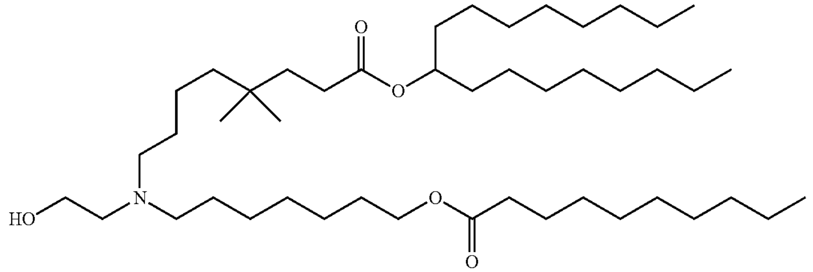
159c
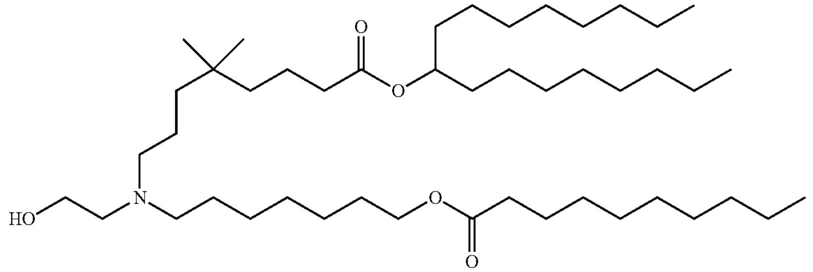
160c
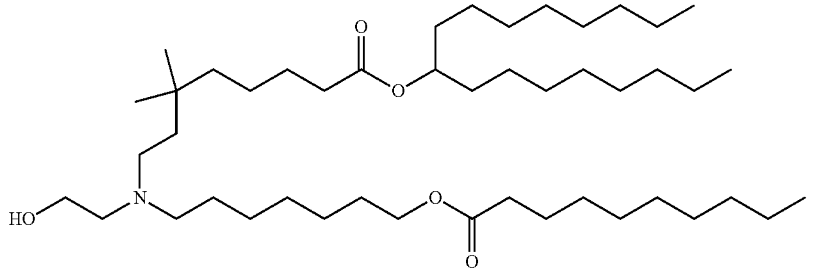
161c
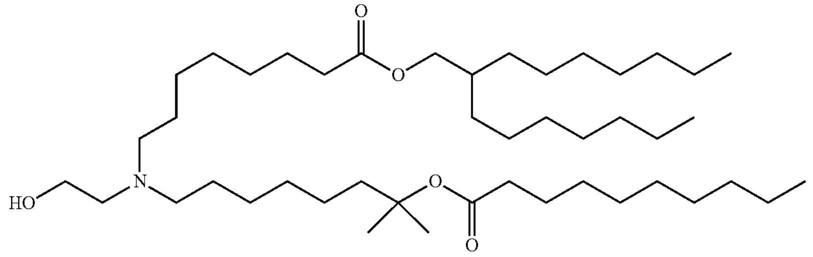

-continued
162c
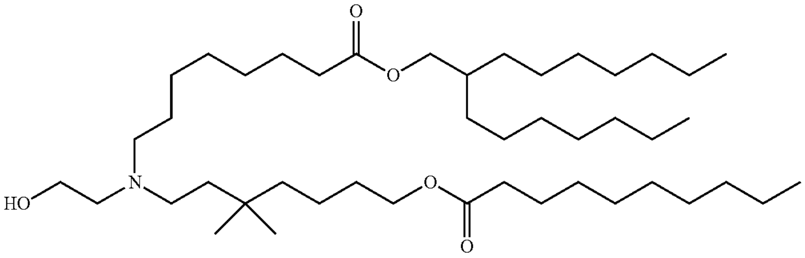
163c
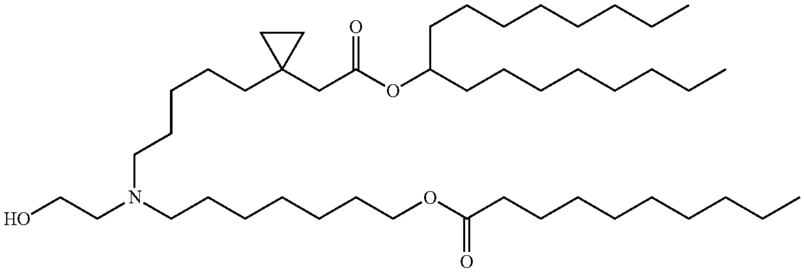
164c
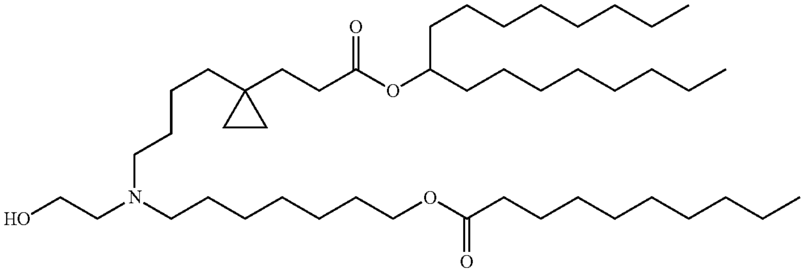
165c
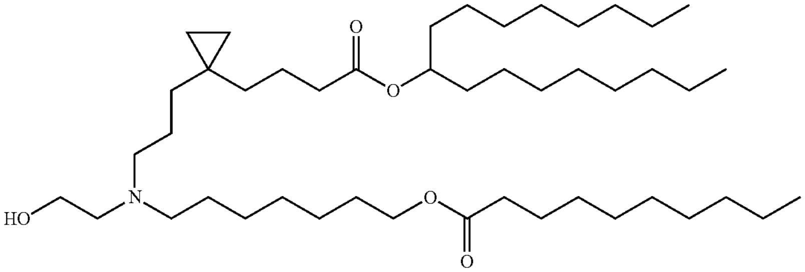
166c
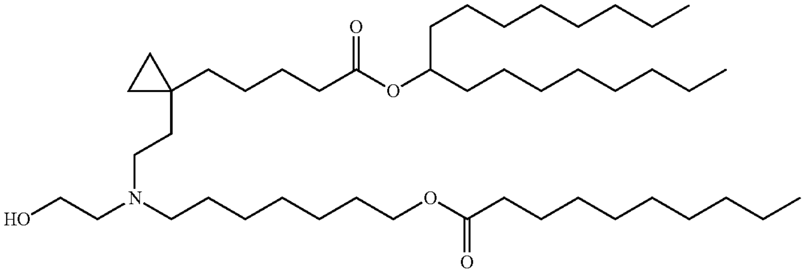
167c
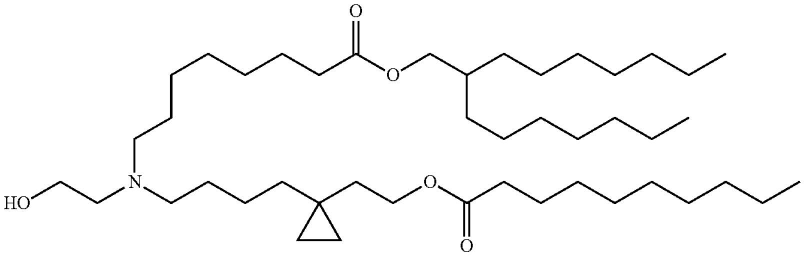

-continued
168c
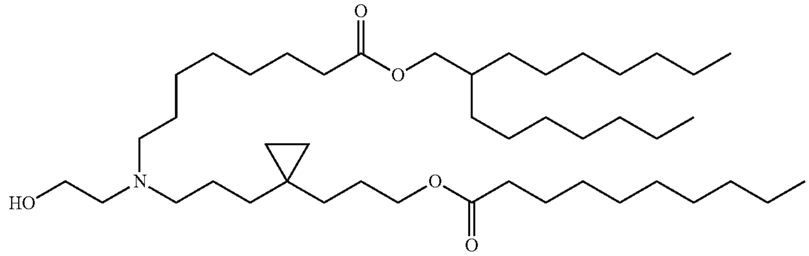
169c
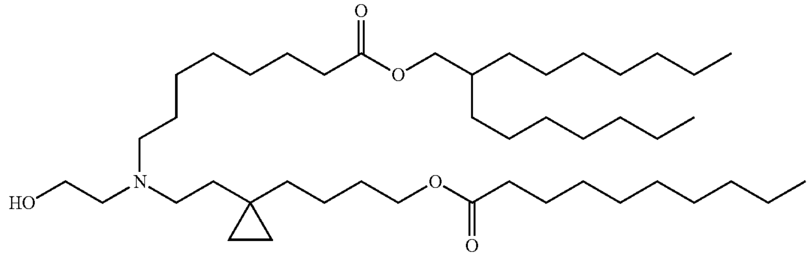
170c
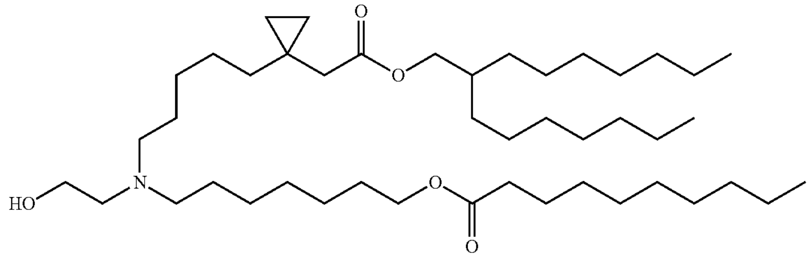
171c
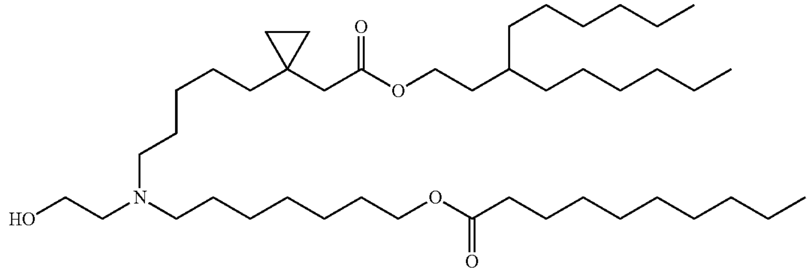
172c
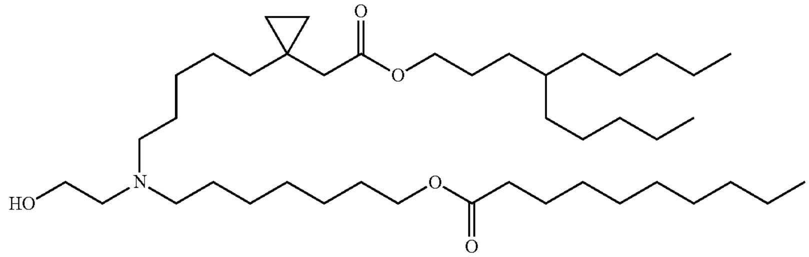
173c
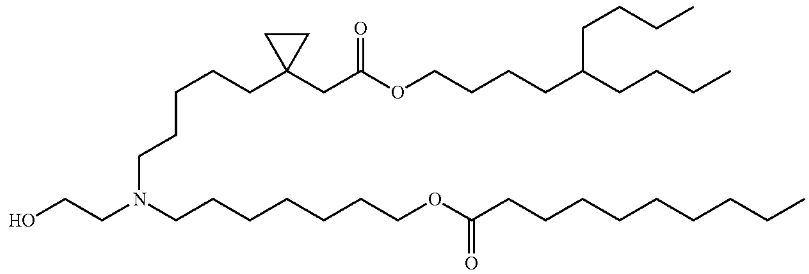

-continued
174c
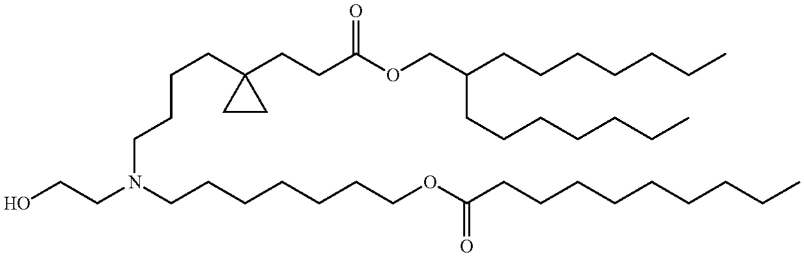
175c
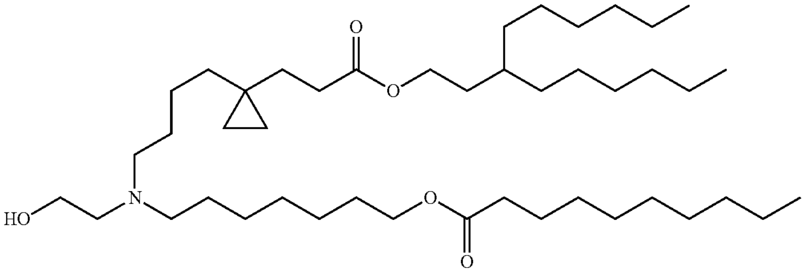
176c
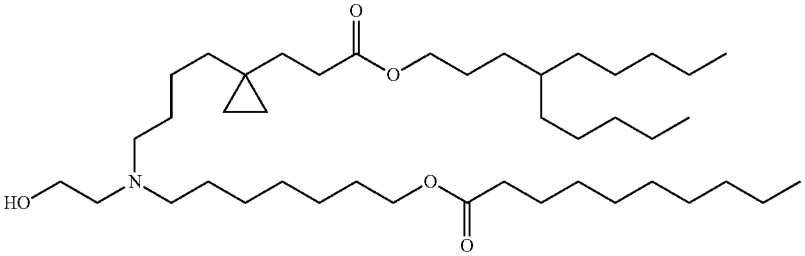
177c
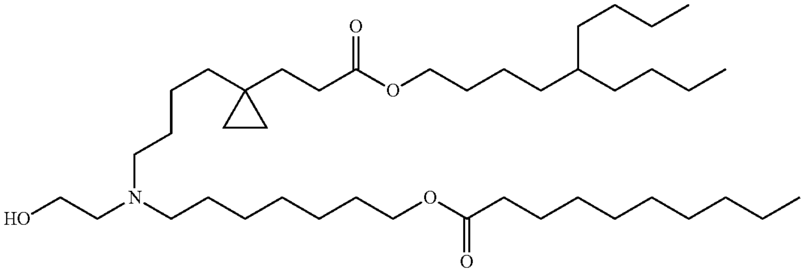
178c
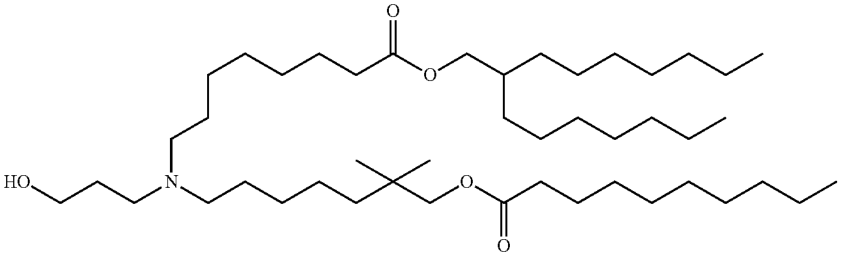
179c
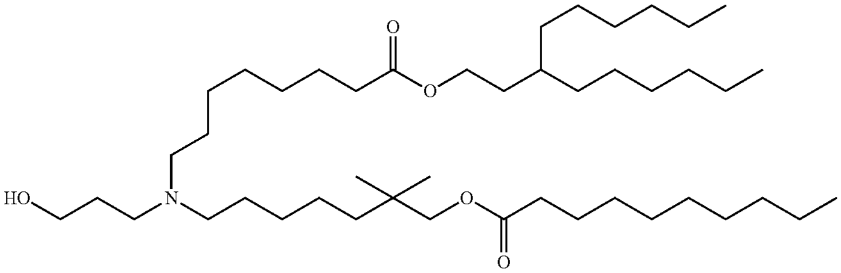

-continued
180c
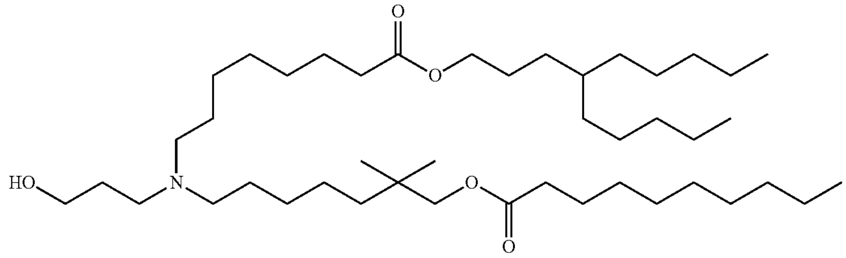
181c
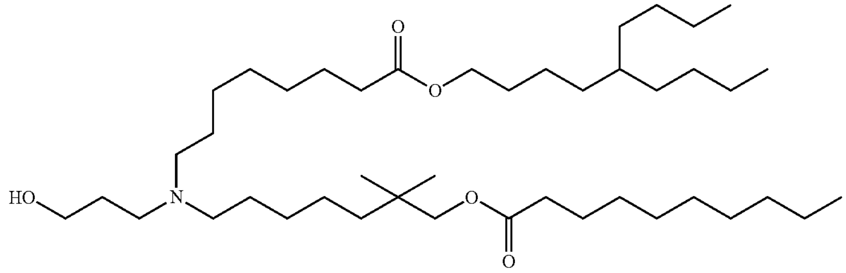
182c
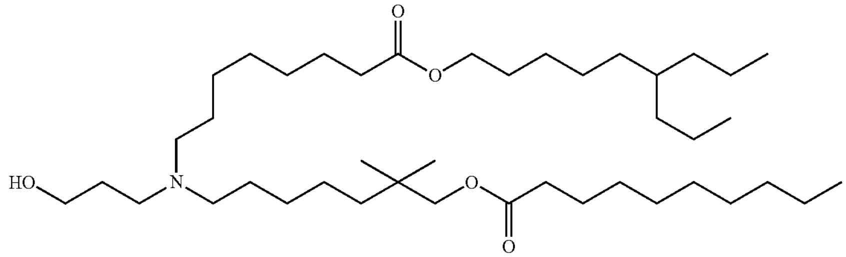
183c
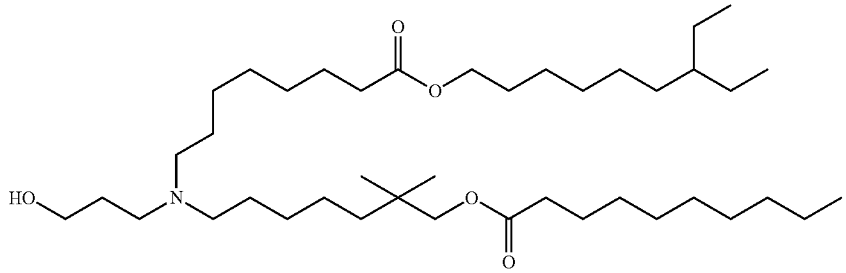
184c
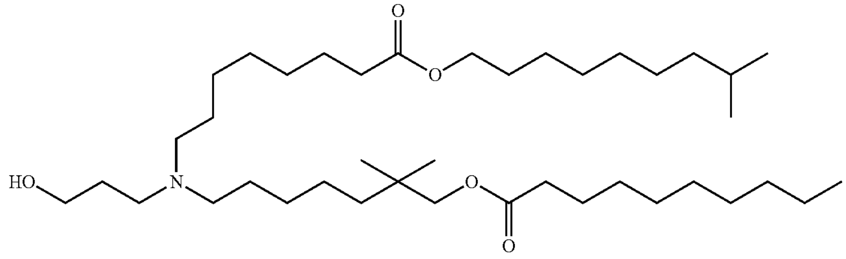
185c
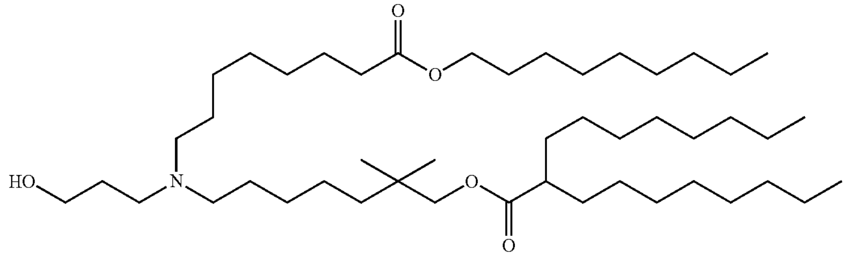

-continued
186c
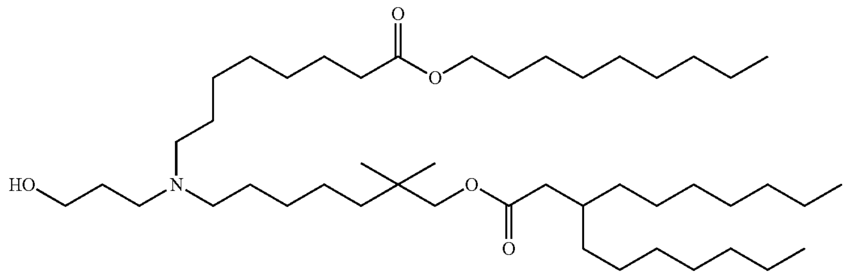
187c
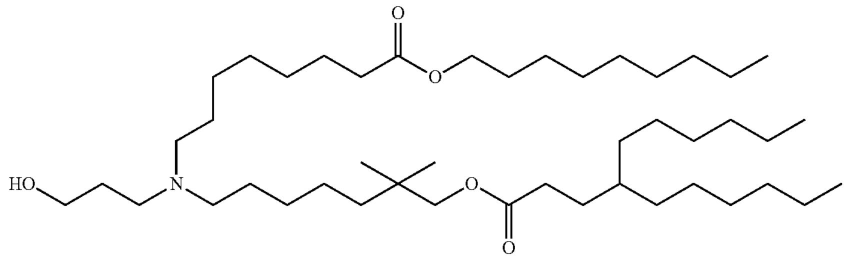
188c
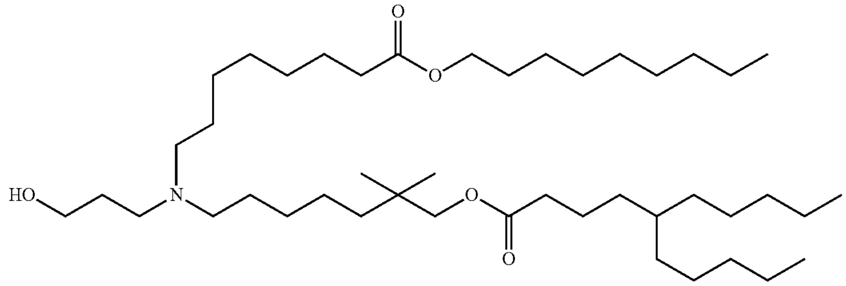
189c
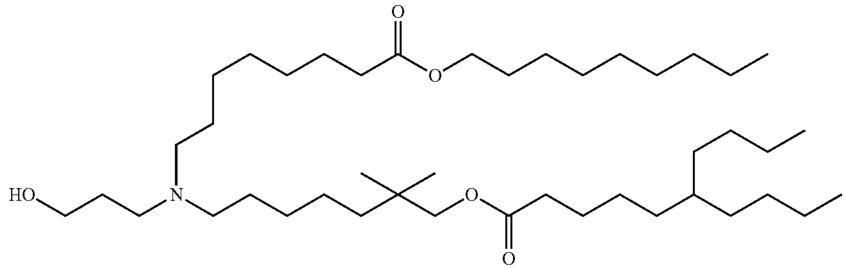
190c
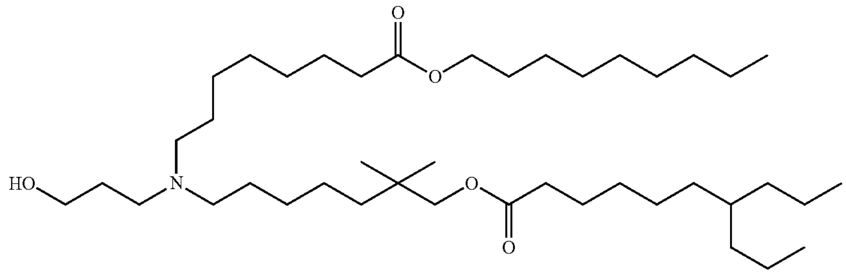

-continued
191c
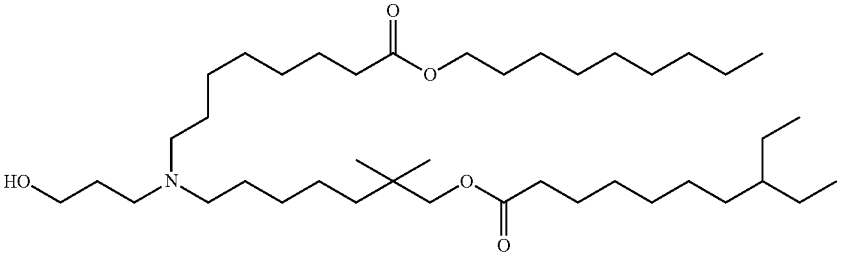
192c
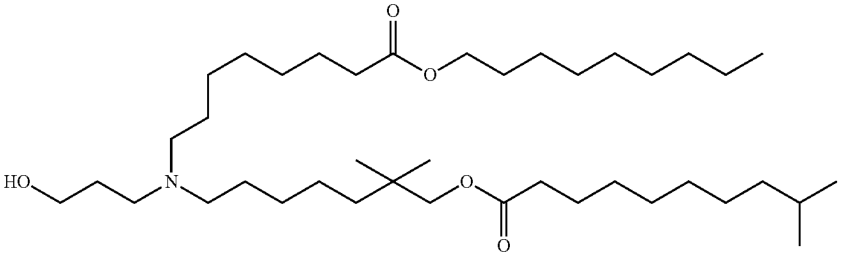
193c
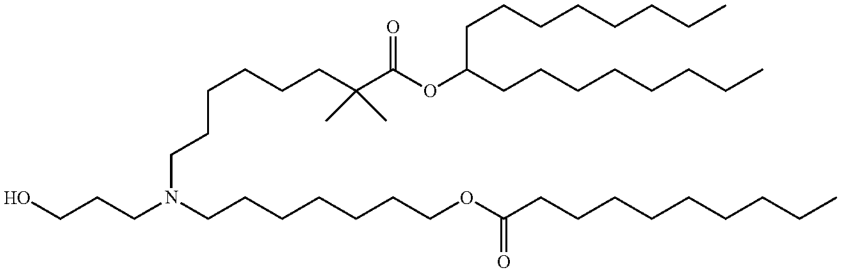
194c
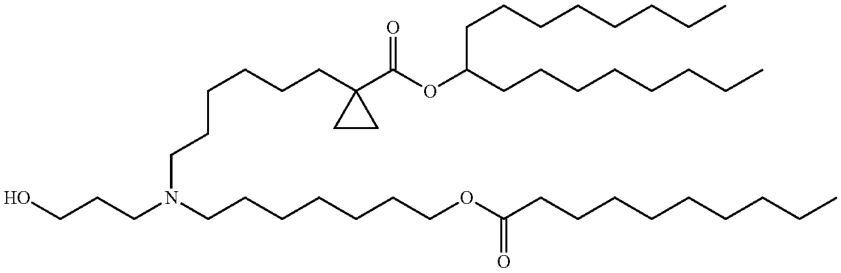
195c
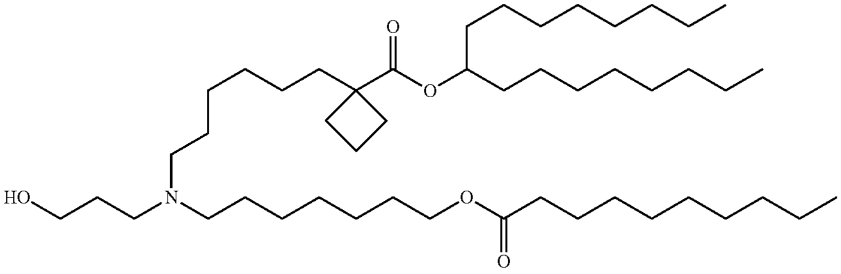
196c
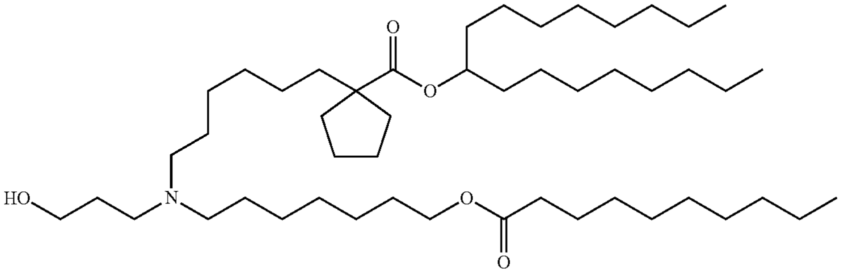

-continued
197c
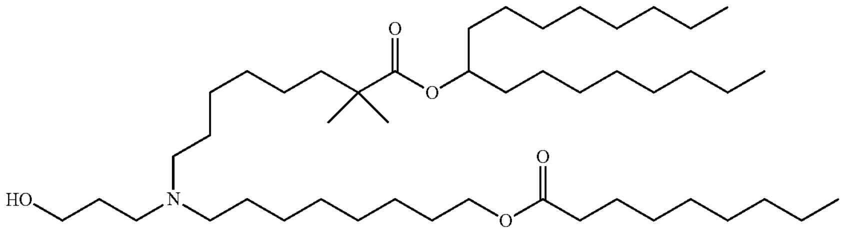
198c
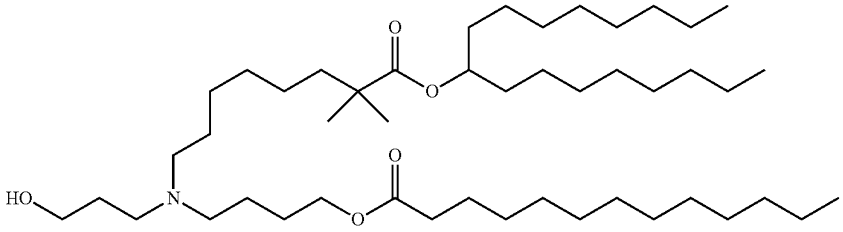
199c
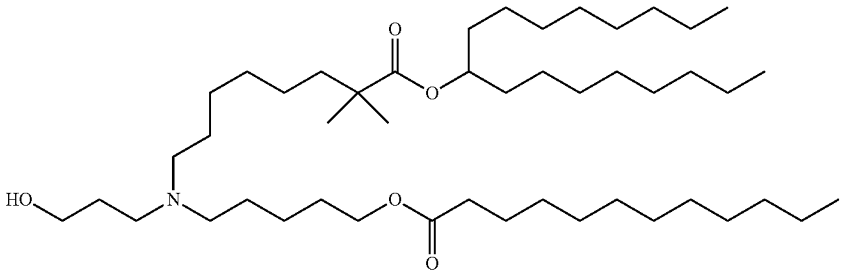
200c
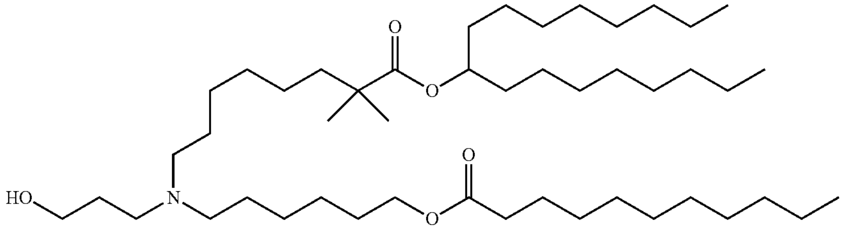
201c
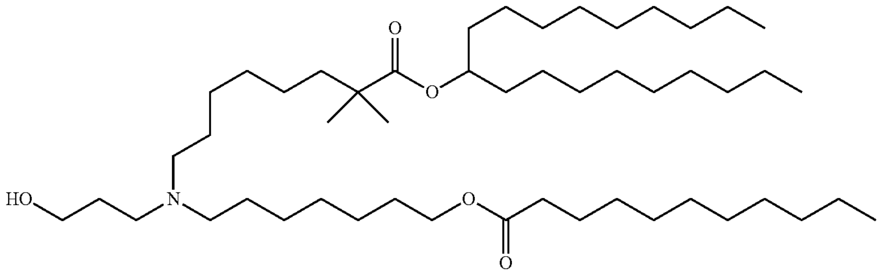
202c
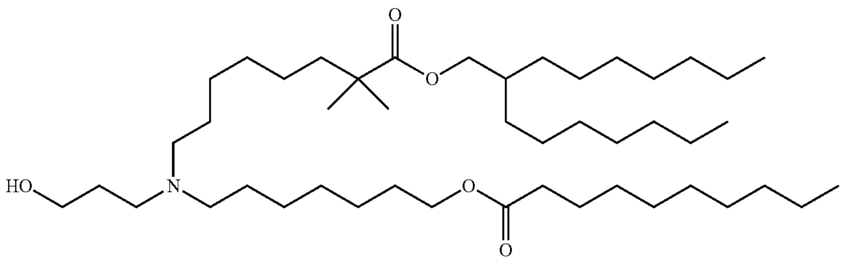

-continued
203c
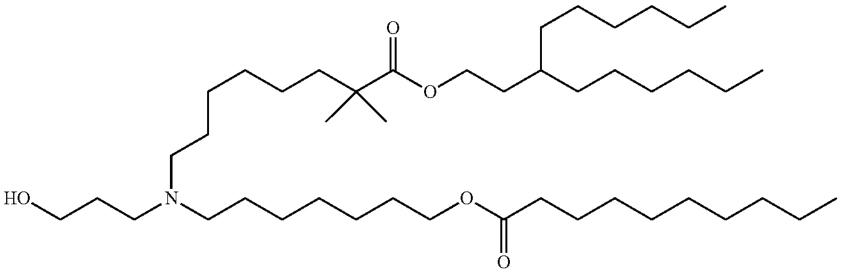
204c
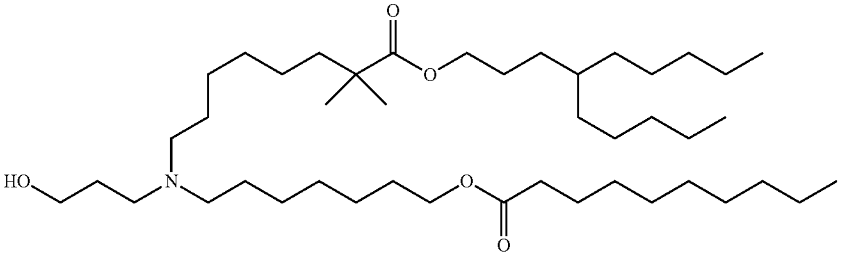
205c
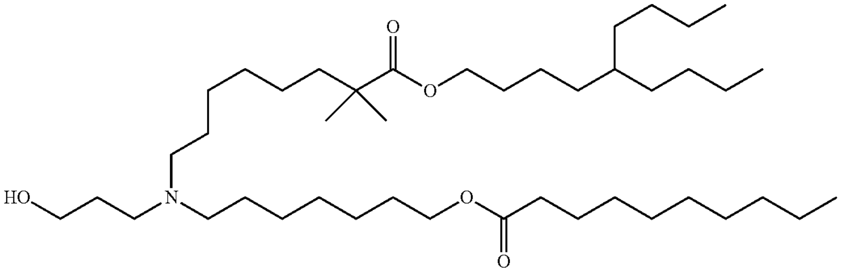
206c
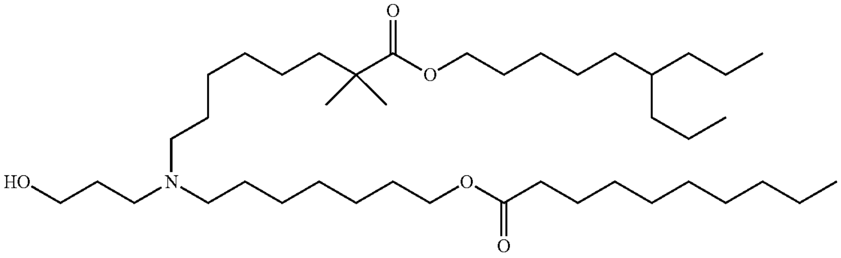
207c
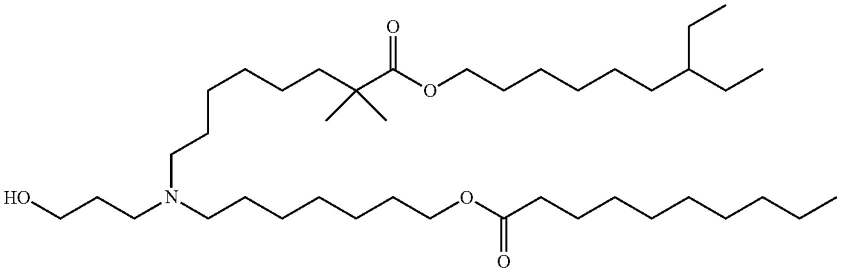
208c
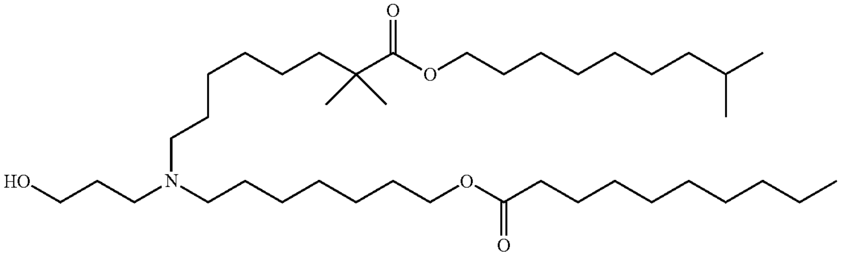

-continued
209c
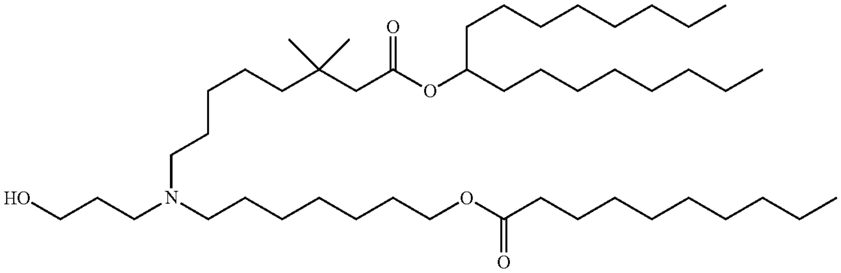
210c
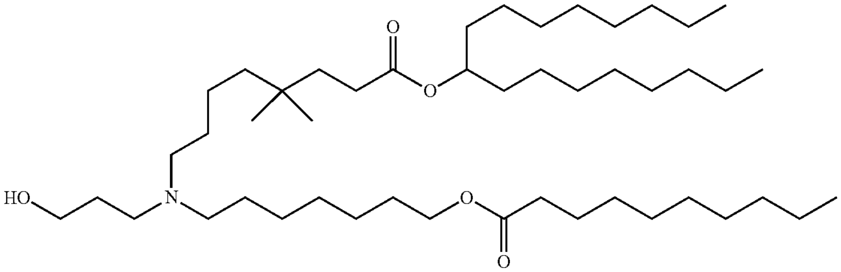
211c
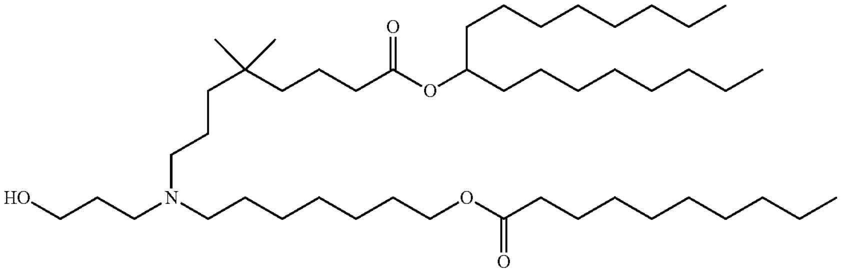
212c
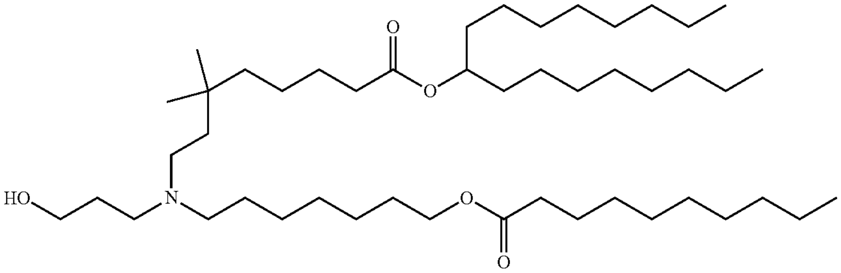
213c
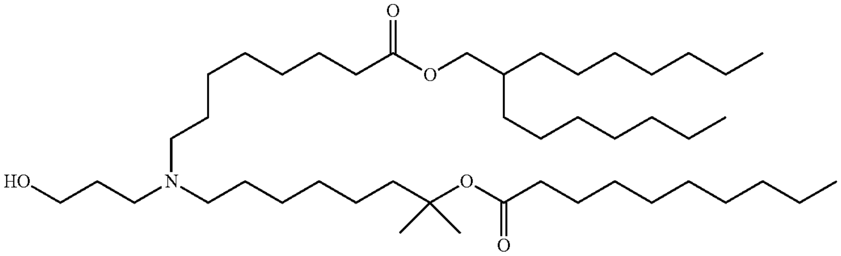
214c
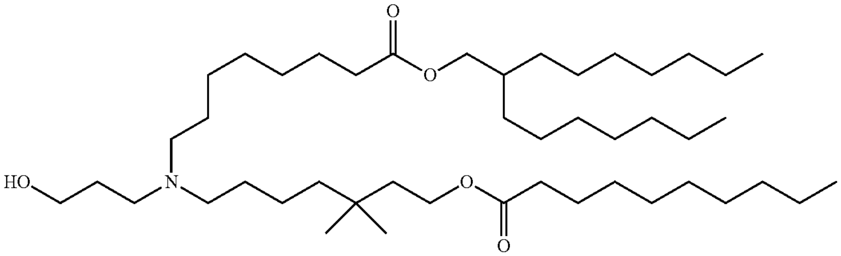

-continued
215c
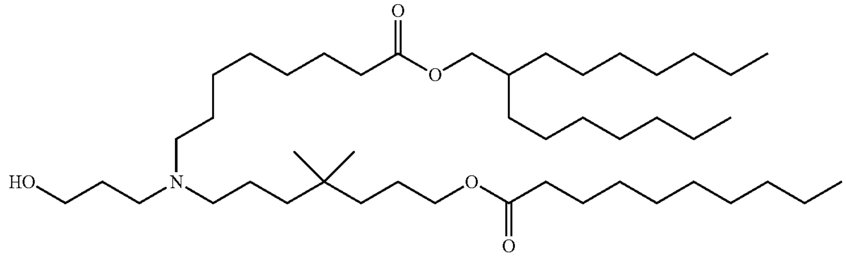
216c
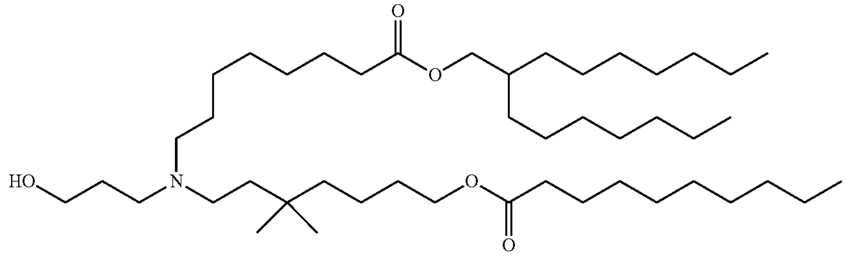
217c
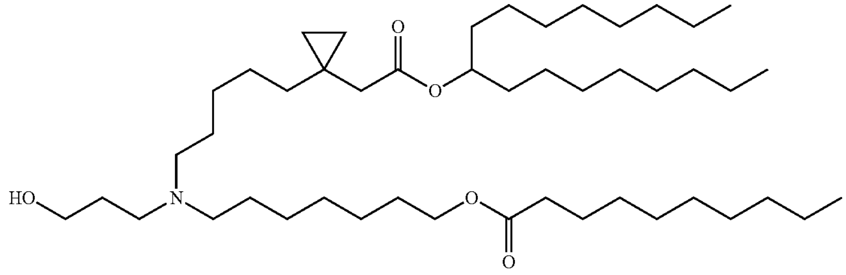
218c
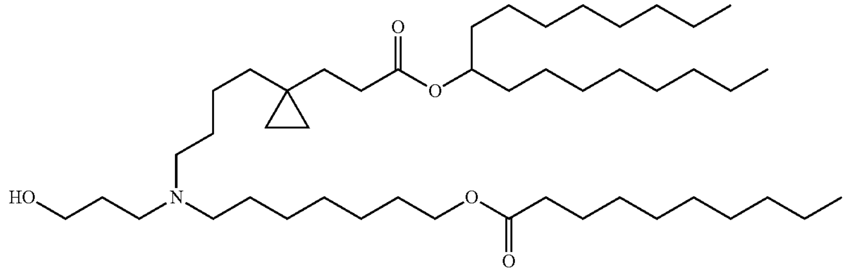
219c
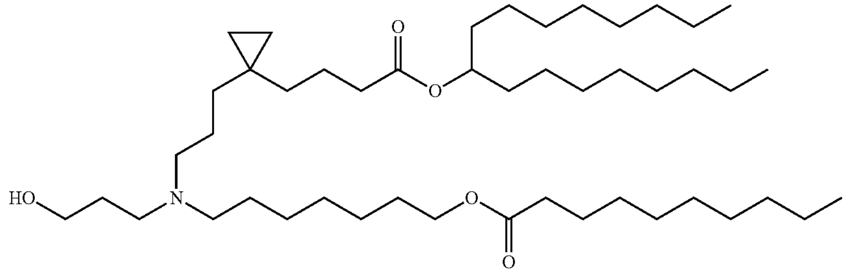
220c
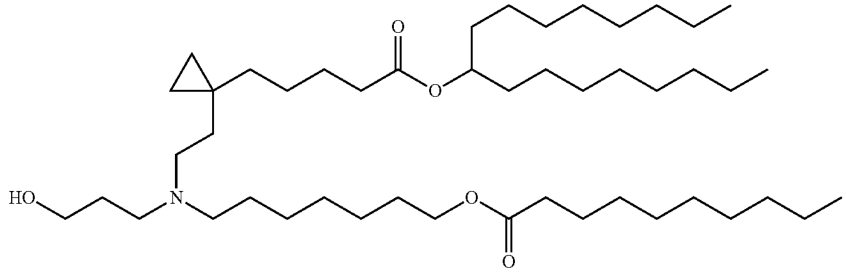

-continued
221c
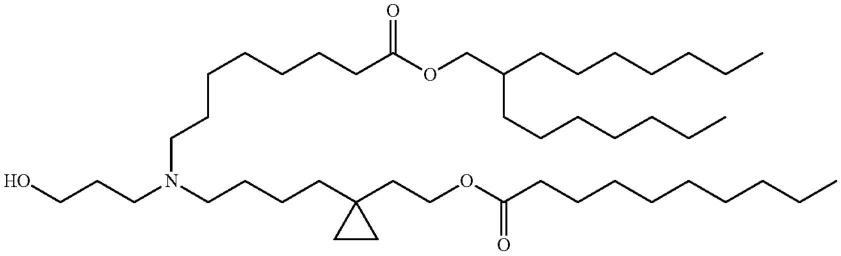
222c
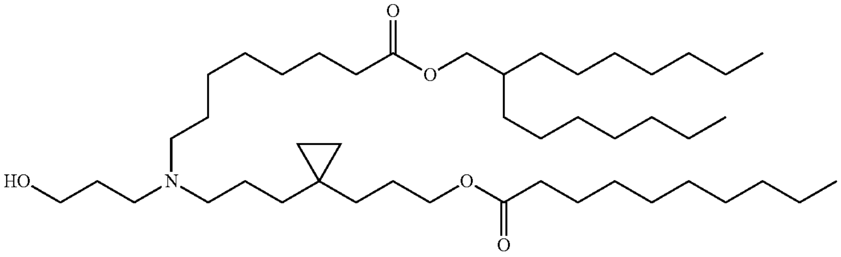
223c
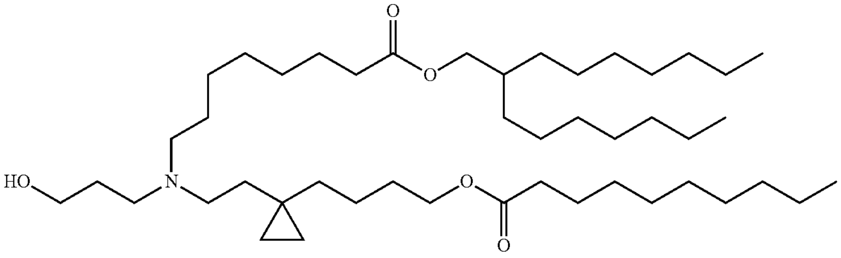
224c
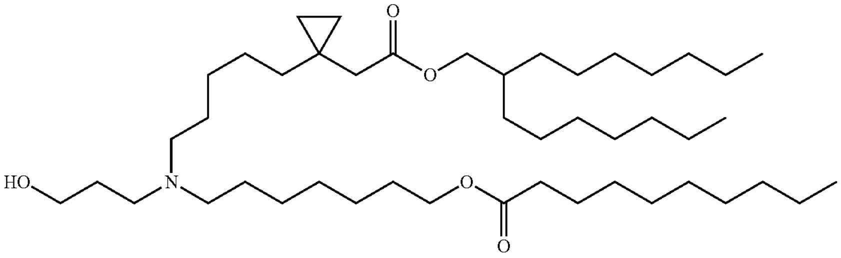
225c
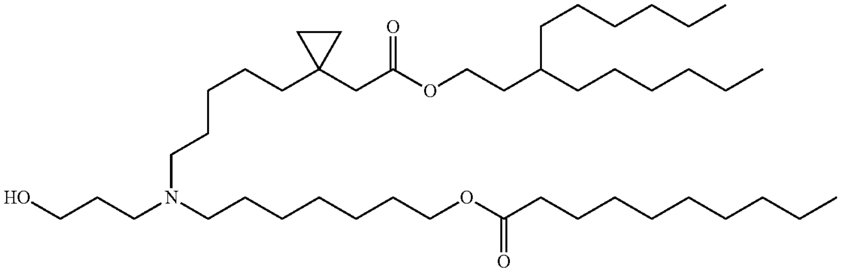

-continued
226c
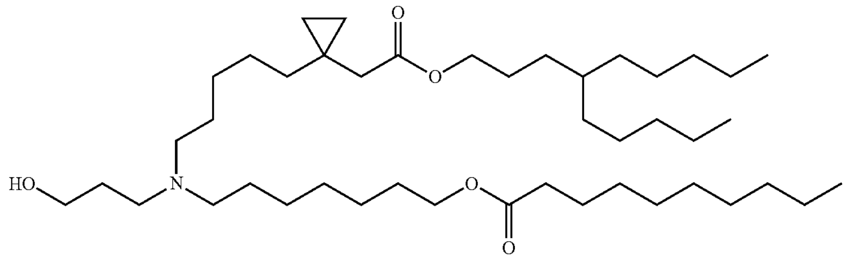
227c
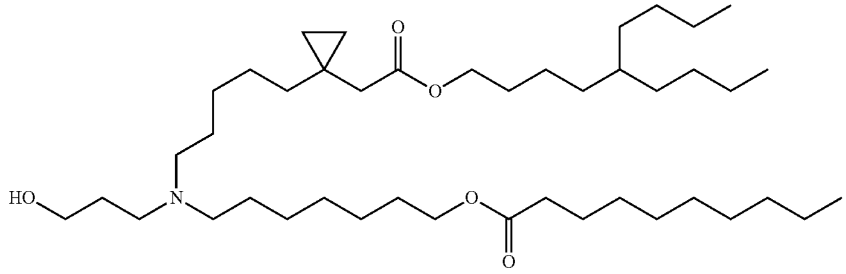
228c
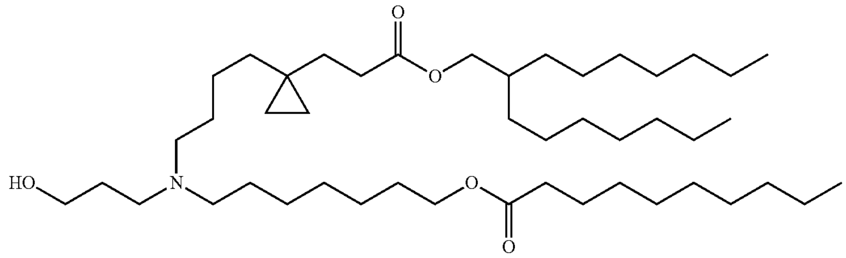
229c
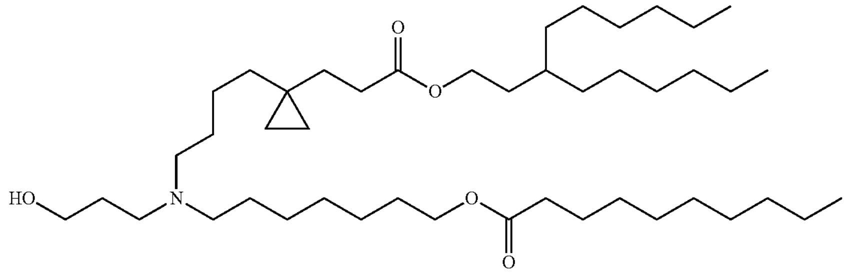
230c
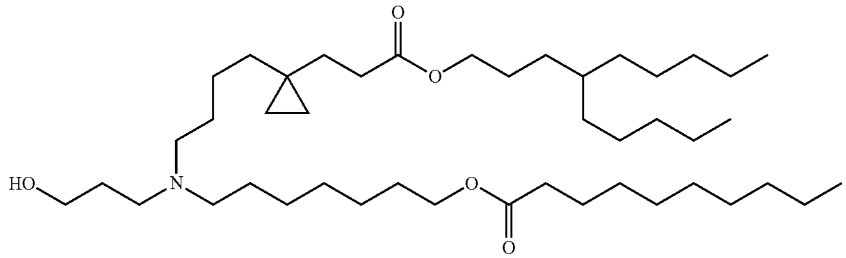
231c
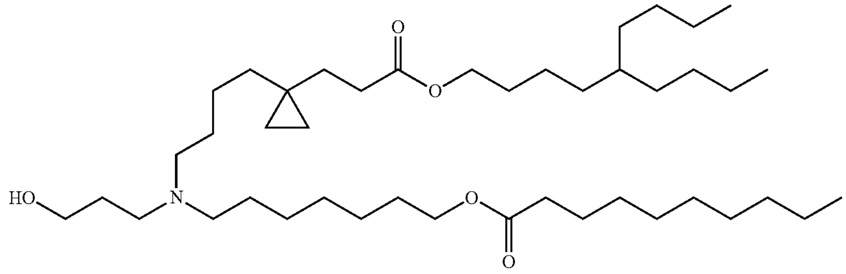

-continued
232c
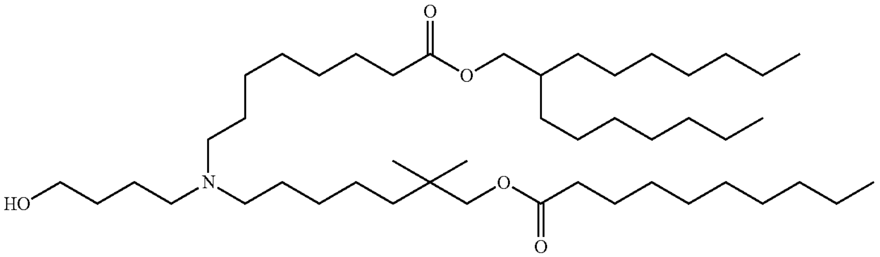
233c
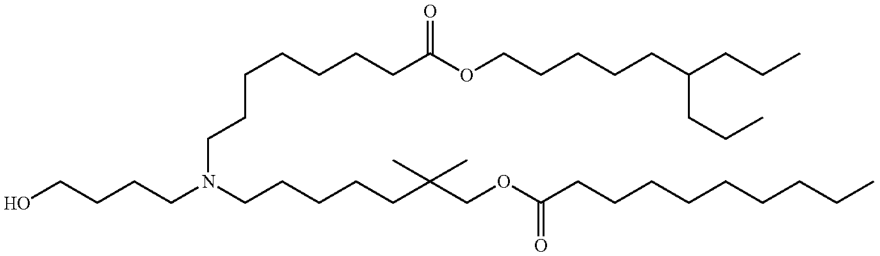
234c
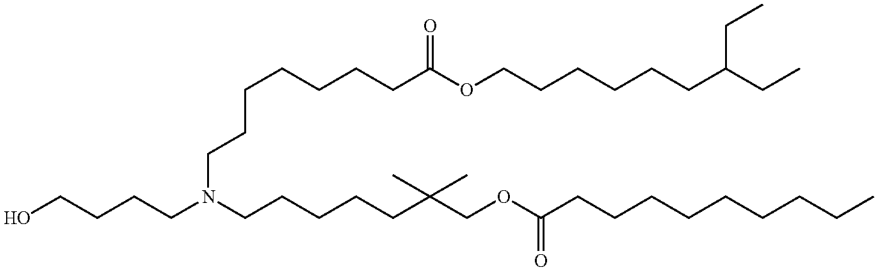
235c
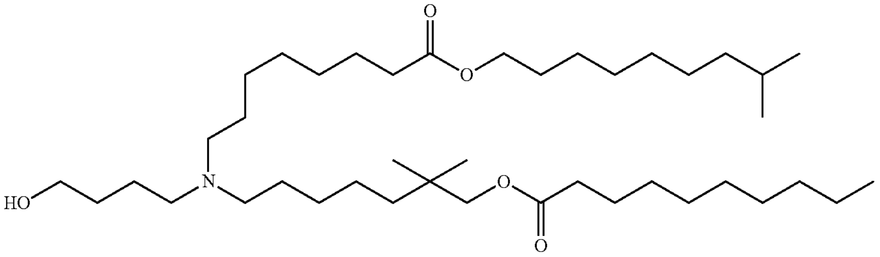
236c
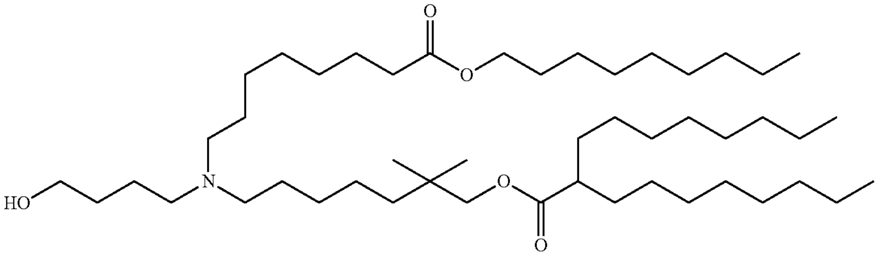
237c
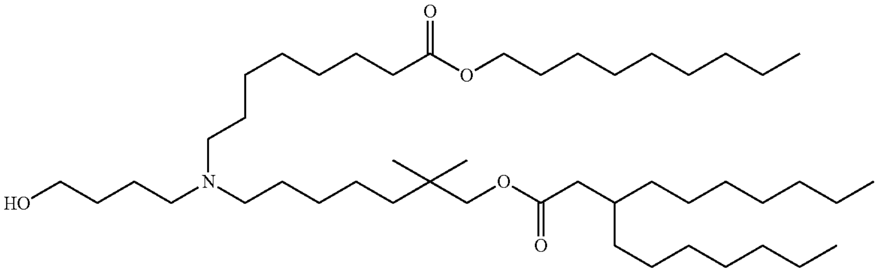

-continued
238c
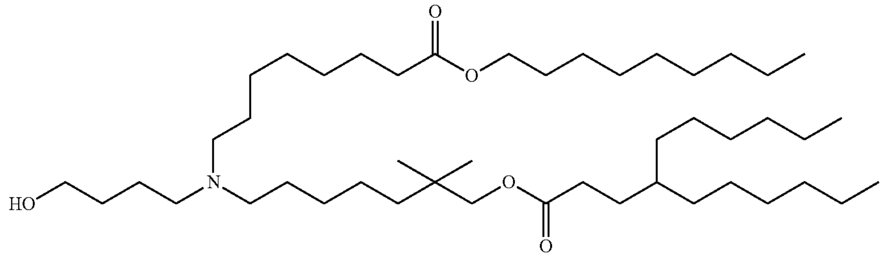
239c
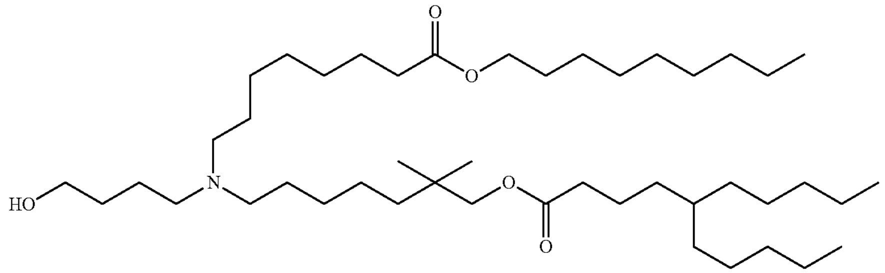
240c
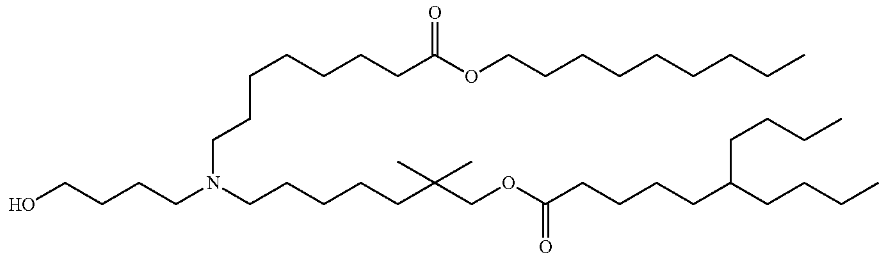
241c
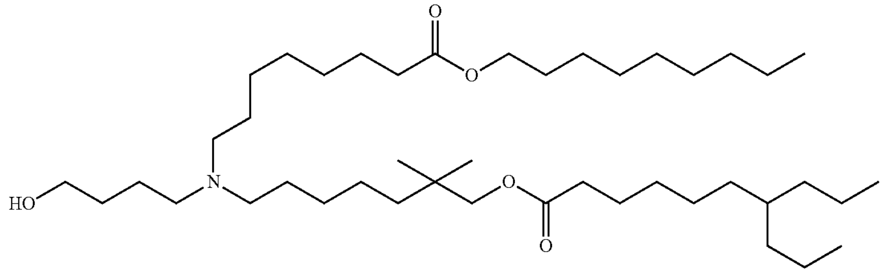
242c
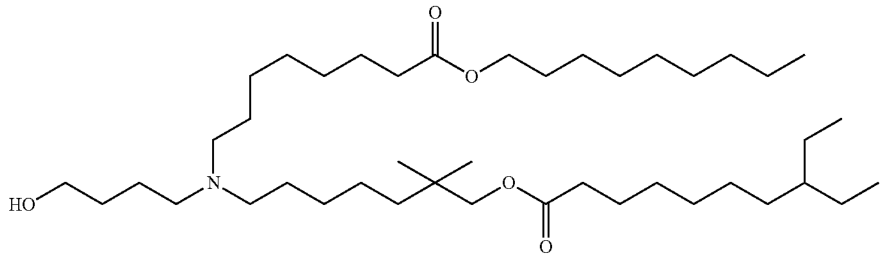
243c
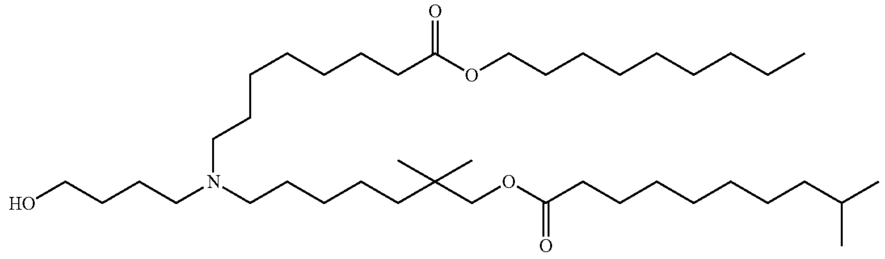

-continued
244c
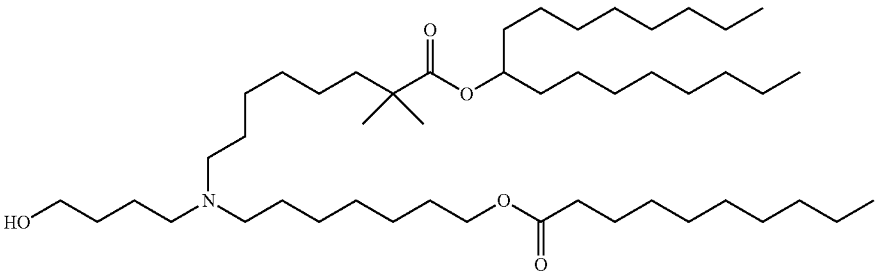
245c
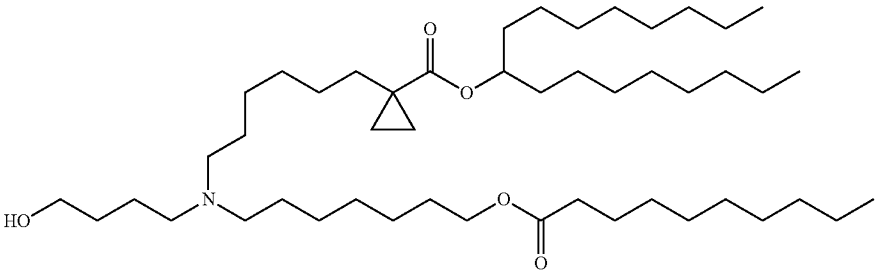
246c
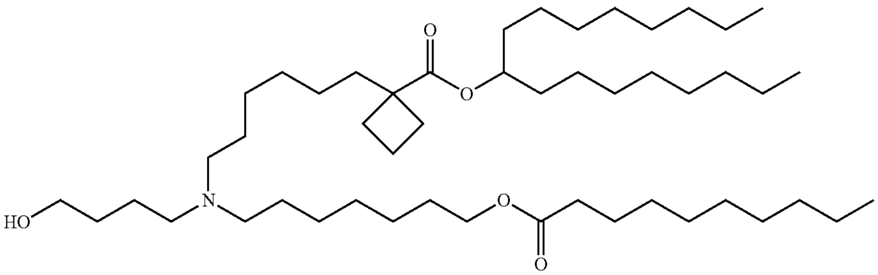
247c
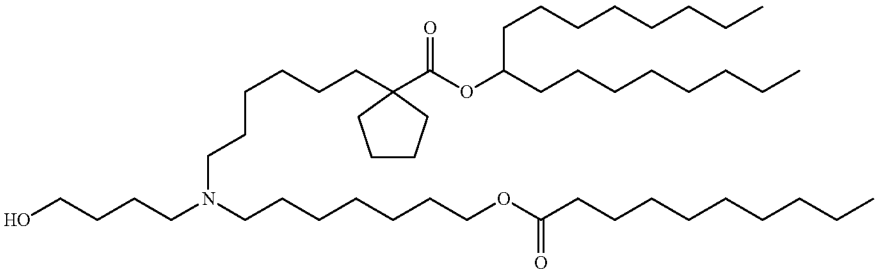
248c
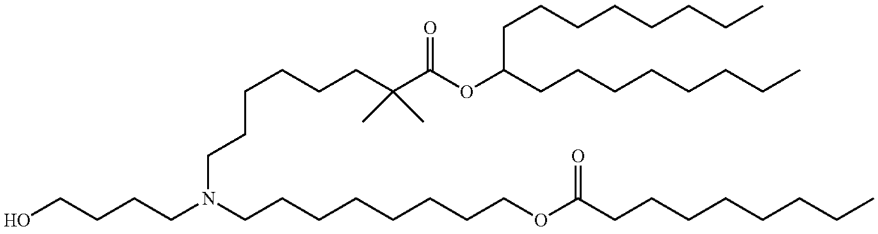
249c
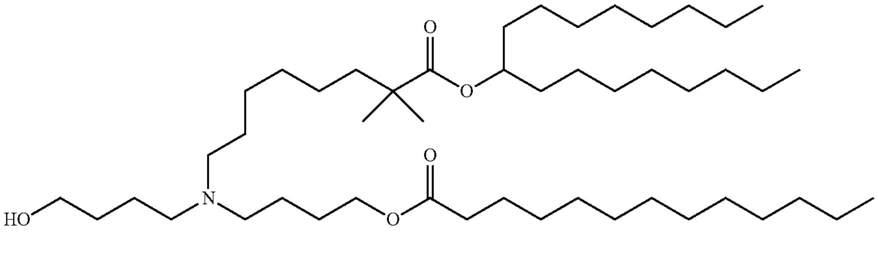

-continued
250c
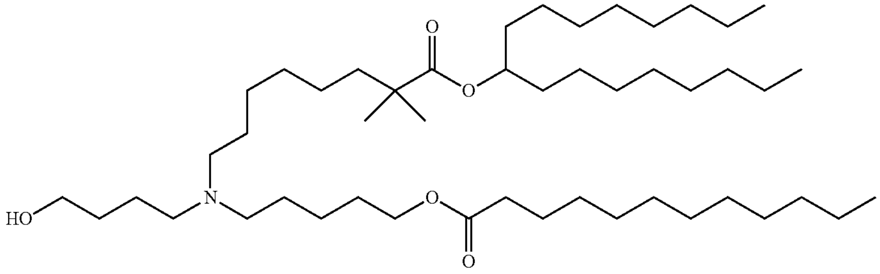
251c
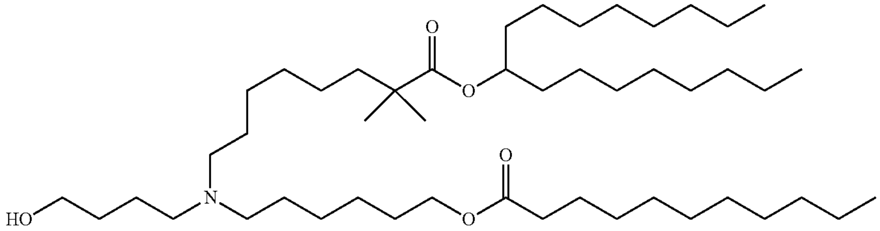
252c
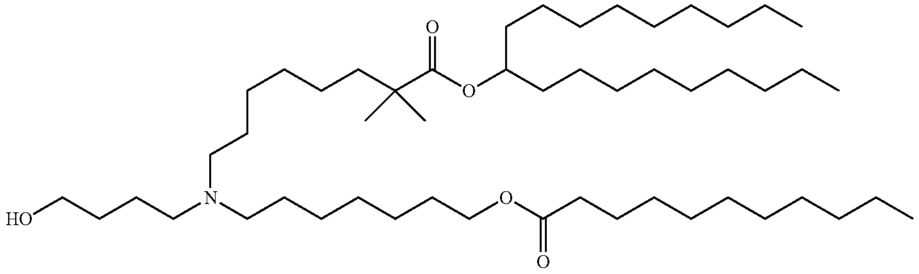
253c
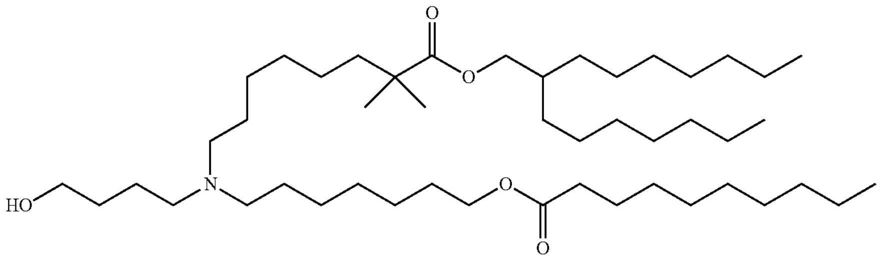
254c
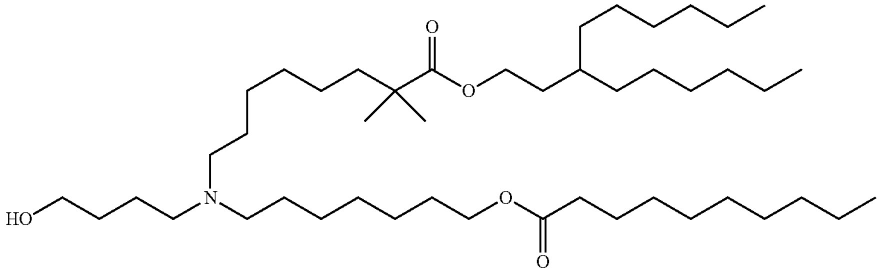
255c
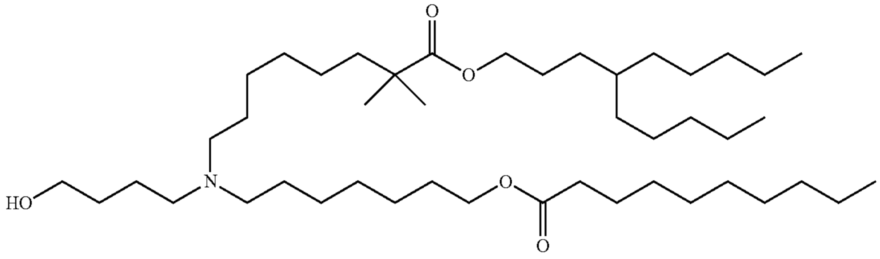

-continued
256c
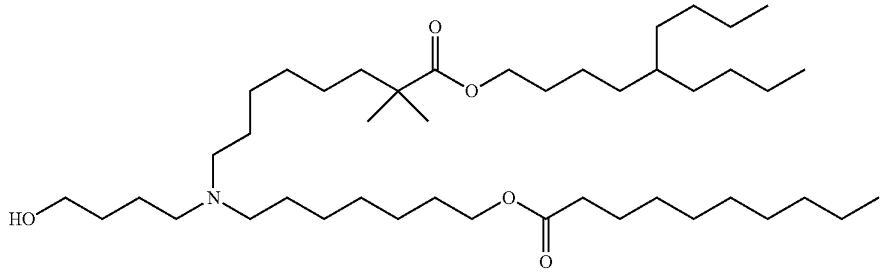
257c
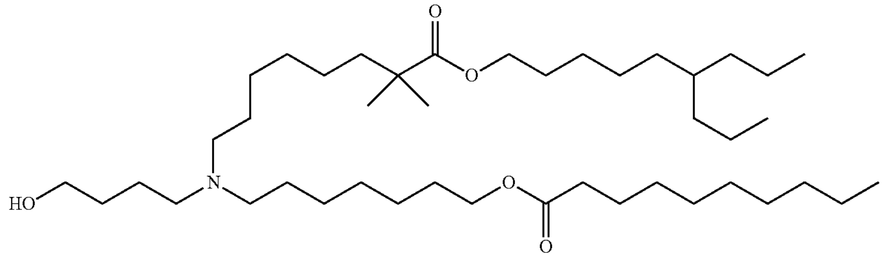
258c
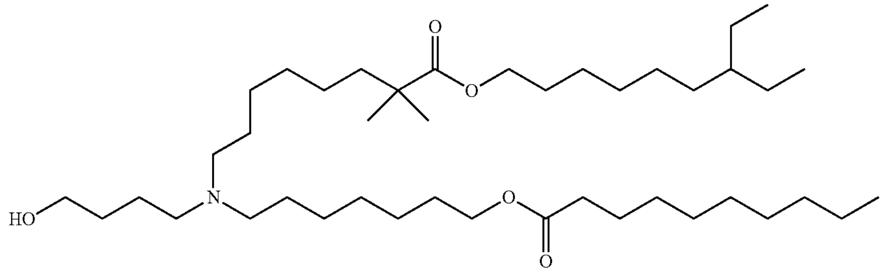
259c
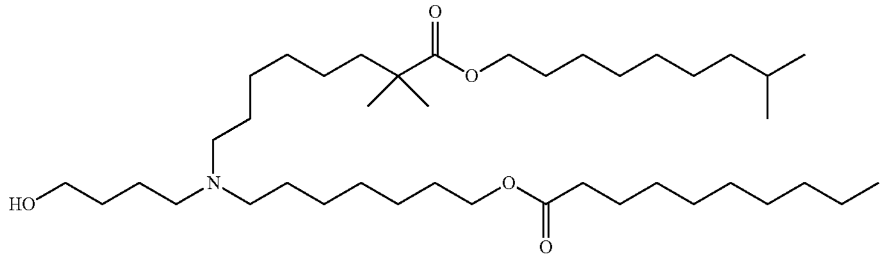
260c
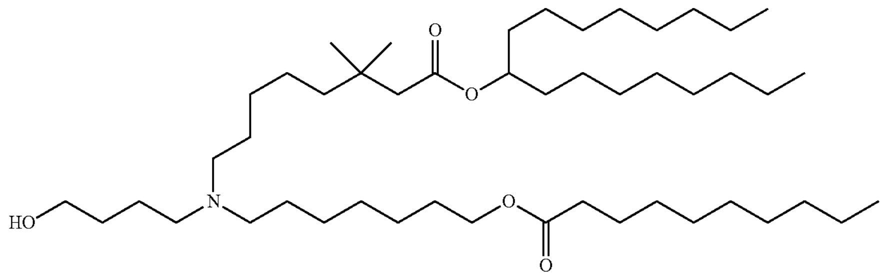
261c
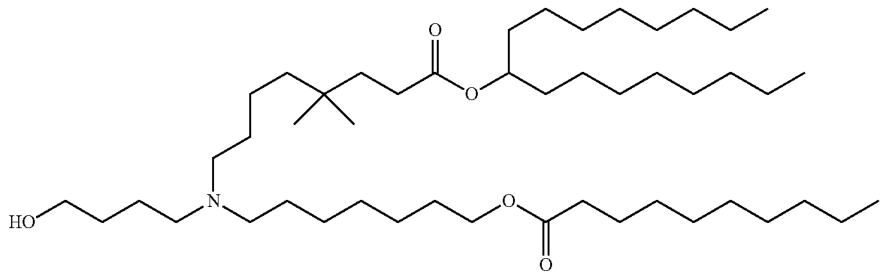

-continued
262c
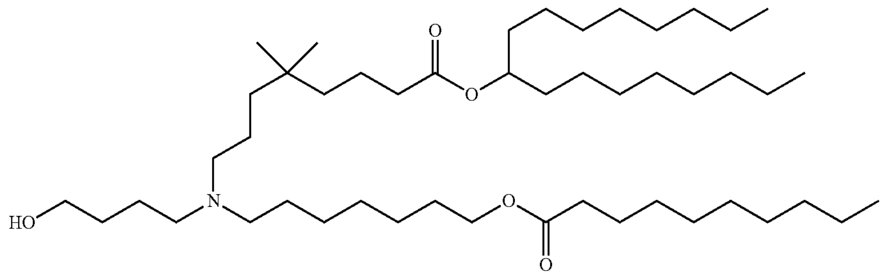
263c
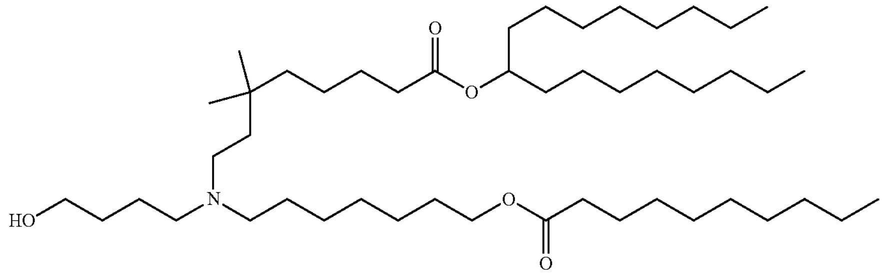
264c
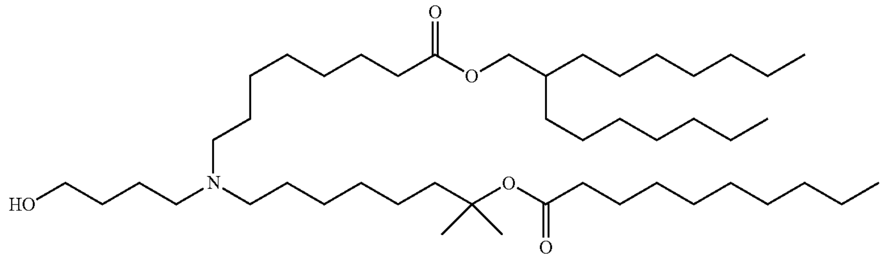
265c
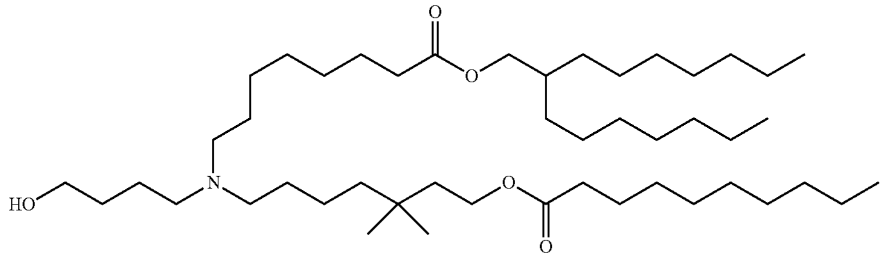
266c
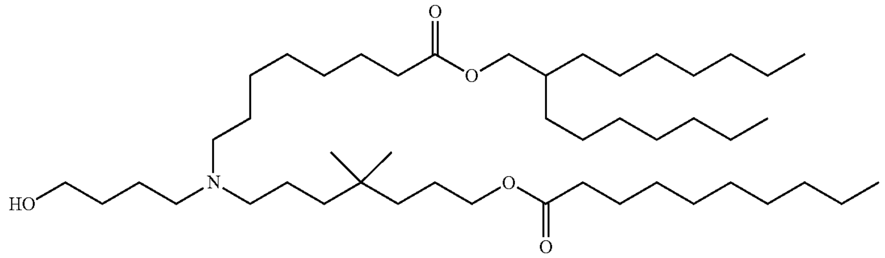
267c
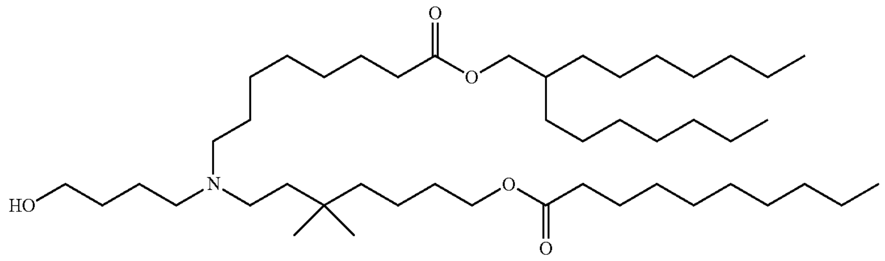

-continued
268c
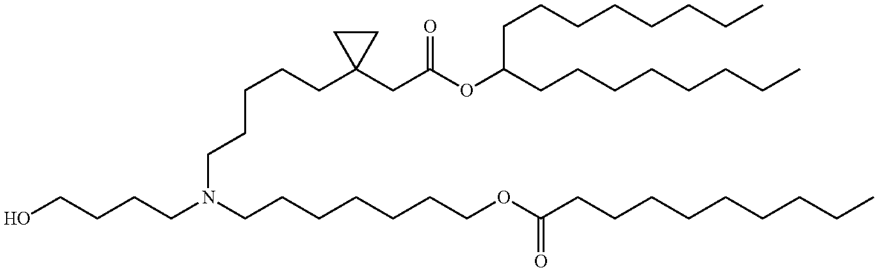
269c
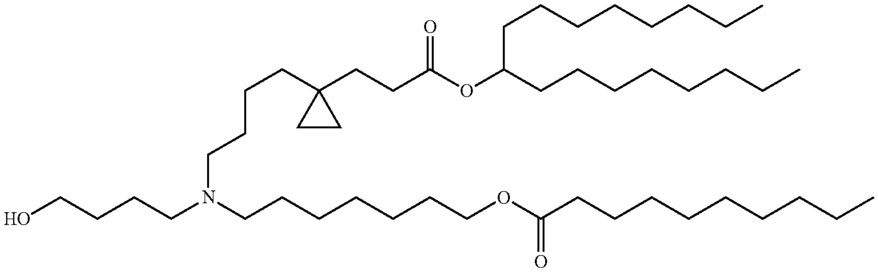
270c
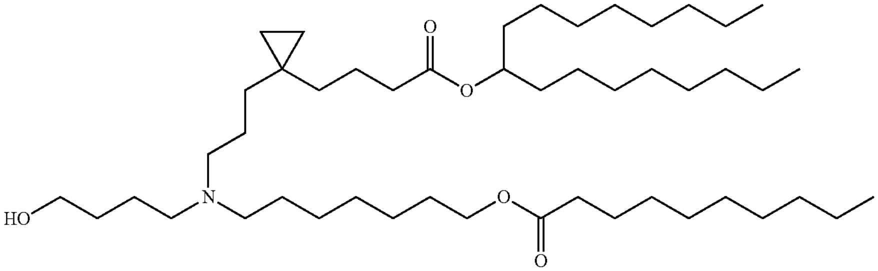
271c
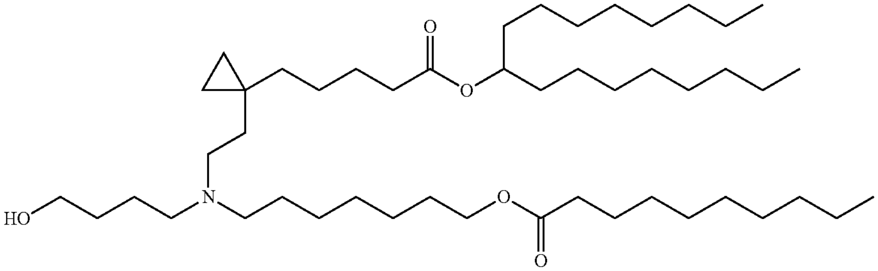
272c
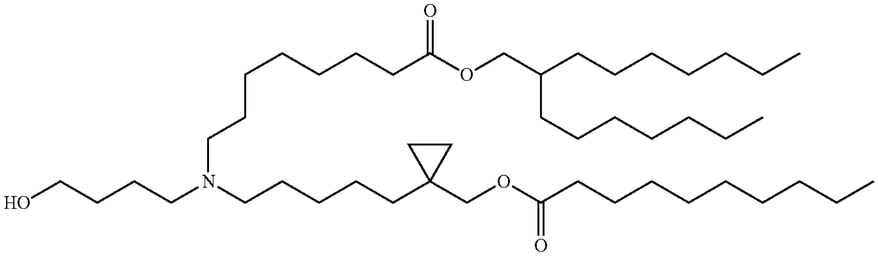
273c
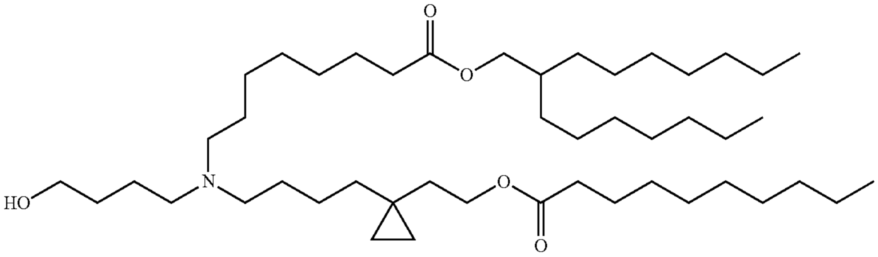

-continued
274c
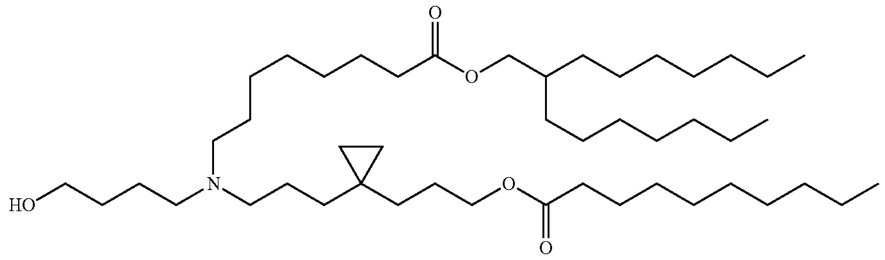
275c
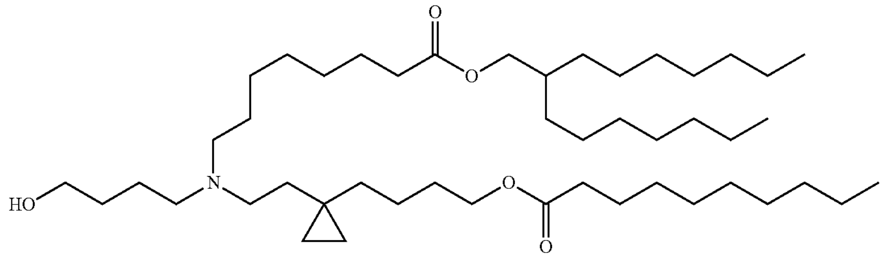
276c
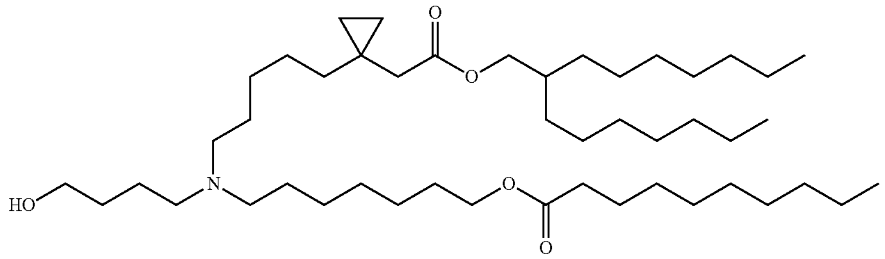
277c
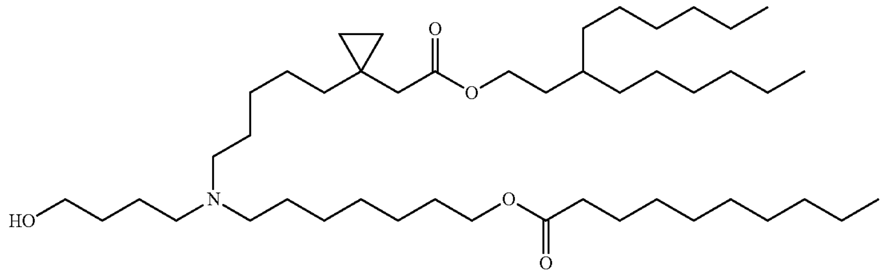
278c
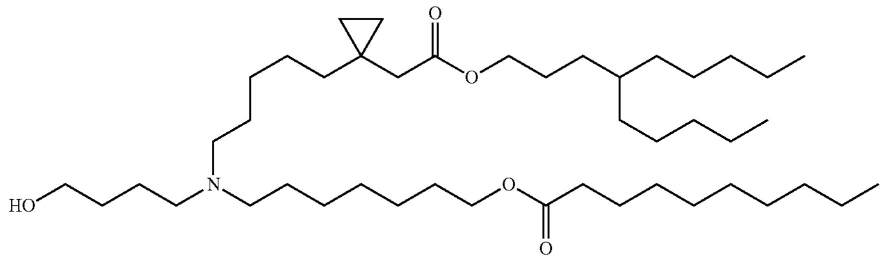
279c
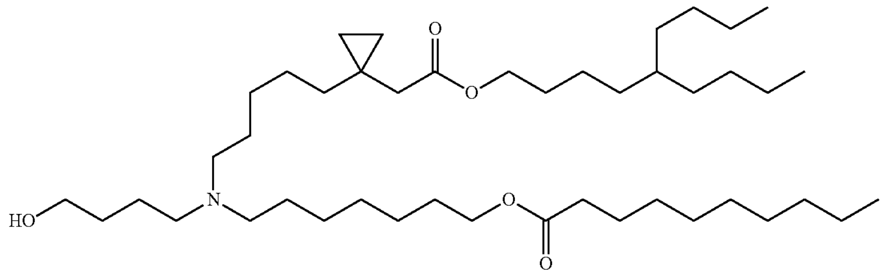

-continued
280c
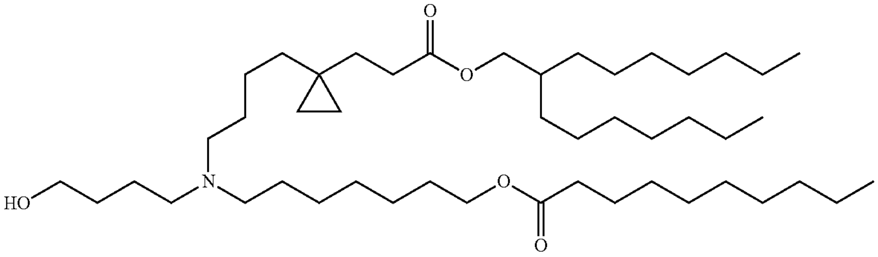
281c
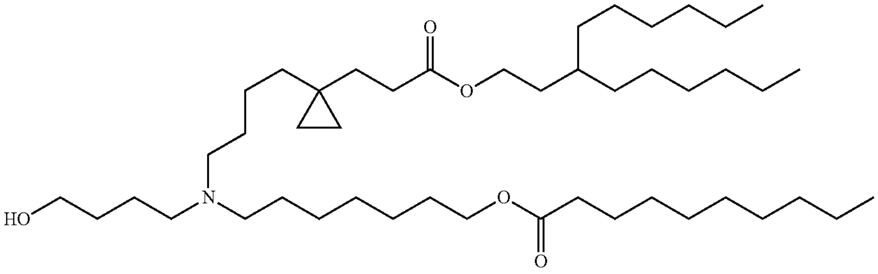
282c
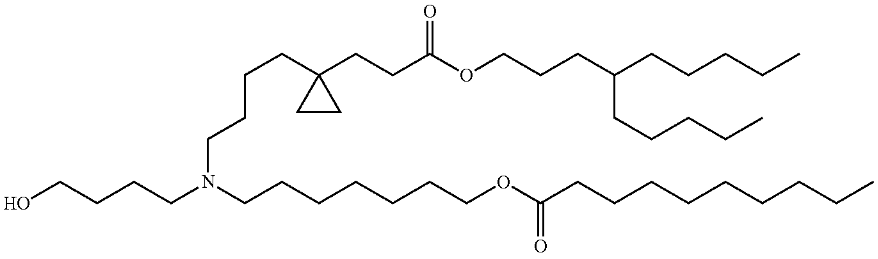
283c
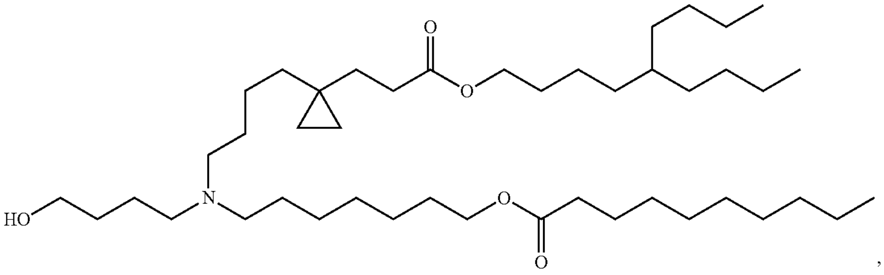
,
or a pharmaceutically acceptable salt, isotopic variant, tautomer or stereoisomer thereof.
* * * * *